US011702431B2

(12) United States Patent
Kanai et al.

(10) Patent No.: US 11,702,431 B2
(45) Date of Patent: *Jul. 18, 2023

(54) OXO-SUBSTITUTED COMPOUND

(71) Applicants: Sumitomo Pharma Co., Ltd., Osaka (JP); THE KITASATO INSTITUTE, Minato-ku (JP)

(72) Inventors: Toshio Kanai, Osaka (JP); Sachiko Koike, Osaka (JP); Takayuki Fukaya, Osaka (JP); Shunichiro Uesugi, Osaka (JP); Shingo Mizushima, Osaka (JP); Hitoshi Suda, Osaka (JP); Yuki Mizukami, Osaka (JP); Yohei Ikuma, Osaka (JP); Toshiaki Sunazuka, Minato-ku (JP); Yoshihiko Noguchi, Minato-ku (JP)

(73) Assignees: Sumitomo Pharma Co., Ltd., Osaka (JP); THE KITASATO INSTITUTE, Minato-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/050,747

(22) PCT Filed: Apr. 26, 2019

(86) PCT No.: PCT/JP2019/018011
§ 371 (c)(1),
(2) Date: Oct. 26, 2020

(87) PCT Pub. No.: WO2019/208797
PCT Pub. Date: Oct. 31, 2019

(65) Prior Publication Data
US 2021/0147448 A1    May 20, 2021

(30) Foreign Application Priority Data

Apr. 27, 2018 (JP) .............................. JP2018-087761

(51) Int. Cl.
*C07F 5/02* (2006.01)
*A61P 31/04* (2006.01)
*A61K 45/06* (2006.01)
*A61K 31/407* (2006.01)
*A61K 31/69* (2006.01)

(52) U.S. Cl.
CPC ............ *C07F 5/025* (2013.01); *A61K 31/407* (2013.01); *A61K 31/69* (2013.01); *A61K 45/06* (2013.01); *A61P 31/04* (2018.01)

(58) Field of Classification Search
CPC . C07F 5/025; C07F 5/027; C07F 5/02; A61K 31/407; A61K 31/69; A61K 45/06; A61P 31/04; A61P 1/02; A61P 1/16; A61P 11/00; A61P 11/02; A61P 11/04; A61P 13/02; A61P 15/08; A61P 17/02; A61P 19/02; A61P 27/02; A61P 27/16; A61P 29/00; A61P 31/10; A61P 31/12; A61P 37/08; A61P 43/00

See application file for complete search history.

(56) References Cited

U.S. PATENT DOCUMENTS

| 2015/0291630 A1 | 10/2015 | Burns et al. |
| 2016/0016978 A1 | 1/2016 | Burns et al. |
| 2017/0073360 A1 | 3/2017 | Burns et al. |
| 2017/0088561 A1 | 3/2017 | Reddy et al. |
| 2017/0136047 A1 | 5/2017 | Reddy et al. |
| 2018/0051041 A1 | 2/2018 | Hecker et al. |

FOREIGN PATENT DOCUMENTS

| WO | WO 2014/089365 A1 | 6/2014 | |
| WO | WO 2014/107535 A1 | 7/2014 | |
| WO | WO 2014/107536 A1 | 7/2014 | |
| WO | WO 2014/110442 A1 | 7/2014 | |
| WO | WO 2014/151958 A1 | 9/2014 | |
| WO | WO 2015/179308 A1 | 11/2015 | |
| WO | WO-2015179308 A1 * | 11/2015 | ........... A61K 31/407 |
| WO | WO 2015/191907 A1 | 12/2015 | |
| WO | WO 2016/003929 A1 | 1/2016 | |
| WO | WO 2016/149393 A1 | 9/2016 | |
| WO | WO 2017/044828 A1 | 3/2017 | |

OTHER PUBLICATIONS

International Search Report dated Jul. 16, 2019 in PCT/JP2019/018011 filed on Apr. 26, 2019, 3 pages.
Buynak, J.D.; "β-Lactamase inhibitors: a review of the patent literature", Expert Opin. Ther. Patents, 2013, vol. 23, No. 11; pp. 1469-1481.
Extended European Search Repori dated Feb. 23, 2022 in European Patent Application No. 19793135.5, 9 pages
Australian Office Action dated Aug. 31, 2022 in Australian Patent Application No. 2019259818, 3 pages.
Mexican Office Action dated Sep. 28, 2022 in Mexican Patent Application No. MX/a/2020/011367 (with unedited computer-generated English translation), 12 pages.
Office Action dated May 5, 2022, in corresponding Indian Patent Application No. 202017048770 (with English Translation), 6 pages
Eurasian Office Action dated Jan. 24, 2022 in Eurasian Patent Application No. 202092579 (with English language translation), 7 pages.
Office Action dated Nov. 4, 2022 in corresponding Indonesian application No. P00202008986 (with English translation).
Office Action and Search Report dated Feb. 15, 2023, issued in a Chinese Patent Application No. 201980028757.2 (with English translation).
Official Acton dated Apr. 17, 2023, issued in the Japanese Patent Application No. 2020-515615 with English translation.
Examination Report dated Apr. 11, 2023, issued in the Australian Patent Application No. 2019259818.

(Continued)

*Primary Examiner* — Samira J Jean-Louis
(74) *Attorney, Agent, or Firm* — Oblon, McClelland, Maier & Neustadt, L.L.P.

(57) ABSTRACT

Provided is a novel compound that has an excellent β-lactamase inhibitory effect. More specifically, provided is a compound represented by formula (1a), (1b) or (11) having an excellent β-lactamase inhibitory effect or a pharmaceutically acceptable salt thereof. By using this compound either in combination with a β-lactam drug or alone, a useful preventive or therapeutic agent for bacterial infections is provided. Also provided are useful preventive or therapeutic agents for treating various diseases with the combined use of the aforesaid compound and β-lactam drugs.

68 Claims, No Drawings

(56) References Cited

OTHER PUBLICATIONS

Office Action dated Mar. 27, 2023, issued in the Israeli Patent Application No. 27826 with English translation.
Preliminary Office Action dated Apr. 11, 2023, issued in the Brazilian Patent Application No. 112020021631-3 with Engtish translation.

* cited by examiner

OXO-SUBSTITUTED COMPOUND

This application is a national stage application of PCT/JP2019/018011, filed Apr. 26, 2019 which claims benefit of JP 2018-087761 filed on Apr. 27, 2018, the contents of each application is incorporated herein by reference.

TECHNICAL FIELD

The present invention relates to an oxo-substituted compound that is useful as a medicament or a pharmaceutically acceptable salt thereof. More specifically, the present invention relates to a pharmaceutical composition comprising a novel oxo-substituted compound or a pharmaceutically acceptable salt thereof. The present invention relates to a therapeutic agent comprising the oxo-substituted compound or a pharmaceutically acceptable salt thereof.

BACKGROUND ART

Since the discovery of penicillin, antimicrobial agents have taken an important role in the treatment of infections.

In particular, β-lactam agents (e.g., penicillin antimicrobial agents, cephalosporin antimicrobial agents, and carbapenem antimicrobial agents) are agents that are most commonly used in the treatment of bacterial infections in view of their potent sterilizing capacity and high degree of safety. However, with increased use of β-lactam agents, emergence and prevalence of pathogenic bacteria that have acquired resistance to β-lactam agents have become a global problem. Examples of the mechanism of acquiring resistance of such pathogens include production of β-lactamase, structural change in the target molecule of a β-lactam agent, reduced drug permeation into microbial cell, elevated drug discharge, and the like. In particular, production of β-lactamase, which degrades and inactivates β-lactam agents, is one of the most influential in the maintenance of efficacy of β-lactam agents. Various bacteria are involved in the evolution of β-lactamase that antagonizes the efficacy of various β-lactam agents. β-lactamases can be classified into 4 classes based on their amino acid sequences, i.e., Ambler classes A, B, C, and D. Since class A, C, and D enzymes have a serine residue at the center of enzymatic activity, they are known as serine-β-lactamases. Since class B enzymes do not have a serine residue at the center of enzymatic activity but have metal ion zinc ($Zn^{2+}$), they are known as metallo-β-lactamases (zinc-β-lactamases).

It has been already confirmed that concomitant use of a β-lactamase inhibiting agent and a β-lactam agent is effective for solving the problem of resistance acquisition due to production of β-lactamase. It is known that commercially available β-lactamase inhibiting agents clavulanic acid, sulbactam, and tazobactam primarily inhibit class A β-lactamases excluding KPC (*Klebsiella pneumoniae* Carbapenemase), and avibactam inhibits class A β-lactamases (including KPC), class C β-lactamases, and some class D β-lactamases including OXA-48 (Non Patent Literature 1). However, these existing β-lactamase inhibiting agents cannot effectively and broadly inhibit all β-lactamases produced by various bacteria. For example, such inhibiting agents do not exert an effect on class B metallo-β lactamases. Recently, β-lactamases called ESBLs (Extended Spectrum β-Lactamases) that can degrade more substrates (β-lactam agent) compared to conventional β-lactamases were isolated, which have led to a problem as a new resistant bacteria, especially as a causative bacteria for hospital-acquired infections in the US and Europe. In addition, emergence and prevalence of metallo-β-lactamase producing bacteria is becoming a problem in Japan. In view of such a circumstance, it is very important to address β-lactamase producing bacteria including ESBLs and metallo-β-lactamase for the prophylaxis of hospital-acquired infections. Furthermore, pathogenic bacteria evolve quickly, such that emergence of new β-lactamase resistant bacteria is very likely. Accordingly, as a solution to such problems or as a safeguard against such issues to be addressed, there is a demand for the development of a novel β-lactamase inhibiting agent that has a different structure from existing β-lactamase inhibiting agents, whereby a broader β-lactamase inhibitory action or metallo-β-lactamase inhibitory action is expected.

Recently, boronic acid derivatives with β-lactamase inhibitory action have been reported in Patent Literatures 1 to 9 and the like. These Patent Literatures do not disclose a structure related to the oxo-substituted compounds encompassed by the present invention, i.e., a boronic acid compound group having a non-aryl heterocycle (preferably a nitrogen-containing non-aryl heterocycle) on a side chain at a specific position and an oxo substituent (—C(=O)—, —S(=O)—, —S(=O)$_2$—, or the like) that attaches to the ring.

CITATION LIST

Patent Literature

[PTL 1] WO 2014/107535
[PTL 2] WO 2014/107536
[PTL 3] WO 2015/179308
[PTL 4] WO 2016/003929
[PTL 5] WO 2016/149393
[PTL 6] WO 2014/089365
[PTL 7] WO 2014/110442
[PTL 8] WO 2014/151958
[PTL 9] WO 2015/191907

Non Patent Literature

[NPL 1] Buynak. J D. Expert Opinion on Therapeutic Patents, 2013, 23(11), 1469-1481.

SUMMARY OF INVENTION

Solution to Problem

The present invention provides a novel compound having excellent β-lactamase inhibitory action and provides a prophylactic or therapeutic agent that is useful for a bacteria infection, alone or in concomitant use with a β-lactam agent. Specifically, the present invention provides a prophylactic or therapeutic agent that is useful for therapy, by concomitant use with a β-lactam agent, of a disease such as sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, deep skin infection, lymphangitis/lymphadenitis, secondary infection of trauma, burn injury, surgical wound, or the like, urinary tract infection, genital infection, eye infection, or odontogenic infection.

More specifically, the inventors completed the present invention by finding that a compound represented by formula (1a), (1b), or (11) described below or a pharmaceutically acceptable salt thereof (also referred to as the "compound of the invention" hereinafter) has excellent β-lactamase inhibitory action. Specifically, the present invention is the following.

[Item A1]

A compound represented by formula (1a) or (1b):

[Chemical Formula 1]

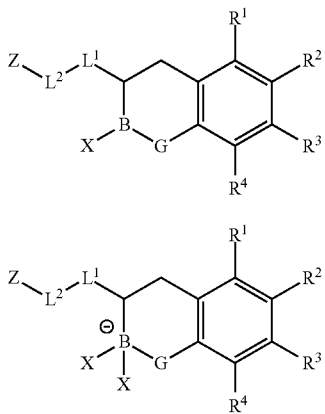

or a pharmaceutically acceptable salt thereof
wherein
G is an oxygen atom, a sulfur atom, or —$NR^{a1}$—,
X is a hydroxyl group, an optionally substituted $C_{1-6}$ alkoxy group, or —$NR^{a2}R^{b1}$,
$R^{a1}$, $R^{a2}$, and $R^{b1}$ are the same or different, each independently
1) a hydrogen atom,
2) a $C_{1-6}$ alkyl group,
3) a $C_{3-10}$ alicyclic group,
4) $C_{6-10}$ aryl,
5) 5- or 6-membered heteroaryl,
6) a 4- to 10-membered non-aryl heterocycle,
7) a $C_{1-6}$ alkylcarbonyl group,
8) a $C_{3-10}$ alicyclic carbonyl group,
9) a $C_{6-10}$ arylcarbonyl group,
10) a 5- or 6-membered heteroarylcarbonyl group,
11) a $C_{1-6}$ alkylsulfonyl group,
12) a $C_{3-10}$ alicyclic sulfonyl group,
13) a $C_{6-10}$ arylsulfonyl group,
14) a 5- or 6-membered heteroarylsulfonyl group, or
15) —$OR^{c1}$,
(wherein each substituent from 2) to 14) is optionally substituted),
wherein $R^{a2}$ and $R^{b1}$ together may form an optionally substituted 4- to 10-membered nitrogen-containing non-aryl heterocycle,
$R^{c1}$ is
1) a hydrogen atom,
2) a $C_{1-6}$ alkyl group,
3) a $C_{3-10}$ alicyclic group,
4) $C_{6-10}$ aryl,
5) 5- or 6-membered heteroaryl, or
6) a 4- to 10-membered non-aryl heterocycle,
(wherein each substituent from 2) to 6) is optionally substituted),
$L^1$ is a single bond, an oxygen atom, a sulfur atom, —SO—, —$SO_2$—, —$NR^d$—, —$NR^dC(=O)$—, or —$NR^dSO_2$—, $L^2$ is a single bond or an optionally substituted $C_{1-6}$ alkylene group,
Z is
1) a hydrogen atom,
2) a hydroxyl group,
3) a cyano group,
4) a carboxyl group,
5) a $C_{3-10}$ alicyclic group,
6) $C_{6-10}$ aryl,
7) 5- or 6-membered heteroaryl,
8) a 4- to 10-membered non-aryl heterocycle,
9) a $C_{1-6}$ alkoxy group,
10) a $C_{3-10}$ alicyclic oxy group,
11) a $C_{6-10}$ aryloxy group,
12) a 5- or 6-membered heteroaryloxy group,
13) a 4- to 10-membered non-aryl heterocyclyl oxy group,
14) a $C_{1-6}$ alkylthio group,
15) a $C_{3-10}$ alicyclic thio group,
16) a $C_{6-10}$ arylthio group,
17) a 5- or 6-membered heteroarylthio group,
18) a 4- to 10-membered non-aryl heterocyclyl thio group,
(wherein each substituent from 5) to 18) is optionally substituted),
19) —$SO_2$—$NR^{e1}R^{f1}$,
20) —$NR^{e1}$—C(=O)$OR^{f1}$,
21) —$NR^{g1}$—C(=O)$NR^{e1}R^{f1}$,
22) —$NR^{e1}$—C(=S)$R^{f1}$,
23) —$NR^{i1}$—C(=S)$OR^{f1}$,
24) —$NR^{g1}$—C(=S)$NR^{f1}$,
25) —$NR^{g1}$—$CR^{e1}$(=$NR^{f1}$),
26) —$NR^{g1}$—$CR^{e1}$(=N—$OR^{f1}$),
27) —$NR^{h1}$—C(=$NR^{g1}$)$NR^{e1}R^{f1}$,
28) —$NR^{h1}$—C(=N—$OR^{g1}$)$NR^{e1}R^{f1}$,
29) —$NR^{i1}$—C(—$NR^{h1}$)$NR^{g1}$—$NR^{e1}R^{f1}$,
30) —$NR^{i1}$—C(=N—$OR^{h1}$)$NR^{g1}$—$NR^{e1}R^{f1}$,
31) —$NR^{e1}$—$SO_2$—$R^{f1}$,
32) —$NR^{g1}$—$SO_2$—$NR^{e1}R^{f1}$,
33) —C(=O)$OR^{e1}$,
34) —C(=S)$OR^{e1}$,
35) —C(=S)$NR^{e1}R^{f1}$,
36) —C(=S)$NR^{e1}OR^{f1}$,
37) —C(=S)$NR^{g1}$—$NR^{e1}R^{f1}$,
38) —C(=$NR^{e1}$)$R^{f1}$,
39) —C(=N—$OR^{e1}$)$R^{f1}$,
40) —C(=$NR^{h1}$)$NR^{g1}$—$NR^{e1}R^{f1}$,
41) —C(=N—$OR^{h1}$)$NR^{g1}$—$NR^{e1}R^{f1}$,
42) —$NR^{e1}R^{f1}$,
43) —$NR^{g1}$—$NR^{e1}R^{f1}$,
44) —$NR^{e1}OR^{f1}$,
45) —$NR^{e1}$—C(=O)$R^{f1}$,
46) —C(=O) $NR^{e1}R^{f1}$,
47) —C(=O) $NR^{e1}OR^{f1}$,
48) —C(=O)$NR^{g1}$—$NR^{e1}R^{f1}$,
49) —C(=O)$R^{e1}$,
50) —C(=$NR^{g1}$)$NR^{e1}R^{f1}$, or
51) —C(=N—$OR^{h1}$)$NR^{e1}R^{f1}$,
one of $R^1$, $R^2$, and $R^3$ is a group represented by formula (2):

[Chemical Formula 2]

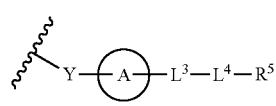

wherein
Y is an oxygen atom, a sulfur atom, or —NR$^j$—,
ring A is an optionally substituted 4- to 20-membered non-aryl heterocycle,
L$^3$ is —C(=O)—, —S(=O)—, or —S(=O)$_2$—,
L$^4$ is
1) a single bond,
2) a C$_{1-6}$ alkylene group,
3) a C$_{1-10}$ cycloalkylene group,
4) a C$_{6-10}$ arylene group
5) a 5- or 6-membered heteroarylene group,
6) a 4- to 10-membered non-aryl heterocyclylene group, or
7) —C(=N—OR$^{h1}$)—
(wherein each substituent from 2) to 6) is optionally substituted), and
R$^5$ is
1) a hydrogen atom,
2) a C$_{1-6}$ alkyl group,
3) a C$_{3-10}$ alicyclic group,
4) a 4- to 10-membered non-aryl heterocycle,
5) C$_{6-10}$ aryl,
6) 5- or 6-membered heteroaryl,
7) a C$_{1-6}$ alkylthio group,
(wherein each substituent from 2) to 7) is optionally substituted), or
8) —NR$^{e1}$OH,
the remaining two (without the structure of formula (2) among R$^1$, R$^2$, and R$^3$) are the same or different, each independently a hydrogen atom, a halogen atom, an optionally substituted C$_{1-6}$ alkyl group, an optionally substituted C$_{1-6}$ alkoxy group, an optionally substituted C$_{1-6}$ alkylthio group, an optionally substituted 5- or 6-membered heteroaryl, or —NR$^{a3}$R$^{b2}$,
R$^d$, R$^{e1}$, R$^{e2}$, R$^{f1}$, R$^{f2}$, R$^{g1}$, R$^{g2}$, R$^{h1}$, R$^{h2}$, R$^{i1}$, R$^{i2}$, and R$^j$ are the same or different, each independently a hydrogen atom, an optionally substituted C$_{1-6}$ alkyl group, an optionally substituted C$_{3-10}$ alicyclic group, optionally substituted C$_{6-10}$ aryl, optionally substituted 5- or 6-membered heteroaryl, or an optionally substituted 4- to 10-membered non-aryl heterocycle,
a combination of R$^{e1}$ and R$^{f1}$ or R$^{e2}$ and R$^{f2}$, when attached to the same nitrogen atom, together may form an optionally substituted 4- to 10-membered nitrogen-containing non-aryl heterocycle,
R$^4$ is
1) —C(=O)R$^8$,
2) —SO$_2$-L$^6$-R$^8$,
(wherein R$^8$ in 1) and 2) is —NR$^{a5}$R$^{b4}$, —NR$^{a5}$-L$^7$-B(OR$^{m1}$)$_2$, —OR$^{m1}$, or an optionally substituted C$_{1-6}$ alkyl group, and L$^6$ is a single bond or —NR$^{a6}$—),
3) —NR$^{a4}$R$^{b3}$,
4) —B(OR$^{m1}$)$_2$,
5) —PO(OR$^{m1}$)(OR$^{m2}$),
6) optionally substituted 5-membered heteroaryl,
7) an optionally substituted 5-membered non-aryl heterocycle, or
8) a bioisostere of one of 1) to 7),
(wherein the formulas of 2), 4), 5), and 6) include a carboxylic acid isostere, and 8) may include them in duplicates),
R$^{a3}$, R$^{a4}$, R$^{a5}$, R$^{a6}$, R$^{b2}$, R$^{b3}$, and R$^{b4}$ are the same or different, each independently having the same definition as R$^{a1}$, R$^{a2}$, and R$^{b1}$, wherein a combination of R$^{a3}$ and R$^{b2}$, R$^{a4}$ and R$^{b3}$, or R$^{a5}$ and R$^{b4}$, when attached to the same nitrogen atom, together may form an optionally substituted 4- to 10-membered nitrogen-containing non-aryl heterocycle, R$^{m1}$ is
1) a hydrogen atom,
2) a C$_{1-6}$ alkyl group,
3) a C$_{3-10}$ alicyclic group,
4) C$_{6-10}$ aryl,
5) 5- or 6-membered heteroaryl, or
6) a 4- to 10-membered non-aryl heterocycle
(wherein each substituent from 2) to 6) is optionally substituted),
wherein if R$^{m1}$ is attached to a boron atom via an oxygen atom, two R$^{m1}$, as C$_{2-4}$ alkylene, together with the boron atom and two oxygen atoms, may form a 5- to 7-membered non-aryl heterocycle (wherein an alkylene moiety is optionally substituted in the non-aryl heterocycle),
R$^{m2}$ is a hydrogen atom, an optionally substituted C$_{1-6}$ alkyl group, or an optionally substituted C$_{3-10}$ alicyclic group, and
L$^7$ is an optionally substituted C$_{1-3}$ alkylene group.
[Item A2]
The compound or the pharmaceutically acceptable salt thereof according to item A1, wherein
L$^1$ is a single bond, a sulfur atom, —NR$^d$C(=O)—, or —NR$^d$SO$_2$—,
L$^2$ is a single bond or an optionally substituted C$_{1-6}$ alkylene group, and
Z is
1) a hydrogen atom,
2) a hydroxyl group,
3) a C$_{3-10}$ alicyclic group,
4) C$_{6-10}$ aryl,
5) 5- or 6-membered heteroaryl,
6) a 4- to 10-membered non-aryl heterocycle,
7) —C(=N—OR$^{e1}$)R$^{f1}$, or
8) —NR$^{e1}$R$^{f1}$.
[Item A3]
The compound or the pharmaceutically acceptable salt thereof according to item A1 or A2, wherein
Z-L$^2$-L$^1$ is a hydrogen atom, an optionally substituted C$_{1-6}$ alkyl group, or an optionally substituted C$_{1-6}$ alkylthio group.
[Item A4]
The compound or the pharmaceutically acceptable salt thereof according to any one of items A1 to A3, wherein Z-L$^2$-L$^1$ is a hydrogen atom.
[Item A5]
The compound or the pharmaceutically acceptable salt thereof according to any one of items A1 to A4, wherein G is an oxygen atom.
[Item A6]
The compound or the pharmaceutically acceptable salt thereof according to any one of items A1 to A5, wherein X is a hydroxyl group or an optionally substituted C$_{1-6}$ alkoxy group.
[Item A7]
The compound or the pharmaceutically acceptable salt thereof according to any one of items A1 to A6, wherein X is a hydroxyl group.
[Item A8]
The compound or the pharmaceutically acceptable salt thereof according to any one of items A1 to A7, wherein the compounds of formulas (1a) and (1b) are represented by formulas (3a) and (3b), respectively:

[Chemical Formula 3]

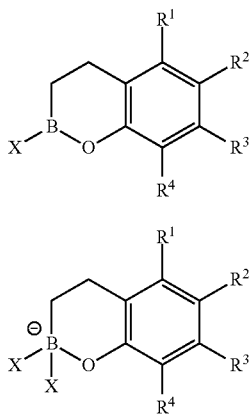

wherein X, $R^1$, $R^2$, and $R^3$ are defined the same as any one of items A1 to A7, and $R^4$ is selected from the group consisting of
1) —COOR$^{m1}$ (wherein R$^{m1}$ is a hydrogen atom, a $C_{1-6}$ alkyl group, a $C_{3-10}$ alicyclic group, $C_{6-10}$ aryl, 5- or 6-membered heteroaryl, or a 4- to 10-membered non-aryl heterocycle, and wherein the $C_{1-6}$ alkyl group, the $C_{3-10}$ alicyclic group, the $C_{6-10}$ aryl, the 5- or 6-membered heteroaryl, and the 4- to 10-membered non-aryl heterocycle are each optionally substituted), and
2) a bioisostere of 1).

[Item A9]

The compound or the pharmaceutically acceptable salt thereof according to item A8, wherein $R^4$ is
1) —COOH (i.e., a carboxyl group), or
2) a carboxylic acid isostere.

[Item A10]

The compound or the pharmaceutically acceptable salt thereof according to any one of items A1 to A9, wherein the compounds of formulas (1a) and (1b) or the compounds of formulas (3a) and (3b) are represented by formulas (4a) and (4b), respectively:

[Chemical Formula 4]

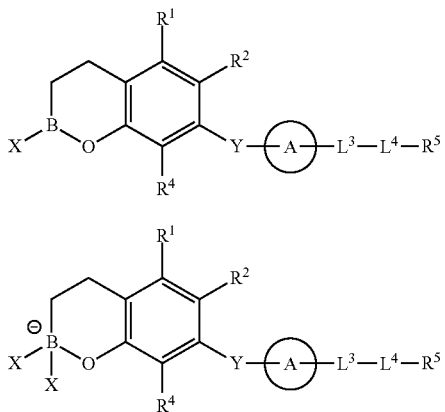

wherein X, $R^4$, Y, ring A, $L^3$, $L^4$, and $R^5$ are defined the same as any one of items A1 to A9, and $R^1$ and $R^2$ are the same or different, each independently a hydrogen atom, a halogen atom, a $C_{1-6}$ alkyl group, or a $C_{1-6}$ alkoxy group (wherein the $C_{1-6}$ alkyl group and $C_{1-6}$ alkoxy group are optionally substituted with 1 to 5 halogen atoms).

[Item A11]

The compound or the pharmaceutically acceptable salt thereof according to any one of items A1 to A10, wherein ring A is an optionally substituted 4- to 10-membered non-aryl heterocycle.

[Item A12]

The compound or the pharmaceutically acceptable salt thereof according to any one of items A1 to A11, wherein ring A is an optionally substituted 4- to 7-membered non-aryl heterocycle.

[Item A13]

The compound or the pharmaceutically acceptable salt thereof according to any one of items A1 to A12, wherein Y is an oxygen atom or a sulfur atom.

[Item A14]

The compound or the pharmaceutically acceptable salt thereof according to any one of items A1 to A13, wherein Y is an oxygen atom.

[Item A15]

The compound or the pharmaceutically acceptable salt thereof according to any one of items A1 to A14, wherein the compounds of formulas (1a) and (1b), the compounds of formulas (3a) and (3b), or the compounds of formulas (4a) and (4b) are represented by formulas (5a) and (5b), respectively:

[Chemical Formula 5]

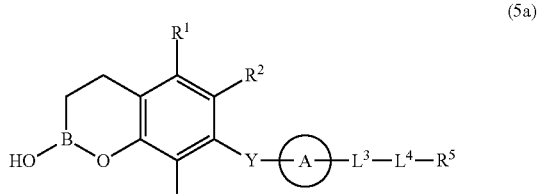

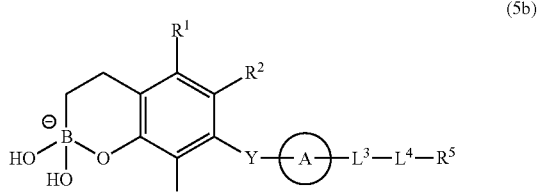

wherein ring A is an optionally substituted 4- to 6-membered nitrogen-containing non-aryl heterocycle.

[Item A16]

The compound or the pharmaceutically acceptable salt thereof according to any one of items A1 to A15, wherein $L^3$ is —C(=O)— or —S(=O)$_2$—.

[Item A17]

The compound or the pharmaceutically acceptable salt thereof according to any one of items A1 to A16, wherein $L^3$ is —C(=O)—.

[Item A18]

The compound or the pharmaceutically acceptable salt thereof according to any one of items A1 to A17, wherein $L^4$ is a single bond, —C(=N—OR$^{h1}$)—, or an optionally substituted $C_{1-6}$ alkylene group, wherein R$^{h1}$ is an optionally substituted $C_{1-6}$ alkyl group.

[Item A19]
The compound or the pharmaceutically acceptable salt thereof according to any one of items A1 to A18, wherein $L^4$ is a single bond, or a $C_{1-6}$ alkylene group optionally substituted with —$NR^{21}R^{22}$ or —$NOR^{23}$, wherein $R^{21}$, $R^{22}$, and $R^{23}$ are each independently a hydrogen atom, an optionally substituted $C_{1-6}$ alkyl group, or an optionally substituted 4- to 10-membered non-aryl heterocyclyl carbonyl group.

[Item A20]
The compound or the pharmaceutically acceptable salt thereof according to any one of items A1 to A19, wherein $L^4$ is a single bond, —$CH_2$—, —$CH(NH_2)$—, or —CH($NH_2$)—$CH_2$—, wherein if an amino group is present in $L^4$, carbon that attaches to the amino group attaches to $L^3$.

[Item A21]
The compound or the pharmaceutically acceptable salt thereof according to any one of items A1 to A20, wherein $R^5$ is a hydrogen atom, an optionally substituted $C_{1-6}$ alkyl group, an optionally substituted 4- to 10-membered non-aryl heterocycle, optionally substituted $C_{6-10}$ aryl, optionally substituted 5- or 6-membered heteroaryl, an optionally substituted $C_{1-6}$ alkylthio group, or —$NR^{e1}OH$, wherein $R^{e1}$ is a hydrogen atom or an optionally substituted $C_{1-6}$ alkyl group.

[Item A22]
The compound or the pharmaceutically acceptable salt thereof according to any one of items A1 to A21, wherein $R^5$ is optionally substituted 5- or 6-membered heteroaryl or optionally substituted $C_{6-10}$ aryl.

[Item A23]
The compound or the pharmaceutically acceptable salt thereof according to any one of items A1 to A21, wherein $L^4$ is a single bond, and $R^5$ is —$NR^{e1}OH$, wherein $R^{e1}$ is a hydrogen atom or an optionally substituted $C_{1-6}$ alkyl group.

[Item A24]
The compound or the pharmaceutically acceptable salt thereof according to any one of items A1 to A22, wherein
$R^5$ is selected from the group consisting of

[Chemical Formula 6]

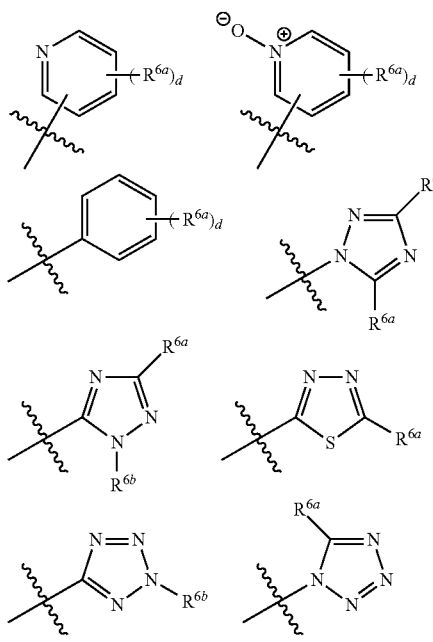

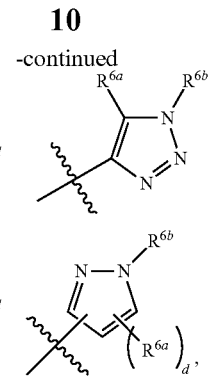

-continued subscript d is the number of substitutable positions on a ring of $R^5$, each $R^{6a}$ is independently selected from the group consisting of
1) a hydrogen atom,
2) a hydroxyl group,
3) a cyano group,
4) halogen,
5) a $C_{1-4}$ alkyl group,
6) a $C_{3-10}$ alicyclic group,
7) a $C_{1-4}$ alkoxy group,
8) a $C_{3-10}$ alicyclic oxy group,
9) a $C_{6-10}$ aryloxy group,
10) a 5- or 6-membered heteroaryloxy group,
11) a 4- to 10-membered non-aryl heterocyclyl oxy group, (wherein each substituent from 5) to 11) is optionally substituted),
12) —$SO_2$—$NR^{e2}R^{f2}$,
13) —$NR^{g2}$—$CR^{e2}(=NR^{f2})$,
14) —$NR^{g2}$—$CR^{e2}(=N$—$OR^{f2})$,
15) —$NR^{h2}$—$C(=NR^{g2})$ $NR^{e2}R^{f2}$,
16) —$NR^{h2}$—$C(=N$—$OR^{g2})$ $NR^{e2}R^{f2}$,
17) —$NR^{i2}$—$C(=NR^{h2})$ $NR^{g2}$—$NR^{e2}R^{f2}$,
18) —$NR^{i2}$—$C(=N$—$OR^{h2})NR^{g2}$—$NR^{e2}R^{f2}$
19) —$C(=NR^{e2})R^{f2}$,
20) —$C(=N$—$OR^{e2})R^{f2}$,
21) —$C(=NR^{h2})$—$NR^{e2}R^{f2}$,
22) —$C(=NR^{h2})NR^{g2}$—$NR^{e2}R^{f2}$,
23) —$C(=N$—$OR^{h2})NR^{g2}$—$NR^{e2}R^{f2}$,
24) —$NR^{e2}R^{f2}$,
25) —$NR^{g2}$—$NR^{e2}R^{f2}$,
26) —$NR^{e2}OR^{f2}$
27) —$NR^{e2}$—$C(=O)R^{f2}$,
28) —$C(=O)NR^{e2}R^{f2}$,
29) —$C(=O)NR^{e2}OR^{f2}$,
30) —$C(=O)NR^{g2}$—$NR^{e2}R^{f2}$,
31) —$C(=O)R^{e2}$,
32) —$C(=O)OR^{e2}$, and
33) —$C(=N$—$OR^{h2})NR^{e2}R^{f2}$, and each $R^{6b}$ is independently selected from the group consisting of
1) a hydrogen atom,
2) a hydroxyl group,
3) a $C_{1-4}$ alkyl group
(wherein the alkyl group is optionally substituted),
4) a $C_{3-10}$ alicyclic group
(wherein the alicyclic group is optionally substituted),
5) —$C(=NR^{e2})R^{f2}$,
6) —$C(=N$—$OR^{e2})R^{f2}$,
7) —$SO_2$—$NR^{e2}R^{f2}$,
8) —$C(=NR^{h2})$—$NR^{e2}R^{f2}$,
9) —$C(=NR^{h2})NR^{g2}$—$NR^{e2}R^{f2}$, 10) —C(=N—OR$^{h2}$)NR$^{g2}$—NR$^{e2}$R$^{f2}$,
11) —C(=O)NR$^{e2}$R$^{f2}$,
12) —C(=O)NR$^{e2}$OR$^{f2}$,
13) —C(=O)NR$^{g2}$—NR$^{e2}$R$^{f2}$,
14) —C(=O)R$^{e2}$, and
15) —C(=N—OR$^{h2}$)NR$^{e2}$R$^{f2}$.

[Item A25]
The compound or the pharmaceutically acceptable salt thereof according to any one of items A1 to A24, wherein R$^1$ and R$^2$ are the same or different, each independently selected from the group consisting of
1) a hydrogen atom,
2) a halogen atom,
3) a C$_{1-6}$ alkyl group,
4) a C$_{1-6}$ alkoxy group, and
5) a C$_{1-6}$ alkylthio group,
(wherein each substituent from 3) to 5) is optionally substituted).

[Item A26]
The compound or the pharmaceutically acceptable salt thereof according to any one of items A1 to A25, wherein R$^1$ and R$^2$ are the same or different, each independently selected from the group consisting of
1) a hydrogen atom,
2) a halogen atom, and
3) an optionally substituted C$_{1-6}$ alkyl group.

[Item A27]
The compound or the pharmaceutically acceptable salt thereof according to any one of items A1 to A26, wherein R$^1$ and R$^2$ are both hydrogen atoms.

[Item A28]
The compound or the pharmaceutically acceptable salt thereof according to any one of items A1 to A27, wherein the compounds of formulas (1a) and (1b), the compounds of formulas (3a) and (3b), the compounds of formulas (4a) and (4b), or the compounds of formulas (5a) and (5b) are represented by formulas (6a) and (6b), respectively:

[Chemical Formula 7]

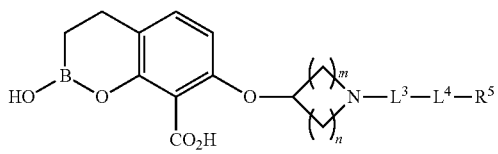

(6a)

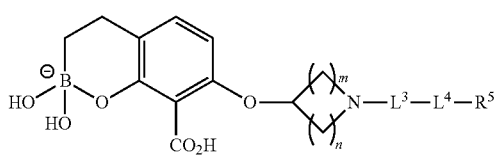

(6b)

wherein
L$^3$, L$^4$, and R$^5$ are defined the same as any one of items A1 to A24,
m is an integer 1, 2, or 3,
n is an integer 1, 2, or 3, and
m+n is 2, 3, or 4.

[Item A29]
The compound or the pharmaceutically acceptable salt thereof according to any one of items A1 to A28, wherein m is 1 or 2, n is 1 or 2, and m+n is 2 or 3.

[Item A30]
The compound or the pharmaceutically acceptable salt thereof according to any one of items A1 to A29, wherein m is 1 and n is 1.

[Item A31]
The compound or the pharmaceutically acceptable salt thereof according to any one of items A1 to A30, wherein R$^5$ is 5- or 6-membered aryl or heteroaryl selected from the group consisting of

[Chemical Formula 8]

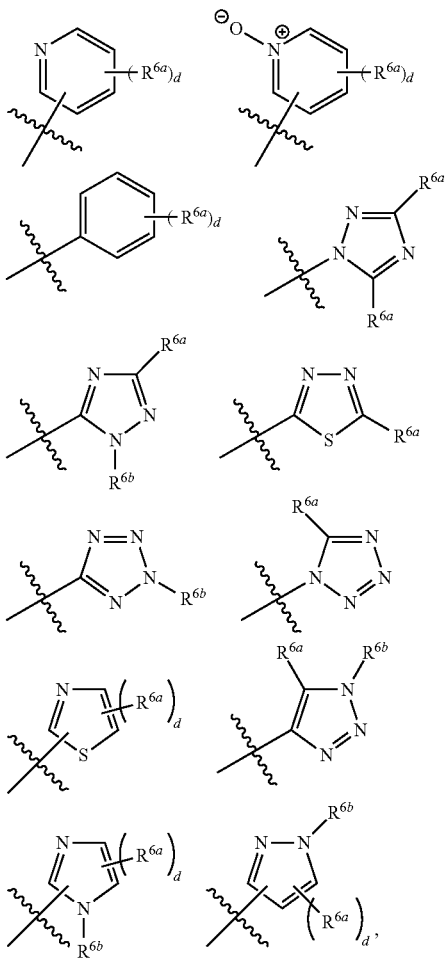

subscript d is the number of substitutable positions on a ring of R$^5$,
each R$^{6a}$ is independently selected from the group consisting of
1) a hydrogen atom,
2) a hydroxyl group,
3) halogen,
4) a C$_{1-4}$ alkyl group
(wherein the alkyl group is optionally substituted with NR$^{e2}$R$^{f2}$, —C(=O)OR$^{f2}$, or a hydroxyl group),
5) a C$_{1-4}$ alkoxy group
6) —NR$^{e2}$R$^{f2}$, and
7) —C(=O)OR$^{e2}$, and
each R$^{6b}$ is independently selected from the group consisting of
1) a hydrogen atom,
2) a hydroxyl group, and
3) a C$_{1-4}$ alkyl group, (wherein the alkyl group is optionally substituted with $NR^{e2}R^{f2}$, —C(=O)$OR^{f2}$, or a hydroxyl group).

[Item A32]

The compound or the pharmaceutically acceptable salt thereof according to any one of items A1 to A31, wherein $R^{e2}$, and $R^{f2}$ are the same or different, each independently a hydrogen atom, an optionally substituted $C_{1-6}$ alkyl group, or an optionally substituted $C_{3-10}$ alicyclic group.

[Item A33]

The compound or the pharmaceutically acceptable salt thereof according to any one of items A1 to A32, wherein $R^{e2}$ and $R^{12}$ are the same or different, each independently a hydrogen atom or an optionally substituted $C_{1-6}$ alkyl group.

[Item A34]

The compound or the pharmaceutically acceptable salt thereof according to any one of items A1 to A33, wherein $R^{e2}$ and $R^{f2}$ are hydrogen atoms.

[Item A35]

The compound or the pharmaceutically acceptable salt thereof according to any one of items A24 to A33, wherein $R^{6a}$ is —$NR^{e2}R^{f2}$, and one of $R^{e2}$ and $R^{f2}$ is a hydrogen atom and the other is a $C_{1-4}$ alkyl group (wherein the alkyl group is optionally substituted with an amino group or a hydroxyl group).

[Item A36]

The compound or the pharmaceutically acceptable salt thereof of item A1, represented by the following compound name or structural formula:

7-[(1-acetylazetidin-3-yl)oxy]-2-hydroxy-3,4-dihydro-2H-1,2-benzoxaborinine-8-carboxylic acid

[Chemical Formula 9]

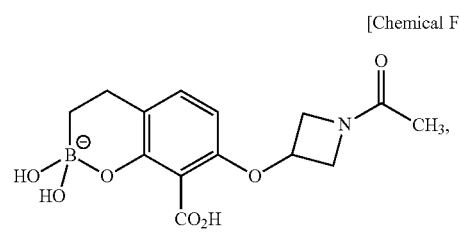

8-[(1-acetylazetidin-3-yl)oxy]-4,4-dihydroxy-5-oxa-4-boranuidabicyclo[4.4.0]deca-1(6),7,9-triene-7-carboxylic acid

[Chemical Formula 10]

2-hydroxy-7-({1-[(1H-imidazol-5-yl)acetyl]azetidin-3-yl}oxy)-3,4-dihydro-2H-1,2-benzoxaborinine-8-carboxylic acid

[Chemical Formula 11]

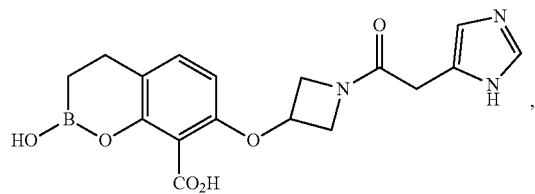

4,4-dihydroxy-8-({1-[(1H-imidazol-5-yl)acetyl]azetidin-3-yl}oxy)-5-oxa-4-boranuidabicyclo[4.4.0]deca-1(6),7,9-triene-7-carboxylic acid

[Chemical Formula 12]

2-hydroxy-7-{[1-(methanesulfonyl)azetidin-3-yl]oxy}-3,4-dihydro-2H-1,2-benzoxaborinine-8-carboxylic acid

[Chemical Formula 13]

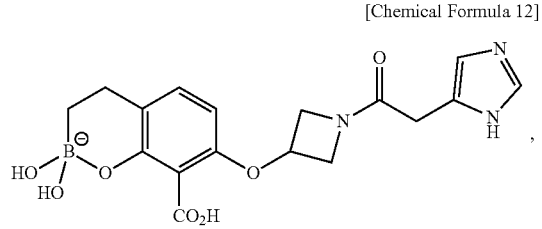 [SMILES: O=C(O)c1c(OC2CN(C(=O)Cc3cnc[nH]3)C2)ccc2c1O[B-](O)(O)CC2]

4,4-dihydroxy-8-{[1-(methanesulfonyl)azetidin-3-yl]oxy}-5-oxa-4-boranuidabicyclo[4.4.0]deca-1(6),7,9-triene-7-carboxylic acid

[Chemical Formula 14]

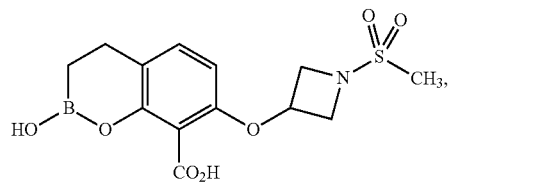

7-({1-[(2R)-2-amino-2-(4-hydroxyphenyl)acetyl]azetidin-3-yl}oxy)-2-hydroxy-3,4-dihydro-2H-1,2-benzoxaborinine-8-carboxylic acid

[Chemical Formula 15]

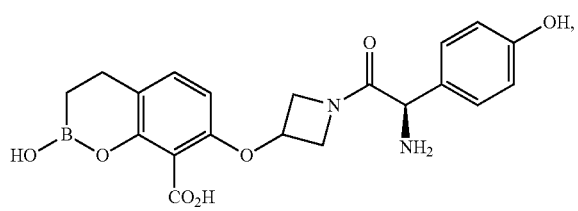

8-({1-[(2R)-2-amino-2-(4-hydroxyphenyl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 16]

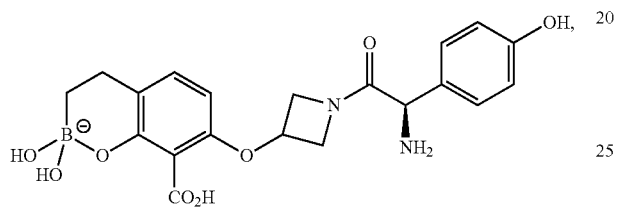

7-({1-[(2-amino-1,3-thiazol-4-yl)(methoxyimino)acetyl]azetidin-3-yl}oxy)-2-hydroxy-3,4-dihydro-2H-1,2-benzoxaborinine-8-carboxylic acid

[Chemical Formula 17]

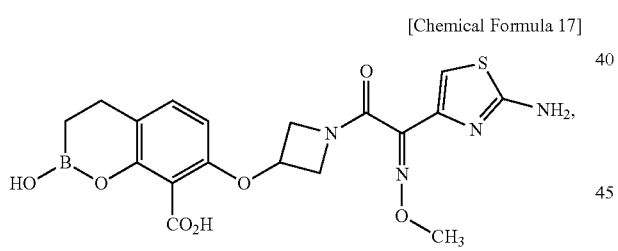

8-({1-[(2-amino-1,3-thiazol-4-yl)(methoxyimino)acetyl]azetidin-3-yl}oxy)-4,4-dihydroxy-5-oxa-4-boranuidabicyclo[4.4.0]deca-1(6),7,9-triene-7-carboxylic acid

[Chemical Formula 18]

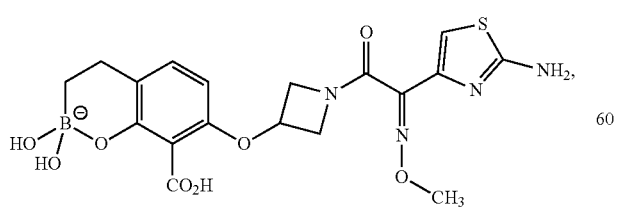

2-hydroxy-7-{[1-(pyridine-2-carbonyl)azetidin-3-yl]oxy}-3,4-dihydro-2H-1,2-benzoxaborinine-8-carboxylic acid

[Chemical Formula 19]

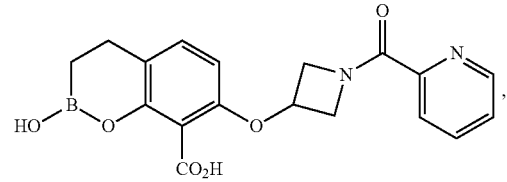

4,4-dihydroxy-8-{[1-(pyridine-2-carbonyl)azetidin-3-yl]oxy}-5-oxa-4-boranuidabicyclo[4.4.0]deca-1(6),7,9-triene-7-carboxylic acid

[Chemical Formula 20]

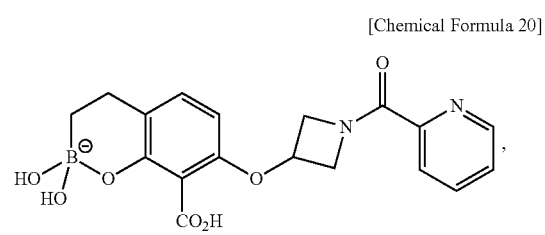 [SMILES: O=C(O)c1c(OC2CN(C(=O)c3ccccn3)C2)ccc2c1O[B-](O)(O)CC2]

2-hydroxy-7-({1-[(methylsulfanyl)acetyl]azetidin-3-yl}oxy)-3,4-dihydro-2H-1,2-benzoxaborinine-8-carboxylic acid

[Chemical Formula 21]

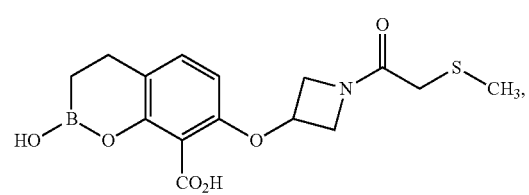

4,4-dihydroxy-8-({1-[(methylsulfanyl)acetyl]azetidin-3-yl}oxy)-5-oxa-4-boranuidabicyclo[4.4.0]deca-1(6),7,9-triene-7-carboxylic acid

[Chemical Formula 22]

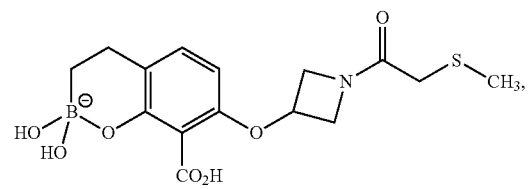

2-hydroxy-7-{[1-(1H-1,2,4-triazole-3-carbonyl)azetidin-3-yl]oxy}-3,4-dihydro-2H-1,2-benzoxaborinine-8-carboxylic acid

[Chemical Formula 23]

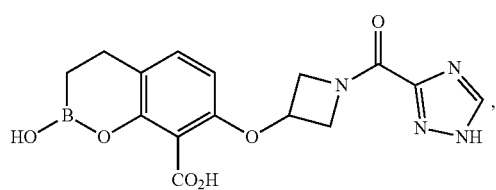

4,4-dihydroxy-8-{[1-(1H-1,2,4-triazole-3-carbonyl)azetidin-3-yl]oxy}-5-oxa-4-boranuidabicyclo[4.4.0]deca-l(6),7,9-triene-7-carboxylic acid

[Chemical Formula 24]

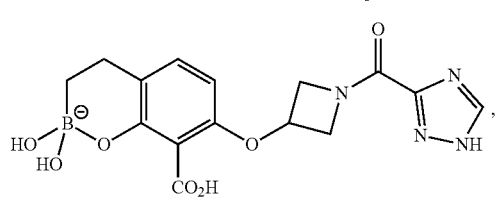

2-hydroxy-7-{[1-(1-oxido-2-pyridinylcarbonyl)azetidin-3-yl]oxy}-3,4-dihydro-2H-1,2-benzoxaborinine-8-carboxylic acid

[Chemical Formula 25]

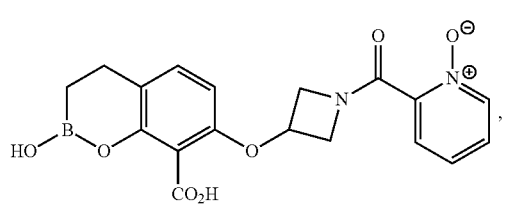

4,4-dihydroxy-8-{[1-(1-oxido-2-pyridinylcarbonyl)azetidin-3-yl]oxy}-5-oxa-4-boranuidabicyclo[4.4.0]deca-l(6),7,9-triene-7-carboxylic acid

[Chemical Formula 26]

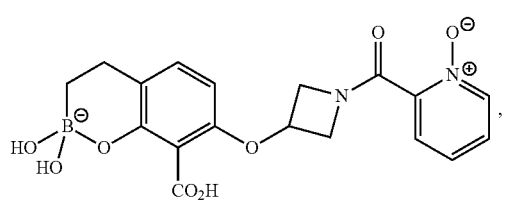

7-({1-[(2R)-2-amino-2-phenylacetyl]azetidin-3-yl}oxy)-2-hydroxy-3,4-dihydro-2H-1,2-benzoxaborinine-8-carboxylic acid

[Chemical Formula 27]

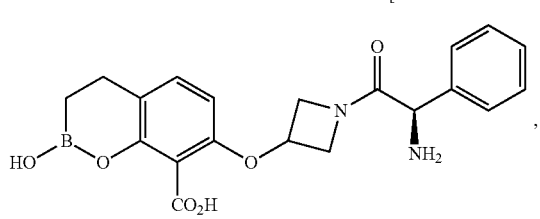

8-({1-[(2R)-2-amino-2-phenylacetyl]azetidin-3-yl}oxy)-4,4-dihydroxy-5-oxa-4-boranuidabicyclo[4.4.0]deca-l(6),7,9-triene-7-carboxylic acid

[Chemical Formula 28]

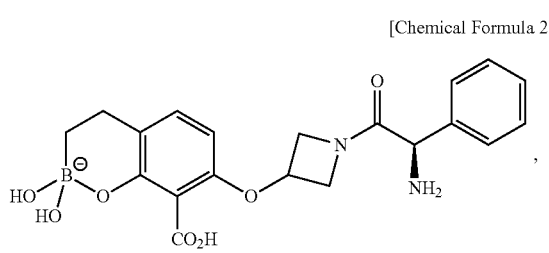

7-[(1-benzoylazetidin-3-yl)oxy]-2-hydroxy-3,4-dihydro-2H-1,2-benzoxaborinine-8-carboxylic acid

[Chemical Formula 29]

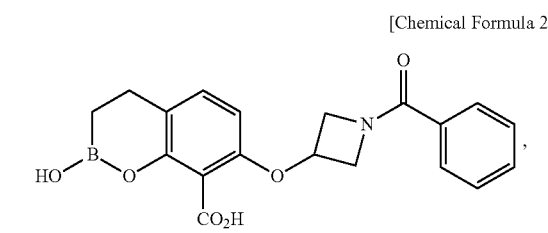

8-[(1-benzoylazetidin-3-yl)oxy]-4,4-dihydroxy-5-oxa-4-boranuidabicyclo[4.4.0]deca-l(6),7,9-triene-7-carboxylic acid

[Chemical Formula 30]

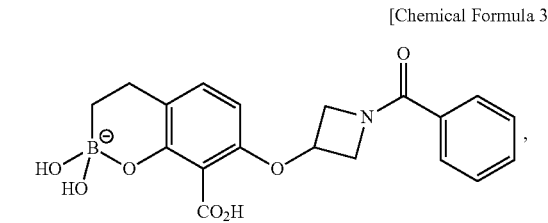

2-hydroxy-7-{[1-(pyridine-3-carbonyl)azetidin-3-yl]oxy}-3,4-dihydro-2H-1,2-benzoxaborinine-8-carboxylic acid

[Chemical Formula 31]

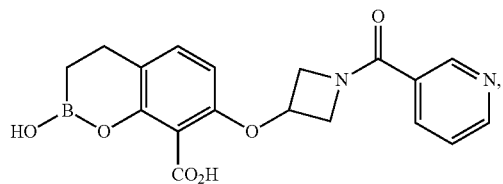

4,4-dihydroxy-8-{[1-(pyridine-3-carbonyl)azetidin-3-yl]oxy}-5-oxa-4-boranuidabicyclo[4.4.0]deca-1(6),7,9-triene-7-carboxylic acid

[Chemical Formula 32]

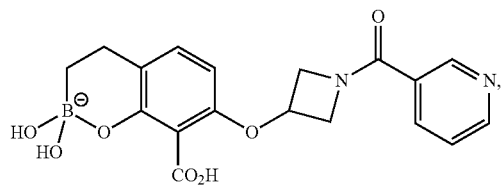

2-hydroxy-7-({1-[(pyridin-2-yl)acetyl]azetidin-3-yl}oxy)-3,4-dihydro-2H-1,2-benzoxaborinine-8-carboxylic acid

[Chemical Formula 33]

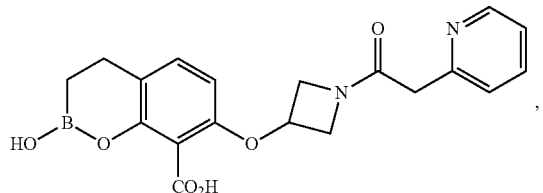

4,4-dihydroxy-8-({1-[(pyridin-2-yl)acetyl]azetidin-3-yl}oxy)-5-oxa-4-boranuidabicyclo[4.4.0]deca-1(6),7,9-triene-7-carboxylic acid

[Chemical Formula 34]

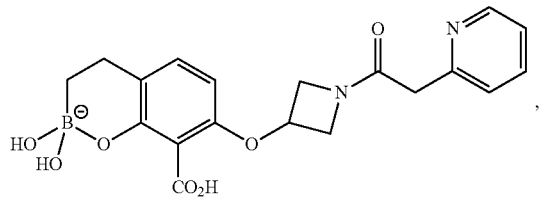

2-hydroxy-7-({1-[(pyridin-3-yl)acetyl]azetidin-3-yl}oxy)-3,4-dihydro-2H-1,2-benzoxaborinine-8-carboxylic acid

[Chemical Formula 35]

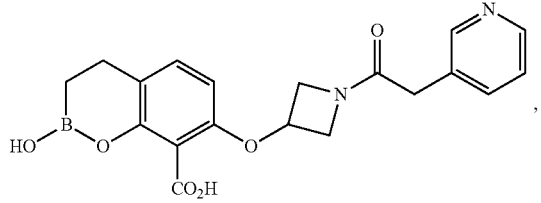

4,4-dihydroxy-8-({1-[(pyridin-3-yl)acetyl]azetidin-3-yl}oxy)-5-oxa-4-boranuidabicyclo[4.4.0]deca-1(6),7,9-triene-7-carboxylic acid

[Chemical Formula 36]

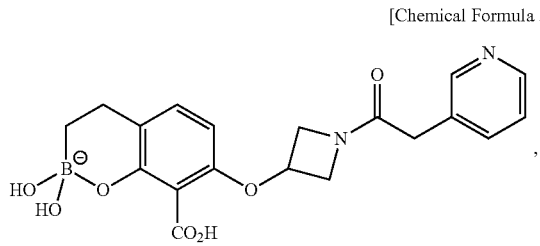

7-({1-[(2S)-2-amino-2-phenylacetyl]azetidin-3-yl}oxy)-2-hydroxy-3,4-dihydro-2H-1,2-benzoxaborinine-8-carboxylic acid

[Chemical Formula 37]

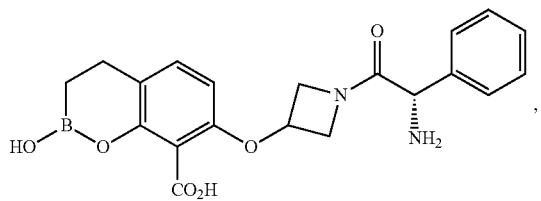

8-({1-[(2S)-2-amino-2-phenylacetyl]azetidin-3-yl}oxy)-4,4-dihydroxy-5-oxa-4-boranuidabicyclo[4.4.0]deca-1(6),7,9-triene-7-carboxylic acid

[Chemical Formula 38]

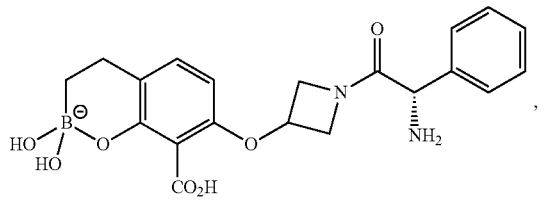

2-hydroxy-7-({1-[(pyridin-4-yl)acetyl]azetidin-3-yl}oxy)-3,4-dihydro-2H-1,2-benzoxaborinine-8-carboxylic acid

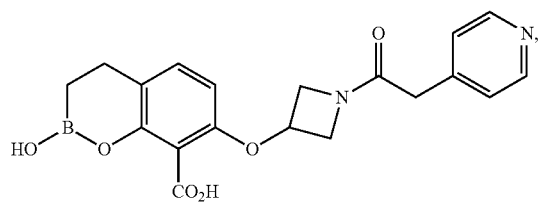

4,4-dihydroxy-8-({1-[(pyridin-4-yl)acetyl]azetidin-3-yl}oxy)-5-oxa-4-boranuidabicyclo[4.4.0]deca-1(6),7,9-triene-7-carboxylic acid

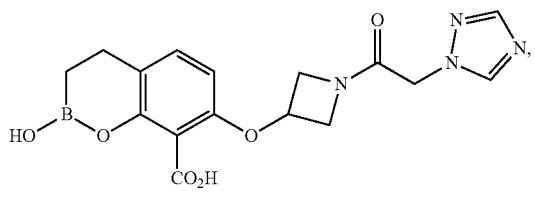

4,4-dihydroxy-8-({1-[(1H-1,2,4-triazol-1-yl)acetyl]azetidin-3-yl}oxy)-5-oxa-4-boranuidabicyclo[4.4.0]deca-1(6),7,9-triene-7-carboxylic acid

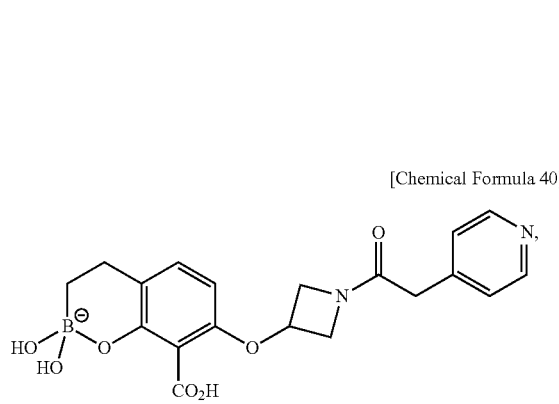

2-hydroxy-7-({1-[(4-hydroxyphenyl)acetyl]azetidin-3-yl}oxy)-3,4-dihydro-2H-1,2-benzoxaborinine-8-carboxylic acid

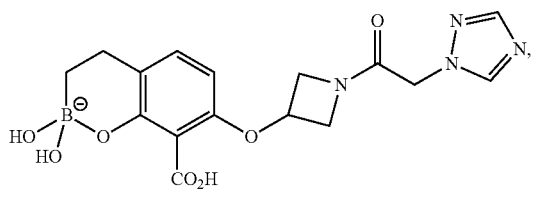

7-({1-[amino(1H-imidazol-5-yl)acetyl]azetidin-3-yl}oxy)-2-hydroxy-3,4-dihydro-2H-1,2-benzoxaborinine-8-carboxylic acid

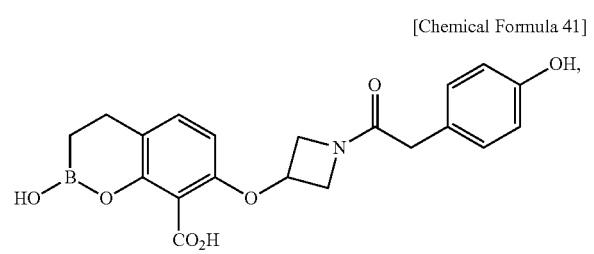 [SMILES: O=C(O)c1c(OC2CN(C(=O)Cc3ccc(O)cc3)C2)ccc2c1OB(O)CC2]

4,4-dihydroxy-8-({1-[(4-hydroxyphenyl)acetyl]azetidin-3-yl}oxy)-5-oxa-4-boranuidabicyclo[4.4.0]deca-1(6),7,9-triene-7-carboxylic acid

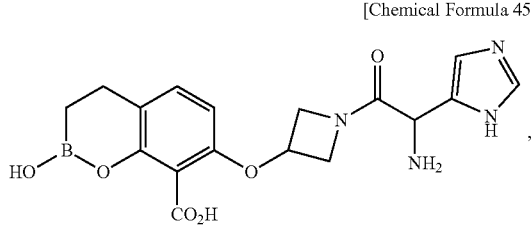 [SMILES: NC(C(=O)N1CC(Oc2ccc3c(c2C(=O)O)OB(O)CC3)C1)c1cnc[nH]1]

8-({1-[amino(1H-imidazol-5-yl)acetyl]azetidin-3-yl}oxy)-4,4-dihydroxy-5-oxa-4-boranuidabicyclo[4.4.0]deca-1(6),7,9-triene-7-carboxylic acid

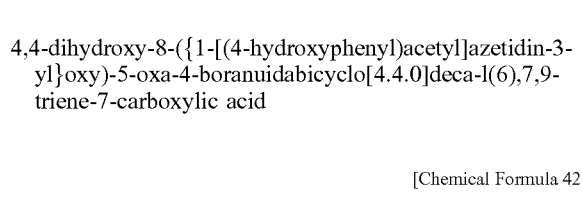

2-hydroxy-7-({1-[(1H-1,2,4-triazol-1-yl)acetyl]azetidin-3-yl}oxy)-3,4-dihydro-2H-1,2-benzoxaborinine-8-carboxylic acid

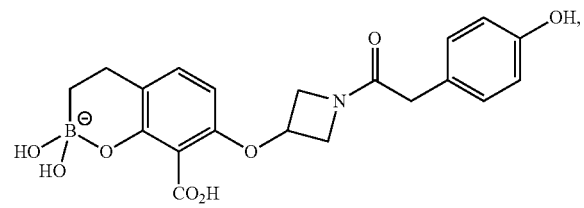

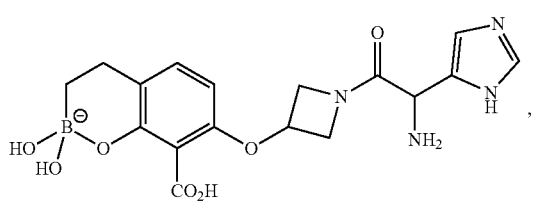

2-hydroxy-7-{[1-(phenylacetyl)azetidin-3-yl]oxy}-3,4-dihydro-2H-1,2-benzoxaborinine-8-carboxylic acid

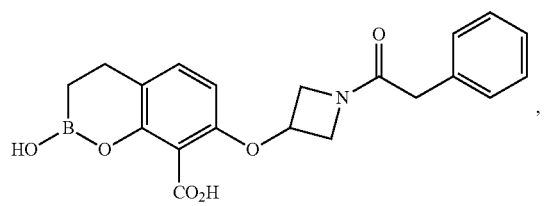

4,4-dihydroxy-8-{[1-(phenylacetyl)azetidin-3-yl]oxy}-5-oxa-4-boranuidabicyclo[4.4.0]deca-1(6),7,9-triene-7-carboxylic acid

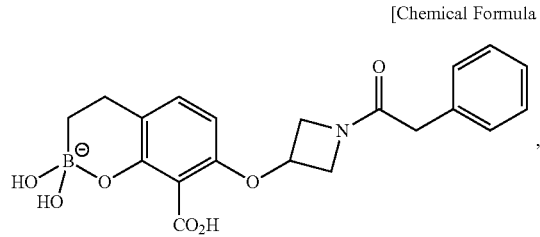

2-hydroxy-7-{[1-(3-phenylpropanoyl)azetidin-3-yl]oxy}-3,4-dihydro-2H-1,2-benzoxaborinine-8-carboxylic acid

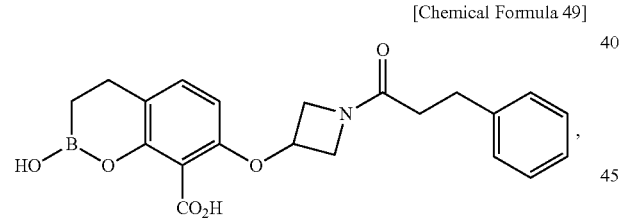

4,4-dihydroxy-8-{[1-(3-phenylpropanoyl)azetidin-3-yl]oxy}-5-oxa-4-boranuidabicyclo[4.4.0]deca-1(6),7,9-triene-7-carboxylic acid

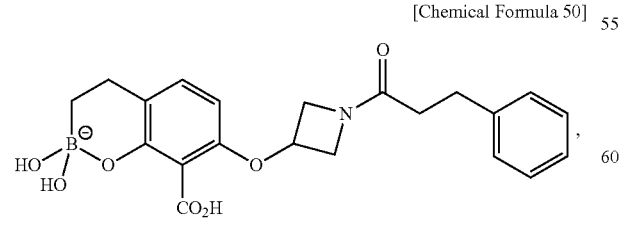

2-hydroxy-7-({1-[(1H-imidazol-1-yl)acetyl]azetidin-3-yl}oxy)-3,4-dihydro-2H-1,2-benzoxaborinine-8-carboxylic acid

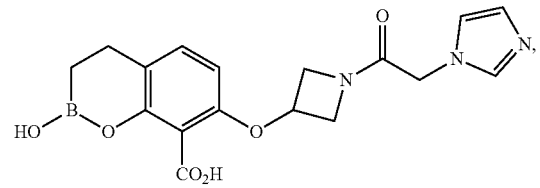

4,4-dihydroxy-8-({1-[(1H-imidazol-1-yl)acetyl]azetidin-3-yl}oxy)-5-oxa-4-boranuidabicyclo[4.4.0]deca-1(6),7,9-triene-7-carboxylic acid

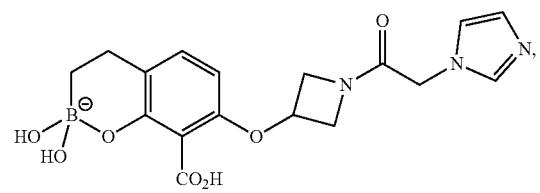

2-hydroxy-7-({1-[(1H-tetrazol-1-yl)acetyl]azetidin-3-yl}oxy)-3,4-dihydro-2H-1,2-benzoxaborinine-8-carboxylic acid

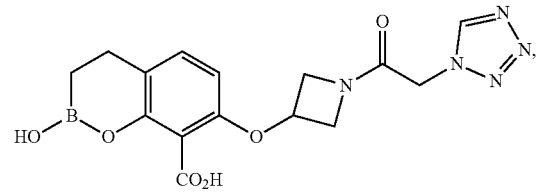

4,4-dihydroxy-8-({1-[(1H-tetrazol-1-yl)acetyl]azetidin-3-yl}oxy)-5-oxa-4-boranuidabicyclo[4.4.0]deca-1(6),7,9-triene-7-carboxylic acid

2-hydroxy-7-({1-[(2H-tetrazol-5-yl)acetyl]azetidin-3-yl}oxy)-3,4-dihydro-2H-1,2-benzoxaborinine-8-carboxylic acid

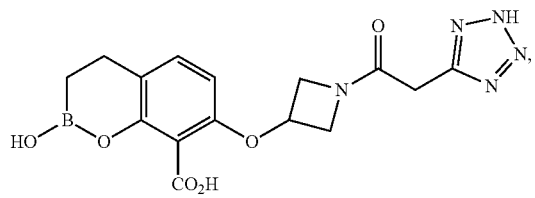

4,4-dihydroxy-8-({1-[(2H-tetrazol-5-yl)acetyl]azetidin-3-yl}oxy)-5-oxa-4-boranuidabicyclo[4.4.0]deca-1(6),7,9-triene-7-carboxylic acid

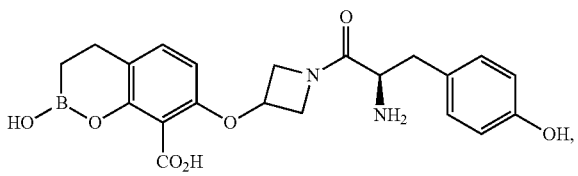

4,4-dihydroxy-8-[(1-D-tyrosylazetidin-3-yl)oxy]-5-oxa-4-boranuidabicyclo[4.4.0]deca-1(6),7,9-triene-7-carboxylic acid

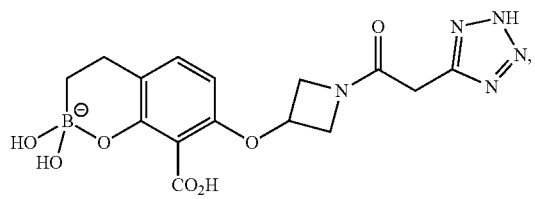

2-hydroxy-7-[(1-D-phenylalanylazetidin-3-yl)oxy]-3,4-dihydro-2H-1,2-benzoxaborinine-8-carboxylic acid

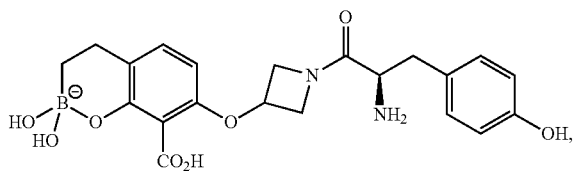

7-[(1-D-histidylazetidin-3-yl)oxy]-2-hydroxy-3,4-dihydro-2H-1,2-benzoxaborinine-8-carboxylic acid

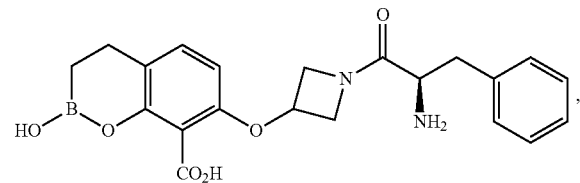

4,4-dihydroxy-8-[(1-D-phenylalanylazetidin-3-yl)oxy]-5-oxa-4-boranuidabicyclo[4.4.0]deca-1(6),7,9-triene-7-carboxylic acid

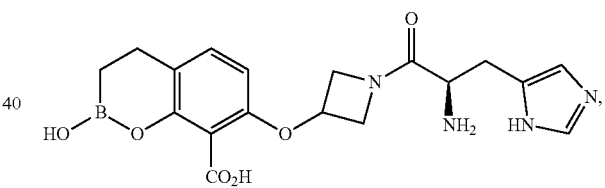

8-[(1-D-histidylazetidin-3-yl)oxy]-4,4-dihydroxy-5-oxa-4-boranuidabicyclo[4.4.0]deca-1(6),7,9-triene-7-carboxylic acid

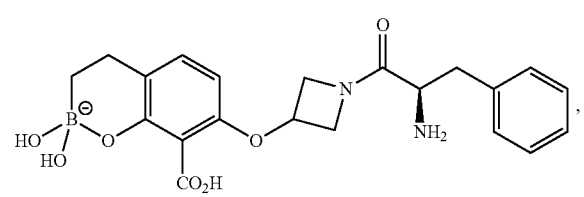

2-hydroxy-7-[(1-D-tyrosylazetidin-3-yl)oxy]-3,4-dihydro-2H-1,2-benzoxaborinine-8-carboxylic acid

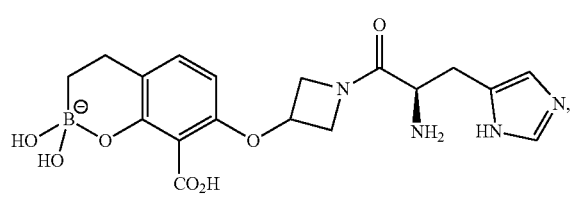

2-hydroxy-7-[(1-D-valylazetidin-3-yl)oxy]-3,4-dihydro-2H-1,2-benzoxaborinine-8-carboxylic acid

[Chemical Formula 63]

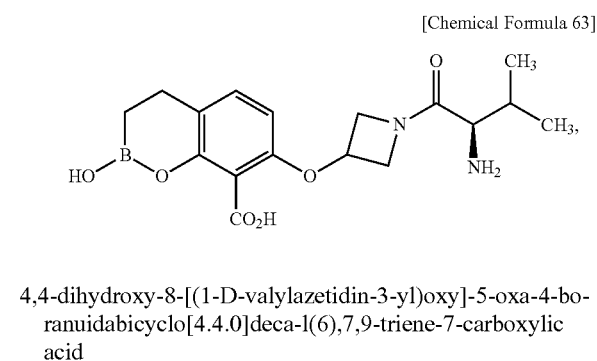

4,4-dihydroxy-8-[(1-D-valylazetidin-3-yl)oxy]-5-oxa-4-boranuidabicyclo[4.4.0]deca-1(6),7,9-triene-7-carboxylic acid

[Chemical Formula 64]

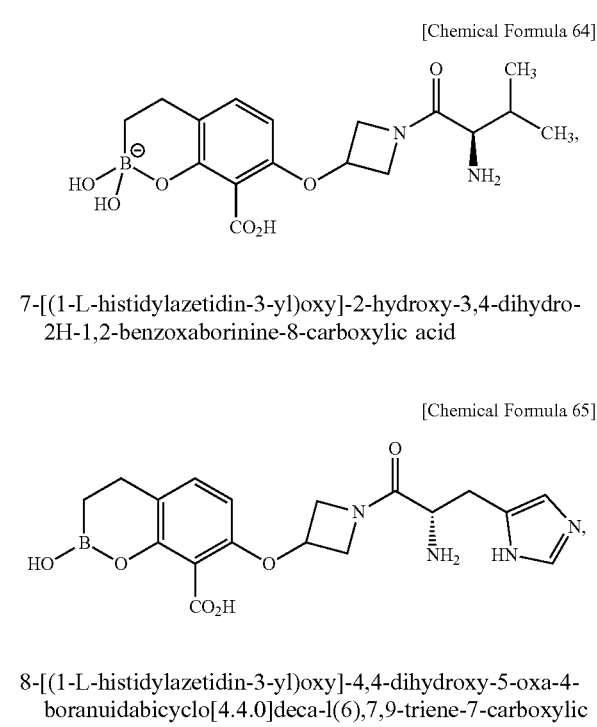

7-[(1-L-histidylazetidin-3-yl)oxy]-2-hydroxy-3,4-dihydro-2H-1,2-benzoxaborinine-8-carboxylic acid

[Chemical Formula 65]

8-[(1-L-histidylazetidin-3-yl)oxy]-4,4-dihydroxy-5-oxa-4-boranuidabicyclo[4.4.0]deca-1(6),7,9-triene-7-carboxylic acid

[Chemical Formula 66]

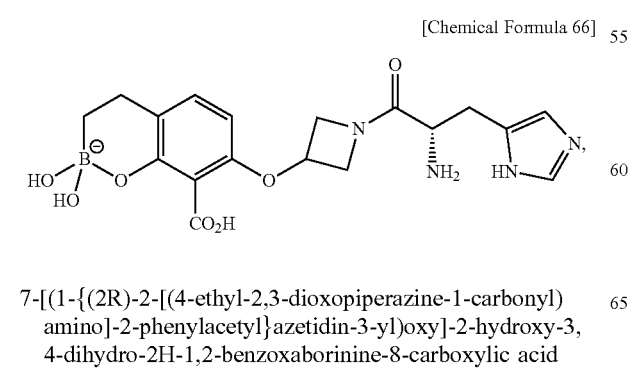

7-[(1-{(2R)-2-[(4-ethyl-2,3-dioxopiperazine-1-carbonyl)amino]-2-phenylacetyl}azetidin-3-yl)oxy]-2-hydroxy-3,4-dihydro-2H-1,2-benzoxaborinine-8-carboxylic acid

[Chemical Formula 67]

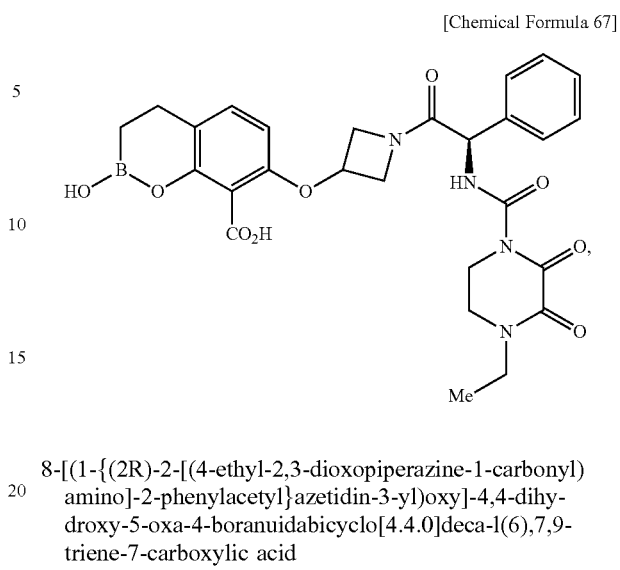

8-[(1-{(2R)-2-[(4-ethyl-2,3-dioxopiperazine-1-carbonyl)amino]-2-phenylacetyl}azetidin-3-yl)oxy]-4,4-dihydroxy-5-oxa-4-boranuidabicyclo[4.4.0]deca-1(6),7,9-triene-7-carboxylic acid

[Chemical Formula 68]

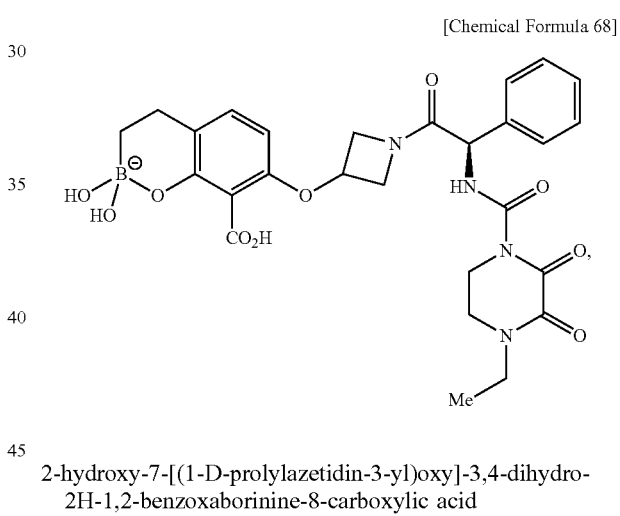

2-hydroxy-7-[(1-D-prolylazetidin-3-yl)oxy]-3,4-dihydro-2H-1,2-benzoxaborinine-8-carboxylic acid

[Chemical Formula 69]

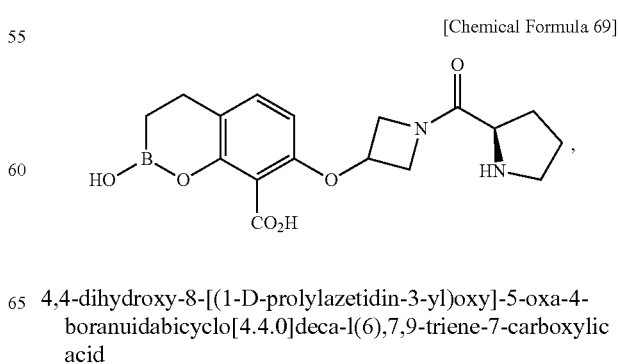

4,4-dihydroxy-8-[(1-D-prolylazetidin-3-yl)oxy]-5-oxa-4-boranuidabicyclo[4.4.0]deca-1(6),7,9-triene-7-carboxylic acid

[Chemical Formula 70]

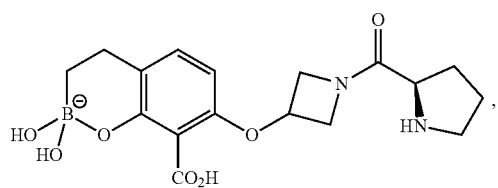

2-hydroxy-7-[(1-L-prolylazetidin-3-yl)oxy]-3,4-dihydro-2H-1,2-benzoxaborinine-8-carboxylic acid

[Chemical Formula 71]

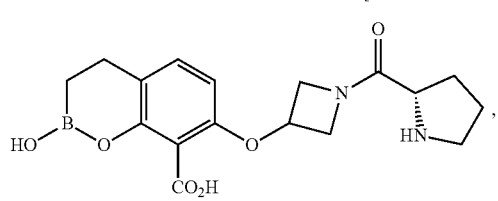

4,4-dihydroxy-8-[(1-L-prolylazetidin-3-yl)oxy]-5-oxa-4-boranuidabicyclo[4.4.0]deca-1(6),7,9-triene-7-carboxylic acid

[Chemical Formula 72]

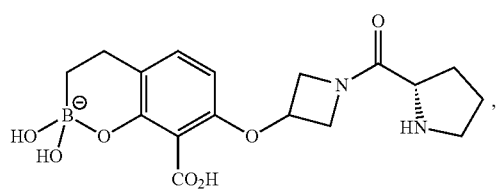

7-[(1-{[4-(2-aminoethyl)-1H-imidazol-1-yl]acetyl}azetidin-3-yl)oxy]-2-hydroxy-3,4-dihydro-2H-1,2-benzoxaborinine-8-carboxylic acid

[Chemical Formula 73]

8-[(1-{[4-(2-aminoethyl)-1H-imidazol-1-yl]acetyl}azetidin-3-yl)oxy]-4,4-dihydroxy-5-oxa-4-boranuidabicyclo[4.4.0]deca-1(6),7,9-triene-7-carboxylic acid

[Chemical Formula 74]

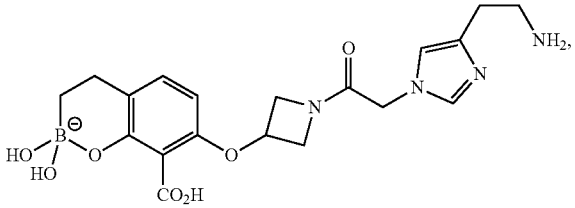

7-{[1-(3,4-dihydroxybenzoyl)azetidin-3-yl]oxy}-2-hydroxy-3,4-dihydro-2H-1,2-benzoxaborinine-8-carboxylic acid

[Chemical Formula 75]

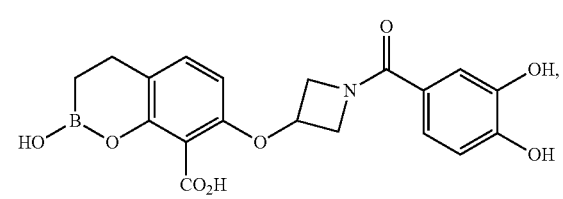

8-{[1-(3,4-dihydroxybenzoyl)azetidin-3-yl]oxy}-4,4-dihydroxy-5-oxa-4-boranuidabicyclo[4.4.0]deca-1(6),7,9-triene-7-carboxylic acid

[Chemical Formula 76]

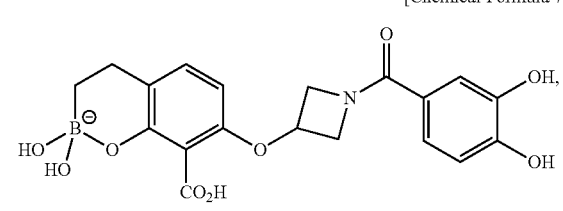

2-hydroxy-7-([1-(hydroxycarbamoyl)azetidin-3-yl]oxy)-3,4-dihydro-2H-1,2-benzoxaborinine-8-carboxylic acid

[Chemical Formula 77]

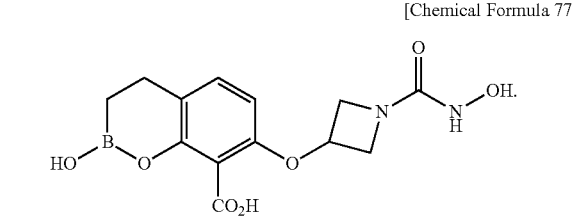 [SMILES: O=C(O)c1c(OC2CN(C(=O)NO)C2)ccc2c1OB(O)CC2]

4,4-dihydroxy-8-{[1-(hydroxycarbamoyl)azetidin-3-yl]oxy}-5-oxa-4-boranuidabicyclo[4.4.0]deca-1(6),7,9-triene-7-carboxylic acid

[Chemical Formula 78]

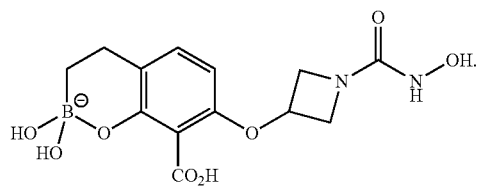

[Item A37]

A salt of the compound of item A36, represented by the following compound name or structural formula:

8-({1-[(2R)-2-amino-2-(4-hydroxyphenyl)acetyl]azetidin-3-yl}oxy)-4,4-dihydroxy-5-oxa-4-boranuidabicyclo[4.4.0]deca-1(6),7,9-triene-7-carboxylic acid disodium salt

[Chemical Formula 79]

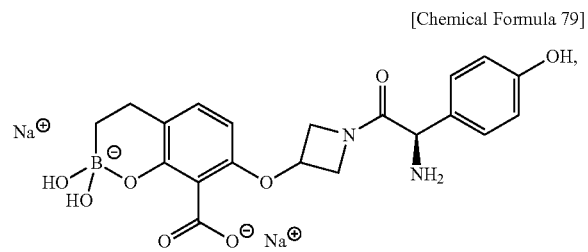 [SMILES: [Na+] ; N[C@@H](C(=O)N1CC(Oc2ccc3c(c2C(=O)[O-])O[B-](O)(O)CC3)C1)c1ccc(O)cc1 ; [Na+]]

4,4-dihydroxy-8-({1-[(methylsulfanyl)acetyl]azetidin-3-yl}oxy)-5-oxa-4-boranuidabicyclo[4.4.0]deca-1(6),7,9-triene-7-carboxylic acid disodium salt

[Chemical Formula 80]

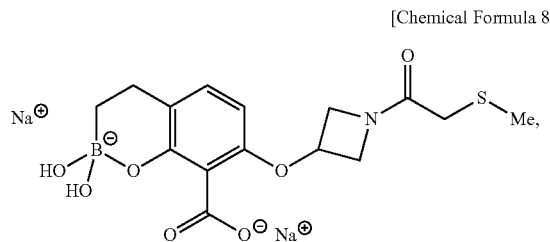

4,4-dihydroxy-8-{[1-(1H-1,2,4-triazole-3-carbonyl)azetidin-3-yl]oxy}-5-oxa-4-boranuidabicyclo[4.4.0]deca-1(6),7,9-triene-7-carboxylic acid disodium salt

[Chemical Formula 81]

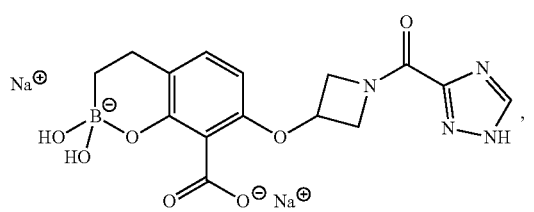

4,4-dihydroxy-8-{[1-(1-oxido-2-pyridinylcarbonyl)azetidin-3-yl]oxy}-5-oxa-4-boranuidabicyclo[4.4.0]deca-1(6),7,9-triene-7-carboxylic acid disodium salt

[Chemical Formula 82]

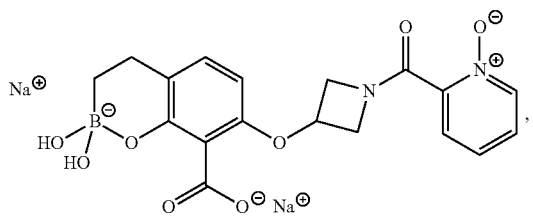

8-({1-[(2R)-2-amino-2-phenylacetyl]azetidin-3-yl}oxy)-4,4-dihydroxy-5-oxa-4-boranuidabicyclo[4.4.0]deca-1(6),7,9-triene-7-carboxylic acid disodium salt

[Chemical Formula 83]

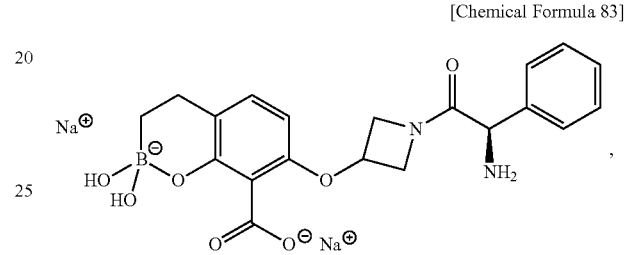

8-[(1-benzoylazetidin-3-yl)oxy]-4,4-dihydroxy-5-oxa-4-boranuidabicyclo[4.4.0]deca-1(6),7,9-triene-7-carboxylic acid disodium salt

[Chemical Formula 84]

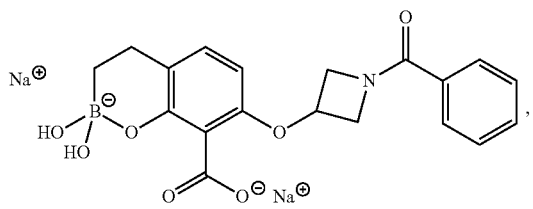

4,4-dihydroxy-8-{[1-(pyridine-3-carbonyl)azetidin-3-yl]oxy}-5-oxa-4-boranuidabicyclo[4.4.0]deca-1(6),7,9-triene-7-carboxylic acid disodium salt

[Chemical Formula 85]

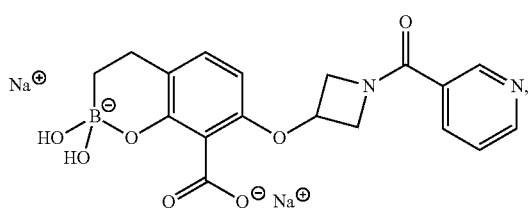

4,4-dihydroxy-8-({1-[(pyridin-2-yl)acetyl]azetidin-3-yl}oxy)-5-oxa-4-boranuidabicyclo[4.4.0]deca-1(6),7,9-triene-7-carboxylic acid disodium salt

[Chemical Formula 86]

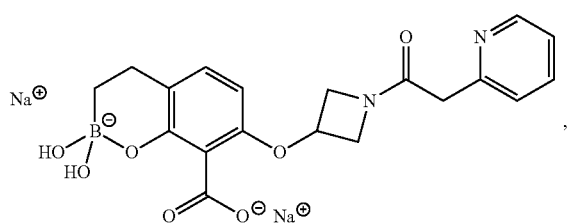

4,4-dihydroxy-8-({1-[(pyridin-3-yl)acetyl]azetidin-3-yl}oxy)-5-oxa-4-boranuidabicyclo[4.4.0]deca-l(6),7,9-triene-7-carboxylic acid disodium salt

[Chemical Formula 87]

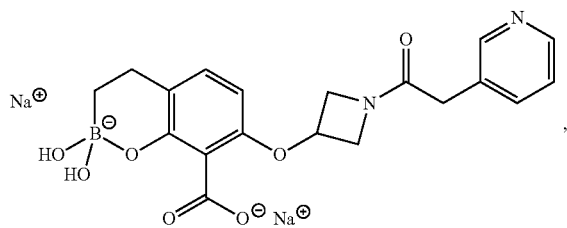

8-({1-[(2S)-2-amino-2-phenylacetyl]azetidin-3-yl}oxy)-4,4-dihydroxy-5-oxa-4-boranuidabicyclo[4.4.0]deca-l(6),7,9-triene-7-carboxylic acid disodium salt

[Chemical Formula 88]

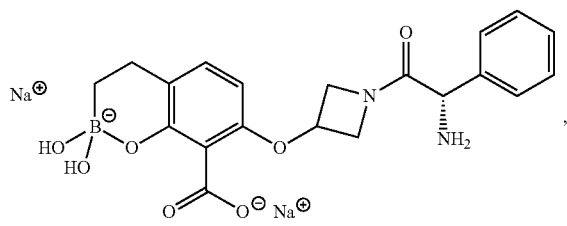

4,4-dihydroxy-8-({1-[(pyridin-4-yl)acetyl]azetidin-3-yl}oxy)-5-oxa-4-boranuidabicyclo[4.4.0]deca-l(6),7,9-triene-7-carboxylic acid disodium salt

[Chemical Formula 89]

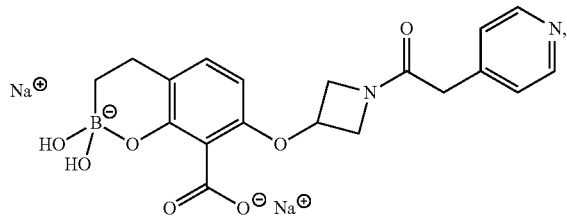

4,4-dihydroxy-8-({1-[(4-hydroxyphenyl)acetyl]azetidin-3-yl}oxy)-5-oxa-4-boranuidabicyclo[4.4.0]deca-l(6),7,9-triene-7-carboxylic acid disodium salt

[Chemical Formula 90]

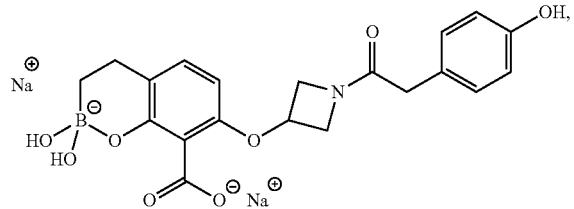

4,4-dihydroxy-8-({1-[(1H-1,2,4-triazol-1-yl)acetyl]azetidin-3-yl}oxy)-5-oxa-4-boranuidabicyclo[4.4.0]deca-l(6),7,9-triene-7-carboxylic acid disodium salt

[Chemical Formula 91]

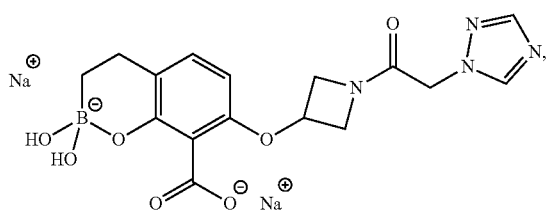

8-({1-[amino(1H-imidazol-5-yl)acetyl]azetidin-3-yl}oxy)-4,4-dihydroxy-5-oxa-4-boranuidabicyclo[4.4.0]deca-l(6),7,9-triene-7-carboxylic acid disodium salt

[Chemical Formula 92]

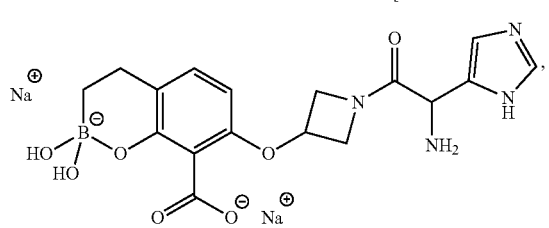

4,4-dihydroxy-8-{[1-(phenylacetyl)azetidin-3-yl]oxy}-5-oxa-4-boranuidabicyclo[4.4.0]deca-l(6),7,9-triene-7-carboxylic acid disodium salt

[Chemical Formula 93]

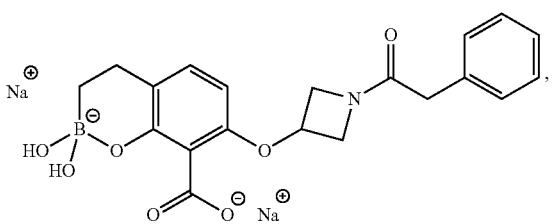

4,4-dihydroxy-8-{[1-(3-phenylpropanoyl)azetidin-3-yl]oxy}-5-oxa-4-boranuidabicyclo[4.4.0]deca-l(6),7,9-triene-7-carboxylic acid disodium salt

[Chemical Formula 94]

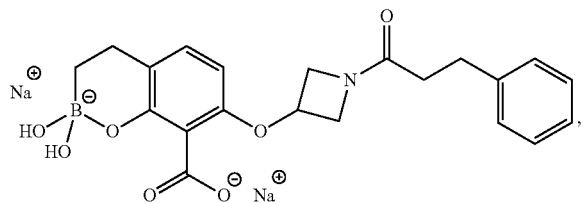

4,4-dihydroxy-8-({1-[(1H-imidazol-1-yl)acetyl]azetidin-3-yl}oxy)-5-oxa-4-boranuidabicyclo[4.4.0]deca-1(6),7,9-triene-7-carboxylic acid disodium salt

[Chemical Formula 95]

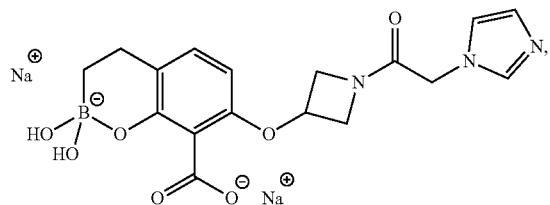

4,4-dihydroxy-8-({1-[(1H-tetrazol-1-yl)acetyl]azetidin-3-yl}oxy)-5-oxa-4-boranuidabicyclo[4.4.0]deca-1(6),7,9-triene-7-carboxylic acid disodium salt

[Chemical Formula 96]

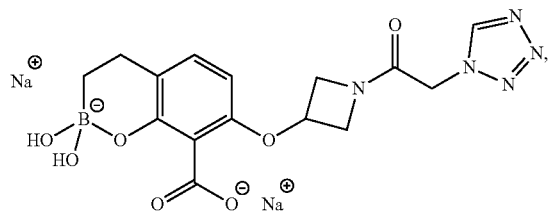

4,4-dihydroxy-8-({1-[(2H-tetrazol-5-yl)acetyl]azetidin-3-yl}oxy)-5-oxa-4-boranuidabicyclo[4.4.0]deca-1(6),7,9-triene-7-carboxylic acid disodium salt

[Chemical Formula 97]

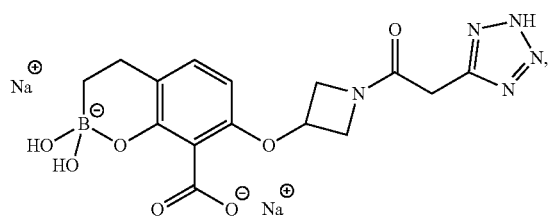

4,4-dihydroxy-8-[(1-D-phenylalanylazetidin-3-yl)oxy]-5-oxa-4-boranuidabicyclo[4.4.0]deca-1(6),7,9-triene-7-carboxylic acid disodium salt

[Chemical Formula 98]

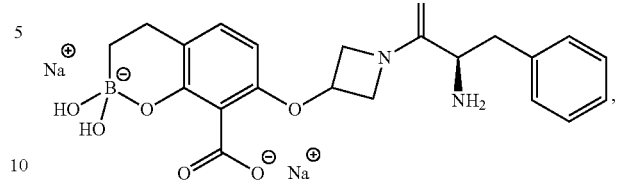

4,4-dihydroxy-8-[(1-D-tyrosylazetidin-3-yl)oxy]-5-oxa-4-boranuidabicyclo[4.4.0]deca-1(6),7,9-triene-7-carboxylic acid disodium salt

[Chemical Formula 99]

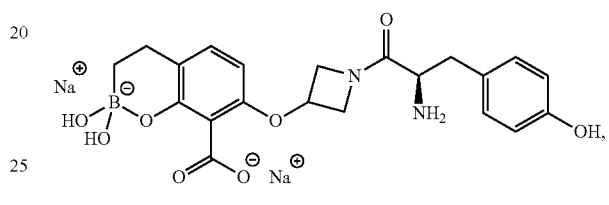

8-[(1-D-histidylazetidin-3-yl)oxy]-4,4-dihydroxy-5-oxa-4-boranuidabicyclo[4.4.0]deca-1(6),7,9-triene-7-carboxylic acid disodium salt

[Chemical Formula 100]

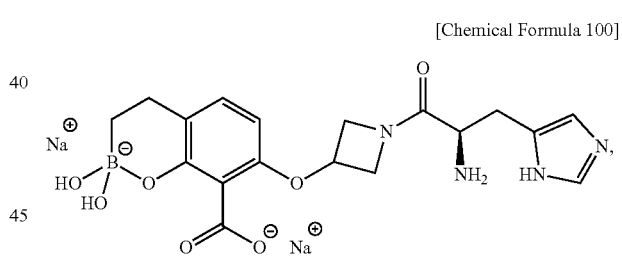

4,4-dihydroxy-8-[(1-D-valylazetidin-3-yl)oxy]-5-oxa-4-boranuidabicyclo[4.4.0]deca-1(6),7,9-triene-7-carboxylic acid disodium salt

[Chemical Formula 101]

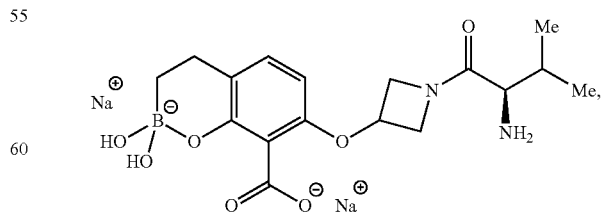

8-[(1-L-histidylazetidin-3-yl)oxy]-4,4-dihydroxy-5-oxa-4-boranuidabicyclo[4.4.0]deca-1(6),7,9-triene-7-carboxylic acid disodium salt

[Chemical Formula 102]

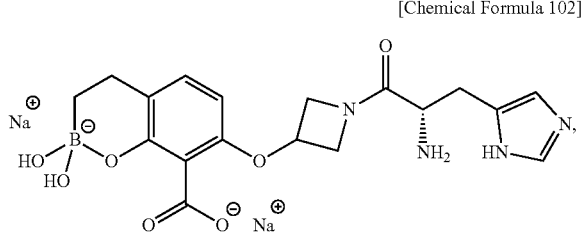 [SMILES: [Na+] ; N[C@@H](Cc1cnc[nH]1)C(=O)N1CC(Oc2ccc3c(c2C(=O)[O-])O[B-](O)(O)CC3)C1 ; [Na+]]

8-[(1-{(2R)-2-[(4-ethyl-2,3-dioxopiperazine-1-carbonyl)amino]-2-phenylacetyl}azetidin-3-yl)oxy]-4,4-dihydroxy-5-oxa-4-boranuidabicyclo[4.4.0]deca-1(6),7,9-triene-7-carboxylic acid disodium salt

[Chemical Formula 103]

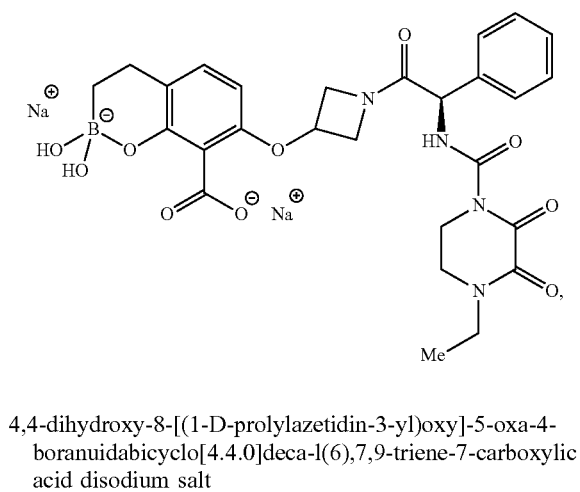

4,4-dihydroxy-8-[(1-D-prolylazetidin-3-yl)oxy]-5-oxa-4-boranuidabicyclo[4.4.0]deca-1(6),7,9-triene-7-carboxylic acid disodium salt

[Chemical Formula 104]

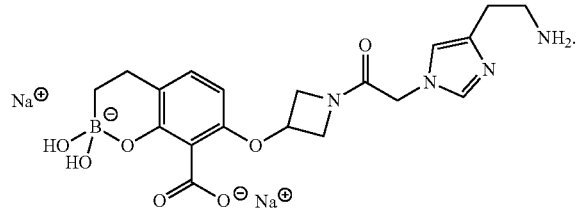

4,4-dihydroxy-8-[(1-L-prolylazetidin-3-yl)oxy]-5-oxa-4-boranuidabicyclo[4.4.0]deca-1(6),7,9-triene-7-carboxylic acid disodium salt

[Chemical Formula 105]

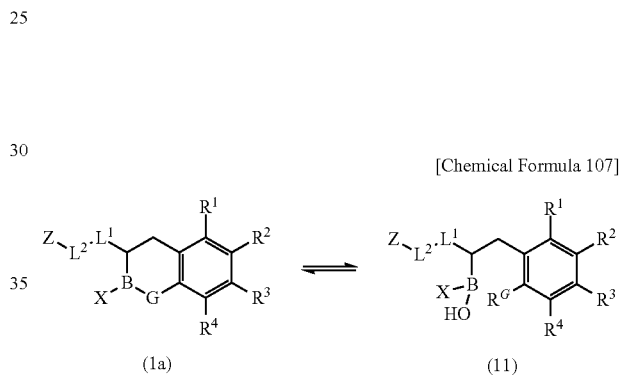

8-[(1-{[4-(2-aminoethyl)-1H-imidazol-1-yl]acetyl}azetidin-3-yl)oxy]-4,4-dihydroxy-5-oxa-4-boranuidabicyclo[4.4.0]deca-1(6),7,9-triene-7-carboxylic acid disodium salt

[Chemical Formula 106]

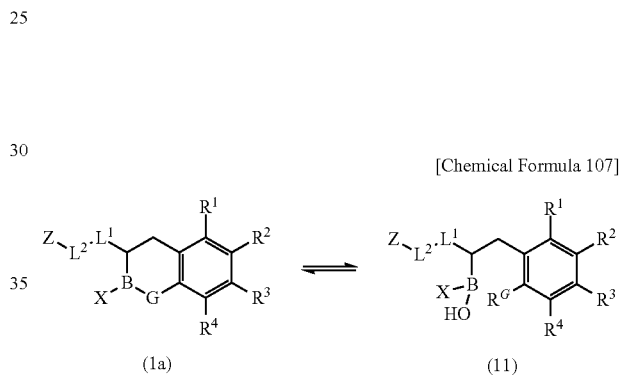

[Item A38]

A compound represented by formula (11):

[Chemical Formula 107]

$$Z_{\diagdown L^2} \diagdown L^1 \diagdown \text{(1a)} \rightleftharpoons Z_{\diagdown L^2} \diagdown L^1 \diagdown \text{(11)}$$

or a pharmaceutically acceptable salt thereof, wherein $R^G$ is a hydroxyl group, a thiol group, or $-NHR^{a1}$, $R^{a1}$, Z, $L^1$, $L^2$, X, $R^1$, $R^2$, $R^3$, and $R^4$ are defined the same as the definition according to item A1, and formula (1a) is defined the same as item A1.

[Item A39]

The compound or the pharmaceutically acceptable salt thereof according to item A38, wherein the compound of formula (11) is represented by formula (12):

[Chemical Formula 108]

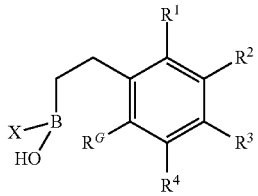

(12)

wherein X, $R^1$, $R^2$, $R^3$, and $R^4$ are defined by the same the definition according to item A8.

[Item A40]

The compound or the pharmaceutically acceptable salt thereof according to item A38 or A39, wherein the compound of formula (12) is represented by formula (13):

[Chemical Formula 109]

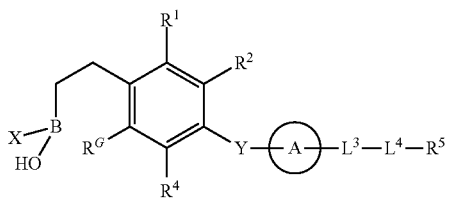

(13)

wherein X, Y, ring A, $L^3$, $L^4$, $R^1$, $R^2$, $R^4$, and $R^5$ are defined the same as the definition according to any one of items A10 to A14 and items A16 to A27.

[Item A41]

The compound or the pharmaceutically acceptable salt thereof according to item A40, wherein X and $R^G$ are hydroxyl groups, $R^4$ is a carboxyl group, and ring A is an optionally substituted 4- to 6-membered nitrogen-containing non-aryl heterocycle.

[Item A42]

The compound or the pharmaceutically acceptable salt thereof according to any one of items A38 to A41, wherein the compound of formula (13) is represented by formula (14):

[Chemical Formula 110]

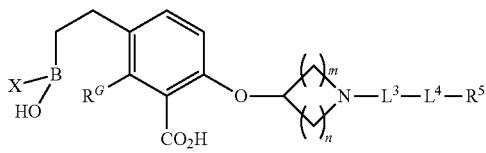

(14)

wherein X, $L^3$, $L^4$, m, n, and $R^5$ are defined the same as the definition according to item A28.

[Item A43]

The compound or the pharmaceutically acceptable salt thereof according to any one of items A38 to A42, wherein $R^G$ is a hydroxyl group or a thiol group.

[Item A44]

The compound or the pharmaceutically acceptable salt thereof according to any one of items A38 to A43, wherein $R^G$ is a hydroxyl group.

[Item A45]

The compound or the pharmaceutically acceptable salt thereof according to any one of items A38 to A44, wherein X is a hydroxyl group or a $C_{1-6}$ alkoxy group.

[Item A46]

The compound or the pharmaceutically acceptable salt thereof according to any one of items A38 to A45, wherein X is a hydroxyl group.

[Item A47]

The compound or the pharmaceutically acceptable salt thereof according to any one of items A42 to A46, wherein m is 1 or 2, n is 1 or 2, and m+n is 2 or 3.

[Item A48]

The compound or the pharmaceutically acceptable salt thereof according to any one of items A42 to A47, wherein m is 1, and n is 1.

[Item A49]

The compound or the pharmaceutically acceptable salt thereof according to any one of items A38 to A48, wherein $L^3$ is defined the same as the definition according to item A16 or A17.

[Item A50]

The compound or the pharmaceutically acceptable salt thereof according to any one of items A38 to A49, wherein $L^4$ is defined the same as the definition according to any one of items A18 to A20.

[Item A51]

The compound or the pharmaceutically acceptable salt thereof according to item A38, selected from the group consisting of the following compounds:

6-[(1-acetylazetidin-3-yl)oxy]-3-(2-boronoethyl)-2-hydroxybenzoic acid

[Chemical Formula 111]

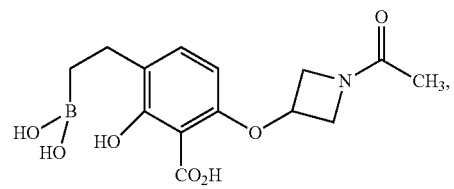

3-(2-boronoethyl)-2-hydroxy-6-({1-[(1H-imidazol-5-yl)acetyl]azetidin-3-yl}oxy)benzoic acid

[Chemical Formula 112]

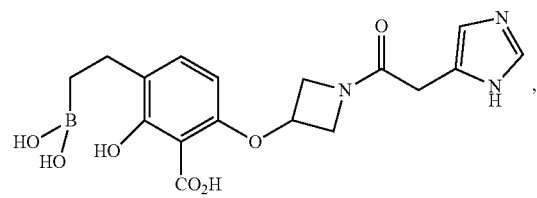

3-(2-boronoethyl)-2-hydroxy-6-{[1-(methanesulfonyl)azetidin-3-yl]oxy}benzoic acid

[Chemical Formula 113]

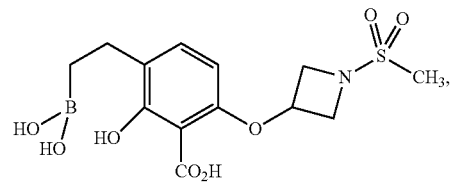

6-({1-[(2R)-2-amino-2-(4-hydroxyphenyl)acetyl]azetidin-3-yl}oxy)-3-(2-boronoethyl)-2-hydroxybenzoic acid

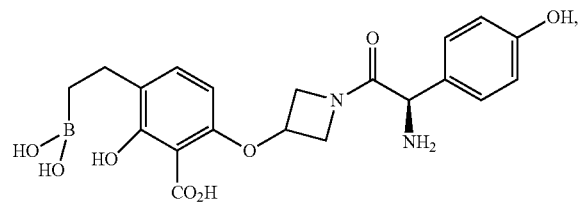

6-({1-[(2-amino-1,3-thiazol-4-yl)(methoxyimino)acetyl]azetidin-3-yl}oxy)-3-(2-boronoethyl)-2-hydroxybenzoic acid

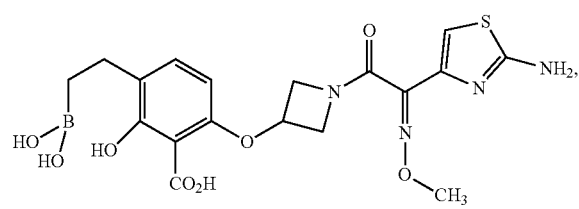

3-(2-boronoethyl)-2-hydroxy-6-{[1-(pyridine-2-carbonyl)azetidin-3-yl]oxy}benzoic acid

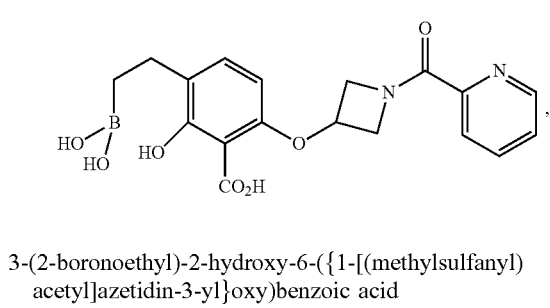

3-(2-boronoethyl)-2-hydroxy-6-({1-[(methylsulfanyl)acetyl]azetidin-3-yl}oxy)benzoic acid

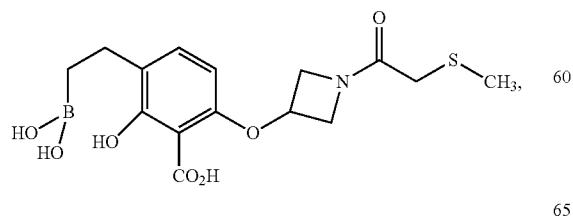

3-(2-boronoethyl)-2-hydroxy-6-{[1-(1H-1,2,4-triazole-3-carbonyl)azetidin-3-yl]oxy}benzoic acid

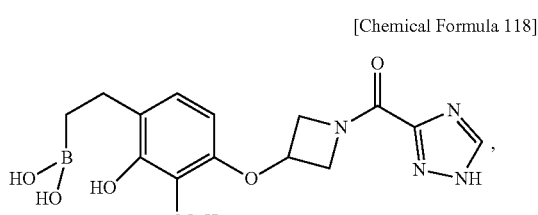

3-(2-boronoethyl)-2-hydroxy-6-{[1-(1-oxido-2-pyridinyl-carbonyl)azetidin-3-yl]oxy}benzoic acid

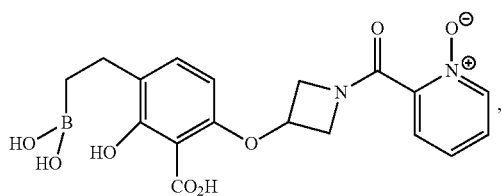

6-({1-[(2R)-2-amino-2-phenylacetyl]azetidin-3-yl}oxy)-3-(2-boronoethyl)-2-hydroxybenzoic acid

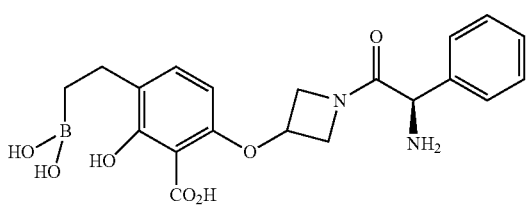

6-[(1-benzoylazetidin-3-yl)oxy]-3-(2-boronoethyl)-2-hydroxybenzoic acid

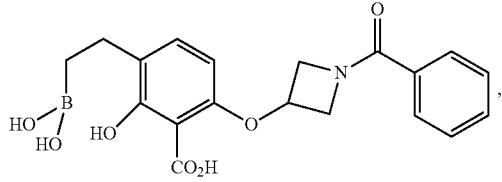

[Chemical Formula 122]

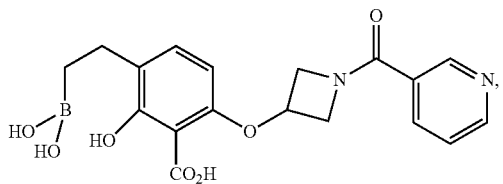

3-(2-boronoethyl)-2-hydroxy-6-({1-[(pyridin-2-yl)acetyl]
azetidin-3-yl}oxy)benzoic acid

[Chemical Formula 123]

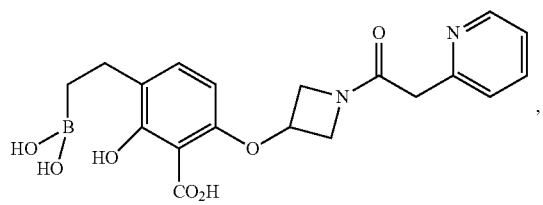

3-(2-boronoethyl)-2-hydroxy-6-({1-[(pyridin-3-yl)acetyl]
azetidin-3-yl}oxy)benzoic acid

[Chemical Formula 124]

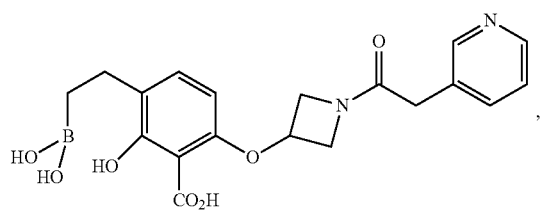

6-({1-[(2S)-2-amino-2-phenylacetyl]azetidin-3-yl}oxy)-3-
(2-boronoethyl)-2-hydroxybenzoic acid

[Chemical Formula 125]

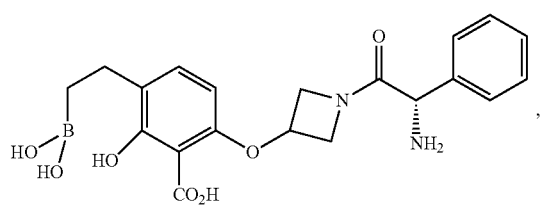

[Chemical Formula 126]

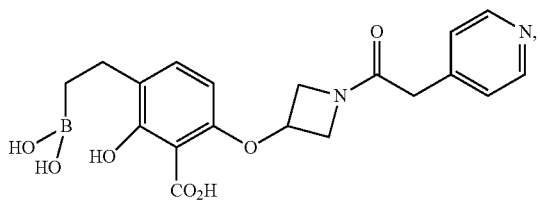

3-(2-boronoethyl)-2-hydroxy-6-({1-[(4-hydroxyphenyl)
acetyl]azetidin-3-yl}oxy)benzoic acid

[Chemical Formula 127]

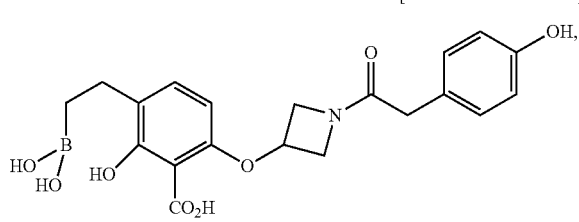

3-(2-boronoethyl)-2-hydroxy-6-({1-[(1H-1,2,4-triazol-1-yl)
acetyl]azetidin-3-yl}oxy)benzoic acid

[Chemical Formula 128]

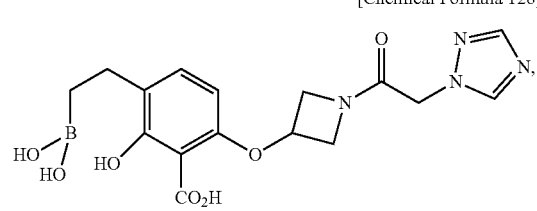

6-({1-[amino(1H-imidazol-5-yl)acetyl]azetidin-3-yl}oxy)-
3-(2-boronoethyl)-2-hydroxybenzoic acid

[Chemical Formula 129]

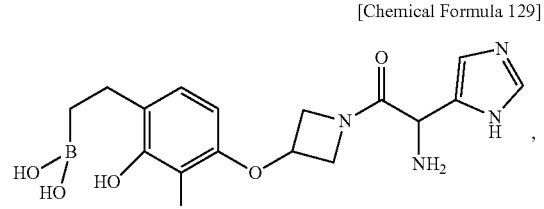

3-(2-boronoethyl)-2-hydroxy-6-{[1-(phenylacetyl)azetidin-3-yl]oxy}benzoic acid

[Chemical Formula 130]

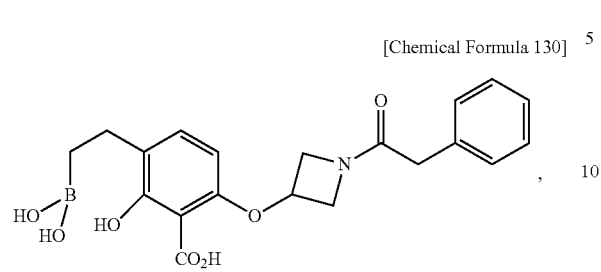

3-(2-boronoethyl)-2-hydroxy-6-{[1-(3-phenylpropanoyl)azetidin-3-yl]oxy}benzoic acid

[Chemical Formula 131]

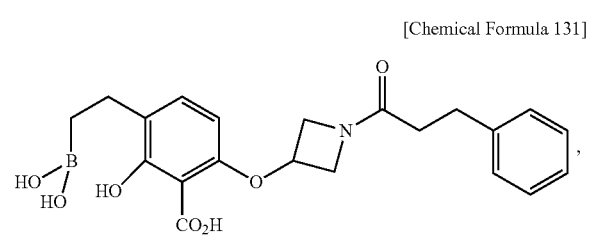 [SMILES: O=C(O)c1c(OC2CN(C(=O)CCc3ccccc3)C2)ccc(CCB(O)O)c1O]

3-(2-boronoethyl)-2-hydroxy-6-({1-[(1H-imidazol-1-yl)acetyl]azetidin-3-yl}oxy)benzoic acid

[Chemical Formula 132]

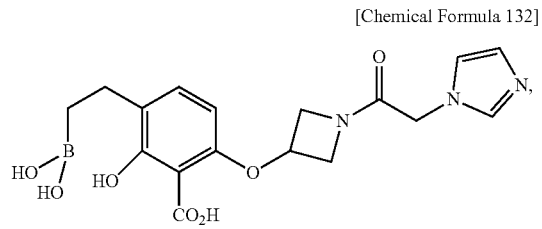 [SMILES: O=C(O)c1c(OC2CN(C(=O)Cn3ccnc3)C2)ccc(CCB(O)O)c1O]

3-(2-boronoethyl)-2-hydroxy-6-({1-[(1H-tetrazol-1-yl)acetyl]azetidin-3-yl}oxy)benzoic acid

[Chemical Formula 133]

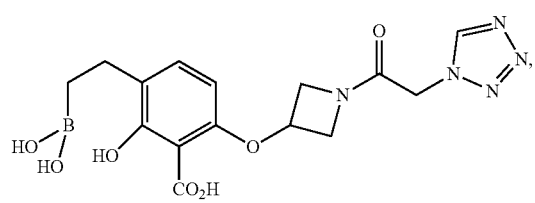

3-(2-boronoethyl)-2-hydroxy-6-({1-[(2H-tetrazol-5-yl)acetyl]azetidin-3-yl}oxy)benzoic acid

[Chemical Formula 134]

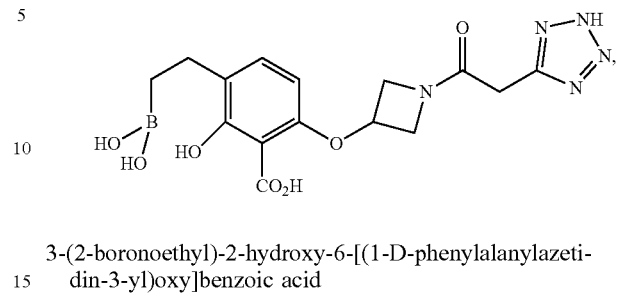

3-(2-boronoethyl)-2-hydroxy-6-[(1-D-phenylalanylazetidin-3-yl)oxy]benzoic acid

[Chemical Formula 135]

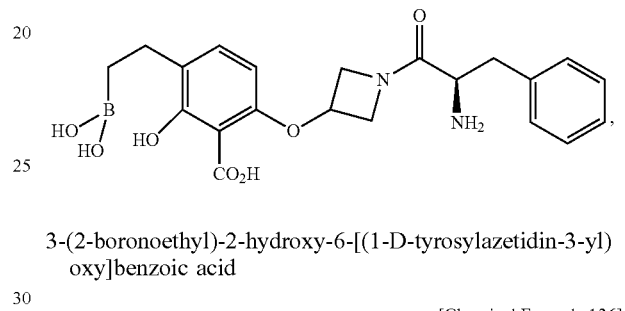

3-(2-boronoethyl)-2-hydroxy-6-[(1-D-tyrosylazetidin-3-yl)oxy]benzoic acid

[Chemical Formula 136]

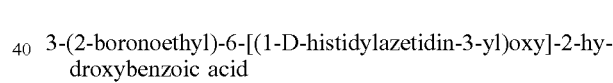

3-(2-boronoethyl)-6-[(1-D-histidylazetidin-3-yl)oxy]-2-hydroxybenzoic acid

[Chemical Formula 137]

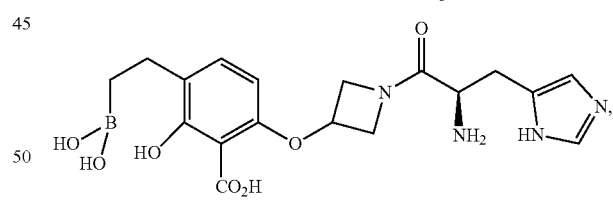

3-(2-boronoethyl)-2-hydroxy-6-[(1-D-valylazetidin-3-yl)oxy]benzoic acid

[Chemical Formula 138]

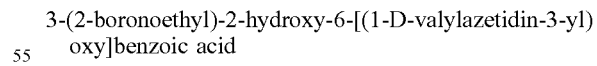
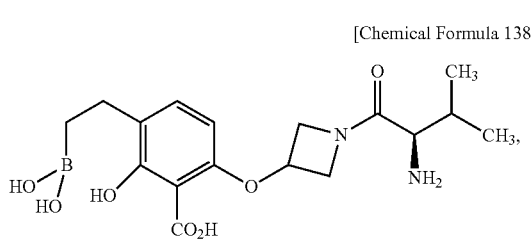

3-(2-boronoethyl)-6-[(1-L-histidylazetidin-3-yl)oxy]-2-hydroxybenzoic acid

[Chemical Formula 139]

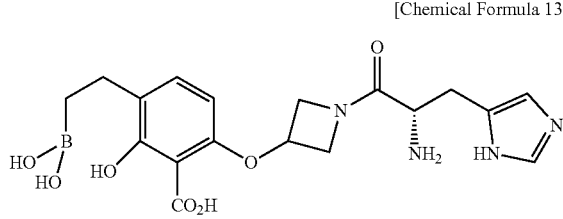

3-(2-boronoethyl)-6-[(1-{(2R)-2-[(4-ethyl-2,3-dioxopiperazine-1-carbonyl)amino]-2-phenylacetyl}azetidin-3-yl)oxy]-2-hydroxybenzoic acid

[Chemical Formula 140]

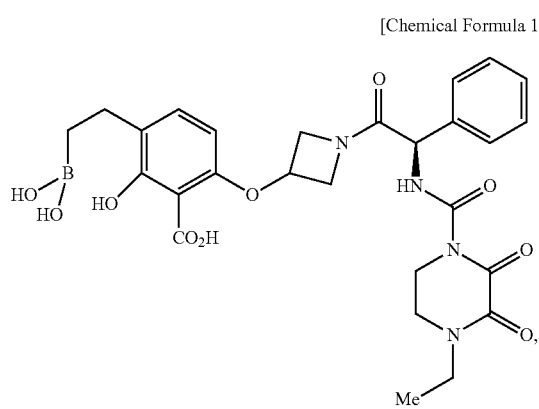

3-(2-boronoethyl)-2-hydroxy-6-[(1-D-prolylazetidin-3-yl)oxy]benzoic acid

[Chemical Formula 141]

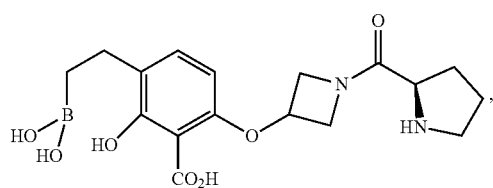

3-(2-boronoethyl)-2-hydroxy-6-[(1-L-prolylazetidin-3-yl)oxy]benzoic acid

[Chemical Formula 142]

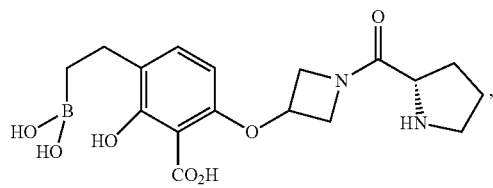

6-[(1-{[4-(2-aminoethyl)-1H-imidazol-1-yl]acetyl}azetidin-3-yl)oxy]-3-(2-boronoethyl)-2-hydroxybenzoic acid

[Chemical Formula 143]

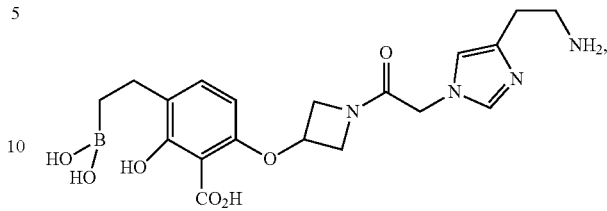

3-(2-boronoethyl)-6-{[1-(3,4-dihydroxybenzoyl)azetidin-3-yl]oxy}-2-hydroxybenzoic acid

[Chemical Formula 144]

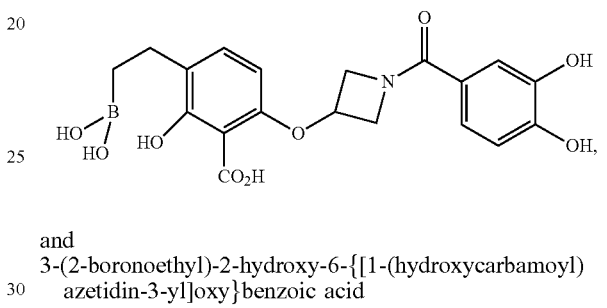

and
3-(2-boronoethyl)-2-hydroxy-6-{[1-(hydroxycarbamoyl)azetidin-3-yl]oxy}benzoic acid

[Chemical Formula 145]

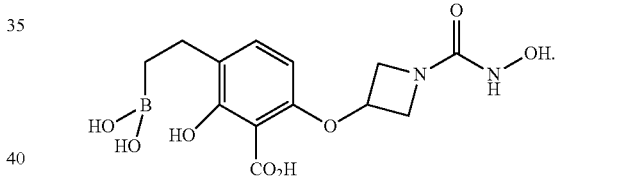

[Item A52]
A medicament comprising the compound or the pharmaceutically acceptable salt thereof according to any one of items A1 to A51.

[Item A53]
The medicament according to item A52, which is a therapeutic drug or a prophylactic drug for a bacterial infection.

[Item A54]
A β-lactamase inhibiting agent comprising the compound or the pharmaceutically acceptable salt thereof according to any one of items A1 to A51 as an active ingredient.

[Item A55]
A pharmaceutical composition comprising the compound or the pharmaceutically acceptable salt thereof according to any one of items A1 to A51 and a pharmaceutically acceptable carrier.

[Item A56]
The pharmaceutical composition according to item A55, further comprising an additional agent.

[Item A57]
The pharmaceutical composition according to item A56, wherein the additional agent is selected from the group consisting of an antibacterial agent, an antifungal agent, an antiviral agent, an anti-inflammatory agent, and an anti-allergic agent.

[Item A58]

The pharmaceutical composition according to item A56 or A57, wherein the additional agent is a β-lactam agent.

[Item A59]

The pharmaceutical composition according to item A57 or A58, wherein a β-lactam agent, which is the additional agent, is selected from the group consisting of amoxicillin, ampicillin (pivampicillin, hetacillin, bacampicillin, metampicillin, and talampicillin), epicillin, carbenicillin (carindacillin), ticarcillin, temocillin, azlocillin, piperacillin, mezlocillin, mecillinam (pivmecillinam), sulbenicillin, benzylpenicillin (G), clometocillin, benzathine benzylpenicillin, procaine benzylpenicillin, azidocillin, penamecillin, phenoxymethyl penicillin (V), propicillin, benzathine phenoxymethylpenicillin, phenethicillin, cloxacillin (dicloxacillin and flucloxacillin), oxacillin, methicillin, nafcillin, faropenem, biapenem, doripenem, ertapenem, imipenem, meropenem, panipenem, tomopenem, razupenem, cefazolin, cefacetrile, cefadroxil, cephalexin, cefaloglycin, cefalonium, cefaloridine, cephalothin, cephapirin, cefatrizine, cefazedone, cefazaflur, cefradine, cefroxadine, ceftezole, cefaclor, cefamandole, cefminox, cefonicide, ceforanide, cefotiam, cefprozil, cefbuperazone, cefuroxime, cefuzonam, cefoxitin, cefotetan, cefmetazole, loracarbef, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, flomoxef, latamoxef, cefepime, cefozopran, cefpirome, cefquinome, ceftobiprole, ceftaroline, CXA-101, RWJ-54428, MC-04546, ME1036, BAL30072, SYN2416, ceftiofur, cefquinome, cefovecin, aztreonam, tigemonam, carumonam, RWJ-442831, RWJ-333441, and RWJ-333442.

[Item A60]

The pharmaceutical composition according to item A58 or A59, wherein the β-lactam agent is selected from ceftazidime, biapenem, doripenem, ertapenem, imipenem, meropenem, or panipenem.

[Item A61]

The pharmaceutical composition according to item A58 or A59, wherein the β-lactam agent is selected from aztreonam, tigemonam, BAL30072, SYN2416, or carumonam.

[Item A62]

The pharmaceutical composition according to item A55, characterized in that an additional agent is concomitantly administered.

[Item A63]

The pharmaceutical composition according to item A62, wherein the additional agent is selected from an antibacterial agent, an antifungal agent, an antiviral agent, an anti-inflammatory agent, or an anti-allergic agent.

[Item A64]

The pharmaceutical composition according to item A62 or A63, wherein the additional agent is a β-lactam agent.

[Item A65]

The pharmaceutical composition according to item A63 or A64, wherein a β-lactam agent, which is the additional agent, is selected from the group consisting of amoxicillin, ampicillin (pivampicillin, hetacillin, bacampicillin, metampicillin, and talampicillin), epicillin, carbenicillin (carindacillin), ticarcillin, temocillin, azlocillin, piperacillin, mezlocillin, mecillinam (pivmecillinam), sulbenicillin, benzylpenicillin (G), clometocillin, benzathine benzylpenicillin, procaine benzylpenicillin, azidocillin, penamecillin, phenoxymethyl penicillin (V), propicillin, benzathine phenoxymethylpenicillin, phenethicillin, cloxacillin (dicloxacillin and flucloxacillin), oxacillin, methicillin, nafcillin, faropenem, biapenem, doripenem, ertapenem, imipenem, meropenem, panipenem, tomopenem, razupenem, cefazolin, cefacetrile, cefadroxil, cephalexin, cefaloglycin, cefalonium, cefaloridine, cephalothin, cephapirin, cefatrizine, cefazedone, cefazaflur, cefradine, cefroxadine, ceftezole, cefaclor, cefamandole, cefminox, cefonicide, ceforanide, cefotiam, cefprozil, cefbuperazone, cefuroxime, cefuzonam, cefoxitin, cefotetan, cefmetazole, loracarbef, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, flomoxef, latamoxef, cefepime, cefozopran, cefpirome, cefquinome, ceftobiprole, ceftaroline, CXA-101, RWJ-54428, MC-04546, ME1036, BAL30072, SYN2416, ceftiofur, cefquinome, cefovecin, aztreonam, tigemonam, carumonam, RWJ-442831, RWJ-333441, and RWJ-333442.

[Item A66]

The pharmaceutical composition according to item A64 or A65, wherein the β-lactam agent is selected from the group consisting of ceftazidime, biapenem, doripenem, ertapenem, imipenem, meropenem, and panipenem.

[Item A67]

The pharmaceutical composition according to item A64 or A65, wherein the D-lactam agent is selected from the group consisting of aztreonam, tigemonam, BAL30072, SYN2416, and carumonam.

[Item A68]

The compound or the pharmaceutically acceptable salt thereof according to any one of items A1 to A51 for treating a bacterial infection.

[Item A69]

The compound or the pharmaceutically acceptable salt thereof according to item A68, wherein the bacterial infection is a bacterial infection in which a bacteria that can have a β-lactamase is involved.

[Item A70]

The compound or the pharmaceutically acceptable salt thereof according to item A68 or A69, wherein the bacterial infection is sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, or an odontogenic infection.

[Item A71]

A medicament comprised of a combination of the compound or the pharmaceutically acceptable salt thereof according to any one of items A1 to A51 and at least one agent selected from the group consisting of therapeutic agents for sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, and an odontogenic infection.

[Item A72]

A pharmaceutical composition comprising a R-lactam agent, wherein the pharmaceutical composition is administered with the compound or the pharmaceutically acceptable salt thereof according to any one of items A1 to A51.

[Item A73]

A method for treating a bacterial infection, characterized in that a therapeutically effective amount of the compound or the pharmaceutically acceptable salt thereof according to any one of items A1 to A51 is administered to a patient in need thereof.

[Item A74]

The method according to item A73, wherein the bacterial infection is a bacterial infection in which a bacteria that can have a β-lactamase is involved.

[Item A75]

The method according to item A73 or A74, wherein the bacterial infection is sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, or an odontogenic infection.

[Item A76]

The method according to any one of items A73 to A75, characterized in that an additional agent is concomitantly administered.

The present invention also provides the following.

[Item 1]

A compound represented by formula (1a) or (1b):

[Chemical Formula 146]

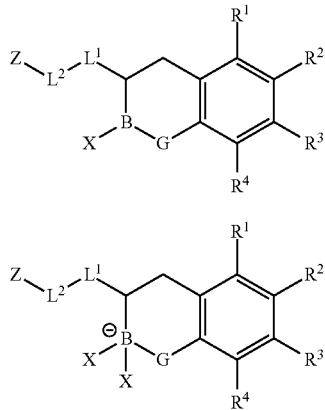

or a pharmaceutically acceptable salt thereof,
wherein
G is an oxygen atom, a sulfur atom, or —$NR^{a1}$—,
X is a hydroxyl group, an optionally substituted $C_{1-6}$ alkoxy group, or —$NR^{a2}R^{b1}$,
$R^{a1}$, $R^{a2}$, and $R^{b1}$ are the same or different, each independently
1) a hydrogen atom,
2) a $C_{1-6}$ alkyl group,
3) a $C_{3-10}$ alicyclic group,
4) $C_{6-10}$ aryl
5) 5- or 6-membered heteroaryl,
6) a 4- to 10-membered non-aryl heterocycle,
7) a $C_{1-6}$ alkylcarbonyl group,
8) a $C_{3-10}$ alicyclic carbonyl group,
9) a $C_{6-10}$ arylcarbonyl group,
10) a 5- or 6-membered heteroarylcarbonyl group,
11) a $C_{1-6}$ alkylsulfonyl group,
12) a $C_{3-10}$ alicyclic sulfonyl group,
13) a $C_{6-10}$ arylsulfonyl group,
14) a 5- or 6-membered heteroarylsulfonyl group, or
15) —$OR^{c1}$,
(wherein each substituent from 2) to 14) is optionally substituted),
wherein $R^{a2}$ and $R^{b1}$ together may form an optionally substituted 4- to 10-membered nitrogen-containing non-aryl heterocycle,
$R^{c1}$ is
1) a hydrogen atom,
2) a $C_{1-6}$ alkyl group,
3) a $C_{3-10}$ alicyclic group,
4) $C_{6-10}$ aryl,
5) 5- or 6-membered heteroaryl, or
6) a 4- to 10-membered non-aryl heterocycle,
(wherein each substituent from 2) to 6) is optionally substituted),
$L^1$ is a single bond, an oxygen atom, a sulfur atom, —SO—, —$SO_2$—, —$NR^d$—, —$NR^dC(=O)$—, or —$NR^dSO_2$—,
$L^2$ is a single bond or an optionally substituted $C_{1-6}$ alkylene group,
Z is
1) a hydrogen atom,
2) a hydroxyl group,
3) a cyano group,
4) a carboxyl group,
5) a $C_{3-10}$ alicyclic group,
6) $C_{6-10}$ aryl,
7) 5- or 6-membered heteroaryl,
8) a 4- to 10-membered non-aryl heterocycle,
9) a $C_{1-6}$ alkoxy group,
10) a $C_{3-10}$ alicyclic oxy group,
11) a $C_{6-10}$ aryloxy group,
12) a 5- or 6-membered heteroaryloxy group,
13) a 4- to 10-membered non-aryl heterocyclyl oxy group,
14) a $C_{1-6}$ alkylthio group,
15) a $C_{3-10}$ alicyclic thio group,
16) a $C_{6-10}$ arylthio group,
17) a 5- or 6-membered heteroarylthio group,
18) a 4- to 10-membered non-aryl heterocyclyl thio group,
(wherein each substituent from 5) to 18) is optionally substituted),
19) —$SO_2$—$NR^{e1}R^{f1}$,
20) —$NR^{e1}$—$C(=O)OR^{f1}$,
21) —$NR^{g1}$—$C(=O)NR^{e1}R^{f1}$,
22) —$NR^{e1}$—$C(=S)R^{f1}$,
23) —$NR^{e1}$—$C(=S)OR^{f1}$,
24) —$NR^{g1}$—$C(=S)NR^{e1}R^{f1}$,
25) —$NR^{g1}$—$CR^{e1}(=NR^{f1})$,
26) —$NR^{g1}$—$CR^{e1}(=N$—$OR^{f1})$,
27) —$NR^{h1}$—$C(=NR^{g1})NR^{e1}R^{f1}$,
28) —$NR^{h1}$—$C(=N$—$OR^{g1})NR^{e1}R^{f1}$,
29) —$NR^{i1}$—$C(=NR^{h1})NR^{g1}$—$NR^{e1}R^{f1}$,
30) —$NR^{i1}$—$C(=N$—$OR^{h1})NR^{g1}$—$NR^{e1}R^{f1}$,
31) —$NR^{e1}$—$SO_2$—$R^{f1}$,
32) —$NR^{g1}$—$SO_2$—$NR^{e1}R^{f1}$,
33) —$C(=O)OR^{e1}$,
34) —$C(=S)OR^{e1}$,
35) —$C(=S)NR^{e1}R^{f1}$,
36) —$C(=S)NR^{e1}OR^{f1}$,
37) —$C(=S)$ $NR^{g1}$—$NR^{e1}R^{f1}$, 38) —C(=NR$^{e1}$)R$^{f1}$,
39) —C(=N—OR$^{e1}$)R$^{f1}$,
40) —C(=NR$^{h1}$)NR$^{g1}$—NR$^{e1}$R$^{f1}$,
41) —C(=N—OR$^{h1}$)NR$^{g1}$—NR$^{e1}$R$^{f1}$,
42) —NR$^{e1}$R$^{f1}$,
43) —NR$^{g1}$—NR$^{e1}$R$^{f1}$,
44) —NR$^{e1}$OR$^{f1}$,
45) —NR$^{e1}$—C(=O)R$^{f1}$,
46) —C(=O)NR$^{e1}$R$^{f1}$,
47) —C(=O)NR$^{e1}$OR$^{f1}$,
48) —C(=O)NR$^{g1}$—NR$^{e1}$R$^{f1}$,
49) —C(=O)R$^{e1}$,
50) —C(=NR$^{g1}$)NR$^{e1}$R$^{f1}$, or
51) —C(=N—OR$^{h1}$)NR$^{e1}$R$^{f1}$, one of R$^1$, R$^2$, and R$^3$ is a group represented by formula (2):

[Chemical Formula 147]

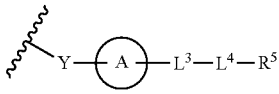

(2)

wherein
Y is an oxygen atom, a sulfur atom, or —NR$^j$—,
ring A is an optionally substituted 4- to 20-membered non-aryl heterocycle,
L$^3$ is —C(=O)—, —S(=O)—, or —S(=O)$_2$—,
L$^4$ is
1) a single bond,
2) a C$_{1-6}$ alkylene group,
3) a C$_{3-10}$ cycloalkylene group,
4) a C$_{6-10}$ arylene group,
5) a 5- or 6-membered heteroarylene group,
6) a 4- to 10-membered non-aryl heterocyclylene group, or
7) —C(=N—OR$^{h1}$)—,
(wherein each substituent from 2) to 6) is optionally substituted), and
R$^5$ is
1) a hydrogen atom,
2) a C$_{1-6}$ alkyl group,
3) a C$_{3-10}$ alicyclic group,
4) a 4- to 10-membered non-aryl heterocycle,
5) C$_{6-10}$ aryl,
6) 5- or 6-membered heteroaryl,
7) a C$_{1-6}$ alkylthio group,
(wherein each substituent from 2) to 7) is optionally substituted), or
8) —NR$^{e1}$OH,
the remaining two (without the structure of formula (2) among R$^1$, R$^2$, and R$^3$) are the same or different, each independently a hydrogen atom, a halogen atom, an optionally substituted C$_{1-6}$ alkyl group, an optionally substituted C$_{1-6}$ alkoxy group, an optionally substituted C$_{1-6}$ alkylthio group, an optionally substituted 5- or 6-membered heteroaryl, or —NR$^{a3}$R$^{b2}$, R$^d$, R$^{e1}$, R$^{e2}$, R$^{f1}$, R$^{f2}$, R$^{g1}$, R$^{g2}$, R$^{h1}$, R$^{h2}$, R$^{i1}$, R$^{i2}$, and R$^j$ are the same or different, each independently a hydrogen atom, an optionally substituted C$_{1-6}$ alkyl group, an optionally substituted C$_{1-6}$ alicyclic group, optionally substituted C$_{6-10}$ aryl, optionally substituted 5- or 6-membered heteroaryl, or an optionally substituted 4- to 10-membered non-aryl heterocycle, a combination of R$^{e1}$ and R$^{f1}$ or R$^{e2}$ and R$^{f2}$, when attached to the same nitrogen atom, together may form an optionally substituted 4- to 10-membered nitrogen-containing non-aryl heterocycle, R$^4$ is
1) —C(=O)R$^8$,
2) —SO$_2$-L$^6$-R$^8$,
(wherein R$^8$ in 1) and 2) is —NR$^{a5}$R$^{b4}$, —NR$^{a5}$-L$^7$-B(OR$^{m1}$)$_2$, —OR$^{m1}$, or an optionally substituted C$_{1-6}$ alkyl group, and L$^6$ is a single bond or —NR$^{a6}$—),
3) —NR$^{a4}$R$^{b3}$,
4) —B(OR$^{m1}$)$_2$,
5) —PO(OR$^{m1}$)(OR$^{m2}$),
6) optionally substituted 5-membered heteroaryl,
7) an optionally substituted 5-membered non-aryl heterocycle, or
8) a bioisostere of one of 1) to 7), (wherein the formulas of 2), 4), 5), and 6) include a carboxylic acid isostere, and 8) may include them in duplicates), R$^{a3}$, R$^{a4}$, R$^{a5}$, R$^{a6}$, R$^{b2}$, R$^{b3}$, and R$^{b4}$ are the same or different, each independently having the same definition as R$^{a1}$, R$^{a2}$, and R$^{b1}$, wherein a combination of R$^{a3}$ and R$^{b2}$, R$^{a4}$ and R$^{b3}$, or R$^{a5}$ and R$^{b4}$, when attached to the same nitrogen atom, together may form an optionally substituted 4- to 10-membered nitrogen-containing non-aryl heterocycle, R$^{m1}$ is
1) a hydrogen atom,
2) a C$_{1-6}$ alkyl group,
3) a C$_{3-10}$ alicyclic group,
4) C$_{6-10}$ aryl,
5) 5- or 6-membered heteroaryl, or
6) a 4- to 10-membered non-aryl heterocycle,
(wherein each substituent from 2) to 6) is optionally substituted),
wherein if R$^{m1}$ is attached to a boron atom via an oxygen atom, two R$^{m1}$, as C$_{2-4}$ alkylene, together with the boron atom and two oxygen atoms, may form a 5- to 7-membered non-aryl heterocycle (wherein an alkylene moiety is optionally substituted in the non-aryl heterocycle), R$^{m2}$ is a hydrogen atom, an optionally substituted C$_{1-6}$ alkyl group, or an optionally substituted C$_{3-10}$ alicyclic group, and L$^7$ is an optionally substituted C$_{1-3}$ alkylene group.

[Item 2]
The compound or the pharmaceutically acceptable salt thereof according to item 1, wherein
L$^1$ is a single bond, a sulfur atom, —NR$^d$C(=O)—, or —NR$^d$SO$_2$—,
L$^2$ is a single bond or an optionally substituted C$_{1-6}$ alkylene group, and
Z is
1) a hydrogen atom,
2) a hydroxyl group,
3) a C$_{3-10}$ alicyclic group,
4) C$_{6-10}$ aryl,
5) 5- or 6-membered heteroaryl,
6) a 4- to 10-membered non-aryl heterocycle,
7) —C(=N—OR$^{e1}$)R$^{f1}$, or
8) —NR$^{e1}$R$^{f1}$.

[Item 3]
The compound or the pharmaceutically acceptable salt thereof according to item 1 or 2, wherein
Z-L$^2$-L$^1$ is a hydrogen atom, an optionally substituted C$_{1-6}$ alkyl group, or an optionally substituted C$_{1-6}$ alkylthio group.

[Item 4]
The compound or the pharmaceutically acceptable salt thereof according to any one of the preceding items, wherein $Z-L^2-L^1$ is a hydrogen atom.

[Item 5]
The compound or the pharmaceutically acceptable salt thereof according to any one of the preceding items, wherein G is an oxygen atom.

[Item 6]
The compound or the pharmaceutically acceptable salt thereof according to any one of the preceding items, wherein X is a hydroxyl group or an optionally substituted $C_{1-6}$ alkoxy group.

[Item 7]
The compound or the pharmaceutically acceptable salt thereof according to any one of the preceding items, wherein X is a hydroxyl group.

[Item 8]
The compound or the pharmaceutically acceptable salt thereof according to any one of the preceding items, wherein the compounds of formulas (1a) and (1b) are represented by formulas (3a) and (3b), respectively:

[Chemical Formula 148]

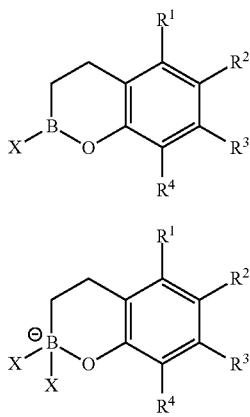

wherein X, $R^1$, $R^2$, and $R^3$ are defined the same as any one of the preceding items, and
$R^4$ is selected from the group consisting of
1) —COOR$^{m1}$ (wherein R$^{m1}$ is a hydrogen atom, a $C_{1-6}$ alkyl group, a $C_{3-10}$ alicyclic group, $C_{6-10}$ aryl, 5- or 6-membered heteroaryl, or a 4- to 10-membered non-aryl heterocycle, wherein the $C_{1-6}$ alkyl group, the $C_{3-10}$ alicyclic group, the $C_{6-10}$ aryl, the 5- or 6-membered heteroaryl, and the 4- to 10-membered non-aryl heterocycle are each optionally substituted), and
2) a bioisostere of 1).

[Item 9]
The compound or the pharmaceutically acceptable salt thereof according to item 8, wherein $R^4$ is
1) —COOH (i.e., a carboxyl group), or
2) a carboxylic acid isostere.

[Item 10]
The compound or the pharmaceutically acceptable salt thereof according to any one of the preceding items, wherein the compounds of formulas (1a) and (1b) or the compounds of formulas (3a) and (3b) are represented by formulas (4a) and (4b), respectively:

[Chemical Formula 149]

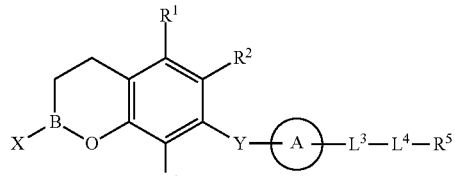

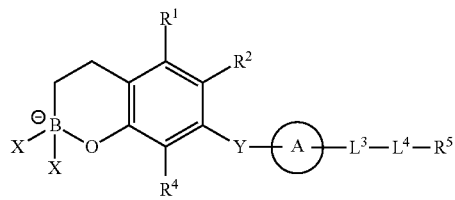

wherein X, $R^4$, Y, ring A, $L^3$, $L^4$, and $R^5$ are defined the same as any one of the preceding items, and
$R^1$ and $R^2$ are the same or different, each independently a hydrogen atom, a halogen atom, a $C_{1-6}$ alkyl group, or a $C_{1-6}$ alkoxy group (wherein the $C_{1-6}$ alkyl group and the $C_{1-6}$ alkoxy group are optionally substituted with 1 to 5 halogen atoms).

[Item 11]
The compound or the pharmaceutically acceptable salt thereof according to any one of the preceding items, wherein ring A is an optionally substituted 4- to 10-membered non-aryl heterocycle.

[Item 12]
The compound or the pharmaceutically acceptable salt thereof according to any one of the preceding items, wherein ring A is an optionally substituted 4- to 7-membered non-aryl heterocycle.

[Item 13]
The compound or the pharmaceutically acceptable salt thereof according to any one of the preceding items, wherein Y is an oxygen atom or a sulfur atom.

[Item 14]
The compound or the pharmaceutically acceptable salt thereof according to any one of the preceding items, wherein Y is an oxygen atom.

[Item 15]
The compound or the pharmaceutically acceptable salt thereof according to any one of the preceding items, wherein the compounds of formulas (1a) and (1b), the compounds of formulas (3a) and (3b), or the compounds of formulas (4a) and (4b) are represented by formulas (5a) and (5b), respectively:

[Chemical Formula 150]

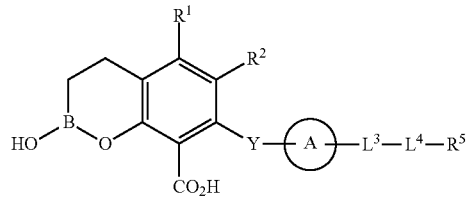

(5b)

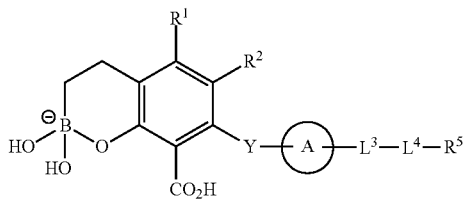

wherein ring A is an optionally substituted 4- to 6-membered nitrogen-containing non-aryl heterocycle.

[Item 16]
The compound or the pharmaceutically acceptable salt thereof according to any one of the preceding items, wherein $L^3$ is —C(=O)— or —S(=O)$_2$—.

[Item 17]
The compound or the pharmaceutically acceptable salt thereof according to any one of the preceding items, wherein $L^3$ is —C(=O)—.

[Item 18]
The compound or the pharmaceutically acceptable salt thereof according to any one of the preceding items, wherein $L^4$ is a single bond, —C(=N—OR$^{h1}$)—, or an optionally substituted $C_{1-6}$ alkylene group, wherein R$^{h1}$ is an optionally substituted $C_{1-6}$ alkyl group.

[Item 19]
The compound or the pharmaceutically acceptable salt thereof according to any one of the preceding items, wherein $R^1$ and $R^2$ are the same or different, each independently selected from the group consisting of
1) a hydrogen atom,
2) a halogen atom,
3) a $C_{1-6}$ alkyl group,
4) a $C_{1-6}$ alkoxy group, and
5) a $C_{1-6}$ alkylthio group,
(wherein each substituent from 3) to 5) is optionally substituted).

[Item 20]
The compound or the pharmaceutically acceptable salt thereof according to any one of the preceding items, wherein $R^1$ and $R^2$ are the same or different, each independently selected from the group consisting of
1) a hydrogen atom,
2) a halogen atom, and
3) an optionally substituted $C_{1-6}$ alkyl group.

[Item 21]
The compound or the pharmaceutically acceptable salt thereof according to any one of the preceding items, wherein $R^1$ and $R^2$ are both hydrogen atoms.

[Item 22]
The compound or the pharmaceutically acceptable salt thereof according to any one of the preceding items, wherein the compounds of formulas (1a) and (1b), the compounds of formulas (3a) and (3b), the compounds of formulas (4a) and (4b), or the compounds of formulas (5a) and (5b) are represented by formulas (6a) and (6b), respectively:

[Chemical Formula 151]

(6a)

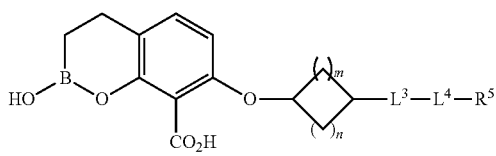

(6b)

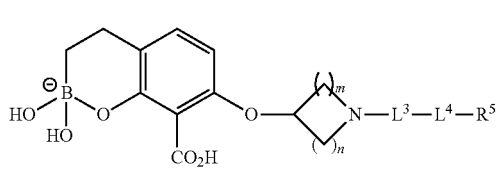

wherein $L^3$, $L^4$, and $R^5$ are defined the same as any one of the preceding items,
m is an integer 1, 2, or 3,
n is an integer 1, 2, or 3, and
m+n is 2, 3, or 4.

[Item 23]
The compound or the pharmaceutically acceptable salt thereof according to any one of the preceding items, wherein m is 1 or 2, n is 1 or 2, and m+n is 2 or 3.

[Item 24]
The compound or the pharmaceutically acceptable salt thereof according to any one of the preceding items, wherein m is 1 and n is 1.

[Item 25]
The compound or the pharmaceutically acceptable salt thereof according to any one of the preceding items, wherein $L^4$ is a single bond, or a $C_{1-6}$ alkylene group optionally substituted with —NR$^{21}$R$^{22}$ or =NOR$^{23}$, wherein R$^{21}$, R$^{22}$, and R$^{23}$ are each independently a hydrogen atom, an optionally substituted $C_{1-6}$ alkyl group, or an optionally substituted 4- to 10-membered non-aryl heterocyclyl carbonyl group.

[Item 26]
The compound or the pharmaceutically acceptable salt thereof according to any one of the preceding items, wherein $L^4$ is a single bond, —CH$_2$—, —CH(NH$_2$)—, or —CH(NH$_2$)—CH$_2$—, wherein if an amino group is present in $L^4$, carbon that attaches to the amino group attaches to $L^3$.

[Item 27]
The compound or the pharmaceutically acceptable salt thereof according to any one of the preceding items, wherein $L^4$ is a single bond, —CH$_2$—, —CMe(NH$_2$)—, —CH(NHMe)-, —CD(NH$_2$)— (wherein D represents a heavy hydrogen atom), —CH(NH$_2$)—, or —CH$_2$CH$_2$—.

[Item 28]
The compound or the pharmaceutically acceptable salt thereof according to any one of the preceding items, wherein $L^4$ is a single bond, —CH$_2$—, or —CH(NH$_2$)—.

[Item 29]
The compound or the pharmaceutically acceptable salt thereof according to any one of the preceding items, wherein $R^5$ is a hydrogen atom, an optionally substituted $C_{1-6}$ alkyl group, an optionally substituted 4- to 10-membered non-aryl heterocycle, optionally substituted $C_{6-10}$ aryl, optionally substituted 5- or 6-membered heteroaryl, an optionally substituted $C_{1-6}$ alkylthio group, or —NR$^{e1}$OH, wherein R$^{e1}$ is a hydrogen atom or an optionally substituted $C_{1-4}$ alkyl group.

[Item 30]
The compound or the pharmaceutically acceptable salt thereof according to any one of the preceding items, wherein $R^5$ is optionally substituted 5- or 6-membered heteroaryl or optionally substituted $C_{6-10}$ aryl.

[Item 31]
The compound or the pharmaceutically acceptable salt thereof according to any one of the preceding items, wherein $R^5$ is optionally substituted 5- or 6-membered heteroaryl.

[Item 32]
The compound or the pharmaceutically acceptable salt thereof according to any one of the preceding items, wherein $R^5$ is an optionally substituted 4- to 10-membered non-aryl heterocycle.

[Item 33]
The compound or the pharmaceutically acceptable salt thereof according to any one of the preceding items, wherein $L^4$ is a single bond, and $R^5$ is —$NR^{e1}OH$, wherein $R^{e1}$ is a hydrogen atom or an optionally substituted $C_{1-6}$ alkyl group.

[Item 34]
The compound or the pharmaceutically acceptable salt thereof according to any one of the preceding items, wherein $L^4$ is
1) —$(CH_2)_p$—$CR^{10}(NHR^{11})$—,
2) —$(CH_2)_q$—$CR^{12}R^{13}$—, or
3) —$(CH_2)_p$—$CR^{10}(NHR^{11})$—$(CH_2)_q$—$CR^{12}R^{13}$— (wherein p and q are independently 0 or 1),
$R^{10}$ is
1) a hydrogen atom,
2) a carboxyl group, or
3) —$C(=O)NR^{10a}R^{10b}$,
$R^{11}$ is
1) a hydrogen atom,
2) —$C(=O)R^{11a}$, or
3) an optionally substituted 5- or 6-membered non-aryl heterocyclyl carbonyl group,
wherein if $R^{10}$ is —$C(=O)NR^{10a}R^{10b}$, $R^{10b}$ and $R^{11}$ together may form —$CH_2CH_2$—,
$R^{12}$ is
1) a hydrogen atom, or
2) an optionally substituted $C_{1-4}$ alkyl group,
$R^{13}$ is
1) a hydrogen atom,
2) a hydroxyl group,
3) an optionally substituted $C_{1-4}$ alkyl group,
4) a sulfanyl group,
5) a carboxyl group,
6) an optionally substituted $C_{1-4}$ alkylthio group,
7) —$NR^{13a}R^{13b}$,
8) —$NR^{13a}$—$C(=O)R^{13b}$,
9) an optionally substituted 5- or 6-membered non-aryl heterocyclyl carbonylamino group,
10) —$NR^{13a}$—$C(=O)NR^{13b}R^{13c}$,
11) —$C(=O)NR^{13a}R^{13b}$,
12) —$C(=O)$ $NR^{13a}OR^{13b}$,
13) —$S(=O)_2$—$R^{13a}$,
14) —$S(=O)_2$—$NR^{13a}R^{13b}$,
15) —$C(=O)NR^{13a}$—$S(=O)_2$—$R^{13b}$, or
16) —$C(=O)NR^{13a}$—$S(=O)_2$—$NR^{13b}R^{13c}$, and
$R^{10a}$, $R^{10b}$, $R^{11a}$, $R^{13a}$, $R^{13b}$, and $R^{13c}$ are each independently a hydrogen atom or an optionally substituted $C_{1-4}$ alkyl group.

[Item 35]
The compound or the pharmaceutically acceptable salt thereof according to any one of the preceding items, wherein $R^5$ is a hydrogen atom or an optionally substituted $C_{1-4}$ alkyl group.

[Item 36]
The compound or the pharmaceutically acceptable salt thereof according to any one of items 1 to 31, wherein $R^5$ is selected from the group consisting of

[Chemical Formula 152]

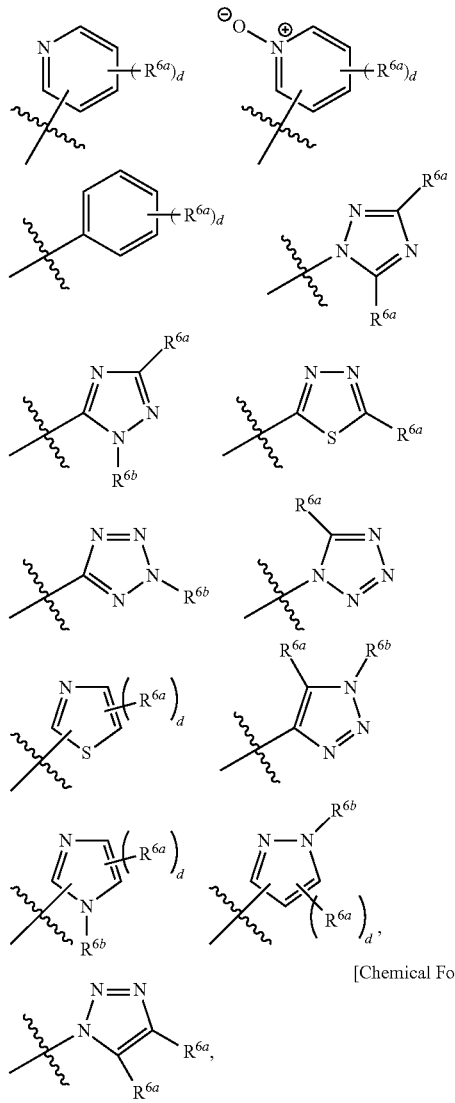

[Chemical Formula 153]

subscript d is the number of substitutable positions on a ring of $R^5$,
each $R^{6a}$ is independently selected from the group consisting of
1) a hydrogen atom,
2) a hydroxyl group,
3) a cyano group,
4) a nitro group,
5) halogen,
6) a $C_{1-4}$ alkyl group,
7) a $C_{3-10}$ alicyclic group,
8) a $C_{1-4}$ alkoxy group,
9) a $C_{3-10}$ alicyclic oxy group,
10) a $C_{6-10}$ aryloxy group,
11) a 5- or 6-membered heteroaryloxy group,
12) a 4- to 10-membered non-aryl heterocyclyl oxy group, (wherein each substituent from 6) to 12) is optionally substituted),
13) —$SO_2$—$NR^{e2}R^{f2}$,
14) —$NR^{g2}$—$CR^{e2}(=NR^{f2})$
15) —$NR^{g2}$—$CR^{e2}(=N$—$OR^{f2})$, 16) —NR$^{h2}$—C(=NR$^{g2}$)NR$^{e2}$R$^{f2}$,
17) —NR$^{h2}$—C(=N—OR$^{g2}$)NR$^{e2}$R$^{f2}$,
18) —NR$^{i2}$—C(=NR$^{h2}$)NR$^{g2}$—NR$^{e2}$R$^{f2}$,
19) —NR$^{i2}$C(=N—OR$^{h2}$)NR$^{g2}$—NR$^{e2}$R$^{f2}$,
20) —C(=NR$^{e2}$)R$^{f2}$,
21) —C(=N—OR$^{e2}$)R$^{f2}$,
22) —C(—NR$^{h2}$)—NR$^{e2}$R$^{f2}$,
23) —C(=NR$^{h2}$)NR$^{g2}$—NR$^{e2}$R$^{f2}$,
24) —C(=N—OR$^{h2}$)NR$^{g2}$—NR$^{e2}$R$^{f2}$,
25) —NR$^{e2}$R$^{f2}$,
26) —NR$^{g2}$—NR$^{e2}$R$^{f2}$,
27) —N$^{e2}$OR$^{f2}$,
28) —NR$^{e2}$—C(=O)R$^{f2}$,
29) —C(=O)NR$^{e2}$R$^{f2}$,
30) —C(=O)NR$^{e2}$OR$^{f2}$,
31) —C(=O)NR$^{g2}$—NR$^{e2}$R$^{f2}$,
32) —C(=O)R$^{e2}$,
33) —C(=O)OR$^{e2}$, and
34) —C(=N—OR$^{h2}$)NR$^{e2}$R$^{f2}$, and each R$^{6b}$ is independently selected from the group consisting of
1) a hydrogen atom,
2) a hydroxyl group,
3) a C$_{1-4}$ alkyl group
(wherein the alkyl group is optionally substituted)
4) a C$_{3-10}$ alicyclic group
(wherein the alicyclic group is optionally substituted),
5) —C(=NR$^{e2}$)R$^{f2}$,
6) —C(=N—OR$^{e2}$)R$^{f2}$,
7) —SO$_2$—NR$^{e2}$R$^{f2}$,
8) —C(=NR$^{h2}$)—NR$^{e2}$R$^{f2}$,
9) —C(=NR$^{h2}$)NR$^{g2}$—NR$^{e2}$R$^{f2}$,
10) —C(=N—OR$^{h2}$)NR$^{g2}$—NR$^{e2}$R$^{f2}$,
11) —C(=O)NR$^{e2}$R$^{f2}$,
12) —C(=O) NR$^{e2}$OR$^{f2}$,
13) —C(=O)NR$^{g2}$—NR$^{e2}$R$^{f2}$,
14) —C(=O)R$^{e2}$, and
15) —C(=N—OR$^{h2}$)NR$^{e2}$R$^{f2}$.

[Item 37]

The compound or the pharmaceutically acceptable salt thereof according to any one of items 1 to 31 and 36, wherein R$^5$ is 5- or 6-membered aryl or heteroaryl selected from the group consisting of

[Chemical Formula 154]

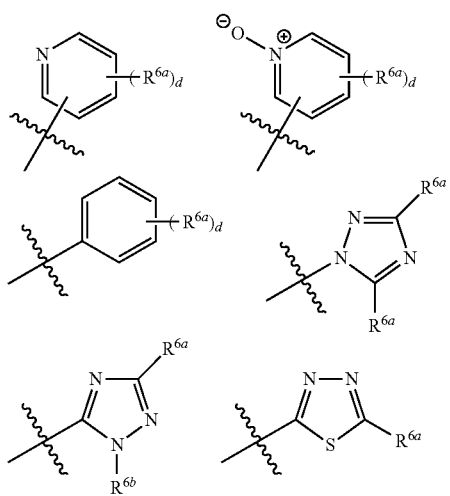

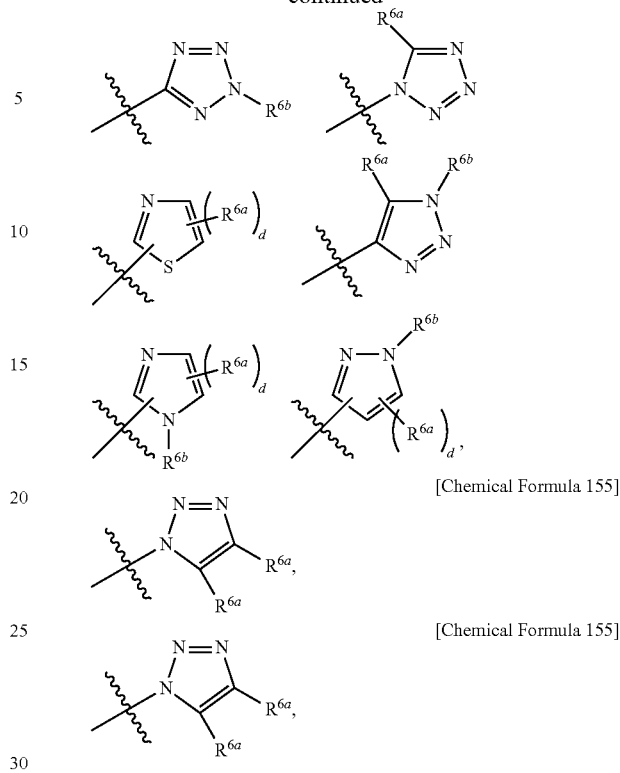

[Chemical Formula 155]

[Chemical Formula 155]

subscript d is the number of substitutable positions on a ring of R$^5$, each R$^{6a}$ is independently selected from the group consisting of
1) a hydrogen atom,
2) a hydroxyl group,
3) halogen,
4) a C$_{1-4}$ alkyl group
(wherein the alkyl group is optionally substituted with NR$^{e2}$R$^{f2}$, a 5- or 6-membered non-aryl heterocycle, —C(=O)OR$^{f2}$, or a hydroxyl group),
5) a C$_{1-4}$ alkoxy group
6) —NR$^{e2}$R$^{f2}$, and
7) —C(=O)OR$^{e2}$, and each R$^{6b}$ is independently selected from the group consisting of
1) a hydrogen atom,
2) a hydroxyl group, and
3) a C$_{1-4}$ alkyl group
(wherein the alkyl group is optionally substituted with NR$^{e2}$R$^{f2}$, —C(=O) NR$^{e2}$R$^{f2}$, —C(=O) OR$^{f2}$, or a hydroxyl group).

[Item 38]

The compound or the pharmaceutically acceptable salt thereof according to any one of items 1 to 31, 36, and 37, wherein R$^{e2}$ and R$^{f2}$ are the same or different, each independently a hydrogen atom, an optionally substituted C$_{1-6}$ alkyl group, or an optionally substituted C$_{3-10}$ alicyclic group.

[Item 39]

The compound or the pharmaceutically acceptable salt thereof according to any one of items 1 to 31 and 36 to 38, wherein R$^{e2}$ and R$^{f2}$ are the same or different, each independently a hydrogen atom or an optionally substituted C$_{1-6}$ alkyl group.

[Item 40]
The compound or the pharmaceutically acceptable salt thereof according to any one of items 1 to 31 and 36 to 39, wherein $R^{e2}$ and $R^{f2}$ are hydrogen atoms.

[Item 41]
The compound or the pharmaceutically acceptable salt thereof according to any one of items 36 to 39, wherein $R^{6a}$ is $-NR^{e2}R^{f2}$, and one of $R^{e2}$ and $R^{f2}$ is a hydrogen atom and the other is a $C_{1-4}$ alkyl group (wherein the alkyl group is optionally substituted with an amino group or a hydroxyl group).

[Item 42]
The compound or the pharmaceutically acceptable salt thereof according to any one of items 1 to 29 and 32, wherein $R^5$ is a 4- to 6-membered non-aryl heterocycle selected from the group consisting of

[Chemical Formula 156]

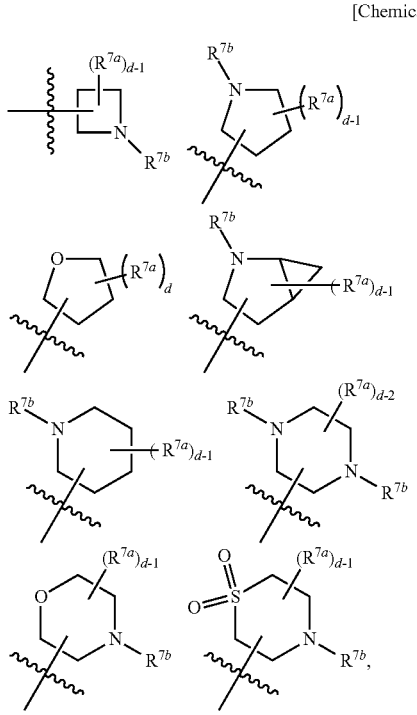

subscript d is the number of substitutable positions on a ring of $R^5$,
each $R^{7a}$ is independently selected from the group consisting of
1) a hydrogen atom,
2) a hydroxyl group,
3) a cyano group,
4) halogen,
5) a $C_{1-4}$ alkyl group,
6) a $C_{3-10}$ alicyclic group,
7) a $C_{1-4}$ alkoxy group,
8) a $C_{3-10}$ alicyclic oxy group,
9) a $C_{6-10}$ aryloxy group,
10) a 5- or 6-membered heteroaryloxy group,
11) a 4- to 10-membered non-aryl heterocyclyl oxy group, (wherein each substituent from 5) to 11) is optionally substituted),
12) $-SO_2-NR^{e3}R^{f3}$,
13) $-NR^{g2}-CR^{e3}(=NR^{f3})$,
14) $-NR^{g2}-CR^{e3}(=N-OR^{f3})$,
15) $-NR^{h2}-C(=NR^{g2})NR^{e3}R^{f3}$,
16) $-NR^{h2}-C(=N-OR^{g2})NR^{e3}R^{f3}$,
17) $-NR^{i2}-C(=NR^{h2})NR^{g2}-NR^{e3}R^{f3}$,
18) $-NR^{i2}C(=N-OR^{h2})NR^{g2}-NR^{e3}R^{f3}$,
19) $-C(=NR^{e3})R^{f3}$,
20) $-C(=N-OR^{e3})R^{f3}$,
21) $-C(=NR^{h2})-NR^{e3}R^{f3}$,
22) $-C(=NR^{h2})NR^{g2}-NR^{e3}R^{f3}$,
23) $-C(=N-OR^{h2})NR^{g2}-NR^{e3}R^{f3}$,
24) $-NR^{e3}R^{f3}$,
25) $-NR^{g2}-NR^{e3}R^{f3}$,
26) $-NR^{e3}OR^{f3}$,
27) $-NR^{e3}-C(=O)R^{f3}$,
28) $-C(=O)NR^{e3}R^{f3}$,
29) $-C(=O)NR^{e3}OR^{f3}$,
30) $-C(=O)NR^{g2}-NR^{e3}R^{f3}$,
31) $-C(=O) R^{e3}$,
32) $-C(=O)OR^{e3}$, and
33) $-C(=N-OR^{h2}) NR^{e3}R^{f3}$, each $R^{7b}$ is independently selected from the group consisting of
1) a hydrogen atom,
2) a hydroxyl group,
3) a $C_{1-4}$ alkyl group
(wherein the alkyl group is optionally substituted),
4) a $C_{3-10}$ alicyclic group
(wherein the alicyclic group is optionally substituted),
5) $-C(=NR^{e3})R^{f3}$,
6) $-C(=N-OR^{e3})R^{f3}$,
7) $-SO_2-NR^{e3}R^{f3}$,
8) $-C(=NR^{h2})-NR^{e3}R^{f3}$,
9) $-C(=NR^{h2})NR^{g2}-NR^{e3}R^{f3}$,
10) $-C(=N-OR^{h2})R^{g2}-R^{e3}R^{f3}$,
11) $-C(=O)NR^{e3}R^{f3}$,
12) $-C(=O)NR^{e3}OR^{f3}$,
13) $-C(=O)NR^{g2}-NR^{e3}R^{f3}$
14) $-C(=O)R^{e3}$, and
15) $-C(=N-OR^{h2})NR^{e3}R^{f3}$, and $R^{e3}$ and $R^{f3}$ are defined the same as $R^{e2}$ and $R^{f2}$ according to item 1.

[Item 43]
The compound or the pharmaceutically acceptable salt thereof according to any one of items 1 to 29, 32, and 42, wherein
$R^5$ is a 4- to 6-membered non-aryl heterocycle selected from the group consisting of

[Chemical Formula 157]

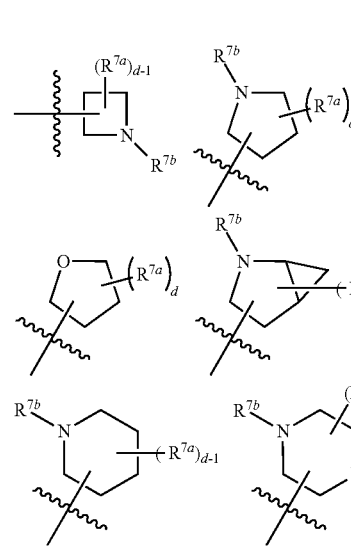

-continued

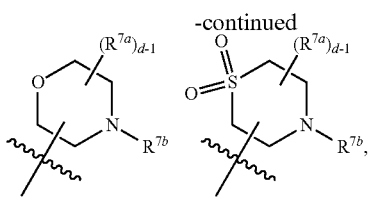

subscript d is the number of substitutable positions on a ring of $R^5$, each $R^{7a}$ is independently selected from the group consisting of
1) a hydrogen atom,
2) a hydroxyl group,
3) halogen,
4) a $C_{1-4}$ alkyl group
(wherein the alkyl group is optionally substituted with $NR^{e3}R^{f3}$, a 5- or 6-membered non-aryl heterocycle, —C(=O)OR$^{f3}$, or a hydroxyl group),
5) a $C_{1-4}$ alkoxy group
6) —NR$^{e3}$R$^{f3}$,
7) —C(=O)OR$^{e3}$,
8) $C_{6-10}$ aryl, and
9) —C(=O)NR$^{e3}$R$^{f3}$, each $R^{7b}$ is independently selected from the group consisting of
1) a hydrogen atom,
2) a hydroxyl group, and
3) a $C_{1-4}$ alkyl group
(wherein the alkyl group is optionally substituted with $NR^{e3}R^{f3}$, —C(=O) OR$^{f3}$, or a hydroxyl group), and $R^{e3}$ and $R^{f3}$ are defined the same as $R^{e2}$ and $R^{f2}$ according to any one of items 38 to 40.

[Item 44]

The compound or the pharmaceutically acceptable salt thereof according to any one of the preceding items, wherein
$L^4$ is —CH(NH$_2$)—CHR$^{13}$—, wherein carbon that attaches to the NH$_2$ attaches to $L^3$,
$R^5$ is a hydrogen atom, and
$R^{13}$ is
1) —NH—C(=O)CH$_3$,
2) —NH—C(=O)NH$_2$,
3) —NH—C(=O)CH(NH$_2$)—CH$_2$C(=O)NH$_2$,
4) —NH—C(=O)CH$_2$—NH$_2$,
5) —NH—C(=O)CH(NH$_2$)—CH$_2$OH, or
6) a pyrrolidin-2-ylcarbonylamino group.

[Item 45]

The compound or the pharmaceutically acceptable salt thereof according to any one of the preceding items, wherein $L^4$ is —CH(NH$_2$) —CR$^{12}$R$^{13}$—, wherein carbon that attaches to the NH$_2$ attaches to $L^3$,
$R^5$ is a hydrogen atom or methyl,
$R^{12}$ is a hydrogen atom or methyl, and
$R^{13}$ is a benzylthio group or a sulfanyl group.

[Item 46]

The compound or the pharmaceutically acceptable salt thereof according to any one of the preceding items, wherein $L^4$ is —CH(NH$_2$)—(CH$_2$)$_q$—CHR$^{13}$—, wherein q is 0 or 1, and carbon that attaches to the NH$_2$ attaches to $L^3$,
$R^5$ is a hydrogen atom, and
$R^{13}$ is
1) a carboxyl group,
2) —C(=O)NH$_2$,
3) —C(=O)NH(CH$_3$),
4) —C(=O)N(CH$_3$)$_2$,
5) —C(=O)NH—(CH$_2$)$_2$—OH,
6) —C(=O)NH—(CH$_2$)$_2$—NH$_2$,
7) —C(=O)NH—S(=O)$_2$—CH$_3$,
8) —C(=O)NHOH,
9) —S(=O)$_2$—NH$_2$,
10) —S(=O)$_2$—CH$_3$, or
11) a hydroxyl group.

[Item 47]

The compound or the pharmaceutically acceptable salt thereof according to any one of the preceding items, wherein
$L^4$ is —CH(NHR$^{11}$)—CH$_2$—, wherein carbon that attaches to the NHR$^{11}$ attaches to $L^3$,
$R^5$ is hydrogen, and
$R^{11}$ is
1) —C(=O)CH(NH$_2$)—CH$_2$C(=O)NH$_2$,
2) —C(=O)CH$_2$—NH$_2$,
3) —C(=O)CH(CH$_3$)—NH$_2$,
4) —C(=O)CH(NH$_2$)—CH$_2$OH, or
5) pyrrolidin-2-ylcarbonyl.

[Item 48]

The compound or the pharmaceutically acceptable salt thereof according to any one of the preceding items, wherein
$L^4$ is —CH(NHR$^{11}$)—CH(COOH)—, wherein carbon that attaches to the NHR$^{11}$ attaches to $L^3$,
$R^5$ is hydrogen, and
$R^{11}$ is
1) —C(=O)CH(NH$_2$)—CH$_2$C(=O)NH$_2$,
2) —C(=O)CH$_2$—NH$_2$,
3) —C(=O)CH(CH$_3$)—NH$_2$,
4) —C(=O)CH(NH$_2$)—CH$_2$OH, or
5) pyrrolidin-2-ylcarbonyl.

[Item 49]

The compound or the pharmaceutically acceptable salt thereof according to any one of the preceding items, wherein
$L^4$ is —CHR$^{13}$— or —CH$_2$—CHR$^{13}$
$R^5$ is hydrogen, and
$R^{13}$ is —C(=O)NH$_2$ or —C(=O)NHOH.

[Item 50]

The compound or the pharmaceutically acceptable salt thereof according to any one of the preceding items, wherein
$L^4$ is —CH$_2$—CR$^{10}$(NH$_2$)—, wherein the CH$_2$ attaches to $L^3$,
$R^5$ is hydrogen, and
$R^{10}$ is a carboxy group or —C(=O)NH$_2$.

[Item 51]

The compound or the pharmaceutically acceptable salt thereof according to any one of the preceding items, wherein
$L^4$ is —(CH$_2$)$_p$—CR$^{10}$(NHR$^{11}$)—(CH$_2$)$_q$—CHR$^{13}$— or —CHR$^{13}$—(CH$_2$)$_q$—CR$^{10}$(NHR$^{11}$)—(CH$_2$)$_p$—, wherein q is 0 or 1,
$R^5$ is hydrogen,
(1) if $L^4$ is —CHR$^{13}$—(CH$_2$)$_q$—CR$^{10}$(NHR$^{11}$)—(CH$_2$)$_p$—, carbon of the —CHR$^{13}$— group attaches to $L^3$,
p is 0,
$R^{10}$ is a hydrogen atom, a carboxyl group, or —C(=O) NHR$^{10b}$,
$R^{11}$ is a hydrogen atom,
$R^{10b}$ is a hydrogen atom,
wherein if $R^{10}$ is —C(=O)NHR$^{10b}$, $R^{10b}$ and $R^{11}$ together may form —CH$_2$CH$_2$—, and
$R^{13}$ is a hydrogen atom, and
(2) if $L^4$ is —(CH$_2$)$_p$—CR$^{10}$(NHR$^{11}$)—(CH$_2$)$_q$—CHR$^{13}$—, carbon of the —(CH$_2$)$_p$— group attaches to $L^3$,
p is 1,
$R^{10}$ and $R^{11}$ are both hydrogen atoms,
$R^{13}$ is a carboxyl group or —C(=O) NR$^{13a}$R$^{13b}$, and
$R^{13a}$ and $R^{13b}$ are each independently a hydrogen atom or an optionally substituted $C_{1-4}$ alkyl group.

[Item 52]

The compound or the pharmaceutically acceptable salt thereof according to any one of the preceding items, wherein $L^4$ is —$CR^{12}(NH_2)$—, $R^{12}$ is a hydrogen atom or a methyl group, and $R^5$ is a $C_{1-4}$ alkyl group optionally substituted with a hydroxyl group.

[Item 53]

The compound or the pharmaceutically acceptable salt thereof according to item 1, represented by the following compound name or structural formula:

7-[(1-acetylazetidin-3-yl)oxy]-2-hydroxy-3,4-dihydro-2H-1,2-benzoxaborinine-8-carboxylic acid 4,4-dihydroxy-8-({1-[(1H-imidazol-5-yl)acetyl]azetidin-3-yl}oxy)-5-oxa-4-boranuidabicyclo[4.4.0]deca-1(6),7,9-triene-7-carboxylic acid

[Chemical Formula 161]

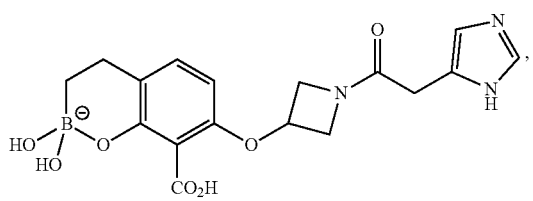

2-hydroxy-7-{[1-(methanesulfonyl)azetidin-3-yl]oxy}-3,4-dihydro-2H-1,2-benzoxaborinine-8-carboxylic acid

[Chemical Formula 158]

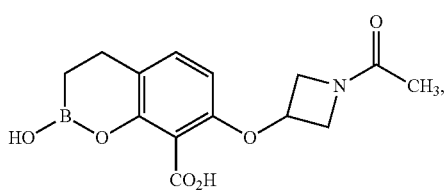

8-[(1-acetylazetidin-3-yl)oxy]-4,4-dihydroxy-5-oxa-4-boranuidabicyclo[4.4.0]deca-1(6),7,9-triene-7-carboxylic acid

[Chemical Formula 162]

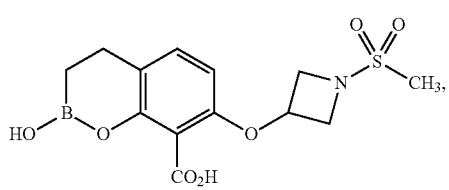

4,4-dihydroxy-8-{[1-(methanesulfonyl)azetidin-3-yl]oxy}-5-oxa-4-boranuidabicyclo[4.4.0]deca-1(6),7,9-triene-7-carboxylic acid

[Chemical Formula 159]

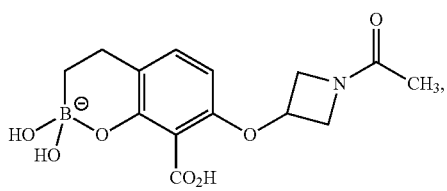

2-hydroxy-7-({1-[(1H-imidazol-5-yl)acetyl]azetidin-3-yl}oxy)-3,4-dihydro-2H-1,2-benzoxaborinine-8-carboxylic acid

[Chemical Formula 163]

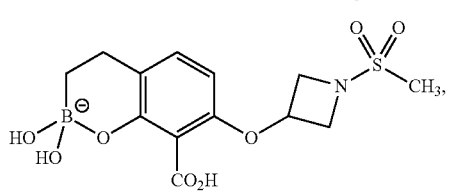

7-({1-[(2R)-2-amino-2-(4-hydroxyphenyl)acetyl]azetidin-3-yl}oxy)-2-hydroxy-3,4-dihydro-2H-1,2-benzoxaborinine-8-carboxylic acid

[Chemical Formula 160]

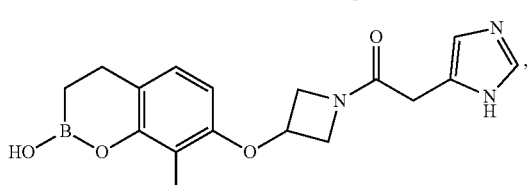

[Chemical Formula 164]

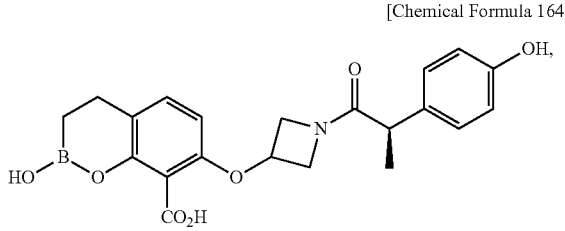 [SMILES: C[C@@H](C(=O)N1CC(Oc2ccc3c(c2C(=O)O)OB(O)CC3)C1)c1ccc(O)cc1]

8-({1-[(2R)-2-amino-2-(4-hydroxyphenyl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 165]

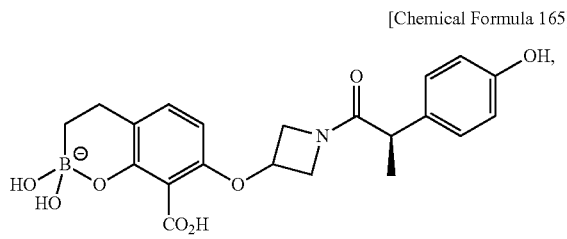

7-({1-[(2-amino-1,3-thiazol-4-yl)(methoxyimino)acetyl]azetidin-3-yl}oxy)-2-hydroxy-3,4-dihydro-2H-1,2-benzoxaborinine-8-carboxylic acid

[Chemical Formula 166]

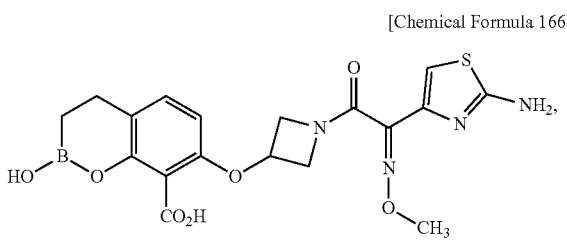 [SMILES: CON=C(C(=O)N1CC(Oc2ccc3c(c2C(=O)O)OB(O)CC3)C1)c1csc(N)n1]

8-({1-[(2-amino-1,3-thiazol-4-yl)(methoxyimino)acetyl]azetidin-3-yl}oxy)-4,4-dihydroxy-5-oxa-4-boranuidabicyclo[4.4.0]deca-1(6),7,9-triene-7-carboxylic acid

[Chemical Formula 167]

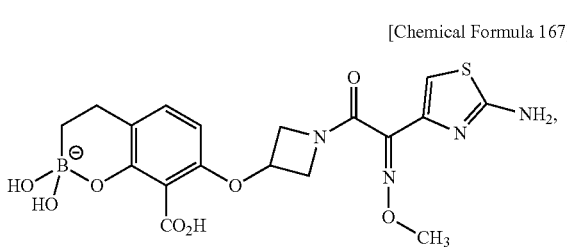 [SMILES: CON=C(C(=O)N1CC(Oc2ccc3c(c2C(=O)O)O[B-](O)(O)CC3)C1)c1csc(N)n1]

2-hydroxy-7-{[1-(pyridine-2-carbonyl)azetidin-3-yl]oxy}-3,4-dihydro-2H-1,2-benzoxaborinine-8-carboxylic acid

[Chemical Formula 168]

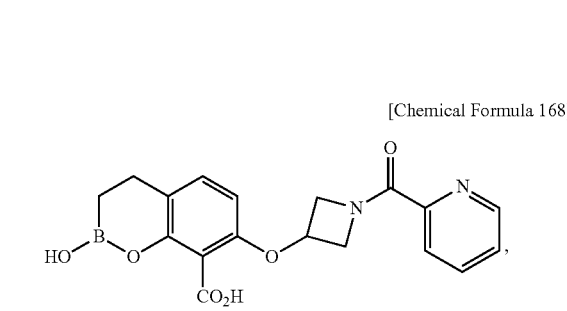

4,4-dihydroxy-8-{[1-(pyridine-2-carbonyl)azetidin-3-yl]oxy}-5-oxa-4-boranuidabicyclo[4.4.0]deca-1(6),7,9-triene-7-carboxylic acid

[Chemical Formula 169]

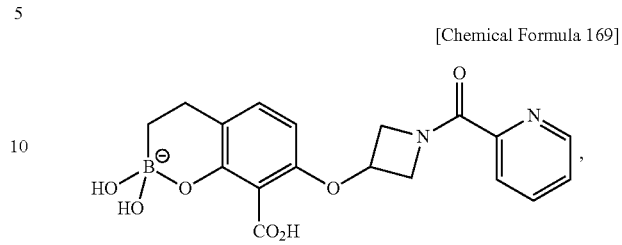

2-hydroxy-7-({1-[(methylsulfanyl)acetyl]azetidin-3-yl}oxy)-3,4-dihydro-2H-1,2-benzoxaborinine-8-carboxylic acid

[Chemical Formula 170]

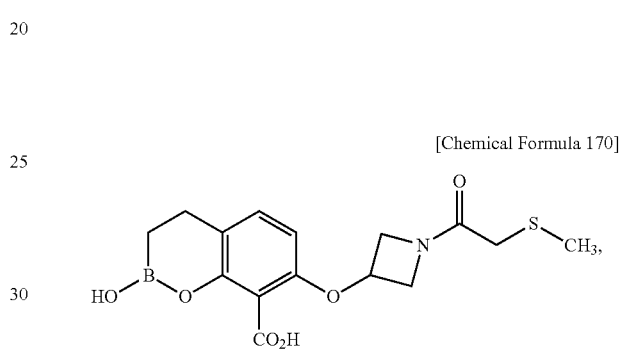

4,4-dihydroxy-8-({1-[(methylsulfanyl)acetyl]azetidin-3-yl}oxy)-5-oxa-4-boranuidabicyclo[4.4.0]deca-1(6),7,9-triene-7-carboxylic acid

[Chemical Formula 171]

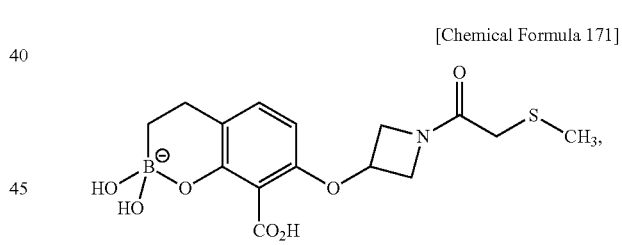

2-hydroxy-7-{[1-(1H-1,2,4-triazole-3-carbonyl)azetidin-3-yl]oxy}-3,4-dihydro-2H-1,2-benzoxaborinine-8-carboxylic acid

[Chemical Formula 172]

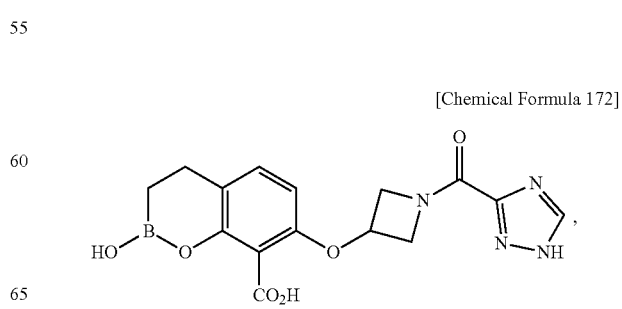

4,4-dihydroxy-8-{[1-(1H-1,2,4-triazole-3-carbonyl)azetidin-3-yl]oxy}-5-oxa-4-boranuidabicyclo[4.4.0]deca-1(6),7,9-triene-7-carboxylic acid 8-({1-[(2R)-2-amino-2-phenylacetyl]azetidin-3-yl}oxy)-4,4-dihydroxy-5-oxa-4-boranuidabicyclo[4.4.0]deca-1(6),7,9-triene-7-carboxylic acid

[Chemical Formula 173]

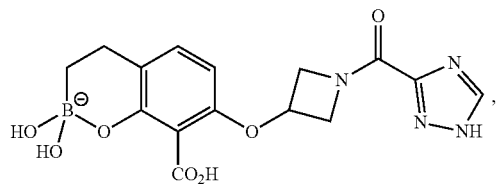

[Chemical Formula 177]

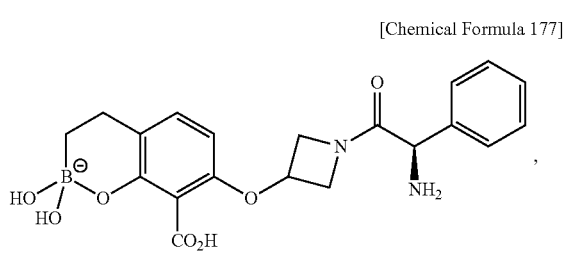 [SMILES: N[C@@H](C(=O)N1CC(Oc2ccc3c(c2C(=O)O)O[B-](O)(O)CC3)C1)c1ccccc1]

2-hydroxy-7-{[1-(1-oxido-2-pyridinylcarbonyl)azetidin-3-yl]oxy}-3,4-dihydro-2H-1,2-benzoxaborinine-8-carboxylic acid 7-[(1-benzoylazetidin-3-yl)oxy]-2-hydroxy-3,4-dihydro-2H-1,2-benzoxaborinine-8-carboxylic acid

[Chemical Formula 174]

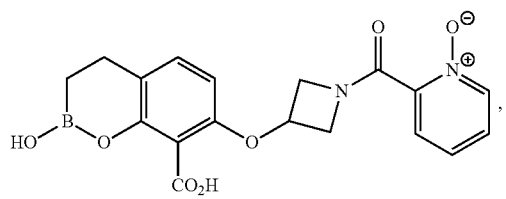

[Chemical Formula 178]

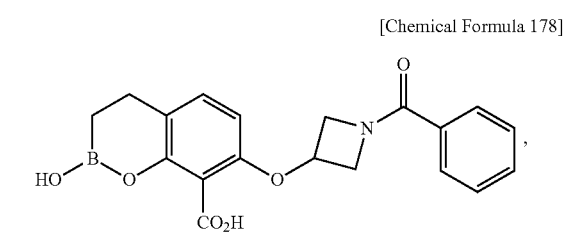 [SMILES: O=C(O)c1c(OC2CN(C(=O)c3ccccc3)C2)ccc2c1OB(O)CC2]

4,4-dihydroxy-8-{[1-(1-oxido-2-pyridinylcarbonyl)azetidin-3-yl]oxy}-5-oxa-4-boranuidabicyclo[4.4.0]deca-1(6),7,9-triene-7-carboxylic acid 8-[(1-benzoylazetidin-3-yl)oxy]-4,4-dihydroxy-5-oxa-4-boranuidabicyclo[4.4.0]deca-1(6),7,9-triene-7-carboxylic acid

[Chemical Formula 175]

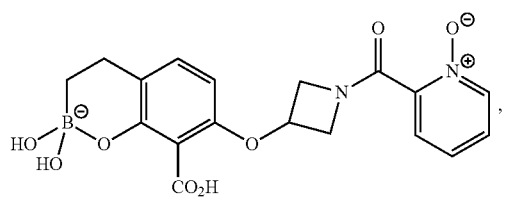

[Chemical Formula 179]

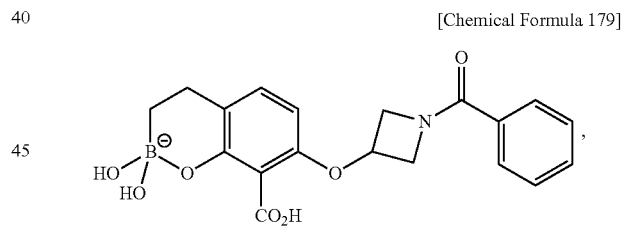

7-({1-[(2R)-2-amino-2-phenylacetyl]azetidin-3-yl}oxy)-2-hydroxy-3,4-dihydro-2H-1,2-benzoxaborinine-8-carboxylic acid 2-hydroxy-7-{[1-(pyridine-3-carbonyl)azetidin-3-yl]oxy}-3,4-dihydro-2H-1,2-benzoxaborinine-8-carboxylic acid

[Chemical Formula 176]

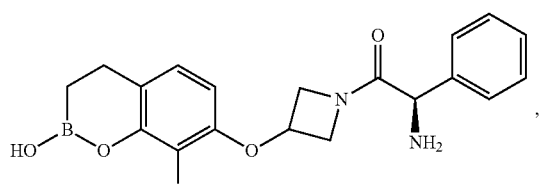

[Chemical Formula 180]

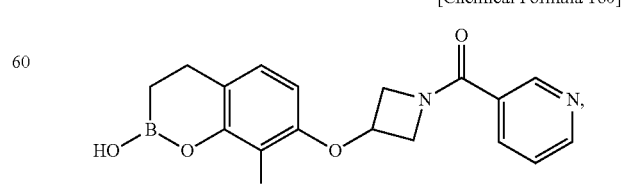

4,4-dihydroxy-8-{[1-(pyridine-3-carbonyl)azetidin-3-yl]
oxy}-5-oxa-4-boranuidabicyclo[4.4.0]deca-1(6),7,9-
triene-7-carboxylic acid

[Chemical Formula 181]

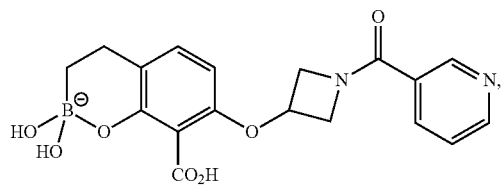

2-hydroxy-7-({1-[(pyridin-2-yl)acetyl]azetidin-3-yl}oxy)-
3,4-dihydro-2H-1,2-benzoxaborinine-8-carboxylic acid

[Chemical Formula 182]

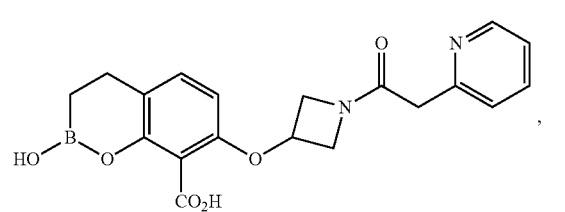

4,4-dihydroxy-8-({1-[(pyridin-2-yl)acetyl]azetidin-3-
yl}oxy)-5-oxa-4-boranuidabicyclo[4.4.0]deca-1(6),7,9-
triene-7-carboxylic acid

[Chemical Formula 183]

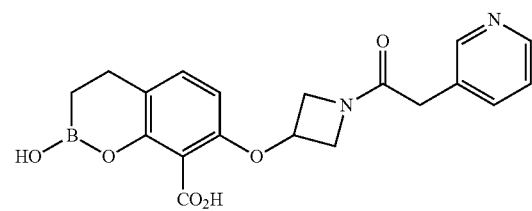

2-hydroxy-7-({1-[(pyridin-3-yl)acetyl]azetidin-3-yl}oxy)-
3,4-dihydro-2H-1,2-benzoxaborinine-8-carboxylic acid

[Chemical Formula 184]

4,4-dihydroxy-8-({1-[(pyridin-3-yl)acetyl]azetidin-3-
yl}oxy)-5-oxa-4-boranuidabicyclo[4.4.0]deca-1(6),7,9-
triene-7-carboxylic acid

[Chemical Formula 185]

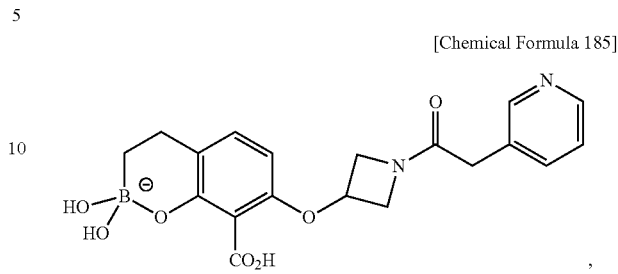

7-({1-[(2S)-2-amino-2-phenylacetyl]azetidin-3-yl}oxy)-2-
hydroxy-3,4-dihydro-2H-1,2-benzoxaborinine-8-carbox-
ylic acid

[Chemical Formula 186]

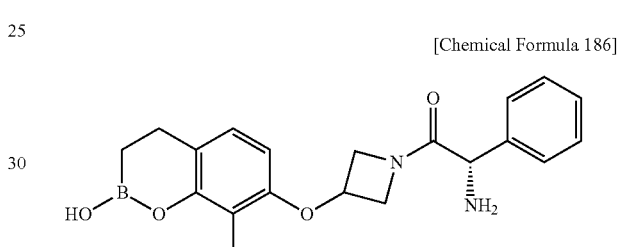

8-({1-[(2S)-2-amino-2-phenylacetyl]azetidin-3-yl}oxy)-4,
4-dihydroxy-5-oxa-4-boranuidabicyclo[4.4.0]deca-1(6),7,
9-triene-7-carboxylic acid

[Chemical Formula 187]

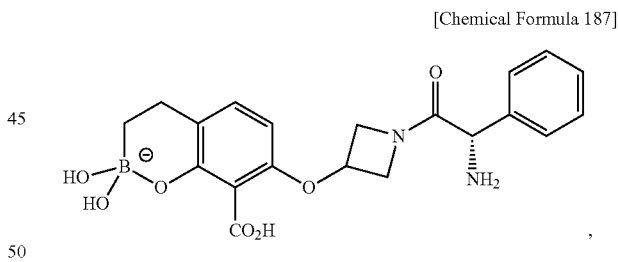

2-hydroxy-7-({1-[(pyridin-4-yl)acetyl]azetidin-3-yl}oxy)-
3,4-dihydro-2H-1,2-benzoxaborinine-8-carboxylic acid

[Chemical Formula 188]

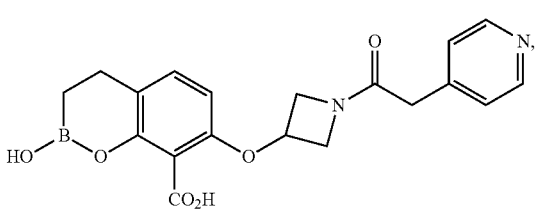

4,4-dihydroxy-8-({1-[(pyridin-4-yl)acetyl]azetidin-3-yl}oxy)-5-oxa-4-boranuidabicyclo[4.4.0]deca-1(6),7,9-triene-7-carboxylic acid

[Chemical Formula 189]

2-hydroxy-7-({1-[(4-hydroxyphenyl)acetyl]azetidin-3-yl}oxy)-3,4-dihydro-2H-1,2-benzoxaborinine-8-carboxylic acid

[Chemical Formula 190]

4,4-dihydroxy-8-({1-[(4-hydroxyphenyl)acetyl]azetidin-3-yl}oxy)-5-oxa-4-boranuidabicyclo[4.4.0]deca-1(6),7,9-triene-7-carboxylic acid

[Chemical Formula 191]

2-hydroxy-7-({1-[(1H-1,2,4-triazol-1-yl)acetyl]azetidin-3-yl}oxy)-3,4-dihydro-2H-1,2-benzoxaborinine-8-carboxylic acid

[Chemical Formula 192]

4,4-dihydroxy-8-({1-[(1H-1,2,4-triazol-1-yl)acetyl]azetidin-3-yl}oxy)-5-oxa-4-boranuidabicyclo[4.4.0]deca-1(6),7,9-triene-7-carboxylic acid

[Chemical Formula 193]

7-({1-[amino(1H-imidazol-5-yl)acetyl]azetidin-3-yl}oxy)-2-hydroxy-3,4-dihydro-2H-1,2-benzoxaborinine-8-carboxylic acid

[Chemical Formula 194]

8-({1-[amino(1H-imidazol-5-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 195]

2-hydroxy-7-{[1-(phenylacetyl)azetidin-3-yl]oxy}-3,4-dihydro-2H-1,2-benzoxaborinine-8-carboxylic acid

[Chemical Formula 196]

77

4,4-dihydroxy-8-{[1-(phenylacetyl)azetidin-3-yl]oxy}-5-oxa-4-boranuidabicyclo[4.4.0]deca-1(6),7,9-triene-7-carboxylic acid

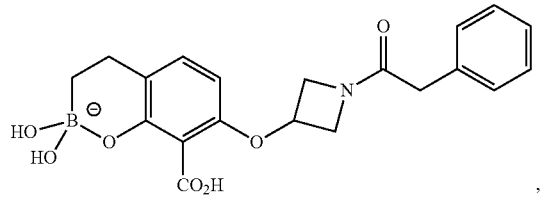

2-hydroxy-7-{[1-(3-phenylpropanoyl)azetidin-3-yl]oxy}-3,4-dihydro-2H-1,2-benzoxaborinine-8-carboxylic acid

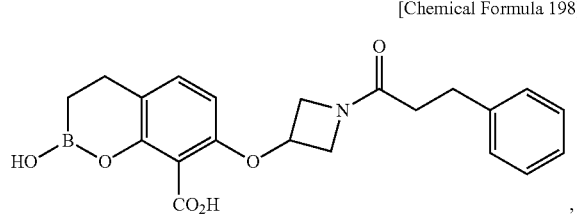

4,4-dihydroxy-8-{[1-(3-phenylpropanoyl)azetidin-3-yl]oxy}-5-oxa-4-boranuidabicyclo[4.4.0]deca-1(6),7,9-triene-7-carboxylic acid

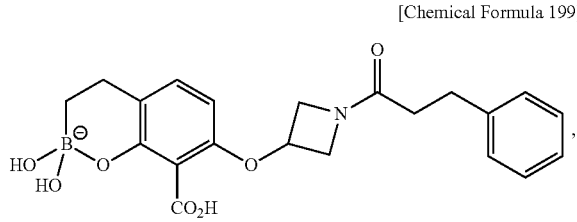 [SMILES: O=C(O)c1c(OC2CN(C(=O)CCc3ccccc3)C2)ccc2c1O[B-](O)(O)CC2]

2-hydroxy-7-({1-[(1H-imidazol-1-yl)acetyl]azetidin-3-yl}oxy)-3,4-dihydro-2H-1,2-benzoxaborinine-8-carboxylic acid

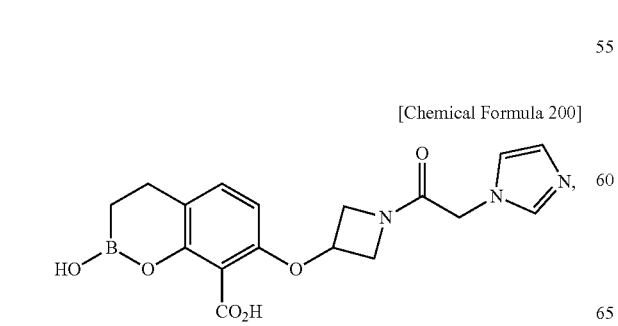

78

4,4-dihydroxy-8-({1-[(1H-imidazol-1-yl)acetyl]azetidin-3-yl}oxy)-5-oxa-4-boranuidabicyclo[4.4.0]deca-1(6),7,9-triene-7-carboxylic acid

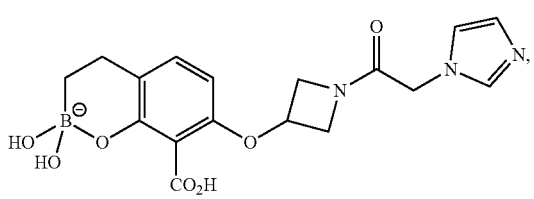

2-hydroxy-7-({1-[(1H-tetrazol-1-yl)acetyl]azetidin-3-yl}oxy)-3,4-dihydro-2H-1,2-benzoxaborinine-8-carboxylic acid 4,4-dihydroxy-8-({1-[(1H-tetrazol-1-yl)acetyl]azetidin-3-yl}oxy)-5-oxa-4-boranuidabicyclo[4.4.0]deca-1(6),7,9-triene-7-carboxylic acid

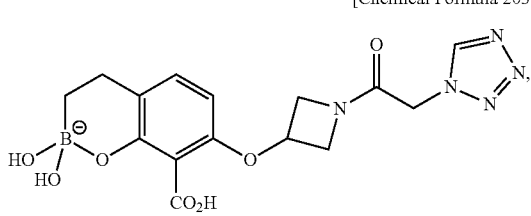

2-hydroxy-7-({1-[(2H-tetrazol-5-yl)acetyl]azetidin-3-yl}oxy)-3,4-dihydro-2H-1,2-benzoxaborinine-8-carboxylic acid

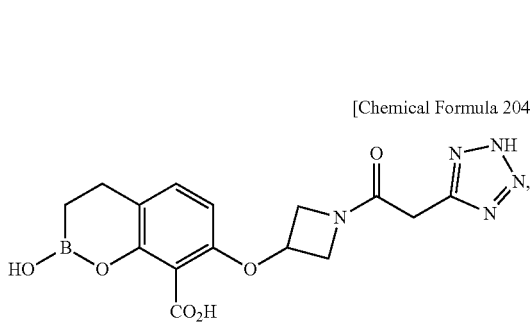 [SMILES: O=C(O)c1c(OC2CN(C(=O)Cc3nn[nH]n3)C2)ccc2c1OB(O)CC2]

4,4-dihydroxy-8-({1-[(2H-tetrazol-5-yl)acetyl]azetidin-3-yl}oxy)-5-oxa-4-boranuidabicyclo[4.4.0]deca-1(6),7,9-triene-7-carboxylic acid

[Chemical Formula 205]

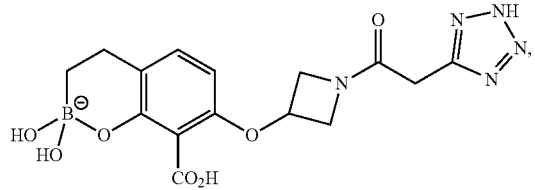

2-hydroxy-7-[(1-D-phenylalanylazetidin-3-yl)oxy]-3,4-dihydro-2H-1,2-benzoxaborinine-8-carboxylic acid

[Chemical Formula 206]

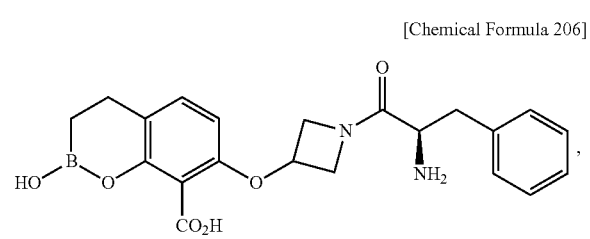 [SMILES: N[C@H](Cc1ccccc1)C(=O)N1CC(Oc2ccc3c(c2C(=O)O)OB(O)CC3)C1]

4,4-dihydroxy-8-[(1-D-phenylalanylazetidin-3-yl)oxy]-5-oxa-4-boranuidabicyclo[4.4.0]deca-1(6),7,9-triene-7-carboxylic acid

[Chemical Formula 207]

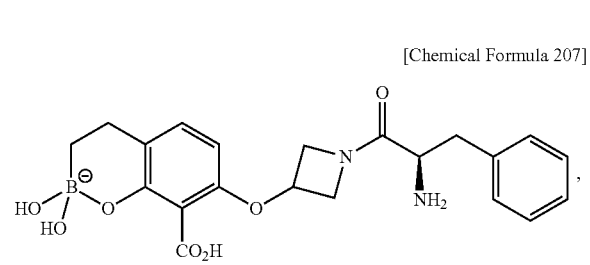 [SMILES: N[C@H](Cc1ccccc1)C(=O)N1CC(Oc2ccc3c(c2C(=O)O)O[B-](O)(O)CC3)C1]

2-hydroxy-7-[(1-D-tyrosylazetidin-3-yl)oxy]-3,4-dihydro-2H-1,2-benzoxaborinine-8-carboxylic acid

[Chemical Formula 208]

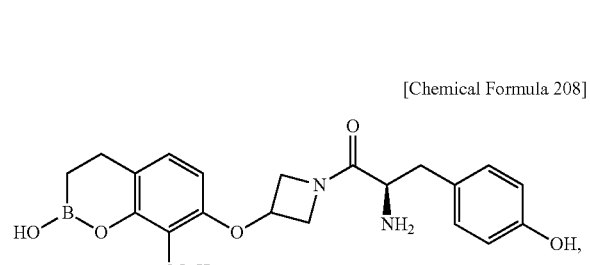

4,4-dihydroxy-8-[(1-D-tyrosylazetidin-3-yl)oxy]-5-oxa-4-boranuidabicyclo[4.4.0]deca-1(6),7,9-triene-7-carboxylic acid

[Chemical Formula 209]

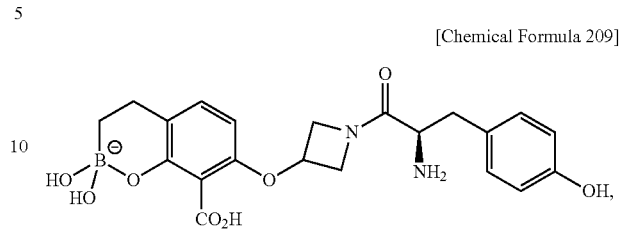

7-[(1-D-histidylazetidin-3-yl)oxy]-2-hydroxy-3,4-dihydro-2H-1,2-benzoxaborinine-8-carboxylic acid

[Chemical Formula 210]

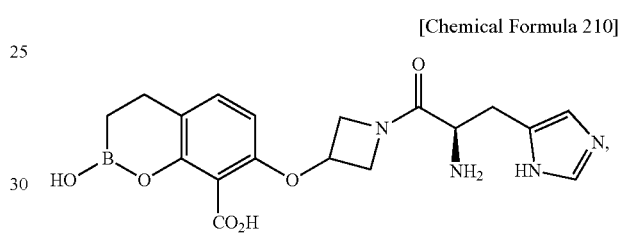

8-[(1-D-histidylazetidin-3-yl)oxy]-4,4-dihydroxy-5-oxa-4-boranuidabicyclo[4.4.0]deca-1(6),7,9-triene-7-carboxylic acid

[Chemical Formula 211]

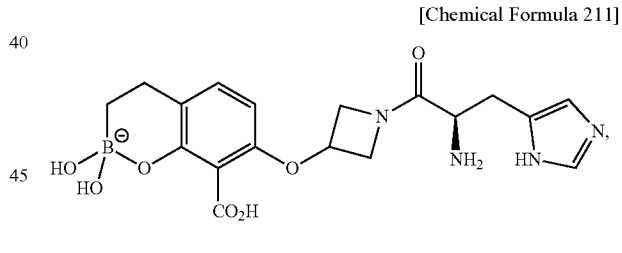

2-hydroxy-7-[(1-D-valylazetidin-3-yl)oxy]-3,4-dihydro-2H-1,2-benzoxaborinine-8-carboxylic acid

[Chemical Formula 212]

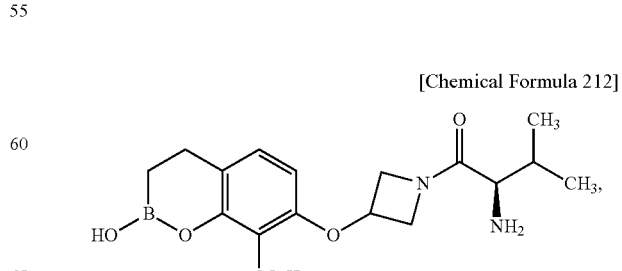

4,4-dihydroxy-8-[(1-D-valylazetidin-3-yl)oxy]-5-oxa-4-bo-
ranuidabicyclo[4.4.0]deca-1(6),7,9-triene-7-carboxylic
acid

[Chemical Formula 213]

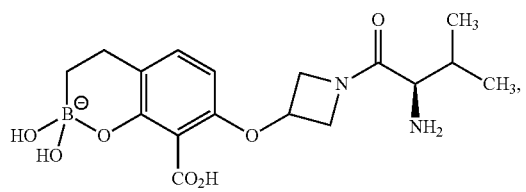

7-[(1-L-histidylazetidin-3-yl)oxy]-2-hydroxy-3,4-dihydro-
2H-1,2-benzoxaborinine-8-carboxylic acid

[Chemical Formula 214]

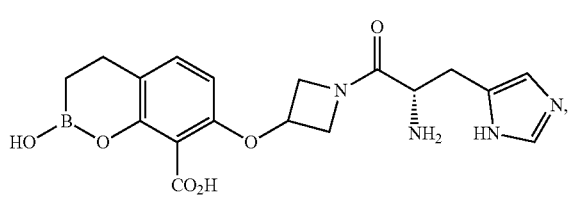

8-[(1-L-histidylazetidin-3-yl)oxy]-4,4-dihydroxy-5-oxa-4-
boranuidabicyclo[4.4.0]deca-1(6),7,9-triene-7-carboxylic
acid

[Chemical Formula 215]

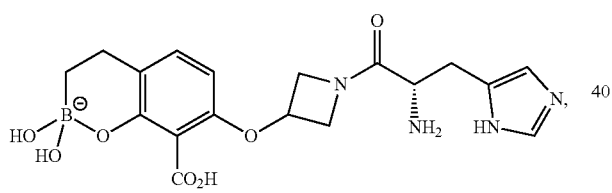

7-[(1-{(2R)-2-[(4-ethyl-2,3-dioxopiperazine-1-carbonyl)
amino]-2-phenylacetyl}azetidin-3-yl)oxy]-2-hydroxy-3,
4-dihydro-2H-1,2-benzoxaborinine-8-carboxylic acid

[Chemical Formula 216]

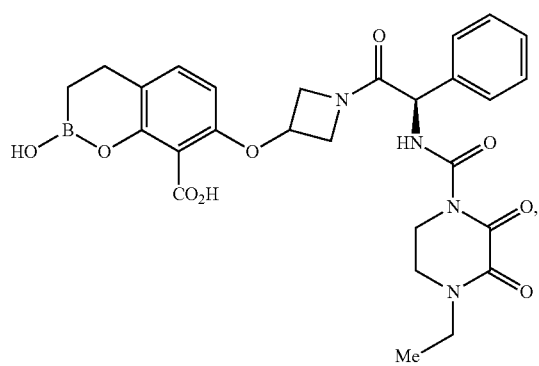

8-[(1-{(2R)-2-[(4-ethyl-2,3-dioxopiperazine-1-carbonyl)
amino]-2-phenylacetyl}azetidin-3-yl)oxy]-4,4-dihy-
droxy-5-oxa-4-boranuidabicyclo[4.4.0]deca-1(6),7,9-
triene-7-carboxylic acid

[Chemical Formula 217]

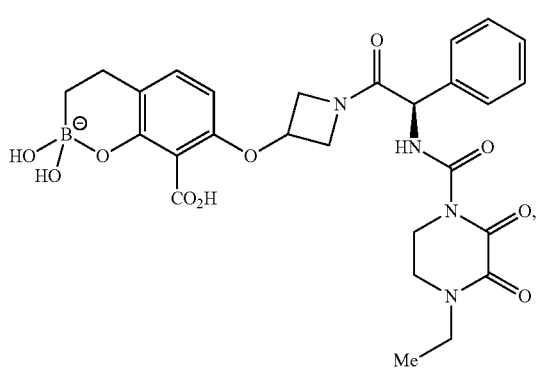

2-hydroxy-7-[(1-D-prolylazetidin-3-yl)oxy]-3,4-dihydro-
2H-1,2-benzoxaborinine-8-carboxylic acid

[Chemical Formula 218]

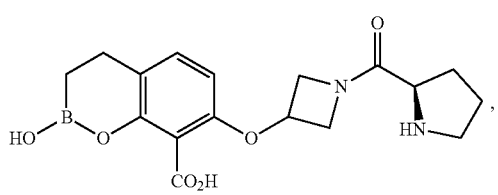

4,4-dihydroxy-8-[(1-D-prolylazetidin-3-yl)oxy]-5-oxa-4-
boranuidabicyclo[4.4.0]deca-1(6),7,9-triene-7-carboxylic
acid

[Chemical Formula 219]

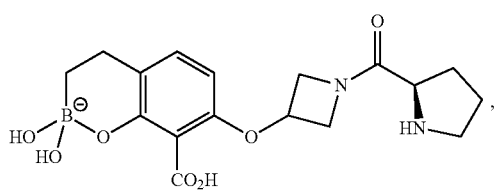

2-hydroxy-7-[(1-L-prolylazetidin-3-yl)oxy]-3,4-dihydro-
2H-1,2-benzoxaborinine-8-carboxylic acid

[Chemical Formula 220]

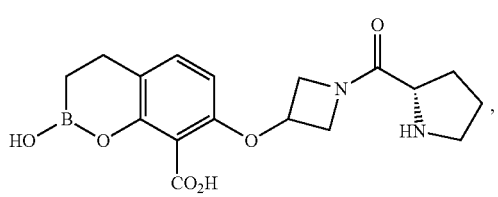

83

4,4-dihydroxy-8-[(1-L-prolylazetidin-3-yl)oxy]-5-oxa-4-boranuidabicyclo[4.4.0]deca-l(6),7,9-triene-7-carboxylic acid

[Chemical Formula 221]

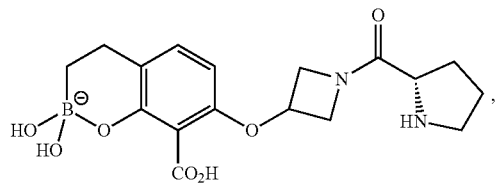

7-[(1-{[4-(2-aminoethyl)-1H-imidazol-1-yl]acetyl}azetidin-3-yl)oxy]-2-hydroxy-3,4-dihydro-2H-1,2-benzoxaborinine-8-carboxylic acid

[Chemical Formula 222]

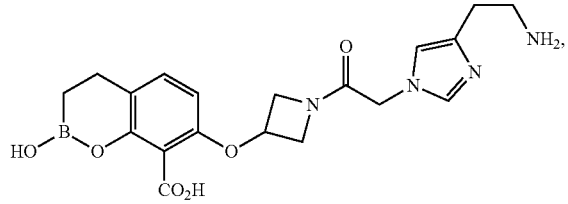

8-[(1-{[4-(2-aminoethyl)-1H-imidazol-1-yl]acetyl}azetidin-3-yl)oxy]-4,4-dihydroxy-5-oxa-4-boranuidabicyclo[4.4.0]deca-l(6),7,9-triene-7-carboxylic acid

[Chemical Formula 223]

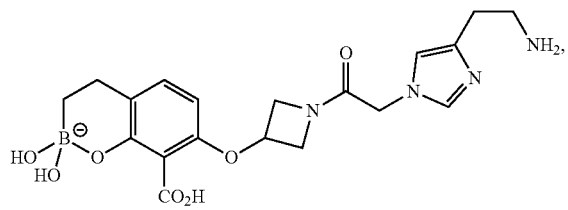

7-{[1-(3,4-dihydroxybenzoyl)azetidin-3-yl]oxy}-2-hydroxy-3,4-dihydro-2H-1,2-benzoxaborinine-8-carboxylic acid

[Chemical Formula 224]

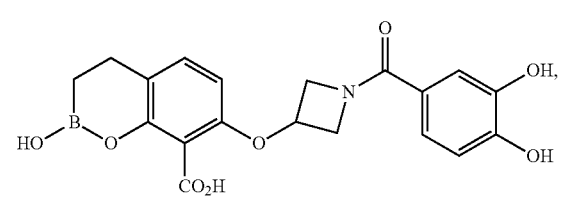

84

8-{[1-(3,4-dihydroxybenzoyl)azetidin-3-yl]oxy}-4,4-dihydroxy-5-oxa-4-boranuidabicyclo[4.4.0]deca-l(6),7,9-triene-7-carboxylic acid

[Chemical Formula 225]

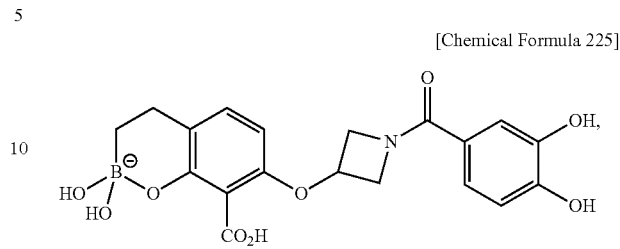

2-hydroxy-7-{[1-(hydroxycarbamoyl)azetidin-3-yl]oxy}-3,4-dihydro-2H-1,2-benzoxaborinine-8-carboxylic acid

[Chemical Formula 226]

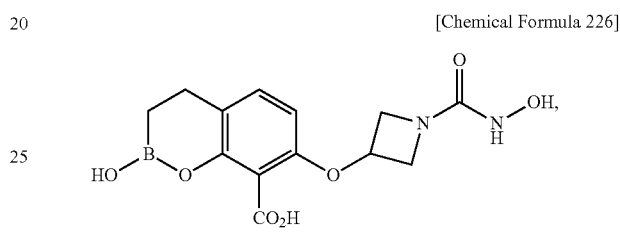

4,4-dihydroxy-8-{[1-(hydroxycarbamoyl)azetidin-3-yl]oxy}-5-oxa-4-boranuidabicyclo[4.4.0]deca-l(6),7,9-triene-7-carboxylic acid

[Chemical Formula 227]

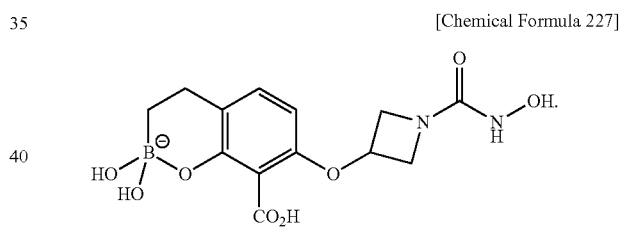

[Item 54]

The compound or the pharmaceutically acceptable salt thereof of item 1, represented by the following compound name or structural formula:

7-({1-[(2R)-2-amino-2-(1H-imidazol-4-yl)acetyl]azetidin-3-yl}oxy)-2-hydroxy-3,4-dihydro-2H-1,2-benzoxaborinine-8-carboxylic acid

[Chemical Formula 228]

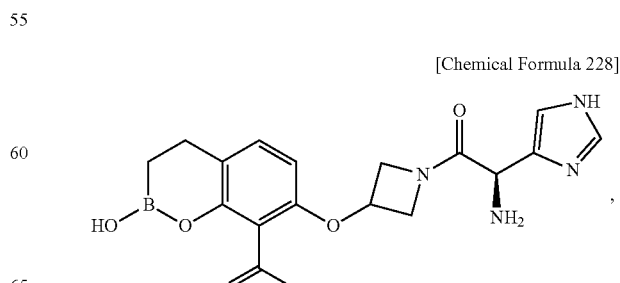

85

8-({1-[(2R)-2-amino-2-(1H-imidazol-4-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 229]

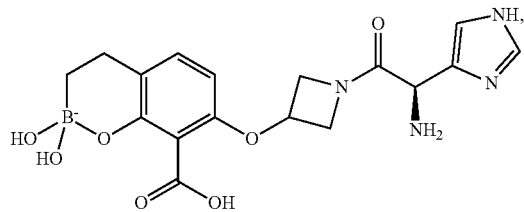

7-({1-[(2S)-2-amino-2-(1H-imidazol-4-yl)acetyl]azetidin-3-yl}oxy)-2-hydroxy-3,4-dihydro-2H-1,2-benzoxaborinine-8-carboxylic acid

[Chemical Formula 230]

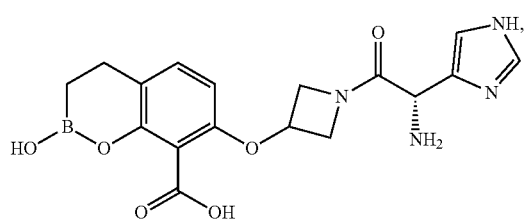

8-({1-[(2S)-2-amino-2-(1H-imidazol-4-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 231]

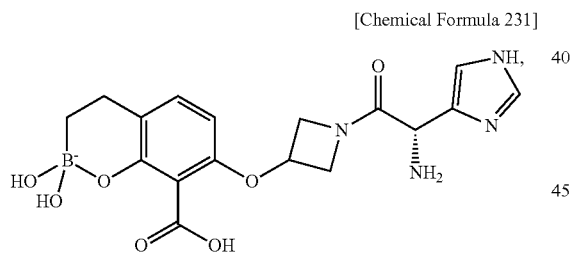

7-({1-[amino(1-methyl-1H-imidazol-4-yl)acetyl]azetidin-3-yl}oxy)-2-hydroxy-3,4-dihydro-2H-1,2-benzoxaborinine-8-carboxylic acid

[Chemical Formula 232]

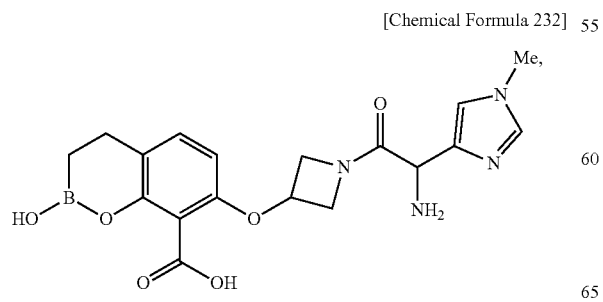

86

8-({1-[amino(1-methyl-1H-imidazol-4-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 233]

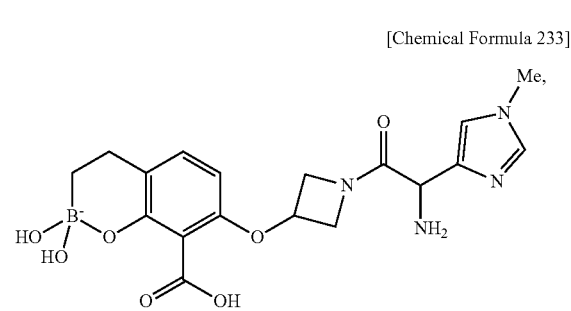 [SMILES: Cn1cnc(C(N)C(=O)N2CC(Oc3ccc4c(c3C(=O)O)O[B-](O)(O)CC4)C2)c1]

2-hydroxy-7-{[1-(4H-1,2,4-triazole-3-sulfonyl)azetidin-3-yl]oxy}-3,4-dihydro-2H-1,2-benzoxaborinine-8-carboxylic acid

[Chemical Formula 234]

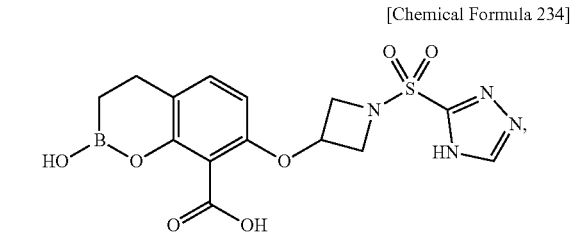 [SMILES: O=C(O)c1c(OC2CN(S(=O)(=O)c3nnc[nH]3)C2)ccc2c1OB(O)CC2]

4,4-dihydroxy-8-{[1-(4H-1,2,4-triazole-3-sulfonyl)azetidin-3-yl]oxy}-5-oxa-4-boranuidabicyclo[4.4.0]deca-1(6),7,9-triene-7-carboxylic acid

[Chemical Formula 235]

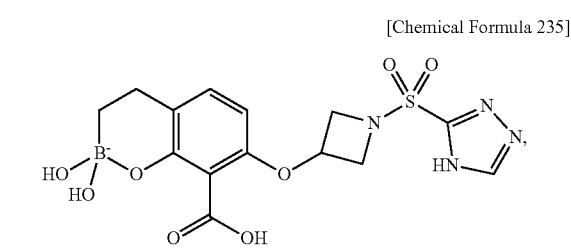 [SMILES: O=C(O)c1c(OC2CN(S(=O)(=O)c3nnc[nH]3)C2)ccc2c1O[B-](O)(O)CC2]

7-({1-[2-amino-2-(1H-imidazol-4-yl)($^{2}$H)ethanoyl]azetidin-3-yl}oxy)-2-hydroxy-3,4-dihydro-2H-1,2-benzoxaborinine-8-carboxylic acid

[Chemical Formula 236]

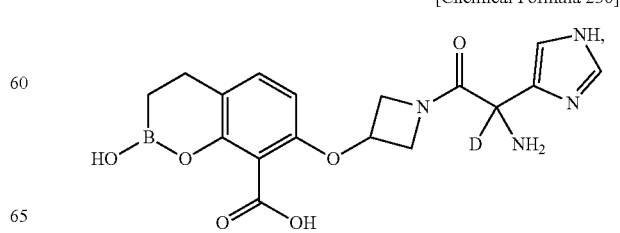

8-({1-[2-amino-2-(1H-imidazol-4-yl)(²H)ethanoyl]azeti-
din-3-yl}oxy)-4,4-dihydroxy-5-oxa-4-boranuidabicyclo
[4.4.0]deca-1(6),7,9-triene-7-carboxylic acid

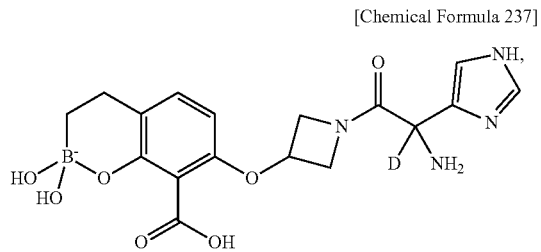 [SMILES: [2H]C(N)(C(=O)N1CC(Oc2ccc3c(c2C(=O)O)O[B-](O)(O)CC3)C1)c1c[nH]cn1]

7-({1-[2-amino-2-(1H-imidazol-4-yl)propanoyl]azetidin-3-
yl}oxy)-2-hydroxy-3,4-dihydro-2H-1,2-benzoxabori-
nine-8-carboxylic acid

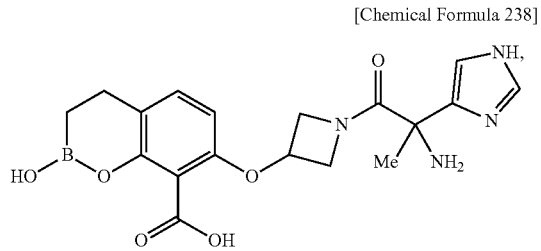 [SMILES: CC(N)(C(=O)N1CC(Oc2ccc3c(c2C(=O)O)OB(O)CC3)C1)c1c[nH]cn1]

8-({1-[2-amino-2-(1H-imidazol-4-yl)propanoyl]azetidin-3-
yl}oxy)-4,4-dihydroxy-5-oxa-4-boranuidabicyclo[4.4.0]
deca-1(6),7,9-triene-7-carboxylic acid

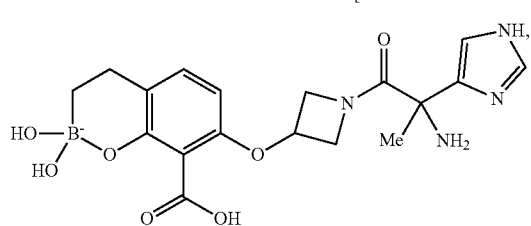

7-({(3S)-1-[amino(1H-imidazol-4-yl)acetyl]pyrrolidin-3-
yl}oxy)-2-hydroxy-3,4-dihydro-2H-1,2-benzoxabori-
nine-8-carboxylic acid

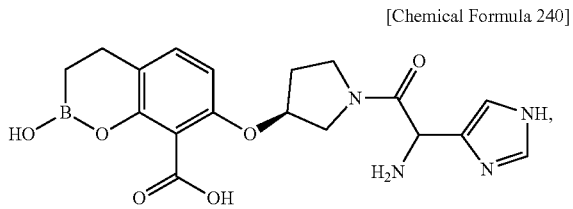 [SMILES: NC(C(=O)N1CC[C@H](Oc2ccc3c(c2C(=O)O)OB(O)CC3)C1)c1c[nH]cn1]

8-({(3S)-1-[amino(1H-imidazol-4-yl)acetyl]pyrrolidin-3-
yl}oxy)-4,4-dihydroxy-5-oxa-4-boranuidabicyclo[4.4.0]
deca-1(6),7,9-triene-7-carboxylic acid

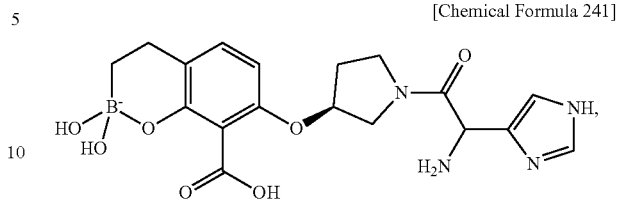

2-hydroxy-7-{[1-(4-hydroxy-6-methylpyridine-3-carbonyl)
azetidin-3-yl]oxy}-3,4-dihydro-2H-1,2-benzoxaborinine-
8-carboxylic acid

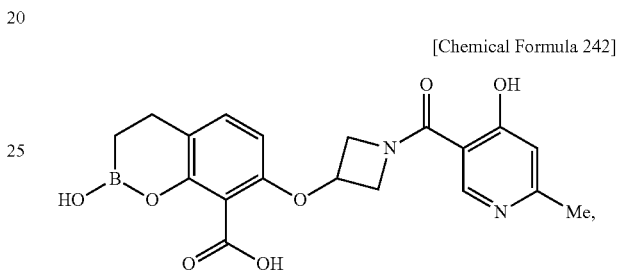

4,4-dihydroxy-8-{[1-(4-hydroxy-6-methylpyridine-3-carbo-
nyl)azetidin-3-yl]oxy}-5-oxa-4-boranuidabicyclo[4.4.0]
deca-1(6),7,9-triene-7-carboxylic acid

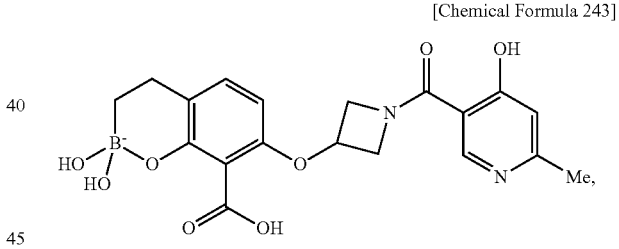

7-({1-[amino(1-methyl-1H-imidazol-5-yl)acetyl]azetidin-3-
yl}oxy)-2-hydroxy-3,4-dihydro-2H-1,2-benzoxabori-
nine-8-carboxylic acid

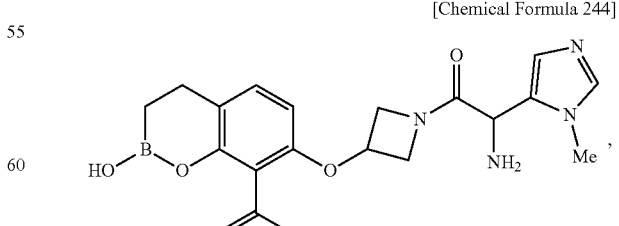

8-({1-[amino(1-methyl-1H-imidazol-5-yl)acetyl]azetidin-3-
yl}oxy)-4,4-dihydroxy-5-oxa-4-boranuidabicyclo[4.4.0]
deca-1(6),7,9-triene-7-carboxylic acid

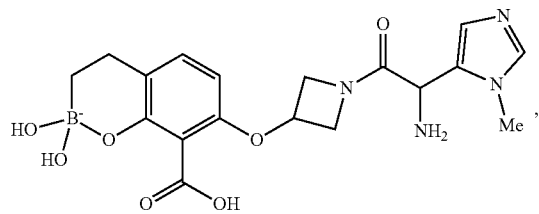

7-[(1-{amino[1-(carboxymethyl)-1H-imidazol-4-yl]
acetyl}azetidin-3-yl)oxy]-2-hydroxy-3,4-dihydro-2H-1,
2-benzoxaborinine-8-carboxylic acid

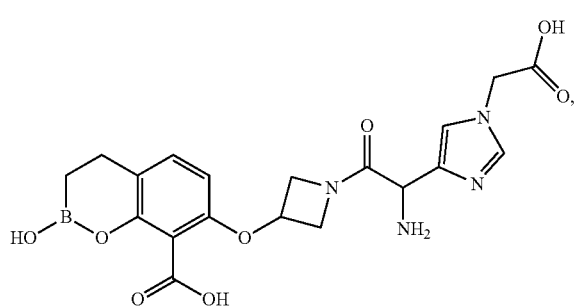

8-[(1-{amino[1-(carboxymethyl)-1H-imidazol-4-yl]
acetyl}azetidin-3-yl)oxy]-4,4-dihydroxy-5-oxa-4-bo-
ranuidabicyclo[4.4.0]deca-1(6),7,9-triene-7-carboxylic
acid

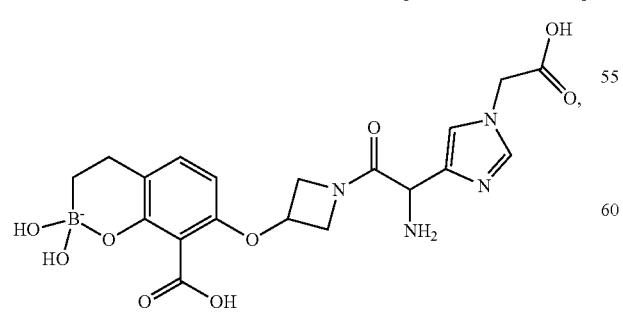

7-[(1-{amino[1-(2-amino-2-oxoethyl)-1H-imidazol-4-yl]
acetyl}azetidin-3-yl)oxy]-2-hydroxy-3,4-dihydro-2H-1,
2-benzoxaborinine-8-carboxylic acid

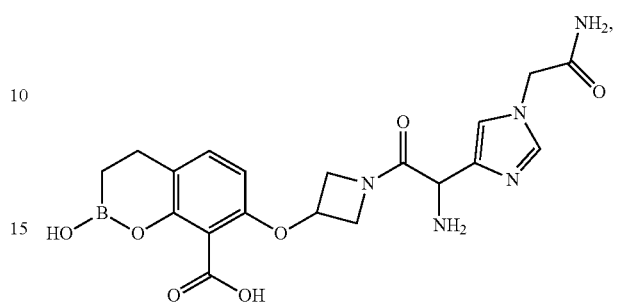

8-[(1-{amino[1-(2-amino-2-oxoethyl)-1H-imidazol-4-yl]
acetyl}azetidin-3-yl)oxy]-4,4-dihydroxy-5-oxa-4-bo-
ranuidabicyclo[4.4.0]deca-1(6),7,9-triene-7-carboxylic
acid

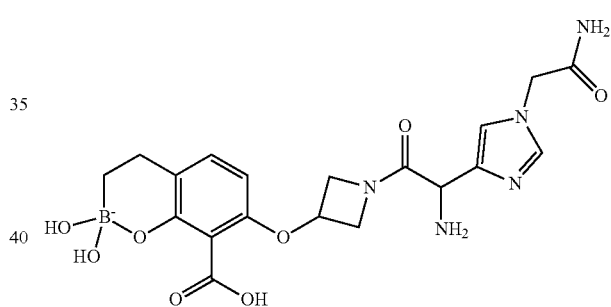

7-({1-[amino(pyridin-3-yl)acetyl]azetidin-3-yl}oxy)-2-hy-
droxy-3,4-dihydro-2H-1,2-benzoxaborinine-8-carboxylic
acid

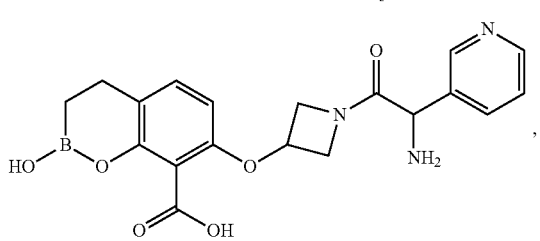

8-({1-[amino(pyridin-3-yl)acetyl]azetidin-3-yl}oxy)-4,4-dihydroxy-5-oxa-4-boranuidabicyclo[4.4.0]deca-1(6),7,9-triene-7-carboxylic acid 8-({(3R)-1-[amino (1H-imidazol-4-yl)acetyl]pyrrolidin-3-yl}oxy)-4,4-dihydroxy-5-oxa-4-boranuidabicyclo[4.4.0]deca-1(6),7,9-triene-7-carboxylic acid

[Chemical Formula 251]

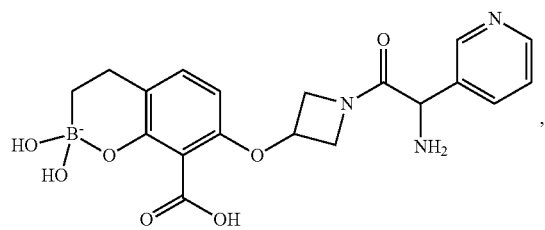

[Chemical Formula 255]

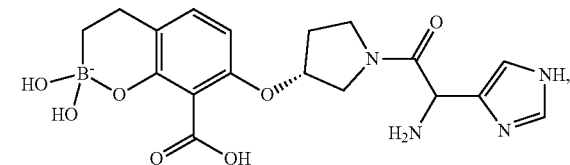

7-({1-[amino(1-methyl-1H-pyrazol-4-yl)acetyl]azetidin-3-yl}oxy)-2-hydroxy-3,4-dihydro-2H-1,2-benzoxaborinine-8-carboxylic acid 7-({1-[amino(2-methyl-1H-imidazol-4-yl)acetyl]azetidin-3-yl}oxy)-2-hydroxy-3,4-dihydro-2H-1,2-benzoxaborinine-8-carboxylic acid

[Chemical Formula 252]

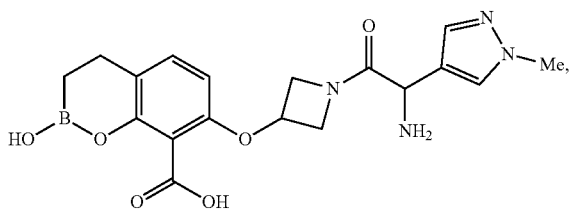

[Chemical Formula 256]

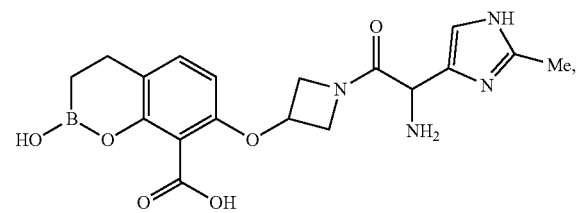

8-({1-[amino(1-methyl-1H-pyrazol-4-yl)acetyl]azetidin-3-yl}oxy)-4,4-dihydroxy-5-oxa-4-boranuidabicyclo[4.4.0]deca-1(6),7,9-triene-7-carboxylic acid 8-({1-[amino(2-methyl-1H-imidazol-4-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 253]

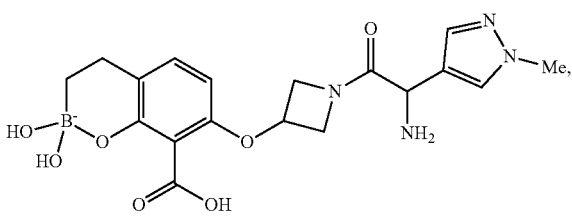

[Chemical Formula 257]

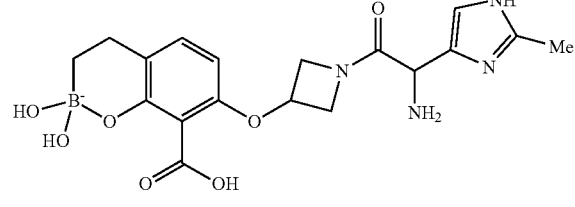

7-({(3R)-1-[amino(1H-imidazol-4-yl)acetyl]pyrrolidin-3-yl}oxy)-2-hydroxy-3,4-dihydro-2H-1,2-benzoxaborinine-8-carboxylic acid 7-({1-[amino(1,3-thiazol-4-yl)acetyl]azetidin-3-yl}oxy)-2-hydroxy-3,4-dihydro-2H-1,2-benzoxaborinine-8-carboxylic acid

[Chemical Formula 254]

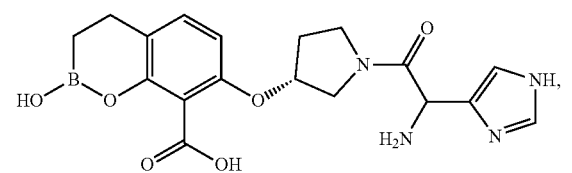

[Chemical Formula 258]

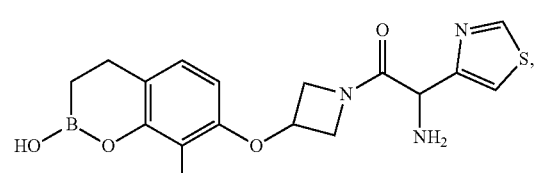

8-({1-[amino(1,3-thiazol-4-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 259]

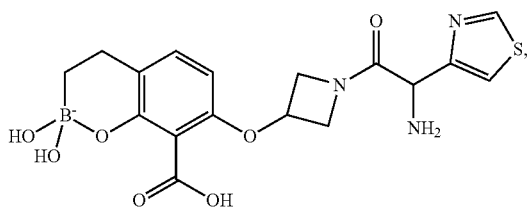

2-hydroxy-7-{[1-(1H-imidazole-4-sulfonyl)azetidin-3-yl]oxy}-3,4-dihydro-2H-1,2-benzoxaborinine-8-carboxylic acid

[Chemical Formula 260]

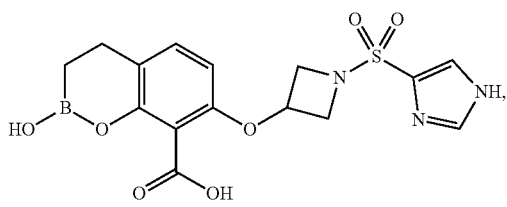

4,4-dihydroxy-8-{[1-(1H-imidazole-4-sulfonyl)azetidin-3-yl]oxy}-5-oxa-4-boranuidabicyclo[4.4.0]deca-1(6),7,9-triene-7-carboxylic acid

[Chemical Formula 261]

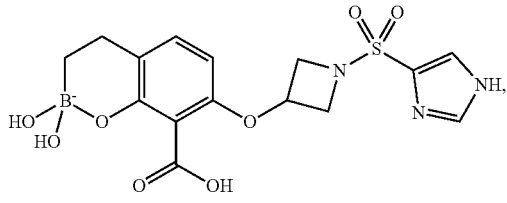

2-hydroxy-7-{[1-(pyridine-3-sulfonyl)azetidin-3-yl]oxy}-3,4-dihydro-2H-1,2-benzoxaborinine-8-carboxylic acid

[Chemical Formula 262]

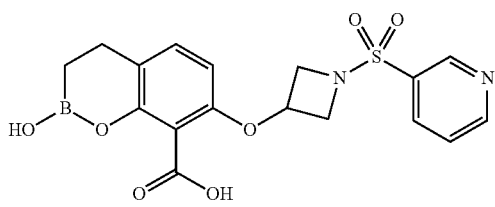

4,4-dihydroxy-8-{[1-(pyridine-3-sulfonyl)azetidin-3-yl]oxy}-5-oxa-4-boranuidabicyclo[4.4.0]deca-1(6),7,9-triene-7-carboxylic acid

[Chemical Formula 263]

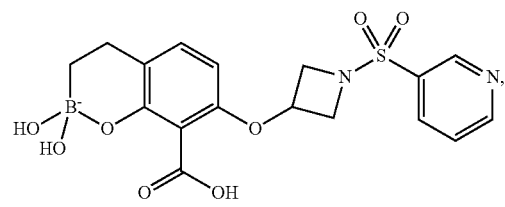

2-hydroxy-7-{[1-(1-oxo-1λ⁵-pyridine-2-sulfonyl)azetidin-3-yl]oxy}-3,4-dihydro-2H-1,2-benzoxaborinine-8-carboxylic acid

[Chemical Formula 264]

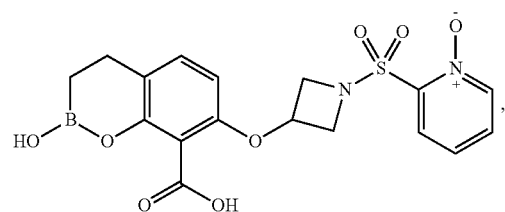

4,4-dihydroxy-8-{[1-(1-oxo-1λ⁵-pyridine-2-sulfonyl)azetidin-3-yl]oxy}-5-oxa-4-boranuidabicyclo[4.4.0]deca-1(6),7,9-triene-7-carboxylic acid

[Chemical Formula 265]

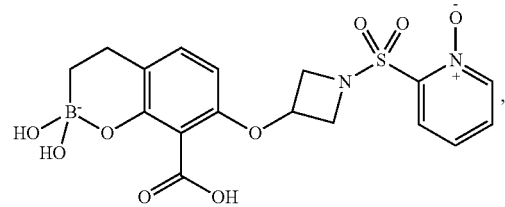

7-({1-[(2-amino-1,3-thiazol-4-yl)acetyl]azetidin-3-yl}oxy)-2-hydroxy-3,4-dihydro-2H-1,2-benzoxaborinine-8-carboxylic acid

[Chemical Formula 266]

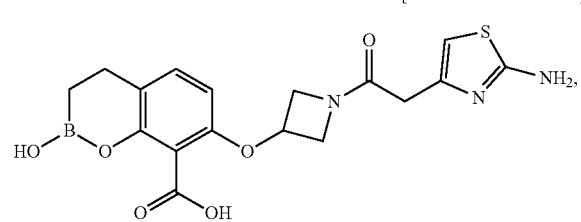

8-({1-[(2-amino-1,3-thiazol-4-yl)acetyl]azetidin-3-yl}oxy)-4,4-dihydroxy-5-oxa-4-boranuidabicyclo[4.4.0]deca-l(6),7,9-triene-7-carboxylic acid 4,4-dihydroxy-8-({1-[(1H-1,2,3-triazol-1-yl)acetyl]azetidin-3-yl}oxy)-5-oxa-4-boranuidabicyclo[4.4.0]deca-l(6),7,9-triene-7-carboxylic acid

[Chemical Formula 267]

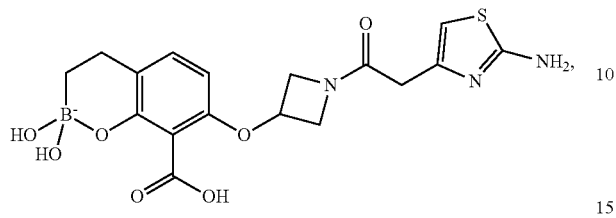

[Chemical Formula 271]

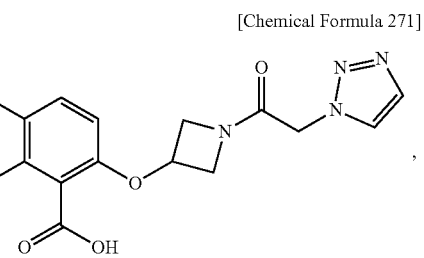

7-{[1-(2-amino-1,3-thiazole-4-carbonyl)azetidin-3-yl]oxy}-2-hydroxy-3,4-dihydro-2H-1,2-benzoxaborinine-8-carboxylic acid 7-[(1-{[1-(2-aminoethyl)-1H-imidazol-4-yl]acetyl}azetidin-3-yl)oxy]-2-hydroxy-3,4-dihydro-2H-1,2-benzoxaborinine-8-carboxylic acid

[Chemical Formula 268]

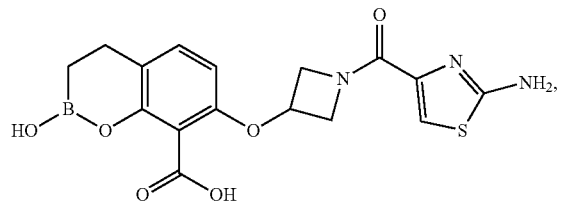

[Chemical Formula 272]

8-{[1-(2-amino-1,3-thiazole-4-carbonyl)azetidin-3-yl]oxy}-4,4-dihydroxy-5-oxa-4-boranuidabicyclo[4.4.0]deca-l(6),7,9-triene-7-carboxylic acid 8-[(1-{[1-(2-aminoethyl)-1H-imidazol-4-yl]acetyl}azetidin-3-yl)oxy]-4,4-dihydroxy-5-oxa-4-boranuidabicyclo[4.4.0]deca-l(6),7,9-triene-7-carboxylic acid

[Chemical Formula 269]

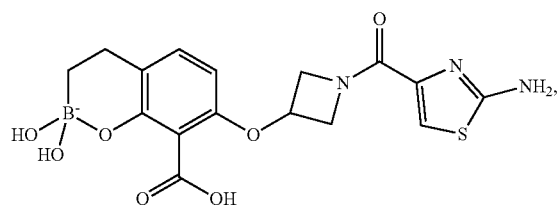

[Chemical Formula 273]

2-hydroxy-7-({1-[(1H-1,2,3-triazol-1-yl)acetyl]azetidin-3-yl}oxy)-3,4-dihydro-2H-1,2-benzoxaborinine-8-carboxylic acid 2-hydroxy-7-{[1-(1H-imidazole-4-carbonyl)azetidin-3-yl]oxy}-3,4-dihydro-2H-1,2-benzoxaborinine-8-carboxylic acid

[Chemical Formula 270]

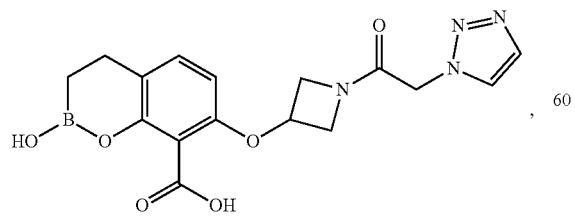

[Chemical Formula 274]

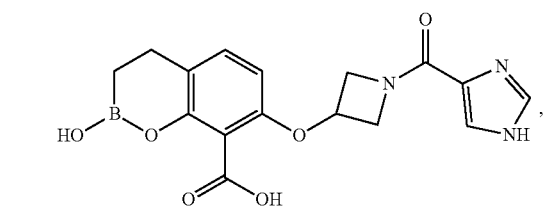

4,4-dihydroxy-8-{[1-(1H-imidazole-4-carbonyl)azetidin-3-yl]oxy}-5-oxa-4-boranuidabicyclo[4.4.0]deca-1(6),7,9-triene-7-carboxylic acid

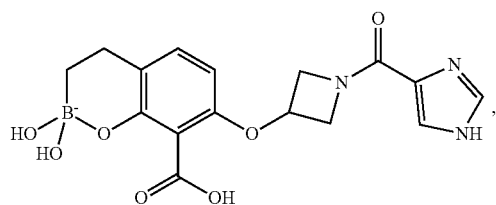

2-hydroxy-7-{[1-(1H-imidazole-2-carbonyl)azetidin-3-yl]oxy}-3,4-dihydro-2H-1,2-benzoxaborinine-8-carboxylic acid

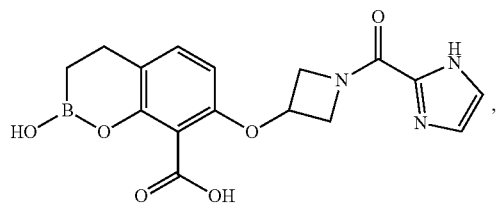

4,4-dihydroxy-8-{[1-(1H-imidazole-2-carbonyl)azetidin-3-yl]oxy}-5-oxa-4-boranuidabicyclo[4.4.0]deca-1(6),7,9-triene-7-carboxylic acid

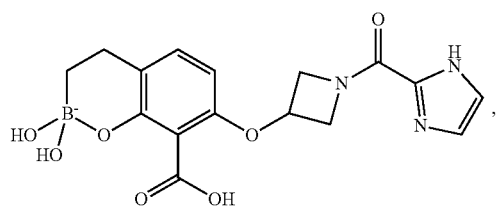

2-hydroxy-7-[(1-{[4-(hydroxymethyl)-1H-1,2,3-triazol-1-yl]acetyl}azetidin-3-yl)oxy]-3,4-dihydro-2H-1,2-benzoxaborinine-8-carboxylic acid 4,4-dihydroxy-8-[(1-{[4-(hydroxymethyl)-1H-1,2,3-triazol-1-yl]acetyl}azetidin-3-yl)oxy]-5-oxa-4-boranuidabicyclo[4.4.0]deca-1(6),7,9-triene-7-carboxylic acid

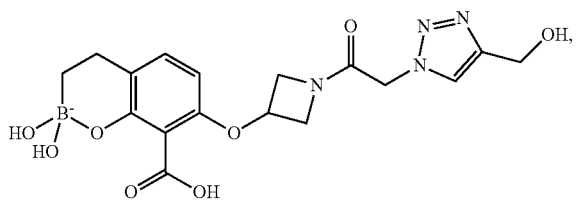

2-hydroxy-7-{[1-({4-[(methylamino)methyl]-1H-1,2,3-triazol-1-yl}acetyl)azetidin-3-yl]oxy}-3,4-dihydro-2H-1,2-benzoxaborinine-8-carboxylic acid

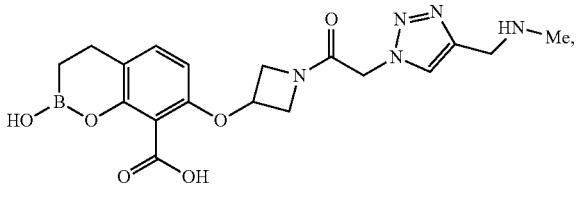

4,4-dihydroxy-8-{[1-({4-[(methylamino)methyl]-1H-1,2,3-triazol-1-yl}acetyl)azetidin-3-yl]oxy}-5-oxa-4-boranuidabicyclo[4.4.0]deca-1(6),7,9-triene-7-carboxylic acid

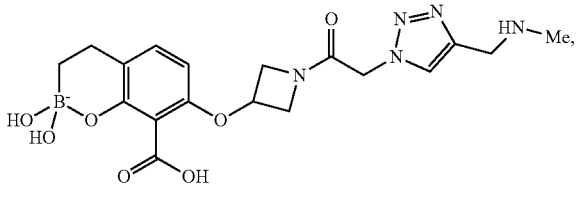

2-hydroxy-7-{[1-({4-[(piperazin-1-yl)methyl]-1H-1,2,3-triazol-1-yl}acetyl)azetidin-3-yl]oxy}-3,4-dihydro-2H-1,2-benzoxaborinine-8-carboxylic acid

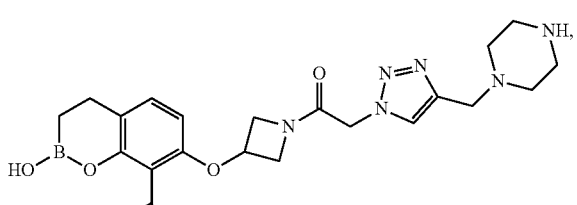

4,4-dihydroxy-8-{[1-({4-[(piperazin-1-yl)methyl]-1H-1,2,3-triazol-1-yl}acetyl)azetidin-3-yl]oxy}-5-oxa-4-boranuidabicyclo[4.4.0]deca-1(6),7,9-triene-7-carboxylic acid

[Chemical Formula 283]

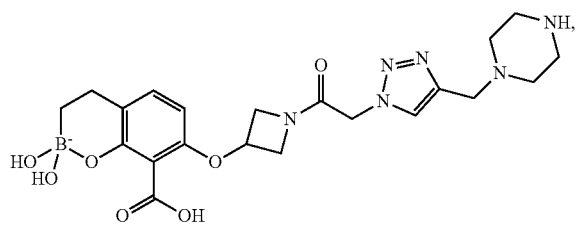

2-hydroxy-7-[(1-{[4-(2-hydroxyethyl)-1H-1,2,3-triazol-1-yl]acetyl}azetidin-3-yl)oxy]-3,4-dihydro-2H-1,2-benzoxaborinine-8-carboxylic acid

[Chemical Formula 284]

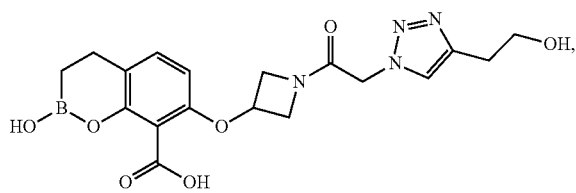

4,4-dihydroxy-8-[(1-{[4-(2-hydroxyethyl)-1H-1,2,3-triazol-1-yl]acetyl}azetidin-3-yl)oxy]-5-oxa-4-boranuidabicyclo[4.4.0]deca-1(6),7,9-triene-7-carboxylic acid

[Chemical Formula 285]

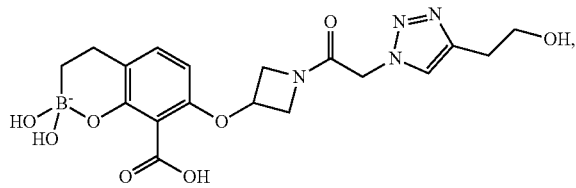

2-hydroxy-7-[(1-{[5-(hydroxymethyl)-1H-1,2,3-triazol-1-yl]acetyl}azetidin-3-yl)oxy]-3,4-dihydro-2H-1,2-benzoxaborinine-8-carboxylic acid

[Chemical Formula 286]

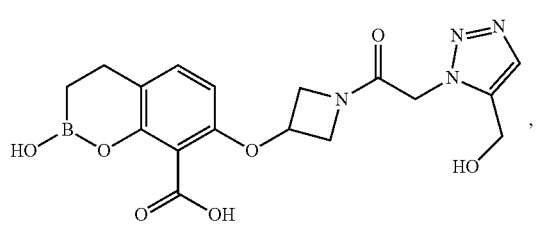

4,4-dihydroxy-8-[(1-{[5-(hydroxymethyl)-1H-1,2,3-triazol-1-yl]acetyl}azetidin-3-yl)oxy]-5-oxa-4-boranuidabicyclo[4.4.0]deca-1(6),7,9-triene-7-carboxylic acid

[Chemical Formula 287]

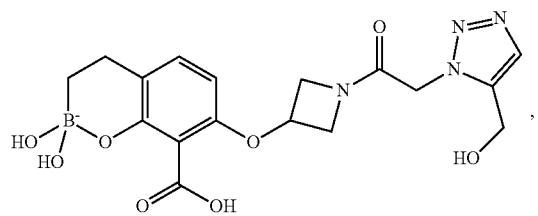

2-hydroxy-7-{[1-({5-[(methylamino)methyl]-1H-1,2,3-triazol-1-yl}acetyl)azetidin-3-yl]oxy}-3,4-dihydro-2H-1,2-benzoxaborinine-8-carboxylic acid

[Chemical Formula 288]

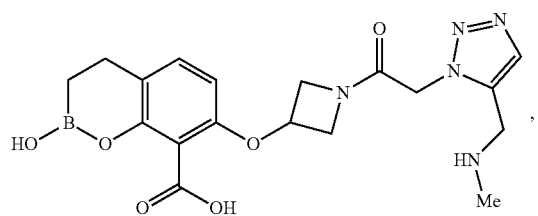

4,4-dihydroxy-8-{[1-({5-[(methylamino)methyl]-1H-1,2,3-triazol-1-yl}acetyl)azetidin-3-yl]oxy}-5-oxa-4-boranuidabicyclo[4.4.0]deca-1(6),7,9-triene-7-carboxylic acid

[Chemical Formula 289]

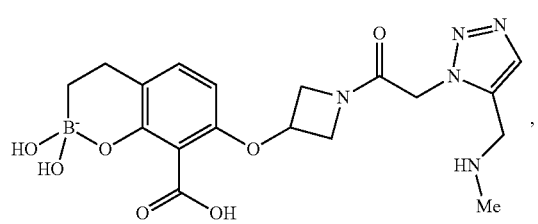

2-hydroxy-7-({1-[(1H-1,2,3-triazol-4-yl)acetyl]azetidin-3-yl}oxy)-3,4-dihydro-2H-1,2-benzoxaborinine-8-carboxylic acid

[Chemical Formula 290]

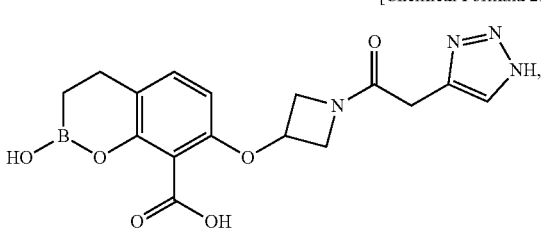

101

4,4-dihydroxy-8-({1-[(1H-1,2,3-triazol-4-yl)acetyl]azetidin-3-yl}oxy)-5-oxa-4-boranuidabicyclo[4.4.0]deca-l(6),7,9-triene-7-carboxylic acid

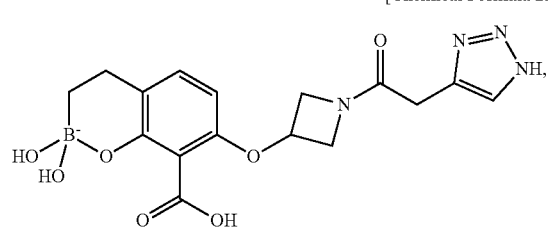

[Chemical Formula 291]

7-[(1-{[4-(carboxymethyl)-1H-1,2,3-triazol-1-yl]acetyl}azetidin-3-yl)oxy]-2-hydroxy-3,4-dihydro-2H-1,2-benzoxaborinine-8-carboxylic acid

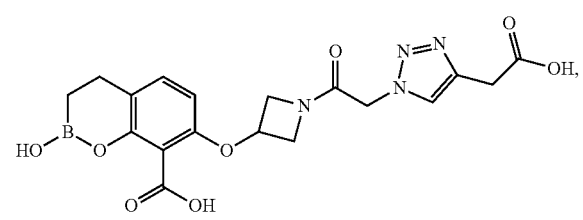

[Chemical Formula 292]

8-[(1-{[4-(carboxymethyl)-1H-1,2,3-triazol-1-yl]acetyl}azetidin-3-yl)oxy]-4,4-dihydroxy-5-oxa-4-boranuidabicyclo[4.4.0]deca-l(6),7,9-triene-7-carboxylic acid

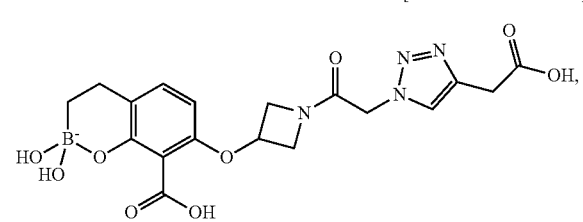

[Chemical Formula 293]

7-[(1-{[1-(carboxymethyl)-1H-1,2,3-triazol-4-yl]acetyl}azetidin-3-yl)oxy]-2-hydroxy-3,4-dihydro-2H-1,2-benzoxaborinine-8-carboxylic acid

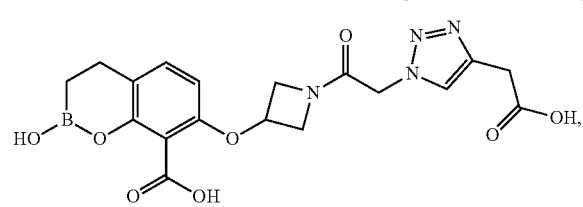

[Chemical Formula 294]

102

8-[(1-{[1-(carboxymethyl)-1H-1,2,3-triazol-4-yl]acetyl}azetidin-3-yl)oxy]-4,4-dihydroxy-5-oxa-4-boranuidabicyclo[4.4.0]deca-l(6),7,9-triene-7-carboxylic acid

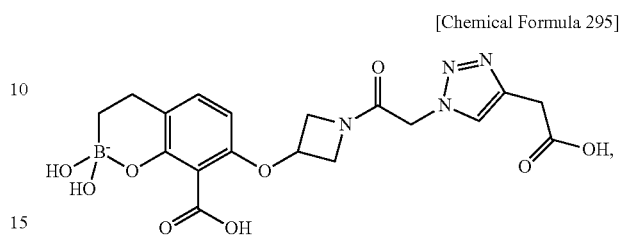

[Chemical Formula 295]

7-({1-[amino(1H-1,2,3-triazol-4-yl)acetyl]azetidin-3-yl}oxy)-2-hydroxy-3,4-dihydro-2H-1,2-benzoxaborinine-8-carboxylic acid

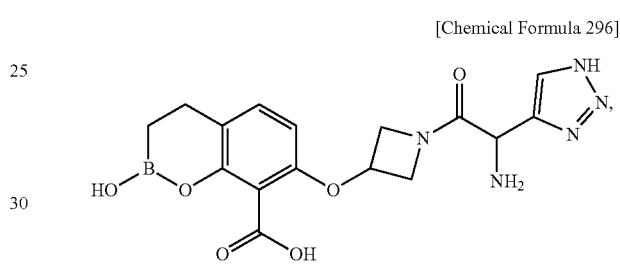

[Chemical Formula 296]

8-({1-[amino(1H-1,2,3-triazol-4-yl)acetyl]azetidin-3-yl}oxy-4,4-dihydroxy-5-oxa-4-boranuidabicyclo[4.4.0]deca-l(6),7,9-triene-7-carboxylic acid

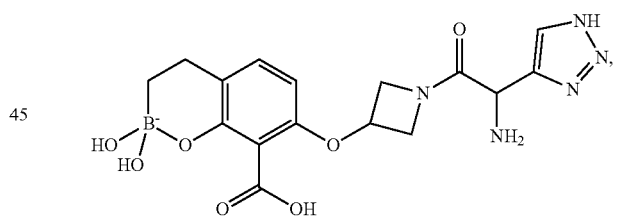

[Chemical Formula 297]

2-hydroxy-7-({1-[(4-nitro-1H-1,2,3-triazol-1-yl)acetyl]azetidin-3-yl}oxy)-3,4-dihydro-2H-1,2-benzoxaborinine-8-carboxylic acid

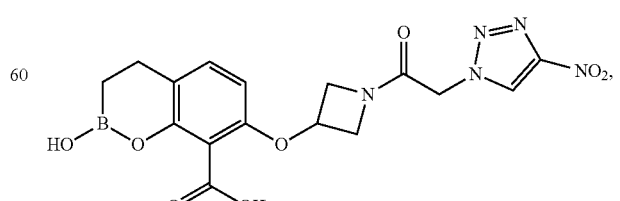

[Chemical Formula 298]

103

4,4-dihydroxy-8-({1-[(4-nitro-1H-1,2,3-triazol-1-yl)acetyl]azetidin-3-yl}oxy)-5-oxa-4-boranuidabicyclo[4.4.0]deca-1(6),7,9-triene-7-carboxylic acid

[Chemical Formula 299]

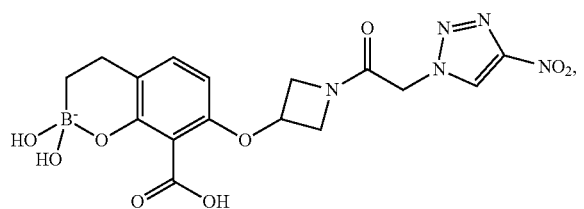

7-({1-[amino(3,4-dihydroxyphenyl)acetyl]azetidin-3-yl}oxy)-2-hydroxy-3,4-dihydro-2H-1,2-benzoxaborinine-8-carboxylic acid

[Chemical Formula 300]

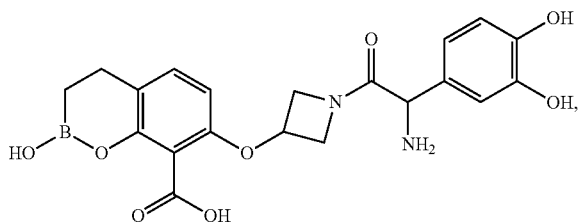

8-({1-[amino(3,4-dihydroxyphenyl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 301]

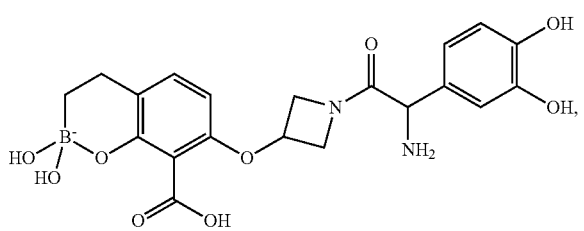

7-({1-[amino(2,4-dihydroxyphenyl)acetyl]azetidin-3-yl}oxy)-2-hydroxy-3,4-dihydro-2H-1,2-benzoxaborinine-8-carboxylic acid

[Chemical Formula 302]

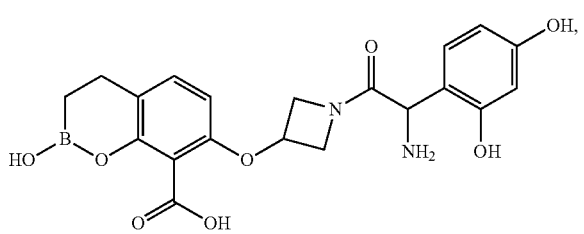

104

8-({1-[amino(2,4-dihydroxyphenyl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 303]

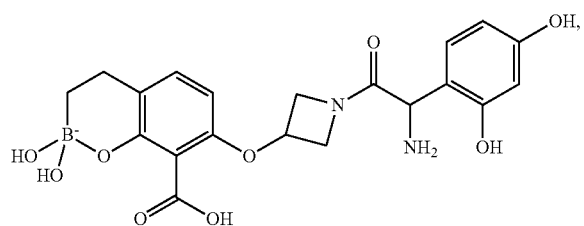

7-{[1-(S-benzyl-D-cysteinyl)azetidin-3-yl]oxy}-2-hydroxy-3,4-dihydro-2H-1,2-benzoxaborinine-8-carboxylic acid

[Chemical Formula 304]

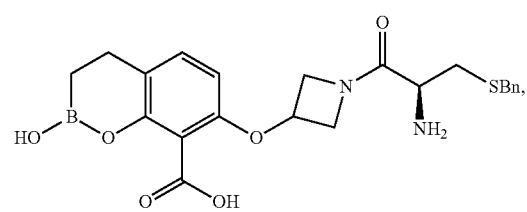

8-{[1-(S-benzyl-D-cysteinyl)azetidin-3-yl]oxy}-4,4-dihydroxy-5-oxa-4-boranuidabicyclo[4.4.0]deca-1(6),7,9-triene-7-carboxylic acid

[Chemical Formula 305]

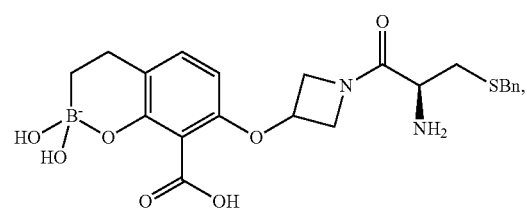

7-[(1-D-cysteinylazetidin-3-yl)oxy]-2-hydroxy-3,4-dihydro-2H-1,2-benzoxaborinine-8-carboxylic acid

[Chemical Formula 306]

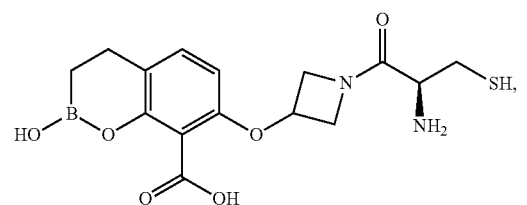

105

7-[(1-D-cysteinylazetidin-3-yl)oxy]-4,4-dihydroxy-5-oxa-4-boranuidabicyclo[4.4.0]deca-l(6), 7,9-triene-7-carboxylic acid

[Chemical Formula 307]

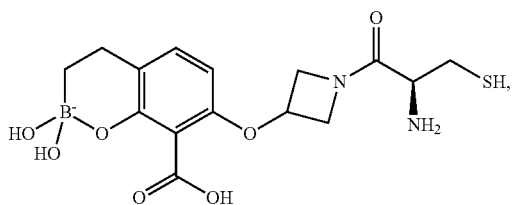

2-hydroxy-7-{[1-(3-sulfanyl-D-valyl)azetidin-3-yl]oxy}-3,4-dihydro-2H-1,2-benzoxaborinine-8-carboxylic acid

[Chemical Formula 308]

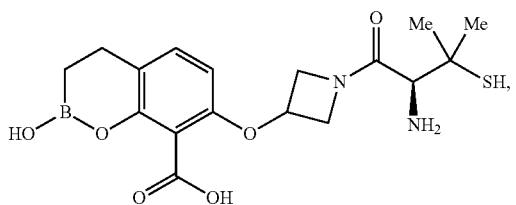

4,4-dihydroxy-8-{[1-(3-sulfanyl-D-valyl)azetidin-3-yl]oxy}-5-oxa-4-boranuidabicyclo[4.4.0]deca-l(6),7,9-triene-7-carboxylic acid

[Chemical Formula 309]

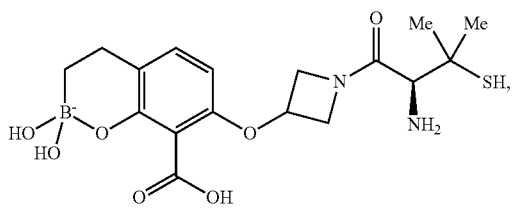

7-({1-[(2S)-2-amino-3-carboxypropanoyl]azetidin-3-yl}oxy)-2-hydroxy-3,4-dihydro-2H-1,2-benzoxaborinine-8-carboxylic acid

[Chemical Formula 310]

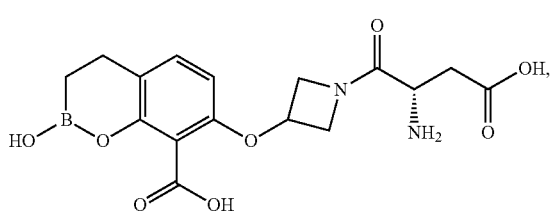

106

8-({1-[(2S)-2-amino-3-carboxypropanoyl]azetidin-3-yl}oxy)-4,4-dihydroxy-5-oxa-4-boranuidabicyclo[4.4.0]deca-l(6),7,9-triene-7-carboxylic acid

[Chemical Formula 311]

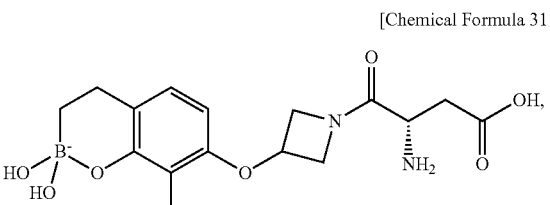

7-{[1-(D-alanyl-D-alanyl)azetidin-3-yl]oxy}-2-hydroxy-3,4-dihydro-2H-1,2-benzoxaborinine-8-carboxylic acid

[Chemical Formula 312]

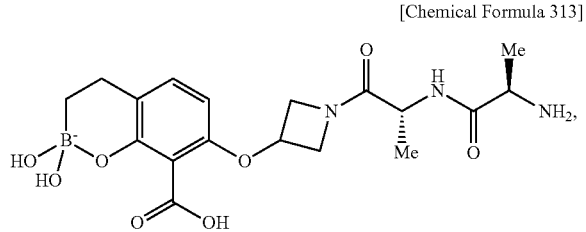 [SMILES: C[C@@H](N)C(=O)N[C@H](C)C(=O)N1CC(Oc2ccc3c(c2C(=O)O)O[B-](O)(O)CC3)C1]

8-{[1-(D-alanyl-D-alanyl)azetidin-3-yl]oxy}-4,4-dihydroxy-5-oxa-4-boranuidabicyclo[4.4.0]deca-l(6),7,9-triene-7-carboxylic acid

[Chemical Formula 313]

7-[(1-L-asparaginylazetidin-3-yl)oxy]-2-hydroxy-3,4-dihydro-2H-1,2-benzoxaborinine-8-carboxylic acid

[Chemical Formula 314]

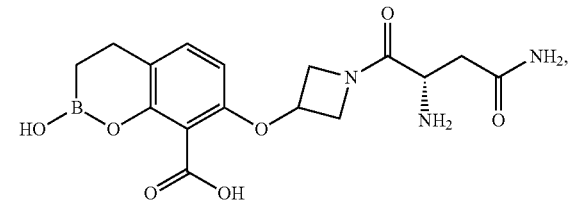

8-[(1-L-asparaginylazetidin-3-yl)oxy]-4,4-dihydroxy-5-oxa-4-boranuidabicyclo[4.4.0]deca-1(6),7,9-triene-7-carboxylic acid

[Chemical Formula 315]

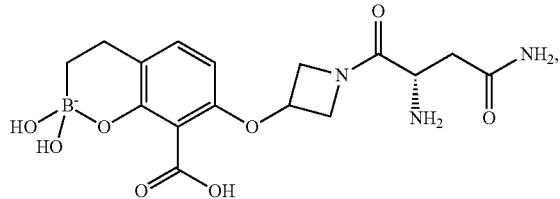

7-[(1-D-asparaginylazetidin-3-yl)oxy]-2-hydroxy-3,4-dihydro-2H-1,2-benzoxaborinine-8-carboxylic acid

[Chemical Formula 316]

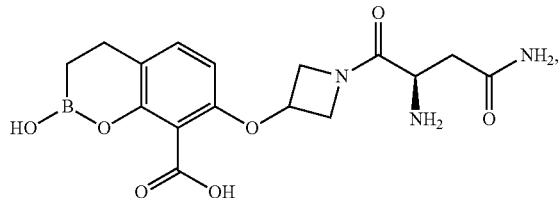

8-[(1-D-asparaginylazetidin-3-yl)oxy]-4,4-dihydroxy-5-oxa-4-boranuidabicyclo[4.4.0]deca-1(6),7,9-triene-7-carboxylic acid

[Chemical Formula 317]

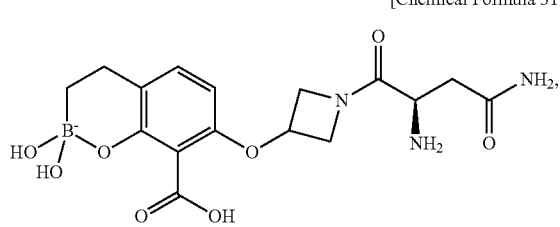

7-({1-[(2R)-2-amino-3-carboxypropanoyl]azetidin-3-yl}oxy)-2-hydroxy-3,4-dihydro-2H-1,2-benzoxaborinine-8-carboxylic acid

[Chemical Formula 318]

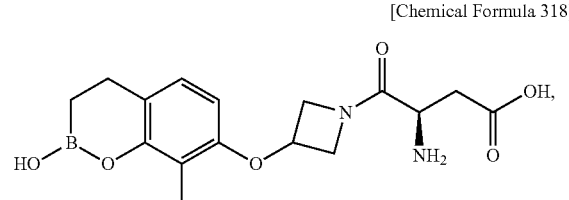

8-({1-[(2R)-2-amino-3-carboxypropanoyl]azetidin-3-yl}oxy)-4,4-dihydroxy-5-oxa-4-boranuidabicyclo[4.4.0]deca-1(6),7,9-triene-7-carboxylic acid

[Chemical Formula 319]

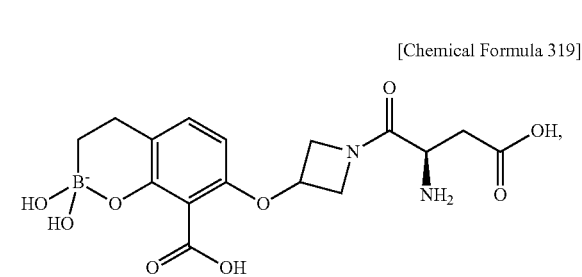 [SMILES: NC(=O)C[C@@H](N)C(=O)N1CC(Oc2ccc3c(c2C(=O)O)O[B-](O)(O)CC3)C1]

2-hydroxy-7-[(1-D-serylazetidin-3-yl)oxy]-3,4-dihydro-2H-1,2-benzoxaborinine-8-carboxylic acid

[Chemical Formula 320]

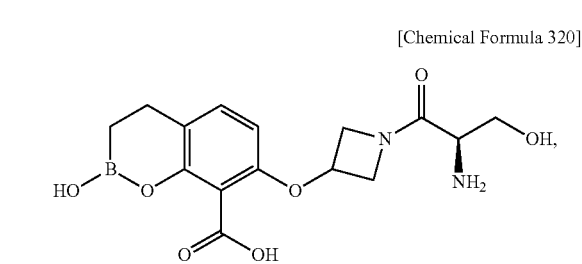 [SMILES: N[C@H](CO)C(=O)N1CC(Oc2ccc3c(c2C(=O)O)OB(O)CC3)C1]

4,4-dihydroxy-8-[(1-D-serylazetidin-3-yl)oxy]-5-oxa-4-boranuidabicyclo[4.4.0]deca-1(6),7,9-triene-7-carboxylic acid

[Chemical Formula 321]

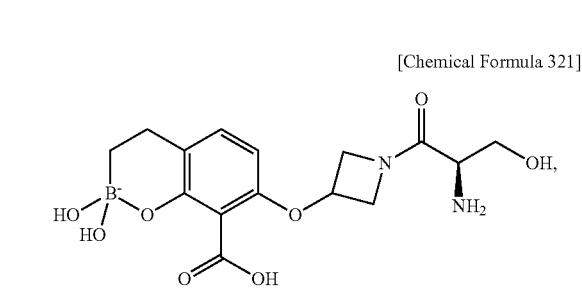 [SMILES: N[C@H](CO)C(=O)N1CC(Oc2ccc3c(c2C(=O)O)O[B-](O)(O)CC3)C1]

7-{[1-(4-amino-4-oxobutanoyl)azetidin-3-yl]oxy}-2-hydroxy-3,4-dihydro-2H-1,2-benzoxaborinine-8-carboxylic acid

[Chemical Formula 322]

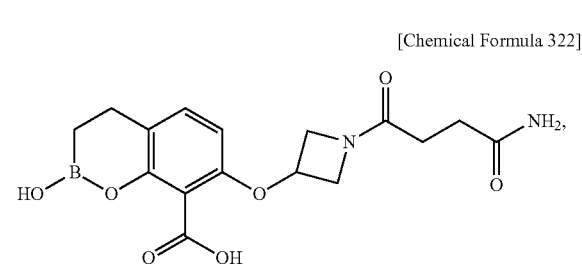 [SMILES: NC(=O)CCC(=O)N1CC(Oc2ccc3c(c2C(=O)O)OB(O)CC3)C1]

8-{[1-(4-amino-4-oxobutanoyl)azetidin-3-yl]oxy}-4,4-dihydroxy-5-oxa-4-boranuidabicyclo[4.4.0]deca-1(6),7,9-triene-7-carboxylic acid

[Chemical Formula 323]

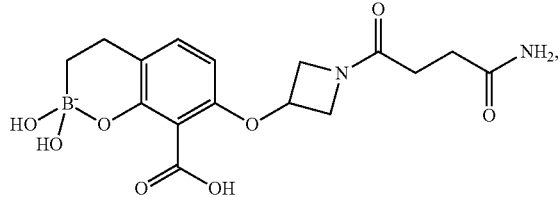

7-[(1-D-glutaminylazetidin-3-yl)oxy]-2-hydroxy-3,4-dihydro-2H-1,2-benzoxaborinine-8-carboxylic acid

[Chemical Formula 324]

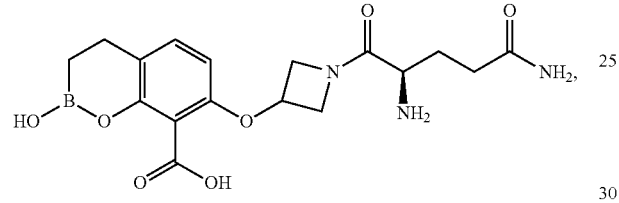

8-[(1-D-glutaminylazetidin-3-yl)oxy]-4,4-dihydroxy-5-oxa-4-boranuidabicyclo[4.4.0]deca-1(6),7,9-triene-7-carboxylic acid

[Chemical Formula 325]

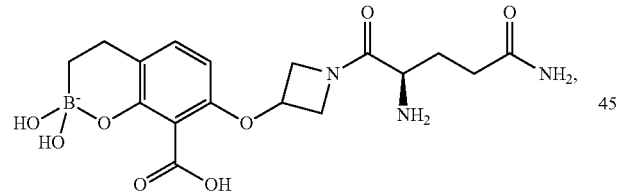

7-({1-[3-(carbamoylamino)-D-alanyl]azetidin-3-yl}oxy)-2-hydroxy-3,4-dihydro-2H-1,2-benzoxaborinine-8-carboxylic acid

[Chemical Formula 326]

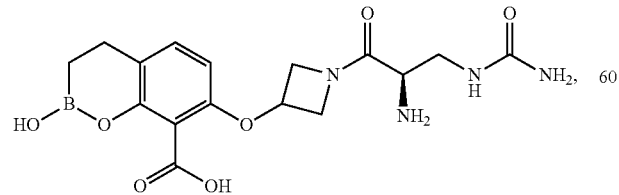

8-({1-[3-(carbamoylamino)-D-alanyl]azetidin-3-yl}oxy)-4,4-dihydroxy-5-oxa-4-boranuidabicyclo[4.4.0]deca-1(6),7,9-triene-7-carboxylic acid

[Chemical Formula 327]

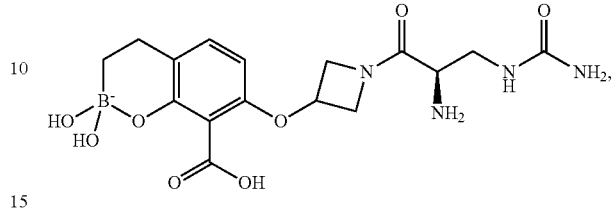

7-{[1-(3-acetamido-D-alanyl)azetidin-3-yl]oxy}-2-hydroxy-3,4-dihydro-2H-1,2-benzoxaborinine-8-carboxylic acid

[Chemical Formula 328]

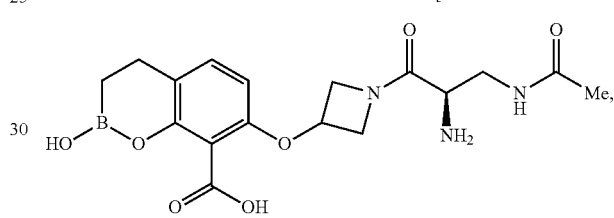

8-{[1-(3-acetamido-D-alanyl)azetidin-3-yl]oxy}-4,4-dihydroxy-5-oxa-4-boranuidabicyclo[4.4.0]deca-1(6),7,9-triene-7-carboxylic acid

[Chemical Formula 329]

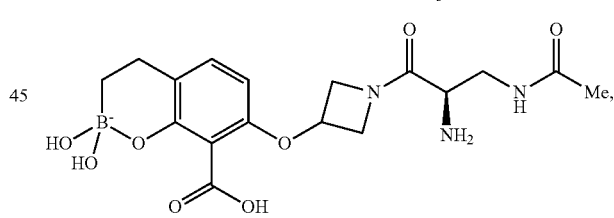

7-{[1-(N,N-dimethyl-D-asparaginyl)azetidin-3-yl]oxy}-2-hydroxy-3,4-dihydro-2H-1,2-benzoxaborinine-8-carboxylic acid

[Chemical Formula 330]

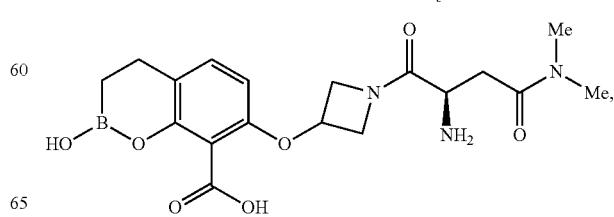

111

8-{[1-(N,N-dimethyl-D-asparaginyl) azetidin-3-yl]oxy}-4,4-dihydroxy-5-oxa-4-boranuidabicyclo[4.4.0]deca-1(6),7,9-triene-7-carboxylic acid

[Chemical Formula 331]

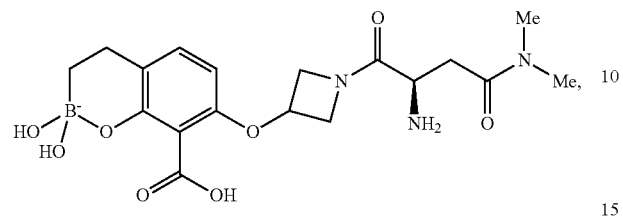

2-hydroxy-7-{[1-(N-methyl-D-asparaginyl)azetidin-3-yl]oxy}-3,4-dihydro-2H-1,2-benzoxaborinine-8-carboxylic acid

[Chemical Formula 332]

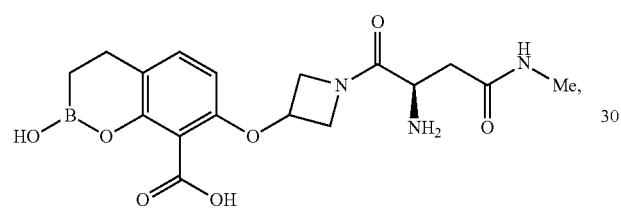

4,4-dihydroxy-8-{[1-(N-methyl-D-asparaginyl)azetidin-3-yl]oxy}-5-oxa-4-boranuidabicyclo[4.4.0]deca-1(6),7,9-triene-7-carboxylic acid

[Chemical Formula 333]

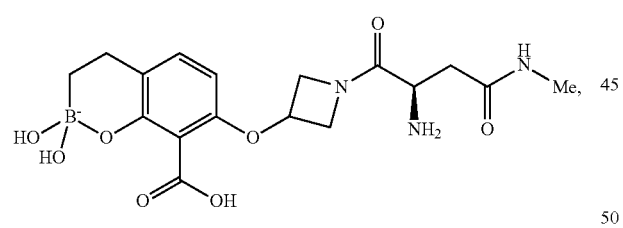

2-hydroxy-7-[(1-L-serylazetidin-3-yl)oxy]-3,4-dihydro-2H-1,2-benzoxaborine-8-carboxylic acid

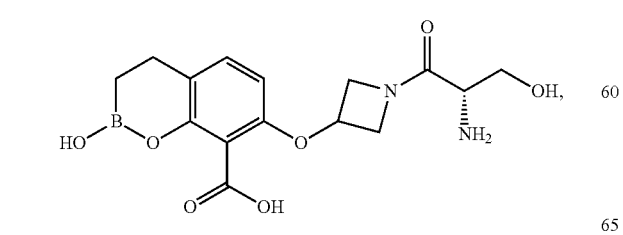

112

4,4-dihydroxy-8-[(1-L-serylazetidin-3-yl)oxy]-5-oxa-4-boranuidabicyclo[4.4.0]deca-1(6),7,9-triene-7-carboxylic acid

[Chemical Formula 335]

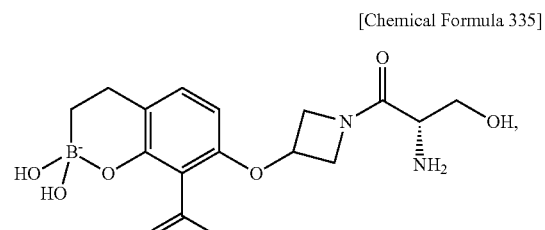

2-hydroxy-7-{[1-(4-hydroxyprolyl)azetidin-3-yl]oxy}-3,4-dihydro-2H-1,2-benzoxaborinine-8-carboxylic acid

[Chemical Formula 336]

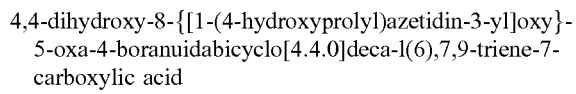

4,4-dihydroxy-8-{[1-(4-hydroxyprolyl)azetidin-3-yl]oxy}-5-oxa-4-boranuidabicyclo[4.4.0]deca-1(6),7,9-triene-7-carboxylic acid

[Chemical Formula 337]

2-hydroxy-7-({1-[(4R)-4-(trifluoromethyl)-D-prolyl]azetidin-3-yl}oxy)-3,4-dihydro-2H-1,2-benzoxaborinine-8-carboxylic acid

[Chemical Formula 338]

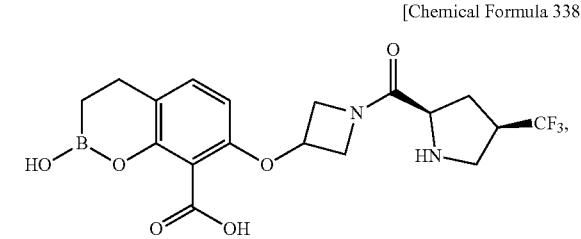 [SMILES: O=C(O)c1c(OC2CN(C(=O)[C@H]3C[C@@H](C(F)(F)F)CN3)C2)ccc2c1OB(O)CC2]

113

4,4-dihydroxy-8-({1-[(4R)-4-(trifluoromethyl)-D-prolyl]
azetidin-3-yl}oxy)-5-oxa-4-boranuidabicyclo[4.4.0]deca-
1(6),7,9-triene-7-carboxylic acid

[Chemical Formula 339]

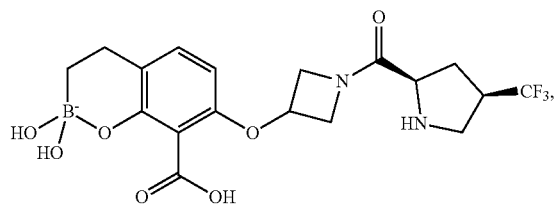

7-({1-[(4S)-4-fluoro-L-prolyl]azetidin-3-yl}oxy)-2-hy-
droxy-3,4-dihydro-2H-1,2-benzoxaborinine-8-carboxylic
acid

[Chemical Formula 340]

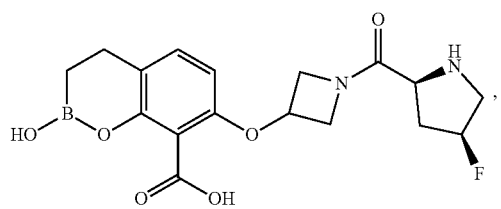

8-({1-[(4S)-4-fluoro-L-prolyl]azetidin-3-yl}oxy)-4,4-dihy-
droxy-5-oxa-4-boranuidabicyclo[4.4.0]deca-1(6),7,9-
triene-7-carboxylic acid

[Chemical Formula 341]

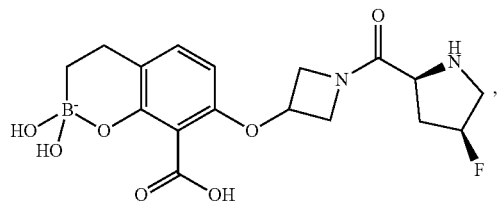

2-hydroxy-7-({1-[(pyrrolidin-3-yl)acetyl]azetidin-3-
yl}oxy)-3,4-dihydro-2H-1,2-benzoxaborinine-8-carbox-
ylic acid

[Chemical Formula 342]

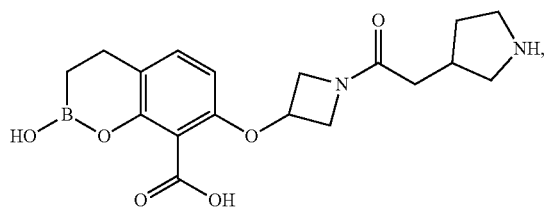

114

4,4-dihydroxy-8-({1-[(pyrrolidin-3-yl)acetyl]azetidin-3-
yl}oxy)-5-oxa-4-boranuidabicyclo[4.4.0]deca-1(6),7,9-
triene-7-carboxylic acid

[Chemical Formula 343]

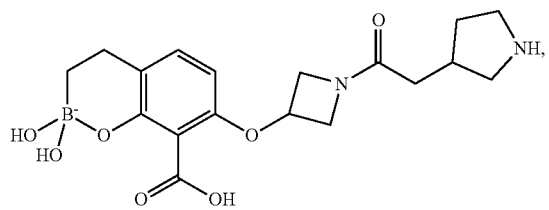

7-[(1-{[(3R,5S)-5-(dimethylcarbamoyl)pyrrolidin-3-yl]
acetyl}azetidin-3-yl)oxy]-2-hydroxy-3,4-dihydro-2H-1,
2-benzoxaborinine-8-carboxylic acid

[Chemical Formula 344]

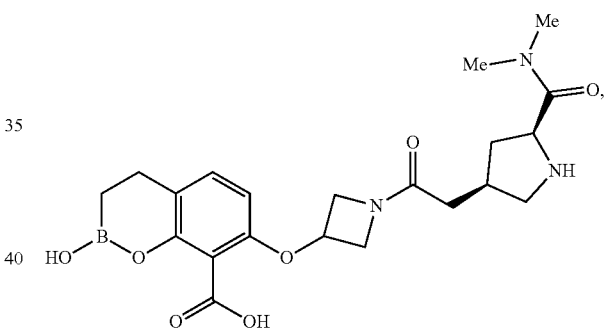

8-[(1-{[(3R,5S)-5-(dimethylcarbamoyl)pyrrolidin-3-yl]
acetyl}azetidin-3-yl)oxy]-4,4-dihydroxy-5-oxa-4-bo-
ranuidabicyclo[4.4.0]deca-1(6),7,9-triene-7-carboxylic
acid

[Chemical Formula 345]

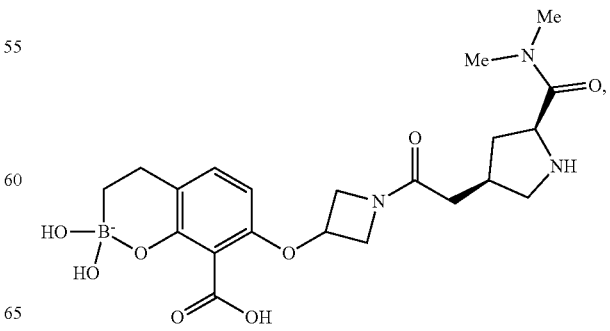

7-[(1-{[(3S,5R)-5-(dimethylcarbamoyl)pyrrolidin-3-yl]
acetyl}azetidin-3-yl)oxy]-2-hydroxy-3,4-dihydro-2H-1,
2-benzoxaborinine-8-carboxylic acid

[Chemical Formula 346]

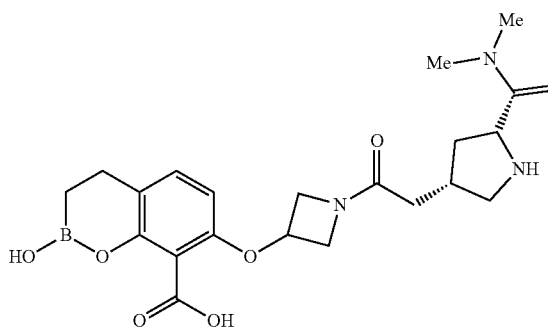

8-[(1-{[(3S,5R)-5-(dimethylcarbamoyl)pyrrolidin-3-yl]
acetyl}azetidin-3-yl)oxy]-4,4-dihydroxy-5-oxa-4-bo-
ranuidabicyclo[4.4.0]deca-1(6),7,9-triene-7-carboxylic
acid

[Chemical Formula 347]

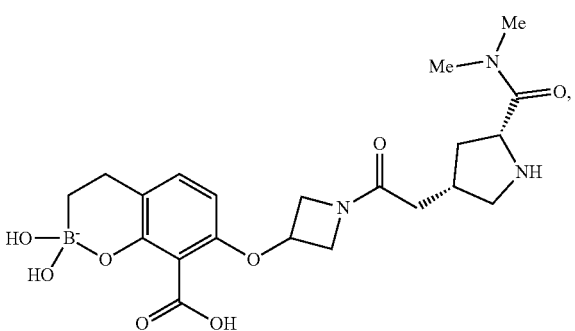

7-[(1-{[(2R,4S)-4-fluoropyrrolidin-2-yl]acetyl}azetidin-3-
yl)oxy]-2-hydroxy-3,4-dihydro-2H-1,2-benzoxaborinine-
8-carboxylic acid

[Chemical Formula 348]

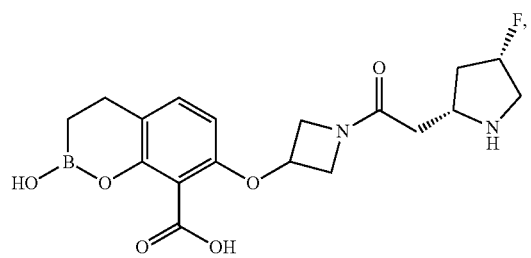

8-[(1-{[(2R,4S)-4-fluoropyrrolidin-2-yl]acetyl}azetidin-3-
yl)oxy]-4,4-dihydroxy-5-oxa-4-boranuidabicyclo[4.4.0]
deca-1(6), 7,9-triene-7-carboxylic acid

[Chemical Formula 349]

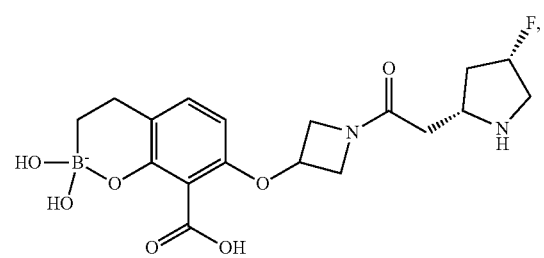

7-{[1-(4,4-difluoro-L-prolyl)azetidin-3-yl]oxy}-2-hydroxy-
3,4-dihydro-2H-1,2-benzoxaborinine-8-carboxylic acid

[Chemical Formula 350]

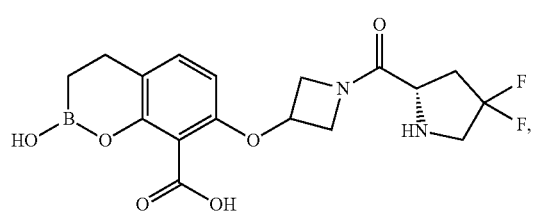

8-{[1-(4,4-difluoro-L-prolyl)azetidin-3-yl]oxy}-4,4-dihy-
droxy-5-oxa-4-boranuidabicyclo[4.4.0]deca-1(6),7,9-
triene-7-carboxylic acid

[Chemical Formula 351]

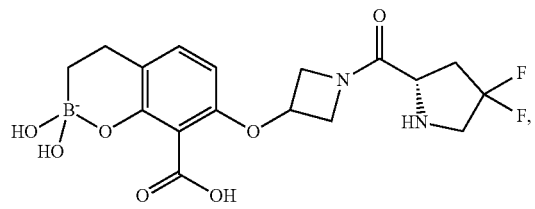

2-hydroxy-7-({1-[(4R)-4-hydroxy-L-prolyl]azetidin-3-
yl}oxy)-3,4-dihydro-2H-1,2-benzoxaborinine-8-carbox-
ylic acid

[Chemical Formula 352]

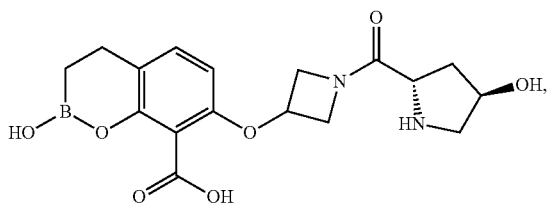

117

4,4-dihydroxy-8-({1-[(4R)-4-hydroxy-L-prolyl]azetidin-3-yl}oxy)-5-oxa-4-boranuidabicyclo[4.4.0]deca-1(6),7,9-triene-7-carboxylic acid

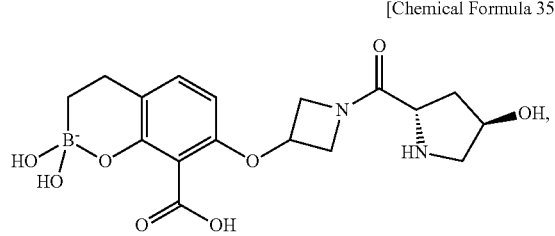

2-hydroxy-7-({1-[(piperidin-4-yl)acetyl]azetidin-3-yl}oxy)-3,4-dihydro-2H-1,2-benzoxaborinine-8-carboxylic acid

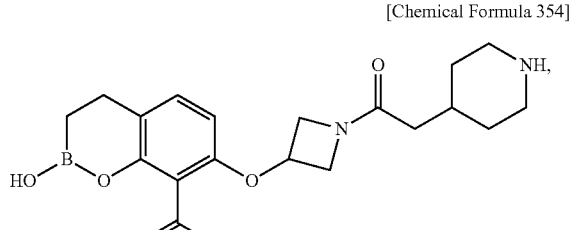

4,4-dihydroxy-8-({1-[(piperidin-4-yl)acetyl]azetidin-3-yl}oxy)-5-oxa-4-boranuidabicyclo[4.4.0]deca-1(6),7,9-triene-7-carboxylic acid

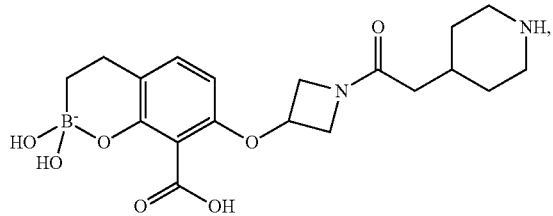

2-hydroxy-7-{[1-(pyrrolidine-3-carbonyl)azetidin-3-yl]oxy}-3,4-dihydro-2H-1,2-benzoxaborinine-8-carboxylic acid

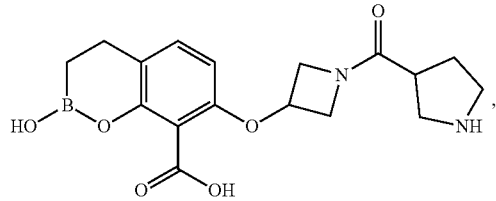

118

4,4-dihydroxy-8-{[1-(pyrrolidine-3-carbonyl)azetidin-3-yl]oxy}-5-oxa-4-boranuidabicyclo[4.4.0]deca-1(6),7,9-triene-7-carboxylic acid

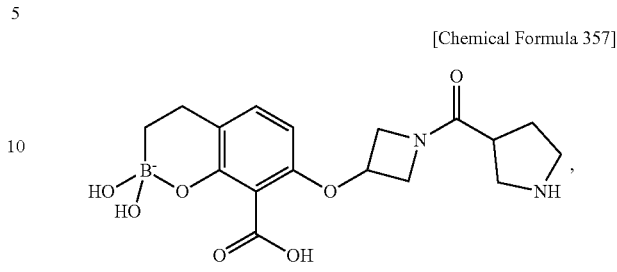

2-hydroxy-7-({1-[(4S)-4-hydroxy-L-prolyl]azetidin-3-yl}oxy)-3,4-dihydro-2H-1,2-benzoxaborinine-8-carboxylic acid

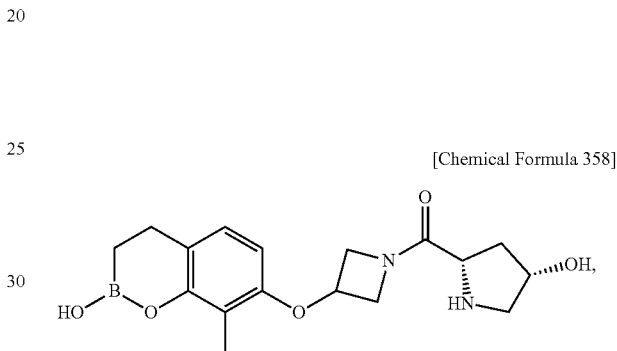

4,4-dihydroxy-8-({1-[(4S)-4-hydroxy-L-prolyl]azetidin-3-yl}oxy)-5-oxa-4-boranuidabicyclo[4.4.0]deca-1(6),7,9-triene-7-carboxylic acid

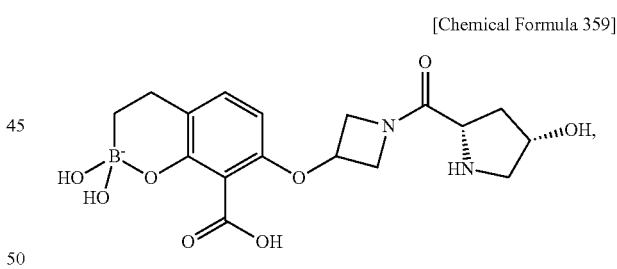

7-({1-[(4S)-4-amino-L-prolyl]azetidin-3-yl}oxy)-2-hydroxy-3,4-dihydro-2H-1,2-benzoxaborinine-8-carboxylic acid

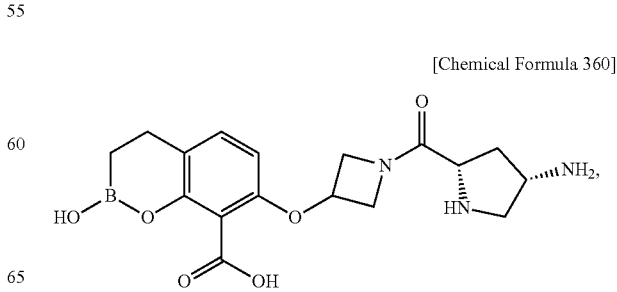

8-({1-[(4S)-4-amino-L-prolyl]azetidin-3-yl}oxy)-4,4-dihydroxy-5-oxa-4-boranuidabicyclo[4.4.0]deca-l(6),7,9-triene-7-carboxylic acid

[Chemical Formula 361]

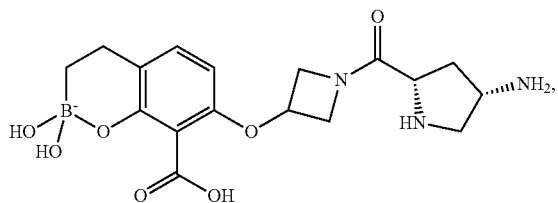

7-({1-[(4S)-4-acetamido-L-prolyl]azetidin-3-yl}oxy)-2-hydroxy-3,4-dihydro-2H-1,2-benzoxaborinine-8-carboxylic acid

[Chemical Formula 362]

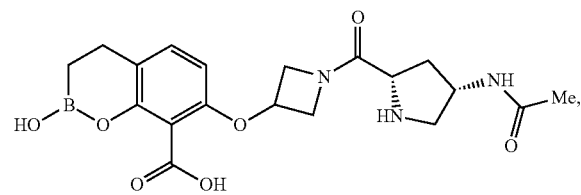

8-({1-[(4S)-4-acetamido-L-prolyl]azetidin-3-yl}oxy)-4,4-dihydroxy-5-oxa-4-boranuidabicyclo[4.4.0]deca-l(6),7,9-triene-7-carboxylic acid

[Chemical Formula 363]

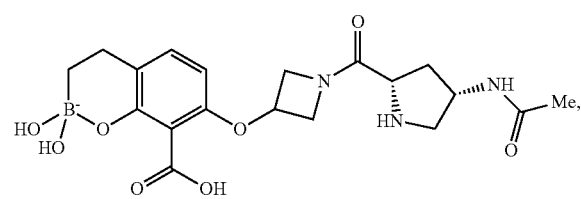

2-hydroxy-7-({1-[(3R)-3-hydroxy-L-prolyl]azetidin-3-yl}oxy)-3,4-dihydro-2H-1,2-benzoxaborinine-8-carboxylic acid

[Chemical Formula 364]

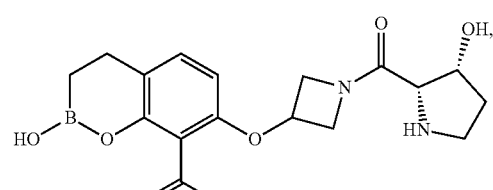

4,4-dihydroxy-8-({1-[(3R)-3-hydroxy-L-prolyl]azetidin-3-yl}oxy)-5-oxa-4-boranuidabicyclo[4.4.0]deca-l(6),7,9-triene-7-carboxylic acid

[Chemical Formula 365]

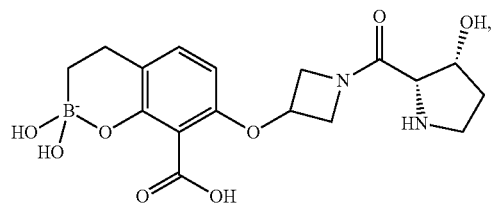

7-{[1-(4,4-dimethyl-L-prolyl)azetidin-3-yl]oxy}-2-hydroxy-3,4-dihydro-2H-1,2-benzoxaborinine-8-carboxylic acid

[Chemical Formula 366]

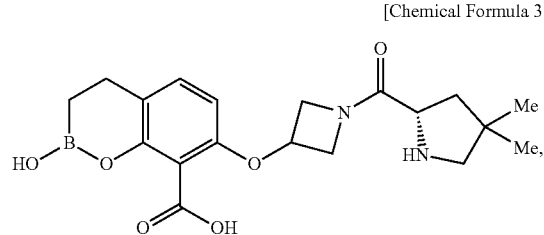

8-{[1-(4,4-dimethyl-L-prolyl)azetidin-3-yl]oxy}-4,4-dihydroxy-5-oxa-4-boranuidabicyclo[4.4.0]deca-l(6),7,9-triene-7-carboxylic acid

[Chemical Formula 367]

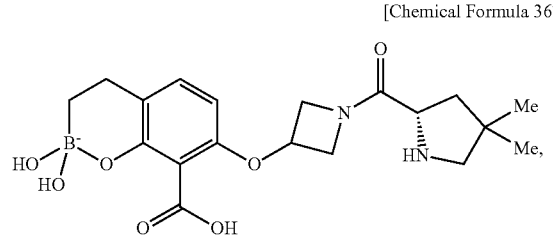

2-hydroxy-7-({1-[(pyrrolidin-2-yl)acetyl]azetidin-3-yl}oxy)-3,4-dihydro-2H-1,2-benzoxaborinine-8-carboxylic acid

[Chemical Formula 368]

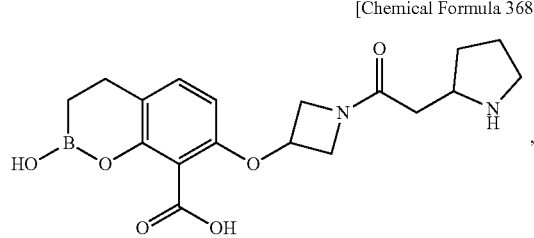 [SMILES: O=C(O)c1c(OC2CN(C(=O)CC3CCCN3)C2)ccc2c1OB(O)CC2]

121

4,4-dihydroxy-8-({1-[(pyrrolidin-2-yl)acetyl]azetidin-3-yl}oxy)-5-oxa-4-boranuidabicyclo[4.4.0]deca-1(6),7,9-triene-7-carboxylic acid

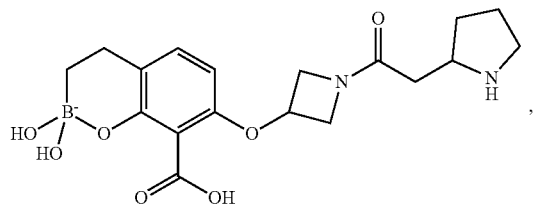

2-hydroxy-7-([1-(piperidine-2-carbonyl)azetidin-3-yl]oxy)-3,4-dihydro-2H-1,2-benzoxaborinine-8-carboxylic acid

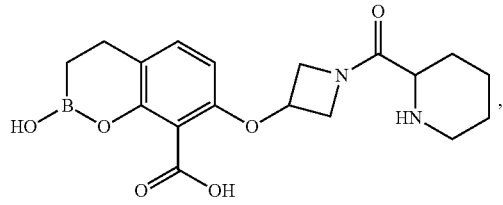

4,4-dihydroxy-8-{[1-(piperidine-2-carbonyl)azetidin-3-yl]oxy}-5-oxa-4-boranuidabicyclo[4.4.0]deca-1(6),7,9-triene-7-carboxylic acid

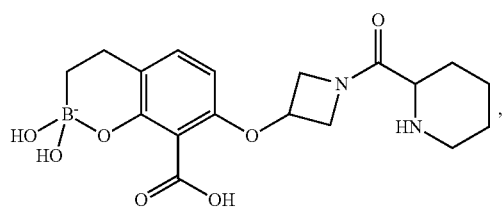

2-hydroxy-7-([1-(piperidine-3-carbonyl)azetidin-3-yl]oxy)-3,4-dihydro-2H-1,2-benzoxaborinine-8-carboxylic acid

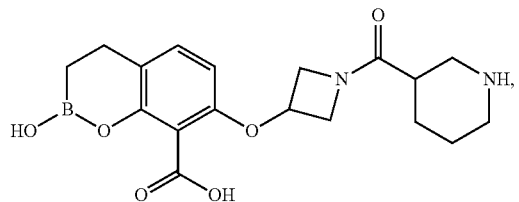

122

4,4-dihydroxy-8-{[1-(piperidine-3-carbonyl)azetidin-3-yl]oxy}-5-oxa-4-boranuidabicyclo[4.4.0]deca-1(6),7,9-triene-7-carboxylic acid

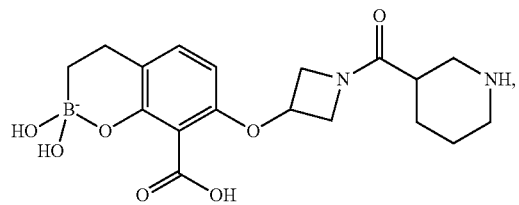

2-hydroxy-7-{[1-(piperidine-4-carbonyl)azetidin-3-yl]oxy}-3,4-dihydro-2H-1,2-benzoxaborinine-8-carboxylic acid

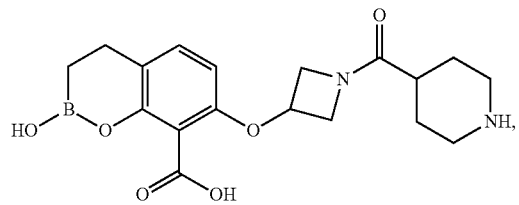

4,4-dihydroxy-8-{[1-(piperidine-4-carbonyl)azetidin-3-yl]oxy}-5-oxa-4-boranuidabicyclo[4.4.0]deca-1(6),7,9-triene-7-carboxylic acid

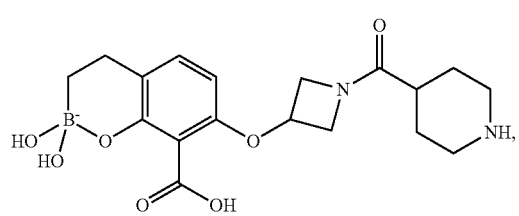

2-hydroxy-7-({1-[(2S)-oxolane-2-carbonyl]azetidin-3-yl}oxy)-3,4-dihydro-2H-1,2-benzoxaborinine-8-carboxylic acid

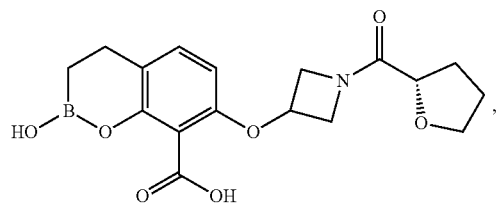

123

4,4-dihydroxy-8-({1-[(2S)-oxolane-2-carbonyl]azetidin-3-yl}oxy)-5-oxa-4-boranuidabicyclo[4.4.0]deca-1(6),7,9-triene-7-carboxylic acid

[Chemical Formula 377]

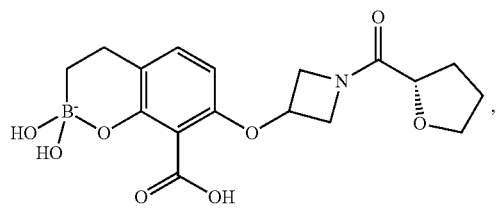

2-hydroxy-7-({1-[(4R)-4-phenyl-L-prolyl]azetidin-3-yl}oxy)-3,4-dihydro-2H-1,2-benzoxaborinine-8-carboxylic acid

[Chemical Formula 378]

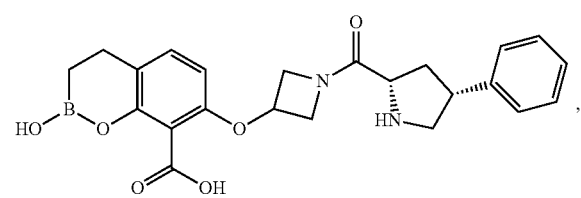

4,4-dihydroxy-8-({1-[(4R)-4-phenyl-L-prolyl]azetidin-3-yl}oxy)-5-oxa-4-boranuidabicyclo[4.4.0]deca-1(6),7,9-triene-7-carboxylic acid

[Chemical Formula 379]

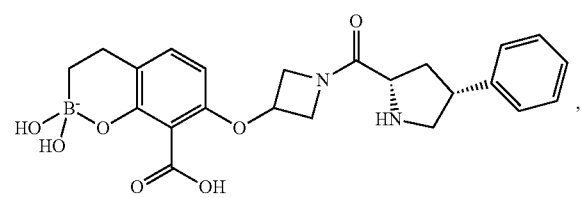

7-({1-[(1S,3S,5S)-2-azabicyclo[3.1.0]hexane-3-carbonyl]azetidin-3-yl}oxy)-2-hydroxy-3,4-dihydro-2H-1,2-benzoxaborinine-8-carboxylic acid

[Chemical Formula 380]

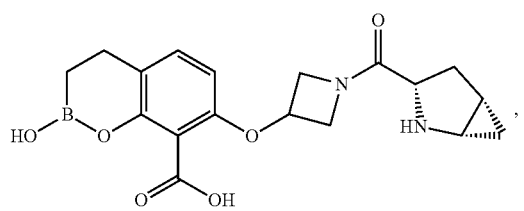

124

8-({1-[(1S,3S,5S)-2-azabicyclo[3.1.0]hexane-3-carbonyl]azetidin-3-yl}oxy)-4,4-dihydroxy-5-oxa-4-boranuidabicyclo[4.4.0]deca-1(6),7,9-triene-7-carboxylic acid

[Chemical Formula 381]

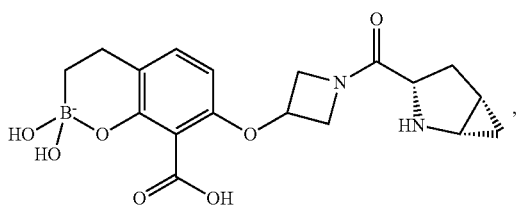

2-hydroxy-7-{[1-(1-methyl-L-prolyl)azetidin-3-yl]oxy}-3,4-dihydro-2H-1,2-benzoxaborinine-8-carboxylic acid

[Chemical Formula 382]

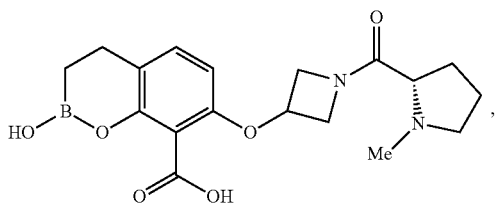

4,4-dihydroxy-8-{[1-(1-methyl-L-prolyl)azetidin-3-yl]oxy}-5-oxa-4-boranuidabicyclo[4.4.0]deca-1(6),7,9-triene-7-carboxylic acid

[Chemical Formula 383]

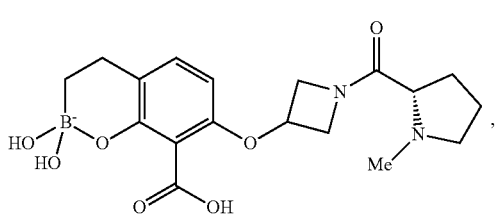

2-hydroxy-7-({1-[(piperidin-3-yl)acetyl]azetidin-3-yl}oxy)-3,4-dihydro-2H-1,2-benzoxaborinine-8-carboxylic acid

[Chemical Formula 384]

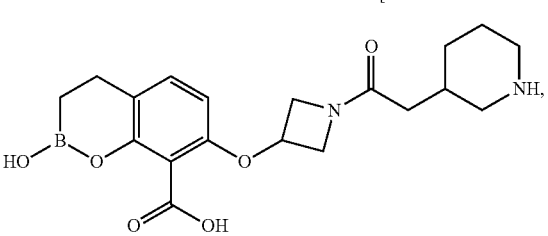

125

4,4-dihydroxy-8-({1-[(piperidin-3-yl)acetyl]azetidin-3-yl}oxy)-5-oxa-4-boranuidabicyclo[4.4.0]deca-1(6),7,9-triene-7-carboxylic acid

[Chemical Formula 385]

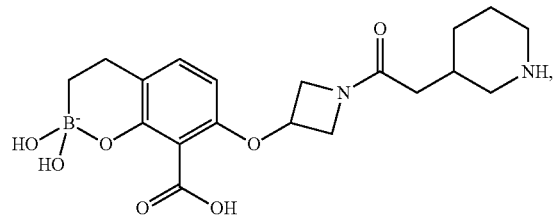

2-hydroxy-7-({1-[(morpholin-2-yl)acetyl]azetidin-3-yl}oxy)-3,4-dihydro-2H-1,2-benzoxaborinine-8-carboxylic acid

[Chemical Formula 386]

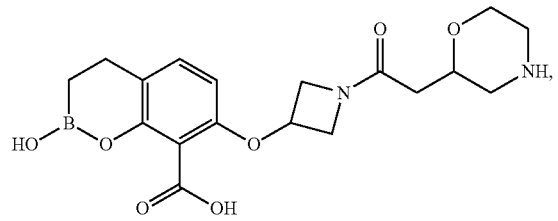

4,4-dihydroxy-8-({1-[(morpholin-2-yl)acetyl]azetidin-3-yl}oxy)-5-oxa-4-boranuidabicyclo[4.4.0]deca-1(6),7,9-triene-7-carboxylic acid

[Chemical Formula 387]

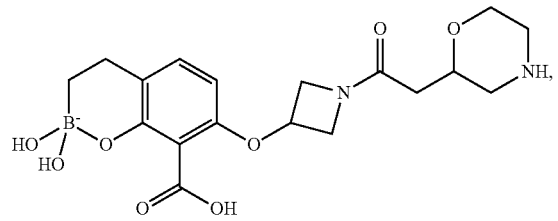

7-({1-[(azetidin-3-yl)acetyl]azetidin-3-yl}oxy)-2-hydroxy-3,4-dihydro-2H-1,2-benzoxaborinine-8-carboxylic acid

[Chemical Formula 388]

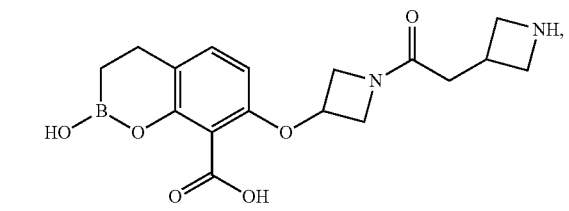

126

8-({1-[(azetidin-3-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 389]

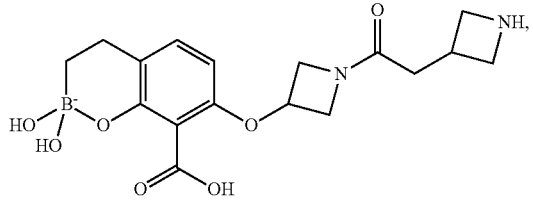

7-({1-[amino(pyrrolidin-3-yl)acetyl]azetidin-3-yl}oxy)-2-hydroxy-3,4-dihydro-2H-1,2-benzoxaborinine-8-carboxylic acid

[Chemical Formula 390]

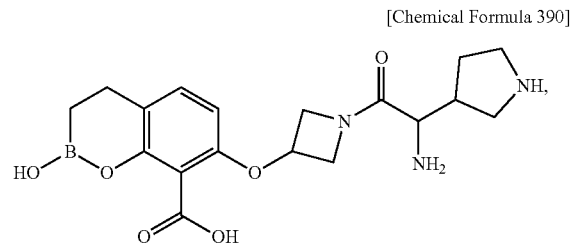 [SMILES: NC(C(=O)N1CC(Oc2ccc3c(c2C(=O)O)OB(O)CC3)C1)C1CCNC1]

8-({1-[amino(pyrrolidin-3-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 391]

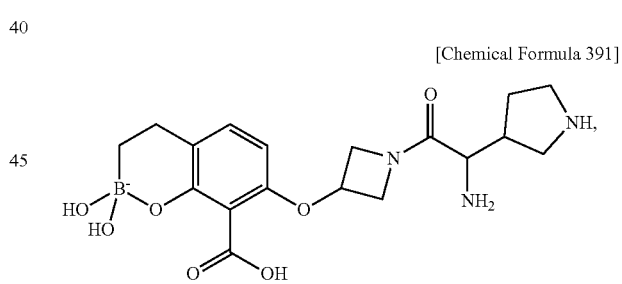

2-hydroxy-7-({1-[3-(pyrrolidin-2-yl)propanoyl]azetidin-3-yl}oxy)-3,4-dihydro-2H-1,2-benzoxaborinine-8-carboxylic acid

[Chemical Formula 392]

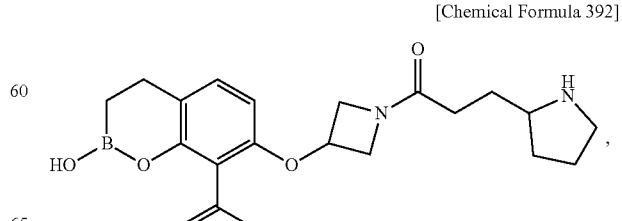

127

4,4-dihydroxy-8-({1-[3-(pyrrolidin-2-yl)propanoyl]azetidin-3-yl}oxy)-5-oxa-4-boranuidabicyclo[4.4.0]deca-1(6),7,9-triene-7-carboxylic acid

[Chemical Formula 393]

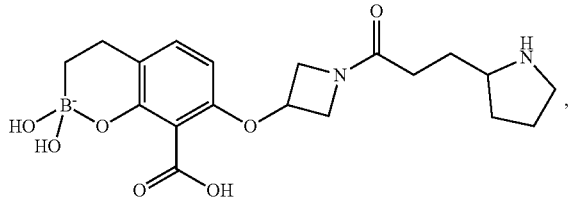

7-({1-[(4R)-4-amino-L-prolyl]azetidin-3-yl}oxy)-2-hydroxy-3,4-dihydro-2H-1,2-benzoxaborinine-8-carboxylic acid

[Chemical Formula 394]

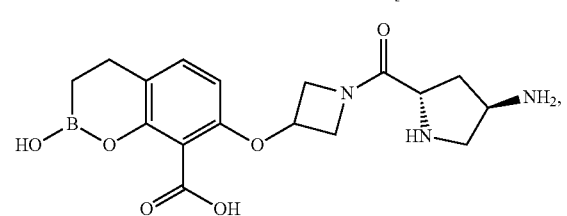

8-({1-[(4R)-4-amino-L-prolyl]azetidin-3-yl}oxy)-4,4-dihydroxy-5-oxa-4-boranuidabicyclo[4.4.0]deca-1(6),7,9-triene-7-carboxylic acid

[Chemical Formula 395]

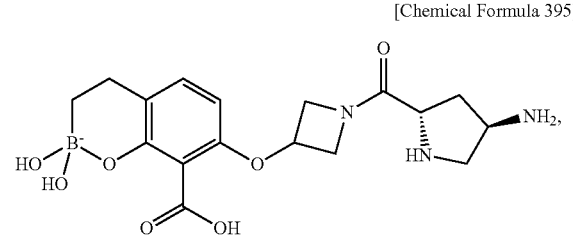

7-({1-[(4R)-4-acetamido-L-prolyl]azetidin-3-yl}oxy)-2-hydroxy-3,4-dihydro-2H-1,2-benzoxaborinine-8-carboxylic acid

[Chemical Formula 396]

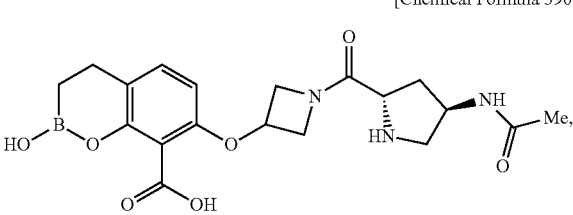

128

8-({1-[(4R)-4-acetamido-L-prolyl]azetidin-3-yl}oxy)-4,4-dihydroxy-5-oxa-4-boranuidabicyclo[4.4.0]deca-1(6),7,9-triene-7-carboxylic acid

[Chemical Formula 397]

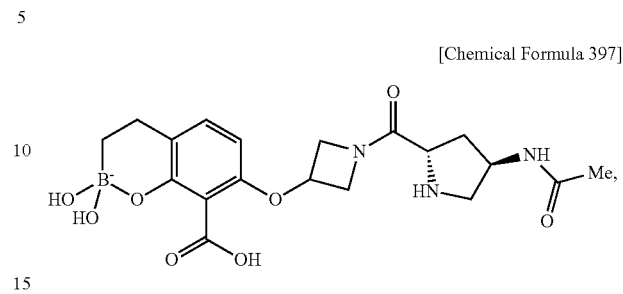

7-({1-[amino(piperidin-4-yl)acetyl]azetidin-3-yl}oxy)-2-hydroxy-3,4-dihydro-2H-1,2-benzoxaborinine-8-carboxylic acid

[Chemical Formula 398]

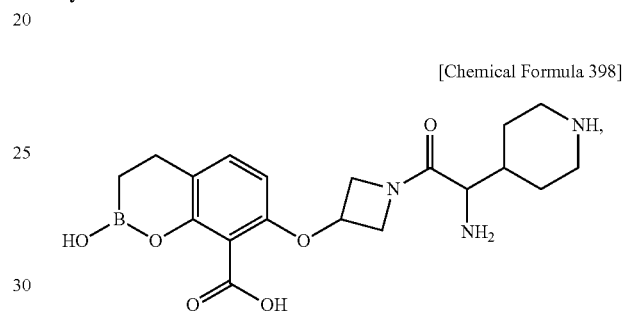

8-({1-[amino(piperidin-4-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 399]

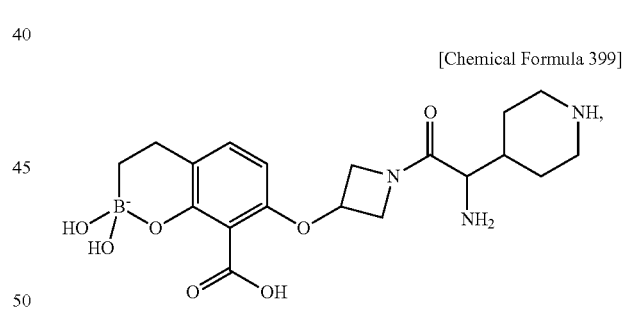

2-hydroxy-7-({1-[(piperidin-2-yl)acetyl]azetidin-3-yl}oxy)-3,4-dihydro-2H-1,2-benzoxaborinine-8-carboxylic acid

[Chemical Formula 400]

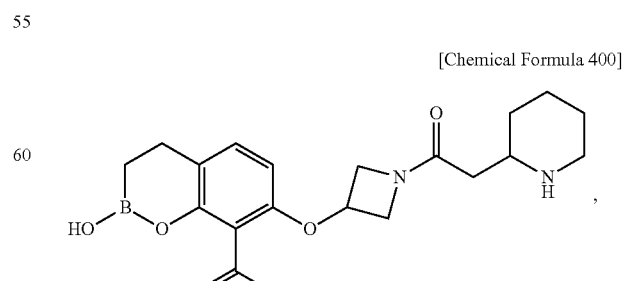

4,4-dihydroxy-8-({1-[(piperidin-2-yl)acetyl]azetidin-3-yl}oxy)-5-oxa-4-boranuidabicyclo[4.4.0]deca-1(6),7,9-triene-7-carboxylic acid

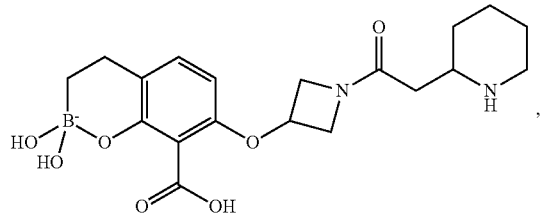

7-({1-[(4S)-4-carbamoyl-L-prolyl]azetidin-3-yl}oxy)-2-hydroxy-3,4-dihydro-2H-1,2-benzoxaborinine-8-carboxylic acid

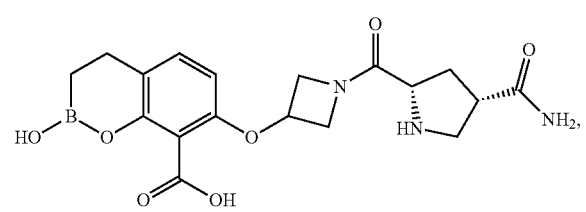

8-({1-[(4S)-4-carbamoyl-L-prolyl]azetidin-3-yl}oxy)-4,4-dihydroxy-5-oxa-4-boranuidabicyclo[4.4.0]deca-1(6),7,9-triene-7-carboxylic acid

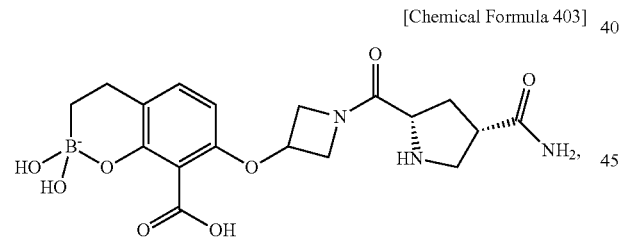

2-hydroxy-7-[(1-{[(3R)-pyrrolidin-3-yl]acetyl}azetidin-3-yl)oxy]-3,4-dihydro-2H-1,2-benzoxaborine-8-carboxylic acid

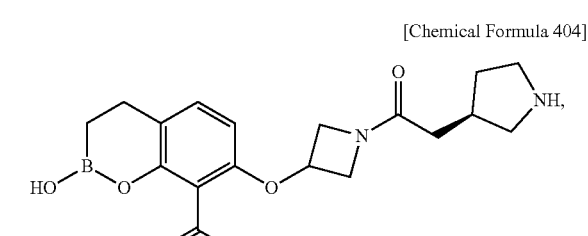

4,4-dihydroxy-8-[(1-{[(3R)-pyrrolidin-3-yl]acetyl}azetidin-3-yl)oxy]-5-oxa-4-boranuidabicyclo[4.4.0]deca-1(6),7,9-triene-7-carboxylic acid

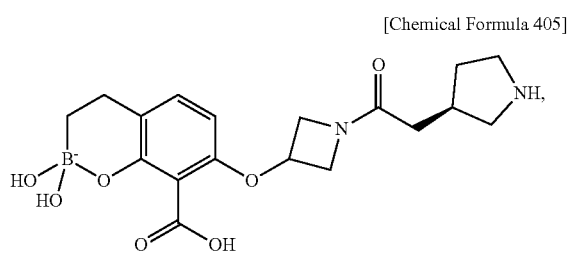 [SMILES: O=C(O)c1c(OC2CN(C(=O)C[C@H]3CCNC3)C2)ccc2c1O[B-](O)(O)CC2]

2-hydroxy-7-[(1-{[(3S)-pyrrolidin-3-yl]acetyl}azetidin-3-yl)oxy]-3,4-dihydro-2H-1,2-benzoxaborine-8-carboxylic acid

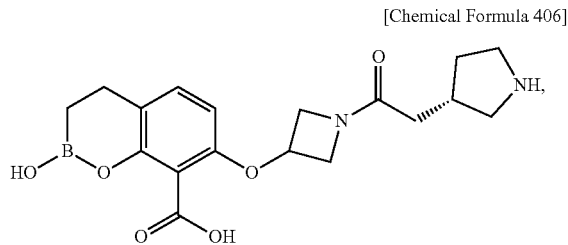 [SMILES: O=C(O)c1c(OC2CN(C(=O)C[C@@H]3CCNC3)C2)ccc2c1OB(O)CC2]

4,4-dihydroxy-8-[(1-{[(3S)-pyrrolidin-3-yl]acetyl}azetidin-3-yl)oxy]-5-oxa-4-boranuidabicyclo[4.4.0]deca-1(6),7,9-triene-7-carboxylic acid

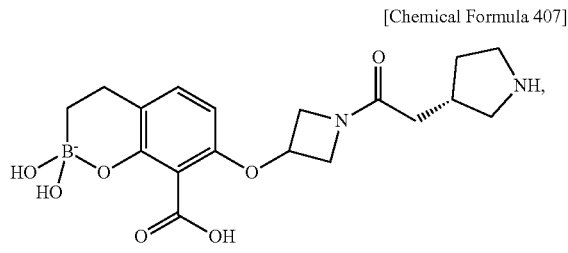 [SMILES: O=C(O)c1c(OC2CN(C(=O)C[C@@H]3CCNC3)C2)ccc2c1O[B-](O)(O)CC2]

2-hydroxy-7-[(1-{[(2R)-pyrrolidin-2-yl]acetyl}azetidin-3-yl)oxy]-3,4-dihydro-2H-1,2-benzoxaborine-8-carboxylic acid

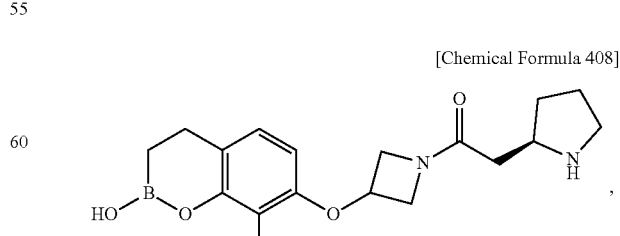

131

4,4-dihydroxy-8-[(1-{[(2R)-pyrrolidin-2-yl]acetyl}azetidin-3-yl)oxy]-5-oxa-4-boranuidabicyclo[4.4.0]deca-1(6),7,9-triene-7-carboxylic acid

[Chemical Formula 409]

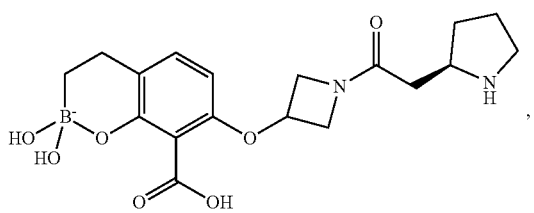

2-hydroxy-7-[(1-{[(2S)-pyrrolidin-2-yl]acetyl}azetidin-3-yl)oxy]-3,4-dihydro-2H-1,2-benzoxaborine-8-carboxylic acid

[Chemical Formula 410]

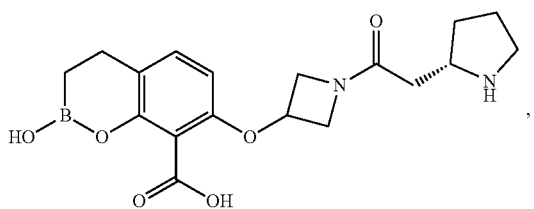

4,4-dihydroxy-8-[(1-{[(2S)-pyrrolidin-2-yl]acetyl}azetidin-3-yl)oxy]-5-oxa-4-boranuidabicyclo[4.4.0]deca-1(6),7,9-triene-7-carboxylic acid

[Chemical Formula 411]

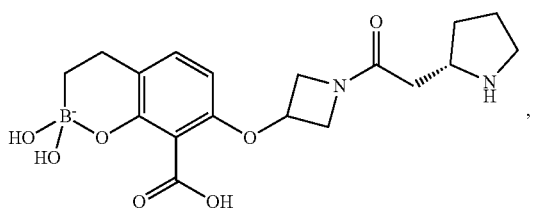

2-hydroxy-7-({1-[(piperazin-2-yl)acetyl]azetidin-3-yl}oxy)-3,4-dihydro-2H-1,2-benzoxaborinine-8-carboxylic acid

[Chemical Formula 412]

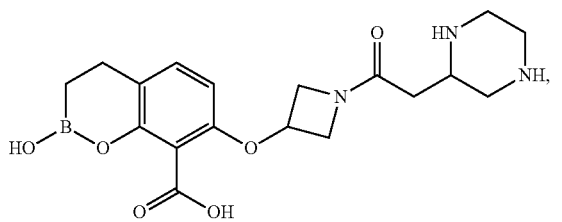

132

4,4-dihydroxy-8-({1-[(piperazin-2-yl)acetyl]azetidin-3-yl}oxy)-5-oxa-4-boranuidabicyclo[4.4.0]deca-1(6),7,9-triene-7-carboxylic acid

[Chemical Formula 413]

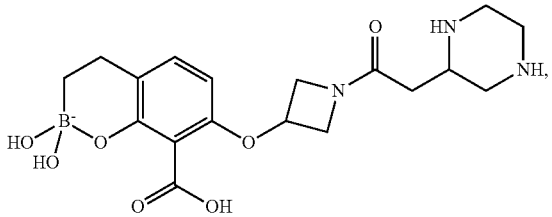

7-({1-[(1,1-dioxo-1$\lambda^6$-thiomorpholin-2-yl)acetyl]azetidin-3-yl}oxy)-2-hydroxy-3,4-dihydro-2H-1,2-benzoxaborinine-8-carboxylic acid

[Chemical Formula 414]

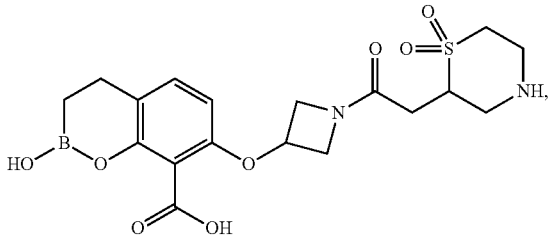

8-({1-[(1,1-dioxo-1$\lambda^6$-thiomorpholin-2-yl)acetyl]azetidin-3-yl}oxy)-4,4-dihydroxy-5-oxa-4-boranuidabicyclo[4.4.0]deca-1(6),7,9-triene-7-carboxylic acid

[Chemical Formula 415]

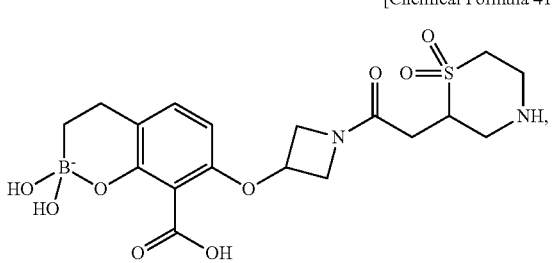

7-({1-[(2S)-4-acetamido-2-aminobutanoyl]azetidin-3-yl}oxy)-2-hydroxy-3,4-dihydro-2H-1,2-benzoxaborinine-8-carboxylic acid

[Chemical Formula 416]

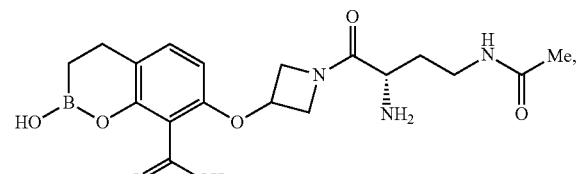

8-({1-[(2S)-4-acetamido-2-aminobutanoyl]azetidin-3-yl}oxy)-4,4-dihydroxy-5-oxa-4-boranuidabicyclo[4.4.0]deca-1(6),7,9-triene-7-carboxylic acid 8-{[1-(L-alanyl-L-alanyl)azetidin-3-yl]oxy}-4,4-dihydroxy-5-oxa-4-boranuidabicyclo[4.4.0]deca-1(6),7,9-triene-7-carboxylic acid

[Chemical Formula 417]

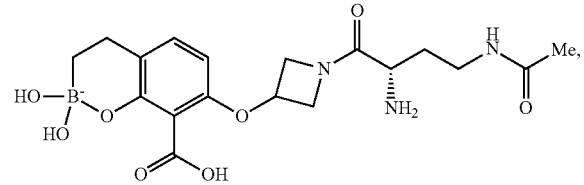

7-{[1-(L-α-asparaginyl)azetidin-3-yl]oxy}-2-hydroxy-3,4-dihydro-2H-1,2-benzoxaborinine-8-carboxylic acid

[Chemical Formula 421]

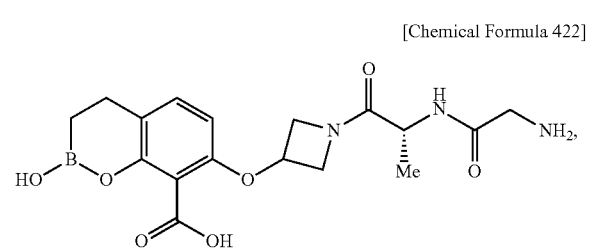 [SMILES: C[C@@H](NC(=O)CN)C(=O)N1CC(Oc2ccc3c(c2C(=O)O)OB(O)CC3)C1]

7-{[1-(glycyl-D-alanyl)azetidin-3-yl]oxy}-2-hydroxy-3,4-dihydro-2H-1,2-benzoxaborinine-8-carboxylic acid

[Chemical Formula 418]

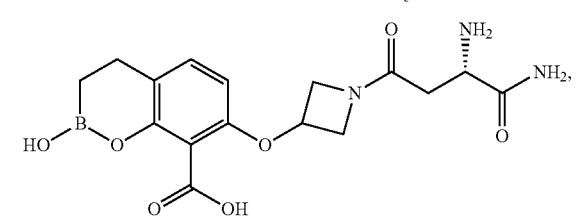

8-{[1-(L-α-asparaginyl)azetidin-3-yl]oxy}-4,4-dihydroxy-5-oxa-4-boranuidabicyclo[4.4.0]deca-1(6),7,9-triene-7-carboxylic acid

[Chemical Formula 422]

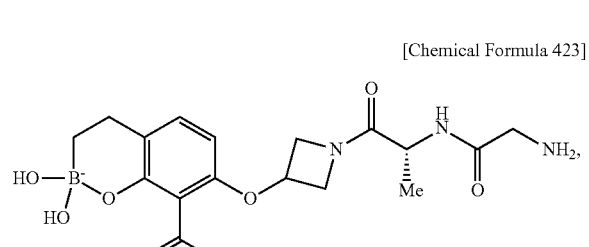

8-{[1-(glycyl-D-alanyl)azetidin-3-yl]oxy}-4,4-dihydroxy-5-oxa-4-boranuidabicyclo[4.4.0]deca-1(6),7,9-triene-7-carboxylic acid

[Chemical Formula 419]

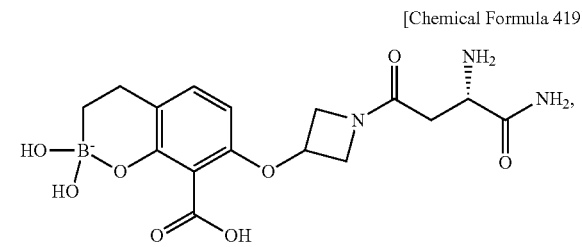

7-{[1-(L-alanyl-L-alanyl)azetidin-3-yl]oxy}-2-hydroxy-3,4-dihydro-2H-1,2-benzoxaborinine-8-carboxylic acid

[Chemical Formula 423]

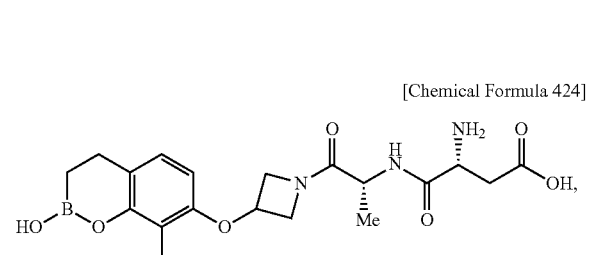

N-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-α-asparagine

[Chemical Formula 420]

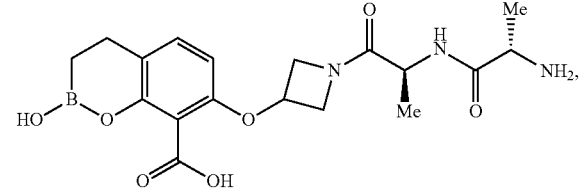

[Chemical Formula 424]

135

N-[(2R)-1-{3-[(7-carboxy-4,4-hydroxy-5-oxa-4-boranuid-abicyclo[4.4.0]deca-1(6),7,9-trien-8-yl)oxy]azetidin-1-yl}-1-oxopropan-2-yl]-D-α-asparagine

[Chemical Formula 425]

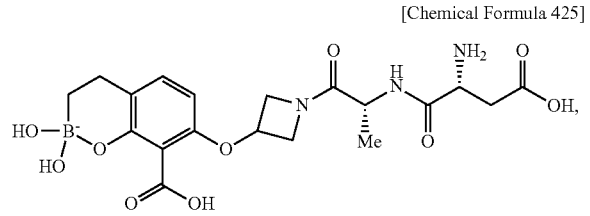

N¹-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-aspartamide

[Chemical Formula 426]

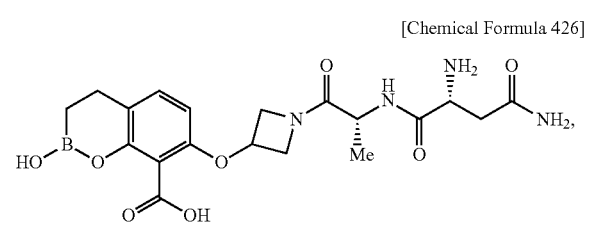 [SMILES: C[C@@H](NC(=O)[C@H](N)CC(N)=O)C(=O)N1CC(Oc2ccc3c(c2C(=O)O)OB(O)CC3)C1]

N¹-[(2R)-1-{3-[(7-carboxy-4,4-hydroxy-5-oxa-4-boranuid-abicyclo[4.4.0]deca-1(6),7,9-trien-8-yl)oxy]azetidin-1-yl}-1-oxopropan-2-yl]-D-aspartamide

[Chemical Formula 427]

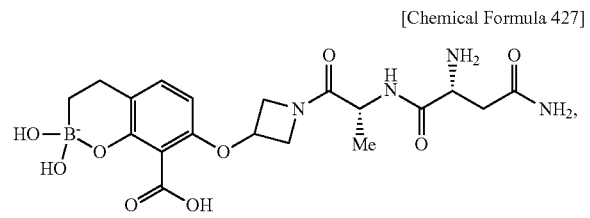 [SMILES: C[C@@H](NC(=O)[C@H](N)CC(N)=O)C(=O)N1CC(Oc2ccc3c(c2C(=O)O)O[B-](O)(O)CC3)C1]

N-[(2R)-1-{3-[(8-carboxy-2-hydroxy-3,4-dihydro-2H-1,2-benzoxaborinine-7-yl}oxy]azetidin-1-yl)-1-oxopropan-2-yl]-D-serinamide

[Chemical Formula 428]

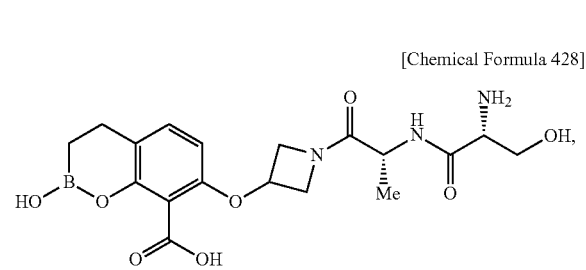 [SMILES: C[C@@H](NC(=O)[C@H](N)CO)C(=O)N1CC(Oc2ccc3c(c2C(=O)O)OB(O)CC3)C1]

136

N-[(2R)-1-{3-[(7-carboxy-4,4-hydroxy-5-oxa-4-boranuid-abicyclo[4.4.0]deca-1(6),7,9-trien-8-yl)oxy]azetidin-1-yl}-1-oxopropan-2-yl]-D-serinamide

[Chemical Formula 429]

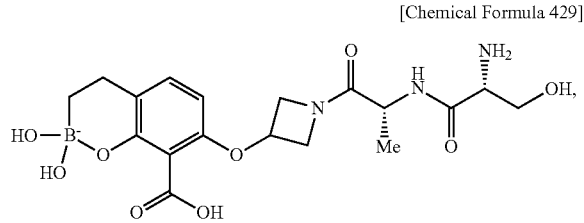 [SMILES: C[C@@H](NC(=O)[C@H](N)CO)C(=O)N1CC(Oc2ccc3c(c2C(=O)O)O[B-](O)(O)CC3)C1]

7-({1-[(3S)-3-amino-3-carboxypropanoyl]azetidin-3-yl}oxy)-2-hydroxy-3,4-dihydro-2H-1,2-benzoxaborinine-8-carboxylic acid

[Chemical Formula 430]

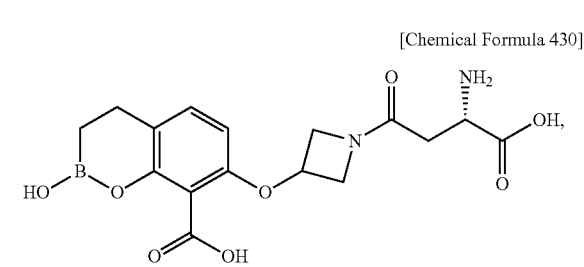

8-({1-[(3S)-3-amino-3-carboxypropanoyl]azetidin-3-yl}oxy)-4,4-dihydroxy-5-oxa-4-boranuidabicyclo[4.4.0]deca-1(6),7,9-triene-7-carboxylic acid

[Chemical Formula 431]

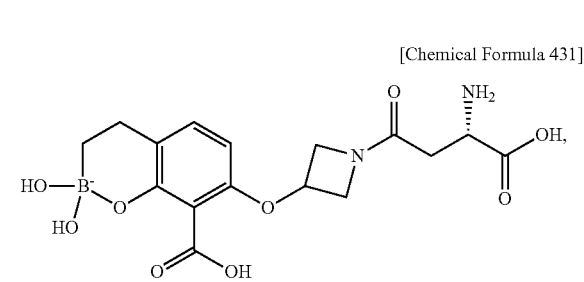

2-hydroxy-7-({1-[(1H-imidazol-4-yl)(methylamino)acetyl]azetidin-3-yl}oxy)-3,4-dihydro-2H-1,2-benzoxaborinine-8-carboxylic acid

[Chemical Formula 432]

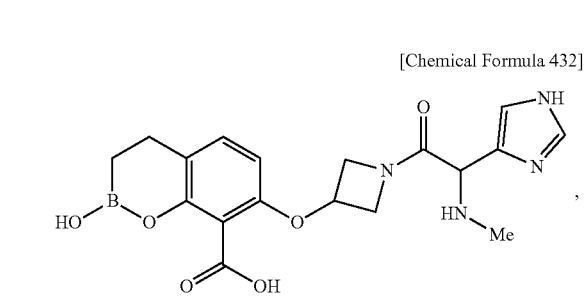 [SMILES: CNC(C(=O)N1CC(Oc2ccc3c(c2C(=O)O)OB(O)CC3)C1)c1c[nH]cn1]

137

4,4-dihydroxy-8-({1-[(1H-imidazol-4-yl)(methylamino)
acetyl]azetidin-3-yl}oxy)-5-oxa-4-boranuidabicyclo
[4.4.0]deca-1(6), 7,9-triene-7-carboxylic acid

[Chemical Formula 433]

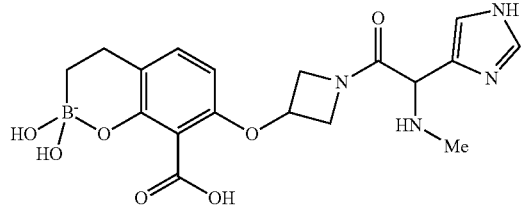

2-hydroxy-7-({1-[(1H-imidazol-4-yl)(methylamino)acetyl]
azetidin-3-yl}oxy)-3,4-dihydro-2H-1,2-benzoxaborinine-
8-carboxylic acid

[Chemical Formula 434]

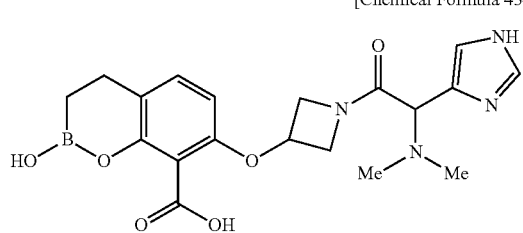

4,4-dihydroxy-8-({1-[(1H-imidazol-4-yl)(methylamino)
acetyl]azetidin-3-yl}oxy)-5-oxa-4-boranuidabicyclo
[4.4.0]deca-1(6), 7,9-triene-7-carboxylic acid

[Chemical Formula 435]

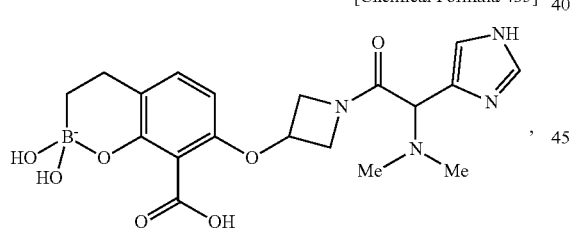

2-hydroxy-7-{[1-(2-methyl-D-seryl)azetidin-3-yl]oxy}-3,4-
dihydro-2H-1,2-benzoxaborinine-8-carboxylic acid

[Chemical Formula 436]

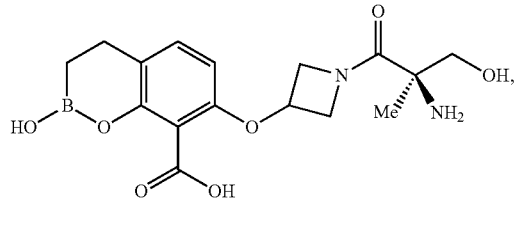

138

4,4-dihydroxy-8-{[1-(2-methyl-D-seryl)azetidin-3-yl]oxy}-
5-oxa-4-boranuidabicyclo[4.4.0]deca-1(6),7,9-triene-7-
carboxylic acid

[Chemical Formula 437]

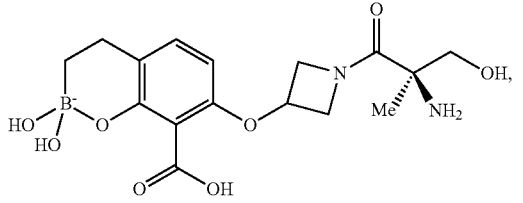

2-hydroxy-7-{[1-(2-methyl-L-seryl)azetidin-3-yl]oxy}-3,4-
dihydro-2H-1,2-benzoxaborinine-8-carboxylic acid

[Chemical Formula 438]

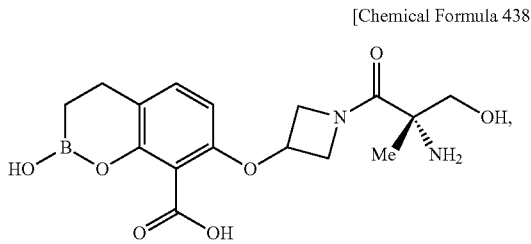

4,4-dihydroxy-8-{[1-(2-methyl-L-seryl)azetidin-3-yl]oxy}-
5-oxa-4-boranuidabicyclo[4.4.0]deca-1(6),7,9-triene-7-
carboxylic acid

[Chemical Formula 439]

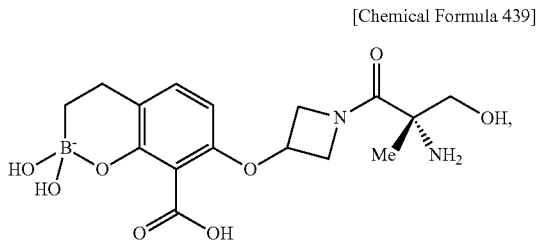 [SMILES: C[C@](N)(CO)C(=O)N1CC(Oc2ccc3c(c2C(=O)O)O[B-](O)(O)CC3)C1]

2-hydroxy-7-({1-[(3-oxopiperazin-2-yl)acetyl]azetidin-3-
yl}oxy)-3,4-dihydro-2H-1,2-benzoxaborinine-8-carbox-
ylic acid

[Chemical Formula 440]

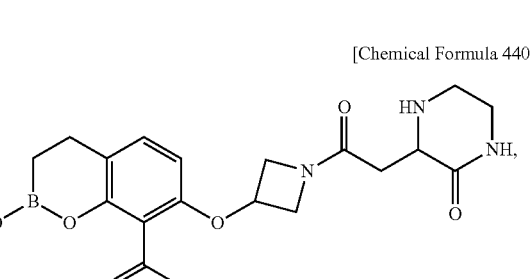

4,4-dihydroxy-8-({1-[(3-oxopiperazin-2-yl)acetyl]azetidin-3-yl}oxy)-5-oxa-4-boranuidabicyclo[4.4.0]deca-l(6),7,9-triene-7-carboxylic acid

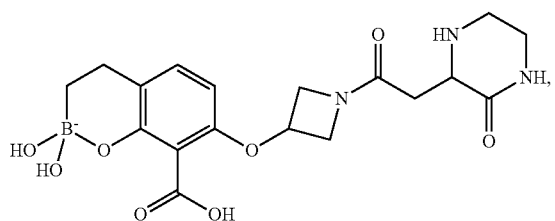

7-({1-[(3S)-3-amino-5-carboxypentanoyl]azetidin-3-yl}oxy)-2-hydroxy-3,4-dihydro-2H-1,2-benzoxaborinine-8-carboxylic acid

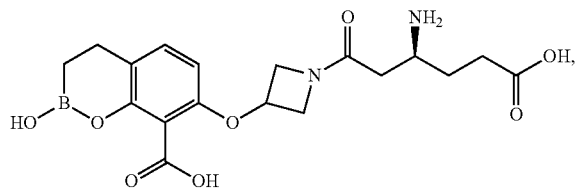

8-({1-[(3S)-3-amino-5-carboxypentanoyl]azetidin-3-yl}oxy)-4,4-dihydroxy-5-oxa-4-boranuidabicyclo[4.4.0]deca-l(6),7,9-triene-7-carboxylic acid

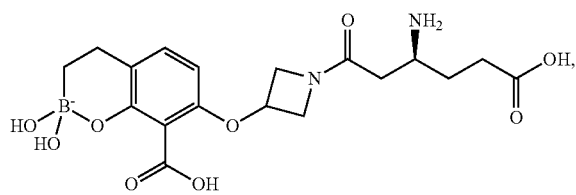

7-({1-[(3R)-3-amino-3-carboxypropanoyl]azetidin-3-yl}oxy)-2-hydroxy-3,4-dihydro-2H-1,2-benzoxaborinine-8-carboxylic acid

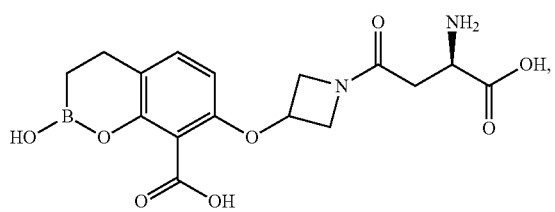

8-({1-[(3R)-3-amino-3-carboxypropanoyl]azetidin-3-yl}oxy)-4,4-dihydroxy-5-oxa-4-boranuidabicyclo[4.4.0]deca-l(6),7,9-triene-7-carboxylic acid

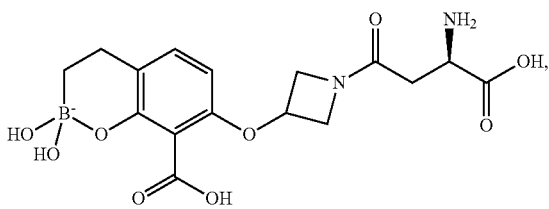

7-({1-[(4R)-4-amino-4-carboxybutanoyl]azetidin-3-yl}oxy)-2-hydroxy-3,4-dihydro-2H-1,2-benzoxaborinine-8-carboxylic acid

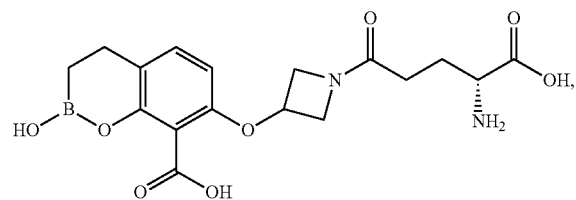

8-({1-[(3R)-3-amino-3-carboxypropanoyl]azetidin-3-yl}oxy)-4,4-dihydroxy-5-oxa-4-boranuidabicyclo[4.4.0]deca-l(6),7,9-triene-7-carboxylic acid

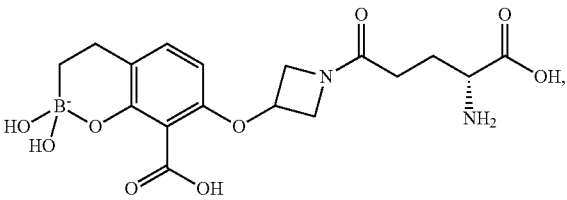

7-({1-[(3S)-3,6-diamino-6-oxohexanoyl]azetidin-3-yl}oxy)-2-hydroxy-3,4-dihydro-2H-1,2-benzoxaborinine-8-carboxylic acid

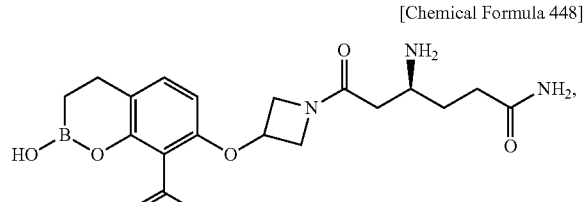

141

8-({1-[(3S)-3,6-diamino-6-oxohexanoyl]azetidin-3-yl}oxy)-4,4-dihydroxy-5-oxa-4-boranuidabicyclo[4.4.0]deca-1(6),7,9-triene-7-carboxylic acid

[Chemical Formula 449]

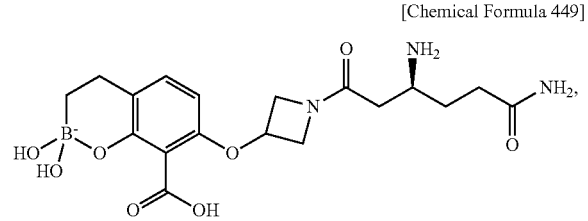

7-{[1-(D-α-asparaginyl)azetidin-3-yl]oxy}-2-hydroxy-3,4-dihydro-2H-1,2-benzoxaborinine-8-carboxylic acid

[Chemical Formula 450]

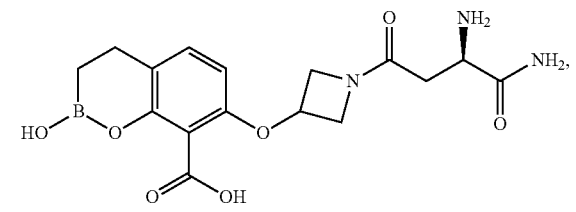

8-{[1-(D-α-asparaginyl)azetidin-3-yl]oxy}-4,4-dihydroxy-5-oxa-4-boranuidabicyclo[4.4.0]deca-1(6),7,9-triene-7-carboxylic acid

[Chemical Formula 451]

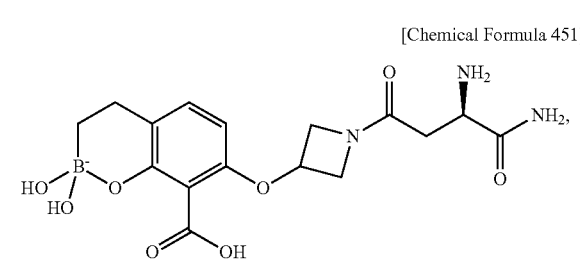 [SMILES: N[C@H](CC(=O)N1CC(Oc2ccc3c(c2C(=O)O)O[B-](O)(O)CC3)C1)C(=O)O]

7-{[1-(D-α-glutaminyl)azetidin-3-yl]oxy}-2-hydroxy-3,4-dihydro-2H-1,2-benzoxaborinine-8-carboxylic acid

[Chemical Formula 452]

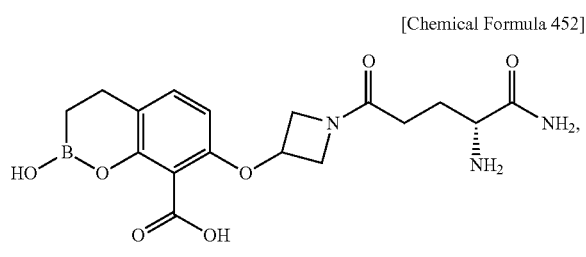 [SMILES: NC(=O)[C@H](N)CCC(=O)N1CC(Oc2ccc3c(c2C(=O)O)OB(O)CC3)C1]

142

8-{[1-(D-α-glutaminyl)azetidin-3-yl]oxy}-4,4-dihydroxy-5-oxa-4-boranuidabicyclo[4.4.0]deca-1(6),7,9-triene-7-carboxylic acid

[Chemical Formula 453]

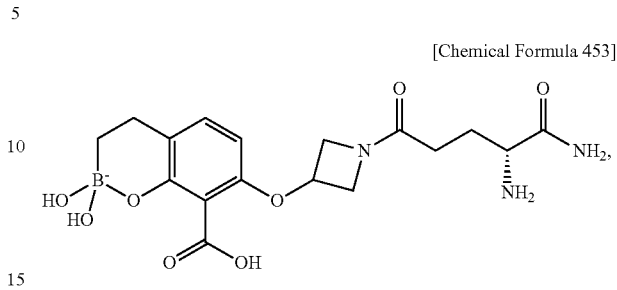

7-({1-[(4S)-4-amino-4-carboxybutanoyl]azetidin-3-yl}oxy)-2-hydroxy-3,4-dihydro-2H-1,2-benzoxaborinine-8-carboxylic acid

[Chemical Formula 454]

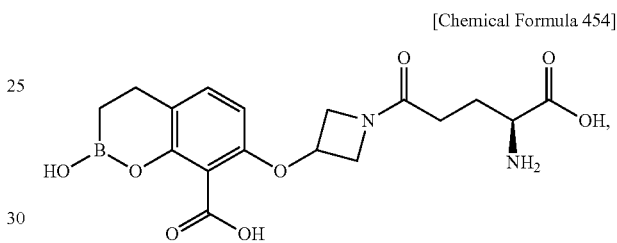

8-({1-[(4S)-4-amino-4-carboxybutanoyl]azetidin-3-yl}oxy)-4,4-dihydroxy-5-oxa-4-boranuidabicyclo[4.4.0]deca-1(6),7,9-triene-7-carboxylic acid

[Chemical Formula 455]

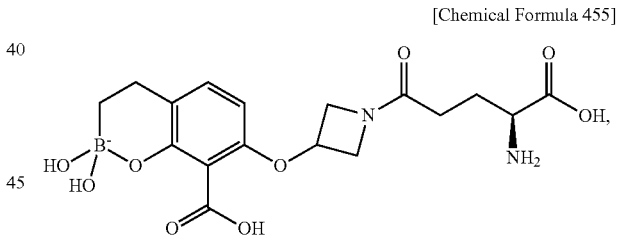

7-{[1-(L-α-glutaminyl)azetidin-3-yl]oxy}-2-hydroxy-3,4-dihydro-2H-1,2-benzoxaborinine-8-carboxylic acid

[Chemical Formula 456]

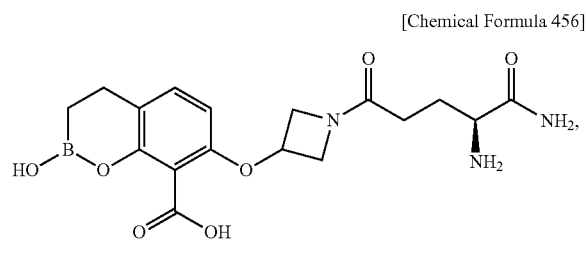 [SMILES: NC(=O)[C@@H](N)CCC(=O)N1CC(Oc2ccc3c(c2C(=O)O)OB(O)CC3)C1]

8-{[1-(L-α-glutaminyl)azetidin-3-yl]oxy}-4,4-dihydroxy-5-oxa-4-boranuidabicyclo[4.4.0]deca-1(6),7,9-triene-7-carboxylic acid

[Chemical Formula 457]

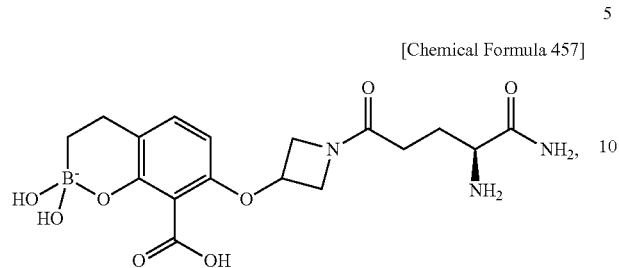

2-hydroxy-7-[(1-D-threonylazetidin-3-yl)oxy]-3,4-dihydro-2H-1,2-benzoxaborinine-8-carboxylic acid

[Chemical Formula 458]

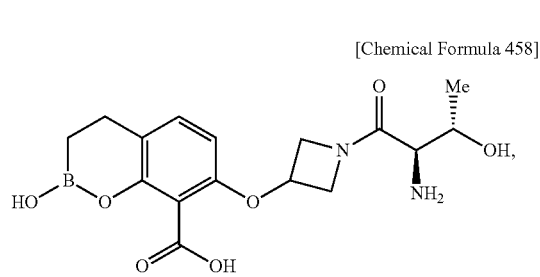 [SMILES: C[C@H](O)[C@@H](N)C(=O)N1CC(Oc2ccc3c(c2C(=O)O)OB(O)CC3)C1]

4,4-dihydroxy-8-[(1-D-threonylazetidin-3-yl)oxy]-5-oxa-4-boranuidabicyclo[4.4.0]deca-1(6),7,9-triene-7-carboxylic acid

[Chemical Formula 459]

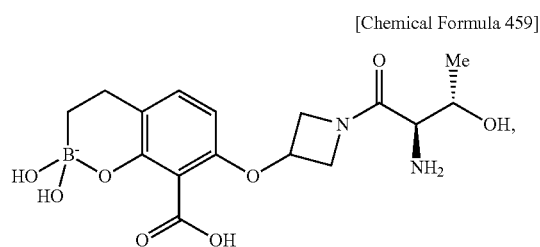 [SMILES: C[C@H](O)[C@@H](N)C(=O)N1CC(Oc2ccc3c(c2C(=O)O)O[B-](O)(O)CC3)C1]

2-hydroxy-7-[(1-L-threonylazetidin-3-yl)oxy]-3,4-dihydro-2H-1,2-benzoxaborinine-8-carboxylic acid

[Chemical Formula 460]

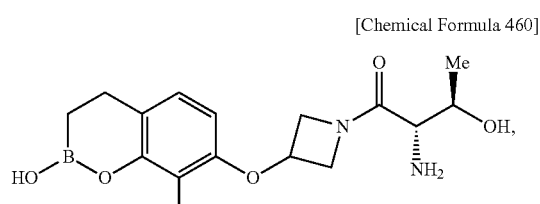

4,4-dihydroxy-8-[(1-L-threonylazetidin-3-yl)oxy]-5-oxa-4-boranuidabicyclo[4.4.0]deca-1(6),7,9-triene-7-carboxylic

[Chemical Formula 461]

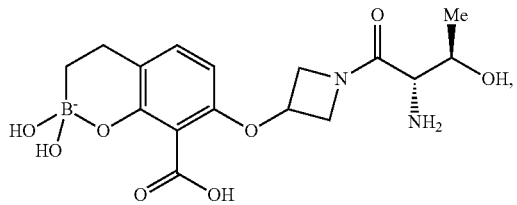

[Item 55]
A compound represented by formula (11):

[Chemical Formula 462]

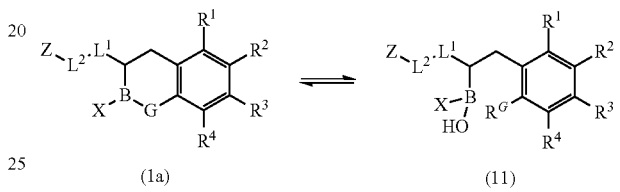

or a pharmaceutically acceptable salt thereof, wherein $R^G$ is a hydroxyl group, a thiol group, or $-NHR^{a1}$, $R^{a1}$, Z, $L^1$, $L^2$, X, $R^1$, $R^2$, $R^3$, and $R^4$ are defined the same as the definition according to item 1, and formula (1a) is defined the same as item 1.

[Item 56]
The compound or the pharmaceutically acceptable salt thereof according to item 55, wherein the compound of formula (11) is represented by formula (12):

[Chemical Formula 463]

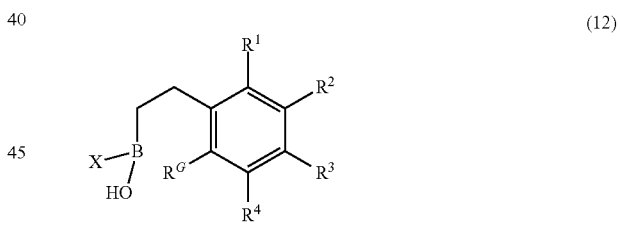

wherein X, $R^1$, $R^2$, $R^3$, and $R^4$ are defined the same as the definition according to any one of the preceding items.

[Item 57]
The compound or the pharmaceutically acceptable salt thereof according to item 55 or 56, wherein the compound of formula (12) is represented by formula (13):

[Chemical Formula 464]

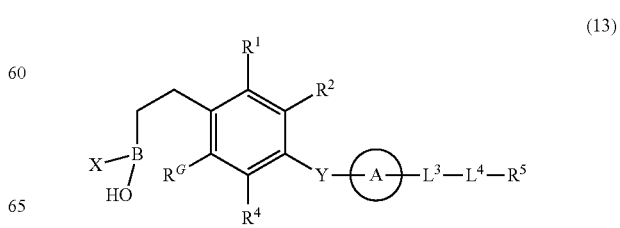

wherein X, Y, ring A, $L^3$, $L^4$, $R^1$, $R^2$, $R^4$, and $R^5$ are defined the same as the definition according to any one of the preceding items.

[Item 58]

The compound or the pharmaceutically acceptable salt thereof according to any one of items 55 to 57, wherein X and $R^G$ are hydroxyl groups, $R^4$ is a carboxyl group, and ring A is an optionally substituted 4- to 6-membered nitrogen-containing non-aryl heterocycle.

[Item 59]

The compound or the pharmaceutically acceptable salt thereof according to any one of items 55 to 58, wherein the compound of formula (13) is represented by formula (14):

[Chemical Formula 465]

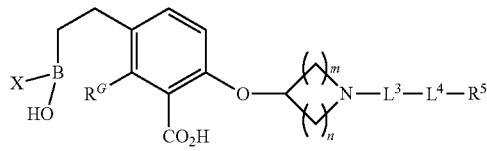

(14)

wherein X, $L^3$, $L^4$, m, n, and $R^5$ are defined the same as the definition according to any one of the preceding items.

[Item 60]

The compound or the pharmaceutically acceptable salt thereof according to any one of items 55 to 59, wherein $R^G$ is a hydroxyl group or a thiol group.

[Item 61]

The compound or the pharmaceutically acceptable salt thereof according to any one of items 55 to 60, wherein $R^G$ is a hydroxyl group.

[Item 62]

The compound or the pharmaceutically acceptable salt thereof according to any one of items 55 to 61, wherein X is a hydroxyl group or a $C_{1-6}$ alkoxy group.

[Item 63]

The compound or the pharmaceutically acceptable salt thereof according to any one of items 55 to 62, wherein X is a hydroxyl group.

[Item 64]

The compound or the pharmaceutically acceptable salt thereof according to any one of items 55 to 63, wherein m is 1 or 2, n is 1 or 2, and m+n is 2 or 3.

[Item 65]

The compound or the pharmaceutically acceptable salt thereof according to any one of items 55 to 64, wherein m is 1, and n is 1.

[Item 66]

The compound or the pharmaceutically acceptable salt thereof according to any one of items 55 to 65, wherein $L^3$ is defined the same as the definition according to any one of the preceding items.

[Item 67]

The compound or the pharmaceutically acceptable salt thereof according to any one of items 55 to 66, wherein $L^4$ and $R^5$ are defined the same as the definitions according to any one of the preceding items.

[Item 68]

The compound or the pharmaceutically acceptable salt thereof according to item 55, selected from the group consisting of the following compounds:

6-[(1-acetylazetidin-3-yl)oxy]-3-(2-boronoethyl)-2-hydroxybenzoic acid

[Chemical Formula 466]

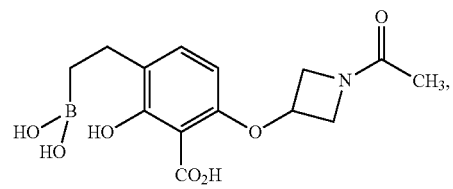

3-(2-boronoethyl)-2-hydroxy-6-({1-[(1H-imidazol-5-yl)acetyl]azetidin-3-yl}oxy)benzoic acid

[Chemical Formula 467]

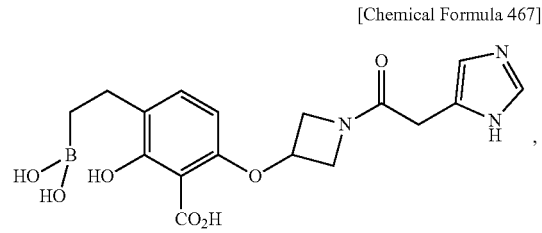 [SMILES: O=C(O)c1c(OC2CN(C(=O)Cc3cnc[nH]3)C2)ccc(CCB(O)O)c1O]

3-(2-boronoethyl)-2-hydroxy-6-{[1-(methanesulfonyl)azetidin-3-yl]oxy}benzoic acid

[Chemical Formula 468]

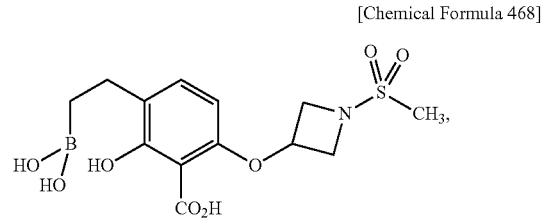 [SMILES: CS(=O)(=O)N1CC(Oc2ccc(CCB(O)O)c(O)c2C(=O)O)C1]

6-({1-[(2R)-2-amino-2-(4-hydroxyphenyl)acetyl]azetidin-3-yl}oxy)-3-(2-boronoethyl)-2-hydroxybenzoic acid

[Chemical Formula 469]

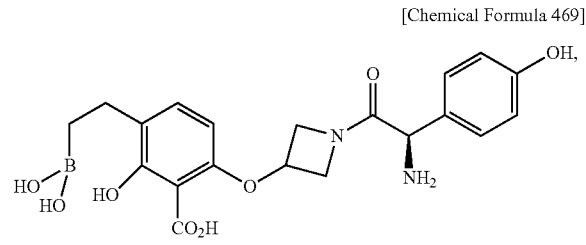 [SMILES: N[C@@H](C(=O)N1CC(Oc2ccc(CCB(O)O)c(O)c2C(=O)O)C1)c1ccc(O)cc1]

147

6-({1-[(2-amino-1,3-thiazol-4-yl)(methoxyimino)acetyl]azetidin-3-yl}oxy)-3-(2-boronoethyl)-2-hydroxybenzoic acid

[Chemical Formula 470]

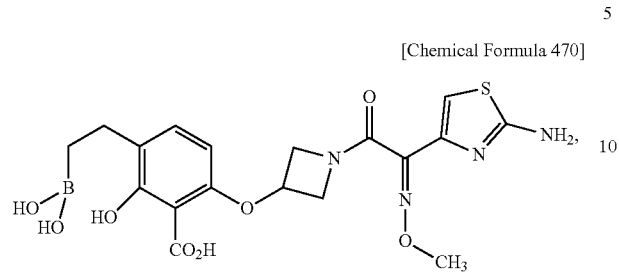

3-(2-boronoethyl)-2-hydroxy-6-{[1-(pyridine-2-carbonyl)azetidin-3-yl]oxy}benzoic acid

[Chemical Formula 471]

3-(2-boronoethyl)-2-hydroxy-6-({1-[(methylsulfanyl)acetyl]azetidin-3-yl}oxy)benzoic acid

[Chemical Formula 472]

3-(2-boronoethyl)-2-hydroxy-6-{[1-(1H-1,2,4-triazole-3-carbonyl)azetidin-3-yl]oxy}benzoic acid

[Chemical Formula 473]

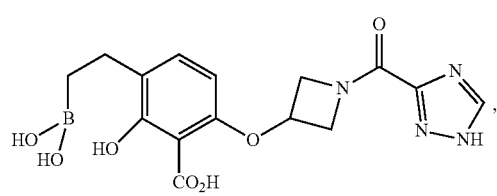

148

3-(2-boronoethyl)-2-hydroxy-6-{[1-(1-oxido-2-pyridinylcarbonyl)azetidin-3-yl]oxy}benzoic acid

[Chemical Formula 474]

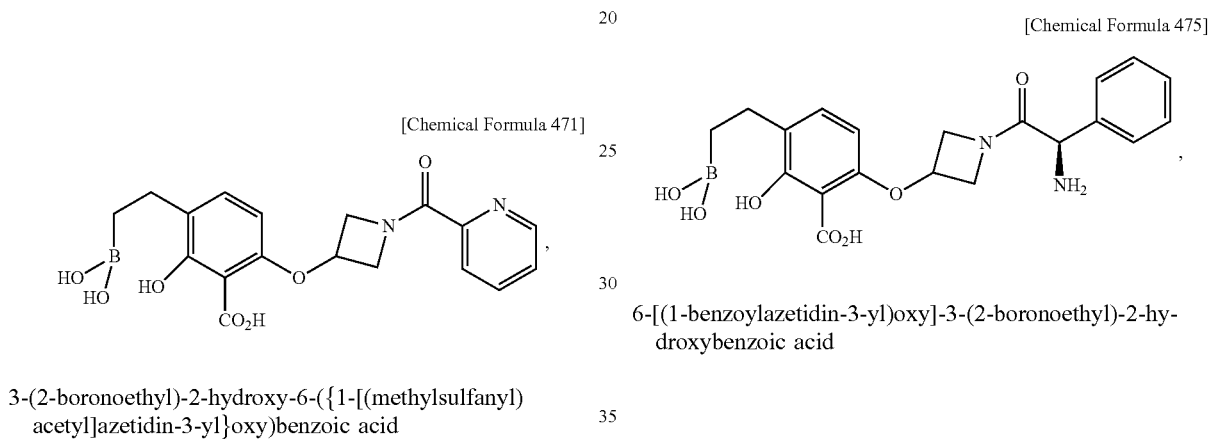

6-({1-[(2R)-2-amino-2-phenylacetyl]azetidin-3-yl}oxy)-3-(2-boronoethyl)-2-hydroxybenzoic acid

[Chemical Formula 475]

6-[(1-benzoylazetidin-3-yl)oxy]-3-(2-boronoethyl)-2-hydroxybenzoic acid

[Chemical Formula 476]

3-(2-boronoethyl)-2-hydroxy-6-{[1-(pyridine-3-carbonyl)azetidin-3-yl]oxy}benzoic acid

[Chemical Formula 477]

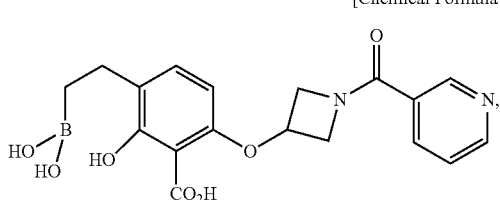

3-(2-boronoethyl)-2-hydroxy-6-({1-[(pyridin-2-yl)acetyl]azetidin-3-yl}oxy)benzoic acid 3-(2-boronoethyl)-2-hydroxy-6-({1-[(4-hydroxyphenyl)acetyl]azetidin-3-yl}oxy)benzoic acid

[Chemical Formula 478]

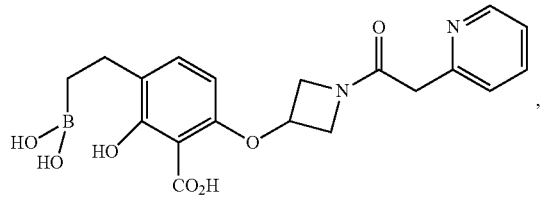

[Chemical Formula 482]

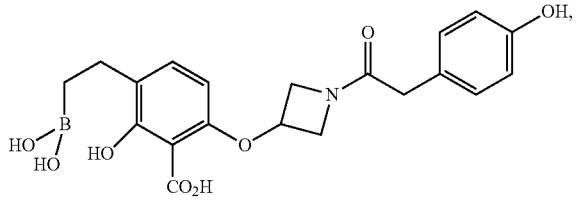

3-(2-boronoethyl)-2-hydroxy-6-({1-[(pyridin-3-yl)acetyl]azetidin-3-yl}oxy)benzoic acid 3-(2-boronoethyl)-2-hydroxy-6-({1-[(1H-1,2,4-triazol-1-yl)acetyl]azetidin-3-yl}oxy)benzoic acid

[Chemical Formula 479]

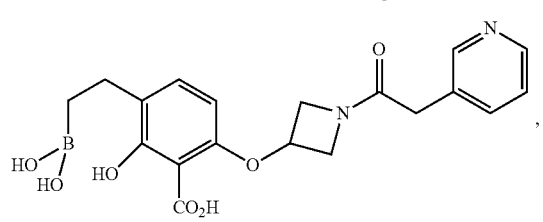

[Chemical Formula 483]

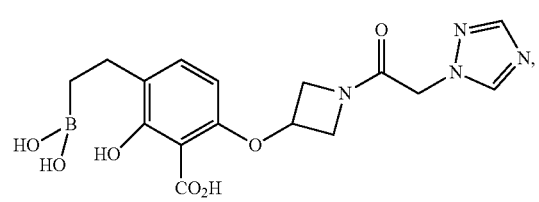

6-({1-[(2S)-2-amino-2-phenylacetyl]azetidin-3-yl}oxy)-3-(2-boronoethyl)-2-hydroxybenzoic acid 6-({1-[amino(1H-imidazol-5-yl)acetyl]azetidin-3-yl}oxy)-3-(2-boronoethyl)-2-hydroxybenzoic acid

[Chemical Formula 480]

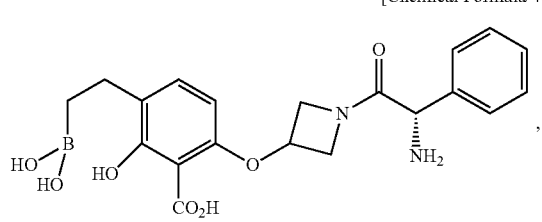

[Chemical Formula 484]

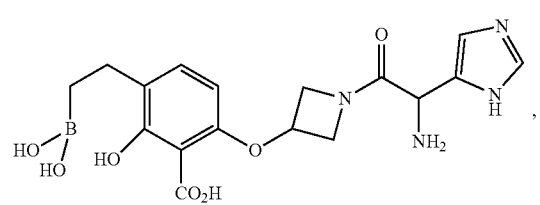

3-(2-boronoethyl)-2-hydroxy-6-({1-[(pyridin-4-yl)acetyl]azetidin-3-yl}oxy)benzoic acid 3-(2-boronoethyl)-2-hydroxy-6-{[1-(phenylacetyl)azetidin-3-yl]oxy}benzoic acid

[Chemical Formula 481]

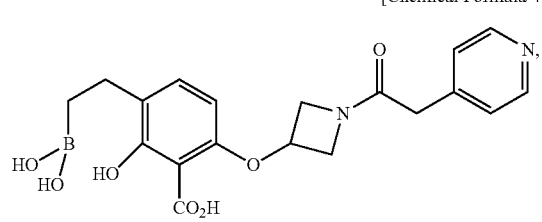

[Chemical Formula 485]

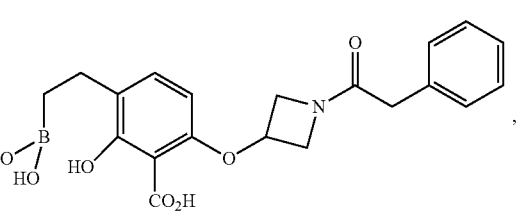

151

3-(2-boronoethyl)-2-hydroxy-6-{[1-(3-phenylpropanoyl)azetidin-3-yl]oxy}benzoic acid

[Chemical Formula 486]

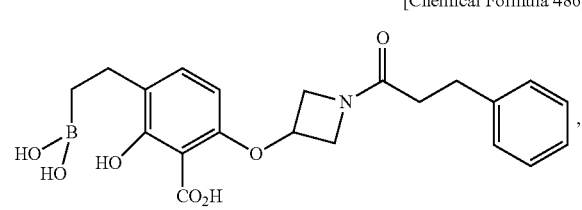

3-(2-boronoethyl)-2-hydroxy-6-({1-[(1H-imidazol-1-yl)acetyl]azetidin-3-yl}oxy)benzoic acid

[Chemical Formula 487]

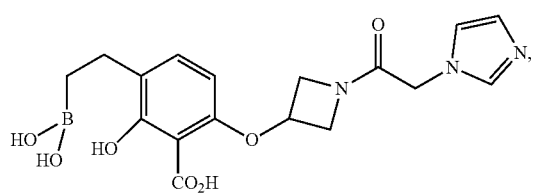

3-(2-boronoethyl)-2-hydroxy-6-({1-[(1H-tetrazol-1-yl)acetyl]azetidin-3-yl}oxy)benzoic acid

[Chemical Formula 488]

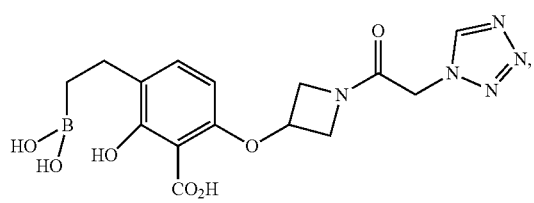

3-(2-boronoethyl)-2-hydroxy-6-({1-[(2H-tetrazol-5-yl)acetyl]azetidin-3-yl}oxy)benzoic acid

[Chemical Formula 489]

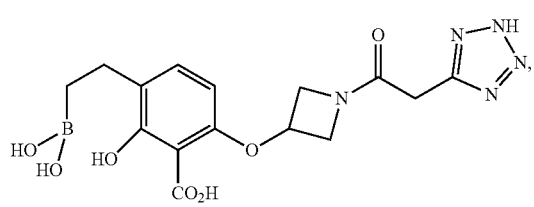

152

3-(2-boronoethyl)-2-hydroxy-6-[(1-D-phenylalanylazetidin-3-yl)oxy]benzoic acid

[Chemical Formula 490]

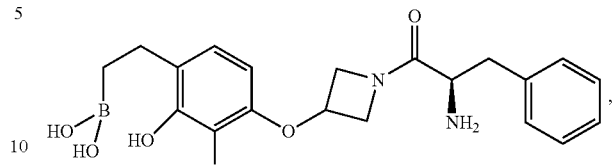

3-(2-boronoethyl)-2-hydroxy-6-[(1-D-tyrosylazetidin-3-yl)oxy]benzoic acid

[Chemical Formula 491]

3-(2-boronoethyl)-6-[(1-D-histidylazetidin-3-yl)oxy]-2-hydroxybenzoic acid

[Chemical Formula 492]

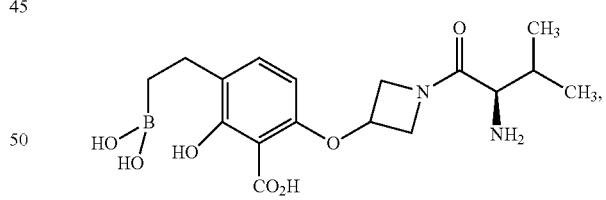

3-(2-boronoethyl)-2-hydroxy-6-[(1-D-valylazetidin-3-yl)oxy]benzoic acid

[Chemical Formula 493]

3-(2-boronoethyl)-6-[(1-L-histidylazetidin-3-yl)oxy]-2-hydroxybenzoic acid

[Chemical Formula 494]

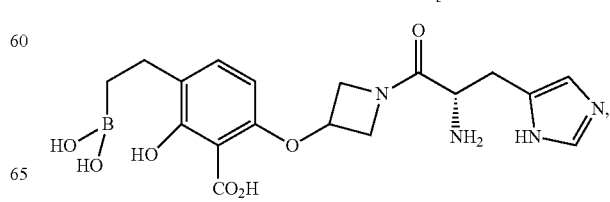

3-(2-boronoethyl)-6-[(1-{(2R)-2-[(4-ethyl-2,3-dioxopiperazine-1-carbonyl)amino]-2-phenylacetyl}azetidin-3-yl)oxy]-2-hydroxybenzoic acid 3-(2-boronoethyl)-6-{[1-(3,4-dihydroxybenzoyl)azetidin-3-yl]oxy}-2-hydroxybenzoic acid

[Chemical Formula 495]

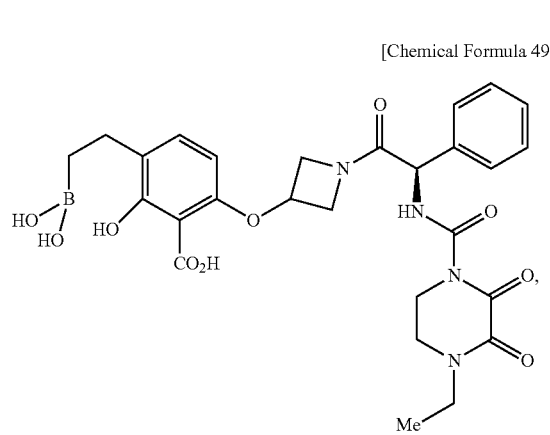

[Chemical Formula 499]

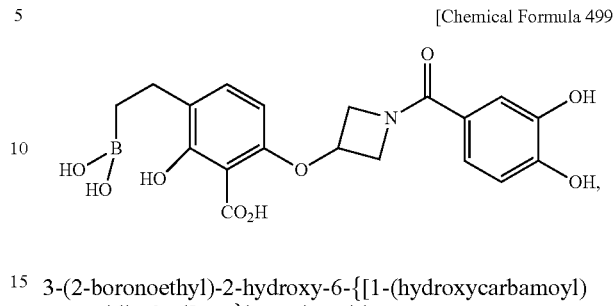

3-(2-boronoethyl)-2-hydroxy-6-{[1-(hydroxycarbamoyl)azetidin-3-yl]oxy}benzoic acid 3-(2-boronoethyl)-2-hydroxy-6-[(1-D-prolylazetidin-3-yl)oxy]benzoic acid

[Chemical Formula 500]

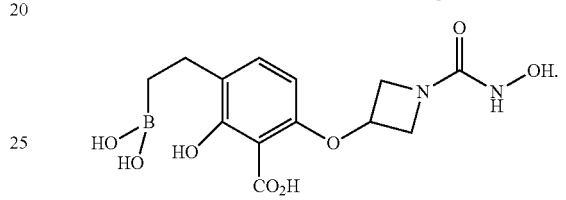

[Chemical Formula 496]

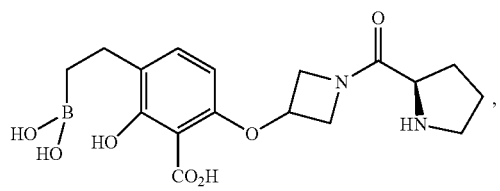

[Item 69]

The compound or the pharmaceutically acceptable salt thereof according to item 55, selected from the group consisting of the following compounds:

6-({1-[(2R)-2-amino-2-(1H-imidazol-4-yl)acetyl]azetidin-3-yl}oxy)-3-(2-boronoethyl)-2-hydroxybenzoic acid 3-(2-boronoethyl)-2-hydroxy-6-[(1-L-prolylazetidin-3-yl)oxy]benzoic acid

[Chemical Formula 501]

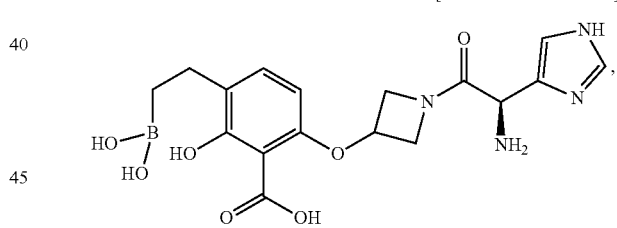

[Chemical Formula 497]

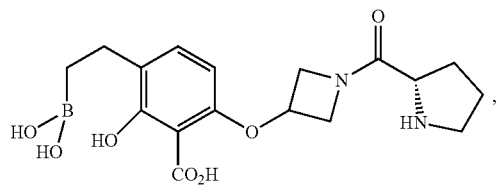

6-({1-[(2S)-2-amino-2-(1H-imidazol-4-yl)acetyl]azetidin-3-yl}oxy)-3-(2-boronoethyl)-2-hydroxybenzoic acid 6-[(1-{[4-(2-aminoethyl)-1H-imidazol-1-yl]acetyl}azetidin-3-yl)oxy]-3-(2-boronoethyl)-2-hydroxybenzoic acid

[Chemical Formula 498]

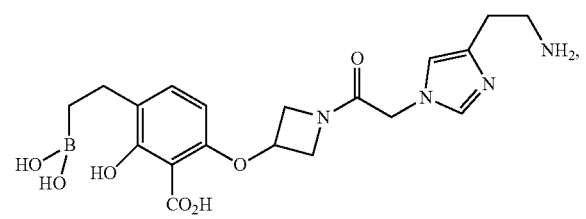

[Chemical Formula 502]

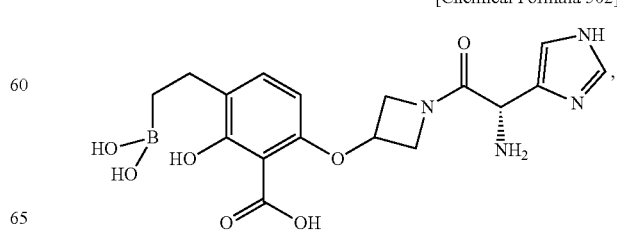

6-({1-[amino(1-methyl-1H-imidazol-4-yl)acetyl]azetidin-3-yl}oxy)-3-(2-boronoethyl)-2-hydroxybenzoic acid 6-({(3S)-1-[amino(1H-imidazol-4-yl)acetyl]pyrrolidin-3-yl}oxy)-3-(2-boronoethyl)-2-hydroxybenzoic acid

[Chemical Formula 503]

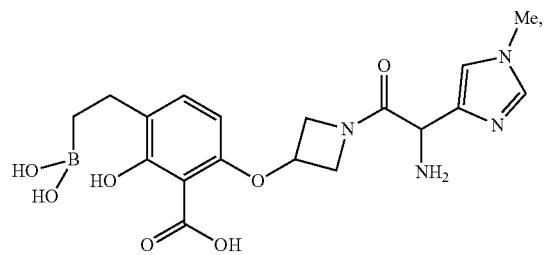

3-(2-boronoethyl)-2-hydroxy-6-{[1-(4H-1,2,4-triazole-3-sulfonyl)azetidin-3-yl]oxy}benzoic acid

[Chemical Formula 507]

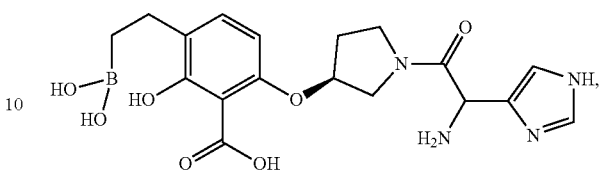

3-(2-boronoethyl)-2-hydroxy-6-{[1-(4-hydroxy-6-methylpyridine-3-carbonyl)azetidin-3-yl]oxy}benzoic acid

[Chemical Formula 504]

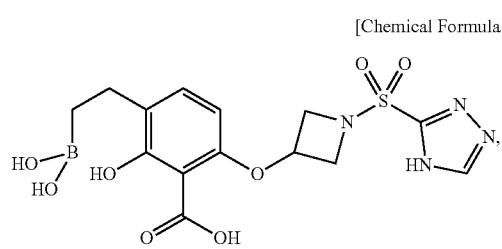

6-({1-[2-amino-2-(1H-imidazol-4-yl)($^2$H)ethanoyl]azetidin-3-yl}oxy)-3-(2-boronoethyl)-2-hydroxybenzoic acid

[Chemical Formula 508]

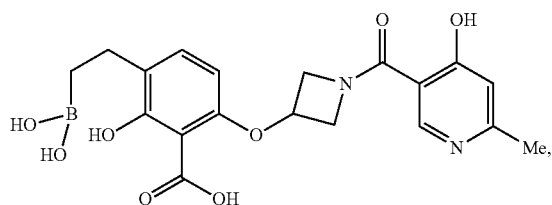

6-({1-[amino(1-methyl-1H-imidazol-5-yl)acetyl]azetidin-3-yl}oxy)-3-(2-boronoethyl)-2-hydroxybenzoic acid

[Chemical Formula 505]

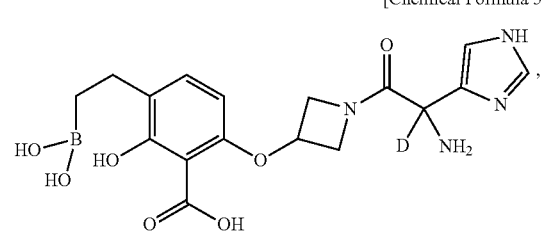

6-({1-[2-amino-2-(1H-imidazol-4-yl)propanoyl]azetidin-3-yl}oxy)-3-(2-boronoethyl)-2-hydroxybenzoic acid

[Chemical Formula 509]

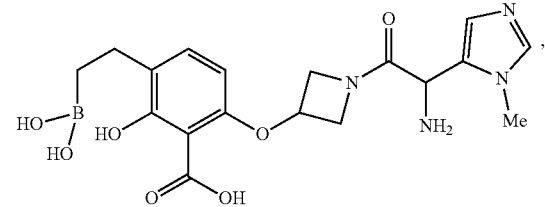

6-[(1-{amino[1-(carboxymethyl)-1H-imidazol-4-yl]acetyl}azetidin-3-yl)oxy]-3-(2-boronoethyl)-2-hydroxybenzoic acid

[Chemical Formula 506]

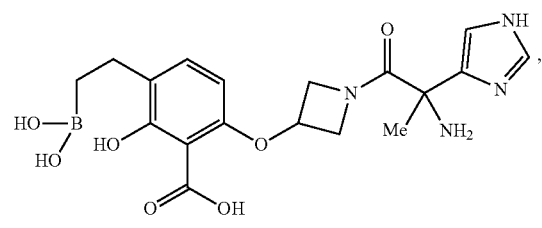

[Chemical Formula 510]

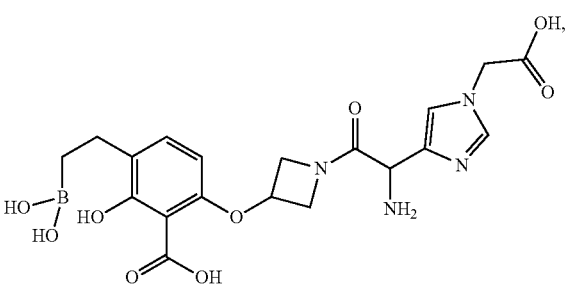

157

6-[(1-{amino[1-(2-amino-2-oxoethyl)-1H-imidazol-4-yl]acetyl}azetidin-3-yl)oxy]-3-(2-boronoethyl)-2-hydroxybenzoic acid

[Chemical Formula 511]

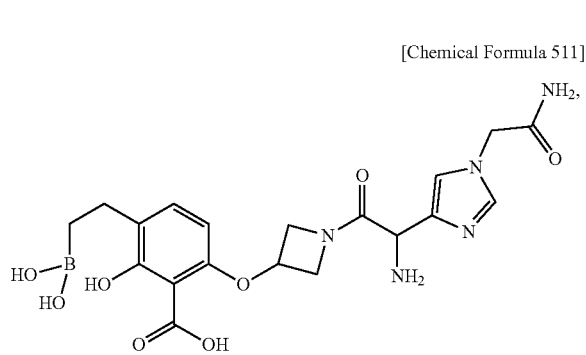 [SMILES: NC(=O)Cn1cnc(C(N)C(=O)N2CC(Oc3ccc(CCB(O)O)c(O)c3C(=O)O)C2)c1]

6-({1-[amino(pyridin-3-yl)acetyl]azetidin-3-yl}oxy)-3-(2-boronoethyl)-2-hydroxybenzoic acid

[Chemical Formula 512]

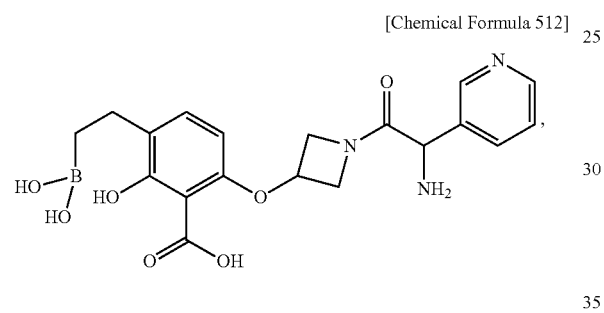

6-({1-[amino(1-methyl-1H-pyrazol-4-yl)acetyl]azetidin-3-yl}oxy)-3-(2-boronoethyl)-2-hydroxybenzoic acid

[Chemical Formula 513]

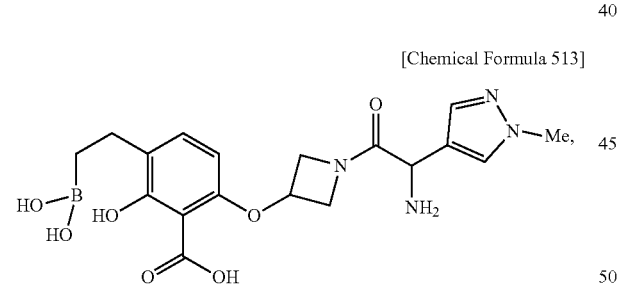

6-({(3R)-1-[amino(1H-imidazol-4-yl)acetyl]pyrrolidin-3-yl}oxy)-3-(2-boronoethyl)-2-hydroxybenzoic acid

[Chemical Formula 514]

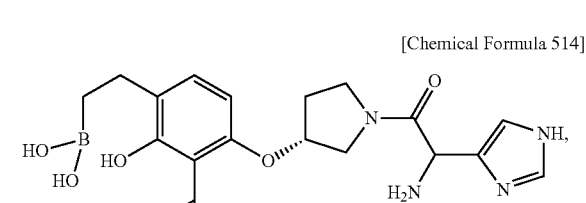

158

6-({1-[amino(2-methyl-1H-imidazol-4-yl)acetyl]azetidin-3-yl}oxy)-3-(2-boronoethyl)-2-hydroxybenzoic acid

[Chemical Formula 515]

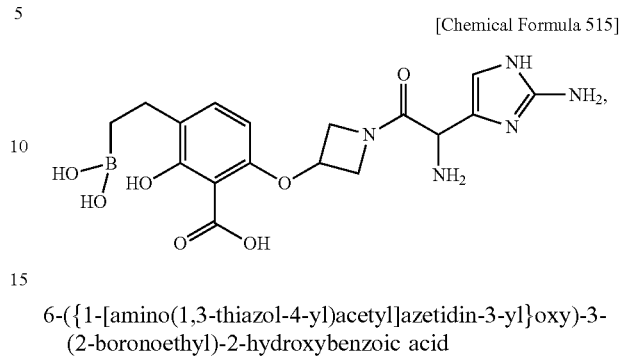

6-({1-[amino(1,3-thiazol-4-yl)acetyl]azetidin-3-yl}oxy)-3-(2-boronoethyl)-2-hydroxybenzoic acid

[Chemical Formula 516]

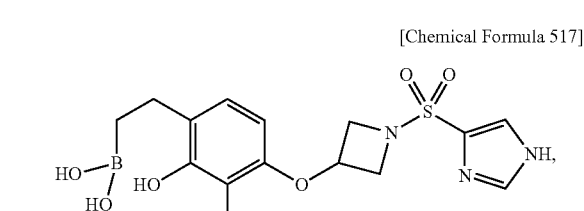

3-(2-boronoethyl)-2-hydroxy-6-{[1-(1H-imidazole-4-sulfonyl)azetidin-3-yl]oxy}benzoic acid

[Chemical Formula 517]

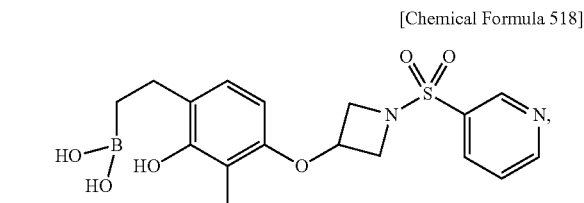

3-(2-boronoethyl)-2-hydroxy-6-{[1-(pyridine-3-sulfonyl)azetidin-3-yl]oxy}benzoic acid

[Chemical Formula 518]

3-(2-boronoethyl)-2-hydroxy-6-{[1-(1-oxo-1λ⁵-pyridine-2-sulfonyl)azetidin-3-yl]oxy}benzoic acid 6-[(1-{[1-(2-aminoethyl)-1H-imidazol-4-yl]acetyl}azetidin-3-yl)oxy]-3-(2-boronoethyl)-2-hydroxybenzoic acid

[Chemical Formula 519]

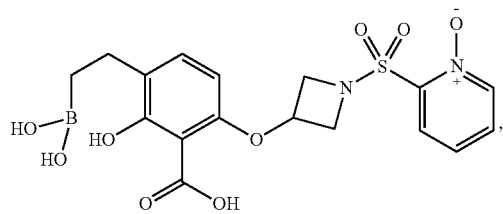

[Chemical Formula 523]

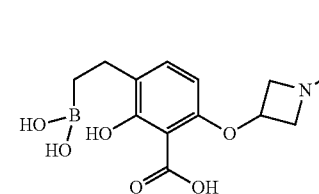

6-({1-[(2-amino-1,3-thiazol-4-yl)acetyl]azetidin-3-yl}oxy)-3-(2-boronoethyl)-2-hydroxybenzoic acid 3-(2-boronoethyl)-2-hydroxy-6-{[1-(1H-imidazole-4-carbonyl)azetidin-3-yl]oxy}benzoic acid

[Chemical Formula 520]

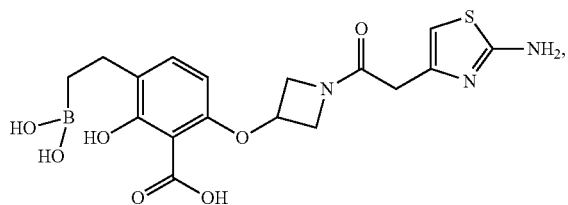

[Chemical Formula 524]

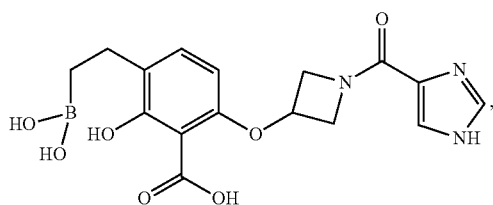

6-{[1-(2-amino-1,3-thiazole-4-carbonyl)azetidin-3-yl]oxy}-3-(2-boronoethyl)-2-hydroxybenzoic acid 3-(2-boronoethyl)-2-hydroxy-6-{[1-(1H-imidazole-2-carbonyl)azetidin-3-yl]oxy}benzoic acid

[Chemical Formula 521]

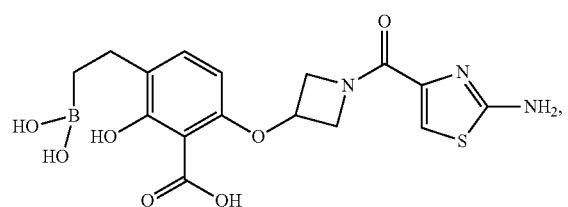

[Chemical Formula 525]

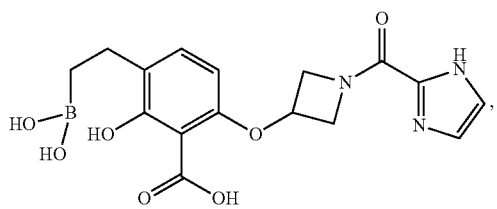

3-(2-boronoethyl)-2-hydroxy-6-({1-[(1H-1,2,3-triazol-1-yl)acetyl]azetidin-3-yl}oxy)benzoic acid 3-(2-boronoethyl)-2-hydroxy-6-[(1-{[4-(hydroxymethyl)-1H-1,2,3-triazol-1-yl]acetyl}azetidin-3-yl)oxy]benzoic acid

[Chemical Formula 522]

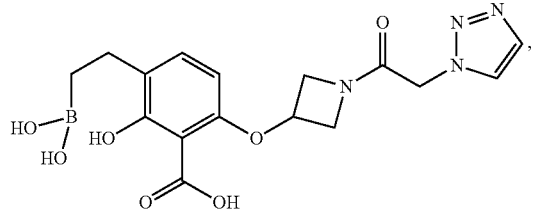

[Chemical Formula 526]

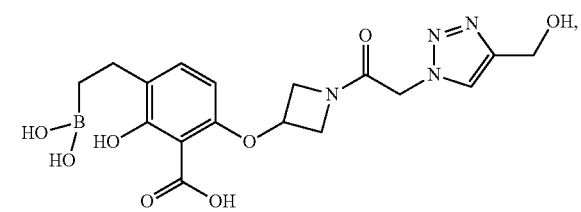

3-(2-boronoethyl)-2-hydroxy-6-{[1-({4-[(methylamino)
methyl]-1H-1,2,3-triazol-1-yl}acetyl)azetidin-3-yl]
oxy}benzoic acid 3-(2-boronoethyl)-2-hydroxy-6-{[1-({5-[(methylamino)
methyl]-1H-1,2,3-triazol-1-yl}acetyl)azetidin-3-yl]
oxy}benzoic acid

[Chemical Formula 527]

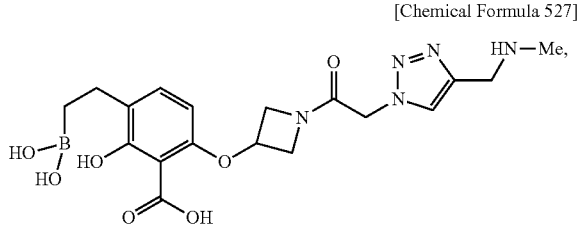 [SMILES: CNCc1cn(CC(=O)N2CC(Oc3ccc(CCB(O)O)c(O)c3C(=O)O)C2)nn1]

[Chemical Formula 531]

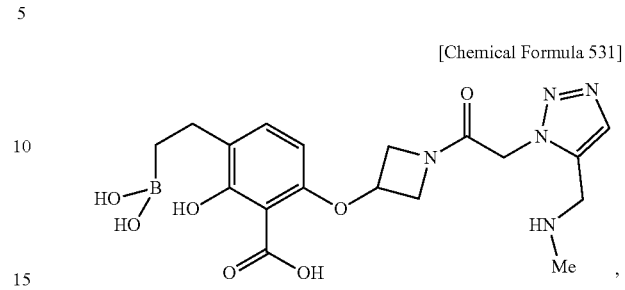

3-(2-boronoethyl)-2-hydroxy-6-{[1-({4-[(piperazin-1-yl)
methyl]-1H-1,2,3-triazol-1-yl}acetyl)azetidin-3-yl]
oxy}benzoic acid 3-(2-boronoethyl)-2-hydroxy-6-({1-[(1H-1,2,3-triazol-4-yl)
acetyl]azetidin-3-yl}oxy)benzoic acid

[Chemical Formula 528]

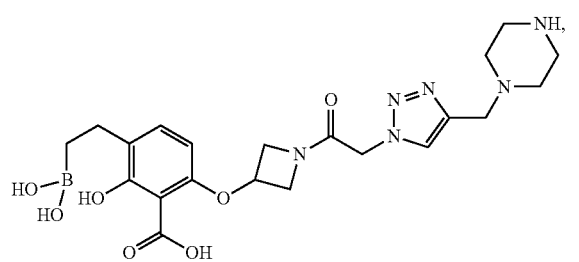

[Chemical Formula 532]

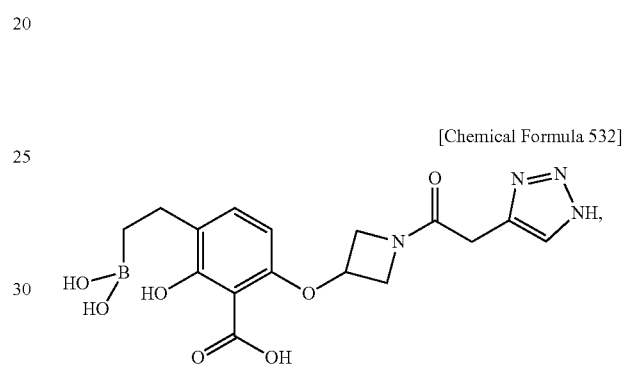

3-(2-boronoethyl)-2-hydroxy-6-[(1-{[4-(2-hydroxyethyl)-
1H-1,2,3-triazol-1-yl]acetyl}azetidin-3-yl)oxy]benzoic
acid 3-(2-boronoethyl)-6-[(1-{[4-(carboxymethyl)-1H-1,2,3-tri-
azol-1-yl]acetyl}azetidin-3-yl)oxy]-2-hydroxybenzoic
acid

[Chemical Formula 529]

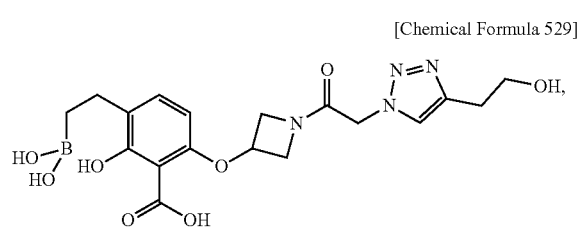 [SMILES: O=C(O)c1c(OC2CN(C(=O)Cn3cc(CCO)nn3)C2)ccc(CCB(O)O)c1O]

[Chemical Formula 533]

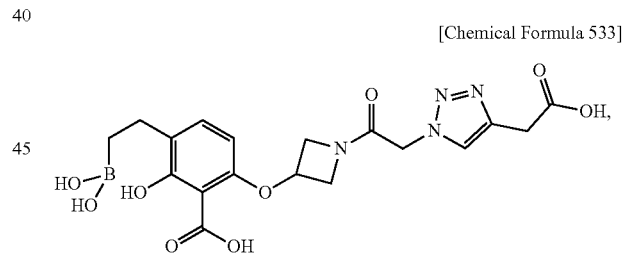

3-(2-boronoethyl)-2-hydroxy-6-[(1-{[5-(hydroxymethyl)-
1H-1,2,3-triazol-1-yl]acetyl}azetidin-3-yl)oxy]benzoic
acid 3-(2-boronoethyl)-6-[(1-{[1-(carboxymethyl)-1H-1,2,3-tri-
azol-4-yl]acetyl}azetidin-3-yl)oxy]-2-hydroxybenzoic

[Chemical Formula 530]

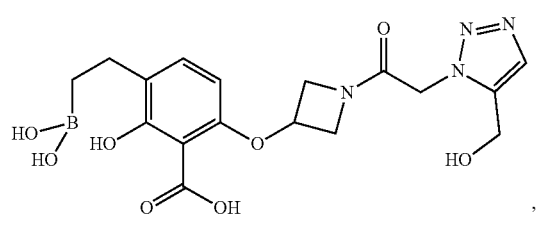

[Chemical Formula 534]

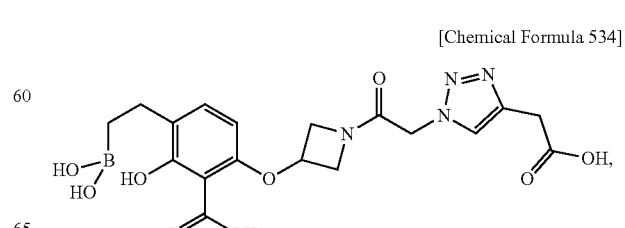

6-({1-[amino(1H-1,2,3-triazol-4-yl)acetyl]azetidin-3-yl}oxy)-3-(2-boronoethyl)-2-hydroxybenzoic acid 6-{[1-(S-benzyl-D-cysteinyl) azetidin-3-yl]oxy}-3-(2-boronoethyl)-2-hydroxybenzoic acid

[Chemical Formula 535]

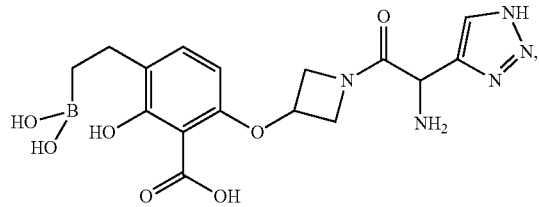

[Chemical Formula 539]

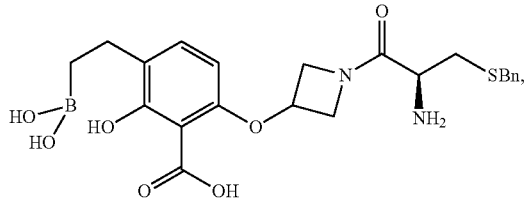

3-(2-boronoethyl)-2-hydroxy-6-({1-[(4-nitro-1H-1,2,3-triazol-1-yl)acetyl]azetidin-3-yl}oxy)benzoic acid 3-(2-boronoethyl)-6-[(1-D-cysteinylazetidin-3-yl)oxy]-2-hydroxybenzoic acid

[Chemical Formula 536]

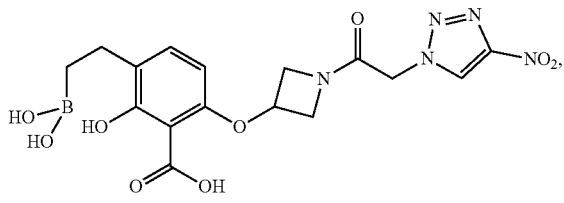

[Chemical Formula 540]

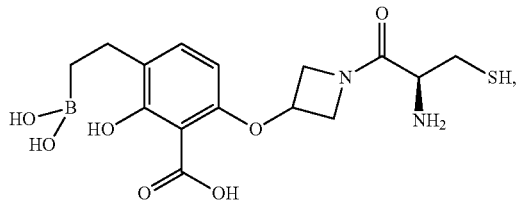

6-({1-[amino(3,4-dihydroxyphenyl)acetyl]azetidin-3-yl}oxy)-3-(2-boronoethyl)-2-hydroxybenzoic acid 3-(2-boronoethyl)-2-hydroxy-6-{[1-(3-sulfanyl-D-valyl)azetidin-3-yl]oxy}benzoic acid

[Chemical Formula 537]

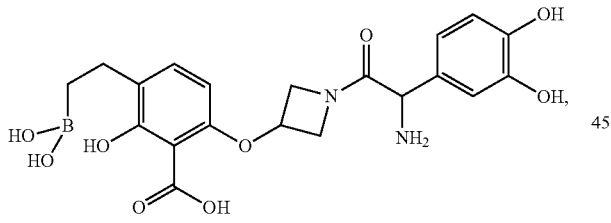

[Chemical Formula 541]

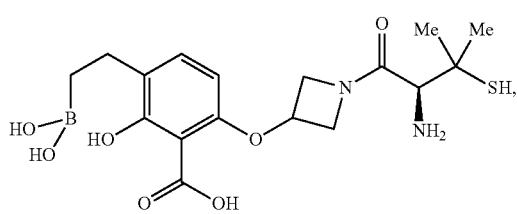

6-({1-[amino(2,4-dihydroxyphenyl)acetyl]azetidin-3-yl}oxy)-3-(2-boronoethyl)-2-hydroxybenzoic acid 6-({1-[(2S)-2-amino-3-carboxypropanoyl]azetidin-3-yl}oxy)-3-(2-boronoethyl)-2-hydroxybenzoic acid

[Chemical Formula 538]

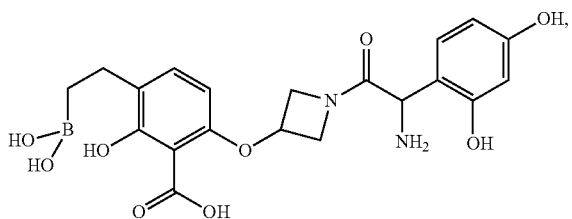

[Chemical Formula 542]

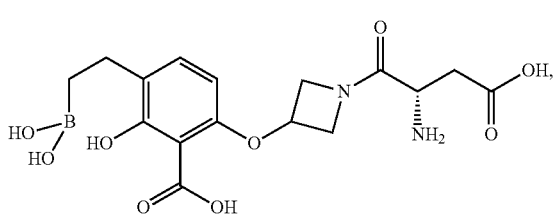

165

6-{[1-(D-alanyl-D-alanyl)azetidin-3-yl]oxy}-3-(2-borono-ethyl)-2-hydroxybenzoic acid

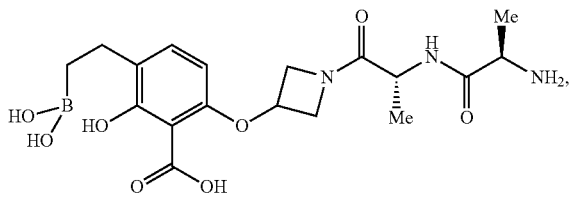

[Chemical Formula 543]

6-[(1-L-asparaginylazetidin-3-yl)oxy]-3-(2-boronoethyl)-2-hydroxybenzoic acid

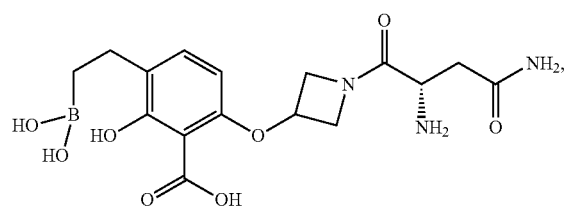

[Chemical Formula 544]

6-[(1-D-asparaginylazetidin-3-yl)oxy]-3-(2-boronoethyl)-2-hydroxybenzoic acid

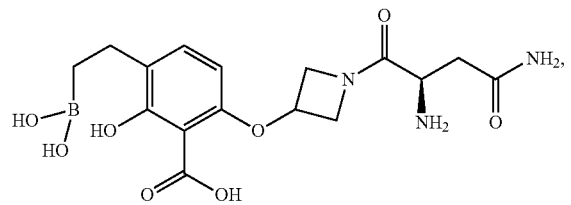

[Chemical Formula 545]

6-({1-[(2R)-2-amino-3-carboxypropanoyl]azetidin-3-yl}oxy)-3-(2-boronoethyl)-2-hydroxybenzoic acid

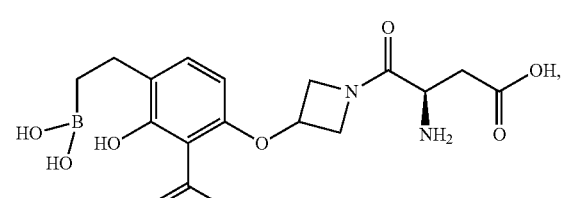

[Chemical Formula 546]

166

3-(2-boronoethyl)-2-hydroxy-6-[(1-D-serylazetidin-3-yl)oxy]benzoic acid

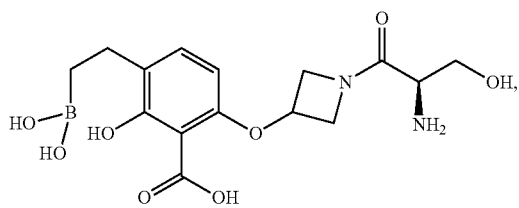

[Chemical Formula 547]

6-{[1-(4-amino-4-oxobutanoyl)azetidin-3-yl]oxy}-3-(2-boronoethyl)-2-hydroxybenzoic acid

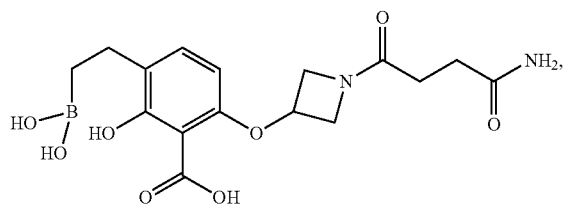

[Chemical Formula 548]

3-(2-boronoethyl)-6-[(1-D-glutaminylazetidin-3-yl)oxy]-2-hydroxybenzoic acid

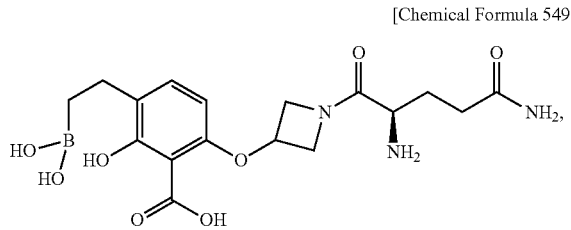 [SMILES: CC(=O)NC[C@@H](N)C(=O)N1CC(Oc2ccc(CCB(O)O)c(O)c2C(=O)O)C1]

[Chemical Formula 549]

3-(2-boronoethyl)-6-({1-[3-(carbamoylamino)-D-alanyl]azetidin-3-yl}oxy)-2-hydroxybenzoic acid

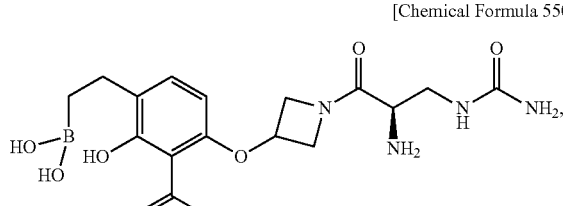

[Chemical Formula 550]

6-{[1-(3-acetamido-D-alanyl)azetidin-3-yl]oxy}-3-(2-boronoethyl)-2-hydroxybenzoic acid

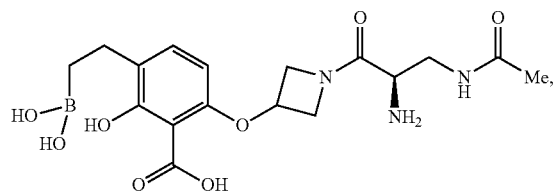

3-(2-boronoethyl)-6-{[1-(N,N-dimethyl-D-asparaginyl)azetidin-3-yl]oxy}-2-hydroxybenzoic acid

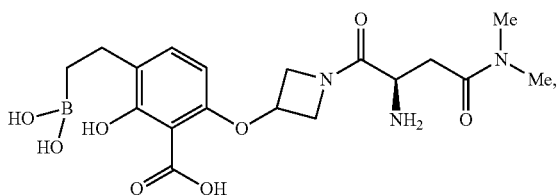

3-(2-boronoethyl)-2-hydroxy-6-{[1-(N-methyl-D-asparaginyl)azetidin-3-yl]oxy}benzoic acid

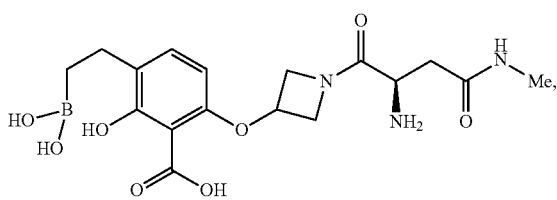

3-(2-boronoethyl)-2-hydroxy-6-[(1-L-serylazetidin-3-yl)oxy]benzoic acid

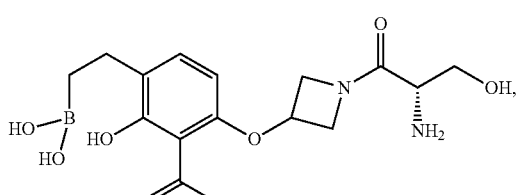

3-(2-boronoethyl)-2-hydroxy-6-{[1-(4-hydroxyprolyl)azetidin-3-yl]oxy}benzoic acid

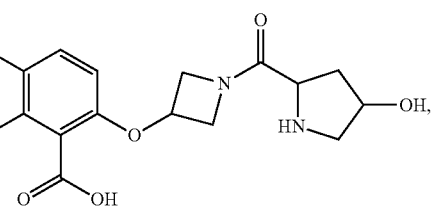

3-(2-boronoethyl)-2-hydroxy-6-({1-[(4R)-4-(trifluoromethyl)-D-prolyl]azetidin-3-yl}oxy)benzoic acid

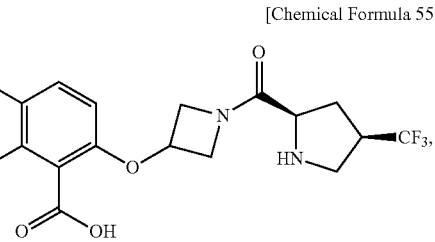

3-(2-boronoethyl)-6-({1-[(4S)-4-fluoro-L-prolyl]azetidin-3-yl}oxy)-2-hydroxybenzoic acid

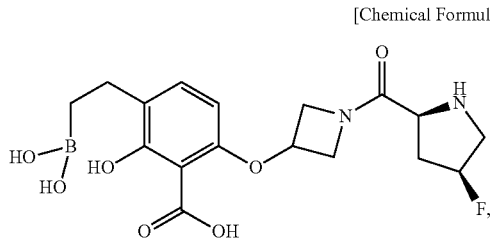

3-(2-boronoethyl)-2-hydroxy-6-({1-[(pyrrolidin-3-yl)acetyl]azetidin-3-yl}oxy)benzoic acid

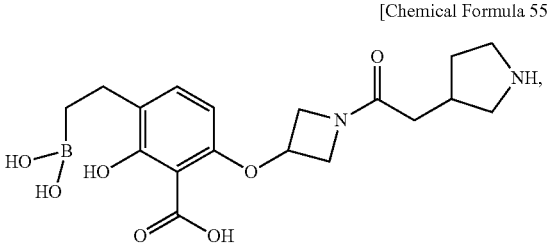

3-(2-boronoethyl)-6-[(1-{[(3R,5S)-5-(dimethylcarbamoyl)pyrrolidin-3-yl]acetyl}azetidin-3-yl)oxy]-2-hydroxybenzoic acid 3-(2-boronoethyl)-6-{[1-(4,4-difluoro-L-prolyl)azetidin-3-yl]oxy}-2-hydroxybenzoic acid

[Chemical Formula 559]

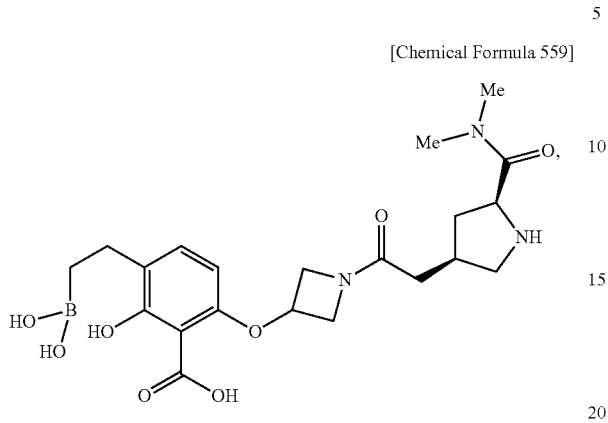

[Chemical Formula 562]

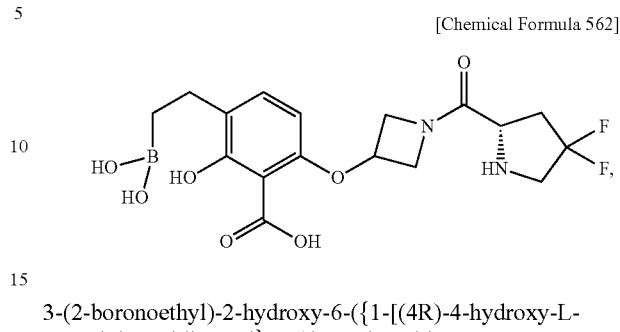

3-(2-boronoethyl)-2-hydroxy-6-({1-[(4R)-4-hydroxy-L-prolyl]azetidin-3-yl}oxy)benzoic acid 3-(2-boronoethyl)-6-[(1-{[(3S,5R)-5-(dimethylcarbamoyl)pyrrolidin-3-yl]acetyl}azetidin-3-yl)oxy]-2-hydroxybenzoic acid

[Chemical Formula 563]

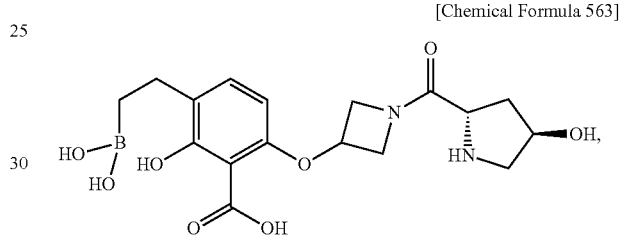

[Chemical Formula 560]

3-(2-boronoethyl)-2-hydroxy-6-({1-[(piperidin-4-yl)acetyl]azetidin-3-yl}oxy)benzoic acid

[Chemical Formula 564]

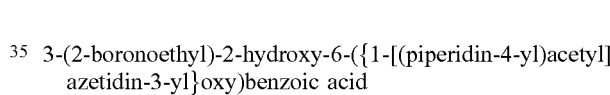

3-(2-boronoethyl)-6-[(1-{[(2R,4S)-4-fluoropyrrolidin-2-yl]acetyl}azetidin-3-yl)oxy]-2-hydroxybenzoic acid 3-(2-boronoethyl)-2-hydroxy-6-{[1-(pyrrolidine-3-carbonyl)azetidin-3-yl]oxy}benzoic acid

[Chemical Formula 561]

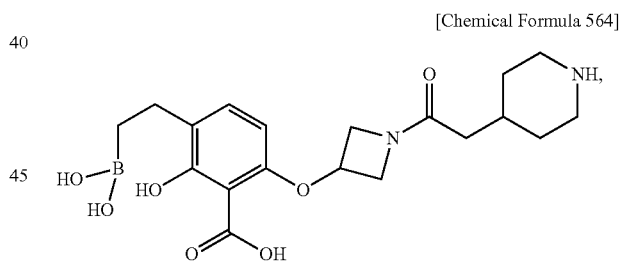

[Chemical Formula 565]

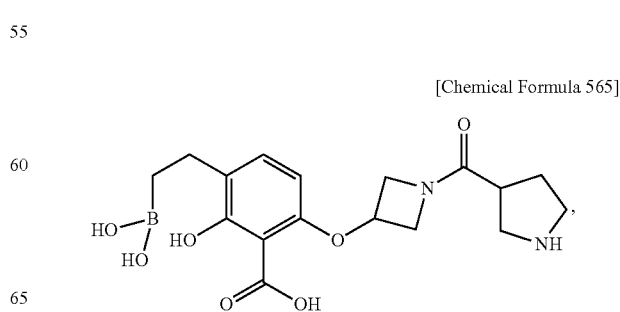

171

3-(2-boronoethyl)-2-hydroxy-6-({1-[(4S)-4-hydroxy-L-prolyl]azetidin-3-yl}oxy)benzoic acid

[Chemical Formula 566]

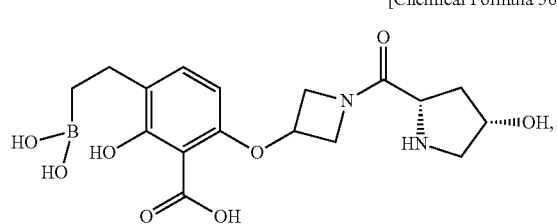

6-({1-[(4S)-4-amino-L-prolyl]azetidin-3-yl}oxy)-3-(2-boronoethyl)-2-hydroxybenzoic acid

[Chemical Formula 567]

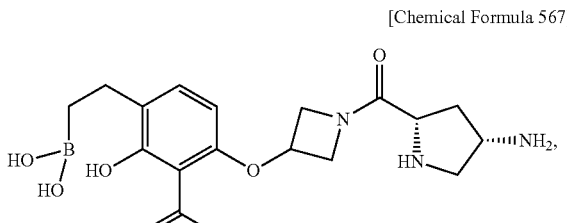

6-({1-[(4S)-4-acetamido-L-prolyl]azetidin-3-yl}oxy)-3-(2-boronoethyl)-2-hydroxybenzoic acid

[Chemical Formula 568]

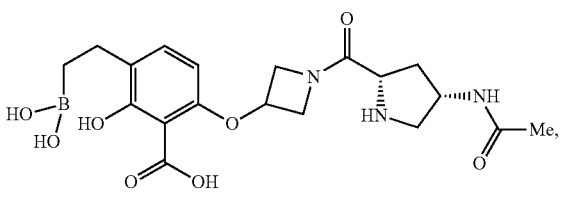

3-(2-boronoethyl)-2-hydroxy-6-({1-[(3R)-3-hydroxy-L-prolyl]azetidin-3-yl}oxy)benzoic acid

[Chemical Formula 569]

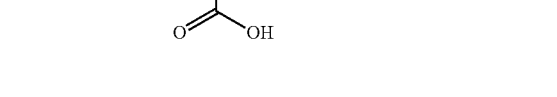

172

3-(2-boronoethyl)-6-{[1-(4,4-dimethyl-L-prolyl)azetidin-3-yl]oxy}-2-hydroxybenzoic acid

[Chemical Formula 570]

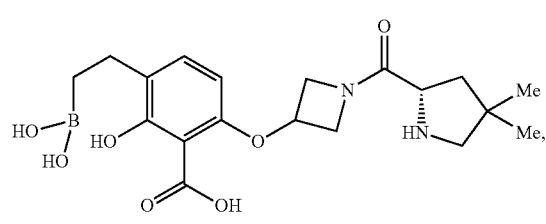

3-(2-boronoethyl)-2-hydroxy-6-({1-[(pyrrolidin-2-yl)acetyl]azetidin-3-yl}oxy)benzoic acid

[Chemical Formula 571]

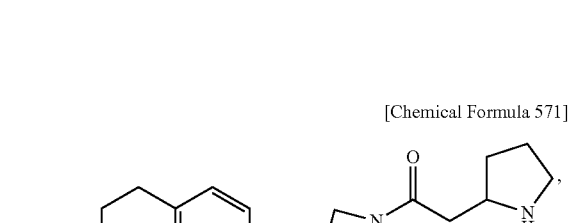

3-(2-boronoethyl)-2-hydroxy-6-{[1-(piperidine-2-carbonyl)azetidin-3-yl]oxy}benzoic acid

[Chemical Formula 572]

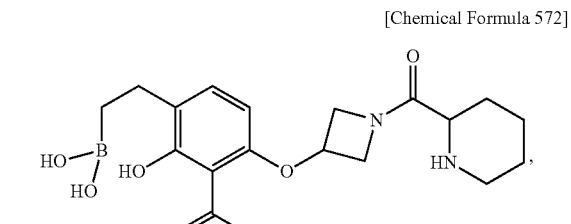

3-(2-boronoethyl)-2-hydroxy-6-{[1-(piperidine-3-carbonyl)azetidin-3-yl]oxy}benzoic acid

[Chemical Formula 573]

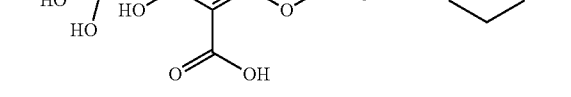

3-(2-boronoethyl)-2-hydroxy-6-{[1-(piperidine-4-carbonyl)azetidin-3-yl]oxy}benzoic acid 3-(2-boronoethyl)-2-hydroxy-6-{[1-(1-methyl-L-prolyl)azetidin-3-yl]oxy}benzoic acid

[Chemical Formula 574]

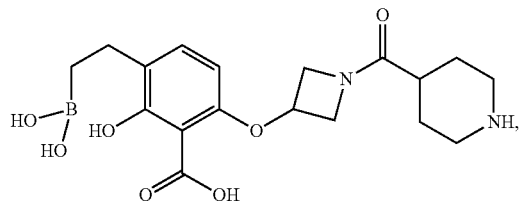

[Chemical Formula 578]

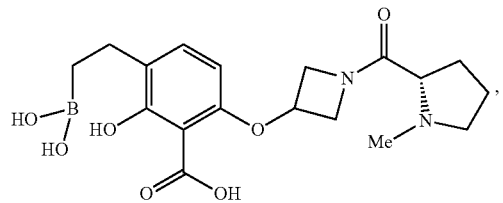

3-(2-boronoethyl)-2-hydroxy-6-({1-[(2S)-oxolane-2-carbonyl]azetidin-3-yl}oxy)benzoic acid 3-(2-boronoethyl)-2-hydroxy-6-({1-[(piperidin-3-yl)acetyl]azetidin-3-yl}oxy)benzoic acid

[Chemical Formula 575]

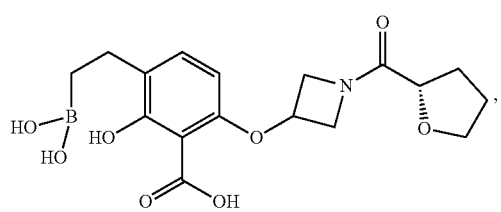

[Chemical Formula 579]

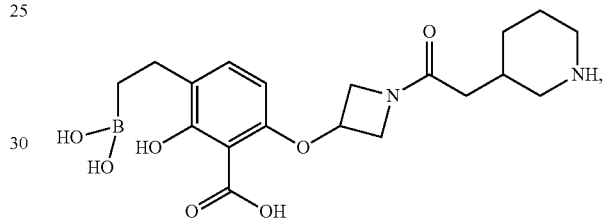

3-(2-boronoethyl)-2-hydroxy-6-({1-[(4R)-4-phenyl-L-prolyl]azetidin-3-yl}oxy)benzoic acid 3-(2-boronoethyl)-2-hydroxy-6-({1-[(morpholin-2-yl)acetyl]azetidin-3-yl}oxy)benzoic acid

[Chemical Formula 576]

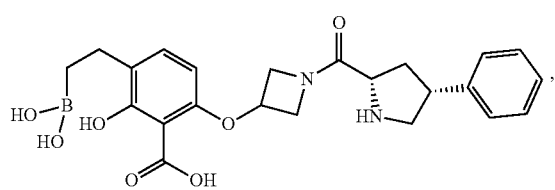

[Chemical Formula 580]

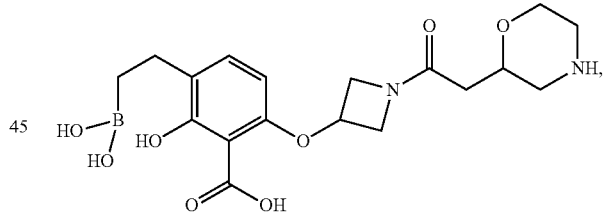

6-({1-[(1S,3S,5S)-2-azabicyclo[3.1.0]hexane-3-carbonyl]azetidin-3-yl}oxy)-3-(2-boronoethyl)-2-hydroxybenzoic acid 6-({1-[(azetidin-3-yl)acetyl]azetidin-3-yl}oxy)-3-(2-boronoethyl)-2-hydroxybenzoic acid

[Chemical Formula 577]

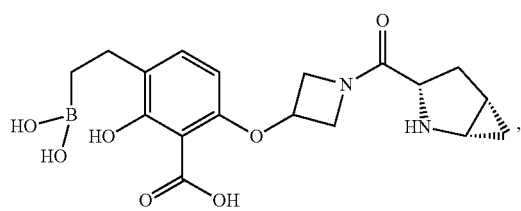

[Chemical Formula 581]

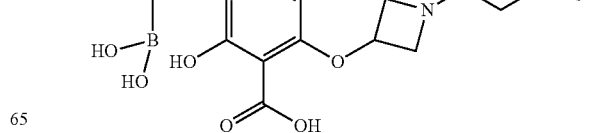

175

6-({1-[amino(pyrrolidin-3-yl)acetyl]azetidin-3-yl}oxy)-3-(2-boronoethyl)-2-hydroxybenzoic acid

[Chemical Formula 582]

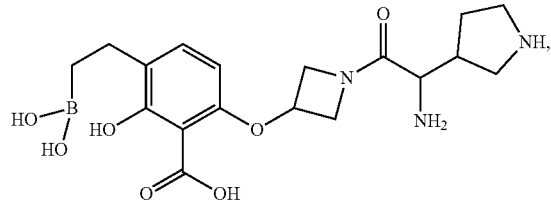

3-(2-boronoethyl)-2-hydroxy-6-({1-[3-(pyrrolidin-2-yl)propanoyl]azetidin-3-yl}oxy)benzoic acid

[Chemical Formula 583]

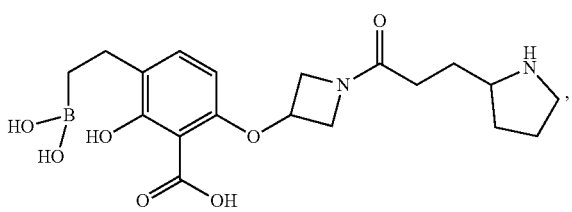

6-({1-[(4R)-4-amino-L-prolyl]azetidin-3-yl}oxy)-3-(2-boronoethyl)-2-hydroxybenzoic acid

[Chemical Formula 584]

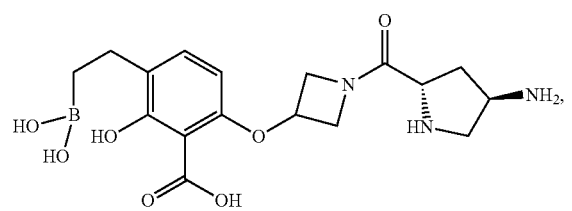

6-({1-[(4R)-4-acetamido-L-prolyl]azetidin-3-yl}oxy)-3-(2-boronoethyl)-2-hydroxybenzoic acid

[Chemical Formula 585]

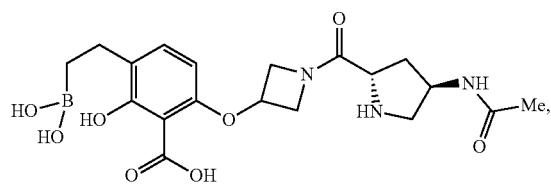

176

6-({1-[amino(piperidin-4-yl)acetyl]azetidin-3-yl}oxy)-3-(2-boronoethyl)-2-hydroxybenzoic acid

[Chemical Formula 586]

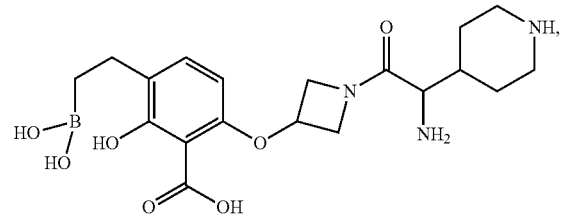

3-(2-boronoethyl)-2-hydroxy-6-({1-[(piperidin-2-yl)acetyl]azetidin-3-yl}oxy)benzoic acid

[Chemical Formula 587]

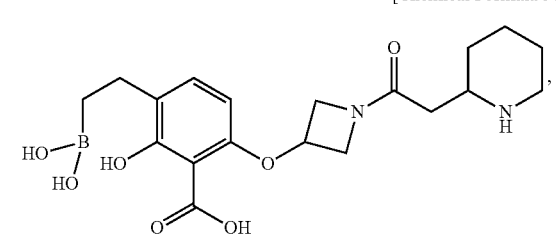

3-(2-boronoethyl)-6-({1-[(4S)-4-carbamoyl-L-prolyl]azetidin-3-yl}oxy)-2-hydroxybenzoic acid

[Chemical Formula 588]

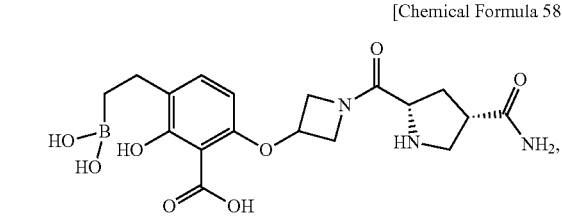

3-(2-boronoethyl)-2-hydroxy-6-[(1-{[(3R)-pyrrolidin-3-yl]acetyl}azetidin-3-yl)oxy]benzoic acid

[Chemical Formula 589]

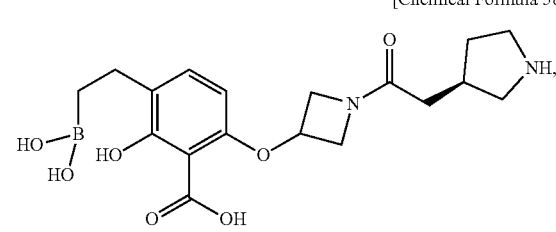

3-(2-boronoethyl)-2-hydroxy-6-[(1-{[(3S)-pyrrolidin-3-yl]acetyl}azetidin-3-yl)oxy]benzoic acid 3-(2-boronoethyl)-6-({1-[(1,1-dioxo-1λ⁶-thiomorpholin-2-yl)acetyl]azetidin-3-yl}oxy)-2-hydroxybenzoic acid

[Chemical Formula 590]

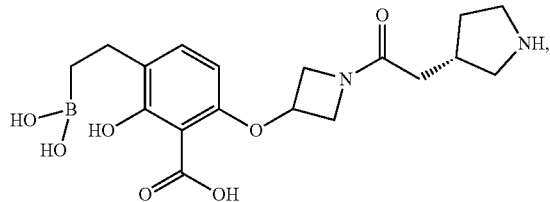

[Chemical Formula 594]

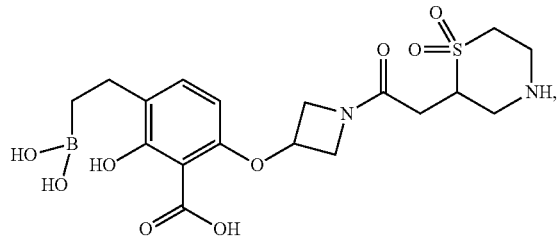

3-(2-boronoethyl)-2-hydroxy-6-[(1-{[(2R)-pyrrolidin-2-yl]acetyl}azetidin-3-yl)oxy]benzoic acid 6-({1-[(2S)-4-acetamido-2-aminobutanoyl]azetidin-3-yl}oxy)-3-(2-boronoethyl)-2-hydroxybenzoic acid

[Chemical Formula 591]

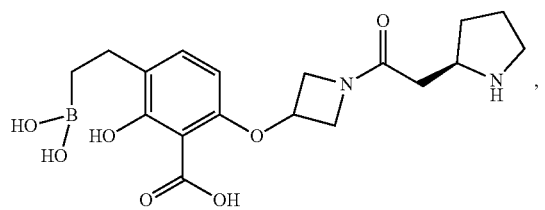

[Chemical Formula 595]

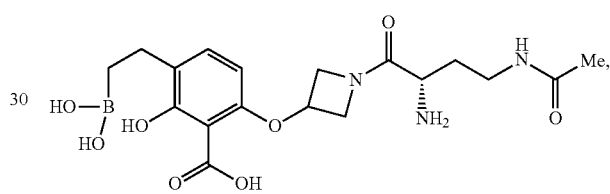

3-(2-boronoethyl)-2-hydroxy-6-[(1-{[(2S)-pyrrolidin-2-yl]acetyl}azetidin-3-yl)oxy]benzoic acid 6-{[1-(L-α-asparaginyl)azetidin-3-yl]oxy}-3-(2-borono-ethyl)-2-hydroxybenzoic acid

[Chemical Formula 592]

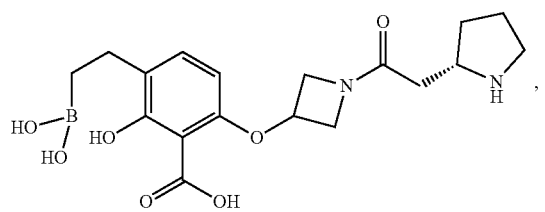

[Chemical Formula 596]

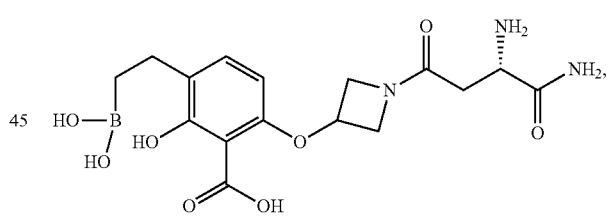

3-(2-boronoethyl)-2-hydroxy-6-({1-[(piperazin-2-yl)acetyl]azetidin-3-yl}oxy)benzoic acid 6-{[1-(L-alanyl-L-alanyl)azetidin-3-yl]oxy}-3-(2-borono-ethyl)-2-hydroxybenzoic acid

[Chemical Formula 593]

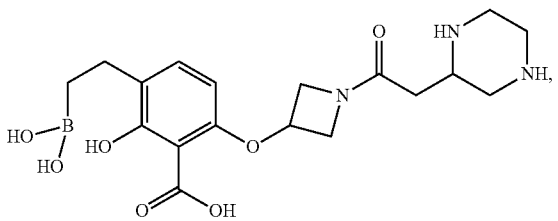

[Chemical Formula 597]

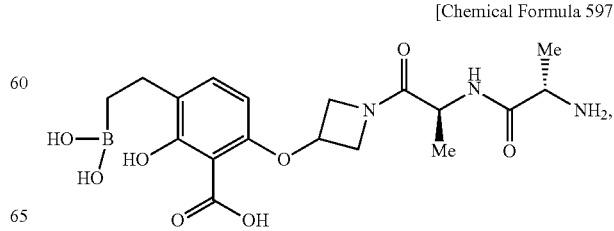

3-(2-boronoethyl)-6-{[1-(glycyl-D-alanyl)azetidin-3-yl]oxy}-2-hydroxybenzoic acid 6-({1-[(3S)-3-amino-3-carboxypropanoyl]azetidin-3-yl}oxy)-3-(2-boronoethyl)-2-hydroxybenzoic acid

[Chemical Formula 598]

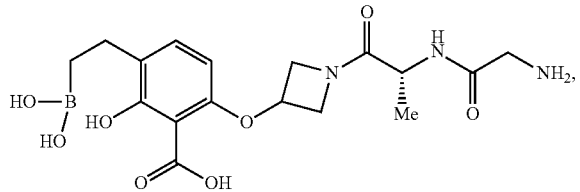

[Chemical Formula 602]

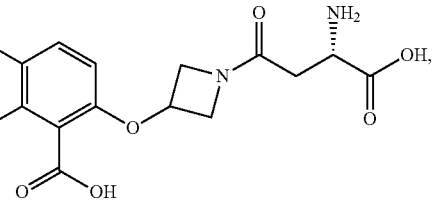

N-[(2R)-1-{3-[4-(2-boronoethyl)-2-carboxy-3-hydroxyphenoxy]azetidin-1-yl}-1-oxopropan-2-yl]-D-α-asparagine 3-(2-boronoethyl)-2-hydroxy-6-({1-[(1H-imidazol-4-yl)(methylamino)acetyl]azetidin-3-yl}oxy)benzoic acid

[Chemical Formula 599]

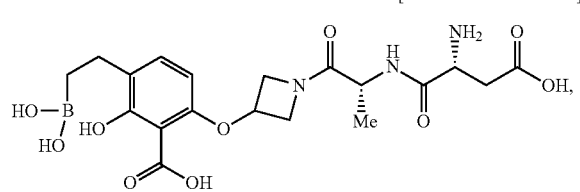

[Chemical Formula 603]

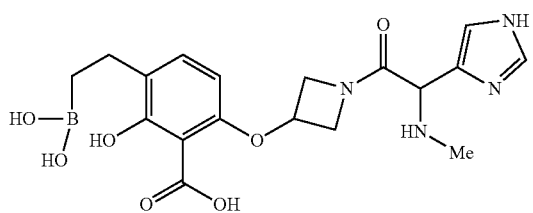

N¹-[(2R)-1-{3-[4-(2-boronoethyl)-2-carboxy-3-hydroxyphenoxy]azetidin-1-yl}-1-oxopropan-2-yl]-D-aspartamide 3-(2-boronoethyl)-6-({1-[(dimethylamino)(1H-imidazol-4-yl)acetyl]azetidin-3-yl)oxy}-2-hydroxybenzoic acid

[Chemical Formula 600]

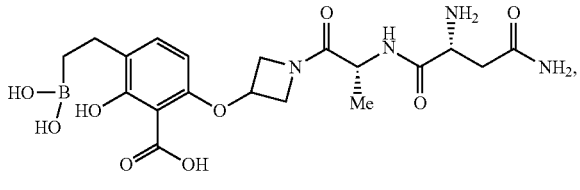

[Chemical Formula 604]

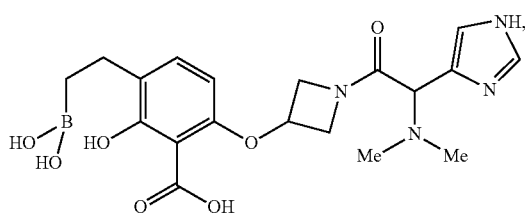

N-[(2R)-1-{3-[4-(2-boronoethyl)-2-carboxy-3-hydroxyphenoxy]azetidin-1-yl}-1-oxopropan-2-yl]-D-serinamide 3-(2-boronoethyl)-2-hydroxy-6-{[1-(2-methyl-D-seryl)azetidin-3-yl]oxy}benzoic acid

[Chemical Formula 601]

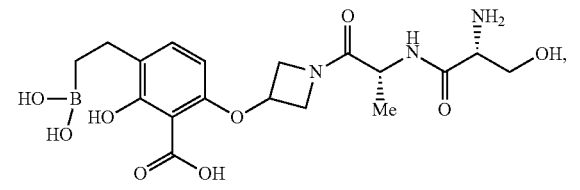

[Chemical Formula 605]

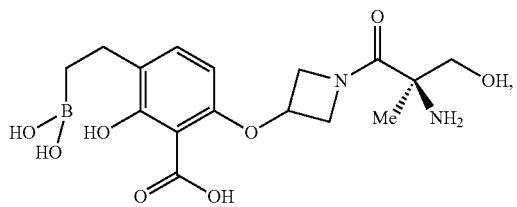

181

3-(2-boronoethyl)-2-hydroxy-6-{[1-(2-methyl-L-seryl)azetidin-3-yl]oxy}benzoic acid

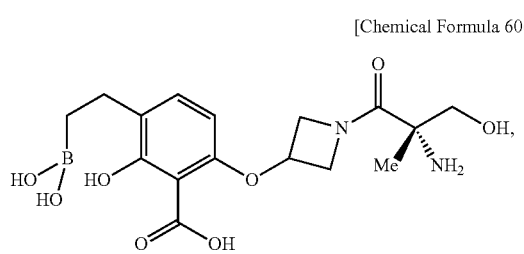

[Chemical Formula 606]

3-(2-boronoethyl)-2-hydroxy-6-({1-[(3-oxopiperazin-2-yl)acetyl]azetidin-3-yl}oxy)benzoic acid

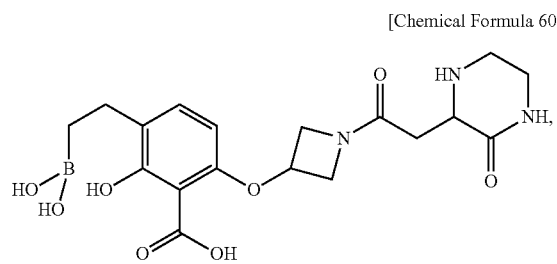

[Chemical Formula 607]

6-({1-[(3S)-3-amino-5-carboxypentanoyl]azetidin-3-yl}oxy)-3-(2-boronoethyl)-2-hydroxybenzoic acid

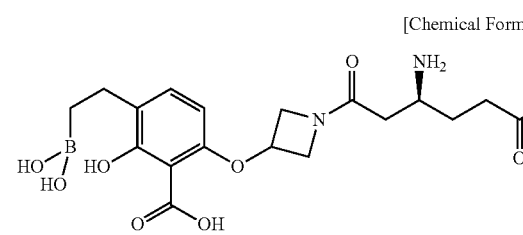

[Chemical Formula 608]

6-({1-[(3R)-3-amino-3-carboxypropanoyl]azetidin-3-yl}oxy)-3-(2-boronoethyl)-2-hydroxybenzoic acid

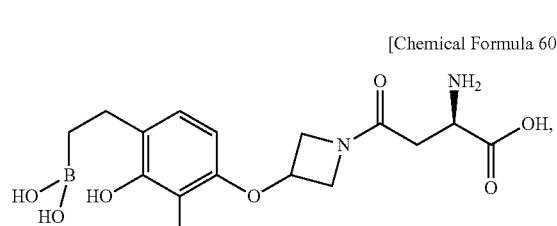

[Chemical Formula 609]

182

6-({1-[(4R)-4-amino-4-carboxybutanoyl]azetidin-3-yl}oxy)-3-(2-boronoethyl)-2-hydroxybenzoic acid

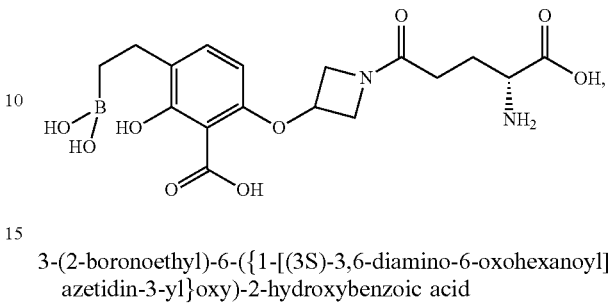

[Chemical Formula 610]

3-(2-boronoethyl)-6-({1-[(3S)-3,6-diamino-6-oxohexanoyl]azetidin-3-yl}oxy)-2-hydroxybenzoic acid

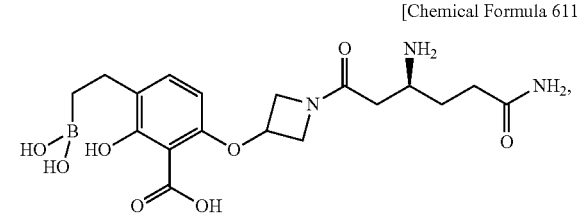

[Chemical Formula 611]

6-{[1-(D-α-asparaginyl) azetidin-3-yl]oxy}-3-(2-boronoethyl)-2-hydroxybenzoic acid

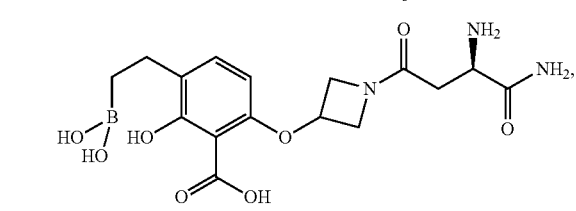

[Chemical Formula 612]

3-(2-boronoethyl)-6-{[1-(D-α-glutaminyl)azetidin-3-yl]oxy}-2-hydroxybenzoic acid

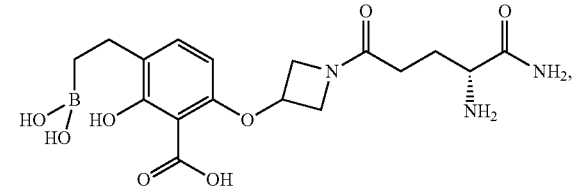

[Chemical Formula 613]

6-({1-[(4S)-4-amino-4-carboxybutanoyl]azetidin-3-yl}oxy)-3-(2-boronoethyl)-2-hydroxybenzoic acid

[Chemical Formula 614]

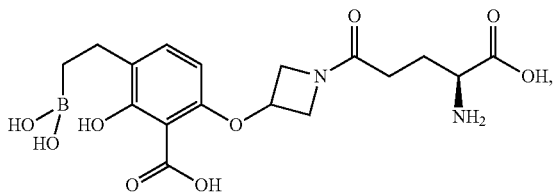

3-(2-boronoethyl)-6-{[1-(L-α-glutaminyl)azetidin-3-yl]oxy}-2-hydroxybenzoic acid

[Chemical Formula 615]

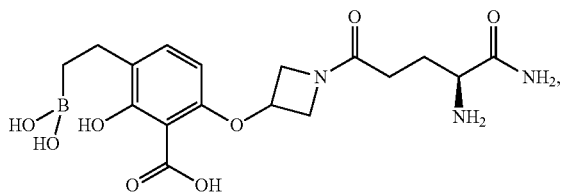

3-(2-boronoethyl)-2-hydroxy-6-[(1-D-threonylazetidin-3-yl)oxy]benzoic acid

[Chemical Formula 616]

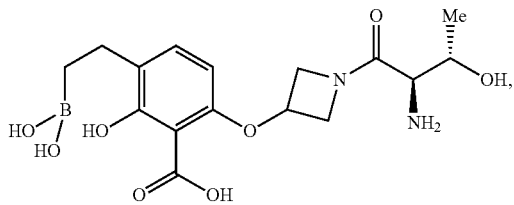

and
3-(2-boronoethyl)-2-hydroxy-6-[(1-L-threonylazetidin-3-yl)oxy]benzoic acid

[Chemical Formula 617]

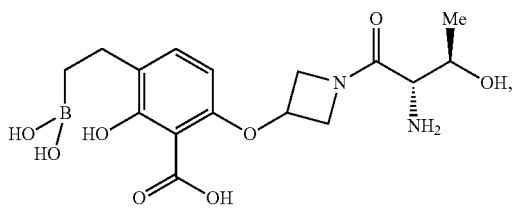

[Item 70]
A medicament comprising the compound or the pharmaceutically acceptable salt thereof according to any one of items 1 to 69.

[Item 71]
The medicament according to item 70, which is a therapeutic drug or a prophylactic drug for a bacterial infection.

[Item 72]
A β-lactamase inhibiting agent comprising the compound or the pharmaceutically acceptable salt thereof according to any one of items 1 to 69 as an active ingredient.

[Item 73]
A pharmaceutical composition comprising the compound or the pharmaceutically acceptable salt thereof according to any one of items 1 to 69 and a pharmaceutically acceptable carrier.

[Item 74]
The pharmaceutical composition according to item 73, further comprising an additional agent.

[Item 75]
The pharmaceutical composition according to item 74, wherein the additional agent is selected from the group consisting of an antibacterial agent, an antifungal agent, an antiviral agent, an anti-inflammatory agent, and an anti-allergic agent.

[Item 76]
The pharmaceutical composition according to item 74 or 75, wherein the additional agent is a β-lactam agent.

[Item 77]
The pharmaceutical composition according to item 75 or 76, wherein a β-lactam agent, which is the additional agent, is selected from the group consisting of amoxicillin, ampicillin (pivampicillin, hetacillin, bacampicillin, metampicillin, and talampicillin), epicillin, carbenicillin (carindacillin), ticarcillin, temocillin, azlocillin, piperacillin, mezlocillin, mecillinam (pivmecillinam), sulbenicillin, benzylpenicillin (G), clometocillin, benzathine benzylpenicillin, procaine benzylpenicillin, azidocillin, penamecillin, phenoxymethyl penicillin (V), propicillin, benzathine phenoxymethylpenicillin, phenethicillin, cloxacillin (dicloxacillin and flucloxacillin), oxacillin, methicillin, nafcillin, faropenem, biapenem, doripenem, ertapenem, imipenem, meropenem, panipenem, tomopenem, razupenem, cefazolin, cefacetrile, cefadroxil, cephalexin, cefaloglycin, cefalonium, cefaloridine, cephalothin, cephapirin, cefatrizine, cefazedone, cefazaflur, cefradine, cefroxadine, ceftezole, cefaclor, cefamandole, cefminox, cefonicide, ceforanide, cefotiam, cefprozil, cefbuperazone, cefuroxime, cefuzonam, cefoxitin, cefotetan, cefmetazole, loracarbef, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, flomoxef, latamoxef, cefepime, cefozopran, cefpirome, cefquinome, ceftobiprole, ceftaroline, CXA-101, RWJ-54428, MC-04546, ME1036, BAL30072, SYN2416, ceftiofur, cefquinome, cefovecin, aztreonam, tigemonam, carumonam, RWJ-442831, RWJ-333441, and RWJ-333442.

[Item 78]
The pharmaceutical composition according to item 76 or 77, wherein the β-lactam agent is selected from ceftazidime, biapenem, doripenem, ertapenem, imipenem, meropenem, or panipenem.

[Item 79]
The pharmaceutical composition according to item 76 or 77, wherein the β-lactam agent is selected from aztreonam, tigemonam, BAL30072, SYN2416, or carumonam.

[Item 80]
The pharmaceutical composition according to item 73, characterized in that an additional agent is concomitantly administered.

[Item 81]
The pharmaceutical composition according to item 80, wherein the additional agent is selected from an antibacterial agent, an antifungal agent, an antiviral agent, an anti-inflammatory agent, or an anti-allergic agent.

[Item 82]

The pharmaceutical composition according to item 80 or 81, wherein the additional agent is a R-lactam agent.

[Item 83]

The pharmaceutical composition according to item 81 or 82, wherein a β-lactam agent, which is the additional agent, is selected from the group consisting of amoxicillin, ampicillin (pivampicillin, hetacillin, bacampicillin, metampicillin, and talampicillin), epicillin, carbenicillin (carindacillin), ticarcillin, temocillin, azlocillin, piperacillin, mezlocillin, mecillinam (pivmecillinam), sulbenicillin, benzylpenicillin (G), clometocillin, benzathine benzylpenicillin, procaine benzylpenicillin, azidocillin, penamecillin, phenoxymethyl penicillin (V), propicillin, benzathine phenoxymethylpenicillin, phenethicillin, cloxacillin (dicloxacillin and flucloxacillin), oxacillin, methicillin, nafcillin, faropenem, biapenem, doripenem, ertapenem, imipenem, meropenem, panipenem, tomopenem, razupenem, cefazolin, cefacetrile, cefadroxil, cephalexin, cefaloglycin, cefalonium, cefaloridine, cephalothin, cephapirin, cefatrizine, cefazedone, cefazaflur, cefradine, cefroxadine, ceftezole, cefaclor, cefamandole, cefminox, cefonicide, ceforanide, cefotiam, cefprozil, cefbuperazone, cefuroxime, cefuzonam, cefoxitin, cefotetan, cefmetazole, loracarbef, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, flomoxef, latamoxef, cefepime, cefozopran, cefpirome, cefquinome, ceftobiprole, ceftaroline, CXA-101, RWJ-54428, MC-04546, ME1036, BAL30072, SYN2416, ceftiofur, cefquinome, cefovecin, aztreonam, tigemonam, carumonam, RWJ-442831, RWJ-333441, and RWJ-333442.

[Item 84]

The pharmaceutical composition according to item 82 or 83, wherein the β-lactam agent is selected from the group consisting of ceftazidime, biapenem, doripenem, ertapenem, imipenem, meropenem, and panipenem.

[Item 85]

The pharmaceutical composition according to item 82 or 83, wherein the β-lactam agent is selected from the group consisting of aztreonam, tigemonam, BAL30072, SYN2416, and carumonam.

[Item 86]

The compound or the pharmaceutically acceptable salt thereof according to any one of the preceding items for treating a bacterial infection.

[Item 87]

The compound or the pharmaceutically acceptable salt thereof according to any one of the preceding items, wherein the bacterial infection is a bacterial infection in which a bacteria that can have a β-lactamase is involved.

[Item 88]

The compound or the pharmaceutically acceptable salt thereof according to any one of the preceding items, wherein the bacterial infection is sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, or an odontogenic infection.

[Item 89]

A medicament comprised of a combination of the compound or the pharmaceutically acceptable salt thereof according to any one of the preceding items and at least one agent selected from the group consisting of therapeutic agents for sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, and an odontogenic infection.

[Item 90]

A pharmaceutical composition comprising a β-lactam agent, wherein the pharmaceutical composition is administered with the compound or the pharmaceutically acceptable salt thereof according to any one of the preceding items.

[Item 91]

A method for treating a bacterial infection, characterized in that a therapeutically effective amount of the compound or the pharmaceutically acceptable salt thereof according to any one of the preceding items is administered to a patient in need thereof.

[Item 92]

The method according to any one of the preceding items, wherein the bacterial infection is a bacterial infection in which a bacteria that can have a β-lactamase is involved.

[Item 93]

The method according to any one of the preceding items, wherein the bacterial infection is sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, or an odontogenic infection.

[Item 94]

The method of any one of the preceding items, characterized in that an additional agent is concomitantly administered.

The present invention is intended so that one or more of the features described above can be provided not only as the explicitly disclosed combinations, but also as other combinations thereof. Additional embodiments and advantages of the invention are recognized by those skilled in the art by reading and understanding the following detailed description as needed.

Advantageous Effects of Invention

The compound of the invention has excellent inhibitory action against serine-β-lactamase with a serine residue at the center of enzymatic activity. A better embodiment of the compound of the invention is expected to have a broad β-lactamase inhibitory action or metallo-β-lactamase inhibitory action with zinc ($Zn^{2+}$) at the center of enzymatic activity against multiple types of β-lactamases. Therefore, the compound of the invention is useful alone or in concomitant use with a β-lactam agent as a therapeutic agent and/or prophylactic agent for a bacterial infection in which a bacteria that can have a β-lactamase is involved, i.e., sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, or an odontogenic infection.

DESCRIPTION OF EMBODIMENTS

The present invention is described hereinafter in more detail.

Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The terms and the general technologies that are used herein are first described.

Unless specifically noted otherwise, the term "group" refers to a monovalent group. Examples of groups that are not a monovalent group include alkylene groups (divalent). The term "group" may also be omitted in the following descriptions of substituents or the like.

Unless specifically limited, the number of substituents when defined as "optionally substituted" or "substituted" is not particularly limited herein, as long as a substitution is possible. The number of substituents is one or multiple substituents. Moreover, unless indicated otherwise, the description for each substituent is also applicable when the substituent is a part of or a substituent of another group.

A substituent in "optionally substituted" is selected from substituent group α that consists of the following. The substitution is optionally substituted with 1 to 5 of the same or different substituents. While not particularly limited by the type of substituent, if an atom to which the substituent attaches is an oxygen atom, a nitrogen atom, or a sulfur atom, the substituent is limited to the following substituents that attaches to a carbon atom.

Substituent group α includes
1) a halogen atom
2) a hydroxyl group
3) a carboxyl group
4) a cyano group
5) a sulfanyl group,
6) a nitro group,
7) a $C_{1-6}$ alkyl group
8) a $C_{2-6}$ alkenyl group
9) a $C_{2-6}$ alkynyl group
10) a $C_{1-6}$ alkoxy group
11) a $C_{1-6}$ alkylthio group
12) a $C_{1-6}$ alkylcarbonyl group
13) a $C_{1-6}$ alkylsulfonyl group (wherein each substituent from 7) to 13) is optionally substituent with 1 to 5 of the same or different sub substituents selected from substituent group β)
14) a $C_{3-10}$ alicyclic group
15) a $C_{3-10}$ alicyclic oxy group
16) a $C_{6-10}$ aryloxy group
17) a 5- or 6-membered heteroaryloxy group
18) a 4- to 10-membered non-aryl heterocyclyl oxy group
19) a $C_{3-10}$ alicyclic thio group
20) a $C_{6-10}$ arylthio group
21) a 5- or 6-membered heteroarylthio group
22) a 4- to 10-membered non-aryl heterocyclyl thio group
23) $C_{6-10}$ aryl
24) 5- or 6-membered heteroaryl
25) a 4- to 10-membered non-aryl heterocycle
26) a $C_{3-10}$ alicyclic carbonyl group
27) a $C_{6-10}$ arylcarbonyl group
28) a 5- or 6-membered heteroarylcarbonyl group
29) a 4- to 10-membered non-aryl heterocyclyl carbonyl group
30) a 4- to 10-membered non-aryl heterocyclyl carbonylamino group
31) a $C_{3-10}$ alicyclic sulfonyl group
32) a $C_{6-10}$ arylsulfonyl group
33) a 5- or 6-membered heteroarylsulfonyl group
34) a 4- to 10-membered non-aryl heterocyclyl sulfonyl group
(wherein each substituent from 14) to 34) is optionally substituted with 1 to 5 of substituent group β or 1) a $C_{1-6}$ alkyl group)
35) —$NR^{10a}R^{11a}$
36) —$SO_2$—$R^{10b}$
37) —$SO_2$—$NR^{10b}R^{11b}$
38) —$NR^{10c}$—C(=O)$R^{11c}$
39) $NR^{10d}$—C(=O)O$R^{11d}$
40) —$NR^{12a}$—C(=O)$NR^{10e}R^{11e}$
41) —$NR^{10f}$—C(=S)$R^{11f}$
42) —$NR^{10g}$—C(=S)O$R^{11g}$,
43) —$NR^{12b}$—C(=S)$NR^{10h}R^{11h}$
44) —$NR^{10i}$—$SO_2$—$R^{11i}$
45) —$NR^{12c}$—$SO_2$—$NR^{10j}R^{11j}$
46) —C(=O)O$R^{10k}$
47) —C(=O)$NR^{10l}R^{11k}$
48) —C(=O)$NR^{10m}OR^{11l}$
49) —C(=O)$NR^{12d}$—$NR^{10n}R^{11m}$
50) —C(=S)O$R^{10o}$
51) —C(=S)$NR^{10p}R^{11m}$
52) —C(=S)$NR^{10q}OR^{10o}$
53) —C(=S)$NR^{12e}$—$NR^{10r}R^{11p}$
54) —C(=$NR^{13a}$)$R^{10s}$
55) —C(=$NR^{13b}$)CHO
56) —C(=$NR^{13c}$)$NR^{10t}R^{11q}$
57) —C(=$NR^{13d}$)$NR^{12f}$—$NR^{10u}R^{11r}$
58) —$NR^{17c}$—C(=$NR^{13k}$)$R^{17d}$
59) —$NR^{12g}$—C(=$NR^{13e}$)—$NR^{10v}R^{11s}$
60) —$NR^{14}$—C(=$NR^{13f}$)—$NR^{12h}$—$NR^{10w}R^{11t}$
61) —OC(=O)$R^{10x}$
62) —OC(=O)O$R^{10y}$
63) —OC(=O)$NR^{10z1}R^{11u}$
64) —$NR^{12i}$—$NR^{10z2}R^{11v}$
65) —$NR^{10z3}$ $OR^{11w}$
66) —C(=N—$OR^{13a}$)$R^{10s}$
67) —C(=N—$OR^{13b}$)CHO
68) —C(=N—$OR^{13c}$)$NR^{10t}R^{11q}$
69) —C(=N—$OR^{13d}$)$NR^{12f}$—$NR^{10u}R^{11r}$
70) —C(=O)$NR^{12j}$—S(=O)$_2$—$R^{10a1}$ and
71) —C(=O)$NR^{12k}$—S(=O)$_2$—$NR^{10a2}R^{11x}$, substituent group β is a group consisting of
1) a halogen atom,
2) a hydroxyl group,
3) a carboxyl group,
4) a cyano group,
5) a $C_{3-10}$ alicyclic group,
6) a $C_{1-6}$ alkoxy group,
7) a $C_{3-10}$ alicyclic oxy group,
8) a $C_{1-6}$ alkylthio group,
9) a 5- or 6-membered heteroarylthio group,
10) $C_{6-10}$ aryl,
11) 5- or 6-membered heteroaryl,
12) a 4- to 10-membered non-aryl heterocycle,
13) a $C_{1-6}$ alkylcarbonyl group,
14) a $C_{3-10}$ alicyclic carbonyl group,
15) a $C_{6-10}$ arylcarbonyl group,
16) a 5- or 6-membered heteroarylcarbonyl group,
17) a 4- to 10-membered non-aryl heterocyclyl carbonyl group,
18) —$NR^{15a}R^{16a}$,
19) —$SO_2$—$NR^{15b}R^{16b}$,
20) —$NR^{15c}$—C(=O)$R^{16c}$
21) —$NR^{17a}$—C(=O) $NR^{15d}R^{16d}$,
22) —C(=O)$NR^{15e}R^{16e}$,
23) —C(=$NR^{13g}$)$R^{15f}$,
24) —C(=$NR^{13h}$)$NR^{15g}R^{16f}$
25) —$NR^{16g}$—C(=$NR^{13i}$)$R^{15h}$
26) —$NR^{17b}$—C(=$NR^{13j}$)$NR^{15i}R^{16h}$
27) —C(=N—$OR^{13g}$)$R^{15f}$, and
28) —C(=N—$OR^{13h}$)$R^{15g}R^{16f}$
(wherein each substituent from 5) to 17) in substituent group β is optionally substituted with 1 to 5 substituents selected from the group consisting of a halogen atom, a hydroxyl group, a cyano group, a carboxyl group, and —$NR^{18a}R^{18b}$)
$R^{13a}$, $R^{13b}$, $R^{13c}$, $R^{13d}$, $R^{13e}$, $R^{13f}$, $R^{13g}$, $R^{13h}$, $R^{13i}$, $R^{13j}$, and $R^{13k}$ are the same or different, each independently a hydrogen atom, a hydroxyl group, a $C_{1-6}$ alkyl group, or a $C_{1-6}$ alkoxy group,
$R^{10a}$, $R^{10b}$, $R^{10c}$, $R^{10d}$, $R^{10e}$, $R^{10f}$, $R^{10g}$, $R^{10h}$, $R^{10i}$, $R^{10j}$, $R^{10k}$, $R^{10l}$, $R^{10m}$, $R^{10n}$, $R^{10o}$, $R^{10p}$, $R^{10q}$, $R^{10r}$, $R^{10s}$, $R^{10t}$, $R^{10u}$, $R^{10v}$, $R^{10w}$, $R^{10x}$, $R^{10y}$, $R^{10a1}$, $R^{10a2}$, $R^{10z1}$, $R^{10z2}$, $R^{10z3}$, $R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11k}$, $R^{11l}$, $R^{11m}$, $R^{11n}$, $R^{11o}$, $R^{11p}$, $R^{11q}$, $R^{11r}$, $R^{11s}$, $R^{11t}$, $R^{11u}$, $R^{11v}$, $R^{11w}$, $R^{11x}$, $R^{12a}$, $R^{12b}$, $R^{12c}$, $R^{12d}$, $R^{12e}$, $R^{12f}$, $R^{12g}$, $R^{12h}$, $R^{12i}$, $R^{12j}$, $R^{12k}$, $R^{14}$, $R^{15a}$, $R^{15b}$, $R^{15c}$, $R^{15d}$, $R^{15e}$, $R^{15f}$, $R^{15g}$, $R^{15h}$, $R^{15i}$, $R^{16a}$, $R^{16b}$, $R^{16c}$, $R^{16d}$, $R^{16e}$, $R^{16f}$, $R^{16g}$, $R^{16h}$, $R^{17a}$, $R^{17b}$, $R^{17c}$, and $R^{17d}$ are the same or different, each independently a hydrogen atom, a 5- or 6-membered non-aryl heterocycle, or a $C_{1-6}$ alkyl group (wherein the 5- or 6-membered non-aryl heterocycle and the $C_{1-6}$ alkyl group are optionally substituted with 1 to 3 of the same or different substituents, each independently selected from the group consisting of a hydroxyl group, a cyano group, a $C_{1-6}$ alkoxy group, —$NR^{18a}R^{18b}$, a carboxyl group, and —C(=O)$NR^{18c}R^{18d}$), and
$R^{18a}$, $R^{18b}$, $R^{18c}$, and $R^{18d}$ are the same or different, each independently a hydrogen atom or a $C_{1-6}$ alkyl group.

Preferred examples of substituents in "optionally substituted" include the following substituents.

Preferred substituent group α includes
1) a halogen atom
2) a hydroxyl group
3) a carboxyl group
4) a cyano group
5) a $C_{1-6}$ alkyl group
6) a $C_{1-6}$ alkoxy group
7) a $C_{1-6}$ alkylthio group 8) a $C_{1-6}$ alkylcarbonyl group
(wherein each substituent from 5) to 8) is optionally substituted with 1 to 5 of the same or different substituents selected from substituent group β)
9) a $C_{3-10}$ alicyclic group
10) a $C_{3-10}$ alicyclic oxy group
11) a $C_{6-10}$ aryloxy group
12) a 5- or 6-membered heteroaryloxy group
13) a 4- to 10-membered non-aryl heterocyclyl oxy group
14) a $C_{3-10}$ alicyclic thio group
15) a $C_{6-10}$ arylthio group
16) a 5- or 6-membered heteroarylthio group
17) a 4- to 10-membered non-aryl heterocyclyl thio group
18) $C_{6-10}$ aryl
19) 5- or 6-membered heteroaryl
20) a 4- to 10-membered non-aryl heterocycle
21) a $C_{3-10}$ alicyclic carbonyl group
22) a $C_{6-10}$ arylcarbonyl group
23) a 5- or 6-membered heteroarylcarbonyl group
24) a 4- to 10-membered non-aryl heterocyclyl carbonyl group
(wherein each substituent from 9) to 24) is optionally substituted with 1 to 5 of substituent group β or 1) a $C_{1-6}$ alkyl group)
25) —$NR^{10a}R^{11a}$
26) —$SO_2$—$NR^{10b}R^{11b}$
27) —$NR^{10c}$—C(=O)$R^{11c}$
28) —$NR^{12a}$—C(=O)$NR^{10d}R^{11d}$
29) —$NR^{10e}$—$SO_2$—$R^{11e}$
30) —$NR^{12b}$—$SO_2$—$NR^{10f}R^{11f}$
31) —C(=O)$NR^{10g}R^{11g}$
32) —C(=$NR^{13a}$)$R^{10h}$
33) —C(=$NR^{13b}$) $NR^{10i}R^{11h}$
34) —$NR^{11f}$—C(=$NR^{13a}$)$R^{10h}$
35) —$NR^{12c}$—C(=$NR^{13d}$)—$NR^{10j}R^{11i}$
36) —C(=N—$OR^{13a}$)$R^{10h}$, and
37) —C(=N—$OR^{13b}$)$NR^{10i}R^{11h}$, substituent group β is preferably selected from the group consisting of
1) a halogen atom
2) a hydroxyl group
3) a cyano group
4) a $C_{3-10}$ alicyclic group
5) a $C_{1-6}$ alkoxy group
6) a $C_{1-6}$ alkylthio group
7) a 5- or 6-membered heteroarylthio group
8) 5- or 6-membered heteroaryl
9) a 4- to 10-membered non-aryl heterocycle
10) a $C_{1-6}$ alkylcarbonyl group
11) a $C_{3-10}$ alicyclic carbonyl group
12) a $C_{6-10}$ arylcarbonyl group
13) a 5- or 6-membered heteroarylcarbonyl group
14) a 4- to 10-membered non-aryl heterocyclyl carbonyl group
15) —$NR^{15a}R^{16a}$
16) —$NR^{15b}$—C(=O)$R^{16b}$
17) —$NR^{17a}$—C(=O)$NR^{15c}R^{16c}$
18) —C(=O)$NR^{15d}R^{16d}$
19) —C(=$NR^{13e}$)$R^{15e}$
20) —C(=$NR^{13f}$)$NR^{15f}R^{16e}$
21) —$NR^{16f}$—C(=$NR^{13g}$)$R^{15g}$
22) —$NR^{17b}$—C(=$NR^{13h}$)—$R^{15h}R^{16g}$
23) —C(=N—$OR^{13e}$)$R^{15e}$ and
24) —C(=N—$OR^{13f}$)$NR^{15f}R^{16e}$
(wherein each substituent from 4) to 14) in substituent group β is optionally substituted with 1 to 5 substituents selected from the group consisting of a halogen atom, a hydroxyl group, a cyano group, a carboxyl group, and —NR$^{18a}$R$^{18b}$)

R$^{13a}$, R$^{13b}$, R$^{13c}$, R$^{13d}$, R$^{13e}$, R$^{13f}$, R$^{13g}$, and R$^{13h}$ are the same or different, each independently a hydrogen atom, a hydroxyl group, a C$_{1-6}$ alkyl group, or a C$_{1-6}$ alkoxy group, R$^{10a}$, R$^{10b}$, R$^{10c}$, R$^{10d}$, R$^{10e}$, R$^{10f}$, R$^{10g}$, R$^{10h}$, R$^{10i}$, R$^{10j}$, R$^{11a}$, R$^{11b}$, R$^{11c}$, R$^{11d}$, R$^{11e}$, R$^{11f}$, R$^{11g}$, R$^{11h}$, R$^{11i}$, R$^{12a}$, R$^{12b}$, R$^{12c}$, R$^{15a}$, R$^{15b}$, R$^{15c}$, R$^{15d}$, R$^{15e}$, R$^{15f}$, R$^{15g}$, R$^{16a}$, R$^{16b}$, R$^{16c}$, R$^{16d}$, R$^{16e}$, R$^{16f}$, R$^{16g}$, R$^{17a}$, and R$^{17b}$ are the same or different, each independently a hydrogen atom or a C$_{1-6}$ alkyl group (wherein the group is optionally substituted with 1 to 3 of the same or different substituents selected from a hydroxyl group, a cyano group, C$_{1-6}$ alkoxy group, and —NR$^{18a}$R$^{18b}$), and R$^{18a}$ and R$^{18b}$ are the same or different, each independently a hydrogen atom or a C$_{1-6}$ alkyl group.

More preferred examples of substituents in "optionally substituted" include the following substituents.

More preferred substituent group α includes
1) a halogen atom
2) a hydroxyl group
3) a cyano group
4) a C$_{1-6}$ alkyl group
5) a C$_{1-6}$ alkoxy group
6) a C$_{1-6}$ alkylthio group
7) a C$_{1-6}$ alkylcarbonyl group
(wherein each substituent from 4) to 7) is optionally substituted with 1 to 5 of the same or different substituents selected from substituent group β)
8) a 5- or 6-membered heteroaryloxy group
9) a 4- to 10-membered non-aryl heterocyclyl oxy group
10) a 5- or 6-membered heteroarylthio group
11) a 4- to 10-membered non-aryl heterocyclyl thio group
12) C$_{6-10}$ aryl
13) 5- or 6-membered heteroaryl
14) a 4- to 10-membered non-aryl heterocycle
(wherein each substituent from 4) to 14) is optionally substituted with 1 to 5 of substituent group β or 1) a C$_{1-6}$ alkyl group)
15) —NR$^{10a}$R$^{11a}$
16) —NR$^{11b}$—C(=O)R$^{10b}$
17) —NR$^{12a}$—C(=O)NR$^{10c}$R$^{11c}$
18) —C(=O)NR$^{10d}$R$^{11d}$
19) —C(=NR$^{13a}$)R$^{10e}$
20) —C(=NR$^{13b}$)NR$^{10f}$R$^{11e}$
21) —NR$^{11f}$—C(=NR$^{13c}$)R$^{10g}$
22) —NR$^{12b}$—C(=NR$^{13d}$)—NR$^{10h}$R$^{11g}$
23) —C(=N—OR$^{13a}$)R$^{10e}$ and
24) —C(=N—OR$^{13b}$)NR$^{10f}$R$^{11e}$, substituent group β is more preferably
1) a halogen atom,
2) a hydroxyl group,
3) a cyano group,
4) —NR$^{15a}$R$^{16a}$,
5) —NR$^{15b}$—C(=O)R$^{16b}$,
6) —NR$^{17a}$—C(=O)NR$^{15c}$R$^{16c}$,
7) —C(=O)NR$^{15d}$R$^{16d}$,
8) —C(=NR$^{13e}$)R$^{15e}$,
9) —C(=NR$^{13f}$)NR$^{15f}$R$^{16e}$,
10) —NR$^{16f}$—C(=NR$^{13g}$)R$^{15g}$,
11) —NR$^{17b}$—C(=NR$^{13h}$)—NR$^{15h}$R$^{16g}$,
12) —C(=N—OR$^{13e}$)R$^{15e}$, or
13) —C(=N—OR$^{13f}$)NR$^{15f}$R$^{16e}$, R$^{13a}$, R$^{13b}$, R$^{13c}$, R$^{13d}$, R$^{13e}$, R$^{13f}$, R$^{13g}$, and R$^{13h}$ are the same or different, each independently a hydrogen atom, a hydroxyl group, a C$_{1-6}$ alkyl group, or a C$_{1-6}$ alkoxy group, R$^{10a}$, R$^{10b}$, R$^{10c}$, R$^{10d}$, R$^{10e}$, R$^{10f}$, R$^{10g}$, R$^{10h}$, R$^{11a}$, R$^{11b}$, R$^{11c}$, R$^{11d}$, R$^{11e}$, R$^{11f}$, R$^{11g}$, R$^{12a}$, R$^{12b}$, R$^{15a}$, R$^{15b}$, R$^{15c}$, R$^{15d}$, R$^{15e}$, R$^{15f}$, R$^{15g}$, R$^{15h}$, R$^{16a}$, R$^{16b}$, R$^{16c}$, R$^{16d}$, R$^{16e}$, R$^{16f}$, R$^{16g}$, R$^{17a}$, and R$^{17b}$ are the same or different, each independently a hydrogen atom or a C$_{1-6}$ alkyl group (wherein the group is optionally substituted with 1 to 3 of the same or different substituents selected from a hydroxyl group, a cyano group, a C$_{1-6}$ alkoxy group, and —NR$^{18a}$R$^{18b}$), and R$^{18a}$ and R$^{18b}$ are the same or different, each independently a hydrogen atom or a C$_{1-6}$ alkyl group.

"C$_{1-6}$" means that the number of carbon atoms is 1 to 6. The same applies to other numbers. For example, "C$_{1-4}$" means that the number of carbon atoms is 1 to 4.

A "heteroatom" refers to an oxygen atom, a nitrogen atom, a sulfur atom, or the like.

A "halogen atom" refers to a fluorine atom, chlorine atom, bromine atom, or iodine atom, preferably a fluorine atom or chlorine atom, and still more preferably a fluorine atom. A "halogen atom" is also referred to as "halogen".

"C$_{1-6}$ alkyl group" refers to a linear or branched saturated hydrocarbon group with 1 to 6 carbon atoms. "C$_{1-6}$ alkyl group" is preferably a "C$_{1-4}$ alkyl group", more preferably a "C$_{1-3}$ alkyl group", and still more preferably a "C$_{1-2}$ alkyl group". Specific examples of "C$_{1-6}$ alkyl group" include, but are not limited to, methyl, ethyl, propyl, butyl, isopropyl, isobutyl, tert-butyl, sec-butyl, isopentyl, neopentyl, tert-pentyl, 1,2-dimethylpropyl, and the like.

"C$_{2-6}$ alkenyl group" refers to a linear or branched unsaturated hydrocarbon group with 2 to 6 carbon atoms, comprising one or more carbon-carbon double bonds. "C$_{2-6}$ alkenyl group" is preferably a "C$_{2-4}$ alkenyl group". Specific examples of "C$_{2-6}$ alkenyl group" include, but are not limited to, a vinyl group, 1-propylenyl group, 2-propylenyl group, 1-butenyl group, 2-butenyl group, 3-butenyl group, 2-methyl-1-propylenyl group, 2-methyl-2-propylenyl group, and the like.

"C$_{2-6}$ alkynyl group" refers to a linear or branched unsaturated aliphatic hydrocarbon group comprising one or more carbon-carbon triple bonds. "C$_{2-6}$ alkynyl group" is preferably a "C$_{2-4}$ alkynyl group". Specific examples thereof include, but are not limited to, an ethynyl group, 1-propynyl group, 2-propynyl group, 1-butynyl group, 1-methyl-2-propynyl group, 3-butynyl group, 1-pentynyl group, 1-hexynyl group, and the like.

"C$_{3-20}$ alicyclic group" refers to a monocyclic or bicyclic non-aromatic hydrocarbon ring with 3 to 20 carbon atoms, including those with a partially unsaturated bond, those with a partially crosslinked structure, those that have a partially spiro form, and those having 1 or 2 carbonyl structures. "Alicyclic group" encompasses cycloalkyl groups, cycloalkenyl groups, and cycloalkynyl groups. "C$_{3-20}$ alicyclic group" is preferably a "C$_{3-10}$ alicyclic group", and more preferably a "C$_{3-6}$ alicyclic group". Specific examples of "C$_{3-20}$ alicyclic group" include, but are not limited to, a cyclopropyl group, cyclobutyl group, cyclopentyl group, cyclohexyl group, cycloheptyl group, cyclooctyl group, cyclohexadinyl group, cycloheptadinyl group, cyclooctadinyl group, adamantyl, norbornyl, and the like.

Specific examples of "C$_{3-20}$ alicyclic group" with a partially crosslinked structure include, but are not limited to, those with a structure shown below and the like.

[Chemical Formula 618]

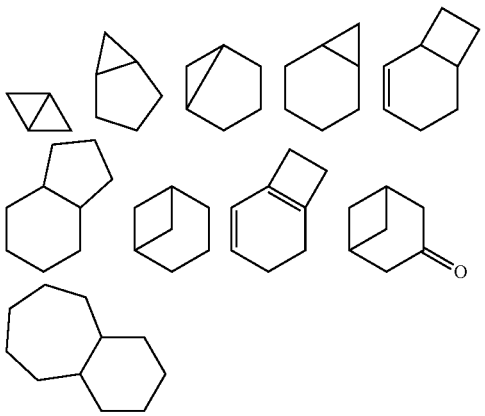

"$C_{3-20}$ alicyclic group" also encompasses compounds fused to an aromatic ring. Specific examples thereof include the groups represented by the following and the like.

[Chemical Formula 619]

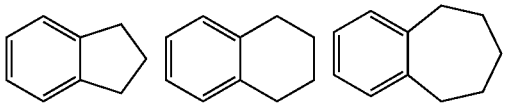

"$C_{3-10}$ alicyclic group" refers to the "$C_{3-20}$ alicyclic group" described above wherein the "$C_{3-10}$ alicyclic group" is a monovalent group.

"$C_{6-10}$ aryl" refers to a monocyclic or bicyclic aromatic hydrocarbon ring with 6 to 10 carbon atoms. Specific examples thereof include a phenyl group, 1-naphthyl group, 2-naphthyl group, and the like. Preferred $C_{6-10}$ aryl includes $C_6$ aryl and $C_{10}$ aryl.

"5- or 6-membered heteroaryl" refers to a monocyclic aromatic heterocycle consisting of 5 to 6 atoms, comprising 1 to 4 of the same or different heteroatoms selected from the group consisting of an oxygen atom, a nitrogen atom, and a sulfur atom.

"5- to 10-membered heteroaryl" refers to a monocyclic or bicyclic aromatic heterocycle consisting of 5 to 10 atoms, comprising 1 to 4 of the same or different heteroatoms selected from the group consisting of an oxygen atom, a nitrogen atom, and a sulfur atom.

"9- or 10-membered heteroaryl" refers to a bicyclic aromatic heterocycle consisting of 9 to 10 atoms, comprising 1 to 4 of the same or different heteroatoms selected from the group consisting of an oxygen atom, a nitrogen atom, and a sulfur atom.

"5- or 6-membered nitrogen-containing heteroaryl" refers to a monocyclic aromatic heterocycle consisting of 5 to 6 atoms, comprising 0 to 3 of the same or different heteroatoms selected from the group consisting of an oxygen atom, a nitrogen atom, and a sulfur atom, in addition to 1 nitrogen atom.

Specific examples of "6-membered heteroaryl" include, but are not limited to, pyridine, pyridazine, pyrimidine, pyrazine, and the like.

Specific examples of "5-membered heteroaryl" include, but are not limited to, thiophene, pyrrole, thiazole, isothiazole, pyrazole, imidazole, furan, oxazole, isoxazole, oxadiazole, thiadiazole, triazole, tetrazole, and the like. 5-membered heteroaryl is preferably triazole, tetrazole, or thiadiazole, and more preferably thiadiazole.

Specific examples of "5- or 6-membered heteroaryl" include the specific examples for "5-membered heteroaryl" and "6-membered heteroaryl" described above.

"4- to 20-membered non-aryl heterocycle" refers to a monocyclic or bicyclic non-aromatic heterocycle comprised of 4 to 20 atoms, comprising 1 to 2 of the same or different heteroatoms selected from the group consisting of an oxygen atom, a nitrogen atom, and a sulfur atom, including those with a partially unsaturated bond, those with a partially crosslinked structure, and those that have a partially spiro form. A non-aryl heterocycle may form a fused ring with aryl or heteroaryl. When fused to, for example, $C_{6-10}$ aryl or 5- or 6-membered heteroaryl, such a heterocycle is still encompassed by a heterocycle. Such a heterocycle may comprise 1 or 2 carbonyl, thiocarbonyl, sulfinyl, or sulfonyl to make up the non-aryl heterocycle. For example, lactam, thiolactam, lactone, thiolactone, cyclic imide, cyclic carbamate, cyclic thiocarbamate, and other cyclic groups are also encompassed by said non-aryl heterocycle. In this regard, oxygen atoms of carbonyl, sulfinyl, and sulfonyl and sulfur atoms of thiocarbonyl are not included in the number of 4 to 20 members (size of ring) or the number of heteroatoms constituting the ring. Specific examples of "4- to 20-membered non-aryl heterocycle" include, but are not limited to, azetidine, pyrrolidine, piperidine, piperazine, morpholine, homopiperidine, oxetane, tetrahydrofuran, tetrahydropyran, and the like, those with a structure shown below, and the like.

[Chemical Formula 620]

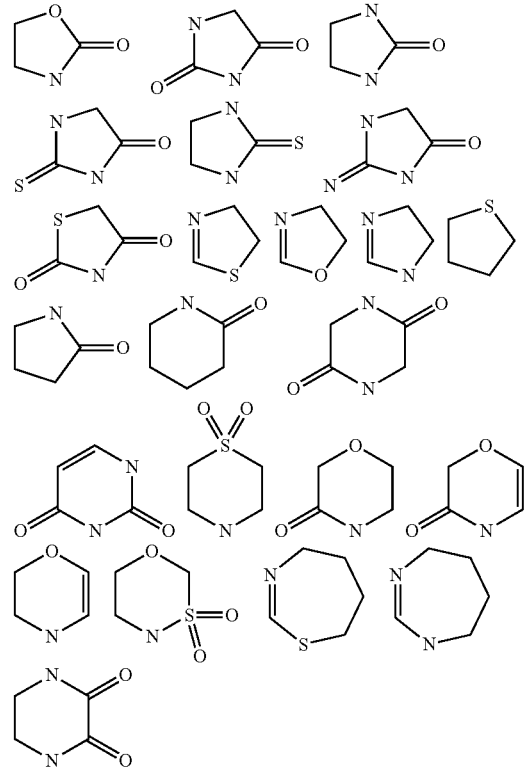

Specific examples of "4- to 20-membered non-aryl heterocycle" with partial crosslinking or spiro structure include, but are not limited to, those with a structure shown below and the like.

[Chemical Formula 621]

"4- to 20-membered nitrogen-containing non-aryl heterocycle" refers to a monocyclic or bicyclic non-aromatic heterocycle comprised of 4 to 20 atoms, comprising 0 or 1 of the same or different heteroatoms selected from the group consisting of an oxygen atom, a nitrogen atom, and a sulfur atom, in addition to 1 nitrogen atom, including those with a partially unsaturated bond, those with a partially crosslinked structure, and those that have a partially spiro form.

"4- to 10-membered non-aryl heterocycle" refers to the "4- to 20-membered non-aryl heterocycle" described above wherein "4- to 10-membered non-aryl heterocycle" is a monovalent group.

"4- to 10-membered nitrogen-containing non-aryl heterocycle" refers to the "4- to 20-membered nitrogen-containing non-aryl heterocycle" wherein the "4- to 10-membered nitrogen-containing non-aryl heterocycle" is a monovalent group.

"5- to 7-membered non-aryl heterocycle" refers to the "4- to 20-membered non-aryl heterocycle" described above wherein "5- to 7-membered non-aryl heterocycle" is a monovalent group.

"4- to 7-membered non-aryl heterocycle" refers to the "4- to 20-membered non-aryl heterocycle" described above wherein "4- to 7-membered non-aryl heterocycle" is a monovalent group.

Specific examples of "4-membered non-aryl heterocycle" include, but are not limited to, azetidine, oxetane, thietane, and the like.

Specific examples of "4-membered non-aryl heterocycle" with a partially unsaturated bond include, but are not limited to, those with a structure shown below and the like.

[Chemical Formula 622]

Specific examples of "5-membered non-aryl heterocycle" include, but are not limited to, pyrrolidine, pyrrolidone, oxazolidinone, tetrahydrofuran, tetrahydrothiophene, and the like.

Specific examples of "5-membered non-aryl heterocycle" with a partially unsaturated bond include, but are not limited to, those with a structure shown below and the like.

[Chemical Formula 623]

Specific examples of "5-membered non-aryl heterocycle" with a partially crosslinked structure include, but are not limited to, those with a structure shown below and the like.

[Chemical Formula 624]

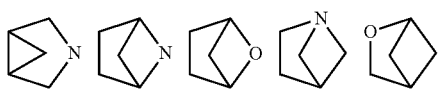

Specific examples of "5-membered non-aryl heterocycle" comprising carbonyl, thiocarbonyl, or the like include, but are not limited to, those with a structure shown below and the like.

[Chemical Formula 625]

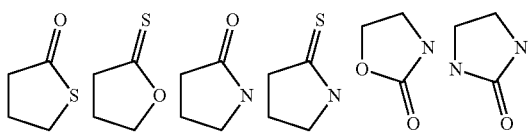

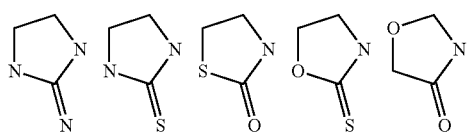

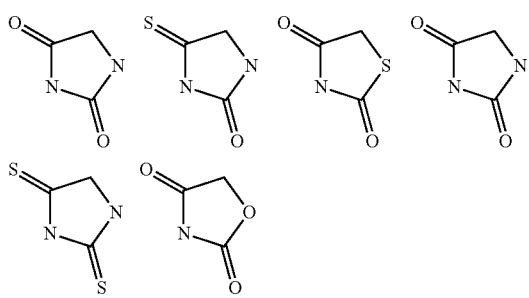

Specific examples of "6-membered non-aryl heterocycle" include, but are not limited to, piperidine, piperazine, morpholine, tetrahydropyran, tetrahydrothiopyran, and the like.

Specific examples of "6-membered non-aryl heterocycle" with a partially unsaturated bond include, but are not limited to, those with a structure shown below and the like.

[Chemical Formula 626]

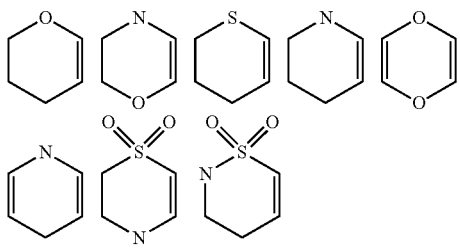

Specific examples of "6-membered non-aryl heterocycle" with a partially crosslinked structure include, but are not limited to, those with a structure shown below and the like.

[Chemical Formula 627]

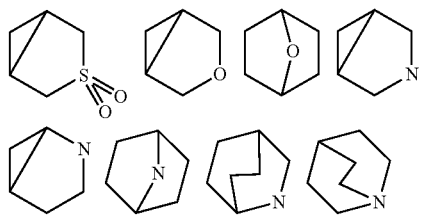

"$C_{1-6}$ alkoxy group" refers to a "$C_{1-6}$ alkyloxy group", and the $C_{1-6}$ alkyl moiety is defined the same as the $C_{1-6}$ alkyl group described above. "$C_{1-6}$ alkoxy group" is preferably a "$C_{1-4}$ alkoxy group", more preferably a "$C_{1-3}$ alkoxy group", and still more preferably a "$C_{1-2}$ alkoxy group". Specific examples of "$C_{1-6}$ alkoxy group" include, but are not limited to, a methoxy group, ethoxy group, propoxy group, butoxy group, isopropoxy group, isobutoxy group, tert-butoxy group, sec-butoxy group, isopentyloxy group, neopentyloxy group, tert-pentyloxy group, 1,2-dimethylpropoxy group, and the like.

"$C_{3-10}$ alicyclic oxy group" refers to a ($C_{3-10}$ alicyclic group)-O-group, and the $C_{3-10}$ alicyclic moiety is defined the same as a $C_{3-10}$ alicyclic group. "$C_{3-6}$ alicyclic oxy group" refers to a ($C_{3-6}$ alicyclic group)-O-group, and the $C_{3-6}$ alicyclic moiety is defined the same as a $C_{3-6}$ alicyclic group. "$C_{3-6}$ alicyclic oxy group" is preferably a "$C_{3-5}$ alicyclic oxy group". Specific examples of "$C_{3-6}$ alicyclic oxy group" include, but are not limited to, a cyclopropyloxy group, cyclobutyloxy group, cyclopentyloxy group, cyclohexyloxy group, and the like.

The $C_{6-10}$ aryl moiety of a "$C_{6-10}$ aryloxy group" is defined the same as the $C_{6-10}$ aryl described above. "$C_{6-10}$ aryloxy group" is preferably a "$C_6$ or $C_{10}$ aryloxy group". Specific examples of "$C_{6-10}$ aryloxy group" include, but are not limited to, a phenoxy group, 1-naphthyloxy group, 2-naphthyloxy group, and the like.

The 5- or 6-membered heteroaryl moiety of "5- or 6-membered heteroaryloxy group" is defined the same as the "5-membered heteroaryl" or "6-membered heteroaryl" described above. Specific examples of "5- or 6-membered heteroaryloxy group" include, but are not limited to, a pyrazoyloxy group, triazoyloxy group, thiazoyloxy group, thiadiazoyloxy group, pyridyloxy group, pyridazoyloxy group, and the like.

The 4- to 10-membered non-aryl heterocycle moiety of "4- to 10-membered non-aryl heterocyclyl oxy group" is defined the same as the "4- to 10-membered non-aryl heterocycle" described above. "4- to 10-membered non-aryl heterocyclyl oxy group" is preferably a "4- to 6-membered non-aryl heterocyclyl oxy group". Specific examples of "4- to 10-membered non-aryl heterocyclyl oxy group" include, but are not limited to, a tetrahydrofuranyloxy group, tetrahydropyranyloxy group, azetidinyloxy group, pyrrolidinyloxy group, piperidinyloxy group, and the like.

The $C_{1-6}$ alkyl moiety of "$C_{1-6}$ alkylthio group" is defined the same as the $C_{1-6}$ alkyl described above. "$C_{1-6}$ alkylthio group" is preferably a "$C_{1-4}$ alkylthio group", and more preferably a "$C_{1-3}$ alkylthio group". Specific examples of "$C_{1-6}$ alkylthio group" include, but are not limited to, a methylthio group, ethylthio group, propylthio group, butylthio group, isopropylthio group, isobutylthio group, tert-butylthio group, sec-butylthio group, isopentylthio group, neopentylthio group, tert-pentylthio group, 1,2-dimethylpropylthio group, and the like.

"$C_{3-10}$ alicyclic thio group" refers to a ($C_{3-10}$ alicyclic group)-S-group, and the $C_{3-10}$ alicyclic moiety is defined the same as the $C_{3-10}$ alicyclic group described above. "$C_{3-10}$ alicyclic thio group" is preferably a "$C_{3-6}$ alicyclic thio group". Specific examples of "$C_{3-6}$ alicyclic thio group" include, but are not limited to, a cyclopropylthio group, cyclobutylthio group, cyclopentylthio group, cyclohexylthio group, and the like.

The $C_{6-10}$ aryl moiety of "$C_{6-10}$ arylthio group" is defined the same as the $C_{6-10}$ aryl described above. "$C_{6-10}$ arylthio group" is preferably a "$C_6$ or $C_{10}$ arylthio group". Specific examples of "$C_{6-10}$ aryloxy group" include, but are not limited to, a phenylthio group, 1-naphthylthio group, 2-naphthylthio group, and the like.

The 5- or 6-membered heteroaryl moiety of "5- or 6-membered heteroarylthio group" is defined the same as the "5-membered heteroaryl" or "6-membered heteroaryl" described above. Specific examples of "5- or 6-membered heteroarylthio group" include, but are not limited to, a pyrazoylthio group, triazoylthio group, thiazoylthio group, thiadiazoylthio group, pyridylthio group, pyridazoylthio group, and the like.

The 4- to 10-membered non-aryl heterocycle moiety of "4- to 10-membered non-aryl heterocyclyl thio group" is defined the same as the "4- to 10-membered non-aryl heterocycle" described above. "4- to 10-membered non-aryl heterocyclyl thio group" is preferably a "4- to 6-membered non-aryl heterocyclyl thio group". Specific examples of "4- to 10-membered non-aryl heterocyclyl thio group" include, but are not limited to, a tetrahydropyranylthio group, piperidinylthio group, and the like.

"$C_{1-6}$ alkylcarbonyl group" refers to a carbonyl group substituted with the "$C_{1-6}$ alkyl group" described above. "$C_{1-6}$ alkylcarbonyl group" is preferably a "$C_{1-4}$ alkylcarbonyl group". Specific examples of "$C_{1-6}$ alkylcarbonyl group" include, but are not limited to, an acetyl group, propionyl group, butyryl group, and the like.

"$C_{3-10}$ alicyclic carbonyl group" refers to a carbonyl group substituted with the "$C_{3-10}$ alicyclic group" described above. "$C_{3-10}$ alicyclic carbonyl group" is preferably a "$C_{3-6}$ alicyclic carbonyl group". Specific examples of "$C_{3-10}$ alicyclic carbonyl group" include, but are not limited to, a cyclopropylcarbonyl group, cyclopentylcarbonyl group, and the like.

"$C_{6-10}$ arylcarbonyl group" refers to a carbonyl group substituted with the "$C_{6-10}$ aryl" described above. "$C_{6-10}$ arylcarbonyl group" is preferably a "$C_6$ or $C_{10}$ arylcarbonyl group". Specific examples of "$C_{6-10}$ arylcarbonyl group" include, but are not limited to, a benzoyl group, 1-naphthylcarbonyl group, 2-naphthylcarbonyl group, and the like.

"5- or 6-membered heteroarylcarbonyl group" refers to a carbonyl group substituted with the "5- or 6-membered heteroaryl" described above. Specific examples of "5- or 6-membered heteroarylcarbonyl group" include, but are not limited to, a pyrazoylcarbonyl group, triazoylcarbonyl group, thiazoylcarbonyl group, thiadiazoylcarbonyl group, pyridylcarbonyl group, pyridazoylcarbonyl group, and the like.

"4- to 10-membered non-aryl heterocyclyl carbonyl group" refers to a carbonyl group substituted with the "4- to 10-membered non-aryl heterocycle" described above. "4- to 10-membered non-aryl heterocyclyl carbonyl group" is preferably a "4- to 6-membered non-aryl heterocyclyl carbonyl group". Specific examples of "4- to 10-membered non-aryl heterocyclyl carbonyl group" include, but are not limited to, an azetidinylcarbonyl group, pyrrolidinylcarbonyl group, piperidinylcarbonyl group, morpholinylcarbonyl group, and the like.

"$C_{1-6}$ alkylsulfonyl group" refers to a sulfonyl group substituted with the "$C_{1-6}$ alkyl group" described above. "$C_{1-6}$ alkylsulfonyl group" is preferably a "$C_{1-4}$ alkylsulfonyl group". Specific examples of "$C_{1-6}$ alkylsulfonyl group" include, but are not limited to, a methylsulfonyl group, propionylsulfonyl group, butyrylsulfonyl group, and the like.

"$C_{3-10}$ alicyclic sulfonyl group" refers to a sulfonyl group substituted with the "$C_{3-10}$ alicyclic group" described above. "$C_{3-10}$ alicyclic sulfonyl group" is preferably a "$C_{3-6}$ alicyclic sulfonyl group". Specific examples of "$C_{3-10}$ alicyclic sulfonyl group" include, but are not limited to, a cyclopropylsulfonyl group, cyclobutylsulfonyl group, cyclopentylsulfonyl group, cyclohexylsulfonyl group, and the like.

"$C_{6-10}$ arylsulfonyl group" refers to a sulfonyl group substituted with the "$C_{6-10}$ aryl" described above. "$C_{6-10}$ arylsulfonyl group" is preferably a "$C_6$ or $C_{10}$ arylsulfonyl group". Specific examples of "$C_{6-10}$ arylsulfonyl group" include, but are not limited to, a phenylsulfonyl group, 1-naphthylsulfonyl group, 2-naphthylsulfonyl group, and the like.

"5- or 6-membered heteroarylsulfonyl group" refers to a sulfonyl group substituted with the "5- or 6-membered heteroaryl" described above. Specific examples of "5- or 6-membered heteroarylsulfonyl group" include a pyrazoylsulfonyl group, triazoylsulfonyl group, thiazoylsulfonyl group, thiadiazoylsulfonyl group, pyridylsulfonyl group, pyridazoylsulfonyl group, and the like.

"$C_{1-6}$ alkylene group" refers to a substituent that is a divalent group due to removing two hydrogen atoms from saturated hydrocarbon with 1 to 6 carbon atoms. "$C_{1-3}$ alkylene group" and "$C_{2-4}$ alkylene group" refer to substituents that are divalent groups due to removing two hydrogen atoms from saturated hydrocarbon with 1 to 3 carbon atoms and 2 to 4 carbon atoms, respectively.

"$C_{3-10}$ cycloalkylene group" refers to a substituent that is a divalent group due to removing two hydrogen atoms from saturated cyclic hydrocarbon with 3 to 10 carbon atoms. "$C_{3-6}$ cycloalkylene group" and "$C_{4-6}$ cycloalkylene group" refer to substituents that are divalent groups due to removing two hydrogen atoms from saturated cyclic hydrocarbon with 3 to 6 carbon atoms and 4 to 6 carbon atoms, respectively.

"$C_{6-10}$ arylene group" refers to a substituent that is a divalent group due to removing two hydrogen atoms from aromatic hydrocarbon with 6 to 10 carbon atoms. "$C_6$ arylene group" refers to a substituent that is a divalent group due to removing two hydrogen atoms from aromatic hydrocarbon with 6 carbon atoms.

"5- or 6-membered heteroarylene group" refers to a substituent that is a divalent group due to removing two hydrogen atoms from a 5- or 6-membered heteroaryl ring. "5-membered heteroarylene group" and "6-membered heteroarylene group" refer to substituents that are divalent groups due to removing two hydrogen atoms from 5-membered and 6-membered heteroaryl rings, respectively.

"4- to 10-membered non-aryl heterocyclylene group" refers to a substituent that is a divalent group due to removing two hydrogen atoms from a 4- to 10-membered non-aryl heterocycle. "4- to 5-membered non-aryl heterocyclylene group" and "4- to 6-membered non-aryl heterocyclylene group" refer to substituents that are divalent groups due to removing two hydrogen atoms from 4- to 5-membered and 4- to 6-membered non-aryl heterocycles, respectively.

A bond intersecting a wavy line in the description of a specific structure of $R^5$ indicates a bond with $L^4$. A bond intersecting a bond between ring atoms means that there are variables (e.g., $R^{6a}$, $R^{7a}$, and the like) at each of the substitutable positions on a monocycle or fused polycycle including the ring atoms. For example, for a monocyclic 5-membered ring (heteroaryl),

[Chemical Formula 628]

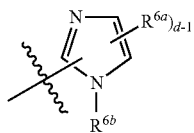

(wherein d is 3) is one of

[Chemical Formula 629]

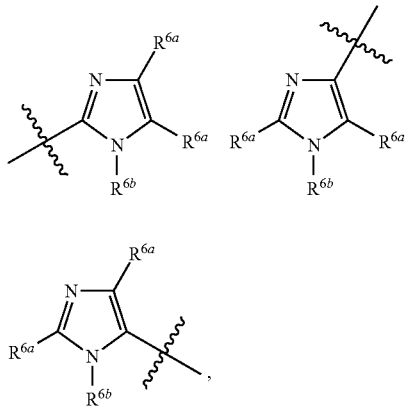

$L^4$ attaches to a ring carbon atom of the 5-membered ring. For example, for a monocyclic 6-membered ring (heteroaryl),

[Chemical Formula 630]

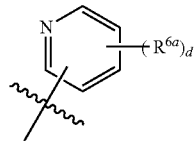

(wherein d is 4) is one of

[Chemical Formula 631]

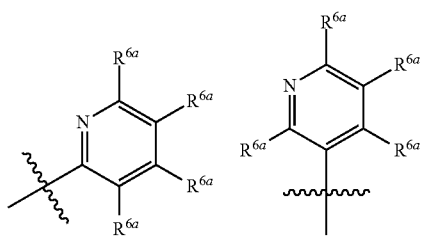

-continued

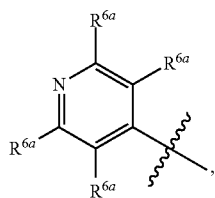

$L^4$ attaches to a ring carbon atom of the 6-membered ring. Alternatively, for example, for a monocyclic 5-membered ring (non-aryl heterocycle),

[Chemical Formula 632]

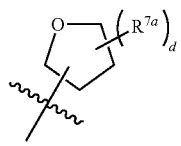

(wherein d is 7) is one of

[Chemical Formula 633]

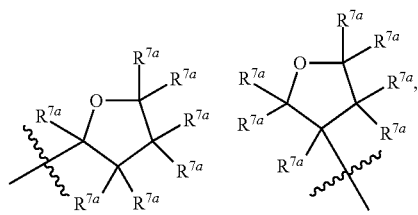

and
$L^4$ attaches to a ring carbon atom of the 5-membered ring. For example, for a monocyclic 6-membered ring (non-aryl heterocycle),

[Chemical Formula 634]

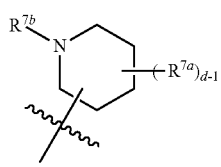

(wherein d is 10) is one of

[Chemical Formula 635]

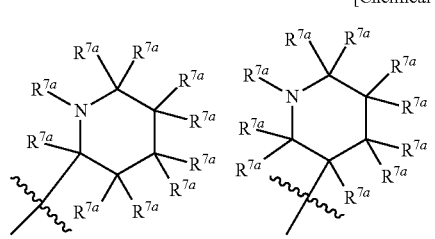

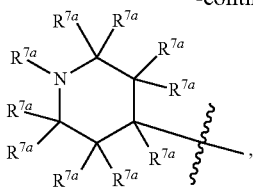

and $L^4$ attaches to a ring carbon atom of the 6-membered ring.

Subscript d is the number of substitutable positions on a ring of $R^5$, but is a number of substitutable positions excluding the attachment position to $L^4$.

"Bioisostere" refers to another partial structure (functional group) serving the same biological role as a group (e.g., carboxyl group) in a drug molecule (prodrug structures are also encompassed as a concept of a bioisostere in the present invention). "Carboxylic acid isostere" refers to a bioisostere of carboxylic acid. Examples of the carboxylic acid isostere include, but are not limited to, —SO$_3$H, —SO$_2$NHR$^{19a}$, —B(OR$^{m1}$)$_2$, —PO(OR$^{m1}$)(OR$^{m2}$), —CONHR$^{19a}$, —CONHSO$_2$R$^{19a}$, —CONR$^{19a}$CN, —CONHNHSO$_2$R$^{19a}$, and substituents represented by the formulas (8A), (8B), (8C), (8D), (8E), (8F), (8G), (8H), (8I), (8J), (8K), (8L), (8M), (8N), (8O), (8P), (8Q), (8R), (8S), (BT), (8U), (8V), and (8W) described below (each of the substituents is further optionally substituted with 1 to 3 of the same or different R$^{19b}$ at a chemical substitutable position),

[Chemical Formula 636]

Formulas (8A); (8B); (8C); (8D); (8E); (8F); (8G); (8H); (8I); (8J); (8K); (8L); (8M); (8N); (8O); (8P); (8Q); (8R); (8S); (8T); (8U); (8V); (8W);

(8A)

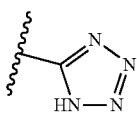

(8B)

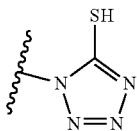

(8C)

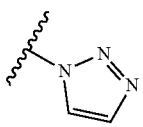

(8D)

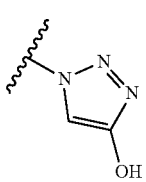

(8E)

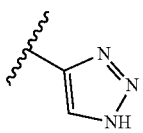

(8F)

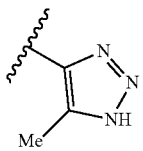

(8G)

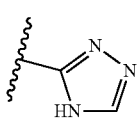

(8H)

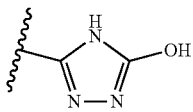

(8I)

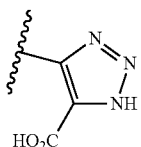

(8J)

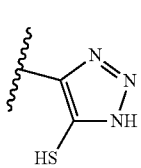

(8K)

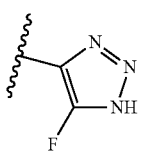

(8L)

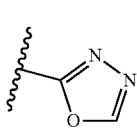

(8M)

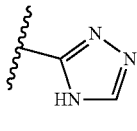

(8N)

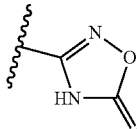

(8O)

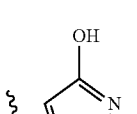

(8P)

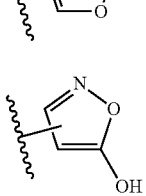

-continued (8Q) 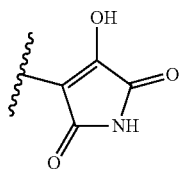

(8R) 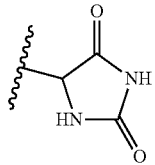

(8S) 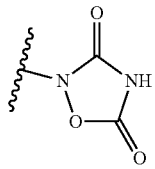

(8T) 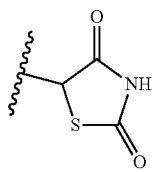

(8U) 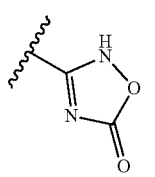

(8V) 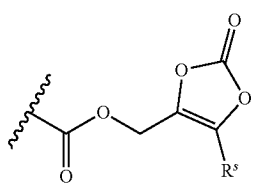

(8W) 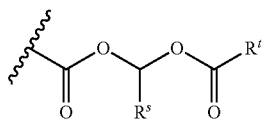

wherein [in (8V) and (8W), $R^s$ is a hydrogen atom, a $C_{1-6}$ alkyl group, or a $C_{3-10}$ alicyclic group (wherein the $C_{1-6}$ alkyl group or $C_{3-10}$ alicyclic group is optionally substituted with 1 to 5 halogen atoms), $R^t$ is a hydrogen atom, a $C_{1-6}$ alkyl group, a $C_{1-6}$ alkoxy group, (wherein the $C_{1-6}$ alkyl group or $C_{1-6}$ alkoxy group is optionally substituted with 1 to 5 halogen atoms), a $C_{3-10}$ alicyclic group, a $C_{3-10}$ alicyclic oxy group, a phenyl group, a phenoxy group, a pyridyl group, or a pyridyloxy group, (wherein the $C_{3-10}$ alicyclic group, $C_{3-10}$ alicyclic oxy group, phenyl group, phenoxy group, pyridyl group, or pyridyloxy group is optionally substituted with 1 to 5 substituents selected from the group consisting of a halogen atom, a $C_{1-6}$ alkyl group, and a $C_{1-6}$ alkoxy group)], $R^{19a}$ and $R^{19b}$ are the same or different, each independently representing a hydrogen atom, a hydroxyl group, a $C_{1-6}$ alkyl group, $C_{6-10}$ aryl, 5- or 6-membered heteroaryl, or a 4- to 10-membered non-aryl heterocycle, $R^{m1}$ represents
1) a hydrogen atom,
2) a $C_{1-6}$ alkyl group,
3) a $C_{3-10}$ alicyclic group,
4) $C_{6-10}$ aryl,
5) 5- or 6-membered heteroaryl, or
6) a 4- to 10-membered non-aryl heterocycle,
(wherein each substituent from 2) to 6) is optionally substituted), wherein if $R^{m1}$ is attached to a boron atom via an oxygen atom, two $R^{m1}$, as $C_{2-4}$ alkylene, together with the boron atom and two oxygen atoms, may form a 5- to 7-membered non-aryl heterocycle (wherein an alkylene moiety is optionally substituted in the non-aryl heterocycle), and $R^{m2}$ represents a hydrogen atom, an optionally substituted $C_{1-6}$ alkyl group, or an optionally substituted $C_{3-10}$ alicyclic group, wherein, preferably, $R^s$ is a hydrogen atom or a $C_{1-5}$ alkyl group, and
$R^t$ is a hydrogen atom, a $C_{1-6}$ alkyl group, a $C_{1-6}$ alkoxy group, a $C_{3-10}$ alicyclic group, or a $C_{3-10}$ alicyclic oxy group, or alternatively preferably, $R^{19a}$ and $R^{19b}$ are the same or different, each independently a hydrogen atom, a hydroxyl group, or a $C_{1-6}$ alkyl group,
or also preferably $R^{m1}$ and $R^{m2}$ are the same or different, each independently a hydrogen atom, a $C_{1-6}$ alkyl group, or a $C_{3-10}$ alicyclic group.

An exemplary embodiment of the compounds of the invention is a compound represented by formula (1a) or (1b)

[Chemical Formula 637]

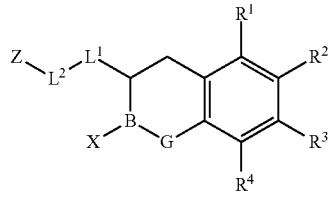

(1a)

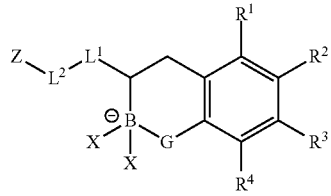

(1b)

or a pharmaceutically acceptable salt thereof,
wherein
G is an oxygen atom, a sulfur atom, or —$NR^{a1}$—,
X is a hydroxyl group, an optionally substituted $C_{1-6}$ alkoxy group, or —$NR^{a2}R^{b1}$,
$R^{a1}$, $R^{a2}$, and $R^{b1}$ are the same or different, each independently
1) a hydrogen atom,
2) a $C_{1-6}$ alkyl group,
3) a $C_{3-10}$ alicyclic group,
4) $C_{6-10}$ aryl
5) 5- or 6-membered heteroaryl,
6) a 4- to 10-membered non-aryl heterocycle, 7) a $C_{1-6}$ alkylcarbonyl group,
8) a $C_{3-10}$ alicyclic carbonyl group,
9) a $C_{6-10}$ arylcarbonyl group,
10) a 5- or 6-membered heteroarylcarbonyl group,
11) a $C_{1-6}$ alkylsulfonyl group,
12) a $C_{3-10}$ alicyclic sulfonyl group,
13) a $C_{6-10}$ arylsulfonyl group,
14) a 5- or 6-membered heteroarylsulfonyl group, or
15) —$OR^{e1}$,
(wherein each substituent from 2) to 14) is optionally substituted),
wherein $R^{a2}$ and $R^{b1}$ together may form an optionally substituted 4- to 10-membered nitrogen-containing non-aryl heterocycle,
$R^{e1}$ is
1) a hydrogen atom,
2) a $C_{1-6}$ alkyl group,
3) a $C_{3-10}$ alicyclic group,
4) $C_{6-10}$ aryl,
5) 5- or 6-membered heteroaryl, or
6) a 4- to 10-membered non-aryl heterocycle,
(wherein each substituent from 2) to 6) is optionally substituted),
$L^1$ is a single bond, an oxygen atom, a sulfur atom, —SO—, —$SO_2$—, —$NR^d$—, —$NR^dC(=O)$—, or —$NR^dSO_2$—,
$L^2$ is a single bond or an optionally substituted $C_{1-6}$ alkylene group,
Z is
1) a hydrogen atom,
2) a hydroxyl group,
3) a cyano group,
4) a carboxyl group,
5) a $C_{3-10}$ alicyclic group,
6) $C_{6-10}$ aryl,
7) 5- or 6-membered heteroaryl,
8) a 4- to 10-membered non-aryl heterocycle,
9) a $C_{1-6}$ alkoxy group,
10) a $C_{3-10}$ alicyclic oxy group,
11) a $C_{6-10}$ aryloxy group,
12) a 5- or 6-membered heteroaryloxy group,
13) a 4- to 10-membered non-aryl heterocyclyl oxy group,
14) a $C_{1-6}$ alkylthio group,
15) a $C_{3-10}$ alicyclic thio group,
16) a $C_{6-10}$ arylthio group,
17) a 5- or 6-membered heteroarylthio group,
18) a 4- to 10-membered non-aryl heterocyclyl thio group,
(wherein each substituent from 5) to 18) is optionally substituted),
19) —$SO_2$—$NR^{e1}R^{f1}$,
20) —$NR^{e1}$—$C(=O)OR^{f1}$,
21) —$NR^{g1}$—$C(=O)NR^{e1}R^{f1}$,
22) —$NR^{e1}$—$C(=S)R^{f1}$,
23) —$NR^{e1}$—$C(=S)OR^{f1}$,
24) —$NR^{g1}$—$C(=S)NR^{e1}R^{f1}$,
25) —$NR^{g1}$—$CR^{e1}(=NR^{f1})$,
26) —$NR^{g1}$—$CR^{e1}(=N-OR^{f1})$,
27) —$NR^{h1}$—$C(=NR^{g1})NR^{e1}R^{f1}$,
28) —$NR^{h1}$—$C(=N-OR^{g1})NR^{e1}R^{f1}$,
29) —$NR^{i1}$—$C(=NR^{h1})NR^{g1}$—$NR^{e1}R^{f1}$,
30) —$NR^{i1}$—$C(=N-OR^{h1})NR^{g1}$—$NR^{e1}R^{f1}$,
31) —$NR^{e1}$—$SO_2$—$R^{f1}$,
32) —$NR^{g1}$—$SO_2$—$NR^{e1}R^{f1}$,
33) —$C(=O)OR^{e1}$,
34) —$C(=S)OR^{e1}$,
35) —$C(=S)NR^{e1}R^{f1}$,
36) —$C(=S) NR^{e1}OR^{f1}$,
37) —$C(=S)NR^{g1}$—$NR^{e1}R^{f1}$,
38) —$C(=NR^{e1})R^{f1}$,
39) —$C(=N-OR^{e1})R^{f1}$,
40) —$C(=NR^{h1})NR^{g1}$—$NR^{e1}R^{f1}$,
41) —$C(=N-OR^{h1})NR^{g1}$—$R^{e1}R^{f1}$,
42) —$NR^{e1}R^{f1}$,
43) —$NR^{g1}$—$NR^{e1}R^{f1}$,
44) —$NR^{e1}OR^{f1}$,
45) —$NR^{e1}$—$C(=O)R^{f1}$,
46) —$C(=O) NR^{e1}R^{f1}$,
47) —$C(=O)NR^{e1}OR^{f1}$,
48) —$C(=O)NR^{g1}$—$NR^{e1}R^{f1}$,
49) —$C(=O)R^{e1}$,
50) —$C(=NR^{g1})NR^{e1}$, or
51) —$C(=N-OR^{h1})NR^{e1}R^{f1}$,
one of $R^1$, $R^2$, and $R^3$ is formula (2):

[Chemical Formula 638]

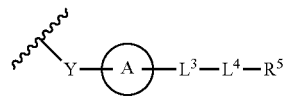

(2)

wherein,
Y is an oxygen atom, a sulfur atom, or —$NR^j$—,
ring A is an optionally substituted 4- to 20-membered non-aryl heterocycle,
$L^3$ is —$C(=O)$—, —$S(=O)$—, or —$S(=O)_2$—,
$L^4$ is
1) a single bond,
2) a $C_{1-6}$ alkylene group,
3) a $C_{3-10}$ cycloalkylene group,
4) a $C_{6-10}$ arylene group,
5) a 5- or 6-membered heteroarylene group,
6) a 4- to 10-membered non-aryl heterocyclylene group, or
7) —$C(=N-OR^{h1})$—,
(wherein each substituent from 2) to 6) is optionally substituted), and
$R^5$ is
1) a hydrogen atom,
2) a $C_{1-6}$ alkyl group,
3) a $C_{3-10}$ alicyclic group,
4) a 4- to 10-membered non-aryl heterocycle,
5) $C_{6-10}$ aryl,
6) 5- or 6-membered heteroaryl,
7) a $C_{1-6}$ alkylthio group,
(wherein each substituent from 2) to 7) is optionally substituted), or
8) —$NR^{e1}OH$,
the remaining two (without the structure of formula (2) among $R^1$, $R^2$, and $R^3$) are the same or different, each independently a hydrogen atom, a halogen atom, an optionally substituted $C_{1-6}$ alkyl group, an optionally substituted $C_{1-6}$ alkoxy group, an optionally substituted $C_{1-6}$ alkylthio group, an optionally substituted 5- or 6-membered heteroaryl, or —$NR^{a3}R^{b2}$,
$R^d$, $R^{e1}$, $R^{e2}$, $R^{f1}$, $R^{f2}$, $R^{g1}$, $R^{g2}$, $R^{h1}$, $R^{h2}$, $R^{i1}$, $R^{i2}$, and $R^j$ are the same or different, each independently a hydrogen atom, an optionally substituted $C_{1-6}$ alkyl group, an optionally substituted $C_{3-10}$ alicyclic group, optionally substituted $C_{6-10}$ aryl, optionally substituted 5- or 6-membered heteroaryl, or an optionally substituted 4- to 10-membered non-aryl heterocycle, a combination of $R^{e1}$ and $R^{f1}$ or $R^{e2}$ and $R^{f2}$, when attached to the same nitrogen atom, together may form an optionally substituted 4- to 10-membered nitrogen-containing non-aryl heterocycle, $R^4$ is
1) —C(=O)R$^8$,
2) —SO$_2$-L$^6$-R$^8$,
(wherein R$^8$ in 1) and 2) is —NR$^{a5}$R$^{b4}$, —NR$^{a5}$-L$^7$-B(OR$^{m1}$)$_2$, —OR$^{m1}$, or an optionally substituted C$_{1-6}$ alkyl group, and L$^6$ is a single bond or —NR$^{a6}$—),
3) —NR$^{a4}$R$^{b3}$,
4) —B(OR$^{m1}$)$_2$,
5) —PO(OR$^{m1}$)(OR$^{m2}$),
6) optionally substituted 5-membered heteroaryl,
7) an optionally substituted 5-membered non-aryl heterocycle, or
8) a bioisostere of one of 1) to 7),
(wherein the formulas of 2), 4), 5), and 6) include a carboxylic acid isostere, and 8) may include them in duplicates), R$^{a3}$, R$^{a4}$, R$^{a5}$, R$^{a6}$, R$^{b2}$, R$^{b3}$, and R$^{b4}$ are the same or different, each independently having the same definition as R$^{a1}$, R$^{a2}$, and R$^{b1}$, wherein a combination of R$^{a3}$ and R$^{b2}$, R$^{a4}$ and R$^{b3}$, or R$^{a5}$ and R$^{b4}$, when attached to the same nitrogen atom, together may form an optionally substituted 4- to 10-membered nitrogen-containing non-aryl heterocycle, R$^{m1}$ s
1) a hydrogen atom,
2) a C$_{1-6}$ alkyl group,
3) a C$_{3-10}$ alicyclic group,
4) C$_{6-10}$ aryl,
5) 5- or 6-membered heteroaryl, or
6) a 4- to 10-membered non-aryl heterocycle,
(wherein each substituent from 2) to 6) is optionally substituted), wherein if R$^{m1}$ is attached to a boron atom via an oxygen atom, two R$^{m1}$, as C$_{2-4}$ alkylene, together with the boron atom and two oxygen atoms, may form a 5- to 7-membered non-aryl heterocycle (wherein an alkylene moiety is optionally substituted in the non-aryl heterocycle), R$^{m2}$ is a hydrogen atom, an optionally substituted C$_{1-6}$ alkyl group, or an optionally substituted C$_{3-10}$ alicyclic group, and L$^7$ is an optionally substituted C$_{1-3}$ alkylene group.

In some embodiments, Z-L$^2$-L$^1$ is a hydrogen atom, an optionally substituted C$_{1-6}$ alkyl group, or an optionally substituted C$_{1-6}$ alkylthio group. In one embodiment, L$^1$ is a single bond.

In some embodiments, L$^2$ is a single bond or an optionally substituted C$_{1-6}$ alkylene group. In one embodiment, L$^2$ is a single bond.

In some embodiments, Z is
1) a hydrogen atom,
2) a hydroxyl group,
3) a cyano group,
4) a carboxyl group,
5) a C$_{3-10}$ alicyclic group,
6) C$_{6-10}$ aryl,
7) 5- or 6-membered heteroaryl,
8) a 4- to 10-membered non-aryl heterocycle,
9) a C$_{1-6}$ alkoxy group,
10) a C$_{3-10}$ alicyclic oxy group,
11) a C$_{6-10}$ aryloxy group,
12) a 5- or 6-membered heteroaryloxy group,
13) a 4- to 10-membered non-aryl heterocyclyl oxy group,
14) a C$_{1-6}$ alkylthio group,
15) a C$_{3-10}$ alicyclic thio group,
16) a C$_{6-10}$ arylthio group,
17) a 5- or 6-membered heteroarylthio group,
18) a 4- to 10-membered non-aryl heterocyclyl thio group,
(wherein each substituent from 5) to 18) is optionally substituted),
19) —SO$_2$—NR$^{e1}$R$^{f1}$,
20) —NR$^{e1}$—C(=O)OR$^{f1}$,
21) —NR$^{g1}$—C(=O)NR$^{e1}$R$^{f1}$,
22) —NR$^{e1}$—C(=S)R$^{f1}$,
23) —NR$^{e1}$—C(=S)OR$^{f1}$,
24) —NR$^{g1}$—C(=S)NR$^{e1}$R$^{f1}$,
25) —NR$^{g1}$—CR$^{e1}$(=NR$^{f1}$),
26) —NR$^{g1}$—CR$^{e1}$(=N—OR$^{f1}$),
27) —NR$^{h1}$—C(=NR$^{g1}$)NR$^{e1}$R$^{f1}$,
28) —NR$^{h1}$—C(=N—OR$^{g1}$)NR$^{e1}$R$^{f1}$,
29) —NR$^{i1}$—C(=NR$^{h1}$)NR$^{g1}$—NR$^{e1}$R$^{f1}$,
30) —NR$^{i1}$—C(=N—OR$^{h1}$)NR$^{g1}$—NR$^{e1}$R$^{f1}$,
31) —NR$^{e1}$—SO$_2$—R$^{f1}$,
32) —NR$^{g1}$—SO$_2$—NR$^{e1}$R$^{f1}$,
33) —C(=O)OR$^{e1}$,
34) —C(=S)OR$^{e1}$,
35) —C(=S) NR$^{e1}$OR$^{f1}$,
36) —C(=S)NR$^{e1}$OR$^{f1}$,
37) —C(=S)NR$^{g1}$—NR$^{g1}$R$^{f1}$,
38) —C(=NR$^{e1}$)R$^{f1}$,
39) —C(=N—OR$^{e1}$)R$^{f1}$,
40) —C(=NR$^{h1}$)NR$^{g1}$—NR$^{e1}$R$^{f1}$,
41) —C(=N—OR$^{h1}$)NR$^{g1}$—NR$^{e1}$R$^{f1}$,
42) —NR$^{e1}$R$^{f1}$,
43) —NR$^{g1}$—NR$^{e1}$R$^{f2}$,
44) —NR$^{e1}$OR$^{f1}$,
45) —NR$^{e1}$—C(=O)R$^{f1}$,
46) —C(=O)NR$^{e1}$R$^{f1}$,
47) —C(=O)NR$^{e1}$OR$^{f1}$,
48) —C(=O)NR$^{g1}$—NR$^{e1}$R$^{f1}$,
49) —C(=O)R$^{e1}$,
50) —C(=NR$^{g1}$)NR$^{e1}$R$^{f1}$, or
51) —C(=N—OR$^{h1}$)NR$^{e1}$R$^{f1}$.

The R$^{e1}$, R$^{f1}$, R$^{g1}$, and R$^{h1}$ are the same as the definitions herein. In a preferred embodiment, Z is one of 1), 2), 5) to 8), 39), and 42). In one embodiment, Z is a hydrogen atom. Alternatively, in another embodiment, Z is an optionally substituted C$_{1-6}$ alkylthio group. In still another embodiment, Z is an optionally substituted C$_{1-6}$ alkyl group.

In a preferred embodiment, Z-L$^2$-L$^1$ is a hydrogen atom. Alternatively, in another embodiment, Z-L$^2$-L$^1$ is an optionally substituted C$_{1-6}$ alkylthio group. In still another embodiment, Z-L$^2$-L$^1$ is an optionally substituted C$_{1-6}$ alkyl group.

In some embodiments, G is an oxygen atom, a sulfur atom, or —NR$^{a1}$—. In one embodiment, G is an oxygen atom or a sulfur atom. In a preferred embodiment, G is an oxygen atom. The R$^{a1}$ is the same as the definition herein.

In some embodiments, X is a hydroxyl group, an optionally substituted C$_{1-6}$ alkoxy group, or —NR$^{a2}$R$^{b1}$. In one embodiment, X is a hydroxyl group or an optionally substituted C$_{1-6}$ alkoxy group. In a preferred embodiment, X is a hydroxyl group. The R$^{a2}$ and R$^{b1}$ are the same as the definitions herein.

In some embodiments, one of $R^1$, $R^2$, and $R^3$ is a group represented by formula (2):

[Chemical Formula 639]

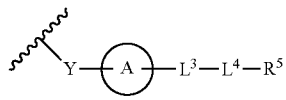

(2)

wherein
Y is an oxygen atom, a sulfur atom, or —$NR^j$—,
ring A is an optionally substituted 4- to 20-membered non-aryl heterocycle,
$L^3$ is —C(=O)—, —S(=O)—, or —S(=O)$_2$—,
$L^4$ is
1) a single bond,
2) a $C_{1-6}$ alkylene group,
3) a $C_{3-10}$ cycloalkylene group,
4) a $C_{6-10}$ arylene group
5) a 5- or 6-membered heteroarylene group,
6) a 4- to 10-membered non-aryl heterocyclylene group, or
7) —C(=N—$OR^{h1}$)—,
(wherein each substituent from 2) to 6) is optionally substituted), and
$R^5$ is
1) a hydrogen atom,
2) a $C_{1-6}$ alkyl group,
3) a $C_{3-10}$ alicyclic group,
4) a 4- to 10-membered non-aryl heterocycle,
5) $C_{6-10}$ aryl,
6) 5- or 6-membered heteroaryl,
7) a $C_{1-6}$ alkylthio group,
(wherein each substituent from 2) to 7) is optionally substituted), or
8) —$NR^{e1}$OH], and
the remaining two (without the structure of formula (2) among $R^1$, $R^2$, and $R^3$) are the same or different, each independently a hydrogen atom, a halogen atom, an optionally substituted $C_{1-6}$ alkyl group, an optionally substituted $C_{1-6}$ alkoxy group, an optionally substituted $C_{1-6}$ alkylthio group, optionally substituted 5- or 6-membered heteroaryl, or —$NR^{a3}R^{b2}$, wherein $R^{a3}$ and $R^{b2}$ are the same as the definitions herein. In a preferred embodiment, $R^3$ has the structure of formula (2).

In one embodiment, if $R^5$ in formula (2) is 2) a $C_{1-6}$ alkyl group, 3) a $C_{3-10}$ alicyclic group, 4) a 4- to 10-membered non-aryl heterocycle, 5) $C_{6-10}$ aryl, 6) 5- or 6-membered heteroaryl, or 7) a $C_{1-6}$ alkylthio group, 2), 3), 4), 5), 6), and 7) are optionally substituted with a carboxyl group or a $C_{1-6}$ alkyl group substituted with a carboxyl group. In one embodiment, said 2), 3), 4), 5), 6), and 7) are optionally substituted with a carboxyl group. In one embodiment, said 2), 3), 4), 5), 6), and 7) are optionally substituted with a $C_{1-6}$ alkyl group substituted with a carboxyl group.

In one embodiment, if one of $R^1$, $R^2$, and $R^3$ is represented by formula (2), the remaining two without the structure of formula (2) among $R^1$, $R^2$, and $R^3$ are each independently selected from the group consisting of a hydrogen atom, a halogen atom, methyl, trifluoromethyl, methoxy, and trifluoromethoxy. In a preferred embodiment, $R^3$ is represented by formula (2), and $R^1$ and $R^2$ are each independently selected from the group consisting of a hydrogen atom, a halogen atom, methyl, trifluoromethyl, methoxy, and trifluoromethoxy.

In some embodiments, Y is an oxygen atom, a sulfur atom, or —$NR^j$—. In one embodiment, Y is an oxygen atom or a sulfur atom. In a preferred embodiment, Y is an oxygen atom. The $R^j$ is the same as the definition herein.

In some embodiments, ring A is an optionally substituted 4- to 20-membered non-aryl heterocycle. In one embodiment, ring A is an optionally substituted 4- to 10-membered non-aryl heterocycle. In one embodiment, ring A is an optionally substituted 4- to 7-membered non-aryl heterocycle. In one embodiment, ring A is an optionally substituted 4- to 7-membered nitrogen-containing non-aryl heterocycle. In one embodiment, ring A is an optionally substituted 4- to 6-membered non-aryl heterocycle. In one embodiment, ring A is an optionally substituted 4- to 6-membered nitrogen-containing non-aryl heterocycle. In one embodiment, ring A is an optionally substituted azetidine ring. In a specific embodiment of said embodiment, ring A is

[Chemical Formula 640-1]

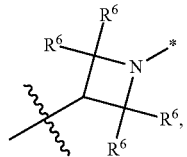

wherein $R^6$ represents a substituent on an azetidine ring and is defined the same as $R^{6a}$, a bond that is orthogonal to a wavy line indicates a bond with Y, and a bond with * indicates a bond with $L^3$. In a preferred embodiment, $R^6$ are the same or different, each independently selected from the group consisting of
1) a hydrogen atom,
2) a halogen atom,
3) a $C_{1-6}$ alkyl group, and
4) a $C_{1-6}$ alkoxy group
(wherein each of substituents 3) and 4) is optionally substituted with a halogen atom), and
in a preferred embodiment, are selected from the group consisting of
1) a hydrogen atom,
2) a halogen atom, and
3) a $C_{1-6}$ alkyl group optionally substituted with a halogen atom, and
most preferably are hydrogen atoms.

In a specific embodiment, ring A is

[Chemical Formula 640-2]

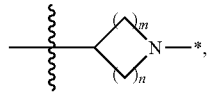

wherein m is 1, 2, or 3, n is 1, 2, or 3, m+n is 2, 3, 4, or 5, a bond that is orthogonal to a wavy line indicates a bond with Y, and a bond with * indicates a bond with $L^3$. In one embodiment, m+n is 2, 3, or 4. In one embodiment, m+n is 2 or 3. In a preferred embodiment, m+n is 2. In a more preferred embodiment, m=1 and n=1.

In some embodiments, $L^3$ is —C(=O)—, —S(=O)—, or —S(=O)$_2$—. In one embodiment, $L^3$ is —C(=O)— or —S(=O)$_2$—. In a preferred embodiment, $L^3$ is —C(=O)—.

In some embodiments, $L^4$ is
1) a single bond,
2) a $C_{1-6}$ alkylene group,
3) a $C_{3-10}$ cycloalkylene group,
4) a $C_{6-10}$ arylene group
5) a 5- or 6-membered heteroarylene group,
6) a 4- to 10-membered non-aryl heterocyclylene group, or
7) —C(=N—OR$^{h1}$)—,
(wherein each substituent from 2) to 6) is optionally substituted).

In one embodiment, $L^4$ is a single bond, —C(=N—OR$^{h1}$)— or an optionally substituted $C_{1-6}$ alkylene group, wherein $R^{h1}$ is an optionally substituted $C_{1-6}$ alkyl group. In one embodiment, $L^4$ is a single bond or a $C_{1-6}$ alkylene group optionally substituted with —NR$^{21}$R$^{22}$ or =NOR$^{23}$, wherein $R^{21}$, $R^{22}$, and $R^{23}$ are each independently a hydrogen atom, an optionally substituted $C_{1-6}$ alkyl group, or an optionally substituted 4- to 10-membered non-aryl heterocyclyl carbonyl group. In a preferred embodiment, $L^4$ is a bond, —CH$_2$—, —CH(NH$_2$)—, or —CH(NH$_2$)—CH$_2$—, wherein if an amino group is present in $L^4$, carbon that attaches to the amino group attaches to $L^3$.

In one embodiment, $L^4$ is a single bond, —CH$_2$—, —CMe(NH$_2$)—, —CH(NHMe)-, —CD(NH$_2$)— (wherein D represents a heavy hydrogen atom), —CH(NH$_2$)—, or —CH$_2$CH$_2$—. In one embodiment, $L^4$ is a single bond, —CH$_2$—, or —CH(NH$_2$)—.

In one embodiment, $L^4$ is
1) —(CH$_2$)$_p$—CR$^{10}$(NHR$^{11}$)—,
2) —(CH$_2$)$_q$—CR$^{12}$R$^{13}$—, or
3) —(CH$_2$)$_p$—CR$^{10}$(NHR$^{11}$)—(CH$_2$)$_q$—CR$^{12}$R$^{13}$—,
wherein p and q are independently 0 or 1, $R^{10}$ is
1) a hydrogen atom,
2) a carboxyl group, or
3) —C(=O)NR$^{10a}$R$^{10b}$,
$R^{11}$ is
1) a hydrogen atom,
2) —C(=O)R$^{11a}$, or
3) an optionally substituted 5- or 6-membered non-aryl heterocyclyl carbonyl group,
wherein if $R^{10}$ is —C(=O)NR$^{10a}$R$^{10b}$, $R^{10b}$ and $R^{11}$ together may form —CH$_2$CH$_2$—,
$R^{12}$ is
1) a hydrogen atom, or
2) an optionally substituted $C_{1-4}$ alkyl group,
$R^{13}$ is
1) a hydrogen atom,
2) a hydroxyl group
3) an optionally substituted $C_{1-4}$ alkyl group
4) a sulfanyl group,
5) a carboxyl group,
6) an optionally substituted $C_{1-4}$ alkylthio group,
7) —NR$^{13a}$R$^{13b}$,
8) —NR$^{13a}$—C(=O)R$^{13b}$,
9) an optionally substituted 5- or 6-membered non-aryl heterocyclyl carbonylamino group,
10) —NR$^{13a}$C(=O)NR$^{13b}$R$^{13c}$,
11) —C(=O)NR$^{13a}$R$^{13b}$,
12) —C(=O)NR$^{13a}$OR$^{13b}$,
13) —S(=O)$_2$—R$^{13a}$,
14) —S(=O)$_2$—NR$^{13a}$R$^{13b}$,
15) —C(=O)NR$^{13a}$—S(=O)$_2$—R$^{13b}$, or
16) —C(=O)NR$^{13a}$—S(=O)$_2$—NR$^{13b}$R$^{13c}$, and
$R^{10a}$, $R^{10b}$, $R^{11a}$, $R^{13a}$, $R^{13b}$, and $R^{13c}$ are each independently a hydrogen atom or an optionally substituted $C_{1-4}$ alkyl group.

In one embodiment, $L^4$ is —CH(NH$_2$)—CHR$^{13}$—, wherein carbon that attaches to the NH$_2$ attaches to $L^3$, $R^5$ is a hydrogen atom, and
$R^{13}$ is
1) —NH—C(=O)CH$_3$,
2) —NH—C(=O)NH$_2$,
3) —NH—C(=O)CH(NH$_2$)—CH$_2$C(=O)NH$_2$,
4) —NH—C(=O)CH$_2$—NH$_2$,
5) —NH—C(=O)CH(NH$_2$)—CH$_2$OH, or
6) a pyrrolidin-2-ylcarbonylamino group.

In one embodiment, $L^4$ is —CH(NH$_2$)—CR$^{12}$R$^{13}$—, wherein carbon that attaches to the NH$_2$ attaches to $L^3$,
$R^5$ is a hydrogen atom or methyl,
$R^{12}$ is a hydrogen atom or methyl, and
$R^{13}$ is a benzylthio group or a sulfanyl group.

In one embodiment, $L^4$ is —CH(NH$_2$)—(CH$_2$)$_q$—CHR$^{13}$—, wherein q is 0 or 1, and carbon that attaches to the NH$_2$ attaches to $L^3$,
$R^5$ is a hydrogen atom, and
$R^{13}$ is
1) a carboxyl group,
2) —C(=O)NH$_2$,
3) —C(=O)NH(CH$_3$),
4) —C(=O)N(CH$_3$)$_2$,
5) —C(=O)NH—(CH$_2$)$_2$—OH,
6) —C(=O)NH—(CH$_2$)$_2$—NH$_2$,
7) —C(=O)NH—S(=O)$_2$—CH$_3$,
8) —C(=O)NHOH,
9) —S(=O)$_2$—NH$_2$,
10) —S(=O)$_2$—CH$_3$, or
11) a hydroxyl group.

In one embodiment, $L^4$ is —CH(NHR$^{11}$)—CH$_2$—, wherein carbon that attaches to the NHR$^{11}$ attaches to $L^3$,
$R^5$ is hydrogen, and
$R^{11}$ is
1) —C(=O)CH(NH$_2$)—CH$_2$C(=O)NH$_2$,
2) —C(=O)CH$_2$—NH$_2$,
3) —C(=O)CH(CH)—NH$_2$,
4) —C(=O)CH(NH$_2$)—CH$_2$OH, or
5) pyrrolidin-2-ylcarbonyl.

In one embodiment, $L^4$ is —CH(NHR$^{11}$)—CH(COOH)—, wherein carbon that attaches to the NHR$^{11}$ attaches to $L^3$,
$R^5$ is hydrogen, and
$R^{11}$ is
1) —C(=O)CH(NH$_2$)—CH$_2$C(=O)NH$_2$,
2) —C(=O)CH$_2$—NH$_2$,
3) —C(=O)CH(CH$_3$)—NH$_2$,
4) —C(=O)CH(NH$_2$)—CH$_2$OH, or
5) pyrrolidin-2-ylcarbonyl.

In one embodiment, $L^4$ is —CHR$^{13}$— or —CH$_2$—CHR$^{13}$
$R^5$ is hydrogen, and
$R^3$ is —C(=O)NH$_2$ or —C(=O)NHOH.

In one embodiment, $L^4$ is —CH$_2$—CR$^{10}$(NH$_2$)—, and the CH$_2$ group attaches to $L^3$,
$R^5$ is hydrogen, and
$R^{10}$ is a carboxy group or —C(=O)NH$_2$.

In one embodiment, $L^4$ is —(CH$_2$)$_p$—CR$^{10}$(NHR$^{11}$)—(CH$_2$)$_q$—CHR$^{13}$— or —CHR$^{13}$—(CH$_2$)$_q$—CR$^{10}$(NHR$^{11}$)—(CH$_2$)$_p$—, wherein q is 0 or 1,
$R^5$ is hydrogen,
(1) if $L^4$ is —CHR$^{13}$—(CH$_2$)$_q$—CR$^{10}$(NHR$^{11}$)—(CH$_2$)$_p$—, carbon of the —CHR$^{13}$— group attaches to $L^3$,
p is 0,
$R^{10}$ is a hydrogen atom, a carboxyl group, or —C(=O)NHR$^{10b}$,
$R^{11}$ is a hydrogen atom,

215

$R^{10b}$ is a hydrogen atom,
wherein if $R^{10}$ is —C(=O)NHR$^{10b}$, $R^{10b}$ and $R^{11}$ together may form —CH$_2$CH$_2$—, and
$R^{13}$ is a hydrogen atom, and
(2) if $L^4$ is —(CH$_2$)$_p$—CR$^{10}$(NHR$^{11}$)—(CH$_2$)$_q$—CHR$^{13}$—, carbon of the —(CH$_2$)$_p$— group attaches to $L^3$,
p is 1,
$R^{10}$ and $R^{11}$ are both hydrogen atoms,
$R^{13}$ is a carboxyl group or —C(=O)NR$^{13a}$R$^{13b}$, and
$R^{13a}$ and $R^{13b}$ are each independently a hydrogen atom or an optionally substituted C$_{1-4}$ alkyl group.

In one embodiment, $L^4$ is —CR$^{12}$(NH$_2$)—,
$R^{12}$ is a hydrogen atom or a methyl group, and
$R^5$ is a C$_{1-4}$ alkyl group optionally substituted with a hydroxyl group.

In some embodiments, $R^5$ is
1) a hydrogen atom,
2) a C$_{1-6}$ alkyl group,
3) a C$_{3-10}$ alicyclic group,
4) a 4- to 10-membered non-aryl heterocycle,
5) C$_{6-10}$ aryl,
6) 5- or 6-membered heteroaryl,
7) a C$_{1-6}$ alkylthio group,
(wherein each substituent from 2) to 7) is optionally substituted), or
8) —NR$^{e1}$OH.

In one embodiment, $R^5$ is a hydrogen atom, an optionally substituted C$_{1-6}$ alkyl group, an optionally substituted 4- to 10-membered non-aryl heterocycle, optionally substituted C$_{6-10}$ aryl, optionally substituted 5- or 6-membered heteroaryl, an optionally substituted C$_{1-6}$ alkylthio group, or —NR$^{e1}$OH, wherein R$^{e1}$ is a hydrogen atom or an optionally substituted C$_{1-6}$ alkyl group. In one embodiment, $R^5$ is an optionally substituted 5- or 6-membered heteroaryl or optionally substituted C$_{6-10}$ aryl.

In one embodiment, $R^5$ is optionally substituted 5- or 6-membered heteroaryl. In one embodiment, $R^5$ is an optionally substituted 4- to 10-membered non-aryl heterocycle. In one embodiment, $R^5$ is a hydrogen atom or an optionally substituted C$_{1-4}$ alkyl group.

In one embodiment, $R^5$ is selected from the group consisting of

[Chemical Formula 641]

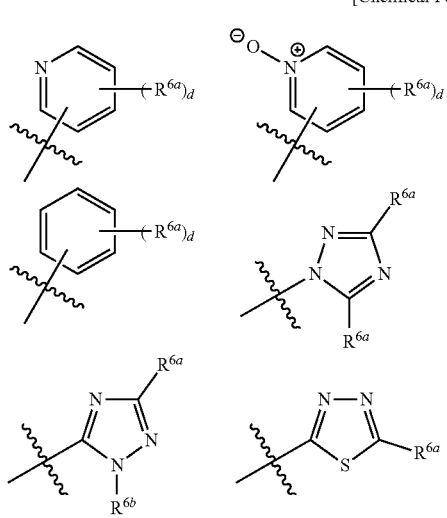

216

-continued

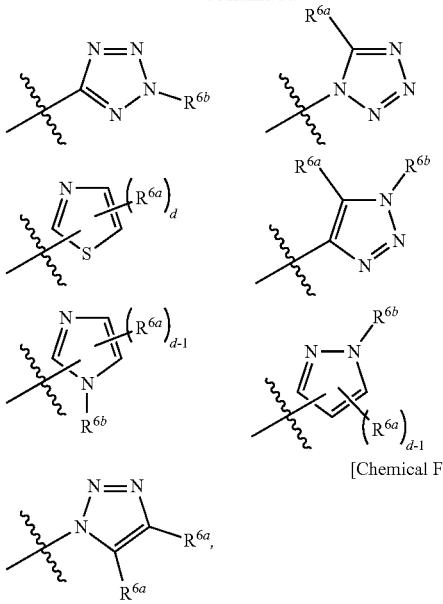

[Chemical Formula 642]

subscript d is the number of substitutable positions on a ring of $R^5$,
each $R^{6a}$ is independently selected from the group consisting of
1) a hydrogen atom,
2) a hydroxyl group,
3) a cyano group,
4) a nitro group,
5) halogen,
6) a C$_{1-4}$ alkyl group,
7) a C$_{3-10}$ alicyclic group,
8) a C$_{1-4}$ alkoxy group,
9) a C$_{3-10}$ alicyclic oxy group,
10) a C$_{6-10}$ aryloxy group,
11) a 5- or 6-membered heteroaryloxy group,
12) a 4- to 10-membered non-aryl heterocyclyl oxy group,
(wherein each substituent from 6) to 12) is optionally substituted),
13) —SO$_2$—NR$^{e2}$R$^{f2}$,
14) —NR$^{g2}$—CR$^{e2}$(=NR$^{f2}$)
15) —NR$^{g2}$—CR$^{e2}$(=N—OR$^{f2}$),
16) —NR$^{h2}$—C(=NR$^{g2}$)NR$^{e2}$R$^{f2}$,
17) —NR$^{h2}$—C(=N—OR$^{g2}$)NR$^{e2}$R$^{f2}$,
18) —NR$^{i2}$—C(=NR$^{h2}$)NR$^{g2}$—NR$^{e2}$R$^{f2}$,
19) —NR$^{i2}$—C(=N—OR$^{h2}$)NR$^{g2}$—NR$^{e2}$R$^{f2}$,
20) —C(=NR$^{e2}$)R$^{f2}$,
21) —C(=N—OR$^{e2}$)R$^{f2}$,
22) —C(=NR$^{h2}$)—NR$^{e2}$R$^{f2}$,
23) —C(=NR$^{h2}$)NR$^{g2}$—NR$^{e2}$R$^{f2}$,
24) —C(=N—OR$^{h2}$)NR$^{g2}$—NR$^{e2}$R$^{f2}$,
25) —NR$^{e2}$R$^{f2}$,
26) —NR$^{g2}$—NR$^{e2}$R$^{f2}$,
27) —NR$^{e2}$OR$^{f2}$
28) —NR$^{e2}$—C(=O)R$^{f2}$,
29) —C(=O)NR$^{e2}$R$^{f2}$,
30) —C(=O)NR$^{e2}$OR$^{f2}$,
31) —C(=O)NR$^{g2}$—NR$^{e2}$R$^{f2}$,
32) —C(=O)R$^{e2}$,
33) —C(=O)OR$^{e2}$, and
34) —C(=N—OR$^{h2}$)NR$^{e2}$R$^{f2}$, and each $R^{6b}$ is independently selected from the group consisting of
1) a hydrogen atom,
2) a hydroxyl group,
3) a $C_{1-4}$ alkyl group
(wherein the alkyl group is optionally substituted),
4) a $C_{3-10}$ alicyclic group
(wherein the alicyclic group is optionally substituted),
5) —C(=NR$^{e2}$)R$^{f2}$,
6) —C(=N—OR$^{e2}$)R$^{f2}$,
7) —SO$_2$—NR$^{e2}$R$^{f2}$,
8) —C(=NR$^{h2}$)—NR$^{e2}$R$^{f2}$,
9) —C(=NR$^{h2}$)NR$^{g2}$—NR$^{e2}$R$^{f2}$,
10) —C(=N—OR$^{h2}$)NR$^{g2}$—NR$^{e2}$R$^{f2}$,
11) —C(=O)NR$^{e2}$R$^{f2}$,
12) —C(=O)NR$^{e2}$OR$^{f2}$,
13) —C(=O)NR$^{g2}$—NR$^{e2}$R$^{f2}$,
14) —C(=O)R$^{e2}$, and
15) —C(=N—OR$^{h2}$)NR$^{e2}$R$^{f2}$.

In one embodiment, $R^5$ is 5- or 6-membered aryl or heteroaryl selected from the group consisting of

[Chemical Formula 643]

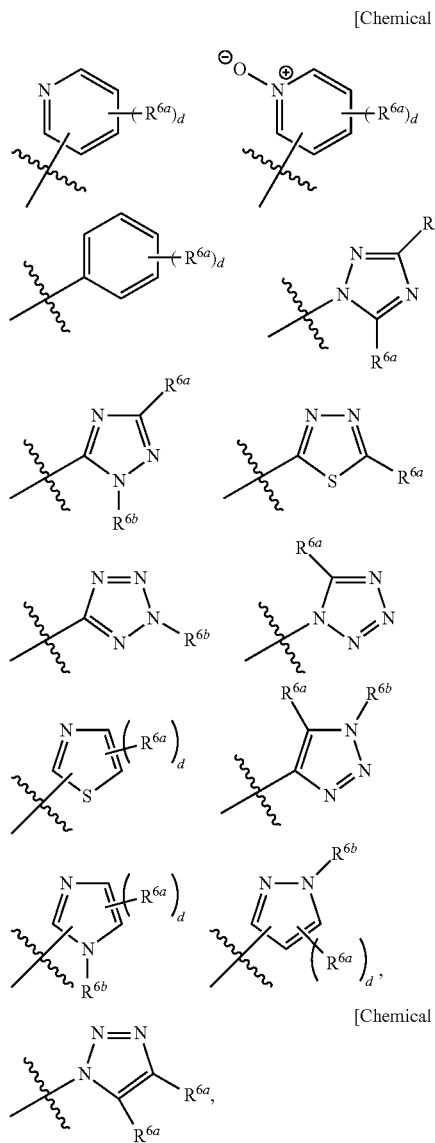

[Chemical Formula 644]

subscript d is the number of substitutable positions on a ring of $R^5$,
each $R^{6a}$ is independently selected from the group consisting of
1) a hydrogen atom,
2) a hydroxyl group,
3) halogen,
4) a $C_{1-4}$ alkyl group
(wherein the alkyl group is optionally substituted with NR$^{e2}$R$^{f2}$, a 5- or 6-membered non-aryl heterocycle, —C(=O)OR$^{f2}$, or a hydroxyl group),
5) a $C_{1-4}$ alkoxy group
6) —NR$^{e2}$R$^{f2}$, and
7) —C(=O)OR$^{e2}$, and
each $R^{6b}$ is independently selected from the group consisting of
1) a hydrogen atom,
2) a hydroxyl group, and
3) a $C_{1-4}$ alkyl group
(wherein the alkyl group is optionally substituted with NR$^{e2}$R$^{f2}$, —C(=O)NR$^{e2}$R$^{f2}$, —C(=O)OR$^{f2}$, or a hydroxyl group).

In one embodiment, $R^{e2}$ and $R^{f2}$ are the same or different, each independently a hydrogen atom, an optionally substituted $C_{1-6}$ alkyl group, or an optionally substituted $C_{3-10}$ alicyclic group. In one embodiment, $R^{e2}$ and $R^{f2}$ are the same or different, each independently a hydrogen atom or an optionally substituted $C_{1-6}$ alkyl group. In one embodiment, $R^{e2}$ and $R^{f2}$ are hydrogen atoms. In one embodiment, $R^{6a}$ is —NR$^{e2}$R$^{f2}$, and one of R$^{e2}$ and R$^{f2}$ is a hydrogen atom and the other is a $C_{1-4}$ alkyl group (wherein the alkyl group is optionally substituted with an amino group or a hydroxyl group).

In one embodiment, each $R^{6a}$ may be independently halogen.

In one embodiment, each $R^{6a}$ may be independently an alkylamino group substituted with an amino group. In one embodiment, each $R^{6a}$ may be independently NR$^{e2}$R$^{f2}$, wherein $R^{e2}$ is a $C_{1-6}$ alkyl group, the $C_{1-6}$ alkyl group is substituted with —NR$^{10a}$R$^{11a}$, and $R^{10a}$ and $R^{11a}$ are each independently defined the same as the description herein.

In one embodiment, each $R^{6a}$ may be independently —C(=O)OH.

In one embodiment, each $R^{6a}$ and/or each $R^{6b}$ may be independently an alkyl group substituted with a carboxyl group. In one embodiment, each $R^{6a}$ and/or each $R^{6b}$ may be independently a $C_{1-4}$ alkyl group substituted with a —C(=O)OH group.

In one embodiment, $R^5$ is a 4- to 6-membered non-aryl heterocycle selected from the group consisting of

[Chemical Formula 645]

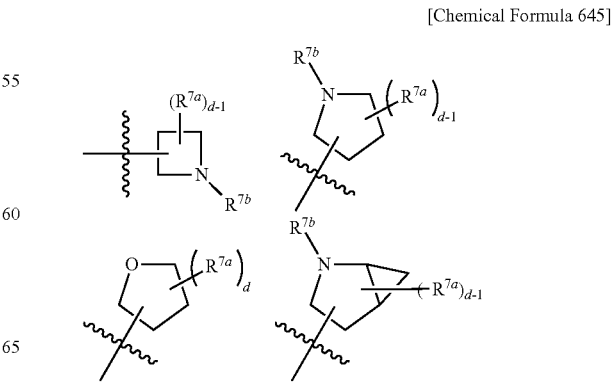

-continued

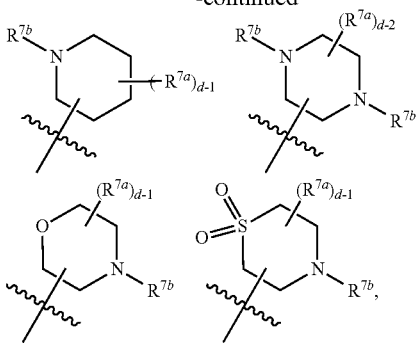

subscript d is the number of substitutable positions on a ring of $R^5$,
each $R^{7a}$ is independently selected from the group consisting of
1) a hydrogen atom,
2) a hydroxyl group,
3) a cyano group,
4) halogen,
5) a $C_{1-4}$ alkyl group,
6) a $C_{3-10}$ alicyclic group,
7) a $C_{1-4}$ alkoxy group,
8) a $C_{3-10}$ alicyclic oxy group,
9) a $C_{6-10}$ aryloxy group,
10) a 5- or 6-membered heteroaryloxy group,
11) a 4- to 10-membered non-aryl heterocyclyl oxy group,
(wherein each substituent from 5) to 11) is optionally substituted),
12) —$SO_2$—$NR^{e3}R^{f3}$,
13) —$NR^{g2}$—$CR^{e3}(=NR^{f3})$,
14) —$NR^{g2}$—$CR^{e3}(=N$—$OR^{f3})$,
15) —$NR^{h2}$—$C(=NR^{g2})NR^{e3}R^{f3}$,
16) —$NR^{h2}$—$C(=N$—$OR^{g2})NR^{e3}R^{f3}$,
17) —$NR^{i2}$—$C(—NR^{h2})NR^{g2}$—$NR^{e3}R^{f3}$,
18) —$NR^{i2}$—$C(=N$—$OR^{h2})NR^{g2}$—$NR^{e3}R^{f3}$,
19) —$C(=NR^{e3})R^{f3}$,
20) —$C(=N$—$OR^{e3})R^{f3}$,
21) —$C(=NR^{h2})$—$NR^{e3}R^{f3}$,
22) —$C(=R^{h2})NR^{g2}$—$NR^{e3}R^{f3}$,
23) —$C(=N$—$OR^{h2})NR^{g2}$—$NR^{e3}R^{f3}$,
24) —$NR^{e3}OR^{f3}$,
25) —$NR^{g2}$—$NR^{e3}R^{f3}$,
26) —$NR^{e3}OR^{f3}$,
27) —$NR^{e3}$—$C(=O)R^{f3}$,
28) —$C(=O)NR^{e3}R^{f3}$,
29) —$C(=O)NR^{e3}OR^{f3}$,
30) —$C(=O)NR^{g2}$—$NR^{e3}R^{f3}$,
31) —$C(=O)R^{e3}$,
32) —$C(=O)OR^{e3}$, and
33) —$C(=N$—$OR^{h2})NR^{e3}R^{f3}$,
each $R^{7b}$ is independently selected from the group consisting of
1) a hydrogen atom,
2) a hydroxyl group,
3) a $C_{1-4}$ alkyl group
(wherein the alkyl group is optionally substituted),
4) a $C_{3-10}$ alicyclic group
(wherein the alicyclic group is optionally substituted),
5) —$C(=NR^{e3})R^{f3}$,
6) —$C(=N$—$OR^{e3})R^{f3}$,
7) —$SO_2$—$NR^{e3}R^{f3}$,
8) —$C(=NR^{h2})$—$NR^{e3}R^{f3}$,
9) —$C(=NR^{h2})NR^{g2}$—$NR^{e3}R^{f3}$,
11) —$C(=O)NR^{e3}R^{f3}$,
12) —$C(=O)NR^{e3}OR^{f3}$,
13) —$C(=O)NR^{g2}$—$NR^{e3}R^{f3}$,
14) —$C(=O)R^{e3}$, and
15) —$C(=N$—$OR^{h2})NR^{e3}R^{f3}$, and
$R^{e3}$ and $R^{f3}$ are defined the same as $R^{e2}$ and $R^{f2}$ according to item B1.

In one embodiment, $R^5$ is a 4- to 6-membered non-aryl heterocycle selected from the group consisting of

[Chemical Formula 646]

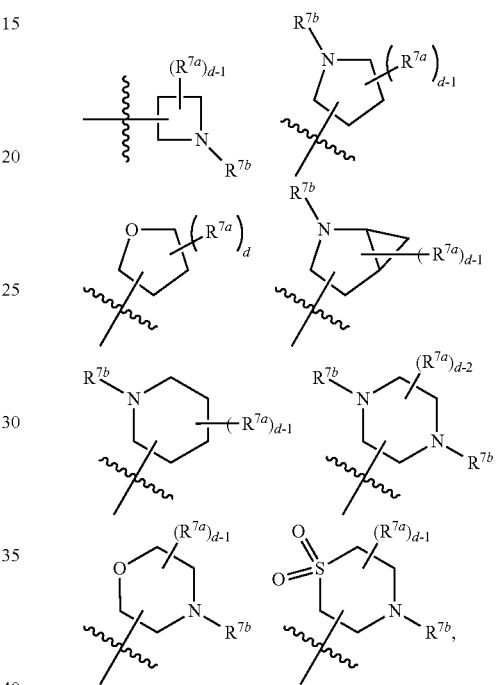

subscript d is the number of substitutable positions on a ring of $R^5$,
each $R^{7a}$ is independently selected from the group consisting of
1) a hydrogen atom,
2) a hydroxyl group,
3) halogen,
4) a $C_{1-4}$ alkyl group
(wherein the alkyl group is optionally substituted with $NR^{e3}R^{f3}$, a 5- or 6-membered non-aryl heterocycle, —$C(=O)OR^{f3}$, or a hydroxyl group),
5) a $C_{1-4}$ alkoxy group
6) —$NR^{e3}R^{f3}$,
7) —$C(=O)OR^{e3}$,
8) $C_{6-10}$ aryl, and
9) —$C(=O)NR^{e3}R^{f3}$,
each $R^{7b}$ is independently selected from the group consisting of
1) a hydrogen atom,
2) a hydroxyl group, and
3) a $C_{1-4}$ alkyl group
(wherein the alkyl group is optionally substituted with $NR^{e3}R^{f3}$, —$C(=O)OR^{f3}$, or a hydroxyl group), and
$R^{e3}$ and $R^{f3}$ are defined the same as $R^{e2}$ and $R^{f2}$ according to any one of items B38 to B40.

In some embodiments, if one of $R^1$, $R^2$, and $R^3$ is represented by formula (2), the remaining two are the same or different, each independently a hydrogen atom, a halogen atom, an optionally substituted $C_{1-6}$ alkyl group, an optionally substituted $C_{1-6}$ alkoxy group, an optionally substituted $C_{1-6}$ alkylthio group, optionally substituted 5- or 6-membered heteroaryl, or —$NR^{a3}R^{b2}$, wherein $R^{a3}$ and $R^{b2}$ are the same as the descriptions herein. In a preferred embodiment, $R^3$ is represented by formula (2).

In one embodiment where $R^3$ is represented by formula (2), $R^1$ and $R^2$ are the same or different, each independently selected from the group consisting of
1) a hydrogen atom,
2) a halogen atom,
3) a $C_{1-6}$ alkyl group,
4) a $C_{1-6}$ alkoxy group, and
5) a $C_{1-6}$ alkylthio group,
(wherein each substituent from 3) to 5) is optionally substituted).

In said embodiment, $R^1$ and $R^2$ are the same or different, each independently selected from the group consisting of
1) a hydrogen atom,
2) a halogen atom, and
3) an optionally substituted $C_{1-6}$ alkyl group.
In a preferred embodiment, $R^1$ and $R^2$ are both hydrogen atoms.

In some embodiments, $R^4$ in formulas (1a) and (1b) is
1) —C(=O)$R^8$,
2) —$SO_2$-$L^6$-$R^8$,
(wherein $R^8$ in 1) and 2) is —$NR^{a5}R^{b4}$, —$NR^{a5}$-$L^7$-B(OR$^{m1}$)$_2$, —$OR^{m1}$, or an optionally substituted $C_{1-6}$ alkyl group, and $L^6$ is a single bond or —$NR^{a6}$—),
3) —$NR^{a4}R^{b3}$,
4) —B(OR$^{m1}$)$_2$,
5) —PO(OR$^{m1}$)(OR$^{m2}$),
6) optionally substituted 5-membered heteroaryl,
7) an optionally substituted 5-membered non-aryl heterocycle, or
8) a bioisostere of one of 1) to 7),
(wherein the formulas of 2), 4), 5), and 6) include a carboxylic acid isostere, and 8) may include them in duplicates).

In one embodiment, $R^4$ is —C(=O)—OR$^{m1}$ or a carboxylic acid isostere thereof. In a preferred embodiment, $R^4$ is 1) —COOH (i.e., a carboxyl group), or 2) a carboxylic acid isostere. The $R^{a4}$, $R^{a5}$, $R^{a6}$, $R^{b3}$, $R^{b4}$, $L^7$, $R^{m1}$, and $R^{m2}$ are the same as the definitions herein.

A specific example of a specific embodiment of the compound of the invention includes a compound represented by formula (3a) or (3b):

[Chemical Formula 647]

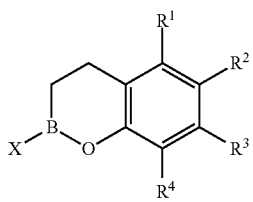

(3a)

-continued

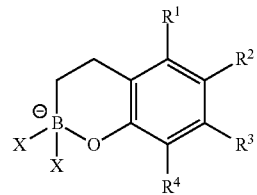

(3b)

or a pharmaceutically acceptable salt thereof. X, $R^1$, $R^2$, and $R^3$ in formula (3a) or (3b) are defined the same as the definitions herein, and $R^4$ is selected from the group consisting of
1) —COOR$^{m1}$ (wherein R$^{m1}$ is a hydrogen atom, a $C_{1-6}$ alkyl group, a $C_{3-10}$ alicyclic group, $C_{6-10}$ aryl, 5- or 6-membered heteroaryl, or a 4- to 10-membered non-aryl heterocycle, wherein the $C_{1-6}$ alkyl group, the $C_{3-10}$ alicyclic group, the $C_{6-10}$ aryl, the 5- or 6-membered heteroaryl, and the 4- to 10-membered non-aryl heterocycle are each optionally substituted), and
2) a bioisostere of 1).

In a preferred embodiment, $R^4$ is 1) —COOH (i.e., a carboxyl group) or 2) a carboxylic acid isostere.

A specific example of a preferred embodiment of the compound of the invention includes compounds represented by formulas (4a) and (4b):

[Chemical Formula 648]

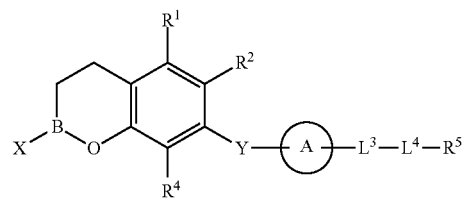

(4a)

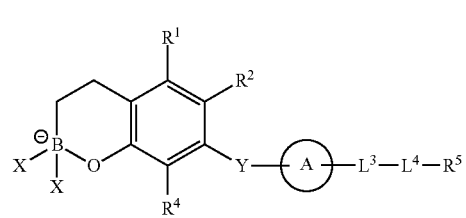

(4b)

or a pharmaceutically acceptable salt thereof. X, $R^4$, Y, ring A, $L^3$, $L^4$, and $R^5$ in formulas (4a) and (4b) are defined the same as the definitions herein, and $R^1$ and $R^2$ are the same or different, each independently a hydrogen atom, a halogen atom, a $C_{1-6}$ alkyl group, or a $C_{1-6}$ alkoxy group (wherein the $C_{1-6}$ alkyl group and $C_{1-6}$ alkoxy group are optionally substituted with 1 to 5 halogens).

A specific example of a still more preferred embodiment of the compound of the invention includes compounds represented by formulas (5a) and (5b):

[Chemical Formula 649]

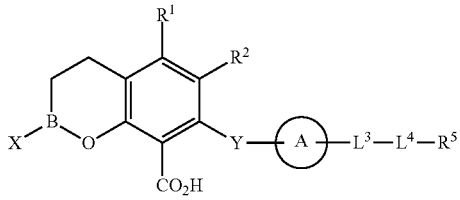
(5a)

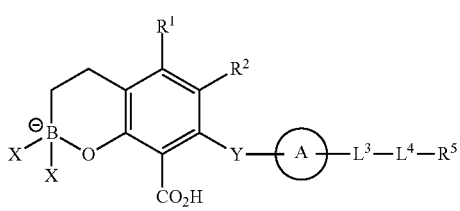
(5b)

or a pharmaceutically acceptable salt thereof. $R^1$, $R^2$, Y, $L^3$, $L^4$, $R^5$, and ring A in formulas (5a) and (5b) are defined the same as the definitions herein, and ring A is an optionally substituted 4- to 6-membered nitrogen-containing non-aryl heterocycle.

A specific example of a yet still more preferred embodiment of the compound of the invention includes compounds represented by formulas (6a) and (6b):

[Chemical Formula 650]

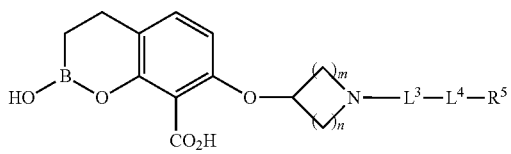
(6a)

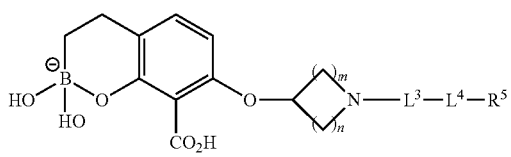
(6b)

or a pharmaceutically acceptable salt thereof. $L^3$, $L^4$, and $R^5$ in formulas (6a) and (6b) are defined the same as the definitions herein, m is an integer 1, 2, or 3, n is an integer 1, 2, or 3, and m+n is 2, 3, or 4. In one embodiment, m is 1 or 2, n is 1 or 2, and m+n is 2 or 3. In a preferred embodiment, m is 1, and n is 1.

A specific example of a preferred embodiment of the compound of the invention includes the following compound: a compound represented by

[Chemical Formula 651]

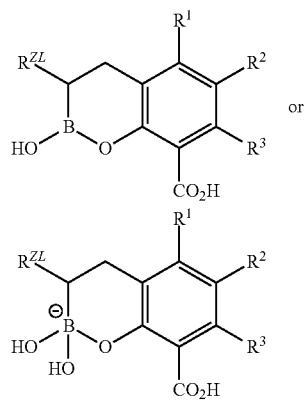
or or a pharmaceutically acceptable salt thereof, wherein $R^{ZL}$ is a substituent selected from the group consisting of the Z1 to Z4 described below,
one of $R^1$, $R^2$, and $R^3$ is

[Chemical Formula 652]

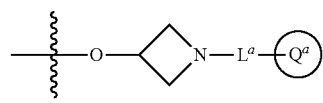

and
the remaining two are hydrogen atoms, linking group $L^a$ is a substituent selected from the group consisting of L1 to L36 described below, and substituent $Q^a$ is a substituent selected from the group consisting of Q1 to Q103 described below;
$R^{ZL}$:

[Chemical Formula 653]

(Z1)

(Z2)

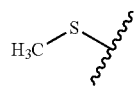
(Z3)

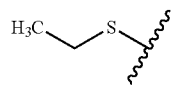
(Z4)

linking group $L^a$:

[Chemical Formula 654]

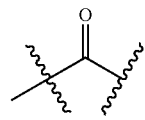
(L1)

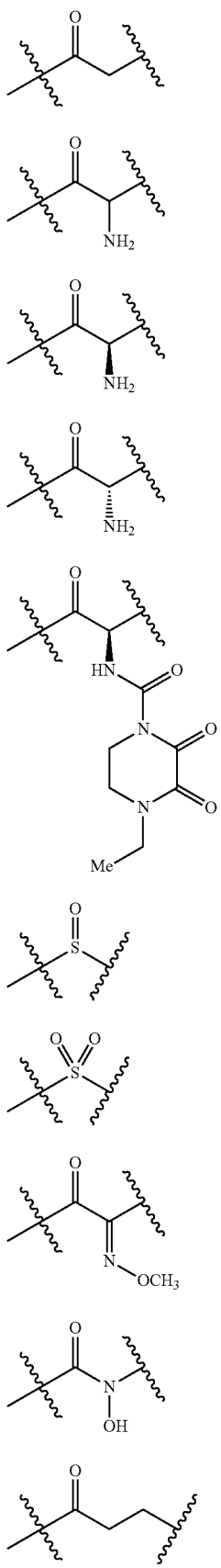
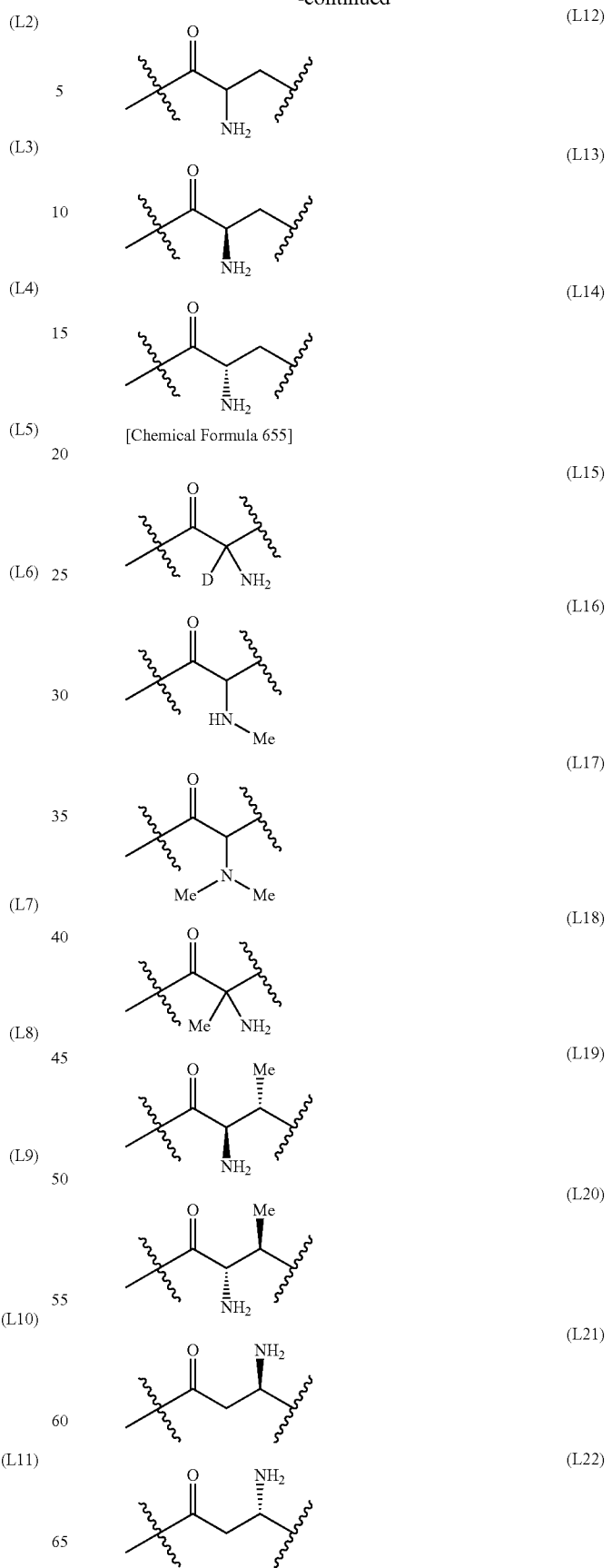
[Chemical Formula 655]

-continued
(L23) 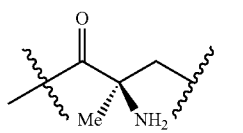
(L24) 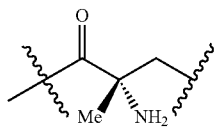
(L25) 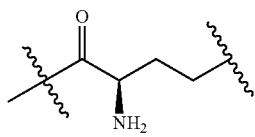
(L26) 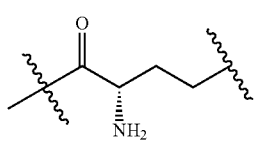
(L27) 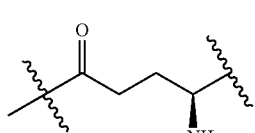
(L28) 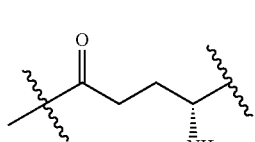
(L29) 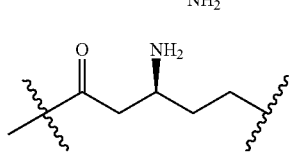
(L30) 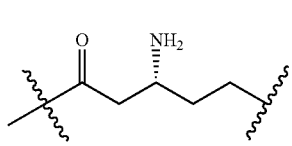
[Chemical Formula 656]
(L31) 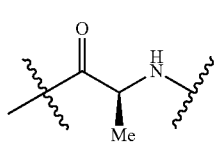
(L32) 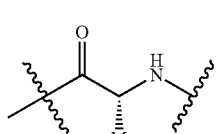
(L33) 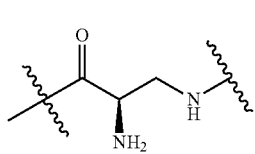
-continued
(L34) 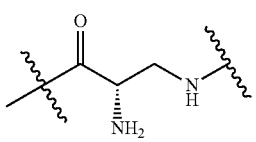
(L35) 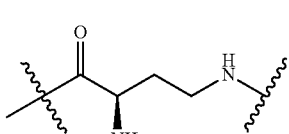
(L36) 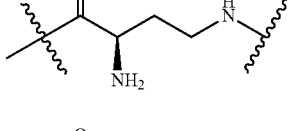
,
and substituent $Q^a$:
[Chemical Formula 657]
(Q1) 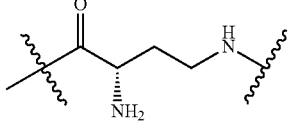
(Q2) 
(Q3) 
(Q4) 
(Q5) 
(Q6) 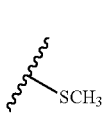
(Q7) 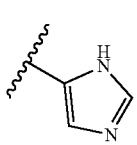
(Q8) 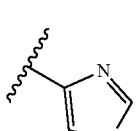

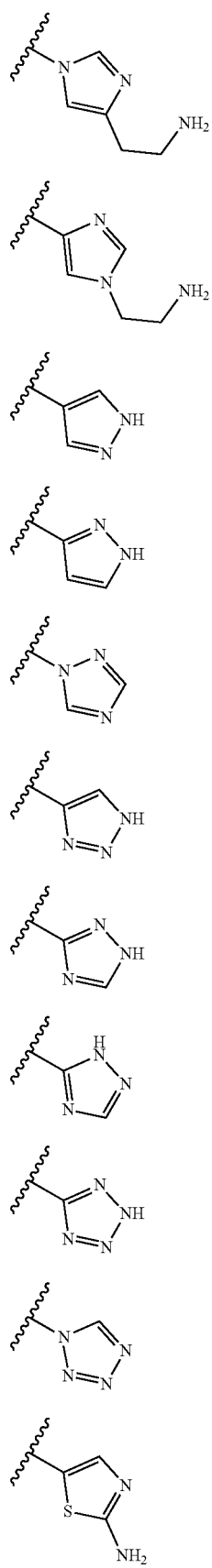
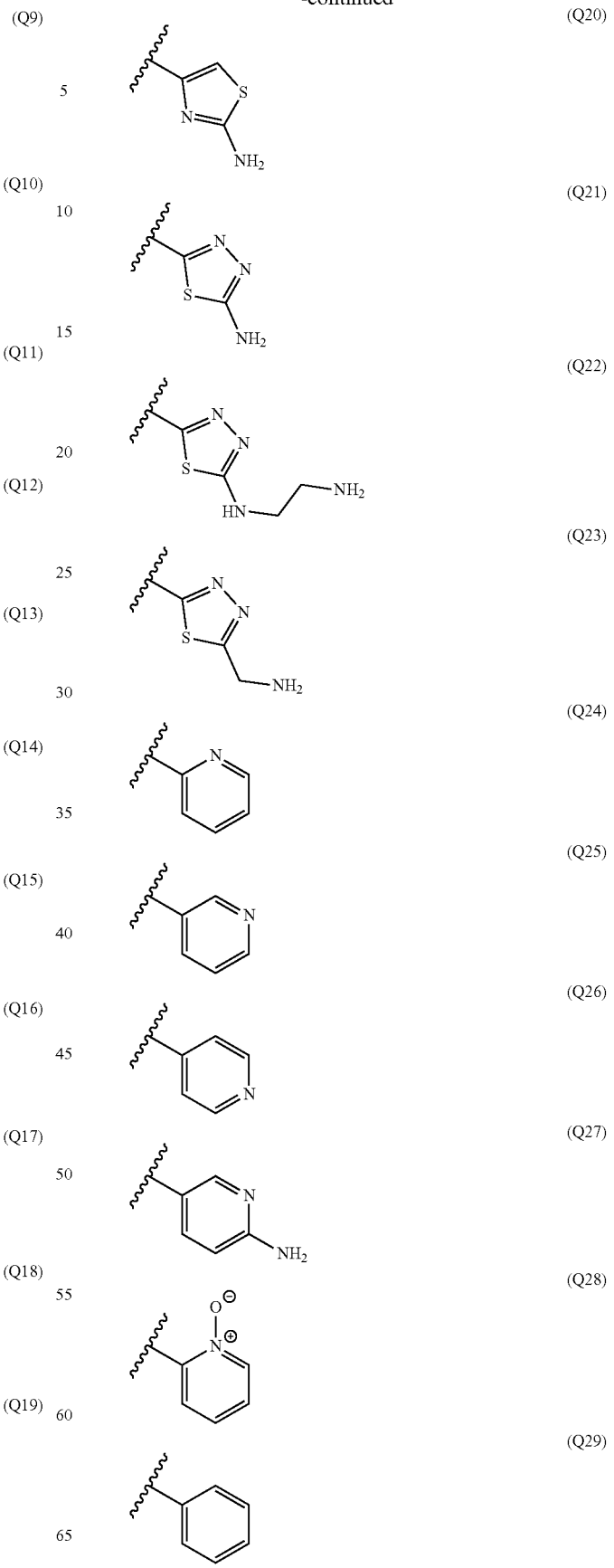

231
-continued
(Q30)
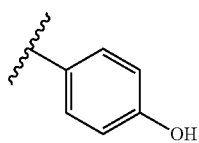
(Q31)
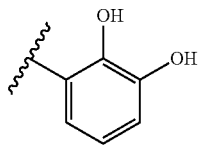
(Q32)
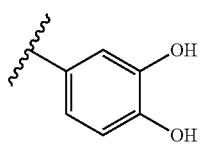
(Q33)
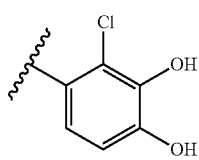
(Q34)
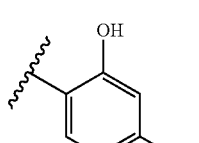
(Q35)
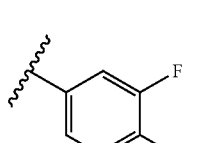
(Q36)
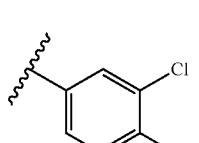
(Q37)
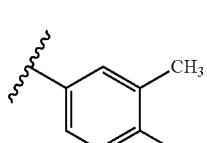
(Q38)
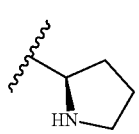
(Q39)
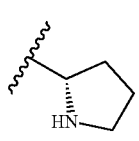
232
-continued
[Chemical Formula 658]
(Q40)
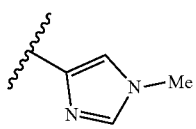
(Q41)
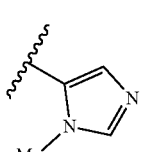
(Q42)
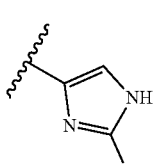
(Q43)
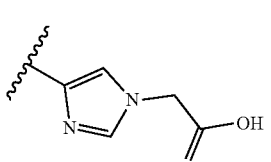
(Q44)
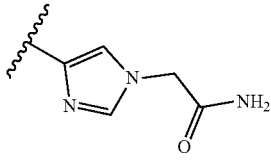
(Q45)
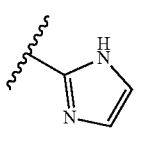
(Q46)
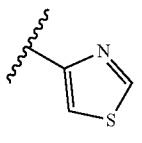
(Q47)
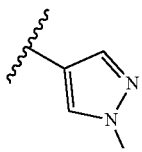
(Q48)
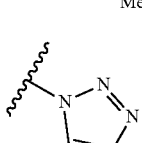
(Q49)
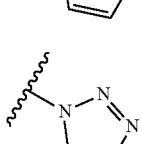

(Q50) 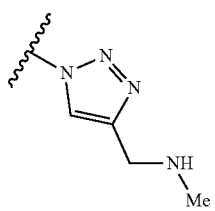
(Q51) 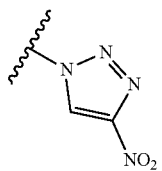
(Q52) 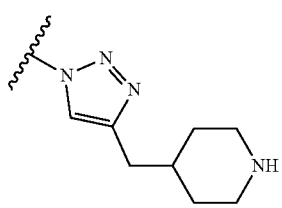
(Q53) 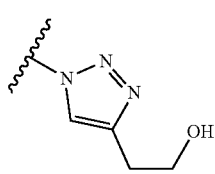
(Q54) 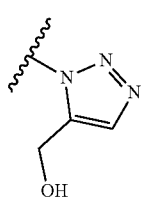
(Q55) 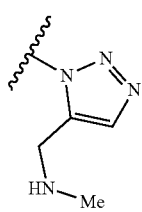
(Q56) 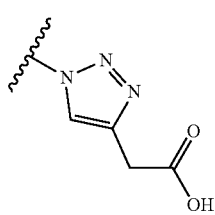
(Q57) 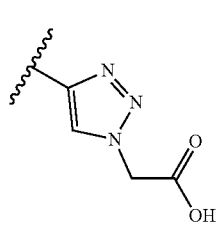
(Q58) 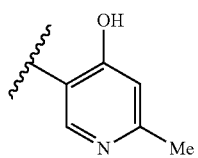
(Q59) 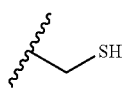
(Q60) 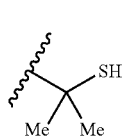
(Q61) 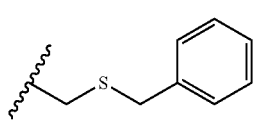
(Q62) 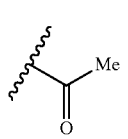
(Q63) 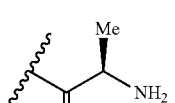
(Q64) 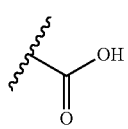
(Q65) 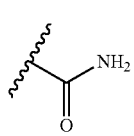
(Q66) 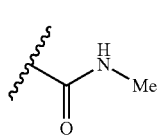
(Q67) 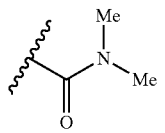
(Q68) 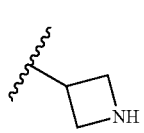
(Q69) 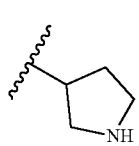

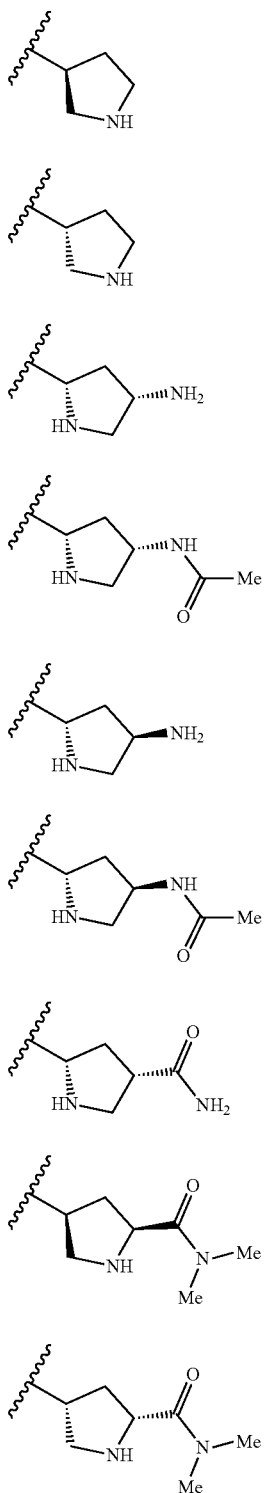
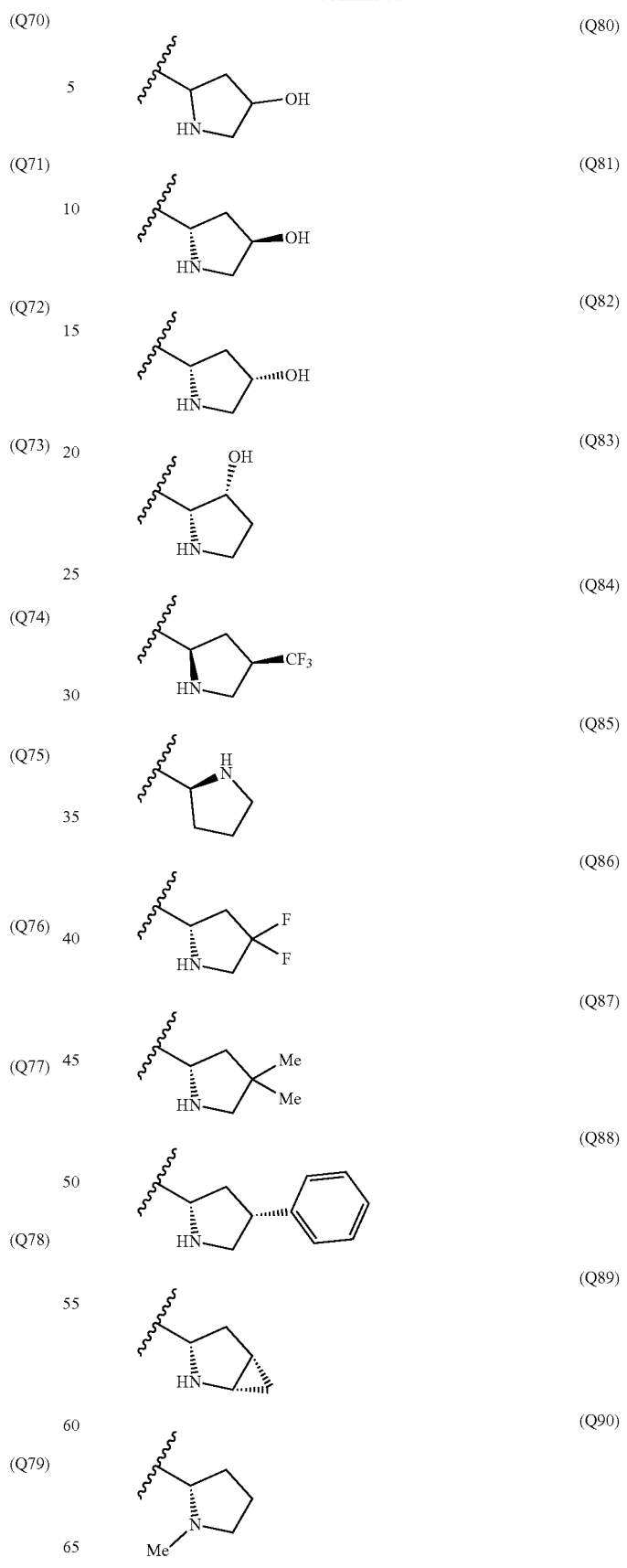
[Chemical Formula 659]

(Q91) 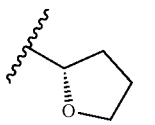

(Q92) 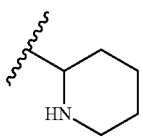

(Q93) 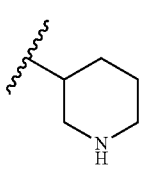

(Q94) 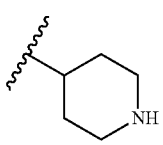

(Q95) 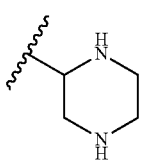

(Q96) 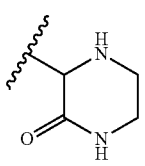

(Q97) 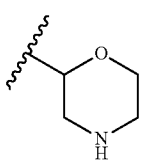

(Q98) 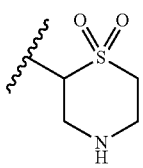

(Q99) 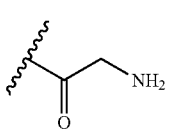

(Q100) 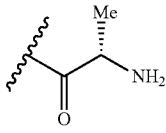

(Q101) 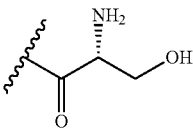

(Q102)

(Q103)

A specific example of a more preferred embodiment of the compound of the invention includes a compound of the following formula:

a compound represented by

[Chemical Formula 660]

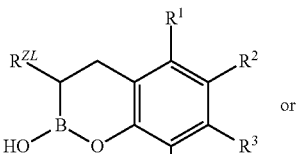

or

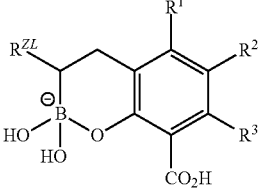

or a pharmaceutically acceptable salt thereof, wherein $R^{ZL}$ is a substituent selected from the group consisting of Z1 to Z4 described above, $R^1$ and $R^2$ are hydrogen atoms, and $R^3$ is

[Chemical Formula 661]

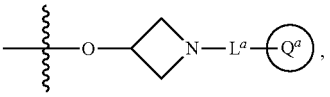

wherein linking group $L^a$ is a substituent selected from the group consisting of L1 to L36 described above, and substituent $Q^a$ is a substituent selected from the group consisting of Q1 to Q103 described above.

Examples of a more preferred embodiment of the compound of the invention include the compounds of the following Table (1) or a pharmaceutically acceptable salt thereof.

[Chemical Formula 662]

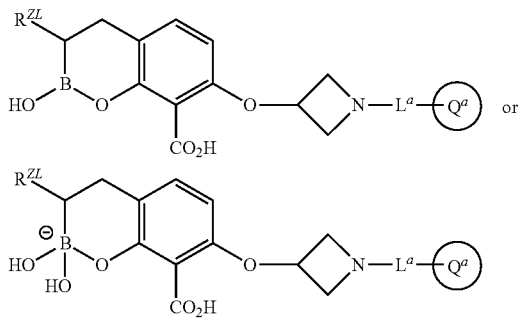

TABLE 1-1

| Example | $R^{ZL}$ | $L^a$ | $Q^a$ |
|---|---|---|---|
| 1 | Z1 | L1 | Q1 |
| 2 | Z1 | L1 | Q2 |
| 3 | Z1 | L1 | Q3 |
| 4 | Z1 | L1 | Q4 |
| 5 | Z1 | L1 | Q5 |
| 6 | Z1 | L1 | Q6 |
| 7 | Z1 | L1 | Q7 |
| 8 | Z1 | L1 | Q8 |
| 9 | Z1 | L1 | Q9 |
| 10 | Z1 | L1 | Q10 |
| 11 | Z1 | L1 | Q11 |
| 12 | Z1 | L1 | Q12 |
| 13 | Z1 | L1 | Q13 |
| 14 | Z1 | L1 | Q14 |
| 15 | Z1 | L1 | Q15 |
| 16 | Z1 | L1 | Q16 |
| 17 | Z1 | L1 | Q17 |
| 18 | Z1 | L1 | Q18 |
| 19 | Z1 | L1 | Q19 |
| 20 | Z1 | L1 | Q20 |
| 21 | Z1 | L1 | Q21 |
| 22 | Z1 | L1 | Q22 |
| 23 | Z1 | L1 | Q23 |
| 24 | Z1 | L1 | Q24 |
| 25 | Z1 | L1 | Q25 |
| 26 | Z1 | L1 | Q26 |
| 27 | Z1 | L1 | Q27 |
| 28 | Z1 | L1 | Q28 |
| 29 | Z1 | L1 | Q29 |
| 30 | Z1 | L1 | Q30 |
| 31 | Z1 | L1 | Q31 |
| 32 | Z1 | L1 | Q32 |
| 33 | Z1 | L1 | Q33 |
| 34 | Z1 | L1 | Q34 |
| 35 | Z1 | L1 | Q35 |
| 36 | Z1 | L1 | Q36 |
| 37 | Z1 | L1 | Q37 |
| 38 | Z1 | L1 | Q38 |
| 39 | Z1 | L1 | Q39 |
| 40 | Z1 | L2 | Q1 |
| 41 | Z1 | L2 | Q2 |
| 42 | Z1 | L2 | Q3 |
| 43 | Z1 | L2 | Q4 |
| 44 | Z1 | L2 | Q5 |
| 45 | Z1 | L2 | Q6 |
| 46 | Z1 | L2 | Q7 |
| 47 | Z1 | L2 | Q8 |
| 48 | Z1 | L2 | Q9 |
| 49 | Z1 | L2 | Q10 |
| 50 | Z1 | L2 | Q11 |
| 51 | Z1 | L2 | Q12 |
| 52 | Z1 | L2 | Q13 |
| 53 | Z1 | L2 | Q14 |
| 54 | Z1 | L2 | Q15 |
| 55 | Z1 | L2 | Q16 |
| 56 | Z1 | L2 | Q17 |
| 57 | Z1 | L2 | Q18 |

TABLE 1-1-continued

| Example | $R^{ZL}$ | $L^a$ | $Q^a$ |
|---|---|---|---|
| 58 | Z1 | L2 | Q19 |
| 59 | Z1 | L2 | Q20 |
| 60 | Z1 | L2 | Q21 |
| 61 | Z1 | L2 | Q22 |
| 62 | Z1 | L2 | Q23 |
| 63 | Z1 | L2 | Q24 |
| 64 | Z1 | L2 | Q25 |
| 65 | Z1 | L2 | Q26 |
| 66 | Z1 | L2 | Q27 |
| 67 | Z1 | L2 | Q28 |
| 68 | Z1 | L2 | Q29 |
| 69 | Z1 | L2 | Q30 |
| 70 | Z1 | L2 | Q31 |
| 71 | Z1 | L2 | Q32 |
| 72 | Z1 | L2 | Q33 |
| 73 | Z1 | L2 | Q34 |
| 74 | Z1 | L2 | Q35 |
| 75 | Z1 | L2 | Q36 |
| 76 | Z1 | L2 | Q37 |
| 77 | Z1 | L2 | Q38 |
| 78 | Z1 | L2 | Q39 |
| 79 | Z1 | L3 | Q1 |
| 80 | Z1 | L3 | Q2 |

TABLE 1-2

| Example | $R^{ZL}$ | $L^a$ | $Q^a$ |
|---|---|---|---|
| 81 | Z1 | L3 | Q3 |
| 82 | Z1 | L3 | Q4 |
| 83 | Z1 | L3 | Q5 |
| 84 | Z1 | L3 | Q6 |
| 85 | Z1 | L3 | Q7 |
| 86 | Z1 | L3 | Q8 |
| 87 | Z1 | L3 | Q9 |
| 88 | Z1 | L3 | Q10 |
| 89 | Z1 | L3 | Q11 |
| 90 | Z1 | L3 | Q12 |
| 91 | Z1 | L3 | Q13 |
| 92 | Z1 | L3 | Q14 |
| 93 | Z1 | L3 | Q15 |
| 94 | Z1 | L3 | Q16 |
| 95 | Z1 | L3 | Q17 |
| 96 | Z1 | L3 | Q18 |
| 97 | Z1 | L3 | Q19 |
| 98 | Z1 | L3 | Q20 |
| 99 | Z1 | L3 | Q21 |
| 100 | Z1 | L3 | Q22 |
| 101 | Z1 | L3 | Q23 |
| 102 | Z1 | L3 | Q24 |
| 103 | Z1 | L3 | Q25 |
| 104 | Z1 | L3 | Q26 |
| 105 | Z1 | L3 | Q27 |
| 106 | Z1 | L3 | Q28 |
| 107 | Z1 | L3 | Q29 |
| 108 | Z1 | L3 | Q30 |
| 109 | Z1 | L3 | Q31 |
| 110 | Z1 | L3 | Q32 |
| 111 | Z1 | L3 | Q33 |
| 112 | Z1 | L3 | Q34 |
| 113 | Z1 | L3 | Q35 |
| 114 | Z1 | L3 | Q36 |
| 115 | Z1 | L3 | Q37 |
| 116 | Z1 | L3 | Q38 |
| 117 | Z1 | L3 | Q39 |
| 118 | Z1 | L4 | Q1 |
| 119 | Z1 | L4 | Q2 |
| 120 | Z1 | L4 | Q3 |
| 121 | Z1 | L4 | Q4 |
| 122 | Z1 | L4 | Q5 |
| 123 | Z1 | L4 | Q6 |
| 124 | Z1 | L4 | Q7 |
| 125 | Z1 | L4 | Q8 |
| 126 | Z1 | L4 | Q9 |
| 127 | Z1 | L4 | Q10 |
| 128 | Z1 | L4 | Q11 |
| 129 | Z1 | L4 | Q12 |

TABLE 1-2-continued

| | | | |
|---|---|---|---|
| 130 | Z1 | L4 | Q13 |
| 131 | Z1 | L4 | Q14 |
| 132 | Z1 | L4 | Q15 |
| 133 | Z1 | L4 | Q16 |
| 134 | Z1 | L4 | Q17 |
| 135 | Z1 | L4 | Q18 |
| 136 | Z1 | L4 | Q19 |
| 137 | Z1 | L4 | Q20 |
| 138 | Z1 | L4 | Q21 |
| 139 | Z1 | L4 | Q22 |
| 140 | Z1 | L4 | Q23 |
| 141 | Z1 | L4 | Q24 |
| 142 | Z1 | L4 | Q25 |
| 143 | Z1 | L4 | Q26 |
| 144 | Z1 | L4 | Q27 |
| 145 | Z1 | L4 | Q28 |
| 146 | Z1 | L4 | Q29 |
| 147 | Z1 | L4 | Q30 |
| 148 | Z1 | L4 | Q31 |
| 149 | Z1 | L4 | Q32 |
| 150 | Z1 | L4 | Q33 |
| 151 | Z1 | L4 | Q34 |
| 152 | Z1 | L4 | Q35 |
| 153 | Z1 | L4 | Q36 |
| 154 | Z1 | L4 | Q37 |
| 155 | Z1 | L4 | Q38 |
| 156 | Z1 | L4 | Q39 |
| 157 | Z1 | L5 | Q1 |
| 158 | Z1 | L5 | Q2 |
| 159 | Z1 | L5 | Q3 |
| 160 | Z1 | L5 | Q4 |
| 161 | Z1 | L5 | Q5 |
| 162 | Z1 | L5 | Q6 |
| 163 | Z1 | L5 | Q7 |
| 164 | Z1 | L5 | Q8 |
| 165 | Z1 | L5 | Q9 |
| 166 | Z1 | L5 | Q10 |
| 167 | Z1 | L5 | Q11 |
| 168 | Z1 | L5 | Q12 |
| 169 | Z1 | L5 | Q13 |
| 170 | Z1 | L5 | Q14 |
| 171 | Z1 | L5 | Q15 |
| 172 | Z1 | L5 | Q16 |
| 173 | Z1 | L5 | Q17 |
| 174 | Z1 | L5 | Q18 |
| 175 | Z1 | L5 | Q19 |
| 176 | Z1 | L5 | Q20 |
| 177 | Z1 | L5 | Q21 |
| 178 | Z1 | L5 | Q22 |
| 179 | Z1 | L5 | Q23 |
| 180 | Z1 | L5 | Q24 |
| 181 | Z1 | L5 | Q25 |
| 182 | Z1 | L5 | Q26 |
| 183 | Z1 | L5 | Q27 |
| 184 | Z1 | L5 | Q28 |
| 185 | Z1 | L5 | Q29 |
| 186 | Z1 | L5 | Q30 |
| 187 | Z1 | L5 | Q31 |
| 188 | Z1 | L5 | Q32 |
| 189 | Z1 | L5 | Q33 |
| 190 | Z1 | L5 | Q34 |
| 191 | Z1 | L5 | Q35 |
| 192 | Z1 | L5 | Q36 |
| 193 | Z1 | L5 | Q37 |
| 194 | Z1 | L5 | Q38 |
| 195 | Z1 | L5 | Q39 |
| 196 | Z1 | L6 | Q1 |
| 197 | Z1 | L6 | Q2 |
| 198 | Z1 | L6 | Q3 |
| 199 | Z1 | L6 | Q4 |
| 200 | Z1 | L6 | Q5 |
| 201 | Z1 | L6 | Q6 |
| 202 | Z1 | L6 | Q7 |
| 203 | Z1 | L6 | Q8 |
| 204 | Z1 | L6 | Q9 |
| 205 | Z1 | L6 | Q10 |
| 206 | Z1 | L6 | Q11 |
| 207 | Z1 | L6 | Q12 |
| 208 | Z1 | L6 | Q13 |
| 209 | Z1 | L6 | Q14 |
| 210 | Z1 | L6 | Q15 |
| 211 | Z1 | L6 | Q16 |
| 212 | Z1 | L6 | Q17 |
| 213 | Z1 | L6 | Q18 |
| 214 | Z1 | L6 | Q19 |
| 215 | Z1 | L6 | Q20 |
| 216 | Z1 | L6 | Q21 |
| 217 | Z1 | L6 | Q22 |
| 218 | Z1 | L6 | Q23 |
| 219 | Z1 | L6 | Q24 |
| 220 | Z1 | L6 | Q25 |
| 221 | Z1 | L6 | Q26 |

TABLE 1-3

| | | | |
|---|---|---|---|
| 222 | Z1 | L6 | Q27 |
| 223 | Z1 | L6 | Q28 |
| 224 | Z1 | L6 | Q29 |
| 225 | Z1 | L6 | Q30 |
| 226 | Z1 | L6 | Q31 |
| 227 | Z1 | L6 | Q32 |
| 228 | Z1 | L6 | Q33 |
| 229 | Z1 | L6 | Q34 |
| 230 | Z1 | L6 | Q35 |
| 231 | Z1 | L6 | Q36 |
| 232 | Z1 | L6 | Q37 |
| 233 | Z1 | L6 | Q38 |
| 234 | Z1 | L6 | Q39 |
| 235 | Z1 | L7 | Q1 |
| 236 | Z1 | L7 | Q2 |
| 237 | Z1 | L7 | Q3 |
| 238 | Z1 | L7 | Q4 |
| 239 | Z1 | L7 | Q5 |
| 240 | Z1 | L7 | Q6 |
| 241 | Z1 | L7 | Q7 |
| 242 | Z1 | L7 | Q8 |
| 243 | Z1 | L7 | Q9 |
| 244 | Z1 | L7 | Q10 |
| 245 | Z1 | L7 | Q11 |
| 246 | Z1 | L7 | Q12 |
| 247 | Z1 | L7 | Q13 |
| 248 | Z1 | L7 | Q14 |
| 249 | Z1 | L7 | Q15 |
| 250 | Z1 | L7 | Q16 |
| 251 | Z1 | L7 | Q17 |
| 252 | Z1 | L7 | Q18 |
| 253 | Z1 | L7 | Q19 |
| 254 | Z1 | L7 | Q20 |
| 255 | Z1 | L7 | Q21 |
| 256 | Z1 | L7 | Q22 |
| 257 | Z1 | L7 | Q23 |
| 258 | Z1 | L7 | Q24 |
| 259 | Z1 | L7 | Q25 |
| 260 | Z1 | L7 | Q26 |
| 261 | Z1 | L7 | Q27 |
| 262 | Z1 | L7 | Q28 |
| 263 | Z1 | L7 | Q29 |
| 264 | Z1 | L7 | Q30 |
| 265 | Z1 | L7 | Q31 |
| 266 | Z1 | L7 | Q32 |
| 267 | Z1 | L7 | Q33 |
| 268 | Z1 | L7 | Q34 |
| 269 | Z1 | L7 | Q35 |
| 270 | Z1 | L7 | Q36 |
| 271 | Z1 | L7 | Q37 |
| 272 | Z1 | L7 | Q38 |
| 273 | Z1 | L7 | Q39 |
| 274 | Z1 | L8 | Q1 |
| 275 | Z1 | L8 | Q2 |
| 276 | Z1 | L8 | Q3 |
| 277 | Z1 | L8 | Q4 |
| 278 | Z1 | L8 | Q5 |
| 279 | Z1 | L8 | Q6 |
| 280 | Z1 | L8 | Q7 |
| 281 | Z1 | L8 | Q8 |
| 282 | Z1 | L8 | Q9 |
| 283 | Z1 | L8 | Q10 |

TABLE 1-3-continued

| | | | |
|---|---|---|---|
| 284 | Z1 | L8 | Q11 |
| 285 | Z1 | L8 | Q12 |
| 286 | Z1 | L8 | Q13 |
| 287 | Z1 | L8 | Q14 |
| 288 | Z1 | L8 | Q15 |
| 289 | Z1 | L8 | Q16 |
| 290 | Z1 | L8 | Q17 |
| 291 | Z1 | L8 | Q18 |
| 292 | Z1 | L8 | Q19 |
| 293 | Z1 | L8 | Q20 |
| 294 | Z1 | L8 | Q21 |
| 295 | Z1 | L8 | Q22 |
| 296 | Z1 | L8 | Q23 |
| 297 | Z1 | L8 | Q24 |
| 298 | Z1 | L8 | Q25 |
| 299 | Z1 | L8 | Q26 |
| 300 | Z1 | L8 | Q27 |
| 301 | Z1 | L8 | Q28 |
| 302 | Z1 | L8 | Q29 |
| 303 | Z1 | L8 | Q30 |
| 304 | Z1 | L8 | Q31 |
| 305 | Z1 | L8 | Q32 |
| 306 | Z1 | L8 | Q33 |
| 307 | Z1 | L8 | Q34 |
| 308 | Z1 | L8 | Q35 |
| 309 | Z1 | L8 | Q36 |
| 310 | Z1 | L8 | Q37 |
| 311 | Z1 | L8 | Q38 |
| 312 | Z1 | L8 | Q39 |
| 313 | Z1 | L9 | Q1 |
| 314 | Z1 | L9 | Q2 |
| 315 | Z1 | L9 | Q3 |
| 316 | Z1 | L9 | Q4 |
| 317 | Z1 | L9 | Q5 |
| 318 | Z1 | L9 | Q6 |
| 319 | Z1 | L9 | Q7 |
| 320 | Z1 | L9 | Q8 |
| 321 | Z1 | L9 | Q9 |
| 322 | Z1 | L9 | Q10 |
| 323 | Z1 | L9 | Q11 |
| 324 | Z1 | L9 | Q12 |
| 325 | Z1 | L9 | Q13 |
| 326 | Z1 | L9 | Q14 |
| 327 | Z1 | L9 | Q15 |
| 328 | Z1 | L9 | Q16 |
| 329 | Z1 | L9 | Q17 |
| 330 | Z1 | L9 | Q18 |
| 331 | Z1 | L9 | Q19 |
| 332 | Z1 | L9 | Q20 |
| 333 | Z1 | L9 | Q21 |
| 334 | Z1 | L9 | Q22 |
| 335 | Z1 | L9 | Q23 |
| 336 | Z1 | L9 | Q24 |
| 337 | Z1 | L9 | Q25 |
| 338 | Z1 | L9 | Q26 |
| 339 | Z1 | L9 | Q27 |
| 340 | Z1 | L9 | Q28 |
| 341 | Z1 | L9 | Q29 |
| 342 | Z1 | L9 | Q30 |
| 343 | Z1 | L9 | Q31 |
| 344 | Z1 | L9 | Q32 |
| 345 | Z1 | L9 | Q33 |
| 346 | Z1 | L9 | Q34 |
| 347 | Z1 | L9 | Q35 |
| 348 | Z1 | L9 | Q36 |
| 349 | Z1 | L9 | Q37 |
| 350 | Z1 | L9 | Q38 |
| 351 | Z1 | L9 | Q39 |
| 352 | Z1 | L10 | Q1 |
| 353 | Z1 | L10 | Q2 |
| 354 | Z1 | L10 | Q3 |
| 355 | Z1 | L10 | Q4 |
| 356 | Z1 | L10 | Q5 |
| 357 | Z1 | L10 | Q6 |
| 358 | Z1 | L10 | Q7 |
| 359 | Z1 | L10 | Q8 |
| 360 | Z1 | L10 | Q9 |
| 361 | Z1 | L10 | Q10 |
| 362 | Z1 | L10 | Q11 |

TABLE 1-4

| | | | |
|---|---|---|---|
| 363 | Z1 | L10 | Q12 |
| 364 | Z1 | L10 | Q13 |
| 365 | Z1 | L10 | Q14 |
| 366 | Z1 | L10 | Q15 |
| 367 | Z1 | L10 | Q16 |
| 368 | Z1 | L10 | Q17 |
| 369 | Z1 | L10 | Q18 |
| 370 | Z1 | L10 | Q19 |
| 371 | Z1 | L10 | Q20 |
| 372 | Z1 | L10 | Q21 |
| 373 | Z1 | L10 | Q22 |
| 374 | Z1 | L10 | Q23 |
| 375 | Z1 | L10 | Q24 |
| 376 | Z1 | L10 | Q25 |
| 377 | Z1 | L10 | Q26 |
| 378 | Z1 | L10 | Q27 |
| 379 | Z1 | L10 | Q28 |
| 380 | Z1 | L10 | Q29 |
| 381 | Z1 | L10 | Q30 |
| 382 | Z1 | L10 | Q31 |
| 383 | Z1 | L10 | Q32 |
| 384 | Z1 | L10 | Q33 |
| 385 | Z1 | L10 | Q34 |
| 386 | Z1 | L10 | Q35 |
| 387 | Z1 | L10 | Q36 |
| 388 | Z1 | L10 | Q37 |
| 389 | Z1 | L10 | Q38 |
| 390 | Z1 | L10 | Q39 |
| 391 | Z1 | L11 | Q1 |
| 392 | Z1 | L11 | Q2 |
| 393 | Z1 | L11 | Q3 |
| 394 | Z1 | L11 | Q4 |
| 395 | Z1 | L11 | Q5 |
| 396 | Z1 | L11 | Q6 |
| 397 | Z1 | L11 | Q7 |
| 398 | Z1 | L11 | Q8 |
| 399 | Z1 | L11 | Q9 |
| 400 | Z1 | L11 | Q10 |
| 401 | Z1 | L11 | Q11 |
| 402 | Z1 | L11 | Q12 |
| 403 | Z1 | L11 | Q13 |
| 404 | Z1 | L11 | Q14 |
| 405 | Z1 | L11 | Q15 |
| 406 | Z1 | L11 | Q16 |
| 407 | Z1 | L11 | Q17 |
| 408 | Z1 | L11 | Q18 |
| 409 | Z1 | L11 | Q19 |
| 410 | Z1 | L11 | Q20 |
| 411 | Z1 | L11 | Q21 |
| 412 | Z1 | L11 | Q22 |
| 413 | Z1 | L11 | Q23 |
| 414 | Z1 | L11 | Q24 |
| 415 | Z1 | L11 | Q25 |
| 416 | Z1 | L11 | Q26 |
| 417 | Z1 | L11 | Q27 |
| 418 | Z1 | L11 | Q28 |
| 419 | Z1 | L11 | Q29 |
| 420 | Z1 | L11 | Q30 |
| 421 | Z1 | L11 | Q31 |
| 422 | Z1 | L11 | Q32 |
| 423 | Z1 | L11 | Q33 |
| 424 | Z1 | L11 | Q34 |
| 425 | Z1 | L11 | Q35 |
| 426 | Z1 | L11 | Q36 |
| 427 | Z1 | L11 | Q37 |
| 428 | Z1 | L11 | Q38 |
| 429 | Z1 | L11 | Q39 |
| 430 | Z1 | L12 | Q1 |
| 431 | Z1 | L12 | Q2 |
| 432 | Z1 | L12 | Q3 |
| 433 | Z1 | L12 | Q4 |
| 434 | Z1 | L12 | Q5 |
| 435 | Z1 | L12 | Q6 |
| 436 | Z1 | L12 | Q7 |
| 437 | Z1 | L12 | Q8 |
| 438 | Z1 | L12 | Q9 |
| 439 | Z1 | L12 | Q10 |
| 440 | Z1 | L12 | Q11 |
| 441 | Z1 | L12 | Q12 |
| 442 | Z1 | L12 | Q13 |

TABLE 1-4-continued

| | | | |
|---|---|---|---|
| 443 | Z1 | L12 | Q14 |
| 444 | Z1 | L12 | Q15 |
| 445 | Z1 | L12 | Q16 |
| 446 | Z1 | L12 | Q17 |
| 447 | Z1 | L12 | Q18 |
| 448 | Z1 | L12 | Q19 |
| 449 | Z1 | L12 | Q20 |
| 450 | Z1 | L12 | Q21 |
| 451 | Z1 | L12 | Q22 |
| 452 | Z1 | L12 | Q23 |
| 453 | Z1 | L12 | Q24 |
| 454 | Z1 | L12 | Q25 |
| 455 | Z1 | L12 | Q26 |
| 456 | Z1 | L12 | Q27 |
| 457 | Z1 | L12 | Q28 |
| 458 | Z1 | L12 | Q29 |
| 459 | Z1 | L12 | Q30 |
| 460 | Z1 | L12 | Q31 |
| 461 | Z1 | L12 | Q32 |
| 462 | Z1 | L12 | Q33 |
| 463 | Z1 | L12 | Q34 |
| 464 | Z1 | L12 | Q35 |
| 465 | Z1 | L12 | Q36 |
| 466 | Z1 | L12 | Q37 |
| 467 | Z1 | L12 | Q38 |
| 468 | Z1 | L12 | Q39 |
| 469 | Z1 | L13 | Q1 |
| 470 | Z1 | L13 | Q2 |
| 471 | Z1 | L13 | Q3 |
| 472 | Z1 | L13 | Q4 |
| 473 | Z1 | L13 | Q5 |
| 474 | Z1 | L13 | Q6 |
| 475 | Z1 | L13 | Q7 |
| 476 | Z1 | L13 | Q8 |
| 477 | Z1 | L13 | Q9 |
| 478 | Z1 | L13 | Q10 |
| 479 | Z1 | L13 | Q11 |
| 480 | Z1 | L13 | Q12 |
| 481 | Z1 | L13 | Q13 |
| 482 | Z1 | L13 | Q14 |
| 483 | Z1 | L13 | Q15 |
| 484 | Z1 | L13 | Q16 |
| 485 | Z1 | L13 | Q17 |
| 486 | Z1 | L13 | Q18 |
| 487 | Z1 | L13 | Q19 |
| 488 | Z1 | L13 | Q20 |
| 489 | Z1 | L13 | Q21 |
| 490 | Z1 | L13 | Q22 |
| 491 | Z1 | L13 | Q23 |
| 492 | Z1 | L13 | Q24 |
| 493 | Z1 | L13 | Q25 |
| 494 | Z1 | L13 | Q26 |
| 495 | Z1 | L13 | Q27 |
| 496 | Z1 | L13 | Q28 |
| 497 | Z1 | L13 | Q29 |
| 498 | Z1 | L13 | Q30 |
| 499 | Z1 | L13 | Q31 |
| 500 | Z1 | L13 | Q32 |
| 501 | Z1 | L13 | Q33 |
| 502 | Z1 | L13 | Q34 |
| 503 | Z1 | L13 | Q35 |

TABLE 1-5

| | | | |
|---|---|---|---|
| 504 | Z1 | L13 | Q36 |
| 505 | Z1 | L13 | Q37 |
| 506 | Z1 | L13 | Q38 |
| 507 | Z1 | L13 | Q39 |
| 508 | Z1 | L14 | Q1 |
| 509 | Z1 | L14 | Q2 |
| 510 | Z1 | L14 | Q3 |
| 511 | Z1 | L14 | Q4 |
| 512 | Z1 | L14 | Q5 |
| 513 | Z1 | L14 | Q6 |
| 514 | Z1 | L14 | Q7 |
| 515 | Z1 | L14 | Q8 |
| 516 | Z1 | L14 | Q9 |

TABLE 1-5-continued

| | | | |
|---|---|---|---|
| 517 | Z1 | L14 | Q10 |
| 518 | Z1 | L14 | Q11 |
| 519 | Z1 | L14 | Q12 |
| 520 | Z1 | L14 | Q13 |
| 521 | Z1 | L14 | Q14 |
| 522 | Z1 | L14 | Q15 |
| 523 | Z1 | L14 | Q16 |
| 524 | Z1 | L14 | Q17 |
| 525 | Z1 | L14 | Q18 |
| 526 | Z1 | L14 | Q19 |
| 527 | Z1 | L14 | Q20 |
| 528 | Z1 | L14 | Q21 |
| 529 | Z1 | L14 | Q22 |
| 530 | Z1 | L14 | Q23 |
| 531 | Z1 | L14 | Q24 |
| 532 | Z1 | L14 | Q25 |
| 533 | Z1 | L14 | Q26 |
| 534 | Z1 | L14 | Q27 |
| 535 | Z1 | L14 | Q28 |
| 536 | Z1 | L14 | Q29 |
| 537 | Z1 | L14 | Q30 |
| 538 | Z1 | L14 | Q31 |
| 539 | Z1 | L14 | Q32 |
| 540 | Z1 | L14 | Q33 |
| 541 | Z1 | L14 | Q34 |
| 542 | Z1 | L14 | Q35 |
| 543 | Z1 | L14 | Q36 |
| 544 | Z1 | L14 | Q37 |
| 545 | Z1 | L14 | Q38 |
| 546 | Z1 | L14 | Q39 |
| 547 | Z2 | L1 | Q1 |
| 548 | Z2 | L1 | Q2 |
| 549 | Z2 | L1 | Q3 |
| 550 | Z2 | L1 | Q4 |
| 551 | Z2 | L1 | Q5 |
| 552 | Z2 | L1 | Q6 |
| 553 | Z2 | L1 | Q7 |
| 554 | Z2 | L1 | Q8 |
| 555 | Z2 | L1 | Q9 |
| 556 | Z2 | L1 | Q10 |
| 557 | Z2 | L1 | Q11 |
| 558 | Z2 | L1 | Q12 |
| 559 | Z2 | L1 | Q13 |
| 560 | Z2 | L1 | Q14 |
| 561 | Z2 | L1 | Q15 |
| 562 | Z2 | L1 | Q16 |
| 563 | Z2 | L1 | Q17 |
| 564 | Z2 | L1 | Q18 |
| 565 | Z2 | L1 | Q19 |
| 566 | Z2 | L1 | Q20 |
| 567 | Z2 | L1 | Q21 |
| 568 | Z2 | L1 | Q22 |
| 569 | Z2 | L1 | Q23 |
| 570 | Z2 | L1 | Q24 |
| 571 | Z2 | L1 | Q25 |
| 572 | Z2 | L1 | Q26 |
| 573 | Z2 | L1 | Q27 |
| 574 | Z2 | L1 | Q28 |
| 575 | Z2 | L1 | Q29 |
| 576 | Z2 | L1 | Q30 |
| 577 | Z2 | L1 | Q31 |
| 578 | Z2 | L1 | Q32 |
| 579 | Z2 | L1 | Q33 |
| 580 | Z2 | L1 | Q34 |
| 581 | Z2 | L1 | Q35 |
| 582 | Z2 | L1 | Q36 |
| 583 | Z2 | L1 | Q37 |
| 584 | Z2 | L1 | Q38 |
| 585 | Z2 | L1 | Q39 |
| 586 | Z2 | L2 | Q1 |
| 587 | Z2 | L2 | Q2 |
| 588 | Z2 | L2 | Q3 |
| 589 | Z2 | L2 | Q4 |
| 590 | Z2 | L2 | Q5 |
| 591 | Z2 | L2 | Q6 |
| 592 | Z2 | L2 | Q7 |
| 593 | Z2 | L2 | Q8 |
| 594 | Z2 | L2 | Q9 |
| 595 | Z2 | L2 | Q10 |
| 596 | Z2 | L2 | Q11 |

TABLE 1-5-continued

| | | | |
|---|---|---|---|
| 597 | Z2 | L2 | Q12 |
| 598 | Z2 | L2 | Q13 |
| 599 | Z2 | L2 | Q14 |
| 600 | Z2 | L2 | Q15 |
| 601 | Z2 | L2 | Q16 |
| 602 | Z2 | L2 | Q17 |
| 603 | Z2 | L2 | Q18 |
| 604 | Z2 | L2 | Q19 |
| 605 | Z2 | L2 | Q20 |
| 606 | Z2 | L2 | Q21 |
| 607 | Z2 | L2 | Q22 |
| 608 | Z2 | L2 | Q23 |
| 609 | Z2 | L2 | Q24 |
| 610 | Z2 | L2 | Q25 |
| 611 | Z2 | L2 | Q26 |
| 612 | Z2 | L2 | Q27 |
| 613 | Z2 | L2 | Q28 |
| 614 | Z2 | L2 | Q29 |
| 615 | Z2 | L2 | Q30 |
| 616 | Z2 | L2 | Q31 |
| 617 | Z2 | L2 | Q32 |
| 618 | Z2 | L2 | Q33 |
| 619 | Z2 | L2 | Q34 |
| 620 | Z2 | L2 | Q35 |
| 621 | Z2 | L2 | Q36 |
| 622 | Z2 | L2 | Q37 |
| 623 | Z2 | L2 | Q38 |
| 624 | Z2 | L2 | Q39 |
| 625 | Z2 | L3 | Q1 |
| 626 | Z2 | L3 | Q2 |
| 627 | Z2 | L3 | Q3 |
| 628 | Z2 | L3 | Q4 |
| 629 | Z2 | L3 | Q5 |
| 630 | Z2 | L3 | Q6 |
| 631 | Z2 | L3 | Q7 |
| 632 | Z2 | L3 | Q8 |
| 633 | Z2 | L3 | Q9 |
| 634 | Z2 | L3 | Q10 |
| 635 | Z2 | L3 | Q11 |
| 636 | Z2 | L3 | Q12 |
| 637 | Z2 | L3 | Q13 |
| 638 | Z2 | L3 | Q14 |
| 639 | Z2 | L3 | Q15 |
| 640 | Z2 | L3 | Q16 |
| 641 | Z2 | L3 | Q17 |
| 642 | Z2 | L3 | Q18 |
| 643 | Z2 | L3 | Q19 |
| 644 | Z2 | L3 | Q20 |

TABLE 1-6

| | | | |
|---|---|---|---|
| 645 | Z2 | L3 | Q21 |
| 646 | Z2 | L3 | Q22 |
| 647 | Z2 | L3 | Q23 |
| 648 | Z2 | L3 | Q24 |
| 649 | Z2 | L3 | Q25 |
| 650 | Z2 | L3 | Q26 |
| 651 | Z2 | L3 | Q27 |
| 652 | Z2 | L3 | Q28 |
| 653 | Z2 | L3 | Q29 |
| 654 | Z2 | L3 | Q30 |
| 655 | Z2 | L3 | Q31 |
| 656 | Z2 | L3 | Q32 |
| 657 | Z2 | L3 | Q33 |
| 658 | Z2 | L3 | Q34 |
| 659 | Z2 | L3 | Q35 |
| 660 | Z2 | L3 | Q36 |
| 661 | Z2 | L3 | Q37 |
| 662 | Z2 | L3 | Q38 |
| 663 | Z2 | L3 | Q39 |
| 664 | Z2 | L4 | Q1 |
| 665 | Z2 | L4 | Q2 |
| 666 | Z2 | L4 | Q3 |
| 667 | Z2 | L4 | Q4 |
| 668 | Z2 | L4 | Q5 |
| 669 | Z2 | L4 | Q6 |
| 670 | Z2 | L4 | Q7 |

TABLE 1-6-continued

| | | | |
|---|---|---|---|
| 671 | Z2 | L4 | Q8 |
| 672 | Z2 | L4 | Q9 |
| 673 | Z2 | L4 | Q10 |
| 674 | Z2 | L4 | Q11 |
| 675 | Z2 | L4 | Q12 |
| 676 | Z2 | L4 | Q13 |
| 677 | Z2 | L4 | Q14 |
| 678 | Z2 | L4 | Q15 |
| 679 | Z2 | L4 | Q16 |
| 680 | Z2 | L4 | Q17 |
| 681 | Z2 | L4 | Q18 |
| 682 | Z2 | L4 | Q19 |
| 683 | Z2 | L4 | Q20 |
| 684 | Z2 | L4 | Q21 |
| 685 | Z2 | L4 | Q22 |
| 686 | Z2 | L4 | Q23 |
| 687 | Z2 | L4 | Q24 |
| 688 | Z2 | L4 | Q25 |
| 689 | Z2 | L4 | Q26 |
| 690 | Z2 | L4 | Q27 |
| 691 | Z2 | L4 | Q28 |
| 692 | Z2 | L4 | Q29 |
| 693 | Z2 | L4 | Q30 |
| 694 | Z2 | L4 | Q31 |
| 695 | Z2 | L4 | Q32 |
| 696 | Z2 | L4 | Q33 |
| 697 | Z2 | L4 | Q34 |
| 698 | Z2 | L4 | Q35 |
| 699 | Z2 | L4 | Q36 |
| 700 | Z2 | L4 | Q37 |
| 701 | Z2 | L4 | Q38 |
| 702 | Z2 | L4 | Q39 |
| 703 | Z2 | L5 | Q1 |
| 704 | Z2 | L5 | Q2 |
| 705 | Z2 | L5 | Q3 |
| 706 | Z2 | L5 | Q4 |
| 707 | Z2 | L5 | Q5 |
| 708 | Z2 | L5 | Q6 |
| 709 | Z2 | L5 | Q7 |
| 710 | Z2 | L5 | Q8 |
| 711 | Z2 | L5 | Q9 |
| 712 | Z2 | L5 | Q10 |
| 713 | Z2 | L5 | Q11 |
| 714 | Z2 | L5 | Q12 |
| 715 | Z2 | L5 | Q13 |
| 716 | Z2 | L5 | Q14 |
| 717 | Z2 | L5 | Q15 |
| 718 | Z2 | L5 | Q16 |
| 719 | Z2 | L5 | Q17 |
| 720 | Z2 | L5 | Q18 |
| 721 | Z2 | L5 | Q19 |
| 722 | Z2 | L5 | Q20 |
| 723 | Z2 | L5 | Q21 |
| 724 | Z2 | L5 | Q22 |
| 725 | Z2 | L5 | Q23 |
| 726 | Z2 | L5 | Q24 |
| 727 | Z2 | L5 | Q25 |
| 728 | Z2 | L5 | Q26 |
| 729 | Z2 | L5 | Q27 |
| 730 | Z2 | L5 | Q28 |
| 731 | Z2 | L5 | Q29 |
| 732 | Z2 | L5 | Q30 |
| 733 | Z2 | L5 | Q31 |
| 734 | Z2 | L5 | Q32 |
| 735 | Z2 | L5 | Q33 |
| 736 | Z2 | L5 | Q34 |
| 737 | Z2 | L5 | Q35 |
| 738 | Z2 | L5 | Q36 |
| 739 | Z2 | L5 | Q37 |
| 740 | Z2 | L5 | Q38 |
| 741 | Z2 | L5 | Q39 |
| 742 | Z2 | L6 | Q1 |
| 743 | Z2 | L6 | Q2 |
| 744 | Z2 | L6 | Q3 |
| 745 | Z2 | L6 | Q4 |
| 746 | Z2 | L6 | Q5 |
| 747 | Z2 | L6 | Q6 |
| 748 | Z2 | L6 | Q7 |
| 749 | Z2 | L6 | Q8 |
| 750 | Z2 | L6 | Q9 |

TABLE 1-6-continued

| | | | |
|---|---|---|---|
| 751 | Z2 | L6 | Q10 |
| 752 | Z2 | L6 | Q11 |
| 753 | Z2 | L6 | Q12 |
| 754 | Z2 | L6 | Q13 |
| 755 | Z2 | L6 | Q14 |
| 756 | Z2 | L6 | Q15 |
| 757 | Z2 | L6 | Q16 |
| 758 | Z2 | L6 | Q17 |
| 759 | Z2 | L6 | Q18 |
| 760 | Z2 | L6 | Q19 |
| 761 | Z2 | L6 | Q20 |
| 762 | Z2 | L6 | Q21 |
| 763 | Z2 | L6 | Q22 |
| 764 | Z2 | L6 | Q23 |
| 765 | Z2 | L6 | Q24 |
| 766 | Z2 | L6 | Q25 |
| 767 | Z2 | L6 | Q26 |
| 768 | Z2 | L6 | Q27 |
| 769 | Z2 | L6 | Q28 |
| 770 | Z2 | L6 | Q29 |
| 771 | Z2 | L6 | Q30 |
| 772 | Z2 | L6 | Q31 |
| 773 | Z2 | L6 | Q32 |
| 774 | Z2 | L6 | Q33 |
| 775 | Z2 | L6 | Q34 |
| 776 | Z2 | L6 | Q35 |
| 777 | Z2 | L6 | Q36 |
| 778 | Z2 | L6 | Q37 |
| 779 | Z2 | L6 | Q38 |
| 780 | Z2 | L6 | Q39 |
| 781 | Z2 | L7 | Q1 |
| 782 | Z2 | L7 | Q2 |
| 783 | Z2 | L7 | Q3 |
| 784 | Z2 | L7 | Q4 |
| 785 | Z2 | L7 | Q5 |

TABLE 1-7

| | | | |
|---|---|---|---|
| 786 | Z2 | L7 | Q6 |
| 787 | Z2 | L7 | Q7 |
| 788 | Z2 | L7 | Q8 |
| 789 | Z2 | L7 | Q9 |
| 790 | Z2 | L7 | Q10 |
| 791 | Z2 | L7 | Q11 |
| 792 | Z2 | L7 | Q12 |
| 793 | Z2 | L7 | Q13 |
| 794 | Z2 | L7 | Q14 |
| 795 | Z2 | L7 | Q15 |
| 796 | Z2 | L7 | Q16 |
| 797 | Z2 | L7 | Q17 |
| 798 | Z2 | L7 | Q18 |
| 799 | Z2 | L7 | Q19 |
| 800 | Z2 | L7 | Q20 |
| 801 | Z2 | L7 | Q21 |
| 802 | Z2 | L7 | Q22 |
| 803 | Z2 | L7 | Q23 |
| 804 | Z2 | L7 | Q24 |
| 805 | Z2 | L7 | Q25 |
| 806 | Z2 | L7 | Q26 |
| 807 | Z2 | L7 | Q27 |
| 808 | Z2 | L7 | Q28 |
| 809 | Z2 | L7 | Q29 |
| 810 | Z2 | L7 | Q30 |
| 811 | Z2 | L7 | Q31 |
| 812 | Z2 | L7 | Q32 |
| 813 | Z2 | L7 | Q33 |
| 814 | Z2 | L7 | Q34 |
| 815 | Z2 | L7 | Q35 |
| 816 | Z2 | L7 | Q36 |
| 817 | Z2 | L7 | Q37 |
| 818 | Z2 | L7 | Q38 |
| 819 | Z2 | L7 | Q39 |
| 820 | Z2 | L8 | Q1 |
| 821 | Z2 | L8 | Q2 |
| 822 | Z2 | L8 | Q3 |
| 823 | Z2 | L8 | Q4 |
| 824 | Z2 | L8 | Q5 |

TABLE 1-7-continued

| | | | |
|---|---|---|---|
| 825 | Z2 | L8 | Q6 |
| 826 | Z2 | L8 | Q7 |
| 827 | Z2 | L8 | Q8 |
| 828 | Z2 | L8 | Q9 |
| 829 | Z2 | L8 | Q10 |
| 830 | Z2 | L8 | Q11 |
| 831 | Z2 | L8 | Q12 |
| 832 | Z2 | L8 | Q13 |
| 833 | Z2 | L8 | Q14 |
| 834 | Z2 | L8 | Q15 |
| 835 | Z2 | L8 | Q16 |
| 836 | Z2 | L8 | Q17 |
| 837 | Z2 | L8 | Q18 |
| 838 | Z2 | L8 | Q19 |
| 839 | Z2 | L8 | Q20 |
| 840 | Z2 | L8 | Q21 |
| 841 | Z2 | L8 | Q22 |
| 842 | Z2 | L8 | Q23 |
| 843 | Z2 | L8 | Q24 |
| 844 | Z2 | L8 | Q25 |
| 845 | Z2 | L8 | Q26 |
| 846 | Z2 | L8 | Q27 |
| 847 | Z2 | L8 | Q28 |
| 848 | Z2 | L8 | Q29 |
| 849 | Z2 | L8 | Q30 |
| 850 | Z2 | L8 | Q31 |
| 851 | Z2 | L8 | Q32 |
| 852 | Z2 | L8 | Q33 |
| 853 | Z2 | L8 | Q34 |
| 854 | Z2 | L8 | Q35 |
| 855 | Z2 | L8 | Q36 |
| 856 | Z2 | L8 | Q37 |
| 857 | Z2 | L8 | Q38 |
| 858 | Z2 | L8 | Q39 |
| 859 | Z2 | L9 | Q1 |
| 860 | Z2 | L9 | Q2 |
| 861 | Z2 | L9 | Q3 |
| 862 | Z2 | L9 | Q4 |
| 863 | Z2 | L9 | Q5 |
| 864 | Z2 | L9 | Q6 |
| 865 | Z2 | L9 | Q7 |
| 866 | Z2 | L9 | Q8 |
| 867 | Z2 | L9 | Q9 |
| 868 | Z2 | L9 | Q10 |
| 869 | Z2 | L9 | Q11 |
| 870 | Z2 | L9 | Q12 |
| 871 | Z2 | L9 | Q13 |
| 872 | Z2 | L9 | Q14 |
| 873 | Z2 | L9 | Q15 |
| 874 | Z2 | L9 | Q16 |
| 875 | Z2 | L9 | Q17 |
| 876 | Z2 | L9 | Q18 |
| 877 | Z2 | L9 | Q19 |
| 878 | Z2 | L9 | Q20 |
| 879 | Z2 | L9 | Q21 |
| 880 | Z2 | L9 | Q22 |
| 881 | Z2 | L9 | Q23 |
| 882 | Z2 | L9 | Q24 |
| 883 | Z2 | L9 | Q25 |
| 884 | Z2 | L9 | Q26 |
| 885 | Z2 | L9 | Q27 |
| 886 | Z2 | L9 | Q28 |
| 887 | Z2 | L9 | Q29 |
| 888 | Z2 | L9 | Q30 |
| 889 | Z2 | L9 | Q31 |
| 890 | Z2 | L9 | Q32 |
| 891 | Z2 | L9 | Q33 |
| 892 | Z2 | L9 | Q34 |
| 893 | Z2 | L9 | Q35 |
| 894 | Z2 | L9 | Q36 |
| 895 | Z2 | L9 | Q37 |
| 896 | Z2 | L9 | Q38 |
| 897 | Z2 | L9 | Q39 |
| 898 | Z2 | L10 | Q1 |
| 899 | Z2 | L10 | Q2 |
| 900 | Z2 | L10 | Q3 |
| 901 | Z2 | L10 | Q4 |
| 902 | Z2 | L10 | Q5 |
| 903 | Z2 | L10 | Q6 |
| 904 | Z2 | L10 | Q7 |

TABLE 1-7-continued

| | | | |
|---|---|---|---|
| 905 | Z2 | L10 | Q8 |
| 906 | Z2 | L10 | Q9 |
| 907 | Z2 | L10 | Q10 |
| 908 | Z2 | L10 | Q11 |
| 909 | Z2 | L10 | Q12 |
| 910 | Z2 | L10 | Q13 |
| 911 | Z2 | L10 | Q14 |
| 912 | Z2 | L10 | Q15 |
| 913 | Z2 | L10 | Q16 |
| 914 | Z2 | L10 | Q17 |
| 915 | Z2 | L10 | Q18 |
| 916 | Z2 | L10 | Q19 |
| 917 | Z2 | L10 | Q20 |
| 918 | Z2 | L10 | Q21 |
| 919 | Z2 | L10 | Q22 |
| 920 | Z2 | L10 | Q23 |
| 921 | Z2 | L10 | Q24 |
| 922 | Z2 | L10 | Q25 |
| 923 | Z2 | L10 | Q26 |
| 924 | Z2 | L10 | Q27 |
| 925 | Z2 | L10 | Q28 |
| 926 | Z2 | L10 | Q29 |

TABLE 1-8

| | | | |
|---|---|---|---|
| 927 | Z2 | L10 | Q30 |
| 928 | Z2 | L10 | Q31 |
| 929 | Z2 | L10 | Q32 |
| 930 | Z2 | L10 | Q33 |
| 931 | Z2 | L10 | Q34 |
| 932 | Z2 | L10 | Q35 |
| 933 | Z2 | L10 | Q36 |
| 934 | Z2 | L10 | Q37 |
| 935 | Z2 | L10 | Q38 |
| 936 | Z2 | L10 | Q39 |
| 937 | Z2 | L11 | Q1 |
| 938 | Z2 | L11 | Q2 |
| 939 | Z2 | L11 | Q3 |
| 940 | Z2 | L11 | Q4 |
| 941 | Z2 | L11 | Q5 |
| 942 | Z2 | L11 | Q6 |
| 943 | Z2 | L11 | Q7 |
| 944 | Z2 | L11 | Q8 |
| 945 | Z2 | L11 | Q9 |
| 946 | Z2 | L11 | Q10 |
| 947 | Z2 | L11 | Q11 |
| 948 | Z2 | L11 | Q12 |
| 949 | Z2 | L11 | Q13 |
| 950 | Z2 | L11 | Q14 |
| 951 | Z2 | L11 | Q15 |
| 952 | Z2 | L11 | Q16 |
| 953 | Z2 | L11 | Q17 |
| 954 | Z2 | L11 | Q18 |
| 955 | Z2 | L11 | Q19 |
| 956 | Z2 | L11 | Q20 |
| 957 | Z2 | L11 | Q21 |
| 958 | Z2 | L11 | Q22 |
| 959 | Z2 | L11 | Q23 |
| 960 | Z2 | L11 | Q24 |
| 961 | Z2 | L11 | Q25 |
| 962 | Z2 | L11 | Q26 |
| 963 | Z2 | L11 | Q27 |
| 964 | Z2 | L11 | Q28 |
| 965 | Z2 | L11 | Q29 |
| 966 | Z2 | L11 | Q30 |
| 967 | Z2 | L11 | Q31 |
| 968 | Z2 | L11 | Q32 |
| 969 | Z2 | L11 | Q33 |
| 970 | Z2 | L11 | Q34 |
| 971 | Z2 | L11 | Q35 |
| 972 | Z2 | L11 | Q36 |
| 973 | Z2 | L11 | Q37 |
| 974 | Z2 | L11 | Q38 |
| 975 | Z2 | L11 | Q39 |
| 976 | Z2 | L12 | Q1 |
| 977 | Z2 | L12 | Q2 |
| 978 | Z2 | L12 | Q3 |

TABLE 1-8-continued

| | | | |
|---|---|---|---|
| 979 | Z2 | L12 | Q4 |
| 980 | Z2 | L12 | Q5 |
| 981 | Z2 | L12 | Q6 |
| 982 | Z2 | L12 | Q7 |
| 983 | Z2 | L12 | Q8 |
| 984 | Z2 | L12 | Q9 |
| 985 | Z2 | L12 | Q10 |
| 986 | Z2 | L12 | Q11 |
| 987 | Z2 | L12 | Q12 |
| 988 | Z2 | L12 | Q13 |
| 989 | Z2 | L12 | Q14 |
| 990 | Z2 | L12 | Q15 |
| 991 | Z2 | L12 | Q16 |
| 992 | Z2 | L12 | Q17 |
| 993 | Z2 | L12 | Q18 |
| 994 | Z2 | L12 | Q19 |
| 995 | Z2 | L12 | Q20 |
| 996 | Z2 | L12 | Q21 |
| 997 | Z2 | L12 | Q22 |
| 998 | Z2 | L12 | Q23 |
| 999 | Z2 | L12 | Q24 |
| 1000 | Z2 | L12 | Q25 |
| 1001 | Z2 | L12 | Q26 |
| 1002 | Z2 | L12 | Q27 |
| 1003 | Z2 | L12 | Q28 |
| 1004 | Z2 | L12 | Q29 |
| 1005 | Z2 | L12 | Q30 |
| 1006 | Z2 | L12 | Q31 |
| 1007 | Z2 | L12 | Q32 |
| 1008 | Z2 | L12 | Q33 |
| 1009 | Z2 | L12 | Q34 |
| 1010 | Z2 | L12 | Q35 |
| 1011 | Z2 | L12 | Q36 |
| 1012 | Z2 | L12 | Q37 |
| 1013 | Z2 | L12 | Q38 |
| 1014 | Z2 | L12 | Q39 |
| 1015 | Z2 | L13 | Q1 |
| 1016 | Z2 | L13 | Q2 |
| 1017 | Z2 | L13 | Q3 |
| 1018 | Z2 | L13 | Q4 |
| 1019 | Z2 | L13 | Q5 |
| 1020 | Z2 | L13 | Q6 |
| 1021 | Z2 | L13 | Q7 |
| 1022 | Z2 | L13 | Q8 |
| 1023 | Z2 | L13 | Q9 |
| 1024 | Z2 | L13 | Q10 |
| 1025 | Z2 | L13 | Q11 |
| 1026 | Z2 | L13 | Q12 |
| 1027 | Z2 | L13 | Q13 |
| 1028 | Z2 | L13 | Q14 |
| 1029 | Z2 | L13 | Q15 |
| 1030 | Z2 | L13 | Q16 |
| 1031 | Z2 | L13 | Q17 |
| 1032 | Z2 | L13 | Q18 |
| 1033 | Z2 | L13 | Q19 |
| 1034 | Z2 | L13 | Q20 |
| 1035 | Z2 | L13 | Q21 |
| 1036 | Z2 | L13 | Q22 |
| 1037 | Z2 | L13 | Q23 |
| 1038 | Z2 | L13 | Q24 |
| 1039 | Z2 | L13 | Q25 |
| 1040 | Z2 | L13 | Q26 |
| 1041 | Z2 | L13 | Q27 |
| 1042 | Z2 | L13 | Q28 |
| 1043 | Z2 | L13 | Q29 |
| 1044 | Z2 | L13 | Q30 |
| 1045 | Z2 | L13 | Q31 |
| 1046 | Z2 | L13 | Q32 |
| 1047 | Z2 | L13 | Q33 |
| 1048 | Z2 | L13 | Q34 |
| 1049 | Z2 | L13 | Q35 |
| 1050 | Z2 | L13 | Q36 |
| 1051 | Z2 | L13 | Q37 |
| 1052 | Z2 | L13 | Q38 |
| 1053 | Z2 | L13 | Q39 |
| 1054 | Z2 | L14 | Q1 |
| 1055 | Z2 | L14 | Q2 |
| 1056 | Z2 | L14 | Q3 |
| 1057 | Z2 | L14 | Q4 |
| 1058 | Z2 | L14 | Q5 |

TABLE 1-8-continued

| | | | |
|---|---|---|---|
| 1059 | Z2 | L14 | Q6 |
| 1060 | Z2 | L14 | Q7 |
| 1061 | Z2 | L14 | Q8 |
| 1062 | Z2 | L14 | Q9 |
| 1063 | Z2 | L14 | Q10 |
| 1064 | Z2 | L14 | Q11 |
| 1065 | Z2 | L14 | Q12 |
| 1066 | Z2 | L14 | Q13 |
| 1067 | Z2 | L14 | Q14 |

TABLE 1-9

| | | | |
|---|---|---|---|
| 1068 | Z2 | L14 | Q15 |
| 1069 | Z2 | L14 | Q16 |
| 1070 | Z2 | L14 | Q17 |
| 1071 | Z2 | L14 | Q18 |
| 1072 | Z2 | L14 | Q19 |
| 1073 | Z2 | L14 | Q20 |
| 1074 | Z2 | L14 | Q21 |
| 1075 | Z2 | L14 | Q22 |
| 1076 | Z2 | L14 | Q23 |
| 1077 | Z2 | L14 | Q24 |
| 1078 | Z2 | L14 | Q25 |
| 1079 | Z2 | L14 | Q26 |
| 1080 | Z2 | L14 | Q27 |
| 1081 | Z2 | L14 | Q28 |
| 1082 | Z2 | L14 | Q29 |
| 1083 | Z2 | L14 | Q30 |
| 1084 | Z2 | L14 | Q31 |
| 1085 | Z2 | L14 | Q32 |
| 1086 | Z2 | L14 | Q33 |
| 1087 | Z2 | L14 | Q34 |
| 1088 | Z2 | L14 | Q35 |
| 1089 | Z2 | L14 | Q36 |
| 1090 | Z2 | L14 | Q37 |
| 1091 | Z2 | L14 | Q38 |
| 1092 | Z2 | L14 | Q39 |
| 1093 | Z3 | L1 | Q1 |
| 1094 | Z3 | L1 | Q2 |
| 1095 | Z3 | L1 | Q3 |
| 1096 | Z3 | L1 | Q4 |
| 1097 | Z3 | L1 | Q5 |
| 1098 | Z3 | L1 | Q6 |
| 1099 | Z3 | L1 | Q7 |
| 1100 | Z3 | L1 | Q8 |
| 1101 | Z3 | L1 | Q9 |
| 1102 | Z3 | L1 | Q10 |
| 1103 | Z3 | L1 | Q11 |
| 1104 | Z3 | L1 | Q12 |
| 1105 | Z3 | L1 | Q13 |
| 1106 | Z3 | L1 | Q14 |
| 1107 | Z3 | L1 | Q15 |
| 1108 | Z3 | L1 | Q16 |
| 1109 | Z3 | L1 | Q17 |
| 1110 | Z3 | L1 | Q18 |
| 1111 | Z3 | L1 | Q19 |
| 1112 | Z3 | L1 | Q20 |
| 1113 | Z3 | L1 | Q21 |
| 1114 | Z3 | L1 | Q22 |
| 1115 | Z3 | L1 | Q23 |
| 1116 | Z3 | L1 | Q24 |
| 1117 | Z3 | L1 | Q25 |
| 1118 | Z3 | L1 | Q26 |
| 1119 | Z3 | L1 | Q27 |
| 1120 | Z3 | L1 | Q28 |
| 1121 | Z3 | L1 | Q29 |
| 1122 | Z3 | L1 | Q30 |
| 1123 | Z3 | L1 | Q31 |
| 1124 | Z3 | L1 | Q32 |
| 1125 | Z3 | L1 | Q33 |
| 1126 | Z3 | L1 | Q34 |
| 1127 | Z3 | L1 | Q35 |
| 1128 | Z3 | L1 | Q36 |
| 1129 | Z3 | L1 | Q37 |
| 1130 | Z3 | L1 | Q38 |
| 1131 | Z3 | L1 | Q39 |
| 1132 | Z3 | L2 | Q1 |

TABLE 1-9-continued

| | | | |
|---|---|---|---|
| 1133 | Z3 | L2 | Q2 |
| 1134 | Z3 | L2 | Q3 |
| 1135 | Z3 | L2 | Q4 |
| 1136 | Z3 | L2 | Q5 |
| 1137 | Z3 | L2 | Q6 |
| 1138 | Z3 | L2 | Q7 |
| 1139 | Z3 | L2 | Q8 |
| 1140 | Z3 | L2 | Q9 |
| 1141 | Z3 | L2 | Q10 |
| 1142 | Z3 | L2 | Q11 |
| 1143 | Z3 | L2 | Q12 |
| 1144 | Z3 | L2 | Q13 |
| 1145 | Z3 | L2 | Q14 |
| 1146 | Z3 | L2 | Q15 |
| 1147 | Z3 | L2 | Q16 |
| 1148 | Z3 | L2 | Q17 |
| 1149 | Z3 | L2 | Q18 |
| 1150 | Z3 | L2 | Q19 |
| 1151 | Z3 | L2 | Q20 |
| 1152 | Z3 | L2 | Q21 |
| 1153 | Z3 | L2 | Q22 |
| 1154 | Z3 | L2 | Q23 |
| 1155 | Z3 | L2 | Q24 |
| 1156 | Z3 | L2 | Q25 |
| 1157 | Z3 | L2 | Q26 |
| 1158 | Z3 | L2 | Q27 |
| 1159 | Z3 | L2 | Q28 |
| 1160 | Z3 | L2 | Q29 |
| 1161 | Z3 | L2 | Q30 |
| 1162 | Z3 | L2 | Q31 |
| 1163 | Z3 | L2 | Q32 |
| 1164 | Z3 | L2 | Q33 |
| 1165 | Z3 | L2 | Q34 |
| 1166 | Z3 | L2 | Q35 |
| 1167 | Z3 | L2 | Q36 |
| 1168 | Z3 | L2 | Q37 |
| 1169 | Z3 | L2 | Q38 |
| 1170 | Z3 | L2 | Q39 |
| 1171 | Z3 | L3 | Q1 |
| 1172 | Z3 | L3 | Q2 |
| 1173 | Z3 | L3 | Q3 |
| 1174 | Z3 | L3 | Q4 |
| 1175 | Z3 | L3 | Q5 |
| 1176 | Z3 | L3 | Q6 |
| 1177 | Z3 | L3 | Q7 |
| 1178 | Z3 | L3 | Q8 |
| 1179 | Z3 | L3 | Q9 |
| 1180 | Z3 | L3 | Q10 |
| 1181 | Z3 | L3 | Q11 |
| 1182 | Z3 | L3 | Q12 |
| 1183 | Z3 | L3 | Q13 |
| 1184 | Z3 | L3 | Q14 |
| 1185 | Z3 | L3 | Q15 |
| 1186 | Z3 | L3 | Q16 |
| 1187 | Z3 | L3 | Q17 |
| 1188 | Z3 | L3 | Q18 |
| 1189 | Z3 | L3 | Q19 |
| 1190 | Z3 | L3 | Q20 |
| 1191 | Z3 | L3 | Q21 |
| 1192 | Z3 | L3 | Q22 |
| 1193 | Z3 | L3 | Q23 |
| 1194 | Z3 | L3 | Q24 |
| 1195 | Z3 | L3 | Q25 |
| 1196 | Z3 | L3 | Q26 |
| 1197 | Z3 | L3 | Q27 |
| 1198 | Z3 | L3 | Q28 |
| 1199 | Z3 | L3 | Q29 |
| 1200 | Z3 | L3 | Q30 |
| 1201 | Z3 | L3 | Q31 |
| 1202 | Z3 | L3 | Q32 |
| 1203 | Z3 | L3 | Q33 |
| 1204 | Z3 | L3 | Q34 |
| 1205 | Z3 | L3 | Q35 |
| 1206 | Z3 | L3 | Q36 |
| 1207 | Z3 | L3 | Q37 |
| 1208 | Z3 | L3 | Q38 |

TABLE 1-10

| | | | |
|---|---|---|---|
| 1209 | Z3 | L3 | Q39 |
| 1210 | Z3 | L4 | Q1 |
| 1211 | Z3 | L4 | Q2 |
| 1212 | Z3 | L4 | Q3 |
| 1213 | Z3 | L4 | Q4 |
| 1214 | Z3 | L4 | Q5 |
| 1215 | Z3 | L4 | Q6 |
| 1216 | Z3 | L4 | Q7 |
| 1217 | Z3 | L4 | Q8 |
| 1218 | Z3 | L4 | Q9 |
| 1219 | Z3 | L4 | Q10 |
| 1220 | Z3 | L4 | Q11 |
| 1221 | Z3 | L4 | Q12 |
| 1222 | Z3 | L4 | Q13 |
| 1223 | Z3 | L4 | Q14 |
| 1224 | Z3 | L4 | Q15 |
| 1225 | Z3 | L4 | Q16 |
| 1226 | Z3 | L4 | Q17 |
| 1227 | Z3 | L4 | Q18 |
| 1228 | Z3 | L4 | Q19 |
| 1229 | Z3 | L4 | Q20 |
| 1230 | Z3 | L4 | Q21 |
| 1231 | Z3 | L4 | Q22 |
| 1232 | Z3 | L4 | Q23 |
| 1233 | Z3 | L4 | Q24 |
| 1234 | Z3 | L4 | Q25 |
| 1235 | Z3 | L4 | Q26 |
| 1236 | Z3 | L4 | Q27 |
| 1237 | Z3 | L4 | Q28 |
| 1238 | Z3 | L4 | Q29 |
| 1239 | Z3 | L4 | Q30 |
| 1240 | Z3 | L4 | Q31 |
| 1241 | Z3 | L4 | Q32 |
| 1242 | Z3 | L4 | Q33 |
| 1243 | Z3 | L4 | Q34 |
| 1244 | Z3 | L4 | Q35 |
| 1245 | Z3 | L4 | Q36 |
| 1246 | Z3 | L4 | Q37 |
| 1247 | Z3 | L4 | Q38 |
| 1248 | Z3 | L4 | Q39 |
| 1249 | Z3 | L5 | Q1 |
| 1250 | Z3 | L5 | Q2 |
| 1251 | Z3 | L5 | Q3 |
| 1252 | Z3 | L5 | Q4 |
| 1253 | Z3 | L5 | Q5 |
| 1254 | Z3 | L5 | Q6 |
| 1255 | Z3 | L5 | Q7 |
| 1256 | Z3 | L5 | Q8 |
| 1257 | Z3 | L5 | Q9 |
| 1258 | Z3 | L5 | Q10 |
| 1259 | Z3 | L5 | Q11 |
| 1260 | Z3 | L5 | Q12 |
| 1261 | Z3 | L5 | Q13 |
| 1262 | Z3 | L5 | Q14 |
| 1263 | Z3 | L5 | Q15 |
| 1264 | Z3 | L5 | Q16 |
| 1265 | Z3 | L5 | Q17 |
| 1266 | Z3 | L5 | Q18 |
| 1267 | Z3 | L5 | Q19 |
| 1268 | Z3 | L5 | Q20 |
| 1269 | Z3 | L5 | Q21 |
| 1270 | Z3 | L5 | Q22 |
| 1271 | Z3 | L5 | Q23 |
| 1272 | Z3 | L5 | Q24 |
| 1273 | Z3 | L5 | Q25 |
| 1274 | Z3 | L5 | Q26 |
| 1275 | Z3 | L5 | Q27 |
| 1276 | Z3 | L5 | Q28 |
| 1277 | Z3 | L5 | Q29 |
| 1278 | Z3 | L5 | Q30 |
| 1279 | Z3 | L5 | Q31 |
| 1280 | Z3 | L5 | Q32 |
| 1281 | Z3 | L5 | Q33 |
| 1282 | Z3 | L5 | Q34 |
| 1283 | Z3 | L5 | Q35 |
| 1284 | Z3 | L5 | Q36 |
| 1285 | Z3 | L5 | Q37 |
| 1286 | Z3 | L5 | Q38 |
| 1287 | Z3 | L5 | Q39 |
| 1288 | Z3 | L6 | Q1 |
| 1289 | Z3 | L6 | Q2 |
| 1290 | Z3 | L6 | Q3 |
| 1291 | Z3 | L6 | Q4 |
| 1292 | Z3 | L6 | Q5 |
| 1293 | Z3 | L6 | Q6 |
| 1294 | Z3 | L6 | Q7 |
| 1295 | Z3 | L6 | Q8 |
| 1296 | Z3 | L6 | Q9 |
| 1297 | Z3 | L6 | Q10 |
| 1298 | Z3 | L6 | Q11 |
| 1299 | Z3 | L6 | Q12 |
| 1300 | Z3 | L6 | Q13 |
| 1301 | Z3 | L6 | Q14 |
| 1302 | Z3 | L6 | Q15 |
| 1303 | Z3 | L6 | Q16 |
| 1304 | Z3 | L6 | Q17 |
| 1305 | Z3 | L6 | Q18 |
| 1306 | Z3 | L6 | Q19 |
| 1307 | Z3 | L6 | Q20 |
| 1308 | Z3 | L6 | Q21 |
| 1309 | Z3 | L6 | Q22 |
| 1310 | Z3 | L6 | Q23 |
| 1311 | Z3 | L6 | Q24 |
| 1312 | Z3 | L6 | Q25 |
| 1313 | Z3 | L6 | Q26 |
| 1314 | Z3 | L6 | Q27 |
| 1315 | Z3 | L6 | Q28 |
| 1316 | Z3 | L6 | Q29 |
| 1317 | Z3 | L6 | Q30 |
| 1318 | Z3 | L6 | Q31 |
| 1319 | Z3 | L6 | Q32 |
| 1320 | Z3 | L6 | Q33 |
| 1321 | Z3 | L6 | Q34 |
| 1322 | Z3 | L6 | Q35 |
| 1323 | Z3 | L6 | Q36 |
| 1324 | Z3 | L6 | Q37 |
| 1325 | Z3 | L6 | Q38 |
| 1326 | Z3 | L6 | Q39 |
| 1327 | Z3 | L7 | Q1 |
| 1328 | Z3 | L7 | Q2 |
| 1329 | Z3 | L7 | Q3 |
| 1330 | Z3 | L7 | Q4 |
| 1331 | Z3 | L7 | Q5 |
| 1332 | Z3 | L7 | Q6 |
| 1333 | Z3 | L7 | Q7 |
| 1334 | Z3 | L7 | Q8 |
| 1335 | Z3 | L7 | Q9 |
| 1336 | Z3 | L7 | Q10 |
| 1337 | Z3 | L7 | Q11 |
| 1338 | Z3 | L7 | Q12 |
| 1339 | Z3 | L7 | Q13 |
| 1340 | Z3 | L7 | Q14 |
| 1341 | Z3 | L7 | Q15 |
| 1342 | Z3 | L7 | Q16 |
| 1343 | Z3 | L7 | Q17 |
| 1344 | Z3 | L7 | Q18 |
| 1345 | Z3 | L7 | Q19 |
| 1346 | Z3 | L7 | Q20 |
| 1347 | Z3 | L7 | Q21 |
| 1348 | Z3 | L7 | Q22 |
| 1349 | Z3 | L7 | Q23 |

TABLE 1-11

| | | | |
|---|---|---|---|
| 1350 | Z3 | L7 | Q24 |
| 1351 | Z3 | L7 | Q25 |
| 1352 | Z3 | L7 | Q26 |
| 1353 | Z3 | L7 | Q27 |
| 1354 | Z3 | L7 | Q28 |
| 1355 | Z3 | L7 | Q29 |
| 1356 | Z3 | L7 | Q30 |
| 1357 | Z3 | L7 | Q31 |
| 1358 | Z3 | L7 | Q32 |
| 1359 | Z3 | L7 | Q33 |
| 1360 | Z3 | L7 | Q34 |
| 1361 | Z3 | L7 | Q35 |
| 1362 | Z3 | L7 | Q36 |

TABLE 1-11-continued

| | | | |
|---|---|---|---|
| 1363 | Z3 | L7 | Q37 |
| 1364 | Z3 | L7 | Q38 |
| 1365 | Z3 | L7 | Q39 |
| 1366 | Z3 | L8 | Q1 |
| 1367 | Z3 | L8 | Q2 |
| 1368 | Z3 | L8 | Q3 |
| 1369 | Z3 | L8 | Q4 |
| 1370 | Z3 | L8 | Q5 |
| 1371 | Z3 | L8 | Q6 |
| 1372 | Z3 | L8 | Q7 |
| 1373 | Z3 | L8 | Q8 |
| 1374 | Z3 | L8 | Q9 |
| 1375 | Z3 | L8 | Q10 |
| 1376 | Z3 | L8 | Q11 |
| 1377 | Z3 | L8 | Q12 |
| 1378 | Z3 | L8 | Q13 |
| 1379 | Z3 | L8 | Q14 |
| 1380 | Z3 | L8 | Q15 |
| 1381 | Z3 | L8 | Q16 |
| 1382 | Z3 | L8 | Q17 |
| 1383 | Z3 | L8 | Q18 |
| 1384 | Z3 | L8 | Q19 |
| 1385 | Z3 | L8 | Q20 |
| 1386 | Z3 | L8 | Q21 |
| 1387 | Z3 | L8 | Q22 |
| 1388 | Z3 | L8 | Q23 |
| 1389 | Z3 | L8 | Q24 |
| 1390 | Z3 | L8 | Q25 |
| 1391 | Z3 | L8 | Q26 |
| 1392 | Z3 | L8 | Q27 |
| 1393 | Z3 | L8 | Q28 |
| 1394 | Z3 | L8 | Q29 |
| 1395 | Z3 | L8 | Q30 |
| 1396 | Z3 | L8 | Q31 |
| 1397 | Z3 | L8 | Q32 |
| 1398 | Z3 | L8 | Q33 |
| 1399 | Z3 | L8 | Q34 |
| 1400 | Z3 | L8 | Q35 |
| 1401 | Z3 | L8 | Q36 |
| 1402 | Z3 | L8 | Q37 |
| 1403 | Z3 | L8 | Q38 |
| 1404 | Z3 | L8 | Q39 |
| 1405 | Z3 | L9 | Q1 |
| 1406 | Z3 | L9 | Q2 |
| 1407 | Z3 | L9 | Q3 |
| 1408 | Z3 | L9 | Q4 |
| 1409 | Z3 | L9 | Q5 |
| 1410 | Z3 | L9 | Q6 |
| 1411 | Z3 | L9 | Q7 |
| 1412 | Z3 | L9 | Q8 |
| 1413 | Z3 | L9 | Q9 |
| 1414 | Z3 | L9 | Q10 |
| 1415 | Z3 | L9 | Q11 |
| 1416 | Z3 | L9 | Q12 |
| 1417 | Z3 | L9 | Q13 |
| 1418 | Z3 | L9 | Q14 |
| 1419 | Z3 | L9 | Q15 |
| 1420 | Z3 | L9 | Q16 |
| 1421 | Z3 | L9 | Q17 |
| 1422 | Z3 | L9 | Q18 |
| 1423 | Z3 | L9 | Q19 |
| 1424 | Z3 | L9 | Q20 |
| 1425 | Z3 | L9 | Q21 |
| 1426 | Z3 | L9 | Q22 |
| 1427 | Z3 | L9 | Q23 |
| 1428 | Z3 | L9 | Q24 |
| 1429 | Z3 | L9 | Q25 |
| 1430 | Z3 | L9 | Q26 |
| 1431 | Z3 | L9 | Q27 |
| 1432 | Z3 | L9 | Q28 |
| 1433 | Z3 | L9 | Q29 |
| 1434 | Z3 | L9 | Q30 |
| 1435 | Z3 | L9 | Q31 |
| 1436 | Z3 | L9 | Q32 |
| 1437 | Z3 | L9 | Q33 |
| 1438 | Z3 | L9 | Q34 |
| 1439 | Z3 | L9 | Q35 |
| 1440 | Z3 | L9 | Q36 |
| 1441 | Z3 | L9 | Q37 |
| 1442 | Z3 | L9 | Q38 |
| 1443 | Z3 | L9 | Q39 |
| 1444 | Z3 | L10 | Q1 |
| 1445 | Z3 | L10 | Q2 |
| 1446 | Z3 | L10 | Q3 |
| 1447 | Z3 | L10 | Q4 |
| 1448 | Z3 | L10 | Q5 |
| 1449 | Z3 | L10 | Q6 |
| 1450 | Z3 | L10 | Q7 |
| 1451 | Z3 | L10 | Q8 |
| 1452 | Z3 | L10 | Q9 |
| 1453 | Z3 | L10 | Q10 |
| 1454 | Z3 | L10 | Q11 |
| 1455 | Z3 | L10 | Q12 |
| 1456 | Z3 | L10 | Q13 |
| 1457 | Z3 | L10 | Q14 |
| 1458 | Z3 | L10 | Q15 |
| 1459 | Z3 | L10 | Q16 |
| 1460 | Z3 | L10 | Q17 |
| 1461 | Z3 | L10 | Q18 |
| 1462 | Z3 | L10 | Q19 |
| 1463 | Z3 | L10 | Q20 |
| 1464 | Z3 | L10 | Q21 |
| 1465 | Z3 | L10 | Q22 |
| 1466 | Z3 | L10 | Q23 |
| 1467 | Z3 | L10 | Q24 |
| 1468 | Z3 | L10 | Q25 |
| 1469 | Z3 | L10 | Q26 |
| 1470 | Z3 | L10 | Q27 |
| 1471 | Z3 | L10 | Q28 |
| 1472 | Z3 | L10 | Q29 |
| 1473 | Z3 | L10 | Q30 |
| 1474 | Z3 | L10 | Q31 |
| 1475 | Z3 | L10 | Q32 |
| 1476 | Z3 | L10 | Q33 |
| 1477 | Z3 | L10 | Q34 |
| 1478 | Z3 | L10 | Q35 |
| 1479 | Z3 | L10 | Q36 |
| 1480 | Z3 | L10 | Q37 |
| 1481 | Z3 | L10 | Q38 |
| 1482 | Z3 | L10 | Q39 |
| 1483 | Z3 | L11 | Q1 |
| 1484 | Z3 | L11 | Q2 |
| 1485 | Z3 | L11 | Q3 |
| 1486 | Z3 | L11 | Q4 |
| 1487 | Z3 | L11 | Q5 |
| 1488 | Z3 | L11 | Q6 |
| 1489 | Z3 | L11 | Q7 |
| 1490 | Z3 | L11 | Q8 |

TABLE 1-12

| | | | |
|---|---|---|---|
| 1491 | Z3 | L11 | Q9 |
| 1492 | Z3 | L11 | Q10 |
| 1493 | Z3 | L11 | Q11 |
| 1494 | Z3 | L11 | Q12 |
| 1495 | Z3 | L11 | Q13 |
| 1496 | Z3 | L11 | Q14 |
| 1497 | Z3 | L11 | Q15 |
| 1498 | Z3 | L11 | Q16 |
| 1499 | Z3 | L11 | Q17 |
| 1500 | Z3 | L11 | Q18 |
| 1501 | Z3 | L11 | Q19 |
| 1502 | Z3 | L11 | Q20 |
| 1503 | Z3 | L11 | Q21 |
| 1504 | Z3 | L11 | Q22 |
| 1505 | Z3 | L11 | Q23 |
| 1506 | Z3 | L11 | Q24 |
| 1507 | Z3 | L11 | Q25 |
| 1508 | Z3 | L11 | Q26 |
| 1509 | Z3 | L11 | Q27 |
| 1510 | Z3 | L11 | Q28 |
| 1511 | Z3 | L11 | Q29 |
| 1512 | Z3 | L11 | Q30 |
| 1513 | Z3 | L11 | Q31 |
| 1514 | Z3 | L11 | Q32 |
| 1515 | Z3 | L11 | Q33 |
| 1516 | Z3 | L11 | Q34 |

TABLE 1-12-continued

| | | | |
|---|---|---|---|
| 1517 | Z3 | L11 | Q35 |
| 1518 | Z3 | L11 | Q36 |
| 1519 | Z3 | L11 | Q37 |
| 1520 | Z3 | L11 | Q38 |
| 1521 | Z3 | L11 | Q39 |
| 1522 | Z3 | L12 | Q1 |
| 1523 | Z3 | L12 | Q2 |
| 1524 | Z3 | L12 | Q3 |
| 1525 | Z3 | L12 | Q4 |
| 1526 | Z3 | L12 | Q5 |
| 1527 | Z3 | L12 | Q6 |
| 1528 | Z3 | L12 | Q7 |
| 1529 | Z3 | L12 | Q8 |
| 1530 | Z3 | L12 | Q9 |
| 1531 | Z3 | L12 | Q10 |
| 1532 | Z3 | L12 | Q11 |
| 1533 | Z3 | L12 | Q12 |
| 1534 | Z3 | L12 | Q13 |
| 1535 | Z3 | L12 | Q14 |
| 1536 | Z3 | L12 | Q15 |
| 1537 | Z3 | L12 | Q16 |
| 1538 | Z3 | L12 | Q17 |
| 1539 | Z3 | L12 | Q18 |
| 1540 | Z3 | L12 | Q19 |
| 1541 | Z3 | L12 | Q20 |
| 1542 | Z3 | L12 | Q21 |
| 1543 | Z3 | L12 | Q22 |
| 1544 | Z3 | L12 | Q23 |
| 1545 | Z3 | L12 | Q24 |
| 1546 | Z3 | L12 | Q25 |
| 1547 | Z3 | L12 | Q26 |
| 1548 | Z3 | L12 | Q27 |
| 1549 | Z3 | L12 | Q28 |
| 1550 | Z3 | L12 | Q29 |
| 1551 | Z3 | L12 | Q30 |
| 1552 | Z3 | L12 | Q31 |
| 1553 | Z3 | L12 | Q32 |
| 1554 | Z3 | L12 | Q33 |
| 1555 | Z3 | L12 | Q34 |
| 1556 | Z3 | L12 | Q35 |
| 1557 | Z3 | L12 | Q36 |
| 1558 | Z3 | L12 | Q37 |
| 1559 | Z3 | L12 | Q38 |
| 1560 | Z3 | L12 | Q39 |
| 1561 | Z3 | L13 | Q1 |
| 1562 | Z3 | L13 | Q2 |
| 1563 | Z3 | L13 | Q3 |
| 1564 | Z3 | L13 | Q4 |
| 1565 | Z3 | L13 | Q5 |
| 1566 | Z3 | L13 | Q6 |
| 1567 | Z3 | L13 | Q7 |
| 1568 | Z3 | L13 | Q8 |
| 1569 | Z3 | L13 | Q9 |
| 1570 | Z3 | L13 | Q10 |
| 1571 | Z3 | L13 | Q11 |
| 1572 | Z3 | L13 | Q12 |
| 1573 | Z3 | L13 | Q13 |
| 1574 | Z3 | L13 | Q14 |
| 1575 | Z3 | L13 | Q15 |
| 1576 | Z3 | L13 | Q16 |
| 1577 | Z3 | L13 | Q17 |
| 1578 | Z3 | L13 | Q18 |
| 1579 | Z3 | L13 | Q19 |
| 1580 | Z3 | L13 | Q20 |
| 1581 | Z3 | L13 | Q21 |
| 1582 | Z3 | L13 | Q22 |
| 1583 | Z3 | L13 | Q23 |
| 1584 | Z3 | L13 | Q24 |
| 1585 | Z3 | L13 | Q25 |
| 1586 | Z3 | L13 | Q26 |
| 1587 | Z3 | L13 | Q27 |
| 1588 | Z3 | L13 | Q28 |
| 1589 | Z3 | L13 | Q29 |
| 1590 | Z3 | L13 | Q30 |
| 1591 | Z3 | L13 | Q31 |
| 1592 | Z3 | L13 | Q32 |
| 1593 | Z3 | L13 | Q33 |
| 1594 | Z3 | L13 | Q34 |
| 1595 | Z3 | L13 | Q35 |
| 1596 | Z3 | L13 | Q36 |
| 1597 | Z3 | L13 | Q37 |
| 1598 | Z3 | L13 | Q38 |
| 1599 | Z3 | L13 | Q39 |
| 1600 | Z3 | L14 | Q1 |
| 1601 | Z3 | L14 | Q2 |
| 1602 | Z3 | L14 | Q3 |
| 1603 | Z3 | L14 | Q4 |
| 1604 | Z3 | L14 | Q5 |
| 1605 | Z3 | L14 | Q6 |
| 1606 | Z3 | L14 | Q7 |
| 1607 | Z3 | L14 | Q8 |
| 1608 | Z3 | L14 | Q9 |
| 1609 | Z3 | L14 | Q10 |
| 1610 | Z3 | L14 | Q11 |
| 1611 | Z3 | L14 | Q12 |
| 1612 | Z3 | L14 | Q13 |
| 1613 | Z3 | L14 | Q14 |
| 1614 | Z3 | L14 | Q15 |
| 1615 | Z3 | L14 | Q16 |
| 1616 | Z3 | L14 | Q17 |
| 1617 | Z3 | L14 | Q18 |
| 1618 | Z3 | L14 | Q19 |
| 1619 | Z3 | L14 | Q20 |
| 1620 | Z3 | L14 | Q21 |
| 1621 | Z3 | L14 | Q22 |
| 1622 | Z3 | L14 | Q23 |
| 1623 | Z3 | L14 | Q24 |
| 1624 | Z3 | L14 | Q25 |
| 1625 | Z3 | L14 | Q26 |
| 1626 | Z3 | L14 | Q27 |
| 1627 | Z3 | L14 | Q28 |
| 1628 | Z3 | L14 | Q29 |
| 1629 | Z3 | L14 | Q30 |
| 1630 | Z3 | L14 | Q31 |
| 1631 | Z3 | L14 | Q32 |

TABLE 1-13

| | | | |
|---|---|---|---|
| 1632 | Z3 | L14 | Q33 |
| 1633 | Z3 | L14 | Q34 |
| 1634 | Z3 | L14 | Q35 |
| 1635 | Z3 | L14 | Q36 |
| 1636 | Z3 | L14 | Q37 |
| 1637 | Z3 | L14 | Q38 |
| 1638 | Z3 | L14 | Q39 |
| 1639 | Z4 | L1 | Q1 |
| 1640 | Z4 | L1 | Q2 |
| 1641 | Z4 | L1 | Q3 |
| 1642 | Z4 | L1 | Q4 |
| 1643 | Z4 | L1 | Q5 |
| 1644 | Z4 | L1 | Q6 |
| 1645 | Z4 | L1 | Q7 |
| 1646 | Z4 | L1 | Q8 |
| 1647 | Z4 | L1 | Q9 |
| 1648 | Z4 | L1 | Q10 |
| 1649 | Z4 | L1 | Q11 |
| 1650 | Z4 | L1 | Q12 |
| 1651 | Z4 | L1 | Q13 |
| 1652 | Z4 | L1 | Q14 |
| 1653 | Z4 | L1 | Q15 |
| 1654 | Z4 | L1 | Q16 |
| 1655 | Z4 | L1 | Q17 |
| 1656 | Z4 | L1 | Q18 |
| 1657 | Z4 | L1 | Q19 |
| 1658 | Z4 | L1 | Q20 |
| 1659 | Z4 | L1 | Q21 |
| 1660 | Z4 | L1 | Q22 |
| 1661 | Z4 | L1 | Q23 |
| 1662 | Z4 | L1 | Q24 |
| 1663 | Z4 | L1 | Q25 |
| 1664 | Z4 | L1 | Q26 |
| 1665 | Z4 | L1 | Q27 |
| 1666 | Z4 | L1 | Q28 |
| 1667 | Z4 | L1 | Q29 |
| 1668 | Z4 | L1 | Q30 |
| 1669 | Z4 | L1 | Q31 |
| 1670 | Z4 | L1 | Q32 |

TABLE 1-13-continued

| | | | |
|---|---|---|---|
| 1671 | Z4 | L1 | Q33 |
| 1672 | Z4 | L1 | Q34 |
| 1673 | Z4 | L1 | Q35 |
| 1674 | Z4 | L1 | Q36 |
| 1675 | Z4 | L1 | Q37 |
| 1676 | Z4 | L1 | Q38 |
| 1677 | Z4 | L1 | Q39 |
| 1678 | Z4 | L2 | Q1 |
| 1679 | Z4 | L2 | Q2 |
| 1680 | Z4 | L2 | Q3 |
| 1681 | Z4 | L2 | Q4 |
| 1682 | Z4 | L2 | Q5 |
| 1683 | Z4 | L2 | Q6 |
| 1684 | Z4 | L2 | Q7 |
| 1685 | Z4 | L2 | Q8 |
| 1686 | Z4 | L2 | Q9 |
| 1687 | Z4 | L2 | Q10 |
| 1688 | Z4 | L2 | Q11 |
| 1689 | Z4 | L2 | Q12 |
| 1690 | Z4 | L2 | Q13 |
| 1691 | Z4 | L2 | Q14 |
| 1692 | Z4 | L2 | Q15 |
| 1693 | Z4 | L2 | Q16 |
| 1694 | Z4 | L2 | Q17 |
| 1695 | Z4 | L2 | Q18 |
| 1696 | Z4 | L2 | Q19 |
| 1697 | Z4 | L2 | Q20 |
| 1698 | Z4 | L2 | Q21 |
| 1699 | Z4 | L2 | Q22 |
| 1700 | Z4 | L2 | Q23 |
| 1701 | Z4 | L2 | Q24 |
| 1702 | Z4 | L2 | Q25 |
| 1703 | Z4 | L2 | Q26 |
| 1704 | Z4 | L2 | Q27 |
| 1705 | Z4 | L2 | Q28 |
| 1706 | Z4 | L2 | Q29 |
| 1707 | Z4 | L2 | Q30 |
| 1708 | Z4 | L2 | Q31 |
| 1709 | Z4 | L2 | Q32 |
| 1710 | Z4 | L2 | Q33 |
| 1711 | Z4 | L2 | Q34 |
| 1712 | Z4 | L2 | Q35 |
| 1713 | Z4 | L2 | Q36 |
| 1714 | Z4 | L2 | Q37 |
| 1715 | Z4 | L2 | Q38 |
| 1716 | Z4 | L2 | Q39 |
| 1717 | Z4 | L3 | Q1 |
| 1718 | Z4 | L3 | Q2 |
| 1719 | Z4 | L3 | Q3 |
| 1720 | Z4 | L3 | Q4 |
| 1721 | Z4 | L3 | Q5 |
| 1722 | Z4 | L3 | Q6 |
| 1723 | Z4 | L3 | Q7 |
| 1724 | Z4 | L3 | Q8 |
| 1725 | Z4 | L3 | Q9 |
| 1726 | Z4 | L3 | Q10 |
| 1727 | Z4 | L3 | Q11 |
| 1728 | Z4 | L3 | Q12 |
| 1729 | Z4 | L3 | Q13 |
| 1730 | Z4 | L3 | Q14 |
| 1731 | Z4 | L3 | Q15 |
| 1732 | Z4 | L3 | Q16 |
| 1733 | Z4 | L3 | Q17 |
| 1734 | Z4 | L3 | Q18 |
| 1735 | Z4 | L3 | Q19 |
| 1736 | Z4 | L3 | Q20 |
| 1737 | Z4 | L3 | Q21 |
| 1738 | Z4 | L3 | Q22 |
| 1739 | Z4 | L3 | Q23 |
| 1740 | Z4 | L3 | Q24 |
| 1741 | Z4 | L3 | Q25 |
| 1742 | Z4 | L3 | Q26 |
| 1743 | Z4 | L3 | Q27 |
| 1744 | Z4 | L3 | Q28 |
| 1745 | Z4 | L3 | Q29 |
| 1746 | Z4 | L3 | Q30 |
| 1747 | Z4 | L3 | Q31 |
| 1748 | Z4 | L3 | Q32 |
| 1749 | Z4 | L3 | Q33 |
| 1750 | Z4 | L3 | Q34 |
| 1751 | Z4 | L3 | Q35 |
| 1752 | Z4 | L3 | Q36 |
| 1753 | Z4 | L3 | Q37 |
| 1754 | Z4 | L3 | Q38 |
| 1755 | Z4 | L3 | Q39 |
| 1756 | Z4 | L4 | Q1 |
| 1757 | Z4 | L4 | Q2 |
| 1758 | Z4 | L4 | Q3 |
| 1759 | Z4 | L4 | Q4 |
| 1760 | Z4 | L4 | Q5 |
| 1761 | Z4 | L4 | Q6 |
| 1762 | Z4 | L4 | Q7 |
| 1763 | Z4 | L4 | Q8 |
| 1764 | Z4 | L4 | Q9 |
| 1765 | Z4 | L4 | Q10 |
| 1766 | Z4 | L4 | Q11 |
| 1767 | Z4 | L4 | Q12 |
| 1768 | Z4 | L4 | Q13 |
| 1769 | Z4 | L4 | Q14 |
| 1770 | Z4 | L4 | Q15 |
| 1771 | Z4 | L4 | Q16 |
| 1772 | Z4 | L4 | Q17 |

TABLE 1-14

| | | | |
|---|---|---|---|
| 1773 | Z4 | L4 | Q18 |
| 1774 | Z4 | L4 | Q19 |
| 1775 | Z4 | L4 | Q20 |
| 1776 | Z4 | L4 | Q21 |
| 1777 | Z4 | L4 | Q22 |
| 1778 | Z4 | L4 | Q23 |
| 1779 | Z4 | L4 | Q24 |
| 1780 | Z4 | L4 | Q25 |
| 1781 | Z4 | L4 | Q26 |
| 1782 | Z4 | L4 | Q27 |
| 1783 | Z4 | L4 | Q28 |
| 1784 | Z4 | L4 | Q29 |
| 1785 | Z4 | L4 | Q30 |
| 1786 | Z4 | L4 | Q31 |
| 1787 | Z4 | L4 | Q32 |
| 1788 | Z4 | L4 | Q33 |
| 1789 | Z4 | L4 | Q34 |
| 1790 | Z4 | L4 | Q35 |
| 1791 | Z4 | L4 | Q36 |
| 1792 | Z4 | L4 | Q37 |
| 1793 | Z4 | L4 | Q38 |
| 1794 | Z4 | L4 | Q39 |
| 1795 | Z4 | L5 | Q1 |
| 1796 | Z4 | L5 | Q2 |
| 1797 | Z4 | L5 | Q3 |
| 1798 | Z4 | L5 | Q4 |
| 1799 | Z4 | L5 | Q5 |
| 1800 | Z4 | L5 | Q6 |
| 1801 | Z4 | L5 | Q7 |
| 1802 | Z4 | L5 | Q8 |
| 1803 | Z4 | L5 | Q9 |
| 1804 | Z4 | L5 | Q10 |
| 1805 | Z4 | L5 | Q11 |
| 1806 | Z4 | L5 | Q12 |
| 1807 | Z4 | L5 | Q13 |
| 1808 | Z4 | L5 | Q14 |
| 1809 | Z4 | L5 | Q15 |
| 1810 | Z4 | L5 | Q16 |
| 1811 | Z4 | L5 | Q17 |
| 1812 | Z4 | L5 | Q18 |
| 1813 | Z4 | L5 | Q19 |
| 1814 | Z4 | L5 | Q20 |
| 1815 | Z4 | L5 | Q21 |
| 1816 | Z4 | L5 | Q22 |
| 1817 | Z4 | L5 | Q23 |
| 1818 | Z4 | L5 | Q24 |
| 1819 | Z4 | L5 | Q25 |
| 1820 | Z4 | L5 | Q26 |
| 1821 | Z4 | L5 | Q27 |
| 1822 | Z4 | L5 | Q28 |
| 1823 | Z4 | L5 | Q29 |
| 1824 | Z4 | L5 | Q30 |

TABLE 1-14-continued

| | | | |
|---|---|---|---|
| 1825 | Z4 | L5 | Q31 |
| 1826 | Z4 | L5 | Q32 |
| 1827 | Z4 | L5 | Q33 |
| 1828 | Z4 | L5 | Q34 |
| 1829 | Z4 | L5 | Q35 |
| 1830 | Z4 | L5 | Q36 |
| 1831 | Z4 | L5 | Q37 |
| 1832 | Z4 | L5 | Q38 |
| 1833 | Z4 | L5 | Q39 |
| 1834 | Z4 | L6 | Q1 |
| 1835 | Z4 | L6 | Q2 |
| 1836 | Z4 | L6 | Q3 |
| 1837 | Z4 | L6 | Q4 |
| 1838 | Z4 | L6 | Q5 |
| 1839 | Z4 | L6 | Q6 |
| 1840 | Z4 | L6 | Q7 |
| 1841 | Z4 | L6 | Q8 |
| 1842 | Z4 | L6 | Q9 |
| 1843 | Z4 | L6 | Q10 |
| 1844 | Z4 | L6 | Q11 |
| 1845 | Z4 | L6 | Q12 |
| 1846 | Z4 | L6 | Q13 |
| 1847 | Z4 | L6 | Q14 |
| 1848 | Z4 | L6 | Q15 |
| 1849 | Z4 | L6 | Q16 |
| 1850 | Z4 | L6 | Q17 |
| 1851 | Z4 | L6 | Q18 |
| 1852 | Z4 | L6 | Q19 |
| 1853 | Z4 | L6 | Q20 |
| 1854 | Z4 | L6 | Q21 |
| 1855 | Z4 | L6 | Q22 |
| 1856 | Z4 | L6 | Q23 |
| 1857 | Z4 | L6 | Q24 |
| 1858 | Z4 | L6 | Q25 |
| 1859 | Z4 | L6 | Q26 |
| 1860 | Z4 | L6 | Q27 |
| 1861 | Z4 | L6 | Q28 |
| 1862 | Z4 | L6 | Q29 |
| 1863 | Z4 | L6 | Q30 |
| 1864 | Z4 | L6 | Q31 |
| 1865 | Z4 | L6 | Q32 |
| 1866 | Z4 | L6 | Q33 |
| 1867 | Z4 | L6 | Q34 |
| 1868 | Z4 | L6 | Q35 |
| 1869 | Z4 | L6 | Q36 |
| 1870 | Z4 | L6 | Q37 |
| 1871 | Z4 | L6 | Q38 |
| 1872 | Z4 | L6 | Q39 |
| 1873 | Z4 | L7 | Q1 |
| 1874 | Z4 | L7 | Q2 |
| 1875 | Z4 | L7 | Q3 |
| 1876 | Z4 | L7 | Q4 |
| 1877 | Z4 | L7 | Q5 |
| 1878 | Z4 | L7 | Q6 |
| 1879 | Z4 | L7 | Q7 |
| 1880 | Z4 | L7 | Q8 |
| 1881 | Z4 | L7 | Q9 |
| 1882 | Z4 | L7 | Q10 |
| 1883 | Z4 | L7 | Q11 |
| 1884 | Z4 | L7 | Q12 |
| 1885 | Z4 | L7 | Q13 |
| 1886 | Z4 | L7 | Q14 |
| 1887 | Z4 | L7 | Q15 |
| 1888 | Z4 | L7 | Q16 |
| 1889 | Z4 | L7 | Q17 |
| 1890 | Z4 | L7 | Q18 |
| 1891 | Z4 | L7 | Q19 |
| 1892 | Z4 | L7 | Q20 |
| 1893 | Z4 | L7 | Q21 |
| 1894 | Z4 | L7 | Q22 |
| 1895 | Z4 | L7 | Q23 |
| 1896 | Z4 | L7 | Q24 |
| 1897 | Z4 | L7 | Q25 |
| 1898 | Z4 | L7 | Q26 |
| 1899 | Z4 | L7 | Q27 |
| 1900 | Z4 | L7 | Q28 |
| 1901 | Z4 | L7 | Q29 |
| 1902 | Z4 | L7 | Q30 |
| 1903 | Z4 | L7 | Q31 |
| 1904 | Z4 | L7 | Q32 |
| 1905 | Z4 | L7 | Q33 |
| 1906 | Z4 | L7 | Q34 |
| 1907 | Z4 | L7 | Q35 |
| 1908 | Z4 | L7 | Q36 |
| 1909 | Z4 | L7 | Q37 |
| 1910 | Z4 | L7 | Q38 |
| 1911 | Z4 | L7 | Q39 |
| 1912 | Z4 | L8 | Q1 |
| 1913 | Z4 | L8 | Q2 |

TABLE 1-15

| | | | |
|---|---|---|---|
| 1914 | Z4 | L8 | Q3 |
| 1915 | Z4 | L8 | Q4 |
| 1916 | Z4 | L8 | Q5 |
| 1917 | Z4 | L8 | Q6 |
| 1918 | Z4 | L8 | Q7 |
| 1919 | Z4 | L8 | Q8 |
| 1920 | Z4 | L8 | Q9 |
| 1921 | Z4 | L8 | Q10 |
| 1922 | Z4 | L8 | Q11 |
| 1923 | Z4 | L8 | Q12 |
| 1924 | Z4 | L8 | Q13 |
| 1925 | Z4 | L8 | Q14 |
| 1926 | Z4 | L8 | Q15 |
| 1927 | Z4 | L8 | Q16 |
| 1928 | Z4 | L8 | Q17 |
| 1929 | Z4 | L8 | Q18 |
| 1930 | Z4 | L8 | Q19 |
| 1931 | Z4 | L8 | Q20 |
| 1932 | Z4 | L8 | Q21 |
| 1933 | Z4 | L8 | Q22 |
| 1934 | Z4 | L8 | Q23 |
| 1935 | Z4 | L8 | Q24 |
| 1936 | Z4 | L8 | Q25 |
| 1937 | Z4 | L8 | Q26 |
| 1938 | Z4 | L8 | Q27 |
| 1939 | Z4 | L8 | Q28 |
| 1940 | Z4 | L8 | Q29 |
| 1941 | Z4 | L8 | Q30 |
| 1942 | Z4 | L8 | Q31 |
| 1943 | Z4 | L8 | Q32 |
| 1944 | Z4 | L8 | Q33 |
| 1945 | Z4 | L8 | Q34 |
| 1946 | Z4 | L8 | Q35 |
| 1947 | Z4 | L8 | Q36 |
| 1948 | Z4 | L8 | Q37 |
| 1949 | Z4 | L8 | Q38 |
| 1950 | Z4 | L8 | Q39 |
| 1951 | Z4 | L9 | Q1 |
| 1952 | Z4 | L9 | Q2 |
| 1953 | Z4 | L9 | Q3 |
| 1954 | Z4 | L9 | Q4 |
| 1955 | Z4 | L9 | Q5 |
| 1956 | Z4 | L9 | Q6 |
| 1957 | Z4 | L9 | Q7 |
| 1958 | Z4 | L9 | Q8 |
| 1959 | Z4 | L9 | Q9 |
| 1960 | Z4 | L9 | Q10 |
| 1961 | Z4 | L9 | Q11 |
| 1962 | Z4 | L9 | Q12 |
| 1963 | Z4 | L9 | Q13 |
| 1964 | Z4 | L9 | Q14 |
| 1965 | Z4 | L9 | Q15 |
| 1966 | Z4 | L9 | Q16 |
| 1967 | Z4 | L9 | Q17 |
| 1968 | Z4 | L9 | Q18 |
| 1969 | Z4 | L9 | Q19 |
| 1970 | Z4 | L9 | Q20 |
| 1971 | Z4 | L9 | Q21 |
| 1972 | Z4 | L9 | Q22 |
| 1973 | Z4 | L9 | Q23 |
| 1974 | Z4 | L9 | Q24 |
| 1975 | Z4 | L9 | Q25 |
| 1976 | Z4 | L9 | Q26 |
| 1977 | Z4 | L9 | Q27 |
| 1978 | Z4 | L9 | Q28 |

TABLE 1-15-continued

| | | | |
|---|---|---|---|
| 1979 | Z4 | L9 | Q29 |
| 1980 | Z4 | L9 | Q30 |
| 1981 | Z4 | L9 | Q31 |
| 1982 | Z4 | L9 | Q32 |
| 1983 | Z4 | L9 | Q33 |
| 1984 | Z4 | L9 | Q34 |
| 1985 | Z4 | L9 | Q35 |
| 1986 | Z4 | L9 | Q36 |
| 1987 | Z4 | L9 | Q37 |
| 1988 | Z4 | L9 | Q38 |
| 1989 | Z4 | L9 | Q39 |
| 1990 | Z4 | L10 | Q1 |
| 1991 | Z4 | L10 | Q2 |
| 1992 | Z4 | L10 | Q3 |
| 1993 | Z4 | L10 | Q4 |
| 1994 | Z4 | L10 | Q5 |
| 1995 | Z4 | L10 | Q6 |
| 1996 | Z4 | L10 | Q7 |
| 1997 | Z4 | L10 | Q8 |
| 1998 | Z4 | L10 | Q9 |
| 1999 | Z4 | L10 | Q10 |
| 2000 | Z4 | L10 | Q11 |
| 2001 | Z4 | L10 | Q12 |
| 2002 | Z4 | L10 | Q13 |
| 2003 | Z4 | L10 | Q14 |
| 2004 | Z4 | L10 | Q15 |
| 2005 | Z4 | L10 | Q16 |
| 2006 | Z4 | L10 | Q17 |
| 2007 | Z4 | L10 | Q18 |
| 2008 | Z4 | L10 | Q19 |
| 2009 | Z4 | L10 | Q20 |
| 2010 | Z4 | L10 | Q21 |
| 2011 | Z4 | L10 | Q22 |
| 2012 | Z4 | L10 | Q23 |
| 2013 | Z4 | L10 | Q24 |
| 2014 | Z4 | L10 | Q25 |
| 2015 | Z4 | L10 | Q26 |
| 2016 | Z4 | L10 | Q27 |
| 2017 | Z4 | L10 | Q28 |
| 2018 | Z4 | L10 | Q29 |
| 2019 | Z4 | L10 | Q30 |
| 2020 | Z4 | L10 | Q31 |
| 2021 | Z4 | L10 | Q32 |
| 2022 | Z4 | L10 | Q33 |
| 2023 | Z4 | L10 | Q34 |
| 2024 | Z4 | L10 | Q35 |
| 2025 | Z4 | L10 | Q36 |
| 2026 | Z4 | L10 | Q37 |
| 2027 | Z4 | L10 | Q38 |
| 2028 | Z4 | L10 | Q39 |
| 2029 | Z4 | L11 | Q1 |
| 2030 | Z4 | L11 | Q2 |
| 2031 | Z4 | L11 | Q3 |
| 2032 | Z4 | L11 | Q4 |
| 2033 | Z4 | L11 | Q5 |
| 2034 | Z4 | L11 | Q6 |
| 2035 | Z4 | L11 | Q7 |
| 2036 | Z4 | L11 | Q8 |
| 2037 | Z4 | L11 | Q9 |
| 2038 | Z4 | L11 | Q10 |
| 2039 | Z4 | L11 | Q11 |
| 2040 | Z4 | L11 | Q12 |
| 2041 | Z4 | L11 | Q13 |
| 2042 | Z4 | L11 | Q14 |
| 2043 | Z4 | L11 | Q15 |
| 2044 | Z4 | L11 | Q16 |
| 2045 | Z4 | L11 | Q17 |
| 2046 | Z4 | L11 | Q18 |
| 2047 | Z4 | L11 | Q19 |
| 2048 | Z4 | L11 | Q20 |
| 2049 | Z4 | L11 | Q21 |
| 2050 | Z4 | L11 | Q22 |
| 2051 | Z4 | L11 | Q23 |
| 2052 | Z4 | L11 | Q24 |
| 2053 | Z4 | L11 | Q25 |
| 2054 | Z4 | L11 | Q26 |

TABLE 1-16

| | | | |
|---|---|---|---|
| 2055 | Z4 | L11 | Q27 |
| 2056 | Z4 | L11 | Q28 |
| 2057 | Z4 | L11 | Q29 |
| 2058 | Z4 | L11 | Q30 |
| 2059 | Z4 | L11 | Q31 |
| 2060 | Z4 | L11 | Q32 |
| 2061 | Z4 | L11 | Q33 |
| 2062 | Z4 | L11 | Q34 |
| 2063 | Z4 | L11 | Q35 |
| 2064 | Z4 | L11 | Q36 |
| 2065 | Z4 | L11 | Q37 |
| 2066 | Z4 | L11 | Q38 |
| 2067 | Z4 | L11 | Q39 |
| 2068 | Z4 | L12 | Q1 |
| 2069 | Z4 | L12 | Q2 |
| 2070 | Z4 | L12 | Q3 |
| 2071 | Z4 | L12 | Q4 |
| 2072 | Z4 | L12 | Q5 |
| 2073 | Z4 | L12 | Q6 |
| 2074 | Z4 | L12 | Q7 |
| 2075 | Z4 | L12 | Q8 |
| 2076 | Z4 | L12 | Q9 |
| 2077 | Z4 | L12 | Q10 |
| 2078 | Z4 | L12 | Q11 |
| 2079 | Z4 | L12 | Q12 |
| 2080 | Z4 | L12 | Q13 |
| 2081 | Z4 | L12 | Q14 |
| 2082 | Z4 | L12 | Q15 |
| 2083 | Z4 | L12 | Q16 |
| 2084 | Z4 | L12 | Q17 |
| 2085 | Z4 | L12 | Q18 |
| 2086 | Z4 | L12 | Q19 |
| 2087 | Z4 | L12 | Q20 |
| 2088 | Z4 | L12 | Q21 |
| 2089 | Z4 | L12 | Q22 |
| 2090 | Z4 | L12 | Q23 |
| 2091 | Z4 | L12 | Q24 |
| 2092 | Z4 | L12 | Q25 |
| 2093 | Z4 | L12 | Q26 |
| 2094 | Z4 | L12 | Q27 |
| 2095 | Z4 | L12 | Q28 |
| 2096 | Z4 | L12 | Q29 |
| 2097 | Z4 | L12 | Q30 |
| 2098 | Z4 | L12 | Q31 |
| 2099 | Z4 | L12 | Q32 |
| 2100 | Z4 | L12 | Q33 |
| 2101 | Z4 | L12 | Q34 |
| 2102 | Z4 | L12 | Q35 |
| 2103 | Z4 | L12 | Q36 |
| 2104 | Z4 | L12 | Q37 |
| 2105 | Z4 | L12 | Q38 |
| 2106 | Z4 | L12 | Q39 |
| 2107 | Z4 | L13 | Q1 |
| 2108 | Z4 | L13 | Q2 |
| 2109 | Z4 | L13 | Q3 |
| 2110 | Z4 | L13 | Q4 |
| 2111 | Z4 | L13 | Q5 |
| 2112 | Z4 | L13 | Q6 |
| 2113 | Z4 | L13 | Q7 |
| 2114 | Z4 | L13 | Q8 |
| 2115 | Z4 | L13 | Q9 |
| 2116 | Z4 | L13 | Q10 |
| 2117 | Z4 | L13 | Q11 |
| 2118 | Z4 | L13 | Q12 |
| 2119 | Z4 | L13 | Q13 |
| 2120 | Z4 | L13 | Q14 |
| 2121 | Z4 | L13 | Q15 |
| 2122 | Z4 | L13 | Q16 |
| 2123 | Z4 | L13 | Q17 |
| 2124 | Z4 | L13 | Q18 |
| 2125 | Z4 | L13 | Q19 |
| 2126 | Z4 | L13 | Q20 |
| 2127 | Z4 | L13 | Q21 |
| 2128 | Z4 | L13 | Q22 |
| 2129 | Z4 | L13 | Q23 |
| 2130 | Z4 | L13 | Q24 |
| 2131 | Z4 | L13 | Q25 |
| 2132 | Z4 | L13 | Q26 |
| 2133 | Z4 | L13 | Q27 |
| 2134 | Z4 | L13 | Q28 |

TABLE 1-16-continued

| | | | |
|---|---|---|---|
| 2135 | Z4 | L13 | Q29 |
| 2136 | Z4 | L13 | Q30 |
| 2137 | Z4 | L13 | Q31 |
| 2138 | Z4 | L13 | Q32 |
| 2139 | Z4 | L13 | Q33 |
| 2140 | Z4 | L13 | Q34 |
| 2141 | Z4 | L13 | Q35 |
| 2142 | Z4 | L13 | Q36 |
| 2143 | Z4 | L13 | Q37 |
| 2144 | Z4 | L13 | Q38 |
| 2145 | Z4 | L13 | Q39 |
| 2146 | Z4 | L14 | Q1 |
| 2147 | Z4 | L14 | Q2 |
| 2148 | Z4 | L14 | Q3 |
| 2149 | Z4 | L14 | Q4 |
| 2150 | Z4 | L14 | Q5 |
| 2151 | Z4 | L14 | Q6 |
| 2152 | Z4 | L14 | Q7 |
| 2153 | Z4 | L14 | Q8 |
| 2154 | Z4 | L14 | Q9 |
| 2155 | Z4 | L14 | Q10 |
| 2156 | Z4 | L14 | Q11 |
| 2157 | Z4 | L14 | Q12 |
| 2158 | Z4 | L14 | Q13 |
| 2159 | Z4 | L14 | Q14 |
| 2160 | Z4 | L14 | Q15 |
| 2161 | Z4 | L14 | Q16 |
| 2162 | Z4 | L14 | Q17 |
| 2163 | Z4 | L14 | Q18 |
| 2164 | Z4 | L14 | Q19 |
| 2165 | Z4 | L14 | Q20 |
| 2166 | Z4 | L14 | Q21 |
| 2167 | Z4 | L14 | Q22 |
| 2168 | Z4 | L14 | Q23 |
| 2169 | Z4 | L14 | Q24 |
| 2170 | Z4 | L14 | Q25 |
| 2171 | Z4 | L14 | Q26 |
| 2172 | Z4 | L14 | Q27 |
| 2173 | Z4 | L14 | Q28 |
| 2174 | Z4 | L14 | Q29 |
| 2175 | Z4 | L14 | Q30 |
| 2176 | Z4 | L14 | Q31 |
| 2177 | Z4 | L14 | Q32 |
| 2178 | Z4 | L14 | Q33 |
| 2179 | Z4 | L14 | Q34 |
| 2180 | Z4 | L14 | Q35 |
| 2181 | Z4 | L14 | Q36 |
| 2182 | Z4 | L14 | Q37 |
| 2183 | Z4 | L14 | Q38 |
| 2184 | Z4 | L14 | Q39 |

TABLE 1-17

| Example | $R^{ZL}$ | $L^a$ | $Q^a$ |
|---|---|---|---|
| 2185 | Z1 | L1 | Q40 |
| 2186 | Z1 | L1 | Q41 |
| 2187 | Z1 | L1 | Q42 |
| 2188 | Z1 | L1 | Q43 |
| 2189 | Z1 | L1 | Q44 |
| 2190 | Z1 | L1 | Q45 |
| 2191 | Z1 | L1 | Q46 |
| 2192 | Z1 | L1 | Q47 |
| 2193 | Z1 | L1 | Q48 |
| 2194 | Z1 | L1 | Q49 |
| 2195 | Z1 | L1 | Q50 |
| 2196 | Z1 | L1 | Q51 |
| 2197 | Z1 | L1 | Q52 |
| 2198 | Z1 | L1 | Q53 |
| 2199 | Z1 | L1 | Q54 |
| 2200 | Z1 | L1 | Q55 |
| 2201 | Z1 | L1 | Q56 |
| 2202 | Z1 | L1 | Q57 |
| 2203 | Z1 | L1 | Q58 |
| 2204 | Z1 | L1 | Q59 |
| 2205 | Z1 | L1 | Q60 |
| 2206 | Z1 | L1 | Q61 |

TABLE 1-17-continued

| Example | $R^{ZL}$ | $L^a$ | $Q^a$ |
|---|---|---|---|
| 2207 | Z1 | L1 | Q62 |
| 2208 | Z1 | L1 | Q63 |
| 2209 | Z1 | L1 | Q64 |
| 2210 | Z1 | L1 | Q65 |
| 2211 | Z1 | L1 | Q66 |
| 2212 | Z1 | L1 | Q67 |
| 2213 | Z1 | L1 | Q68 |
| 2214 | Z1 | L1 | Q69 |
| 2215 | Z1 | L1 | Q70 |
| 2216 | Z1 | L1 | Q71 |
| 2217 | Z1 | L1 | Q72 |
| 2218 | Z1 | L1 | Q73 |
| 2219 | Z1 | L1 | Q74 |
| 2220 | Z1 | L1 | Q75 |
| 2221 | Z1 | L1 | Q76 |
| 2222 | Z1 | L1 | Q77 |
| 2223 | Z1 | L1 | Q78 |
| 2224 | Z1 | L1 | Q79 |
| 2225 | Z1 | L1 | Q80 |
| 2226 | Z1 | L1 | Q81 |
| 2227 | Z1 | L1 | Q82 |
| 2228 | Z1 | L1 | Q83 |
| 2229 | Z1 | L1 | Q84 |
| 2230 | Z1 | L1 | Q85 |
| 2231 | Z1 | L1 | Q86 |
| 2232 | Z1 | L1 | Q87 |
| 2233 | Z1 | L1 | Q88 |
| 2234 | Z1 | L1 | Q89 |
| 2235 | Z1 | L1 | Q90 |
| 2236 | Z1 | L1 | Q91 |
| 2237 | Z1 | L1 | Q92 |
| 2238 | Z1 | L1 | Q93 |
| 2239 | Z1 | L1 | Q94 |
| 2240 | Z1 | L1 | Q95 |
| 2241 | Z1 | L1 | Q96 |
| 2242 | Z1 | L1 | Q97 |
| 2243 | Z1 | L1 | Q98 |
| 2244 | Z1 | L1 | Q99 |
| 2245 | Z1 | L1 | Q100 |
| 2246 | Z1 | L1 | Q101 |
| 2247 | Z1 | L1 | Q102 |
| 2248 | Z1 | L1 | Q103 |
| 2249 | Z1 | L2 | Q40 |
| 2250 | Z1 | L2 | Q41 |
| 2251 | Z1 | L2 | Q42 |
| 2252 | Z1 | L2 | Q43 |
| 2253 | Z1 | L2 | Q44 |
| 2254 | Z1 | L2 | Q45 |
| 2255 | Z1 | L2 | Q46 |
| 2256 | Z1 | L2 | Q47 |
| 2257 | Z1 | L2 | Q48 |
| 2258 | Z1 | L2 | Q49 |
| 2259 | Z1 | L2 | Q50 |
| 2260 | Z1 | L2 | Q51 |
| 2261 | Z1 | L2 | Q52 |
| 2262 | Z1 | L2 | Q53 |
| 2263 | Z1 | L2 | Q54 |
| 2264 | Z1 | L2 | Q55 |
| 2265 | Z1 | L2 | Q56 |
| 2266 | Z1 | L2 | Q57 |
| 2267 | Z1 | L2 | Q58 |
| 2268 | Z1 | L2 | Q59 |
| 2269 | Z1 | L2 | Q60 |
| 2270 | Z1 | L2 | Q61 |
| 2271 | Z1 | L2 | Q62 |
| 2272 | Z1 | L2 | Q63 |
| 2273 | Z1 | L2 | Q64 |
| 2274 | Z1 | L2 | Q65 |
| 2275 | Z1 | L2 | Q66 |
| 2276 | Z1 | L2 | Q67 |
| 2277 | Z1 | L2 | Q68 |
| 2278 | Z1 | L2 | Q69 |
| 2279 | Z1 | L2 | Q70 |
| 2280 | Z1 | L2 | Q71 |
| 2281 | Z1 | L2 | Q72 |
| 2282 | Z1 | L2 | Q73 |
| 2283 | Z1 | L2 | Q74 |
| 2284 | Z1 | L2 | Q75 |

TABLE 1-17-continued

| Example | R$^{ZL}$ | L$^a$ | Q$^a$ |
|---|---|---|---|
| 2285 | Z1 | L2 | Q76 |
| 2286 | Z1 | L2 | Q77 |
| 2287 | Z1 | L2 | Q78 |
| 2288 | Z1 | L2 | Q79 |
| 2289 | Z1 | L2 | Q80 |
| 2290 | Z1 | L2 | Q81 |
| 2291 | Z1 | L2 | Q82 |
| 2292 | Z1 | L2 | Q83 |
| 2293 | Z1 | L2 | Q84 |
| 2294 | Z1 | L2 | Q85 |
| 2295 | Z1 | L2 | Q86 |
| 2296 | Z1 | L2 | Q87 |
| 2297 | Z1 | L2 | Q88 |
| 2298 | Z1 | L2 | Q89 |
| 2299 | Z1 | L2 | Q90 |
| 2300 | Z1 | L2 | Q91 |
| 2301 | Z1 | L2 | Q92 |
| 2302 | Z1 | L2 | Q93 |
| 2303 | Z1 | L2 | Q94 |
| 2304 | Z1 | L2 | Q95 |
| 2305 | Z1 | L2 | Q96 |
| 2306 | Z1 | L2 | Q97 |
| 2307 | Z1 | L2 | Q98 |
| 2308 | Z1 | L2 | Q99 |
| 2309 | Z1 | L2 | Q100 |
| 2310 | Z1 | L2 | Q101 |
| 2311 | Z1 | L2 | Q102 |
| 2312 | Z1 | L2 | Q103 |
| 2313 | Z1 | L3 | Q40 |
| 2314 | Z1 | L3 | Q41 |
| 2315 | Z1 | L3 | Q42 |
| 2316 | Z1 | L3 | Q43 |
| 2317 | Z1 | L3 | Q44 |
| 2318 | Z1 | L3 | Q45 |
| 2319 | Z1 | L3 | Q46 |
| 2320 | Z1 | L3 | Q47 |
| 2321 | Z1 | L3 | Q48 |
| 2322 | Z1 | L3 | Q49 |
| 2323 | Z1 | L3 | Q50 |
| 2324 | Z1 | L3 | Q51 |
| 2325 | Z1 | L3 | Q52 |
| 2326 | Z1 | L3 | Q53 |
| 2327 | Z1 | L3 | Q54 |
| 2328 | Z1 | L3 | Q55 |
| 2329 | Z1 | L3 | Q56 |
| 2330 | Z1 | L3 | Q57 |
| 2331 | Z1 | L3 | Q58 |
| 2332 | Z1 | L3 | Q59 |
| 2333 | Z1 | L3 | Q60 |
| 2334 | Z1 | L3 | Q61 |
| 2335 | Z1 | L3 | Q62 |
| 2336 | Z1 | L3 | Q63 |
| 2337 | Z1 | L3 | Q64 |
| 2338 | Z1 | L3 | Q65 |
| 2339 | Z1 | L3 | Q66 |
| 2340 | Z1 | L3 | Q67 |
| 2341 | Z1 | L3 | Q68 |
| 2342 | Z1 | L3 | Q69 |
| 2343 | Z1 | L3 | Q70 |
| 2344 | Z1 | L3 | Q71 |
| 2345 | Z1 | L3 | Q72 |
| 2346 | Z1 | L3 | Q73 |
| 2347 | Z1 | L3 | Q74 |
| 2348 | Z1 | L3 | Q75 |
| 2349 | Z1 | L3 | Q76 |
| 2350 | Z1 | L3 | Q77 |
| 2351 | Z1 | L3 | Q78 |
| 2352 | Z1 | L3 | Q79 |
| 2353 | Z1 | L3 | Q80 |
| 2354 | Z1 | L3 | Q81 |
| 2355 | Z1 | L3 | Q82 |
| 2356 | Z1 | L3 | Q83 |
| 2357 | Z1 | L3 | Q84 |
| 2358 | Z1 | L3 | Q85 |
| 2359 | Z1 | L3 | Q86 |
| 2360 | Z1 | L3 | Q87 |
| 2361 | Z1 | L3 | Q88 |
| 2362 | Z1 | L3 | Q89 |
| 2363 | Z1 | L3 | Q90 |
| 2364 | Z1 | L3 | Q91 |
| 2365 | Z1 | L3 | Q92 |
| 2366 | Z1 | L3 | Q93 |
| 2367 | Z1 | L3 | Q94 |
| 2368 | Z1 | L3 | Q95 |
| 2369 | Z1 | L3 | Q96 |
| 2370 | Z1 | L3 | Q97 |
| 2371 | Z1 | L3 | Q98 |
| 2372 | Z1 | L3 | Q99 |
| 2373 | Z1 | L3 | Q100 |
| 2374 | Z1 | L3 | Q101 |
| 2375 | Z1 | L3 | Q102 |
| 2376 | Z1 | L3 | Q103 |
| 2377 | Z1 | L4 | Q40 |
| 2378 | Z1 | L4 | Q41 |
| 2379 | Z1 | L4 | Q42 |
| 2380 | Z1 | L4 | Q43 |
| 2381 | Z1 | L4 | Q44 |
| 2382 | Z1 | L4 | Q45 |
| 2383 | Z1 | L4 | Q46 |
| 2384 | Z1 | L4 | Q47 |

TABLE 1-18

| Example | R$^{ZL}$ | L$^a$ | Q$^a$ |
|---|---|---|---|
| 2385 | Z1 | L4 | Q48 |
| 2386 | Z1 | L4 | Q49 |
| 2387 | Z1 | L4 | Q50 |
| 2388 | Z1 | L4 | Q51 |
| 2389 | Z1 | L4 | Q52 |
| 2390 | Z1 | L4 | Q53 |
| 2391 | Z1 | L4 | Q54 |
| 2392 | Z1 | L4 | Q55 |
| 2393 | Z1 | L4 | Q56 |
| 2394 | Z1 | L4 | Q57 |
| 2395 | Z1 | L4 | Q58 |
| 2396 | Z1 | L4 | Q59 |
| 2397 | Z1 | L4 | Q60 |
| 2398 | Z1 | L4 | Q61 |
| 2399 | Z1 | L4 | Q62 |
| 2400 | Z1 | L4 | QS3 |
| 2401 | Z1 | L4 | Q64 |
| 2402 | Z1 | L4 | Q65 |
| 2403 | Z1 | L4 | Q66 |
| 2404 | Z1 | L4 | Q67 |
| 2405 | Z1 | L4 | Q68 |
| 2406 | Z1 | L4 | Q69 |
| 2407 | Z1 | L4 | Q70 |
| 2408 | Z1 | L4 | Q71 |
| 2409 | Z1 | L4 | Q72 |
| 2410 | Z1 | L4 | Q73 |
| 2411 | Z1 | L4 | Q74 |
| 2412 | Z1 | L4 | Q75 |
| 2413 | Z1 | L4 | Q76 |
| 2414 | Z1 | L4 | Q77 |
| 2415 | Z1 | L4 | Q78 |
| 2416 | Z1 | L4 | Q79 |
| 2417 | Z1 | L4 | Q80 |
| 2418 | Z1 | L4 | Q81 |
| 2419 | Z1 | L4 | Q82 |
| 2420 | Z1 | L4 | Q83 |
| 2421 | Z1 | L4 | Q84 |
| 2422 | Z1 | L4 | Q85 |
| 2423 | Z1 | L4 | Q86 |
| 2424 | Z1 | L4 | Q87 |
| 2425 | Z1 | L4 | Q88 |
| 2426 | Z1 | L4 | Q89 |
| 2427 | Z1 | L4 | Q90 |
| 2428 | Z1 | L4 | Q91 |
| 2429 | Z1 | L4 | Q92 |
| 2430 | Z1 | L4 | Q93 |
| 2431 | Z1 | L4 | Q94 |
| 2432 | Z1 | L4 | Q95 |
| 2433 | Z1 | L4 | Q96 |
| 2434 | Z1 | L4 | Q97 |

TABLE 1-18-continued

| | | | |
|---|---|---|---|
| 2435 | Z1 | L4 | Q98 |
| 2436 | Z1 | L4 | Q99 |
| 2437 | Z1 | L4 | Q100 |
| 2438 | Z1 | L4 | Q101 |
| 2439 | Z1 | L4 | Q102 |
| 2440 | Z1 | L4 | Q103 |
| 2441 | Z1 | L5 | Q40 |
| 2442 | Z1 | L5 | Q41 |
| 2443 | Z1 | L5 | Q42 |
| 2444 | Z1 | L5 | Q43 |
| 2445 | Z1 | L5 | Q44 |
| 2446 | Z1 | L5 | Q45 |
| 2447 | Z1 | L5 | Q46 |
| 2448 | Z1 | L5 | Q47 |
| 2449 | Z1 | L5 | Q48 |
| 2450 | Z1 | L5 | Q49 |
| 2451 | Z1 | L5 | Q50 |
| 2452 | Z1 | L5 | Q51 |
| 2453 | Z1 | L5 | Q52 |
| 2454 | Z1 | L5 | Q53 |
| 2455 | Z1 | L5 | Q54 |
| 2456 | Z1 | L5 | Q55 |
| 2457 | Z1 | L5 | Q56 |
| 2458 | Z1 | L5 | Q57 |
| 2459 | Z1 | L5 | Q58 |
| 2460 | Z1 | L5 | Q59 |
| 2461 | Z1 | L5 | Q60 |
| 2462 | Z1 | L5 | Q61 |
| 2463 | Z1 | L5 | Q62 |
| 2464 | Z1 | L5 | Q63 |
| 2465 | Z1 | L5 | Q64 |
| 2466 | Z1 | L5 | Q65 |
| 2467 | Z1 | L5 | Q66 |
| 2468 | Z1 | L5 | Q67 |
| 2469 | Z1 | L5 | Q68 |
| 2470 | Z1 | L5 | Q69 |
| 2471 | Z1 | L5 | Q70 |
| 2472 | Z1 | L5 | Q71 |
| 2473 | Z1 | L5 | Q72 |
| 2474 | Z1 | L5 | Q73 |
| 2475 | Z1 | L5 | Q74 |
| 2476 | Z1 | L5 | Q75 |
| 2477 | Z1 | L5 | Q76 |
| 2478 | Z1 | L5 | Q77 |
| 2479 | Z1 | L5 | Q78 |
| 2480 | Z1 | L5 | Q79 |
| 2481 | Z1 | L5 | Q80 |
| 2482 | Z1 | L5 | Q81 |
| 2483 | Z1 | L5 | Q82 |
| 2484 | Z1 | L5 | Q83 |
| 2485 | Z1 | L5 | Q84 |
| 2486 | Z1 | L5 | Q85 |
| 2487 | Z1 | L5 | Q86 |
| 2488 | Z1 | L5 | Q87 |
| 2489 | Z1 | L5 | Q88 |
| 2490 | Z1 | L5 | Q89 |
| 2491 | Z1 | L5 | Q90 |
| 2492 | Z1 | L5 | Q91 |
| 2493 | Z1 | L5 | Q92 |
| 2494 | Z1 | L5 | Q93 |
| 2495 | Z1 | L5 | Q94 |
| 2496 | Z1 | L5 | Q95 |
| 2497 | Z1 | L5 | Q96 |
| 2498 | Z1 | L5 | Q97 |
| 2499 | Z1 | L5 | Q98 |
| 2500 | Z1 | L5 | Q99 |
| 2501 | Z1 | L5 | Q100 |
| 2502 | Z1 | L5 | Q101 |
| 2503 | Z1 | L5 | Q102 |
| 2504 | Z1 | L5 | Q103 |
| 2505 | Z1 | L6 | Q40 |
| 2506 | Z1 | L6 | Q41 |
| 2507 | Z1 | L6 | Q42 |
| 2508 | Z1 | L6 | Q43 |
| 2509 | Z1 | L6 | Q44 |
| 2510 | Z1 | L6 | Q45 |
| 2511 | Z1 | L6 | Q46 |
| 2512 | Z1 | L6 | Q47 |
| 2513 | Z1 | L6 | Q48 |
| 2514 | Z1 | L6 | Q49 |
| 2515 | Z1 | L6 | Q50 |
| 2516 | Z1 | L6 | Q51 |
| 2517 | Z1 | L6 | Q52 |
| 2518 | Z1 | L6 | Q53 |
| 2519 | Z1 | L6 | Q54 |
| 2520 | Z1 | L6 | Q55 |
| 2521 | Z1 | L6 | Q56 |
| 2522 | Z1 | L6 | Q57 |
| 2523 | Z1 | L6 | Q58 |
| 2524 | Z1 | L6 | Q59 |
| 2525 | Z1 | L6 | Q60 |
| 2526 | Z1 | L6 | Q61 |
| 2527 | Z1 | L6 | Q62 |
| 2528 | Z1 | L6 | Q63 |
| 2529 | Z1 | L6 | Q64 |
| 2530 | Z1 | L6 | Q65 |
| 2531 | Z1 | L6 | Q66 |
| 2532 | Z1 | L6 | Q67 |
| 2533 | Z1 | L6 | Q68 |
| 2534 | Z1 | L6 | Q69 |
| 2535 | Z1 | L6 | Q70 |
| 2536 | Z1 | L6 | Q71 |
| 2537 | Z1 | L6 | Q72 |
| 2538 | Z1 | L6 | Q73 |
| 2539 | Z1 | L6 | Q74 |
| 2540 | Z1 | L6 | Q75 |
| 2541 | Z1 | L6 | Q76 |
| 2542 | Z1 | L6 | Q77 |
| 2543 | Z1 | L6 | Q78 |
| 2544 | Z1 | L6 | Q79 |
| 2545 | Z1 | L6 | Q80 |
| 2546 | Z1 | L6 | Q81 |
| 2547 | Z1 | L6 | Q82 |
| 2548 | Z1 | L6 | Q83 |
| 2549 | Z1 | L6 | Q84 |
| 2550 | Z1 | L6 | Q85 |
| 2551 | Z1 | L6 | Q86 |
| 2552 | Z1 | L6 | Q87 |
| 2553 | Z1 | L6 | Q88 |
| 2554 | Z1 | L6 | Q89 |
| 2555 | Z1 | L6 | Q90 |
| 2556 | Z1 | L6 | Q91 |
| 2557 | Z1 | L6 | Q92 |
| 2558 | Z1 | L6 | Q93 |
| 2559 | Z1 | L6 | Q94 |
| 2560 | Z1 | L6 | Q95 |
| 2561 | Z1 | L6 | Q96 |
| 2562 | Z1 | L6 | Q97 |
| 2563 | Z1 | L6 | Q98 |
| 2564 | Z1 | L6 | Q99 |
| 2565 | Z1 | L6 | Q100 |
| 2566 | Z1 | L6 | Q101 |
| 2567 | Z1 | L6 | Q102 |
| 2568 | Z1 | L6 | Q103 |
| 2569 | Z1 | L7 | Q40 |
| 2570 | Z1 | L7 | Q41 |
| 2571 | Z1 | L7 | Q42 |
| 2572 | Z1 | L7 | Q43 |
| 2573 | Z1 | L7 | Q44 |
| 2574 | Z1 | L7 | Q45 |
| 2575 | Z1 | L7 | Q46 |
| 2576 | Z1 | L7 | Q47 |
| 2577 | Z1 | L7 | Q48 |
| 2578 | Z1 | L7 | Q49 |
| 2579 | Z1 | L7 | Q50 |
| 2580 | Z1 | L7 | Q51 |
| 2581 | Z1 | L7 | Q52 |
| 2582 | Z1 | L7 | Q53 |
| 2583 | Z1 | L7 | Q54 |
| 2584 | Z1 | L7 | Q55 |
| 2585 | Z1 | L7 | Q56 |

TABLE 1-19

| | | | |
|---|---|---|---|
| 2586 | Z1 | L7 | Q57 |
| 2587 | Z1 | L7 | Q58 |
| 2588 | Z1 | L7 | Q59 |

TABLE 1-19-continued

| | | | |
|---|---|---|---|
| 2589 | Z1 | L7 | Q60 |
| 2590 | Z1 | L7 | Q61 |
| 2591 | Z1 | L7 | Q62 |
| 2592 | Z1 | L7 | Q63 |
| 2593 | Z1 | L7 | Q64 |
| 2594 | Z1 | L7 | Q65 |
| 2595 | Z1 | L7 | Q66 |
| 2596 | Z1 | L7 | Q67 |
| 2597 | Z1 | L7 | Q68 |
| 2598 | Z1 | L7 | Q69 |
| 2599 | Z1 | L7 | Q70 |
| 2600 | Z1 | L7 | Q71 |
| 2601 | Z1 | L7 | Q72 |
| 2602 | Z1 | L7 | Q73 |
| 2603 | Z1 | L7 | Q74 |
| 2604 | Z1 | L7 | Q75 |
| 2605 | Z1 | L7 | Q76 |
| 2606 | Z1 | L7 | Q77 |
| 2607 | Z1 | L7 | Q78 |
| 2608 | Z1 | L7 | Q79 |
| 2609 | Z1 | L7 | Q80 |
| 2610 | Z1 | L7 | Q81 |
| 2611 | Z1 | L7 | Q82 |
| 2612 | Z1 | L7 | Q83 |
| 2613 | Z1 | L7 | Q84 |
| 2614 | Z1 | L7 | Q85 |
| 2615 | Z1 | L7 | Q86 |
| 2616 | Z1 | L7 | Q87 |
| 2617 | Z1 | L7 | Q88 |
| 2618 | Z1 | L7 | Q89 |
| 2619 | Z1 | L7 | Q90 |
| 2620 | Z1 | L7 | Q91 |
| 2621 | Z1 | L7 | Q92 |
| 2622 | Z1 | L7 | Q93 |
| 2623 | Z1 | L7 | Q94 |
| 2624 | Z1 | L7 | Q95 |
| 2625 | Z1 | L7 | Q96 |
| 2626 | Z1 | L7 | Q97 |
| 2627 | Z1 | L7 | Q98 |
| 2628 | Z1 | L7 | Q99 |
| 2629 | Z1 | L7 | Q100 |
| 2630 | Z1 | L7 | Q101 |
| 2631 | Z1 | L7 | Q102 |
| 2632 | Z1 | L7 | Q103 |
| 2633 | Z1 | L8 | Q40 |
| 2634 | Z1 | L8 | Q41 |
| 2635 | Z1 | L8 | Q42 |
| 2636 | Z1 | L8 | Q43 |
| 2637 | Z1 | L8 | Q44 |
| 2638 | Z1 | L8 | Q45 |
| 2639 | Z1 | L8 | Q46 |
| 2640 | Z1 | L8 | Q47 |
| 2641 | Z1 | L8 | Q48 |
| 2642 | Z1 | L8 | Q49 |
| 2643 | Z1 | L8 | Q50 |
| 2644 | Z1 | L8 | Q51 |
| 2645 | Z1 | L8 | Q52 |
| 2646 | Z1 | L8 | Q53 |
| 2647 | Z1 | L8 | Q54 |
| 2648 | Z1 | L8 | Q55 |
| 2649 | Z1 | L8 | Q56 |
| 2650 | Z1 | L8 | Q57 |
| 2651 | Z1 | L8 | Q58 |
| 2652 | Z1 | L8 | Q59 |
| 2653 | Z1 | L8 | Q60 |
| 2654 | Z1 | L8 | Q61 |
| 2655 | Z1 | L8 | Q62 |
| 2656 | Z1 | L8 | Q63 |
| 2657 | Z1 | L8 | Q64 |
| 2658 | Z1 | L8 | Q65 |
| 2659 | Z1 | L8 | Q66 |
| 2660 | Z1 | L8 | Q67 |
| 2661 | Z1 | L8 | Q68 |
| 2662 | Z1 | L8 | Q69 |
| 2663 | Z1 | L8 | Q70 |
| 2664 | Z1 | L8 | Q71 |
| 2665 | Z1 | L8 | Q72 |
| 2666 | Z1 | L8 | Q73 |
| 2667 | Z1 | L8 | Q74 |
| 2668 | Z1 | L8 | Q75 |
| 2669 | Z1 | L8 | Q76 |
| 2670 | Z1 | L8 | Q77 |
| 2671 | Z1 | L8 | Q78 |
| 2672 | Z1 | L8 | Q79 |
| 2673 | Z1 | L8 | Q80 |
| 2674 | Z1 | L8 | Q81 |
| 2675 | Z1 | L8 | Q82 |
| 2676 | Z1 | L8 | Q83 |
| 2677 | Z1 | L8 | Q84 |
| 2678 | Z1 | L8 | Q85 |
| 2679 | Z1 | L8 | Q86 |
| 2680 | Z1 | L8 | Q87 |
| 2681 | Z1 | L8 | Q88 |
| 2682 | Z1 | L8 | Q89 |
| 2683 | Z1 | L8 | Q90 |
| 2684 | Z1 | L8 | Q91 |
| 2685 | Z1 | L8 | Q92 |
| 2686 | Z1 | L8 | Q93 |
| 2687 | Z1 | L8 | Q94 |
| 2688 | Z1 | L8 | Q95 |
| 2689 | Z1 | L8 | Q96 |
| 2690 | Z1 | L8 | Q97 |
| 2691 | Z1 | L8 | Q98 |
| 2692 | Z1 | L8 | Q99 |
| 2693 | Z1 | L8 | Q100 |
| 2694 | Z1 | L8 | Q101 |
| 2695 | Z1 | L8 | Q102 |
| 2696 | Z1 | L8 | Q103 |
| 2697 | Z1 | L9 | Q40 |
| 2698 | Z1 | L9 | Q41 |
| 2699 | Z1 | L9 | Q42 |
| 2700 | Z1 | L9 | Q43 |
| 2701 | Z1 | L9 | Q44 |
| 2702 | Z1 | L9 | Q45 |
| 2703 | Z1 | L9 | Q46 |
| 2704 | Z1 | L9 | Q47 |
| 2705 | Z1 | L9 | Q48 |
| 2706 | Z1 | L9 | Q49 |
| 2707 | Z1 | L9 | Q50 |
| 2708 | Z1 | L9 | Q51 |
| 2709 | Z1 | L9 | Q52 |
| 2710 | Z1 | L9 | Q53 |
| 2711 | Z1 | L9 | Q54 |
| 2712 | Z1 | L9 | Q55 |
| 2713 | Z1 | L9 | Q56 |
| 2714 | Z1 | L9 | Q57 |
| 2715 | Z1 | L9 | Q58 |
| 2716 | Z1 | L9 | Q59 |
| 2717 | Z1 | L9 | Q60 |
| 2718 | Z1 | L9 | Q61 |
| 2719 | Z1 | L9 | Q62 |
| 2720 | Z1 | L9 | Q63 |
| 2721 | Z1 | L9 | Q64 |
| 2722 | Z1 | L9 | Q65 |
| 2723 | Z1 | L9 | Q66 |
| 2724 | Z1 | L9 | Q67 |
| 2725 | Z1 | L9 | Q68 |
| 2726 | Z1 | L9 | Q69 |
| 2727 | Z1 | L9 | Q70 |
| 2728 | Z1 | L9 | Q71 |
| 2729 | Z1 | L9 | Q72 |
| 2730 | Z1 | L9 | Q73 |
| 2731 | Z1 | L9 | Q74 |
| 2732 | Z1 | L9 | Q75 |
| 2733 | Z1 | L9 | Q76 |
| 2734 | Z1 | L9 | Q77 |
| 2735 | Z1 | L9 | Q78 |
| 2736 | Z1 | L9 | Q79 |
| 2737 | Z1 | L9 | Q80 |
| 2738 | Z1 | L9 | Q81 |
| 2739 | Z1 | L9 | Q82 |
| 2740 | Z1 | L9 | Q83 |
| 2741 | Z1 | L9 | Q84 |
| 2742 | Z1 | L9 | Q85 |
| 2743 | Z1 | L9 | Q86 |
| 2744 | Z1 | L9 | Q87 |
| 2745 | Z1 | L9 | Q88 |
| 2746 | Z1 | L9 | Q89 |
| 2747 | Z1 | L9 | Q90 |
| 2748 | Z1 | L9 | Q91 |

TABLE 1-19-continued

| | | | |
|---|---|---|---|
| 2749 | Z1 | L9 | Q92 |
| 2750 | Z1 | L9 | Q93 |
| 2751 | Z1 | L9 | Q94 |
| 2752 | Z1 | L9 | Q95 |
| 2753 | Z1 | L9 | Q96 |
| 2754 | Z1 | L9 | Q97 |
| 2755 | Z1 | L9 | Q98 |
| 2756 | Z1 | L9 | Q99 |
| 2757 | Z1 | L9 | Q100 |
| 2758 | Z1 | L9 | Q101 |
| 2759 | Z1 | L9 | Q102 |
| 2760 | Z1 | L9 | Q103 |
| 2761 | Z1 | L10 | Q40 |
| 2762 | Z1 | L10 | Q41 |
| 2763 | Z1 | L10 | Q42 |
| 2764 | Z1 | L10 | Q43 |
| 2765 | Z1 | L10 | Q44 |
| 2766 | Z1 | L10 | Q45 |
| 2767 | Z1 | L10 | Q46 |
| 2768 | Z1 | L10 | Q47 |
| 2769 | Z1 | L10 | Q48 |
| 2770 | Z1 | L10 | Q49 |
| 2771 | Z1 | L10 | Q50 |
| 2772 | Z1 | L10 | Q51 |
| 2773 | Z1 | L10 | Q52 |
| 2774 | Z1 | L10 | Q53 |
| 2775 | Z1 | L10 | Q54 |
| 2776 | Z1 | L10 | Q55 |
| 2777 | Z1 | L10 | Q56 |
| 2778 | Z1 | L10 | Q57 |
| 2779 | Z1 | L10 | Q58 |
| 2780 | Z1 | L10 | Q59 |
| 2781 | Z1 | L10 | Q60 |
| 2782 | Z1 | L10 | Q61 |
| 2783 | Z1 | L10 | Q62 |
| 2784 | Z1 | L10 | Q63 |
| 2785 | Z1 | L10 | Q64 |
| 2786 | Z1 | L10 | Q65 |

TABLE 1-20

| | | | |
|---|---|---|---|
| 2787 | Z1 | L10 | Q66 |
| 2788 | Z1 | L10 | Q67 |
| 2789 | Z1 | L10 | Q68 |
| 2790 | Z1 | L10 | Q69 |
| 2791 | Z1 | L10 | Q70 |
| 2792 | Z1 | L10 | Q71 |
| 2793 | Z1 | L10 | Q72 |
| 2794 | Z1 | L10 | Q73 |
| 2795 | Z1 | L10 | Q74 |
| 2796 | Z1 | L10 | Q75 |
| 2797 | Z1 | L10 | Q76 |
| 2798 | Z1 | L10 | Q77 |
| 2799 | Z1 | L10 | Q78 |
| 2800 | Z1 | L10 | Q79 |
| 2801 | Z1 | L10 | Q80 |
| 2302 | Z1 | L10 | Q81 |
| 2803 | Z1 | L10 | Q82 |
| 2804 | Z1 | L10 | Q83 |
| 2805 | Z1 | L10 | Q84 |
| 2806 | Z1 | L10 | Q85 |
| 2807 | Z1 | L10 | Q86 |
| 2808 | Z1 | L10 | Q87 |
| 2809 | Z1 | L10 | Q88 |
| 2810 | Z1 | L10 | Q89 |
| 2811 | Z1 | L10 | Q90 |
| 2812 | Z1 | L10 | Q91 |
| 2813 | Z1 | L10 | Q92 |
| 2814 | Z1 | L10 | Q93 |
| 2815 | Z1 | L10 | Q94 |
| 2816 | Z1 | L10 | Q95 |
| 2817 | Z1 | L10 | Q96 |
| 2818 | Z1 | L10 | Q97 |
| 2819 | Z1 | L10 | Q98 |
| 2820 | Z1 | L10 | Q99 |
| 2821 | Z1 | L10 | Q100 |
| 2822 | Z1 | L10 | Q101 |

TABLE 1-20-continued

| | | | |
|---|---|---|---|
| 2823 | Z1 | L10 | Q102 |
| 2824 | Z1 | L10 | Q103 |
| 2825 | Z1 | L11 | Q40 |
| 2826 | Z1 | L11 | Q41 |
| 2827 | Z1 | L11 | Q42 |
| 2828 | Z1 | L11 | Q43 |
| 2829 | Z1 | L11 | Q44 |
| 2830 | Z1 | L11 | Q45 |
| 2831 | Z1 | L11 | Q46 |
| 2832 | Z1 | L11 | Q47 |
| 2833 | Z1 | L11 | Q48 |
| 2834 | Z1 | L11 | Q49 |
| 2835 | Z1 | L11 | Q50 |
| 2836 | Z1 | L11 | Q51 |
| 2837 | Z1 | L11 | Q52 |
| 2838 | Z1 | L11 | Q53 |
| 2839 | Z1 | L11 | Q54 |
| 2840 | Z1 | L11 | Q55 |
| 2841 | Z1 | L11 | Q56 |
| 2842 | Z1 | L11 | Q57 |
| 2843 | Z1 | L11 | Q58 |
| 2844 | Z1 | L11 | Q59 |
| 2845 | Z1 | L11 | Q60 |
| 2846 | Z1 | L11 | Q61 |
| 2847 | Z1 | L11 | Q62 |
| 2848 | Z1 | L11 | Q63 |
| 2849 | Z1 | L11 | Q64 |
| 2850 | Z1 | L11 | Q65 |
| 2851 | Z1 | L11 | Q66 |
| 2852 | Z1 | L11 | Q67 |
| 2853 | Z1 | L11 | Q68 |
| 2854 | Z1 | L11 | Q69 |
| 2855 | Z1 | L11 | Q70 |
| 2856 | Z1 | L11 | Q71 |
| 2857 | Z1 | L11 | Q72 |
| 2858 | Z1 | L11 | Q73 |
| 2859 | Z1 | L11 | Q74 |
| 2860 | Z1 | L11 | Q75 |
| 2861 | Z1 | L11 | Q76 |
| 2862 | Z1 | L11 | Q77 |
| 2863 | Z1 | L11 | Q78 |
| 2864 | Z1 | L11 | Q79 |
| 2865 | Z1 | L11 | Q80 |
| 2866 | Z1 | L11 | Q81 |
| 2867 | Z1 | L11 | Q82 |
| 2868 | Z1 | L11 | Q83 |
| 2869 | Z1 | L11 | Q84 |
| 2870 | Z1 | L11 | Q85 |
| 2871 | Z1 | L11 | Q86 |
| 2872 | Z1 | L11 | Q87 |
| 2873 | Z1 | L11 | Q88 |
| 2874 | Z1 | L11 | Q89 |
| 2875 | Z1 | L11 | Q90 |
| 2876 | Z1 | L11 | Q91 |
| 2877 | Z1 | L11 | Q92 |
| 2878 | Z1 | L11 | Q93 |
| 2879 | Z1 | L11 | Q94 |
| 2880 | Z1 | L11 | Q95 |
| 2881 | Z1 | L11 | Q96 |
| 2882 | Z1 | L11 | Q97 |
| 2883 | Z1 | L11 | Q98 |
| 2884 | Z1 | L11 | Q99 |
| 2885 | Z1 | L11 | Q100 |
| 2886 | Z1 | L11 | Q101 |
| 2887 | Z1 | L11 | Q102 |
| 2888 | Z1 | L11 | Q103 |
| 2889 | Z1 | L12 | Q40 |
| 2890 | Z1 | L12 | Q41 |
| 2891 | Z1 | L12 | Q42 |
| 2892 | Z1 | L12 | Q43 |
| 2893 | Z1 | L12 | Q44 |
| 2894 | Z1 | L12 | Q45 |
| 2895 | Z1 | L12 | Q46 |
| 2896 | Z1 | L12 | Q47 |
| 2897 | Z1 | L12 | Q48 |
| 2898 | Z1 | L12 | Q49 |
| 2899 | Z1 | L12 | Q50 |
| 2900 | Z1 | L12 | Q51 |
| 2901 | Z1 | L12 | Q52 |
| 2902 | Z1 | L12 | Q53 |

TABLE 1-20-continued

| | | | |
|---|---|---|---|
| 2903 | Z1 | L12 | Q54 |
| 2904 | Z1 | L12 | Q55 |
| 2905 | Z1 | L12 | Q56 |
| 2906 | Z1 | L12 | Q57 |
| 2907 | Z1 | L12 | Q58 |
| 2908 | Z1 | L12 | Q59 |
| 2909 | Z1 | L12 | Q60 |
| 2910 | Z1 | L12 | Q61 |
| 2911 | Z1 | L12 | Q62 |
| 2912 | Z1 | L12 | Q63 |
| 2913 | Z1 | L12 | Q64 |
| 2914 | Z1 | L12 | Q65 |
| 2915 | Z1 | L12 | Q66 |
| 2916 | Z1 | L12 | Q67 |
| 2917 | Z1 | L12 | Q68 |
| 2918 | Z1 | L12 | Q69 |
| 2919 | Z1 | L12 | Q70 |
| 2920 | Z1 | L12 | Q71 |
| 2921 | Z1 | L12 | Q72 |
| 2922 | Z1 | L12 | Q73 |
| 2923 | Z1 | L12 | Q74 |
| 2924 | Z1 | L12 | Q75 |
| 2925 | Z1 | L12 | Q76 |
| 2926 | Z1 | L12 | Q77 |
| 2927 | Z1 | L12 | Q78 |
| 2928 | Z1 | L12 | Q79 |
| 2929 | Z1 | L12 | Q80 |
| 2930 | Z1 | L12 | Q81 |
| 2931 | Z1 | L12 | Q82 |
| 2932 | Z1 | L12 | Q83 |
| 2933 | Z1 | L12 | Q84 |
| 2934 | Z1 | L12 | Q85 |
| 2935 | Z1 | L12 | Q86 |
| 2936 | Z1 | L12 | Q87 |
| 2937 | Z1 | L12 | Q88 |
| 2938 | Z1 | L12 | Q89 |
| 2939 | Z1 | L12 | Q90 |
| 2940 | Z1 | L12 | Q91 |
| 2941 | Z1 | L12 | Q92 |
| 2942 | Z1 | L12 | Q93 |
| 2943 | Z1 | L12 | Q94 |
| 2944 | Z1 | L12 | Q95 |
| 2945 | Z1 | L12 | Q96 |
| 2946 | Z1 | L12 | Q97 |
| 2947 | Z1 | L12 | Q98 |
| 2948 | Z1 | L12 | Q99 |
| 2949 | Z1 | L12 | Q100 |
| 2950 | Z1 | L12 | Q101 |
| 2951 | Z1 | L12 | Q102 |
| 2952 | Z1 | L12 | Q103 |
| 2953 | Z1 | L13 | Q40 |
| 2954 | Z1 | L13 | Q41 |
| 2955 | Z1 | L13 | Q42 |
| 2956 | Z1 | L13 | Q43 |
| 2957 | Z1 | L13 | Q44 |
| 2958 | Z1 | L13 | Q45 |
| 2959 | Z1 | L13 | Q46 |
| 2960 | Z1 | L13 | Q47 |
| 2961 | Z1 | L13 | Q48 |
| 2962 | Z1 | L13 | Q49 |
| 2963 | Z1 | L13 | Q50 |
| 2964 | Z1 | L13 | Q51 |
| 2965 | Z1 | L13 | Q52 |
| 2966 | Z1 | L13 | Q53 |
| 2967 | Z1 | L13 | Q54 |
| 2968 | Z1 | L13 | Q55 |
| 2969 | Z1 | L13 | Q56 |
| 2970 | Z1 | L13 | Q57 |
| 2971 | Z1 | L13 | Q58 |
| 2972 | Z1 | L13 | Q59 |
| 2973 | Z1 | L13 | Q60 |
| 2974 | Z1 | L13 | Q61 |
| 2975 | Z1 | L13 | Q62 |
| 2976 | Z1 | L13 | Q63 |
| 2977 | Z1 | L13 | Q64 |
| 2978 | Z1 | L13 | Q65 |
| 2979 | Z1 | L13 | Q66 |
| 2980 | Z1 | L13 | Q67 |
| 2981 | Z1 | L13 | Q68 |
| 2982 | Z1 | L13 | Q69 |
| 2983 | Z1 | L13 | Q70 |
| 2984 | Z1 | L13 | Q71 |
| 2985 | Z1 | L13 | Q72 |
| 2986 | Z1 | L13 | Q73 |
| 2987 | Z1 | L13 | Q74 |

TABLE 1-21

| | | | |
|---|---|---|---|
| 2988 | Z1 | L13 | Q75 |
| 2989 | Z1 | L13 | Q76 |
| 2990 | Z1 | L13 | Q77 |
| 2991 | Z1 | L13 | Q78 |
| 2992 | Z1 | L13 | Q79 |
| 2993 | Z1 | L13 | Q80 |
| 2994 | Z1 | L13 | Q81 |
| 2995 | Z1 | L13 | Q82 |
| 2996 | Z1 | L13 | Q83 |
| 2997 | Z1 | L13 | Q84 |
| 2998 | Z1 | L13 | Q85 |
| 2999 | Z1 | L13 | Q86 |
| 3000 | Z1 | L13 | Q87 |
| 3001 | Z1 | L13 | Q88 |
| 3002 | Z1 | L13 | Q89 |
| 3003 | Z1 | L13 | Q90 |
| 3004 | Z1 | L13 | Q91 |
| 3005 | Z1 | L13 | Q92 |
| 3006 | Z1 | L13 | Q93 |
| 3007 | Z1 | L13 | Q94 |
| 3008 | Z1 | L13 | Q95 |
| 3009 | Z1 | L13 | Q96 |
| 3010 | Z1 | L13 | Q97 |
| 3011 | Z1 | L13 | Q98 |
| 3012 | Z1 | L13 | Q99 |
| 3013 | Z1 | L13 | Q100 |
| 3014 | Z1 | L13 | Q101 |
| 3015 | Z1 | L13 | Q102 |
| 3016 | Z1 | L13 | Q103 |
| 3017 | Z1 | L14 | Q40 |
| 3018 | Z1 | L14 | Q41 |
| 3019 | Z1 | L14 | Q42 |
| 3020 | Z1 | L14 | Q43 |
| 3021 | Z1 | L14 | Q44 |
| 3022 | Z1 | L14 | Q45 |
| 3023 | Z1 | L14 | Q46 |
| 3024 | Z1 | L14 | Q47 |
| 3025 | Z1 | L14 | Q48 |
| 3026 | Z1 | L14 | Q49 |
| 3027 | Z1 | L14 | Q50 |
| 3028 | Z1 | L14 | Q51 |
| 3029 | Z1 | L14 | Q52 |
| 3030 | Z1 | L14 | Q53 |
| 3031 | Z1 | L14 | Q54 |
| 3032 | Z1 | L14 | Q55 |
| 3033 | Z1 | L14 | Q56 |
| 3034 | Z1 | L14 | Q57 |
| 3035 | Z1 | L14 | Q58 |
| 3036 | Z1 | L14 | Q59 |
| 3037 | Z1 | L14 | Q60 |
| 3038 | Z1 | L14 | Q61 |
| 3039 | Z1 | L14 | Q62 |
| 3040 | Z1 | L14 | Q63 |
| 3041 | Z1 | L14 | Q64 |
| 3042 | Z1 | L14 | Q65 |
| 3043 | Z1 | L14 | Q66 |
| 3044 | Z1 | L14 | Q67 |
| 3045 | Z1 | L14 | Q68 |
| 3046 | Z1 | L14 | Q69 |
| 3047 | Z1 | L14 | Q70 |
| 3048 | Z1 | L14 | Q71 |
| 3049 | Z1 | L14 | Q72 |
| 3050 | Z1 | L14 | Q73 |
| 3051 | Z1 | L14 | Q74 |
| 3052 | Z1 | L14 | Q75 |
| 3053 | Z1 | L14 | Q76 |
| 3054 | Z1 | L14 | Q77 |
| 3055 | Z1 | L14 | Q78 |
| 3056 | Z1 | L14 | Q79 |

TABLE 1-21-continued

| | | | |
|---|---|---|---|
| 3057 | Z1 | LI4 | Q80 |
| 3058 | Z1 | L14 | Q81 |
| 3059 | Z1 | L14 | Q82 |
| 3060 | Z1 | L14 | Q83 |
| 3061 | Z1 | L14 | Q84 |
| 3062 | Z1 | L14 | Q85 |
| 3063 | Z1 | L14 | Q86 |
| 3064 | Z1 | L14 | Q87 |
| 3065 | Z1 | L14 | Q88 |
| 3066 | Z1 | L14 | Q89 |
| 3067 | Z1 | L14 | Q90 |
| 3068 | Z1 | L14 | Q91 |
| 3069 | Z1 | L14 | Q92 |
| 3070 | Z1 | L14 | Q93 |
| 3071 | Z1 | L14 | Q94 |
| 3072 | Z1 | L14 | Q95 |
| 3073 | Z1 | L14 | Q96 |
| 3074 | Z1 | L14 | Q97 |
| 3075 | Z1 | L14 | Q98 |
| 3076 | Z1 | L14 | Q99 |
| 3077 | Z1 | L14 | Q100 |
| 3078 | Z1 | L14 | Q101 |
| 3079 | Z1 | L14 | Q102 |
| 3080 | Z1 | L14 | Q103 |
| 3081 | Z2 | L1 | Q40 |
| 3082 | Z2 | L1 | Q41 |
| 3083 | Z2 | L1 | Q42 |
| 3084 | Z2 | L1 | Q43 |
| 3085 | Z2 | L1 | Q44 |
| 3086 | Z2 | L1 | Q45 |
| 3087 | Z2 | L1 | Q46 |
| 3088 | Z2 | L1 | Q47 |
| 3089 | Z2 | L1 | Q48 |
| 3090 | Z2 | L1 | Q49 |
| 3091 | Z2 | L1 | Q50 |
| 3092 | Z2 | L1 | Q51 |
| 3093 | Z2 | L1 | Q52 |
| 3094 | Z2 | L1 | Q53 |
| 3095 | Z2 | L1 | Q54 |
| 3096 | Z2 | L1 | Q55 |
| 3097 | Z2 | L1 | Q56 |
| 3098 | Z2 | L1 | Q57 |
| 3099 | Z2 | L1 | Q58 |
| 3100 | Z2 | L1 | Q59 |
| 3101 | Z2 | L1 | Q60 |
| 3102 | Z2 | L1 | Q61 |
| 3103 | Z2 | L1 | Q62 |
| 3104 | Z2 | L1 | Q63 |
| 3105 | Z2 | L1 | Q64 |
| 3106 | Z2 | L1 | Q65 |
| 3107 | Z2 | L1 | Q66 |
| 3108 | Z2 | L1 | Q67 |
| 3109 | Z2 | L1 | Q68 |
| 3110 | Z2 | L1 | Q69 |
| 3111 | Z2 | L1 | Q70 |
| 3112 | Z2 | L1 | Q71 |
| 3113 | Z2 | L1 | Q72 |
| 3114 | Z2 | L1 | Q73 |
| 3115 | Z2 | L1 | Q74 |
| 3116 | Z2 | L1 | Q75 |
| 3117 | Z2 | L1 | Q76 |
| 3118 | Z2 | L1 | Q77 |
| 3119 | Z2 | L1 | Q78 |
| 3120 | Z2 | L1 | Q79 |
| 3121 | Z2 | L1 | Q80 |
| 3122 | Z2 | L1 | Q81 |
| 3123 | Z2 | L1 | Q82 |
| 3124 | Z2 | L1 | Q83 |
| 3125 | Z2 | L1 | Q84 |
| 3126 | Z2 | L1 | Q85 |
| 3127 | Z2 | L1 | Q86 |
| 3128 | Z2 | L1 | Q87 |
| 3129 | Z2 | L1 | Q88 |
| 3130 | Z2 | L1 | Q89 |
| 3131 | Z2 | L1 | Q90 |
| 3132 | Z2 | L1 | Q91 |
| 3133 | Z2 | L1 | Q92 |
| 3134 | Z2 | L1 | Q93 |
| 3135 | Z2 | L1 | Q94 |
| 3136 | Z2 | L1 | Q95 |
| 3137 | Z2 | L1 | Q96 |
| 3138 | Z2 | L1 | Q97 |
| 3139 | Z2 | L1 | Q98 |
| 3140 | Z2 | L1 | Q99 |
| 3141 | Z2 | L1 | Q100 |
| 3142 | Z2 | L1 | Q101 |
| 3143 | Z2 | L1 | Q102 |
| 3144 | Z2 | L1 | Q103 |
| 3145 | Z2 | L2 | Q40 |
| 3146 | Z2 | L2 | Q41 |
| 3147 | Z2 | L2 | Q42 |
| 3148 | Z2 | L2 | Q43 |
| 3149 | Z2 | L2 | Q44 |
| 3150 | Z2 | L2 | Q45 |
| 3151 | Z2 | L2 | Q46 |
| 3152 | Z2 | L2 | Q47 |
| 3153 | Z2 | L2 | Q48 |
| 3154 | Z2 | L2 | Q49 |
| 3155 | Z2 | L2 | Q50 |
| 3156 | Z2 | L2 | Q51 |
| 3157 | Z2 | L2 | Q52 |
| 3158 | Z2 | L2 | Q53 |
| 3159 | Z2 | L2 | Q54 |
| 3160 | Z2 | L2 | Q55 |
| 3161 | Z2 | L2 | Q56 |
| 3162 | Z2 | L2 | Q57 |
| 3163 | Z2 | L2 | Q58 |
| 3164 | Z2 | L2 | Q59 |
| 3165 | Z2 | L2 | Q60 |
| 3166 | Z2 | L2 | Q61 |
| 3167 | Z2 | L2 | Q62 |
| 3168 | Z2 | L2 | Q63 |
| 3169 | Z2 | L2 | Q64 |
| 3170 | Z2 | L2 | Q65 |
| 3171 | Z2 | L2 | Q66 |
| 3172 | Z2 | L2 | Q67 |
| 3173 | Z2 | L2 | Q68 |
| 3174 | Z2 | L2 | Q69 |
| 3175 | Z2 | L2 | Q70 |
| 3176 | Z2 | L2 | Q71 |
| 3177 | Z2 | L2 | Q72 |
| 3178 | Z2 | L2 | Q73 |
| 3179 | Z2 | L2 | Q74 |
| 3180 | Z2 | L2 | Q75 |
| 3181 | Z2 | L2 | Q76 |
| 3182 | Z2 | L2 | Q77 |
| 3183 | Z2 | L2 | Q78 |
| 3184 | Z2 | L2 | Q79 |
| 3185 | Z2 | L2 | Q80 |
| 3186 | Z2 | L2 | Q81 |
| 3187 | Z2 | L2 | Q82 |
| 3188 | Z2 | L2 | Q83 |

TABLE 1-22

| | | | |
|---|---|---|---|
| 3189 | Z2 | L2 | Q84 |
| 3190 | Z2 | L2 | Q85 |
| 3191 | Z2 | L2 | Q86 |
| 3192 | Z2 | L2 | Q87 |
| 3193 | Z2 | L2 | Q88 |
| 3194 | Z2 | L2 | Q89 |
| 3195 | Z2 | L2 | Q90 |
| 3196 | Z2 | L2 | Q91 |
| 3197 | Z2 | L2 | Q92 |
| 3198 | Z2 | L2 | Q93 |
| 3199 | Z2 | L2 | Q94 |
| 3200 | Z2 | L2 | Q95 |
| 3201 | Z2 | L2 | Q96 |
| 3202 | Z2 | L2 | Q97 |
| 3203 | Z2 | L2 | Q98 |
| 3204 | Z2 | L2 | Q99 |
| 3205 | Z2 | L2 | Q100 |
| 3206 | Z2 | L2 | Q101 |
| 3207 | Z2 | L2 | Q102 |
| 3208 | Z2 | L2 | Q103 |
| 3209 | Z2 | L3 | Q40 |
| 3210 | Z2 | L3 | Q41 |

TABLE 1-22-continued

| | | | |
|---|---|---|---|
| 3211 | Z2 | L3 | Q42 |
| 3212 | Z2 | L3 | Q43 |
| 3213 | Z2 | L3 | Q44 |
| 3214 | Z2 | L3 | Q45 |
| 3215 | Z2 | L3 | Q46 |
| 3216 | Z2 | L3 | Q47 |
| 3217 | Z2 | L3 | Q48 |
| 3218 | Z2 | L3 | Q49 |
| 3219 | Z2 | L3 | Q50 |
| 3220 | Z2 | L3 | Q51 |
| 3221 | Z2 | L3 | Q52 |
| 3222 | Z2 | L3 | Q53 |
| 3223 | Z2 | L3 | Q54 |
| 3224 | Z2 | L3 | Q55 |
| 3225 | Z2 | L3 | Q56 |
| 3226 | Z2 | L3 | Q57 |
| 3227 | Z2 | L3 | Q58 |
| 3228 | Z2 | L3 | Q59 |
| 3229 | Z2 | L3 | Q60 |
| 3230 | Z2 | L3 | Q61 |
| 3231 | Z2 | L3 | Q62 |
| 3232 | Z2 | L3 | Q63 |
| 3233 | Z2 | L3 | Q64 |
| 3234 | Z2 | L3 | Q65 |
| 3235 | Z2 | L3 | Q66 |
| 3236 | Z2 | L3 | Q67 |
| 3237 | Z2 | L3 | Q68 |
| 3238 | Z2 | L3 | Q69 |
| 3239 | Z2 | L3 | Q70 |
| 3240 | Z2 | L3 | Q71 |
| 3241 | Z2 | L3 | Q72 |
| 3242 | Z2 | L3 | Q73 |
| 3243 | Z2 | L3 | Q74 |
| 3244 | Z2 | L3 | Q75 |
| 3245 | Z2 | L3 | Q76 |
| 3246 | Z2 | L3 | Q77 |
| 3247 | Z2 | L3 | Q78 |
| 3248 | Z2 | L3 | Q79 |
| 3249 | Z2 | L3 | Q80 |
| 3250 | Z2 | L3 | Q81 |
| 3251 | Z2 | L3 | Q82 |
| 3252 | Z2 | L3 | Q83 |
| 3253 | Z2 | L3 | Q84 |
| 3254 | Z2 | L3 | Q85 |
| 3255 | Z2 | L3 | Q86 |
| 3256 | Z2 | L3 | Q87 |
| 3257 | Z2 | L3 | Q88 |
| 3258 | Z2 | L3 | Q89 |
| 3259 | Z2 | L3 | Q90 |
| 3260 | Z2 | L3 | Q91 |
| 3261 | Z2 | L3 | Q92 |
| 3262 | Z2 | L3 | Q93 |
| 3263 | Z2 | L3 | Q94 |
| 3264 | Z2 | L3 | Q95 |
| 3265 | Z2 | L3 | Q96 |
| 3266 | Z2 | L3 | Q97 |
| 3267 | Z2 | L3 | Q98 |
| 3268 | Z2 | L3 | Q99 |
| 3269 | Z2 | L3 | Q100 |
| 3270 | Z2 | L3 | Q101 |
| 3271 | Z2 | L3 | Q102 |
| 3272 | Z2 | L3 | Q103 |
| 3273 | Z2 | L4 | Q40 |
| 3274 | Z2 | L4 | Q41 |
| 3275 | Z2 | L4 | Q42 |
| 3276 | Z2 | L4 | Q43 |
| 3277 | Z2 | L4 | Q44 |
| 3278 | Z2 | L4 | Q45 |
| 3279 | Z2 | L4 | Q46 |
| 3280 | Z2 | L4 | Q47 |
| 3281 | Z2 | L4 | Q48 |
| 3282 | Z2 | L4 | Q49 |
| 3283 | Z2 | L4 | Q50 |
| 3284 | Z2 | L4 | Q51 |
| 3285 | Z2 | L4 | Q52 |
| 3286 | Z2 | L4 | Q53 |
| 3287 | Z2 | L4 | Q54 |
| 3288 | Z2 | L4 | Q55 |
| 3289 | Z2 | L4 | Q56 |
| 3290 | Z2 | L4 | Q57 |
| 3291 | Z2 | L4 | Q58 |
| 3292 | Z2 | L4 | Q59 |
| 3293 | Z2 | L4 | Q60 |
| 3294 | Z2 | L4 | Q61 |
| 3295 | Z2 | L4 | Q62 |
| 3296 | Z2 | L4 | Q63 |
| 3297 | Z2 | L4 | Q64 |
| 3298 | Z2 | L4 | Q65 |
| 3299 | Z2 | L4 | Q66 |
| 3300 | Z2 | L4 | Q67 |
| 3301 | Z2 | L4 | Q68 |
| 3302 | Z2 | L4 | Q69 |
| 3303 | Z2 | L4 | Q70 |
| 3304 | Z2 | L4 | Q71 |
| 3305 | Z2 | L4 | Q72 |
| 3306 | Z2 | L4 | Q73 |
| 3307 | Z2 | L4 | Q74 |
| 3308 | Z2 | L4 | Q75 |
| 3309 | Z2 | L4 | Q76 |
| 3310 | Z2 | L4 | Q77 |
| 3311 | Z2 | L4 | Q78 |
| 3312 | Z2 | L4 | Q79 |
| 3313 | Z2 | L4 | Q80 |
| 3314 | Z2 | L4 | Q81 |
| 3315 | Z2 | L4 | Q82 |
| 3316 | Z2 | L4 | Q83 |
| 3317 | Z2 | L4 | Q84 |
| 3318 | Z2 | L4 | Q85 |
| 3319 | Z2 | L4 | Q86 |
| 3320 | Z2 | L4 | Q87 |
| 3321 | Z2 | L4 | Q88 |
| 3322 | Z2 | L4 | Q89 |
| 3323 | Z2 | L4 | Q90 |
| 3324 | Z2 | L4 | Q91 |
| 3325 | Z2 | L4 | Q92 |
| 3326 | Z2 | L4 | Q93 |
| 3327 | Z2 | L4 | Q94 |
| 3328 | Z2 | L4 | Q95 |
| 3329 | Z2 | L4 | Q96 |
| 3330 | Z2 | L4 | Q97 |
| 3331 | Z2 | L4 | Q98 |
| 3332 | Z2 | L4 | Q99 |
| 3333 | Z2 | L4 | Q100 |
| 3334 | Z2 | L4 | Q101 |
| 3335 | Z2 | L4 | Q102 |
| 3336 | Z2 | L4 | Q103 |
| 3337 | Z2 | L5 | Q40 |
| 3338 | Z2 | L5 | Q41 |
| 3339 | Z2 | L5 | Q42 |
| 3340 | Z2 | L5 | Q43 |
| 3341 | Z2 | L5 | Q44 |
| 3342 | Z2 | L5 | Q45 |
| 3343 | Z2 | L5 | Q46 |
| 3344 | Z2 | L5 | Q47 |
| 3345 | Z2 | L5 | Q48 |
| 3346 | Z2 | L5 | Q49 |
| 3347 | Z2 | L5 | Q50 |
| 3348 | Z2 | L5 | Q51 |
| 3349 | Z2 | L5 | Q52 |
| 3350 | Z2 | L5 | Q53 |
| 3351 | Z2 | L5 | Q54 |
| 3352 | Z2 | L5 | Q55 |
| 3353 | Z2 | L5 | Q56 |
| 3354 | Z2 | L5 | Q57 |
| 3355 | Z2 | L5 | Q58 |
| 3356 | Z2 | L5 | Q59 |
| 3357 | Z2 | L5 | Q60 |
| 3358 | Z2 | L5 | Q61 |
| 3359 | Z2 | L5 | Q62 |
| 3360 | Z2 | L5 | Q63 |
| 3361 | Z2 | L5 | Q64 |
| 3362 | Z2 | L5 | Q65 |
| 3363 | Z2 | L5 | Q66 |
| 3364 | Z2 | L5 | Q67 |
| 3365 | Z2 | L5 | Q68 |
| 3366 | Z2 | L5 | Q69 |
| 3367 | Z2 | L5 | Q70 |
| 3368 | Z2 | L5 | Q71 |
| 3369 | Z2 | L5 | Q72 |
| 3370 | Z2 | L5 | Q73 |

TABLE 1-22-continued

| | | | |
|---|---|---|---|
| 3371 | Z2 | L5 | Q74 |
| 3372 | Z2 | L5 | Q75 |
| 3373 | Z2 | L5 | Q76 |
| 3374 | Z2 | L5 | Q77 |
| 3375 | Z2 | L5 | Q78 |
| 3376 | Z2 | L5 | Q79 |
| 3377 | Z2 | L5 | Q80 |
| 3378 | Z2 | L5 | Q81 |
| 3379 | Z2 | L5 | Q82 |
| 3380 | Z2 | L5 | Q83 |
| 3381 | Z2 | L5 | Q84 |
| 3382 | Z2 | L5 | Q85 |
| 3383 | Z2 | L5 | Q86 |
| 3384 | Z2 | L5 | Q87 |
| 3385 | Z2 | L5 | Q88 |
| 3386 | Z2 | L5 | Q89 |
| 3387 | Z2 | L5 | Q90 |
| 3388 | Z2 | L5 | Q91 |
| 3389 | Z2 | L5 | Q92 |

TABLE 1-23

| | | | |
|---|---|---|---|
| 3390 | Z2 | L5 | Q93 |
| 3391 | Z2 | L5 | Q94 |
| 3392 | Z2 | L5 | Q95 |
| 3393 | Z2 | L5 | Q96 |
| 3394 | Z2 | L5 | Q97 |
| 3395 | Z2 | L5 | Q98 |
| 3396 | Z2 | L5 | Q99 |
| 3397 | Z2 | L5 | Q100 |
| 3398 | Z2 | L5 | Q101 |
| 3399 | Z2 | L5 | Q102 |
| 3400 | Z2 | L5 | Q103 |
| 3401 | Z2 | L6 | Q40 |
| 3402 | Z2 | L6 | Q41 |
| 3403 | Z2 | L5 | Q42 |
| 3404 | Z2 | L6 | Q43 |
| 3405 | Z2 | L6 | Q44 |
| 3406 | Z2 | L6 | Q45 |
| 3407 | Z2 | L6 | Q46 |
| 3408 | Z2 | L6 | Q47 |
| 3409 | Z2 | L6 | Q48 |
| 3410 | Z2 | L6 | Q49 |
| 3411 | Z2 | L6 | Q50 |
| 3412 | Z2 | L6 | Q51 |
| 3413 | Z2 | L6 | Q52 |
| 3414 | Z2 | L6 | Q53 |
| 3415 | Z2 | L6 | Q54 |
| 3416 | Z2 | L6 | Q55 |
| 3417 | Z2 | L6 | Q56 |
| 3418 | Z2 | L6 | Q57 |
| 3419 | Z2 | L6 | Q58 |
| 3420 | Z2 | L6 | Q59 |
| 3421 | Z2 | L6 | Q60 |
| 3422 | Z2 | L6 | Q61 |
| 3423 | Z2 | L6 | Q62 |
| 3424 | Z2 | L6 | Q63 |
| 3425 | Z2 | L6 | Q64 |
| 3426 | Z2 | L6 | Q65 |
| 3427 | Z2 | L6 | Q66 |
| 3428 | Z2 | L6 | Q67 |
| 3429 | Z2 | L6 | Q68 |
| 3430 | Z2 | L6 | Q69 |
| 3431 | Z2 | L6 | Q70 |
| 3432 | Z2 | L6 | Q71 |
| 3433 | Z2 | L6 | Q72 |
| 3434 | Z2 | L6 | Q73 |
| 3435 | Z2 | L6 | Q74 |
| 3436 | Z2 | L6 | Q75 |
| 3437 | Z2 | L6 | Q76 |
| 3438 | Z2 | L6 | Q77 |
| 3439 | Z2 | L6 | Q78 |
| 3440 | Z2 | L6 | Q79 |
| 3441 | Z2 | L6 | Q80 |
| 3442 | Z2 | L6 | Q81 |
| 3443 | Z2 | L6 | Q82 |
| 3444 | Z2 | L6 | Q83 |

TABLE 1-23-continued

| | | | |
|---|---|---|---|
| 3445 | Z2 | L6 | Q84 |
| 3446 | Z2 | L6 | Q85 |
| 3447 | Z2 | L6 | Q86 |
| 3448 | Z2 | L6 | Q87 |
| 3449 | Z2 | L6 | Q88 |
| 3450 | Z2 | L6 | Q89 |
| 3451 | Z2 | L6 | Q90 |
| 3452 | Z2 | L6 | Q91 |
| 3453 | Z2 | L6 | Q92 |
| 3454 | Z2 | L6 | Q93 |
| 3455 | Z2 | L6 | Q94 |
| 3456 | Z2 | L6 | Q95 |
| 3457 | Z2 | L6 | Q96 |
| 3458 | Z2 | L6 | Q97 |
| 3459 | Z2 | L6 | Q98 |
| 3460 | Z2 | L6 | Q99 |
| 3461 | Z2 | L6 | Q100 |
| 3462 | Z2 | L6 | Q101 |
| 3463 | Z2 | L6 | Q102 |
| 3464 | Z2 | L6 | Q103 |
| 3465 | Z2 | L7 | Q40 |
| 3466 | Z2 | L7 | Q41 |
| 3467 | Z2 | L7 | Q42 |
| 3468 | Z2 | L7 | Q43 |
| 3469 | Z2 | L7 | Q44 |
| 3470 | Z2 | L7 | Q45 |
| 3471 | Z2 | L7 | Q46 |
| 3472 | Z2 | L7 | Q47 |
| 3473 | Z2 | L7 | Q48 |
| 3474 | Z2 | L7 | Q49 |
| 3475 | Z2 | L7 | Q50 |
| 3476 | Z2 | L7 | Q51 |
| 3477 | Z2 | L7 | Q52 |
| 3478 | Z2 | L7 | Q53 |
| 3479 | Z2 | L7 | Q54 |
| 3480 | Z2 | L7 | Q55 |
| 3481 | Z2 | L7 | Q56 |
| 3482 | Z2 | L7 | Q57 |
| 3483 | Z2 | L7 | Q58 |
| 3484 | Z2 | L7 | Q59 |
| 3485 | Z2 | L7 | Q60 |
| 3486 | Z2 | L7 | Q61 |
| 3487 | Z2 | L7 | Q62 |
| 3488 | Z2 | L7 | Q63 |
| 3489 | Z2 | L7 | Q64 |
| 3490 | Z2 | L7 | Q65 |
| 3491 | Z2 | L7 | Q66 |
| 3492 | Z2 | L7 | Q67 |
| 3493 | Z2 | L7 | Q68 |
| 3494 | Z2 | L7 | Q69 |
| 3495 | Z2 | L7 | Q70 |
| 3496 | Z2 | L7 | Q71 |
| 3497 | Z2 | L7 | Q72 |
| 3498 | Z2 | L7 | Q73 |
| 3499 | Z2 | L7 | Q74 |
| 3500 | Z2 | L7 | Q75 |
| 3501 | Z2 | L7 | Q76 |
| 3502 | Z2 | L7 | Q77 |
| 3503 | Z2 | L7 | Q78 |
| 3504 | Z2 | L7 | Q79 |
| 3505 | Z2 | L7 | Q80 |
| 3506 | Z2 | L7 | Q81 |
| 3507 | Z2 | L7 | Q82 |
| 3508 | Z2 | L7 | Q83 |
| 3509 | Z2 | L7 | Q84 |
| 3510 | Z2 | L7 | Q85 |
| 3511 | Z2 | L7 | Q86 |
| 3512 | Z2 | L7 | Q87 |
| 3513 | Z2 | L7 | Q88 |
| 3514 | Z2 | L7 | Q89 |
| 3515 | Z2 | L7 | Q90 |
| 3516 | Z2 | L7 | Q91 |
| 3517 | Z2 | L7 | Q92 |
| 3518 | Z2 | L7 | Q93 |
| 3519 | Z2 | L7 | Q94 |
| 3520 | Z2 | L7 | Q95 |
| 3521 | Z2 | L7 | Q96 |
| 3522 | Z2 | L7 | Q97 |
| 3523 | Z2 | L7 | Q98 |
| 3524 | Z2 | L7 | Q99 |

TABLE 1-23-continued

| | | | |
|---|---|---|---|
| 3525 | Z2 | L7 | Q100 |
| 3526 | Z2 | L7 | Q101 |
| 3527 | Z2 | L7 | Q102 |
| 3528 | Z2 | L7 | Q103 |
| 3529 | Z2 | L8 | Q40 |
| 3530 | Z2 | L8 | Q41 |
| 3531 | Z2 | L8 | Q42 |
| 3532 | Z2 | L8 | Q43 |
| 3533 | Z2 | L8 | Q44 |
| 3534 | Z2 | L8 | Q45 |
| 3535 | Z2 | L8 | Q46 |
| 3536 | Z2 | L8 | Q47 |
| 3537 | Z2 | L8 | Q48 |
| 3538 | Z2 | L8 | Q49 |
| 3539 | Z2 | L8 | Q50 |
| 3540 | Z2 | L8 | Q51 |
| 3541 | Z2 | L8 | Q52 |
| 3542 | Z2 | L8 | Q53 |
| 3543 | Z2 | L8 | Q54 |
| 3544 | Z2 | L8 | Q55 |
| 3545 | Z2 | L8 | Q56 |
| 3546 | Z2 | L8 | Q57 |
| 3547 | Z2 | L8 | Q58 |
| 3548 | Z2 | L8 | Q59 |
| 3549 | Z2 | L8 | Q60 |
| 3550 | Z2 | L8 | Q61 |
| 3551 | Z2 | L8 | Q62 |
| 3552 | Z2 | L8 | Q63 |
| 3553 | Z2 | L8 | Q64 |
| 3554 | Z2 | L8 | Q65 |
| 3555 | Z2 | L8 | Q66 |
| 3556 | Z2 | L8 | Q67 |
| 3557 | Z2 | L8 | Q68 |
| 3558 | Z2 | L8 | Q69 |
| 3559 | Z2 | L8 | Q70 |
| 3560 | Z2 | L8 | Q71 |
| 3561 | Z2 | L8 | Q72 |
| 3562 | Z2 | L8 | Q73 |
| 3563 | Z2 | L8 | Q74 |
| 3564 | Z2 | L8 | Q75 |
| 3565 | Z2 | L8 | Q76 |
| 3566 | Z2 | L8 | Q77 |
| 3567 | Z2 | L8 | Q78 |
| 3568 | Z2 | L8 | Q79 |
| 3569 | Z2 | L8 | Q80 |
| 3570 | Z2 | L8 | Q81 |
| 3571 | Z2 | L8 | Q82 |
| 3572 | Z2 | L8 | Q83 |
| 3573 | Z2 | L8 | Q84 |
| 3574 | Z2 | L8 | Q85 |
| 3575 | Z2 | L8 | Q86 |
| 3576 | Z2 | L8 | Q87 |
| 3577 | Z2 | L8 | Q88 |
| 3578 | Z2 | L8 | Q89 |
| 3579 | Z2 | L8 | Q90 |
| 3580 | Z2 | L8 | Q91 |
| 3581 | Z2 | L8 | Q92 |
| 3582 | Z2 | L8 | Q93 |
| 3583 | Z2 | L8 | Q94 |
| 3584 | Z2 | L8 | Q95 |
| 3585 | Z2 | L8 | Q96 |
| 3586 | Z2 | L8 | Q97 |
| 3587 | Z2 | L8 | Q98 |
| 3588 | Z2 | L8 | Q99 |
| 3589 | Z2 | L8 | Q100 |
| 3590 | Z2 | L8 | Q101 |

TABLE 1-24

| | | | |
|---|---|---|---|
| 3591 | Z2 | L8 | Q102 |
| 3592 | Z2 | L8 | Q103 |
| 3593 | Z2 | L9 | Q40 |
| 3594 | Z2 | L9 | Q41 |
| 3595 | Z2 | L9 | Q42 |
| 3596 | Z2 | L9 | Q43 |
| 3597 | Z2 | L9 | Q44 |
| 3598 | Z2 | L9 | Q45 |

TABLE 1-24-continued

| | | | |
|---|---|---|---|
| 3599 | Z2 | L9 | Q46 |
| 3600 | Z2 | L9 | Q47 |
| 3601 | Z2 | L9 | Q48 |
| 3602 | Z2 | L9 | Q49 |
| 3603 | Z2 | L9 | Q50 |
| 3604 | Z2 | L9 | Q51 |
| 3605 | Z2 | L9 | Q52 |
| 3606 | Z2 | L9 | Q53 |
| 3607 | Z2 | L9 | Q54 |
| 3608 | Z2 | L9 | Q55 |
| 3609 | Z2 | L9 | Q56 |
| 3610 | Z2 | L9 | Q57 |
| 3611 | Z2 | L9 | Q58 |
| 3612 | Z2 | L9 | Q59 |
| 3613 | Z2 | L9 | Q60 |
| 3614 | Z2 | L9 | Q61 |
| 3615 | Z2 | L9 | Q62 |
| 3616 | Z2 | L9 | Q63 |
| 3617 | Z2 | L9 | Q64 |
| 3618 | Z2 | L9 | Q65 |
| 3619 | Z2 | L9 | Q66 |
| 3620 | Z2 | L9 | Q67 |
| 3621 | Z2 | L9 | Q68 |
| 3622 | Z2 | L9 | Q69 |
| 3623 | Z2 | L9 | Q70 |
| 3624 | Z2 | L9 | Q71 |
| 3625 | Z2 | L9 | Q72 |
| 3626 | Z2 | L9 | Q73 |
| 3627 | Z2 | L9 | Q74 |
| 3628 | Z2 | L9 | Q75 |
| 3629 | Z2 | L9 | Q76 |
| 3630 | Z2 | L9 | Q77 |
| 3631 | Z2 | L9 | Q78 |
| 3632 | Z2 | L9 | Q79 |
| 3633 | Z2 | L9 | Q80 |
| 3634 | Z2 | L9 | Q81 |
| 3635 | Z2 | L9 | Q82 |
| 3636 | Z2 | L9 | Q83 |
| 3637 | Z2 | L9 | Q84 |
| 3638 | Z2 | L9 | Q85 |
| 3639 | Z2 | L9 | Q86 |
| 3640 | Z2 | L9 | Q87 |
| 3641 | Z2 | L9 | Q88 |
| 3642 | Z2 | L9 | Q89 |
| 3643 | Z2 | L9 | Q90 |
| 3644 | Z2 | L9 | Q91 |
| 3645 | Z2 | L9 | Q92 |
| 3646 | Z2 | L9 | Q93 |
| 3647 | Z2 | L9 | Q94 |
| 3648 | Z2 | L9 | Q95 |
| 3649 | Z2 | L9 | Q96 |
| 3650 | Z2 | L9 | Q97 |
| 3651 | Z2 | L9 | Q98 |
| 3652 | Z2 | L9 | Q99 |
| 3653 | Z2 | L9 | Q100 |
| 3654 | Z2 | L9 | Q101 |
| 3655 | Z2 | L9 | Q102 |
| 3656 | Z2 | L9 | Q103 |
| 3657 | Z2 | L10 | Q40 |
| 3658 | Z2 | L10 | Q41 |
| 3659 | Z2 | L10 | Q42 |
| 3660 | Z2 | L10 | Q43 |
| 3661 | Z2 | L10 | Q44 |
| 3662 | Z2 | L10 | Q45 |
| 3663 | Z2 | L10 | Q46 |
| 3664 | Z2 | L10 | Q47 |
| 3665 | Z2 | L10 | Q48 |
| 3666 | Z2 | L10 | Q49 |
| 3667 | Z2 | L10 | Q50 |
| 3668 | Z2 | L10 | Q51 |
| 3669 | Z2 | L10 | Q52 |
| 3670 | Z2 | L10 | Q53 |
| 3671 | Z2 | L10 | Q54 |
| 3672 | Z2 | L10 | Q55 |
| 3673 | Z2 | L10 | Q56 |
| 3674 | Z2 | L10 | Q57 |
| 3675 | Z2 | L10 | Q58 |
| 3676 | Z2 | L10 | Q59 |
| 3677 | Z2 | L10 | Q60 |
| 3678 | Z2 | L10 | Q61 |

TABLE 1-24-continued

| | | | |
|---|---|---|---|
| 3679 | Z2 | L10 | Q62 |
| 3680 | Z2 | L10 | Q63 |
| 3681 | Z2 | L10 | Q64 |
| 3682 | Z2 | L10 | Q65 |
| 3683 | Z2 | L10 | Q66 |
| 3684 | Z2 | L10 | Q67 |
| 3685 | Z2 | L10 | Q68 |
| 3686 | Z2 | L10 | Q69 |
| 3687 | Z2 | L10 | Q70 |
| 3688 | Z2 | L10 | Q71 |
| 3689 | Z2 | L10 | Q72 |
| 3690 | Z2 | L10 | Q73 |
| 3691 | Z2 | L10 | Q74 |
| 3692 | Z2 | L10 | Q75 |
| 3693 | Z2 | L10 | Q76 |
| 3694 | Z2 | L10 | Q77 |
| 3695 | Z2 | L10 | Q78 |
| 3696 | Z2 | L10 | Q79 |
| 3697 | Z2 | L10 | Q80 |
| 3698 | Z2 | L10 | Q81 |
| 3699 | Z2 | L10 | Q82 |
| 3700 | Z2 | L10 | Q83 |
| 3701 | Z2 | L10 | Q84 |
| 3702 | Z2 | L10 | Q85 |
| 3703 | Z2 | L10 | Q86 |
| 3704 | Z2 | L10 | Q87 |
| 3705 | Z2 | L10 | Q88 |
| 3706 | Z2 | L10 | Q89 |
| 3707 | Z2 | L10 | Q90 |
| 3708 | Z2 | L10 | Q91 |
| 3709 | Z2 | L10 | Q92 |
| 3710 | Z2 | L10 | Q93 |
| 3711 | Z2 | L10 | Q94 |
| 3712 | Z2 | L10 | Q95 |
| 3713 | Z2 | L10 | Q96 |
| 3714 | Z2 | L10 | Q97 |
| 3715 | Z2 | L10 | Q98 |
| 3716 | Z2 | L10 | Q99 |
| 3717 | Z2 | L10 | Q100 |
| 3718 | Z2 | L10 | Q101 |
| 3719 | Z2 | L10 | Q102 |
| 3720 | Z2 | L10 | Q103 |
| 3721 | Z2 | L11 | Q40 |
| 3722 | Z2 | L11 | Q41 |
| 3723 | Z2 | L11 | Q42 |
| 3724 | Z2 | L11 | Q43 |
| 3725 | Z2 | L11 | Q44 |
| 3726 | Z2 | L11 | Q45 |
| 3727 | Z2 | L11 | Q46 |
| 3728 | Z2 | L11 | Q47 |
| 3729 | Z2 | L11 | Q48 |
| 3730 | Z2 | L11 | Q49 |
| 3731 | Z2 | L11 | Q50 |
| 3732 | Z2 | L11 | Q51 |
| 3733 | Z2 | L11 | Q52 |
| 3734 | Z2 | L11 | Q53 |
| 3735 | Z2 | L11 | Q54 |
| 3736 | Z2 | L11 | Q55 |
| 3737 | Z2 | L11 | Q56 |
| 3738 | Z2 | L11 | Q57 |
| 3739 | Z2 | L11 | Q58 |
| 3740 | Z2 | L11 | Q59 |
| 3741 | Z2 | L11 | Q60 |
| 3742 | Z2 | L11 | Q61 |
| 3743 | Z2 | L11 | Q62 |
| 3744 | Z2 | L11 | Q63 |
| 3745 | Z2 | L11 | Q64 |
| 3746 | Z2 | L11 | Q65 |
| 3747 | Z2 | L11 | Q66 |
| 3748 | Z2 | L11 | Q67 |
| 3749 | Z2 | L11 | Q68 |
| 3750 | Z2 | L11 | Q69 |
| 3751 | Z2 | L11 | Q70 |
| 3752 | Z2 | L11 | Q71 |
| 3753 | Z2 | L11 | Q72 |
| 3754 | Z2 | L11 | Q73 |
| 3755 | Z2 | L11 | Q74 |
| 3756 | Z2 | L11 | Q75 |
| 3757 | Z2 | L11 | Q76 |
| 3758 | Z2 | L11 | Q77 |
| 3759 | Z2 | L11 | Q78 |
| 3760 | Z2 | L11 | Q79 |
| 3761 | Z2 | L11 | Q80 |
| 3762 | Z2 | L11 | Q81 |
| 3763 | Z2 | L11 | Q82 |
| 3764 | Z2 | L11 | Q83 |
| 3765 | Z2 | L11 | Q84 |
| 3766 | Z2 | L11 | Q85 |
| 3767 | Z2 | L11 | Q86 |
| 3768 | Z2 | L11 | Q87 |
| 3769 | Z2 | L11 | Q88 |
| 3770 | Z2 | L11 | Q89 |
| 3771 | Z2 | L11 | Q90 |
| 3772 | Z2 | L11 | Q91 |
| 3773 | Z2 | L11 | Q92 |
| 3774 | Z2 | L11 | Q93 |
| 3775 | Z2 | L11 | Q94 |
| 3776 | Z2 | L11 | Q95 |
| 3777 | Z2 | L11 | Q96 |
| 3778 | Z2 | L11 | Q97 |
| 3779 | Z2 | L11 | Q98 |
| 3780 | Z2 | L11 | Q99 |
| 3781 | Z2 | L11 | Q100 |
| 3782 | Z2 | L11 | Q101 |
| 3783 | Z2 | L11 | Q102 |
| 3784 | Z2 | L11 | Q103 |
| 3785 | Z2 | L12 | Q40 |
| 3786 | Z2 | L12 | Q41 |
| 3787 | Z2 | L12 | Q42 |
| 3788 | Z2 | L12 | Q43 |
| 3789 | Z2 | L12 | Q44 |
| 3790 | Z2 | L12 | Q45 |
| 3791 | Z2 | L12 | Q46 |

TABLE 1-25

| | | | |
|---|---|---|---|
| 3792 | Z2 | L12 | Q47 |
| 3793 | Z2 | L12 | Q48 |
| 3794 | Z2 | L12 | Q49 |
| 3795 | Z2 | L12 | Q50 |
| 3796 | Z2 | L12 | Q51 |
| 3797 | Z2 | L12 | Q52 |
| 3798 | Z2 | L12 | Q53 |
| 3799 | Z2 | L12 | Q54 |
| 3800 | Z2 | L12 | Q55 |
| 3801 | Z2 | L12 | Q56 |
| 3802 | Z2 | L12 | Q57 |
| 3803 | Z2 | L12 | Q58 |
| 3804 | Z2 | L12 | Q59 |
| 3805 | Z2 | L12 | Q60 |
| 3806 | Z2 | L12 | Q61 |
| 3807 | Z2 | L12 | Q62 |
| 3808 | Z2 | L12 | Q63 |
| 3809 | Z2 | L12 | Q64 |
| 3810 | Z2 | L12 | Q65 |
| 3811 | Z2 | L12 | Q66 |
| 3812 | Z2 | L12 | Q67 |
| 3813 | Z2 | L12 | Q68 |
| 3814 | Z2 | L12 | Q69 |
| 3815 | Z2 | L12 | Q70 |
| 3816 | Z2 | L12 | Q71 |
| 3817 | Z2 | L12 | Q72 |
| 3818 | Z2 | L12 | Q73 |
| 3819 | Z2 | L12 | Q74 |
| 3820 | Z2 | L12 | Q75 |
| 3821 | Z2 | L12 | Q76 |
| 3822 | Z2 | L12 | Q77 |
| 3823 | Z2 | L12 | Q78 |
| 3824 | Z2 | L12 | Q79 |
| 3825 | Z2 | L12 | Q80 |
| 3826 | Z2 | L12 | Q81 |
| 3827 | Z2 | L12 | Q82 |
| 3828 | Z2 | L12 | Q83 |
| 3829 | Z2 | L12 | Q84 |
| 3830 | Z2 | L12 | Q85 |
| 3831 | Z2 | L12 | Q86 |
| 3832 | Z2 | L12 | Q87 |

TABLE 1-25-continued

| | | | |
|---|---|---|---|
| 3833 | Z2 | L12 | Q88 |
| 3834 | Z2 | L12 | Q89 |
| 3835 | Z2 | L12 | Q90 |
| 3836 | Z2 | L12 | Q91 |
| 3837 | Z2 | L12 | Q92 |
| 3838 | Z2 | L12 | Q93 |
| 3839 | Z2 | LI2 | Q94 |
| 3840 | Z2 | L12 | Q95 |
| 3841 | Z2 | L12 | Q96 |
| 3842 | Z2 | L12 | Q97 |
| 3843 | Z2 | L12 | Q98 |
| 3844 | Z2 | L12 | Q99 |
| 3845 | Z2 | L12 | Q100 |
| 3846 | Z2 | L12 | Q101 |
| 3847 | Z2 | L12 | Q102 |
| 3848 | Z2 | L12 | Q103 |
| 3849 | Z2 | L13 | Q40 |
| 3850 | Z2 | L13 | Q41 |
| 3851 | Z2 | L13 | Q42 |
| 3852 | Z2 | L13 | Q43 |
| 3853 | Z2 | L13 | Q44 |
| 3854 | Z2 | L13 | Q45 |
| 3855 | Z2 | L13 | Q46 |
| 3856 | Z2 | L13 | Q47 |
| 3857 | Z2 | L13 | Q48 |
| 3858 | Z2 | L13 | Q49 |
| 3859 | Z2 | L13 | Q50 |
| 3860 | Z2 | L13 | Q51 |
| 3861 | Z2 | L13 | Q52 |
| 3862 | Z2 | L13 | Q53 |
| 3863 | Z2 | L13 | Q54 |
| 3864 | Z2 | L13 | Q55 |
| 3865 | Z2 | L13 | Q56 |
| 3866 | Z2 | L13 | Q57 |
| 3867 | Z2 | L13 | Q58 |
| 3868 | Z2 | L13 | Q59 |
| 3869 | Z2 | L13 | Q60 |
| 3870 | Z2 | L13 | Q61 |
| 3871 | Z2 | L13 | Q62 |
| 3872 | Z2 | L13 | Q63 |
| 3873 | Z2 | L13 | Q64 |
| 3874 | Z2 | L13 | Q65 |
| 3875 | Z2 | L13 | Q66 |
| 3876 | Z2 | L13 | Q67 |
| 3877 | Z2 | L13 | Q68 |
| 3878 | Z2 | L13 | Q69 |
| 3879 | Z2 | L13 | Q70 |
| 3880 | Z2 | L13 | Q71 |
| 3881 | Z2 | L13 | Q72 |
| 3882 | Z2 | L13 | Q73 |
| 3883 | Z2 | L13 | Q74 |
| 3884 | Z2 | L13 | Q75 |
| 3885 | Z2 | L13 | Q76 |
| 3886 | Z2 | L13 | Q77 |
| 3887 | Z2 | L13 | Q78 |
| 3888 | Z2 | L13 | Q79 |
| 3889 | Z2 | L13 | Q80 |
| 3890 | Z2 | L13 | Q81 |
| 3891 | Z2 | L13 | Q82 |
| 3892 | Z2 | L13 | Q83 |
| 3893 | Z2 | L13 | Q84 |
| 3894 | Z2 | L13 | Q85 |
| 3895 | Z2 | L13 | Q86 |
| 3896 | Z2 | L13 | Q87 |
| 3897 | Z2 | L13 | Q88 |
| 3898 | Z2 | L13 | Q89 |
| 3899 | Z2 | L13 | Q90 |
| 3900 | Z2 | L13 | Q91 |
| 3901 | Z2 | L13 | Q92 |
| 3902 | Z2 | L13 | Q93 |
| 3903 | Z2 | L13 | Q94 |
| 3904 | Z2 | L13 | Q95 |
| 3905 | Z2 | L13 | Q96 |
| 3906 | Z2 | L13 | Q97 |
| 3907 | Z2 | L13 | Q98 |
| 3908 | Z2 | L13 | Q99 |
| 3909 | Z2 | L13 | Q100 |
| 3910 | Z2 | L13 | Q101 |
| 3911 | Z2 | L13 | Q102 |
| 3912 | Z2 | L13 | Q103 |
| 3913 | Z2 | L14 | Q40 |
| 3914 | Z2 | L14 | Q41 |
| 3915 | Z2 | L14 | Q42 |
| 3916 | Z2 | L14 | Q43 |
| 3917 | Z2 | L14 | Q44 |
| 3918 | Z2 | L14 | Q45 |
| 3919 | Z2 | L14 | Q46 |
| 3920 | Z2 | L14 | Q47 |
| 3921 | Z2 | L14 | Q48 |
| 3922 | Z2 | L14 | Q49 |
| 3923 | Z2 | L14 | Q50 |
| 3924 | Z2 | L14 | Q51 |
| 3925 | Z2 | L14 | Q52 |
| 3926 | Z2 | L14 | Q53 |
| 3927 | Z2 | L14 | Q54 |
| 3928 | Z2 | L14 | Q55 |
| 3929 | Z2 | L14 | Q56 |
| 3930 | Z2 | L14 | Q57 |
| 3931 | Z2 | L14 | Q58 |
| 3932 | Z2 | L14 | Q59 |
| 3933 | Z2 | L14 | Q60 |
| 3934 | Z2 | L14 | Q61 |
| 3935 | Z2 | L14 | Q62 |
| 3936 | Z2 | L14 | Q63 |
| 3937 | Z2 | L14 | Q64 |
| 3938 | Z2 | L14 | Q65 |
| 3939 | Z2 | L14 | Q66 |
| 3940 | Z2 | L14 | Q67 |
| 3941 | Z2 | L14 | Q68 |
| 3942 | Z2 | L14 | Q69 |
| 3943 | Z2 | L14 | Q70 |
| 3944 | Z2 | L14 | Q71 |
| 3945 | Z2 | L14 | Q72 |
| 3946 | Z2 | L14 | Q73 |
| 3947 | Z2 | L14 | Q74 |
| 3948 | Z2 | L14 | Q75 |
| 3949 | Z2 | L14 | Q76 |
| 3950 | Z2 | L14 | Q77 |
| 3951 | Z2 | L14 | Q78 |
| 3952 | Z2 | L14 | Q79 |
| 3953 | Z2 | L14 | Q80 |
| 3954 | Z2 | L14 | Q81 |
| 3955 | Z2 | L14 | Q82 |
| 3956 | Z2 | L14 | Q83 |
| 3957 | Z2 | L14 | Q84 |
| 3958 | Z2 | L14 | Q85 |
| 3959 | Z2 | L14 | Q86 |
| 3960 | Z2 | L14 | Q87 |
| 3961 | Z2 | L14 | Q88 |
| 3962 | Z2 | L14 | Q89 |
| 3963 | Z2 | L14 | Q90 |
| 3964 | Z2 | L14 | Q91 |
| 3965 | Z2 | L14 | Q92 |
| 3966 | Z2 | L14 | Q93 |
| 3967 | Z2 | L14 | Q94 |
| 3968 | Z2 | L14 | Q95 |
| 3969 | Z2 | L14 | Q96 |
| 3970 | Z2 | L14 | Q97 |
| 3971 | Z2 | L14 | Q98 |
| 3972 | Z2 | L14 | Q99 |
| 3973 | Z2 | L14 | Q100 |
| 3974 | Z2 | L14 | Q101 |
| 3975 | Z2 | L14 | Q102 |
| 3976 | Z2 | L14 | Q103 |
| 3977 | Z3 | L1 | Q40 |
| 3978 | Z3 | L1 | Q41 |
| 3979 | Z3 | L1 | Q42 |
| 3980 | Z3 | L1 | Q43 |
| 3981 | Z3 | L1 | Q44 |
| 3982 | Z3 | L1 | Q45 |
| 3983 | Z3 | L1 | Q46 |
| 3984 | Z3 | L1 | Q47 |
| 3985 | Z3 | L1 | Q48 |
| 3986 | Z3 | L1 | Q49 |
| 3987 | Z3 | L1 | Q50 |
| 3988 | Z3 | L1 | Q51 |
| 3989 | Z3 | L1 | Q52 |

TABLE 1-25-continued

| | | | |
|---|---|---|---|
| 3990 | Z3 | L1 | Q53 |
| 3991 | Z3 | L1 | Q54 |
| 3992 | Z3 | L1 | Q55 |

TABLE 1-26

| | | | |
|---|---|---|---|
| 3993 | Z3 | L1 | Q56 |
| 3994 | Z3 | L1 | Q57 |
| 3995 | Z3 | L1 | Q58 |
| 3996 | Z3 | L1 | Q59 |
| 3997 | Z3 | L1 | Q60 |
| 3998 | Z3 | L1 | Q61 |
| 3999 | Z3 | L1 | Q62 |
| 4000 | Z3 | L1 | Q63 |
| 4001 | Z3 | L1 | Q64 |
| 4002 | Z3 | L1 | Q65 |
| 4003 | Z3 | L1 | Q66 |
| 4004 | Z3 | L1 | Q67 |
| 4005 | Z3 | L1 | Q68 |
| 4006 | Z3 | L1 | Q69 |
| 4007 | Z3 | L1 | Q70 |
| 4008 | Z3 | L1 | Q71 |
| 4009 | Z3 | L1 | Q72 |
| 4010 | Z3 | L1 | Q73 |
| 4011 | Z3 | L1 | Q74 |
| 4012 | Z3 | L1 | Q75 |
| 4013 | Z3 | L1 | Q76 |
| 4014 | Z3 | L1 | Q77 |
| 4015 | Z3 | L1 | Q78 |
| 4016 | Z3 | L1 | Q79 |
| 4017 | Z3 | L1 | Q80 |
| 4018 | Z3 | L1 | Q81 |
| 4019 | Z3 | L1 | Q82 |
| 4020 | Z3 | L1 | Q83 |
| 4021 | Z3 | L1 | Q84 |
| 4022 | Z3 | L1 | Q85 |
| 4023 | Z3 | L1 | Q86 |
| 4024 | Z3 | L1 | Q87 |
| 4025 | Z3 | L1 | Q88 |
| 4026 | Z3 | L1 | Q89 |
| 4027 | Z3 | L1 | Q90 |
| 4028 | Z3 | L1 | Q91 |
| 4029 | Z3 | L1 | Q92 |
| 4030 | Z3 | L1 | Q93 |
| 4031 | Z3 | L1 | Q94 |
| 4032 | Z3 | L1 | Q95 |
| 4033 | Z3 | L1 | Q96 |
| 4034 | Z3 | L1 | Q97 |
| 4035 | Z3 | L1 | Q98 |
| 4036 | Z3 | L1 | Q99 |
| 4037 | Z3 | L1 | Q100 |
| 4038 | Z3 | L1 | Q101 |
| 4039 | Z3 | L1 | Q102 |
| 4040 | Z3 | L1 | Q103 |
| 4041 | Z3 | L2 | Q40 |
| 4042 | Z3 | L2 | Q41 |
| 4043 | Z3 | L2 | Q42 |
| 4044 | Z3 | L2 | Q43 |
| 4045 | Z3 | L2 | Q44 |
| 4046 | Z3 | L2 | Q45 |
| 4047 | Z3 | L2 | Q46 |
| 4048 | Z3 | L2 | Q47 |
| 4049 | Z3 | L2 | Q48 |
| 4050 | Z3 | L2 | Q49 |
| 4051 | Z3 | L2 | Q50 |
| 4052 | Z3 | L2 | Q51 |
| 4053 | Z3 | L2 | Q52 |
| 4054 | Z3 | L2 | Q53 |
| 4055 | Z3 | L2 | Q54 |
| 4056 | Z3 | L2 | Q55 |
| 4057 | Z3 | L2 | Q56 |
| 4058 | Z3 | L2 | Q57 |
| 4059 | Z3 | L2 | Q58 |
| 4060 | Z3 | L2 | Q59 |
| 4061 | Z3 | L2 | Q60 |
| 4062 | Z3 | L2 | Q61 |
| 4063 | Z3 | L2 | Q62 |

TABLE 1-26-continued

| | | | |
|---|---|---|---|
| 4064 | Z3 | L2 | Q63 |
| 4065 | Z3 | L2 | Q64 |
| 4066 | Z3 | L2 | Q65 |
| 4067 | Z3 | L2 | Q66 |
| 4068 | Z3 | L2 | Q67 |
| 4069 | Z3 | L2 | Q68 |
| 4070 | Z3 | L2 | Q69 |
| 4071 | Z3 | L2 | Q70 |
| 4072 | Z3 | L2 | Q71 |
| 4073 | Z3 | L2 | Q72 |
| 4074 | Z3 | L2 | Q73 |
| 4075 | Z3 | L2 | Q74 |
| 4076 | Z3 | L2 | Q75 |
| 4077 | Z3 | L2 | Q76 |
| 4078 | Z3 | L2 | Q77 |
| 4079 | Z3 | L2 | Q78 |
| 4080 | Z3 | L2 | Q79 |
| 4081 | Z3 | L2 | Q80 |
| 4082 | Z3 | L2 | Q81 |
| 4083 | Z3 | L2 | Q82 |
| 4084 | Z3 | L2 | Q83 |
| 4085 | Z3 | L2 | Q84 |
| 4086 | Z3 | L2 | Q85 |
| 4087 | Z3 | L2 | Q86 |
| 4088 | Z3 | L2 | Q87 |
| 4089 | Z3 | L2 | Q88 |
| 4090 | Z3 | L2 | Q89 |
| 4091 | Z3 | L2 | Q90 |
| 4092 | Z3 | L2 | Q91 |
| 4093 | Z3 | L2 | Q92 |
| 4094 | Z3 | L2 | Q93 |
| 4095 | Z3 | L2 | Q94 |
| 4096 | Z3 | L2 | Q95 |
| 4097 | Z3 | L2 | Q96 |
| 4098 | Z3 | L2 | Q97 |
| 4099 | Z3 | L2 | Q98 |
| 4100 | Z3 | L2 | Q99 |
| 4101 | Z3 | L2 | Q100 |
| 4102 | Z3 | L2 | Q101 |
| 4103 | Z3 | L2 | Q102 |
| 4104 | Z3 | L2 | Q103 |
| 4105 | Z3 | L3 | Q40 |
| 4106 | Z3 | L3 | Q41 |
| 4107 | Z3 | L3 | Q42 |
| 4108 | Z3 | L3 | Q43 |
| 4109 | Z3 | L3 | Q44 |
| 4110 | Z3 | L3 | Q45 |
| 4111 | Z3 | L3 | Q46 |
| 4112 | Z3 | L3 | Q47 |
| 4113 | Z3 | L3 | Q48 |
| 4114 | Z3 | L3 | Q49 |
| 4115 | Z3 | L3 | Q50 |
| 4116 | Z3 | L3 | Q51 |
| 4117 | Z3 | L3 | Q52 |
| 4118 | Z3 | L3 | Q53 |
| 4119 | Z3 | L3 | Q54 |
| 4120 | Z3 | L3 | Q55 |
| 4121 | Z3 | L3 | Q56 |
| 4122 | Z3 | L3 | Q57 |
| 4123 | Z3 | L3 | Q58 |
| 4124 | Z3 | L3 | Q59 |
| 4125 | Z3 | L3 | Q60 |
| 4126 | Z3 | L3 | Q61 |
| 4127 | Z3 | L3 | Q62 |
| 4128 | Z3 | L3 | Q63 |
| 4129 | 73 | L3 | Q64 |
| 4130 | Z3 | L3 | Q65 |
| 4131 | Z3 | L3 | Q66 |
| 4132 | Z3 | L3 | Q67 |
| 4133 | Z3 | L3 | Q68 |
| 4134 | Z3 | L3 | Q69 |
| 4135 | Z3 | L3 | Q70 |
| 4136 | Z3 | L3 | Q71 |
| 4137 | Z3 | L3 | Q72 |
| 4138 | Z3 | L3 | Q73 |
| 4139 | Z3 | L3 | Q74 |
| 4140 | Z3 | L3 | Q75 |
| 4141 | Z3 | L3 | Q76 |
| 4142 | Z3 | L3 | Q77 |
| 4143 | Z3 | L3 | Q78 |

TABLE 1-26-continued

| | | | |
|---|---|---|---|
| 4144 | Z3 | L3 | Q79 |
| 4145 | Z3 | L3 | Q80 |
| 4146 | Z3 | L3 | Q81 |
| 4147 | Z3 | L3 | Q82 |
| 4148 | Z3 | L3 | Q83 |
| 4149 | Z3 | L3 | Q84 |
| 4150 | Z3 | L3 | Q85 |
| 4151 | Z3 | L3 | Q86 |
| 4152 | Z3 | L3 | Q87 |
| 4153 | Z3 | L3 | Q88 |
| 4154 | Z3 | L3 | Q89 |
| 4155 | Z3 | L3 | Q90 |
| 4156 | Z3 | L3 | Q91 |
| 4157 | Z3 | L3 | Q92 |
| 4158 | Z3 | L3 | Q93 |
| 4159 | Z3 | L3 | Q94 |
| 4160 | Z3 | L3 | Q95 |
| 4161 | Z3 | L3 | Q96 |
| 4162 | Z3 | L3 | Q97 |
| 4163 | Z3 | L3 | Q98 |
| 4164 | Z3 | L3 | Q99 |
| 4165 | Z3 | L3 | Q100 |
| 4166 | Z3 | L3 | Q101 |
| 4167 | Z3 | L3 | Q102 |
| 4168 | Z3 | L3 | Q103 |
| 4169 | Z3 | L4 | Q40 |
| 4170 | Z3 | L4 | Q41 |
| 4171 | Z3 | L4 | Q42 |
| 4172 | Z3 | L4 | Q43 |
| 4173 | Z3 | L4 | Q44 |
| 4174 | Z3 | L4 | Q45 |
| 4175 | Z3 | L4 | Q46 |
| 4176 | Z3 | L4 | Q47 |
| 4177 | Z3 | L4 | Q48 |
| 4178 | Z3 | L4 | Q49 |
| 4179 | Z3 | L4 | Q50 |
| 4180 | Z3 | L4 | Q51 |
| 4181 | Z3 | L4 | Q52 |
| 4182 | Z3 | L4 | Q53 |
| 4183 | Z3 | L4 | Q54 |
| 4184 | Z3 | L4 | Q55 |
| 4185 | Z3 | L4 | Q56 |
| 4186 | Z3 | L4 | Q57 |
| 4187 | Z3 | L4 | Q58 |
| 4188 | Z3 | L4 | Q59 |
| 4189 | Z3 | L4 | Q60 |
| 4190 | Z3 | L4 | Q61 |
| 4191 | Z3 | L4 | Q62 |
| 4192 | Z3 | L4 | Q63 |
| 4193 | Z3 | L4 | Q64 |

TABLE 1-27

| | | | |
|---|---|---|---|
| 4194 | Z3 | L4 | Q65 |
| 4195 | Z3 | L4 | Q66 |
| 4196 | Z3 | L4 | Q67 |
| 4197 | Z3 | L4 | Q68 |
| 4198 | Z3 | L4 | Q69 |
| 4199 | Z3 | L4 | Q70 |
| 4200 | Z3 | L4 | Q71 |
| 4201 | Z3 | L4 | Q72 |
| 4202 | Z3 | L4 | Q73 |
| 4203 | Z3 | L4 | Q74 |
| 4204 | Z3 | L4 | Q75 |
| 4205 | Z3 | L4 | Q76 |
| 4206 | Z3 | L4 | Q77 |
| 4207 | Z3 | L4 | Q78 |
| 4208 | Z3 | L4 | Q79 |
| 4209 | Z3 | L4 | Q80 |
| 4210 | Z3 | L4 | Q81 |
| 4211 | Z3 | L4 | Q82 |
| 4212 | Z3 | L4 | Q83 |
| 4213 | Z3 | L4 | Q84 |
| 4214 | Z3 | L4 | Q85 |
| 4215 | Z3 | L4 | Q86 |
| 4216 | Z3 | L4 | Q87 |
| 4217 | Z3 | L4 | Q88 |

TABLE 1-27-continued

| | | | |
|---|---|---|---|
| 4218 | Z3 | L4 | Q89 |
| 4219 | Z3 | L4 | Q90 |
| 4220 | Z3 | L4 | Q91 |
| 4221 | Z3 | L4 | Q92 |
| 4222 | Z3 | L4 | Q93 |
| 4223 | Z3 | L4 | Q94 |
| 4224 | Z3 | L4 | Q95 |
| 4225 | Z3 | L4 | Q96 |
| 4226 | Z3 | L4 | Q97 |
| 4227 | Z3 | L4 | Q98 |
| 4228 | Z3 | L4 | Q99 |
| 4229 | Z3 | L4 | Q100 |
| 4230 | Z3 | L4 | Q101 |
| 4231 | Z3 | L4 | Q102 |
| 4232 | Z3 | L4 | Q103 |
| 4233 | Z3 | L5 | Q40 |
| 4234 | Z3 | L5 | Q41 |
| 4235 | Z3 | L5 | Q42 |
| 4236 | Z3 | L5 | Q43 |
| 4237 | Z3 | L5 | Q44 |
| 4238 | Z3 | L5 | Q45 |
| 4239 | Z3 | L5 | Q46 |
| 4240 | Z3 | L5 | Q47 |
| 4241 | Z3 | L5 | Q48 |
| 4242 | Z3 | L5 | Q49 |
| 4243 | Z3 | L5 | Q50 |
| 4244 | Z3 | L5 | Q51 |
| 4245 | Z3 | L5 | Q52 |
| 4246 | Z3 | L5 | Q53 |
| 4247 | Z3 | L5 | Q54 |
| 4248 | Z3 | L5 | Q55 |
| 4249 | Z3 | L5 | Q56 |
| 4250 | Z3 | L5 | Q57 |
| 4251 | Z3 | L5 | Q58 |
| 4252 | Z3 | L5 | Q59 |
| 4253 | Z3 | L5 | Q60 |
| 4254 | Z3 | L5 | Q61 |
| 4255 | Z3 | L5 | Q62 |
| 4256 | Z3 | L5 | Q63 |
| 4257 | Z3 | L5 | Q64 |
| 4258 | Z3 | L5 | Q65 |
| 4259 | Z3 | L5 | Q66 |
| 4260 | Z3 | L5 | Q67 |
| 4261 | Z3 | L5 | Q68 |
| 4262 | Z3 | L5 | Q69 |
| 4263 | Z3 | L5 | Q70 |
| 4264 | Z3 | L5 | Q71 |
| 4265 | Z3 | L5 | Q72 |
| 4266 | Z3 | L5 | Q73 |
| 4267 | Z3 | L5 | Q74 |
| 4268 | Z3 | L5 | Q75 |
| 4269 | Z3 | L5 | Q76 |
| 4270 | Z3 | L5 | Q77 |
| 4271 | Z3 | L5 | Q78 |
| 4272 | Z3 | L5 | Q79 |
| 4273 | Z3 | L5 | Q80 |
| 4274 | Z3 | L5 | Q81 |
| 4275 | Z3 | L5 | Q82 |
| 4276 | Z3 | L5 | Q83 |
| 4277 | Z3 | L5 | Q84 |
| 4278 | Z3 | L5 | Q85 |
| 4279 | Z3 | L5 | Q86 |
| 4280 | Z3 | L5 | Q87 |
| 4281 | Z3 | L5 | Q88 |
| 4282 | Z3 | L5 | Q89 |
| 4283 | Z3 | L5 | Q90 |
| 4284 | Z3 | L5 | Q91 |
| 4285 | Z3 | L5 | Q92 |
| 4286 | Z3 | L5 | Q93 |
| 4287 | Z3 | L5 | Q94 |
| 4288 | Z3 | L5 | Q95 |
| 4289 | Z3 | L5 | Q96 |
| 4290 | Z3 | L5 | Q97 |
| 4291 | Z3 | L5 | Q98 |
| 4292 | Z3 | L5 | Q99 |
| 4293 | Z3 | L5 | Q100 |
| 4294 | Z3 | L5 | Q101 |
| 4295 | Z3 | L5 | Q102 |
| 4296 | Z3 | L5 | Q103 |
| 4297 | Z3 | L6 | Q40 |

TABLE 1-27-continued

| | | | |
|---|---|---|---|
| 4298 | Z3 | L6 | Q41 |
| 4299 | Z3 | L6 | Q42 |
| 4300 | Z3 | L6 | Q43 |
| 4301 | Z3 | L6 | Q44 |
| 4302 | Z3 | L6 | Q45 |
| 4303 | Z3 | L6 | Q46 |
| 4304 | Z3 | L6 | Q47 |
| 4305 | Z3 | L6 | Q48 |
| 4306 | Z3 | L6 | Q49 |
| 4307 | Z3 | L6 | Q50 |
| 4308 | Z3 | L6 | Q51 |
| 4309 | Z3 | L6 | Q52 |
| 4310 | Z3 | L6 | Q53 |
| 4311 | Z3 | L6 | Q54 |
| 4312 | Z3 | L6 | Q55 |
| 4313 | Z3 | L6 | Q56 |
| 4314 | Z3 | L6 | Q57 |
| 4315 | Z3 | L6 | Q58 |
| 4316 | Z3 | L6 | Q59 |
| 4317 | Z3 | L6 | Q60 |
| 4318 | Z3 | L6 | Q61 |
| 4319 | Z3 | L6 | Q62 |
| 4320 | Z3 | L6 | Q63 |
| 4321 | Z3 | L6 | Q64 |
| 4322 | Z3 | L6 | Q65 |
| 4323 | Z3 | L6 | Q66 |
| 4324 | Z3 | L6 | Q67 |
| 4325 | Z3 | L6 | Q68 |
| 4326 | Z3 | L6 | Q69 |
| 4327 | Z3 | L6 | Q70 |
| 4328 | Z3 | L6 | Q71 |
| 4329 | Z3 | L6 | Q72 |
| 4330 | Z3 | L6 | Q73 |
| 4331 | Z3 | L6 | Q74 |
| 4332 | Z3 | L6 | Q75 |
| 4333 | Z3 | L6 | Q76 |
| 4334 | Z3 | L6 | Q77 |
| 4335 | Z3 | L6 | Q78 |
| 4336 | Z3 | L6 | Q79 |
| 4337 | Z3 | L6 | Q80 |
| 4338 | Z3 | L6 | Q81 |
| 4339 | Z3 | L6 | Q82 |
| 4340 | Z3 | L6 | Q83 |
| 4341 | Z3 | L6 | Q84 |
| 4342 | Z3 | L6 | Q85 |
| 4343 | Z3 | L6 | Q86 |
| 4344 | Z3 | L6 | Q87 |
| 4345 | Z3 | L6 | Q88 |
| 4346 | Z3 | L6 | Q89 |
| 4347 | Z3 | L6 | Q90 |
| 4348 | Z3 | L6 | Q91 |
| 4349 | Z3 | L6 | Q92 |
| 4350 | Z3 | L6 | Q93 |
| 4351 | Z3 | L6 | Q94 |
| 4352 | Z3 | L6 | Q95 |
| 4353 | Z3 | L6 | Q96 |
| 4354 | Z3 | L6 | Q97 |
| 4355 | Z3 | L6 | Q98 |
| 4356 | Z3 | L6 | Q99 |
| 4357 | Z3 | L6 | Q100 |
| 4358 | Z3 | L6 | Q101 |
| 4359 | Z3 | L6 | Q102 |
| 4360 | Z3 | L6 | Q103 |
| 4361 | Z3 | L7 | Q40 |
| 4362 | Z3 | L7 | Q41 |
| 4363 | Z3 | L7 | Q42 |
| 4364 | Z3 | L7 | Q43 |
| 4365 | Z3 | L7 | Q44 |
| 4366 | Z3 | L7 | Q45 |
| 4367 | Z3 | L7 | Q46 |
| 4368 | Z3 | L7 | Q47 |
| 4369 | Z3 | L7 | Q48 |
| 4370 | Z3 | L7 | Q49 |
| 4371 | Z3 | L7 | Q50 |
| 4372 | Z3 | L7 | Q51 |
| 4373 | Z3 | L7 | Q52 |
| 4374 | Z3 | L7 | Q53 |
| 4375 | Z3 | L7 | Q54 |
| 4376 | Z3 | L7 | Q55 |
| 4377 | Z3 | L7 | Q56 |
| 4378 | Z3 | L7 | Q57 |
| 4379 | Z3 | L7 | Q58 |
| 4380 | Z3 | L7 | Q59 |
| 4381 | Z3 | L7 | Q60 |
| 4382 | Z3 | L7 | Q61 |
| 4383 | Z3 | L7 | Q62 |
| 4384 | Z3 | L7 | Q63 |
| 4385 | Z3 | L7 | Q64 |
| 4386 | Z3 | L7 | Q65 |
| 4387 | Z3 | L7 | Q66 |
| 4388 | Z3 | L7 | Q67 |
| 4389 | Z3 | L7 | Q68 |
| 4390 | Z3 | L7 | Q69 |
| 4391 | Z3 | L7 | Q70 |
| 4392 | Z3 | L7 | Q71 |
| 4393 | Z3 | L7 | Q72 |
| 4394 | Z3 | L7 | Q73 |

TABLE 1-28

| | | | |
|---|---|---|---|
| 4395 | Z3 | L7 | Q74 |
| 4396 | Z3 | L7 | Q75 |
| 4397 | Z3 | L7 | Q76 |
| 4398 | Z3 | L7 | Q77 |
| 4399 | Z3 | L7 | Q78 |
| 4400 | Z3 | L7 | Q79 |
| 4401 | Z3 | L7 | Q80 |
| 4402 | Z3 | L7 | Q81 |
| 4403 | Z3 | L7 | Q82 |
| 4404 | Z3 | L7 | Q83 |
| 4405 | Z3 | L7 | Q84 |
| 4406 | Z3 | L7 | Q85 |
| 4407 | Z3 | L7 | Q86 |
| 4408 | Z3 | L7 | Q87 |
| 4409 | Z3 | L7 | Q88 |
| 4410 | Z3 | L7 | Q89 |
| 4411 | Z3 | L7 | Q90 |
| 4412 | Z3 | L7 | Q91 |
| 4413 | Z3 | L7 | Q92 |
| 4414 | Z3 | L7 | Q93 |
| 4415 | Z3 | L7 | Q94 |
| 4416 | Z3 | L7 | Q95 |
| 4417 | Z3 | L7 | Q96 |
| 4418 | Z3 | L7 | Q97 |
| 4419 | Z3 | L7 | Q98 |
| 4420 | Z3 | L7 | Q99 |
| 4421 | Z3 | L7 | Q100 |
| 4422 | Z3 | L7 | Q101 |
| 4423 | Z3 | L7 | Q102 |
| 4424 | Z3 | L7 | Q103 |
| 4425 | Z3 | L8 | Q40 |
| 4426 | Z3 | L8 | Q41 |
| 4427 | Z3 | L8 | Q42 |
| 4428 | Z3 | L8 | Q43 |
| 4429 | Z3 | L8 | Q44 |
| 4430 | Z3 | L8 | Q45 |
| 4431 | Z3 | L8 | Q46 |
| 4432 | Z3 | L8 | Q47 |
| 4433 | Z3 | L8 | Q48 |
| 4434 | Z3 | L8 | Q49 |
| 4435 | Z3 | L8 | Q50 |
| 4436 | Z3 | L8 | Q51 |
| 4437 | Z3 | L8 | Q52 |
| 4438 | Z3 | L8 | Q53 |
| 4439 | Z3 | L8 | Q54 |
| 4440 | Z3 | L8 | Q55 |
| 4441 | Z3 | L8 | Q56 |
| 4442 | Z3 | L8 | Q57 |
| 4443 | Z3 | L8 | Q58 |
| 4444 | Z3 | L8 | Q59 |
| 4445 | Z3 | L8 | Q60 |
| 4446 | Z3 | L8 | Q61 |
| 4447 | Z3 | L8 | Q62 |
| 4448 | Z3 | L8 | Q63 |
| 4449 | Z3 | L8 | Q64 |
| 4450 | Z3 | L8 | Q65 |
| 4451 | Z3 | L8 | Q66 |

TABLE 1-28-continued

| | | | |
|---|---|---|---|
| 4452 | Z3 | L8 | Q67 |
| 4453 | Z3 | L8 | Q68 |
| 4454 | Z3 | L8 | Q69 |
| 4455 | Z3 | L8 | Q70 |
| 4456 | Z3 | L8 | Q71 |
| 4457 | Z3 | L8 | Q72 |
| 4458 | Z3 | L8 | Q73 |
| 4459 | Z3 | L8 | Q74 |
| 4460 | Z3 | L8 | Q75 |
| 4461 | Z3 | L8 | Q76 |
| 4462 | Z3 | L8 | Q77 |
| 4463 | Z3 | L8 | Q78 |
| 4464 | Z3 | L8 | Q79 |
| 4465 | Z3 | L8 | Q80 |
| 4466 | Z3 | L8 | Q81 |
| 4467 | Z3 | L8 | Q82 |
| 4468 | Z3 | L8 | Q83 |
| 4469 | Z3 | L8 | Q84 |
| 4470 | Z3 | L8 | Q85 |
| 4471 | Z3 | L8 | Q86 |
| 4472 | Z3 | L8 | Q87 |
| 4473 | Z3 | L8 | Q88 |
| 4474 | Z3 | L8 | Q89 |
| 4475 | Z3 | L8 | Q90 |
| 4476 | Z3 | L8 | Q91 |
| 4477 | Z3 | L8 | Q92 |
| 4478 | Z3 | L8 | Q93 |
| 4479 | Z3 | L8 | Q94 |
| 4480 | Z3 | L8 | Q95 |
| 4481 | Z3 | L8 | Q96 |
| 4482 | Z3 | L8 | Q97 |
| 4483 | Z3 | L8 | Q98 |
| 4484 | Z3 | L8 | Q99 |
| 4485 | Z3 | L8 | Q100 |
| 4486 | Z3 | L8 | Q101 |
| 4487 | Z3 | L8 | Q102 |
| 4488 | Z3 | L8 | Q103 |
| 4489 | Z3 | L9 | Q40 |
| 4490 | Z3 | L9 | Q41 |
| 4491 | Z3 | L9 | Q42 |
| 4492 | Z3 | L9 | Q43 |
| 4493 | Z3 | L9 | Q44 |
| 4494 | Z3 | L9 | Q45 |
| 4495 | Z3 | L9 | Q46 |
| 4496 | Z3 | L9 | Q47 |
| 4497 | Z3 | L9 | Q48 |
| 4498 | Z3 | L9 | Q49 |
| 4499 | Z3 | L9 | Q50 |
| 4500 | Z3 | L9 | Q51 |
| 4501 | Z3 | L9 | Q52 |
| 4502 | Z3 | L9 | Q53 |
| 4503 | Z3 | L9 | Q54 |
| 4504 | Z3 | L9 | Q55 |
| 4505 | Z3 | L9 | Q56 |
| 4506 | Z3 | L9 | Q57 |
| 4507 | Z3 | L9 | Q58 |
| 4508 | Z3 | L9 | Q59 |
| 4509 | Z3 | L9 | Q60 |
| 4510 | Z3 | L9 | Q61 |
| 4511 | Z3 | L9 | Q62 |
| 4512 | Z3 | L9 | Q63 |
| 4513 | Z3 | L9 | Q64 |
| 4514 | Z3 | L9 | Q65 |
| 4515 | Z3 | L9 | Q66 |
| 4516 | Z3 | L9 | Q67 |
| 4517 | Z3 | L9 | Q68 |
| 4518 | Z3 | L9 | Q69 |
| 4519 | Z3 | L9 | Q70 |
| 4520 | Z3 | L9 | Q71 |
| 4521 | Z3 | L9 | Q72 |
| 4522 | Z3 | L9 | Q73 |
| 4523 | Z3 | L9 | Q74 |
| 4524 | Z3 | L9 | Q75 |
| 4525 | Z3 | L9 | Q76 |
| 4526 | Z3 | L9 | Q77 |
| 4527 | Z3 | L9 | Q78 |
| 4528 | Z3 | L9 | Q79 |
| 4529 | Z3 | L9 | Q80 |
| 4530 | Z3 | L9 | Q81 |
| 4531 | Z3 | L9 | Q82 |
| 4532 | Z3 | L9 | Q83 |
| 4533 | Z3 | L9 | Q84 |
| 4534 | Z3 | L9 | Q85 |
| 4535 | Z3 | L9 | Q86 |
| 4536 | Z3 | L9 | Q87 |
| 4537 | Z3 | L9 | Q88 |
| 4538 | Z3 | L9 | Q89 |
| 4539 | Z3 | L9 | Q90 |
| 4540 | Z3 | L9 | Q91 |
| 4541 | Z3 | L9 | Q92 |
| 4542 | Z3 | L9 | Q93 |
| 4543 | Z3 | L9 | Q94 |
| 4544 | Z3 | L9 | Q95 |
| 4545 | Z3 | L9 | Q96 |
| 4546 | Z3 | L9 | Q97 |
| 4547 | Z3 | L9 | Q98 |
| 4548 | Z3 | L9 | Q99 |
| 4549 | Z3 | L9 | Q100 |
| 4550 | Z3 | L9 | Q101 |
| 4551 | Z3 | L9 | Q102 |
| 4552 | Z3 | L9 | Q103 |
| 4553 | Z3 | L10 | Q40 |
| 4554 | Z3 | L10 | Q41 |
| 4555 | Z3 | L10 | Q42 |
| 4556 | Z3 | L10 | Q43 |
| 4557 | Z3 | L10 | Q44 |
| 4558 | Z3 | L10 | Q45 |
| 4559 | Z3 | L10 | Q46 |
| 4560 | Z3 | L10 | Q47 |
| 4561 | Z3 | L10 | Q48 |
| 4562 | Z3 | L10 | Q49 |
| 4563 | Z3 | L10 | Q50 |
| 4564 | Z3 | L10 | Q51 |
| 4565 | Z3 | L10 | Q52 |
| 4566 | Z3 | L10 | Q53 |
| 4567 | Z3 | L10 | Q54 |
| 4568 | Z3 | L10 | Q55 |
| 4569 | Z3 | L10 | Q56 |
| 4570 | Z3 | L10 | Q57 |
| 4571 | Z3 | L10 | Q58 |
| 4572 | Z3 | L10 | Q59 |
| 4573 | Z3 | L10 | Q60 |
| 4574 | Z3 | L10 | Q61 |
| 4575 | Z3 | L10 | Q62 |
| 4576 | Z3 | L10 | Q63 |
| 4577 | Z3 | L10 | Q64 |
| 4578 | Z3 | L10 | Q65 |
| 4579 | Z3 | L10 | Q66 |
| 4580 | Z3 | L10 | Q67 |
| 4581 | Z3 | L10 | Q68 |
| 4582 | Z3 | L10 | Q69 |
| 4583 | Z3 | L10 | Q70 |
| 4584 | Z3 | L10 | Q71 |
| 4585 | Z3 | L10 | Q72 |
| 4586 | Z3 | L10 | Q73 |
| 4587 | Z3 | L10 | Q74 |
| 4588 | Z3 | L10 | Q75 |
| 4589 | Z3 | L10 | Q76 |
| 4590 | Z3 | L10 | Q77 |
| 4591 | Z3 | L10 | Q78 |
| 4592 | Z3 | L10 | Q79 |
| 4593 | Z3 | L10 | Q80 |
| 4594 | Z3 | L10 | Q81 |
| 4595 | Z3 | L10 | Q82 |

TABLE 1-29

| | | | |
|---|---|---|---|
| 4596 | Z3 | L10 | Q83 |
| 4597 | Z3 | L10 | Q84 |
| 4598 | Z3 | L10 | Q85 |
| 4599 | Z3 | L10 | Q86 |
| 4600 | Z3 | L10 | Q87 |
| 4601 | Z3 | L10 | Q88 |
| 4602 | Z3 | L10 | Q89 |
| 4603 | Z3 | L10 | Q90 |
| 4604 | Z3 | L10 | Q91 |
| 4605 | Z3 | L10 | Q92 |

TABLE 1-29-continued

| | | | |
|---|---|---|---|
| 4606 | Z3 | L10 | Q93 |
| 4607 | Z3 | L10 | Q94 |
| 4608 | Z3 | L10 | Q95 |
| 4609 | Z3 | L10 | Q96 |
| 4610 | Z3 | L10 | Q97 |
| 4611 | Z3 | L10 | Q98 |
| 4612 | Z3 | L10 | Q99 |
| 4613 | Z3 | L10 | Q100 |
| 4614 | Z3 | L10 | Q101 |
| 4615 | Z3 | L10 | Q102 |
| 4616 | Z3 | L10 | Q103 |
| 4617 | Z3 | L11 | Q40 |
| 4618 | Z3 | L11 | Q41 |
| 4619 | Z3 | L11 | Q42 |
| 4620 | Z3 | L11 | Q43 |
| 4621 | Z3 | L11 | Q44 |
| 4622 | Z3 | L11 | Q45 |
| 4623 | Z3 | L11 | Q46 |
| 4624 | Z3 | L11 | Q47 |
| 4625 | Z3 | L11 | Q48 |
| 4626 | Z3 | L11 | Q49 |
| 4627 | Z3 | L11 | Q50 |
| 4628 | Z3 | L11 | Q51 |
| 4629 | Z3 | L11 | Q52 |
| 4630 | Z3 | L11 | Q53 |
| 4631 | Z3 | L11 | Q54 |
| 4632 | Z3 | L11 | Q55 |
| 4633 | Z3 | L11 | Q56 |
| 4634 | Z3 | L11 | Q57 |
| 4635 | Z3 | L11 | Q58 |
| 4636 | Z3 | L11 | Q59 |
| 4637 | Z3 | L11 | Q60 |
| 4638 | Z3 | L11 | Q61 |
| 4639 | Z3 | L11 | Q62 |
| 4640 | Z3 | L11 | Q63 |
| 4641 | Z3 | L11 | Q64 |
| 4642 | Z3 | L11 | Q65 |
| 4643 | Z3 | L11 | Q66 |
| 4644 | Z3 | L11 | Q67 |
| 4645 | Z3 | L11 | Q68 |
| 4646 | Z3 | L11 | Q69 |
| 4647 | Z3 | L11 | Q70 |
| 4648 | Z3 | L11 | Q71 |
| 4649 | Z3 | L11 | Q72 |
| 4650 | Z3 | L11 | Q73 |
| 4651 | Z3 | L11 | Q74 |
| 4652 | Z3 | L11 | Q75 |
| 4653 | Z3 | L11 | Q76 |
| 4654 | Z3 | L11 | Q77 |
| 4655 | Z3 | L11 | Q78 |
| 4656 | Z3 | L11 | Q79 |
| 4657 | Z3 | L11 | Q80 |
| 4658 | Z3 | L11 | Q81 |
| 4659 | Z3 | L11 | Q82 |
| 4660 | Z3 | L11 | Q83 |
| 4661 | Z3 | L11 | Q84 |
| 4662 | Z3 | L11 | Q85 |
| 4663 | Z3 | L11 | Q86 |
| 4664 | Z3 | L11 | Q87 |
| 4665 | Z3 | L11 | Q88 |
| 4666 | Z3 | L11 | Q89 |
| 4667 | Z3 | L11 | Q90 |
| 4668 | Z3 | L11 | Q91 |
| 4669 | Z3 | L11 | Q92 |
| 4670 | Z3 | L11 | Q93 |
| 4671 | Z3 | L11 | Q94 |
| 4672 | Z3 | L11 | Q95 |
| 4673 | Z3 | L11 | Q96 |
| 4674 | Z3 | L11 | Q97 |
| 4675 | Z3 | L11 | Q98 |
| 4676 | Z3 | L11 | Q99 |
| 4677 | Z3 | L11 | Q100 |
| 4678 | Z3 | L11 | Q101 |
| 4679 | Z3 | L11 | Q102 |
| 4680 | Z3 | L11 | Q103 |
| 4681 | Z3 | L12 | Q40 |
| 4682 | Z3 | L12 | Q41 |
| 4683 | Z3 | L12 | Q42 |
| 4684 | Z3 | L12 | Q43 |
| 4685 | Z3 | L12 | Q44 |
| 4686 | Z3 | L12 | Q45 |
| 4687 | Z3 | L12 | Q46 |
| 4688 | Z3 | L12 | Q47 |
| 4689 | Z3 | L12 | Q48 |
| 4690 | Z3 | L12 | Q49 |
| 4691 | Z3 | L12 | Q50 |
| 4692 | Z3 | L12 | Q51 |
| 4693 | Z3 | L12 | Q52 |
| 4694 | Z3 | L12 | Q53 |
| 4695 | Z3 | L12 | Q54 |
| 4696 | Z3 | L12 | Q55 |
| 4697 | Z3 | L12 | Q56 |
| 4698 | Z3 | L12 | Q57 |
| 4699 | Z3 | L12 | Q58 |
| 4700 | Z3 | L12 | Q59 |
| 4701 | Z3 | L12 | Q60 |
| 4702 | Z3 | L12 | Q61 |
| 4703 | Z3 | L12 | Q62 |
| 4704 | Z3 | L12 | Q63 |
| 4705 | Z3 | L12 | Q64 |
| 4706 | Z3 | L12 | Q65 |
| 4707 | Z3 | L12 | Q66 |
| 4708 | Z3 | L12 | Q67 |
| 4709 | Z3 | L12 | Q68 |
| 4710 | Z3 | L12 | Q69 |
| 4711 | Z3 | L12 | Q70 |
| 4712 | Z3 | L12 | Q71 |
| 4713 | Z3 | L12 | Q72 |
| 4714 | Z3 | L12 | Q73 |
| 4715 | Z3 | L12 | Q74 |
| 4716 | Z3 | L12 | Q75 |
| 4717 | Z3 | L12 | Q76 |
| 4718 | Z3 | L12 | Q77 |
| 4719 | Z3 | LI2 | Q78 |
| 4720 | Z3 | L12 | Q79 |
| 4721 | Z3 | L12 | Q80 |
| 4722 | Z3 | L12 | Q81 |
| 4723 | Z3 | L12 | Q82 |
| 4724 | Z3 | L12 | Q83 |
| 4725 | Z3 | L12 | Q84 |
| 4726 | Z3 | L12 | Q85 |
| 4727 | Z3 | L12 | Q86 |
| 4728 | Z3 | L12 | Q87 |
| 4729 | Z3 | L12 | Q88 |
| 4730 | Z3 | L12 | Q89 |
| 4731 | Z3 | L12 | Q90 |
| 4732 | Z3 | L12 | Q91 |
| 4733 | Z3 | L12 | Q92 |
| 4734 | Z3 | L12 | Q93 |
| 4735 | Z3 | L12 | Q94 |
| 4736 | Z3 | L12 | Q95 |
| 4737 | Z3 | L12 | Q96 |
| 4738 | Z3 | L12 | Q97 |
| 4739 | Z3 | L12 | Q98 |
| 4740 | Z3 | L12 | Q99 |
| 4741 | Z3 | L12 | Q100 |
| 4742 | Z3 | L12 | Q101 |
| 4743 | Z3 | L12 | Q102 |
| 4744 | Z3 | L12 | Q103 |
| 4745 | Z3 | L13 | Q40 |
| 4746 | Z3 | L13 | Q41 |
| 4747 | Z3 | L13 | Q42 |
| 4748 | Z3 | L13 | Q43 |
| 4749 | Z3 | L13 | Q44 |
| 4750 | Z3 | L13 | Q45 |
| 4751 | Z3 | L13 | Q46 |
| 4752 | Z3 | L13 | Q47 |
| 4753 | Z3 | L13 | Q48 |
| 4754 | Z3 | L13 | Q49 |
| 4755 | Z3 | L13 | Q50 |
| 4756 | Z3 | L13 | Q51 |
| 4757 | Z3 | L13 | Q52 |
| 4758 | Z3 | L13 | Q53 |
| 4759 | Z3 | L13 | Q54 |
| 4760 | Z3 | L13 | Q55 |
| 4761 | Z3 | L13 | Q56 |
| 4762 | Z3 | L13 | Q57 |
| 4763 | Z3 | L13 | Q58 |
| 4764 | Z3 | L13 | Q59 |
| 4765 | Z3 | L13 | Q60 |

TABLE 1-29-continued

| | | | |
|---|---|---|---|
| 4766 | Z3 | L13 | Q61 |
| 4767 | Z3 | L13 | Q62 |
| 4768 | Z3 | L13 | Q63 |
| 4769 | Z3 | L13 | Q64 |
| 4770 | Z3 | L13 | Q65 |
| 4771 | Z3 | L13 | Q66 |
| 4772 | Z3 | L13 | Q67 |
| 4773 | Z3 | L13 | Q68 |
| 4774 | Z3 | L13 | Q69 |
| 4775 | Z3 | L13 | Q70 |
| 4776 | Z3 | L13 | Q71 |
| 4777 | Z3 | L13 | Q72 |
| 4778 | Z3 | L13 | Q73 |
| 4779 | Z3 | L13 | Q74 |
| 4780 | Z3 | L13 | Q75 |
| 4781 | Z3 | L13 | Q76 |
| 4782 | Z3 | L13 | Q77 |
| 4783 | Z3 | L13 | Q78 |
| 4784 | Z3 | L13 | Q79 |
| 4785 | Z3 | L13 | Q80 |
| 4786 | Z3 | L13 | Q81 |
| 4787 | Z3 | L13 | Q82 |
| 4788 | Z3 | L13 | Q83 |
| 4789 | Z3 | L13 | Q84 |
| 4790 | Z3 | L13 | Q85 |
| 4791 | Z3 | L13 | Q86 |
| 4792 | Z3 | L13 | Q87 |
| 4793 | Z3 | L13 | Q88 |
| 4794 | Z3 | L13 | Q89 |
| 4795 | Z3 | L13 | Q90 |
| 4796 | Z3 | L13 | Q91 |

TABLE 1-30

| | | | |
|---|---|---|---|
| 4797 | Z3 | L13 | Q92 |
| 4798 | Z3 | L13 | Q93 |
| 4799 | Z3 | L13 | Q94 |
| 4800 | Z3 | L13 | Q95 |
| 4801 | Z3 | L13 | Q96 |
| 4802 | Z3 | L13 | Q97 |
| 4803 | Z3 | L13 | Q98 |
| 4804 | Z3 | L13 | Q99 |
| 4805 | Z3 | L13 | Q100 |
| 4806 | Z3 | L13 | Q101 |
| 4807 | Z3 | L13 | Q102 |
| 4808 | Z3 | L13 | Q103 |
| 4809 | Z3 | L14 | Q40 |
| 4810 | Z3 | L14 | Q41 |
| 4811 | Z3 | L14 | Q42 |
| 4812 | Z3 | L14 | Q43 |
| 4813 | Z3 | L14 | Q44 |
| 4814 | Z3 | L14 | Q45 |
| 4815 | Z3 | L14 | Q46 |
| 4816 | Z3 | L14 | Q47 |
| 4817 | Z3 | L14 | Q48 |
| 4818 | Z3 | L14 | Q49 |
| 4819 | Z3 | L14 | Q50 |
| 4820 | Z3 | L14 | Q51 |
| 4821 | Z3 | L14 | Q52 |
| 4822 | Z3 | L14 | Q53 |
| 4823 | Z3 | L14 | Q54 |
| 4824 | Z3 | L14 | Q55 |
| 4825 | Z3 | L14 | Q56 |
| 4826 | Z3 | L14 | Q57 |
| 4827 | Z3 | L14 | Q58 |
| 4828 | Z3 | L14 | Q59 |
| 4829 | Z3 | L14 | Q60 |
| 4830 | Z3 | L14 | Q61 |
| 4831 | Z3 | L14 | Q62 |
| 4832 | Z3 | L14 | Q63 |
| 4833 | Z3 | L14 | Q64 |
| 4834 | Z3 | L14 | Q65 |
| 4835 | Z3 | L14 | Q66 |
| 4836 | Z3 | L14 | Q67 |
| 4837 | Z3 | L14 | Q68 |
| 4838 | Z3 | L14 | Q69 |
| 4839 | Z3 | L14 | Q70 |

TABLE 1-30-continued

| | | | |
|---|---|---|---|
| 4840 | Z3 | L14 | Q71 |
| 4841 | Z3 | L14 | Q72 |
| 4842 | Z3 | L14 | Q73 |
| 4843 | Z3 | L14 | Q74 |
| 4844 | Z3 | L14 | Q75 |
| 4845 | Z3 | L14 | Q76 |
| 4846 | Z3 | L14 | Q77 |
| 4847 | Z3 | L14 | Q78 |
| 4848 | Z3 | L14 | Q79 |
| 4849 | Z3 | L14 | Q80 |
| 4850 | Z3 | L14 | Q81 |
| 4851 | Z3 | L14 | Q82 |
| 4852 | Z3 | L14 | Q83 |
| 4853 | Z3 | L14 | Q84 |
| 4854 | Z3 | L14 | Q85 |
| 4855 | Z3 | L14 | Q86 |
| 4856 | Z3 | L14 | Q87 |
| 4857 | Z3 | L14 | Q88 |
| 4858 | Z3 | L14 | Q89 |
| 4859 | Z3 | L14 | Q90 |
| 4860 | Z3 | L14 | Q91 |
| 4861 | Z3 | L14 | Q92 |
| 4862 | Z3 | L14 | Q93 |
| 4863 | Z3 | L14 | Q94 |
| 4864 | Z3 | L14 | Q95 |
| 4865 | Z3 | L14 | Q96 |
| 4866 | Z3 | L14 | Q97 |
| 4867 | Z3 | L14 | Q98 |
| 4868 | Z3 | L14 | Q99 |
| 4869 | Z3 | L14 | Q100 |
| 4870 | Z3 | L14 | Q101 |
| 4371 | Z3 | L14 | Q102 |
| 4872 | Z3 | L14 | Q103 |
| 4873 | Z4 | L1 | Q40 |
| 4874 | Z4 | L1 | Q41 |
| 4875 | Z4 | L1 | Q42 |
| 4876 | Z4 | L1 | Q43 |
| 4877 | Z4 | L1 | Q44 |
| 4878 | Z4 | L1 | Q45 |
| 4879 | Z4 | L1 | Q46 |
| 4880 | Z4 | L1 | Q47 |
| 4881 | Z4 | L1 | Q48 |
| 4882 | Z4 | L1 | Q49 |
| 4883 | Z4 | L1 | Q50 |
| 4884 | Z4 | L1 | Q51 |
| 4885 | Z4 | L1 | Q52 |
| 4886 | Z4 | L1 | Q53 |
| 4887 | Z4 | L1 | Q54 |
| 4888 | Z4 | L1 | Q55 |
| 4889 | Z4 | L1 | Q56 |
| 4890 | Z4 | L1 | Q57 |
| 4891 | Z4 | L1 | Q58 |
| 4892 | Z4 | L1 | Q59 |
| 4893 | Z4 | L1 | Q60 |
| 4894 | Z4 | L1 | Q61 |
| 4895 | Z4 | L1 | Q62 |
| 4896 | Z4 | L1 | Q63 |
| 4897 | Z4 | L1 | Q64 |
| 4898 | Z4 | L1 | Q65 |
| 4899 | Z4 | L1 | Q66 |
| 4900 | Z4 | L1 | Q67 |
| 4901 | Z4 | L1 | Q68 |
| 4902 | Z4 | L1 | Q69 |
| 4903 | Z4 | L1 | Q70 |
| 4904 | Z4 | L1 | Q71 |
| 4905 | Z4 | L1 | Q72 |
| 4906 | Z4 | L1 | Q73 |
| 4907 | Z4 | L1 | Q74 |
| 4908 | Z4 | L1 | Q75 |
| 4909 | Z4 | L1 | Q76 |
| 4910 | Z4 | L1 | Q77 |
| 4911 | Z4 | L1 | Q78 |
| 4912 | Z4 | L1 | Q79 |
| 4913 | Z4 | L1 | Q80 |
| 4914 | Z4 | L1 | Q81 |
| 4915 | Z4 | L1 | Q82 |
| 4916 | Z4 | L1 | Q83 |
| 4917 | Z4 | L1 | Q84 |
| 4918 | Z4 | L1 | Q85 |
| 4919 | Z4 | L1 | Q86 |

TABLE 1-30-continued

| | | | |
|---|---|---|---|
| 4920 | Z4 | L1 | Q87 |
| 4921 | Z4 | L1 | Q88 |
| 4922 | Z4 | L1 | Q89 |
| 4923 | Z4 | L1 | Q90 |
| 4924 | Z4 | L1 | Q91 |
| 4925 | Z4 | L1 | Q92 |
| 4926 | Z4 | L1 | Q93 |
| 4927 | Z4 | L1 | Q94 |
| 4928 | Z4 | L1 | Q95 |
| 4929 | Z4 | L1 | Q96 |
| 4930 | Z4 | L1 | Q97 |
| 4931 | Z4 | L1 | Q98 |
| 4932 | Z4 | L1 | Q99 |
| 4933 | Z4 | L1 | Q100 |
| 4934 | Z4 | L1 | Q101 |
| 4935 | Z4 | L1 | Q102 |
| 4936 | Z4 | L1 | Q103 |
| 4937 | Z4 | L2 | Q40 |
| 4938 | Z4 | L2 | Q41 |
| 4939 | Z4 | L2 | Q42 |
| 4940 | Z4 | L2 | Q43 |
| 4941 | Z4 | L2 | Q44 |
| 4942 | Z4 | L2 | Q45 |
| 4943 | Z4 | L2 | Q46 |
| 4944 | Z4 | L2 | Q47 |
| 4945 | Z4 | L2 | Q48 |
| 4946 | Z4 | L2 | Q49 |
| 4947 | Z4 | L2 | Q50 |
| 4948 | Z4 | L2 | Q51 |
| 4949 | Z4 | L2 | Q52 |
| 4950 | Z4 | L2 | Q53 |
| 4951 | Z4 | L2 | Q54 |
| 4952 | Z4 | L2 | Q55 |
| 4953 | Z4 | L2 | Q56 |
| 4954 | Z4 | L2 | Q57 |
| 4955 | Z4 | L2 | Q58 |
| 4956 | Z4 | L2 | Q59 |
| 4957 | Z4 | L2 | Q60 |
| 4958 | Z4 | L2 | Q61 |
| 4959 | Z4 | L2 | Q62 |
| 4960 | Z4 | L2 | Q63 |
| 4961 | Z4 | L2 | Q64 |
| 4962 | Z4 | L2 | Q65 |
| 4963 | Z4 | L2 | Q66 |
| 4964 | Z4 | L2 | Q67 |
| 4965 | Z4 | L2 | Q68 |
| 4966 | Z4 | L2 | Q69 |
| 4967 | Z4 | L2 | Q70 |
| 4968 | Z4 | L2 | Q71 |
| 4969 | Z4 | L2 | Q72 |
| 4970 | Z4 | L2 | Q73 |
| 4971 | Z4 | L2 | Q74 |
| 4972 | Z4 | L2 | Q75 |
| 4973 | Z4 | L2 | Q76 |
| 4974 | Z4 | L2 | Q77 |
| 4975 | Z4 | L2 | Q78 |
| 4976 | Z4 | L2 | Q79 |
| 4977 | Z4 | L2 | Q80 |
| 4978 | Z4 | L2 | Q81 |
| 4979 | Z4 | L2 | Q82 |
| 4980 | Z4 | L2 | Q83 |
| 4981 | Z4 | L2 | Q84 |
| 4982 | Z4 | L2 | Q85 |
| 4983 | Z4 | L2 | Q86 |
| 4984 | Z4 | L2 | Q87 |
| 4985 | Z4 | L2 | Q88 |
| 4986 | Z4 | L2 | Q89 |
| 4987 | Z4 | L2 | Q90 |
| 4988 | Z4 | L2 | Q91 |
| 4989 | Z4 | L2 | Q92 |
| 4990 | Z4 | L2 | Q93 |
| 4991 | Z4 | L2 | Q94 |
| 4992 | Z4 | L2 | Q95 |
| 4993 | Z4 | L2 | Q96 |
| 4994 | Z4 | L2 | Q97 |
| 4995 | Z4 | L2 | Q98 |
| 4996 | Z4 | L2 | Q99 |
| 4997 | Z4 | L2 | Q100 |

TABLE 1-31

| | | | |
|---|---|---|---|
| 4993 | Z4 | L2 | Q101 |
| 4999 | Z4 | L2 | Q102 |
| 5000 | Z4 | L2 | Q103 |
| 5001 | Z4 | L3 | Q40 |
| 5002 | Z4 | L3 | Q41 |
| 5003 | Z4 | L3 | Q42 |
| 5004 | Z4 | L3 | Q43 |
| 5005 | Z4 | L3 | Q44 |
| 5006 | Z4 | L3 | Q45 |
| 5007 | Z4 | L3 | Q46 |
| 5008 | Z4 | L3 | Q47 |
| 5009 | Z4 | L3 | Q48 |
| 5010 | Z4 | L3 | Q49 |
| 5011 | Z4 | L3 | Q50 |
| 5012 | Z4 | L3 | Q51 |
| 5013 | Z4 | L3 | Q52 |
| 5014 | Z4 | L3 | Q53 |
| 5015 | Z4 | L3 | Q54 |
| 5016 | Z4 | L3 | Q55 |
| 5017 | Z4 | L3 | Q56 |
| 5018 | Z4 | L3 | Q57 |
| 5019 | Z4 | L3 | Q58 |
| 5020 | Z4 | L3 | Q59 |
| 5021 | Z4 | L3 | Q60 |
| 5022 | Z4 | L3 | Q61 |
| 5023 | Z4 | L3 | Q62 |
| 5024 | Z4 | L3 | Q63 |
| 5025 | Z4 | L3 | Q64 |
| 5026 | Z4 | L3 | Q65 |
| 5027 | Z4 | L3 | Q66 |
| 5028 | Z4 | L3 | Q67 |
| 5029 | Z4 | L3 | Q68 |
| 5030 | Z4 | L3 | Q69 |
| 5031 | Z4 | L3 | Q70 |
| 5032 | Z4 | L3 | Q71 |
| 5033 | Z4 | L3 | Q72 |
| 5034 | Z4 | L3 | Q73 |
| 5035 | Z4 | L3 | Q74 |
| 5036 | Z4 | L3 | Q75 |
| 5037 | Z4 | L3 | Q76 |
| 5038 | Z4 | L3 | Q77 |
| 5039 | Z4 | L3 | Q78 |
| 5040 | Z4 | L3 | Q79 |
| 5041 | Z4 | L3 | Q80 |
| 5042 | Z4 | L3 | Q81 |
| 5043 | Z4 | L3 | Q82 |
| 5044 | Z4 | L3 | Q83 |
| 5045 | Z4 | L3 | Q84 |
| 5046 | Z4 | L3 | Q85 |
| 5047 | Z4 | L3 | Q86 |
| 5048 | Z4 | L3 | Q87 |
| 5049 | Z4 | L3 | Q88 |
| 5050 | Z4 | L3 | Q89 |
| 5051 | Z4 | L3 | Q90 |
| 5052 | Z4 | L3 | Q91 |
| 5053 | Z4 | L3 | Q92 |
| 5054 | Z4 | L3 | Q93 |
| 5055 | Z4 | L3 | Q94 |
| 5056 | Z4 | L3 | Q95 |
| 5057 | Z4 | L3 | Q96 |
| 5058 | Z4 | L3 | Q97 |
| 5059 | Z4 | L3 | Q98 |
| 5060 | 74 | L3 | Q99 |
| 5061 | Z4 | L3 | Q100 |
| 5062 | Z4 | L3 | Q101 |
| 5063 | Z4 | L3 | Q102 |
| 5064 | Z4 | L3 | Q103 |
| 5065 | Z4 | L4 | Q40 |
| 5066 | Z4 | L4 | Q41 |
| 5067 | Z4 | L4 | Q42 |
| 5068 | Z4 | L4 | Q43 |
| 5069 | Z4 | L4 | Q44 |
| 5070 | Z4 | L4 | Q45 |
| 5071 | Z4 | L4 | Q46 |
| 5072 | Z4 | L4 | Q47 |
| 5073 | Z4 | L4 | Q48 |
| 5074 | Z4 | L4 | Q49 |
| 5075 | Z4 | L4 | Q50 |
| 5076 | Z4 | L4 | Q51 |
| 5077 | Z4 | L4 | Q52 |

TABLE 1-31-continued

| | | | |
|---|---|---|---|
| 5078 | Z4 | L4 | Q53 |
| 5079 | Z4 | L4 | Q54 |
| 5080 | Z4 | L4 | Q55 |
| 5081 | Z4 | L4 | Q56 |
| 5082 | Z4 | L4 | Q57 |
| 5083 | Z4 | L4 | Q58 |
| 5084 | Z4 | L4 | Q59 |
| 5085 | Z4 | L4 | Q60 |
| 5086 | Z4 | L4 | Q61 |
| 5087 | Z4 | L4 | Q62 |
| 5088 | Z4 | L4 | Q63 |
| 5089 | Z4 | L4 | Q64 |
| 5090 | Z4 | L4 | Q65 |
| 5091 | Z4 | L4 | Q66 |
| 5092 | Z4 | L4 | Q67 |
| 5093 | Z4 | L4 | Q68 |
| 5094 | Z4 | L4 | Q69 |
| 5095 | Z4 | L4 | Q70 |
| 5096 | Z4 | L4 | Q71 |
| 5097 | Z4 | L4 | Q72 |
| 5098 | Z4 | L4 | Q73 |
| 5099 | Z4 | L4 | Q74 |
| 5100 | Z4 | L4 | Q75 |
| 5101 | Z4 | L4 | Q76 |
| 5102 | Z4 | L4 | Q77 |
| 5103 | Z4 | L4 | Q78 |
| 5104 | Z4 | L4 | Q79 |
| 5105 | Z4 | L4 | Q80 |
| 5106 | Z4 | L4 | Q81 |
| 5107 | Z4 | L4 | Q82 |
| 5108 | Z4 | L4 | Q83 |
| 5109 | Z4 | L4 | Q84 |
| 5110 | Z4 | L4 | Q85 |
| 5111 | Z4 | L4 | Q86 |
| 5112 | Z4 | L4 | Q87 |
| 5113 | Z4 | L4 | Q88 |
| 5114 | Z4 | L4 | Q89 |
| 5115 | Z4 | L4 | Q90 |
| 5116 | Z4 | L4 | Q91 |
| 5117 | Z4 | L4 | Q92 |
| 5118 | Z4 | L4 | Q93 |
| 5119 | Z4 | L4 | Q94 |
| 5120 | Z4 | L4 | Q95 |
| 5121 | Z4 | L4 | Q96 |
| 5122 | Z4 | L4 | Q97 |
| 5123 | Z4 | L4 | Q98 |
| 5124 | Z4 | L4 | Q99 |
| 5125 | Z4 | L4 | Q100 |
| 5126 | Z4 | L4 | Q101 |
| 5127 | Z4 | L4 | Q102 |
| 5128 | Z4 | L4 | Q103 |
| 5129 | Z4 | L5 | Q40 |
| 5130 | Z4 | L5 | Q41 |
| 5131 | Z4 | L5 | Q42 |
| 5132 | Z4 | L5 | Q43 |
| 5133 | Z4 | L5 | Q44 |
| 5134 | Z4 | L5 | Q45 |
| 5135 | Z4 | L5 | Q46 |
| 5136 | Z4 | L5 | Q47 |
| 5137 | Z4 | L5 | Q48 |
| 5138 | Z4 | L5 | Q49 |
| 5139 | Z4 | L5 | Q50 |
| 5140 | Z4 | L5 | Q51 |
| 5141 | Z4 | L5 | Q52 |
| 5142 | Z4 | L5 | Q53 |
| 5143 | Z4 | L5 | Q54 |
| 5144 | Z4 | L5 | Q55 |
| 5145 | Z4 | L5 | Q56 |
| 5146 | Z4 | L5 | Q57 |
| 5147 | Z4 | L5 | Q58 |
| 5148 | Z4 | L5 | Q59 |
| 5149 | Z4 | L5 | Q60 |
| 5150 | Z4 | L5 | Q61 |
| 5151 | Z4 | L5 | Q62 |
| 5152 | Z4 | L5 | Q63 |
| 5153 | Z4 | L5 | Q64 |
| 5154 | Z4 | L5 | Q65 |
| 5155 | Z4 | L5 | Q66 |
| 5156 | Z4 | L5 | Q67 |
| 5157 | Z4 | L5 | Q68 |
| 5158 | Z4 | L5 | Q69 |
| 5159 | Z4 | L5 | Q70 |
| 5160 | Z4 | L5 | Q71 |
| 5161 | Z4 | L5 | Q72 |
| 5162 | Z4 | L5 | Q73 |
| 5163 | Z4 | L5 | Q74 |
| 5164 | Z4 | L5 | Q75 |
| 5165 | Z4 | L5 | Q76 |
| 5166 | Z4 | L5 | Q77 |
| 5167 | Z4 | L5 | Q78 |
| 5168 | Z4 | L5 | Q79 |
| 5169 | Z4 | L5 | Q80 |
| 5170 | Z4 | L5 | Q81 |
| 5171 | Z4 | L5 | Q82 |
| 5172 | Z4 | L5 | Q83 |
| 5173 | Z4 | L5 | Q84 |
| 5174 | Z4 | L5 | Q85 |
| 5175 | Z4 | L5 | Q86 |
| 5176 | Z4 | L5 | Q87 |
| 5177 | Z4 | L5 | Q88 |
| 5178 | Z4 | L5 | Q89 |
| 5179 | Z4 | L5 | Q90 |
| 5180 | Z4 | L5 | Q91 |
| 5181 | Z4 | L5 | Q92 |
| 5182 | Z4 | L5 | Q93 |
| 5183 | Z4 | L5 | Q94 |
| 5184 | Z4 | L5 | Q95 |
| 5185 | Z4 | L5 | Q96 |
| 5186 | Z4 | L5 | Q97 |
| 5187 | Z4 | L5 | Q98 |
| 5188 | Z4 | L5 | Q99 |
| 5189 | Z4 | L5 | Q100 |
| 5190 | Z4 | L5 | Q101 |
| 5191 | Z4 | L5 | Q102 |
| 5192 | Z4 | L5 | Q103 |
| 5193 | Z4 | L6 | Q40 |
| 5194 | Z4 | L6 | Q41 |
| 5195 | Z4 | L6 | Q42 |
| 5196 | Z4 | L6 | Q43 |
| 5197 | Z4 | L6 | Q44 |
| 5198 | Z4 | L6 | Q45 |

TABLE 1-32

| | | | |
|---|---|---|---|
| 5199 | Z4 | L6 | Q46 |
| 5200 | Z4 | L6 | Q47 |
| 5201 | Z4 | L6 | Q48 |
| 5202 | Z4 | L6 | Q49 |
| 5203 | Z4 | L6 | Q50 |
| 5204 | Z4 | L6 | Q51 |
| 5205 | Z4 | L6 | Q52 |
| 5206 | Z4 | L6 | Q53 |
| 5207 | Z4 | L6 | Q54 |
| 5208 | Z4 | L6 | Q55 |
| 5209 | Z4 | L6 | Q56 |
| 5210 | Z4 | L6 | Q57 |
| 5211 | Z4 | L6 | Q58 |
| 5212 | Z4 | L6 | Q59 |
| 5213 | Z4 | L6 | Q60 |
| 5214 | Z4 | L6 | Q61 |
| 5215 | Z4 | L6 | Q62 |
| 5216 | Z4 | L6 | Q63 |
| 5217 | Z4 | L6 | Q64 |
| 5218 | Z4 | L6 | Q65 |
| 5219 | Z4 | L6 | Q66 |
| 5220 | Z4 | L6 | Q67 |
| 5221 | Z4 | L6 | Q68 |
| 5222 | Z4 | L6 | Q69 |
| 5223 | Z4 | L6 | Q70 |
| 5224 | Z4 | L6 | Q71 |
| 5225 | Z4 | L6 | Q72 |
| 5226 | Z4 | L6 | Q73 |
| 5227 | Z4 | L6 | Q74 |
| 5228 | Z4 | L6 | Q75 |
| 5229 | Z4 | L6 | Q76 |
| 5230 | Z4 | L6 | Q77 |
| 5231 | Z4 | L6 | Q78 |

TABLE 1-32-continued

| | | | |
|---|---|---|---|
| 5232 | Z4 | L6 | Q79 |
| 5233 | Z4 | L6 | Q80 |
| 5234 | Z4 | L6 | Q81 |
| 5235 | Z4 | L6 | Q82 |
| 5236 | Z4 | L6 | Q83 |
| 5237 | Z4 | L6 | Q84 |
| 5238 | Z4 | L6 | Q85 |
| 5239 | Z4 | L6 | Q86 |
| 5240 | Z4 | L6 | Q87 |
| 5241 | Z4 | L6 | Q88 |
| 5242 | Z4 | L6 | Q89 |
| 5243 | Z4 | L6 | Q90 |
| 5244 | Z4 | L6 | Q91 |
| 5245 | Z4 | L6 | Q92 |
| 5246 | Z4 | L6 | Q93 |
| 5247 | Z4 | L6 | Q94 |
| 5248 | Z4 | L6 | Q95 |
| 5249 | Z4 | L6 | Q96 |
| 5250 | Z4 | L6 | Q97 |
| 5251 | Z4 | L6 | Q98 |
| 5252 | Z4 | L6 | Q99 |
| 5253 | Z4 | L6 | Q100 |
| 5254 | Z4 | L6 | Q101 |
| 5255 | Z4 | L6 | Q102 |
| 5256 | Z4 | L6 | Q103 |
| 5257 | Z4 | L7 | Q40 |
| 5258 | Z4 | L7 | Q41 |
| 5259 | Z4 | L7 | Q42 |
| 5260 | Z4 | L7 | Q43 |
| 5261 | Z4 | L7 | Q44 |
| 5262 | Z4 | L7 | Q45 |
| 5263 | Z4 | L7 | Q46 |
| 5264 | Z4 | L7 | Q47 |
| 5265 | Z4 | L7 | Q48 |
| 5266 | Z4 | L7 | Q49 |
| 5267 | Z4 | L7 | Q50 |
| 5268 | Z4 | L7 | Q51 |
| 5269 | Z4 | L7 | Q52 |
| 5270 | Z4 | L7 | Q53 |
| 5271 | Z4 | L7 | Q54 |
| 5272 | Z4 | L7 | Q55 |
| 5273 | Z4 | L7 | Q56 |
| 5274 | Z4 | L7 | Q57 |
| 5275 | Z4 | L7 | Q58 |
| 5276 | Z4 | L7 | Q59 |
| 5277 | Z4 | L7 | Q60 |
| 5278 | Z4 | L7 | Q61 |
| 5279 | Z4 | L7 | Q62 |
| 5280 | Z4 | L7 | Q63 |
| 5281 | Z4 | L7 | Q64 |
| 5282 | Z4 | L7 | Q65 |
| 5283 | Z4 | L7 | Q66 |
| 5284 | Z4 | L7 | Q67 |
| 5285 | Z4 | L7 | Q68 |
| 5286 | Z4 | L7 | Q69 |
| 5287 | Z4 | L7 | Q70 |
| 5288 | Z4 | L7 | Q71 |
| 5289 | Z4 | L7 | Q72 |
| 5290 | Z4 | L7 | Q73 |
| 5291 | Z4 | L7 | Q74 |
| 5292 | Z4 | L7 | Q75 |
| 5293 | Z4 | L7 | Q76 |
| 5294 | Z4 | L7 | Q77 |
| 5295 | Z4 | L7 | Q78 |
| 5296 | Z4 | L7 | Q79 |
| 5297 | Z4 | L7 | Q80 |
| 5298 | Z4 | L7 | Q81 |
| 5299 | Z4 | L7 | Q82 |
| 5300 | Z4 | L7 | Q83 |
| 5301 | Z4 | L7 | Q84 |
| 5302 | Z4 | L7 | Q85 |
| 5303 | Z4 | L7 | Q86 |
| 5304 | Z4 | L7 | Q87 |
| 5305 | Z4 | L7 | Q88 |
| 5306 | Z4 | L7 | Q89 |
| 5307 | Z4 | L7 | Q90 |
| 5308 | Z4 | L7 | Q91 |
| 5309 | Z4 | L7 | Q92 |
| 5310 | Z4 | L7 | Q93 |
| 5311 | Z4 | L7 | Q94 |
| 5312 | Z4 | L7 | Q95 |
| 5313 | Z4 | L7 | Q96 |
| 5314 | Z4 | L7 | Q97 |
| 5315 | Z4 | L7 | Q98 |
| 5316 | Z4 | L7 | Q99 |
| 5317 | Z4 | L7 | Q100 |
| 5318 | Z4 | L7 | Q101 |
| 5319 | Z4 | L7 | Q102 |
| 5320 | Z4 | L7 | Q103 |
| 5321 | Z4 | L8 | Q40 |
| 5322 | Z4 | L8 | Q41 |
| 5323 | Z4 | L8 | Q42 |
| 5324 | Z4 | L8 | Q43 |
| 5325 | Z4 | L8 | Q44 |
| 5326 | Z4 | L8 | Q45 |
| 5327 | Z4 | L8 | Q46 |
| 5328 | Z4 | L8 | Q47 |
| 5329 | Z4 | L8 | Q48 |
| 5330 | Z4 | L8 | Q49 |
| 5331 | Z4 | L8 | Q50 |
| 5332 | Z4 | L8 | Q51 |
| 5333 | Z4 | L8 | Q52 |
| 5334 | Z4 | L8 | Q53 |
| 5335 | Z4 | L8 | Q54 |
| 5336 | Z4 | L8 | Q55 |
| 5337 | Z4 | L8 | Q56 |
| 5338 | Z4 | L8 | Q57 |
| 5339 | Z4 | L8 | Q58 |
| 5340 | Z4 | L8 | Q59 |
| 5341 | Z4 | L8 | Q60 |
| 5342 | Z4 | L8 | Q61 |
| 5343 | Z4 | L8 | Q62 |
| 5344 | Z4 | L8 | Q63 |
| 5345 | Z4 | L8 | Q64 |
| 5346 | Z4 | L8 | Q65 |
| 5347 | Z4 | L8 | Q66 |
| 5348 | Z4 | L8 | Q67 |
| 5349 | Z4 | L8 | Q68 |
| 5350 | Z4 | L8 | Q69 |
| 5351 | Z4 | L8 | Q70 |
| 5352 | Z4 | L8 | Q71 |
| 5353 | Z4 | L8 | Q72 |
| 5354 | Z4 | L8 | Q73 |
| 5355 | Z4 | L8 | Q74 |
| 5356 | Z4 | L8 | Q75 |
| 5357 | Z4 | L8 | Q76 |
| 5358 | Z4 | L8 | Q77 |
| 5359 | Z4 | L8 | Q78 |
| 5360 | Z4 | L8 | Q79 |
| 5361 | Z4 | L8 | Q80 |
| 5362 | Z4 | L8 | Q81 |
| 5363 | Z4 | L8 | Q82 |
| 5364 | Z4 | L8 | Q83 |
| 5365 | Z4 | L8 | Q84 |
| 5366 | Z4 | L8 | Q85 |
| 5367 | Z4 | L8 | Q86 |
| 5368 | Z4 | L8 | Q87 |
| 5369 | Z4 | L8 | Q88 |
| 5370 | Z4 | L8 | Q89 |
| 5371 | Z4 | L8 | Q90 |
| 5372 | Z4 | L8 | Q91 |
| 5373 | Z4 | L8 | Q92 |
| 5374 | Z4 | L8 | Q93 |
| 5375 | Z4 | L8 | Q94 |
| 5376 | Z4 | L8 | Q95 |
| 5377 | Z4 | L8 | Q96 |
| 5378 | Z4 | L8 | Q97 |
| 5379 | Z4 | L8 | Q98 |
| 5380 | Z4 | L8 | Q99 |
| 5381 | Z4 | L8 | Q100 |
| 5382 | Z4 | L8 | Q101 |
| 5383 | Z4 | L8 | Q102 |
| 5384 | Z4 | L8 | Q103 |
| 5385 | Z4 | L9 | Q40 |
| 5386 | Z4 | L9 | Q41 |
| 5387 | Z4 | L9 | Q42 |
| 5388 | Z4 | L9 | Q43 |
| 5389 | Z4 | L9 | Q44 |
| 5390 | Z4 | L9 | Q45 |
| 5391 | Z4 | L9 | Q46 |

TABLE 1-32-continued

| | | | |
|---|---|---|---|
| 5392 | Z4 | L9 | Q47 |
| 5393 | Z4 | L9 | Q48 |
| 5394 | Z4 | L9 | Q49 |
| 5395 | Z4 | L9 | Q50 |
| 5396 | Z4 | L9 | Q51 |
| 5397 | Z4 | L9 | Q52 |
| 5398 | Z4 | L9 | Q53 |
| 5399 | Z4 | L9 | Q54 |

TABLE 1-33

| | | | |
|---|---|---|---|
| 5400 | Z4 | L9 | Q55 |
| 5401 | Z4 | L9 | Q56 |
| 5402 | Z4 | L9 | Q57 |
| 5403 | Z4 | L9 | Q58 |
| 5404 | Z4 | L9 | Q59 |
| 5405 | Z4 | L9 | Q60 |
| 5406 | Z4 | L9 | Q61 |
| 5407 | Z4 | L9 | Q62 |
| 5408 | Z4 | L9 | Q63 |
| 5409 | Z4 | L9 | Q64 |
| 5410 | Z4 | L9 | Q65 |
| 5411 | Z4 | L9 | Q66 |
| 5412 | Z4 | L9 | Q67 |
| 5413 | Z4 | L9 | Q68 |
| 5414 | Z4 | L9 | Q69 |
| 5415 | Z4 | L9 | Q70 |
| 5416 | Z4 | L9 | Q71 |
| 5417 | Z4 | L9 | Q72 |
| 5418 | Z4 | L9 | Q73 |
| 5419 | Z4 | L9 | Q74 |
| 5420 | Z4 | L9 | Q75 |
| 5421 | Z4 | L9 | Q76 |
| 5422 | Z4 | L9 | Q77 |
| 5423 | Z4 | L9 | Q78 |
| 5424 | Z4 | L9 | Q79 |
| 5425 | Z4 | L9 | Q80 |
| 5426 | Z4 | L9 | Q81 |
| 5427 | Z4 | L9 | Q82 |
| 5428 | Z4 | L9 | Q83 |
| 5429 | Z4 | L9 | Q84 |
| 5430 | Z4 | L9 | Q85 |
| 5431 | Z4 | L9 | Q86 |
| 5432 | Z4 | L9 | Q87 |
| 5433 | Z4 | L9 | Q88 |
| 5434 | Z4 | L9 | Q89 |
| 5435 | Z4 | L9 | Q90 |
| 5436 | Z4 | L9 | Q91 |
| 5437 | Z4 | L9 | Q92 |
| 5438 | Z4 | L9 | Q93 |
| 5439 | Z4 | L9 | Q94 |
| 5440 | Z4 | L9 | Q95 |
| 5441 | Z4 | L9 | Q96 |
| 5442 | Z4 | L9 | Q97 |
| 5443 | Z4 | L9 | Q98 |
| 5444 | Z4 | L9 | Q99 |
| 5445 | Z4 | L9 | Q100 |
| 5446 | Z4 | L9 | Q101 |
| 5447 | Z4 | L9 | Q102 |
| 5448 | Z4 | L9 | Q103 |
| 5449 | Z4 | L10 | Q40 |
| 5450 | Z4 | L10 | Q41 |
| 5451 | Z4 | L10 | Q42 |
| 5452 | Z4 | L10 | Q43 |
| 5453 | Z4 | L10 | Q44 |
| 5454 | Z4 | L10 | Q45 |
| 5455 | Z4 | L10 | Q46 |
| 5456 | Z4 | L10 | Q47 |
| 5457 | Z4 | L10 | Q48 |
| 5458 | Z4 | L10 | Q49 |
| 5459 | Z4 | L10 | Q50 |
| 5460 | Z4 | L10 | Q51 |
| 5461 | Z4 | L10 | Q52 |
| 5462 | Z4 | L10 | Q53 |
| 5463 | Z4 | L10 | Q54 |
| 5464 | Z4 | L10 | Q55 |
| 5465 | Z4 | L10 | Q56 |

TABLE 1-33-continued

| | | | |
|---|---|---|---|
| 5466 | Z4 | L10 | Q57 |
| 5467 | Z4 | L10 | Q58 |
| 5468 | Z4 | L10 | Q59 |
| 5469 | Z4 | L10 | Q60 |
| 5470 | Z4 | L10 | Q61 |
| 5471 | Z4 | L10 | Q62 |
| 5472 | Z4 | L10 | Q63 |
| 5473 | Z4 | L10 | Q64 |
| 5474 | Z4 | L10 | Q65 |
| 5475 | Z4 | L10 | Q66 |
| 5476 | Z4 | L10 | Q67 |
| 5477 | Z4 | L10 | Q68 |
| 5478 | Z4 | L10 | Q69 |
| 5479 | Z4 | L10 | Q70 |
| 5480 | Z4 | L10 | Q71 |
| 5481 | Z4 | L10 | Q72 |
| 5482 | Z4 | L10 | Q73 |
| 5483 | Z4 | L10 | Q74 |
| 5484 | Z4 | L10 | Q75 |
| 5485 | Z4 | L10 | Q76 |
| 5486 | Z4 | L10 | Q77 |
| 5487 | Z4 | L10 | Q78 |
| 5488 | Z4 | L10 | Q79 |
| 5489 | Z4 | L10 | Q80 |
| 5490 | Z4 | L10 | Q81 |
| 5491 | Z4 | L10 | Q82 |
| 5492 | Z4 | L10 | Q83 |
| 5493 | Z4 | L10 | Q84 |
| 5494 | Z4 | L10 | Q85 |
| 5495 | Z4 | L10 | Q86 |
| 5496 | Z4 | L10 | Q87 |
| 5497 | Z4 | L10 | Q88 |
| 5498 | Z4 | L10 | Q89 |
| 5499 | Z4 | L10 | Q90 |
| 5500 | Z4 | L10 | Q91 |
| 5501 | Z4 | L10 | Q92 |
| 5502 | Z4 | L10 | Q93 |
| 5503 | Z4 | L10 | Q94 |
| 5504 | Z4 | L10 | Q95 |
| 5505 | Z4 | L10 | Q96 |
| 5506 | Z4 | L10 | Q97 |
| 5507 | Z4 | L10 | Q98 |
| 5508 | Z4 | L10 | Q99 |
| 5509 | Z4 | L10 | Q100 |
| 5510 | Z4 | L10 | Q101 |
| 5511 | Z4 | L10 | Q102 |
| 5512 | Z4 | L10 | Q103 |
| 5513 | Z4 | L11 | Q40 |
| 5514 | Z4 | L11 | Q41 |
| 5515 | Z4 | L11 | Q42 |
| 5516 | Z4 | L11 | Q43 |
| 5517 | Z4 | L11 | Q44 |
| 5518 | Z4 | L11 | Q45 |
| 5519 | Z4 | L11 | Q46 |
| 5520 | Z4 | L11 | Q47 |
| 5521 | Z4 | L11 | Q48 |
| 5522 | Z4 | L11 | Q49 |
| 5523 | Z4 | L11 | Q50 |
| 5524 | Z4 | L11 | Q51 |
| 5525 | Z4 | L11 | Q52 |
| 5526 | Z4 | L11 | Q53 |
| 5527 | Z4 | L11 | Q54 |
| 5528 | Z4 | L11 | Q55 |
| 5529 | Z4 | L11 | Q56 |
| 5530 | Z4 | L11 | Q57 |
| 5531 | Z4 | L11 | Q58 |
| 5532 | Z4 | L11 | Q59 |
| 5533 | Z4 | L11 | Q60 |
| 5534 | Z4 | L11 | Q61 |
| 5535 | Z4 | L11 | Q62 |
| 5536 | Z4 | L11 | Q63 |
| 5537 | Z4 | L11 | Q64 |
| 5538 | Z4 | L11 | Q65 |
| 5539 | Z4 | L11 | Q66 |
| 5540 | Z4 | L11 | Q67 |
| 5541 | Z4 | L11 | Q68 |
| 5542 | Z4 | L11 | Q69 |
| 5543 | Z4 | L11 | Q70 |
| 5544 | Z4 | L11 | Q71 |
| 5545 | Z4 | L11 | Q72 |

TABLE 1-33-continued

| | | | |
|---|---|---|---|
| 5546 | Z4 | L11 | Q73 |
| 5547 | Z4 | L11 | Q74 |
| 5548 | Z4 | L11 | Q75 |
| 5549 | Z4 | L11 | Q76 |
| 5550 | Z4 | L11 | Q77 |
| 5551 | Z4 | L11 | Q78 |
| 5552 | Z4 | L11 | Q79 |
| 5553 | Z4 | L11 | Q80 |
| 5554 | Z4 | L11 | Q81 |
| 5555 | Z4 | L11 | Q82 |
| 5556 | Z4 | L11 | Q83 |
| 5557 | Z4 | L11 | Q84 |
| 5558 | Z4 | L11 | Q85 |
| 5559 | Z4 | L11 | Q86 |
| 5560 | Z4 | L11 | Q87 |
| 5561 | Z4 | L11 | Q88 |
| 5562 | Z4 | L11 | Q89 |
| 5563 | Z4 | L11 | Q90 |
| 5564 | Z4 | L11 | Q91 |
| 5565 | Z4 | L11 | Q92 |
| 5566 | Z4 | L11 | Q93 |
| 5567 | Z4 | L11 | Q94 |
| 5568 | Z4 | L11 | Q95 |
| 5569 | Z4 | L11 | Q96 |
| 5570 | Z4 | L11 | Q97 |
| 5571 | Z4 | L11 | Q98 |
| 5572 | Z4 | L11 | Q99 |
| 5573 | Z4 | L11 | Q100 |
| 5574 | Z4 | L11 | Q101 |
| 5575 | Z4 | L11 | Q102 |
| 5576 | Z4 | L11 | Q103 |
| 5577 | Z4 | L12 | Q40 |
| 5578 | Z4 | L12 | Q41 |
| 5579 | Z4 | L12 | Q42 |
| 5580 | Z4 | L12 | Q43 |
| 5581 | Z4 | L12 | Q44 |
| 5582 | Z4 | L12 | Q45 |
| 5583 | Z4 | L12 | Q46 |
| 5584 | Z4 | L12 | Q47 |
| 5585 | Z4 | L12 | Q48 |
| 5586 | Z4 | L12 | Q49 |
| 5587 | Z4 | L12 | Q50 |
| 5588 | Z4 | L12 | Q51 |
| 5589 | Z4 | L12 | Q52 |
| 5590 | Z4 | L12 | Q53 |
| 5591 | Z4 | L12 | Q54 |
| 5592 | Z4 | L12 | Q55 |
| 5593 | Z4 | L12 | Q56 |
| 5594 | Z4 | L12 | Q57 |
| 5595 | Z4 | L12 | Q58 |
| 5596 | Z4 | L12 | Q59 |
| 5597 | Z4 | L12 | Q60 |
| 5598 | Z4 | L12 | Q61 |
| 5599 | Z4 | L12 | Q62 |
| 5600 | Z4 | L12 | Q63 |

TABLE 1-34

| | | | |
|---|---|---|---|
| 5601 | Z4 | L12 | Q64 |
| 5602 | Z4 | L12 | Q65 |
| 5603 | Z4 | L12 | Q66 |
| 5604 | Z4 | L12 | Q67 |
| 5605 | Z4 | L12 | Q68 |
| 5606 | Z4 | L12 | Q69 |
| 5607 | Z4 | L12 | Q70 |
| 5608 | Z4 | L12 | Q71 |
| 5609 | Z4 | L12 | Q72 |
| 5610 | Z4 | L12 | Q73 |
| 5611 | Z4 | L12 | Q74 |
| 5612 | Z4 | L12 | Q75 |
| 5613 | Z4 | L12 | Q76 |
| 5614 | Z4 | L12 | Q77 |
| 5615 | Z4 | L12 | Q78 |
| 5616 | Z4 | L12 | Q79 |
| 5617 | Z4 | L12 | Q80 |
| 5618 | Z4 | L12 | Q81 |
| 5619 | Z4 | L12 | Q82 |

TABLE 1-34-continued

| | | | |
|---|---|---|---|
| 5620 | Z4 | L12 | Q83 |
| 5621 | Z4 | L12 | Q84 |
| 5622 | Z4 | L12 | Q85 |
| 5623 | Z4 | L12 | Q86 |
| 5624 | Z4 | L12 | Q87 |
| 5625 | Z4 | L12 | Q88 |
| 5626 | Z4 | L12 | Q89 |
| 5627 | Z4 | L12 | Q90 |
| 5628 | Z4 | L12 | Q91 |
| 5629 | Z4 | L12 | Q92 |
| 5630 | Z4 | L12 | Q93 |
| 5631 | Z4 | L12 | Q94 |
| 5632 | Z4 | L12 | Q95 |
| 5633 | Z4 | L12 | Q96 |
| 5634 | Z4 | L12 | Q97 |
| 5635 | Z4 | L12 | Q98 |
| 5636 | Z4 | L12 | Q99 |
| 5637 | Z4 | L12 | Q100 |
| 5638 | Z4 | L12 | Q101 |
| 5639 | Z4 | L12 | Q102 |
| 5640 | Z4 | L12 | Q103 |
| 5641 | Z4 | L13 | Q40 |
| 5642 | Z4 | L13 | Q41 |
| 5643 | Z4 | L13 | Q42 |
| 5644 | Z4 | L13 | Q43 |
| 5645 | Z4 | L13 | Q44 |
| 5646 | Z4 | L13 | Q45 |
| 5647 | Z4 | L13 | Q46 |
| 5648 | Z4 | L13 | Q47 |
| 5649 | Z4 | L13 | Q48 |
| 5650 | Z4 | L13 | Q49 |
| 5651 | Z4 | L13 | Q50 |
| 5652 | Z4 | L13 | Q51 |
| 5653 | Z4 | L13 | Q52 |
| 5654 | Z4 | L13 | Q53 |
| 5655 | Z4 | L13 | Q54 |
| 5656 | Z4 | L13 | Q55 |
| 5657 | Z4 | L13 | Q56 |
| 5658 | Z4 | L13 | Q57 |
| 5659 | Z4 | L13 | Q58 |
| 5660 | Z4 | L13 | Q59 |
| 5661 | Z4 | L13 | Q60 |
| 5662 | Z4 | L13 | Q61 |
| 5663 | Z4 | L13 | Q62 |
| 5664 | Z4 | L13 | Q63 |
| 5665 | Z4 | L13 | Q64 |
| 5666 | Z4 | L13 | Q65 |
| 5667 | Z4 | L13 | Q66 |
| 5668 | Z4 | L13 | Q67 |
| 5669 | Z4 | L13 | Q68 |
| 5670 | Z4 | L13 | Q69 |
| 5671 | Z4 | L13 | Q70 |
| 5672 | Z4 | L13 | Q71 |
| 5673 | Z4 | L13 | Q72 |
| 5674 | Z4 | L13 | Q73 |
| 5675 | Z4 | L13 | Q74 |
| 5676 | Z4 | L13 | Q75 |
| 5677 | Z4 | L13 | Q76 |
| 5678 | Z4 | L13 | Q77 |
| 5679 | Z4 | L13 | Q78 |
| 5680 | Z4 | L13 | Q79 |
| 5681 | Z4 | L13 | Q80 |
| 5682 | Z4 | L13 | Q81 |
| 5683 | Z4 | L13 | Q82 |
| 5684 | Z4 | L13 | Q83 |
| 5685 | Z4 | L13 | Q84 |
| 5686 | Z4 | L13 | Q85 |
| 5687 | Z4 | L13 | Q86 |
| 5688 | Z4 | L13 | Q87 |
| 5689 | Z4 | L13 | Q88 |
| 5690 | Z4 | L13 | Q89 |
| 5691 | Z4 | L13 | Q90 |
| 5692 | Z4 | L13 | Q91 |
| 5693 | Z4 | L13 | Q92 |
| 5694 | Z4 | L13 | Q93 |
| 5695 | Z4 | L13 | Q94 |
| 5696 | Z4 | L13 | Q95 |
| 5697 | Z4 | L13 | Q96 |
| 5698 | Z4 | L13 | Q97 |
| 5699 | Z4 | L13 | Q98 |

TABLE 1-34-continued

| | | | |
|---|---|---|---|
| 5700 | Z4 | L13 | Q99 |
| 5701 | Z4 | L13 | Q100 |
| 5702 | Z4 | L13 | Q101 |
| 5703 | Z4 | L13 | Q102 |
| 5704 | Z4 | L13 | Q103 |
| 5705 | Z4 | L14 | Q40 |
| 5706 | Z4 | L14 | Q41 |
| 5707 | Z4 | L14 | Q42 |
| 5708 | Z4 | L14 | Q43 |
| 5709 | Z4 | L14 | Q44 |
| 5710 | Z4 | L14 | Q45 |
| 5711 | Z4 | L14 | Q46 |
| 5712 | Z4 | L14 | Q47 |
| 5713 | Z4 | L14 | Q48 |
| 5714 | Z4 | L14 | Q49 |
| 5715 | Z4 | L14 | Q50 |
| 5716 | Z4 | L14 | Q51 |
| 5717 | Z4 | L14 | Q52 |
| 5718 | Z4 | L14 | Q53 |
| 5719 | Z4 | L14 | Q54 |
| 5720 | Z4 | L14 | Q55 |
| 5721 | Z4 | L14 | Q56 |
| 5722 | Z4 | L14 | Q57 |
| 5723 | Z4 | L14 | Q58 |
| 5724 | Z4 | L14 | Q59 |
| 5725 | Z4 | L14 | Q60 |
| 5726 | Z4 | L14 | Q61 |
| 5727 | Z4 | L14 | Q62 |
| 5728 | Z4 | L14 | Q63 |
| 5729 | Z4 | L14 | Q64 |
| 5730 | Z4 | L14 | Q65 |
| 5731 | Z4 | L14 | Q66 |
| 5732 | Z4 | L14 | Q67 |
| 5733 | Z4 | L14 | Q68 |
| 5734 | Z4 | L14 | Q69 |
| 5735 | Z4 | L14 | Q70 |
| 5736 | Z4 | L14 | Q71 |
| 5737 | Z4 | L14 | Q72 |
| 5738 | Z4 | L14 | Q73 |
| 5739 | Z4 | L14 | Q74 |
| 5740 | Z4 | L14 | Q75 |
| 5741 | Z4 | L14 | Q76 |
| 5742 | Z4 | L14 | Q77 |
| 5743 | Z4 | L14 | Q78 |
| 5744 | Z4 | L14 | Q79 |
| 5745 | Z4 | L14 | Q80 |
| 5746 | Z4 | L14 | Q81 |
| 5747 | Z4 | L14 | Q82 |
| 5748 | Z4 | L14 | Q83 |
| 5749 | Z4 | L14 | Q84 |
| 5750 | Z4 | L14 | Q85 |
| 5751 | Z4 | L14 | Q86 |
| 5752 | Z4 | L14 | Q87 |
| 5753 | Z4 | L14 | Q88 |
| 5754 | Z4 | L14 | Q89 |
| 5755 | Z4 | L14 | Q90 |
| 5756 | Z4 | L14 | Q91 |
| 5757 | Z4 | L14 | Q92 |
| 5758 | Z4 | L14 | Q93 |
| 5759 | Z4 | L14 | Q94 |
| 5760 | Z4 | L14 | Q95 |
| 5761 | Z4 | L14 | Q96 |
| 5762 | Z4 | L14 | Q97 |
| 5763 | Z4 | L14 | Q98 |
| 5764 | Z4 | L14 | Q99 |
| 5765 | Z4 | L14 | Q100 |
| 5766 | Z4 | L14 | Q101 |
| 5767 | Z4 | L14 | Q102 |
| 5768 | Z4 | L14 | Q103 |
| 5769 | Z1 | L15 | Q1 |
| 5770 | Z1 | L15 | Q2 |
| 5771 | Z1 | L15 | Q3 |
| 5772 | Z1 | L15 | Q4 |
| 5773 | Z1 | L15 | Q5 |
| 5774 | Z1 | L15 | Q6 |
| 5775 | Z1 | L15 | Q7 |
| 5776 | Z1 | L15 | Q8 |
| 5777 | Z1 | L15 | Q9 |
| 5778 | Z1 | L15 | Q10 |
| 5779 | Z1 | L15 | Q11 |

TABLE 1-34-continued

| | | | |
|---|---|---|---|
| 5780 | Z1 | L15 | Q12 |
| 5781 | Z1 | L15 | Q13 |
| 5782 | Z1 | L15 | Q14 |
| 5783 | Z1 | L15 | Q15 |
| 5784 | Z1 | L15 | Q16 |
| 5785 | Z1 | L15 | Q17 |
| 5786 | Z1 | L15 | Q18 |
| 5787 | Z1 | L15 | Q19 |
| 5788 | Z1 | L15 | Q20 |
| 5789 | Z1 | L15 | Q21 |
| 5790 | Z1 | L15 | Q22 |
| 5791 | Z1 | L15 | Q23 |
| 5792 | Z1 | L15 | Q24 |
| 5793 | Z1 | L15 | Q25 |
| 5794 | Z1 | L15 | Q26 |
| 5795 | Z1 | L15 | Q27 |
| 5796 | Z1 | L15 | Q28 |
| 5797 | Z1 | L15 | Q29 |
| 5798 | Z1 | L15 | Q30 |
| 5799 | Z1 | L15 | Q31 |
| 5800 | Z1 | L15 | Q32 |
| 5801 | Z1 | L15 | Q33 |

TABLE 1-35

| | | | |
|---|---|---|---|
| 5802 | Z1 | L15 | Q34 |
| 5803 | Z1 | L15 | Q35 |
| 5804 | Z1 | L15 | Q36 |
| 5805 | Z1 | L15 | Q37 |
| 5806 | Z1 | L15 | Q38 |
| 5807 | Z1 | L15 | Q39 |
| 5808 | Z1 | L15 | Q40 |
| 5809 | Z1 | L15 | Q41 |
| 5810 | Z1 | L15 | Q42 |
| 5811 | Z1 | L15 | Q43 |
| 5812 | Z1 | L15 | Q44 |
| 5813 | Z1 | L15 | Q45 |
| 5814 | Z1 | L15 | Q46 |
| 5815 | Z1 | L15 | Q47 |
| 5816 | Z1 | L15 | Q48 |
| 5817 | Z1 | L15 | Q49 |
| 5818 | Z1 | L15 | Q50 |
| 5819 | Z1 | L15 | Q51 |
| 5820 | Z1 | L15 | Q52 |
| 5821 | Z1 | L15 | Q53 |
| 5822 | Z1 | L15 | Q54 |
| 5823 | Z1 | L15 | Q55 |
| 5824 | Z1 | L15 | Q56 |
| 5825 | Z1 | L15 | Q57 |
| 5826 | Z1 | L15 | Q58 |
| 5827 | Z1 | L15 | Q59 |
| 5828 | Z1 | L15 | Q60 |
| 5829 | Z1 | L15 | Q61 |
| 5830 | Z1 | L15 | Q62 |
| 5831 | Z1 | L15 | Q63 |
| 5832 | Z1 | L15 | Q64 |
| 5833 | Z1 | L15 | Q65 |
| 5834 | Z1 | L15 | Q66 |
| 5835 | Z1 | L15 | Q67 |
| 5836 | Z1 | L15 | Q68 |
| 5837 | Z1 | L15 | Q69 |
| 5838 | Z1 | L15 | Q70 |
| 5839 | Z1 | L15 | Q71 |
| 5840 | Z1 | L15 | Q72 |
| 5841 | Z1 | L15 | Q73 |
| 5842 | Z1 | L15 | Q74 |
| 5843 | Z1 | L15 | Q75 |
| 5844 | Z1 | L15 | Q76 |
| 5845 | Z1 | L15 | Q77 |
| 5846 | Z1 | L15 | Q78 |
| 5847 | Z1 | L15 | Q79 |
| 5848 | Z1 | L15 | Q80 |
| 5849 | Z1 | L15 | Q81 |
| 5850 | Z1 | L15 | Q82 |
| 5851 | Z1 | L15 | Q83 |
| 5852 | Z1 | L15 | Q84 |
| 5853 | Z1 | L15 | Q85 |

TABLE 1-35-continued

| | | | |
|---|---|---|---|
| 5854 | Z1 | L15 | Q86 |
| 5855 | Z1 | L15 | Q87 |
| 5856 | Z1 | L15 | Q88 |
| 5857 | Z1 | L15 | Q89 |
| 5858 | Z1 | L15 | Q90 |
| 5859 | Z1 | L15 | Q91 |
| 5860 | Z1 | L15 | Q92 |
| 5861 | Z1 | L15 | Q93 |
| 5862 | Z1 | L15 | Q94 |
| 5863 | Z1 | L15 | Q95 |
| 5864 | Z1 | L15 | Q96 |
| 5865 | Z1 | L15 | Q97 |
| 5866 | Z1 | L15 | Q98 |
| 5867 | Z1 | L15 | Q99 |
| 5868 | Z1 | L15 | Q100 |
| 5869 | Z1 | L15 | Q101 |
| 5870 | Z1 | L15 | Q102 |
| 5871 | Z1 | L15 | Q103 |
| 5872 | Z1 | L16 | Q1 |
| 5873 | Z1 | L16 | Q2 |
| 5874 | Z1 | L16 | Q3 |
| 5875 | Z1 | L16 | Q4 |
| 5876 | Z1 | L16 | Q5 |
| 5877 | Z1 | L16 | Q6 |
| 5878 | Z1 | L16 | Q7 |
| 5879 | Z1 | L16 | Q8 |
| 5880 | Z1 | L16 | Q9 |
| 5881 | Z1 | L16 | Q10 |
| 5882 | Z1 | L16 | Q11 |
| 5883 | Z1 | L16 | Q12 |
| 5884 | Z1 | L16 | Q13 |
| 5885 | Z1 | L16 | Q14 |
| 5886 | Z1 | L16 | Q15 |
| 5887 | Z1 | L16 | Q16 |
| 5888 | Z1 | L16 | Q17 |
| 5889 | Z1 | L16 | Q18 |
| 5890 | Z1 | L16 | Q19 |
| 5891 | Z1 | L16 | Q20 |
| 5892 | Z1 | L16 | Q21 |
| 5893 | Z1 | L16 | Q22 |
| 5894 | Z1 | L16 | Q23 |
| 5895 | Z1 | L16 | Q24 |
| 5896 | Z1 | L16 | Q25 |
| 5897 | Z1 | L16 | Q26 |
| 5898 | Z1 | L16 | Q27 |
| 5899 | Z1 | L16 | Q28 |
| 5900 | Z1 | L16 | Q29 |
| 5901 | Z1 | L16 | Q30 |
| 5902 | Z1 | L16 | Q31 |
| 5903 | Z1 | L16 | Q32 |
| 5904 | Z1 | L16 | Q33 |
| 5905 | Z1 | L16 | Q34 |
| 5906 | Z1 | L16 | Q35 |
| 5907 | Z1 | L16 | Q36 |
| 5908 | Z1 | L16 | Q37 |
| 5909 | Z1 | L16 | Q38 |
| 5910 | Z1 | L16 | Q39 |
| 5911 | Z1 | L16 | Q40 |
| 5912 | Z1 | L16 | Q41 |
| 5913 | Z1 | L16 | Q42 |
| 5914 | Z1 | L16 | Q43 |
| 5915 | Z1 | L16 | Q44 |
| 5916 | Z1 | L16 | Q45 |
| 5917 | Z1 | L16 | Q46 |
| 5918 | Z1 | L16 | Q47 |
| 5919 | Z1 | L16 | Q48 |
| 5920 | Z1 | L16 | Q49 |
| 5921 | Z1 | L16 | Q50 |
| 5922 | Z1 | L16 | Q51 |
| 5923 | Z1 | L16 | Q52 |
| 5924 | Z1 | L16 | Q53 |
| 5925 | Z1 | L16 | Q54 |
| 5926 | Z1 | L16 | Q55 |
| 5927 | Z1 | L16 | Q56 |
| 5928 | Z1 | L16 | Q57 |
| 5929 | Z1 | L16 | Q58 |
| 5930 | Z1 | L16 | Q59 |
| 5931 | Z1 | L16 | Q60 |
| 5932 | Z1 | L16 | Q61 |
| 5933 | Z1 | L16 | Q62 |
| 5934 | Z1 | L16 | Q63 |
| 5935 | Z1 | L16 | Q64 |
| 5936 | Z1 | L16 | Q65 |
| 5937 | Z1 | L16 | Q66 |
| 5938 | Z1 | L16 | Q67 |
| 5939 | Z1 | L16 | Q68 |
| 5940 | Z1 | L16 | Q69 |
| 5941 | Z1 | L16 | Q70 |
| 5942 | Z1 | L16 | Q71 |
| 5943 | Z1 | L16 | Q72 |
| 5944 | Z1 | L16 | Q73 |
| 5945 | Z1 | L16 | Q74 |
| 5946 | Z1 | L16 | Q75 |
| 5947 | Z1 | L16 | Q76 |
| 5948 | Z1 | L16 | Q77 |
| 5949 | Z1 | L16 | Q78 |
| 5950 | Z1 | L16 | Q79 |
| 5951 | Z1 | L16 | Q80 |
| 5952 | Z1 | L16 | Q81 |
| 5953 | Z1 | L16 | Q82 |
| 5954 | Z1 | L16 | Q83 |
| 5955 | Z1 | L16 | Q84 |
| 5956 | Z1 | L16 | Q85 |
| 5957 | Z1 | L16 | Q86 |
| 5958 | Z1 | L16 | Q87 |
| 5959 | Z1 | L16 | Q88 |
| 5960 | Z1 | L16 | Q89 |
| 5961 | Z1 | L16 | Q90 |
| 5962 | Z1 | L16 | Q91 |
| 5963 | Z1 | L16 | Q92 |
| 5964 | Z1 | L16 | Q93 |
| 5965 | Z1 | L16 | Q94 |
| 5966 | Z1 | L16 | Q95 |
| 5967 | Z1 | L16 | Q96 |
| 5968 | Z1 | L16 | Q97 |
| 5969 | Z1 | L16 | Q98 |
| 5970 | Z1 | L16 | Q99 |
| 5971 | Z1 | L16 | Q100 |
| 5972 | Z1 | L16 | Q101 |
| 5973 | Z1 | L16 | Q102 |
| 5974 | Z1 | L16 | Q103 |
| 5975 | Z1 | L17 | Q1 |
| 5976 | Z1 | L17 | Q2 |
| 5977 | Z1 | L17 | Q3 |
| 5978 | Z1 | L17 | Q4 |
| 5979 | Z1 | L17 | Q5 |
| 5980 | Z1 | L17 | Q6 |
| 5981 | Z1 | L17 | Q7 |
| 5982 | Z1 | L17 | Q8 |
| 5983 | Z1 | L17 | Q9 |
| 5984 | Z1 | L17 | Q10 |
| 5985 | Z1 | L17 | Q11 |
| 5986 | Z1 | L17 | Q12 |
| 5987 | Z1 | L17 | Q13 |
| 5988 | Z1 | L17 | Q14 |
| 5989 | Z1 | L17 | Q15 |
| 5990 | Z1 | L17 | Q16 |
| 5991 | Z1 | L17 | Q17 |
| 5992 | Z1 | L17 | Q18 |
| 5993 | Z1 | L17 | Q19 |
| 5994 | Z1 | L17 | Q20 |
| 5995 | Z1 | L17 | Q21 |
| 5996 | Z1 | L17 | Q22 |
| 5997 | Z1 | L17 | Q23 |
| 5998 | Z1 | L17 | Q24 |
| 5999 | Z1 | L17 | Q25 |
| 6000 | Z1 | L17 | Q26 |
| 6001 | Z1 | L17 | Q27 |
| 6002 | Z1 | L17 | Q28 |

TABLE 1-36

| | | | |
|---|---|---|---|
| 6003 | Z1 | L17 | Q29 |
| 6004 | Z1 | L17 | Q30 |
| 6005 | Z1 | L17 | Q31 |
| 6006 | Z1 | L17 | Q32 |
| 6007 | Z1 | L17 | Q33 |

TABLE 1-36-continued

| | | | | | | | |
|---|---|---|---|---|---|---|---|
| 6003 | Z1 | L17 | Q34 | | 6088 | Z1 | L18 | Q11 |
| 6009 | Z1 | L17 | Q35 | | 6089 | Z1 | L18 | Q12 |
| 6010 | Z1 | L17 | Q36 | | 6090 | Z1 | L18 | Q13 |
| 6011 | Z1 | L17 | Q37 | | 6091 | Z1 | L18 | Q14 |
| 6012 | Z1 | L17 | Q38 | | 6092 | Z1 | L18 | Q15 |
| 6013 | Z1 | L17 | Q39 | | 6093 | Z1 | L18 | Q16 |
| 6014 | Z1 | L17 | Q40 | | 6094 | Z1 | L18 | Q17 |
| 6015 | Z1 | L17 | Q41 | | 6095 | Z1 | L18 | Q18 |
| 6016 | Z1 | L17 | Q42 | | 6096 | Z1 | L18 | Q19 |
| 6017 | Z1 | L17 | Q43 | | 6097 | Z1 | L18 | Q20 |
| 6013 | Z1 | L17 | Q44 | | 6098 | Z1 | L18 | Q21 |
| 6019 | Z1 | L17 | Q45 | | 6099 | Z1 | L18 | Q22 |
| 6020 | Z1 | L17 | Q46 | | 6100 | Z1 | L18 | Q23 |
| 6021 | Z1 | L17 | Q47 | | 6101 | Z1 | L18 | Q24 |
| 6022 | Z1 | L17 | Q48 | | 6102 | Z1 | L18 | Q25 |
| 6023 | Z1 | L17 | Q49 | | 6103 | Z1 | L18 | Q26 |
| 6024 | Z1 | L17 | Q50 | | 6104 | Z1 | L18 | Q27 |
| 6025 | Z1 | L17 | Q51 | | 6105 | Z1 | L18 | Q28 |
| 6026 | Z1 | L17 | Q52 | | 6106 | Z1 | L18 | Q29 |
| 6027 | Z1 | L17 | Q53 | | 6107 | Z1 | L18 | Q30 |
| 6028 | Z1 | L17 | Q54 | | 6108 | Z1 | L18 | Q31 |
| 6029 | Z1 | L17 | Q55 | | 6109 | Z1 | L18 | Q32 |
| 6030 | Z1 | L17 | Q56 | | 6110 | Z1 | L18 | Q33 |
| 6031 | Z1 | L17 | Q57 | | 6111 | Z1 | L18 | Q34 |
| 6032 | Z1 | L17 | Q58 | | 6112 | Z1 | L18 | Q35 |
| 6033 | Z1 | L17 | Q59 | | 6113 | Z1 | L18 | Q36 |
| 6034 | Z1 | L17 | Q60 | | 6114 | Z1 | L18 | Q37 |
| 6035 | Z1 | L17 | Q61 | | 6115 | Z1 | L18 | Q38 |
| 6036 | Z1 | L17 | Q62 | | 6116 | Z1 | L18 | Q39 |
| 6037 | Z1 | L17 | Q63 | | 6117 | Z1 | L18 | Q40 |
| 6038 | Z1 | L17 | Q64 | | 6118 | Z1 | L18 | Q41 |
| 6039 | Z1 | L17 | Q65 | | 6119 | Z1 | L18 | Q42 |
| 6040 | Z1 | L17 | Q66 | | 6120 | Z1 | L18 | Q43 |
| 6041 | Z1 | L17 | Q67 | | 6121 | Z1 | L18 | Q44 |
| 6042 | Z1 | L17 | Q68 | | 6122 | Z1 | L18 | Q45 |
| 6043 | Z1 | L17 | Q69 | | 6123 | Z1 | L18 | Q46 |
| 6044 | Z1 | L17 | Q70 | | 6124 | Z1 | L18 | Q47 |
| 6045 | Z1 | L17 | Q71 | | 6125 | Z1 | L18 | Q48 |
| 6046 | Z1 | L17 | Q72 | | 6126 | Z1 | L18 | Q49 |
| 6047 | Z1 | L17 | Q73 | | 6127 | Z1 | L18 | Q50 |
| 6048 | Z1 | L17 | Q74 | | 6128 | Z1 | L18 | Q51 |
| 6049 | Z1 | L17 | Q75 | | 6129 | Z1 | L18 | Q52 |
| 6050 | Z1 | L17 | Q76 | | 6130 | Z1 | L18 | Q53 |
| 6051 | Z1 | L17 | Q77 | | 6131 | Z1 | L18 | Q54 |
| 6052 | Z1 | L17 | Q78 | | 6132 | Z1 | L18 | Q55 |
| 6053 | Z1 | L17 | Q79 | | 6133 | Z1 | L18 | Q56 |
| 6054 | Z1 | L17 | Q80 | | 6134 | Z1 | L18 | Q57 |
| 6055 | Z1 | L17 | Q81 | | 6135 | Z1 | L18 | Q58 |
| 6056 | Z1 | L17 | Q82 | | 6136 | Z1 | L18 | Q59 |
| 6057 | Z1 | L17 | Q83 | | 6137 | Z1 | L18 | Q60 |
| 6058 | Z1 | L17 | Q84 | | 6138 | Z1 | L18 | Q61 |
| 6059 | Z1 | L17 | Q85 | | 6139 | Z1 | L18 | Q62 |
| 6060 | Z1 | L17 | Q86 | | 6140 | Z1 | L18 | Q63 |
| 6061 | Z1 | L17 | Q87 | | 6141 | Z1 | L18 | Q64 |
| 6062 | Z1 | L17 | Q88 | | 6142 | Z1 | L18 | Q65 |
| 6063 | Z1 | L17 | Q89 | | 6143 | Z1 | L18 | Q66 |
| 6064 | Z1 | L17 | Q90 | | 6144 | Z1 | L18 | Q67 |
| 6065 | Z1 | L17 | Q91 | | 6145 | Z1 | L18 | Q68 |
| 6066 | Z1 | L17 | Q92 | | 6146 | Z1 | L18 | Q69 |
| 6067 | Z1 | L17 | Q93 | | 6147 | Z1 | L18 | Q70 |
| 6068 | Z1 | L17 | Q94 | | 6148 | Z1 | L18 | Q71 |
| 6069 | Z1 | L17 | Q95 | | 6149 | Z1 | L18 | Q72 |
| 6070 | Z1 | L17 | Q96 | | 6150 | Z1 | L18 | Q73 |
| 6071 | Z1 | L17 | Q97 | | 6151 | Z1 | L18 | Q74 |
| 6072 | Z1 | L17 | Q98 | | 6152 | Z1 | L18 | Q75 |
| 6073 | Z1 | L17 | Q99 | | 6153 | Z1 | L18 | Q76 |
| 6074 | Z1 | L17 | Q100 | | 6154 | Z1 | L18 | Q77 |
| 6075 | Z1 | L17 | Q101 | | 6155 | Z1 | L18 | Q78 |
| 6076 | Z1 | L17 | Q102 | | 6156 | Z1 | L18 | Q79 |
| 6077 | Z1 | L17 | Q103 | | 6157 | Z1 | L18 | Q80 |
| 6078 | Z1 | L18 | Q1 | | 6158 | Z1 | L18 | Q81 |
| 6079 | Z1 | L18 | Q2 | | 6159 | Z1 | L18 | Q82 |
| 6080 | Z1 | L18 | Q3 | | 6160 | Z1 | L18 | Q83 |
| 6081 | Z1 | L18 | Q4 | | 6161 | Z1 | L18 | Q84 |
| 6082 | Z1 | L18 | Q5 | | 6162 | Z1 | L18 | Q85 |
| 6083 | Z1 | L18 | Q6 | | 6163 | Z1 | L18 | Q86 |
| 6084 | Z1 | L18 | Q7 | | 6164 | Z1 | L18 | Q87 |
| 6085 | Z1 | L18 | Q8 | | 6165 | Z1 | L18 | Q88 |
| 6086 | Z1 | L18 | Q9 | | 6166 | Z1 | L18 | Q89 |
| 6087 | Z1 | L18 | Q10 | | 6167 | Z1 | L18 | Q90 |

TABLE 1-36-continued

| | | | |
|---|---|---|---|
| 6168 | Z1 | L18 | Q91 |
| 6169 | Z1 | L18 | Q92 |
| 6170 | Z1 | L18 | Q93 |
| 6171 | Z1 | L18 | Q94 |
| 6172 | Z1 | L18 | Q95 |
| 6173 | Z1 | L18 | Q96 |
| 6174 | Z1 | L18 | Q97 |
| 6175 | Z1 | L18 | Q98 |
| 6176 | Z1 | L18 | Q99 |
| 6177 | Z1 | L18 | Q100 |
| 6178 | Z1 | L18 | Q101 |
| 6179 | Z1 | L18 | Q102 |
| 6180 | Z1 | L18 | Q103 |
| 6181 | Z1 | L19 | Q1 |
| 6182 | Z1 | L19 | Q2 |
| 6183 | Z1 | L19 | Q3 |
| 6184 | Z1 | L19 | Q4 |
| 6185 | Z1 | L19 | Q5 |
| 6186 | Z1 | L19 | Q6 |
| 6187 | Z1 | L19 | Q7 |
| 6188 | Z1 | L19 | Q8 |
| 6189 | Z1 | L19 | Q9 |
| 6190 | Z1 | L19 | Q10 |
| 6191 | Z1 | L19 | Q11 |
| 6192 | Z1 | L19 | Q12 |
| 6193 | Z1 | L19 | Q13 |
| 6194 | Z1 | L19 | Q14 |
| 6195 | Z1 | L19 | Q15 |
| 6196 | Z1 | L19 | Q16 |
| 6197 | Z1 | L19 | Q17 |
| 6198 | Z1 | L19 | Q18 |
| 6199 | Z1 | L19 | Q19 |
| 6200 | Z1 | L19 | Q20 |
| 6201 | Z1 | L19 | Q21 |
| 6202 | Z1 | L19 | Q22 |
| 6203 | Z1 | L19 | Q23 |

TABLE 1-37

| | | | |
|---|---|---|---|
| 6204 | Z1 | L19 | Q24 |
| 6205 | Z1 | L19 | Q25 |
| 6206 | Z1 | L19 | Q26 |
| 6207 | Z1 | L19 | Q27 |
| 6208 | Z1 | L19 | Q28 |
| 6209 | Z1 | L19 | Q29 |
| 6210 | Z1 | L19 | Q30 |
| 6211 | Z1 | L19 | Q31 |
| 6212 | Z1 | L19 | Q32 |
| 6213 | Z1 | L19 | Q33 |
| 6214 | Z1 | L19 | Q34 |
| 6215 | Z1 | L19 | Q35 |
| 6216 | Z1 | L19 | Q36 |
| 6217 | Z1 | L19 | Q37 |
| 6218 | Z1 | L19 | Q38 |
| 6219 | Z1 | L19 | Q39 |
| 6220 | Z1 | L19 | Q40 |
| 6221 | Z1 | L19 | Q41 |
| 6222 | Z1 | L19 | Q42 |
| 6223 | Z1 | L19 | Q43 |
| 6224 | Z1 | L19 | Q44 |
| 6225 | Z1 | L19 | Q45 |
| 6226 | Z1 | L19 | Q46 |
| 6227 | Z1 | L19 | Q47 |
| 6228 | Z1 | L19 | Q48 |
| 6229 | Z1 | L19 | Q49 |
| 6230 | Z1 | L19 | Q50 |
| 6231 | Z1 | L19 | Q51 |
| 6232 | Z1 | L19 | Q52 |
| 6233 | Z1 | L19 | Q53 |
| 6234 | Z1 | L19 | Q54 |
| 6235 | Z1 | L19 | Q55 |
| 6236 | Z1 | L19 | Q56 |
| 6237 | Z1 | L19 | Q57 |
| 6238 | Z1 | L19 | Q58 |
| 6239 | Z1 | L19 | Q59 |
| 6240 | Z1 | L19 | Q60 |
| 6241 | Z1 | L19 | Q61 |

TABLE 1-37-continued

| | | | |
|---|---|---|---|
| 6242 | Z1 | L19 | Q62 |
| 6243 | Z1 | L19 | Q63 |
| 6244 | Z1 | L19 | Q64 |
| 6245 | Z1 | L19 | Q65 |
| 6246 | Z1 | L19 | Q66 |
| 6247 | Z1 | L19 | Q67 |
| 6248 | Z1 | L19 | Q68 |
| 6249 | Z1 | L19 | Q69 |
| 6250 | Z1 | L19 | Q70 |
| 6251 | Z1 | L19 | Q71 |
| 6252 | Z1 | L19 | Q72 |
| 6253 | Z1 | L19 | Q73 |
| 6254 | Z1 | L19 | Q74 |
| 6255 | Z1 | L19 | Q75 |
| 6256 | Z1 | L19 | Q76 |
| 6257 | Z1 | L19 | Q77 |
| 6258 | Z1 | L19 | Q78 |
| 6259 | Z1 | L19 | Q79 |
| 6260 | Z1 | L19 | Q80 |
| 6261 | Z1 | L19 | Q81 |
| 6262 | Z1 | L19 | Q82 |
| 6263 | Z1 | L19 | Q83 |
| 6264 | Z1 | L19 | Q84 |
| 6265 | Z1 | L19 | Q85 |
| 6266 | Z1 | L19 | Q86 |
| 6267 | Z1 | L19 | Q87 |
| 6268 | Z1 | L19 | Q88 |
| 6269 | Z1 | L19 | Q89 |
| 6270 | Z1 | L19 | Q90 |
| 6271 | Z1 | L19 | Q91 |
| 6272 | Z1 | L19 | Q92 |
| 6273 | Z1 | L19 | Q93 |
| 6274 | Z1 | L19 | Q94 |
| 6275 | Z1 | L19 | Q95 |
| 6276 | Z1 | L19 | Q96 |
| 6277 | Z1 | L19 | Q97 |
| 6278 | Z1 | L19 | Q98 |
| 6279 | Z1 | L19 | Q99 |
| 6280 | Z1 | L19 | Q100 |
| 6281 | Z1 | L19 | Q101 |
| 6282 | Z1 | L19 | Q102 |
| 6283 | Z1 | L19 | Q103 |
| 6284 | Z1 | L20 | Q1 |
| 6285 | Z1 | L20 | Q2 |
| 6286 | Z1 | L20 | Q3 |
| 6287 | Z1 | L20 | Q4 |
| 6288 | Z1 | L20 | Q5 |
| 6289 | Z1 | L20 | Q6 |
| 6290 | Z1 | L20 | Q7 |
| 6291 | Z1 | L20 | Q8 |
| 6292 | Z1 | L20 | Q9 |
| 6293 | Z1 | L20 | Q10 |
| 6294 | Z1 | L20 | Q11 |
| 6295 | Z1 | L20 | Q12 |
| 6296 | Z1 | L20 | Q13 |
| 6297 | Z1 | L20 | Q14 |
| 6298 | Z1 | L20 | Q15 |
| 6299 | Z1 | L20 | Q16 |
| 6300 | Z1 | L20 | Q17 |
| 6301 | Z1 | L20 | Q18 |
| 6302 | Z1 | L20 | Q19 |
| 6303 | Z1 | L20 | Q20 |
| 6304 | Z1 | L20 | Q21 |
| 6305 | Z1 | L20 | Q22 |
| 6306 | Z1 | L20 | Q23 |
| 6307 | Z1 | L20 | Q24 |
| 6308 | Z1 | L20 | Q25 |
| 6309 | Z1 | L20 | Q26 |
| 6310 | Z1 | L20 | Q27 |
| 6311 | Z1 | L20 | Q28 |
| 6312 | Z1 | L20 | Q29 |
| 6313 | Z1 | L20 | Q30 |
| 6314 | Z1 | L20 | Q31 |
| 6315 | Z1 | L20 | Q32 |
| 6316 | Z1 | L20 | Q33 |
| 6317 | Z1 | L20 | Q34 |
| 6318 | Z1 | L20 | Q35 |
| 6319 | Z1 | L20 | Q36 |
| 6320 | Z1 | L20 | Q37 |
| 6321 | Z1 | L20 | Q38 |

TABLE 1-37-continued

| | | | |
|---|---|---|---|
| 6322 | Z1 | L20 | Q39 |
| 6323 | Z1 | L20 | Q40 |
| 6324 | Z1 | L20 | Q41 |
| 6325 | Z1 | L20 | Q42 |
| 6326 | Z1 | L20 | Q43 |
| 6327 | Z1 | L20 | Q44 |
| 6328 | Z1 | L20 | Q45 |
| 6329 | Z1 | L20 | Q46 |
| 6330 | Z1 | L20 | Q47 |
| 6331 | Z1 | L20 | Q48 |
| 6332 | Z1 | L20 | Q49 |
| 6333 | Z1 | L20 | Q50 |
| 6334 | Z1 | L20 | Q51 |
| 6335 | Z1 | L20 | Q52 |
| 6336 | Z1 | L20 | Q53 |
| 6337 | Z1 | L20 | Q54 |
| 6338 | Z1 | L20 | Q55 |
| 6339 | Z1 | L20 | Q56 |
| 6340 | Z1 | L20 | Q57 |
| 6341 | Z1 | L20 | Q58 |
| 6342 | Z1 | L20 | Q59 |
| 6343 | Z1 | L20 | Q60 |
| 6344 | Z1 | L20 | Q61 |
| 6345 | Z1 | L20 | Q62 |
| 6346 | Z1 | L20 | Q63 |
| 6347 | Z1 | L20 | Q64 |
| 6348 | Z1 | L20 | Q65 |
| 6349 | Z1 | L20 | Q66 |
| 6350 | Z1 | L20 | Q67 |
| 6351 | Z1 | L20 | Q68 |
| 6352 | Z1 | L20 | Q69 |
| 6353 | Z1 | L20 | Q70 |
| 6354 | Z1 | L20 | Q71 |
| 6355 | Z1 | L20 | Q72 |
| 6356 | Z1 | L20 | Q73 |
| 6357 | Z1 | L20 | Q74 |
| 6358 | Z1 | L20 | Q75 |
| 6359 | Z1 | L20 | Q76 |
| 6360 | Z1 | L20 | Q77 |
| 6361 | Z1 | L20 | Q78 |
| 6362 | Z1 | L20 | Q79 |
| 6363 | Z1 | L20 | Q80 |
| 6364 | Z1 | L20 | Q81 |
| 6365 | Z1 | L20 | Q82 |
| 6366 | Z1 | L20 | Q83 |
| 6367 | Z1 | L20 | Q84 |
| 6368 | Z1 | L20 | Q85 |
| 6369 | Z1 | L20 | Q86 |
| 6370 | Z1 | L20 | Q87 |
| 6371 | Z1 | L20 | Q88 |
| 6372 | Z1 | L20 | Q89 |
| 6373 | Z1 | L20 | Q90 |
| 6374 | Z1 | L20 | Q91 |
| 6375 | Z1 | L20 | Q92 |
| 6376 | Z1 | L20 | Q93 |
| 6377 | Z1 | L20 | Q94 |
| 6378 | Z1 | L20 | Q95 |
| 6379 | Z1 | L20 | Q96 |
| 6380 | Z1 | L20 | Q97 |
| 6381 | Z1 | L20 | Q98 |
| 6382 | Z1 | L20 | Q99 |
| 6383 | Z1 | L20 | Q100 |
| 6384 | Z1 | L20 | Q101 |
| 6385 | Z1 | L20 | Q102 |
| 6386 | Z1 | L20 | Q103 |
| 6387 | Z1 | L21 | Q1 |
| 6388 | Z1 | L21 | Q2 |
| 6389 | Z1 | L21 | Q3 |
| 6390 | Z1 | L21 | Q4 |
| 6391 | Z1 | L21 | Q5 |
| 6392 | Z1 | L21 | Q6 |
| 6393 | Z1 | L21 | Q7 |
| 6394 | Z1 | L21 | Q8 |
| 6395 | Z1 | L21 | Q9 |
| 6396 | Z1 | L21 | Q10 |
| 6397 | Z1 | L21 | Q11 |
| 6398 | Z1 | L21 | Q12 |
| 6399 | Z1 | L21 | Q13 |
| 6400 | Z1 | L21 | Q14 |
| 6401 | Z1 | L21 | Q15 |
| 6402 | Z1 | L21 | Q16 |
| 6403 | Z1 | L21 | Q17 |
| 6404 | Z1 | L21 | Q18 |

TABLE 1-38

| | | | |
|---|---|---|---|
| 6405 | Z1 | L21 | Q19 |
| 6406 | Z1 | L21 | Q20 |
| 6407 | Z1 | L21 | Q21 |
| 6408 | Z1 | L21 | Q22 |
| 6409 | Z1 | L21 | Q23 |
| 6410 | Z1 | L21 | Q24 |
| 6411 | Z1 | L21 | Q25 |
| 6412 | Z1 | L21 | Q26 |
| 6413 | Z1 | L21 | Q27 |
| 6414 | Z1 | L21 | Q28 |
| 6415 | Z1 | L21 | Q29 |
| 6416 | Z1 | L21 | Q30 |
| 6417 | Z1 | L21 | Q31 |
| 6418 | Z1 | L21 | Q32 |
| 6419 | Z1 | L21 | Q33 |
| 6420 | Z1 | L21 | Q34 |
| 6421 | Z1 | L21 | Q35 |
| 6422 | Z1 | L21 | Q36 |
| 6423 | Z1 | L21 | Q37 |
| 6424 | Z1 | L21 | Q38 |
| 6425 | Z1 | L21 | Q39 |
| 6426 | Z1 | L21 | Q40 |
| 6427 | Z1 | L21 | Q41 |
| 6428 | Z1 | L21 | Q42 |
| 6429 | Z1 | L21 | Q43 |
| 6430 | Z1 | L21 | Q44 |
| 6431 | Z1 | L21 | Q45 |
| 6432 | Z1 | L21 | Q46 |
| 6433 | Z1 | L21 | Q47 |
| 6434 | Z1 | L21 | Q48 |
| 6435 | Z1 | L21 | Q49 |
| 6436 | Z1 | L21 | Q50 |
| 6437 | Z1 | L21 | Q51 |
| 6438 | Z1 | L21 | Q52 |
| 6439 | Z1 | L21 | Q53 |
| 6440 | Z1 | L21 | Q54 |
| 6441 | Z1 | L21 | Q55 |
| 6442 | Z1 | L21 | Q56 |
| 6443 | Z1 | L21 | Q57 |
| 6444 | Z1 | L21 | Q58 |
| 6445 | Z1 | L21 | Q59 |
| 6446 | Z1 | L21 | Q60 |
| 6447 | Z1 | L21 | Q61 |
| 6448 | Z1 | L21 | Q62 |
| 6449 | Z1 | L21 | Q63 |
| 6450 | Z1 | L21 | Q64 |
| 6451 | Z1 | L21 | Q65 |
| 6452 | Z1 | L21 | Q66 |
| 6453 | Z1 | L21 | Q67 |
| 6454 | Z1 | L21 | Q68 |
| 6455 | Z1 | L21 | Q69 |
| 6456 | Z1 | L21 | Q70 |
| 6457 | Z1 | L21 | Q71 |
| 6458 | Z1 | L21 | Q72 |
| 6459 | Z1 | L21 | Q73 |
| 6460 | Z1 | L21 | Q74 |
| 6461 | Z1 | L21 | Q75 |
| 6462 | Z1 | L21 | Q76 |
| 6463 | Z1 | L21 | Q77 |
| 6464 | Z1 | L21 | Q78 |
| 6465 | Z1 | L21 | Q79 |
| 6466 | Z1 | L21 | Q80 |
| 6467 | Z1 | L21 | Q81 |
| 6468 | Z1 | L21 | Q82 |
| 6469 | Z1 | L21 | Q83 |
| 6470 | Z1 | L21 | Q84 |
| 6471 | Z1 | L21 | Q85 |
| 6472 | Z1 | L21 | Q86 |
| 6473 | Z1 | L21 | Q87 |
| 6474 | Z1 | L21 | Q88 |
| 6475 | Z1 | L21 | Q89 |

TABLE 1-38-continued

| | | | |
|---|---|---|---|
| 6476 | Z1 | L21 | Q90 |
| 6477 | Z1 | L21 | Q91 |
| 6478 | Z1 | L21 | Q92 |
| 6479 | Z1 | L21 | Q93 |
| 6480 | Z1 | L21 | Q94 |
| 6481 | Z1 | L21 | Q95 |
| 6482 | Z1 | L21 | Q96 |
| 6483 | Z1 | L21 | Q97 |
| 6484 | Z1 | L21 | Q98 |
| 6485 | Z1 | L21 | Q99 |
| 6486 | Z1 | L21 | Q100 |
| 6487 | Z1 | L21 | Q101 |
| 6488 | Z1 | L21 | Q102 |
| 6489 | Z1 | L21 | Q103 |
| 6490 | Z1 | L22 | Q1 |
| 6491 | Z1 | L22 | Q2 |
| 6492 | Z1 | L22 | Q3 |
| 6493 | Z1 | L22 | Q4 |
| 6494 | Z1 | L22 | Q5 |
| 6495 | Z1 | L22 | Q6 |
| 6496 | Z1 | L22 | Q7 |
| 6497 | Z1 | L22 | Q8 |
| 6498 | Z1 | L22 | Q9 |
| 6499 | Z1 | L22 | Q10 |
| 6500 | Z1 | L22 | Q11 |
| 6501 | Z1 | L22 | Q12 |
| 6502 | Z1 | L22 | Q13 |
| 6503 | Z1 | L22 | Q14 |
| 6504 | Z1 | L22 | Q15 |
| 6505 | Z1 | L22 | Q16 |
| 6506 | Z1 | L22 | Q17 |
| 6507 | Z1 | L22 | Q18 |
| 6508 | Z1 | L22 | Q19 |
| 6509 | Z1 | L22 | Q20 |
| 6510 | Z1 | L22 | Q21 |
| 6511 | Z1 | L22 | Q22 |
| 6512 | Z1 | L22 | Q23 |
| 6513 | Z1 | L22 | Q24 |
| 6514 | Z1 | L22 | Q25 |
| 6515 | Z1 | L22 | Q26 |
| 6516 | Z1 | L22 | Q27 |
| 6517 | Z1 | L22 | Q28 |
| 6518 | Z1 | L22 | Q29 |
| 6519 | Z1 | L22 | Q30 |
| 6520 | Z1 | L22 | Q31 |
| 6521 | Z1 | L22 | Q32 |
| 6522 | Z1 | L22 | Q33 |
| 6523 | Z1 | L22 | Q34 |
| 6524 | Z1 | L22 | Q35 |
| 6525 | Z1 | L22 | Q36 |
| 6526 | Z1 | L22 | Q37 |
| 6527 | Z1 | L22 | Q38 |
| 6528 | Z1 | L22 | Q39 |
| 6529 | Z1 | L22 | Q40 |
| 6530 | Z1 | L22 | Q41 |
| 6531 | Z1 | L22 | Q42 |
| 6532 | Z1 | L22 | Q43 |
| 6533 | Z1 | L22 | Q44 |
| 6534 | Z1 | L22 | Q45 |
| 6535 | Z1 | L22 | Q46 |
| 6536 | Z1 | L22 | Q47 |
| 6537 | Z1 | L22 | Q48 |
| 6538 | Z1 | L22 | Q49 |
| 6539 | Z1 | L22 | Q50 |
| 6540 | Z1 | L22 | Q51 |
| 6541 | Z1 | L22 | Q52 |
| 6542 | Z1 | L22 | Q53 |
| 6543 | Z1 | L22 | Q54 |
| 6544 | Z1 | L22 | Q55 |
| 6545 | Z1 | L22 | Q56 |
| 6546 | Z1 | L22 | Q57 |
| 6547 | Z1 | L22 | Q58 |
| 6548 | Z1 | L22 | Q59 |
| 6549 | Z1 | L22 | Q60 |
| 6550 | Z1 | L22 | Q61 |
| 6551 | Z1 | L22 | Q62 |
| 6552 | Z1 | L22 | Q63 |
| 6553 | Z1 | L22 | Q64 |
| 6554 | Z1 | L22 | Q65 |
| 6555 | Z1 | L22 | Q66 |
| 6556 | Z1 | L22 | Q67 |
| 6557 | Z1 | L22 | Q68 |
| 6558 | Z1 | L22 | Q69 |
| 6559 | Z1 | L22 | Q70 |
| 6560 | Z1 | L22 | Q71 |
| 6561 | Z1 | L22 | Q72 |
| 6562 | Z1 | L22 | Q73 |
| 6563 | Z1 | L22 | Q74 |
| 6564 | Z1 | L22 | Q75 |
| 6565 | Z1 | L22 | Q76 |
| 6566 | Z1 | L22 | Q77 |
| 6567 | Z1 | L22 | Q78 |
| 6568 | Z1 | L22 | Q79 |
| 6569 | Z1 | L22 | Q80 |
| 6570 | Z1 | L22 | Q81 |
| 6571 | Z1 | L22 | Q82 |
| 6572 | Z1 | L22 | Q83 |
| 6573 | Z1 | L22 | Q84 |
| 6574 | Z1 | L22 | Q85 |
| 6575 | Z1 | L22 | Q86 |
| 6576 | Z1 | L22 | Q87 |
| 6577 | Z1 | L22 | Q88 |
| 6578 | Z1 | L22 | Q89 |
| 6579 | Z1 | L22 | Q90 |
| 6580 | Z1 | L22 | Q91 |
| 6581 | Z1 | L22 | Q92 |
| 6582 | Z1 | L22 | Q93 |
| 6583 | Z1 | L22 | Q94 |
| 6584 | Z1 | L22 | Q95 |
| 6585 | Z1 | L22 | Q96 |
| 6586 | Z1 | L22 | Q97 |
| 6587 | Z1 | L22 | Q98 |
| 6588 | Z1 | L22 | Q99 |
| 6589 | Z1 | L22 | Q100 |
| 6590 | Z1 | L22 | Q101 |
| 6591 | Z1 | L22 | Q102 |
| 6592 | Z1 | L22 | Q103 |
| 6593 | Z1 | L23 | Q1 |
| 6594 | Z1 | L23 | Q2 |
| 6595 | Z1 | L23 | Q3 |
| 6596 | Z1 | L23 | Q4 |
| 6597 | Z1 | L23 | Q5 |
| 6598 | Z1 | L23 | Q6 |
| 6599 | Z1 | L23 | Q7 |
| 6600 | Z1 | L23 | Q8 |
| 6601 | Z1 | L23 | Q9 |
| 6602 | Z1 | L23 | Q10 |
| 6603 | Z1 | L23 | Q11 |
| 6604 | Z1 | L23 | Q12 |
| 6605 | Z1 | L23 | Q13 |

TABLE 1-39

| | | | |
|---|---|---|---|
| 6606 | Z1 | L23 | Q14 |
| 6607 | Z1 | L23 | Q15 |
| 6608 | Z1 | L23 | Q16 |
| 6609 | Z1 | L23 | Q17 |
| 6610 | Z1 | L23 | Q18 |
| 6611 | Z1 | L23 | Q19 |
| 6612 | Z1 | L23 | Q20 |
| 6613 | Z1 | L23 | Q21 |
| 6614 | Z1 | L23 | Q22 |
| 6615 | Z1 | L23 | Q23 |
| 6616 | Z1 | L23 | Q24 |
| 6617 | Z1 | L23 | Q25 |
| 6618 | Z1 | L23 | Q26 |
| 6619 | Z1 | L23 | Q27 |
| 6620 | Z1 | L23 | Q28 |
| 6621 | Z1 | L23 | Q29 |
| 6622 | Z1 | L23 | Q30 |
| 6623 | Z1 | L23 | Q31 |
| 6624 | Z1 | L23 | Q32 |
| 6625 | Z1 | L23 | Q33 |
| 6626 | Z1 | L23 | Q34 |
| 6627 | Z1 | L23 | Q35 |
| 6628 | Z1 | L23 | Q36 |
| 6629 | Z1 | L23 | Q37 |

TABLE 1-39-continued

| | | | |
|---|---|---|---|
| 6630 | Z1 | L23 | Q38 |
| 6631 | Z1 | L23 | Q39 |
| 6632 | Z1 | L23 | Q40 |
| 6633 | Z1 | L23 | Q41 |
| 6634 | Z1 | L23 | Q42 |
| 6635 | Z1 | L23 | Q43 |
| 6636 | Z1 | L23 | Q44 |
| 6637 | Z1 | L23 | Q45 |
| 6638 | Z1 | L23 | Q46 |
| 6639 | Z1 | L23 | Q47 |
| 6640 | Z1 | L23 | Q48 |
| 6641 | Z1 | L23 | Q49 |
| 6642 | Z1 | L23 | Q50 |
| 6643 | Z1 | L23 | Q51 |
| 6644 | Z1 | L23 | Q52 |
| 6645 | Z1 | L23 | Q53 |
| 6646 | Z1 | L23 | Q54 |
| 6647 | Z1 | L23 | Q55 |
| 6648 | Z1 | L23 | Q56 |
| 6649 | Z1 | L23 | Q57 |
| 6650 | Z1 | L23 | Q58 |
| 6651 | Z1 | L23 | Q59 |
| 6652 | Z1 | L23 | Q60 |
| 6653 | Z1 | L23 | Q61 |
| 6654 | Z1 | L23 | Q62 |
| 6655 | Z1 | L23 | Q63 |
| 6656 | Z1 | L23 | Q64 |
| 6657 | Z1 | L23 | Q65 |
| 6658 | Z1 | L23 | Q66 |
| 6659 | Z1 | L23 | Q67 |
| 6660 | Z1 | L23 | Q68 |
| 6661 | Z1 | L23 | Q69 |
| 6662 | Z1 | L23 | Q70 |
| 6663 | Z1 | L23 | Q71 |
| 6664 | Z1 | L23 | Q72 |
| 6665 | Z1 | L23 | Q73 |
| 6666 | Z1 | L23 | Q74 |
| 6667 | Z1 | L23 | Q75 |
| 6668 | Z1 | L23 | Q76 |
| 6669 | Z1 | L23 | Q77 |
| 6670 | Z1 | L23 | Q78 |
| 6671 | Z1 | L23 | Q79 |
| 6672 | Z1 | L23 | Q80 |
| 6673 | Z1 | L23 | Q81 |
| 6674 | Z1 | L23 | Q82 |
| 6675 | Z1 | L23 | Q83 |
| 6676 | Z1 | L23 | Q84 |
| 6677 | Z1 | L23 | Q85 |
| 6678 | Z1 | L23 | Q86 |
| 6679 | Z1 | L23 | Q87 |
| 6680 | Z1 | L23 | Q88 |
| 6681 | Z1 | L23 | Q89 |
| 6682 | Z1 | L23 | Q90 |
| 6683 | Z1 | L23 | Q91 |
| 6684 | Z1 | L23 | Q92 |
| 6685 | Z1 | L23 | Q93 |
| 6686 | Z1 | L23 | Q94 |
| 6687 | Z1 | L23 | Q95 |
| 6688 | Z1 | L23 | Q96 |
| 6689 | Z1 | L23 | Q97 |
| 6690 | Z1 | L23 | Q98 |
| 6691 | Z1 | L23 | Q99 |
| 6692 | Z1 | L23 | Q100 |
| 6693 | Z1 | L23 | Q101 |
| 6694 | Z1 | L23 | Q102 |
| 6695 | Z1 | L23 | Q103 |
| 6696 | Z1 | L24 | Q1 |
| 6697 | Z1 | L24 | Q2 |
| 6698 | Z1 | L24 | Q3 |
| 6699 | Z1 | L24 | Q4 |
| 6700 | Z1 | L24 | Q5 |
| 6701 | Z1 | L24 | Q6 |
| 6702 | Z1 | L24 | Q7 |
| 6703 | Z1 | L24 | Q8 |
| 6704 | Z1 | L24 | Q9 |
| 6705 | Z1 | L24 | Q10 |
| 6706 | Z1 | L24 | Q11 |
| 6707 | Z1 | L24 | Q12 |
| 6708 | Z1 | L24 | Q13 |
| 6709 | Z1 | L24 | Q14 |
| 6710 | Z1 | L24 | Q15 |
| 6711 | Z1 | L24 | Q16 |
| 6712 | Z1 | L24 | Q17 |
| 6713 | Z1 | L24 | Q18 |
| 6714 | Z1 | L24 | Q19 |
| 6715 | Z1 | L24 | Q20 |
| 6716 | Z1 | L24 | Q21 |
| 6717 | Z1 | L24 | Q22 |
| 6718 | Z1 | L24 | Q23 |
| 6719 | Z1 | L24 | Q24 |
| 6720 | Z1 | L24 | Q25 |
| 6721 | Z1 | L24 | Q26 |
| 6722 | Z1 | L24 | Q27 |
| 6723 | Z1 | L24 | Q28 |
| 6724 | Z1 | L24 | Q29 |
| 6725 | Z1 | L24 | Q30 |
| 6726 | Z1 | L24 | Q31 |
| 6727 | Z1 | L24 | Q32 |
| 6728 | Z1 | L24 | Q33 |
| 6729 | Z1 | L24 | Q34 |
| 6730 | Z1 | L24 | Q35 |
| 6731 | Z1 | L24 | Q36 |
| 6732 | Z1 | L24 | Q37 |
| 6733 | Z1 | L24 | Q38 |
| 6734 | Z1 | L24 | Q39 |
| 6735 | Z1 | L24 | Q40 |
| 6736 | Z1 | L24 | Q41 |
| 6737 | Z1 | L24 | Q42 |
| 6738 | Z1 | L24 | Q43 |
| 6739 | Z1 | L24 | Q44 |
| 6740 | Z1 | L24 | Q45 |
| 6741 | Z1 | L24 | Q46 |
| 6742 | Z1 | L24 | Q47 |
| 6743 | Z1 | L24 | Q48 |
| 6744 | Z1 | L24 | Q49 |
| 6745 | Z1 | L24 | Q50 |
| 6746 | Z1 | L24 | Q51 |
| 6747 | Z1 | L24 | Q52 |
| 6748 | Z1 | L24 | Q53 |
| 6749 | Z1 | L24 | Q54 |
| 6750 | Z1 | L24 | Q55 |
| 6751 | Z1 | L24 | Q56 |
| 6752 | Z1 | L24 | Q57 |
| 6753 | Z1 | L24 | Q58 |
| 6754 | Z1 | L24 | Q59 |
| 6755 | Z1 | L24 | Q60 |
| 6756 | Z1 | L24 | Q61 |
| 6757 | Z1 | L24 | Q62 |
| 6758 | Z1 | L24 | Q63 |
| 6759 | Z1 | L24 | Q64 |
| 6760 | Z1 | L24 | Q65 |
| 6761 | Z1 | L24 | Q66 |
| 6762 | Z1 | L24 | Q67 |
| 6763 | Z1 | L24 | Q68 |
| 6764 | Z1 | L24 | Q69 |
| 6765 | Z1 | L24 | Q70 |
| 6766 | Z1 | L24 | Q71 |
| 6767 | Z1 | L24 | Q72 |
| 6768 | Z1 | L24 | Q73 |
| 6769 | Z1 | L24 | Q74 |
| 6770 | Z1 | L24 | Q75 |
| 6771 | Z1 | L24 | Q76 |
| 6772 | Z1 | L24 | Q77 |
| 6773 | Z1 | L24 | Q78 |
| 6774 | Z1 | L24 | Q79 |
| 6775 | Z1 | L24 | Q80 |
| 6776 | Z1 | L24 | Q81 |
| 6777 | Z1 | L24 | Q82 |
| 6778 | Z1 | L24 | Q83 |
| 6779 | Z1 | L24 | Q84 |
| 6780 | Z1 | L24 | Q85 |
| 6781 | Z1 | L24 | Q86 |
| 6782 | Z1 | L24 | Q87 |
| 6783 | Z1 | L24 | Q88 |
| 6784 | Z1 | L24 | Q89 |
| 6785 | Z1 | L24 | Q90 |
| 6786 | Z1 | L24 | Q91 |
| 6787 | Z1 | L24 | Q92 |
| 6788 | Z1 | L24 | Q93 |
| 6789 | Z1 | L24 | Q94 |

TABLE 1-39-continued

| | | | |
|---|---|---|---|
| 6790 | Z1 | L24 | Q95 |
| 6791 | Z1 | L24 | Q96 |
| 6792 | Z1 | L24 | Q97 |
| 6793 | Z1 | L24 | Q98 |
| 6794 | Z1 | L24 | Q99 |
| 6795 | Z1 | L24 | Q100 |
| 6796 | Z1 | L24 | Q101 |
| 6797 | Z1 | L24 | Q102 |
| 6798 | Z1 | L24 | Q103 |
| 6799 | Z1 | L25 | Q1 |
| 6800 | Z1 | L25 | Q2 |
| 6801 | Z1 | L25 | Q3 |
| 6802 | Z1 | L25 | Q4 |
| 6803 | Z1 | L25 | Q5 |
| 6804 | Z1 | L25 | Q6 |
| 6805 | Z1 | L25 | Q7 |
| 6806 | Z1 | L25 | Q8 |

TABLE 1-40

| | | | |
|---|---|---|---|
| 6807 | Z1 | L25 | Q9 |
| 6808 | Z1 | L25 | Q10 |
| 6809 | Z1 | L25 | Q11 |
| 6810 | Z1 | L25 | Q12 |
| 6811 | Z1 | L25 | Q13 |
| 6812 | Z1 | L25 | Q14 |
| 6813 | Z1 | L25 | Q15 |
| 6814 | Z1 | L25 | Q16 |
| 6815 | Z1 | L25 | Q17 |
| 6816 | Z1 | L25 | Q18 |
| 6817 | Z1 | L25 | Q19 |
| 6818 | Z1 | L25 | Q20 |
| 6819 | Z1 | L25 | Q21 |
| 6820 | Z1 | L25 | Q22 |
| 6821 | Z1 | L25 | Q23 |
| 6822 | Z1 | L25 | Q24 |
| 6823 | Z1 | L25 | Q25 |
| 6824 | Z1 | L25 | Q26 |
| 6825 | Z1 | L25 | Q27 |
| 6826 | Z1 | L25 | Q28 |
| 6827 | Z1 | L25 | Q29 |
| 6828 | Z1 | L25 | Q30 |
| 6829 | Z1 | L25 | Q31 |
| 6830 | Z1 | L25 | Q32 |
| 6831 | Z1 | L25 | Q33 |
| 6832 | Z1 | L25 | Q34 |
| 6833 | Z1 | L25 | Q35 |
| 6834 | Z1 | L25 | Q36 |
| 6835 | Z1 | L25 | Q37 |
| 6836 | Z1 | L25 | Q38 |
| 6837 | Z1 | L25 | Q39 |
| 6838 | Z1 | L25 | Q40 |
| 6839 | Z1 | L25 | Q41 |
| 6840 | Z1 | L25 | Q42 |
| 6841 | Z1 | L25 | Q43 |
| 6842 | Z1 | L25 | Q44 |
| 6843 | Z1 | L25 | Q45 |
| 6844 | Z1 | L25 | Q46 |
| 6845 | Z1 | L25 | Q47 |
| 6846 | Z1 | L25 | Q48 |
| 6847 | Z1 | L25 | Q49 |
| 6848 | Z1 | L25 | Q50 |
| 6849 | Z1 | L25 | Q51 |
| 6850 | Z1 | L25 | Q52 |
| 6851 | Z1 | L25 | Q53 |
| 6852 | Z1 | L25 | Q54 |
| 6853 | Z1 | L25 | Q55 |
| 6354 | Z1 | L25 | Q56 |
| 6855 | Z1 | L25 | Q57 |
| 6856 | Z1 | L25 | Q58 |
| 6857 | Z1 | L25 | Q59 |
| 6858 | Z1 | L25 | Q60 |
| 6859 | Z1 | L25 | Q61 |
| 6860 | Z1 | L25 | Q62 |
| 6861 | Z1 | L25 | Q63 |
| 6862 | Z1 | L25 | Q64 |
| 6863 | Z1 | L25 | Q65 |

TABLE 1-40-continued

| | | | |
|---|---|---|---|
| 6864 | Z1 | L25 | Q66 |
| 6865 | Z1 | L25 | Q67 |
| 6866 | Z1 | L25 | Q68 |
| 6867 | Z1 | L25 | Q69 |
| 6868 | Z1 | L25 | Q70 |
| 6869 | Z1 | L25 | Q71 |
| 6870 | Z1 | L25 | Q72 |
| 6871 | Z1 | L25 | Q73 |
| 6872 | Z1 | L25 | Q74 |
| 6873 | Z1 | L25 | Q75 |
| 6874 | Z1 | L25 | Q76 |
| 6875 | Z1 | L25 | Q77 |
| 6876 | Z1 | L25 | Q78 |
| 6877 | Z1 | L25 | Q79 |
| 6878 | Z1 | L25 | Q80 |
| 6879 | Z1 | L25 | Q81 |
| 6880 | Z1 | L25 | Q82 |
| 6881 | Z1 | L25 | Q83 |
| 6882 | Z1 | L25 | Q84 |
| 6883 | Z1 | L25 | Q85 |
| 6884 | Z1 | L25 | Q86 |
| 6885 | Z1 | L25 | Q87 |
| 6886 | Z1 | L25 | Q88 |
| 6887 | Z1 | L25 | Q89 |
| 6888 | Z1 | L25 | Q90 |
| 6889 | Z1 | L25 | Q91 |
| 6890 | Z1 | L25 | Q92 |
| 6891 | Z1 | L25 | Q93 |
| 6892 | Z1 | L25 | Q94 |
| 6893 | Z1 | L25 | Q95 |
| 6894 | Z1 | L25 | Q96 |
| 6895 | Z1 | L25 | Q97 |
| 6896 | Z1 | L25 | Q98 |
| 6897 | Z1 | L25 | Q99 |
| 6898 | Z1 | L25 | Q100 |
| 6899 | Z1 | L25 | Q101 |
| 6900 | Z1 | L25 | Q102 |
| 6901 | Z1 | L25 | Q103 |
| 6902 | Z1 | L26 | Q1 |
| 6903 | Z1 | L26 | Q2 |
| 6904 | Z1 | L26 | Q3 |
| 6905 | Z1 | L26 | Q4 |
| 6906 | Z1 | L26 | Q5 |
| 6907 | Z1 | L26 | Q6 |
| 6908 | Z1 | L26 | Q7 |
| 6909 | Z1 | L26 | Q8 |
| 6910 | Z1 | L26 | Q9 |
| 6911 | Z1 | L26 | Q10 |
| 6912 | Z1 | L26 | Q11 |
| 6913 | Z1 | L26 | Q12 |
| 6914 | Z1 | L26 | Q13 |
| 6915 | Z1 | L26 | Q14 |
| 6916 | Z1 | L26 | Q15 |
| 6917 | Z1 | L26 | Q16 |
| 6918 | Z1 | L26 | Q17 |
| 6919 | Z1 | L26 | Q18 |
| 6920 | Z1 | L26 | Q19 |
| 6921 | Z1 | L26 | Q20 |
| 6922 | Z1 | L26 | Q21 |
| 6923 | Z1 | L26 | Q22 |
| 6924 | Z1 | L26 | Q23 |
| 6925 | Z1 | L26 | Q24 |
| 6926 | Z1 | L26 | Q25 |
| 6927 | Z1 | L26 | Q26 |
| 6928 | Z1 | L26 | Q27 |
| 6929 | Z1 | L26 | Q28 |
| 6930 | Z1 | L26 | Q29 |
| 6931 | Z1 | L26 | Q30 |
| 6932 | Z1 | L26 | Q31 |
| 6933 | Z1 | L26 | Q32 |
| 6934 | Z1 | L26 | Q33 |
| 6935 | Z1 | L26 | Q34 |
| 6936 | Z1 | L26 | Q35 |
| 6937 | Z1 | L26 | Q36 |
| 6938 | Z1 | L26 | Q37 |
| 6939 | Z1 | L26 | Q38 |
| 6940 | Z1 | L26 | Q39 |
| 6941 | Z1 | L26 | Q40 |
| 6942 | Z1 | L26 | Q41 |
| 6943 | Z1 | L26 | Q42 |

TABLE 1-40-continued

| | | | |
|---|---|---|---|
| 6944 | Z1 | L26 | Q43 |
| 6945 | Z1 | L26 | Q44 |
| 6946 | Z1 | L26 | Q45 |
| 6947 | Z1 | L26 | Q46 |
| 6948 | Z1 | L26 | Q47 |
| 6949 | Z1 | L26 | Q48 |
| 6950 | Z1 | L26 | Q49 |
| 6951 | Z1 | L26 | Q50 |
| 6952 | Z1 | L26 | Q51 |
| 6953 | Z1 | L26 | Q52 |
| 6954 | Z1 | L26 | Q53 |
| 6955 | Z1 | L26 | Q54 |
| 6956 | Z1 | L26 | Q55 |
| 6957 | Z1 | L26 | Q56 |
| 6958 | Z1 | L26 | Q57 |
| 6959 | Z1 | L26 | Q58 |
| 6960 | Z1 | L26 | Q59 |
| 6961 | Z1 | L26 | Q60 |
| 6962 | Z1 | L26 | Q61 |
| 6963 | Z1 | L26 | Q62 |
| 6964 | Z1 | L26 | Q63 |
| 6965 | Z1 | L26 | Q64 |
| 6966 | Z1 | L26 | Q65 |
| 6967 | Z1 | L26 | Q66 |
| 6968 | Z1 | L26 | Q67 |
| 6969 | Z1 | L26 | Q68 |
| 6970 | Z1 | L26 | Q69 |
| 6971 | Z1 | L26 | Q70 |
| 6972 | Z1 | L26 | Q71 |
| 6973 | Z1 | L26 | Q72 |
| 6974 | Z1 | L26 | Q73 |
| 6975 | Z1 | L26 | Q74 |
| 6976 | Z1 | L26 | Q75 |
| 6977 | Z1 | L26 | Q76 |
| 6978 | Z1 | L26 | Q77 |
| 6979 | Z1 | L26 | Q78 |
| 6980 | Z1 | L26 | Q79 |
| 6981 | Z1 | L26 | Q80 |
| 6982 | Z1 | L26 | Q81 |
| 6983 | Z1 | L26 | Q82 |
| 6984 | Z1 | L26 | Q83 |
| 6985 | Z1 | L26 | Q84 |
| 6986 | Z1 | L26 | Q85 |
| 6987 | Z1 | L26 | Q86 |
| 6988 | Z1 | L26 | Q87 |
| 6989 | Z1 | L26 | Q88 |
| 6990 | Z1 | L26 | Q89 |
| 6991 | Z1 | L26 | Q90 |
| 6992 | Z1 | L26 | Q91 |
| 6993 | Z1 | L26 | Q92 |
| 6994 | Z1 | L26 | Q93 |
| 6995 | Z1 | L26 | Q94 |
| 6996 | Z1 | L26 | Q95 |
| 6997 | Z1 | L26 | Q96 |
| 6998 | Z1 | L26 | Q97 |
| 6999 | Z1 | L26 | Q98 |
| 7000 | Z1 | L26 | Q99 |
| 7001 | Z1 | L26 | Q100 |
| 7002 | Z1 | L26 | Q101 |
| 7003 | Z1 | L26 | Q102 |
| 7004 | Z1 | L26 | Q103 |
| 7005 | Z1 | L27 | Q1 |
| 7006 | Z1 | L27 | Q2 |
| 7007 | Z1 | L27 | Q3 |

TABLE 1-41

| | | | |
|---|---|---|---|
| 7008 | Z1 | L27 | Q4 |
| 7009 | Z1 | L27 | Q5 |
| 7010 | Z1 | L27 | Q6 |
| 7011 | Z1 | L27 | Q7 |
| 7012 | Z1 | L27 | Q8 |
| 7013 | Z1 | L27 | Q9 |
| 7014 | Z1 | L27 | Q10 |
| 7015 | Z1 | L27 | Q11 |
| 7016 | Z1 | L27 | Q12 |
| 7017 | Z1 | L27 | Q13 |

TABLE 1-41-continued

| | | | |
|---|---|---|---|
| 7018 | Z1 | L27 | Q14 |
| 7019 | Z1 | L27 | Q15 |
| 7020 | Z1 | L27 | Q16 |
| 7021 | Z1 | L27 | Q17 |
| 7022 | Z1 | L27 | Q18 |
| 7023 | Z1 | L27 | Q19 |
| 7024 | Z1 | L27 | Q20 |
| 7025 | Z1 | L27 | Q21 |
| 7026 | Z1 | L27 | Q22 |
| 7027 | Z1 | L27 | Q23 |
| 7028 | Z1 | L27 | Q24 |
| 7029 | Z1 | L27 | Q25 |
| 7030 | Z1 | L27 | Q26 |
| 7031 | Z1 | L27 | Q27 |
| 7032 | Z1 | L27 | Q28 |
| 7033 | Z1 | L27 | Q29 |
| 7034 | Z1 | L27 | Q30 |
| 7035 | Z1 | L27 | Q31 |
| 7036 | Z1 | L27 | Q32 |
| 7037 | Z1 | L27 | Q33 |
| 7038 | Z1 | L27 | Q34 |
| 7039 | Z1 | L27 | Q35 |
| 7040 | Z1 | L27 | Q36 |
| 7041 | Z1 | L27 | Q37 |
| 7042 | Z1 | L27 | Q38 |
| 7043 | Z1 | L27 | Q39 |
| 7044 | Z1 | L27 | Q40 |
| 7045 | Z1 | L27 | Q41 |
| 7046 | Z1 | L27 | Q42 |
| 7047 | Z1 | L27 | Q43 |
| 7048 | Z1 | L27 | Q44 |
| 7049 | Z1 | L27 | Q45 |
| 7050 | Z1 | L27 | Q46 |
| 7051 | Z1 | L27 | Q47 |
| 7052 | Z1 | L27 | Q48 |
| 7053 | Z1 | L27 | Q49 |
| 7054 | Z1 | L27 | Q50 |
| 7055 | Z1 | L27 | Q51 |
| 7056 | Z1 | L27 | Q52 |
| 7057 | Z1 | L27 | Q53 |
| 7058 | Z1 | L27 | Q54 |
| 7059 | Z1 | L27 | Q55 |
| 7060 | Z1 | L27 | Q56 |
| 7061 | Z1 | L27 | Q57 |
| 7062 | Z1 | L27 | Q58 |
| 7063 | Z1 | L27 | Q59 |
| 7064 | Z1 | L27 | Q60 |
| 7065 | Z1 | L27 | Q61 |
| 7066 | Z1 | L27 | Q62 |
| 7067 | Z1 | L27 | Q63 |
| 7068 | Z1 | L27 | Q64 |
| 7069 | Z1 | L27 | Q65 |
| 7070 | Z1 | L27 | Q66 |
| 7071 | Z1 | L27 | Q67 |
| 7072 | Z1 | L27 | Q68 |
| 7073 | Z1 | L27 | Q69 |
| 7074 | Z1 | L27 | Q70 |
| 7075 | Z1 | L27 | Q71 |
| 7076 | Z1 | L27 | Q72 |
| 7077 | Z1 | L27 | Q73 |
| 7078 | Z1 | L27 | Q74 |
| 7079 | Z1 | L27 | Q75 |
| 7080 | Z1 | L27 | Q76 |
| 7081 | Z1 | L27 | Q77 |
| 7082 | Z1 | L27 | Q78 |
| 7083 | Z1 | L27 | Q79 |
| 7084 | Z1 | L27 | Q80 |
| 7085 | Z1 | L27 | Q81 |
| 7086 | Z1 | L27 | Q82 |
| 7087 | Z1 | L27 | Q83 |
| 7088 | Z1 | L27 | Q84 |
| 7089 | Z1 | L27 | Q85 |
| 7090 | Z1 | L27 | Q86 |
| 7091 | Z1 | L27 | Q87 |
| 7092 | Z1 | L27 | Q88 |
| 7093 | Z1 | L27 | Q89 |
| 7094 | Z1 | L27 | Q90 |
| 7095 | Z1 | L27 | Q91 |
| 7096 | Z1 | L27 | Q92 |
| 7097 | Z1 | L27 | Q93 |

TABLE 1-41-continued

| | | | |
|---|---|---|---|
| 7098 | Z1 | L27 | Q94 |
| 7099 | Z1 | L27 | Q95 |
| 7100 | Z1 | L27 | Q96 |
| 7101 | Z1 | L27 | Q97 |
| 7102 | Z1 | L27 | Q98 |
| 7103 | Z1 | L27 | Q99 |
| 7104 | Z1 | L27 | Q100 |
| 7105 | Z1 | L27 | Q101 |
| 7106 | Z1 | L27 | Q102 |
| 7107 | Z1 | L27 | Q103 |
| 7108 | Z1 | L28 | Q1 |
| 7109 | Z1 | L28 | Q2 |
| 7110 | Z1 | L28 | Q3 |
| 7111 | Z1 | L28 | Q4 |
| 7112 | Z1 | L28 | Q5 |
| 7113 | Z1 | L28 | Q6 |
| 7114 | Z1 | L28 | Q7 |
| 7115 | Z1 | L28 | Q8 |
| 7116 | Z1 | L28 | Q9 |
| 7117 | Z1 | L28 | Q10 |
| 7118 | Z1 | L28 | Q11 |
| 7119 | Z1 | L28 | Q12 |
| 7120 | Z1 | L28 | Q13 |
| 7121 | Z1 | L28 | Q14 |
| 7122 | Z1 | L28 | Q15 |
| 7123 | Z1 | L28 | Q16 |
| 7124 | Z1 | L28 | Q17 |
| 7125 | Z1 | L28 | Q18 |
| 7126 | Z1 | L28 | Q19 |
| 7127 | Z1 | L28 | Q20 |
| 7128 | Z1 | L28 | Q21 |
| 7129 | Z1 | L28 | Q22 |
| 7130 | Z1 | L28 | Q23 |
| 7131 | Z1 | L28 | Q24 |
| 7132 | Z1 | L28 | Q25 |
| 7133 | Z1 | L28 | Q26 |
| 7134 | Z1 | L28 | Q27 |
| 7135 | Z1 | L28 | Q28 |
| 7136 | Z1 | L28 | Q29 |
| 7137 | Z1 | L28 | Q30 |
| 7138 | Z1 | L28 | Q31 |
| 7139 | Z1 | L28 | Q32 |
| 7140 | Z1 | L28 | Q33 |
| 7141 | Z1 | L28 | Q34 |
| 7142 | Z1 | L28 | Q35 |
| 7143 | Z1 | L28 | Q36 |
| 7144 | Z1 | L28 | Q37 |
| 7145 | Z1 | L28 | Q38 |
| 7146 | Z1 | L28 | Q39 |
| 7147 | Z1 | L28 | Q40 |
| 7148 | Z1 | L28 | Q41 |
| 7149 | Z1 | L28 | Q42 |
| 7150 | Z1 | L28 | Q43 |
| 7151 | Z1 | L28 | Q44 |
| 7152 | Z1 | L28 | Q45 |
| 7153 | Z1 | L28 | Q46 |
| 7154 | Z1 | L28 | Q47 |
| 7155 | Z1 | L28 | Q48 |
| 7156 | Z1 | L28 | Q49 |
| 7157 | Z1 | L28 | Q50 |
| 7158 | Z1 | L28 | Q51 |
| 7159 | Z1 | L28 | Q52 |
| 7160 | Z1 | L28 | Q53 |
| 7161 | Z1 | L28 | Q54 |
| 7162 | Z1 | L28 | Q55 |
| 7163 | Z1 | L28 | Q56 |
| 7164 | Z1 | L28 | Q57 |
| 7165 | Z1 | L28 | Q58 |
| 7166 | Z1 | L28 | Q59 |
| 7167 | Z1 | L28 | Q60 |
| 7168 | Z1 | L28 | Q61 |
| 7169 | Z1 | L28 | Q62 |
| 7170 | Z1 | L28 | Q63 |
| 7171 | Z1 | L28 | Q64 |
| 7172 | Z1 | L28 | Q65 |
| 7173 | Z1 | L28 | Q66 |
| 7174 | Z1 | L28 | Q67 |
| 7175 | Z1 | L28 | Q68 |
| 7176 | Z1 | L28 | Q69 |
| 7177 | Z1 | L28 | Q70 |
| 7178 | Z1 | L28 | Q71 |
| 7179 | Z1 | L28 | Q72 |
| 7180 | Z1 | L28 | Q73 |
| 7181 | Z1 | L28 | Q74 |
| 7182 | Z1 | L28 | Q75 |
| 7183 | Z1 | L28 | Q76 |
| 7184 | Z1 | L28 | Q77 |
| 7185 | Z1 | L28 | Q78 |
| 7186 | Z1 | L28 | Q79 |
| 7187 | Z1 | L28 | Q80 |
| 7188 | Z1 | L28 | Q81 |
| 7189 | Z1 | L28 | Q82 |
| 7190 | Z1 | L28 | Q83 |
| 7191 | Z1 | L28 | Q84 |
| 7192 | Z1 | L28 | Q85 |
| 7193 | Z1 | L28 | Q86 |
| 7194 | Z1 | L28 | Q87 |
| 7195 | Z1 | L28 | Q88 |
| 7196 | Z1 | L28 | Q89 |
| 7197 | Z1 | L28 | Q90 |
| 7198 | Z1 | L28 | Q91 |
| 7199 | Z1 | L28 | Q92 |
| 7200 | Z1 | L28 | Q93 |
| 7201 | Z1 | L28 | Q94 |
| 7202 | Z1 | L28 | Q95 |
| 7203 | Z1 | L28 | Q96 |
| 7204 | Z1 | L28 | Q97 |
| 7205 | Z1 | L28 | Q98 |
| 7206 | Z1 | L28 | Q99 |
| 7207 | Z1 | L28 | Q100 |
| 7208 | Z1 | L28 | Q101 |

TABLE 1-42

| | | | |
|---|---|---|---|
| 7209 | Z1 | L28 | Q102 |
| 7210 | Z1 | L28 | Q103 |
| 7211 | Z1 | L29 | Q1 |
| 7212 | Z1 | L29 | Q2 |
| 7213 | Z1 | L29 | Q3 |
| 7214 | Z1 | L29 | Q4 |
| 7215 | Z1 | L29 | Q5 |
| 7216 | Z1 | L29 | Q6 |
| 7217 | Z1 | L29 | Q7 |
| 7218 | Z1 | L29 | Q8 |
| 7219 | Z1 | L29 | Q9 |
| 7220 | Z1 | L29 | Q10 |
| 7221 | Z1 | L29 | Q11 |
| 7222 | Z1 | L29 | Q12 |
| 7223 | Z1 | L29 | Q13 |
| 7224 | Z1 | L29 | Q14 |
| 7225 | Z1 | L29 | Q15 |
| 7226 | Z1 | L29 | Q16 |
| 7227 | Z1 | L29 | Q17 |
| 7228 | Z1 | L29 | Q18 |
| 7229 | Z1 | L29 | Q19 |
| 7230 | Z1 | L29 | Q20 |
| 7231 | Z1 | L29 | Q21 |
| 7232 | Z1 | L29 | Q22 |
| 7233 | Z1 | L29 | Q23 |
| 7234 | Z1 | L29 | Q24 |
| 7235 | Z1 | L29 | Q25 |
| 7236 | Z1 | L29 | Q26 |
| 7237 | Z1 | L29 | Q27 |
| 7238 | Z1 | L29 | Q28 |
| 7239 | Z1 | L29 | Q29 |
| 7240 | Z1 | L29 | Q30 |
| 7241 | Z1 | L29 | Q31 |
| 7242 | Z1 | L29 | Q32 |
| 7243 | Z1 | L29 | Q33 |
| 7244 | Z1 | L29 | Q34 |
| 7245 | Z1 | L29 | Q35 |
| 7246 | Z1 | L29 | Q36 |
| 7247 | Z1 | L29 | Q37 |
| 7248 | Z1 | L29 | Q38 |
| 7249 | Z1 | L29 | Q39 |
| 7250 | Z1 | L29 | Q40 |
| 7251 | Z1 | L29 | Q41 |

TABLE 1-42-continued

| | | | |
|---|---|---|---|
| 7252 | Z1 | L29 | Q42 |
| 7253 | Z1 | L29 | Q43 |
| 7254 | Z1 | L29 | Q44 |
| 7255 | Z1 | L29 | Q45 |
| 7256 | Z1 | L29 | Q46 |
| 7257 | Z1 | L29 | Q47 |
| 7258 | Z1 | L29 | Q48 |
| 7259 | Z1 | L29 | Q49 |
| 7260 | Z1 | L29 | Q50 |
| 7261 | Z1 | L29 | Q51 |
| 7262 | Z1 | L29 | Q52 |
| 7263 | Z1 | L29 | Q53 |
| 7264 | Z1 | L29 | Q54 |
| 7265 | Z1 | L29 | Q55 |
| 7266 | Z1 | L29 | Q56 |
| 7267 | Z1 | L29 | Q57 |
| 7268 | Z1 | L29 | Q58 |
| 7269 | Z1 | L29 | Q59 |
| 7270 | Z1 | L29 | Q60 |
| 7271 | Z1 | L29 | Q61 |
| 7272 | Z1 | L29 | Q62 |
| 7273 | Z1 | L29 | Q63 |
| 7274 | Z1 | L29 | Q64 |
| 7275 | Z1 | L29 | Q65 |
| 7276 | Z1 | L29 | Q66 |
| 7277 | Z1 | L29 | Q67 |
| 7278 | Z1 | L29 | Q68 |
| 7279 | Z1 | L29 | Q69 |
| 7280 | Z1 | L29 | Q70 |
| 7281 | Z1 | L29 | Q71 |
| 7282 | Z1 | L29 | Q72 |
| 7283 | Z1 | L29 | Q73 |
| 7284 | Z1 | L29 | Q74 |
| 7285 | Z1 | L29 | Q75 |
| 7286 | Z1 | L29 | Q76 |
| 7287 | Z1 | L29 | Q77 |
| 7288 | Z1 | L29 | Q78 |
| 7289 | Z1 | L29 | Q79 |
| 7290 | Z1 | L29 | Q80 |
| 7291 | Z1 | L29 | Q81 |
| 7292 | Z1 | L29 | Q82 |
| 7293 | Z1 | L29 | Q83 |
| 7294 | Z1 | L29 | Q84 |
| 7295 | Z1 | L29 | Q85 |
| 7296 | Z1 | L29 | Q86 |
| 7297 | Z1 | L29 | Q87 |
| 7298 | Z1 | L29 | Q88 |
| 7299 | Z1 | L29 | Q89 |
| 7300 | Z1 | L29 | Q90 |
| 7301 | Z1 | L29 | Q91 |
| 7302 | Z1 | L29 | Q92 |
| 7303 | Z1 | L29 | Q93 |
| 7304 | Z1 | L29 | Q94 |
| 7305 | Z1 | L29 | Q95 |
| 7306 | Z1 | L29 | Q96 |
| 7307 | Z1 | L29 | Q97 |
| 7308 | Z1 | L29 | Q98 |
| 7309 | Z1 | L29 | Q99 |
| 7310 | Z1 | L29 | Q100 |
| 7311 | Z1 | L29 | Q101 |
| 7312 | Z1 | L29 | Q102 |
| 7313 | Z1 | L29 | Q103 |
| 7314 | Z1 | L30 | Q1 |
| 7315 | Z1 | L30 | Q2 |
| 7316 | Z1 | L30 | Q3 |
| 7317 | Z1 | L30 | Q4 |
| 7318 | Z1 | L30 | Q5 |
| 7319 | Z1 | L30 | Q6 |
| 7320 | Z1 | L30 | Q7 |
| 7321 | Z1 | L30 | Q8 |
| 7322 | Z1 | L30 | Q9 |
| 7323 | Z1 | L30 | Q10 |
| 7324 | Z1 | L30 | Q11 |
| 7325 | Z1 | L30 | Q12 |
| 7326 | Z1 | L30 | Q13 |
| 7327 | Z1 | L30 | Q14 |
| 7328 | Z1 | L30 | Q15 |
| 7329 | Z1 | L30 | Q16 |
| 7330 | Z1 | L30 | Q17 |
| 7331 | Z1 | L30 | Q18 |
| 7332 | Z1 | L30 | Q19 |
| 7333 | Z1 | L30 | Q20 |
| 7334 | Z1 | L30 | Q21 |
| 7335 | Z1 | L30 | Q22 |
| 7336 | Z1 | L30 | Q23 |
| 7337 | Z1 | L30 | Q24 |
| 7338 | Z1 | L30 | Q25 |
| 7339 | Z1 | L30 | Q26 |
| 7340 | Z1 | L30 | Q27 |
| 7341 | Z1 | L30 | Q28 |
| 7342 | Z1 | L30 | Q29 |
| 7343 | Z1 | L30 | Q30 |
| 7344 | Z1 | L30 | Q31 |
| 7345 | Z1 | L30 | Q32 |
| 7346 | Z1 | L30 | Q33 |
| 7347 | Z1 | L30 | Q34 |
| 7348 | Z1 | L30 | Q35 |
| 7349 | Z1 | L30 | Q36 |
| 7350 | Z1 | L30 | Q37 |
| 7351 | Z1 | L30 | Q38 |
| 7352 | Z1 | L30 | Q39 |
| 7353 | Z1 | L30 | Q40 |
| 7354 | Z1 | L30 | Q41 |
| 7355 | Z1 | L30 | Q42 |
| 7356 | Z1 | L30 | Q43 |
| 7357 | Z1 | L30 | Q44 |
| 7358 | Z1 | L30 | Q45 |
| 7359 | Z1 | L30 | Q46 |
| 7360 | Z1 | L30 | Q47 |
| 7361 | Z1 | L30 | Q48 |
| 7362 | Z1 | L30 | Q49 |
| 7363 | Z1 | L30 | Q50 |
| 7364 | Z1 | L30 | Q51 |
| 7365 | Z1 | L30 | Q52 |
| 7366 | Z1 | L30 | Q53 |
| 7367 | Z1 | L30 | Q54 |
| 7368 | Z1 | L30 | Q55 |
| 7369 | Z1 | L30 | Q56 |
| 7370 | Z1 | L30 | Q57 |
| 7371 | Z1 | L30 | Q58 |
| 7372 | Z1 | L30 | Q59 |
| 7373 | Z1 | L30 | Q60 |
| 7374 | Z1 | L30 | Q61 |
| 7375 | Z1 | L30 | Q62 |
| 7376 | Z1 | L30 | Q63 |
| 7377 | Z1 | L30 | Q64 |
| 7378 | Z1 | L30 | Q65 |
| 7379 | Z1 | L30 | Q66 |
| 7380 | Z1 | L30 | Q67 |
| 7381 | Z1 | L30 | Q68 |
| 7382 | Z1 | L30 | Q69 |
| 7383 | Z1 | L30 | Q70 |
| 7384 | Z1 | L30 | Q71 |
| 7385 | Z1 | L30 | Q72 |
| 7386 | Z1 | L30 | Q73 |
| 7387 | Z1 | L30 | Q74 |
| 7388 | Z1 | L30 | Q75 |
| 7389 | Z1 | L30 | Q76 |
| 7390 | Z1 | L30 | Q77 |
| 7391 | Z1 | L30 | Q78 |
| 7392 | Z1 | L30 | Q79 |
| 7393 | Z1 | L30 | Q80 |
| 7394 | Z1 | L30 | Q81 |
| 7395 | Z1 | L30 | Q82 |
| 7396 | Z1 | L30 | Q83 |
| 7397 | Z1 | L30 | Q84 |
| 7398 | Z1 | L30 | Q85 |
| 7399 | Z1 | L30 | Q86 |
| 7400 | Z1 | L30 | Q87 |
| 7401 | Z1 | L30 | Q88 |
| 7402 | Z1 | L30 | Q89 |
| 7403 | Z1 | L30 | Q90 |
| 7404 | Z1 | L30 | Q91 |
| 7405 | Z1 | L30 | Q92 |
| 7406 | Z1 | L30 | Q93 |
| 7407 | Z1 | L30 | Q94 |
| 7408 | Z1 | L30 | Q95 |
| 7409 | Z1 | L30 | Q96 |

TABLE 1-43

| | | | |
|---|---|---|---|
| 7410 | Z1 | L30 | Q97 |
| 7411 | Z1 | L30 | Q98 |
| 7412 | Z1 | L30 | Q99 |
| 7413 | Z1 | L30 | Q100 |
| 7414 | Z1 | L30 | Q101 |
| 7415 | Z1 | L30 | Q102 |
| 7416 | Z1 | L30 | Q103 |
| 7417 | Z1 | L31 | Q1 |
| 7418 | Z1 | L31 | Q2 |
| 7419 | Z1 | L31 | Q3 |
| 7420 | Z1 | L31 | Q4 |
| 7421 | Z1 | L31 | Q5 |
| 7422 | Z1 | L31 | Q6 |
| 7423 | Z1 | L31 | Q7 |
| 7424 | Z1 | L31 | Q8 |
| 7425 | Z1 | L31 | Q9 |
| 7426 | Z1 | L31 | Q10 |
| 7427 | Z1 | L31 | Q11 |
| 7428 | Z1 | L31 | Q12 |
| 7429 | Z1 | L31 | Q13 |
| 7430 | Z1 | L31 | Q14 |
| 7431 | Z1 | L31 | Q15 |
| 7432 | Z1 | L31 | Q16 |
| 7433 | Z1 | L31 | Q17 |
| 7434 | Z1 | L31 | Q18 |
| 7435 | Z1 | L31 | Q19 |
| 7436 | Z1 | L31 | Q20 |
| 7437 | Z1 | L31 | Q21 |
| 7438 | Z1 | L31 | Q22 |
| 7439 | Z1 | L31 | Q23 |
| 7440 | Z1 | L31 | Q24 |
| 7441 | Z1 | L31 | Q25 |
| 7442 | Z1 | L31 | Q26 |
| 7443 | Z1 | L31 | Q27 |
| 7444 | Z1 | L31 | Q28 |
| 7445 | Z1 | L31 | Q29 |
| 7446 | Z1 | L31 | Q30 |
| 7447 | Z1 | L31 | Q31 |
| 7448 | Z1 | L31 | Q32 |
| 7449 | Z1 | L31 | Q33 |
| 7450 | Z1 | L31 | Q34 |
| 7451 | Z1 | L31 | Q35 |
| 7452 | Z1 | L31 | Q36 |
| 7453 | Z1 | L31 | Q37 |
| 7454 | Z1 | L31 | Q38 |
| 7455 | Z1 | L31 | Q39 |
| 7456 | Z1 | L31 | Q40 |
| 7457 | Z1 | L31 | Q41 |
| 7458 | Z1 | L31 | Q42 |
| 7459 | Z1 | L31 | Q43 |
| 7460 | Z1 | L31 | Q44 |
| 7461 | Z1 | L31 | Q45 |
| 7462 | Z1 | L31 | Q46 |
| 7463 | Z1 | L31 | Q47 |
| 7464 | Z1 | L31 | Q48 |
| 7465 | Z1 | L31 | Q49 |
| 7466 | Z1 | L31 | Q50 |
| 7467 | Z1 | L31 | Q51 |
| 7468 | Z1 | L31 | Q52 |
| 7469 | Z1 | L31 | Q53 |
| 7470 | Z1 | L31 | Q54 |
| 7471 | Z1 | L31 | Q55 |
| 7472 | Z1 | L31 | Q56 |
| 7473 | Z1 | L31 | Q57 |
| 7474 | Z1 | L31 | Q58 |
| 7475 | Z1 | L31 | Q59 |
| 7476 | Z1 | L31 | Q60 |
| 7477 | Z1 | L31 | Q61 |
| 7478 | Z1 | L31 | Q62 |
| 7479 | Z1 | L31 | Q63 |
| 7480 | Z1 | L31 | Q64 |
| 7481 | Z1 | L31 | Q65 |
| 7482 | Z1 | L31 | Q66 |
| 7483 | Z1 | L31 | Q67 |
| 7484 | Z1 | L31 | Q68 |
| 7485 | Z1 | L31 | Q69 |
| 7486 | Z1 | L31 | Q70 |
| 7487 | Z1 | L31 | Q71 |
| 7488 | Z1 | L31 | Q72 |
| 7489 | Z1 | L31 | Q73 |
| 7490 | Z1 | L31 | Q74 |
| 7491 | Z1 | L31 | Q75 |
| 7492 | Z1 | L31 | Q76 |
| 7493 | Z1 | L31 | Q77 |
| 7494 | Z1 | L31 | Q78 |
| 7495 | Z1 | L31 | Q79 |
| 7496 | Z1 | L31 | Q80 |
| 7497 | Z1 | L31 | Q81 |
| 7498 | Z1 | L31 | Q82 |
| 7499 | Z1 | L31 | Q83 |
| 7500 | Z1 | L31 | Q84 |
| 7501 | Z1 | L31 | Q85 |
| 7502 | Z1 | L31 | Q86 |
| 7503 | Z1 | L31 | Q87 |
| 7504 | Z1 | L31 | Q88 |
| 7505 | Z1 | L31 | Q89 |
| 7506 | Z1 | L31 | Q90 |
| 7507 | Z1 | L31 | Q91 |
| 7508 | Z1 | L31 | Q92 |
| 7509 | Z1 | L31 | Q93 |
| 7510 | Z1 | L31 | Q94 |
| 7511 | Z1 | L31 | Q95 |
| 7512 | Z1 | L31 | Q96 |
| 7513 | Z1 | L31 | Q97 |
| 7514 | Z1 | L31 | Q98 |
| 7515 | Z1 | L31 | Q99 |
| 7516 | Z1 | L31 | Q100 |
| 7517 | Z1 | L31 | Q101 |
| 7518 | Z1 | L31 | Q102 |
| 7519 | Z1 | L31 | Q103 |
| 7520 | Z1 | L32 | Q1 |
| 7521 | Z1 | L32 | Q2 |
| 7522 | Z1 | L32 | Q3 |
| 7523 | Z1 | L32 | Q4 |
| 7524 | Z1 | L32 | Q5 |
| 7525 | Z1 | L32 | Q6 |
| 7526 | Z1 | L32 | Q7 |
| 7527 | Z1 | L32 | Q8 |
| 7528 | Z1 | L32 | Q9 |
| 7529 | Z1 | L32 | Q10 |
| 7530 | Z1 | L32 | Q11 |
| 7531 | Z1 | L32 | Q12 |
| 7532 | Z1 | L32 | Q13 |
| 7533 | Z1 | L32 | Q14 |
| 7534 | Z1 | L32 | Q15 |
| 7535 | Z1 | L32 | Q16 |
| 7536 | Z1 | L32 | Q17 |
| 7537 | Z1 | L32 | Q18 |
| 7538 | Z1 | L32 | Q19 |
| 7539 | Z1 | L32 | Q20 |
| 7540 | Z1 | L32 | Q21 |
| 7541 | Z1 | L32 | Q22 |
| 7542 | Z1 | L32 | Q23 |
| 7543 | Z1 | L32 | Q24 |
| 7544 | Z1 | L32 | Q25 |
| 7545 | Z1 | L32 | Q26 |
| 7546 | Z1 | L32 | Q27 |
| 7547 | Z1 | L32 | Q28 |
| 7548 | Z1 | L32 | Q29 |
| 7549 | Z1 | L32 | Q30 |
| 7550 | Z1 | L32 | Q31 |
| 7551 | Z1 | L32 | Q32 |
| 7552 | Z1 | L32 | Q33 |
| 7553 | Z1 | L32 | Q34 |
| 7554 | Z1 | L32 | Q35 |
| 7555 | Z1 | L32 | Q36 |
| 7556 | Z1 | L32 | Q37 |
| 7557 | Z1 | L32 | Q38 |
| 7558 | Z1 | L32 | Q39 |
| 7559 | Z1 | L32 | Q40 |
| 7560 | Z1 | L32 | Q41 |
| 7561 | Z1 | L32 | Q42 |
| 7562 | Z1 | L32 | Q43 |
| 7563 | Z1 | L32 | Q44 |
| 7564 | Z1 | L32 | Q45 |
| 7565 | Z1 | L32 | Q46 |
| 7566 | Z1 | L32 | Q47 |
| 7567 | Z1 | L32 | Q48 |
| 7568 | Z1 | L32 | Q49 |
| 7569 | Z1 | L32 | Q50 |

TABLE 1-43-continued

| | | | |
|---|---|---|---|
| 7570 | Z1 | L32 | Q51 |
| 7571 | Z1 | L32 | Q52 |
| 7572 | Z1 | L32 | Q53 |
| 7573 | Z1 | L32 | Q54 |
| 7574 | Z1 | L32 | Q55 |
| 7575 | Z1 | L32 | Q56 |
| 7576 | Z1 | L32 | Q57 |
| 7577 | Z1 | L32 | Q58 |
| 7578 | Z1 | L32 | Q59 |
| 7579 | Z1 | L32 | Q60 |
| 7580 | Z1 | L32 | Q61 |
| 7581 | Z1 | L32 | Q62 |
| 7582 | Z1 | L32 | Q63 |
| 7583 | Z1 | L32 | Q64 |
| 7584 | Z1 | L32 | Q65 |
| 7585 | Z1 | L32 | Q66 |
| 7586 | Z1 | L32 | Q67 |
| 7587 | Z1 | L32 | Q68 |
| 7588 | Z1 | L32 | Q69 |
| 7589 | Z1 | L32 | Q70 |
| 7590 | Z1 | L32 | Q71 |
| 7591 | Z1 | L32 | Q72 |
| 7592 | Z1 | L32 | Q73 |
| 7593 | Z1 | L32 | Q74 |
| 7594 | Z1 | L32 | Q75 |
| 7595 | Z1 | L32 | Q76 |
| 7596 | Z1 | L32 | Q77 |
| 7597 | Z1 | L32 | Q78 |
| 7598 | Z1 | L32 | Q79 |
| 7599 | Z1 | L32 | Q80 |
| 7600 | Z1 | L32 | Q81 |
| 7601 | Z1 | L32 | Q82 |
| 7602 | Z1 | L32 | Q83 |
| 7603 | Z1 | L32 | Q84 |
| 7604 | Z1 | L32 | Q85 |
| 7605 | Z1 | L32 | Q86 |
| 7606 | Z1 | L32 | Q87 |
| 7607 | Z1 | L32 | Q88 |
| 7608 | Z1 | L32 | Q89 |
| 7609 | Z1 | L32 | Q90 |
| 7610 | Z1 | L32 | Q91 |

TABLE 1-44

| | | | |
|---|---|---|---|
| 7611 | Z1 | L32 | Q92 |
| 7612 | Z1 | L32 | Q93 |
| 7613 | Z1 | L32 | Q94 |
| 7614 | Z1 | L32 | Q95 |
| 7615 | Z1 | L32 | Q96 |
| 7616 | Z1 | L32 | Q97 |
| 7617 | Z1 | L32 | Q98 |
| 7618 | Z1 | L32 | Q99 |
| 7619 | Z1 | L32 | Q100 |
| 7620 | Z1 | L32 | Q101 |
| 7621 | Z1 | L32 | Q102 |
| 7622 | Z1 | L32 | Q103 |
| 7623 | Z1 | L33 | Q1 |
| 7624 | Z1 | L33 | Q2 |
| 7625 | Z1 | L33 | Q3 |
| 7626 | Z1 | L33 | Q4 |
| 7627 | Z1 | L33 | Q5 |
| 7628 | Z1 | L33 | Q6 |
| 7629 | Z1 | L33 | Q7 |
| 7630 | Z1 | L33 | Q8 |
| 7631 | Z1 | L33 | Q9 |
| 7632 | Z1 | L33 | Q10 |
| 7633 | Z1 | L33 | Q11 |
| 7634 | Z1 | L33 | Q12 |
| 7635 | Z1 | L33 | Q13 |
| 7636 | Z1 | L33 | Q14 |
| 7637 | Z1 | L33 | Q15 |
| 7638 | Z1 | L33 | Q16 |
| 7639 | Z1 | L33 | Q17 |
| 7640 | Z1 | L33 | Q18 |
| 7641 | Z1 | L33 | Q19 |
| 7642 | Z1 | L33 | Q20 |
| 7643 | Z1 | L33 | Q21 |

TABLE 1-44-continued

| | | | |
|---|---|---|---|
| 7644 | Z1 | L33 | Q22 |
| 7645 | Z1 | L33 | Q23 |
| 7646 | Z1 | L33 | Q24 |
| 7647 | Z1 | L33 | Q25 |
| 7648 | Z1 | L33 | Q26 |
| 7649 | Z1 | L33 | Q27 |
| 7650 | Z1 | L33 | Q28 |
| 7651 | Z1 | L33 | Q29 |
| 7652 | Z1 | L33 | Q30 |
| 7653 | Z1 | L33 | Q31 |
| 7654 | Z1 | L33 | Q32 |
| 7655 | Z1 | L33 | Q33 |
| 7656 | Z1 | L33 | Q34 |
| 7657 | Z1 | L33 | Q35 |
| 7658 | Z1 | L33 | Q36 |
| 7659 | Z1 | L33 | Q37 |
| 7660 | Z1 | L33 | Q38 |
| 7661 | Z1 | L33 | Q39 |
| 7662 | Z1 | L33 | Q40 |
| 7663 | Z1 | L33 | Q41 |
| 7664 | Z1 | L33 | Q42 |
| 7665 | Z1 | L33 | Q43 |
| 7666 | Z1 | L33 | Q44 |
| 7667 | Z1 | L33 | Q45 |
| 7668 | Z1 | L33 | Q46 |
| 7669 | Z1 | L33 | Q47 |
| 7670 | Z1 | L33 | Q48 |
| 7671 | Z1 | L33 | Q49 |
| 7672 | Z1 | L33 | Q50 |
| 7673 | 71 | L33 | Q51 |
| 7674 | Z1 | L33 | Q52 |
| 7675 | Z1 | L33 | Q53 |
| 7676 | Z1 | L33 | Q54 |
| 7677 | Z1 | L33 | Q55 |
| 7678 | Z1 | L33 | Q56 |
| 7679 | Z1 | L33 | Q57 |
| 7680 | Z1 | L33 | Q58 |
| 7681 | Z1 | L33 | Q59 |
| 7682 | Z1 | L33 | Q60 |
| 7683 | Z1 | L33 | Q61 |
| 7684 | Z1 | L33 | Q62 |
| 7685 | Z1 | L33 | Q63 |
| 7686 | Z1 | L33 | Q64 |
| 7687 | Z1 | L33 | Q65 |
| 7688 | Z1 | L33 | Q66 |
| 7689 | Z1 | L33 | Q67 |
| 7690 | Z1 | L33 | Q68 |
| 7691 | Z1 | L33 | Q69 |
| 7692 | Z1 | L33 | Q70 |
| 7693 | Z1 | L33 | Q71 |
| 7694 | Z1 | L33 | Q72 |
| 7695 | Z1 | L33 | Q73 |
| 7696 | Z1 | L33 | Q74 |
| 7697 | Z1 | L33 | Q75 |
| 7698 | Z1 | L33 | Q76 |
| 7699 | Z1 | L33 | Q77 |
| 7700 | Z1 | L33 | Q78 |
| 7701 | Z1 | L33 | Q79 |
| 7702 | Z1 | L33 | Q80 |
| 7703 | Z1 | L33 | Q81 |
| 7704 | Z1 | L33 | Q82 |
| 7705 | Z1 | L33 | Q83 |
| 7706 | Z1 | L33 | Q84 |
| 7707 | Z1 | L33 | Q85 |
| 7708 | Z1 | L33 | Q86 |
| 7709 | Z1 | L33 | Q87 |
| 7710 | Z1 | L33 | Q88 |
| 7711 | Z1 | L33 | Q89 |
| 7712 | Z1 | L33 | Q90 |
| 7713 | Z1 | L33 | Q91 |
| 7714 | Z1 | L33 | Q92 |
| 7715 | Z1 | L33 | Q93 |
| 7716 | Z1 | L33 | Q94 |
| 7717 | Z1 | L33 | Q95 |
| 7718 | Z1 | L33 | Q96 |
| 7719 | Z1 | L33 | Q97 |
| 7720 | Z1 | L33 | Q98 |
| 7721 | Z1 | L33 | Q99 |
| 7722 | Z1 | L33 | Q100 |
| 7723 | Z1 | L33 | Q101 |

TABLE 1-44-continued

| | | | |
|---|---|---|---|
| 7724 | Z1 | L33 | Q102 |
| 7725 | Z1 | L33 | Q103 |
| 7726 | Z1 | L34 | Q1 |
| 7727 | Z1 | L34 | Q2 |
| 7728 | Z1 | L34 | Q3 |
| 7729 | Z1 | L34 | Q4 |
| 7730 | Z1 | L34 | Q5 |
| 7731 | Z1 | L34 | Q6 |
| 7732 | Z1 | L34 | Q7 |
| 7733 | Z1 | L34 | Q8 |
| 7734 | Z1 | L34 | Q9 |
| 7735 | Z1 | L34 | Q10 |
| 7736 | Z1 | L34 | Q11 |
| 7737 | Z1 | L34 | Q12 |
| 7738 | Z1 | L34 | Q13 |
| 7739 | Z1 | L34 | Q14 |
| 7740 | 71 | L34 | Q15 |
| 7741 | Z1 | L34 | Q16 |
| 7742 | Z1 | L34 | Q17 |
| 7743 | Z1 | L34 | Q18 |
| 7744 | Z1 | L34 | Q19 |
| 7745 | Z1 | L34 | Q20 |
| 7746 | Z1 | L34 | Q21 |
| 7747 | Z1 | L34 | Q22 |
| 7748 | Z1 | L34 | Q23 |
| 7749 | Z1 | L34 | Q24 |
| 7750 | Z1 | L34 | Q25 |
| 7751 | Z1 | L34 | Q26 |
| 7752 | Z1 | L34 | Q27 |
| 7753 | Z1 | L34 | Q28 |
| 7754 | Z1 | L34 | Q29 |
| 7755 | Z1 | L34 | Q30 |
| 7756 | Z1 | L34 | Q31 |
| 7757 | Z1 | L34 | Q32 |
| 7758 | Z1 | L34 | Q33 |
| 7759 | Z1 | L34 | Q34 |
| 7760 | Z1 | L34 | Q35 |
| 7761 | Z1 | L34 | Q36 |
| 7762 | Z1 | L34 | Q37 |
| 7763 | Z1 | L34 | Q38 |
| 7764 | Z1 | L34 | Q39 |
| 7765 | Z1 | L34 | Q40 |
| 7766 | Z1 | L34 | Q41 |
| 7767 | Z1 | L34 | Q42 |
| 7768 | Z1 | L34 | Q43 |
| 7769 | Z1 | L34 | Q44 |
| 7770 | Z1 | L34 | Q45 |
| 7771 | Z1 | L34 | Q46 |
| 7772 | Z1 | L34 | Q47 |
| 7773 | Z1 | L34 | Q48 |
| 7774 | Z1 | L34 | Q49 |
| 7775 | Z1 | L34 | Q50 |
| 7776 | Z1 | L34 | Q51 |
| 7777 | Z1 | L34 | Q52 |
| 7778 | Z1 | L34 | Q53 |
| 7779 | Z1 | L34 | Q54 |
| 7780 | Z1 | L34 | Q55 |
| 7781 | Z1 | L34 | Q56 |
| 7782 | Z1 | L34 | Q57 |
| 7783 | Z1 | L34 | Q58 |
| 7784 | Z1 | L34 | Q59 |
| 7785 | Z1 | L34 | Q60 |
| 7786 | Z1 | L34 | Q61 |
| 7787 | Z1 | L34 | Q62 |
| 7788 | Z1 | L34 | Q63 |
| 7789 | Z1 | L34 | Q64 |
| 7790 | Z1 | L34 | Q65 |
| 7791 | Z1 | L34 | Q66 |
| 7792 | Z1 | L34 | Q67 |
| 7793 | Z1 | L34 | Q68 |
| 7794 | Z1 | L34 | Q69 |
| 7795 | Z1 | L34 | Q70 |
| 7796 | Z1 | L34 | Q71 |
| 7797 | Z1 | L34 | Q72 |
| 7798 | Z1 | L34 | Q73 |
| 7799 | Z1 | L34 | Q74 |
| 7800 | Z1 | L34 | Q75 |
| 7801 | Z1 | L34 | Q76 |
| 7802 | Z1 | L34 | Q77 |
| 7803 | Z1 | L34 | Q78 |
| 7804 | Z1 | L34 | Q79 |
| 7805 | Z1 | L34 | Q80 |
| 7806 | Z1 | L34 | Q81 |
| 7807 | Z1 | L34 | Q82 |
| 7808 | Z1 | L34 | Q83 |
| 7809 | Z1 | L34 | Q84 |
| 7810 | Z1 | L34 | Q85 |
| 7811 | Z1 | L34 | Q86 |

TABLE 1-45

| | | | |
|---|---|---|---|
| 7812 | Z1 | L34 | Q87 |
| 7813 | Z1 | L34 | Q88 |
| 7814 | Z1 | L34 | Q89 |
| 7815 | Z1 | L34 | Q90 |
| 7816 | Z1 | L34 | Q91 |
| 7817 | Z1 | L34 | Q92 |
| 7818 | Z1 | L34 | Q93 |
| 7819 | Z1 | L34 | Q94 |
| 7820 | Z1 | L34 | Q95 |
| 7821 | Z1 | L34 | Q96 |
| 7822 | Z1 | L34 | Q97 |
| 7823 | Z1 | L34 | Q98 |
| 7824 | Z1 | L34 | Q99 |
| 7825 | Z1 | L34 | Q100 |
| 7826 | Z1 | L34 | Q101 |
| 7827 | Z1 | L34 | Q102 |
| 7828 | Z1 | L34 | Q103 |
| 7829 | Z1 | L35 | Q1 |
| 7830 | Z1 | L35 | Q2 |
| 7831 | Z1 | L35 | Q3 |
| 7832 | Z1 | L35 | Q4 |
| 7833 | Z1 | L35 | Q5 |
| 7834 | Z1 | L35 | Q6 |
| 7835 | Z1 | L35 | Q7 |
| 7836 | Z1 | L35 | Q8 |
| 7837 | Z1 | L35 | Q9 |
| 7838 | Z1 | L35 | Q10 |
| 7839 | Z1 | L35 | Q11 |
| 7840 | Z1 | L35 | Q12 |
| 7841 | Z1 | L35 | Q13 |
| 7842 | Z1 | L35 | Q14 |
| 7843 | Z1 | L35 | Q15 |
| 7844 | Z1 | L35 | Q16 |
| 7845 | Z1 | L35 | Q17 |
| 7846 | Z1 | L35 | Q18 |
| 7847 | Z1 | L35 | Q19 |
| 7848 | Z1 | L35 | Q20 |
| 7849 | Z1 | L35 | Q21 |
| 7850 | Z1 | L35 | Q22 |
| 7851 | Z1 | L35 | Q23 |
| 7852 | Z1 | L35 | Q24 |
| 7853 | Z1 | L35 | Q25 |
| 7854 | Z1 | L35 | Q26 |
| 7855 | Z1 | L35 | Q27 |
| 7856 | Z1 | L35 | Q28 |
| 7857 | Z1 | L35 | Q29 |
| 7858 | Z1 | L35 | Q30 |
| 7859 | Z1 | L35 | Q31 |
| 7860 | Z1 | L35 | Q32 |
| 7861 | Z1 | L35 | Q33 |
| 7862 | Z1 | L35 | Q34 |
| 7863 | Z1 | L35 | Q35 |
| 7864 | Z1 | L35 | Q36 |
| 7865 | Z1 | L35 | Q37 |
| 7866 | Z1 | L35 | Q38 |
| 7867 | Z1 | L35 | Q39 |
| 7868 | Z1 | L35 | Q40 |
| 7869 | Z1 | L35 | Q41 |
| 7870 | Z1 | L35 | Q42 |
| 7871 | Z1 | L35 | Q43 |
| 7872 | Z1 | L35 | Q44 |
| 7873 | Z1 | L35 | Q45 |
| 7874 | Z1 | L35 | Q46 |
| 7875 | Z1 | L35 | Q47 |
| 7876 | Z1 | L35 | Q48 |
| 7877 | Z1 | L35 | Q49 |

TABLE 1-45-continued

| | | | |
|---|---|---|---|
| 7878 | Z1 | L35 | Q50 |
| 7879 | Z1 | L35 | Q51 |
| 7880 | Z1 | L35 | Q52 |
| 7881 | Z1 | L35 | Q53 |
| 7882 | Z1 | L35 | Q54 |
| 7883 | Z1 | L35 | Q55 |
| 7884 | Z1 | L35 | Q56 |
| 7885 | Z1 | L35 | Q57 |
| 7886 | Z1 | L35 | Q58 |
| 7887 | Z1 | L35 | Q59 |
| 7888 | Z1 | L35 | Q60 |
| 7889 | Z1 | L35 | Q61 |
| 7890 | Z1 | L35 | Q62 |
| 7891 | Z1 | L35 | Q63 |
| 7892 | Z1 | L35 | Q64 |
| 7893 | Z1 | L35 | Q65 |
| 7894 | Z1 | L35 | Q66 |
| 7895 | Z1 | L35 | Q67 |
| 7896 | Z1 | L35 | Q68 |
| 7897 | Z1 | L35 | Q69 |
| 7898 | Z1 | L35 | Q70 |
| 7899 | Z1 | L35 | Q71 |
| 7900 | Z1 | L35 | Q72 |
| 7901 | Z1 | L35 | Q73 |
| 7902 | Z1 | L35 | Q74 |
| 7903 | Z1 | L35 | Q75 |
| 7904 | Z1 | L35 | Q76 |
| 7905 | Z1 | L35 | Q77 |
| 7906 | Z1 | L35 | Q78 |
| 7907 | Z1 | L35 | Q79 |
| 7908 | Z1 | L35 | Q80 |
| 7909 | Z1 | L35 | Q81 |
| 7910 | Z1 | L35 | Q82 |
| 7911 | Z1 | L35 | Q83 |
| 7912 | Z1 | L35 | Q84 |
| 7913 | Z1 | L35 | Q85 |
| 7914 | Z1 | L35 | Q86 |
| 7915 | Z1 | L35 | Q87 |
| 7916 | Z1 | L35 | Q88 |
| 7917 | Z1 | L35 | Q89 |
| 7918 | Z1 | L35 | Q90 |
| 7919 | Z1 | L35 | Q91 |
| 7920 | Z1 | L35 | Q92 |
| 7921 | Z1 | L35 | Q93 |
| 7922 | Z1 | L35 | Q94 |
| 7923 | Z1 | L35 | Q95 |
| 7924 | Z1 | L35 | Q96 |
| 7925 | Z1 | L35 | Q97 |
| 7926 | Z1 | L35 | Q98 |
| 7927 | Z1 | L35 | Q99 |
| 7928 | Z1 | L35 | Q100 |
| 7929 | Z1 | L35 | Q101 |
| 7930 | Z1 | L35 | Q102 |
| 7931 | Z1 | L35 | Q103 |
| 7932 | Z1 | L36 | Q1 |
| 7933 | Z1 | L36 | Q2 |
| 7934 | Z1 | L36 | Q3 |
| 7935 | Z1 | L36 | Q4 |
| 7936 | Z1 | L36 | Q5 |
| 7937 | Z1 | L36 | Q6 |
| 7938 | Z1 | L36 | Q7 |
| 7939 | Z1 | L36 | Q8 |
| 7940 | Z1 | L36 | Q9 |
| 7941 | Z1 | L36 | Q10 |
| 7942 | Z1 | L36 | Q11 |
| 7943 | Z1 | L36 | Q12 |
| 7944 | Z1 | L36 | Q13 |
| 7945 | Z1 | L36 | Q14 |
| 7946 | Z1 | L36 | Q15 |
| 7947 | Z1 | L36 | Q16 |
| 7948 | Z1 | L36 | Q17 |
| 7949 | Z1 | L36 | Q18 |
| 7950 | Z1 | L36 | Q19 |
| 7951 | Z1 | L36 | Q20 |
| 7952 | Z1 | L36 | Q21 |
| 7953 | Z1 | L36 | Q22 |
| 7954 | Z1 | L36 | Q23 |
| 7955 | Z1 | L36 | Q24 |
| 7956 | Z1 | L36 | Q25 |
| 7957 | Z1 | L36 | Q26 |
| 7958 | Z1 | L36 | Q27 |
| 7959 | Z1 | L36 | Q28 |
| 7960 | Z1 | L36 | Q29 |
| 7961 | Z1 | L36 | Q30 |
| 7962 | Z1 | L36 | Q31 |
| 7963 | Z1 | L36 | Q32 |
| 7964 | Z1 | L36 | Q33 |
| 7965 | Z1 | L36 | Q34 |
| 7966 | Z1 | L36 | Q35 |
| 7967 | Z1 | L36 | Q36 |
| 7968 | Z1 | L36 | Q37 |
| 7969 | Z1 | L36 | Q38 |
| 7970 | Z1 | L36 | Q39 |
| 7971 | Z1 | L36 | Q40 |
| 7972 | Z1 | L36 | Q41 |
| 7973 | Z1 | L36 | Q42 |
| 7974 | Z1 | L36 | Q43 |
| 7975 | Z1 | L36 | Q44 |
| 7976 | Z1 | L36 | Q45 |
| 7977 | Z1 | L36 | Q46 |
| 7978 | Z1 | L36 | Q47 |
| 7979 | Z1 | L36 | Q48 |
| 7980 | Z1 | L36 | Q49 |
| 7981 | Z1 | L36 | Q50 |
| 7982 | Z1 | L36 | Q51 |
| 7983 | Z1 | L36 | Q52 |
| 7984 | Z1 | L36 | Q53 |
| 7985 | Z1 | L36 | Q54 |
| 7986 | Z1 | L36 | Q55 |
| 7987 | Z1 | L36 | Q56 |
| 7988 | Z1 | L36 | Q57 |
| 7989 | Z1 | L36 | Q58 |
| 7990 | Z1 | L36 | Q59 |
| 7991 | Z1 | L36 | Q60 |
| 7992 | Z1 | L36 | Q61 |
| 7993 | Z1 | L36 | Q62 |
| 7994 | Z1 | L36 | Q63 |
| 7995 | Z1 | L36 | Q64 |
| 7996 | Z1 | L36 | Q65 |
| 7997 | Z1 | L36 | Q66 |
| 7998 | Z1 | L36 | Q67 |
| 7999 | Z1 | L36 | Q68 |
| 8000 | Z1 | L36 | Q69 |
| 8001 | Z1 | L36 | Q70 |
| 8002 | Z1 | L36 | Q71 |
| 8003 | Z1 | L36 | Q72 |
| 8004 | Z1 | L36 | Q73 |
| 8005 | Z1 | L36 | Q74 |
| 8006 | Z1 | L36 | Q75 |
| 8007 | Z1 | L36 | Q76 |
| 8008 | Z1 | L36 | Q77 |
| 8009 | Z1 | L36 | Q78 |
| 8010 | Z1 | L36 | Q79 |
| 8011 | Z1 | L36 | Q80 |
| 8012 | Z1 | L36 | Q81 |

TABLE 1-46

| | | | |
|---|---|---|---|
| 8013 | Z1 | L36 | Q82 |
| 8014 | Z1 | L36 | Q83 |
| 8015 | Z1 | L36 | Q84 |
| 8016 | Z1 | L36 | Q85 |
| 8017 | Z1 | L36 | Q86 |
| 8018 | Z1 | L36 | Q87 |
| 8019 | Z1 | L36 | Q88 |
| 8020 | Z1 | L36 | Q89 |
| 8021 | Z1 | L36 | Q90 |
| 8022 | Z1 | L36 | Q91 |
| 8023 | Z1 | L36 | Q92 |
| 8024 | Z1 | L36 | Q93 |
| 8025 | Z1 | L36 | Q94 |
| 8026 | Z1 | L36 | Q95 |
| 8027 | Z1 | L36 | Q96 |
| 8028 | Z1 | L36 | Q97 |
| 8029 | Z1 | L36 | Q98 |
| 8030 | Z1 | L36 | Q99 |
| 8031 | Z1 | L36 | Q100 |

TABLE 1-46-continued

| | | | |
|---|---|---|---|
| 8032 | Z1 | L36 | Q101 |
| 8033 | Z1 | L36 | Q102 |
| 8034 | Z1 | L36 | Q103 |
| 8035 | Z2 | L15 | Q1 |
| 8036 | Z2 | L15 | Q2 |
| 8037 | Z2 | L15 | Q3 |
| 8038 | Z2 | L15 | Q4 |
| 8039 | Z2 | L15 | Q5 |
| 8040 | Z2 | L15 | Q6 |
| 8041 | Z2 | L15 | Q7 |
| 8042 | Z2 | L15 | Q8 |
| 8043 | Z2 | L15 | Q9 |
| 8044 | Z2 | L15 | Q10 |
| 8045 | Z2 | L15 | Q11 |
| 8046 | Z2 | L15 | Q12 |
| 8047 | Z2 | L15 | Q13 |
| 8048 | Z2 | L15 | Q14 |
| 8049 | Z2 | L15 | Q15 |
| 8050 | Z2 | L15 | Q16 |
| 8051 | Z2 | L15 | Q17 |
| 8052 | Z2 | L15 | Q18 |
| 8053 | Z2 | L15 | Q19 |
| 8054 | Z2 | L15 | Q20 |
| 8055 | Z2 | L15 | Q21 |
| 8056 | Z2 | L15 | Q22 |
| 8057 | Z2 | L15 | Q23 |
| 8058 | Z2 | L15 | Q24 |
| 8059 | Z2 | L15 | Q25 |
| 8060 | Z2 | L15 | Q26 |
| 8061 | Z2 | L15 | Q27 |
| 8062 | Z2 | L15 | Q28 |
| 8063 | Z2 | L15 | Q29 |
| 8064 | Z2 | L15 | Q30 |
| 8065 | Z2 | L15 | Q31 |
| 8066 | Z2 | L15 | Q32 |
| 8067 | Z2 | L15 | Q33 |
| 8068 | Z2 | L15 | Q34 |
| 8069 | Z2 | L15 | Q35 |
| 8070 | Z2 | L15 | Q36 |
| 8071 | Z2 | L15 | Q37 |
| 8072 | Z2 | L15 | Q38 |
| 8073 | Z2 | L15 | Q39 |
| 8074 | Z2 | L15 | Q40 |
| 8075 | Z2 | L15 | Q41 |
| 8076 | Z2 | L15 | Q42 |
| 8077 | Z2 | L15 | Q43 |
| 8078 | Z2 | L15 | Q44 |
| 8079 | Z2 | L15 | Q45 |
| 8080 | Z2 | L15 | Q46 |
| 8081 | Z2 | L15 | Q47 |
| 8082 | Z2 | L15 | Q48 |
| 8083 | Z2 | L15 | Q49 |
| 8084 | Z2 | L15 | Q50 |
| 8085 | Z2 | L15 | Q51 |
| 8086 | Z2 | L15 | Q52 |
| 8087 | Z2 | L15 | Q53 |
| 8088 | Z2 | L15 | Q54 |
| 8089 | Z2 | L15 | Q55 |
| 8090 | Z2 | L15 | Q56 |
| 8091 | Z2 | L15 | Q57 |
| 8092 | Z2 | L15 | Q58 |
| 8093 | Z2 | L15 | Q59 |
| 8094 | Z2 | L15 | Q60 |
| 8095 | Z2 | L15 | Q61 |
| 8096 | Z2 | L15 | Q62 |
| 8097 | Z2 | L15 | Q63 |
| 8098 | Z2 | L15 | Q64 |
| 8099 | Z2 | L15 | Q65 |
| 8100 | Z2 | L15 | Q66 |
| 8101 | Z2 | L15 | Q67 |
| 8102 | Z2 | L15 | Q68 |
| 8103 | Z2 | L15 | Q69 |
| 8104 | Z2 | L15 | Q70 |
| 8105 | Z2 | L15 | Q71 |
| 8106 | Z2 | L15 | Q72 |
| 8107 | Z2 | L15 | Q73 |
| 8108 | Z2 | L15 | Q74 |
| 8109 | Z2 | L15 | Q75 |
| 8110 | Z2 | L15 | Q76 |
| 8111 | Z2 | L15 | Q77 |
| 8112 | Z2 | L15 | Q78 |
| 8113 | Z2 | L15 | Q79 |
| 8114 | Z2 | L15 | Q80 |
| 8115 | Z2 | L15 | Q81 |
| 8116 | Z2 | L15 | Q82 |
| 8117 | Z2 | L15 | Q83 |
| 8118 | Z2 | L15 | Q84 |
| 8119 | Z2 | L15 | Q85 |
| 8120 | Z2 | L15 | Q86 |
| 8121 | Z2 | L15 | Q87 |
| 8122 | Z2 | L15 | Q88 |
| 8123 | Z2 | L15 | Q89 |
| 8124 | Z2 | L15 | Q90 |
| 8125 | Z2 | L15 | Q91 |
| 8126 | Z2 | L15 | Q92 |
| 8127 | Z2 | L15 | Q93 |
| 8128 | Z2 | L15 | Q94 |
| 8129 | Z2 | L15 | Q95 |
| 8130 | Z2 | L15 | Q96 |
| 8131 | Z2 | L15 | Q97 |
| 8132 | Z2 | L15 | Q98 |
| 8133 | Z2 | L15 | Q99 |
| 8134 | Z2 | L15 | Q100 |
| 8135 | Z2 | L15 | Q101 |
| 8136 | Z2 | L15 | Q102 |
| 8137 | Z2 | L15 | Q103 |
| 8138 | Z2 | L16 | Q1 |
| 8139 | Z2 | L16 | Q2 |
| 8140 | Z2 | L16 | Q3 |
| 8141 | Z2 | L16 | Q4 |
| 8142 | Z2 | L16 | Q5 |
| 8143 | Z2 | L16 | Q6 |
| 8144 | Z2 | L16 | Q7 |
| 8145 | Z2 | L16 | Q8 |
| 8146 | Z2 | L16 | Q9 |
| 8147 | Z2 | L16 | Q10 |
| 8148 | Z2 | L16 | Q11 |
| 8149 | Z2 | L16 | Q12 |
| 8150 | Z2 | L16 | Q13 |
| 8151 | Z2 | L16 | Q14 |
| 8152 | Z2 | L16 | Q15 |
| 8153 | Z2 | L16 | Q16 |
| 8154 | Z2 | L16 | Q17 |
| 8155 | Z2 | L16 | Q18 |
| 8156 | Z2 | L16 | Q19 |
| 8157 | Z2 | L16 | Q20 |
| 8158 | Z2 | L16 | Q21 |
| 8159 | Z2 | L16 | Q22 |
| 8160 | Z2 | L16 | Q23 |
| 8161 | Z2 | L16 | Q24 |
| 8162 | Z2 | L16 | Q25 |
| 8163 | Z2 | L16 | Q26 |
| 8164 | Z2 | L16 | Q27 |
| 8165 | Z2 | L16 | Q28 |
| 8166 | Z2 | L16 | Q29 |
| 8167 | Z2 | L16 | Q30 |
| 8168 | Z2 | L16 | Q31 |
| 8169 | Z2 | L16 | Q32 |
| 8170 | Z2 | L16 | Q33 |
| 8171 | Z2 | L16 | Q34 |
| 8172 | Z2 | L16 | Q35 |
| 8173 | Z2 | L16 | Q36 |
| 8174 | Z2 | L16 | Q37 |
| 8175 | Z2 | L16 | Q38 |
| 8176 | Z2 | L16 | Q39 |
| 8177 | Z2 | L16 | Q40 |
| 8178 | Z2 | L16 | Q41 |
| 8179 | Z2 | L16 | Q42 |
| 8180 | Z2 | L16 | Q43 |
| 8181 | Z2 | L16 | Q44 |
| 8182 | Z2 | L16 | Q45 |
| 8183 | Z2 | L16 | Q46 |
| 8184 | Z2 | L16 | Q47 |
| 8185 | Z2 | L16 | Q48 |
| 8186 | Z2 | L16 | Q49 |
| 8187 | Z2 | L16 | Q50 |
| 8188 | Z2 | L16 | Q51 |
| 8189 | Z2 | L16 | Q52 |
| 8190 | Z2 | L16 | Q53 |
| 8191 | Z2 | L16 | Q54 |

TABLE 1-46-continued

| | | | |
|---|---|---|---|
| 8192 | Z2 | L16 | Q55 |
| 8193 | Z2 | L16 | Q56 |
| 8194 | Z2 | L16 | Q57 |
| 8195 | Z2 | L16 | Q58 |
| 8196 | Z2 | L16 | Q59 |
| 8197 | Z2 | L16 | Q60 |
| 8198 | Z2 | L16 | Q61 |
| 8199 | Z2 | L16 | Q62 |
| 8200 | Z2 | L16 | Q63 |
| 8201 | Z2 | L16 | Q64 |
| 8202 | Z2 | L16 | Q65 |
| 8203 | Z2 | L16 | Q66 |
| 8204 | Z2 | L16 | Q67 |
| 8205 | Z2 | L16 | Q68 |
| 8206 | Z2 | L16 | Q69 |
| 8207 | Z2 | L16 | Q70 |
| 8208 | Z2 | L16 | Q71 |
| 8209 | Z2 | L16 | Q72 |
| 8210 | Z2 | L16 | Q73 |
| 8211 | Z2 | L16 | Q74 |
| 8212 | Z2 | L16 | Q75 |
| 8213 | Z2 | L16 | Q76 |

TABLE 1-47

| | | | |
|---|---|---|---|
| 8214 | Z2 | L16 | Q77 |
| 8215 | Z2 | L16 | Q78 |
| 8216 | Z2 | L16 | Q79 |
| 8217 | Z2 | L16 | Q80 |
| 8218 | Z2 | L16 | Q81 |
| 8219 | Z2 | L16 | Q82 |
| 8220 | Z2 | L16 | Q83 |
| 8221 | Z2 | L16 | Q84 |
| 8222 | Z2 | L16 | Q85 |
| 8223 | Z2 | L16 | Q86 |
| 8224 | Z2 | L16 | Q87 |
| 8225 | Z2 | L16 | Q88 |
| 8226 | Z2 | L16 | Q89 |
| 8227 | Z2 | L16 | Q90 |
| 8228 | Z2 | L16 | Q91 |
| 8229 | Z2 | L16 | Q92 |
| 8230 | Z2 | L16 | Q93 |
| 8231 | Z2 | L16 | Q94 |
| 8232 | Z2 | L16 | Q95 |
| 8233 | Z2 | L16 | Q96 |
| 8234 | Z2 | L16 | Q97 |
| 8235 | Z2 | L16 | Q98 |
| 8236 | Z2 | L16 | Q99 |
| 8237 | Z2 | L16 | Q100 |
| 8238 | Z2 | L16 | Q101 |
| 8239 | Z2 | L16 | Q102 |
| 8240 | Z2 | L16 | Q103 |
| 8241 | Z2 | L17 | Q1 |
| 8242 | Z2 | L17 | Q2 |
| 8243 | Z2 | L17 | Q3 |
| 8244 | Z2 | L17 | Q4 |
| 8245 | Z2 | L17 | Q5 |
| 8246 | Z2 | L17 | Q6 |
| 8247 | Z2 | L17 | Q7 |
| 8248 | Z2 | L17 | Q8 |
| 8249 | Z2 | L17 | Q9 |
| 8250 | Z2 | L17 | Q10 |
| 8251 | Z2 | L17 | Q11 |
| 8252 | Z2 | L17 | Q12 |
| 8253 | Z2 | L17 | Q13 |
| 8254 | Z2 | L17 | Q14 |
| 8255 | Z2 | L17 | Q15 |
| 8256 | Z2 | L17 | Q16 |
| 8257 | Z2 | L17 | Q17 |
| 8258 | Z2 | L17 | Q18 |
| 8259 | Z2 | L17 | Q19 |
| 8260 | Z2 | L17 | Q20 |
| 8261 | Z2 | L17 | Q21 |
| 8262 | Z2 | L17 | Q22 |
| 8263 | Z2 | L17 | Q23 |
| 8264 | Z2 | L17 | Q24 |
| 8265 | Z2 | L17 | Q25 |

TABLE 1-47-continued

| | | | |
|---|---|---|---|
| 8266 | Z2 | L17 | Q26 |
| 8267 | Z2 | L17 | Q27 |
| 8268 | Z2 | L17 | Q28 |
| 8269 | Z2 | L17 | Q29 |
| 8270 | Z2 | L17 | Q30 |
| 8271 | Z2 | L17 | Q31 |
| 8272 | Z2 | L17 | Q32 |
| 8273 | Z2 | L17 | Q33 |
| 8274 | Z2 | L17 | Q34 |
| 8275 | Z2 | L17 | Q35 |
| 8276 | Z2 | L17 | Q36 |
| 8277 | Z2 | L17 | Q37 |
| 8278 | Z2 | L17 | Q38 |
| 8279 | Z2 | L17 | Q39 |
| 8280 | Z2 | L17 | Q40 |
| 8281 | Z2 | L17 | Q41 |
| 8282 | Z2 | L17 | Q42 |
| 8283 | Z2 | L17 | Q43 |
| 8284 | Z2 | L17 | Q44 |
| 8285 | Z2 | L17 | Q45 |
| 8286 | Z2 | L17 | Q46 |
| 8287 | Z2 | L17 | Q47 |
| 8288 | Z2 | L17 | Q48 |
| 8289 | Z2 | L17 | Q49 |
| 8290 | Z2 | L17 | Q50 |
| 8291 | Z2 | L17 | Q51 |
| 8292 | Z2 | L17 | Q52 |
| 8293 | Z2 | L17 | Q53 |
| 8294 | Z2 | L17 | Q54 |
| 8295 | Z2 | L17 | Q55 |
| 8296 | Z2 | L17 | Q56 |
| 8297 | Z2 | L17 | Q57 |
| 8298 | Z2 | L17 | Q58 |
| 8299 | Z2 | L17 | Q59 |
| 8300 | Z2 | L17 | Q60 |
| 8301 | Z2 | L17 | Q61 |
| 8302 | Z2 | L17 | Q62 |
| 8303 | Z2 | L17 | Q63 |
| 8304 | Z2 | L17 | Q64 |
| 8305 | Z2 | L17 | Q65 |
| 8306 | Z2 | L17 | Q66 |
| 8307 | Z2 | L17 | Q67 |
| 8308 | Z2 | L17 | Q68 |
| 8309 | Z2 | L17 | Q69 |
| 8310 | Z2 | L17 | Q70 |
| 8311 | Z2 | L17 | Q71 |
| 8312 | Z2 | L17 | Q72 |
| 8313 | Z2 | L17 | Q73 |
| 8314 | Z2 | L17 | Q74 |
| 8315 | Z2 | L17 | Q75 |
| 8316 | Z2 | L17 | Q76 |
| 8317 | Z2 | L17 | Q77 |
| 8318 | Z2 | L17 | Q78 |
| 8319 | Z2 | L17 | Q79 |
| 8320 | Z2 | L17 | Q80 |
| 8321 | Z2 | L17 | Q81 |
| 8322 | Z2 | L17 | Q82 |
| 8323 | Z2 | L17 | Q83 |
| 8324 | Z2 | L17 | Q84 |
| 8325 | Z2 | L17 | Q85 |
| 8326 | Z2 | L17 | Q86 |
| 8327 | Z2 | L17 | Q87 |
| 8328 | Z2 | L17 | Q88 |
| 8329 | Z2 | L17 | Q89 |
| 8330 | Z2 | L17 | Q90 |
| 8331 | Z2 | L17 | Q91 |
| 8332 | Z2 | L17 | Q92 |
| 8333 | Z2 | L17 | Q93 |
| 8334 | Z2 | L17 | Q94 |
| 8335 | Z2 | L17 | Q95 |
| 8336 | Z2 | L17 | Q96 |
| 8337 | Z2 | L17 | Q97 |
| 8338 | Z2 | L17 | Q98 |
| 8339 | Z2 | L17 | Q99 |
| 8340 | Z2 | L17 | Q100 |
| 8341 | Z2 | L17 | Q101 |
| 8342 | Z2 | L17 | Q102 |
| 8343 | Z2 | L17 | Q103 |
| 8344 | Z2 | L18 | Q1 |
| 8345 | Z2 | L18 | Q2 |

TABLE 1-47-continued

| | | | |
|---|---|---|---|
| 8346 | Z2 | L18 | Q3 |
| 8347 | Z2 | L18 | Q4 |
| 8348 | Z2 | L18 | Q5 |
| 8349 | Z2 | L18 | Q6 |
| 8350 | Z2 | L18 | Q7 |
| 8351 | Z2 | L18 | Q8 |
| 8352 | Z2 | L18 | Q9 |
| 8353 | Z2 | L18 | Q10 |
| 8354 | Z2 | L18 | Q11 |
| 8355 | Z2 | L18 | Q12 |
| 8356 | Z2 | L18 | Q13 |
| 8357 | Z2 | L18 | Q14 |
| 8358 | Z2 | L18 | Q15 |
| 8359 | Z2 | L18 | Q16 |
| 8360 | Z2 | L18 | Q17 |
| 8361 | Z2 | L18 | Q18 |
| 8362 | Z2 | L18 | Q19 |
| 8363 | Z2 | L18 | Q20 |
| 8364 | Z2 | L18 | Q21 |
| 8365 | Z2 | L18 | Q22 |
| 8366 | Z2 | L18 | Q23 |
| 8367 | Z2 | L18 | Q24 |
| 8368 | Z2 | L18 | Q25 |
| 8369 | Z2 | L18 | Q26 |
| 8370 | Z2 | L18 | Q27 |
| 8371 | Z2 | L18 | Q28 |
| 8372 | Z2 | L18 | Q29 |
| 8373 | Z2 | L18 | Q30 |
| 8374 | Z2 | L18 | Q31 |
| 8375 | Z2 | L18 | Q32 |
| 8376 | Z2 | L18 | Q33 |
| 8377 | Z2 | L18 | Q34 |
| 8378 | Z2 | L18 | Q35 |
| 8379 | Z2 | L18 | Q36 |
| 8380 | Z2 | L18 | Q37 |
| 8381 | Z2 | L18 | Q38 |
| 8382 | Z2 | L18 | Q39 |
| 8383 | Z2 | L18 | Q40 |
| 8384 | Z2 | L18 | Q41 |
| 8385 | Z2 | L18 | Q42 |
| 8386 | Z2 | L18 | Q43 |
| 8387 | Z2 | L18 | Q44 |
| 8388 | Z2 | L18 | Q45 |
| 8389 | Z2 | L18 | Q46 |
| 8390 | Z2 | L18 | Q47 |
| 8391 | Z2 | L18 | Q48 |
| 8392 | Z2 | L18 | Q49 |
| 8393 | Z2 | L18 | Q50 |
| 8394 | Z2 | L18 | Q51 |
| 8395 | Z2 | L18 | Q52 |
| 8396 | Z2 | L18 | Q53 |
| 8397 | Z2 | L18 | Q54 |
| 8398 | Z2 | L18 | Q55 |
| 8399 | Z2 | L18 | Q56 |
| 8400 | Z2 | L18 | Q57 |
| 8401 | Z2 | L18 | Q58 |
| 8402 | Z2 | L18 | Q59 |
| 8403 | Z2 | L18 | Q60 |
| 8404 | Z2 | L18 | Q61 |
| 8405 | Z2 | L18 | Q62 |
| 8406 | Z2 | L18 | Q63 |
| 8407 | Z2 | L18 | Q64 |
| 8408 | Z2 | L18 | Q65 |
| 8409 | Z2 | L18 | Q66 |
| 8410 | Z2 | L18 | Q67 |
| 8411 | Z2 | L18 | Q68 |
| 8412 | Z2 | L18 | Q69 |
| 8413 | Z2 | L18 | Q70 |
| 8414 | Z2 | L18 | Q71 |

TABLE 1-48

| | | | |
|---|---|---|---|
| 8415 | Z2 | L18 | Q72 |
| 8416 | Z2 | L18 | Q73 |
| 8417 | Z2 | L18 | Q74 |
| 8418 | Z2 | L18 | Q75 |
| 8419 | Z2 | L18 | Q76 |

TABLE 1-48-continued

| | | | |
|---|---|---|---|
| 8420 | Z2 | L18 | Q77 |
| 8421 | Z2 | L18 | Q78 |
| 8422 | Z2 | L18 | Q79 |
| 8423 | Z2 | L18 | Q80 |
| 8424 | Z2 | L18 | Q81 |
| 8425 | Z2 | L18 | Q82 |
| 8426 | Z2 | L18 | Q83 |
| 8427 | Z2 | L18 | Q84 |
| 8428 | Z2 | L18 | Q85 |
| 8429 | Z2 | L18 | Q86 |
| 8430 | Z2 | L18 | Q87 |
| 8431 | Z2 | L18 | Q88 |
| 8432 | Z2 | L18 | Q89 |
| 8433 | Z2 | L18 | Q90 |
| 8434 | Z2 | L18 | Q91 |
| 8435 | Z2 | L18 | Q92 |
| 8436 | Z2 | L18 | Q93 |
| 8437 | Z2 | L18 | Q94 |
| 8438 | Z2 | L18 | Q95 |
| 8439 | Z2 | L18 | Q96 |
| 8440 | Z2 | L18 | Q97 |
| 8441 | Z2 | L18 | Q98 |
| 8442 | Z2 | L18 | Q99 |
| 8443 | Z2 | L18 | Q100 |
| 8444 | Z2 | L18 | Q101 |
| 8445 | Z2 | L18 | Q102 |
| 8446 | Z2 | L18 | Q103 |
| 8447 | Z2 | L19 | Q1 |
| 8448 | Z2 | L19 | Q2 |
| 8449 | Z2 | L19 | Q3 |
| 8450 | Z2 | L19 | Q4 |
| 8451 | Z2 | L19 | Q5 |
| 8452 | Z2 | L19 | Q6 |
| 8453 | Z2 | L19 | Q7 |
| 8454 | Z2 | L19 | Q8 |
| 8455 | Z2 | L19 | Q9 |
| 8456 | Z2 | L19 | Q10 |
| 8457 | Z2 | L19 | Q11 |
| 8458 | Z2 | L19 | Q12 |
| 8459 | Z2 | L19 | Q13 |
| 8460 | Z2 | L19 | Q14 |
| 8461 | Z2 | L19 | Q15 |
| 8462 | Z2 | L19 | Q16 |
| 8463 | Z2 | L19 | Q17 |
| 8464 | Z2 | L19 | Q18 |
| 8465 | Z2 | L19 | Q19 |
| 8466 | Z2 | L19 | Q20 |
| 8467 | Z2 | L19 | Q21 |
| 8468 | Z2 | L19 | Q22 |
| 8469 | Z2 | L19 | Q23 |
| 8470 | Z2 | L19 | Q24 |
| 8471 | Z2 | L19 | Q25 |
| 8472 | Z2 | L19 | Q26 |
| 8473 | Z2 | L19 | Q27 |
| 8474 | Z2 | L19 | Q28 |
| 8475 | Z2 | L19 | Q29 |
| 8476 | Z2 | L19 | Q30 |
| 8477 | Z2 | L19 | Q31 |
| 8478 | Z2 | L19 | Q32 |
| 8479 | Z2 | L19 | Q33 |
| 8480 | Z2 | L19 | Q34 |
| 8481 | Z2 | L19 | Q35 |
| 8482 | Z2 | L19 | Q36 |
| 8483 | Z2 | L19 | Q37 |
| 8484 | Z2 | L19 | Q38 |
| 8485 | Z2 | L19 | Q39 |
| 8486 | Z2 | L19 | Q40 |
| 8487 | Z2 | L19 | Q41 |
| 8488 | Z2 | L19 | Q42 |
| 8489 | Z2 | L19 | Q43 |
| 8490 | Z2 | L19 | Q44 |
| 8491 | Z2 | L19 | Q45 |
| 8492 | Z2 | L19 | Q46 |
| 8493 | Z2 | L19 | Q47 |
| 8494 | Z2 | L19 | Q48 |
| 8495 | Z2 | L19 | Q49 |
| 8496 | Z2 | L19 | Q50 |
| 8497 | Z2 | L19 | Q51 |
| 8498 | Z2 | L19 | Q52 |
| 8499 | Z2 | L19 | Q53 |

TABLE 1-48-continued

| | | | |
|---|---|---|---|
| 8500 | Z2 | L19 | Q54 |
| 8501 | Z2 | L19 | Q55 |
| 8502 | Z2 | L19 | Q56 |
| 8503 | Z2 | L19 | Q57 |
| 8504 | Z2 | L19 | Q58 |
| 8505 | Z2 | L19 | Q59 |
| 8506 | Z2 | L19 | Q60 |
| 8507 | Z2 | L19 | Q61 |
| 8508 | Z2 | L19 | Q62 |
| 8509 | Z2 | L19 | Q63 |
| 8510 | Z2 | L19 | Q64 |
| 8511 | Z2 | L19 | Q65 |
| 8512 | Z2 | L19 | Q66 |
| 8513 | Z2 | L19 | Q67 |
| 8514 | Z2 | L19 | Q68 |
| 8515 | Z2 | L19 | Q69 |
| 8516 | Z2 | L19 | Q70 |
| 8517 | Z2 | L19 | Q71 |
| 8518 | Z2 | L19 | Q72 |
| 8519 | Z2 | L19 | Q73 |
| 8520 | Z2 | L19 | Q74 |
| 8521 | Z2 | L19 | Q75 |
| 8522 | Z2 | L19 | Q76 |
| 8523 | Z2 | L19 | Q77 |
| 8524 | Z2 | L19 | Q78 |
| 8525 | Z2 | L19 | Q79 |
| 8526 | Z2 | L19 | Q80 |
| 8527 | Z2 | L19 | Q81 |
| 8528 | Z2 | L19 | Q82 |
| 8529 | Z2 | L19 | Q83 |
| 8530 | Z2 | L19 | Q84 |
| 8531 | Z2 | L19 | Q85 |
| 8532 | Z2 | L19 | Q86 |
| 8533 | Z2 | L19 | Q87 |
| 8534 | Z2 | L19 | Q88 |
| 8535 | Z2 | L19 | Q89 |
| 8536 | Z2 | L19 | Q90 |
| 8537 | Z2 | L19 | Q91 |
| 8538 | Z2 | L19 | Q92 |
| 8539 | Z2 | L19 | Q93 |
| 8540 | Z2 | L19 | Q94 |
| 8541 | Z2 | L19 | Q95 |
| 8542 | Z2 | L19 | Q96 |
| 8543 | Z2 | L19 | Q97 |
| 8544 | Z2 | L19 | Q98 |
| 8545 | Z2 | L19 | Q99 |
| 8546 | Z2 | L19 | Q100 |
| 8547 | Z2 | L19 | Q101 |
| 8548 | Z2 | L19 | Q102 |
| 8549 | Z2 | L19 | Q103 |
| 8550 | Z2 | L20 | Q1 |
| 8551 | Z2 | L20 | Q2 |
| 8552 | Z2 | L20 | Q3 |
| 8553 | Z2 | L20 | Q4 |
| 8554 | Z2 | L20 | Q5 |
| 8555 | Z2 | L20 | Q6 |
| 8556 | Z2 | L20 | Q7 |
| 8557 | Z2 | L20 | Q8 |
| 8558 | Z2 | L20 | Q9 |
| 8559 | Z2 | L20 | Q10 |
| 8560 | Z2 | L20 | Q11 |
| 8561 | Z2 | L20 | Q12 |
| 8562 | Z2 | L20 | Q13 |
| 8563 | Z2 | L20 | Q14 |
| 8564 | Z2 | L20 | Q15 |
| 8565 | Z2 | L20 | Q16 |
| 8566 | Z2 | L20 | Q17 |
| 8567 | Z2 | L20 | Q18 |
| 8568 | Z2 | L20 | Q19 |
| 8569 | Z2 | L20 | Q20 |
| 8570 | Z2 | L20 | Q21 |
| 8571 | Z2 | L20 | Q22 |
| 8572 | Z2 | L20 | Q23 |
| 8573 | Z2 | L20 | Q24 |
| 8574 | Z2 | L20 | Q25 |
| 8575 | Z2 | L20 | Q26 |
| 8576 | Z2 | L20 | Q27 |
| 8577 | Z2 | L20 | Q28 |
| 8578 | Z2 | L20 | Q29 |
| 8579 | Z2 | L20 | Q30 |
| 8580 | Z2 | L20 | Q31 |
| 8581 | Z2 | L20 | Q32 |
| 8582 | Z2 | L20 | Q33 |
| 8583 | Z2 | L20 | Q34 |
| 8584 | Z2 | L20 | Q35 |
| 8585 | Z2 | L20 | Q36 |
| 8586 | Z2 | L20 | Q37 |
| 8587 | Z2 | L20 | Q38 |
| 8588 | Z2 | L20 | Q39 |
| 8589 | Z2 | L20 | Q40 |
| 8590 | Z2 | L20 | Q41 |
| 8591 | Z2 | L20 | Q42 |
| 8592 | Z2 | L20 | Q43 |
| 8593 | Z2 | L20 | Q44 |
| 8594 | Z2 | L20 | Q45 |
| 8595 | Z2 | L20 | Q46 |
| 8596 | Z2 | L20 | Q47 |
| 8597 | Z2 | L20 | Q48 |
| 8598 | Z2 | L20 | Q49 |
| 8599 | Z2 | L20 | Q50 |
| 8600 | Z2 | L20 | Q51 |
| 8601 | Z2 | L20 | Q52 |
| 8602 | Z2 | L20 | Q53 |
| 8603 | Z2 | L20 | Q54 |
| 8604 | Z2 | L20 | Q55 |
| 8605 | Z2 | L20 | Q56 |
| 8606 | Z2 | L20 | Q57 |
| 8607 | Z2 | L20 | Q58 |
| 8608 | Z2 | L20 | Q59 |
| 8609 | Z2 | L20 | Q60 |
| 8610 | Z2 | L20 | Q61 |
| 8611 | Z2 | L20 | Q62 |
| 8612 | Z2 | L20 | Q63 |
| 8613 | Z2 | L20 | Q64 |
| 8614 | Z2 | L20 | Q65 |
| 8615 | Z2 | L20 | Q66 |

TABLE 1-49

| | | | |
|---|---|---|---|
| 8616 | Z2 | L20 | Q67 |
| 8617 | Z2 | L20 | Q68 |
| 8618 | Z2 | L20 | Q69 |
| 8619 | Z2 | L20 | Q70 |
| 8620 | Z2 | L20 | Q71 |
| 8621 | Z2 | L20 | Q72 |
| 8622 | Z2 | L20 | Q73 |
| 8623 | Z2 | L20 | Q74 |
| 8624 | Z2 | L20 | Q75 |
| 8625 | Z2 | L20 | Q76 |
| 8626 | Z2 | L20 | Q77 |
| 8627 | Z2 | L20 | Q78 |
| 8628 | Z2 | L20 | Q79 |
| 8629 | Z2 | L20 | Q80 |
| 8630 | Z2 | L20 | Q81 |
| 8631 | Z2 | L20 | Q82 |
| 8632 | Z2 | L20 | Q83 |
| 8633 | Z2 | L20 | Q84 |
| 8634 | Z2 | L20 | Q85 |
| 8635 | Z2 | L20 | Q86 |
| 8636 | Z2 | L20 | Q87 |
| 8637 | Z2 | L20 | Q88 |
| 8638 | Z2 | L20 | Q89 |
| 8639 | Z2 | L20 | Q90 |
| 8640 | Z2 | L20 | Q91 |
| 8641 | Z2 | L20 | Q92 |
| 8642 | Z2 | L20 | Q93 |
| 8643 | Z2 | L20 | Q94 |
| 8644 | Z2 | L20 | Q95 |
| 8645 | Z2 | L20 | Q96 |
| 8646 | Z2 | L20 | Q97 |
| 8647 | Z2 | L20 | Q98 |
| 8648 | Z2 | L20 | Q99 |
| 8649 | Z2 | L20 | Q100 |
| 8650 | Z2 | L20 | Q101 |
| 8651 | Z2 | L20 | Q102 |
| 8652 | Z2 | L20 | Q103 |
| 8653 | Z2 | L21 | Q1 |

TABLE 1-49-continued

| | | | |
|---|---|---|---|
| 8654 | Z2 | L21 | Q2 |
| 8655 | Z2 | L21 | Q3 |
| 8656 | Z2 | L21 | Q4 |
| 8657 | Z2 | L21 | Q5 |
| 8658 | Z2 | L21 | Q6 |
| 8659 | Z2 | L21 | Q7 |
| 8660 | Z2 | L21 | Q8 |
| 8661 | Z2 | L21 | Q9 |
| 8662 | Z2 | L21 | Q10 |
| 8663 | Z2 | L21 | Q11 |
| 8664 | Z2 | L21 | Q12 |
| 8665 | Z2 | L21 | Q13 |
| 8666 | Z2 | L21 | Q14 |
| 8667 | Z2 | L21 | Q15 |
| 8668 | Z2 | L21 | Q16 |
| 8669 | Z2 | L21 | Q17 |
| 8670 | Z2 | L21 | Q18 |
| 8671 | Z2 | L21 | Q19 |
| 8672 | Z2 | L21 | Q20 |
| 8673 | Z2 | L21 | Q21 |
| 8674 | Z2 | L21 | Q22 |
| 8675 | Z2 | L21 | Q23 |
| 8676 | Z2 | L21 | Q24 |
| 8677 | Z2 | L21 | Q25 |
| 8678 | Z2 | L21 | Q26 |
| 8679 | Z2 | L21 | Q27 |
| 8680 | Z2 | L21 | Q28 |
| 8681 | Z2 | L21 | Q29 |
| 8682 | Z2 | L21 | Q30 |
| 8683 | Z2 | L21 | Q31 |
| 8684 | Z2 | L21 | Q32 |
| 8685 | Z2 | L21 | Q33 |
| 8686 | Z2 | L21 | Q34 |
| 8687 | Z2 | L21 | Q35 |
| 8688 | Z2 | L21 | Q36 |
| 8689 | Z2 | L21 | Q37 |
| 8690 | Z2 | L21 | Q38 |
| 8691 | Z2 | L21 | Q39 |
| 8692 | Z2 | L21 | Q40 |
| 8693 | Z2 | L21 | Q41 |
| 8694 | Z2 | L21 | Q42 |
| 8695 | Z2 | L21 | Q43 |
| 8696 | Z2 | L21 | Q44 |
| 8697 | Z2 | L21 | Q45 |
| 8698 | Z2 | L21 | Q46 |
| 8699 | Z2 | L21 | Q47 |
| 8700 | Z2 | L21 | Q48 |
| 8701 | Z2 | L21 | Q49 |
| 8702 | Z2 | L21 | Q50 |
| 8703 | Z2 | L21 | Q51 |
| 8704 | Z2 | L21 | Q52 |
| 8705 | Z2 | L21 | Q53 |
| 8706 | Z2 | L21 | Q54 |
| 8707 | Z2 | L21 | Q55 |
| 8708 | Z2 | L21 | Q56 |
| 8709 | Z2 | L21 | Q57 |
| 8710 | Z2 | L21 | Q58 |
| 8711 | Z2 | L21 | Q59 |
| 8712 | Z2 | L21 | Q60 |
| 8713 | Z2 | L21 | Q61 |
| 8714 | Z2 | L21 | Q62 |
| 8715 | Z2 | L21 | Q63 |
| 8716 | Z2 | L21 | Q64 |
| 8717 | Z2 | L21 | Q65 |
| 8718 | Z2 | L21 | Q66 |
| 8719 | Z2 | L21 | Q67 |
| 8720 | Z2 | L21 | Q68 |
| 8721 | Z2 | L21 | Q69 |
| 8722 | Z2 | L21 | Q70 |
| 8723 | Z2 | L21 | Q71 |
| 8724 | Z2 | L21 | Q72 |
| 8725 | Z2 | L21 | Q73 |
| 8726 | Z2 | L21 | Q74 |
| 8727 | Z2 | L21 | Q75 |
| 8728 | Z2 | L21 | Q76 |
| 8729 | Z2 | L21 | Q77 |
| 8730 | Z2 | L21 | Q78 |
| 8731 | Z2 | L21 | Q79 |
| 8732 | Z2 | L21 | Q80 |
| 8733 | Z2 | L21 | Q81 |
| 8734 | Z2 | L21 | Q82 |
| 8735 | Z2 | L21 | Q83 |
| 8736 | Z2 | L21 | Q84 |
| 8737 | Z2 | L21 | Q85 |
| 8738 | Z2 | L21 | Q86 |
| 8739 | Z2 | L21 | Q87 |
| 8740 | Z2 | L21 | Q88 |
| 8741 | Z2 | L21 | Q89 |
| 8742 | Z2 | L21 | Q90 |
| 8743 | Z2 | L21 | Q91 |
| 8744 | Z2 | L21 | Q92 |
| 8745 | Z2 | L21 | Q93 |
| 8746 | Z2 | L21 | Q94 |
| 8747 | Z2 | L21 | Q95 |
| 8748 | Z2 | L21 | Q96 |
| 8749 | Z2 | L21 | Q97 |
| 8750 | Z2 | L21 | Q98 |
| 8751 | Z2 | L21 | Q99 |
| 8752 | Z2 | L21 | Q100 |
| 8753 | Z2 | L21 | Q101 |
| 8754 | Z2 | L21 | Q102 |
| 8755 | Z2 | L21 | Q103 |
| 8756 | Z2 | L22 | Q1 |
| 8757 | Z2 | L22 | Q2 |
| 8758 | Z2 | L22 | Q3 |
| 8759 | Z2 | L22 | Q4 |
| 8760 | Z2 | L22 | Q5 |
| 8761 | Z2 | L22 | Q6 |
| 8762 | Z2 | L22 | Q7 |
| 8763 | Z2 | L22 | Q8 |
| 8764 | Z2 | L22 | Q9 |
| 8765 | Z2 | L22 | Q10 |
| 8766 | Z2 | L22 | Q11 |
| 8767 | Z2 | L22 | Q12 |
| 8768 | Z2 | L22 | Q13 |
| 8769 | Z2 | L22 | Q14 |
| 8770 | Z2 | L22 | Q15 |
| 8771 | Z2 | L22 | Q16 |
| 8772 | Z2 | L22 | Q17 |
| 8773 | Z2 | L22 | Q18 |
| 8774 | Z2 | L22 | Q19 |
| 8775 | Z2 | L22 | Q20 |
| 8776 | Z2 | L22 | Q21 |
| 8777 | Z2 | L22 | Q22 |
| 8778 | Z2 | L22 | Q23 |
| 8779 | Z2 | L22 | Q24 |
| 8780 | Z2 | L22 | Q25 |
| 8781 | Z2 | L22 | Q26 |
| 8782 | Z2 | L22 | Q27 |
| 8783 | Z2 | L22 | Q28 |
| 8784 | Z2 | L22 | Q29 |
| 8785 | Z2 | L22 | Q30 |
| 8786 | Z2 | L22 | Q31 |
| 8787 | Z2 | L22 | Q32 |
| 8788 | Z2 | L22 | Q33 |
| 8789 | Z2 | L22 | Q34 |
| 8790 | Z2 | L22 | Q35 |
| 8791 | Z2 | L22 | Q36 |
| 8792 | Z2 | L22 | Q37 |
| 8793 | Z2 | L22 | Q38 |
| 8794 | Z2 | L22 | Q39 |
| 8795 | Z2 | L22 | Q40 |
| 8796 | Z2 | L22 | Q41 |
| 8797 | Z2 | L22 | Q42 |
| 8798 | Z2 | L22 | Q43 |
| 8799 | Z2 | L22 | Q44 |
| 8800 | Z2 | L22 | Q45 |
| 8801 | Z2 | L22 | Q46 |
| 8802 | Z2 | L22 | Q47 |
| 8803 | Z2 | L22 | Q48 |
| 8804 | Z2 | L22 | Q49 |
| 8805 | Z2 | L22 | Q50 |
| 8806 | Z2 | L22 | Q51 |
| 8807 | Z2 | L22 | Q52 |
| 8808 | Z2 | L22 | Q53 |
| 8809 | Z2 | L22 | Q54 |
| 8810 | Z2 | L22 | Q55 |
| 8811 | Z2 | L22 | Q56 |
| 8812 | Z2 | L22 | Q57 |
| 8813 | Z2 | L22 | Q58 |

TABLE 1-49-continued

| | | | |
|---|---|---|---|
| 8814 | Z2 | L22 | Q59 |
| 8815 | Z2 | L22 | Q60 |
| 8816 | Z2 | L22 | Q61 |

TABLE 1-50

| | | | |
|---|---|---|---|
| 8817 | Z2 | L22 | Q62 |
| 8818 | Z2 | L22 | Q63 |
| 8819 | Z2 | L22 | Q64 |
| 8820 | Z2 | L22 | Q65 |
| 8821 | Z2 | L22 | Q66 |
| 8822 | Z2 | L22 | Q67 |
| 8823 | Z2 | L22 | Q68 |
| 8824 | Z2 | L22 | Q69 |
| 8825 | Z2 | L22 | Q70 |
| 8826 | Z2 | L22 | Q71 |
| 8827 | Z2 | L22 | Q72 |
| 8828 | Z2 | L22 | Q73 |
| 8829 | Z2 | L22 | Q74 |
| 8830 | Z2 | L22 | Q75 |
| 8831 | Z2 | L22 | Q76 |
| 8832 | Z2 | L22 | Q77 |
| 8833 | Z2 | L22 | Q78 |
| 8834 | Z2 | L22 | Q79 |
| 8835 | Z2 | L22 | Q80 |
| 8836 | Z2 | L22 | Q81 |
| 8837 | Z2 | L22 | Q82 |
| 8838 | Z2 | L22 | Q83 |
| 8839 | Z2 | L22 | Q84 |
| 8840 | Z2 | L22 | Q85 |
| 8841 | Z2 | L22 | Q86 |
| 8842 | Z2 | L22 | Q87 |
| 8843 | Z2 | L22 | Q88 |
| 8844 | Z2 | L22 | Q89 |
| 8845 | Z2 | L22 | Q90 |
| 8846 | Z2 | L22 | Q91 |
| 8847 | Z2 | L22 | Q92 |
| 8848 | Z2 | L22 | Q93 |
| 8849 | Z2 | L22 | Q94 |
| 8850 | Z2 | L22 | Q95 |
| 8851 | Z2 | L22 | Q96 |
| 8852 | Z2 | L22 | Q97 |
| 8853 | Z2 | L22 | Q98 |
| 8854 | Z2 | L22 | Q99 |
| 8855 | Z2 | L22 | Q100 |
| 8856 | Z2 | L22 | Q101 |
| 8857 | Z2 | L22 | Q102 |
| 8858 | Z2 | L22 | Q103 |
| 8859 | Z2 | L23 | Q1 |
| 8860 | Z2 | L23 | Q2 |
| 8861 | Z2 | L23 | Q3 |
| 8862 | Z2 | L23 | Q4 |
| 8863 | Z2 | L23 | Q5 |
| 8864 | Z2 | L23 | Q6 |
| 8865 | Z2 | L23 | Q7 |
| 8866 | Z2 | L23 | Q8 |
| 8867 | Z2 | L23 | Q9 |
| 8868 | Z2 | L23 | Q10 |
| 8869 | Z2 | L23 | Q11 |
| 8870 | Z2 | L23 | Q12 |
| 8871 | Z2 | L23 | Q13 |
| 8872 | Z2 | L23 | Q14 |
| 8873 | Z2 | L23 | Q15 |
| 8874 | Z2 | L23 | Q16 |
| 8875 | Z2 | L23 | Q17 |
| 8876 | Z2 | L23 | Q18 |
| 8877 | Z2 | L23 | Q19 |
| 8878 | Z2 | L23 | Q20 |
| 8879 | Z2 | L23 | Q21 |
| 8880 | Z2 | L23 | Q22 |
| 8881 | Z2 | L23 | Q23 |
| 8882 | Z2 | L23 | Q24 |
| 8883 | Z2 | L23 | Q25 |
| 8884 | Z2 | L23 | Q26 |
| 8885 | Z2 | L23 | Q27 |
| 8886 | Z2 | L23 | Q28 |
| 8887 | Z2 | L23 | Q29 |

TABLE 1-50-continued

| | | | |
|---|---|---|---|
| 8888 | Z2 | L23 | Q30 |
| 8889 | Z2 | L23 | Q31 |
| 8890 | Z2 | L23 | Q32 |
| 8891 | Z2 | L23 | Q33 |
| 8892 | Z2 | L23 | Q34 |
| 8893 | Z2 | L23 | Q35 |
| 8894 | Z2 | L23 | Q36 |
| 8895 | Z2 | L23 | Q37 |
| 8896 | Z2 | L23 | Q38 |
| 8897 | Z2 | L23 | Q39 |
| 8898 | Z2 | L23 | Q40 |
| 8899 | Z2 | L23 | Q41 |
| 8900 | Z2 | L23 | Q42 |
| 8901 | Z2 | L23 | Q43 |
| 8902 | Z2 | L23 | Q44 |
| 8903 | Z2 | L23 | Q45 |
| 8904 | Z2 | L23 | Q46 |
| 8905 | Z2 | L23 | Q47 |
| 8906 | Z2 | L23 | Q48 |
| 8907 | Z2 | L23 | Q49 |
| 8908 | Z2 | L23 | Q50 |
| 8909 | Z2 | L23 | Q51 |
| 8910 | Z2 | L23 | Q52 |
| 8911 | Z2 | L23 | Q53 |
| 8912 | Z2 | L23 | Q54 |
| 8913 | Z2 | L23 | Q55 |
| 8914 | Z2 | L23 | Q56 |
| 8915 | Z2 | L23 | Q57 |
| 8916 | Z2 | L23 | Q58 |
| 8917 | Z2 | L23 | Q59 |
| 8918 | Z2 | L23 | Q60 |
| 8919 | Z2 | L23 | Q61 |
| 8920 | Z2 | L23 | Q62 |
| 8921 | Z2 | L23 | Q63 |
| 8922 | Z2 | L23 | Q64 |
| 8923 | Z2 | L23 | Q65 |
| 8924 | Z2 | L23 | Q66 |
| 8925 | Z2 | L23 | Q67 |
| 8926 | Z2 | L23 | Q68 |
| 8927 | Z2 | L23 | Q69 |
| 8928 | Z2 | L23 | Q70 |
| 8929 | Z2 | L23 | Q71 |
| 8930 | Z2 | L23 | Q72 |
| 8931 | Z2 | L23 | Q73 |
| 8932 | Z2 | L23 | Q74 |
| 8933 | Z2 | L23 | Q75 |
| 8934 | Z2 | L23 | Q76 |
| 8935 | Z2 | L23 | Q77 |
| 8936 | Z2 | L23 | Q78 |
| 8937 | Z2 | L23 | Q79 |
| 8938 | Z2 | L23 | Q80 |
| 8939 | Z2 | L23 | Q81 |
| 8940 | Z2 | L23 | Q82 |
| 8941 | Z2 | L23 | Q83 |
| 8942 | Z2 | L23 | Q84 |
| 8943 | Z2 | L23 | Q85 |
| 8944 | Z2 | L23 | Q86 |
| 8945 | Z2 | L23 | Q87 |
| 8946 | Z2 | L23 | Q88 |
| 8947 | Z2 | L23 | Q89 |
| 8948 | Z2 | L23 | Q90 |
| 8949 | Z2 | L23 | Q91 |
| 8950 | Z2 | L23 | Q92 |
| 8951 | Z2 | L23 | Q93 |
| 8952 | Z2 | L23 | Q94 |
| 8953 | Z2 | L23 | Q95 |
| 8954 | Z2 | L23 | Q96 |
| 8955 | Z2 | L23 | Q97 |
| 8956 | Z2 | L23 | Q98 |
| 8957 | Z2 | L23 | Q99 |
| 8958 | Z2 | L23 | Q100 |
| 8959 | Z2 | L23 | Q101 |
| 8960 | Z2 | L23 | Q102 |
| 8961 | Z2 | L23 | Q103 |
| 8962 | Z2 | L24 | Q1 |
| 8963 | Z2 | L24 | Q2 |
| 8964 | Z2 | L24 | Q3 |
| 8965 | Z2 | L24 | Q4 |
| 8966 | Z2 | L24 | Q5 |
| 8967 | Z2 | L24 | Q6 |

TABLE 1-50-continued

| | | | |
|---|---|---|---|
| 8968 | Z2 | L24 | Q7 |
| 8969 | Z2 | L24 | Q8 |
| 8970 | Z2 | L24 | Q9 |
| 8971 | Z2 | L24 | Q10 |
| 8972 | Z2 | L24 | Q11 |
| 8973 | Z2 | L24 | Q12 |
| 8974 | Z2 | L24 | Q13 |
| 8975 | Z2 | L24 | Q14 |
| 8976 | Z2 | L24 | Q15 |
| 8977 | Z2 | L24 | Q16 |
| 8978 | Z2 | L24 | Q17 |
| 8979 | Z2 | L24 | Q18 |
| 8980 | Z2 | L24 | Q19 |
| 8981 | Z2 | L24 | Q20 |
| 8982 | Z2 | L24 | Q21 |
| 8983 | Z2 | L24 | Q22 |
| 8984 | Z2 | L24 | Q23 |
| 8985 | Z2 | L24 | Q24 |
| 8986 | Z2 | L24 | Q25 |
| 8987 | Z2 | L24 | Q26 |
| 8988 | Z2 | L24 | Q27 |
| 8989 | Z2 | L24 | Q28 |
| 8990 | Z2 | L24 | Q29 |
| 8991 | Z2 | L24 | Q30 |
| 8992 | Z2 | L24 | Q31 |
| 8993 | Z2 | L24 | Q32 |
| 8994 | Z2 | L24 | Q33 |
| 8995 | Z2 | L24 | Q34 |
| 8996 | Z2 | L24 | Q35 |
| 8997 | Z2 | L24 | Q36 |
| 8998 | Z2 | L24 | Q37 |
| 8999 | Z2 | L24 | Q38 |
| 9000 | Z2 | L24 | Q39 |
| 9001 | Z2 | L24 | Q40 |
| 9002 | Z2 | L24 | Q41 |
| 9003 | Z2 | L24 | Q42 |
| 9004 | Z2 | L24 | Q43 |
| 9005 | Z2 | L24 | Q44 |
| 9006 | Z2 | L24 | Q45 |
| 9007 | Z2 | L24 | Q46 |
| 9008 | Z2 | L24 | Q47 |
| 9009 | Z2 | L24 | Q48 |
| 9010 | Z2 | L24 | Q49 |
| 9011 | Z2 | L24 | Q50 |
| 9012 | Z2 | L24 | Q51 |
| 9013 | Z2 | L24 | Q52 |
| 9014 | Z2 | L24 | Q53 |
| 9015 | Z2 | L24 | Q54 |
| 9016 | Z2 | L24 | Q55 |
| 9017 | Z2 | L24 | Q56 |

TABLE 1-51

| | | | |
|---|---|---|---|
| 9018 | Z2 | L24 | Q57 |
| 9019 | Z2 | L24 | Q58 |
| 9020 | Z2 | L24 | Q59 |
| 9021 | Z2 | L24 | Q60 |
| 9022 | Z2 | L24 | Q61 |
| 9023 | Z2 | L24 | Q62 |
| 9024 | Z2 | L24 | Q63 |
| 9025 | Z2 | L24 | Q64 |
| 9026 | Z2 | L24 | Q65 |
| 9027 | Z2 | L24 | Q66 |
| 9028 | Z2 | L24 | Q67 |
| 9029 | Z2 | L24 | Q68 |
| 9030 | Z2 | L24 | Q69 |
| 9031 | Z2 | L24 | Q70 |
| 9032 | Z2 | L24 | Q71 |
| 9033 | Z2 | L24 | Q72 |
| 9034 | Z2 | L24 | Q73 |
| 9035 | Z2 | L24 | Q74 |
| 9036 | Z2 | L24 | Q75 |
| 9037 | Z2 | L24 | Q76 |
| 9038 | Z2 | L24 | Q77 |
| 9039 | Z2 | L24 | Q78 |
| 9040 | Z2 | L24 | Q79 |
| 9041 | Z2 | L24 | Q80 |

TABLE 1-51-continued

| | | | |
|---|---|---|---|
| 9042 | Z2 | L24 | Q81 |
| 9043 | Z2 | L24 | Q82 |
| 9044 | Z2 | L24 | Q83 |
| 9045 | Z2 | L24 | Q84 |
| 9046 | Z2 | L24 | Q85 |
| 9047 | Z2 | L24 | Q86 |
| 9048 | Z2 | L24 | Q87 |
| 9049 | Z2 | L24 | Q88 |
| 9050 | Z2 | L24 | Q89 |
| 9051 | Z2 | L24 | Q90 |
| 9052 | Z2 | L24 | Q91 |
| 9053 | Z2 | L24 | Q92 |
| 9054 | Z2 | L24 | Q93 |
| 9055 | Z2 | L24 | Q94 |
| 9056 | Z2 | L24 | Q95 |
| 9057 | Z2 | L24 | Q96 |
| 9058 | Z2 | L24 | Q97 |
| 9059 | Z2 | L24 | Q98 |
| 9060 | Z2 | L24 | Q99 |
| 9061 | Z2 | L24 | Q100 |
| 9062 | Z2 | L24 | Q101 |
| 9063 | Z2 | L24 | Q102 |
| 9064 | Z2 | L24 | Q103 |
| 9065 | Z2 | L25 | Q1 |
| 9066 | Z2 | L25 | Q2 |
| 9067 | Z2 | L25 | Q3 |
| 9068 | Z2 | L25 | Q4 |
| 9069 | Z2 | L25 | Q5 |
| 9070 | Z2 | L25 | Q6 |
| 9071 | Z2 | L25 | Q7 |
| 9072 | Z2 | L25 | Q8 |
| 9073 | Z2 | L25 | Q9 |
| 9074 | Z2 | L25 | Q10 |
| 9075 | Z2 | L25 | Q11 |
| 9076 | Z2 | L25 | Q12 |
| 9077 | Z2 | L25 | Q13 |
| 9078 | Z2 | L25 | Q14 |
| 9079 | Z2 | L25 | Q15 |
| 9080 | Z2 | L25 | Q16 |
| 9081 | Z2 | L25 | Q17 |
| 9082 | Z2 | L25 | Q18 |
| 9083 | Z2 | L25 | Q19 |
| 9084 | Z2 | L25 | Q20 |
| 9085 | Z2 | L25 | Q21 |
| 9086 | Z2 | L25 | Q22 |
| 9087 | Z2 | L25 | Q23 |
| 9088 | Z2 | L25 | Q24 |
| 9089 | Z2 | L25 | Q25 |
| 9090 | Z2 | L25 | Q26 |
| 9091 | Z2 | L25 | Q27 |
| 9092 | Z2 | L25 | Q28 |
| 9093 | Z2 | L25 | Q29 |
| 9094 | Z2 | L25 | Q30 |
| 9095 | Z2 | L25 | Q31 |
| 9096 | Z2 | L25 | Q32 |
| 9097 | Z2 | L25 | Q33 |
| 9098 | Z2 | L25 | Q34 |
| 9099 | Z2 | L25 | Q35 |
| 9100 | Z2 | L25 | Q36 |
| 9101 | Z2 | L25 | Q37 |
| 9102 | Z2 | L25 | Q38 |
| 9103 | Z2 | L25 | Q39 |
| 9104 | Z2 | L25 | Q40 |
| 9105 | Z2 | L25 | Q41 |
| 9106 | Z2 | L25 | Q42 |
| 9107 | Z2 | L25 | Q43 |
| 9108 | Z2 | L25 | Q44 |
| 9109 | Z2 | L25 | Q45 |
| 9110 | Z2 | L25 | Q46 |
| 9111 | Z2 | L25 | Q47 |
| 9112 | Z2 | L25 | Q48 |
| 9113 | Z2 | L25 | Q49 |
| 9114 | Z2 | L25 | Q50 |
| 9115 | Z2 | L25 | Q51 |
| 9116 | Z2 | L25 | Q52 |
| 9117 | Z2 | L25 | Q53 |
| 9118 | Z2 | L25 | Q54 |
| 9119 | Z2 | L25 | Q55 |
| 9120 | Z2 | L25 | Q56 |
| 9121 | Z2 | L25 | Q57 |

TABLE 1-51-continued

| | | | |
|---|---|---|---|
| 9122 | Z2 | L25 | Q58 |
| 9123 | Z2 | L25 | Q59 |
| 9124 | Z2 | L25 | Q60 |
| 9125 | Z2 | L25 | Q61 |
| 9126 | Z2 | L25 | Q62 |
| 9127 | Z2 | L25 | Q63 |
| 9128 | Z2 | L25 | Q64 |
| 9129 | Z2 | L25 | Q65 |
| 9130 | Z2 | L25 | Q66 |
| 9131 | Z2 | L25 | Q67 |
| 9132 | Z2 | L25 | Q68 |
| 9133 | Z2 | L25 | Q69 |
| 9134 | Z2 | L25 | Q70 |
| 9135 | Z2 | L25 | Q71 |
| 9136 | Z2 | L25 | Q72 |
| 9137 | Z2 | L25 | Q73 |
| 9138 | Z2 | L25 | Q74 |
| 9139 | Z2 | L25 | Q75 |
| 9140 | Z2 | L25 | Q76 |
| 9141 | Z2 | L25 | Q77 |
| 9142 | Z2 | L25 | Q78 |
| 9143 | Z2 | L25 | Q79 |
| 9144 | Z2 | L25 | Q80 |
| 9145 | Z2 | L25 | Q81 |
| 9146 | Z2 | L25 | Q82 |
| 9147 | Z2 | L25 | Q83 |
| 9148 | Z2 | L25 | Q84 |
| 9149 | Z2 | L25 | Q85 |
| 9150 | Z2 | L25 | Q86 |
| 9151 | Z2 | L25 | Q87 |
| 9152 | Z2 | L25 | Q88 |
| 9153 | Z2 | L25 | Q89 |
| 9154 | Z2 | L25 | Q90 |
| 9155 | Z2 | L25 | Q91 |
| 9156 | Z2 | L25 | Q92 |
| 9157 | Z2 | L25 | Q93 |
| 9158 | Z2 | L25 | Q94 |
| 9159 | Z2 | L25 | Q95 |
| 9160 | Z2 | L25 | Q96 |
| 9161 | Z2 | L25 | Q97 |
| 9162 | Z2 | L25 | Q98 |
| 9163 | Z2 | L25 | Q99 |
| 9164 | Z2 | L25 | Q100 |
| 9165 | Z2 | L25 | Q101 |
| 9166 | Z2 | L25 | Q102 |
| 9167 | Z2 | L25 | Q103 |
| 9168 | Z2 | L26 | Q1 |
| 9169 | Z2 | L26 | Q2 |
| 9170 | Z2 | L26 | Q3 |
| 9171 | Z2 | L26 | Q4 |
| 9172 | Z2 | L26 | Q5 |
| 9173 | Z2 | L26 | Q6 |
| 9174 | Z2 | L26 | Q7 |
| 9175 | Z2 | L26 | Q8 |
| 9176 | Z2 | L26 | Q9 |
| 9177 | Z2 | L26 | Q10 |
| 9178 | Z2 | L26 | Q11 |
| 9179 | Z2 | L26 | Q12 |
| 9180 | Z2 | L26 | Q13 |
| 9181 | Z2 | L26 | Q14 |
| 9182 | Z2 | L26 | Q15 |
| 9183 | Z2 | L26 | Q16 |
| 9184 | Z2 | L26 | Q17 |
| 9185 | Z2 | L26 | Q18 |
| 9186 | Z2 | L26 | Q19 |
| 9187 | Z2 | L26 | Q20 |
| 9188 | Z2 | L26 | Q21 |
| 9189 | Z2 | L26 | Q22 |
| 9190 | Z2 | L26 | Q23 |
| 9191 | Z2 | L26 | Q24 |
| 9192 | Z2 | L26 | Q25 |
| 9193 | Z2 | L26 | Q26 |
| 9194 | Z2 | L26 | Q27 |
| 9195 | Z2 | L26 | Q28 |
| 9196 | Z2 | L26 | Q29 |
| 9197 | Z2 | L26 | Q30 |
| 9198 | Z2 | L76 | Q31 |
| 9199 | Z2 | L26 | Q32 |
| 9200 | Z2 | L26 | Q33 |
| 9201 | Z2 | L26 | Q34 |
| 9202 | Z2 | L26 | Q35 |
| 9203 | Z2 | L26 | Q36 |
| 9204 | Z2 | L26 | Q37 |
| 9205 | Z2 | L26 | Q38 |
| 9206 | Z2 | L26 | Q39 |
| 9207 | Z2 | L26 | Q40 |
| 9208 | Z2 | L26 | Q41 |
| 9209 | Z2 | L26 | Q42 |
| 9210 | Z2 | L26 | Q43 |
| 9211 | Z2 | L26 | Q44 |
| 9212 | Z2 | L26 | Q45 |
| 9213 | Z2 | L26 | Q46 |
| 9214 | Z2 | L26 | Q47 |
| 9215 | Z2 | L26 | Q48 |
| 9216 | Z2 | L26 | Q49 |
| 9217 | Z2 | L26 | Q50 |
| 9218 | Z2 | L26 | Q51 |

TABLE 1-52

| | | | |
|---|---|---|---|
| 9219 | Z2 | L26 | Q52 |
| 9220 | Z2 | L26 | Q53 |
| 9221 | Z2 | L26 | Q54 |
| 9222 | Z2 | L26 | Q55 |
| 9223 | Z2 | L26 | Q56 |
| 9224 | Z2 | L26 | Q57 |
| 9225 | Z2 | L26 | Q58 |
| 9226 | Z2 | L26 | Q59 |
| 9227 | Z2 | L26 | Q60 |
| 9228 | Z2 | L26 | Q61 |
| 9229 | Z2 | L26 | Q62 |
| 9230 | Z2 | L26 | Q63 |
| 9231 | Z2 | L26 | Q64 |
| 9232 | Z2 | L26 | Q65 |
| 9233 | Z2 | L26 | Q66 |
| 9234 | Z2 | L26 | Q67 |
| 9235 | Z2 | L26 | Q68 |
| 9236 | Z2 | L26 | Q69 |
| 9237 | Z2 | L26 | Q70 |
| 9238 | Z2 | L26 | Q71 |
| 9239 | Z2 | L26 | Q72 |
| 9240 | Z2 | L26 | Q73 |
| 9241 | Z2 | L26 | Q74 |
| 9242 | Z2 | L26 | Q75 |
| 9243 | Z2 | L26 | Q76 |
| 9244 | Z2 | L26 | Q77 |
| 9245 | Z2 | L26 | Q78 |
| 9246 | Z2 | L26 | Q79 |
| 9247 | Z2 | L26 | Q80 |
| 9248 | Z2 | L26 | Q81 |
| 9249 | Z2 | L26 | Q82 |
| 9250 | Z2 | L26 | Q83 |
| 9251 | Z2 | L26 | Q84 |
| 9252 | Z2 | L26 | Q85 |
| 9253 | Z2 | L26 | Q86 |
| 9254 | Z2 | L26 | Q87 |
| 9255 | Z2 | L26 | Q88 |
| 9256 | Z2 | L26 | Q89 |
| 9257 | Z2 | L26 | Q90 |
| 9258 | Z2 | L26 | Q91 |
| 9259 | Z2 | L26 | Q92 |
| 9260 | Z2 | L26 | Q93 |
| 9261 | Z2 | L26 | Q94 |
| 9262 | Z2 | L26 | Q95 |
| 9263 | Z2 | L26 | Q96 |
| 9264 | Z2 | L26 | Q97 |
| 9265 | Z2 | L26 | Q98 |
| 9266 | Z2 | L26 | Q99 |
| 9267 | Z2 | L26 | Q100 |
| 9268 | Z2 | L26 | Q101 |
| 9269 | Z2 | L26 | Q102 |
| 9270 | Z2 | L26 | Q103 |
| 9271 | Z2 | L27 | Q1 |
| 9272 | Z2 | L27 | Q2 |
| 9273 | Z2 | L27 | Q3 |
| 9274 | Z2 | L27 | Q4 |
| 9275 | Z2 | L27 | Q5 |

TABLE 1-52-continued

| | | | |
|---|---|---|---|
| 9276 | Z2 | L27 | Q6 |
| 9277 | Z2 | L27 | Q7 |
| 9278 | Z2 | L27 | Q8 |
| 9279 | Z2 | L27 | Q9 |
| 9280 | Z2 | L27 | Q10 |
| 9281 | Z2 | L27 | Q11 |
| 9282 | Z2 | L27 | Q12 |
| 9283 | Z2 | L27 | Q13 |
| 9284 | Z2 | L27 | Q14 |
| 9285 | Z2 | L27 | Q15 |
| 9286 | Z2 | L27 | Q16 |
| 9287 | Z2 | L27 | Q17 |
| 9288 | Z2 | L27 | Q18 |
| 9289 | Z2 | L27 | Q19 |
| 9290 | Z2 | L27 | Q20 |
| 9291 | Z2 | L27 | Q21 |
| 9292 | Z2 | L27 | Q22 |
| 9293 | Z2 | L27 | Q23 |
| 9294 | Z2 | L27 | Q24 |
| 9295 | Z2 | L27 | Q25 |
| 9296 | Z2 | L27 | Q26 |
| 9297 | Z2 | L27 | Q27 |
| 9298 | Z2 | L27 | Q28 |
| 9299 | Z2 | L27 | Q29 |
| 9300 | Z2 | L27 | Q30 |
| 9301 | Z2 | L27 | Q31 |
| 9302 | Z2 | L27 | Q32 |
| 9303 | Z2 | L27 | Q33 |
| 9304 | Z2 | L27 | Q34 |
| 9305 | Z2 | L27 | Q35 |
| 9306 | Z2 | L27 | Q36 |
| 9307 | Z2 | L27 | Q37 |
| 9308 | Z2 | L27 | Q38 |
| 9309 | Z2 | L27 | Q39 |
| 9310 | Z2 | L27 | Q40 |
| 9311 | Z2 | L27 | Q41 |
| 9312 | Z2 | L27 | Q42 |
| 9313 | Z2 | L27 | Q43 |
| 9314 | Z2 | L27 | Q44 |
| 9315 | Z2 | L27 | Q45 |
| 9316 | Z2 | L27 | Q46 |
| 9317 | Z2 | L27 | Q47 |
| 9318 | Z2 | L27 | Q48 |
| 9319 | Z2 | L27 | Q49 |
| 9320 | Z2 | L27 | Q50 |
| 9321 | Z2 | L27 | Q51 |
| 9322 | Z2 | L27 | Q52 |
| 9323 | Z2 | L27 | Q53 |
| 9324 | Z2 | L27 | Q54 |
| 9325 | Z2 | L27 | Q55 |
| 9326 | Z2 | L27 | Q56 |
| 9327 | Z2 | L27 | Q57 |
| 9328 | Z2 | L27 | Q58 |
| 9329 | Z2 | L27 | Q59 |
| 9330 | Z2 | L27 | Q60 |
| 9331 | Z2 | L27 | Q61 |
| 9332 | Z2 | L27 | Q62 |
| 9333 | Z2 | L27 | Q63 |
| 9334 | Z2 | L27 | Q64 |
| 9335 | Z2 | L27 | Q65 |
| 9336 | Z2 | L27 | Q66 |
| 9337 | Z2 | L27 | Q67 |
| 9338 | Z2 | L27 | Q68 |
| 9339 | Z2 | L27 | Q69 |
| 9340 | Z2 | L27 | Q70 |
| 9341 | Z2 | L27 | Q71 |
| 9342 | Z2 | L27 | Q72 |
| 9343 | Z2 | L27 | Q73 |
| 9344 | Z2 | L27 | Q74 |
| 9345 | Z2 | L27 | Q75 |
| 9346 | Z2 | L27 | Q76 |
| 9347 | Z2 | L27 | Q77 |
| 9348 | Z2 | L27 | Q78 |
| 9349 | Z2 | L27 | Q79 |
| 9350 | Z2 | L27 | Q80 |
| 9351 | Z2 | L27 | Q81 |
| 9352 | Z2 | L27 | Q82 |
| 9353 | Z2 | L27 | Q83 |
| 9354 | Z2 | L27 | Q84 |
| 9355 | Z2 | L27 | Q85 |
| 9356 | Z2 | L27 | Q86 |
| 9357 | Z2 | L27 | Q87 |
| 9358 | Z2 | L27 | Q88 |
| 9359 | Z2 | L27 | Q89 |
| 9360 | Z2 | L27 | Q90 |
| 9361 | Z2 | L27 | Q91 |
| 9362 | Z2 | L27 | Q92 |
| 9363 | Z2 | L27 | Q93 |
| 9364 | Z2 | L27 | Q94 |
| 9365 | Z2 | L27 | Q95 |
| 9366 | Z2 | L27 | Q96 |
| 9367 | Z2 | L27 | Q97 |
| 9368 | Z2 | L27 | Q98 |
| 9369 | Z2 | L27 | Q99 |
| 9370 | Z2 | L27 | Q100 |
| 9371 | Z2 | L27 | Q101 |
| 9372 | Z2 | L27 | Q102 |
| 9373 | Z2 | L27 | Q103 |
| 9374 | Z2 | L28 | Q1 |
| 9375 | Z2 | L28 | Q2 |
| 9376 | Z2 | L28 | Q3 |
| 9377 | Z2 | L28 | Q4 |
| 9378 | Z2 | L28 | Q5 |
| 9379 | Z2 | L28 | Q6 |
| 9380 | Z2 | L28 | Q7 |
| 9381 | Z2 | L28 | Q8 |
| 9382 | Z2 | L28 | Q9 |
| 9383 | Z2 | L28 | Q10 |
| 9384 | Z2 | L28 | Q11 |
| 9385 | Z2 | L28 | Q12 |
| 9386 | Z2 | L28 | Q13 |
| 9387 | Z2 | L28 | Q14 |
| 9388 | Z2 | L28 | Q15 |
| 9389 | Z2 | L28 | Q16 |
| 9390 | Z2 | L28 | Q17 |
| 9391 | Z2 | L28 | Q18 |
| 9392 | Z2 | L28 | Q19 |
| 9393 | Z2 | L28 | Q20 |
| 9394 | Z2 | L28 | Q21 |
| 9395 | Z2 | L28 | Q22 |
| 9396 | Z2 | L28 | Q23 |
| 9397 | Z2 | L28 | Q24 |
| 9398 | Z2 | L28 | Q25 |
| 9399 | Z2 | L28 | Q26 |
| 9400 | Z2 | L28 | Q27 |
| 9401 | Z2 | L28 | Q28 |
| 9402 | Z2 | L28 | Q29 |
| 9403 | Z2 | L28 | Q30 |
| 9404 | Z2 | L28 | Q31 |
| 9405 | Z2 | L28 | Q32 |
| 9406 | Z2 | L28 | Q33 |
| 9407 | Z2 | L28 | Q34 |
| 9408 | Z2 | L28 | Q35 |
| 9409 | Z2 | L28 | Q36 |
| 9410 | Z2 | L28 | Q37 |
| 9411 | Z2 | L28 | Q38 |
| 9412 | Z2 | L28 | Q39 |
| 9413 | Z2 | L28 | Q40 |
| 9414 | Z2 | L28 | Q41 |
| 9415 | Z2 | L28 | Q42 |
| 9416 | Z2 | L28 | Q43 |
| 9417 | Z2 | L28 | Q44 |
| 9418 | Z2 | L28 | Q45 |
| 9419 | Z2 | L28 | Q46 |

TABLE 1-53

| | | | |
|---|---|---|---|
| 9420 | Z2 | L28 | Q47 |
| 9421 | Z2 | L28 | Q48 |
| 9422 | Z2 | L28 | Q49 |
| 9423 | Z2 | L28 | Q50 |
| 9424 | Z2 | L28 | Q51 |
| 9425 | Z2 | L28 | Q52 |
| 9426 | Z2 | L28 | Q53 |
| 9427 | Z2 | L28 | Q54 |
| 9428 | Z2 | L28 | Q55 |
| 9429 | Z2 | L28 | Q56 |

TABLE 1-53-continued

| | | | |
|---|---|---|---|
| 9430 | Z2 | L28 | Q57 |
| 9431 | Z2 | L28 | Q58 |
| 9432 | Z2 | L28 | Q59 |
| 9433 | Z2 | L28 | Q60 |
| 9434 | Z2 | L28 | Q61 |
| 9435 | Z2 | L28 | Q62 |
| 9436 | Z2 | L28 | Q63 |
| 9437 | Z2 | L28 | Q64 |
| 9438 | Z2 | L28 | Q65 |
| 9439 | Z2 | L28 | Q66 |
| 9440 | Z2 | L28 | Q67 |
| 9441 | Z2 | L28 | Q68 |
| 9442 | Z2 | L28 | Q69 |
| 9443 | Z2 | L28 | Q70 |
| 9444 | Z2 | L28 | Q71 |
| 9445 | Z2 | L28 | Q72 |
| 9446 | Z2 | L28 | Q73 |
| 9447 | Z2 | L28 | Q74 |
| 9448 | Z2 | L28 | Q75 |
| 9449 | Z2 | L28 | Q76 |
| 9450 | Z2 | L28 | Q77 |
| 9451 | Z2 | L28 | Q78 |
| 9452 | Z2 | L28 | Q79 |
| 9453 | Z2 | L28 | Q80 |
| 9454 | Z2 | L28 | Q81 |
| 9455 | Z2 | L28 | Q82 |
| 9456 | Z2 | L28 | Q83 |
| 9457 | Z2 | L28 | Q84 |
| 9458 | Z2 | L28 | Q85 |
| 9459 | Z2 | L28 | Q86 |
| 9460 | Z2 | L28 | Q87 |
| 9461 | Z2 | L28 | Q88 |
| 9462 | Z2 | L28 | Q89 |
| 9463 | Z2 | L28 | Q90 |
| 9464 | Z2 | L28 | Q91 |
| 9465 | Z2 | L28 | Q92 |
| 9466 | Z2 | L28 | Q93 |
| 9467 | Z2 | L28 | Q94 |
| 9468 | Z2 | L28 | Q95 |
| 9469 | Z2 | L28 | Q96 |
| 9470 | Z2 | L28 | Q97 |
| 9471 | Z2 | L28 | Q98 |
| 9472 | Z2 | L28 | Q99 |
| 9473 | Z2 | L28 | Q100 |
| 9474 | Z2 | L28 | Q101 |
| 9475 | Z2 | L28 | Q102 |
| 9476 | Z2 | L28 | Q103 |
| 9477 | Z2 | L29 | Q1 |
| 9478 | Z2 | L29 | Q2 |
| 9479 | Z2 | L29 | Q3 |
| 9480 | Z2 | L29 | Q4 |
| 9481 | Z2 | L29 | Q5 |
| 9482 | Z2 | L29 | Q6 |
| 9483 | Z2 | L29 | Q7 |
| 9484 | Z2 | L29 | Q8 |
| 9485 | Z2 | L29 | Q9 |
| 9486 | Z2 | L29 | Q10 |
| 9487 | Z2 | L29 | Q11 |
| 9488 | Z2 | L29 | Q12 |
| 9489 | Z2 | L29 | Q13 |
| 9490 | Z2 | L29 | Q14 |
| 9491 | Z2 | L29 | Q15 |
| 9492 | Z2 | L29 | Q16 |
| 9493 | Z2 | L29 | Q17 |
| 9494 | Z2 | L29 | Q18 |
| 9495 | Z2 | L29 | Q19 |
| 9496 | Z2 | L29 | Q20 |
| 9497 | Z2 | L29 | Q21 |
| 9498 | Z2 | L29 | Q22 |
| 9499 | Z2 | L29 | Q23 |
| 9500 | Z2 | L29 | Q24 |
| 9501 | Z2 | L29 | Q25 |
| 9502 | Z2 | L29 | Q26 |
| 9503 | Z2 | L29 | Q27 |
| 9504 | Z2 | L29 | Q28 |
| 9505 | Z2 | L29 | Q29 |
| 9506 | Z2 | L29 | Q30 |
| 9507 | Z2 | L29 | Q31 |
| 9508 | Z2 | L29 | Q32 |
| 9509 | Z2 | L29 | Q33 |
| 9510 | Z2 | L29 | Q34 |
| 9511 | Z2 | L29 | Q35 |
| 9512 | Z2 | L29 | Q36 |
| 9513 | Z2 | L29 | Q37 |
| 9514 | Z2 | L29 | Q38 |
| 9515 | Z2 | L29 | Q39 |
| 9516 | Z2 | L29 | Q40 |
| 9517 | Z2 | L29 | Q41 |
| 9518 | Z2 | L29 | Q42 |
| 9519 | Z2 | L29 | Q43 |
| 9520 | Z2 | L29 | Q44 |
| 9521 | Z2 | L29 | Q45 |
| 9522 | Z2 | L29 | Q46 |
| 9523 | Z2 | L29 | Q47 |
| 9524 | Z2 | L29 | Q48 |
| 9525 | Z2 | L29 | Q49 |
| 9526 | Z2 | L29 | Q50 |
| 9527 | Z2 | L29 | Q51 |
| 9528 | Z2 | L29 | Q52 |
| 9529 | Z2 | L29 | Q53 |
| 9530 | Z2 | L29 | Q54 |
| 9531 | Z2 | L29 | Q55 |
| 9532 | Z2 | L29 | Q56 |
| 9533 | Z2 | L29 | Q57 |
| 9534 | Z2 | L29 | Q58 |
| 9535 | Z2 | L29 | Q59 |
| 9536 | Z2 | L29 | Q60 |
| 9537 | Z2 | L29 | Q61 |
| 9538 | Z2 | L29 | Q62 |
| 9539 | Z2 | L29 | Q63 |
| 9540 | Z2 | L29 | Q64 |
| 9541 | Z2 | L29 | Q65 |
| 9542 | Z2 | L29 | Q66 |
| 9543 | Z2 | L29 | Q67 |
| 9544 | Z2 | L29 | Q68 |
| 9545 | Z2 | L29 | Q69 |
| 9546 | Z2 | L29 | Q70 |
| 9547 | Z2 | L29 | Q71 |
| 9548 | Z2 | L29 | Q72 |
| 9549 | Z2 | L29 | Q73 |
| 9550 | Z2 | L29 | Q74 |
| 9551 | Z2 | L29 | Q75 |
| 9552 | Z2 | L29 | Q76 |
| 9553 | Z2 | L29 | Q77 |
| 9554 | Z2 | L29 | Q78 |
| 9555 | Z2 | L29 | Q79 |
| 9556 | Z2 | L29 | Q80 |
| 9557 | Z2 | L29 | Q81 |
| 9558 | Z2 | L29 | Q82 |
| 9559 | Z2 | L29 | Q83 |
| 9560 | Z2 | L29 | Q84 |
| 9561 | Z2 | L29 | Q85 |
| 9562 | Z2 | L29 | Q86 |
| 9563 | Z2 | L29 | Q87 |
| 9564 | Z2 | L29 | Q88 |
| 9565 | Z2 | L29 | Q89 |
| 9566 | Z2 | L29 | Q90 |
| 9567 | Z2 | L29 | Q91 |
| 9568 | Z2 | L29 | Q92 |
| 9569 | Z2 | L29 | Q93 |
| 9570 | Z2 | L29 | Q94 |
| 9571 | Z2 | L29 | Q95 |
| 9572 | Z2 | L29 | Q96 |
| 9573 | Z2 | L29 | Q97 |
| 9574 | Z2 | L29 | Q98 |
| 9575 | Z2 | L29 | Q99 |
| 9576 | Z2 | L29 | Q100 |
| 9577 | Z2 | L29 | Q101 |
| 9578 | Z2 | L29 | Q102 |
| 9579 | Z2 | L29 | Q103 |
| 9580 | Z2 | L30 | Q1 |
| 9581 | Z2 | L30 | Q2 |
| 9582 | Z2 | L30 | Q3 |
| 9583 | Z2 | L30 | Q4 |
| 9584 | Z2 | L30 | Q5 |
| 9585 | Z2 | L30 | Q6 |
| 9586 | Z2 | L30 | Q7 |
| 9587 | Z2 | L30 | Q8 |
| 9588 | Z2 | L30 | Q9 |
| 9589 | Z2 | L30 | Q10 |

TABLE 1-53-continued

| | | | |
|---|---|---|---|
| 9590 | Z2 | L30 | Q11 |
| 9591 | Z2 | L30 | Q12 |
| 9592 | Z2 | L30 | Q13 |
| 9593 | Z2 | L30 | Q14 |
| 9594 | Z2 | L30 | Q15 |
| 9595 | Z2 | L30 | Q16 |
| 9596 | Z2 | L30 | Q17 |
| 9597 | Z2 | L30 | Q18 |
| 9598 | Z2 | L30 | Q19 |
| 9599 | Z2 | L30 | Q20 |
| 9600 | Z2 | L30 | Q21 |
| 9601 | Z2 | L30 | Q22 |
| 9602 | Z2 | L30 | Q23 |
| 9603 | Z2 | L30 | Q24 |
| 9604 | Z2 | L30 | Q25 |
| 9605 | Z2 | L30 | Q26 |
| 9606 | Z2 | L30 | Q27 |
| 9607 | Z2 | L30 | Q28 |
| 9608 | Z2 | L30 | Q29 |
| 9609 | Z2 | L30 | Q30 |
| 9610 | Z2 | L30 | Q31 |
| 9611 | Z2 | L30 | Q32 |
| 9612 | Z2 | L30 | Q33 |
| 9613 | Z2 | L30 | Q34 |
| 9614 | Z2 | L30 | Q35 |
| 9615 | Z2 | L30 | Q36 |
| 9616 | Z2 | L30 | Q37 |
| 9617 | Z2 | L30 | Q38 |
| 9618 | Z2 | L30 | Q39 |
| 9619 | Z2 | L30 | Q40 |
| 9620 | Z2 | L30 | Q41 |

TABLE 1-54

| | | | |
|---|---|---|---|
| 9621 | Z2 | L30 | Q42 |
| 9622 | Z2 | L30 | Q43 |
| 9623 | Z2 | L30 | Q44 |
| 9624 | Z2 | L30 | Q45 |
| 9625 | Z2 | L30 | Q46 |
| 9626 | Z2 | L30 | Q47 |
| 9627 | Z2 | L30 | Q48 |
| 9628 | Z2 | L30 | Q49 |
| 9629 | Z2 | L30 | Q50 |
| 9630 | Z2 | L30 | Q51 |
| 9631 | Z2 | L30 | Q52 |
| 9632 | Z2 | L30 | Q53 |
| 9633 | Z2 | L30 | Q54 |
| 9634 | Z2 | L30 | Q55 |
| 9635 | Z2 | L30 | Q56 |
| 9636 | Z2 | L30 | Q57 |
| 9637 | Z2 | L30 | Q58 |
| 9638 | Z2 | L30 | Q59 |
| 9639 | Z2 | L30 | Q60 |
| 9640 | Z2 | L30 | Q61 |
| 9641 | Z2 | L30 | Q62 |
| 9642 | Z2 | L30 | Q63 |
| 9643 | Z2 | L30 | Q64 |
| 9644 | Z2 | L30 | Q65 |
| 9645 | Z2 | L30 | Q66 |
| 9646 | Z2 | L30 | Q67 |
| 9647 | Z2 | L30 | Q68 |
| 9648 | Z2 | L30 | Q69 |
| 9649 | Z2 | L30 | Q70 |
| 9650 | Z2 | L30 | Q71 |
| 9651 | Z2 | L30 | Q72 |
| 9652 | Z2 | L30 | Q73 |
| 9653 | Z2 | L30 | Q74 |
| 9654 | Z2 | L30 | Q75 |
| 9655 | Z2 | L30 | Q76 |
| 9656 | Z2 | L30 | Q77 |
| 9657 | Z2 | L30 | Q78 |
| 9658 | Z2 | L30 | Q79 |
| 9659 | Z2 | L30 | Q80 |
| 9660 | Z2 | L30 | Q81 |
| 9661 | Z2 | L30 | Q82 |
| 9662 | Z2 | L30 | Q83 |
| 9663 | Z2 | L30 | Q84 |

TABLE 1-54-continued

| | | | |
|---|---|---|---|
| 9664 | Z2 | L30 | Q85 |
| 9665 | Z2 | L30 | Q86 |
| 9666 | Z2 | L30 | Q87 |
| 9667 | Z2 | L30 | Q88 |
| 9668 | Z2 | L30 | Q89 |
| 9669 | Z2 | L30 | Q90 |
| 9670 | Z2 | L30 | Q91 |
| 9671 | Z2 | L30 | Q92 |
| 9672 | Z2 | L30 | Q93 |
| 9673 | Z2 | L30 | Q94 |
| 9674 | Z2 | L30 | Q95 |
| 9675 | Z2 | L30 | Q96 |
| 9676 | Z2 | L30 | Q97 |
| 9677 | Z2 | L30 | Q98 |
| 9678 | Z2 | L30 | Q99 |
| 9679 | Z2 | L30 | Q100 |
| 9680 | Z2 | L30 | Q101 |
| 9681 | Z2 | L30 | Q102 |
| 9682 | Z2 | L30 | Q103 |
| 9683 | Z2 | L31 | Q1 |
| 9684 | Z2 | L31 | Q2 |
| 9685 | Z2 | L31 | Q3 |
| 9686 | Z2 | L31 | Q4 |
| 9687 | Z2 | L31 | Q5 |
| 9688 | Z2 | L31 | Q6 |
| 9689 | Z2 | L31 | Q7 |
| 9690 | Z2 | L31 | Q8 |
| 9691 | Z2 | L31 | Q9 |
| 9692 | Z2 | L31 | Q10 |
| 9693 | Z2 | L31 | Q11 |
| 9694 | Z2 | L31 | Q12 |
| 9695 | Z2 | L31 | Q13 |
| 9696 | Z2 | L31 | Q14 |
| 9697 | Z2 | L31 | Q15 |
| 9698 | Z2 | L31 | Q16 |
| 9699 | Z2 | L31 | Q17 |
| 9700 | Z2 | L31 | Q18 |
| 9701 | Z2 | L31 | Q19 |
| 9702 | Z2 | L31 | Q20 |
| 9703 | Z2 | L31 | Q21 |
| 9704 | Z2 | L31 | Q22 |
| 9705 | Z2 | L31 | Q23 |
| 9706 | Z2 | L31 | Q24 |
| 9707 | Z2 | L31 | Q25 |
| 9708 | Z2 | L31 | Q26 |
| 9709 | Z2 | L31 | Q27 |
| 9710 | Z2 | L31 | Q28 |
| 9711 | Z2 | L31 | Q29 |
| 9712 | Z2 | L31 | Q30 |
| 9713 | Z2 | L31 | Q31 |
| 9714 | Z2 | L31 | Q32 |
| 9715 | Z2 | L31 | Q33 |
| 9716 | Z2 | L31 | Q34 |
| 9717 | Z2 | L31 | Q35 |
| 9718 | Z2 | L31 | Q36 |
| 9719 | Z2 | L31 | Q37 |
| 9720 | Z2 | L31 | Q38 |
| 9721 | Z2 | L31 | Q39 |
| 9722 | Z2 | L31 | Q40 |
| 9723 | Z2 | L31 | Q41 |
| 9724 | Z2 | L31 | Q42 |
| 9725 | Z2 | L31 | Q43 |
| 9726 | Z2 | L31 | Q44 |
| 9727 | Z2 | L31 | Q45 |
| 9728 | Z2 | L31 | Q46 |
| 9729 | Z2 | L31 | Q47 |
| 9730 | Z2 | L31 | Q48 |
| 9731 | Z2 | L31 | Q49 |
| 9732 | Z2 | L31 | Q50 |
| 9733 | Z2 | L31 | Q51 |
| 9734 | Z2 | L31 | Q52 |
| 9735 | Z2 | L31 | Q53 |
| 9736 | Z2 | L31 | Q54 |
| 9737 | Z2 | L31 | Q55 |
| 9738 | Z2 | L31 | Q56 |
| 9739 | Z2 | L31 | Q57 |
| 9740 | Z2 | L31 | Q58 |
| 9741 | Z2 | L31 | Q59 |
| 9742 | Z2 | L31 | Q60 |
| 9743 | Z2 | L31 | Q61 |

TABLE 1-54-continued

| | | | |
|---|---|---|---|
| 9744 | Z2 | L31 | Q62 |
| 9745 | Z2 | L31 | Q63 |
| 9746 | Z2 | L31 | Q64 |
| 9747 | Z2 | L31 | Q65 |
| 9748 | Z2 | L31 | Q66 |
| 9749 | Z2 | L31 | Q67 |
| 9750 | Z2 | L31 | Q68 |
| 9751 | Z2 | L31 | Q69 |
| 9752 | Z2 | L31 | Q70 |
| 9753 | Z2 | L31 | Q71 |
| 9754 | Z2 | L31 | Q72 |
| 9755 | Z2 | L31 | Q73 |
| 9756 | Z2 | L31 | Q74 |
| 9757 | Z2 | L31 | Q75 |
| 9758 | Z2 | L31 | Q76 |
| 9759 | Z2 | L31 | Q77 |
| 9760 | Z2 | L31 | Q78 |
| 9761 | Z2 | L31 | Q79 |
| 9762 | Z2 | L31 | Q80 |
| 9763 | Z2 | L31 | Q81 |
| 9764 | Z2 | L31 | Q82 |
| 9765 | Z2 | L31 | Q83 |
| 9766 | Z2 | L31 | Q84 |
| 9767 | Z2 | L31 | Q85 |
| 9768 | Z2 | L31 | Q86 |
| 9769 | Z2 | L31 | Q87 |
| 9770 | Z2 | L31 | Q88 |
| 9771 | Z2 | L31 | Q89 |
| 9772 | Z2 | L31 | Q90 |
| 9773 | Z2 | L31 | Q91 |
| 9774 | Z2 | L31 | Q92 |
| 9775 | Z2 | L31 | Q93 |
| 9776 | Z2 | L31 | Q94 |
| 9777 | Z2 | L31 | Q95 |
| 9778 | Z2 | L31 | Q96 |
| 9779 | Z2 | L31 | Q97 |
| 9780 | Z2 | L31 | Q98 |
| 9781 | Z2 | L31 | Q99 |
| 9782 | Z2 | L31 | Q100 |
| 9783 | Z2 | L31 | Q101 |
| 9784 | Z2 | L31 | Q102 |
| 9785 | Z2 | L31 | Q103 |
| 9786 | Z2 | L32 | Q1 |
| 9787 | Z2 | L32 | Q2 |
| 9788 | Z2 | L32 | Q3 |
| 9789 | Z2 | L32 | Q4 |
| 9790 | Z2 | L32 | Q5 |
| 9791 | Z2 | L32 | Q6 |
| 9792 | Z2 | L32 | Q7 |
| 9793 | Z2 | L32 | Q8 |
| 9794 | Z2 | L32 | Q9 |
| 9795 | Z2 | L32 | Q10 |
| 9796 | Z2 | L32 | Q11 |
| 9797 | Z2 | L32 | Q12 |
| 9798 | Z2 | L32 | Q13 |
| 9799 | Z2 | L32 | Q14 |
| 9800 | Z2 | L32 | Q15 |
| 9801 | Z2 | L32 | Q16 |
| 9802 | Z2 | L32 | Q17 |
| 9803 | Z2 | L32 | Q18 |
| 9804 | Z2 | L32 | Q19 |
| 9805 | Z2 | L32 | Q20 |
| 9806 | Z2 | L32 | Q21 |
| 9807 | Z2 | L32 | Q22 |
| 9808 | Z2 | L32 | Q23 |
| 9809 | Z2 | L32 | Q24 |
| 9810 | Z2 | L32 | Q25 |
| 9811 | Z2 | L32 | Q26 |
| 9812 | Z2 | L32 | Q27 |
| 9813 | Z2 | L32 | Q28 |
| 9814 | Z2 | L32 | Q29 |
| 9815 | Z2 | L32 | Q30 |
| 9816 | Z2 | L32 | Q31 |
| 9817 | Z2 | L32 | Q32 |
| 9818 | Z2 | L32 | Q33 |
| 9819 | Z2 | L32 | Q34 |
| 9820 | Z2 | L32 | Q35 |
| 9821 | Z2 | L32 | Q36 |

TABLE 1-55

| | | | |
|---|---|---|---|
| 9822 | Z2 | L32 | Q37 |
| 9823 | Z2 | L32 | Q38 |
| 9824 | Z2 | L32 | Q39 |
| 9825 | Z2 | L32 | Q40 |
| 9826 | Z2 | L32 | Q41 |
| 9827 | Z2 | L32 | Q42 |
| 9828 | Z2 | L32 | Q43 |
| 9829 | Z2 | L32 | Q44 |
| 9830 | Z2 | L32 | Q45 |
| 9831 | Z2 | L32 | Q46 |
| 9832 | Z2 | L32 | Q47 |
| 9833 | Z2 | L32 | Q48 |
| 9834 | Z2 | L32 | Q49 |
| 9835 | Z2 | L32 | Q50 |
| 9836 | Z2 | L32 | Q51 |
| 9837 | Z2 | L32 | Q52 |
| 9838 | Z2 | L32 | Q53 |
| 9839 | Z2 | L32 | Q54 |
| 9840 | Z2 | L32 | Q55 |
| 9841 | Z2 | L32 | Q56 |
| 9842 | Z2 | L32 | Q57 |
| 9843 | Z2 | L32 | Q58 |
| 9844 | Z2 | L32 | Q59 |
| 9845 | Z2 | L32 | Q60 |
| 9846 | Z2 | L32 | Q61 |
| 9847 | Z2 | L32 | Q62 |
| 9848 | Z2 | L32 | Q63 |
| 9849 | Z2 | L32 | Q64 |
| 9850 | Z2 | L32 | Q65 |
| 9851 | Z2 | L32 | Q66 |
| 9852 | Z2 | L32 | Q67 |
| 9853 | Z2 | L32 | Q68 |
| 9854 | Z2 | L32 | Q69 |
| 9855 | Z2 | L32 | Q70 |
| 9856 | Z2 | L32 | Q71 |
| 9857 | Z2 | L32 | Q72 |
| 9858 | Z2 | L32 | Q73 |
| 9859 | Z2 | L32 | Q74 |
| 9860 | Z2 | L32 | Q75 |
| 9861 | Z2 | L32 | Q76 |
| 9862 | Z2 | L32 | Q77 |
| 9863 | Z2 | L32 | Q78 |
| 9864 | Z2 | L32 | Q79 |
| 9865 | Z2 | L32 | Q80 |
| 9866 | Z2 | L32 | Q81 |
| 9867 | Z2 | L32 | Q82 |
| 9868 | Z2 | L32 | Q83 |
| 9869 | Z2 | L32 | Q84 |
| 9870 | Z2 | L32 | Q85 |
| 9871 | Z2 | L32 | Q86 |
| 9872 | Z2 | L32 | Q87 |
| 9873 | Z2 | L32 | Q88 |
| 9874 | Z2 | L32 | Q89 |
| 9875 | Z2 | L32 | Q90 |
| 9876 | Z2 | L32 | Q91 |
| 9877 | Z2 | L32 | Q92 |
| 9878 | Z2 | L32 | Q93 |
| 9879 | Z2 | L32 | Q94 |
| 9880 | Z2 | L32 | Q95 |
| 9881 | Z2 | L32 | Q96 |
| 9882 | Z2 | L32 | Q97 |
| 9883 | Z2 | L32 | Q98 |
| 9884 | Z2 | L32 | Q99 |
| 9885 | Z2 | L32 | Q100 |
| 9886 | Z2 | L32 | Q101 |
| 9887 | Z2 | L32 | Q102 |
| 9888 | Z2 | L32 | Q103 |
| 9889 | Z2 | L33 | Q1 |
| 9890 | Z2 | L33 | Q2 |
| 9891 | Z2 | L33 | Q3 |
| 9892 | Z2 | L33 | Q4 |
| 9893 | Z2 | L33 | Q5 |
| 9894 | Z2 | L33 | Q6 |
| 9895 | Z2 | L33 | Q7 |
| 9896 | Z2 | L33 | Q8 |
| 9897 | Z2 | L33 | Q9 |
| 9898 | Z2 | L33 | Q10 |
| 9899 | Z2 | L33 | Q11 |
| 9900 | Z2 | L33 | Q12 |
| 9901 | Z2 | L33 | Q13 |

TABLE 1-55-continued

| | | | |
|---|---|---|---|
| 9902 | Z2 | L33 | Q14 |
| 9903 | Z2 | L33 | Q15 |
| 9904 | Z2 | L33 | Q16 |
| 9905 | Z2 | L33 | Q17 |
| 9906 | Z2 | L33 | Q18 |
| 9907 | Z2 | L33 | Q19 |
| 9908 | Z2 | L33 | Q20 |
| 9909 | Z2 | L33 | Q21 |
| 9910 | Z2 | L33 | Q22 |
| 9911 | Z2 | L33 | Q23 |
| 9912 | Z2 | L33 | Q24 |
| 9913 | Z2 | L33 | Q25 |
| 9914 | Z2 | L33 | Q26 |
| 9915 | Z2 | L33 | Q27 |
| 9916 | Z2 | L33 | Q28 |
| 9917 | Z2 | L33 | Q29 |
| 9918 | Z2 | L33 | Q30 |
| 9919 | Z2 | L33 | Q31 |
| 9920 | Z2 | L33 | Q32 |
| 9921 | Z2 | L33 | Q33 |
| 9922 | Z2 | L33 | Q34 |
| 9923 | Z2 | L33 | Q35 |
| 9924 | Z2 | L33 | Q36 |
| 9925 | Z2 | L33 | Q37 |
| 9926 | Z2 | L33 | Q38 |
| 9927 | Z2 | L33 | Q39 |
| 9928 | Z2 | L33 | Q40 |
| 9929 | Z2 | L33 | Q41 |
| 9930 | Z2 | L33 | Q42 |
| 9931 | Z2 | L33 | Q43 |
| 9932 | Z2 | L33 | Q44 |
| 9933 | Z2 | L33 | Q45 |
| 9934 | Z2 | L33 | Q46 |
| 9935 | Z2 | L33 | Q47 |
| 9936 | Z2 | L33 | Q48 |
| 9937 | Z2 | L33 | Q49 |
| 9938 | Z2 | L33 | Q50 |
| 9939 | Z2 | L33 | Q51 |
| 9940 | Z2 | L33 | Q52 |
| 9941 | Z2 | L33 | Q53 |
| 9942 | Z2 | L33 | Q54 |
| 9943 | Z2 | L33 | Q55 |
| 9944 | Z2 | L33 | Q56 |
| 9945 | Z2 | L33 | Q57 |
| 9946 | Z2 | L33 | Q58 |
| 9947 | Z2 | L33 | Q59 |
| 9948 | Z2 | L33 | Q60 |
| 9949 | Z2 | L33 | Q61 |
| 9950 | Z2 | L33 | Q62 |
| 9951 | Z2 | L33 | Q63 |
| 9952 | Z2 | L33 | Q64 |
| 9953 | Z2 | L33 | Q65 |
| 9954 | Z2 | L33 | Q66 |
| 9955 | Z2 | L33 | Q67 |
| 9956 | Z2 | L33 | Q68 |
| 9957 | Z2 | L33 | Q69 |
| 9958 | Z2 | L33 | Q70 |
| 9959 | Z2 | L33 | Q71 |
| 9960 | Z2 | L33 | Q72 |
| 9961 | Z2 | L33 | Q73 |
| 9962 | Z2 | L33 | Q74 |
| 9963 | Z2 | L33 | Q75 |
| 9964 | Z2 | L33 | Q76 |
| 9965 | Z2 | L33 | Q77 |
| 9966 | Z2 | L33 | Q78 |
| 9967 | Z2 | L33 | Q79 |
| 9968 | Z2 | L33 | Q80 |
| 9969 | Z2 | L33 | Q81 |
| 9970 | Z2 | L33 | Q82 |
| 9971 | Z2 | L33 | Q83 |
| 9972 | Z2 | L33 | Q84 |
| 9973 | Z2 | L33 | Q85 |
| 9974 | Z2 | L33 | Q86 |
| 9975 | Z2 | L33 | Q87 |
| 9976 | Z2 | L33 | Q88 |
| 9977 | Z2 | L33 | Q89 |
| 9978 | Z2 | L33 | Q90 |
| 9979 | Z2 | L33 | Q91 |
| 9980 | Z2 | L33 | Q92 |
| 9981 | Z2 | L33 | Q93 |
| 9982 | Z2 | L33 | Q94 |
| 9983 | Z2 | L33 | Q95 |
| 9984 | Z2 | L33 | Q96 |
| 9985 | Z2 | L33 | Q97 |
| 9986 | Z2 | L33 | Q98 |
| 9987 | Z2 | L33 | Q99 |
| 9988 | Z2 | L33 | Q100 |
| 9989 | Z2 | L33 | Q101 |
| 9990 | Z2 | L33 | Q102 |
| 9991 | Z2 | L33 | Q103 |
| 9992 | Z2 | L34 | Q1 |
| 9993 | Z2 | L34 | Q2 |
| 9994 | Z2 | L34 | Q3 |
| 9995 | Z2 | L34 | Q4 |
| 9996 | Z2 | L34 | Q5 |
| 9997 | Z2 | L34 | Q6 |
| 9998 | Z2 | L34 | Q7 |
| 9999 | Z2 | L34 | Q8 |
| 10000 | Z2 | L34 | Q9 |
| 10001 | Z2 | L34 | Q10 |
| 10002 | Z2 | L34 | Q11 |
| 10003 | Z2 | L34 | Q12 |
| 10004 | Z2 | L34 | Q13 |
| 10005 | Z2 | L34 | Q14 |
| 10006 | Z2 | L34 | Q15 |
| 10007 | Z2 | L34 | Q16 |
| 10008 | Z2 | L34 | Q17 |
| 10009 | Z2 | L34 | Q18 |
| 10010 | Z2 | L34 | Q19 |
| 10011 | Z2 | L34 | Q20 |
| 10012 | Z2 | L34 | Q21 |
| 10013 | Z2 | L34 | Q22 |
| 10014 | Z2 | L34 | Q23 |
| 10015 | Z2 | L34 | Q24 |
| 10016 | Z2 | L34 | Q25 |
| 10017 | Z2 | L34 | Q26 |
| 10018 | Z2 | L34 | Q27 |
| 10019 | Z2 | L34 | Q28 |
| 10020 | Z2 | L34 | Q29 |
| 10021 | Z2 | L34 | Q30 |
| 10022 | Z2 | L34 | Q31 |

TABLE 1-56

| | | | |
|---|---|---|---|
| 10023 | Z2 | L34 | Q32 |
| 10024 | Z2 | L34 | Q33 |
| 10025 | Z2 | L34 | Q34 |
| 10026 | Z2 | L34 | Q35 |
| 10027 | Z2 | L34 | Q36 |
| 10028 | Z2 | L34 | Q37 |
| 10029 | Z2 | L34 | Q38 |
| 10030 | Z2 | L34 | Q39 |
| 10031 | Z2 | L34 | Q40 |
| 10032 | Z2 | L34 | Q41 |
| 10033 | Z2 | L34 | Q42 |
| 10034 | Z2 | L34 | Q43 |
| 10035 | Z2 | L34 | Q44 |
| 10036 | Z2 | L34 | Q45 |
| 10037 | Z2 | L34 | Q46 |
| 10038 | Z2 | L34 | Q47 |
| 10039 | Z2 | L34 | Q48 |
| 10040 | Z2 | L34 | Q49 |
| 10041 | Z2 | L34 | Q50 |
| 10042 | Z2 | L34 | Q51 |
| 10043 | Z2 | L34 | Q52 |
| 10044 | Z2 | L34 | Q53 |
| 10045 | Z2 | L34 | Q54 |
| 10046 | Z2 | L34 | Q55 |
| 10047 | Z2 | L34 | Q56 |
| 10048 | Z2 | L34 | Q57 |
| 10049 | Z2 | L34 | Q58 |
| 10050 | Z2 | L34 | Q59 |
| 10051 | Z2 | L34 | Q60 |
| 10052 | Z2 | L34 | Q61 |
| 10053 | Z2 | L34 | Q62 |
| 10054 | Z2 | L34 | Q63 |
| 10055 | Z2 | L34 | Q64 |

TABLE 1-56-continued

| | | | |
|---|---|---|---|
| 10056 | Z2 | L34 | Q65 |
| 10057 | Z2 | L34 | Q66 |
| 10058 | Z2 | L34 | Q67 |
| 10059 | Z2 | L34 | Q68 |
| 10060 | Z2 | L34 | Q69 |
| 10061 | Z2 | L34 | Q70 |
| 10062 | Z2 | L34 | Q71 |
| 10063 | Z2 | L34 | Q72 |
| 10064 | Z2 | L34 | Q73 |
| 10065 | Z2 | L34 | Q74 |
| 10066 | Z2 | L34 | Q75 |
| 10067 | Z2 | L34 | Q76 |
| 10068 | Z2 | L34 | Q77 |
| 10069 | Z2 | L34 | Q78 |
| 10070 | Z2 | L34 | Q79 |
| 10071 | Z2 | L34 | Q80 |
| 10072 | Z2 | L34 | Q81 |
| 10073 | Z2 | L34 | Q82 |
| 10074 | Z2 | L34 | Q83 |
| 10075 | Z2 | L34 | Q84 |
| 10076 | Z2 | L34 | Q85 |
| 10077 | Z2 | L34 | Q86 |
| 10078 | Z2 | L34 | Q87 |
| 10079 | Z2 | L34 | Q88 |
| 10080 | Z2 | L34 | Q89 |
| 10081 | Z2 | L34 | Q90 |
| 10082 | Z2 | L34 | Q91 |
| 10083 | Z2 | L34 | Q92 |
| 10084 | Z2 | L34 | Q93 |
| 10085 | Z2 | L34 | Q94 |
| 10086 | Z2 | L34 | Q95 |
| 10087 | Z2 | L34 | Q96 |
| 10088 | Z2 | L34 | Q97 |
| 10089 | Z2 | L34 | Q98 |
| 10090 | Z2 | L34 | Q99 |
| 10091 | Z2 | L34 | Q100 |
| 10092 | Z2 | L34 | Q101 |
| 10093 | Z2 | L34 | Q102 |
| 10094 | Z2 | L34 | Q103 |
| 10095 | Z2 | L35 | Q1 |
| 10096 | Z2 | L35 | Q2 |
| 10097 | Z2 | L35 | Q3 |
| 10098 | Z2 | L35 | Q4 |
| 10099 | Z2 | L35 | Q5 |
| 10100 | Z2 | L35 | Q6 |
| 10101 | Z2 | L35 | Q7 |
| 10102 | Z2 | L35 | Q8 |
| 10103 | Z2 | L35 | Q9 |
| 10104 | Z2 | L35 | Q10 |
| 10105 | Z2 | L35 | Q11 |
| 10106 | Z2 | L35 | Q12 |
| 10107 | Z2 | L35 | Q13 |
| 10108 | Z2 | L35 | Q14 |
| 10109 | Z2 | L35 | Q15 |
| 10110 | Z2 | L35 | Q16 |
| 10111 | Z2 | L35 | Q17 |
| 10112 | Z2 | L35 | Q18 |
| 10113 | Z2 | L35 | Q19 |
| 10114 | Z2 | L35 | Q20 |
| 10115 | Z2 | L35 | Q21 |
| 10116 | Z2 | L35 | Q22 |
| 10117 | Z2 | L35 | Q23 |
| 10118 | Z2 | L35 | Q24 |
| 10119 | Z2 | L35 | Q25 |
| 10120 | Z2 | L35 | Q26 |
| 10121 | Z2 | L35 | Q27 |
| 10122 | Z2 | L35 | Q28 |
| 10123 | Z2 | L35 | Q29 |
| 10124 | Z2 | L35 | Q30 |
| 10125 | Z2 | L35 | Q31 |
| 10126 | Z2 | L35 | Q32 |
| 10127 | Z2 | L35 | Q33 |
| 10128 | Z2 | L35 | Q34 |
| 10129 | Z2 | L35 | Q35 |
| 10130 | Z2 | L35 | Q36 |
| 10131 | Z2 | L35 | Q37 |
| 10132 | Z2 | L35 | Q38 |
| 10133 | Z2 | L35 | Q39 |
| 10134 | Z2 | L35 | Q40 |
| 10135 | Z2 | L35 | Q41 |
| 10136 | Z2 | L35 | Q42 |
| 10137 | Z2 | L35 | Q43 |
| 10138 | Z2 | L35 | Q44 |
| 10139 | Z2 | L35 | Q45 |
| 10140 | Z2 | L35 | Q46 |
| 10141 | Z2 | L35 | Q47 |
| 10142 | Z2 | L35 | Q48 |
| 10143 | Z2 | L35 | Q49 |
| 10144 | Z2 | L35 | Q50 |
| 10145 | Z2 | L35 | Q51 |
| 10146 | Z2 | L35 | Q52 |
| 10147 | Z2 | L35 | Q53 |
| 10148 | Z2 | L35 | Q54 |
| 10149 | Z2 | L35 | Q55 |
| 10150 | Z2 | L35 | Q56 |
| 10151 | Z2 | L35 | Q57 |
| 10152 | Z2 | L35 | Q58 |
| 10153 | Z2 | L35 | Q59 |
| 10154 | Z2 | L35 | Q60 |
| 10155 | Z2 | L35 | Q61 |
| 10156 | Z2 | L35 | Q62 |
| 10157 | Z2 | L35 | Q63 |
| 10158 | Z2 | L35 | Q64 |
| 10159 | Z2 | L35 | Q65 |
| 10160 | Z2 | L35 | Q66 |
| 10161 | Z2 | L35 | Q67 |
| 10162 | Z2 | L35 | Q68 |
| 10163 | Z2 | L35 | Q69 |
| 10164 | Z2 | L35 | Q70 |
| 10165 | Z2 | L35 | Q71 |
| 10166 | Z2 | L35 | Q72 |
| 10167 | Z2 | L35 | Q73 |
| 10168 | Z2 | L35 | Q74 |
| 10169 | Z2 | L35 | Q75 |
| 10170 | Z2 | L35 | Q76 |
| 10171 | Z2 | L35 | Q77 |
| 10172 | Z2 | L35 | Q78 |
| 10173 | Z2 | L35 | Q79 |
| 10174 | Z2 | L35 | Q80 |
| 10175 | Z2 | L35 | Q81 |
| 10176 | Z2 | L35 | Q82 |
| 10177 | Z2 | L35 | Q83 |
| 10178 | Z2 | L35 | Q84 |
| 10179 | Z2 | L35 | Q85 |
| 10180 | Z2 | L35 | Q86 |
| 10181 | Z2 | L35 | Q87 |
| 10182 | Z2 | L35 | Q88 |
| 10183 | Z2 | L35 | Q89 |
| 10184 | Z2 | L35 | Q90 |
| 10185 | Z2 | L35 | Q91 |
| 10186 | Z2 | L35 | Q92 |
| 10187 | Z2 | L35 | Q93 |
| 10188 | Z2 | L35 | Q94 |
| 10189 | Z2 | L35 | Q95 |
| 10190 | Z2 | L35 | Q96 |
| 10191 | Z2 | L35 | Q97 |
| 10192 | Z2 | L35 | Q98 |
| 10193 | Z2 | L35 | Q99 |
| 10194 | Z2 | L35 | Q100 |
| 10195 | Z2 | L35 | Q101 |
| 10196 | Z2 | L35 | Q102 |
| 10197 | Z2 | L35 | Q103 |
| 10198 | Z2 | L36 | Q1 |
| 10199 | Z2 | L36 | Q2 |
| 10200 | Z2 | L36 | Q3 |
| 10201 | Z2 | L36 | Q4 |
| 10202 | Z2 | L36 | Q5 |
| 10203 | Z2 | L36 | Q6 |
| 10204 | Z2 | L36 | Q7 |
| 10205 | Z2 | L36 | Q8 |
| 10206 | Z2 | L36 | Q9 |
| 10207 | Z2 | L36 | Q10 |
| 10208 | Z2 | L36 | Q11 |
| 10209 | Z2 | L36 | Q12 |
| 10210 | Z2 | L36 | Q13 |
| 10211 | Z2 | L36 | Q14 |
| 10212 | Z2 | L36 | Q15 |
| 10213 | Z2 | L36 | Q16 |
| 10214 | Z2 | L36 | Q17 |
| 10215 | Z2 | L36 | Q18 |

TABLE 1-56-continued

| | | | |
|---|---|---|---|
| 10216 | Z2 | L36 | Q19 |
| 10217 | Z2 | L36 | Q20 |
| 10218 | Z2 | L36 | Q21 |
| 10219 | Z2 | L36 | Q22 |
| 10220 | Z2 | L36 | Q23 |
| 10221 | Z2 | L36 | Q24 |
| 10222 | Z2 | L36 | Q25 |
| 10223 | Z2 | L36 | Q26 |

TABLE 1-57

| | | | |
|---|---|---|---|
| 10224 | Z2 | L36 | Q27 |
| 10225 | Z2 | L36 | Q28 |
| 10226 | Z2 | L36 | Q29 |
| 10227 | Z2 | L36 | Q30 |
| 10228 | Z2 | L36 | Q31 |
| 10229 | Z2 | L36 | Q32 |
| 10230 | Z2 | L36 | Q33 |
| 10231 | Z2 | L36 | Q34 |
| 10232 | Z2 | L36 | Q35 |
| 10233 | Z2 | L36 | Q36 |
| 10234 | Z2 | L36 | Q37 |
| 10235 | Z2 | L36 | Q38 |
| 10236 | Z2 | L36 | Q39 |
| 10237 | Z2 | L36 | Q40 |
| 10238 | Z2 | L36 | Q41 |
| 10239 | Z2 | L36 | Q42 |
| 10240 | Z2 | L36 | Q43 |
| 10241 | Z2 | L36 | Q44 |
| 10242 | Z2 | L36 | Q45 |
| 10243 | Z2 | L36 | Q46 |
| 10244 | Z2 | L36 | Q47 |
| 10245 | Z2 | L36 | Q48 |
| 10246 | Z2 | L36 | Q49 |
| 10247 | Z2 | L36 | Q50 |
| 10248 | Z2 | L36 | Q51 |
| 10249 | Z2 | L36 | Q52 |
| 10250 | Z2 | L36 | Q53 |
| 10251 | Z2 | L36 | Q54 |
| 10252 | Z2 | L36 | Q55 |
| 10253 | Z2 | L36 | Q56 |
| 10254 | Z2 | L36 | Q57 |
| 10255 | Z2 | L36 | Q58 |
| 10256 | Z2 | L36 | Q59 |
| 10257 | Z2 | L36 | Q60 |
| 10258 | Z2 | L36 | Q61 |
| 10259 | Z2 | L36 | Q62 |
| 10260 | Z2 | L36 | Q63 |
| 10261 | Z2 | L36 | Q64 |
| 10262 | Z2 | L36 | Q65 |
| 10263 | Z2 | L36 | Q66 |
| 10264 | Z2 | L36 | Q67 |
| 10265 | Z2 | L36 | Q68 |
| 10266 | Z2 | L36 | Q69 |
| 10267 | Z2 | L36 | Q70 |
| 10268 | Z2 | L36 | Q71 |
| 10269 | Z2 | L36 | Q72 |
| 10270 | Z2 | L36 | Q73 |
| 10271 | Z2 | L36 | Q74 |
| 10272 | Z2 | L36 | Q75 |
| 10273 | Z2 | L36 | Q76 |
| 10274 | Z2 | L36 | Q77 |
| 10275 | Z2 | L36 | Q78 |
| 10276 | Z2 | L36 | Q79 |
| 10277 | Z2 | L36 | Q80 |
| 10278 | Z2 | L36 | Q81 |
| 10279 | Z2 | L36 | Q82 |
| 10280 | Z2 | L36 | Q83 |
| 10281 | Z2 | L36 | Q84 |
| 10282 | Z2 | L36 | Q85 |
| 10283 | Z2 | L36 | Q86 |
| 10284 | Z2 | L36 | Q87 |
| 10285 | Z2 | L36 | Q88 |
| 10286 | Z2 | L36 | Q89 |
| 10287 | Z2 | L36 | Q90 |
| 10288 | Z2 | L36 | Q91 |
| 10289 | Z2 | L36 | Q92 |

TABLE 1-57-continued

| | | | |
|---|---|---|---|
| 10290 | Z2 | L36 | Q93 |
| 10291 | Z2 | L36 | Q94 |
| 10292 | Z2 | L36 | Q95 |
| 10293 | Z2 | L36 | Q96 |
| 10294 | Z2 | L36 | Q97 |
| 10295 | Z2 | L36 | Q98 |
| 10296 | Z2 | L36 | Q99 |
| 10297 | Z2 | L36 | Q100 |
| 10298 | Z2 | L36 | Q101 |
| 10299 | Z2 | L36 | Q102 |
| 10300 | Z2 | L36 | Q103 |
| 10301 | Z3 | L15 | Q1 |
| 10302 | Z3 | L15 | Q2 |
| 10303 | Z3 | L15 | Q3 |
| 10304 | Z3 | L15 | Q4 |
| 10305 | Z3 | L15 | Q5 |
| 10306 | Z3 | L15 | Q6 |
| 10307 | Z3 | L15 | Q7 |
| 10308 | Z3 | L15 | Q8 |
| 10309 | Z3 | L15 | Q9 |
| 10310 | Z3 | L15 | Q10 |
| 10311 | Z3 | L15 | Q11 |
| 10312 | Z3 | L15 | Q12 |
| 10313 | Z3 | L15 | Q13 |
| 10314 | Z3 | L15 | Q14 |
| 10315 | Z3 | L15 | Q15 |
| 10316 | Z3 | L15 | Q16 |
| 10317 | Z3 | L15 | Q17 |
| 10318 | Z3 | L15 | Q18 |
| 10319 | Z3 | L15 | Q19 |
| 10320 | Z3 | L15 | Q20 |
| 10321 | Z3 | L15 | Q21 |
| 10322 | Z3 | L15 | Q22 |
| 10323 | Z3 | L15 | Q23 |
| 10324 | Z3 | L15 | Q24 |
| 10325 | Z3 | L15 | Q25 |
| 10326 | Z3 | L15 | Q26 |
| 10327 | Z3 | L15 | Q27 |
| 10328 | Z3 | L15 | Q28 |
| 10329 | Z3 | L15 | Q29 |
| 10330 | Z3 | L15 | Q30 |
| 10331 | Z3 | L15 | Q31 |
| 10332 | Z3 | L05 | Q32 |
| 10333 | Z3 | L15 | Q33 |
| 10334 | Z3 | L15 | Q34 |
| 10335 | Z3 | L15 | Q35 |
| 10336 | Z3 | L15 | Q36 |
| 10337 | Z3 | L15 | Q37 |
| 10338 | Z3 | L15 | Q38 |
| 10339 | Z3 | L15 | Q39 |
| 10340 | Z3 | L15 | Q40 |
| 10341 | Z3 | L15 | Q41 |
| 10342 | Z3 | L15 | Q42 |
| 10343 | Z3 | L15 | Q43 |
| 10344 | Z3 | L15 | Q44 |
| 10345 | Z3 | L15 | Q45 |
| 10346 | Z3 | L15 | Q46 |
| 10347 | Z3 | L15 | Q47 |
| 10348 | Z3 | L15 | Q48 |
| 10349 | Z3 | L15 | Q49 |
| 10350 | Z3 | L15 | Q50 |
| 10351 | Z3 | L15 | Q51 |
| 10352 | Z3 | L15 | Q52 |
| 10353 | Z3 | L15 | Q53 |
| 10354 | Z3 | L15 | Q54 |
| 10355 | Z3 | L15 | Q55 |
| 10356 | Z3 | L15 | Q56 |
| 10357 | Z3 | L15 | Q57 |
| 10358 | Z3 | L15 | Q58 |
| 10359 | Z3 | L15 | Q59 |
| 10360 | Z3 | L15 | Q60 |
| 10361 | Z3 | L15 | Q61 |
| 10362 | Z3 | L15 | Q62 |
| 10363 | Z3 | L15 | Q63 |
| 10364 | Z3 | L15 | Q64 |
| 10365 | Z3 | L15 | Q65 |
| 10366 | Z3 | L15 | Q66 |
| 10367 | Z3 | L15 | Q67 |
| 10368 | Z3 | L15 | Q68 |
| 10369 | Z3 | L15 | Q69 |

TABLE 1-57-continued

| | | | |
|---|---|---|---|
| 10370 | Z3 | L15 | Q70 |
| 10371 | Z3 | L15 | Q71 |
| 10372 | Z3 | L15 | Q72 |
| 10373 | Z3 | L15 | Q73 |
| 10374 | Z3 | L15 | Q74 |
| 10375 | Z3 | L15 | Q75 |
| 10376 | Z3 | L15 | Q76 |
| 10377 | Z3 | L15 | Q77 |
| 10378 | Z3 | L15 | Q78 |
| 10379 | Z3 | L15 | Q79 |
| 10380 | Z3 | L15 | Q80 |
| 10381 | Z3 | L15 | Q81 |
| 10382 | Z3 | L15 | Q82 |
| 10383 | Z3 | L15 | Q83 |
| 10384 | Z3 | L15 | Q84 |
| 10385 | Z3 | L15 | Q85 |
| 10386 | Z3 | L15 | Q86 |
| 10387 | Z3 | L15 | Q87 |
| 10388 | Z3 | L15 | Q88 |
| 10389 | Z3 | L15 | Q89 |
| 10390 | Z3 | L15 | Q90 |
| 10391 | Z3 | L15 | Q91 |
| 10392 | Z3 | L15 | Q92 |
| 10393 | Z3 | L15 | Q93 |
| 10394 | Z3 | L15 | Q94 |
| 10395 | Z3 | L15 | Q95 |
| 10396 | Z3 | L15 | Q96 |
| 10397 | Z3 | L15 | Q97 |
| 10398 | Z3 | L15 | Q98 |
| 10399 | Z3 | L15 | Q99 |
| 10400 | Z3 | L15 | Q100 |
| 10401 | Z3 | L15 | Q101 |
| 10402 | Z3 | L15 | Q102 |
| 10403 | Z3 | L15 | Q103 |
| 10404 | Z3 | L16 | Q1 |
| 10405 | Z3 | L16 | Q2 |
| 10406 | Z3 | L16 | Q3 |
| 10407 | Z3 | L16 | Q4 |
| 10408 | Z3 | L16 | Q5 |
| 10409 | Z3 | L16 | Q6 |
| 10410 | Z3 | L16 | Q7 |
| 10411 | Z3 | L16 | Q8 |
| 10412 | Z3 | L16 | Q9 |
| 10413 | Z3 | L16 | Q10 |
| 10414 | Z3 | L16 | Q11 |
| 10415 | Z3 | L16 | Q12 |
| 10416 | Z3 | L16 | Q13 |
| 10417 | Z3 | L16 | Q14 |
| 10418 | Z3 | L16 | Q15 |
| 10419 | Z3 | L16 | Q16 |
| 10420 | Z3 | L16 | Q17 |
| 10421 | Z3 | L16 | Q18 |
| 10422 | Z3 | L16 | Q19 |
| 10423 | Z3 | L16 | Q20 |
| 10424 | Z3 | L16 | Q21 |

TABLE 1-58

| | | | |
|---|---|---|---|
| 10425 | Z3 | L16 | Q22 |
| 10426 | Z3 | L16 | Q23 |
| 10427 | Z3 | L16 | Q24 |
| 10428 | Z3 | L16 | Q25 |
| 10429 | Z3 | L16 | Q26 |
| 10430 | Z3 | L16 | Q27 |
| 10431 | Z3 | L16 | Q28 |
| 10432 | Z3 | L16 | Q29 |
| 10433 | Z3 | L16 | Q30 |
| 10434 | Z3 | L16 | Q31 |
| 10435 | Z3 | L16 | Q32 |
| 10436 | Z3 | L16 | Q33 |
| 10437 | Z3 | L16 | Q34 |
| 10438 | Z3 | L16 | Q35 |
| 10439 | Z3 | L16 | Q36 |
| 10440 | Z3 | L16 | Q37 |
| 10441 | Z3 | L16 | Q38 |
| 10442 | Z3 | L16 | Q39 |
| 10443 | Z3 | L16 | Q40 |

TABLE 1-58-continued

| | | | |
|---|---|---|---|
| 10444 | Z3 | L16 | Q41 |
| 10445 | Z3 | L16 | Q42 |
| 10446 | Z3 | L16 | Q43 |
| 10447 | Z3 | L16 | Q44 |
| 10448 | Z3 | L16 | Q45 |
| 10449 | Z3 | L16 | Q46 |
| 10450 | Z3 | L16 | Q47 |
| 10451 | Z3 | L16 | Q48 |
| 10452 | Z3 | L16 | Q49 |
| 10453 | Z3 | L16 | Q50 |
| 10454 | Z3 | L16 | Q51 |
| 10455 | Z3 | L16 | Q52 |
| 10456 | Z3 | L16 | Q53 |
| 10457 | Z3 | L16 | Q54 |
| 10458 | Z3 | L16 | Q55 |
| 10459 | Z3 | L16 | Q56 |
| 10460 | Z3 | L16 | Q57 |
| 10461 | Z3 | L16 | Q58 |
| 10462 | Z3 | L16 | Q59 |
| 10463 | Z3 | L16 | Q60 |
| 10464 | Z3 | L16 | Q61 |
| 10465 | Z3 | L16 | Q62 |
| 10466 | Z3 | L16 | Q63 |
| 10467 | Z3 | L16 | Q64 |
| 10468 | Z3 | L16 | Q65 |
| 10469 | Z3 | L16 | Q66 |
| 10470 | Z3 | L16 | Q67 |
| 10471 | Z3 | L16 | Q68 |
| 10472 | Z3 | L16 | Q68 |
| 10473 | Z3 | L16 | Q70 |
| 10474 | Z3 | L16 | Q71 |
| 10475 | Z3 | L16 | Q72 |
| 10476 | Z3 | L16 | Q73 |
| 10477 | Z3 | L16 | Q74 |
| 10478 | Z3 | L16 | Q75 |
| 10479 | Z3 | L16 | Q76 |
| 10480 | Z3 | L16 | Q77 |
| 10481 | Z3 | L16 | Q78 |
| 10482 | Z3 | L16 | Q79 |
| 10483 | Z3 | L16 | Q80 |
| 10484 | Z3 | L16 | Q81 |
| 10485 | Z3 | L16 | Q82 |
| 10486 | Z3 | L16 | Q83 |
| 10487 | Z3 | L16 | Q84 |
| 10488 | Z3 | L16 | Q85 |
| 10489 | Z3 | L16 | Q86 |
| 10490 | Z3 | L16 | Q87 |
| 10491 | Z3 | L16 | Q88 |
| 10492 | Z3 | L16 | Q89 |
| 10493 | Z3 | L16 | Q90 |
| 10494 | Z3 | L16 | Q91 |
| 10495 | Z3 | L16 | Q92 |
| 10496 | Z3 | L16 | Q93 |
| 10497 | Z3 | L16 | Q94 |
| 10498 | Z3 | L16 | Q95 |
| 10499 | Z3 | L16 | Q96 |
| 10500 | Z3 | L16 | Q97 |
| 10501 | Z3 | L16 | Q98 |
| 10502 | Z3 | L16 | Q99 |
| 10503 | Z3 | L16 | Q100 |
| 10504 | Z3 | L16 | Q101 |
| 10505 | Z3 | L16 | Q102 |
| 10506 | Z3 | L16 | Q103 |
| 10507 | Z3 | L17 | Q1 |
| 10508 | Z3 | L17 | Q2 |
| 10509 | Z3 | L17 | Q3 |
| 10510 | Z3 | L17 | Q4 |
| 10511 | Z3 | L17 | Q5 |
| 10512 | Z3 | L17 | Q6 |
| 10513 | Z3 | L17 | Q7 |
| 10514 | Z3 | L17 | Q8 |
| 10515 | Z3 | L17 | Q9 |
| 10516 | Z3 | L17 | Q10 |
| 10517 | Z3 | L17 | Q11 |
| 10518 | Z3 | L17 | Q12 |
| 10519 | Z3 | L17 | Q13 |
| 10520 | Z3 | L17 | Q14 |
| 10521 | Z3 | L17 | Q15 |
| 10522 | Z3 | L17 | Q16 |
| 10523 | Z3 | L17 | Q17 |

TABLE 1-58-continued

| | | | |
|---|---|---|---|
| 10524 | Z3 | L17 | Q18 |
| 10525 | Z3 | L17 | Q19 |
| 10526 | Z3 | L17 | Q20 |
| 10527 | Z3 | L17 | Q21 |
| 10528 | Z3 | L17 | Q22 |
| 10529 | Z3 | L17 | Q23 |
| 10530 | Z3 | L17 | Q24 |
| 10531 | Z3 | L17 | Q25 |
| 10532 | Z3 | L17 | Q26 |
| 10533 | Z3 | L17 | Q27 |
| 10534 | Z3 | L17 | Q28 |
| 10535 | Z3 | L17 | Q29 |
| 10536 | Z3 | L17 | Q30 |
| 10537 | Z3 | L17 | Q31 |
| 10538 | Z3 | L17 | Q32 |
| 10539 | Z3 | L17 | Q33 |
| 10540 | Z3 | L17 | Q34 |
| 10541 | Z3 | L17 | Q35 |
| 10542 | Z3 | L17 | Q36 |
| 10543 | Z3 | L17 | Q37 |
| 10544 | Z3 | L17 | Q38 |
| 10545 | Z3 | L17 | Q39 |
| 10546 | Z3 | L17 | Q40 |
| 10547 | Z3 | L17 | Q41 |
| 10548 | Z3 | L17 | Q42 |
| 10549 | Z3 | L17 | Q43 |
| 10550 | Z3 | L17 | Q44 |
| 10551 | Z3 | L17 | Q45 |
| 10552 | Z3 | L17 | Q46 |
| 10553 | Z3 | L17 | Q47 |
| 10554 | Z3 | L17 | Q48 |
| 10555 | Z3 | L17 | Q49 |
| 10556 | Z3 | L17 | Q50 |
| 10557 | Z3 | L17 | Q51 |
| 10558 | Z3 | L17 | Q52 |
| 10559 | Z3 | L17 | Q53 |
| 10560 | Z3 | L17 | Q54 |
| 10561 | Z3 | L17 | Q55 |
| 10562 | Z3 | L17 | Q56 |
| 10563 | Z3 | L17 | Q57 |
| 10564 | Z3 | L17 | Q58 |
| 10565 | Z3 | L17 | Q59 |
| 10566 | Z3 | L17 | Q60 |
| 10567 | Z3 | L17 | Q61 |
| 10568 | Z3 | L17 | Q62 |
| 10569 | Z3 | L17 | Q63 |
| 10570 | Z3 | L17 | Q64 |
| 10571 | Z3 | L17 | Q65 |
| 10572 | Z3 | L17 | Q66 |
| 10573 | Z3 | L17 | Q67 |
| 10574 | Z3 | L17 | Q68 |
| 10575 | Z3 | L17 | Q69 |
| 10576 | Z3 | L17 | Q70 |
| 10577 | Z3 | L17 | Q71 |
| 10578 | Z3 | L17 | Q72 |
| 10579 | Z3 | L17 | Q73 |
| 10580 | Z3 | L17 | Q74 |
| 10581 | Z3 | L17 | Q75 |
| 10582 | Z3 | L17 | Q76 |
| 10583 | Z3 | L17 | Q77 |
| 10584 | Z3 | L17 | Q78 |
| 10585 | Z3 | L17 | Q79 |
| 10586 | Z3 | L17 | Q80 |
| 10587 | Z3 | L17 | Q81 |
| 10588 | Z3 | L17 | Q82 |
| 10589 | Z3 | L17 | Q83 |
| 10590 | Z3 | L17 | Q84 |
| 10591 | Z3 | L17 | Q85 |
| 10592 | Z3 | L17 | Q86 |
| 10593 | Z3 | L17 | Q87 |
| 10594 | Z3 | L17 | Q88 |
| 10595 | Z3 | L17 | Q89 |
| 10596 | Z3 | L17 | Q90 |
| 10597 | Z3 | L17 | Q91 |
| 10598 | Z3 | L17 | Q92 |
| 10599 | Z3 | L17 | Q93 |
| 10600 | Z3 | L17 | Q94 |
| 10601 | Z3 | L17 | Q95 |
| 10602 | Z3 | L17 | Q96 |
| 10603 | Z3 | L17 | Q97 |
| 10604 | Z3 | L17 | Q98 |
| 10605 | Z3 | L17 | Q99 |
| 10606 | Z3 | L17 | Q100 |
| 10607 | Z3 | L17 | Q101 |
| 10608 | Z3 | L17 | Q102 |
| 10609 | Z3 | L17 | Q103 |
| 10610 | Z3 | L18 | Q1 |
| 10611 | Z3 | L18 | Q2 |
| 10612 | Z3 | L18 | Q3 |
| 10613 | Z3 | L18 | Q4 |
| 10614 | Z3 | L18 | Q5 |
| 10615 | Z3 | L18 | Q6 |
| 10616 | Z3 | L18 | Q7 |
| 10617 | Z3 | L18 | Q8 |
| 10618 | Z3 | L18 | Q9 |
| 10619 | Z3 | L18 | Q10 |
| 10620 | Z3 | L18 | Q11 |
| 10621 | Z3 | L18 | Q12 |
| 10622 | Z3 | L18 | Q13 |
| 10623 | Z3 | L18 | Q14 |
| 10624 | Z3 | L18 | Q15 |
| 10625 | Z3 | L18 | Q16 |

TABLE 1-59

| | | | |
|---|---|---|---|
| 10626 | Z3 | L18 | Q17 |
| 10627 | Z3 | L18 | Q18 |
| 10628 | Z3 | L18 | Q19 |
| 10629 | Z3 | L18 | Q20 |
| 10630 | Z3 | L18 | Q21 |
| 10631 | Z3 | L18 | Q22 |
| 10632 | Z3 | L18 | Q23 |
| 10633 | Z3 | L18 | Q24 |
| 10634 | Z3 | L18 | Q25 |
| 10635 | Z3 | L18 | Q26 |
| 10636 | Z3 | L18 | Q27 |
| 10637 | Z3 | L18 | Q28 |
| 10638 | Z3 | L18 | Q29 |
| 10639 | Z3 | L18 | Q30 |
| 10640 | Z3 | L18 | Q31 |
| 10641 | Z3 | L18 | Q32 |
| 10642 | Z3 | L18 | Q33 |
| 10643 | Z3 | L18 | Q34 |
| 10644 | Z3 | L18 | Q35 |
| 10645 | Z3 | L18 | Q36 |
| 10646 | Z3 | L18 | Q37 |
| 10647 | Z3 | L18 | Q38 |
| 10648 | Z3 | L18 | Q39 |
| 10649 | Z3 | L18 | Q40 |
| 10650 | Z3 | L18 | Q41 |
| 10651 | Z3 | L18 | Q42 |
| 10652 | Z3 | L18 | Q43 |
| 10653 | Z3 | L18 | Q44 |
| 10654 | Z3 | L18 | Q45 |
| 10655 | Z3 | L18 | Q46 |
| 10656 | Z3 | L18 | Q47 |
| 10657 | Z3 | L18 | Q48 |
| 10658 | Z3 | L18 | Q49 |
| 10659 | Z3 | L18 | Q50 |
| 10660 | Z3 | L18 | Q51 |
| 10661 | Z3 | L18 | Q52 |
| 10662 | Z3 | L18 | Q53 |
| 10663 | Z3 | L18 | Q54 |
| 10664 | Z3 | L18 | Q55 |
| 10665 | Z3 | L18 | Q56 |
| 10666 | Z3 | L18 | Q57 |
| 10667 | Z3 | L18 | Q58 |
| 10668 | Z3 | L18 | Q59 |
| 10669 | Z3 | L18 | Q60 |
| 10670 | Z3 | L18 | Q61 |
| 10671 | Z3 | L18 | Q62 |
| 10672 | Z3 | L18 | Q63 |
| 10673 | Z3 | L18 | Q64 |
| 10674 | Z3 | L18 | Q65 |
| 10675 | Z3 | L18 | Q66 |
| 10676 | Z3 | L18 | Q67 |
| 10677 | Z3 | L18 | Q68 |

TABLE 1-59-continued

| | | | |
|---|---|---|---|
| 10678 | Z3 | L18 | Q69 |
| 10679 | Z3 | L18 | Q70 |
| 10680 | Z3 | L18 | Q71 |
| 10681 | Z3 | L18 | Q72 |
| 10682 | Z3 | L18 | Q73 |
| 10683 | Z3 | L18 | Q74 |
| 10684 | Z3 | L18 | Q75 |
| 10685 | Z3 | L18 | Q76 |
| 10686 | Z3 | L18 | Q77 |
| 10687 | Z3 | L18 | Q78 |
| 10688 | Z3 | L18 | Q79 |
| 10689 | Z3 | L18 | Q80 |
| 10690 | Z3 | L18 | Q81 |
| 10691 | Z3 | L18 | Q82 |
| 10692 | Z3 | L18 | Q83 |
| 10693 | Z3 | L18 | Q84 |
| 10694 | Z3 | L18 | Q85 |
| 10695 | Z3 | L18 | Q86 |
| 10696 | Z3 | L18 | Q87 |
| 10697 | Z3 | L18 | Q88 |
| 10698 | Z3 | L18 | Q89 |
| 10699 | Z3 | L18 | Q90 |
| 10700 | Z3 | L18 | Q91 |
| 10701 | Z3 | L18 | Q92 |
| 10702 | Z3 | L18 | Q93 |
| 10703 | Z3 | L18 | Q94 |
| 10704 | Z3 | L18 | Q95 |
| 10705 | Z3 | L18 | Q96 |
| 10706 | Z3 | L18 | Q97 |
| 10707 | Z3 | L18 | Q98 |
| 10708 | Z3 | L18 | Q99 |
| 10709 | Z3 | L18 | Q100 |
| 10710 | Z3 | L18 | Q101 |
| 10711 | Z3 | L18 | Q102 |
| 10712 | Z3 | L18 | Q103 |
| 10713 | Z3 | L19 | Q1 |
| 10714 | Z3 | L19 | Q2 |
| 10715 | Z3 | L19 | Q3 |
| 10716 | Z3 | L19 | Q4 |
| 10717 | Z3 | L19 | Q5 |
| 10718 | Z3 | L19 | Q6 |
| 10719 | Z3 | L19 | Q7 |
| 10720 | Z3 | L19 | Q8 |
| 10721 | Z3 | L19 | Q9 |
| 10722 | Z3 | L19 | Q10 |
| 10723 | Z3 | L19 | Q11 |
| 10724 | Z3 | L19 | Q12 |
| 10725 | Z3 | L19 | Q13 |
| 10726 | Z3 | L19 | Q14 |
| 10727 | Z3 | L19 | Q15 |
| 10728 | Z3 | L19 | Q16 |
| 10729 | Z3 | L19 | Q17 |
| 10730 | Z3 | L19 | Q18 |
| 10731 | Z3 | L19 | Q19 |
| 10732 | Z3 | L19 | Q20 |
| 10733 | Z3 | L19 | Q21 |
| 10734 | Z3 | L19 | Q22 |
| 10735 | Z3 | L19 | Q23 |
| 10736 | Z3 | L19 | Q24 |
| 10737 | Z3 | L19 | Q25 |
| 10738 | Z3 | L19 | Q26 |
| 10739 | Z3 | L19 | Q27 |
| 10740 | Z3 | L19 | Q28 |
| 10741 | Z3 | L19 | Q29 |
| 10742 | Z3 | L19 | Q30 |
| 10743 | Z3 | L19 | Q31 |
| 10744 | Z3 | L19 | Q32 |
| 10745 | Z3 | L19 | Q33 |
| 10746 | Z3 | L19 | Q34 |
| 10747 | Z3 | L19 | Q35 |
| 10748 | Z3 | L19 | Q36 |
| 10749 | Z3 | L19 | Q37 |
| 10750 | Z3 | L19 | Q38 |
| 10751 | Z3 | L19 | Q39 |
| 10752 | Z3 | L19 | Q40 |
| 10753 | Z3 | L19 | Q41 |
| 10754 | Z3 | L19 | Q42 |
| 10755 | Z3 | L19 | Q43 |
| 10756 | Z3 | L19 | Q44 |
| 10757 | Z3 | L19 | Q45 |
| 10758 | Z3 | L19 | Q46 |
| 10759 | Z3 | L19 | Q47 |
| 10760 | Z3 | L19 | Q48 |
| 10761 | Z3 | L19 | Q49 |
| 10762 | Z3 | L19 | Q50 |
| 10763 | Z3 | L19 | Q51 |
| 10764 | Z3 | L19 | Q52 |
| 10765 | Z3 | L19 | Q53 |
| 10766 | Z3 | L19 | Q54 |
| 10767 | Z3 | L19 | Q55 |
| 10768 | Z3 | L19 | Q56 |
| 10769 | Z3 | L19 | Q57 |
| 10770 | Z3 | L19 | Q58 |
| 10771 | Z3 | L19 | Q59 |
| 10772 | Z3 | L19 | Q60 |
| 10773 | Z3 | L19 | Q61 |
| 10774 | Z3 | L19 | Q62 |
| 10775 | Z3 | L19 | Q63 |
| 10776 | Z3 | L19 | Q64 |
| 10777 | Z3 | L19 | Q65 |
| 10778 | Z3 | L19 | Q66 |
| 10779 | Z3 | L19 | Q67 |
| 10780 | Z3 | L19 | Q68 |
| 10781 | Z3 | L19 | Q69 |
| 10782 | Z3 | L19 | Q70 |
| 10783 | Z3 | L19 | Q71 |
| 10784 | Z3 | L19 | Q72 |
| 10785 | Z3 | L19 | Q73 |
| 10786 | Z3 | L19 | Q74 |
| 10787 | Z3 | L19 | Q75 |
| 10788 | Z3 | L19 | Q76 |
| 10789 | Z3 | L19 | Q77 |
| 10790 | Z3 | L19 | Q78 |
| 10791 | Z3 | L19 | Q79 |
| 10792 | Z3 | L19 | Q80 |
| 10793 | Z3 | L19 | Q81 |
| 10794 | Z3 | L19 | Q82 |
| 10795 | Z3 | L19 | Q83 |
| 10796 | Z3 | L19 | Q84 |
| 10797 | Z3 | L19 | Q85 |
| 10798 | Z3 | L19 | Q86 |
| 10799 | Z3 | L19 | Q87 |
| 10800 | Z3 | L19 | Q88 |
| 10801 | Z3 | L19 | Q89 |
| 10802 | Z3 | L19 | Q90 |
| 10803 | Z3 | L19 | Q91 |
| 10804 | Z3 | L19 | Q92 |
| 10805 | Z3 | L19 | Q93 |
| 10806 | Z3 | L19 | Q94 |
| 10807 | Z3 | L19 | Q95 |
| 10808 | Z3 | L19 | Q96 |
| 10809 | Z3 | L19 | Q97 |
| 10810 | Z3 | L19 | Q98 |
| 10811 | Z3 | L19 | Q99 |
| 10812 | Z3 | L19 | Q100 |
| 10813 | Z3 | L19 | Q101 |
| 10814 | Z3 | L19 | Q102 |
| 10815 | Z3 | L19 | Q103 |
| 10816 | Z3 | L20 | Q1 |
| 10817 | Z3 | L20 | Q2 |
| 10818 | Z3 | L20 | Q3 |
| 10819 | Z3 | L20 | Q4 |
| 10820 | Z3 | L20 | Q5 |
| 10821 | Z3 | L20 | Q6 |
| 10822 | Z3 | L20 | Q7 |
| 10823 | Z3 | L20 | Q8 |
| 10824 | Z3 | L20 | Q9 |
| 10825 | Z3 | L20 | Q10 |
| 10826 | Z3 | L20 | Q11 |

TABLE 1-60

| | | | |
|---|---|---|---|
| 10827 | Z3 | L20 | Q12 |
| 10828 | Z3 | L20 | Q13 |
| 10829 | Z3 | L20 | Q14 |
| 10830 | Z3 | L20 | Q15 |
| 10831 | Z3 | L20 | Q16 |

TABLE 1-60-continued

| | | | |
|---|---|---|---|
| 10832 | Z3 | L20 | Q17 |
| 10833 | Z3 | L20 | Q18 |
| 10834 | Z3 | L20 | Q19 |
| 10835 | Z3 | L20 | Q20 |
| 10836 | Z3 | L20 | Q21 |
| 10837 | Z3 | L20 | Q22 |
| 10838 | Z3 | L20 | Q23 |
| 10839 | Z3 | L20 | Q24 |
| 10840 | Z3 | L20 | Q25 |
| 10841 | Z3 | L20 | Q26 |
| 10842 | Z3 | L20 | Q27 |
| 10843 | Z3 | L20 | Q28 |
| 10844 | Z3 | L20 | Q29 |
| 10845 | Z3 | L20 | Q30 |
| 10846 | Z3 | L20 | Q31 |
| 10847 | Z3 | L20 | Q32 |
| 10848 | Z3 | L20 | Q33 |
| 10849 | Z3 | L20 | Q34 |
| 10850 | Z3 | L20 | Q35 |
| 10851 | Z3 | L20 | Q36 |
| 10852 | Z3 | L20 | Q37 |
| 10853 | Z3 | L20 | Q38 |
| 10854 | Z3 | L20 | Q39 |
| 10855 | Z3 | L20 | Q40 |
| 10856 | Z3 | L20 | Q41 |
| 10857 | Z3 | L20 | Q42 |
| 10858 | Z3 | L20 | Q43 |
| 10859 | Z3 | L20 | Q44 |
| 10860 | Z3 | L20 | Q45 |
| 10861 | Z3 | L20 | Q46 |
| 10862 | Z3 | L20 | Q47 |
| 10863 | Z3 | L20 | Q48 |
| 10864 | Z3 | L20 | Q49 |
| 10865 | Z3 | L20 | Q50 |
| 10866 | Z3 | L20 | Q51 |
| 10867 | Z3 | L20 | Q52 |
| 10868 | Z3 | L20 | Q53 |
| 10869 | Z3 | L20 | Q54 |
| 10870 | Z3 | L20 | Q55 |
| 10871 | Z3 | L20 | Q56 |
| 10872 | Z3 | L20 | Q57 |
| 10873 | Z3 | L20 | Q58 |
| 10874 | Z3 | L20 | Q59 |
| 10875 | Z3 | L20 | Q60 |
| 10876 | Z3 | L20 | Q61 |
| 10877 | Z3 | L20 | Q62 |
| 10878 | Z3 | L20 | Q63 |
| 10879 | Z3 | L20 | Q64 |
| 10880 | Z3 | L20 | Q65 |
| 10881 | Z3 | L20 | Q66 |
| 10882 | Z3 | L20 | Q67 |
| 10883 | Z3 | L20 | Q68 |
| 10884 | Z3 | L20 | Q69 |
| 10885 | Z3 | L20 | Q70 |
| 10886 | Z3 | L20 | Q71 |
| 10887 | Z3 | L20 | Q72 |
| 10888 | Z3 | L20 | Q73 |
| 10889 | Z3 | L20 | Q74 |
| 10890 | Z3 | L20 | Q75 |
| 10891 | Z3 | L20 | Q76 |
| 10892 | Z3 | L20 | Q77 |
| 10893 | Z3 | L20 | Q78 |
| 10894 | Z3 | L20 | Q79 |
| 10895 | Z3 | L20 | Q80 |
| 10896 | Z3 | L20 | Q81 |
| 10897 | Z3 | L20 | Q82 |
| 10898 | Z3 | L20 | Q83 |
| 10899 | Z3 | L20 | Q84 |
| 10900 | Z3 | L20 | Q85 |
| 10901 | Z3 | L20 | Q86 |
| 10902 | Z3 | L20 | Q87 |
| 10903 | Z3 | L20 | Q88 |
| 10904 | Z3 | L20 | Q89 |
| 10905 | Z3 | L20 | Q90 |
| 10906 | Z3 | L20 | Q91 |
| 10907 | Z3 | L20 | Q92 |
| 10908 | Z3 | L20 | Q93 |
| 10909 | Z3 | L20 | Q94 |
| 10910 | Z3 | L20 | Q95 |
| 10911 | Z3 | L20 | Q96 |
| 10912 | Z3 | L20 | Q97 |
| 10913 | Z3 | L20 | Q98 |
| 10914 | Z3 | L20 | Q99 |
| 10915 | Z3 | L20 | Q100 |
| 10916 | Z3 | L20 | Q101 |
| 10917 | Z3 | L20 | Q102 |
| 10918 | Z3 | L20 | Q103 |
| 10919 | Z3 | L21 | Q1 |
| 10920 | Z3 | L21 | Q2 |
| 10921 | Z3 | L21 | Q3 |
| 10922 | Z3 | L21 | Q4 |
| 10923 | Z3 | L21 | Q5 |
| 10924 | Z3 | L21 | Q6 |
| 10925 | Z3 | L21 | Q7 |
| 10926 | Z3 | L21 | Q8 |
| 10927 | Z3 | L21 | Q9 |
| 10928 | Z3 | L21 | Q10 |
| 10929 | Z3 | L21 | Q11 |
| 10930 | Z3 | L21 | Q12 |
| 10931 | Z3 | L21 | Q13 |
| 10932 | Z3 | L21 | Q14 |
| 10933 | Z3 | L21 | Q15 |
| 10934 | Z3 | L21 | Q16 |
| 10935 | Z3 | L21 | Q17 |
| 10936 | Z3 | L21 | Q18 |
| 10937 | Z3 | L21 | Q19 |
| 10938 | Z3 | L21 | Q20 |
| 10939 | Z3 | L21 | Q21 |
| 10940 | Z3 | L21 | Q22 |
| 10941 | Z3 | L21 | Q23 |
| 10942 | Z3 | L21 | Q24 |
| 10943 | Z3 | L21 | Q25 |
| 10944 | Z3 | L21 | Q26 |
| 10945 | Z3 | L21 | Q27 |
| 10946 | Z3 | L21 | Q28 |
| 10947 | Z3 | L21 | Q29 |
| 10948 | Z3 | L21 | Q30 |
| 10949 | Z3 | L21 | Q31 |
| 10950 | Z3 | L21 | Q32 |
| 10951 | Z3 | L21 | Q33 |
| 10952 | Z3 | L21 | Q34 |
| 10953 | Z3 | L21 | Q35 |
| 10954 | Z3 | L21 | Q36 |
| 10955 | Z3 | L21 | Q37 |
| 10956 | Z3 | L21 | Q38 |
| 10957 | Z3 | L21 | Q39 |
| 10958 | Z3 | L21 | Q40 |
| 10959 | Z3 | L21 | Q41 |
| 10960 | Z3 | L21 | Q42 |
| 10961 | Z3 | L21 | Q43 |
| 10962 | Z3 | L21 | Q44 |
| 10963 | Z3 | L21 | Q45 |
| 10964 | Z3 | L21 | Q46 |
| 10965 | Z3 | L21 | Q47 |
| 10966 | Z3 | L21 | Q48 |
| 10967 | Z3 | L21 | Q49 |
| 10968 | Z3 | L21 | Q50 |
| 10969 | Z3 | L21 | Q51 |
| 10970 | Z3 | L21 | Q52 |
| 10971 | Z3 | L21 | Q53 |
| 10972 | Z3 | L21 | Q54 |
| 10973 | Z3 | L21 | Q55 |
| 10974 | Z3 | L21 | Q56 |
| 10975 | Z3 | L21 | Q57 |
| 10976 | Z3 | L21 | Q58 |
| 10977 | Z3 | L21 | Q59 |
| 10978 | Z3 | L21 | Q60 |
| 10979 | Z3 | L21 | Q61 |
| 10980 | Z3 | L21 | Q62 |
| 10981 | Z3 | L21 | Q63 |
| 10982 | Z3 | L21 | Q64 |
| 10983 | Z3 | L21 | Q65 |
| 10984 | Z3 | L21 | Q66 |
| 10985 | Z3 | L21 | Q67 |
| 10986 | Z3 | L21 | Q68 |
| 10987 | Z3 | L21 | Q69 |
| 10988 | Z3 | L21 | Q70 |
| 10989 | Z3 | L21 | Q71 |
| 10990 | Z3 | L21 | Q72 |
| 10991 | Z3 | L21 | Q73 |

TABLE 1-60-continued

| | | | |
|---|---|---|---|
| 10992 | Z3 | L21 | Q74 |
| 10993 | Z3 | L21 | Q75 |
| 10994 | Z3 | L21 | Q76 |
| 10995 | Z3 | L21 | Q77 |
| 10996 | Z3 | L21 | Q78 |
| 10997 | Z3 | L21 | Q79 |
| 10998 | Z3 | L21 | Q80 |
| 10999 | Z3 | L21 | Q81 |
| 11000 | Z3 | L21 | Q82 |
| 11001 | Z3 | L21 | Q83 |
| 11002 | Z3 | L21 | Q84 |
| 11003 | Z3 | L21 | Q85 |
| 11004 | Z3 | L21 | Q86 |
| 11005 | Z3 | L21 | Q87 |
| 11006 | Z3 | L21 | Q88 |
| 11007 | Z3 | L21 | Q89 |
| 11008 | Z3 | L21 | Q90 |
| 11009 | Z3 | L21 | Q91 |
| 11010 | Z3 | L21 | Q92 |
| 11011 | Z3 | L21 | Q93 |
| 11012 | Z3 | L21 | Q94 |
| 11013 | Z3 | L21 | Q95 |
| 11014 | Z3 | L21 | Q96 |
| 11015 | Z3 | L21 | Q97 |
| 11016 | Z3 | L21 | Q98 |
| 11017 | Z3 | L21 | Q99 |
| 11018 | Z3 | L21 | Q100 |
| 11019 | Z3 | L21 | Q101 |
| 11020 | Z3 | L21 | Q102 |
| 11021 | Z3 | L21 | Q103 |
| 11022 | Z3 | L22 | Q1 |
| 11023 | Z3 | L22 | Q2 |
| 11024 | Z3 | L22 | Q3 |
| 11025 | Z3 | L22 | Q4 |
| 11026 | Z3 | L22 | Q5 |
| 11027 | Z3 | L22 | Q6 |

TABLE 1-61

| | | | |
|---|---|---|---|
| 11028 | Z3 | L22 | Q7 |
| 11029 | Z3 | L22 | Q8 |
| 11030 | Z3 | L22 | Q9 |
| 11031 | Z3 | L22 | Q10 |
| 11032 | Z3 | L22 | Q11 |
| 11033 | Z3 | L22 | Q12 |
| 11034 | Z3 | L22 | Q13 |
| 11035 | Z3 | L22 | Q14 |
| 11036 | Z3 | L22 | Q15 |
| 11037 | Z3 | L22 | Q16 |
| 11038 | Z3 | L22 | Q17 |
| 11039 | Z3 | L22 | Q18 |
| 11040 | Z3 | L22 | Q19 |
| 11041 | Z3 | L22 | Q20 |
| 11042 | Z3 | L22 | Q21 |
| 11043 | Z3 | L22 | Q22 |
| 11044 | Z3 | L22 | Q23 |
| 11045 | Z3 | L22 | Q24 |
| 11046 | Z3 | L22 | Q25 |
| 11047 | Z3 | L22 | Q26 |
| 11048 | Z3 | L22 | Q27 |
| 11049 | Z3 | L22 | Q28 |
| 11050 | Z3 | L22 | Q29 |
| 11051 | Z3 | L22 | Q30 |
| 11052 | Z3 | L22 | Q31 |
| 11053 | Z3 | L22 | Q32 |
| 11054 | Z3 | L22 | Q33 |
| 11055 | Z3 | L22 | Q34 |
| 11056 | Z3 | L22 | Q35 |
| 11057 | Z3 | L22 | Q36 |
| 11058 | Z3 | L22 | Q37 |
| 11059 | Z3 | L22 | Q38 |
| 11060 | Z3 | L22 | Q39 |
| 11061 | Z3 | L22 | Q40 |
| 11062 | Z3 | L22 | Q41 |
| 11063 | Z3 | L22 | Q42 |
| 11064 | Z3 | L22 | Q43 |
| 11065 | Z3 | L22 | Q44 |

TABLE 1-61-continued

| | | | |
|---|---|---|---|
| 11066 | Z3 | L22 | Q45 |
| 11067 | Z3 | L22 | Q46 |
| 11068 | Z3 | L22 | Q47 |
| 11069 | Z3 | L22 | Q48 |
| 11070 | Z3 | L22 | Q49 |
| 11071 | Z3 | L22 | Q50 |
| 11072 | Z3 | L22 | Q51 |
| 11073 | Z3 | L22 | Q52 |
| 11074 | Z3 | L22 | Q53 |
| 11075 | Z3 | L22 | Q54 |
| 11076 | Z3 | L22 | Q55 |
| 11077 | Z3 | L22 | Q56 |
| 11078 | Z3 | L22 | Q57 |
| 11079 | Z3 | L22 | Q58 |
| 11080 | Z3 | L22 | Q59 |
| 11081 | Z3 | L22 | Q60 |
| 11082 | Z3 | L22 | Q61 |
| 11083 | Z3 | L22 | Q62 |
| 11084 | Z3 | L22 | Q63 |
| 11085 | Z3 | L22 | Q64 |
| 11086 | Z3 | L22 | Q65 |
| 11087 | Z3 | L22 | Q66 |
| 11088 | Z3 | L22 | Q67 |
| 11089 | Z3 | L22 | Q68 |
| 11090 | Z3 | L22 | Q69 |
| 11091 | Z3 | L22 | Q70 |
| 11092 | Z3 | L22 | Q71 |
| 11093 | Z3 | L22 | Q72 |
| 11094 | Z3 | L22 | Q73 |
| 11095 | Z3 | L22 | Q74 |
| 11096 | Z3 | L22 | Q75 |
| 11097 | Z3 | L22 | Q76 |
| 11098 | Z3 | L22 | Q77 |
| 11099 | Z3 | L22 | Q78 |
| 11100 | Z3 | L22 | Q79 |
| 11101 | Z3 | L22 | Q80 |
| 11102 | Z3 | L22 | Q81 |
| 11103 | Z3 | L22 | Q82 |
| 11104 | Z3 | L22 | Q83 |
| 11105 | Z3 | L22 | Q84 |
| 11106 | Z3 | L22 | Q85 |
| 11107 | Z3 | L22 | Q86 |
| 11108 | Z3 | L22 | Q87 |
| 11109 | Z3 | L22 | Q88 |
| 11110 | Z3 | L22 | Q89 |
| 11111 | Z3 | L22 | Q90 |
| 11112 | Z3 | L22 | Q91 |
| 11113 | Z3 | L22 | Q92 |
| 11114 | Z3 | L22 | Q93 |
| 11115 | Z3 | L22 | Q94 |
| 11116 | Z3 | L22 | Q95 |
| 11117 | Z3 | L22 | Q96 |
| 11118 | Z3 | L22 | Q97 |
| 11119 | Z3 | L22 | Q98 |
| 11120 | Z3 | L22 | Q99 |
| 11121 | Z3 | L22 | Q100 |
| 11122 | Z3 | L22 | Q101 |
| 11123 | Z3 | L22 | Q102 |
| 11124 | Z3 | L22 | Q103 |
| 11125 | Z3 | L23 | Q1 |
| 11126 | Z3 | L23 | Q2 |
| 11127 | Z3 | L23 | Q3 |
| 11128 | Z3 | L23 | Q4 |
| 11129 | Z3 | L23 | Q5 |
| 11130 | Z3 | L23 | Q6 |
| 11131 | Z3 | L23 | Q7 |
| 11132 | Z3 | L23 | Q8 |
| 11133 | Z3 | L23 | Q9 |
| 11134 | Z3 | L23 | Q10 |
| 11135 | Z3 | L23 | Q11 |
| 11136 | Z3 | L23 | Q12 |
| 11137 | Z3 | L23 | Q13 |
| 11138 | Z3 | L23 | Q14 |
| 11139 | Z3 | L23 | Q15 |
| 11140 | Z3 | L23 | Q16 |
| 11141 | Z3 | L23 | Q17 |
| 11142 | Z3 | L23 | Q18 |
| 11143 | Z3 | L23 | Q19 |
| 11144 | Z3 | L23 | Q20 |
| 11145 | Z3 | L23 | Q21 |

TABLE 1-61-continued

| | | | |
|---|---|---|---|
| 11146 | Z3 | L23 | Q22 |
| 11147 | Z3 | L23 | Q23 |
| 11148 | Z3 | L23 | Q24 |
| 11149 | Z3 | L23 | Q25 |
| 11150 | Z3 | L23 | Q26 |
| 11151 | Z3 | L23 | Q27 |
| 11152 | Z3 | L23 | Q28 |
| 11153 | Z3 | L23 | Q29 |
| 11154 | Z3 | L23 | Q30 |
| 11155 | Z3 | L23 | Q31 |
| 11156 | Z3 | L23 | Q32 |
| 11157 | Z3 | L23 | Q33 |
| 11158 | Z3 | L23 | Q34 |
| 11159 | Z3 | L23 | Q35 |
| 11160 | Z3 | L23 | Q36 |
| 11161 | Z3 | L23 | Q37 |
| 11162 | Z3 | L23 | Q38 |
| 11163 | Z3 | L23 | Q39 |
| 11164 | Z3 | L23 | Q40 |
| 11165 | Z3 | L23 | Q41 |
| 11166 | Z3 | L23 | Q42 |
| 11167 | Z3 | L23 | Q43 |
| 11168 | Z3 | L23 | Q44 |
| 11169 | Z3 | L23 | Q45 |
| 11170 | Z3 | L23 | Q46 |
| 11171 | Z3 | L23 | Q47 |
| 11172 | Z3 | L23 | Q48 |
| 11173 | Z3 | L23 | Q49 |
| 11174 | Z3 | L23 | Q50 |
| 11175 | Z3 | L23 | Q51 |
| 11176 | Z3 | L23 | Q52 |
| 11177 | Z3 | L23 | Q53 |
| 11178 | Z3 | L23 | Q54 |
| 11179 | Z3 | L23 | Q55 |
| 11180 | Z3 | L23 | Q56 |
| 11181 | Z3 | L23 | Q57 |
| 11182 | Z3 | L23 | Q58 |
| 11183 | Z3 | L23 | Q59 |
| 11184 | Z3 | L23 | Q60 |
| 11185 | Z3 | L23 | Q61 |
| 11186 | Z3 | L23 | Q62 |
| 11187 | Z3 | L23 | Q63 |
| 11188 | Z3 | L23 | Q64 |
| 11189 | Z3 | L23 | Q65 |
| 11190 | Z3 | L23 | Q66 |
| 11191 | Z3 | L23 | Q67 |
| 11192 | Z3 | L23 | Q68 |
| 11193 | Z3 | L23 | Q69 |
| 11194 | Z3 | L23 | Q70 |
| 11195 | Z3 | L23 | Q71 |
| 11196 | Z3 | L23 | Q72 |
| 11197 | Z3 | L23 | Q73 |
| 11198 | Z3 | L23 | Q74 |
| 11199 | Z3 | L23 | Q75 |
| 11200 | Z3 | L23 | Q76 |
| 11201 | Z3 | L23 | Q77 |
| 11202 | Z3 | L23 | Q78 |
| 11203 | Z3 | L23 | Q79 |
| 11204 | Z3 | L23 | Q80 |
| 11205 | Z3 | L23 | Q81 |
| 11206 | Z3 | L23 | Q82 |
| 11207 | Z3 | L23 | Q83 |
| 11208 | Z3 | L23 | Q84 |
| 11209 | Z3 | L23 | Q85 |
| 11210 | Z3 | L23 | Q86 |
| 11211 | Z3 | L23 | Q87 |
| 11212 | Z3 | L23 | Q88 |
| 11213 | Z3 | L23 | Q89 |
| 11214 | Z3 | L23 | Q90 |
| 11215 | Z3 | L23 | Q91 |
| 11216 | Z3 | L23 | Q92 |
| 11217 | Z3 | L23 | Q93 |
| 11218 | Z3 | L23 | Q94 |
| 11219 | Z3 | L23 | Q95 |
| 11220 | Z3 | L23 | Q96 |
| 11221 | Z3 | L23 | Q97 |
| 11222 | Z3 | L23 | Q98 |
| 11223 | Z3 | L23 | Q99 |
| 11224 | Z3 | L23 | Q100 |
| 11225 | Z3 | L23 | Q101 |
| 11226 | Z3 | L23 | Q102 |
| 11227 | Z3 | L23 | Q103 |
| 11228 | Z3 | L24 | Q1 |

TABLE 1-62

| | | | |
|---|---|---|---|
| 11229 | Z3 | L24 | Q2 |
| 11230 | Z3 | L24 | Q3 |
| 11231 | Z3 | L24 | Q4 |
| 11232 | Z3 | L24 | Q5 |
| 11233 | Z3 | L24 | Q6 |
| 11234 | Z3 | L24 | Q7 |
| 11235 | Z3 | L24 | Q8 |
| 11236 | Z3 | L24 | Q9 |
| 11237 | Z3 | L24 | Q10 |
| 11238 | Z3 | L24 | Q11 |
| 11239 | Z3 | L24 | Q12 |
| 11240 | Z3 | L24 | Q13 |
| 11241 | Z3 | L24 | Q14 |
| 11242 | Z3 | L24 | Q15 |
| 11243 | Z3 | L24 | Q16 |
| 11244 | Z3 | L24 | Q17 |
| 11245 | Z3 | L24 | Q18 |
| 11246 | Z3 | L24 | Q19 |
| 11247 | Z3 | L24 | Q20 |
| 11248 | Z3 | L24 | Q21 |
| 11249 | Z3 | L24 | Q22 |
| 11250 | Z3 | L24 | Q23 |
| 11251 | Z3 | L24 | Q24 |
| 11252 | Z3 | L24 | Q25 |
| 11253 | Z3 | L24 | Q26 |
| 11254 | Z3 | L24 | Q27 |
| 11255 | Z3 | L24 | Q28 |
| 11256 | Z3 | L24 | Q29 |
| 11257 | Z3 | L24 | Q30 |
| 11258 | Z3 | L24 | Q31 |
| 11259 | Z3 | L24 | Q32 |
| 11260 | Z3 | L24 | Q33 |
| 11261 | Z3 | L24 | Q34 |
| 11262 | Z3 | L24 | Q35 |
| 11263 | Z3 | L24 | Q36 |
| 11264 | Z3 | L24 | Q37 |
| 11265 | Z3 | L24 | Q38 |
| 11266 | Z3 | L24 | Q39 |
| 11267 | Z3 | L24 | Q40 |
| 11268 | Z3 | L24 | Q41 |
| 11269 | Z3 | L24 | Q42 |
| 11270 | Z3 | L24 | Q43 |
| 11271 | Z3 | L24 | Q44 |
| 11272 | Z3 | L24 | Q45 |
| 11273 | Z3 | L24 | Q46 |
| 11274 | Z3 | L24 | Q47 |
| 11275 | Z3 | L24 | Q48 |
| 11276 | Z3 | L24 | Q49 |
| 11277 | Z3 | L24 | Q50 |
| 11278 | Z3 | L24 | Q51 |
| 11279 | Z3 | L24 | Q52 |
| 11280 | Z3 | L24 | Q53 |
| 11281 | Z3 | L24 | Q54 |
| 11282 | Z3 | L24 | Q55 |
| 11283 | Z3 | L24 | Q56 |
| 11284 | Z3 | L24 | Q57 |
| 11285 | Z3 | L24 | Q58 |
| 11286 | Z3 | L24 | Q59 |
| 11287 | Z3 | L24 | Q60 |
| 11288 | Z3 | L24 | Q61 |
| 11289 | Z3 | L24 | Q62 |
| 11290 | Z3 | L24 | Q63 |
| 11291 | Z3 | L24 | Q64 |
| 11292 | Z3 | L24 | Q65 |
| 11293 | Z3 | L24 | Q66 |
| 11294 | Z3 | L24 | Q67 |
| 11295 | Z3 | L24 | Q68 |
| 11296 | Z3 | L24 | Q69 |
| 11297 | Z3 | L24 | Q70 |
| 11298 | Z3 | L24 | Q71 |
| 11299 | Z3 | L24 | Q72 |

TABLE 1-62-continued

| | | | |
|---|---|---|---|
| 11300 | Z3 | L24 | Q73 |
| 11301 | Z3 | L24 | Q74 |
| 11302 | Z3 | L24 | Q75 |
| 11303 | Z3 | L24 | Q76 |
| 11304 | Z3 | L24 | Q77 |
| 11305 | Z3 | L24 | Q78 |
| 11306 | Z3 | L24 | Q79 |
| 11307 | Z3 | L24 | Q80 |
| 11308 | Z3 | L24 | Q81 |
| 11309 | Z3 | L24 | Q82 |
| 11310 | Z3 | L24 | Q83 |
| 11311 | Z3 | L24 | Q84 |
| 11312 | Z3 | L24 | Q85 |
| 11313 | Z3 | L24 | Q86 |
| 11314 | Z3 | L24 | Q87 |
| 11315 | Z3 | L24 | Q88 |
| 11316 | Z3 | L24 | Q89 |
| 11317 | Z3 | L24 | Q90 |
| 11318 | Z3 | L24 | Q91 |
| 11319 | Z3 | L24 | Q92 |
| 11320 | Z3 | L24 | Q93 |
| 11321 | Z3 | L24 | Q94 |
| 11322 | Z3 | L24 | Q95 |
| 11323 | Z3 | L24 | Q96 |
| 11324 | Z3 | L24 | Q97 |
| 11325 | Z3 | L24 | Q98 |
| 11326 | Z3 | L24 | Q99 |
| 11327 | Z3 | L24 | Q100 |
| 11328 | Z3 | L24 | Q101 |
| 11329 | Z3 | L24 | Q102 |
| 11330 | Z3 | L24 | Q103 |
| 11331 | Z3 | L25 | Q1 |
| 11332 | Z3 | L25 | Q2 |
| 11333 | Z3 | L25 | Q3 |
| 11334 | Z3 | L25 | Q4 |
| 11335 | Z3 | L25 | Q5 |
| 11336 | Z3 | L25 | Q6 |
| 11337 | Z3 | L25 | Q7 |
| 11338 | Z3 | L25 | Q8 |
| 11339 | Z3 | L25 | Q9 |
| 11340 | Z3 | L25 | Q10 |
| 11341 | Z3 | L25 | Q11 |
| 11342 | Z3 | L25 | Q12 |
| 11343 | Z3 | L25 | Q13 |
| 11344 | Z3 | L25 | Q14 |
| 11345 | Z3 | L25 | Q15 |
| 11346 | Z3 | L25 | Q16 |
| 11347 | Z3 | L25 | Q17 |
| 11348 | Z3 | L25 | Q18 |
| 11349 | Z3 | L25 | Q19 |
| 11350 | Z3 | L25 | Q20 |
| 11351 | Z3 | L25 | Q21 |
| 11352 | Z3 | L25 | Q22 |
| 11353 | Z3 | L25 | Q23 |
| 11354 | Z3 | L25 | Q24 |
| 11355 | Z3 | L25 | Q25 |
| 11356 | Z3 | L25 | Q26 |
| 11357 | Z3 | L25 | Q27 |
| 11358 | Z3 | L25 | Q28 |
| 11359 | Z3 | L25 | Q29 |
| 11360 | Z3 | L25 | Q30 |
| 11361 | Z3 | L25 | Q31 |
| 11362 | Z3 | L25 | Q32 |
| 11363 | Z3 | L25 | Q33 |
| 11364 | Z3 | L25 | Q34 |
| 11365 | Z3 | L25 | Q35 |
| 11366 | Z3 | L25 | Q36 |
| 11367 | Z3 | L25 | Q37 |
| 11368 | Z3 | L25 | Q38 |
| 11369 | Z3 | L25 | Q39 |
| 11370 | Z3 | L25 | Q40 |
| 11371 | Z3 | L25 | Q41 |
| 11372 | Z3 | L25 | Q42 |
| 11373 | Z3 | L25 | Q43 |
| 11374 | Z3 | L25 | Q44 |
| 11375 | Z3 | L25 | Q45 |
| 11376 | Z3 | L25 | Q46 |
| 11377 | Z3 | L25 | Q47 |
| 11378 | Z3 | L25 | Q48 |
| 11379 | Z3 | L25 | Q49 |

TABLE 1-62-continued

| | | | |
|---|---|---|---|
| 11380 | Z3 | L25 | Q50 |
| 11381 | Z3 | L25 | Q51 |
| 11382 | Z3 | L25 | Q52 |
| 11383 | Z3 | L25 | Q53 |
| 11384 | Z3 | L25 | Q54 |
| 11385 | Z3 | L25 | Q55 |
| 11386 | Z3 | L25 | Q56 |
| 11387 | Z3 | L25 | Q57 |
| 11388 | Z3 | L25 | Q58 |
| 11389 | Z3 | L25 | Q59 |
| 11390 | Z3 | L25 | Q60 |
| 11391 | Z3 | L25 | Q61 |
| 11392 | Z3 | L25 | Q62 |
| 11393 | Z3 | L25 | Q63 |
| 11394 | Z3 | L25 | Q64 |
| 11395 | Z3 | L25 | Q65 |
| 11396 | Z3 | L25 | Q66 |
| 11397 | Z3 | L25 | Q67 |
| 11398 | Z3 | L25 | Q68 |
| 11399 | Z3 | L25 | Q69 |
| 11400 | Z3 | L25 | Q70 |
| 11401 | Z3 | L25 | Q71 |
| 11402 | Z3 | L25 | Q72 |
| 11403 | Z3 | L25 | Q73 |
| 11404 | Z3 | L25 | Q74 |
| 11405 | Z3 | L25 | Q75 |
| 11406 | Z3 | L25 | Q76 |
| 11407 | Z3 | L25 | Q77 |
| 11408 | Z3 | L25 | Q78 |
| 11409 | Z3 | L25 | Q79 |
| 11410 | Z3 | L25 | Q80 |
| 11411 | Z3 | L25 | Q81 |
| 11412 | Z3 | L25 | Q82 |
| 11413 | Z3 | L25 | Q83 |
| 11414 | Z3 | L25 | Q84 |
| 11415 | Z3 | l25 | Q85 |
| 11416 | Z3 | L25 | Q86 |
| 11417 | Z3 | L25 | Q87 |
| 11418 | Z3 | L25 | Q38 |
| 11419 | Z3 | L25 | Q89 |
| 11420 | Z3 | L25 | Q90 |
| 11421 | Z3 | L25 | Q91 |
| 11422 | Z3 | L25 | Q92 |
| 11423 | Z3 | L25 | Q93 |
| 11424 | Z3 | L25 | Q94 |
| 11425 | Z3 | L25 | Q95 |
| 11426 | Z3 | L25 | Q96 |
| 11427 | Z3 | L25 | Q97 |
| 11428 | Z3 | L25 | Q98 |
| 11429 | Z3 | L25 | Q99 |

TABLE 1-63

| | | | |
|---|---|---|---|
| 11430 | Z3 | L25 | Q100 |
| 11431 | Z3 | L25 | Q101 |
| 11432 | Z3 | L25 | Q102 |
| 11433 | Z3 | L25 | Q103 |
| 11434 | Z3 | L26 | Q1 |
| 11435 | Z3 | L26 | Q2 |
| 11436 | Z3 | L26 | Q3 |
| 11437 | Z3 | L26 | Q4 |
| 11438 | Z3 | L26 | Q5 |
| 11439 | Z3 | L26 | Q6 |
| 11440 | Z3 | L26 | Q7 |
| 11441 | Z3 | L26 | Q8 |
| 11442 | Z3 | L26 | Q9 |
| 11443 | Z3 | L26 | Q10 |
| 11444 | Z3 | L26 | Q11 |
| 11445 | Z3 | L26 | Q12 |
| 11446 | Z3 | L26 | Q13 |
| 11447 | Z3 | L26 | Q14 |
| 11448 | Z3 | L26 | Q15 |
| 11449 | Z3 | L26 | Q16 |
| 11450 | Z3 | L26 | Q17 |
| 11451 | Z3 | L26 | Q18 |
| 11452 | Z3 | L26 | Q19 |
| 11453 | Z3 | L26 | Q20 |

TABLE 1-63-continued

| | | | |
|---|---|---|---|
| 11454 | Z3 | L26 | Q21 |
| 11455 | Z3 | L26 | Q22 |
| 11456 | Z3 | L26 | Q23 |
| 11457 | Z3 | L26 | Q24 |
| 11458 | Z3 | L26 | Q25 |
| 11459 | Z3 | L26 | Q26 |
| 11460 | Z3 | L26 | Q27 |
| 11461 | Z3 | L26 | Q28 |
| 11462 | Z3 | L26 | Q29 |
| 11463 | Z3 | L26 | Q30 |
| 11464 | Z3 | L26 | Q31 |
| 11465 | Z3 | L26 | Q32 |
| 11466 | Z3 | L26 | Q33 |
| 11467 | Z3 | L26 | Q34 |
| 11468 | Z3 | L26 | Q35 |
| 11469 | Z3 | L26 | Q36 |
| 11470 | Z3 | L26 | Q37 |
| 11471 | Z3 | L26 | Q38 |
| 11472 | Z3 | L26 | Q39 |
| 11473 | Z3 | L26 | Q40 |
| 11474 | Z3 | L26 | Q41 |
| 11475 | Z3 | L26 | Q42 |
| 11476 | Z3 | L26 | Q43 |
| 11477 | Z3 | L26 | Q44 |
| 11478 | Z3 | L26 | Q45 |
| 11479 | Z3 | L26 | Q46 |
| 11480 | Z3 | L26 | Q47 |
| 11481 | Z3 | L26 | Q48 |
| 11482 | Z3 | L26 | Q49 |
| 11483 | Z3 | L26 | Q50 |
| 11484 | Z3 | L26 | Q51 |
| 11485 | Z3 | L26 | Q52 |
| 11486 | Z3 | L26 | Q53 |
| 11487 | Z3 | L26 | Q54 |
| 11488 | Z3 | L26 | Q55 |
| 11489 | Z3 | L26 | Q56 |
| 11490 | Z3 | L26 | Q57 |
| 11491 | Z3 | L26 | Q58 |
| 11492 | Z3 | L26 | Q59 |
| 11493 | Z3 | L26 | Q60 |
| 11494 | Z3 | L26 | Q61 |
| 11495 | Z3 | L26 | Q62 |
| 11496 | Z3 | L26 | Q63 |
| 11497 | Z3 | L26 | Q64 |
| 11498 | Z3 | L26 | Q65 |
| 11499 | Z3 | L26 | Q66 |
| 11500 | Z3 | L26 | Q67 |
| 11501 | Z3 | L26 | Q68 |
| 11502 | Z3 | L26 | Q69 |
| 11503 | Z3 | L26 | Q70 |
| 11504 | Z3 | L26 | Q71 |
| 11505 | Z3 | L26 | Q72 |
| 11506 | Z3 | L26 | Q73 |
| 11507 | Z3 | L26 | Q74 |
| 11508 | Z3 | L26 | Q75 |
| 11509 | Z3 | L26 | Q76 |
| 11510 | Z3 | L26 | Q77 |
| 11511 | Z3 | L26 | Q78 |
| 11512 | Z3 | L26 | Q79 |
| 11513 | Z3 | L26 | Q80 |
| 11514 | Z3 | L26 | Q81 |
| 11515 | Z3 | L26 | Q82 |
| 11516 | Z3 | L26 | Q83 |
| 11517 | Z3 | L26 | Q84 |
| 11518 | Z3 | L26 | Q85 |
| 11519 | Z3 | L26 | Q86 |
| 11520 | Z3 | L26 | Q87 |
| 11521 | Z3 | L26 | Q88 |
| 11522 | Z3 | L26 | Q89 |
| 11523 | Z3 | L26 | Q90 |
| 11524 | Z3 | L26 | Q91 |
| 11525 | Z3 | L26 | Q92 |
| 11526 | Z3 | L26 | Q93 |
| 11527 | Z3 | L26 | Q94 |
| 11528 | Z3 | L26 | Q95 |
| 11529 | Z3 | L26 | Q96 |
| 11530 | Z3 | L26 | Q97 |
| 11531 | Z3 | L26 | Q98 |
| 11532 | Z3 | L26 | Q99 |
| 11533 | Z3 | L26 | Q100 |
| 11534 | Z3 | L26 | Q101 |
| 11535 | Z3 | L26 | Q102 |
| 11536 | Z3 | L26 | Q103 |
| 11537 | Z3 | L27 | Q1 |
| 11538 | Z3 | L27 | Q2 |
| 11539 | Z3 | L27 | Q3 |
| 11540 | Z3 | L27 | Q4 |
| 11541 | Z3 | L27 | Q5 |
| 11542 | Z3 | L27 | Q6 |
| 11543 | Z3 | L27 | Q7 |
| 11544 | Z3 | L27 | Q8 |
| 11545 | Z3 | L27 | Q9 |
| 11546 | Z3 | L27 | Q10 |
| 11547 | Z3 | L27 | Q11 |
| 11548 | Z3 | L27 | Q12 |
| 11549 | Z3 | L27 | Q13 |
| 11550 | Z3 | L27 | Q14 |
| 11551 | Z3 | L27 | Q15 |
| 11552 | Z3 | L27 | Q16 |
| 11553 | Z3 | L27 | Q17 |
| 11554 | Z3 | L27 | Q18 |
| 11555 | Z3 | L27 | Q19 |
| 11556 | Z3 | L27 | Q20 |
| 11557 | Z3 | L27 | Q21 |
| 11558 | Z3 | L27 | Q22 |
| 11559 | Z3 | L27 | Q23 |
| 11560 | Z3 | L27 | Q24 |
| 11561 | Z3 | L27 | Q25 |
| 11562 | Z3 | L27 | Q26 |
| 11563 | Z3 | L27 | Q27 |
| 11564 | Z3 | L27 | Q28 |
| 11565 | Z3 | L27 | Q29 |
| 11566 | Z3 | L27 | Q30 |
| 11567 | Z3 | L27 | Q31 |
| 11568 | Z3 | L27 | Q32 |
| 11569 | Z3 | L27 | Q33 |
| 11570 | Z3 | L27 | Q34 |
| 11571 | Z3 | L27 | Q35 |
| 11572 | Z3 | L27 | Q36 |
| 11573 | Z3 | L27 | Q37 |
| 11574 | Z3 | L27 | Q38 |
| 11575 | Z3 | L27 | Q39 |
| 11576 | Z3 | L27 | Q40 |
| 11577 | Z3 | L27 | Q41 |
| 11578 | Z3 | L27 | Q42 |
| 11579 | Z3 | L27 | Q43 |
| 11580 | Z3 | L27 | Q44 |
| 11581 | Z3 | L27 | Q45 |
| 11582 | Z3 | L27 | Q46 |
| 11583 | Z3 | L27 | Q47 |
| 11584 | Z3 | L27 | Q48 |
| 11585 | Z3 | L27 | Q49 |
| 11586 | Z3 | L27 | Q50 |
| 11587 | Z3 | L27 | Q51 |
| 11588 | Z3 | L27 | Q52 |
| 11589 | Z3 | L27 | Q53 |
| 11590 | Z3 | L27 | Q54 |
| 11591 | Z3 | L27 | Q55 |
| 11592 | Z3 | L27 | Q56 |
| 11593 | Z3 | L27 | Q57 |
| 11594 | Z3 | L27 | Q58 |
| 11595 | Z3 | L27 | Q59 |
| 11596 | Z3 | L27 | Q60 |
| 11597 | Z3 | L27 | Q61 |
| 11598 | Z3 | L27 | Q62 |
| 11599 | Z3 | L27 | Q63 |
| 11600 | Z3 | L27 | Q64 |
| 11601 | Z3 | L27 | Q65 |
| 11602 | Z3 | L27 | Q66 |
| 11603 | Z3 | L27 | Q67 |
| 11604 | Z3 | L27 | Q68 |
| 11605 | Z3 | L27 | Q69 |
| 11606 | Z3 | L27 | Q70 |
| 11607 | Z3 | L27 | Q71 |
| 11608 | Z3 | L27 | Q72 |
| 11609 | Z3 | L27 | Q73 |
| 11610 | Z3 | L27 | Q74 |
| 11611 | Z3 | L27 | Q75 |
| 11612 | Z3 | L27 | Q76 |
| 11613 | Z3 | L27 | Q77 |

TABLE 1-63-continued

| | | | |
|---|---|---|---|
| 11614 | Z3 | L27 | Q78 |
| 11615 | Z3 | L27 | Q79 |
| 11616 | Z3 | L27 | Q80 |
| 11617 | Z3 | L27 | Q81 |
| 11618 | Z3 | L27 | Q82 |
| 11619 | Z3 | L27 | Q83 |
| 11620 | Z3 | L27 | Q84 |
| 11621 | Z3 | L27 | Q85 |
| 11622 | Z3 | L27 | Q86 |
| 11623 | Z3 | L27 | Q87 |
| 11624 | Z3 | L27 | Q88 |
| 11625 | Z3 | L27 | Q89 |
| 11626 | Z3 | L27 | Q90 |
| 11627 | Z3 | L27 | Q91 |
| 11628 | Z3 | L27 | Q92 |
| 11629 | Z3 | L27 | Q93 |
| 11630 | Z3 | L27 | Q94 |

TABLE 1-64

| | | | |
|---|---|---|---|
| 11631 | Z3 | L27 | Q95 |
| 11632 | Z3 | L27 | Q96 |
| 11633 | Z3 | L27 | Q97 |
| 11634 | Z3 | L27 | Q98 |
| 11635 | Z3 | L27 | Q99 |
| 11636 | Z3 | L27 | Q100 |
| 11637 | Z3 | L27 | Q101 |
| 11638 | Z3 | L27 | Q102 |
| 11639 | Z3 | L27 | Q103 |
| 11640 | Z3 | L28 | Q1 |
| 11641 | Z3 | L28 | Q2 |
| 11642 | Z3 | L28 | Q3 |
| 11643 | Z3 | L28 | Q4 |
| 11644 | Z3 | L28 | Q5 |
| 11645 | Z3 | L28 | Q6 |
| 11646 | Z3 | L28 | Q7 |
| 11647 | Z3 | L28 | Q8 |
| 11648 | Z3 | L28 | Q9 |
| 11649 | Z3 | L28 | Q10 |
| 11650 | Z3 | L28 | Q11 |
| 11651 | Z3 | L28 | Q12 |
| 11652 | Z3 | L28 | Q13 |
| 11653 | Z3 | L28 | Q14 |
| 11654 | Z3 | L28 | Q15 |
| 11655 | Z3 | L28 | Q16 |
| 11656 | Z3 | L28 | Q17 |
| 11657 | Z3 | L28 | Q18 |
| 11658 | Z3 | L28 | Q19 |
| 11659 | Z3 | L28 | Q20 |
| 11660 | Z3 | L28 | Q21 |
| 11661 | Z3 | L28 | Q22 |
| 11662 | Z3 | L28 | Q23 |
| 11663 | Z3 | L28 | Q24 |
| 11664 | Z3 | L28 | Q25 |
| 11665 | Z3 | L28 | Q26 |
| 11666 | Z3 | L28 | Q27 |
| 11667 | Z3 | L28 | Q28 |
| 11668 | Z3 | L28 | Q29 |
| 11669 | Z3 | L28 | Q30 |
| 11670 | Z3 | L28 | Q31 |
| 11671 | Z3 | L28 | Q32 |
| 11672 | Z3 | L28 | Q33 |
| 11673 | Z3 | L28 | Q34 |
| 11674 | Z3 | L28 | Q35 |
| 11675 | Z3 | L28 | Q36 |
| 11676 | Z3 | L28 | Q37 |
| 11677 | Z3 | L28 | Q38 |
| 11678 | Z3 | L28 | Q39 |
| 11679 | Z3 | L28 | Q40 |
| 11680 | Z3 | L28 | Q41 |
| 11681 | Z3 | L28 | Q42 |
| 11682 | Z3 | L28 | Q43 |
| 11683 | Z3 | L28 | Q44 |
| 11684 | Z3 | L28 | Q45 |
| 11685 | Z3 | L28 | Q46 |
| 11686 | Z3 | L28 | Q47 |
| 11687 | Z3 | L28 | Q48 |

TABLE 1-64-continued

| | | | |
|---|---|---|---|
| 11688 | Z3 | L28 | Q49 |
| 11689 | Z3 | L28 | Q50 |
| 11690 | Z3 | L28 | Q51 |
| 11691 | Z3 | L28 | Q52 |
| 11692 | Z3 | L28 | Q53 |
| 11693 | Z3 | L28 | Q54 |
| 11694 | Z3 | L28 | Q55 |
| 11695 | Z3 | L28 | Q56 |
| 11696 | Z3 | L28 | Q57 |
| 11697 | Z3 | L28 | Q58 |
| 11698 | Z3 | L28 | Q59 |
| 11699 | Z3 | L28 | Q60 |
| 11700 | Z3 | L28 | Q61 |
| 11701 | Z3 | L28 | Q62 |
| 11702 | Z3 | L28 | Q63 |
| 11703 | Z3 | L28 | Q64 |
| 11704 | Z3 | L28 | Q65 |
| 11705 | Z3 | L28 | Q66 |
| 11706 | Z3 | L28 | Q67 |
| 11707 | Z3 | L28 | Q68 |
| 11708 | Z3 | L28 | Q69 |
| 11709 | Z3 | L28 | Q70 |
| 11710 | Z3 | L28 | Q71 |
| 11711 | Z3 | L28 | Q72 |
| 11712 | Z3 | L28 | Q73 |
| 11713 | Z3 | L28 | Q74 |
| 11714 | Z3 | L28 | Q75 |
| 11715 | Z3 | L28 | Q76 |
| 11716 | Z3 | L28 | Q77 |
| 11717 | Z3 | L28 | Q78 |
| 11718 | Z3 | L28 | Q79 |
| 11719 | Z3 | L28 | Q80 |
| 11720 | Z3 | L28 | Q81 |
| 11721 | Z3 | L28 | Q82 |
| 11722 | Z3 | L28 | Q83 |
| 11723 | Z3 | L28 | Q84 |
| 11724 | Z3 | L28 | Q85 |
| 11725 | Z3 | L28 | Q86 |
| 11726 | Z3 | L28 | Q87 |
| 11727 | Z3 | L28 | Q88 |
| 11728 | Z3 | L28 | Q89 |
| 11729 | Z3 | L28 | Q90 |
| 11730 | Z3 | L28 | Q91 |
| 11731 | Z3 | L28 | Q92 |
| 11732 | Z3 | L28 | Q93 |
| 11733 | Z3 | L28 | Q94 |
| 11734 | Z3 | L28 | Q95 |
| 11735 | Z3 | L28 | Q96 |
| 11736 | Z3 | L28 | Q97 |
| 11737 | Z3 | L28 | Q98 |
| 11738 | Z3 | L28 | Q99 |
| 11739 | Z3 | L28 | Q100 |
| 11740 | Z3 | L28 | Q101 |
| 11741 | Z3 | L28 | Q102 |
| 11742 | Z3 | L28 | Q103 |
| 11743 | Z3 | L29 | Q1 |
| 11744 | Z3 | L29 | Q2 |
| 11745 | Z3 | L29 | Q3 |
| 11746 | Z3 | L29 | Q4 |
| 11747 | Z3 | L29 | Q5 |
| 11748 | Z3 | L29 | Q6 |
| 11749 | Z3 | L29 | Q7 |
| 11750 | Z3 | L29 | Q8 |
| 11751 | Z3 | L29 | Q9 |
| 11752 | Z3 | L29 | Q10 |
| 11753 | Z3 | L29 | Q11 |
| 11754 | Z3 | L29 | Q12 |
| 11755 | Z3 | L29 | Q13 |
| 11756 | Z3 | L29 | Q14 |
| 11757 | Z3 | L29 | Q15 |
| 11758 | Z3 | L29 | Q16 |
| 11759 | Z3 | L29 | Q17 |
| 11760 | Z3 | L29 | Q18 |
| 11761 | Z3 | L29 | Q19 |
| 11762 | Z3 | L29 | Q20 |
| 11763 | Z3 | L29 | Q21 |
| 11764 | Z3 | L29 | Q22 |
| 11765 | Z3 | L29 | Q23 |
| 11766 | Z3 | L29 | Q24 |
| 11767 | Z3 | L29 | Q25 |

TABLE 1-64-continued

| | | | |
|---|---|---|---|
| 11768 | Z3 | L29 | Q26 |
| 11769 | Z3 | L29 | Q27 |
| 11770 | Z3 | L29 | Q28 |
| 11771 | Z3 | L29 | Q29 |
| 11772 | Z3 | L29 | Q30 |
| 11773 | Z3 | L29 | Q31 |
| 11774 | Z3 | L29 | Q32 |
| 11775 | Z3 | L29 | Q33 |
| 11776 | Z3 | L29 | Q34 |
| 11777 | Z3 | L29 | Q35 |
| 11778 | Z3 | L29 | Q36 |
| 11779 | Z3 | L29 | Q37 |
| 11780 | Z3 | L29 | Q38 |
| 11781 | Z3 | L29 | Q39 |
| 11782 | Z3 | L29 | Q40 |
| 11783 | Z3 | L29 | Q41 |
| 11784 | Z3 | L29 | Q42 |
| 11785 | Z3 | L29 | Q43 |
| 11786 | Z3 | L29 | Q44 |
| 11787 | Z3 | L29 | Q45 |
| 11788 | Z3 | L29 | Q46 |
| 11789 | Z3 | L29 | Q47 |
| 11790 | Z3 | L29 | Q48 |
| 11791 | Z3 | L29 | Q49 |
| 11792 | Z3 | L29 | Q50 |
| 11793 | Z3 | L29 | Q51 |
| 11794 | Z3 | L29 | Q52 |
| 11795 | Z3 | L29 | Q53 |
| 11796 | Z3 | L29 | Q54 |
| 11797 | Z3 | L29 | Q55 |
| 11798 | Z3 | L29 | Q56 |
| 11799 | Z3 | L29 | Q57 |
| 11800 | Z3 | L29 | Q58 |
| 11801 | Z3 | L29 | Q59 |
| 11802 | Z3 | L29 | Q60 |
| 11803 | Z3 | L29 | Q61 |
| 11804 | Z3 | L29 | Q62 |
| 11805 | Z3 | L29 | Q63 |
| 11806 | Z3 | L29 | Q64 |
| 11807 | Z3 | L29 | Q65 |
| 11808 | Z3 | L29 | Q66 |
| 11809 | Z3 | L29 | Q67 |
| 11810 | Z3 | L29 | Q68 |
| 11811 | Z3 | L29 | Q69 |
| 11812 | Z3 | L29 | Q70 |
| 11813 | Z3 | L29 | Q71 |
| 11814 | Z3 | L29 | Q72 |
| 11815 | Z3 | L29 | Q73 |
| 11816 | Z3 | L29 | Q74 |
| 11817 | Z3 | L29 | Q75 |
| 11818 | Z3 | L29 | Q76 |
| 11819 | Z3 | L29 | Q77 |
| 11820 | Z3 | L29 | Q78 |
| 11821 | Z3 | L29 | Q79 |
| 11822 | Z3 | L29 | Q80 |
| 11823 | Z3 | L29 | Q81 |
| 11824 | Z3 | L29 | Q82 |
| 11825 | Z3 | L29 | Q83 |
| 11826 | Z3 | L29 | Q84 |
| 11827 | Z3 | L29 | Q85 |
| 11828 | Z3 | L29 | Q86 |
| 11829 | Z3 | L29 | Q87 |
| 11830 | Z3 | L29 | Q88 |
| 11831 | Z3 | L29 | Q89 |

TABLE 1-65

| | | | |
|---|---|---|---|
| 11832 | Z3 | L29 | Q90 |
| 11833 | Z3 | L29 | Q91 |
| 11834 | Z3 | L29 | Q92 |
| 11835 | Z3 | L29 | Q93 |
| 11836 | Z3 | L29 | Q94 |
| 11837 | Z3 | L29 | Q95 |
| 11838 | Z3 | L29 | Q96 |
| 11839 | Z3 | L29 | Q97 |
| 11840 | Z3 | L29 | Q98 |
| 11841 | Z3 | L29 | Q99 |

TABLE 1-65-continued

| | | | |
|---|---|---|---|
| 11842 | Z3 | L29 | Q100 |
| 11843 | Z3 | L29 | Q101 |
| 11844 | Z3 | L29 | Q102 |
| 11845 | Z3 | L29 | Q103 |
| 11846 | Z3 | L30 | Q1 |
| 11847 | Z3 | L30 | Q2 |
| 11848 | Z3 | L30 | Q3 |
| 11849 | Z3 | L30 | Q4 |
| 11850 | Z3 | L30 | Q5 |
| 11851 | Z3 | L30 | Q6 |
| 11852 | Z3 | L30 | Q7 |
| 11853 | Z3 | L30 | Q8 |
| 11854 | Z3 | L30 | Q9 |
| 11855 | Z3 | L30 | Q10 |
| 11856 | Z3 | L30 | Q11 |
| 11857 | Z3 | L30 | Q12 |
| 11858 | Z3 | L30 | Q13 |
| 11859 | Z3 | L30 | Q14 |
| 11860 | Z3 | L30 | Q15 |
| 11861 | Z3 | L30 | Q16 |
| 11862 | Z3 | L30 | Q17 |
| 11863 | Z3 | L30 | Q18 |
| 11864 | Z3 | L30 | Q19 |
| 11865 | Z3 | L30 | Q20 |
| 11866 | Z3 | L30 | Q21 |
| 11867 | Z3 | L30 | Q22 |
| 11868 | Z3 | L30 | Q23 |
| 11869 | Z3 | L30 | Q24 |
| 11870 | Z3 | L30 | Q25 |
| 11871 | Z3 | L30 | Q26 |
| 11872 | Z3 | L30 | Q27 |
| 11873 | Z3 | L30 | Q28 |
| 11874 | Z3 | L30 | Q29 |
| 11875 | Z3 | L30 | Q30 |
| 11876 | Z3 | L30 | Q31 |
| 11877 | Z3 | L30 | Q32 |
| 11878 | Z3 | L30 | Q33 |
| 11879 | Z3 | L30 | Q34 |
| 11880 | Z3 | L30 | Q35 |
| 11881 | Z3 | L30 | Q36 |
| 11882 | Z3 | L30 | Q37 |
| 11883 | Z3 | L30 | Q38 |
| 11884 | Z3 | L30 | Q39 |
| 11885 | Z3 | L30 | Q40 |
| 11886 | Z3 | L30 | Q41 |
| 11887 | Z3 | L30 | Q42 |
| 11888 | Z3 | L30 | Q43 |
| 11889 | Z3 | L30 | Q44 |
| 11890 | Z3 | L30 | Q45 |
| 11891 | Z3 | L30 | Q46 |
| 11892 | Z3 | L30 | Q47 |
| 11893 | Z3 | L30 | Q48 |
| 11894 | Z3 | L30 | Q49 |
| 11895 | Z3 | L30 | Q50 |
| 11896 | Z3 | L30 | Q51 |
| 11897 | Z3 | L30 | Q52 |
| 11898 | Z3 | L30 | Q53 |
| 11899 | Z3 | L30 | Q54 |
| 11900 | Z3 | L30 | Q55 |
| 11901 | Z3 | L30 | Q56 |
| 11902 | Z3 | L30 | Q57 |
| 11903 | Z3 | L30 | Q58 |
| 11904 | Z3 | L30 | Q59 |
| 11905 | Z3 | L30 | Q60 |
| 11906 | Z3 | L30 | Q61 |
| 11907 | Z3 | L30 | Q62 |
| 11908 | Z3 | L30 | Q63 |
| 11909 | Z3 | L30 | Q64 |
| 11910 | Z3 | L30 | Q65 |
| 11911 | Z3 | L30 | Q66 |
| 11912 | Z3 | L30 | Q67 |
| 11913 | Z3 | L30 | Q68 |
| 11914 | Z3 | L30 | Q69 |
| 11915 | Z3 | L30 | Q70 |
| 11916 | Z3 | L30 | Q71 |
| 11917 | Z3 | L30 | Q72 |
| 11918 | Z3 | L30 | Q73 |
| 11919 | Z3 | L30 | Q74 |
| 11920 | Z3 | L30 | Q75 |
| 11921 | Z3 | L30 | Q76 |

TABLE 1-65-continued

| | | | |
|---|---|---|---|
| 11922 | Z3 | L30 | Q77 |
| 11923 | Z3 | L30 | Q78 |
| 11924 | Z3 | L30 | Q79 |
| 11925 | Z3 | L30 | Q80 |
| 11926 | Z3 | L30 | Q81 |
| 11927 | Z3 | L30 | Q82 |
| 11928 | Z3 | L30 | Q83 |
| 11929 | Z3 | L30 | Q84 |
| 11930 | Z3 | L30 | Q85 |
| 11931 | Z3 | L30 | Q86 |
| 11932 | Z3 | L30 | Q87 |
| 11933 | Z3 | L30 | Q88 |
| 11934 | Z3 | L30 | Q89 |
| 11935 | Z3 | L30 | Q90 |
| 11936 | Z3 | L30 | Q91 |
| 11937 | Z3 | L30 | Q92 |
| 11938 | Z3 | L30 | Q93 |
| 11939 | Z3 | L30 | Q94 |
| 11940 | Z3 | L30 | Q95 |
| 11941 | Z3 | L30 | Q96 |
| 11942 | Z3 | L30 | Q97 |
| 11943 | Z3 | L30 | Q98 |
| 11944 | Z3 | L30 | Q99 |
| 11945 | Z3 | L30 | Q100 |
| 11946 | Z3 | L30 | Q101 |
| 11947 | Z3 | L30 | Q102 |
| 11948 | Z3 | L30 | Q103 |
| 11949 | Z3 | L31 | Q1 |
| 11950 | Z3 | L31 | Q2 |
| 11951 | Z3 | L31 | Q3 |
| 11952 | Z3 | L31 | Q4 |
| 11953 | Z3 | L31 | Q5 |
| 11954 | Z3 | L31 | Q6 |
| 11955 | Z3 | L31 | Q7 |
| 11956 | Z3 | L31 | Q8 |
| 11957 | Z3 | L31 | Q9 |
| 11958 | Z3 | L31 | Q10 |
| 11959 | Z3 | L31 | Q11 |
| 11960 | Z3 | L31 | Q12 |
| 11961 | Z3 | L31 | Q13 |
| 11962 | Z3 | L31 | Q14 |
| 11963 | Z3 | L31 | Q15 |
| 11964 | Z3 | L31 | Q16 |
| 11965 | Z3 | L31 | Q17 |
| 11966 | Z3 | L31 | Q18 |
| 11967 | Z3 | L31 | Q19 |
| 11968 | Z3 | L31 | Q20 |
| 11969 | Z3 | L31 | Q21 |
| 11970 | Z3 | L31 | Q22 |
| 11971 | Z3 | L31 | Q23 |
| 11972 | Z3 | L31 | Q24 |
| 11973 | Z3 | L31 | Q25 |
| 11974 | Z3 | L31 | Q26 |
| 11975 | Z3 | L31 | Q27 |
| 11976 | Z3 | L31 | Q28 |
| 11977 | Z3 | L31 | Q29 |
| 11978 | Z3 | L31 | Q30 |
| 11979 | Z3 | L31 | Q31 |
| 11980 | Z3 | L31 | Q32 |
| 11981 | Z3 | L31 | Q33 |
| 11982 | Z3 | L31 | Q34 |
| 11983 | Z3 | L31 | Q35 |
| 11984 | Z3 | L31 | Q36 |
| 11985 | Z3 | L31 | Q37 |
| 11986 | Z3 | L31 | Q38 |
| 11987 | Z3 | L31 | Q39 |
| 11988 | Z3 | L31 | Q40 |
| 11989 | Z3 | L31 | Q41 |
| 11990 | Z3 | L31 | Q42 |
| 11991 | Z3 | L31 | Q43 |
| 11992 | Z3 | L31 | Q44 |
| 11993 | Z3 | L31 | Q45 |
| 11994 | Z3 | L31 | Q46 |
| 11995 | Z3 | L31 | Q47 |
| 11996 | Z3 | L31 | Q48 |
| 11997 | Z3 | L31 | Q49 |
| 11998 | Z3 | L31 | Q50 |
| 11999 | Z3 | L31 | Q51 |
| 12000 | Z3 | L31 | Q52 |
| 12001 | Z3 | L31 | Q53 |
| 12002 | Z3 | L31 | Q54 |
| 12003 | Z3 | L31 | Q55 |
| 12004 | Z3 | L31 | Q56 |
| 12005 | Z3 | L31 | Q57 |
| 12006 | Z3 | L31 | Q58 |
| 12007 | Z3 | L31 | Q59 |
| 12008 | Z3 | L31 | Q60 |
| 12009 | Z3 | L31 | Q61 |
| 12010 | Z3 | L31 | Q62 |
| 12011 | Z3 | L31 | Q63 |
| 12012 | Z3 | L31 | Q64 |
| 12013 | Z3 | L31 | Q65 |
| 12014 | Z3 | L31 | Q66 |
| 12015 | Z3 | L31 | Q67 |
| 12016 | Z3 | L31 | Q68 |
| 12017 | Z3 | L31 | Q69 |
| 12018 | Z3 | L31 | Q70 |
| 12019 | Z3 | L31 | Q71 |
| 12020 | Z3 | L31 | Q72 |
| 12021 | Z3 | L31 | Q73 |
| 12022 | Z3 | L31 | Q74 |
| 12023 | Z3 | L31 | Q75 |
| 12024 | Z3 | L31 | Q76 |
| 12025 | Z3 | L31 | Q77 |
| 12026 | Z3 | L31 | Q78 |
| 12027 | Z3 | L31 | Q79 |
| 12028 | Z3 | L31 | Q80 |
| 12029 | Z3 | L31 | Q81 |
| 12030 | Z3 | L31 | Q82 |
| 12031 | Z3 | L31 | Q83 |
| 12032 | Z3 | L31 | Q84 |

TABLE 1-66

| | | | |
|---|---|---|---|
| 12033 | Z3 | L31 | Q85 |
| 12034 | Z3 | L31 | Q86 |
| 12035 | Z3 | L31 | Q87 |
| 12036 | Z3 | L31 | Q88 |
| 12037 | Z3 | L31 | Q89 |
| 12038 | Z3 | L31 | Q90 |
| 12039 | Z3 | L31 | Q91 |
| 12040 | Z3 | L31 | Q92 |
| 12041 | Z3 | L31 | Q93 |
| 12042 | Z3 | L31 | Q94 |
| 12043 | Z3 | L31 | Q95 |
| 12044 | Z3 | L31 | Q96 |
| 12045 | Z3 | L31 | Q97 |
| 12046 | Z3 | L31 | Q98 |
| 12047 | Z3 | L31 | Q99 |
| 12048 | Z3 | L31 | Q100 |
| 12049 | Z3 | L31 | Q101 |
| 12050 | Z3 | L31 | Q102 |
| 12051 | Z3 | L31 | Q103 |
| 12052 | Z3 | L32 | Q1 |
| 12053 | Z3 | L32 | Q2 |
| 12054 | Z3 | L32 | Q3 |
| 12055 | Z3 | L32 | Q4 |
| 12056 | Z3 | L32 | Q5 |
| 12057 | Z3 | L32 | Q6 |
| 12058 | Z3 | L32 | Q7 |
| 12059 | Z3 | L32 | Q8 |
| 12060 | Z3 | L32 | Q9 |
| 12061 | Z3 | L32 | Q10 |
| 12062 | Z3 | L32 | Q11 |
| 12063 | Z3 | L32 | Q12 |
| 12064 | Z3 | L32 | Q13 |
| 12065 | Z3 | L32 | Q14 |
| 12066 | Z3 | L32 | Q15 |
| 12067 | Z3 | L32 | Q16 |
| 12068 | Z3 | L32 | Q17 |
| 12069 | Z3 | L32 | Q18 |
| 12070 | Z3 | L32 | Q19 |
| 12071 | Z3 | L32 | Q20 |
| 12072 | Z3 | L32 | Q21 |
| 12073 | Z3 | L32 | Q22 |
| 12074 | Z3 | L32 | Q23 |
| 12075 | Z3 | L32 | Q24 |

TABLE 1-66-continued

| | | | |
|---|---|---|---|
| 12076 | Z3 | L32 | Q25 |
| 12077 | Z3 | L32 | Q26 |
| 12078 | Z3 | L32 | Q27 |
| 12079 | Z3 | L32 | Q28 |
| 12080 | Z3 | L32 | Q29 |
| 12081 | Z3 | L32 | Q30 |
| 12082 | Z3 | L32 | Q31 |
| 12083 | Z3 | L32 | Q32 |
| 12084 | Z3 | L32 | Q33 |
| 12085 | Z3 | L32 | Q34 |
| 12086 | Z3 | L32 | Q35 |
| 12087 | Z3 | L32 | Q36 |
| 12088 | Z3 | L32 | Q37 |
| 12089 | Z3 | L32 | Q38 |
| 12090 | Z3 | L32 | Q39 |
| 12091 | Z3 | L32 | Q40 |
| 12092 | Z3 | L32 | Q41 |
| 12093 | Z3 | L32 | Q42 |
| 12094 | Z3 | L32 | Q43 |
| 12095 | Z3 | L32 | Q44 |
| 12096 | Z3 | L32 | Q45 |
| 12097 | Z3 | L32 | Q46 |
| 12098 | Z3 | L32 | Q47 |
| 12099 | Z3 | L32 | Q48 |
| 12100 | Z3 | L32 | Q49 |
| 12101 | Z3 | L32 | Q50 |
| 12102 | Z3 | L32 | Q51 |
| 12103 | Z3 | L32 | Q52 |
| 12104 | Z3 | L32 | Q53 |
| 12105 | Z3 | L32 | Q54 |
| 12106 | Z3 | L32 | Q55 |
| 12107 | Z3 | L32 | Q50 |
| 12108 | Z3 | L32 | Q57 |
| 12109 | Z3 | L32 | Q58 |
| 12110 | Z3 | L32 | Q59 |
| 12111 | Z3 | L32 | Q60 |
| 12112 | Z3 | L32 | Q61 |
| 12113 | Z3 | L32 | Q62 |
| 12114 | Z3 | L32 | Q63 |
| 12115 | Z3 | L32 | Q64 |
| 12116 | Z3 | L32 | Q55 |
| 12117 | Z3 | L32 | Q66 |
| 12118 | Z3 | L32 | Q67 |
| 12119 | Z3 | L32 | Q68 |
| 12120 | Z3 | L32 | Q89 |
| 12121 | Z3 | L32 | Q70 |
| 12122 | Z3 | L32 | Q71 |
| 12123 | Z3 | L32 | Q72 |
| 12124 | Z3 | L32 | Q73 |
| 12125 | Z3 | L32 | Q74 |
| 12126 | Z3 | L32 | Q75 |
| 12127 | Z3 | L32 | Q76 |
| 12128 | Z3 | L32 | Q77 |
| 12129 | Z3 | L32 | Q78 |
| 12130 | Z3 | L32 | Q79 |
| 12131 | Z3 | L32 | Q80 |
| 12132 | Z3 | L32 | Q81 |
| 12133 | Z3 | L32 | Q82 |
| 12134 | Z3 | L32 | Q83 |
| 12135 | Z3 | L32 | Q84 |
| 12135 | Z3 | L32 | Q85 |
| 12137 | Z3 | L32 | Q86 |
| 12138 | Z3 | L32 | Q87 |
| 12139 | Z3 | L32 | Q88 |
| 12140 | Z3 | L32 | Q89 |
| 12141 | Z3 | L32 | Q90 |
| 12142 | Z3 | L32 | Q91 |
| 12143 | Z3 | L32 | Q92 |
| 12144 | Z3 | L32 | Q93 |
| 12145 | Z3 | L32 | Q94 |
| 12145 | Z3 | L32 | Q95 |
| 12147 | Z3 | L32 | Q96 |
| 12148 | Z3 | L32 | Q97 |
| 12149 | Z3 | L32 | Q98 |
| 12150 | Z3 | L32 | Q99 |
| 12151 | Z3 | L32 | Q100 |
| 12152 | Z3 | L32 | Q101 |
| 12153 | Z3 | L32 | Q102 |
| 12154 | Z3 | L32 | Q103 |
| 12155 | Z3 | L33 | Q1 |
| 12156 | Z3 | L33 | Q2 |
| 12157 | Z3 | L33 | Q3 |
| 12158 | Z3 | L33 | Q4 |
| 12159 | Z3 | L33 | Q5 |
| 12160 | Z3 | L33 | Q6 |
| 12161 | Z3 | L33 | Q7 |
| 12162 | Z3 | L33 | Q8 |
| 12163 | Z3 | L33 | Q9 |
| 12164 | Z3 | L33 | Q10 |
| 12165 | Z3 | L33 | Q11 |
| 12166 | Z3 | L33 | Q12 |
| 12167 | Z3 | L33 | Q13 |
| 12168 | Z3 | L33 | Q14 |
| 12169 | Z3 | L33 | Q15 |
| 12170 | Z3 | L33 | Q16 |
| 12171 | Z3 | L33 | Q17 |
| 12172 | Z3 | L33 | Q18 |
| 12173 | Z3 | L33 | Q19 |
| 12174 | Z3 | L33 | Q20 |
| 12175 | Z3 | L33 | Q21 |
| 12176 | Z3 | L33 | Q22 |
| 12177 | Z3 | L33 | Q23 |
| 12178 | Z3 | L33 | Q24 |
| 12179 | Z3 | L33 | Q25 |
| 12180 | Z3 | L33 | Q26 |
| 12181 | Z3 | L33 | Q27 |
| 12182 | Z3 | L33 | Q28 |
| 12183 | Z3 | L33 | Q29 |
| 12184 | Z3 | L33 | Q30 |
| 12185 | Z3 | L33 | Q31 |
| 12186 | Z3 | L33 | Q32 |
| 12187 | Z3 | L33 | Q33 |
| 12188 | Z3 | L33 | Q34 |
| 12189 | Z3 | L33 | Q35 |
| 12190 | Z3 | L33 | Q36 |
| 12191 | Z3 | L33 | Q37 |
| 12192 | Z3 | L33 | Q38 |
| 12193 | Z3 | L33 | Q39 |
| 12194 | Z3 | L33 | Q40 |
| 12195 | Z3 | L33 | Q41 |
| 12196 | Z3 | L33 | Q42 |
| 12197 | Z3 | L33 | Q43 |
| 12198 | Z3 | L33 | Q44 |
| 12199 | Z3 | L33 | Q45 |
| 12200 | Z3 | L33 | Q46 |
| 12201 | Z3 | L33 | Q47 |
| 12202 | Z3 | L33 | Q48 |
| 12203 | Z3 | L33 | Q49 |
| 12204 | Z3 | L33 | Q50 |
| 12205 | Z3 | L33 | Q51 |
| 12206 | Z3 | L33 | Q52 |
| 12207 | Z3 | L33 | Q53 |
| 12208 | Z3 | L33 | Q54 |
| 12209 | Z3 | L33 | Q55 |
| 12210 | Z3 | L33 | Q56 |
| 12211 | Z3 | L33 | Q57 |
| 12212 | Z3 | L33 | Q58 |
| 12213 | Z3 | L33 | Q59 |
| 12214 | Z3 | L33 | Q60 |
| 12215 | Z3 | L33 | Q61 |
| 12216 | Z3 | L33 | Q62 |
| 12217 | Z3 | L33 | Q63 |
| 12218 | Z3 | L33 | Q64 |
| 12219 | Z3 | L33 | Q65 |
| 12220 | Z3 | L33 | Q66 |
| 12221 | Z3 | L33 | Q67 |
| 12222 | Z3 | L33 | Q68 |
| 12223 | Z3 | L33 | Q69 |
| 12224 | Z3 | L33 | Q70 |
| 12225 | Z3 | L33 | Q71 |
| 12226 | Z3 | L33 | Q72 |
| 12227 | Z3 | L33 | Q73 |
| 12228 | Z3 | L33 | Q74 |
| 12229 | Z3 | L33 | Q75 |
| 12230 | Z3 | L33 | Q76 |
| 12231 | Z3 | L33 | Q77 |
| 12232 | Z3 | L33 | Q78 |
| 12233 | Z3 | L33 | Q79 |

TABLE 1-67

| | | | |
|---|---|---|---|
| 12234 | Z3 | L33 | Q80 |
| 12235 | Z3 | L33 | Q81 |
| 12236 | Z3 | L33 | Q82 |
| 12237 | Z3 | L33 | Q83 |
| 12238 | Z3 | L33 | Q84 |
| 12239 | Z3 | L33 | Q85 |
| 12240 | Z3 | L33 | Q86 |
| 12241 | Z3 | L33 | Q87 |
| 12242 | Z3 | L33 | Q88 |
| 12243 | Z3 | L33 | Q89 |
| 12244 | Z3 | L33 | Q90 |
| 12245 | Z3 | L33 | Q91 |
| 12246 | Z3 | L33 | Q92 |
| 12247 | Z3 | L33 | Q93 |
| 12248 | Z3 | L33 | Q94 |
| 12249 | Z3 | L33 | Q95 |
| 12250 | Z3 | L33 | Q96 |
| 12251 | Z3 | L33 | Q97 |
| 12252 | Z3 | L33 | Q98 |
| 12253 | Z3 | L33 | Q99 |
| 12254 | Z3 | L33 | Q100 |
| 12255 | Z3 | L33 | Q101 |
| 12256 | Z3 | L33 | Q102 |
| 12257 | Z3 | L33 | Q103 |
| 12258 | Z3 | L34 | Q1 |
| 12259 | Z3 | L34 | Q2 |
| 12260 | Z3 | L34 | Q3 |
| 12261 | Z3 | L34 | Q4 |
| 12262 | Z3 | L34 | Q5 |
| 12263 | Z3 | L34 | Q6 |
| 12264 | Z3 | L34 | Q7 |
| 12265 | Z3 | L34 | Q8 |
| 12266 | Z3 | L34 | Q9 |
| 12267 | Z3 | L34 | Q10 |
| 12268 | Z3 | L34 | Q11 |
| 12269 | Z3 | L34 | Q12 |
| 12270 | Z3 | L34 | Q13 |
| 12271 | Z3 | L34 | Q14 |
| 12272 | Z3 | L34 | Q15 |
| 12273 | Z3 | L34 | Q16 |
| 12274 | Z3 | L34 | Q17 |
| 12275 | Z3 | L34 | Q18 |
| 12276 | Z3 | L34 | Q19 |
| 12277 | Z3 | L34 | Q20 |
| 12278 | Z3 | L34 | Q21 |
| 12279 | Z3 | L34 | Q22 |
| 12280 | Z3 | L34 | Q23 |
| 12281 | Z3 | L34 | Q24 |
| 12282 | Z3 | L34 | Q25 |
| 12283 | Z3 | L34 | Q26 |
| 12284 | Z3 | L34 | Q27 |
| 12285 | Z3 | L34 | Q28 |
| 12286 | Z3 | L34 | Q29 |
| 12287 | Z3 | L34 | Q30 |
| 12288 | Z3 | L34 | Q31 |
| 12289 | Z3 | L34 | Q32 |
| 12290 | Z3 | L34 | Q33 |
| 12291 | Z3 | L34 | Q34 |
| 12292 | Z3 | L34 | Q35 |
| 12293 | Z3 | L34 | Q36 |
| 12294 | Z3 | L34 | Q37 |
| 12295 | Z3 | L34 | Q38 |
| 12296 | Z3 | L34 | Q39 |
| 12297 | Z3 | L34 | Q40 |
| 12298 | Z3 | L34 | Q41 |
| 12299 | Z3 | L34 | Q42 |
| 12300 | Z3 | L34 | Q43 |
| 12301 | Z3 | L34 | Q44 |
| 12302 | Z3 | L34 | Q45 |
| 12303 | Z3 | L34 | Q46 |
| 12304 | Z3 | L34 | Q47 |
| 12305 | Z3 | L34 | Q48 |
| 12306 | Z3 | L34 | Q49 |
| 12307 | Z3 | L34 | Q50 |
| 12308 | Z3 | L34 | Q51 |
| 12309 | Z3 | L34 | Q52 |
| 12310 | Z3 | L34 | Q53 |
| 12311 | Z3 | L34 | Q54 |
| 12312 | Z3 | L34 | Q55 |
| 12313 | Z3 | L34 | Q56 |
| 12314 | Z3 | L34 | Q57 |
| 12315 | Z3 | L34 | Q58 |
| 12316 | Z3 | L34 | Q59 |
| 12317 | Z3 | L34 | Q60 |
| 12318 | Z3 | L34 | Q61 |
| 12319 | Z3 | L34 | Q62 |
| 12320 | Z3 | L34 | Q63 |
| 12321 | Z3 | L34 | Q64 |
| 12322 | Z3 | L34 | Q65 |
| 12323 | Z3 | L34 | Q66 |
| 12324 | Z3 | L34 | Q67 |
| 12325 | Z3 | L34 | Q68 |
| 12326 | Z3 | L34 | Q69 |
| 12327 | Z3 | L34 | Q70 |
| 12328 | Z3 | L34 | Q71 |
| 12329 | Z3 | L34 | Q72 |
| 12330 | Z3 | L34 | Q73 |
| 12331 | Z3 | L34 | Q74 |
| 12332 | Z3 | L34 | Q75 |
| 12333 | Z3 | L34 | Q76 |
| 12334 | Z3 | L34 | Q77 |
| 12335 | Z3 | L34 | Q78 |
| 12336 | Z3 | L34 | Q79 |
| 12337 | Z3 | L34 | Q80 |
| 12338 | Z3 | L34 | Q81 |
| 12339 | Z3 | L34 | Q82 |
| 12340 | Z3 | L34 | Q83 |
| 12341 | Z3 | L34 | Q84 |
| 12342 | Z3 | L34 | Q85 |
| 12343 | Z3 | L34 | Q86 |
| 12344 | Z3 | L34 | Q87 |
| 12345 | Z3 | L34 | Q88 |
| 12346 | Z3 | L34 | Q89 |
| 12347 | Z3 | L34 | Q90 |
| 12348 | Z3 | L34 | Q91 |
| 12349 | Z3 | L34 | Q92 |
| 12350 | Z3 | L34 | Q93 |
| 12351 | Z3 | L34 | Q94 |
| 12352 | Z3 | L34 | Q95 |
| 12353 | Z3 | L34 | Q96 |
| 12354 | Z3 | L34 | Q97 |
| 12355 | Z3 | L34 | Q98 |
| 12356 | Z3 | L34 | Q99 |
| 12357 | Z3 | L34 | Q100 |
| 12358 | Z3 | L34 | Q101 |
| 12359 | Z3 | L34 | Q102 |
| 12360 | Z3 | L34 | Q103 |
| 12361 | Z3 | L35 | Q1 |
| 12362 | Z3 | L35 | Q2 |
| 12363 | Z3 | L35 | Q3 |
| 12364 | Z3 | L35 | Q4 |
| 12365 | Z3 | L35 | Q5 |
| 12366 | Z3 | L35 | Q5 |
| 12367 | Z3 | L35 | Q7 |
| 12368 | Z3 | L35 | Q8 |
| 12369 | Z3 | L35 | Q9 |
| 12370 | Z3 | L35 | Q10 |
| 12371 | Z3 | L35 | Q11 |
| 12372 | Z3 | L35 | Q12 |
| 12373 | Z3 | L35 | Q13 |
| 12374 | Z3 | L35 | Q14 |
| 12375 | Z3 | L35 | Q15 |
| 12376 | Z3 | L35 | Q16 |
| 12377 | Z3 | L35 | Q17 |
| 12378 | Z3 | L35 | Q18 |
| 12379 | Z3 | L35 | Q19 |
| 12380 | Z3 | L35 | Q20 |
| 12381 | Z3 | L35 | Q21 |
| 12382 | Z3 | L35 | Q22 |
| 12383 | Z3 | L35 | Q23 |
| 12384 | Z3 | L35 | Q24 |
| 12385 | Z3 | L35 | Q25 |
| 12386 | Z3 | L35 | Q26 |
| 12387 | Z3 | L35 | Q27 |
| 12388 | Z3 | L35 | Q28 |
| 12389 | Z3 | L35 | Q29 |
| 12390 | Z3 | L35 | Q30 |
| 12391 | Z3 | L35 | Q31 |
| 12392 | Z3 | L35 | Q32 |
| 12393 | Z3 | L35 | Q33 |

TABLE 1-67-continued

| | | | |
|---|---|---|---|
| 12394 | Z3 | L35 | Q34 |
| 12395 | Z3 | L35 | Q35 |
| 12396 | Z3 | L35 | Q36 |
| 12397 | Z3 | L35 | Q37 |
| 12398 | Z3 | L35 | Q38 |
| 12399 | Z3 | L35 | Q39 |
| 12400 | Z3 | L35 | Q40 |
| 12401 | Z3 | L35 | Q41 |
| 12402 | Z3 | L35 | Q42 |
| 12403 | Z3 | L35 | Q43 |
| 12404 | Z3 | L35 | Q44 |
| 12405 | Z3 | L35 | Q45 |
| 12406 | Z3 | L35 | Q46 |
| 12407 | Z3 | L35 | Q47 |
| 12408 | Z3 | L35 | Q48 |
| 12409 | Z3 | L35 | Q49 |
| 12410 | Z3 | L35 | Q50 |
| 12411 | Z3 | L35 | Q51 |
| 12412 | Z3 | L35 | Q52 |
| 12413 | Z3 | L35 | Q53 |
| 12414 | Z3 | L35 | Q54 |
| 12415 | Z3 | L35 | Q55 |
| 12416 | Z3 | L35 | Q56 |
| 12417 | Z3 | L35 | Q57 |
| 12418 | Z3 | L35 | Q58 |
| 12419 | Z3 | L35 | Q59 |
| 12420 | Z3 | L35 | Q60 |
| 12421 | Z3 | L35 | Q61 |
| 12422 | Z3 | L35 | Q62 |
| 12423 | Z3 | L35 | Q63 |
| 12424 | Z3 | L35 | Q64 |
| 12425 | Z3 | L35 | Q65 |
| 12426 | Z3 | L35 | Q66 |
| 12427 | Z3 | L35 | Q67 |
| 12428 | Z3 | L35 | Q68 |
| 12429 | Z3 | L35 | Q69 |
| 12430 | Z3 | L35 | Q70 |
| 12431 | Z3 | L35 | Q71 |
| 12432 | Z3 | L35 | Q72 |
| 12433 | Z3 | L35 | Q73 |
| 12434 | Z3 | L35 | Q74 |

TABLE 1-68

| | | | |
|---|---|---|---|
| 12435 | Z3 | L35 | Q75 |
| 12436 | Z3 | L35 | Q76 |
| 12437 | Z3 | L35 | Q77 |
| 12438 | Z3 | L35 | Q78 |
| 12439 | Z3 | L35 | Q79 |
| 12440 | Z3 | L35 | Q80 |
| 12441 | Z3 | L35 | Q81 |
| 12442 | Z3 | L35 | Q82 |
| 12443 | Z3 | L35 | Q83 |
| 12444 | Z3 | L35 | Q84 |
| 12445 | Z3 | L35 | Q85 |
| 12446 | Z3 | L35 | Q86 |
| 12447 | Z3 | L35 | Q87 |
| 12448 | Z3 | L35 | Q88 |
| 12449 | Z3 | L35 | Q89 |
| 12450 | Z3 | L35 | Q90 |
| 12451 | Z3 | L35 | Q91 |
| 12452 | Z3 | L35 | Q92 |
| 12453 | Z3 | L35 | Q93 |
| 12454 | Z3 | L35 | Q94 |
| 12455 | Z3 | L35 | Q95 |
| 12456 | Z3 | L35 | Q96 |
| 12457 | Z3 | L35 | Q97 |
| 12458 | Z3 | L35 | Q98 |
| 12459 | Z3 | L35 | Q99 |
| 12460 | Z3 | L35 | Q100 |
| 12461 | Z3 | L35 | Q101 |
| 12462 | Z3 | L35 | Q102 |
| 12463 | Z3 | L35 | Q103 |
| 12464 | Z3 | L36 | Q1 |
| 12465 | Z3 | L36 | Q2 |
| 12466 | Z3 | L36 | Q3 |
| 12467 | Z3 | L36 | Q4 |

TABLE 1-68-continued

| | | | |
|---|---|---|---|
| 12468 | Z3 | L36 | Q5 |
| 12469 | Z3 | L36 | Q6 |
| 12470 | Z3 | L36 | Q7 |
| 12471 | Z3 | L36 | Q8 |
| 12472 | Z3 | L36 | Q9 |
| 12473 | Z3 | L36 | Q10 |
| 12474 | Z3 | L36 | Q11 |
| 12475 | Z3 | L36 | Q12 |
| 12476 | Z3 | L36 | Q13 |
| 12477 | Z3 | L36 | Q14 |
| 12478 | Z3 | L36 | Q15 |
| 12479 | Z3 | L36 | Q16 |
| 12480 | Z3 | L36 | Q17 |
| 12481 | Z3 | L36 | Q18 |
| 12482 | Z3 | L36 | Q19 |
| 12483 | Z3 | L36 | Q20 |
| 12484 | Z3 | L36 | Q21 |
| 12485 | Z3 | L36 | Q22 |
| 12486 | Z3 | L36 | Q23 |
| 12487 | Z3 | L36 | Q24 |
| 12488 | Z3 | L36 | Q25 |
| 12489 | Z3 | L36 | Q26 |
| 12490 | Z3 | L36 | Q27 |
| 12491 | Z3 | L36 | Q28 |
| 12492 | Z3 | L36 | Q29 |
| 12493 | Z3 | L36 | Q30 |
| 12494 | Z3 | L36 | Q31 |
| 12495 | Z3 | L36 | Q32 |
| 12496 | Z3 | L36 | Q33 |
| 12497 | Z3 | L36 | Q34 |
| 12498 | Z3 | L36 | Q35 |
| 12499 | Z3 | L36 | Q36 |
| 12500 | Z3 | L36 | Q37 |
| 12501 | Z3 | L36 | Q38 |
| 12502 | Z3 | L36 | Q39 |
| 12503 | Z3 | L36 | Q40 |
| 12504 | Z3 | L36 | Q41 |
| 12505 | Z3 | L36 | Q42 |
| 12506 | Z3 | L36 | Q43 |
| 12507 | Z3 | L36 | Q44 |
| 12508 | Z3 | L36 | Q45 |
| 12509 | Z3 | L36 | Q46 |
| 12510 | Z3 | L36 | Q47 |
| 12511 | Z3 | L36 | Q48 |
| 12512 | Z3 | L36 | Q49 |
| 12513 | Z3 | L36 | Q50 |
| 12514 | Z3 | L36 | Q51 |
| 12515 | Z3 | L36 | Q52 |
| 12516 | Z3 | L36 | Q53 |
| 12517 | Z3 | L36 | Q54 |
| 12518 | Z3 | L36 | Q55 |
| 12519 | Z3 | L36 | Q56 |
| 12520 | Z3 | L36 | Q57 |
| 12521 | Z3 | L36 | Q58 |
| 12522 | Z3 | L36 | Q59 |
| 12523 | Z3 | L36 | Q60 |
| 12524 | Z3 | L36 | Q61 |
| 12525 | Z3 | L36 | Q62 |
| 12526 | Z3 | L36 | Q63 |
| 12527 | Z3 | L36 | Q64 |
| 12528 | Z3 | L36 | Q65 |
| 12529 | Z3 | L36 | Q66 |
| 12530 | Z3 | L36 | Q67 |
| 12531 | Z3 | L36 | Q68 |
| 12532 | Z3 | L36 | Q69 |
| 12533 | Z3 | L36 | Q70 |
| 12534 | Z3 | L36 | Q71 |
| 12535 | Z3 | L36 | Q72 |
| 12536 | Z3 | L36 | Q73 |
| 12537 | Z3 | L36 | Q74 |
| 12538 | Z3 | L36 | Q75 |
| 12539 | Z3 | L36 | Q76 |
| 12540 | Z3 | L36 | Q77 |
| 12541 | Z3 | L36 | Q78 |
| 12542 | Z3 | L36 | Q79 |
| 12543 | Z3 | L36 | Q80 |
| 12544 | Z3 | L36 | Q81 |
| 12545 | Z3 | L36 | Q82 |
| 12546 | Z3 | L36 | Q83 |
| 12547 | Z3 | L36 | Q84 |

TABLE 1-68-continued

| | | | |
|---|---|---|---|
| 12548 | Z3 | L36 | Q85 |
| 12549 | Z3 | L36 | Q86 |
| 12550 | Z3 | L36 | Q87 |
| 12551 | Z3 | L36 | Q88 |
| 12552 | Z3 | L36 | Q89 |
| 12553 | Z3 | L36 | Q90 |
| 12554 | Z3 | L36 | Q91 |
| 12555 | Z3 | L36 | Q92 |
| 12556 | Z3 | L36 | Q93 |
| 12557 | Z3 | L36 | Q94 |
| 12558 | Z3 | L36 | Q95 |
| 12559 | Z3 | L36 | Q96 |
| 12560 | Z3 | L36 | Q97 |
| 12561 | Z3 | L36 | Q98 |
| 12562 | Z3 | L36 | Q99 |
| 12563 | Z3 | L36 | Q100 |
| 12564 | Z3 | L36 | Q101 |
| 12565 | Z3 | L36 | Q102 |
| 12566 | Z3 | L36 | Q103 |
| 12567 | Z4 | L15 | Q1 |
| 12568 | Z4 | L15 | Q2 |
| 12569 | Z4 | L15 | Q3 |
| 12570 | Z4 | L15 | Q4 |
| 12571 | Z4 | L15 | Q5 |
| 12572 | Z4 | L15 | Q6 |
| 12573 | Z4 | L15 | Q7 |
| 12574 | Z4 | L15 | Q8 |
| 12575 | Z4 | L15 | Q9 |
| 12576 | Z4 | L15 | Q10 |
| 12577 | Z4 | L15 | Q11 |
| 12578 | Z4 | L15 | Q12 |
| 12579 | Z4 | L15 | Q13 |
| 12580 | Z4 | L15 | Q14 |
| 12581 | Z4 | L15 | Q15 |
| 12582 | Z4 | L15 | Q16 |
| 12583 | Z4 | L15 | Q17 |
| 12584 | Z4 | L15 | Q18 |
| 12585 | Z4 | L15 | Q19 |
| 12586 | Z4 | L15 | Q20 |
| 12587 | Z4 | L15 | Q21 |
| 12588 | Z4 | L15 | Q22 |
| 12589 | Z4 | L15 | Q23 |
| 12590 | Z4 | L15 | Q24 |
| 12591 | Z4 | L15 | Q25 |
| 12592 | Z4 | L15 | Q26 |
| 12593 | Z4 | L15 | Q27 |
| 12594 | Z4 | L15 | Q28 |
| 12595 | Z4 | L15 | Q29 |
| 12596 | Z4 | L15 | Q30 |
| 12597 | Z4 | L15 | Q31 |
| 12598 | Z4 | L15 | Q32 |
| 12599 | Z4 | L15 | Q33 |
| 12600 | Z4 | L15 | Q34 |
| 12601 | Z4 | L15 | Q35 |
| 12602 | Z4 | L15 | Q36 |
| 12603 | Z4 | L15 | Q37 |
| 12604 | Z4 | L15 | Q38 |
| 12605 | Z4 | L15 | Q39 |
| 12606 | Z4 | L15 | Q40 |
| 12607 | Z4 | L15 | Q41 |
| 12603 | Z4 | L15 | Q42 |
| 12609 | Z4 | L15 | Q43 |
| 12610 | Z4 | L15 | Q44 |
| 12611 | Z4 | L15 | Q45 |
| 12612 | Z4 | L15 | Q46 |
| 12613 | Z4 | L15 | Q47 |
| 12614 | Z4 | L15 | Q48 |
| 12615 | Z4 | L15 | Q49 |
| 12616 | Z4 | L15 | Q50 |
| 12617 | Z4 | L15 | Q51 |
| 12618 | Z4 | L15 | Q52 |
| 12619 | Z4 | L15 | Q53 |
| 12620 | Z4 | L15 | Q54 |
| 12621 | Z4 | L15 | Q55 |
| 12622 | Z4 | L15 | Q56 |
| 12623 | Z4 | L15 | Q57 |
| 12624 | Z4 | L15 | Q58 |
| 12625 | Z4 | L15 | Q59 |
| 12626 | Z4 | L15 | Q60 |
| 12627 | Z4 | L15 | Q61 |
| 12628 | Z4 | L15 | Q62 |
| 12629 | Z4 | L15 | Q63 |
| 12630 | Z4 | L15 | Q64 |
| 12631 | Z4 | L15 | Q65 |
| 12632 | Z4 | L15 | Q65 |
| 12633 | Z4 | L15 | Q67 |
| 12634 | Z4 | L15 | Q68 |
| 12635 | Z4 | L15 | Q69 |

TABLE 1-69

| | | | |
|---|---|---|---|
| 12636 | Z4 | L15 | Q70 |
| 12637 | Z4 | L15 | Q71 |
| 12638 | Z4 | L15 | Q72 |
| 12639 | Z4 | L15 | Q73 |
| 12640 | Z4 | L15 | Q74 |
| 12641 | Z4 | L15 | Q75 |
| 12642 | Z4 | L15 | Q76 |
| 12643 | Z4 | L15 | Q77 |
| 12644 | Z4 | L15 | Q78 |
| 12645 | Z4 | L15 | Q79 |
| 12646 | Z4 | L15 | Q80 |
| 12647 | Z4 | L15 | Q81 |
| 12648 | Z4 | L15 | Q82 |
| 12649 | Z4 | L15 | Q83 |
| 12650 | Z4 | L15 | Q84 |
| 12651 | Z4 | L15 | Q85 |
| 12652 | Z4 | L15 | Q86 |
| 12653 | Z4 | L15 | Q87 |
| 12654 | Z4 | L15 | Q88 |
| 12655 | Z4 | L15 | Q89 |
| 12656 | Z4 | L15 | Q90 |
| 12657 | Z4 | L15 | Q91 |
| 12658 | Z4 | L15 | Q92 |
| 12659 | Z4 | L15 | Q93 |
| 12660 | Z4 | L15 | Q94 |
| 12661 | Z4 | L15 | Q95 |
| 12662 | Z4 | L15 | Q96 |
| 12663 | Z4 | L15 | Q97 |
| 12664 | Z4 | L15 | Q98 |
| 12665 | Z4 | L15 | Q99 |
| 12666 | Z4 | L15 | Q100 |
| 12667 | Z4 | L15 | Q101 |
| 12668 | Z4 | L15 | Q102 |
| 12669 | Z4 | L15 | Q103 |
| 12670 | Z4 | L16 | Q1 |
| 12671 | Z4 | L16 | Q2 |
| 12672 | Z4 | L16 | Q3 |
| 12673 | Z4 | L16 | Q4 |
| 12674 | Z4 | L16 | Q5 |
| 12675 | Z4 | L16 | Q6 |
| 12676 | Z4 | L16 | Q7 |
| 12677 | Z4 | L16 | Q8 |
| 12678 | Z4 | L16 | Q9 |
| 12679 | Z4 | L16 | Q10 |
| 12680 | Z4 | L16 | Q11 |
| 12681 | Z4 | L16 | Q12 |
| 12682 | Z4 | L16 | Q13 |
| 12683 | Z4 | L16 | Q14 |
| 12684 | Z4 | L16 | Q15 |
| 12685 | Z4 | L16 | Q16 |
| 12686 | Z4 | L16 | Q17 |
| 12687 | Z4 | L16 | Q18 |
| 12688 | Z4 | L16 | Q19 |
| 12689 | Z4 | L16 | Q20 |
| 12690 | Z4 | L16 | Q21 |
| 12691 | Z4 | L16 | Q22 |
| 12692 | Z4 | L16 | Q23 |
| 12693 | Z4 | L16 | Q24 |
| 12694 | Z4 | L16 | Q25 |
| 12695 | Z4 | L16 | Q26 |
| 12696 | Z4 | L16 | Q27 |
| 12697 | Z4 | L16 | Q28 |
| 12698 | Z4 | L16 | Q29 |
| 12699 | Z4 | L16 | Q30 |
| 12700 | Z4 | L16 | Q31 |
| 12701 | Z4 | L16 | Q32 |

TABLE 1-69-continued

| | | | |
|---|---|---|---|
| 12702 | Z4 | L16 | Q33 |
| 12703 | Z4 | L16 | Q34 |
| 12704 | Z4 | L16 | Q35 |
| 12705 | Z4 | L16 | Q36 |
| 12706 | Z4 | L16 | Q37 |
| 12707 | Z4 | L16 | Q38 |
| 12708 | Z4 | L16 | Q39 |
| 12709 | Z4 | L16 | Q40 |
| 12710 | Z4 | L16 | Q41 |
| 12711 | Z4 | L16 | Q42 |
| 12712 | Z4 | L16 | Q43 |
| 12713 | Z4 | L16 | Q44 |
| 12714 | Z4 | L16 | Q45 |
| 12715 | Z4 | L16 | Q46 |
| 12716 | Z4 | L16 | Q47 |
| 12717 | Z4 | L16 | Q48 |
| 12718 | Z4 | L16 | Q49 |
| 12719 | Z4 | L16 | Q50 |
| 12720 | Z4 | L16 | Q51 |
| 12721 | Z4 | L16 | Q52 |
| 12722 | Z4 | L16 | Q53 |
| 12723 | Z4 | L16 | Q54 |
| 12724 | Z4 | L16 | Q55 |
| 12725 | Z4 | L16 | Q56 |
| 12726 | Z4 | L16 | Q57 |
| 12727 | Z4 | L16 | Q58 |
| 12728 | Z4 | L16 | Q59 |
| 12729 | Z4 | L16 | Q60 |
| 12730 | Z4 | L16 | Q61 |
| 12731 | Z4 | L16 | Q62 |
| 12732 | Z4 | L16 | Q63 |
| 12733 | Z4 | L16 | Q64 |
| 12734 | Z4 | L16 | Q65 |
| 12735 | Z4 | L16 | Q66 |
| 12736 | Z4 | L16 | Q67 |
| 12737 | Z4 | L16 | Q68 |
| 12738 | Z4 | L16 | Q69 |
| 12739 | Z4 | L16 | Q70 |
| 12740 | Z4 | L16 | Q71 |
| 12741 | Z4 | L16 | Q72 |
| 12742 | Z4 | L16 | Q73 |
| 12743 | Z4 | L16 | Q74 |
| 12744 | Z4 | L16 | Q75 |
| 12745 | Z4 | L16 | Q76 |
| 12746 | Z4 | L16 | Q77 |
| 12747 | Z4 | L16 | Q78 |
| 12748 | Z4 | L16 | Q79 |
| 12749 | Z4 | L16 | Q80 |
| 12750 | Z4 | L16 | Q81 |
| 12751 | Z4 | L16 | Q82 |
| 12752 | Z4 | L16 | Q83 |
| 12753 | Z4 | L16 | Q84 |
| 12754 | Z4 | L16 | Q85 |
| 12755 | Z4 | L16 | Q86 |
| 12756 | Z4 | L16 | Q87 |
| 12757 | Z4 | L16 | Q88 |
| 12758 | Z4 | L16 | Q89 |
| 12759 | Z4 | L16 | Q90 |
| 12760 | Z4 | L16 | Q91 |
| 12761 | Z4 | L16 | Q92 |
| 12762 | Z4 | L16 | Q93 |
| 12763 | Z4 | L16 | Q94 |
| 12764 | Z4 | L16 | Q95 |
| 12765 | Z4 | L16 | Q96 |
| 12766 | Z4 | L16 | Q97 |
| 12767 | Z4 | L16 | Q98 |
| 12768 | Z4 | L16 | Q99 |
| 12769 | Z4 | L16 | Q100 |
| 12770 | Z4 | L16 | Q101 |
| 12771 | Z4 | L16 | Q102 |
| 12772 | Z4 | L16 | Q103 |
| 12773 | Z4 | L17 | Q1 |
| 12774 | Z4 | L17 | Q2 |
| 12775 | Z4 | L17 | Q3 |
| 12776 | Z4 | L17 | Q4 |
| 12777 | Z4 | L17 | Q5 |
| 12778 | Z4 | L17 | Q6 |
| 12779 | Z4 | L17 | Q7 |
| 12780 | Z4 | L17 | Q8 |
| 12781 | Z4 | L17 | Q9 |
| 12782 | Z4 | L17 | Q10 |
| 12783 | Z4 | L17 | Q11 |
| 12784 | Z4 | L17 | Q12 |
| 12785 | Z4 | L17 | Q13 |
| 12786 | Z4 | L17 | Q14 |
| 12787 | Z4 | L17 | Q15 |
| 12788 | Z4 | L17 | Q16 |
| 12789 | Z4 | L17 | Q17 |
| 12790 | Z4 | L17 | Q18 |
| 12791 | Z4 | L17 | Q19 |
| 12792 | Z4 | L17 | Q20 |
| 12793 | Z4 | L17 | Q21 |
| 12794 | Z4 | L17 | Q22 |
| 12795 | Z4 | L17 | Q23 |
| 12796 | Z4 | L17 | Q24 |
| 12797 | Z4 | L17 | Q25 |
| 12798 | Z4 | L17 | Q26 |
| 12799 | Z4 | L17 | Q27 |
| 12800 | Z4 | L17 | Q28 |
| 12801 | Z4 | L17 | Q29 |
| 12802 | Z4 | L17 | Q30 |
| 12803 | Z4 | L17 | Q31 |
| 12804 | Z4 | L17 | Q32 |
| 12805 | Z4 | L17 | Q33 |
| 12806 | Z4 | L17 | Q34 |
| 12807 | Z4 | L17 | Q35 |
| 12808 | Z4 | L17 | Q36 |
| 12809 | Z4 | L17 | Q37 |
| 12810 | Z4 | L17 | Q38 |
| 12811 | Z4 | L17 | Q39 |
| 12812 | Z4 | L17 | Q40 |
| 12813 | Z4 | L17 | Q41 |
| 12814 | Z4 | L17 | Q42 |
| 12815 | Z4 | L17 | Q43 |
| 12816 | Z4 | L17 | Q44 |
| 12817 | Z4 | L17 | Q45 |
| 12818 | Z4 | L17 | Q46 |
| 12819 | Z4 | L17 | Q47 |
| 12820 | Z4 | L17 | Q48 |
| 12821 | Z4 | L17 | Q49 |
| 12822 | Z4 | L17 | Q50 |
| 12823 | Z4 | L17 | Q51 |
| 12824 | Z4 | L17 | Q52 |
| 12825 | Z4 | L17 | Q53 |
| 12826 | Z4 | L17 | Q54 |
| 12827 | Z4 | L17 | Q55 |
| 12828 | Z4 | L17 | Q56 |
| 12829 | Z4 | L17 | Q57 |
| 12830 | Z4 | L17 | Q58 |
| 12831 | Z4 | L17 | Q59 |
| 12832 | Z4 | L17 | Q60 |
| 12833 | Z4 | L17 | Q61 |
| 12834 | Z4 | L17 | Q62 |
| 12835 | Z4 | L17 | Q63 |
| 12836 | Z4 | L17 | Q64 |

TABLE 1-70

| | | | |
|---|---|---|---|
| 12837 | Z4 | L17 | Q65 |
| 12838 | Z4 | L17 | Q66 |
| 12839 | Z4 | L17 | Q67 |
| 12840 | Z4 | L17 | Q68 |
| 12841 | Z4 | L17 | Q69 |
| 12842 | Z4 | L17 | Q70 |
| 12843 | Z4 | L17 | Q71 |
| 12844 | Z4 | L17 | Q72 |
| 12845 | Z4 | L17 | Q73 |
| 12846 | Z4 | L17 | Q74 |
| 12847 | Z4 | L17 | Q75 |
| 12848 | Z4 | L17 | Q76 |
| 12849 | Z4 | L17 | Q77 |
| 12850 | Z4 | L17 | Q78 |
| 12851 | Z4 | L17 | Q79 |
| 12852 | Z4 | L17 | Q80 |
| 12853 | Z4 | L17 | Q81 |
| 12854 | Z4 | L17 | Q82 |
| 12855 | Z4 | L17 | Q83 |

TABLE 1-70-continued

| | | | |
|---|---|---|---|
| 12856 | Z4 | L17 | Q84 |
| 12857 | Z4 | L17 | Q85 |
| 12858 | Z4 | L17 | Q86 |
| 12859 | Z4 | L17 | Q87 |
| 12860 | Z4 | L17 | Q88 |
| 12861 | Z4 | L17 | Q89 |
| 12862 | Z4 | L17 | Q90 |
| 12863 | Z4 | L17 | Q91 |
| 12864 | Z4 | L17 | Q92 |
| 12865 | Z4 | L17 | Q93 |
| 12866 | Z4 | L17 | Q94 |
| 12867 | Z4 | L17 | Q95 |
| 12868 | Z4 | L17 | Q96 |
| 12869 | Z4 | L17 | Q97 |
| 12870 | Z4 | L17 | Q98 |
| 12871 | Z4 | L17 | Q99 |
| 12872 | Z4 | L17 | Q100 |
| 12873 | Z4 | L17 | Q101 |
| 12874 | Z4 | L17 | Q102 |
| 12875 | Z4 | L17 | Q103 |
| 12876 | Z4 | L18 | Q1 |
| 12877 | Z4 | L18 | Q2 |
| 12878 | Z4 | L18 | Q3 |
| 12879 | Z4 | L18 | Q4 |
| 12880 | Z4 | L18 | Q5 |
| 12881 | Z4 | L18 | Q6 |
| 12882 | Z4 | L18 | Q7 |
| 12883 | Z4 | L18 | Q3 |
| 12884 | Z4 | L18 | Q9 |
| 12885 | Z4 | L18 | Q10 |
| 12886 | Z4 | L18 | Q11 |
| 12887 | Z4 | L18 | Q12 |
| 12888 | Z4 | L18 | Q13 |
| 12889 | Z4 | L18 | Q14 |
| 12890 | Z4 | L18 | Q15 |
| 12891 | Z4 | L18 | Q16 |
| 12892 | Z4 | L18 | Q17 |
| 12893 | Z4 | L18 | Q18 |
| 12894 | Z4 | L18 | Q19 |
| 12895 | Z4 | L18 | Q20 |
| 12896 | Z4 | L18 | Q21 |
| 12897 | Z4 | L18 | Q22 |
| 12898 | Z4 | L18 | Q23 |
| 12899 | Z4 | L18 | Q24 |
| 12900 | Z4 | L18 | Q25 |
| 12901 | Z4 | L18 | Q26 |
| 12902 | Z4 | L18 | Q27 |
| 12903 | Z4 | L18 | Q28 |
| 12904 | Z4 | L18 | Q29 |
| 12905 | Z4 | L18 | Q30 |
| 12906 | Z4 | L18 | Q31 |
| 12907 | Z4 | L18 | Q32 |
| 12908 | Z4 | L18 | Q33 |
| 12909 | Z4 | L18 | Q34 |
| 12910 | Z4 | L18 | Q35 |
| 12911 | Z4 | L18 | Q36 |
| 12912 | Z4 | L18 | Q37 |
| 12913 | Z4 | L18 | Q38 |
| 12914 | Z4 | L18 | Q39 |
| 12915 | Z4 | L18 | Q40 |
| 12916 | Z4 | L18 | Q41 |
| 12917 | Z4 | L18 | Q42 |
| 12918 | Z4 | L18 | Q43 |
| 12919 | Z4 | L18 | Q44 |
| 12920 | Z4 | L18 | Q45 |
| 12921 | Z4 | L18 | Q46 |
| 12922 | Z4 | L18 | Q47 |
| 12923 | Z4 | L18 | Q48 |
| 12924 | Z4 | L18 | Q49 |
| 12925 | Z4 | L18 | Q50 |
| 12926 | Z4 | L18 | Q51 |
| 12927 | Z4 | L18 | Q52 |
| 12928 | Z4 | L18 | Q53 |
| 12929 | Z4 | L18 | Q54 |
| 12930 | Z4 | L18 | Q55 |
| 12931 | Z4 | L18 | Q56 |
| 12932 | Z4 | L18 | Q57 |
| 12933 | Z4 | L18 | Q58 |
| 12934 | Z4 | L18 | Q59 |
| 12935 | Z4 | L18 | Q60 |
| 12936 | Z4 | L18 | Q61 |
| 12937 | Z4 | L18 | Q62 |
| 12938 | Z4 | L18 | Q63 |
| 12939 | Z4 | L18 | Q64 |
| 12940 | Z4 | L18 | Q65 |
| 12941 | Z4 | L18 | Q66 |
| 12942 | Z4 | L18 | Q67 |
| 12943 | Z4 | L18 | Q68 |
| 12944 | Z4 | L18 | Q69 |
| 12945 | Z4 | L18 | Q70 |
| 12946 | Z4 | L18 | Q71 |
| 12947 | Z4 | L18 | Q72 |
| 12948 | Z4 | L18 | Q73 |
| 12949 | Z4 | L18 | Q74 |
| 12950 | Z4 | L18 | Q75 |
| 12951 | Z4 | L18 | Q76 |
| 12952 | Z4 | L18 | Q77 |
| 12953 | Z4 | L18 | Q78 |
| 12954 | Z4 | L18 | Q79 |
| 12955 | Z4 | L18 | Q80 |
| 12956 | Z4 | L18 | Q81 |
| 12957 | Z4 | L18 | Q82 |
| 12958 | Z4 | L18 | Q83 |
| 12959 | Z4 | L18 | Q84 |
| 12960 | Z4 | L18 | Q85 |
| 12961 | Z4 | L18 | Q86 |
| 12962 | Z4 | L18 | Q87 |
| 12963 | Z4 | L18 | Q88 |
| 12964 | Z4 | L18 | Q89 |
| 12965 | Z4 | L18 | Q90 |
| 12966 | Z4 | L18 | Q91 |
| 12967 | Z4 | L18 | Q92 |
| 12968 | Z4 | L18 | Q93 |
| 12969 | Z4 | L18 | Q94 |
| 12970 | Z4 | L18 | Q95 |
| 12971 | Z4 | L18 | Q96 |
| 12972 | Z4 | L13 | Q97 |
| 12973 | Z4 | L18 | Q98 |
| 12974 | Z4 | L18 | Q99 |
| 12975 | Z4 | L18 | Q100 |
| 12976 | Z4 | L18 | Q101 |
| 12977 | Z4 | L18 | Q102 |
| 12978 | Z4 | L18 | Q103 |
| 12979 | Z4 | L19 | Q1 |
| 12980 | Z4 | L19 | Q2 |
| 12981 | Z4 | L19 | Q3 |
| 12982 | Z4 | L19 | Q4 |
| 12983 | Z4 | L19 | Q5 |
| 12984 | Z4 | L19 | Q6 |
| 12985 | Z4 | L19 | Q7 |
| 12986 | Z4 | L19 | Q8 |
| 12987 | Z4 | L19 | Q9 |
| 12988 | Z4 | L19 | Q10 |
| 12989 | Z4 | L19 | Q11 |
| 12990 | Z4 | L19 | Q12 |
| 12991 | Z4 | L19 | Q13 |
| 12992 | Z4 | L19 | Q14 |
| 12993 | Z4 | L19 | Q15 |
| 12994 | Z4 | L19 | Q16 |
| 12995 | Z4 | L19 | Q17 |
| 12996 | Z4 | L19 | Q18 |
| 12997 | Z4 | L19 | Q19 |
| 12998 | Z4 | L19 | Q20 |
| 12999 | Z4 | L19 | Q21 |
| 13000 | Z4 | L19 | Q22 |
| 13001 | Z4 | L19 | Q23 |
| 13002 | Z4 | L19 | Q24 |
| 13003 | Z4 | L19 | Q25 |
| 13004 | Z4 | L19 | Q26 |
| 13005 | Z4 | L19 | Q27 |
| 13006 | Z4 | L19 | Q28 |
| 13007 | Z4 | L19 | Q29 |
| 13008 | Z4 | L19 | Q30 |
| 13009 | Z4 | L19 | Q31 |
| 13010 | Z4 | L19 | Q32 |
| 13011 | Z4 | L19 | Q33 |
| 13012 | Z4 | L19 | Q34 |
| 13013 | Z4 | L19 | Q35 |
| 13014 | Z4 | L19 | Q36 |
| 13015 | Z4 | L19 | Q37 |

TABLE 1-70-continued

| | | | |
|---|---|---|---|
| 13016 | Z4 | L19 | Q38 |
| 13017 | Z4 | L19 | Q39 |
| 13018 | Z4 | L19 | Q40 |
| 13019 | Z4 | L19 | Q41 |
| 13020 | Z4 | L19 | Q42 |
| 13021 | Z4 | L19 | Q43 |
| 13022 | Z4 | L19 | Q44 |
| 13023 | Z4 | L19 | Q45 |
| 13024 | Z4 | L19 | Q46 |
| 13025 | Z4 | L19 | Q47 |
| 13026 | Z4 | L19 | Q48 |
| 13027 | Z4 | L19 | Q49 |
| 13028 | Z4 | L19 | Q50 |
| 13029 | Z4 | L19 | Q51 |
| 13030 | Z4 | L19 | Q52 |
| 13031 | Z4 | L19 | Q53 |
| 13032 | Z4 | L19 | Q54 |
| 13033 | Z4 | L19 | Q55 |
| 13034 | Z4 | L19 | Q56 |
| 13035 | Z4 | L19 | Q57 |
| 13036 | Z4 | L19 | Q58 |
| 13037 | Z4 | L19 | Q59 |

TABLE 1-71

| | | | |
|---|---|---|---|
| 13038 | Z4 | L19 | Q60 |
| 13039 | Z4 | L19 | Q61 |
| 13040 | Z4 | L19 | Q62 |
| 13041 | Z4 | L19 | Q63 |
| 13042 | Z4 | L19 | Q64 |
| 13043 | Z4 | L19 | Q65 |
| 13044 | Z4 | L19 | Q66 |
| 13045 | Z4 | L19 | Q67 |
| 13046 | Z4 | L19 | Q68 |
| 13047 | Z4 | L19 | Q69 |
| 13048 | Z4 | L19 | Q70 |
| 13049 | Z4 | L19 | Q71 |
| 13050 | Z4 | L19 | Q72 |
| 13051 | Z4 | L19 | Q73 |
| 13052 | Z4 | L19 | Q74 |
| 13053 | Z4 | L19 | Q75 |
| 13054 | Z4 | L19 | Q76 |
| 13055 | Z4 | L19 | Q77 |
| 13056 | Z4 | L19 | Q78 |
| 13057 | Z4 | L19 | Q79 |
| 13058 | Z4 | L19 | Q80 |
| 13059 | Z4 | L19 | Q81 |
| 13060 | Z4 | L19 | Q82 |
| 13061 | Z4 | L19 | Q83 |
| 13062 | Z4 | L19 | Q84 |
| 13063 | Z4 | L19 | Q85 |
| 13064 | Z4 | L19 | Q86 |
| 13065 | Z4 | L19 | Q87 |
| 13066 | Z4 | L19 | Q88 |
| 13067 | Z4 | L19 | Q89 |
| 13068 | Z4 | L19 | Q90 |
| 13069 | Z4 | L19 | Q91 |
| 13070 | Z4 | L19 | Q92 |
| 13071 | Z4 | L19 | Q93 |
| 13072 | Z4 | L19 | Q94 |
| 13073 | Z4 | L19 | Q95 |
| 13074 | Z4 | L19 | Q96 |
| 13075 | Z4 | L19 | Q97 |
| 13076 | Z4 | L19 | Q98 |
| 13077 | Z4 | L19 | Q99 |
| 13078 | Z4 | L19 | Q100 |
| 13079 | Z4 | L19 | Q101 |
| 13080 | Z4 | L19 | Q102 |
| 13081 | Z4 | L19 | Q103 |
| 13082 | Z4 | L20 | Q1 |
| 13083 | Z4 | L20 | Q2 |
| 13084 | Z4 | L20 | Q3 |
| 13085 | Z4 | L20 | Q4 |
| 13086 | Z4 | L20 | Q5 |
| 13087 | Z4 | L20 | Q6 |
| 13088 | Z4 | L20 | Q7 |
| 13089 | Z4 | L20 | Q8 |

TABLE 1-71-continued

| | | | |
|---|---|---|---|
| 13090 | Z4 | L20 | Q9 |
| 13091 | Z4 | L20 | Q10 |
| 13092 | Z4 | L20 | Q11 |
| 13093 | Z4 | L20 | Q12 |
| 13094 | Z4 | L20 | Q13 |
| 13095 | Z4 | L20 | Q14 |
| 13096 | Z4 | L20 | Q15 |
| 13097 | Z4 | L20 | Q16 |
| 13098 | Z4 | L20 | Q17 |
| 13099 | Z4 | L20 | Q18 |
| 13100 | Z4 | L20 | Q19 |
| 13101 | Z4 | L20 | Q20 |
| 13102 | Z4 | L20 | Q21 |
| 13103 | Z4 | L20 | Q22 |
| 13104 | Z4 | L20 | Q23 |
| 13105 | Z4 | L20 | Q24 |
| 13106 | Z4 | L20 | Q25 |
| 13107 | Z4 | L20 | Q26 |
| 13108 | Z4 | L20 | Q27 |
| 13109 | Z4 | L20 | Q28 |
| 13110 | Z4 | L20 | Q29 |
| 13111 | Z4 | L20 | Q30 |
| 13112 | Z4 | L20 | Q31 |
| 13113 | Z4 | L20 | Q32 |
| 13114 | Z4 | L20 | Q33 |
| 13115 | Z4 | L20 | Q34 |
| 13116 | Z4 | L20 | Q35 |
| 13117 | Z4 | L20 | Q36 |
| 13118 | Z4 | L20 | Q37 |
| 13119 | Z4 | L20 | Q38 |
| 13120 | Z4 | L20 | Q39 |
| 13121 | Z4 | L20 | Q40 |
| 13122 | Z4 | L20 | Q41 |
| 13123 | Z4 | L20 | Q42 |
| 13124 | Z4 | L20 | Q43 |
| 13125 | Z4 | L20 | Q44 |
| 13126 | Z4 | L20 | Q45 |
| 13127 | Z4 | L20 | Q46 |
| 13128 | Z4 | L20 | Q47 |
| 13129 | Z4 | L20 | Q48 |
| 13130 | Z4 | L20 | Q49 |
| 13131 | Z4 | L20 | Q50 |
| 13132 | Z4 | L20 | Q51 |
| 13133 | Z4 | L20 | Q52 |
| 13134 | Z4 | L20 | Q53 |
| 13135 | Z4 | L20 | Q54 |
| 13136 | Z4 | L20 | Q55 |
| 13137 | Z4 | L20 | Q56 |
| 13138 | Z4 | L20 | Q57 |
| 13139 | Z4 | L20 | Q58 |
| 13140 | Z4 | L20 | Q59 |
| 13141 | Z4 | L20 | Q60 |
| 13142 | Z4 | L20 | Q61 |
| 13143 | Z4 | L20 | Q62 |
| 13144 | Z4 | L20 | Q63 |
| 13145 | Z4 | L20 | Q64 |
| 13146 | Z4 | L20 | Q65 |
| 13147 | Z4 | L20 | Q66 |
| 13148 | Z4 | L20 | Q67 |
| 13149 | Z4 | L20 | Q68 |
| 13150 | Z4 | L20 | Q69 |
| 13151 | Z4 | L20 | Q70 |
| 13152 | Z4 | L20 | Q71 |
| 13153 | Z4 | L20 | Q72 |
| 13154 | Z4 | L20 | Q73 |
| 13155 | Z4 | L20 | Q74 |
| 13156 | Z4 | L20 | Q75 |
| 13157 | Z4 | L20 | Q76 |
| 13158 | Z4 | L20 | Q77 |
| 13159 | Z4 | L20 | Q78 |
| 13160 | Z4 | L20 | Q79 |
| 13161 | Z4 | L20 | Q80 |
| 13162 | Z4 | L20 | Q81 |
| 13163 | Z4 | L20 | Q82 |
| 13164 | Z4 | L20 | Q83 |
| 13165 | Z4 | L20 | Q84 |
| 13166 | Z4 | L20 | Q85 |
| 13167 | Z4 | L20 | Q86 |
| 13168 | Z4 | L20 | Q87 |
| 13169 | Z4 | L20 | Q88 |

TABLE 1-71-continued

| | | | |
|---|---|---|---|
| 13170 | Z4 | L20 | Q89 |
| 13171 | Z4 | L20 | Q90 |
| 13172 | Z4 | L20 | Q91 |
| 13173 | Z4 | L20 | Q92 |
| 13174 | Z4 | L20 | Q93 |
| 13175 | Z4 | L20 | Q94 |
| 13176 | Z4 | L20 | Q95 |
| 13177 | Z4 | L20 | Q96 |
| 13178 | Z4 | L20 | Q97 |
| 13179 | Z4 | L20 | Q98 |
| 13180 | Z4 | L20 | Q99 |
| 13181 | Z4 | L20 | Q100 |
| 13182 | Z4 | L20 | Q101 |
| 13183 | Z4 | L20 | Q102 |
| 13184 | Z4 | L20 | Q103 |
| 13185 | Z4 | L21 | Q1 |
| 13186 | Z4 | L21 | Q2 |
| 13187 | Z4 | L21 | Q3 |
| 13188 | Z4 | L21 | Q4 |
| 13189 | Z4 | L21 | Q5 |
| 13190 | Z4 | L21 | Q6 |
| 13191 | Z4 | L21 | Q7 |
| 13192 | Z4 | L21 | Q8 |
| 13193 | Z4 | L21 | Q9 |
| 13194 | Z4 | L21 | Q10 |
| 13195 | Z4 | L21 | Q11 |
| 13196 | Z4 | L21 | Q12 |
| 13197 | Z4 | L21 | Q13 |
| 13198 | Z4 | L21 | Q14 |
| 13199 | Z4 | L21 | Q15 |
| 13200 | Z4 | L21 | Q16 |
| 13201 | Z4 | L21 | Q17 |
| 13202 | Z4 | L21 | Q18 |
| 13203 | Z4 | L21 | Q19 |
| 13204 | Z4 | L21 | Q20 |
| 13205 | Z4 | L21 | Q21 |
| 13206 | Z4 | L21 | Q22 |
| 13207 | Z4 | L21 | Q23 |
| 13208 | Z4 | L21 | Q24 |
| 13209 | Z4 | L21 | Q25 |
| 13210 | Z4 | L21 | Q26 |
| 13211 | Z4 | L21 | Q27 |
| 13212 | Z4 | L21 | Q28 |
| 13213 | Z4 | L21 | Q29 |
| 13214 | Z4 | L21 | Q30 |
| 13215 | Z4 | L21 | Q31 |
| 13216 | Z4 | L21 | Q32 |
| 13217 | Z4 | L21 | Q33 |
| 13218 | Z4 | L21 | Q34 |
| 13219 | Z4 | L21 | Q35 |
| 13220 | Z4 | L21 | Q36 |
| 13221 | Z4 | L21 | Q37 |
| 13222 | Z4 | L21 | Q38 |
| 13223 | Z4 | L21 | Q39 |
| 13224 | Z4 | L21 | Q40 |
| 13225 | Z4 | L21 | Q41 |
| 13226 | Z4 | L21 | Q42 |
| 13227 | Z4 | L21 | Q43 |
| 13228 | Z4 | L21 | Q44 |
| 13229 | Z4 | L21 | Q45 |
| 13230 | Z4 | L21 | Q46 |
| 13231 | Z4 | L21 | Q47 |
| 13232 | Z4 | L21 | Q48 |
| 13233 | Z4 | L21 | Q49 |
| 13234 | Z4 | L21 | Q50 |
| 13235 | Z4 | L21 | Q51 |
| 13236 | Z4 | L21 | Q52 |
| 13237 | Z4 | L21 | Q53 |
| 13238 | Z4 | L21 | Q54 |

TABLE 1-72

| | | | |
|---|---|---|---|
| 13239 | Z4 | L21 | Q55 |
| 13240 | Z4 | L21 | Q56 |
| 13241 | Z4 | L21 | Q57 |
| 13242 | Z4 | L21 | Q58 |
| 13243 | Z4 | L21 | Q59 |

TABLE 1-72-continued

| | | | |
|---|---|---|---|
| 13244 | Z4 | L21 | Q60 |
| 13245 | Z4 | L21 | Q61 |
| 13246 | Z4 | L21 | Q62 |
| 13247 | Z4 | L21 | Q63 |
| 13248 | Z4 | L21 | Q64 |
| 13249 | Z4 | L21 | Q65 |
| 13250 | Z4 | L21 | Q66 |
| 13251 | Z4 | L21 | Q67 |
| 13252 | Z4 | L21 | Q68 |
| 13253 | Z4 | L21 | Q69 |
| 13254 | Z4 | L21 | Q70 |
| 13255 | Z4 | L21 | Q71 |
| 13256 | Z4 | L21 | Q72 |
| 13257 | Z4 | L21 | Q73 |
| 13258 | Z4 | L21 | Q74 |
| 13259 | Z4 | L21 | Q75 |
| 13260 | Z4 | L21 | Q76 |
| 13261 | Z4 | L21 | Q77 |
| 13262 | Z4 | L21 | Q78 |
| 13263 | Z4 | L21 | Q79 |
| 13264 | Z4 | L21 | Q80 |
| 13265 | Z4 | L21 | Q81 |
| 13266 | Z4 | L21 | Q82 |
| 13267 | Z4 | L21 | Q83 |
| 13268 | Z4 | L21 | Q84 |
| 13269 | Z4 | L21 | Q85 |
| 13270 | Z4 | L21 | Q86 |
| 13271 | Z4 | L21 | Q87 |
| 13272 | Z4 | L21 | Q88 |
| 13273 | Z4 | L21 | Q89 |
| 13274 | Z4 | L21 | Q90 |
| 13275 | Z4 | L21 | Q91 |
| 13276 | Z4 | L21 | Q92 |
| 13277 | Z4 | L21 | Q93 |
| 13278 | Z4 | L21 | Q94 |
| 13279 | Z4 | L21 | Q95 |
| 13280 | Z4 | L21 | Q96 |
| 13281 | Z4 | L21 | Q97 |
| 13282 | Z4 | L21 | Q98 |
| 13283 | Z4 | L21 | Q99 |
| 13284 | Z4 | L21 | Q100 |
| 13285 | Z4 | L21 | Q101 |
| 13286 | Z4 | L21 | Q102 |
| 13287 | Z4 | L21 | Q103 |
| 13288 | Z4 | L22 | Q1 |
| 13289 | Z4 | L22 | Q2 |
| 13290 | Z4 | L22 | Q3 |
| 13291 | Z4 | L22 | Q4 |
| 13292 | Z4 | L22 | Q5 |
| 13293 | Z4 | L22 | Q6 |
| 13294 | Z4 | L22 | Q7 |
| 13295 | Z4 | L22 | Q8 |
| 13296 | Z4 | L22 | Q9 |
| 13297 | Z4 | L22 | Q10 |
| 13298 | Z4 | L22 | Q11 |
| 13299 | Z4 | L22 | Q12 |
| 13300 | Z4 | L22 | Q13 |
| 13301 | Z4 | L22 | Q14 |
| 13302 | Z4 | L22 | Q15 |
| 13303 | Z4 | L22 | Q16 |
| 13304 | Z4 | L22 | Q17 |
| 13305 | Z4 | L22 | Q18 |
| 13306 | Z4 | L22 | Q19 |
| 13307 | Z4 | L22 | Q20 |
| 13308 | Z4 | L22 | Q21 |
| 13309 | Z4 | L22 | Q22 |
| 13310 | Z4 | L22 | Q23 |
| 13311 | Z4 | L22 | Q24 |
| 13312 | Z4 | L22 | Q25 |
| 13313 | Z4 | L22 | Q26 |
| 13314 | Z4 | L22 | Q27 |
| 13315 | Z4 | L22 | Q28 |
| 13316 | Z4 | L22 | Q29 |
| 13317 | Z4 | L22 | Q30 |
| 13318 | Z4 | L22 | Q31 |
| 13319 | Z4 | L22 | Q32 |
| 13320 | Z4 | L22 | Q33 |
| 13321 | Z4 | L22 | Q34 |
| 13322 | Z4 | L22 | Q35 |
| 13323 | Z4 | L22 | Q36 |

TABLE 1-72-continued

| | | | |
|---|---|---|---|
| 13324 | Z4 | L22 | Q37 |
| 13325 | Z4 | L22 | Q38 |
| 13326 | Z4 | L22 | Q39 |
| 13327 | Z4 | L22 | Q40 |
| 13328 | Z4 | L22 | Q41 |
| 13329 | Z4 | L22 | Q42 |
| 13330 | Z4 | L22 | Q43 |
| 13331 | Z4 | L22 | Q44 |
| 13332 | Z4 | L22 | Q45 |
| 13333 | Z4 | L22 | Q46 |
| 13334 | Z4 | L22 | Q47 |
| 13335 | Z4 | L22 | Q48 |
| 13336 | Z4 | L22 | Q49 |
| 13337 | Z4 | L22 | Q50 |
| 13338 | Z4 | L22 | Q51 |
| 13339 | Z4 | L22 | Q52 |
| 13340 | Z4 | L22 | Q53 |
| 13341 | Z4 | L22 | Q54 |
| 13342 | Z4 | L22 | Q55 |
| 13343 | Z4 | L22 | Q56 |
| 13344 | Z4 | L22 | Q57 |
| 13345 | Z4 | L22 | Q58 |
| 13346 | Z4 | L22 | Q59 |
| 13347 | Z4 | L22 | Q60 |
| 13348 | Z4 | L22 | Q61 |
| 13349 | Z4 | L22 | Q62 |
| 13350 | Z4 | L22 | Q63 |
| 13351 | Z4 | L22 | Q64 |
| 13352 | Z4 | L22 | Q65 |
| 13353 | Z4 | L22 | Q66 |
| 13354 | Z4 | L22 | Q67 |
| 13355 | Z4 | L22 | Q68 |
| 13356 | Z4 | L22 | Q69 |
| 13357 | Z4 | L22 | Q70 |
| 13358 | Z4 | L22 | Q71 |
| 13359 | Z4 | L22 | Q72 |
| 13360 | Z4 | L22 | Q73 |
| 13361 | Z4 | L22 | Q74 |
| 13362 | Z4 | L22 | Q75 |
| 13363 | Z4 | L22 | Q76 |
| 13364 | Z4 | L22 | Q77 |
| 13365 | Z4 | L22 | Q78 |
| 13366 | Z4 | L22 | Q79 |
| 13367 | Z4 | L22 | Q80 |
| 13368 | Z4 | L22 | Q81 |
| 13369 | Z4 | L22 | Q82 |
| 13370 | Z4 | L22 | Q83 |
| 13371 | Z4 | L22 | Q84 |
| 13372 | Z4 | L22 | Q85 |
| 13373 | Z4 | L22 | Q86 |
| 13374 | Z4 | L22 | Q87 |
| 13375 | Z4 | L22 | Q88 |
| 13376 | Z4 | L22 | Q89 |
| 13377 | Z4 | L22 | Q90 |
| 13378 | Z4 | L22 | Q91 |
| 13379 | Z4 | L22 | Q92 |
| 13380 | Z4 | L22 | Q93 |
| 13381 | Z4 | L22 | Q94 |
| 13382 | Z4 | L22 | Q95 |
| 13383 | Z4 | L22 | Q96 |
| 13384 | Z4 | L22 | Q97 |
| 13385 | Z4 | L22 | Q98 |
| 13386 | Z4 | L22 | Q99 |
| 13387 | Z4 | L22 | Q100 |
| 13388 | Z4 | L22 | Q101 |
| 13389 | Z4 | L22 | Q102 |
| 13390 | Z4 | L22 | Q103 |
| 13391 | Z4 | L23 | Q1 |
| 13392 | Z4 | L23 | Q2 |
| 13393 | Z4 | L23 | Q3 |
| 13394 | Z4 | L23 | Q4 |
| 13395 | Z4 | L23 | Q5 |
| 13396 | Z4 | L23 | Q6 |
| 13397 | Z4 | L23 | Q7 |
| 13398 | Z4 | L23 | Q8 |
| 13399 | Z4 | L23 | Q9 |
| 13400 | Z4 | L23 | Q10 |
| 13401 | Z4 | L23 | Q11 |
| 13402 | Z4 | L23 | Q12 |
| 13403 | Z4 | L23 | Q13 |
| 13404 | Z4 | L23 | Q14 |
| 13405 | Z4 | L23 | Q15 |
| 13406 | Z4 | L23 | Q16 |
| 13407 | Z4 | L23 | Q17 |
| 13408 | Z4 | L23 | Q18 |
| 13409 | Z4 | L23 | Q19 |
| 13410 | Z4 | L23 | Q20 |
| 13411 | Z4 | L23 | Q21 |
| 13412 | Z4 | L23 | Q22 |
| 13413 | Z4 | L23 | Q23 |
| 13414 | Z4 | L23 | Q24 |
| 13415 | Z4 | L23 | Q25 |
| 13416 | Z4 | L23 | Q26 |
| 13417 | Z4 | L23 | Q27 |
| 13418 | Z4 | L23 | Q28 |
| 13419 | Z4 | L23 | Q29 |
| 13420 | Z4 | L23 | Q30 |
| 13421 | Z4 | L23 | Q31 |
| 13422 | Z4 | L23 | Q32 |
| 13423 | Z4 | L23 | Q33 |
| 13424 | Z4 | L23 | Q34 |
| 13425 | Z4 | L23 | Q35 |
| 13426 | Z4 | L23 | Q36 |
| 13427 | Z4 | L23 | Q37 |
| 13428 | Z4 | L23 | Q38 |
| 13429 | Z4 | L23 | Q39 |
| 13430 | Z4 | L23 | Q40 |
| 13431 | Z4 | L23 | Q41 |
| 13432 | Z4 | L23 | Q42 |
| 13433 | Z4 | L23 | Q43 |
| 13434 | Z4 | L23 | Q44 |
| 13435 | Z4 | L23 | Q45 |
| 13436 | Z4 | L23 | Q46 |
| 13437 | Z4 | L23 | Q47 |
| 13438 | Z4 | L23 | Q48 |
| 13439 | Z4 | L23 | Q49 |

TABLE 1-73

| | | | |
|---|---|---|---|
| 13440 | Z4 | L23 | Q50 |
| 13441 | Z4 | L23 | Q51 |
| 13442 | Z4 | L23 | Q52 |
| 13443 | Z4 | L23 | Q53 |
| 13444 | Z4 | L23 | Q54 |
| 13445 | Z4 | L23 | Q55 |
| 13446 | Z4 | L23 | Q56 |
| 13447 | Z4 | L23 | Q57 |
| 13448 | Z4 | L23 | Q58 |
| 13449 | Z4 | L23 | Q59 |
| 13450 | Z4 | L23 | Q60 |
| 13451 | Z4 | L23 | Q61 |
| 13452 | Z4 | L23 | Q62 |
| 13453 | Z4 | L23 | Q63 |
| 13454 | Z4 | L23 | Q64 |
| 13455 | Z4 | L23 | Q65 |
| 13456 | Z4 | L23 | Q66 |
| 13457 | Z4 | L23 | Q67 |
| 13458 | Z4 | L23 | Q68 |
| 13459 | Z4 | L23 | Q69 |
| 13460 | Z4 | L23 | Q70 |
| 13461 | Z4 | L23 | Q71 |
| 13462 | Z4 | L23 | Q72 |
| 13463 | Z4 | L23 | Q73 |
| 13464 | Z4 | L23 | Q74 |
| 13465 | Z4 | L23 | Q75 |
| 13466 | Z4 | L23 | Q76 |
| 13467 | Z4 | L23 | Q77 |
| 13468 | Z4 | L23 | Q78 |
| 13469 | Z4 | L23 | Q79 |
| 13470 | Z4 | L23 | Q80 |
| 13471 | Z4 | L23 | Q81 |
| 13472 | Z4 | L23 | Q82 |
| 13473 | Z4 | L23 | Q83 |
| 13474 | Z4 | L23 | Q84 |
| 13475 | Z4 | L23 | Q85 |
| 13476 | Z4 | L23 | Q86 |
| 13477 | Z4 | L23 | Q87 |

TABLE 1-73-continued

| | | | |
|---|---|---|---|
| 13478 | Z4 | L23 | Q88 |
| 13479 | Z4 | L23 | Q89 |
| 13480 | Z4 | L23 | Q90 |
| 13481 | Z4 | L23 | Q91 |
| 13482 | Z4 | L23 | Q92 |
| 13483 | Z4 | L23 | Q93 |
| 13484 | Z4 | L23 | Q94 |
| 13485 | Z4 | L23 | Q95 |
| 13486 | Z4 | L23 | Q96 |
| 13487 | Z4 | L23 | Q97 |
| 13488 | Z4 | L23 | Q98 |
| 13489 | Z4 | L23 | Q99 |
| 13490 | Z4 | L23 | Q100 |
| 13491 | Z4 | L23 | Q101 |
| 13492 | Z4 | L23 | Q102 |
| 13493 | Z4 | L23 | Q103 |
| 13494 | Z4 | L24 | Q1 |
| 13495 | Z4 | L24 | Q2 |
| 13496 | Z4 | L24 | Q3 |
| 13497 | Z4 | L24 | Q4 |
| 13498 | Z4 | L24 | Q5 |
| 13499 | Z4 | L24 | Q6 |
| 13500 | Z4 | L24 | Q7 |
| 13501 | Z4 | L24 | Q8 |
| 13502 | Z4 | L24 | Q9 |
| 13503 | Z4 | L24 | Q10 |
| 13504 | Z4 | L24 | Q11 |
| 13505 | Z4 | L24 | Q12 |
| 13506 | Z4 | L24 | Q13 |
| 13507 | Z4 | L24 | Q14 |
| 13508 | Z4 | L24 | Q15 |
| 13509 | Z4 | L24 | Q16 |
| 13510 | Z4 | L24 | Q17 |
| 13511 | Z4 | L24 | Q18 |
| 13512 | Z4 | L24 | Q19 |
| 13513 | Z4 | L24 | Q20 |
| 13514 | Z4 | L24 | Q21 |
| 13515 | Z4 | L24 | Q22 |
| 13516 | Z4 | L24 | Q23 |
| 13517 | Z4 | L24 | Q24 |
| 13518 | Z4 | L24 | Q25 |
| 13519 | Z4 | L24 | Q26 |
| 13520 | Z4 | L24 | Q27 |
| 13521 | Z4 | L24 | Q28 |
| 13522 | Z4 | L24 | Q29 |
| 13523 | Z4 | L24 | Q30 |
| 13524 | Z4 | L24 | Q31 |
| 13525 | Z4 | L24 | Q32 |
| 13526 | Z4 | L24 | Q33 |
| 13527 | Z4 | L24 | Q34 |
| 13528 | Z4 | L24 | Q35 |
| 13529 | Z4 | L24 | Q36 |
| 13530 | Z4 | L24 | Q37 |
| 13531 | Z4 | L24 | Q38 |
| 13532 | Z4 | L24 | Q39 |
| 13533 | Z4 | L24 | Q40 |
| 13534 | Z4 | L24 | Q41 |
| 13535 | Z4 | L24 | Q42 |
| 13536 | Z4 | L24 | Q43 |
| 13537 | Z4 | L24 | Q44 |
| 13538 | Z4 | L24 | Q45 |
| 13539 | Z4 | L24 | Q46 |
| 13540 | Z4 | L24 | Q47 |
| 13541 | Z4 | L24 | Q48 |
| 13542 | Z4 | L24 | Q49 |
| 13543 | Z4 | L24 | Q50 |
| 13544 | Z4 | L24 | Q51 |
| 13545 | Z4 | L24 | Q52 |
| 13546 | Z4 | L24 | Q53 |
| 13547 | Z4 | L24 | Q54 |
| 13548 | Z4 | L24 | Q55 |
| 13549 | Z4 | L24 | Q56 |
| 13550 | Z4 | L24 | Q57 |
| 13551 | Z4 | L24 | Q58 |
| 13552 | Z4 | L24 | Q59 |
| 13553 | Z4 | L24 | Q60 |
| 13554 | Z4 | L24 | Q61 |
| 13555 | Z4 | L24 | Q62 |
| 13556 | Z4 | L24 | Q63 |
| 13557 | Z4 | L24 | Q64 |
| 13558 | Z4 | L24 | Q65 |
| 13559 | Z4 | L24 | Q66 |
| 13560 | Z4 | L24 | Q67 |
| 13561 | Z4 | L24 | Q68 |
| 13562 | Z4 | L24 | Q69 |
| 13563 | Z4 | L24 | Q70 |
| 13564 | Z4 | L24 | Q71 |
| 13565 | Z4 | L24 | Q72 |
| 13566 | Z4 | L24 | Q73 |
| 13567 | Z4 | L24 | Q74 |
| 13568 | Z4 | L24 | Q75 |
| 13569 | Z4 | L24 | Q76 |
| 13570 | Z4 | L24 | Q77 |
| 13571 | Z4 | L24 | Q78 |
| 13572 | Z4 | L24 | Q79 |
| 13573 | Z4 | L24 | Q80 |
| 13574 | Z4 | L24 | Q81 |
| 13575 | Z4 | L24 | Q82 |
| 13576 | Z4 | L24 | Q83 |
| 13577 | Z4 | L24 | Q84 |
| 13578 | Z4 | L24 | Q85 |
| 13579 | Z4 | L24 | Q86 |
| 13580 | Z4 | L24 | Q87 |
| 13581 | Z4 | L24 | Q88 |
| 13582 | Z4 | L24 | Q89 |
| 13583 | Z4 | L24 | Q90 |
| 13584 | Z4 | L24 | Q91 |
| 13585 | Z4 | L24 | Q92 |
| 13586 | Z4 | L24 | Q93 |
| 13587 | Z4 | L24 | Q94 |
| 13588 | Z4 | L24 | Q95 |
| 13589 | Z4 | L24 | Q96 |
| 13590 | Z4 | L24 | Q97 |
| 13591 | Z4 | L24 | Q98 |
| 13592 | Z4 | L24 | Q99 |
| 13593 | Z4 | L24 | Q100 |
| 13594 | Z4 | L24 | Q101 |
| 13595 | Z4 | L24 | Q102 |
| 13596 | Z4 | L24 | Q103 |
| 13597 | Z4 | L25 | Q1 |
| 13598 | Z4 | L25 | Q2 |
| 13599 | Z4 | L25 | Q3 |
| 13600 | Z4 | L25 | Q4 |
| 13601 | Z4 | L25 | Q5 |
| 13602 | Z4 | L25 | Q6 |
| 13603 | Z4 | L25 | Q7 |
| 13604 | Z4 | L25 | Q8 |
| 13605 | Z4 | L25 | Q9 |
| 13606 | Z4 | L25 | Q10 |
| 13607 | Z4 | L25 | Q11 |
| 13608 | Z4 | L25 | Q12 |
| 13609 | Z4 | L25 | Q13 |
| 13610 | Z4 | L25 | Q14 |
| 13611 | Z4 | L25 | Q15 |
| 13612 | Z4 | L25 | Q16 |
| 13613 | Z4 | L25 | Q17 |
| 13614 | Z4 | L25 | Q18 |
| 13615 | Z4 | L25 | Q19 |
| 13616 | Z4 | L25 | Q20 |
| 13617 | Z4 | L25 | Q21 |
| 13618 | Z4 | L25 | Q22 |
| 13619 | Z4 | L25 | Q23 |
| 13620 | Z4 | L25 | Q24 |
| 13621 | Z4 | L25 | Q25 |
| 13622 | Z4 | L25 | Q26 |
| 13623 | Z4 | L25 | Q27 |
| 13624 | Z4 | L25 | Q28 |
| 13625 | Z4 | L25 | Q29 |
| 13626 | Z4 | L25 | Q30 |
| 13627 | Z4 | L25 | Q31 |
| 13628 | Z4 | L25 | Q32 |
| 13629 | Z4 | L25 | Q33 |
| 13630 | Z4 | L25 | Q34 |
| 13631 | Z4 | L25 | Q35 |
| 13632 | Z4 | L25 | Q36 |
| 13633 | Z4 | L25 | Q37 |
| 13634 | Z4 | L25 | Q38 |
| 13635 | Z4 | L25 | Q39 |
| 13636 | Z4 | L25 | Q40 |
| 13637 | Z4 | L25 | Q41 |

TABLE 1-73-continued

| | | | |
|---|---|---|---|
| 13638 | Z4 | L25 | Q42 |
| 13639 | Z4 | L25 | Q43 |
| 13640 | Z4 | L25 | Q44 |

TABLE 1-74

| | | | |
|---|---|---|---|
| 13641 | Z4 | L25 | Q45 |
| 13642 | Z4 | L25 | Q46 |
| 13643 | Z4 | L25 | Q47 |
| 13644 | Z4 | L25 | Q48 |
| 13645 | Z4 | L25 | Q49 |
| 13646 | Z4 | L25 | Q50 |
| 13647 | Z4 | L25 | Q51 |
| 13648 | Z4 | L25 | Q52 |
| 13649 | Z4 | L25 | Q53 |
| 13650 | Z4 | L25 | Q54 |
| 13651 | Z4 | L25 | Q55 |
| 13652 | Z4 | L25 | Q56 |
| 13653 | Z4 | L25 | Q57 |
| 13654 | Z4 | L25 | Q58 |
| 13655 | Z4 | L25 | Q59 |
| 13656 | Z4 | L25 | Q60 |
| 13657 | Z4 | L25 | Q61 |
| 13658 | Z4 | L25 | Q62 |
| 13659 | Z4 | L25 | Q63 |
| 13660 | Z4 | L25 | Q64 |
| 13661 | Z4 | L25 | Q65 |
| 13662 | Z4 | L25 | Q66 |
| 13663 | Z4 | L25 | Q67 |
| 13664 | Z4 | L25 | Q68 |
| 13665 | Z4 | L25 | Q69 |
| 13666 | Z4 | L25 | Q70 |
| 13667 | Z4 | L25 | Q71 |
| 13668 | Z4 | L25 | Q72 |
| 13669 | Z4 | L25 | Q73 |
| 13670 | Z4 | L25 | Q74 |
| 13671 | Z4 | L25 | Q75 |
| 13672 | Z4 | L25 | Q76 |
| 13673 | Z4 | L25 | Q77 |
| 13674 | Z4 | L25 | Q78 |
| 13675 | Z4 | L25 | Q79 |
| 13676 | Z4 | L25 | Q80 |
| 13677 | Z4 | L25 | Q81 |
| 13678 | Z4 | L25 | Q82 |
| 13679 | Z4 | L25 | Q83 |
| 13680 | Z4 | L25 | Q84 |
| 13681 | Z4 | L25 | Q85 |
| 13682 | Z4 | L25 | Q86 |
| 13683 | Z4 | L25 | Q87 |
| 13684 | Z4 | L25 | Q88 |
| 13685 | Z4 | L25 | Q89 |
| 13686 | Z4 | L25 | Q90 |
| 13687 | Z4 | L25 | Q91 |
| 13688 | Z4 | L25 | Q92 |
| 13689 | Z4 | L25 | Q93 |
| 13690 | Z4 | L25 | Q94 |
| 13691 | Z4 | L25 | Q95 |
| 13692 | Z4 | L25 | Q96 |
| 13693 | Z4 | L25 | Q97 |
| 13694 | Z4 | L25 | Q98 |
| 13695 | Z4 | L25 | Q99 |
| 13696 | Z4 | L25 | Q100 |
| 13697 | Z4 | L25 | Q101 |
| 13698 | Z4 | L25 | Q102 |
| 13699 | Z4 | L25 | Q103 |
| 13700 | Z4 | L26 | Q1 |
| 13701 | Z4 | L26 | Q2 |
| 13702 | Z4 | L26 | Q3 |
| 13703 | Z4 | L26 | Q4 |
| 13704 | Z4 | L26 | Q5 |
| 13705 | Z4 | L26 | Q6 |
| 13706 | Z4 | L26 | Q7 |
| 13707 | Z4 | L26 | Q8 |
| 13708 | Z4 | L26 | Q9 |
| 13709 | Z4 | L26 | Q10 |
| 13710 | Z4 | L26 | Q11 |
| 13711 | Z4 | L26 | Q12 |

TABLE 1-74-continued

| | | | |
|---|---|---|---|
| 13712 | Z4 | L26 | Q13 |
| 13713 | Z4 | L26 | Q14 |
| 13714 | Z4 | L26 | Q15 |
| 13715 | Z4 | L26 | Q16 |
| 13716 | Z4 | L26 | Q17 |
| 13717 | Z4 | L26 | Q18 |
| 13718 | Z4 | L26 | Q19 |
| 13719 | Z4 | L26 | Q20 |
| 13720 | Z4 | L26 | Q21 |
| 13721 | Z4 | L26 | Q22 |
| 13722 | Z4 | L26 | Q23 |
| 13723 | Z4 | L26 | Q24 |
| 13724 | Z4 | L26 | Q25 |
| 13725 | Z4 | L26 | Q26 |
| 13726 | Z4 | L26 | Q27 |
| 13727 | Z4 | L26 | Q28 |
| 13728 | Z4 | L26 | Q29 |
| 13729 | Z4 | L26 | Q30 |
| 13730 | Z4 | L26 | Q31 |
| 13731 | Z4 | L26 | Q32 |
| 13732 | Z4 | L26 | Q33 |
| 13733 | Z4 | L26 | Q34 |
| 13734 | Z4 | L26 | Q35 |
| 13735 | Z4 | L26 | Q36 |
| 13736 | Z4 | L26 | Q37 |
| 13737 | Z4 | L26 | Q38 |
| 13738 | Z4 | L26 | Q39 |
| 13739 | Z4 | L26 | Q40 |
| 13740 | Z4 | L26 | Q41 |
| 13741 | Z4 | L26 | Q42 |
| 13742 | Z4 | L26 | Q43 |
| 13743 | Z4 | L26 | Q44 |
| 13744 | Z4 | L26 | Q45 |
| 13745 | Z4 | L26 | Q46 |
| 13746 | Z4 | L26 | Q47 |
| 13747 | Z4 | L26 | Q48 |
| 13748 | Z4 | L26 | Q49 |
| 13749 | Z4 | L26 | Q50 |
| 13750 | Z4 | L26 | Q51 |
| 13751 | Z4 | L26 | Q52 |
| 13752 | Z4 | L26 | Q53 |
| 13753 | Z4 | L26 | Q54 |
| 13754 | Z4 | L26 | Q55 |
| 13755 | Z4 | L26 | Q56 |
| 13756 | Z4 | L26 | Q57 |
| 13757 | Z4 | L26 | Q58 |
| 13758 | Z4 | L26 | Q59 |
| 13759 | Z4 | L26 | Q60 |
| 13760 | Z4 | L26 | Q61 |
| 13761 | Z4 | L26 | Q62 |
| 13762 | Z4 | L26 | Q63 |
| 13763 | Z4 | L26 | Q64 |
| 13764 | Z4 | L26 | Q65 |
| 13765 | Z4 | L26 | Q66 |
| 13766 | Z4 | L26 | Q67 |
| 13767 | Z4 | L26 | Q68 |
| 13768 | Z4 | L26 | Q69 |
| 13769 | Z4 | L26 | Q70 |
| 13770 | Z4 | L26 | Q71 |
| 13771 | Z4 | L26 | Q72 |
| 13772 | Z4 | L26 | Q73 |
| 13773 | Z4 | L26 | Q74 |
| 13774 | Z4 | L26 | Q75 |
| 13775 | Z4 | L26 | Q76 |
| 13776 | Z4 | L26 | Q77 |
| 13777 | Z4 | L26 | Q78 |
| 13778 | Z4 | L26 | Q79 |
| 13779 | Z4 | L26 | Q80 |
| 13780 | Z4 | L26 | Q81 |
| 13781 | Z4 | L26 | Q82 |
| 13782 | Z4 | L26 | Q83 |
| 13783 | Z4 | L26 | Q84 |
| 13784 | Z4 | L26 | Q85 |
| 13785 | Z4 | L26 | Q86 |
| 13786 | Z4 | L26 | Q87 |
| 13787 | Z4 | L26 | Q88 |
| 13788 | Z4 | L26 | Q89 |
| 13789 | Z4 | L26 | Q90 |
| 13790 | Z4 | L26 | Q91 |
| 13791 | Z4 | L26 | Q92 |

TABLE 1-74-continued

| | | | |
|---|---|---|---|
| 13792 | Z4 | L26 | Q93 |
| 13793 | Z4 | L26 | Q94 |
| 13794 | Z4 | L26 | Q95 |
| 13795 | Z4 | L26 | Q96 |
| 13796 | Z4 | L26 | Q97 |
| 13797 | Z4 | L26 | Q98 |
| 13798 | Z4 | L26 | Q99 |
| 13799 | Z4 | L26 | Q100 |
| 13800 | Z4 | L26 | Q101 |
| 13801 | Z4 | L26 | Q102 |
| 13802 | Z4 | L26 | Q103 |
| 13803 | Z4 | L27 | Q1 |
| 13804 | Z4 | L27 | Q2 |
| 13805 | Z4 | L27 | Q3 |
| 13806 | Z4 | L27 | Q4 |
| 13807 | Z4 | L27 | Q5 |
| 13808 | Z4 | L27 | Q6 |
| 13809 | Z4 | L27 | Q7 |
| 13810 | Z4 | L27 | Q8 |
| 13811 | Z4 | L27 | Q9 |
| 13812 | Z4 | L27 | Q10 |
| 13813 | Z4 | L27 | Q11 |
| 13814 | Z4 | L27 | Q12 |
| 13815 | Z4 | L27 | Q13 |
| 13816 | Z4 | L27 | Q14 |
| 13817 | Z4 | L27 | Q15 |
| 13818 | Z4 | L27 | Q16 |
| 13819 | Z4 | L27 | Q17 |
| 13820 | Z4 | L27 | Q18 |
| 13821 | Z4 | L27 | Q19 |
| 13822 | Z4 | L27 | Q20 |
| 13823 | Z4 | L27 | Q21 |
| 13824 | Z4 | L27 | Q22 |
| 13825 | Z4 | L27 | Q23 |
| 13826 | Z4 | L27 | Q24 |
| 13827 | Z4 | L27 | Q25 |
| 13828 | Z4 | L27 | Q26 |
| 13829 | Z4 | L27 | Q27 |
| 13830 | Z4 | L27 | Q28 |
| 13831 | Z4 | L27 | Q29 |
| 13832 | Z4 | L27 | Q30 |
| 13833 | Z4 | L27 | Q31 |
| 13834 | Z4 | L27 | Q32 |
| 13835 | Z4 | L27 | Q33 |
| 13836 | Z4 | L27 | Q34 |
| 13837 | Z4 | L27 | Q35 |
| 13838 | Z4 | L27 | Q36 |
| 13839 | Z4 | L27 | Q37 |
| 13840 | Z4 | L27 | Q38 |
| 13841 | Z4 | L27 | Q39 |

TABLE 1-75

| | | | |
|---|---|---|---|
| 13842 | Z4 | L27 | Q40 |
| 13843 | Z4 | L27 | Q41 |
| 13844 | Z4 | L27 | Q42 |
| 13845 | Z4 | L27 | Q43 |
| 13846 | Z4 | L27 | Q44 |
| 13847 | Z4 | L27 | Q45 |
| 13848 | Z4 | L27 | Q46 |
| 13849 | Z4 | L27 | Q47 |
| 13850 | Z4 | L27 | Q48 |
| 13851 | Z4 | L27 | Q49 |
| 13852 | Z4 | L27 | Q50 |
| 13853 | Z4 | L27 | Q51 |
| 13854 | Z4 | L27 | Q52 |
| 13855 | Z4 | L27 | Q53 |
| 13856 | Z4 | L27 | Q54 |
| 13857 | Z4 | L27 | Q55 |
| 13858 | Z4 | L27 | Q56 |
| 13859 | Z4 | L27 | Q57 |
| 13860 | Z4 | L27 | Q58 |
| 13861 | Z4 | L27 | Q59 |
| 13862 | Z4 | L27 | Q60 |
| 13863 | Z4 | L27 | Q61 |
| 13864 | Z4 | L27 | Q62 |
| 13865 | Z4 | L27 | Q63 |

TABLE 1-75-continued

| | | | |
|---|---|---|---|
| 13866 | Z4 | L27 | Q64 |
| 13867 | Z4 | L27 | Q65 |
| 13868 | Z4 | L27 | Q66 |
| 13869 | Z4 | L27 | Q67 |
| 13870 | Z4 | L27 | Q68 |
| 13871 | Z4 | L27 | Q69 |
| 13872 | Z4 | L27 | Q70 |
| 13873 | Z4 | L27 | Q71 |
| 13874 | Z4 | L27 | Q72 |
| 13875 | Z4 | L27 | Q73 |
| 13876 | Z4 | L27 | Q74 |
| 13877 | Z4 | L27 | Q75 |
| 13878 | Z4 | L27 | Q76 |
| 13879 | Z4 | L27 | Q77 |
| 13880 | Z4 | L27 | Q78 |
| 13881 | Z4 | L27 | Q79 |
| 13882 | Z4 | L27 | Q80 |
| 13883 | Z4 | L27 | Q81 |
| 13884 | Z4 | L27 | Q82 |
| 13885 | Z4 | L27 | Q83 |
| 13886 | Z4 | L27 | Q84 |
| 13887 | Z4 | L27 | Q85 |
| 13888 | Z4 | L27 | Q86 |
| 13889 | Z4 | L27 | Q87 |
| 13890 | Z4 | L27 | Q88 |
| 13891 | Z4 | L27 | Q89 |
| 13892 | Z4 | L27 | Q90 |
| 13893 | Z4 | L27 | Q91 |
| 13894 | Z4 | L27 | Q92 |
| 13895 | Z4 | L27 | Q93 |
| 13896 | Z4 | L27 | Q94 |
| 13897 | Z4 | L27 | Q95 |
| 13898 | Z4 | L27 | Q96 |
| 13899 | Z4 | L27 | Q97 |
| 13900 | Z4 | L27 | Q98 |
| 13901 | Z4 | L27 | Q99 |
| 13902 | Z4 | L27 | Q100 |
| 13903 | Z4 | L27 | Q101 |
| 13904 | Z4 | L27 | Q102 |
| 13905 | Z4 | L27 | Q103 |
| 13906 | Z4 | L28 | Q1 |
| 13907 | Z4 | L28 | Q2 |
| 13908 | Z4 | L28 | Q3 |
| 13909 | Z4 | L28 | Q4 |
| 13910 | Z4 | L28 | Q5 |
| 13911 | Z4 | L28 | Q6 |
| 13912 | Z4 | L28 | Q7 |
| 13913 | Z4 | L28 | Q8 |
| 13914 | Z4 | L28 | Q9 |
| 13915 | Z4 | L28 | Q10 |
| 13916 | Z4 | L28 | Q11 |
| 13917 | Z4 | L28 | Q12 |
| 13918 | Z4 | L28 | Q13 |
| 13919 | Z4 | L28 | Q14 |
| 13920 | Z4 | L28 | Q15 |
| 13921 | Z4 | L28 | Q16 |
| 13922 | Z4 | L28 | Q17 |
| 13923 | Z4 | L28 | Q18 |
| 13924 | Z4 | L28 | Q19 |
| 13925 | Z4 | L28 | Q20 |
| 13926 | Z4 | L28 | Q21 |
| 13927 | Z4 | L28 | Q22 |
| 13928 | Z4 | L28 | Q23 |
| 13929 | Z4 | L28 | Q24 |
| 13930 | Z4 | L28 | Q25 |
| 13931 | Z4 | L28 | Q26 |
| 13932 | Z4 | L28 | Q27 |
| 13933 | Z4 | L28 | Q28 |
| 13934 | Z4 | L28 | Q29 |
| 13935 | Z4 | L28 | Q30 |
| 13936 | Z4 | L28 | Q31 |
| 13937 | Z4 | L28 | Q32 |
| 13938 | Z4 | L28 | Q33 |
| 13939 | Z4 | L28 | Q34 |
| 13940 | Z4 | L28 | Q35 |
| 13941 | Z4 | L28 | Q36 |
| 13942 | Z4 | L28 | Q37 |
| 13943 | Z4 | L28 | Q38 |
| 13944 | Z4 | L28 | Q39 |
| 13945 | Z4 | L28 | Q40 |

TABLE 1-75-continued

| | | | |
|---|---|---|---|
| 13946 | Z4 | L28 | Q41 |
| 13947 | Z4 | L28 | Q42 |
| 13948 | Z4 | L28 | Q43 |
| 13949 | Z4 | L28 | Q44 |
| 13950 | Z4 | L28 | Q45 |
| 13951 | Z4 | L28 | Q46 |
| 13952 | Z4 | L28 | Q47 |
| 13953 | Z4 | L28 | Q48 |
| 13954 | Z4 | L28 | Q49 |
| 13955 | Z4 | L28 | Q50 |
| 13956 | Z4 | L28 | Q51 |
| 13957 | Z4 | L28 | Q52 |
| 13958 | Z4 | L28 | Q53 |
| 13959 | Z4 | L28 | Q54 |
| 13960 | Z4 | L28 | Q55 |
| 13961 | Z4 | L28 | Q56 |
| 13962 | Z4 | L28 | Q57 |
| 13963 | Z4 | L28 | Q58 |
| 13964 | Z4 | L28 | Q59 |
| 13965 | Z4 | L28 | Q60 |
| 13966 | Z4 | L28 | Q61 |
| 13967 | Z4 | L28 | Q62 |
| 13968 | Z4 | L28 | Q63 |
| 13969 | Z4 | L28 | Q64 |
| 13970 | Z4 | L28 | Q65 |
| 13971 | Z4 | L28 | Q66 |
| 13972 | Z4 | L28 | Q67 |
| 13973 | Z4 | L28 | Q68 |
| 13974 | Z4 | L28 | Q69 |
| 13975 | Z4 | L28 | Q70 |
| 13976 | Z4 | L28 | Q71 |
| 13977 | Z4 | L28 | Q72 |
| 13978 | Z4 | L28 | Q73 |
| 13979 | Z4 | L28 | Q74 |
| 13980 | Z4 | L28 | Q75 |
| 13981 | Z4 | L28 | Q76 |
| 13982 | Z4 | L28 | Q77 |
| 13983 | Z4 | L28 | Q78 |
| 13984 | Z4 | L28 | Q79 |
| 13985 | Z4 | L28 | Q80 |
| 13986 | Z4 | L28 | Q81 |
| 13987 | Z4 | L28 | Q82 |
| 13988 | Z4 | L28 | Q83 |
| 13989 | Z4 | L28 | Q84 |
| 13990 | Z4 | L28 | Q85 |
| 13991 | Z4 | L28 | Q86 |
| 13992 | Z4 | L28 | Q87 |
| 13993 | Z4 | L28 | Q88 |
| 13994 | Z4 | L28 | Q89 |
| 13995 | Z4 | L28 | Q90 |
| 13996 | Z4 | L28 | Q91 |
| 13997 | Z4 | L28 | Q92 |
| 13998 | Z4 | L28 | Q93 |
| 13999 | Z4 | L28 | Q94 |
| 14000 | Z4 | L28 | Q95 |
| 14001 | Z4 | L28 | Q96 |
| 14002 | Z4 | L28 | Q97 |
| 14003 | Z4 | L28 | Q98 |
| 14004 | Z4 | L28 | Q99 |
| 14005 | Z4 | L28 | Q100 |
| 14006 | Z4 | L28 | Q101 |
| 14007 | Z4 | L28 | Q102 |
| 14008 | Z4 | L28 | Q103 |
| 14009 | Z4 | L29 | Q1 |
| 14010 | Z4 | L29 | Q2 |
| 14011 | Z4 | L29 | Q3 |
| 14012 | Z4 | L29 | Q4 |
| 14013 | Z4 | L29 | Q5 |
| 14014 | Z4 | L29 | Q6 |
| 14015 | Z4 | L29 | Q7 |
| 14016 | Z4 | L29 | Q8 |
| 14017 | Z4 | L29 | Q9 |
| 14018 | Z4 | L29 | Q10 |
| 14019 | Z4 | L29 | Q11 |
| 14020 | Z4 | L29 | Q12 |
| 14021 | Z4 | L29 | Q13 |
| 14022 | Z4 | L29 | Q14 |
| 14023 | Z4 | L29 | Q15 |
| 14024 | Z4 | L29 | Q16 |
| 14025 | Z4 | L29 | Q17 |
| 14026 | Z4 | L29 | Q18 |
| 14027 | Z4 | L29 | Q19 |
| 14028 | Z4 | L29 | Q20 |
| 14029 | Z4 | L29 | Q21 |
| 14030 | Z4 | L29 | Q22 |
| 14031 | Z4 | L29 | Q23 |
| 14032 | Z4 | L29 | Q24 |
| 14033 | Z4 | L29 | Q25 |
| 14034 | Z4 | L29 | Q26 |
| 14035 | Z4 | L29 | Q27 |
| 14036 | Z4 | L29 | Q28 |
| 14037 | Z4 | L29 | Q29 |
| 14038 | Z4 | L29 | Q30 |
| 14039 | Z4 | L29 | Q31 |
| 14040 | Z4 | L29 | Q32 |
| 14041 | Z4 | L29 | Q33 |
| 14042 | Z4 | L29 | Q34 |

TABLE 1-76

| | | | |
|---|---|---|---|
| 14043 | Z4 | L29 | Q35 |
| 14044 | Z4 | L29 | Q36 |
| 14045 | Z4 | L29 | Q37 |
| 14046 | Z4 | L29 | Q38 |
| 14047 | Z4 | L29 | Q39 |
| 14048 | Z4 | L29 | Q40 |
| 14049 | Z4 | L29 | Q41 |
| 14050 | Z4 | L29 | Q42 |
| 14051 | Z4 | L29 | Q43 |
| 14052 | Z4 | L29 | Q44 |
| 14053 | Z4 | L29 | Q45 |
| 14054 | Z4 | L29 | Q46 |
| 14055 | Z4 | L29 | Q47 |
| 14056 | Z4 | L29 | Q48 |
| 14057 | Z4 | L29 | Q49 |
| 14058 | Z4 | L29 | Q50 |
| 14059 | Z4 | L29 | Q51 |
| 14060 | Z4 | L29 | Q52 |
| 14061 | Z4 | L29 | Q53 |
| 14062 | Z4 | L29 | Q54 |
| 14063 | Z4 | L29 | Q55 |
| 14064 | Z4 | L29 | Q56 |
| 14065 | Z4 | L29 | Q57 |
| 14066 | Z4 | L29 | Q58 |
| 14067 | Z4 | L29 | Q59 |
| 14068 | Z4 | L29 | Q60 |
| 14069 | Z4 | L29 | Q61 |
| 14070 | Z4 | L29 | Q62 |
| 14071 | Z4 | L29 | Q63 |
| 14072 | Z4 | L29 | Q64 |
| 14073 | Z4 | L29 | Q65 |
| 14074 | Z4 | L29 | Q66 |
| 14075 | Z4 | L29 | Q67 |
| 14076 | Z4 | L29 | Q68 |
| 14077 | Z4 | L29 | Q69 |
| 14078 | Z4 | L29 | Q70 |
| 14079 | Z4 | L29 | Q71 |
| 14080 | Z4 | L29 | Q72 |
| 14081 | Z4 | L29 | Q73 |
| 14082 | Z4 | L29 | Q74 |
| 14083 | Z4 | L29 | Q75 |
| 14084 | Z4 | L29 | Q76 |
| 14085 | Z4 | L29 | Q77 |
| 14086 | Z4 | L29 | Q78 |
| 14087 | Z4 | L29 | Q79 |
| 14088 | Z4 | L29 | Q80 |
| 14089 | Z4 | L29 | Q81 |
| 14090 | Z4 | L29 | Q82 |
| 14091 | Z4 | L29 | Q83 |
| 14092 | Z4 | L29 | Q84 |
| 14093 | Z4 | L29 | Q85 |
| 14094 | Z4 | L29 | Q86 |
| 14095 | Z4 | L29 | Q87 |
| 14096 | Z4 | L29 | Q88 |
| 14097 | Z4 | L29 | Q89 |
| 14098 | Z4 | L29 | Q90 |
| 14099 | Z4 | L29 | Q91 |

TABLE 1-76-continued

| | | | |
|---|---|---|---|
| 14100 | Z4 | L29 | Q92 |
| 14101 | Z4 | L29 | Q93 |
| 14102 | Z4 | L29 | Q94 |
| 14103 | Z4 | L29 | Q95 |
| 14104 | Z4 | L29 | Q96 |
| 14105 | Z4 | L29 | Q97 |
| 14106 | Z4 | L29 | Q98 |
| 14107 | Z4 | L29 | Q99 |
| 14108 | Z4 | L29 | Q100 |
| 14109 | Z4 | L29 | Q101 |
| 14110 | Z4 | L29 | Q102 |
| 14111 | Z4 | L29 | Q103 |
| 14112 | Z4 | L30 | Q1 |
| 14113 | Z4 | L30 | Q2 |
| 14114 | Z4 | L30 | Q3 |
| 14115 | Z4 | L30 | Q4 |
| 14116 | Z4 | L30 | Q5 |
| 14117 | Z4 | L30 | Q6 |
| 14118 | Z4 | L30 | Q7 |
| 14119 | Z4 | L30 | Q8 |
| 14120 | Z4 | L30 | Q9 |
| 14121 | Z4 | L30 | Q10 |
| 14122 | Z4 | L30 | Q11 |
| 14123 | Z4 | L30 | Q12 |
| 14124 | Z4 | L30 | Q13 |
| 14125 | Z4 | L30 | Q14 |
| 14126 | Z4 | L30 | Q15 |
| 14127 | Z4 | L30 | Q16 |
| 14128 | Z4 | L30 | Q17 |
| 14129 | Z4 | L30 | Q18 |
| 14130 | Z4 | L30 | Q19 |
| 14131 | Z4 | L30 | Q20 |
| 14132 | Z4 | L30 | Q21 |
| 14133 | Z4 | L30 | Q22 |
| 14134 | Z4 | L30 | Q23 |
| 14135 | Z4 | L30 | Q24 |
| 14136 | Z4 | L30 | Q25 |
| 14137 | Z4 | L30 | Q26 |
| 14138 | Z4 | L30 | Q27 |
| 14139 | Z4 | L30 | Q28 |
| 14140 | Z4 | L30 | Q29 |
| 14141 | Z4 | L30 | Q30 |
| 14142 | Z4 | L30 | Q31 |
| 14143 | Z4 | L30 | Q32 |
| 14144 | Z4 | L30 | Q33 |
| 14145 | Z4 | L30 | Q34 |
| 14146 | Z4 | L30 | Q35 |
| 14147 | Z4 | L30 | Q36 |
| 14148 | Z4 | L30 | Q37 |
| 14149 | Z4 | L30 | Q38 |
| 14150 | Z4 | L30 | Q39 |
| 14151 | Z4 | L30 | Q40 |
| 14152 | Z4 | L30 | Q41 |
| 14153 | Z4 | L30 | Q42 |
| 14154 | Z4 | L30 | Q43 |
| 14155 | Z4 | L30 | Q44 |
| 14156 | Z4 | L30 | Q45 |
| 14157 | Z4 | L30 | Q46 |
| 14158 | Z4 | L30 | Q47 |
| 14159 | Z4 | L30 | Q48 |
| 14160 | Z4 | L30 | Q49 |
| 14161 | Z4 | L30 | Q50 |
| 14162 | Z4 | L30 | Q51 |
| 14163 | Z4 | L30 | Q52 |
| 14164 | Z4 | L30 | Q53 |
| 14165 | Z4 | L30 | Q54 |
| 14166 | Z4 | L30 | Q55 |
| 14167 | Z4 | L30 | Q56 |
| 14168 | Z4 | L30 | Q57 |
| 14169 | Z4 | L30 | Q58 |
| 14170 | Z4 | L30 | Q59 |
| 14171 | Z4 | L30 | Q60 |
| 14172 | Z4 | L30 | Q61 |
| 14173 | Z4 | L30 | Q62 |
| 14174 | Z4 | L30 | Q63 |
| 14175 | Z4 | L30 | Q64 |
| 14176 | Z4 | L30 | Q65 |
| 14177 | Z4 | L30 | Q66 |
| 14178 | Z4 | L30 | Q67 |
| 14179 | Z4 | L30 | Q68 |
| 14180 | Z4 | L30 | Q69 |
| 14181 | Z4 | L30 | Q70 |
| 14182 | Z4 | L30 | Q71 |
| 14183 | Z4 | L30 | Q72 |
| 14184 | Z4 | L30 | Q73 |
| 14185 | Z4 | L30 | Q74 |
| 14186 | Z4 | L30 | Q75 |
| 14187 | Z4 | L30 | Q76 |
| 14188 | Z4 | L30 | Q77 |
| 14189 | Z4 | L30 | Q78 |
| 14190 | Z4 | L30 | Q79 |
| 14191 | Z4 | L30 | Q80 |
| 14192 | Z4 | L30 | Q81 |
| 14193 | Z4 | L30 | Q82 |
| 14194 | Z4 | L30 | Q83 |
| 14195 | Z4 | L30 | Q84 |
| 14196 | Z4 | L30 | Q85 |
| 14197 | Z4 | L30 | Q86 |
| 14198 | Z4 | L30 | Q87 |
| 14199 | Z4 | L30 | Q88 |
| 14200 | Z4 | L30 | Q89 |
| 14201 | Z4 | L30 | Q90 |
| 14202 | Z4 | L30 | Q91 |
| 14203 | Z4 | L30 | Q92 |
| 14204 | Z4 | L30 | Q93 |
| 14205 | Z4 | L30 | Q94 |
| 14206 | Z4 | L30 | Q95 |
| 14207 | Z4 | L30 | Q96 |
| 14208 | Z4 | L30 | Q97 |
| 14209 | Z4 | L30 | Q98 |
| 14210 | Z4 | L30 | Q99 |
| 14211 | Z4 | L30 | Q100 |
| 14212 | Z4 | L30 | Q101 |
| 14213 | Z4 | L30 | Q102 |
| 14214 | Z4 | L30 | Q103 |
| 14215 | Z4 | L31 | Q1 |
| 14216 | Z4 | L31 | Q2 |
| 14217 | Z4 | L31 | Q3 |
| 14218 | Z4 | L31 | Q4 |
| 14219 | Z4 | L31 | Q5 |
| 14220 | Z4 | L31 | Q6 |
| 14221 | Z4 | L31 | Q7 |
| 14222 | Z4 | L31 | Q8 |
| 14223 | Z4 | L31 | Q9 |
| 14224 | Z4 | L31 | Q10 |
| 14225 | Z4 | L31 | Q11 |
| 14226 | Z4 | L31 | Q12 |
| 14227 | Z4 | L31 | Q13 |
| 14228 | Z4 | L31 | Q14 |
| 14229 | Z4 | L31 | Q15 |
| 14230 | Z4 | L31 | Q16 |
| 14231 | Z4 | L31 | Q17 |
| 14232 | Z4 | L31 | Q18 |
| 14233 | Z4 | L31 | Q19 |
| 14234 | Z4 | L31 | Q20 |
| 14235 | Z4 | L31 | Q21 |
| 14236 | Z4 | L31 | Q22 |
| 14237 | Z4 | L31 | Q23 |
| 14238 | Z4 | L31 | Q24 |
| 14239 | Z4 | L31 | Q25 |
| 14240 | Z4 | L31 | Q26 |
| 14241 | Z4 | L31 | Q27 |
| 14242 | Z4 | L31 | Q28 |
| 14243 | Z4 | L31 | Q29 |

TABLE 1-77

| | | | |
|---|---|---|---|
| 14244 | Z4 | L31 | Q30 |
| 14245 | Z4 | L31 | Q31 |
| 14246 | Z4 | L31 | Q32 |
| 14247 | Z4 | L31 | Q33 |
| 14248 | Z4 | L31 | Q34 |
| 14249 | Z4 | L31 | Q35 |
| 14250 | Z4 | L31 | Q36 |
| 14251 | Z4 | L31 | Q37 |
| 14252 | Z4 | L31 | Q38 |
| 14253 | Z4 | L31 | Q39 |

TABLE 1-77-continued

| | | | |
|---|---|---|---|
| 14254 | Z4 | L31 | Q40 |
| 14255 | Z4 | L31 | Q41 |
| 14256 | Z4 | L31 | Q42 |
| 14257 | Z4 | L31 | Q43 |
| 14258 | Z4 | L31 | Q44 |
| 14259 | Z4 | L31 | Q45 |
| 14260 | Z4 | L31 | Q46 |
| 14261 | Z4 | L31 | Q47 |
| 14262 | Z4 | L31 | Q48 |
| 14263 | Z4 | L31 | Q49 |
| 14264 | Z4 | L31 | Q50 |
| 14265 | Z4 | L31 | Q51 |
| 14266 | Z4 | L31 | Q52 |
| 14267 | Z4 | L31 | Q53 |
| 14268 | Z4 | L31 | Q54 |
| 14269 | Z4 | L31 | Q55 |
| 14270 | Z4 | L31 | Q56 |
| 14271 | Z4 | L31 | Q57 |
| 14272 | Z4 | L31 | Q58 |
| 14273 | Z4 | L31 | Q59 |
| 14274 | Z4 | L31 | Q60 |
| 14275 | Z4 | L31 | Q61 |
| 14276 | Z4 | L31 | Q62 |
| 14277 | Z4 | L31 | Q63 |
| 14278 | Z4 | L31 | Q64 |
| 14279 | Z4 | L31 | Q65 |
| 14280 | Z4 | L31 | Q66 |
| 14281 | Z4 | L31 | Q67 |
| 14282 | Z4 | L31 | Q68 |
| 14283 | Z4 | L31 | Q69 |
| 14284 | Z4 | L31 | Q70 |
| 14285 | Z4 | L31 | Q71 |
| 14286 | Z4 | L31 | Q72 |
| 14287 | Z4 | L31 | Q73 |
| 14288 | Z4 | L31 | Q74 |
| 14289 | Z4 | L31 | Q75 |
| 14290 | Z4 | L31 | Q76 |
| 14291 | Z4 | L31 | Q77 |
| 14292 | Z4 | L31 | Q78 |
| 14293 | Z4 | L31 | Q79 |
| 14294 | Z4 | L31 | Q80 |
| 14295 | Z4 | L31 | Q81 |
| 14296 | Z4 | L31 | Q82 |
| 14297 | Z4 | L31 | Q83 |
| 14298 | Z4 | L31 | Q84 |
| 14299 | Z4 | L31 | Q85 |
| 14300 | Z4 | L31 | Q86 |
| 14301 | Z4 | L31 | Q87 |
| 14302 | Z4 | L31 | Q88 |
| 14303 | Z4 | L31 | Q89 |
| 14304 | Z4 | L31 | Q90 |
| 14305 | Z4 | L31 | Q91 |
| 14306 | Z4 | L31 | Q92 |
| 14307 | Z4 | L31 | Q93 |
| 14308 | Z4 | L31 | Q94 |
| 14309 | Z4 | L31 | Q95 |
| 14310 | Z4 | L31 | Q96 |
| 14311 | Z4 | L31 | Q97 |
| 14312 | Z4 | L31 | Q98 |
| 14313 | Z4 | L31 | Q99 |
| 14314 | Z4 | L31 | Q100 |
| 14315 | Z4 | L31 | Q101 |
| 14316 | Z4 | L31 | Q102 |
| 14317 | Z4 | L31 | Q103 |
| 14318 | Z4 | L32 | Q1 |
| 14319 | Z4 | L32 | Q2 |
| 14320 | Z4 | L32 | Q3 |
| 14321 | Z4 | L32 | Q4 |
| 14322 | Z4 | L32 | Q5 |
| 14323 | Z4 | L32 | Q6 |
| 14324 | Z4 | L32 | Q7 |
| 14325 | Z4 | L32 | Q8 |
| 14326 | Z4 | L32 | Q9 |
| 14327 | Z4 | L32 | Q10 |
| 14328 | Z4 | L32 | Q11 |
| 14329 | Z4 | L32 | Q12 |
| 14330 | Z4 | L32 | Q13 |
| 14331 | Z4 | L32 | Q14 |
| 14332 | Z4 | L32 | Q15 |
| 14333 | Z4 | L32 | Q16 |
| 14334 | Z4 | L32 | Q17 |
| 14335 | Z4 | L32 | Q18 |
| 14336 | Z4 | L32 | Q19 |
| 14337 | Z4 | L32 | Q20 |
| 14338 | Z4 | L32 | Q21 |
| 14339 | Z4 | L32 | Q22 |
| 14340 | Z4 | L32 | Q23 |
| 14341 | Z4 | L32 | Q24 |
| 14342 | Z4 | L32 | Q25 |
| 14343 | Z4 | L32 | Q26 |
| 14344 | Z4 | L32 | Q27 |
| 14345 | Z4 | L32 | Q28 |
| 14346 | Z4 | L32 | Q29 |
| 14347 | Z4 | L32 | Q30 |
| 14348 | Z4 | L32 | Q31 |
| 14349 | Z4 | L32 | Q32 |
| 14350 | Z4 | L32 | Q33 |
| 14351 | Z4 | L32 | Q34 |
| 14352 | Z4 | L32 | Q35 |
| 14353 | Z4 | L32 | Q36 |
| 14354 | Z4 | L32 | Q37 |
| 14355 | Z4 | L32 | Q38 |
| 14356 | Z4 | L32 | Q39 |
| 14357 | Z4 | L32 | Q40 |
| 14358 | Z4 | L32 | Q41 |
| 14359 | Z4 | L32 | Q42 |
| 14360 | Z4 | L32 | Q43 |
| 14361 | Z4 | L32 | Q44 |
| 14362 | Z4 | L32 | Q45 |
| 14363 | Z4 | L32 | Q46 |
| 14364 | Z4 | L32 | Q47 |
| 14365 | Z4 | L32 | Q48 |
| 14366 | Z4 | L32 | Q49 |
| 14367 | Z4 | L32 | Q50 |
| 14368 | Z4 | L32 | Q51 |
| 14369 | Z4 | L32 | Q52 |
| 14370 | Z4 | L32 | Q53 |
| 14371 | Z4 | L32 | Q54 |
| 14372 | Z4 | L32 | Q55 |
| 14373 | Z4 | L32 | Q56 |
| 14374 | Z4 | L32 | Q57 |
| 14375 | Z4 | L32 | Q58 |
| 14376 | Z4 | L32 | Q59 |
| 14377 | Z4 | L32 | Q60 |
| 14378 | Z4 | L32 | Q61 |
| 14379 | Z4 | L32 | Q62 |
| 14380 | Z4 | L32 | Q63 |
| 14381 | Z4 | L32 | Q64 |
| 14382 | Z4 | L32 | Q65 |
| 14383 | Z4 | L32 | Q66 |
| 14384 | Z4 | L32 | Q67 |
| 14385 | Z4 | L32 | Q68 |
| 14386 | Z4 | L32 | Q69 |
| 14387 | Z4 | L32 | Q70 |
| 14388 | Z4 | L32 | Q71 |
| 14389 | Z4 | L32 | Q72 |
| 14390 | Z4 | L32 | Q73 |
| 14391 | Z4 | L32 | Q74 |
| 14392 | Z4 | L32 | Q75 |
| 14393 | Z4 | L32 | Q76 |
| 14394 | Z4 | L32 | Q77 |
| 14395 | Z4 | L32 | Q78 |
| 14396 | Z4 | L32 | Q79 |
| 14397 | Z4 | L32 | Q80 |
| 14398 | Z4 | L32 | Q81 |
| 14399 | Z4 | L32 | Q82 |
| 14400 | Z4 | L32 | Q83 |
| 14401 | Z4 | L32 | Q84 |
| 14402 | Z4 | L32 | Q85 |
| 14403 | Z4 | L32 | Q86 |
| 14404 | Z4 | L32 | Q87 |
| 14405 | Z4 | L32 | Q88 |
| 14406 | Z4 | L32 | Q89 |
| 14407 | Z4 | L32 | Q90 |
| 14408 | Z4 | L32 | Q91 |
| 14409 | Z4 | L32 | Q92 |
| 14410 | Z4 | L32 | Q93 |
| 14411 | Z4 | L32 | Q94 |
| 14412 | Z4 | L32 | Q95 |
| 14413 | Z4 | L32 | Q96 |

TABLE 1-77-continued

| | | | |
|---|---|---|---|
| 14414 | Z4 | L32 | Q97 |
| 14415 | Z4 | L32 | Q98 |
| 14416 | Z4 | L32 | Q99 |
| 14417 | Z4 | L32 | Q100 |
| 14418 | Z4 | L32 | Q101 |
| 14419 | Z4 | L32 | Q102 |
| 14420 | Z4 | L32 | Q103 |
| 14421 | Z4 | L33 | Q1 |
| 14422 | Z4 | L33 | Q2 |
| 14423 | Z4 | L33 | Q3 |
| 14424 | Z4 | L33 | Q4 |
| 14425 | Z4 | L33 | Q5 |
| 14426 | Z4 | L33 | Q6 |
| 14427 | Z4 | L33 | Q7 |
| 14428 | Z4 | L33 | Q8 |
| 14429 | Z4 | L33 | Q9 |
| 14430 | Z4 | L33 | Q10 |
| 14431 | Z4 | L33 | Q11 |
| 14432 | Z4 | L33 | Q12 |
| 14433 | Z4 | L33 | Q13 |
| 14434 | Z4 | L33 | Q14 |
| 14435 | Z4 | L33 | Q15 |
| 14436 | Z4 | L33 | Q16 |
| 14437 | Z4 | L33 | Q17 |
| 14438 | Z4 | L33 | Q18 |
| 14439 | Z4 | L33 | Q19 |
| 14440 | Z4 | L33 | Q20 |
| 14441 | Z4 | L33 | Q21 |
| 14442 | Z4 | L33 | Q22 |
| 14443 | Z4 | L33 | Q23 |
| 14444 | Z4 | L33 | Q24 |

TABLE 1-78

| | | | |
|---|---|---|---|
| 14445 | Z4 | L33 | Q25 |
| 14446 | Z4 | L33 | Q26 |
| 14447 | Z4 | L33 | Q27 |
| 14448 | Z4 | L33 | Q28 |
| 14449 | Z4 | L33 | Q29 |
| 14450 | Z4 | L33 | Q30 |
| 14451 | Z4 | L33 | Q31 |
| 14452 | Z4 | L33 | Q32 |
| 14453 | Z4 | L33 | Q33 |
| 14454 | Z4 | L33 | Q34 |
| 14455 | Z4 | L33 | Q35 |
| 14456 | Z4 | L33 | Q36 |
| 14457 | Z4 | L33 | Q37 |
| 14458 | Z4 | L33 | Q38 |
| 14459 | Z4 | L33 | Q39 |
| 14460 | Z4 | L33 | Q40 |
| 14461 | Z4 | L33 | Q41 |
| 14462 | Z4 | L33 | Q42 |
| 14463 | Z4 | L33 | Q43 |
| 14464 | Z4 | L33 | Q44 |
| 14465 | Z4 | L33 | Q45 |
| 14466 | Z4 | L33 | Q46 |
| 14467 | Z4 | L33 | Q47 |
| 14468 | Z4 | L33 | Q48 |
| 14469 | Z4 | L33 | Q49 |
| 14470 | Z4 | L33 | Q50 |
| 14471 | Z4 | L33 | Q51 |
| 14472 | Z4 | L33 | Q52 |
| 14473 | Z4 | L33 | Q53 |
| 14474 | Z4 | L33 | Q54 |
| 14475 | Z4 | L33 | Q55 |
| 14476 | Z4 | L33 | Q56 |
| 14477 | Z4 | L33 | Q57 |
| 14478 | Z4 | L33 | Q58 |
| 14479 | Z4 | L33 | Q59 |
| 14480 | Z4 | L33 | Q60 |
| 14481 | Z4 | L33 | Q61 |
| 14482 | Z4 | L33 | Q62 |
| 14483 | Z4 | L33 | Q63 |
| 14484 | Z4 | L33 | Q64 |
| 14485 | Z4 | L33 | Q65 |
| 14486 | Z4 | L33 | Q66 |
| 14487 | Z4 | L33 | Q67 |

TABLE 1-78-continued

| | | | |
|---|---|---|---|
| 14488 | Z4 | L33 | Q68 |
| 14489 | Z4 | L33 | Q69 |
| 14490 | Z4 | L33 | Q70 |
| 14491 | Z4 | L33 | Q71 |
| 14492 | Z4 | L33 | Q72 |
| 14493 | Z4 | L33 | Q73 |
| 14494 | Z4 | L33 | Q74 |
| 14495 | Z4 | L33 | Q75 |
| 14496 | Z4 | L33 | Q76 |
| 14497 | Z4 | L33 | Q77 |
| 14498 | Z4 | L33 | Q78 |
| 14499 | Z4 | L33 | Q79 |
| 14500 | Z4 | L33 | Q80 |
| 14501 | Z4 | L33 | Q81 |
| 14502 | Z4 | L33 | Q82 |
| 14503 | Z4 | L33 | Q83 |
| 14504 | Z4 | L33 | Q84 |
| 14505 | Z4 | L33 | Q85 |
| 14506 | Z4 | L33 | Q86 |
| 14507 | Z4 | L33 | Q87 |
| 14508 | Z4 | L33 | Q88 |
| 14509 | Z4 | L33 | Q89 |
| 14510 | Z4 | L33 | Q90 |
| 14511 | Z4 | L33 | Q91 |
| 14512 | Z4 | L33 | Q92 |
| 14513 | Z4 | L33 | Q93 |
| 14514 | Z4 | L33 | Q94 |
| 14515 | Z4 | L33 | Q95 |
| 14516 | Z4 | L33 | Q96 |
| 14517 | Z4 | L33 | Q97 |
| 14518 | Z4 | L33 | Q98 |
| 14519 | Z4 | L33 | Q99 |
| 14520 | Z4 | L33 | Q100 |
| 14521 | Z4 | L33 | Q101 |
| 14522 | Z4 | L33 | Q102 |
| 14523 | Z4 | L33 | Q103 |
| 14524 | Z4 | L34 | Q1 |
| 14525 | Z4 | L34 | Q2 |
| 14526 | Z4 | L34 | Q3 |
| 14527 | Z4 | L34 | Q4 |
| 14528 | Z4 | L34 | Q5 |
| 14529 | Z4 | L34 | Q6 |
| 14530 | Z4 | L34 | Q7 |
| 14531 | Z4 | L34 | Q8 |
| 14532 | Z4 | L34 | Q9 |
| 14533 | Z4 | L34 | Q10 |
| 14534 | Z4 | L34 | Q11 |
| 14535 | Z4 | L34 | Q12 |
| 14536 | Z4 | L34 | Q13 |
| 14537 | Z4 | L34 | Q14 |
| 14538 | Z4 | L34 | Q15 |
| 14539 | Z4 | L34 | Q16 |
| 14540 | Z4 | L34 | Q17 |
| 14541 | Z4 | L34 | Q18 |
| 14542 | Z4 | L34 | Q19 |
| 14543 | Z4 | L34 | Q20 |
| 14544 | Z4 | L34 | Q21 |
| 14545 | Z4 | L34 | Q22 |
| 14546 | Z4 | L34 | Q23 |
| 14547 | Z4 | L34 | Q24 |
| 14548 | Z4 | L34 | Q25 |
| 14549 | Z4 | L34 | Q26 |
| 14550 | Z4 | L34 | Q27 |
| 14551 | Z4 | L34 | Q28 |
| 14552 | Z4 | L34 | Q29 |
| 14553 | Z4 | L34 | Q30 |
| 14554 | Z4 | L34 | Q31 |
| 14555 | Z4 | L34 | Q32 |
| 14556 | Z4 | L34 | Q33 |
| 14557 | Z4 | L34 | Q34 |
| 14558 | Z4 | L34 | Q35 |
| 14559 | Z4 | L34 | Q36 |
| 14560 | Z4 | L34 | Q37 |
| 14561 | Z4 | L34 | Q38 |
| 14562 | Z4 | L34 | Q39 |
| 14563 | Z4 | L34 | Q40 |
| 14564 | Z4 | L34 | Q41 |
| 14565 | Z4 | L34 | Q42 |
| 14566 | Z4 | L34 | Q43 |
| 14567 | Z4 | L34 | Q44 |

TABLE 1-78-continued

| | | | |
|---|---|---|---|
| 14568 | Z4 | L34 | Q45 |
| 14569 | Z4 | L34 | Q46 |
| 14570 | Z4 | L34 | Q47 |
| 14571 | Z4 | L34 | Q48 |
| 14572 | Z4 | L34 | Q49 |
| 14573 | Z4 | L34 | Q50 |
| 14574 | Z4 | L34 | Q51 |
| 14575 | Z4 | L34 | Q52 |
| 14576 | Z4 | L34 | Q53 |
| 14577 | Z4 | L34 | Q54 |
| 14578 | Z4 | L34 | Q55 |
| 14579 | Z4 | L34 | Q56 |
| 14580 | Z4 | L34 | Q57 |
| 14581 | Z4 | L34 | Q58 |
| 14582 | Z4 | L34 | Q59 |
| 14583 | Z4 | L34 | Q60 |
| 14584 | Z4 | L34 | Q61 |
| 14585 | Z4 | L34 | Q62 |
| 14586 | Z4 | L34 | Q63 |
| 14587 | Z4 | L34 | Q64 |
| 14588 | Z4 | L34 | Q65 |
| 14589 | Z4 | L34 | Q66 |
| 14590 | Z4 | L34 | Q67 |
| 14591 | Z4 | L34 | Q68 |
| 14592 | Z4 | L34 | Q69 |
| 14593 | Z4 | L34 | Q70 |
| 14594 | Z4 | L34 | Q71 |
| 14595 | Z4 | L34 | Q72 |
| 14596 | Z4 | L34 | Q73 |
| 14597 | Z4 | L34 | Q74 |
| 14598 | Z4 | L34 | Q75 |
| 14599 | Z4 | L34 | Q76 |
| 14600 | Z4 | L34 | Q77 |
| 14601 | Z4 | L34 | Q78 |
| 14602 | Z4 | L34 | Q79 |
| 14603 | Z4 | L34 | Q80 |
| 14604 | Z4 | L34 | Q81 |
| 14605 | Z4 | L34 | Q82 |
| 14606 | Z4 | L34 | Q83 |
| 14607 | Z4 | L34 | Q84 |
| 14608 | Z4 | L34 | Q85 |
| 14609 | Z4 | L34 | Q86 |
| 14610 | Z4 | L34 | Q87 |
| 14611 | Z4 | L34 | Q88 |
| 14612 | Z4 | L34 | Q89 |
| 14613 | Z4 | L34 | Q90 |
| 14614 | Z4 | L34 | Q91 |
| 14615 | Z4 | L34 | Q92 |
| 14616 | Z4 | L34 | Q93 |
| 14617 | Z4 | L34 | Q94 |
| 14618 | Z4 | L34 | Q95 |
| 14619 | Z4 | L34 | Q96 |
| 14620 | Z4 | L34 | Q97 |
| 14621 | Z4 | L34 | Q98 |
| 14622 | Z4 | L34 | Q99 |
| 14623 | Z4 | L34 | Q100 |
| 14624 | Z4 | L34 | Q101 |
| 14625 | Z4 | L34 | Q102 |
| 14626 | Z4 | L34 | Q103 |
| 14627 | Z4 | L35 | Q1 |
| 14628 | Z4 | L35 | Q2 |
| 14629 | Z4 | L35 | Q3 |
| 14630 | Z4 | L35 | Q4 |
| 14631 | Z4 | L35 | Q5 |
| 14632 | Z4 | L35 | Q6 |
| 14633 | Z4 | L35 | Q7 |
| 14634 | Z4 | L35 | Q8 |
| 14635 | Z4 | L35 | Q9 |
| 14636 | Z4 | L35 | Q10 |
| 14637 | Z4 | L35 | Q11 |
| 14638 | Z4 | L35 | Q12 |
| 14639 | Z4 | L35 | Q13 |
| 14640 | Z4 | L35 | Q14 |
| 14641 | Z4 | L35 | Q15 |
| 14642 | Z4 | L35 | Q16 |
| 14643 | Z4 | L35 | Q17 |
| 14644 | Z4 | L35 | Q18 |
| 14845 | Z4 | L35 | Q19 |

TABLE 1-79

| | | | |
|---|---|---|---|
| 14646 | Z4 | L35 | Q20 |
| 14647 | Z4 | L35 | Q21 |
| 14648 | Z4 | L35 | Q22 |
| 14649 | Z4 | L35 | Q23 |
| 14650 | Z4 | L35 | Q24 |
| 14651 | Z4 | L35 | Q25 |
| 14652 | Z4 | L35 | Q26 |
| 14653 | Z4 | L35 | Q27 |
| 14654 | Z4 | L35 | Q28 |
| 14655 | Z4 | L35 | Q29 |
| 14656 | Z4 | L35 | Q30 |
| 14657 | Z4 | L35 | Q31 |
| 14658 | Z4 | L35 | Q32 |
| 14659 | Z4 | L35 | Q33 |
| 14660 | Z4 | L35 | Q34 |
| 14661 | Z4 | L35 | Q35 |
| 14662 | Z4 | L35 | Q36 |
| 14663 | Z4 | L35 | Q37 |
| 14664 | Z4 | L35 | Q38 |
| 14665 | Z4 | L35 | Q39 |
| 14666 | Z4 | L35 | Q40 |
| 14667 | Z4 | L35 | Q41 |
| 14668 | Z4 | L35 | Q42 |
| 14669 | Z4 | L35 | Q43 |
| 14670 | Z4 | L35 | Q44 |
| 14671 | Z4 | L35 | Q45 |
| 14672 | Z4 | L35 | Q46 |
| 14673 | Z4 | L35 | Q47 |
| 14674 | Z4 | L35 | Q48 |
| 14675 | Z4 | L35 | Q49 |
| 14676 | Z4 | L35 | Q50 |
| 14677 | Z4 | L35 | Q51 |
| 14678 | Z4 | L35 | Q52 |
| 14679 | Z4 | L35 | Q53 |
| 14680 | Z4 | L35 | Q54 |
| 14681 | Z4 | L35 | Q55 |
| 14682 | Z4 | L35 | Q56 |
| 14683 | Z4 | L35 | Q57 |
| 14684 | Z4 | L35 | Q58 |
| 14685 | Z4 | L35 | Q59 |
| 14686 | Z4 | L35 | Q60 |
| 14687 | Z4 | L35 | Q61 |
| 14688 | Z4 | L35 | Q62 |
| 14689 | Z4 | L35 | Q63 |
| 14690 | Z4 | L35 | Q64 |
| 14691 | Z4 | L35 | Q65 |
| 14692 | Z4 | L35 | Q66 |
| 14693 | Z4 | L35 | Q67 |
| 14694 | Z4 | L35 | Q68 |
| 14695 | Z4 | L35 | Q69 |
| 14696 | Z4 | L35 | Q70 |
| 14697 | Z4 | L35 | Q71 |
| 14698 | Z4 | L35 | Q72 |
| 14699 | Z4 | L35 | Q73 |
| 14700 | Z4 | L35 | Q74 |
| 14701 | Z4 | L35 | Q75 |
| 14702 | Z4 | L35 | Q76 |
| 14703 | Z4 | L35 | Q77 |
| 14704 | Z4 | L35 | Q78 |
| 14705 | Z4 | L35 | Q79 |
| 14706 | Z4 | L35 | Q80 |
| 14707 | Z4 | L35 | Q81 |
| 14708 | Z4 | L35 | Q82 |
| 14709 | Z4 | L35 | Q83 |
| 14710 | Z4 | L35 | Q84 |
| 14711 | Z4 | L35 | Q85 |
| 14712 | Z4 | L35 | Q86 |
| 14713 | Z4 | L35 | Q87 |
| 14714 | Z4 | L35 | Q88 |
| 14715 | Z4 | L35 | Q89 |
| 14716 | Z4 | L35 | Q90 |
| 14717 | Z4 | L35 | Q91 |
| 14718 | Z4 | L35 | Q92 |
| 14719 | Z4 | L35 | Q93 |
| 14720 | Z4 | L35 | Q94 |
| 14721 | Z4 | L35 | Q95 |
| 14722 | Z4 | L35 | Q96 |
| 14723 | Z4 | L35 | Q97 |
| 14724 | Z4 | L35 | Q98 |
| 14725 | Z4 | L35 | Q99 |

TABLE 1-79-continued

| | | | |
|---|---|---|---|
| 14726 | Z4 | L35 | Q100 |
| 14727 | Z4 | L35 | Q101 |
| 14728 | Z4 | L35 | Q102 |
| 14729 | Z4 | L35 | Q103 |
| 14730 | Z4 | L36 | Q1 |
| 14731 | Z4 | L36 | Q2 |
| 14732 | Z4 | L36 | Q3 |
| 14733 | Z4 | L36 | Q4 |
| 14734 | Z4 | L36 | Q5 |
| 14735 | Z4 | L36 | Q6 |
| 14736 | Z4 | L36 | Q7 |
| 14737 | Z4 | L36 | Q8 |
| 14738 | Z4 | L36 | Q9 |
| 14739 | Z4 | L36 | Q10 |
| 14740 | Z4 | L36 | Q11 |
| 14741 | Z4 | L36 | Q12 |
| 14742 | Z4 | L36 | Q13 |
| 14743 | Z4 | L36 | Q14 |
| 14744 | Z4 | L36 | Q15 |
| 14745 | Z4 | L36 | Q16 |
| 14746 | Z4 | L36 | Q17 |
| 14747 | Z4 | L36 | Q18 |
| 14748 | Z4 | L36 | Q19 |
| 14749 | Z4 | L36 | Q20 |
| 14750 | Z4 | L36 | Q21 |
| 14751 | Z4 | L36 | Q22 |
| 14752 | Z4 | L36 | Q23 |
| 14753 | Z4 | L36 | Q24 |
| 14754 | Z4 | L36 | Q25 |
| 14755 | Z4 | L36 | Q26 |
| 14756 | Z4 | L36 | Q27 |
| 14757 | Z4 | L36 | Q28 |
| 14758 | Z4 | L36 | Q29 |
| 14759 | Z4 | L36 | Q30 |
| 14760 | Z4 | L36 | Q31 |
| 14761 | Z4 | L36 | Q32 |
| 14762 | Z4 | L36 | Q33 |
| 14763 | Z4 | L36 | Q34 |
| 14764 | Z4 | L36 | Q35 |
| 14765 | Z4 | L36 | Q36 |
| 14766 | Z4 | L36 | Q37 |
| 14767 | Z4 | L36 | Q38 |
| 14768 | Z4 | L36 | Q39 |
| 14769 | Z4 | L36 | Q40 |
| 14770 | Z4 | L36 | Q41 |
| 14771 | Z4 | L36 | Q42 |
| 14772 | Z4 | L36 | Q43 |
| 14773 | Z4 | L36 | Q44 |
| 14774 | Z4 | L36 | Q45 |
| 14775 | Z4 | L36 | Q46 |
| 14776 | Z4 | L36 | Q47 |
| 14777 | Z4 | L36 | Q48 |
| 14778 | Z4 | L36 | Q49 |
| 14779 | Z4 | L36 | Q50 |
| 14780 | Z4 | L36 | Q51 |
| 14781 | Z4 | L36 | Q52 |
| 14782 | Z4 | L36 | Q53 |
| 14783 | Z4 | L36 | Q54 |
| 14784 | Z4 | L36 | Q55 |
| 14785 | Z4 | L36 | Q56 |
| 14786 | Z4 | L36 | Q57 |
| 14787 | Z4 | L36 | Q58 |
| 14788 | Z4 | L36 | Q59 |
| 14789 | Z4 | L36 | Q60 |
| 14790 | Z4 | L36 | Q61 |
| 14791 | Z4 | L36 | Q62 |
| 14792 | Z4 | L36 | Q63 |
| 14793 | Z4 | L36 | Q64 |
| 14794 | Z4 | L36 | Q65 |
| 14795 | Z4 | L36 | Q66 |
| 14796 | Z4 | L36 | Q67 |
| 14797 | Z4 | L36 | Q68 |
| 14798 | Z4 | L36 | Q69 |
| 14799 | Z4 | L36 | Q70 |
| 14800 | Z4 | L36 | Q71 |
| 14801 | Z4 | L36 | Q72 |
| 14802 | Z4 | L36 | Q73 |
| 14803 | Z4 | L36 | Q74 |
| 14804 | Z4 | L36 | Q75 |
| 14805 | Z4 | L36 | Q76 |
| 14806 | Z4 | L36 | Q77 |
| 14807 | Z4 | L36 | Q78 |
| 14808 | Z4 | L36 | Q79 |
| 14809 | Z4 | L36 | Q80 |
| 14810 | Z4 | L36 | Q81 |
| 14811 | Z4 | L36 | Q82 |
| 14812 | Z4 | L36 | Q83 |
| 14813 | Z4 | L36 | Q84 |
| 14814 | Z4 | L36 | Q85 |
| 14815 | Z4 | L36 | Q86 |
| 14816 | Z4 | L36 | Q87 |
| 14817 | Z4 | L36 | Q88 |
| 14818 | Z4 | L36 | Q89 |
| 14819 | Z4 | L36 | Q90 |
| 14820 | Z4 | L36 | Q91 |
| 14821 | Z4 | L36 | Q92 |
| 14822 | Z4 | L36 | Q93 |
| 14823 | Z4 | L36 | Q94 |
| 14824 | Z4 | L36 | Q95 |
| 14825 | Z4 | L36 | Q96 |
| 14826 | Z4 | L36 | Q97 |
| 14827 | Z4 | L36 | Q98 |
| 14828 | Z4 | L36 | Q99 |
| 14829 | Z4 | L36 | Q100 |
| 14830 | Z4 | L36 | Q101 |
| 14831 | Z4 | L36 | Q102 |
| 14832 | Z4 | L36 | Q103 |

A specific example of another embodiment of the compound of the invention includes a compound represented by formula (11):

[Chemical Formula 663]

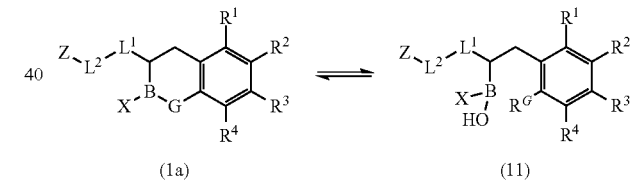

or a pharmaceutically acceptable salt thereof, wherein Z, $L^1$, $L^2$, X, $R^1$, $R^2$, $R^3$, and $R^4$ are the same as the definitions herein, $R^G$ is a hydroxyl group, a thiol group, or $-NHR^{a1}$, and $R^{a1}$ is the same as the definition herein.

A specific example of another embodiment of the compound of the invention includes a compound represented by formula (12):

[Chemical Formula 664]

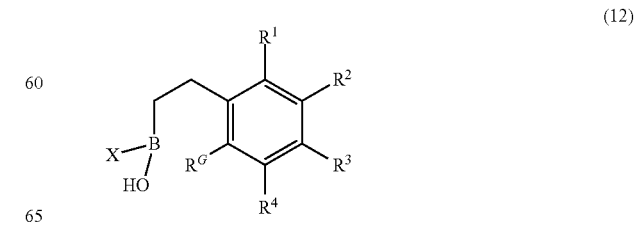

or a pharmaceutically acceptable salt thereof, wherein X, $R^1$, $R^2$, $R^3$, and $R^4$ are the same as the definitions herein, $R^G$ is a hydroxyl group, a thiol group, or —$NHR^{a1}$, and $R^{a1}$ is the same as the definition herein. A compound of formula (12) is in an interchangeable relationship with, and thus can be biologically equivalent with, a compound of formula (1a) or (3a) due to an equilibrium reaction in an aqueous solution or in the body.

A specific example of another embodiment of the compound of the invention includes a compound represented by formula (13):

[Chemical Formula 665]

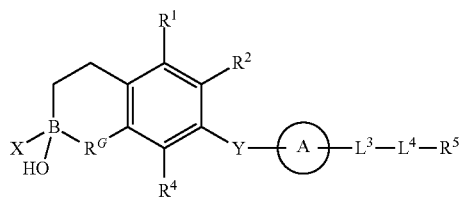

(13)

or a pharmaceutically acceptable salt thereof, wherein X, Y, ring A, $L^3$, $L^4$, $R^1$, $R^2$, $R^4$, and $R^5$ are the same as the definitions herein, $R^G$ is a hydroxyl group, a thiol group, or —$NHR^{a1}$, and $R^{a1}$ is the same as the definition herein.

A specific example of a preferred embodiment of the compound of the invention includes a compound represented by formula (14):

[Chemical Formula 666]

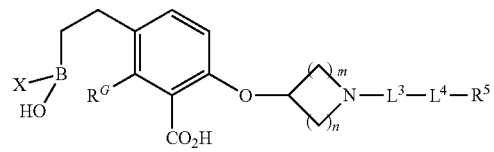

(14)

or a pharmaceutically acceptable salt thereof, wherein X, $L^3$, $L^4$, m, n, and $R^5$ are the same as the definitions herein, $R^G$ is a hydroxyl group, a thiol group, or —$NHR^{a1}$, and $R^{a1}$ is the same as the definition herein.

The compound of the invention is described further hereinafter.

The compound of the invention can have, depending on the type of substituent, a tautomer, stereoisomers such as geometric isomer, and enantiomer, which are encompassed by the present invention. Specifically, if the compound of the invention has one or more asymmetric carbon atoms, there is a diastereomer or an enantiomer, where a mixture of such a diastereomer or enantiomer or isolated diastereomer or enantiomer are also encompassed by the compound of the invention.

The compound of the invention can also have a structure represented by the following formula (11) due to an equilibrium state or the like, depending on the environment conditions such as temperature or humidity, or a physical factor in a solid, liquid, solution, or the like. The compound of the invention also encompasses compounds with such a structure.

[Chemical Formula 667]

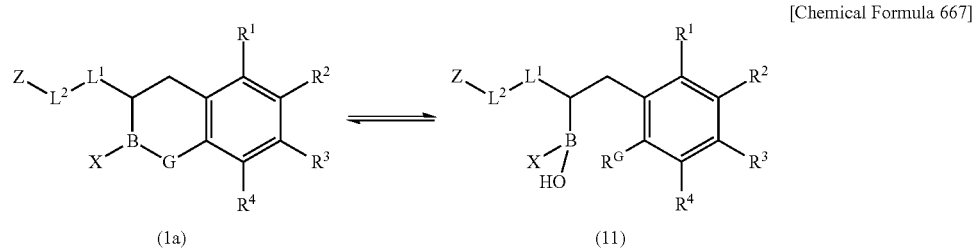

(1a)    (11)

In formula (11), X represents a hydroxyl group, a thiol group, or —NHR$^{a1}$, Z, L$^1$, L$^2$, R, R$^1$, R$^2$, R$^3$, R$^4$, and R$^{a1}$ are defined the same as the definitions herein, and formula (1a) is defined the same as the definition herein.

For example, the structures of the compounds in the Examples herein are based on estimation considered the most appropriate by those skilled in the art using proton nuclear magnetic resonance spectrum ($^1$H-NMR), liquid chromatography mass spectrometry (LCMS), or the like, but the structures are just estimates under each specific measurement environment. In particular, the structure of formula (1a), the structure of formula (1b), and the structure of formula (11) are possibly converted to each other or partially converted to one of the structures and mixed due to a property unique to each compound, various environmental conditions such as temperature or humidity, or physical factor in a solid, liquid, solution or the like.

The compound of the invention also includes various hydrates, solvates, and crystalline polymorphisms.

Furthermore, the compound of the invention may be substituted with an isotope (e.g., $^2$H (or D), $^3$H (or T), $^{11}$C, $^{13}$C, $^{14}$C, $^{13}$N, $^{15}$N, $^{15}$O, $^{35}$S, $^{18}$F, $^{125}$I, or the like). Such compounds are also encompassed by the compound of the invention.

Prodrugs of the compound of the invention are also within the scope of the invention. As used herein, a prodrug refers to a derivative that results in the compound of formula (1a), (1b), or (11) by acid hydrolysis or enzymatic degradation in the body. If, for example, the compound of formula (1a), (1b), or (11) has a hydroxyl group, amino group, or carboxyl group, these groups can be modified in accordance with a conventional method to manufacture a prodrug.

Examples for a compound with a carboxy group include compounds whose carboxyl group has been converted to an alkoxycarbonyl group, alkylthiocarbonyl group, or alkylaminocarbonyl group.

Examples for a compound with an amino group include compounds whose amino group has been substituted with an alkanoyl group to be converted to an alkanoylamino group, substituted with an alkoxycarbonyl group to be converted to an alkoxycarbonylamino group, modified to an alkanoyloxymethylamino group, or converted to a hydroxylamine.

Examples for a compound with a hydroxyl group include compounds whose hydroxyl group has been substituted with the alkanoyl group described above to be converted to an alkanoyloxy group, converted to a phosphate ester, or converted to an alkanoyloxymethyloxy group.

Examples of the alkyl moiety of a group used in producing these prodrugs include the alkyl group described above. The alkyl group is optionally substituted with, for example, an alkoxy group or the like. Preferred examples thereof include the following.

Examples of compounds whose carboxyl group has been converted to an alkoxycarbonyl group include alkoxycarbonyl such as methoxycarbonyl and ethoxycarbonyl, and alkoxycarbonyl substituted with an alkoxy group such as methoxymethoxycarbonyl, ethoxymethoxycarbonyl, 2-methoxyethoxycarbonyl, 2-methoxyethoxymethoxycarbonyl, and pivaloyloxymethoxycarbonyl.

As used herein, "pharmaceutically acceptable salt" refers to an acid addition salt or base addition salt which is pharmaceutically acceptable for use. Examples of "pharmaceutically acceptable salts" include, but are not limited to, acid addition salts such as acetate, propionate, butyrate, formate, trifluoroacetate, maleate, fumarate, tartrate, citrate, stearate, succinate, ethylsuccinate, malonate, lactobionate, gluconate, glucoheptonate, benzoate, methanesulfonate, benzenesulfonate, para-toluenesulfonate (tosylate), laurylsulfate, malate, ascorbate, mandelate, saccharinate, xinafoate, pamoate, cinnamate, adipate, cysteine salt, N-acetyl cysteine salt, hydrochloride, hydrobromide, phosphate, sulfate, hydroiodide, nicotinate, oxalate, picrate, thiocyanate, undecanoate, acrylic acid polymer salt, and carboxyvinyl polymer; inorganic base addition salts such as lithium salt, sodium salt, potassium salt, and calcium salt; organic base addition salts such as morpholine and piperidine; amino acid addition salts wherein the amino acid is aspartic acid or glutamic acid; and the like.

The compounds of the invention can be administered directly, or as a formulation, medicament, or a pharmaceutical composition using a suitable dosage form, by oral or parenteral administration. Specific examples of such dosage forms include, but are not limited to, tablets, capsules, powder, granules, liquid agents, suspension, injections, patches, poultice, and the like. These formulations can be manufactured by a known method using an additive that is commonly used as a pharmaceutical additive.

As these additives, an excipient, disintegrant, binding agent, fluidizer, lubricant, coating agent, solubilizing agent, solubilization promotor, thickener, dispersant, stabilizer, sweetener, flavoring agent, or the like can be used depending on the objective. Specific examples of these additives include, but are not limited to, lactose, mannitol, crystalline cellulose, low-substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide, talc, and the like.

The dosage of the compound of the invention is appropriately selected depending on the animal targeted for administration, route of administration, disease, patient's age, body weight, and symptom. For example, the dosage is 0.01 mg as the lower limit (preferably 100 mg) and 10000 mg as the upper limit (preferably 6000 mg) per day for adults for oral administration. This amount can be administered once daily, or divided into several doses.

The compound of the invention is a compound with inhibitory activity against β-lactamase. Thus, the compound can be a prophylactic or therapeutic agent that is useful for a bacterial infection by combined use with an antimicrobial agent. Specific examples of such bacterial infections include sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, an odontogenic infection, and the like.

The compound of the invention can be used in combination with at least one agent selected from an antimicrobial agent, an antifungal agent, an antiviral agent, an anti-inflammatory agent, or an anti-allergic agent for treating one or more bacterial infections described herein. The agent is preferably an antimicrobial agent, and more preferably a R-lactam agent. Specific examples thereof include amoxicillin, ampicillin (pivampicillin, hetacillin, bacampicillin, metampicillin, and talampicillin), epicillin, carbenicillin (carindacillin), ticarcillin, temocillin, azlocillin, piperacillin, mezlocillin, mecillinam (pivmecillinam), sulbenicillin, benzylpenicillin (G), clometocillin, benzathine benzylpenicillin, procaine benzylpenicillin, azidocillin, penamecillin, phenoxymethyl penicillin (V), propicillin, benzathine phenoxymethylpenicillin, phenethicillin, cloxacillin (dicloxacillin and flucloxacillin), oxacillin, methicillin, nafcillin, faropenem, biapenem, doripenem, ertapenem, imipenem, meropenem, panipenem, tomopenem, razupenem, cefazolin, cefacetrile, cefadroxil, cephalexin, cefaloglycin, cefalonium, cefaloridine, cephalothin, cephapirin, cefatrizine, cefazedone, cefazaflur, cefradine, cefroxadine, ceftezole, cefaclor, cefamandole, cefminox, cefonicide, ceforanide, cefotiam, cefprozil, cefbuperazone, cefuroxime, cefuzonam, cefoxitin, cefotetan, cefmetazole, loracarbef, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, flomoxef, latamoxef, cefepime, cefozopran, cefpirome, cefquinome, ceftobiprole, ceftaroline, CXA-101, RWJ-54428, MC-04546, ME1036, BAL30072, SYN2416, ceftiofur, cefquinome, cefovecin, aztreonam, tigemonam, carumonam, RWJ-442831, RWJ-333441, and RWJ-333442. The timing of dosing of the compound of the invention and therapeutic agents thereof is not limited. The compound and therapeutic agent can be administered concurrently or sequentially to a subject being administered therewith. The compound of the invention and the therapeutic agents can be formulated as a combined agent. The dosage of the therapeutic agent can be appropriately selected based on the clinically used dose. The ratio of the compound of the invention and the therapeutic agents can be appropriately selected depending on the subject of administration, route of administration, target disease, symptom, combination, or the like.

In another embodiment, the compound of the invention can be combined and administered concomitantly or administered at different times upon use of a pharmaceutical composition comprising an antimicrobial agent such as a β-lactam agent. Such a pharmaceutical composition comprising a β-lactam agent is also within the scope of the invention, and can be used for treating or preventing a bacterial infection such as sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, or an odontogenic infection.

Such a medicament, formulation, or pharmaceutical composition can be manufactured by mixing the compound of the invention and/or an addition agent (e.g., antimicrobial agent such as a β-lactam agent) with any suitable component, together or separately, as a combined agent or as separate agents using any technology that is known in the art. An appropriate formulation such as a tablet, capsule, powder, granule, liquid agent, suspension, injection, patch, or poultice can be formulated by using any technology that is known in the art. If the compound of the invention and/or an addition agent (e.g., antimicrobial agent such as a β-lactam agent) are prepared as separate agents, they can be provided as a kit of two agents. The kit can provide one of the components as a single agent, with instructions (package insert or the like) instructing to combine and administer the other component (for the compound of the invention, the additional agent (e.g., antimicrobial agent such as a β-lactam agent); for the addition agent (e.g., antimicrobial agent such as a β-lactam agent), the compound of the invention) concurrently or at different times.

If the compound of the invention is used as an active ingredient of a medicament, the compound can be intended for use in not just humans, but also animals other than humans (cat, dog, cow, chicken, fish, and the like).

Hereinafter, the method of manufacturing the compound of the invention is described with examples, but the present invention is not limited thereto.

The compound of the invention can be manufactured by, for example, the manufacturing methods described below, but the methods are not limited to such methods. These manufacturing methods can be appropriately improved upon based on the expertise of those skilled in the art of organic synthetic chemistry. Salts of the compounds used as a starting material can be used in the manufacturing method described below, as long as the reaction is not affected.

In the manufacturing methods described below, even if use of a protecting group is not specifically described, a functional group other than those at the reaction point can be protected as needed and deprotected after the completion of a reaction or after a series of reactions to obtain a compound of interest if one of the functional groups other than those at the reaction point is altered under the reaction condition or if it is unsuitable for post-reaction processing. Common protecting groups described in the document (T. W. Greene and P. G. M. Wuts, "Protective Group in Organic Synthesis", $3^{rd}$ Ed., John Wiley and Sons, Inc., New York (1999)) or the like can be used as the protecting groups used in these processes. A protecting group can be introduced or removed by a method that is commonly used in organic synthetic chemistry (e.g., method described in the aforementioned document or the like) or a method in accordance therewith.

The starting material and intermediate in the manufacturing methods described below can be purchased as a commercially available product or are available by synthesis in accordance with a method described in a known document or a known method from a known compound. Salts of the starting material and intermediate can also be used, as long as the reaction is not affected.

The intermediate and compound of interest in the manufacturing methods described below can also be converted into another compound encompassed by the present invention by appropriately converting their functional groups. A functional group can be converted, in doing so, by a method that is commonly used in organic synthetic chemistry (e.g., the method described in R. C. Larock, "Comprehensive Organic Transformations", $2^{nd}$ Ed., John Wiley and Sons, Inc., New York (1999) or the like) or a method in accordance therewith.

An inert solvent in the manufacturing methods described below refers to a solvent that does not react with starting materials, reagents, bases, acids, catalysts, ligands, or the like used in a reaction (hereinafter, also referred to as "starting materials or the like used in a reaction"). A solvent used in each step can be used as an inert solvent even if the solvent reacts with the starting materials or the like used in the reaction, as long as the reaction of interest proceeds to result in a compound of interest.

Manufacturing Method 1

The compound of formula (1a), which is represented by formula (1-7) can be manufactured, for example, by the following manufacturing method.

[Chemical Formula 668]

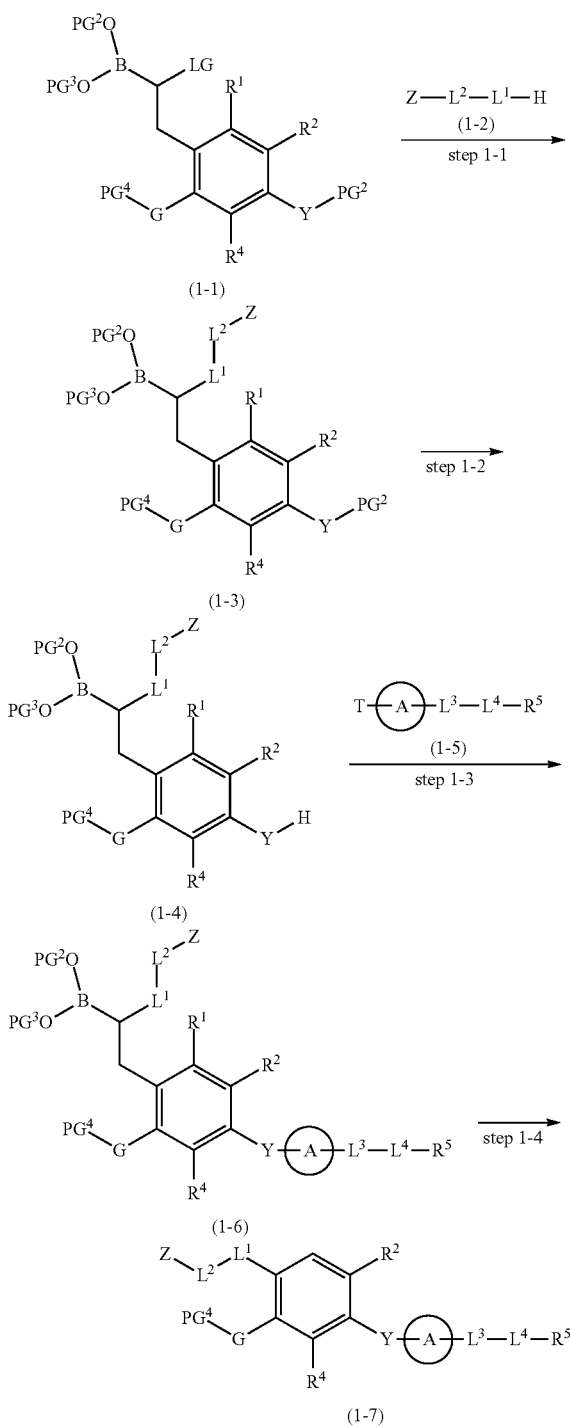

wherein $L^1$, $L^2$, Y, Z, ring A, $L^3$, $L^4$, G, $R^1$, $R^2$, $R^4$, and $R^5$ are defined the same as item 1, s a hydroxyl group or a $C_{1-6}$ alkoxy group, H is a hydrogen atom, LG represents a leaving group (e.g., a halogen atom such as chlorine, bromine, or iodine, a lower alkylsulfonyloxy group such as methanesulfonyloxy, a trihalogenomethanesulfonyloxy group such as trifluoromethanesulfonyloxy, an arylsulfonyloxy group such as benzenesulfonyloxy or p-toluenesulfonyloxy, or the like), T represents a hydroxyl group or a leaving group (e.g., a halogen atom such as chlorine, bromine, or iodine, a lower alkylsulfonyloxy group such as methanesulfonyloxy, a trihalogenomethanesulfonyloxy group such as trifluoromethanesulfonyloxy, an arylsulfonyloxy group such as benzene sulfonyloxy or p-toluenesulfonyloxy, or the like), PG represents a protecting group of a hydroxyl group (e.g., a tert-butoxycarbonyl group, acetyl group, methoxymethyl group, p-methoxybenzyl group, tert-butyldimethylsilyl group, trimethylsilyl group, or the like), and $PG^2$ and $PG^3$ represent protecting groups of boronic acid (e.g., an optionally substituted $C_{1-6}$ alkyl group, a structure represented by the following formula, or the like).

[Chemical Formula 669]

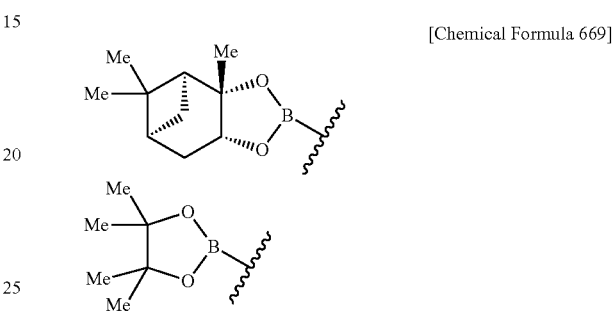

$PG^4$ represents a hydrogen atom, a protecting group of a hydroxyl group (e.g., a tert-butoxycarbonyl group, acetyl group, methoxymethyl group, p-methoxybenzyl group, tert-butyldimethylsilyl group, trimethylsilyl group, or the like), a protecting group of a thiol group (e.g., an acetamidomethyl group or trityl group), or a protecting group of an amino group (e.g., an ethoxycarbonyl group, tert-butoxycarbonyl group, acetyl group, benzoyl group, trifluoroacetyl group, benzyloxycarbonyl group, 3- or 4-chlorobenzyloxycarbonyl group, triphenylmethyl group, methanesulfonyl group, p-toluenesulfonyl group, trimethylsilyl group, benzyloxycarbonyl group, 3- or 4-chlorobenzyloxycarbonyl group, benzylsulfonyl group, benzyl group, 4-nitrobenzyl group, 4-methoxybenzyl group, methyl group, ethyl group, or the like).

A commercially available product or a compound manufactured by a known method (e.g., WO 2016/003929, WO 2016/149393, or the like) can be used as a starting raw material compound (1-1).

A commercially available product that is purchased or a compound synthesized in accordance with a method described in a known document (WO 2016/149393, Journal of Heterocyclic Chemistry, 15(8), 1295, 1978, Journal of Heterocyclic Chemistry, 44(2), 279, 2007, Eur. J. Med. Chem., 64, 54, 2013, J. Med. Chem., 2012, 55, 2945., J. Med. Chem., 2005, 48, 1984, Tetrahedron Letters, 57, 2888, 2016, WO 2012/018668, or the like) or a known method (e.g., the method described in R. C. Larock, "Comprehensive Organic Transformations", $2^{nd}$ Ed., John Wiley and Sons, Inc., New York (1999) or the like) from a known compound can be used as compound (1-2).

A commercially available product that is purchased or a compound synthesized in accordance with a method described in a known document (e.g., WO 2008/008895, WO 2011/118818, J. Med. Chem., 28(11), 1721, 1985, Tetrahedron, 67(52), 10208, 2011, Tetrahedron Letters, 26(39), 4739, 1985, J. Antibiot. 59(4), 241, 2006, or the like) or a known method (e.g., the method described in R. C. Larock, "Comprehensive Organic Transformations", $2^{nd}$ Ed., John Wiley and Sons, Inc., New York (1999) or the like) from a known compound can be used as compound (1-5).

As compound (1-2) and compound (1-5), a salt thereof can also be used, and the compound with a functional group that is protected can also be used as needed, as long as the reaction is not affected.

Step 1-1: Compound (1-3) can be manufactured by reacting compound (1-1) with compound (1-2) in an inert solvent in the presence of a base under normal pressure or under pressure. Specific examples of inert solvents include ether solvents such as THF and DME, halogenated hydrocarbon solvents such as dichloromethane or dichloroethane, aprotic solvents such as N,N-dimethylformamide (DMF), N-methylpyrrolidone (NMP), and dimethyl sulfoxide (DMSO), and the like. Examples of base include potassium tert-butoxy, sodium hydride, triethylamine, diisopropylethylamine, potassium carbonate, sodium carbonate, and the like. A base can be used at 0.001 to 100 equivalents with respect to compound (1-1), which is preferably 0.5 to 10 equivalents. Compound (1-2) can be used at 0.001 to 100 equivalents with respect to compound (1-1), which is preferably 1 to 10 equivalents. The reaction temperature is selected from the range of about $-10°$ C. to about $100°$ C.

Step 1-2: Compound (1-4) can be manufactured by deprotecting the protecting group $PG^1$ of compound (1-3). This step can be performed in accordance with the method described in, for example, the document (T. W. Greene and P. G. M. Wuts, "Protective Group in Organic Synthesis", $3^{rd}$ Ed., John Wiley and Sons, Inc., New York (1999)) or the like.

Step 1-3: Compound (1-6) can be manufactured using Manufacturing Method (1-3-1) or Manufacturing Method (1-3-2) described below.

Step 1-3-1: If Y is an oxygen atom and T is a hydroxyl group, compound (1-6) can be manufactured by reacting compound (1-4) with compound (1-5) under the so-called Mitsunobu reaction in an inert solvent, in the presence of an azo compound analog and organic phosphorous compound or in the presence of a phosphorane compound under normal pressure or under pressure. Specific examples of inert solvents include ether solvents such as THF and DME, hydrocarbon solvents such as toluene and benzene, and the like. Examples of azo compound analog include diethyl azodicarboxylate, diisopropyl azodicarboxylate, and the like. An azo compound analog can be used at 0.001 to 100 molar equivalents with respect to compound (1-4), which is preferably 1 to 10 molar equivalents. Examples of the organic phosphorous compound include triphenylphosphine, tributylphosphine, and the like. An organic phosphorous compound can be used at 0.001 to 100 molar equivalents with respect to compound (1-4), which is preferably 1 to 10 molar equivalents. Examples of phosphorane compounds include (cyanomethylene)tributylphosphorane, (cyanomethylene)trimethylphosphorane, and the like. A phosphorane compound can be used at 0.001 to 100 molar equivalents with respect to compound (1-4), which is preferably 1 to 10 molar equivalents. The reaction temperature is selected from the range of about $-10°$ C. to about $100°$ C.

Step 1-3-2: If Y is an oxygen atom, a sulfur atom, or —$NR^j$— and T is a leaving group (e.g., a halogen atom such as chlorine, bromine, or iodine, a lower alkylsulfonyloxy group such as a methanesulfonyloxy group, a trihalogenomethanesulfonyloxy group such as a trifluoromethanesulfonyloxy group, an arylsulfonyloxy group such as a benzenesulfonyloxy group or p-toluenesulfonyloxy group, or the like), compound (1-6) can be manufactured by reacting compound (1-4) with compound (1-5) in an inert solvent, in the presence of a base under normal pressure or under pressure. Specific examples of inert solvents include ether solvents such as THF and DME, halogenated hydrocarbon solvents such as dichloromethane and dichloroethane, aprotic solvents such as N,N-dimethylformamide (DMF), N-methylpyrrolidone (NMP), and dimethyl sulfoxide (DMSO), and the like. Examples of bases include potassium tert-butoxy, sodium hydride, triethylamine, diisopropylethylamine, potassium carbonate, sodium carbonate, cesium carbonate, and the like. A base can be used at 0.001 to 100 molar equivalents with respect to compound (1-1), which is preferably 0.5 to 10 molar equivalents. Compound (1-5) can be used at 0.001 to 100 molar equivalents with respect to compound (1-4), which is preferably 1 to 10 molar equivalents. The reaction temperature is selected from the range of about $-10°$ C. to about $100°$ C.

Step 1-4: This reaction can manufacture a compound from a corresponding compound (1-6) in accordance with a known method (e.g., WO 2014/151958, WO 2015/191907, WO 2016/003929, or the like). Preferably, a compound can be manufactured using Manufacturing Method (1-4-1) or Manufacturing Method 1-4-2) described below.

Manufacturing Method (1-4-1): Compound (1-7) can be manufactured by using compound (1-6) as a starting material and reacting the compound with boronic acid under acidic conditions in an inert solvent. Examples of boronic acid include phenylboronic acid and 2-methylpropyl boronic acid. The boronic acid can be used in the range of 0.001 to 100 equivalents with respect to compound (1-6), which is preferably 1 to 3 equivalents. Examples of acids include hydrochloric acid, trifluoroacetic acid, and the like. An acid can be used in the range of 0.001 to 100 equivalents with respect to compound (1-6), which is preferably 1 to 10 equivalents. Specific examples of inert solvents include halogenated hydrocarbon solvents such as dichloromethane and dichloroethane, hydrocarbon solvents such as hexane and heptane, ether solvents such as THF and CPME, nitrile solvents such as acetonitrile and propionitrile, and water, which can be used alone or as a mixture solvent. The acids described above can also be directly used as a solvent. A mixture solvent of hexane/acetonitrile is preferably used as a solvent. The reaction temperature is selected from the range of about $-10°$ C. to about $100°$ C.

Manufacturing Method (1-4-2): Compound (1-7) can be manufactured by using compound (1-6) as the starting material and reacting the compound with triethylsilane in a trifluoroacetic acid solvent. Triethylsilane can be used in the range of 0.001 to 100 equivalents with respect to compound (1-6), which is preferably 1 to 50 equivalents. The reaction temperature is selected from the range of about $-10°$ C. to about $70°$ C.

Manufacturing Method 1A

A compound of formula (1a) can be purchased or manufactured from a preparable corresponding material in the same manner as the manufacturing method of compound (1-7) described above. The compound is obtained in some cases as a compound of formula (1b), for example, by reacting with a reagent that generates nucleophilic $X^-$ (X anion) (e.g., alkali metal salt generating a hydroxide anion $HO^-$, alkali metal salt of $C_{1-6}$ alkoxide generating a $C_{1-6}$ alkoxide anion, the alkali metal salt of amide generating amide anion $R^{a2}R^{b1}N^-$, or the like), depending on the property of compound (1a).

[Chemical Formula 670]

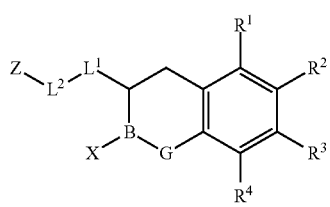
(1a)

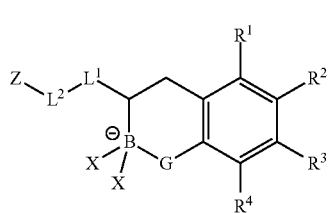
(1b)

wherein X, Z, $L^1$, $L^2$, G, $R^1$, $R^2$, $R^3$, and $R^4$ are defined the same as item 1.

For example, a compound of formula (1a'), which is a compound of formula (1a) wherein X is a hydroxyl group, is obtained in some cases as a sodium salt compound of formula (1b'), depending on the property of the compound, by treatment with an aqueous sodium hydroxide solution.

[Chemical Formula 671]

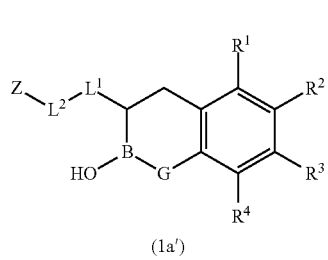
(1a')

Aqueous NaOH solution →

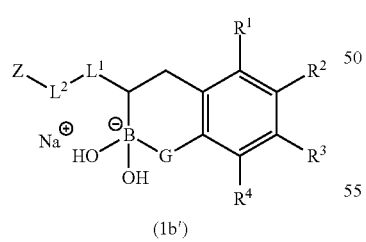
(1b')

wherein Z, $L^1$, $L^2$, G, $R^1$, $R^2$, $R^3$, and $R^4$ are defined the same as item 1.

For example, a compound of formula (1a"), which is a compound of formula (1a) wherein X is a hydroxyl group and $R^4$ is a carboxyl group, is obtained in some cases as a disodium salt compound of formula (1b"), depending on the property of the compound, by treatment with an aqueous sodium hydroxide solution.

[Chemical Formula 672]

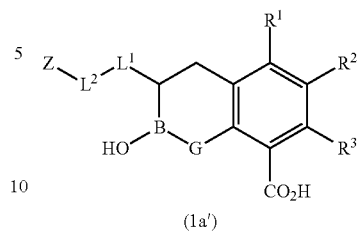
(1a')

Aqueous NaOH solution →

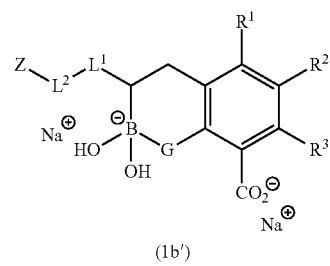
(1b')

wherein Z, $L^1$, $L^2$, G, $R^1$, $R^2$, and $R^3$ are defined the same as item 1.

Manufacturing Method 2

Compounds of formula (1a) represented by formula (2-7) described below can be manufactured, for example, by the manufacturing method described below. Compound (2-7) represents compound (1-7) wherein $L^1$ is —$NR^d$(C=O)— and $R^d$ is a hydrogen atom.

[Chemical Formula 673]

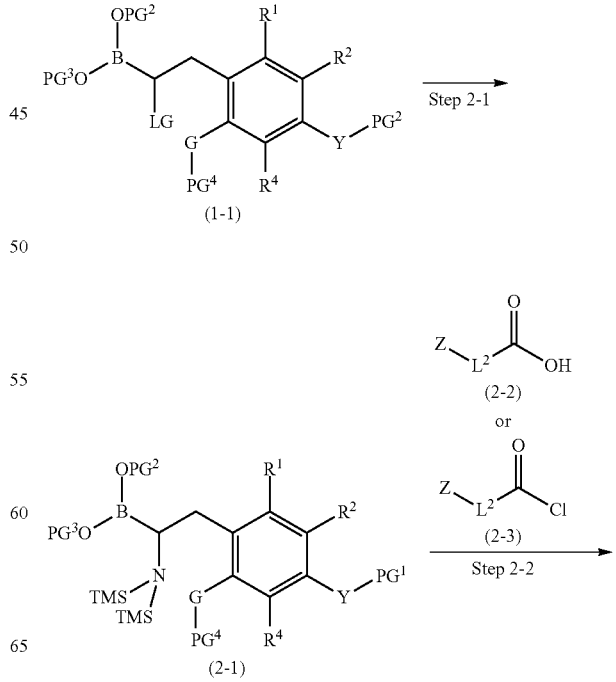

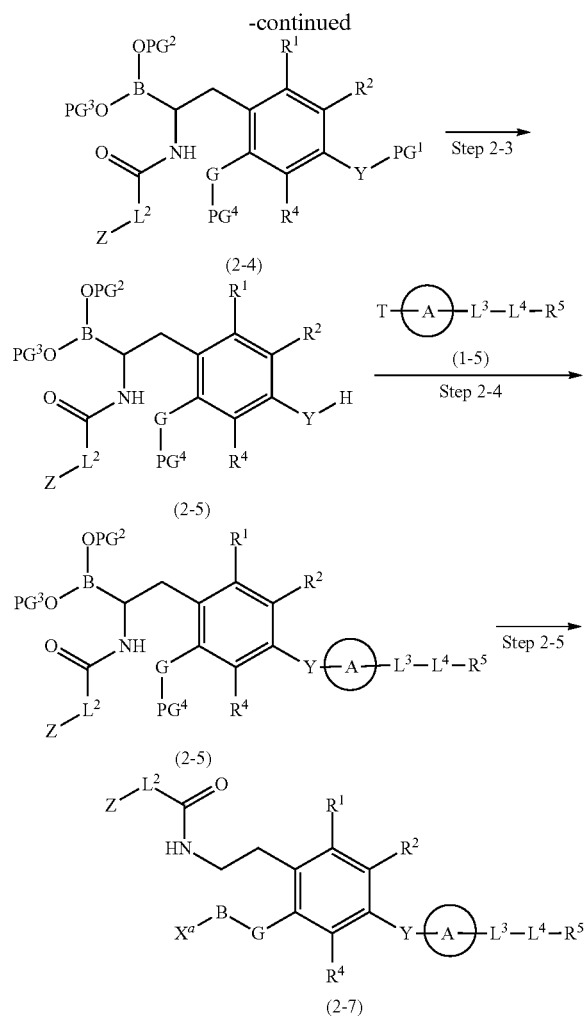

wherein $L^2$, Y, Z, ring A, $L^3$, $L^4$, G, $R^1$, $R^2$, $R^4$, and $R^5$ are defined the same as item 1, $X^a$ is a hydroxyl group or a $C_{1-6}$ alkoxy group, H is a hydrogen atom, T, LG, $PG^1$, $PG^2$, $PG^3$, and $PG^4$ are each defined the same as the definition described in Manufacturing Method 1, and TMS represents a trimethylsilyl group.

A commercially available product that is purchased or a compound manufactured by the method described in Manufacturing Method 1 can be used as the starting material compound (1-1) and compound (1-5). Further, a commercially available product that is purchased or a compound synthesized in accordance with a known method (e.g., the method described in R. C. Larock, "Comprehensive Organic Transformations", $2^{nd}$ Ed., John Wiley and Sons, Inc., New York (1999) or the like) from a known compound can be used as compound (2-2) and compound (2-3). As compound (1-5), compound (2-2), and compound (2-3), a salt thereof can also be used, and the compound with a functional group that is protected can also be used as needed, as long as the reaction is not affected.

Step 2-1: Compound (2-1) can be manufactured by reacting compound (1-1) with hexamethyldisilazane lithium in an inert solvent under normal pressure or under pressure. Specific examples of inert solvents include ether solvents such as THF and diethyl ether, and the like. Hexamethyldisilazane lithium can be used at 0.001 to 100 equivalents with respect to compound (1-1), which is preferably 1 to 10 equivalents. The reaction temperature is selected from the range of about −78° C. to about 50° C.

Step 2-2: Compound (2-4) can be manufactured by reacting compound (2-1) with compound (2-2) or (2-3) in an inert solvent in the presence or absence of a condensing agent and/or base under normal pressure or under pressure. Specific examples of inert solvents include ether solvents such as THF and DME, halogenated hydrocarbon solvents such as dichloromethane and chloroform, aprotic solvents such as DMF, NMP, and DMSO, and the like. (2-2) or (2-3) can be used at 0.001 to 100 equivalents with respect to compound (2-1), which is preferably 1 to 10 equivalents. Various condensing agents that are used in a conventional method can be used as the condensing agent. Examples thereof include 1-ethyl-3-(3-dimethylaminopropyl)carbodiimide (including hydrochloride), 0-(7-azabenzotriazol-1-yl)-N,N,N',N'-tetramethyluronium hexafluorophosphate, N,N'-dicyclohexylcarbodiimide, 4-(4,6-dimethoxy-1,3,5-triazin-2-yl)-4-methylmorpholinium chloride, hydrates thereof, and the like. A condensing agent can be used at 0.001 to 100 equivalents with respect to compound (2-1), which is preferably 1 to 10 equivalents. Examples of bases include diisopropylethylamine, triethylamine, and the like. A base can be used at 0.001 to 100 equivalents with respect to compound (2-1), which is preferably 1 to 10 equivalents. The reaction temperature is selected from the range of about −78° C. to about 100° C.

Step 2-3: Compound (2-5) can be manufactured by using compound (2-4) as a starting material and using conditions in accordance with step 1-2 of Manufacturing Method 1 described above.

Step 2-4: Compound (2-6) can be manufactured by using compound (2-5) as a starting material, and reacting the compound with compound (1-5) by using conditions in accordance with step 1-3 of Manufacturing Method 1 described above.

Step 2-5: Compound (2-7) can be manufactured by using compound (2-6) as a starting material and using conditions in accordance with step 1-4 of Manufacturing Method 1 described above.

Manufacturing Method 3

A compound of formula (1a) represented by formula (3-7) described below can be manufactured, for example, by the manufacturing method described below.

[Chemical Formula 674]

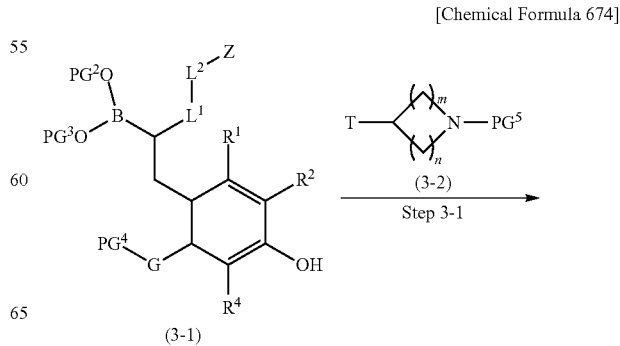

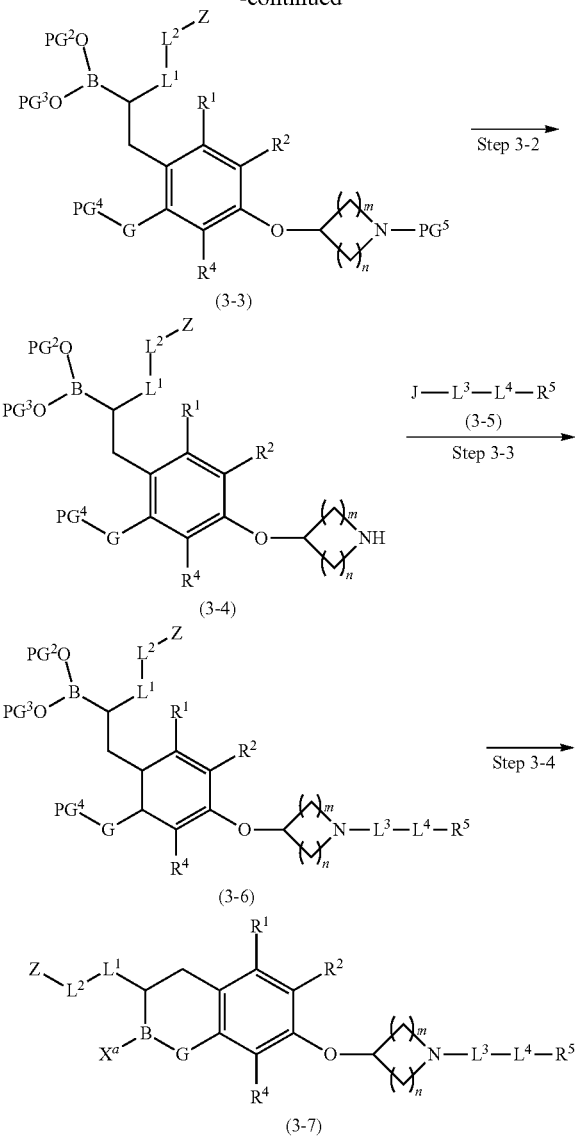

(3-3)

(3-4)

(3-5)

(3-6)

(3-7)

wherein $L^1$, $L^2$, Z, $L^3$, $L^4$, G, $R^1$, $R^2$, $R^4$, and $R^5$ are defined the same as item 1, m and n are defined the same as item 28, $X^a$ is a hydroxyl group or a $C_{1-6}$ alkoxy group, H is a hydrogen atom, T, LG, $PG^2$, $PG^3$, and $PG^4$ are each defined the same as the definition described in Manufacturing Method 1, $PG^5$ represents a protecting group of an amino group (e.g., an ethoxycarbonyl group, tert-butoxycarbonyl group, acetyl group, benzoyl group, trifluoroacetyl group, benzyloxycarbonyl group, 3- or 4-chlorobenzyloxycarbonyl group, triphenylmethyl group, methanesulfonyl group, p-toluenesulfonyl group, trimethylsilyl group, benzyloxycarbonyl group, 3- or 4-chlorobenzyloxycarbonyl group, benzylsulfonyl group, benzyl group, 4-nitrobenzyl group, 4-methoxybenzyl group, methyl group, ethyl group, or the like), and J represents a hydroxyl group or a leaving group (e.g., a halogen atom such as chlorine, bromine, or iodine, a lower alkylsulfonyloxy group such as methanesulfonyloxy, a trihalogenomethanesulfonyloxy group such as trifluoromethanesulfonyloxy, an arylsulfonyloxy group such as benzenesulfonyloxy or p-toluenesulfonyloxy, or the like).

A commercially available product that is purchased or a compound manufactured by the methods described in Manufacturing Method 1 and Manufacturing Method 2 can be used as the starting material compound (3-1) and compound (3-2). Further, a commercially available product that is purchased or a compound synthesized in accordance with a known method (e.g., the method described in R. C. Larock, "Comprehensive Organic Transformations", $2^{nd}$ Ed., John Wiley and Sons, Inc., New York (1999) or the like) from a known compound can be used as compound (3-2) and compound (3-5). As compound (3-2) and compound (3-5), a salt thereof can also be used, and the compound with a functional group that is protected can also be used as needed, as long as the reaction is not affected.

Step 3-1: Compound (3-3) can be manufactured by using compound (3-1) as a starting material, and reacting the compound with compound (3-2) by using conditions in accordance with step 1-3 of Manufacturing Method 1 described above.

Step 3-2: Compound (3-4) can be manufactured by deprotecting the protecting group $PG^5$ of compound (3-3). This step can be performed in accordance with the method described in, for example, the document (T. W. Greene and P. G. M. Wuts, "Protective Group in Organic Synthesis", $3^{rd}$ Ed., John Wiley and Sons, Inc., New York (1999)) or the like.

Step 3-3: Compound (3-6) can be manufactured by using compound (3-4) as a starting material and using conditions in accordance with step 2-2 of Manufacturing Method 2 described above.

Step 3-4: Compound (3-7) can be manufactured by using compound (3-6) as a starting material and using conditions in accordance with step 1-4 of Manufacturing Method 1 described above.

Manufacturing Method 4

A compound of formula (1a) represented by formula (4-4) described below can be manufactured, for example, by the manufacturing method described below.

[Chemical Formula 675]

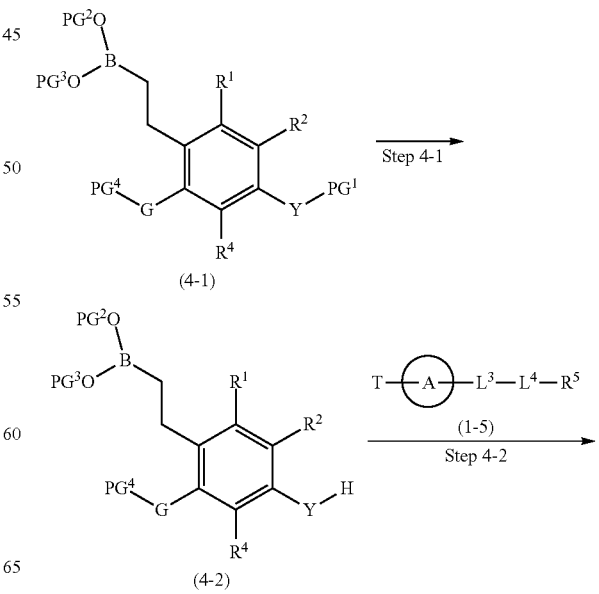

(4-1)

(4-2)

447

-continued

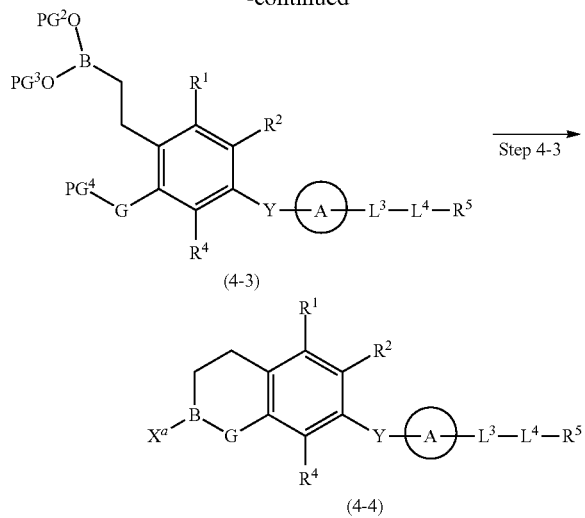

(4-3)

(4-4)

wherein Y, ring A, $L^3$, $L^4$, G, $R^1$, $R^2$, $R^4$, and $R^5$ are defined the same as item 1, $X^a$ is a hydroxyl group or a $C_{1-6}$ alkoxy group, H is a hydrogen atom, and T, $PG^1$, $PG^2$, $PG^3$, and $PG^4$ are each defined the same as the definition described in Manufacturing Method 1.

A commercially available product that is purchased or a compound manufactured by the method described in Manufacturing Method 1 can be used as the starting material compound (4-1) and compound (1-5). As compound (1-5), a salt thereof can also be used, and the compound with a functional group that is protected can also be used as needed, as long as the reaction is not affected.

Step 4-1: Compound (4-2) can be manufactured by using compound (4-1) as a starting material and using conditions in accordance with step 1-2 of Manufacturing Method 1 described above.

Step 4-2: Compound (4-3) can be manufactured by using compound (4-2) as a starting material, and reacting the compound with compound (1-5) by using conditions in accordance with step 1-3 of Manufacturing Method 1 described above.

Step 4-3: Compound (4-4) can be manufactured by using compound (4-3) as a starting material and using conditions in accordance with step 1-4 of Manufacturing Method 1 described above.

Manufacturing Method 5

A compound of formula (1a) represented by formula (5-4) described below can be manufactured, for example, by the manufacturing method described below.

[Chemical Formula 676]

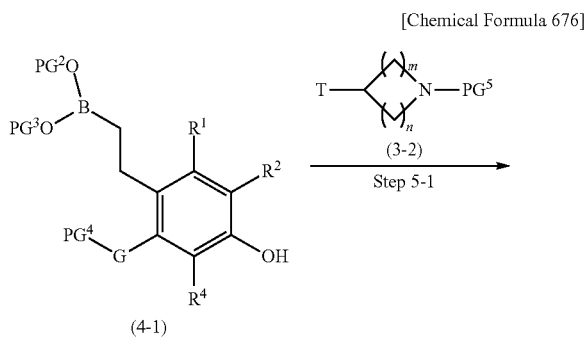

(4-1)

448

-continued

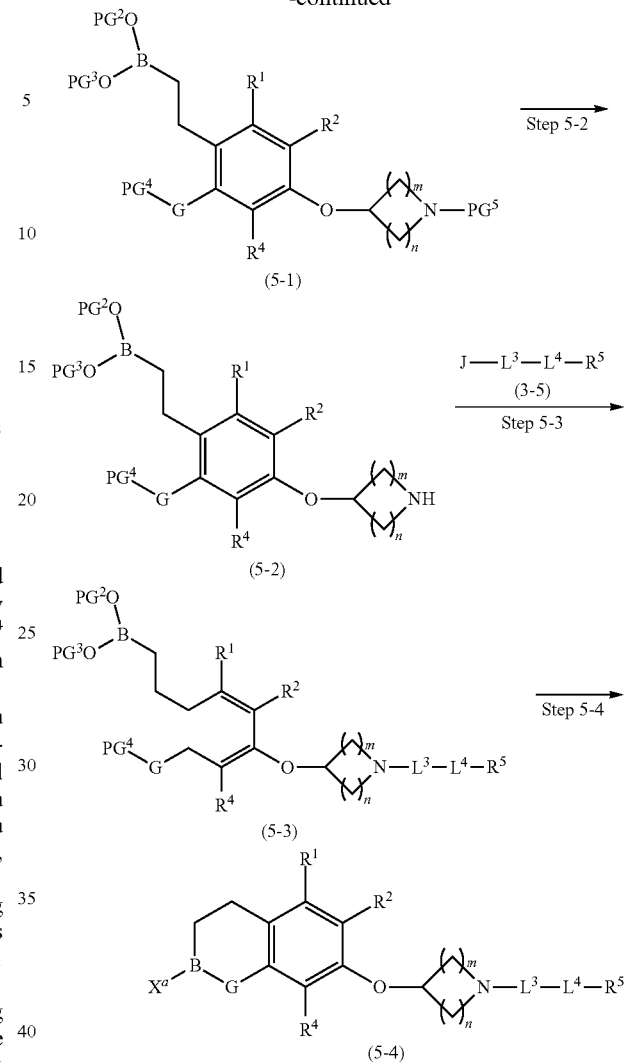

(5-1)

(5-2)

(5-3)

(5-4)

wherein $L^3$, $L^4$, G, $R^1$, $R^2$, $R^4$, and $R^5$ are defined the same as item 1, m and n are defined the same as item 28, $X^a$ is a hydroxyl group or a $C_{1-6}$ alkoxy group, H is a hydrogen atom, T, $PG^2$, $PG^3$, and $PG^4$ are each defined the same as the definition described in Manufacturing Method 1, and $PG^5$ and J are defined the same as the definitions described in Manufacturing Method 3.

A commercially available product that is purchased or a compound manufactured by the methods described in Manufacturing Method 1 and Manufacturing Method 3 can be used as the starting material compound (4-1), compound (3-2), and compound (3-5). As compound (3-2) and compound (3-5), a salt thereof can also be used, and the compound with a functional group that is protected can also be used as needed, as long as the reaction is not affected.

Step 5-1: Compound (5-1) can be manufactured by using compound (4-1) as a starting material, and reacting the compound with compound (3-2) by using conditions in accordance with step 3-1 of Manufacturing Method 3 described above.

Step 5-2: Compound (5-2) can be manufactured by using compound (5-1) as a starting material and using conditions in accordance with step 3-2 of Manufacturing Method 3 described above.

Step 5-3: Compound (5-3) can be manufactured by using compound (5-2) as a starting material, and reacting the compound with compound (3-5) by using conditions in accordance with step 3-3 of Manufacturing Method 3 described above.

Step 5-4: Compound (5-4) can be manufactured by using compound (5-3) as a starting material and using conditions in accordance with step 3-4 of Manufacturing Method 3 described above.

Manufacturing Method 6

A compound of formula (1a) represented by formula (6-5) described below can be manufactured, for example, by the manufacturing method described below.

[Chemical Formula 677]

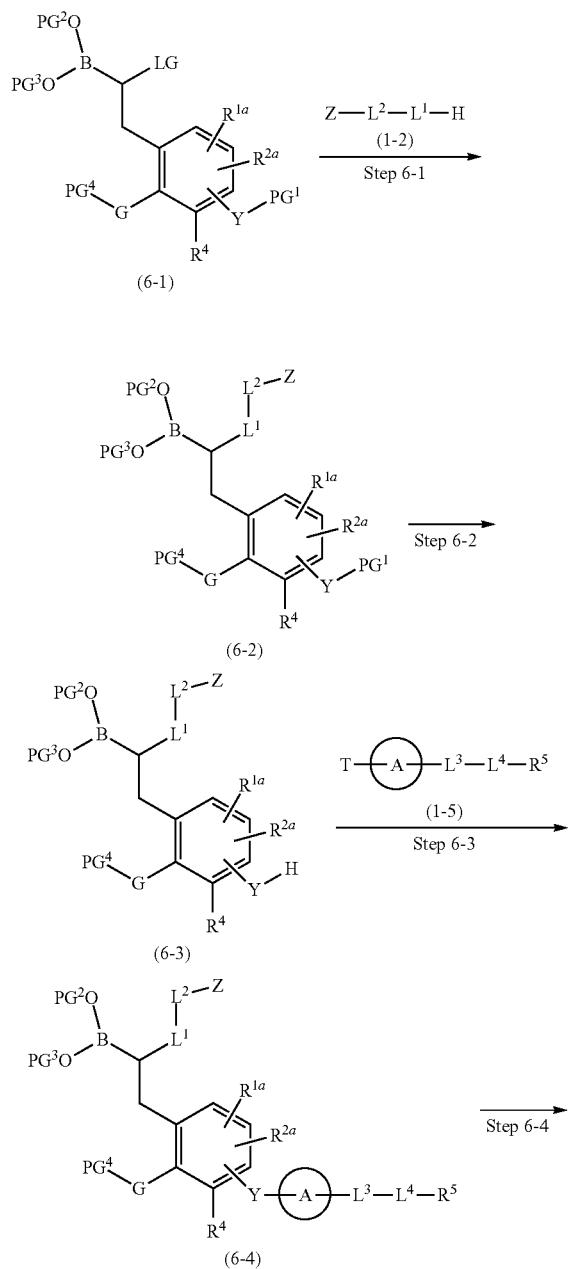

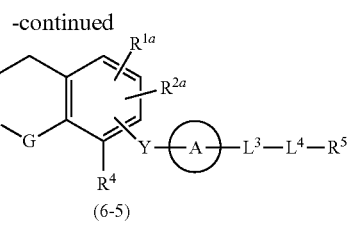

wherein $L^1$, $L^2$, Y, Z, ring A, $L^3$, $L^4$, G, $R^4$, and $R^5$ are defined the same as item 1, wherein one end of Y, $R^{1a}$, and $R^{2a}$ each attach to one of three attachable positions denoted as unsubstituted on a benzene ring in the chemical formula, $R^{1a}$ and $R^{2a}$ represent the remaining two without a structure of formula (2) among $R^1$, $R^2$, and $R^3$ defined in item 1 herein, $X^a$ is a hydroxyl group or a $C_{1-6}$ alkoxy group, H is a hydrogen atom, and T, LG, $PG^1$, $PG^2$, $PG^3$, and $PG^4$ are each defined the same as the definition described in Manufacturing Method 1.

A commercially available product that is purchased or a compound manufactured by the method of Manufacturing Method 1 can be used as the starting material compound (6-1), compound (1-2), and compound (1-5). As compound (3-2) and compound (3-5), a salt thereof can also be used, and the compound with a functional group that is protected can also be used as needed, as long as the reaction is not affected.

Step (6-1): Compound (6-2) can be manufactured by using compound (6-1) as a starting material, and reacting the compound with compound (1-2) by using conditions in accordance with step 1-1 of Manufacturing Method 1 described above.

Step (6-2): Compound (6-3) can be manufactured by using compound (6-2) as a starting material and using conditions in accordance with step 1-2 of Manufacturing Method 1 described above.

Step (6-3): Compound (6-4) can be manufactured by using compound (6-3) as a starting material, and reacting the compound with compound (1-5) by using conditions in accordance with step 1-3 of Manufacturing Method 1 described above.

Step (6-4): Compound (6-5) can be manufactured by using compound (6-4) as a starting material and using conditions in accordance with step 1-4 of Manufacturing Method 1 described above.

Manufacturing Method 7

A compound of formula (1a) represented by formula (7-5) described below can be manufactured, for example, by the manufacturing method described below. Said compound represents compound (6-5) wherein $L^1$ is $-NR^d(C=O)-$ and $R^d$ is a hydrogen atom.

[Chemical Formula 678]

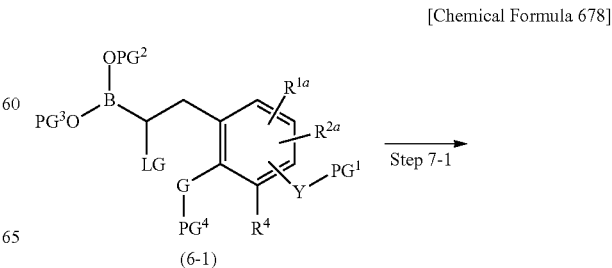

-continued

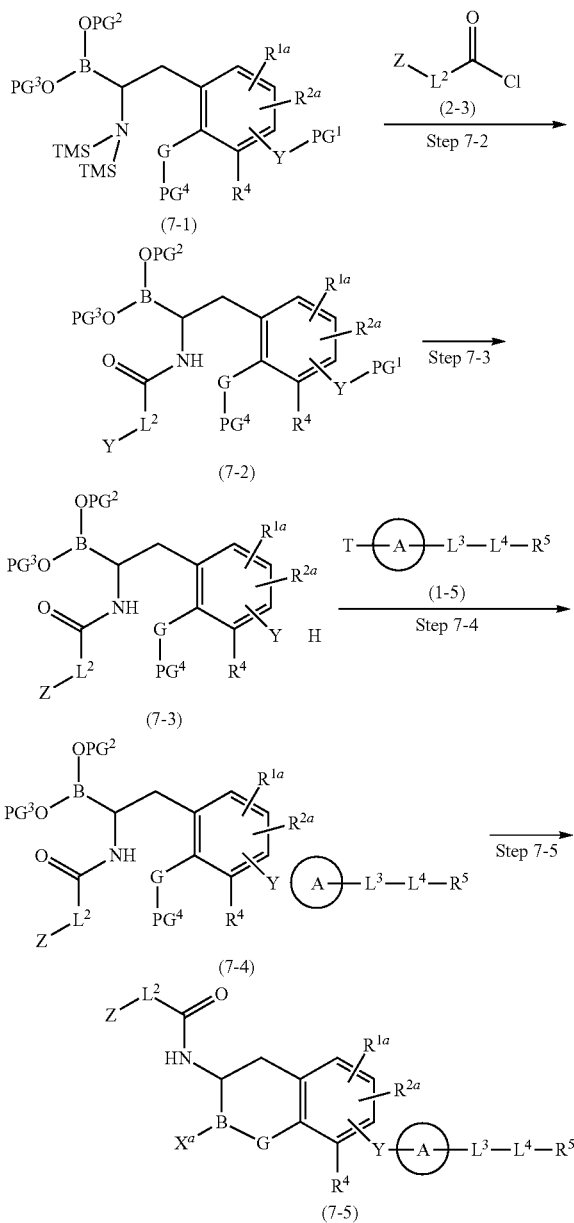

wherein $L^2$, Y, Z, ring A, $L^3$, $L^4$, G, $R^4$, and $R^5$ are defined the same as item 1, wherein one end of Y, $R^{1a}$, and $R^{2a}$ each attach to one of three attachable positions denoted as unsubstituted on a benzene ring in the chemical formula, $R^{1a}$ and $R^{2a}$ represent the remaining two without a structure of formula (2) among $R^1$, $R^2$, and $R^3$ defined in item 1 herein, $X^a$ is a hydroxyl group or a $C_{1-6}$ alkoxy group, H is a hydrogen atom, T, LG, $PG^1$, $PG^2$, $PG^3$, and $PG^4$ are each defined the same as the definition described in Manufacturing Method 1, and TMS represents trimethylsilyl.

A commercially available product that is purchased or a compound manufactured by the method described in Manufacturing Method 1 can be used as the starting material compound (6-1), compound (1-2), and compound (1-5). Further, a commercially available product that is purchased or a compound synthesized in accordance with a known method (e.g., the method described in R. C. Larock, "Comprehensive Organic Transformations", $2^{nd}$ Ed., John Wiley and Sons, Inc., New York (1999) or the like) from a known compound can be used as compound (2-2) and compound (2-3). As compound (2-2), compound (2-3), or compound (1-5), a salt thereof can also be used, and the compound with a functional group that is protected can also be used as needed, as long as the reaction is not affected.

Step 7-1: Compound (7-1) can be manufactured by using compound (6-1) as a starting material and using conditions in accordance with step 2-1 of Manufacturing Method 2 described above.

Step 7-2: Compound (7-2) can be manufactured by using compound (7-3) as a starting material, and reacting the compound with compound (2-2) or compound (2-3) by using conditions in accordance with step 2-2 of Manufacturing Method 2 described above.

Step 7-3: Compound (7-3) can be manufactured by using compound (7-2) as a starting material and using conditions in accordance with step 2-3 of Manufacturing Method 2 described above.

Step 7-4: Compound (7-4) can be manufactured by using compound (7-3) as a starting material, and reacting the compound with compound (1-5) by using conditions in accordance with step 2-4 of Manufacturing Method 2 described above.

Step 7-5: Compound (7-5) can be manufactured by using compound (7-4) as a starting material and using conditions in accordance with step 2-5 of Manufacturing Method 2 described above.

Manufacturing Method 8

A compound of formula (1a) represented by formula (8-4) described below can be manufactured, for example, by the manufacturing method described below.

[Chemical Formula 679]

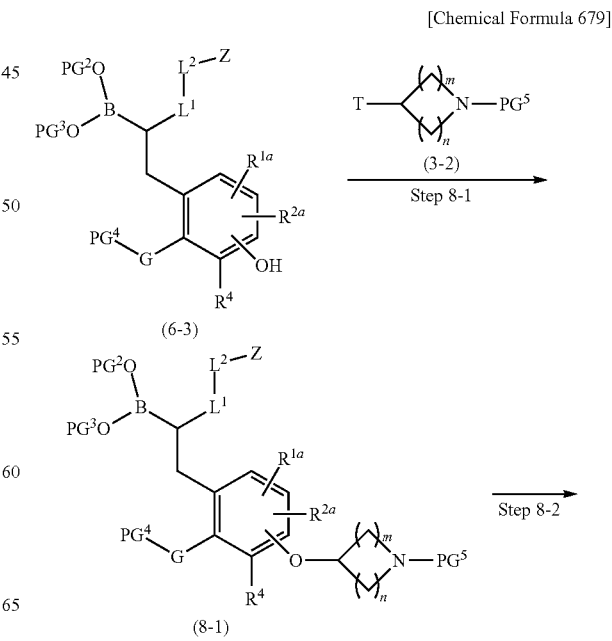

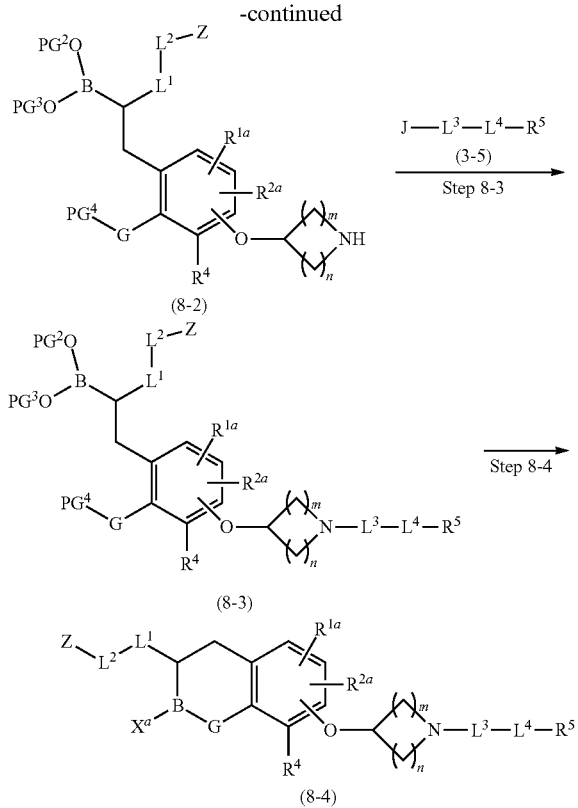

(8-2)

(8-3)

(8-4)

where $L^1$, $L^2$, Z, $L^3$, $L^4$, G, $R^4$, and $R^5$ are defined the same as item 1, wherein one end of an oxygen atom, $R^{1a}$, and $R^{2a}$ for substitution on a benzene ring each attach to one of three attachable positions denoted as unsubstituted on a benzene ring in the chemical formula, $R^{1a}$ and $R^{2a}$ represent the remaining two without a structure of formula (2) among $R^1$, $R^2$, and $R^3$ defined in item 1 herein, m and n are defined the same as item 28, $X^a$ is a hydroxyl group or a $C_{1-6}$ alkoxy group, H is a hydrogen atom, T, $PG^2$, $PG^3$, and $PG^4$ are each defined the same as the definitions described in Manufacturing Method 1, and $PG^5$ and J are each defined the same as the definitions described in Manufacturing Method 3.

A commercially available product that is purchased or a compound manufactured by the methods described in Manufacturing Method 1 and Manufacturing Method 2 can be used as the starting material compound (6-3). Further, a commercially available product that is purchased or a compound manufactured by the method described in Manufacturing Method 3 can be used as compound (3-2) and compound (3-5). As compound (3-2) and compound (3-5), a salt thereof can also be used, and the compound with a functional group that is protected can also be used as needed, as long as the reaction is not affected.

Step 8-1: Compound (8-1) can be manufactured by using compound (6-3) as a starting material, and reacting the compound with compound (3-2) by using conditions in accordance with step 1-3 of Manufacturing Method 1 described above.

Step 8-2: Compound (8-2) can be manufactured by using compound (8-1) as a starting material and using conditions in accordance with step 3-2 of Manufacturing Method 3 described above.

Step 8-3: Compound (8-3) can be manufactured by using compound (8-3) as a starting material, and reacting the compound with compound (3-5) by using conditions in accordance with step 3-3 of Manufacturing Method 3 described above.

Step 8-4: Compound (8-4) can be manufactured by using compound (8-3) as a starting material and using conditions in accordance with step 1-4 of Manufacturing Method 1 described above.

Manufacturing Method 9

A compound of formula (1a) represented by formula (9-4) described below can be manufactured, for example, by the manufacturing method described below.

[Chemical Formula 680]

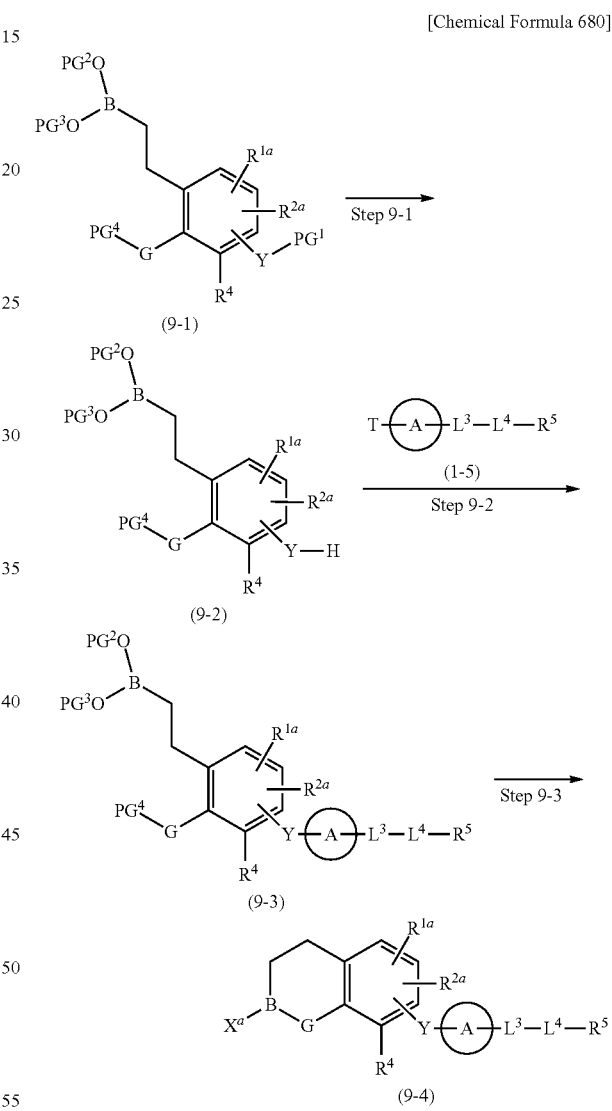

wherein Y, ring A, $L^3$, $L^4$, G, $R^4$, and $R^5$ are defined the same as item 1, wherein one end of Y, $R^{1a}$, and $R^{2a}$ each attach to one of three attachable positions denoted as unsubstituted on a benzene ring in the chemical formula, $R^{1a}$ and $R^{2a}$ represent the remaining two without a structure of formula (2) among $R^1$, $R^2$, and $R^3$ defined in item 1 herein, $X^a$ is a hydroxyl group or a $C_{1-6}$ alkoxy group, H is a hydrogen atom, and T, LG, $PG^1$, $PG^2$, $PG^3$, and $PG^4$ are each defined the same as the definition described in Manufacturing Method 1.

455

A commercially available product that is purchased or a compound manufactured by the method described in Manufacturing Method 1 can be used as the starting material compound (9-1) and compound (1-5). As compound (1-5), a salt thereof can also be used, and the compound with a functional group that is protected can also be used as needed, as long as the reaction is not affected.

Step 9-1: Compound (9-2) can be manufactured by using compound (9-1) as a starting material and using conditions in accordance with step 1-2 of Manufacturing Method 1 described above.

Step 9-2: Compound (9-3) can be manufactured by using compound (9-2) as a starting material, and reacting the compound with compound (1-5) by using conditions in accordance with step 1-3 of Manufacturing Method 1 described above.

Step 9-3: Compound (9-4) can be manufactured by using compound (9-3) as a starting material and using conditions in accordance with step 1-4 of Manufacturing Method 1 described above.

Manufacturing Method 10

A compound of formula (1a) represented by formula (10-4) described below can be manufactured, for example, by the manufacturing method described below.

[Chemical Formula 681]

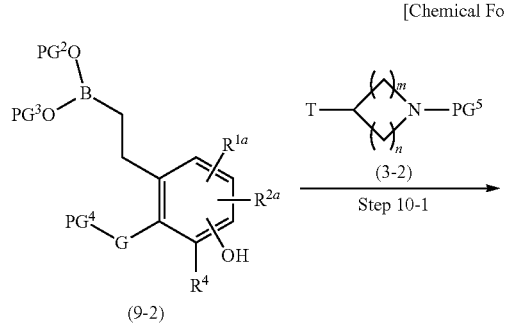

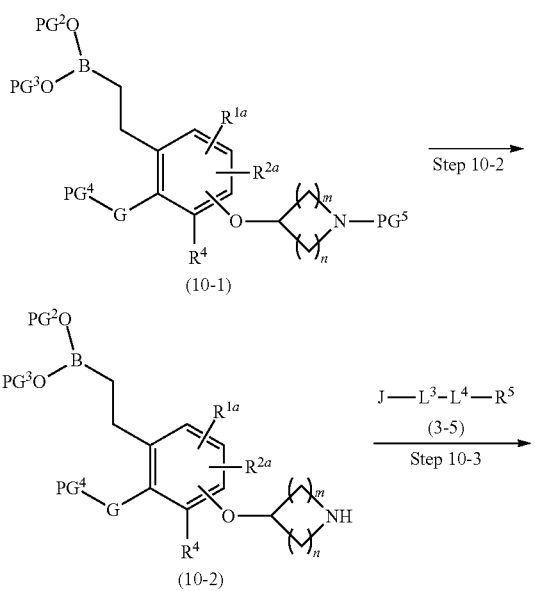

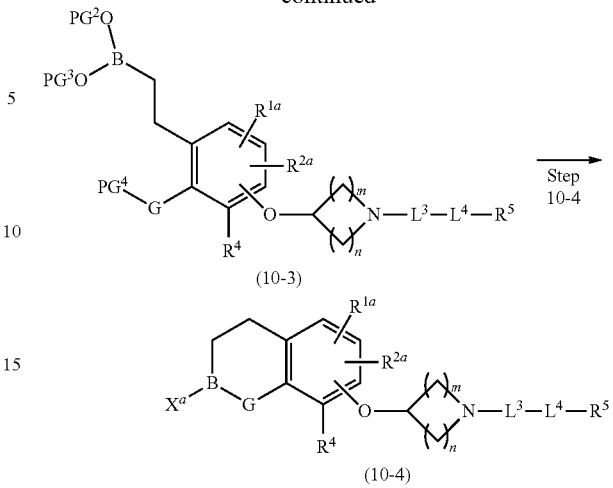

wherein $L^3$, $L^4$, G, $R^4$, and $R^5$ are defined the same as item 1, T, $PG^2$, $PG^3$, and $PG^4$ are each defined the same as the definitions described in Manufacturing Method 1, wherein one end of an oxygen atom, $R^{1a}$, and $R^{2a}$ for substitution on a benzene ring each attach to one of three attachable positions denoted as unsubstituted on a benzene ring in the chemical formula, $R^{1a}$ and $R^{2a}$ represent the remaining two without a structure of formula (2) among $R^1$, $R^2$, and $R^3$ defined in item 1 herein, m and n are defined the same as item 28, $X^a$ is a hydroxyl group or a $C_{1-6}$ alkoxy group, H is a hydrogen atom, and $PG^5$ and J are defined the same as the definitions described in Manufacturing Method 3.

A commercially available product that is purchased or a compound manufactured by the methods described in Manufacturing Method 1 and Manufacturing Method 3 can be used as the starting material compound (9-2), compound (3-2), and compound (3-5). As compound (3-2) and compound (3-5), a salt thereof can also be used, and the compound with a functional group that is protected can also be used as needed, as long as the reaction is not affected.

Step 10-1: Compound (10-1) can be manufactured by using compound (9-2) as a starting material, and reacting the compound with compound (3-2) by using conditions in accordance with step 3-1 of Manufacturing Method 3 described above.

Step 10-2: Compound (10-2) can be manufactured by using compound (10-1) as a starting material and using conditions in accordance with step 3-2 of Manufacturing Method 3 described above.

Step 10-3: Compound (10-3) can be manufactured by using compound (10-2) as a starting material, and reacting the compound with compound (3-5) by using conditions in accordance with step 3-3 of Manufacturing Method 3 described above.

Step 10-4: Compound (10-4) can be manufactured by using compound (10-3) as a starting material and using conditions in accordance with step 3-4 of Manufacturing Method 3 described above.

Manufacturing Method 11

A compound of formula (1a) represented by formula (11-3) described below can be manufactured, for example, by the manufacturing method described below. Said compound (11-3) represents compound (3-7) wherein $L^3$ is $—S(=O)_2—$.

[Chemical Formula 682]

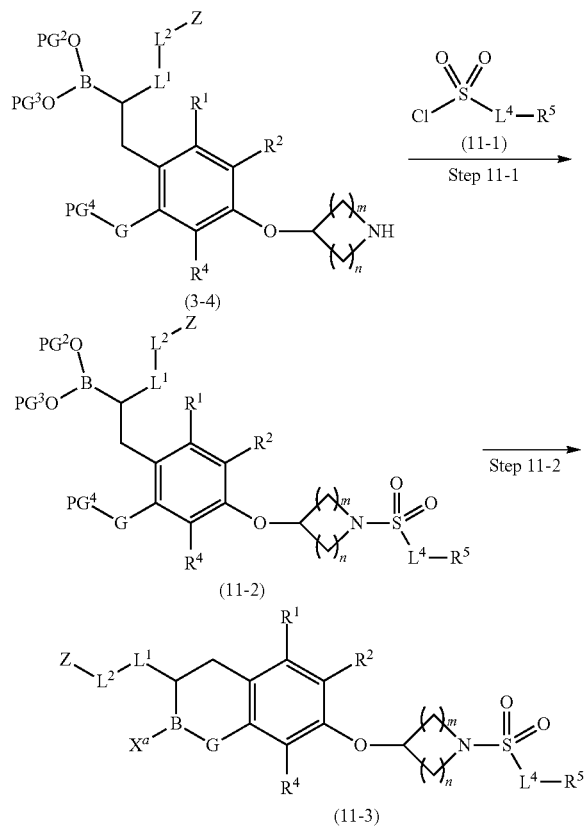

Step 11-2: Compound (11-3) can be manufactured by using compound (11-2) as a starting material and using conditions in accordance with step 1-4 of Manufacturing Method 1 described above.

Manufacturing Method 12

A compound of formula (1a) represented by formula (12-2) described below can be manufactured, for example, by the manufacturing method described below. Said compound (12-2) represents compound (5-4) wherein $L^3$ is —S(=O)$_2$—.

[Chemical Formula 683]

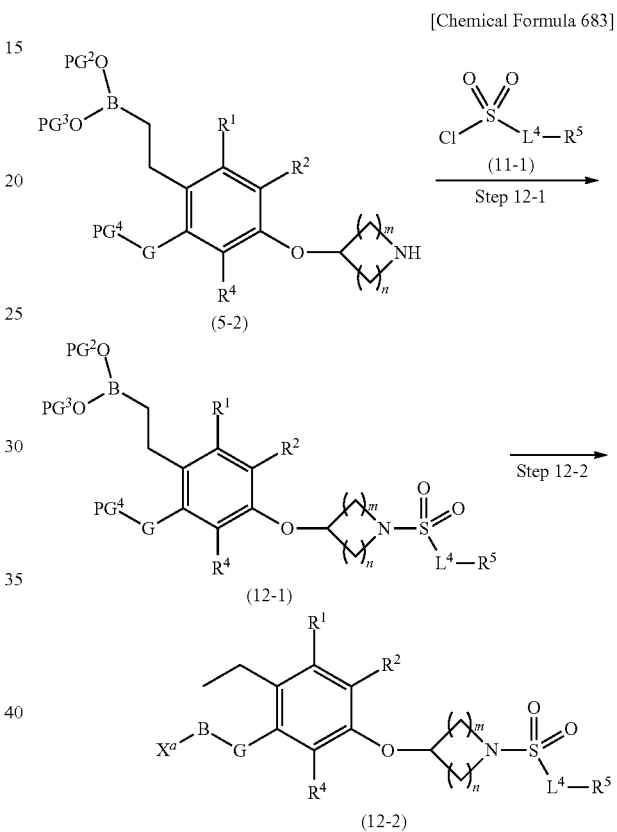

wherein $L^1$, $L^2$, Z, $L^4$, G, $R^1$, $R^2$, $R^4$, and $R^5$ are defined the same as item 1, m and n are defined the same as item 28, $X^a$ is a hydroxyl group or a $C_{1-6}$ alkoxy group, H is a hydrogen atom, and $PG^2$, $PG^3$, and $PG^4$ are each defined the same as the definitions described in Manufacturing Method 1.

A compound manufactured by the method described in Manufacturing Method 3 can be used as the starting material compound (3-4). Further, a commercially available product that is purchased or a compound synthesized in accordance with a known method (e.g., the method described in R. C. Larock, "Comprehensive Organic Transformations", 2$^{nd}$ Ed., John Wiley and Sons, Inc., New York (1999) or the like) from a known compound can be used as compound (11-1). As compound (11-1), a salt thereof can also be used, and the compound with a functional group that is protected can also be used as needed, as long as the reaction is not affected.

Step 11-1: Compound (11-2) can be manufactured by reacting compound (3-4) with compound (11-1) in an inert solvent in the presence or absence of a base under normal pressure or under pressure. Specific examples of inert solvents include ether solvents such as THF and DME, halogenated hydrocarbon solvents such as dichloromethane and chloroform, and aprotic solvents such as DMF, NMP, and DMSO. Compound (11-1) can be used at 0.001 to 100 equivalents with respect to compound (3-4), which is preferably 1 to 10 equivalents. Examples of bases include diisopropylethylamine, triethylamine, and the like. A base can be used at 0.001 to 100 equivalents with respect to compound (3-4), which is preferably 1 to 10 equivalents. The reaction temperature is selected from the range of about −78° C. to about 100° C.

wherein $L^4$, G, $R^1$, $R^2$, $R^4$, and $R^5$ are defined the same as item 1, m and n are defined the same as item 28, $X^a$ is a hydroxyl group or a $C_{1-6}$ alkoxy group, H is a hydrogen atom, and $PG^2$, $PG^3$, and $PG^4$ are each defined the same as the definitions described in Manufacturing Method 1.

A compound manufactured by the method described in Manufacturing Method 5 can be used as the starting material compound (5-2). Further, a commercially available product that is purchased or a compound synthesized in accordance with a known method (e.g., the method described in R. C. Larock, "Comprehensive Organic Transformations", 2$^{nd}$ Ed., John Wiley and Sons, Inc., New York (1999) or the like) from a known compound can be used as compound (11-1). As compound (11-1), a salt thereof can also be used, and the compound with a functional group that is protected can also be used as needed, as long as the reaction is not affected.

Step 12-1: Compound (12-1) can be manufactured by using compound (5-4) as a starting material and using conditions in accordance with step 11-1 of Manufacturing Method 11 described above.

Step 12-2: Compound (12-2) can be manufactured by using compound (12-1) as a starting material and using conditions in accordance with step 1-4 of Manufacturing Method 1 described above.

Manufacturing Method 13

A compound of formula (1a) represented by formula (13-5) described below can be manufactured, for example, by the manufacturing method described below. Said compound (13-5) represents compound (5-4) wherein R is optionally substituted 1H-1,2,3-triazole.

[Chemical Formula 684]

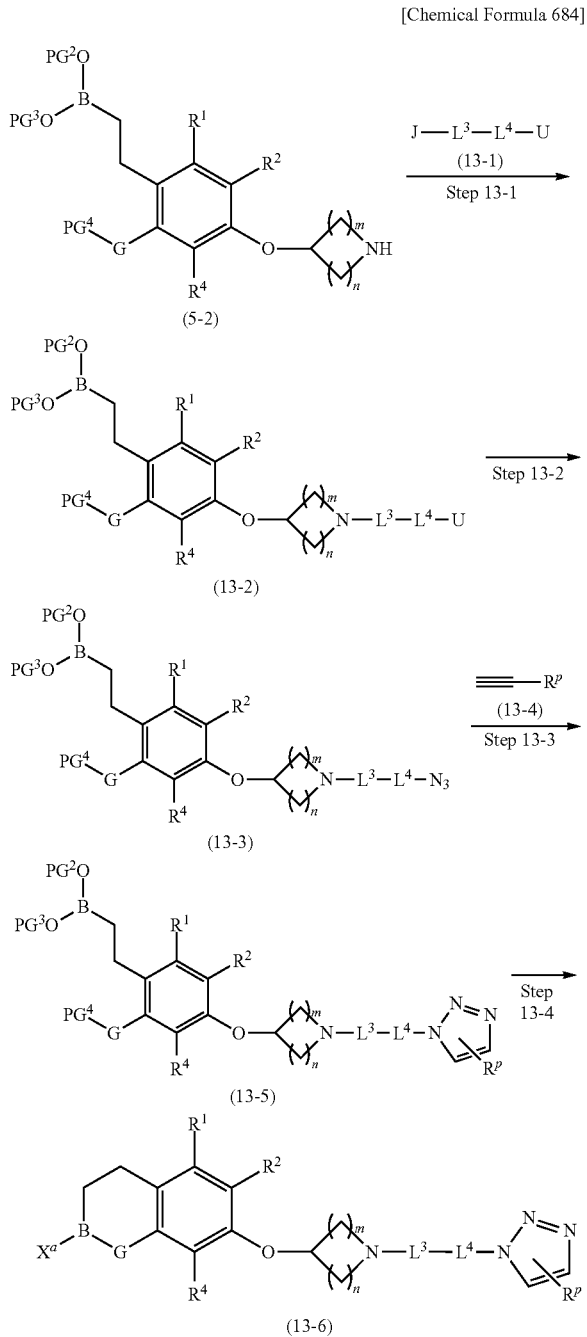

wherein $L^3$, $L^4$, G, $R^1$, $R^2$, and $R^4$ are defined the same as item 1, m and n are defined the same as item 28, $X^a$ is a hydroxyl group or a $C_{1-6}$ alkoxy group, H is a hydrogen atom, U represents an amino group, a nitro group, carboxylic acid, alcohol, or a leaving group (e.g., a halogen atom such as chlorine, bromine, or iodine, a lower alkylsulfonyloxy group such as methanesulfonyloxy, a trihalogenomethanesulfonyloxy group such as trifluoromethanesulfonyloxy, an arylsulfonyloxy group such as benzenesulfonyloxy or p-toluenesulfonyloxy, or the like), $R^P$ is a group that is acceptable as a compound of formula (13-4) in $R^a$ defined in item 36 or a group that can be converted into the $R^a$, $PG^2$, $PG^3$, and $PG^4$ are each defined the same as the definitions described in Manufacturing Method 1, and J is defined the same as the definition described in Manufacturing Method 3.

A compound manufactured by the method described in Manufacturing Method 5 can be used as the starting material compound (5-2). Further, a commercially available product that is purchased or a compound synthesized in accordance with a known method (e.g., the method described in R. C. Larock, "Comprehensive Organic Transformations", 2$^{nd}$ Ed., John Wiley and Sons, Inc., New York (1999) or the like) from a known compound can be used as compound (13-1). As compound (13-1), a salt thereof can also be used, and the compound with a functional group that is protected can also be used as needed, as long as the reaction is not affected.

Step 13-1: Compound (13-2) can be manufactured using compound (5-4) as a starting material and using conditions in accordance with step 5-3 of Manufacturing Method 5 described above.

Step 13-2: Compound (13-3) can be manufactured by reacting compound (13-2) with an aziding agent in an inert solvent in the presence or absence of a base under normal pressure. Specific examples of inert solvents include halogenated hydrocarbon solvents such as dichloromethane and chloroform and aprotic solvents such as DMF, NMP, and DMSO. Specific examples of aziding agents include sodium azide, trimethylsilyl azide, diphenylphosphoryl azide, and the like. An aziding agent can be used at 0.001 to 100 equivalents with respect to compound (13-2), which is preferably 1 to 10 equivalents. Examples of bases include diisopropylethylamine, triethylamine, 4-dimethylaminopyridine, and the like. A base can be used at 0.001 to 100 equivalents with respect to compound (13-2), which is preferably 1 to 10 equivalents. The reaction temperature is selected from the range of about −78° C. to about 100° C.

Step 13-3: Compound (13-5) can be manufactured by reacting compound (13-3) with compound (13-4) in an inert solvent in the presence or absence of a base in the presence or absence of a catalyst under normal pressure or under pressure. Specific examples of inert solvents include ether solvents such as THF and DME, halogenated hydrocarbon solvents such as dichloromethane and chloroform, and aprotic solvents such as acetonitrile, DMF, NMP, and DMSO. Compound (13-4) can be used at 0.001 to 100 equivalents with respect to compound (13-3), which is preferably 1 to equivalents. Examples of bases include diisopropylethylamine, triethylamine, and the like. A base can be used at 0.001 to 100 equivalents with respect to compound (13-3), which is preferably 1 to 10 equivalents. Specific examples of catalysts include copper sulfate, copper iodide, and (chloro [(1,2,3,4,5-h)-1,2,3,4,5-pentamethyl-2,4-cyclopentadien-1-yl]bis(triphenylphosphine)ruthenium(II). A catalyst can be used at 0.001 to 100 equivalents with respect to compound (13-3), which is preferably 0.01 to 10 equivalents. The reaction temperature is selected from the range of about −78° C. to about 100° C.

Step 13-4: Compound (12-6) can be manufactured using compound (12-5) as a starting material and using conditions in accordance with step 1-4 of Manufacturing Method 1 described above.

The intermediate and compound of interest in the manufacturing methods described above can be isolated and purified by subjecting them to a purification method that is commonly used in organic synthesis chemistry (e.g., neutralization, filtration, extraction, washing, drying, concentration, recrystallization, various chromatography, or the like). Each intermediate can also be subjected to the subsequent reaction without any particular purification.

Optically active forms of the compound of the invention can be manufactured by using an optically active starting material or intermediate, or by optically resolving a racemate of the final product or intermediate. Examples of optional resolution methods include, but are not limited to, separation method using an optically active column and a separation method such as fractional crystallization method. A diastereomer of the compound of the invention can be manufactured by, for example, a separation method such as column chromatography or fractional crystallization, but the method is not limited thereto.

A pharmaceutically acceptable salt of a compound represented by formula (1a) or (1b) can be manufactured by, for example, mixing a compound represented by formula (1) with a pharmaceutically acceptable acid or base in a solvent such as water, methanol, ethanol, 2-propanol, ethyl acetate, or acetone, but the manufacturing method is not limited thereto.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. While the present invention is described hereinafter based on the Examples, the above descriptions and the following Examples are provided for the sole purpose of exemplification, not limitation of the present invention. Thus, the scope of the present invention is not limited to the embodiments and Examples that are specifically described herein and is limited only by the scope of claims.

EXAMPLES

While the present invention is described more specifically with Reference Examples, Examples, and Test Examples hereinafter, the preset invention is not limited thereto.

Compounds were identified using proton nuclear magnetic resonance spectrum ($^1$H-NMR), liquid chromatography-mass spectrometry (LCMS), or the like. Tetramethylsilane was used as an internal standard for nuclear magnetic resonance spectrum.

For column chromatography in the Reference Examples and Examples, Yamazen Corporation's silica gel column, YMC's ODS-A column, and YMC's YMC-Actus Triart C18 were used. For TLC (silica gel plate) in purification using a thin layer chromatography (TLC), Silica gel 60F254 (Merck) was used, and for TLC (NH silica gel plate), TLC plate NH (Fuji Silysia) was used.

Various data described in the Reference Examples and Example was obtained with the following equipment.

NMR spectrum: [$^1$H-NMR] 400 MHz: JEOL JNM-AL series AL400, JEOL EX270, and 500 MHz: JEOL ECA-500. 600 Hz: Agilent DD2 600 MHz NMR Spectrometer.

LC-MS spectrum: Waters ACQUITY™ UltraPerformance LC, Waters AQUITY UPLC H-Class System, Shimadzu LCMS-2020.

The compound names described in the Reference Examples and Examples were named using ACD/Name (ACD/Labs 12.0, Advanced Chemistry Development Inc.), which are not necessarily in accordance with the IUPAC nomenclature.

The measuring conditions (hereinafter, also referred to as the measurement methods) for a high performance liquid chromatography-mass spectrometry (LCMS) system are described below. The observed mass spectrometry value [MS(m/z)] is indicated by [M+1]$^+$, and the time of retention at which the mass spectrometry value was observed is indicated by Rt (min). The measurement conditions A to C used for measurement are denoted in each actual measurement value. For example, "LCMS: [M+H]$^+$/Rt=620/1.32$^A$" expresses that measurement was taken under measurement condition A.

Measurement Condition A

Measuring equipment: Waters ACQUITY™ UltraPerformance LC

Column: ACQUITY UPLC BEH C18 1.7 μm 2.1×30 mm column

Solvent: solution A: 0.05% HCOOH/H$_2$O, solution B: CH$_3$CN

Gradient Condition:

0.0 to 1.3 minutes; A/B=90/10 to 5/95 (linear gradient)

1.3 to 1.5 minutes; A/B=90/10

Flow rate: 0.80 mL/min

UV: 220 nm, 254 nm

Column temperature: 40° C.

Measurement Condition B

Measuring equipment: Waters AQUITY UPLC H-Class System

Column: Waters AQUITY UPLC HSS T3 1.8 μm 2.1×50 mm column

Solvent: solution A: 0.1% HCO$_2$H/H$_2$O, solution B: 0.1% HCO$_2$H/MeCN

Gradient Condition:

0.0 to 2.4 minutes; A/B=90/10 to 0/100 (linear gradient)

2.4 to 3.2 minutes; A/B=0/100

Flow rate: 0.70 mL/min

UV: 190 to 800 nm

Column temperature: 40° C.

Measurement Condition C

Measuring equipment: Waters ACQUITY™ UltraPerformance LC

Column: ACQUITY UPLC BEH C18 1.7 μm 2.1×30 mm column

Solvent: solution A: 0.05% HCOOH/H$_2$O, solution B: CH$_3$CN

Gradient Condition:

0.0 to 1.3 minutes; A/B=99/1 to 5/95 (linear gradient)

1.3 to 1.5 minutes; A/B=99/1

Flow rate: 0.80 mL/min

UV: 220 nm, 254 nm

Column temperature: 40° C.

Measurement Condition D

Measuring equipment: Waters AQUITY UPLC H-Class System

Column: ACQUITY UPLC BEH C18 1.7 μm 2.1×50 mm column

Solvent: solution A: HCOOH/CH₃CN/H₂O (0.05/50/49.95), solution B: 0.05% HCOOH/CH₃CN
Gradient condition: 0.0 to 4.0 minutes; A/B=100/0 to 0/100 (linear gradient)
4.0 to 5.0 minutes; A/B=0/100
Flow rate: 0.50 mL/min
UV: 220 nm, 254 nm
Column temperature: 40° C.
Measurement Condition E
Measuring equipment: Waters ACQUITY™ UltraPerformance LC
Column: ACQUITY UPLC BEH C18 1.7 μm 2.1×30 mm column
Solvent: solution A: 0.05% HCOOH/H₂O, solution B: CH₃CN
Gradient Condition:
0.0 to 1.3 minutes; A/B=60/40 to 5/95 (linear gradient)
1.3 to 1.5 minutes; A/B=60/40
Flow rate: 0.80 mL/min
UV: 220 nm, 254 nm
Column temperature: 40° C.
Measurement Condition F
Measuring equipment: Waters ACQUITY™ UltraPerformance LC
Column: ACQUITY UPLC BEH C18 1.7 μm 2.1×30 mm column
Solvent: solution A: 0.05% HCOOH/H₂O, solution B: CH₃CN
Gradient Condition:
0.0 to 1.3 minutes; A/B=98/2 to 4/96 (linear gradient)
1.3 to 1.5 minutes; A/B=98/2
Flow rate: 0.80 mL/min
UV: 220 nm, 254 nm
Column temperature: 40° C.
Measurement Condition G
Measuring equipment: Shimadzu LCMS-2020
Column: Phenomenex Kinetex 1.7 μm C18 (50 mm×2.10 mm)
Solvent: solution A: 0.05% TFA/H₂O, solution B: CH₃CN
Gradient Condition:
0.0 to 1.9 minutes; A/B=99/1 to 1/99 (linear gradient)
1.91 to 3.00 minutes; A/B=1/99
Flow rate: 0.50 mL/min
UV: 220 nm, 254 nm
Column temperature: 40° C.
Measurement Condition H
Measuring equipment: Shimadzu LCMS-2020
Column: Phenomenex Kinetex 1.7 μm C18 (50 mm×2.10 mm)
Solvent: solution A: 0.05% TFA/H₂O, solution B: CH₃CN
Gradient Condition:
0.0 to 1.9 minutes; A/B=90/10 to 1/99 (linear gradient)
1.91 to 3.00 minutes; A/B=1/99
Flow rate: 0.50 mL/min
UV: 220 nm, 254 nm
Column temperature: 40° C.
Measurement Condition I
Measuring equipment: Waters AQUITY™ UPLC H-Class System
Column: Waters AQUITY UPLC BEH C18 1.7 μm 2.1× 50 mm column
Solvent: solution A: 0.05% HCO₂H/H₂O, solution B: 0.05% HCO₂H/MeCN
Gradient Condition:
0.0 to 4.0 minutes; A/B=90/10 to 0/100 (linear gradient)
4.0 to 5.0 minutes; A/B=0/100
Flow rate: 0.50 mL/min
UV: 220, 254 nm
Column temperature: 40° C.

The abbreviations described above and the following abbreviations are used in the Reference Examples, Examples, and Test Examples in some cases to simplify the description.

s: singlet
d: doublet
t: triplet
q: quadruplet
m: multiplet
br: broad
dd: double doublet
J: coupling constant
Hz: Hertz
δ: chemical shift
min: minute
THF: tetrahydrofuran
DMAP: N,N-dimethyl-4-aminopyridine
TFA: trifluoroacetic acid
DIPEA: N,N-diisopropylethylamine
DMF: dimethylformamide
DME: 1,2-dimethoxyethane
NMP: N-methylpyrrolidone
DMSO: dimethyl sulfoxide
Me: methyl
Et: ethyl
MeCN: acetonitrile
CPME: cyclopentyl methyl ether
Boc: tert-butoxycarbonyl
tBu or ᵗBu or t-Bu: tert-butyl
t-: tert-
Bn: benzyl
Cbz: benzyloxycarbonyl
Trt: trityl(triphenylmethyl)
Ms: methanesulfonyl, mesyl
HATU: 1-[bis(dimethylamino)methylene]-1H-1,2,3-triazolo[4,5-b]pyridinium 3-oxide hexafluorophosphate
N: normal
M: mol/L, molarity
MEPM: meropenem
MIC: minimum inhibitory concentration Reference Example 1: tert-butyl [1-(3-hydroxyazetidin-1-yl)ethylidene]carbamate

[Chemical Formula 685]

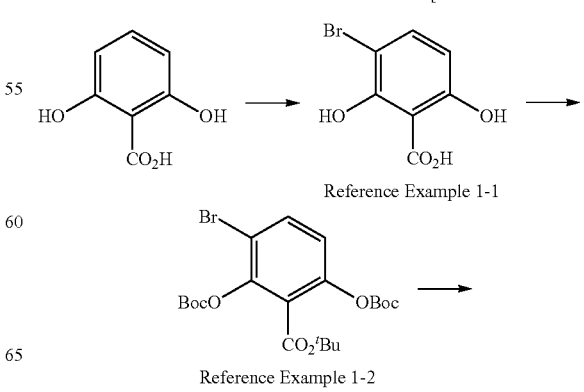

Reference Example 1-1

Reference Example 1-2

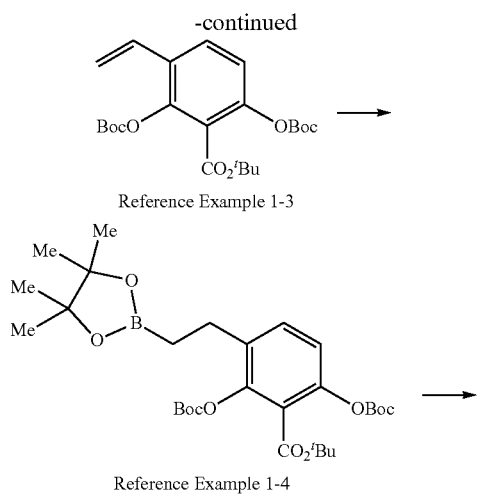

Reference Example 1-3

Reference Example 1-4

Reference Example 1-5

Reference Example 1-6

Reference Example 1-7

Reference Example 1-8

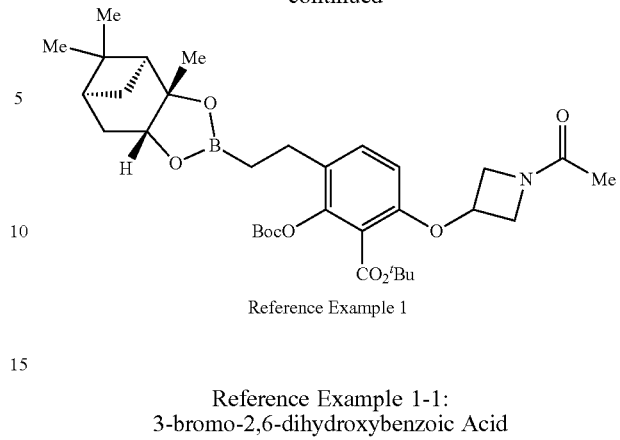

Reference Example 1

Reference Example 1-1: 3-bromo-2,6-dihydroxybenzoic Acid

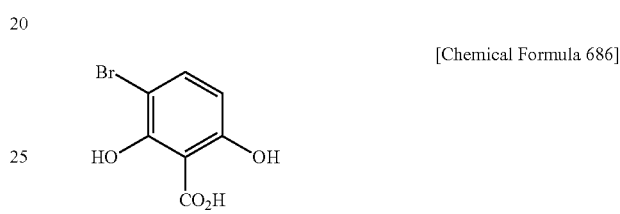

[Chemical Formula 686]

N-bromosuccinimide (6.06 g, 34.1 mmol) was added in small portions to a dichloromethane solution (59 mL) of 2,6-dihydrobenzoic acid (5 g, 32.4 mmol) and N,N-diisopropylethylamine (2.27 mL, 16.2 mmol) at −78° C. The reaction solution was warmed up to room temperature, and stirred for 20 hours at said temperature. The reaction solution was evaporated under reduced pressure. 1 mol/L hydrochloric acid (40 mL) was added to the resulting residue, and the mixture was stirred for 30 minutes at room temperature. The precipitated crystals were filtered out, washed with water, and dried to obtain the title compound (6.03 g).
$^1$H-NMR (CDCl$_3$) δ: 7.58 (1H, d, J=9.2 Hz), 6.53 (1H, d, J=8.5 Hz).
LCMS: [M+H]$^+$/Rt=233/0.412 min$^{-4}$

Reference Example 1-2: tert-butyl 3-bromo-2,6-bis[(tert-butoxycarbonyl)oxy]benzoate

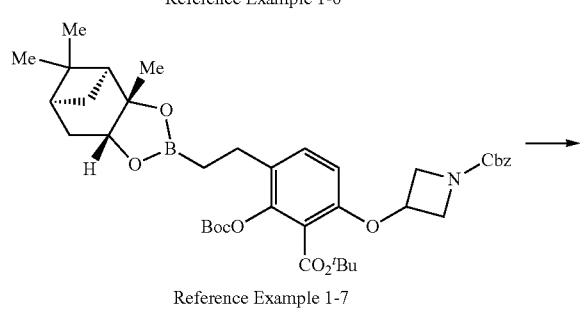

[Chemical Formula 687]

Di-tert-butyl dicarbonate (65.2 g, 299 mmol) and DMAP (0.608 g, 4.98 mmol) were added to a THF (120 mL)/tert-butanol (60 mL) solution of the compound of Reference Example 1-1 (11.6 g, 49.8 mmol), and the reaction mixture was stirred for 18 hours at 60° C. The reaction solution was cooled to room temperature. The reaction solution was evaporated under reduced pressure, and the resulting residue was purified by silica gel column chromatography (eluent: hexane/ethyl acetate=99/1 to 95/5) to obtain the title compound (19.3 g).
$^1$H-NMR (CDCl$_3$) δ: 7.60 (1H, d, J=8.5 Hz), 7.02 (1H, d, J=8.5 Hz), 1.53 (9H, s), 1.51 (9H, s).

Reference Example 1-3: tert-butyl 2,6-bis[(tert-butoxycarbonyl)oxy]-3-ethenylbenzoate

[Chemical Formula 688]

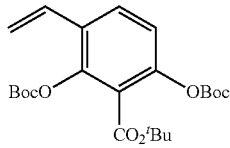

Tri-n-butylvinyltin (2.04 mL, 6.95 mmol) and bis(triphenylphosphine)palladium(II) chloride (0.488 g, 0.695 mmol) were added to a 1,4-dioxane (7 mL) solution of the compound of Reference Example 1-2 (1.7 g, 3.47 mmol) under a nitrogen atmosphere, and the reaction mixture was stirred for 10 hours at 110° C. After cooling the reaction solution to room temperature, the reaction solution was evaporated under reduced pressure, and the resulting residue was purified by silica gel column chromatography (eluent: hexane/ethyl acetate) to obtain the title compound (1.26 g).

$^1$H-NMR (CDCl$_3$) δ: 7.57 (1H, d, J=9.2 Hz), 7.11 (1H, d, J=8.5 Hz), 6.73 (1H, dd, J=17.7, 11.3 Hz), 5.74 (1H, d, J=17.7 Hz), 5.37 (1H, d, J=10.4 Hz), 1.57 (9H, s), 1.54 (9H, s), 1.52 (9H, s).

Reference Example 1-4: tert-butyl 2,6-bis[(tert-butoxycarbonyl)oxy]-3-[2-(4,4,5,5-tetramethyl-1,3,2-dioxaborolan-2-yl)ethyl]benzoate

[Chemical Formula 689]

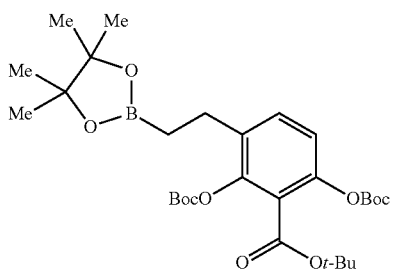

1,4-bis(diphenylphosphino)butane (0.547 g, 1.28 mmol), bis(1,5-cyclooctadiene)diiridium(I) dichloride (0.431 g, 0.641 mmol), and pinacolatodiboron (1.40 mL, 9.62 mmol) were added to a dichloromethane (32 mL) solution of the compound of Reference Example 1-3 (2.8 g, 6.41 mmol) under a nitrogen atmosphere, and the reaction mixture was stirred for 17 hours at room temperature. The reaction solution was evaporated under reduced pressure, and the resulting residue was purified by silica gel column chromatography (eluent: hexane/ethyl acetate) to obtain the title compound (3.59 g).

$^1$H-NMR (CDCl$_3$) δ: 7.30 (1H, d, J=8.5 Hz), 7.01 (1H, d, J=8.5 Hz), 2.66-2.58 (2H, m), 1.53 (9H, s), 1.51 (9H, s), 1.51 (9H, s), 1.20 (12H, s), 1.10-1.02 (2H, m).

Reference Example 1-5: tert-butyl 2,6-bis[(tert-butoxycarbonyl)oxy]-3-{2-[(3aS,4S,6S,7aR)-3a,5,5-trimethylhexahydro-4,6-methano-1,3,2-benzodioxaborol-2-yl]ethyl}benzoate

[Chemical Formula 690]

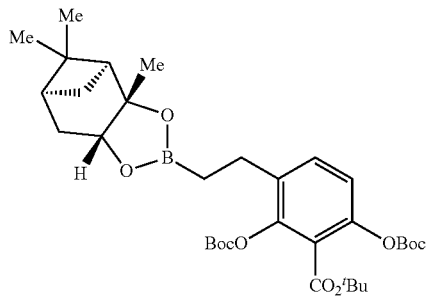

(1S,2S,3R,5S)-(+)-pinanediol (0.736 g, 4.32 mmol) was added to a THF (5 mL) solution of the compound of Reference Example 1-4 (0.976 g, 1.73 mmol), and the reaction mixture was stirred for 62 hours at room temperature. The reaction solution was evaporated under reduced pressure, and the resulting residue was purified by silica gel column chromatography (eluent: hexane/ethyl acetate=99/1 to 85/15) to obtain the title compound (0.90 g).

$^1$H-NMR (CDCl$_3$) δ: 7.31 (1H, d, J=8.5 Hz), 7.01 (1H, d, J=7.9 Hz), 4.23 (1H, dd, J=8.5, 1.8 Hz), 2.69-2.60 (2H, m), 2.35-2.24 (1H, m), 2.20-2.11 (1H, m), 2.04-1.97 (1H, m), 1.91-1.76 (2H, m), 1.54 (9H, s), 1.51 (18H, s), 1.34 (3H, s), 1.26 (3H, s), 1.14-1.07 (2H, m), 1.02 (1H, d, J=11.0 Hz), 0.81 (3H, s).

LCMS: [M−H]$^+$/Rt=615/3.160 min$^B$

Reference Example 1-6: tert-butyl 2-[(tert-butoxycarbonyl)oxy]-6-hydroxy-3-{2-[(3aS,4S,6S,7aR)-3a,5,5-trimethylhexahydro-4,6-methano-1,3,2-benzodioxaborol-2-yl]ethyl}benzoate

[Chemical Formula 691]

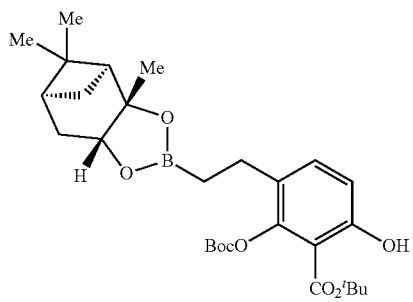

Pyrrolidine (0.121 mL, 1.46 mmol) was added to a THF (5 mL) solution of the compound of Reference Example 1-5 (0.899 g, 1.46 mmol), and the reaction mixture was stirred for 3 hours at room temperature. The reaction solution was evaporated under reduced pressure, and the resulting residue was purified by silica gel column chromatography (eluent: hexane/ethyl acetate=90/10 to 70/30) to obtain the title compound (0.68 g).

¹H-NMR (CDCl₃) δ: 11.26 (1H, s), 7.33 (1H, d, J=8.5 Hz), 6.82 (1H, d, J=8.5 Hz), 4.24 (1H, dd, J=8.8, 2.1 Hz), 2.63-2.54 (2H, m), 2.37-2.25 (1H, m), 2.23-2.11 (1H, m), 2.04-2.00 (1H, m), 1.93-1.78 (2H, m), 1.61 (9H, s), 1.54 (9H, s), 1.36 (3H, s), 1.28 (3H, s), 1.13-1.01 (3H, m), 0.83 (3H, s).

LCMS: [M−H]⁺/Rt=515/3.175 min$^B$

Reference Example 1-7: benzyl 3-[2-(tert-butoxy-carbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carboxylate

[Chemical Formula 692]

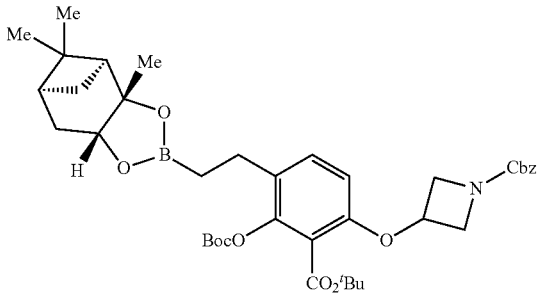

Under a nitrogen atmosphere, cesium carbonate (4.01 g) was added to a DMF (20.5 mL) solution of the compound of Reference Example 1-6 (2.117 g) and benzyl 3-iodoazetidine-1-carboxylic acid (1.95 g), and the reaction mixture was heated to 50° C. After 9 hours, the reaction mixture was cooled to room temperature. The reaction mixture was poured into water, extracted with a mixture solvent of ethyl acetate/hexane (1:1), and concentrated, and the residue was purified by using a silica gel column to obtain the title compound (2.46 g).

¹H-NMR (CDCl₃) δ: 7.36-7.26 (5H, m), 7.18 (1H, d, J=8.5 Hz), 6.36 (1H, d, J=8.5 Hz), 5.08 (2H, s), 4.91-4.84 (1H, m), 4.37-4.27 (2H, m), 4.24-4.18 (1H, m), 4.09-4.03 (2H, m), 2.58 (2H, t, J=8.2 Hz), 2.32-2.25 (1H, m), 2.18-2.08 (1H, m), 2.04-1.95 (1H, m), 1.89-1.84 (1H, m), 1.82-1.74 (1H, m), 1.53 (9H, s), 1.51 (9H, s), 1.34 (3H, s), 1.26 (3H, s), 1.08 (2H, t, J=8.2 Hz), 1.00 (1H, d, J=11.0 Hz), 0.81 (3H, s).

Reference Example 1-8: tert-butyl 6-[(azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate monohydrochloride

[Chemical Formula 693]

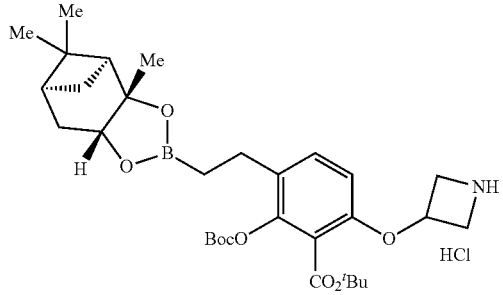

1 N hydrochloric acid (0.567 mL) and 50% water containing 10% palladium on carbon (0.149 g) were added to a methanol (16 mL) solution of the compound of Reference Example 1-7 (0.4 g), and the reaction mixture was stirred for 1 hour under hydrogen atmosphere. After celite filtration, the filtrate was concentrated to obtain the title compound (0.357 g).

¹H-NMR (CD₃OD) δ: 7.31 (1H, d, J=8.5 Hz), 6.66 (1H, d, J=8.5 Hz), 5.14 (1H, m), 4.55-4.42 (2H, m), 4.29-4.22 (1H, m), 4.13-4.05 (2H, m), 2.55 (2H, t, J=8.2 Hz), 2.35-2.30 (1H, m), 2.17-2.13 (1H, m), 1.99-1.92 (1H, m), 1.87-1.80 (1H, m), 1.79-1.72 (1H, m), 1.56 (9H, s), 1.50 (9H, s), 1.33 (3H, s), 1.27 (3H, s), 1.04 (2H, t, J=8.2 Hz), 0.98-0.96 (1H, m), 0.83 (3H, s).

Reference Example 1: tert-butyl 6-[(1-acetylazetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 694]

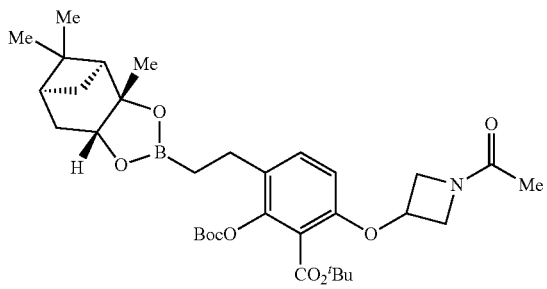

Acetic anhydride (0.023 mL) and triethylamine (0.057 mL) were added to a THF (0.8 mL) solution of the compound of Reference Example 1-8 (0.1 g) in an ice bath, and the reaction mixture was stirred overnight at room temperature. After concentration, the mixture was purified by silica gel column chromatography (ethyl acetate) to obtain the title compound (0.105 g).

¹H-NMR (CDCl₃) δ: 7.19 (1H, d, J=8.5 Hz), 6.39 (1H, d, J=8.5 Hz), 4.93-4.88 (1H, m), 4.46-4.30 (2H, m), 4.24-4.18 (1H, m), 4.16-4.00 (2H, m), 2.59 (2H, t, J=8.7 Hz), 2.35-2.23 (1H, m), 2.20-2.09 (1H, m), 2.01-1.96 (1H, m), 1.91-1.82 (4H, m), 1.82-1.73 (1H, m), 1.54 (9H, s), 1.49 (9H, d, J=15.8 Hz), 1.32 (3H, t, J=7.0 Hz), 1.25 (3H, s), 1.10 (2H, t, J=8.7 Hz), 1.03-0.97 (1H, m), 0.81 (3H, s).

Reference Example 2: tert-butyl 6-[(1-methylsulfonylazetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 695]

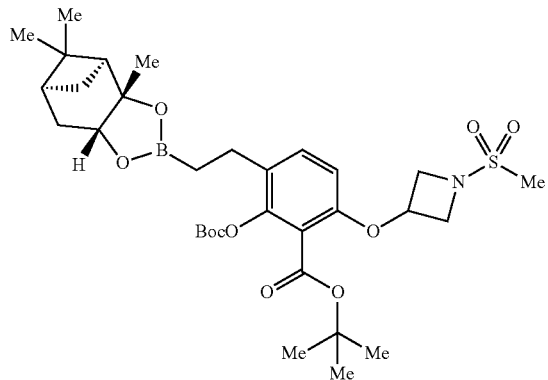

A reaction, work-up, and purification were performed using the compound of Reference Example 1-8 as the starting material by the same method described in Reference Example 1 to obtain the title compound.

¹H-NMR (CDCl₃) δ: 7.20 (1H, d, J=8.5 Hz), 6.41 (1H, d, J=8.5 Hz), 4.93-4.87 (1H, m), 4.29-4.20 (3H, m), 4.00-3.97 (2H, m), 2.89 (3H, s), 2.61-2.57 (2H, m), 2.33-2.26 (1H, m), 2.15 (1H, ddd, J=13.7, 6.1, 3.4 Hz), 2.00 (1H, t, J=5.5 Hz), 1.87 (1H, td, J=6.3, 3.9 Hz), 1.78 (1H, dt, J=14.6, 2.7 Hz), 1.55 (9H, s), 1.51 (9H, s) 1.34 (3H, s), 1.26 (3H, s), 1.11-1.06 (2H, m), 1.00 (2H, d, J=11.0 Hz), 0.81 (3H, a).

Reference Example 3: tert-butyl 2-[(tert-butoxycarbonyl)oxy]-6-((1-[(1H-imidazol-5-yl)acetyl]azetidin-3-yl)oxy)-3-{2-[(3aS,4S,6S,7aR)-3a,5,5-trimethylhexahydro-2H-4,6-methano-1,3,2-benzodioxaborol-2-yl]ethyl}benzoate

[Chemical Formula 696]

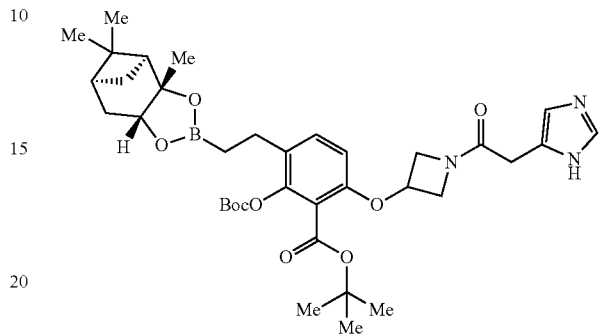

HATU was added to a DMF (0.905 mL) solution of the compound of Reference Example 1-8 (0.11 g), 4-imidazoleacetic acid hydrochloride (0.059 g), and triethylamine (0.076 mL) in an ice bath. The reaction mixture was slowly warmed up to room temperature, and stirred for 18 hours. The reaction mixture was poured into water, extracted with a mixture solvent of ethyl acetate/hexane (2:1), and concentrated, and the residue was purified by using a silica gel column to obtain the title compound (0.096 g).

¹H-NMR (CDCl₃) δ: 8.19 (1H, s), 7.21 (1H, d, J=8.5 Hz), 7.00 (1H, s), 6.39 (1H, d, J=8.5 Hz), 4.90 (1H, m), 4.61-4.59 (1H, m), 4.31-4.27 (1H, m), 4.23-21 (1H, m), 4.7-4.05 (1H, m), 3.81-78 (1H, m), 3.54 (2H, s), 2.58 (2H, m), 2.30-2.26 (2H, m), 2.17-2.13 (1H, m), 2.02-1.98 (1H, m), 1.88-1.87 (1H, m), 1.80-1.77 (1H, s), 1.54 (9H, s), 1.51 (9H, s), 1.33 (3H, s), 1.25 (3H, s), 1.10-1.06 (2H, m), 1.22-1.10 (1H, s), 0.81 (3H, s).

A reaction, work-up, and purification were performed using the compound of Reference Example 1-8 as the starting material by the same method described in Reference Example 3 to obtain each of Reference Example compounds 4 to 34 shown in Table 2.

TABLE 2

| Reference Example | Structural formula | NMR and/or LCMS |
|---|---|---|
| 4 | Me Me Me O B H O BocO O O Me Me Me O N S Trt NH NOMe | ¹H-NMR (CDCl₃) δ: 7.31-7.23 (18H, m), 7.19 (1H, d, J = 8.5 Hz), 6.96 (1H, s), 6.56 (1H, s), 6.35 (1H, d, J = 8.5 Hz), 4.93 (1H, ddd, J = 11.3, 5.8, 3.7 Hz), 4.46 (1H, dd, J = 11.0, 6.7 Hz), 4.32 (1H, dd, J = 9.2, 6.7 Hz), 4.22 (1H, dd, J = 8.5, 1.8 Hz), 4.16-4.04 (3H, m), 4.01 (4H, t, J = 10.7 Hz), 2.59 (2H, t, J = 8.2 Hz), 2.33-2.26 (1H, m), 2.15 (1H, tt, J = 10.7, 3.5 Hz), 1.99 (3H, t, J = 5.8 Hz), 1.89-1.85 (1H, m), 1.78 (1H, dt, J = 14.6, 2.7 Hz), 1.65 (2H, t, J = 6.1 Hz), 1.55-1.46 (19H, m), 1.37-1.29 (4H, m), 1.27 (4H, d, J = 9.8 Hz), 1.07 |

| Reference Example | Structural formula | NMR and/or LCMS |
|---|---|---|
| | | (2H, dd, J = 15.3, 7.3 Hz), 1.01 (1H, t, J = 7.6 Hz), 0.81 (3H, s). |
| 5 | 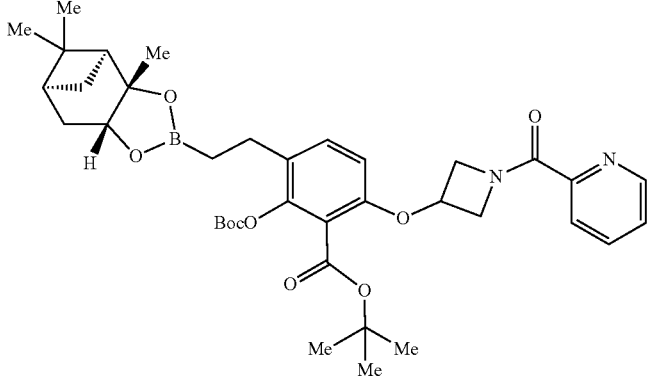 | ¹H-NMR (CDCl₃) δ: 8.54 (1H, d, = 4.3 Hz), 8.10 (1H, d, J = 7.9 Hz), 7.79-7.77 (1H, m), 7.35-7.32 (1H, m), 7.21 (1H, d, J = 8.5 Hz), 6.44 (1H, d, = 8.5 Hz), 5.09-5.06 (1H, m), 4.98-4.97 (1H, m), 4.70-4.67 (1H, m), 4.58-4.55 (1H, m), 4.30-4.19 (2H, m), 2.60 (2H, t, J = 8.2 Hz), 2.31-2.28 (1H, m), 2.18-2.13 (1H, m), 2.02-1.99 (1H, m), 1.87 (1H, br s), 1.81-1.77 (1H, m), 1.53 (9H, s), 1.51 (9H, s), 1.34 (3H, s), 1.26 (3H, s), 1.10 (2H, t, = 7.9 Hz), 1.01 (1H, d, J = 11.0 Hz), 0.81 (3H, s). |
| 6 | 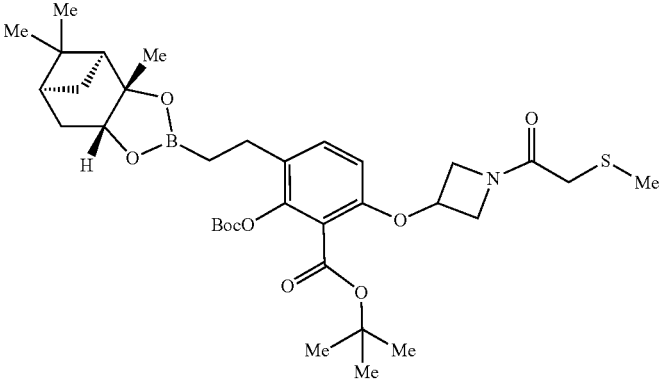 | ¹H-NMR (CDCl₃) δ: 7.22 (1H, d, J = 8.6 Hz), 6.42 (1H, d, J = 8.6 Hz), 5.30 (2H, s), 5.00-4.90 (1H, m), 4.60-4.52 (1H, m), 4.46-4.36 (1H, m), 4.28-4.08 (4H, m), 3.07 (2H, s), 2.66-2.58 (2H, m), 2.39-2.24 (1H, m), 2.22-2.12 (1H, m), 2.07-1.99 (1H, m), 1.93-1.76 (2H, m), 1.57 (9H, s), 1.54 (9H, s), 1.36 (3H, s), 1.28 (3H, s), 1.14-1.01 (3H, m), 0.84 (3H, s). |
| 7 | 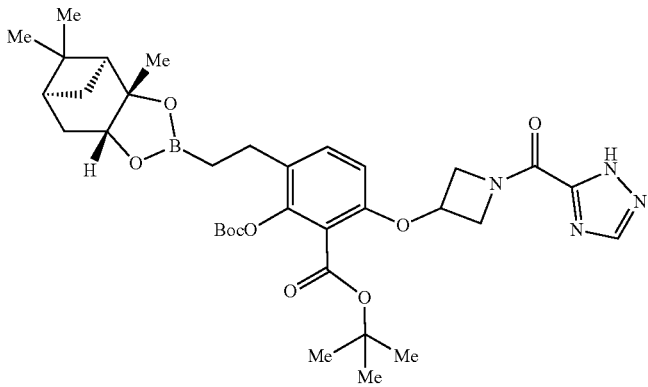 | ¹H-NMR (CDCl₃) δ: 8.19 (1H, s), 7.24 (1H, d, J = 8.6 Hz), 6.46 (1H, d, J = 8.6 Hz), 5.18-5 00 (2H, m) 4.76-4.58 (2H, m), 4.14-4.09 (2H, m), 2.62 (2H, t, J = 8.2 Hz), 2.38-2.25 (1H, m), 2.23-2.09 (1H, m), 2.07-1.99 (1H, m), 1.93-1.75 (2H, m), 1.56 (9H, s), 1.54 (9H, s), 1.34 (3H, s), 1.28 (3H, s), 1.12 (2H, t, J = 8.2 Hz), 1.07-1.00 (1H, m), 0.84 (3H, s). |

TABLE 2-continued

| Reference Example | Structural formula | NMR and/or LCMS |
|---|---|---|
| 8 | | ¹H-NMR (CDCl₃) δ: 8.20-8.17 (1H, m), 7.55-7.51 (1H, m), 7.38-7.12 (4H, m), 6.39 (1H, d, J = 8.6 Hz). 5.13-4.96 (1H, m), 4.77-4.61 (2H, m), 4.28-4.23 (2H, m), 4.14-4.05 (1H, m), 2.72-2.55 (2H, m), 2.32-2.25 (1H, m), 2.23-2.10 (1H, m), 2.07-1.98 (1H, m), 1.95-1.74 (2H, m), 1.56 (9H, s), 1.53 (9H, s), 1.35 (3H, s), 1.28 (3H, 2), 1.13-1.00 (3H, m), 0.83 (3H, s). |
| 9 | | ¹H-NMR (CDCl₃) δ: 7.43-7.28 (4H, m), 7.23-7.14 (1H, m), 6.40-6.27 (1H, m), 5.97-5.78 (1H, m), 5.22-5.10 (1H, m), 4.99-471 (1H, m), 4.65-4.37 (1H, m), 4.35-4.18 (2H, m), 4.18-4.04 (1H, m), 4.04-3.77 (1H, m), 2.66-2.54 (2H, m), 2.38-2.24 (1H, m), 2.205-1.98 (1H, m), 1.94-1.85 (1H, m), 1.84-1.74 (1H, m), 1.57 (9H, m), 1.54-1.48 (9H, m), 1.42-1.36 (9H, m), 1.35 (3H, s), 1.28 (3H, s), 1.14-0.94 (1H, m), 0.83 (3H, s). |
| 10 | | ¹H-NMR (CDCl₃) δ: 7.67-7.59 (2H, m), 7.50-7.36 (3H, m), 7.23-7.19 (1H, d, J = 8.6 Hz), 6.41 (1H, d, J = 8.6 Hz), 5.05-4.95 (1H, m), 4.64-4.50 2H, m), 4.39-4.30 (3H, m), 2.73-2.55 (2H, m), 2.39-2.25 (1H, m), 2.25-2.09 (1H, m), 2.08-1.96 (1H, m), 1.95-1.75 (2H, m), 1.60-1.75 (18H, m), 1.37-1.23 (6H, m), 1.22-0.96 (3H, m), 0.86-0.80 (3H, m). |
| 11 | | LCMS: [M + H]⁺/Rt = 678/2.75 min^B |

TABLE 2-continued
| Reference Example | Structural formula | NMR and/or LCMS |
|---|---|---|
| 12 | 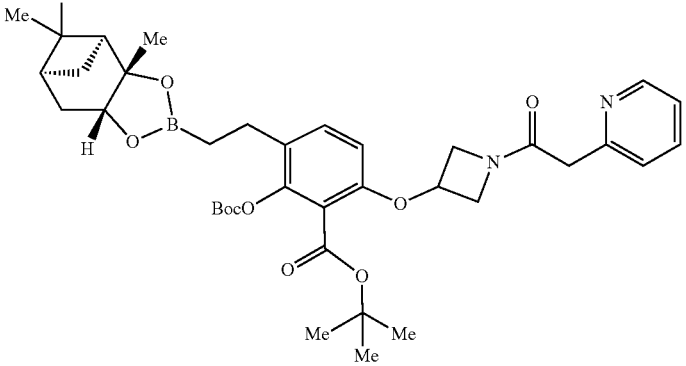 | LCMS: [M + H]⁺/Rt = 692/2.62 min$^B$ |
| 13 | 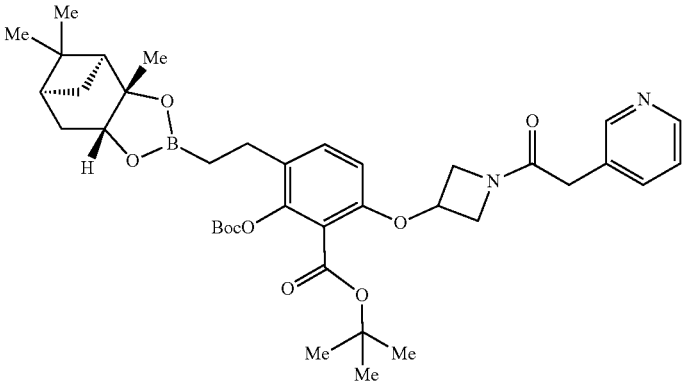 | LCMS: [M + H]⁺/Rt = 692/2.53 min$^B$ |
| 14 | 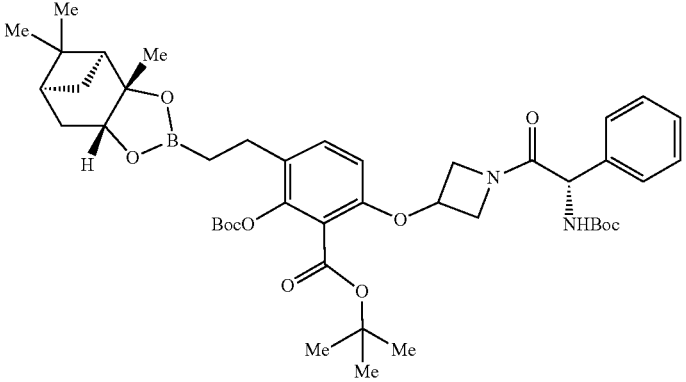 | LCMS: [M + H]⁺/Rt = 828/3.06 min$^B$ |
| 15 | 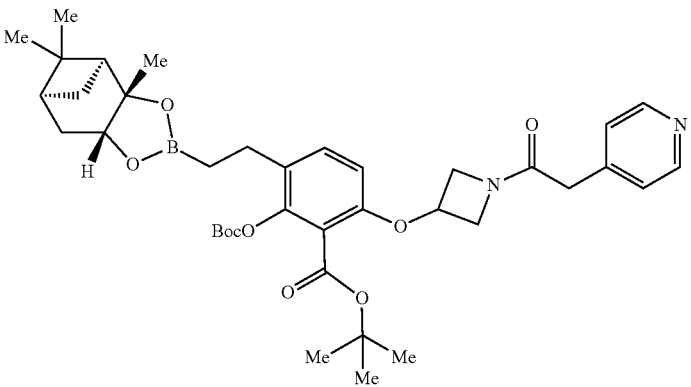 | LCMS: [M + H]⁺/Rt = 692/2.79 min$^B$ |

TABLE 2-continued

| Reference Example | Structural formula | NMR and/or LCMS |
|---|---|---|
| 16 | | $^1$H-NMR (CDCl$_3$) δ: 7.32-7.26 (2H, m), 7.23-7.17 (1H, m), 7.16-7.00 (2H, m), 6.43-6.36 (1H, m), 4.95-4.86 (1H, m), 4.46-4.30 (2H, m), 4.29-4.20 (1H, m), 4.18-4.06 (2H, m), 3.55-3.40 (2H, m), 2.68-2.55 (2H, m), 2.39-2.24 (1H, m), 2.22-2.10 (1H, m), 2.08-1.98 (1H, m), 1.95-1.73 (2H, m), 1.62-1.49 (27H, m), 1.36 (3H, s), 1.28 (3H, m), 1.14-1.01 (3H, m), 0.83 (3H, s). |
| 17 | | LCMS: [M + H]$^+$/Rt = 922/3.08 min$^B$ |
| 18 | | LCMS: [M + H]$^+$/Rt = 682/2.63 min$^B$ |
| 19 | | LCMS: [M + H]$^+$/Rt = 852/3.06 min$^B$ |

TABLE 2-continued

| Reference Example | Structural formula | NMR and/or LCMS |
|---|---|---|
| 20 | | ¹H-NMR (CDCl₃) δ: 7.37-7.17 (6H, m), 6.42-6.34 (1H, m), 4.94-4.84 (1H, m), 4.44-4.32 (2H, m), 4.29-4.19 (1H, m), 4.18-4.02 (2H, m), 3.50 (2H, s), 2.68-2.54 (2H, m), 2.38-2.26 (1H, m), 2.24-2.10 (1H, m), 2.06-1.98 (1H, m), 1.95-1.73 (2H, m), 1.54 (9H, s), 1.54 (9H, s) 1.36 (3H, s), 1.28 (3H, m), 1.13-1.00 (3H, m), 0.83 (3H, s). |
| 21 | | LCMS: [M + H]⁺/Rt = 705/2.98 min$^B$ |
| 22 | | LCMS: [M + H]⁺/Rt = 681/2.22 min$^B$ |
| 23 | | LCMS: [M + H]⁺/Rt = 682/2.66 min$^B$ |

TABLE 2-continued

| Reference Example | Structural formula | NMR and/or LCMS |
|---|---|---|
| 24 | | LCMS: [M + H]⁺/Rt = 683/2.62 min$^B$ |
| 25 | | LCMS: [M + H]⁺/Rt = 820/3.06 min$^B$ |
| 26 | | LCMS: [M + H]⁺/Rt = 936/3.12 min$^B$ |
| 27 | | LCMS: [M + H]⁺/Rt = 810/2.20 min$^B$ |

TABLE 2-continued

| Reference Example | Structural formula | NMR and/or LCMS |
|---|---|---|
| 28 | | LCMS: [M + H]⁺/Rt = 772/3.01 min[B] |
| 29 | | LCMS: [M + H]⁺/Rt = 810/2.20 min[B] |
| 30 | | LCMS: [M + H]⁺/Rt = 874/2.87 min[B] |

TABLE 2-continued

| Reference Example | Structural formula | NMR and/or LCMS |
|---|---|---|
| 31 | | LCMS: [M + H]⁺/Rt = 770/3.01 min$^B$ |
| 32 | | LCMS: [M + H]⁺/Rt = 770/3.01 min$^B$ |
| 33 | | LCMS: [M + H]⁺/Rt = 824/2.20 min$^B$ |

| Reference Example | Structural formula | NMR and/or LCMS |
|---|---|---|
| 34 | (structure shown) | ¹H-NMR (CD₃OD) δ: 7.34 (2H, d, J = 8.5 Hz), 7.30-7.29 (3H, m), 7.22-7.20 (2H, m), 7.06 (1H, d, J = 8.5 Hz), 6.89 (2H, d, J = 8.5 H), 6.84 (2H, d, J = 8.5 Hz), 6.63 (1H, d, J = 8.5 Hz), 5.07 (2H, s), 5.06 (2H, s), 5.05-5.02 (1H, m), 4.52-4.49 (2H, m), 4.27 (1H, d, J = 7.3 Hz), 4.10-4.08 (2H, m), 3.77 (3H, s), 3.74 (3H, s), 2.57 (2H, t, J = 8.2 Hz), 2.34-2.31 (1H, m), 2.16-2.15 (1H, m), 1.97 (1H, t, J = 5.5 Hz), 1.84 (1H, br s), 1.78-1.75 (1H, m), 1.53 (9H, s), 1.51 (9H, s), 1.33 (3H, s), 1.26 (3H, s), 1.07 (2H, t, J = 7.9 Hz), 0.96-0.94 (1H, m), 0.84 (3H, s). |

Reference Example 35: tert-butyl 2-[(tert-butoxycarbonyl)oxy]-6-{[1-(hydroxycarbamoyl)azetidin-3-yl]oxy}-3-{2-[(3aS,4S,6S,7aR)-3a,5,5-trimethylhexahydro-2H-4,6-methano-1,3,2-benzodioxaborol-2-yl]ethyl}benzoate

[Chemical Formula 697]

(structure shown)

Triphosgene (14.92 mg) was added to a toluene solution of the compound of Reference Example 1-8 (76.4 mg) and DIPEA (0.066 mL) at 0° C. The reaction mixture was returned to room temperature and stirred for 1.5 hours. The reaction mixture was concentrated. DMF (2.5 mL), DIPEA (0.5 mL), and hydroxylamine hydrochloride (51 mg) were added to the residue, and the reaction mixture was stirred for 3 hours at room temperature. A saturated aqueous sodium hydrogen carbonate solution was added, and the mixture was extracted with ethyl acetate. The organic phase was washed with saturated saline, dried over anhydrous sodium sulfate, filtered, and concentrated. The residue was subjected to silica gel column chromatography to obtain the title compound (56.5 mg) as a colorless solid.

¹H-NMR (CDCl₃) δ: 7.12 (1H, d, J=8.5 Hz), 7.04 (1H, s), 7.00 (1H, br s), 6.33 (1H, d, J=8.5 Hz), 4.87-4.83 (1H, m), 4.34 (2H, dd, J=9.8, 6.7 Hz), 4.17 (1H, dd, J=8.5, 1.8 Hz), 4.06-4.01 (2H, m), 2.53 (2H, t, J=8.5 Hz), 2.28-2.21 (1H, m), 2.13-2.07 (1H, m), 1.95 (1H, t, J=5.5 Hz), 1.83-1.81 (1H, m), 1.75-1.72 (1H, m), 1.49 (9H, s), 1.46 (9H, s), 1.29 (3H, s), 1.21 (3H, s), 1.03 (2H, t, J=8.5 Hz), 0.96 (1H, d, J=10.4 Hz), 0.76 (3H, s).

Reference Example (R)-36: tert-butyl 6-({1-[(2R)-2-[(tert-butoxycarbonyl)amino]-2-(1H-imidazol-4-yl)acetyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate Reference Example (S)-36: tert-butyl 6-({1-[(2R)-2-[(tert-butoxycarbonyl)amino]-2-(1H-imidazol-4-yl)acetyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 698]

(reaction scheme shown)

Reference Example 36-1

Reference Example 36-2

Reference Example 36-3

491

-continued

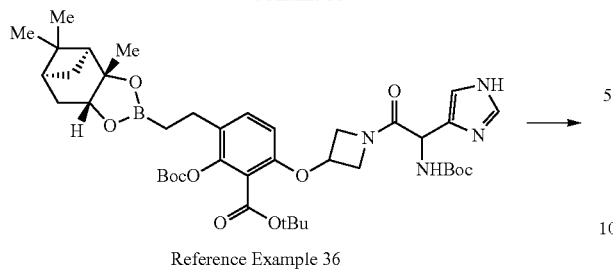

Reference Example 36

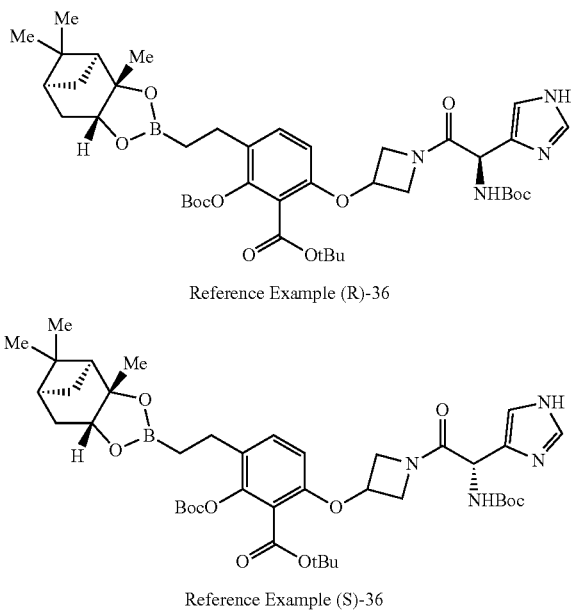

Reference Example 36-1:
4-formyl-N,N-dimethyl-1H-imidazole-1-sulfonamide

[Chemical Formula 699]

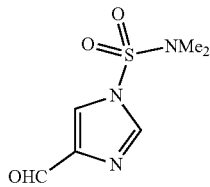

Dimethylsulfamoyl chloride (91 mL, 859 mmol) was added dropwise to a chloroform solution (750 ml) of 1H-imidazole-4-carbaldehyde (75 g, 78 mmol) and triethylamine (163 mL, 1.17 mol) over 50 minutes at room temperature. The reaction solution was stirred for 3 days and then water (900 mL) was added, and the mixture was extracted with chloroform (500 mL, 3 times). The organic phase was dried over sodium sulfate, filtered, and concentrated to obtain the title compound (161 g) as a white solid with a brownish tinge.

$^1$H-NMR (CDCl$_3$) δ: 9.88 (1H, br s), 7.91 (1H, t, J=7.3 Hz), 7.84 (1H, dd, J=8.5, 1.2 Hz), 2.87 (6H, dd, J=9.8, 5.5 Hz).

492

Reference Example 36-2:
amino(1H-imidazol-4-yl)acetic Acid Dihydrochloride

[Chemical Formula 700]

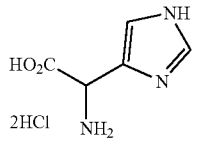

Sodium cyanide (46.7 g, 953 mmol) was added to an ethanol solution (227 mL) of the compound of Reference Example 36-1 (161 g, 794 mmol) and 28% aqueous ammonia (371 mL) while being cooled with ice (internal temperature of 14° C.). The reaction solution was stirred for 4 hours at room temperature and then extracted with chloroform (500 mL, 4 times). The organic phase was dried over sodium sulfate, filtered, and concentrated. 6 N aqueous hydrochloric acid (850 mL) was added to the resulting solid residue, and the reaction mixture was refluxed for 4 hours. The reaction solution was cooled to room temperature and then concentrated under reduced pressure. The resulting solid residue was stirred and washed with a THF-ethanol mixture solvent (1:1, 750 mL) and filtered to obtain the title compound (160 g) as a yellow solid with a brownish tinge.

$^1$H-NMR (D$_2$O) δ: 8.69 (1H, s), 7.54 (1H, s), 5.14 (1H, s).

Reference Example 36-3: [(tert-butoxycarbonyl)amino](1H-imidazol-4-yl)acetic Acid Hydrochloride

[Chemical Formula 701]

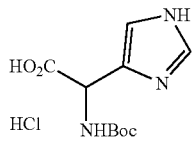

An aqueous 3 N sodium hydroxide solution (374 mL) was added dropwise to a methanol solution (194 mL) of the compound of Reference Example 36-2 (80 g, 374 mmol) over 45 minutes while cooling with ice. After stirring the reaction solution for 15 minutes while cooling with ice, di-tert-butyl dicarbonate was added over 15 minutes. The reaction solution was stirred for 45 minutes while cooling with ice and then warmed up to room temperature. To the reaction solution, N,N-dimethyl-4-aminopyridine (2.28 g, 18.7 mmol) and 2,2,2-trifluoroethanol (53.4 mL, 747 mmol) were added at room temperature, and the reaction solution was refluxed for 2 hours. After the reaction solution was allowed to cool down, 6 N aqueous hydrochloric acid (25 mL) was added while cooling with ice to adjust the pH of the solution to 6.0. After stirring for 1 hour while cooling with ice, the precipitated solid was filtered out, washed with acetone-water mixture solvent (1:1, 1 L), and dried and solidified under reduced pressure to obtain the title compound (40.0 g) as a white solid.

$^1$H-NMR (D$_2$O) δ: 8.50 (1H, d, J=1.2 Hz), 7.27 (1H, s), 5.04 (1H, s), 1.30 (9H, s).

493

Reference Example 36: tert-butyl 6-({1-[2-({tert-butoxycarbonyl}amino)-2-(1H-imidazol-4-yl)acetyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 702]

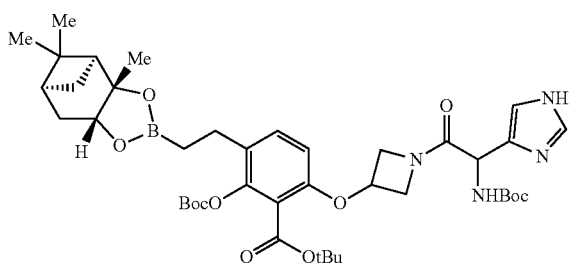

Triethylamine (1.54 ml, 11.1 mmol), 1-hydroxybenzotriazole (0.747 g, 5.53 mmol), and 1-(3-dimethylaminopropyl)-3-ethylcarbodiimide hydrochloride (0.689 g, 3.59 mmol) were added to a DMF solution (9.21 mL) of the compound of Reference Example 36-3 (1.0 g, 4.15 mmol) while cooling with ice. After stirring for 1 hour while cooling with ice, N,N-dimethyl-4-aminopyridine (0.068 g, 0.553 mmol) and the compound of Reference Example 1-8 (1.68 g, 2.76 mmol) were added to the reaction solution. After stirring for 24 hours at room temperature, an aqueous sodium hydrogen carbonate solution was added to the reaction solution, and the mixture was extracted with chloroform. The organic phase was dried over sodium sulfate, filtered, and concentrated, and the resulting residue was purified by silica gel column chromatography (eluent: chloroform/methanol) to obtain the title compound (1.09 g) as a while amorphous compound.

LCMS: [M+H]$^+$/Rt=795.44/0.845 min$^E$

The compound of Reference Example 36 (amount charged per injection: 19.6 mg) was dissolved in 0.300 mL of ethyl acetate. Isomers were obtained by optical resolution by chiral chromatography under the following conditions.

Column: CHIRALPAK IG 20 mmφ×250 mm (Daicel Corporation)

Mobile phase: diethylamine/ethyl acetate (diethylamine: 0.1%)

Flow rate: 10 mL/min

Temperature: 40° C.

Column retention times for both optical isomers were as follows.

(R)-36: 6.056 min (S)-36: 4.225 min

494

Reference Example 37: tert-butyl 6-[(1-{[(tert-butoxycarbonyl)amino](1-methyl-1H-imidazol-4-yl)acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 703]

Reference Example 37-1

Reference Example 37

Reference Example 37-1: [(tert-butoxycarbonyl)amino](1-methyl-1H-imidazol-4-yl) acetic Acid

[Chemical Formula 704]

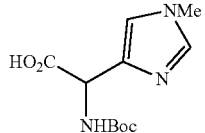

Sodium hydrogen carbonate (1.09 g, 13.0 mmol) and di-tert-butyl dicarbonate (1.30 mL, 5.62 mmol) were added to a methanol/water (1:1, 8.6 mL) solution of amino(1-methyl-1H-imidazol-4-yl) acetic acid (670 mg, 4.32 mmol), and the reaction mixture was stirred at room temperature. After 2 hours, the reaction solution was concentrated, and the residue was dissolved in ethanol (17 mL). Potassium hydrogen sulfate (2.35 g) was added at 0° C. to quench the reaction. Solids were filtered out, the filtrate was concentrated, and the residue was purified by silica gel column chromatography (eluent: chloroform/methanol=100/0 to 40/60) to obtain the title compound (400 mg) as a yellow solid.

LCMS: [M+H]$^+$/Rt=255.94/0.419 min$^C$

Reference Example 37: tert-butyl 6-[(1-{[(tert-butoxycarbonyl)amino](1-methyl-1H-imidazol-4-yl)acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 705]

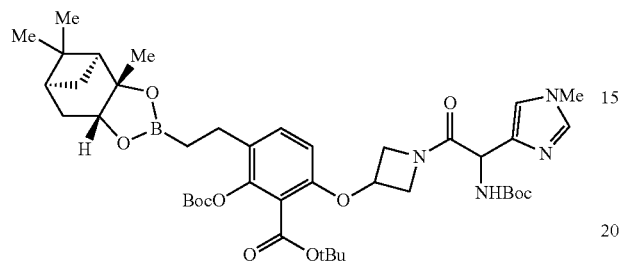

A reaction, work-up, and purification were performed using the compound of Reference Example 1-8 (325 mg, 0.535 mmol) and the compound of Reference Example 37-1 (205 mg, 0.803 mmol) as the starting materials by the same method described in Reference Example 36-4 to obtain the title compound (130 mg).

LCMS: [M+H]$^+$/Rt=809.58/1.246 min$^C$

Reference Example 38: tert-butyl 6-[(1-{[(tert-butoxycarbonyl)amino](2-methyl-1H-imidazol-4-yl)acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 706]

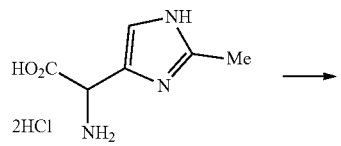

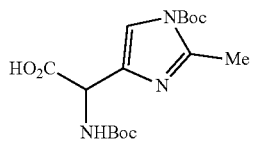

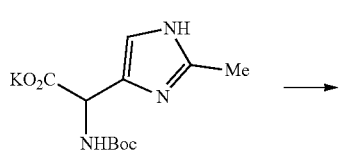

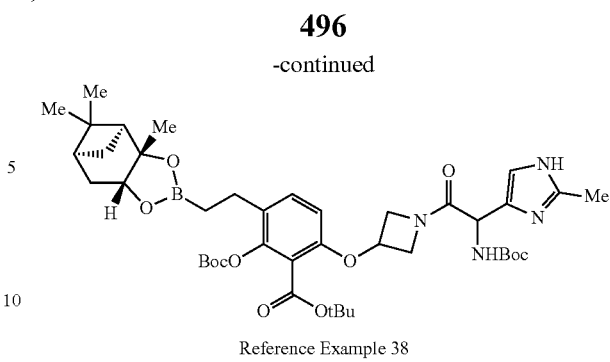

Reference Example 38

Reference Example 38-1: [(tert-butoxycarbonyl)amino][1-(tert-butoxycarbonyl)-2-methyl-1H-imidazol-4-yl]acetic Acid

[Chemical Formula 707]

Di-tert-butyl dicarbonate (1.64 g, 7.52 mmol) was added to a methanol solution (10 mL) of methyl 2-amino-2-(2-methyl-1H-imidazol-4-yl)acetate dihydrochloride (0.828 g, 3.42 mmol), N,N-dimethyl-4-aminopyridine (0.084 g, 0.684 mmol), and triethylamine (1.91 mL, 13.7 mmol) at room temperature, and the reaction mixture was stirred. After the completion of the reaction, a saturated aqueous sodium hydrogen carbonate solution was added, and the mixture was extracted with ethyl acetate and concentrated to obtain the title compound (0.59 g).

$^1$H-NMR (CD$_3$OD) δ: 7.31 (1H, s), 4.91 (1H, s), 2.53 (3H, s), 1.60 (9H, s), 1.42 (9H, s).

Reference Example 38-2: potassium [(tert-butoxycarbonyl)amino](2-methyl-1H-imidazol-4-yl)acetate

[Chemical Formula 708]

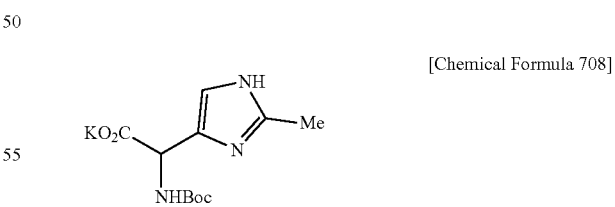

Potassium carbonate (0.331 g, 2.40 mmol) was added to a methanol solution (3.2 mL) of the compound of Reference Example 38-1 (0.59 g, 1.60 mmol). After stirring for 30 minutes at room temperature, the aqueous layer was washed with ethyl acetate and concentrated to obtain the title compound (0.47 g).

$^1$H-NMR (CD$_3$OD) δ: 6.77 (1H, s), 4.98 (1H, s), 2.29 (3H, s), 1.43 (9H, s).

Reference Example 38: tert-butyl 6-[(1-{[(tert-butoxycarbonyl)amino](2-methyl-1H-imidazol-4-yl)acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 709]

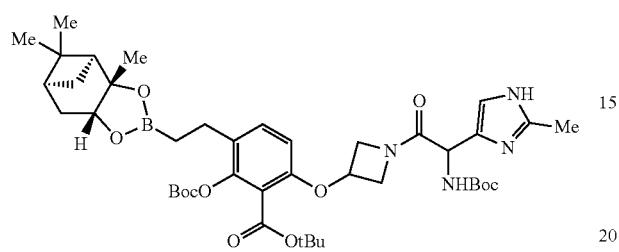

A reaction, work-up, and purification were performed using the compound of Reference Example 1-8 (0.328 g, 0.539 mmol) and the compound of Reference Example 38-2 (0.234 g, 0.799 mmol) as the starting materials by the same method described in Reference Example 36-4 to obtain the title compound (68.3 mg).

LCMS: $[M+H]^+/Rt=809.50/1.162$ $min^C$

Reference Example 39: tert-butyl 6-[(1-{2-[(tert-butoxycarbonyl)amino]-2-(1H-imidazol-4-yl)propanoyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 710]

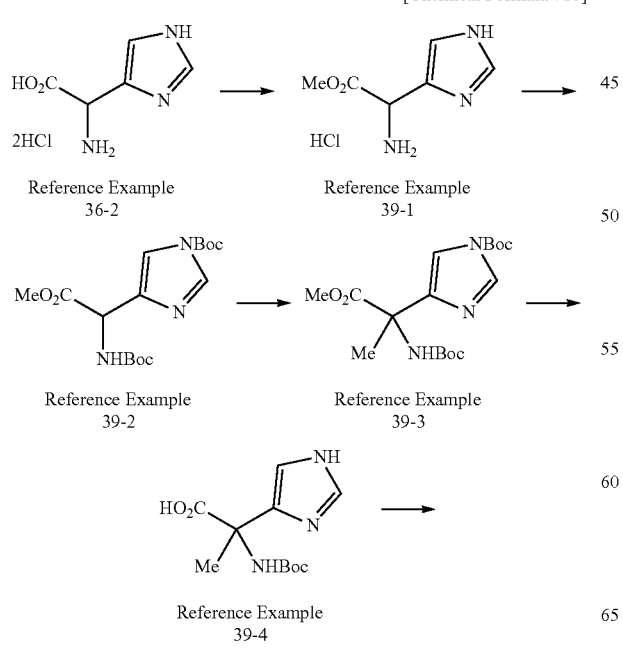

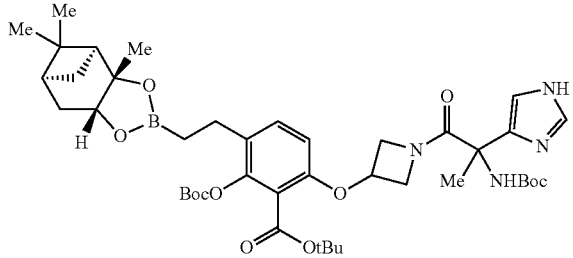

Reference Example 39

Reference Example 39-1: methyl amino(1H-imidazol-4-yl)acetate dihydrochloride

[Chemical Formula 711]

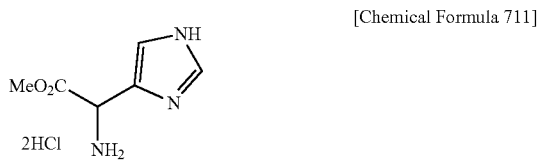 [SMILES: COC(=O)C(N)c1c[nH]cn1]

Thionyl chloride (75 mL, 1.21 mol) was added dropwise to a methanol solution (265 mL) of the compound of Reference Example 36-2 (44 g, 206 mmol) while cooling with ice. The reaction solution was warmed up to room temperature and then stirred for 8 hours at 50° C. The reaction solution was concentrated under reduced pressure to obtain the title compound (46.9 g) as a light yellow oily substance.

LCMS: $[M+H]^+/Rt=155.93/0.142$ $min^C$

Reference Example 39-2: tert-butyl 4-{1-[(tert-butoxycarbonyl)amino]-2-methoxy-2-oxoethyl}-1H-imidazole-1-carboxylate

[Chemical Formula 712]

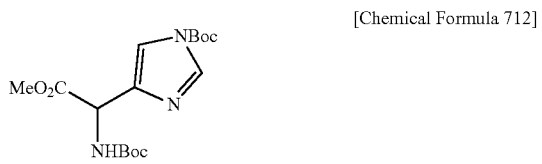 [SMILES: COC(=O)C(NC(=O)OC(C)(C)C)c1cn(C(=O)OC(C)(C)C)cn1]

N,N-dimethyl-4-aminopyridine (0.113 g, 0.928 mmol), triethylamine (0.863 mL, 6.19 mmol), and di-tert-butyl dicarbonate (1.08 mL, 4.64 mmol) were added to a chloroform solution (20 mL) of the compound of Reference Example 39-1 (0.70 g, 3.09 mmol) at room temperature, and the reaction mixture was stirred for 24 hours. The reaction solution was concentrated and the resulting residue was purified by silica gel column chromatography (eluent: hexane/ethyl acetate) to obtain the title compound (1.10 g) as a colorless oily substance.

$^1$H-NMR (CD$_3$OD) δ: 8.14 (1H, d, J=1.2 Hz), 7.51 (1H, s), 5.27 (1H, s), 3.73 (3H, s), 1.63 (9H, s), 1.45 (9H, s).

Reference Example 39-3: tert-butyl 4-{2-[(tert-butoxycarbonyl)amino]-1-methoxy-1-oxopropan-2-yl}-1H-imidazole-1-carboxylate

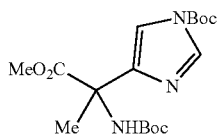

[Chemical Formula 713]

A lithium bis(trimethylsilyl)amide/THF solution (1.3 mol/L, 19.6 mL, 25.4 mmol) was added to a THF solution (43 mL) of the compound of Reference Example 39-2 (4.3 g, 12.1 mmol) at −78° C., and the reaction mixture was stirred for 30 minutes. Methyl iodide (0.832 mL, 13.3 mmol) was added to the reaction solution at −78° C. The reaction solution was warmed up to room temperature, and stirred for 4 hours. Saturated saline was added to the reaction solution, which was extracted with ethyl acetate. The organic phase was dried over sodium sulfate, filtered, and concentrated, and the resulting residue was purified by silica gel column chromatography (eluent: hexane/ethyl acetate) to obtain the title compound (2.15 g) as a light yellow oily substance.

$^1$H-NMR (CDCl$_3$) δ: 8.00 (1H, d, J=1.2 Hz), 7.35 (1H, d, J=1.2 Hz), 6.08 (1H, s), 3.73 (3H, s), 1.91 (3H, s), 1.61 (9H, s), 1.43 (9H, s).

Reference Example 39-4: 2-[(tert-butoxycarbonyl)amino]-2-(1H-imidazol-4-yl)propanoic Acid

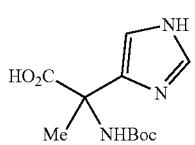

[Chemical Formula 714]

Lithium hydroxide monohydrate (0.513 g, 12.2 mmol) was added to a methanol solution (11.6 mL) of the compound of Reference Example 39-3 (2.15 g, 5.82 mmol) at room temperature, and the reaction mixture was stirred for 3 hours. 6 N aqueous hydrochloric acid (2.1 mL) was added, and the reaction mixture was stirred for 4 hours. Saturated saline was added to the reaction solution, and the solvent was evaporated under reduced pressure to obtain the title compound (1.49 g) as a crude product.

Reference Example 39: tert-butyl 6-[(1-{2-[(tert-butoxycarbonyl)amino]-2-(1H-imidazol-4-yl)propanoyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

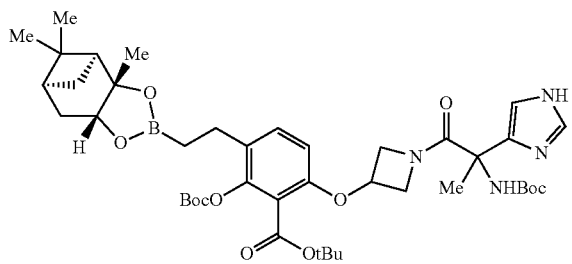

[Chemical Formula 715]

A reaction, work-up, and purification were performed using the compound of Reference Example 1-8 (0.30 g, 0.493 mmol) and the compound of Reference Example 39-4 (0.176 g, 0.691 mmol) as the starting materials by the same method described in Reference Example 36-4 to obtain the title compound (153 mg).

LCMS: [M+H]$^+$/Rt=809.17/1.139 min$^C$

Reference Example 40: tert-butyl 2-[(tert-butoxycarbonyl)oxy]-6-{[1-(1H-imidazole-4-carbonyl)azetidin-3-yl]oxy}-3-{2-[(3aS,4S,6S,7aR)-3a,5,5-trimethylhexahydro-2H-4,6-methano-1,3,2-benzodioxaborol-2-yl]ethyl}benzoate

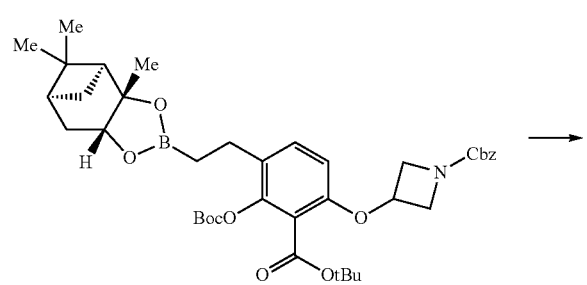

Reference Example 1-7

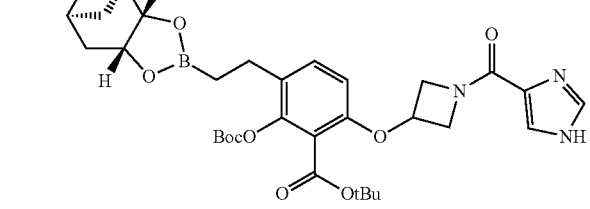

Reference Example 40

Palladium on carbon (20 mg, Pd content: 10%, wetted with ca. 55% water) was added to a methanol solution (3 mL) of the compound of Reference Example 1-7 (200 mg, 0.283 mmol), and the reaction mixture was stirred for 30 minutes under a hydrogen atmosphere at room temperature. The reaction solution was filtered through cellulose. The filtered substance was washed with methylene chloride, and the combined filtrate was concentrated. The resulting residue was dissolved in DMF (3 mL), and triethylamine (0.118 mL, 0.850 mmol) and 1H-imidazole-5-carboxylic acid chloride (40.7 mg, 0.312 mmol) were added. The reaction mixture was stirred for 20 minutes at room temperature, then water was added, and the mixture was extracted with ethyl acetate. The organic phase was washed with saturated saline, dried over sodium sulfate, filtered, and concentrated, and the resulting residue was purified by silica gel column chromatography (eluent: methylene chloride/methanol) to obtain the title compound (149 mg) as a light yellow solid.

$^1$H-NMR (CDCl$_3$) δ: 7.77-7.55 (2H, m), 7.26-722 (1H, m), 7.46 (1H, d, J=8.1 Hz), 5.12-4.90 (2H, m), 4.66-4.40 (2H, m), 4.30-4.15 (2H, m), 2.65-2.59 (2H, m), 2.36-2.26 (1H, m), 2.23-2.13 (1H, m), 2.05-2.00 (1H, m), 1.92-1.70 (2H, m), 1.59 (9H, s), 1.54 (9H, s), 1.36 (3H, s), 1.28 (3H, s), 1.15-1.01 (3H, m), 0.84 (3H, s).

LCMS: [M+H]$^+$/Rt=666.7/2.49 min$^B$

Reference Example 41: tert-butyl 2-[(tert-butoxycarbonyl)oxy]-6-{[1-(4H-1,2,4-triazole-3-sulfonyl)azetidin-3-yl]oxy}-3-{2-[(3aS,4S,6S,7aR)-3a,5,5-trimethylhexahydro-2H-4,6-methano-1,3,2-benzodioxaborol-2-yl]ethyl}benzoate

[Chemical Formula 717]

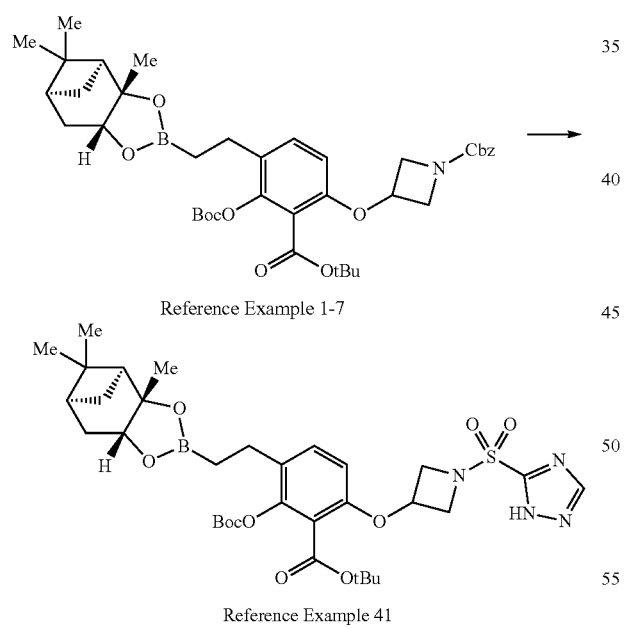

Reference Example 41

Palladium on carbon (20 mg, Pd content: 10%, wetted with ca. 55% water) was added to a methanol solution (3 mL) of the compound of Reference Example 1-7 (200 mg, 0.283 mmol), and the reaction mixture was stirred for 30 minutes at room temperature under a hydrogen atmosphere. The reaction solution was filtered through cellulose. The filtered substance was washed with methylene chloride, and the combined filtrate was concentrated. The resulting residue was dissolved in methylene chloride (3 mL), and triethylamine (0.118 mL, 0.850 mmol) was added. A methylene chloride solution (3 mL) of 1H-1,2,4-triazole-3-sulfonyl chloride (47.5 mg, 0.283 mmol) was added while cooling with ice, and the reaction mixture was stirred for 5 minutes. Water was added to the reaction solution, which was extracted with methylene chloride. The organic phase was washed with saturated saline, dried over sodium sulfate, filtered, and concentrated, and the resulting residue was purified by silica gel column chromatography (eluent: hexane/ethyl acetate) to obtain the title compound (205 mg) as a colorless solid.

$^1$H-NMR (CDCl$_3$) δ: 8.37 (1H, s), 7.20 (1H, d, J=8.1 Hz), 6.26 (1H, d, J=8.1 Hz), 4.43-4.37 (2H, m), 4.24 (1H, dd, J=8.1 Hz, 2.7 Hz), 4.16-4.08 (3H, m), 2.62-2.56 (2H, m), 2.36-2.27 (1H, m), 2.21-2.12 (1H, m), 2.05-2.00 (1H, m), 1.92-1.76 (2H, m), 1.55 (9H, s), 1.52 (9H, s), 1.36 (3H, s), 1.28 (3H, s), 1.12-0.99 (3H, m), 0.83 (3H, s).

LCMS: [M+H]$^+$/Rt=703.6/2.75 min$^B$

Reference Example 42: tert-butyl 6-({1-[N$^2$-(tert-butoxycarbonyl)-L-asparaginyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 718]

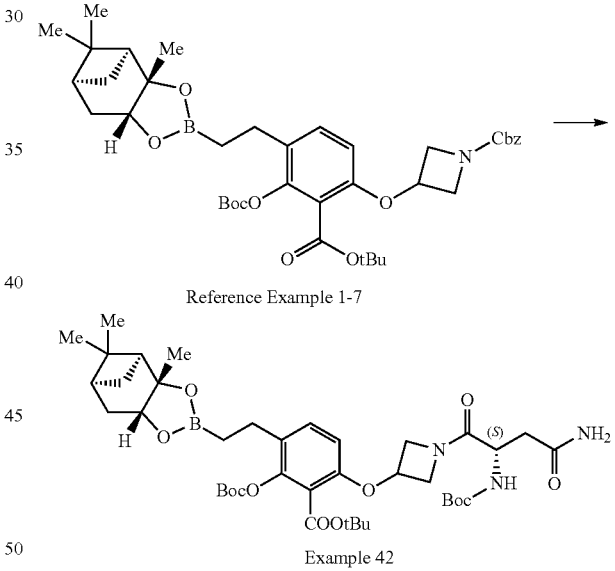

Palladium on carbon (20 mg, Pd content: 10%, wetted with ca. 55% water) was added to a methanol solution (3 mL) of the compound of Reference Example 1-7 (200 mg, 0.283 mmol), and the reaction mixture was stirred for 30 minutes at room temperature under a hydrogen atmosphere. The reaction solution was filtered through cellulose. The filtered substance was washed with methylene chloride, and the combined filtrate was concentrated. The resulting residue was dissolved in THF (3 mL), and tert-butoxycarbonyl-L-asparagine (85.6 mg, 0.368 mmol), N,N'-dicyclohexylcarbodiimide (58.5 mg, 0.340 mmol), 1-hydroxybenzotriazole monohydrate (52.1 mg, 0.340 mmol), and N-methylmorpholine (34.3 μL, 0.312 mmol) were added, and the reaction mixture was stirred for 2 hours at room temperature. Water was added to the reaction solution, which was extracted with ethyl acetate. The organic phase was washed with saturated saline, dried over sodium sulfate, filtered, and concentrated, and the resulting residue was purified by silica gel column chromatography (eluent: hexane/ethyl acetate) to obtain the title compound (198 mg) as a colorless solid.

$^1$H-NMR (CDCl$_3$) δ: 7.22 (1H, d, J=8.1 Hz), 6.41-6.37 (1H, m), 6.03 (1H, br), 5.72-5.61 (1H, m), 5.48-5.39 (1H, m), 4.99-4.89 (1H, m), 4.75-4.51 (2H, m), 4.44-4.31 (2H, m), 4.27-4.23 (1H, m), 4.10-4.03 (1H, m), 2.73-2.56 (4H, m), 2.36-2.27 (1H, m), 2.20-2.14 (1H, m), 2.04-2.00 (1H, m), 1.92-1.77 (2H, m), 1.57 (9H, s), 1.53 (9H, s), 1.43 (9H, s), 1.36 (3H, s), 1.26 (3H, s), 1.14-1.01 (3H, m), 0.83 (3H, s).

LCMS: [M+H]$^+$/Rt=786.8/2.79 min$^B$

Reference Example 43: tert-butyl 2-[(tert-butoxy-carbonyl)oxy]-6-[(1-{[4-(hydroxymethyl)-1H-1,2,3-triazol-1-yl]acetyl}azetidin-3-yl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 719]

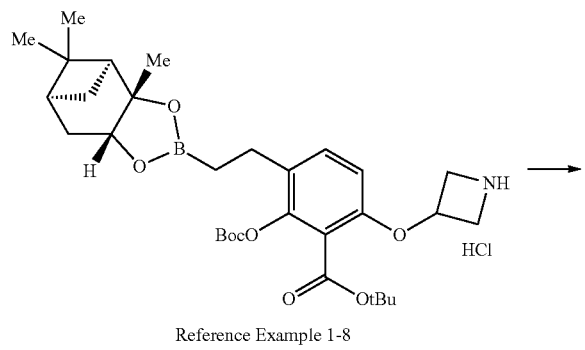

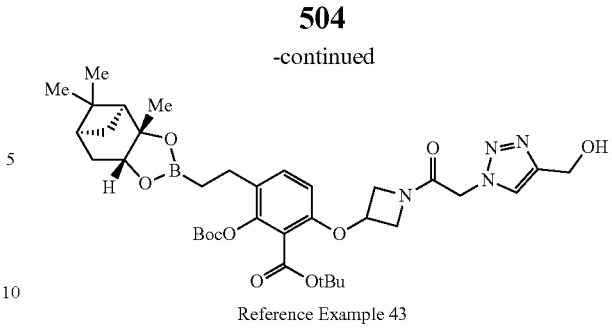

Reference Example 43

Reference Example 43-1: tert-butyl 2-[(tert-butoxy-carbonyl)oxy]-6-{[1-(chloroacetyl) azetidin-3-yl]oxy}-3-{2-[(3aS,4S,6S,7aR)-3a,5,5-trimethylhexahydro-2H-4,6-methano-1,3,2-benzodioxaborol-2-yl] ethyl}benzoate

[Chemical Formula 720]

Under a nitrogen atmosphere, a dichloromethane (5.3 mL) solution of the compound of Reference Example 1-8 (160 mg, 0.263 mmol) was cooled with ice to 0° C. Chloroacetyl chloride (30 μL, 0.377 mmol) and triethylamine (0.11 mL, 0.789 mmol) were added, and the reaction mixture was stirred for 1 hour at room temperature. Subsequently, the reaction solution was cooled with ice, a saturated aqueous sodium hydrogen carbonate solution was added, and the mixture was extracted with ethyl acetate. The organic phase was washed with a saturated aqueous ammonium chloride solution and saturated saline, and then dried over sodium sulfate and filtered, then the filtrate was evaporated under reduced pressure. The resulting residue was purified by silica gel chromatography (eluent: hexane/ethyl acetate=1/1) to obtain the title compound (140 mg).

$^1$H-NMR (CDCl$_3$) δ: 7.21 (1H, d, J=8.6 Hz), 6.40 (1H, d, J=8.6 Hz), 4.99-4.93 (1H, m), 4.64-4.58 (1H, m), 4.44-4.39 (1H, m), 4.32-4.27 (1H, m), 4.24-4.20 (1H, m), 4.15-4.09 (1H, m), 3.89 (2H, s), 2.60 (2H, t, J=8.3 Hz), 2.34-2.26 (1H, m), 2.18-2.12 (1H, m), 2.02-1.98 (1H, m), 1.91-1.85 (1H, m), 1.82-1.75 (1H, m), 1.56-1.51 (18H, m), 1.34 (3H, s), 1.26 (3H, s), 1.11-1.07 (2H, m), 1.00 (1H, d, J=10.9 Hz), 0.81 (3H, s).

Reference Example 43-2: tert-butyl 6-{[1-(azido-acetyl)azetidin-3-yl]oxy}-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 721]

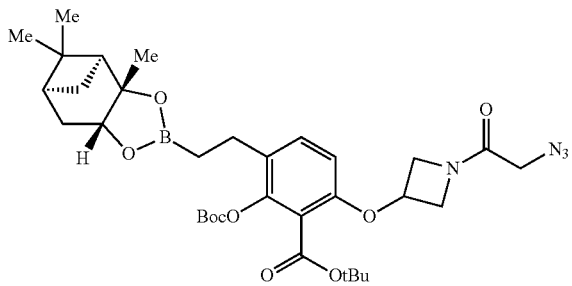

Sodium azide (69.0 mg, 1.06 mmol) was added to a DMSO (4.3 mL) solution of the compound of Reference Example 43-1 (140 mg, 0.216 mmol), and the reaction mixture was stirred for 1.5 hours at room temperature. Subsequently, water was added to the reaction solution, which was diluted with ethyl acetate, and the organic phase was separated. The organic phase was washed with saturated saline, and then dried over sodium sulfate and filtered, then the filtrate was evaporated under reduced pressure. The resulting residue was purified by silica gel chromatography (eluent: hexane/ethyl acetate=1/1) to obtain the title compound (129 mg).

$^1$H-NMR (CDCl$_3$) δ: 7.25-7.21 (1H, m), 6.41 (1H, d, J=8.6 Hz), 5.01-4.93 (1H, m), 4.55-4.48 (1H, m), 4.48-4.40 (1H, m), 4.27-4.19 (2H, m), 4.17-4.11 (1H, m), 3.84-3.72 (2H, m), 2.61 (2H, t, J=8.3 Hz), 2.36-2.28 (1H, m), 2.20-2.13 (1H, m), 2.04-1.99 (1H, m), 1.92-1.86 (1H, m), 1.83-1.77 (1H, m), 1.59-1.51 (18H, m), 1.36 (3H, s), 1.28 (3H, s), 1.13-1.09 (2H, m), 1.04-0.99 (1H, m), 0.83 (3H, s).

Reference Example 43: tert-butyl 2-[(tert-butoxycarbonyl)oxy]-6-[(1-{[4-(hydroxymethyl)-1H-1,2,3-triazol-1-yl]acetyl}azetidin-3-yl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 722]

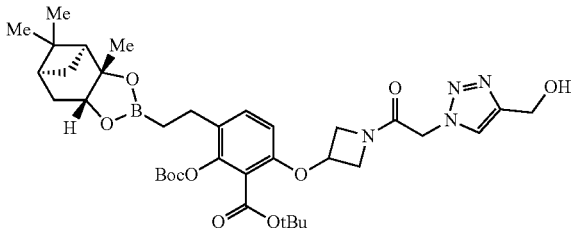

2-propyn-1-ol (47 µL, 0.788 mmol), copper iodide (24.4 mg, 0.128 mmol), and tris[(1-benzyl-1H-1,2,3-triazol-4-yl)methyl]amine (24.3 mg, 46.0 µmol) were added to an acetonitrile (9.2 mL) solution of the compound of Reference Example 43-2 (300 mg, 0.458 mmol), and the reaction mixture was stirred for 2 hours at room temperature. Subsequently, a saturated aqueous potassium sodium tartrate solution was added to the reaction solution, and the mixture was extracted with chloroform. The organic phase was washed with saturated saline, and then dried over sodium sulfate and filtered, then the filtrate was evaporated under reduced pressure. The resulting residue was purified by silica gel chromatography (eluent: chloroform/methanol=50/1 to 30/1) to obtain the title compound (271 mg).

$^1$H-NMR (CDCl$_3$) δ: 7.75 (1H, s), 7.23 (1H, d, J=8.6 Hz), 6.40 (1H, d, J=8.6 Hz), 5.13-5.05 (1H, m), 5.02-4.93 (2H, m), 4.81 (2H, s), 4.56-4.50 (1H, m), 4.47-4.38 (1H, m), 4.27-4.22 (1H, m), 4.21-4.09 (2H, m), 2.66-2.59 (2H, m), 2.38-2.28 (2H, m), 2.22-2.14 (1H, m), 2.05-1.99 (1H, m), 1.93-1.87 (1H, m), 1.84-1.77 (1H, m), 1.57 (9H, s), 1.54 (9H, s), 1.36 (3H, d, J=1.1 Hz), 1.28 (3H, s), 1.14-1.08 (2H, m), 1.06-1.01 (1H, m), 0.84 (3H, s).

LCMS: [M+H]$^+$/Rt=711.42/3.75 min$^D$

Reference Example 44: tert-butyl 2-[(tert-butoxycarbonyl)oxy]-6-[(1-{[5-(hydroxymethyl)-1H-1,2,3-triazol-1-yl]acetyl}azetidin-3-yl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 723]

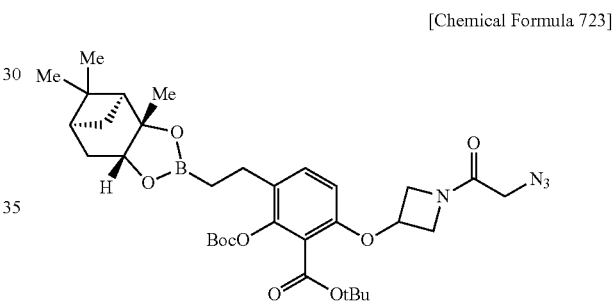

Reference Example 43-2

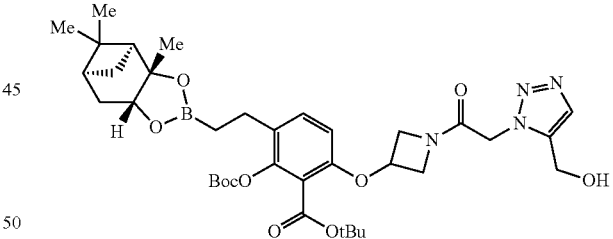

Reference Example 44

The compound of Reference Example 43-2 (74.9 mg, 0.114 mmol) and (chloro[(1,2,3,4,5-h)-1,2,3,4,5-pentamethyl-2,4-cyclopentadien-1-yl]bis(triphenylphosphine)ruthenium(II) (900 µg, 1.14 µmol) were added to a toluene (0.91 mL) solution of 2-propyn-1-ol (11.0 µL, 0.182 mmol), and the reaction mixture was stirred for 19 hours at 80° C. Subsequently, the reaction solution was cooled to room temperature, and stirred again for 4 hours at 80° C. after adding 2-propyn-1-ol (11.0 µL, 0.182 mmol) and chloro[(1,2,3,4,5-h)-1,2,3,4,5-pentamethyl-2,4-cyclopentadien-1-yl]bis(triphenylphosphine)ruthenium(II) (900 µg, 1.14 µmol). Subsequently, the reaction solution was evaporated under reduced pressure, and the resulting residue was purified by silica gel chromatography (eluent: hexane/ethyl acetate=1/1 to chloroform/methanol=10/1) to obtain the title compound (45.3 mg).

$^1$H-NMR (CDCl$_3$) δ: 7.62 (1H, s), 7.22 (1H, d, J=8.6 Hz), 6.41 (1H, d, J=8.6 Hz), 5.14-5.08 (1H, m), 5.02-4.93 (2H, m), 4.71-4.62 (3H, m), 4.42-4.36 (1H, m), 4.29-4.19 (3H, m), 2.60 (2H, t, J=8.3 Hz), 2.36-2.26 (1H, m), 2.20-2.13 (1H, m), 2.03-1.99 (1H, m), 1.92-1.76 (3H, m), 1.56 (9H, s), 1.52 (9H, s), 1.35 (3H, s), 1.27 (3H, s), 1.13-1.07 (2H, m), 1.04-0.99 (1H, m), 0.82 (3H, B).

LCMS: [M+H]$^+$/Rt=711.60/3.75 min$^D$

Reference Example 45: tert-butyl 6-({1-[(5-{[(tert-butoxycarbonyl)(methyl)amino]methyl}-1H-1,2,3-triazol-1-yl)acetyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 724]

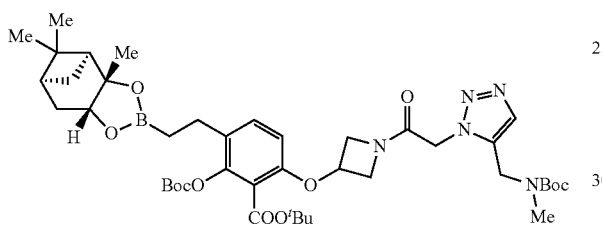

A reaction, work-up, and purification were performed using the compound of Reference Example 43-2 as the starting material by the same method described in Reference Example 44 to obtain the title compound.

$^1$H-NMR (CDCl$_3$) δ: 7.59 (1H, s), 7.21 (1H, d, J=8.6 Hz), 6.38 (1H, d, J=8.6 Hz), 5.23-5.07 (2H, m), 5.01-4.90 (1H, m), 4.62-4.36 (4H, m), 4.29-4.19 (2H, m), 4.13-4.05 (1H, m), 2.82 (3H, s), 2.59 (2H, t, J=8.3 Hz), 2.34-2.26 (1H, m), 2.20-2.11 (1H, m), 2.04-1.96 (1H, m), 1.91-1.85 (1H, m), 1.82-1.75 (1H, m), 1.57-1.51 (18H, m), 1.43 (9H, s), 1.34 (3H, s), 1.26 (3H, s), 1.12-1.07 (2H, m), 1.01 (1H, d, J=10.9 Hz), 0.81 (3H, s).

LCMS: [M+H]$^+$/Rt=824.80/4.16 min$^D$

Reference Example 46: tert-butyl 2-[(tert-butoxycarbonyl)oxy]-6-[(1-{[4-(2-tert-butoxy-2-oxoethyl)-1H-1,2,3-triazol-1-yl]acetyl}azetidin-3-yl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 725]

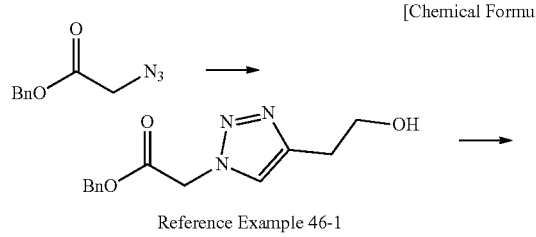

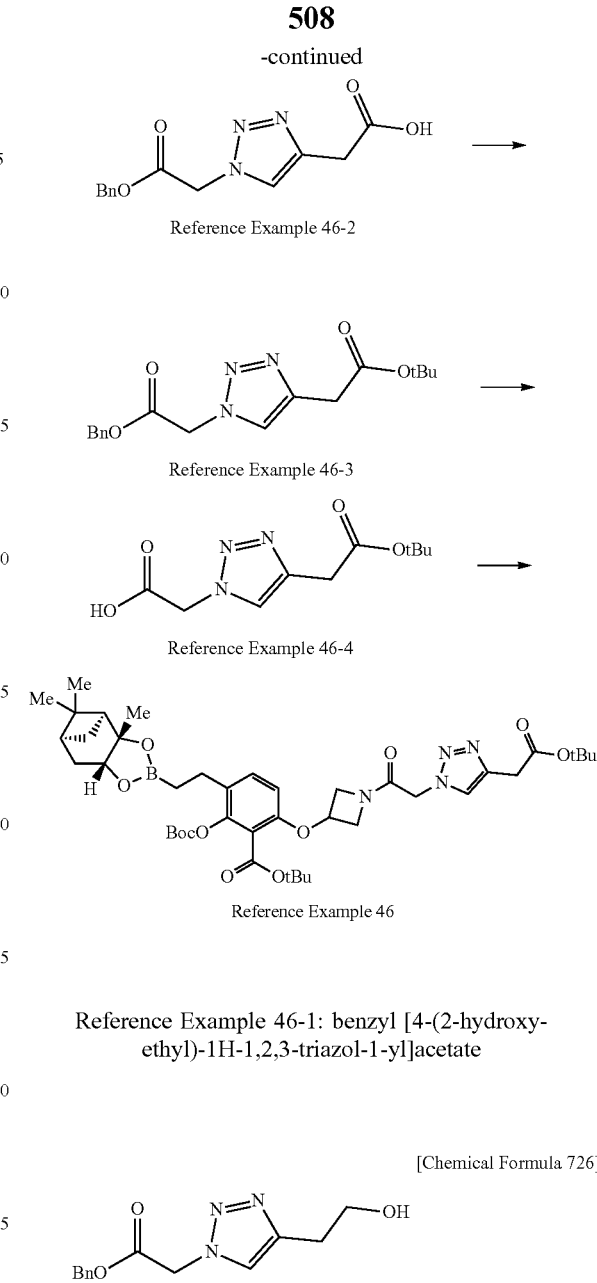

Reference Example 46-1: benzyl [4-(2-hydroxyethyl)-1H-1,2,3-triazol-1-yl]acetate

[Chemical Formula 726]

Water (12 mL) was added to a tert-butyl alcohol (12 mL) solution of benzyl 2-azidoacetate (2.50 g, 13.0 mmol). Sodium L-ascorbate (527 mg, 2.66 mmol), 3-butyn-1-ol (1.5 mL, 19.8 mmol), and copper sulfate pentahydrate (347 mg, 1.39 mmol) were added, and the reaction mixture was stirred for 2 hours at room temperature. Subsequently, water was added to the reaction solution, which was extracted with chloroform. The organic phase was washed with saturated saline, and then dried over sodium sulfate and filtered, then the filtrate was evaporated under reduced pressure. The resulting residue was purified by silica gel chromatography (eluent: chloroform/methanol=100/1 to 30/1) to obtain the title compound (3.13 g).

$^1$H-NMR (CDCl$_3$) δ: 7.52-7.50 (1H, m), 7.38-7.31 (5H, m), 5.21 (2H, s), 5.16 (2H, s), 3.95 (2H, q, J=6.1 Hz), 2.96 (2H, t, J=5.4 Hz).

LCMS: [M+H]$^+$/Rt=262.09/1.88 min$^D$

Reference Example 46-2: {1-[2-(benzyloxy)-2-oxo-ethyl]-1H-1,2,3-triazol-4-yl}acetic Acid

[Chemical Formula 727]

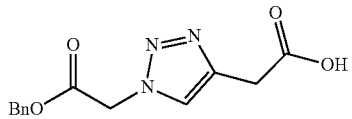

An aqueous 0.67M sodium dihydrogen phosphate solution (28 mL) was added to an acetonitrile (28 mL) solution of the compound of Reference Example 46-1 (1.02 g, 3.90 mmol). 2,2,6,6-tetramethylpiperidine-1-oxyl (56.3 mg, 0.360 mmol), aqueous 5% hypochlorous acid solution (2.1 mL), and aqueous 80% chlorous acid solution (0.88 mL, 7.81 mmol) were added, and the reaction mixture was stirred for 23 hours at room temperature. Subsequently, an aqueous sodium thiosulfate solution was added to the reaction solution, which was then extracted with ethyl acetate. 1M hydrochloric acid was added to the aqueous layer, which was again extracted with chloroform. The organic phase was washed with saturated saline and 1M hydrochloric acid, and then dried over sodium sulfate and filtered, then the filtrate was evaporated under reduced pressure to obtain the title compound (676 mg).
$^1$H-NMR (CDCl$_3$) δ: 7.73 (1H, s), 7.37-7.31 (5H, m), 5.21 (2H, s), 5.18 (2H, s), 3.90 (2H, s).

Reference Example 46-3: benzyl tert-butyl 2,2'-(1H-1,2,3-triazol-1,4-diyl)diacetate

[Chemical Formula 728]

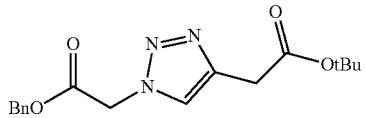

Under a nitrogen atmosphere, a THF (15 mL) solution of the compound of Reference Example 46-2 (676 mg, 2.46 mmol) was cooled with ice. tert-butyl alcohol (10 mL) and N,N'-diisopropyl-O-t-butylisourea (1.8 mL, 0.789 mmol) were added, and the reaction mixture was stirred for 17 hours at room temperature. The reaction solution was evaporated under reduced pressure, and then the resulting residue was purified by silica gel chromatography (eluent: hexane/ethyl acetate=2/1) to obtain the title compound (425 mg).
$^1$H-NMR (CDCl$_3$) δ: 7.72 (1H, s), 7.39-7.31 (5H, m), 5.21 (2H, s), 5.16 (2H, s), 3.75 (2H, s), 1.45 (9H, s).

Reference Example 46-4: [4-(2-tert-butoxy-2-oxo-ethyl)-1H-1,2,3-triazol-1-yl]acetic Acid

[Chemical Formula 729]

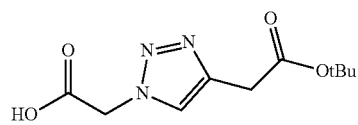

10% palladium on carbon (88.7 mg) was added to an ethyl acetate (12 mL) solution of the compound of Reference Example 46-3 (397 mg, 1.20 mmol). Under a hydrogen atmosphere, the reaction mixture was stirred for 50 minutes at room temperature. Subsequently, the reaction solution was filtered through celite and then the filtrate was evaporated under reduced pressure to obtain the title compound (288 mg).
$^1$H-NMR (CD$_3$OD) δ: 7.91 (1H, s), 5.19 (2H, s), 3.70 (2H, s), 1.45 (9H, s).

Reference Example 46: tert-butyl 2-[(tert-butoxy-carbonyl)oxy]-6-[(1-{[4-(2-tert-butoxy-2-oxoethyl)-1H-1,2,3-triazol-1-yl]acetyl}azetidin-3-yl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 730]

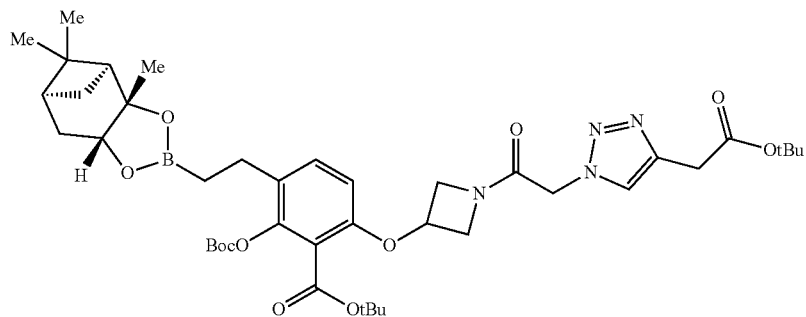

The compound of Reference Example 1-8 (503 mg, 0.828 mmol), triethylamine (0.350 mL, 2.51 mmol), 1-hydroxybenzotriazole (231 mg, 1.71 mmol), and 1-(3-dimethylaminopropyl)-3-ethylcarbodiimide hydrochloride (237 mg, 1.71 mmol) were added to a DMF solution (8.3 mL) of the compound of Reference Example 46-4 (277 mg, 1.15 mmol)

while cooling with ice. After stirring for 1.5 hours at room temperature, water was added to the reaction solution, which was then extracted with a hexane/ethyl acetate (1:1) mixture solution. The organic phase was washed with a saturated aqueous sodium hydrogen carbonate solution, 1 N hydrochloric acid, and saturated saline, and then dried over sodium sulfate and filtered, then the filtrate was evaporated under reduced pressure. The resulting residue was purified by silica gel chromatography (eluent: hexane/ethyl acetate=1/2 to 1/3) to obtain the title compound (394 mg).

$^1$H-NMR (CDCl$_3$) δ: 7.78 (1H, s), 7.22 (1H, d, J=8.6 Hz), 6.38 (1H, d, J=8.6 Hz), 5.10-4.90 (3H, m), 4.50-4.38 (2H, m), 4.27-4.10 (3H, m), 3.76 (2H, s), 2.61 (2H, t, J=8.3 Hz), 2.36-2.28 (1H, m), 2.21-2.14 (1H, m), 2.06-2.00 (1H, m), 1.92-1.87 (1H, m), 1.84-1.76 (1H, m), 1.56 (9H, s), 1.54 (9H, s), 1.46 (9H, s), 1.36 (3H, s), 1.28 (3H, s), 1.14-1.08 (2H, m), 1.03 (1H, d, J=10.9 Hz), 0.84 (3H, s).

LCMS: [M+H]$^+$/Rt=795.55/4.19 min$^D$

Reference Example 47: [4-(2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-1H-1,2,3-triazol-1-yl]acetic Acid

[Chemical Formula 731]

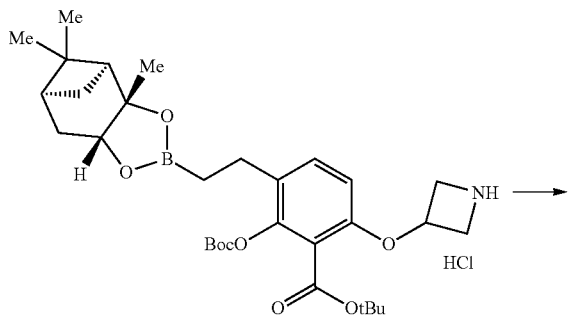

Reference Example 1-8

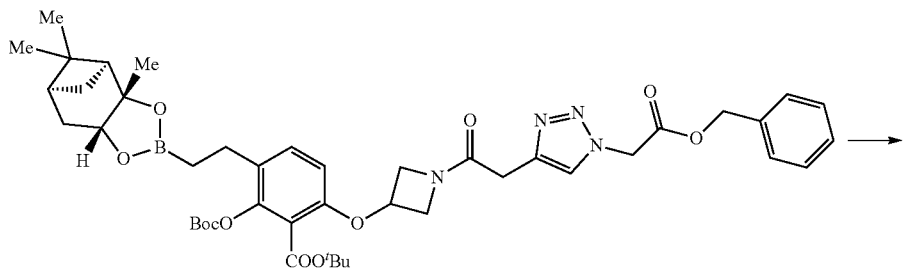

Reference Example 47-1

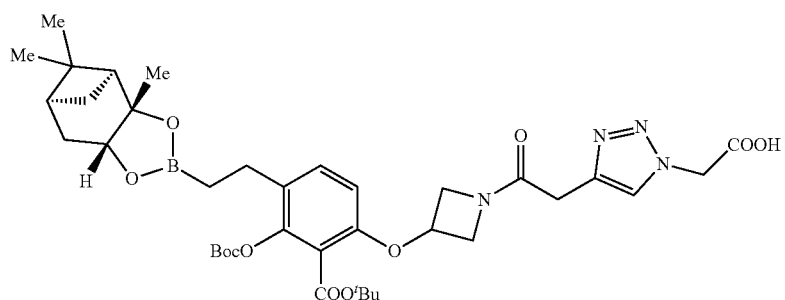

Reference Example 47

Reference Example 47-1: tert-butyl 6-{[1-({1-[2-(benzyloxy)-2-oxoethyl]-1H-1,2,3-triazol-4-yl}acetyl)azetidin-3-yl]oxy}-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

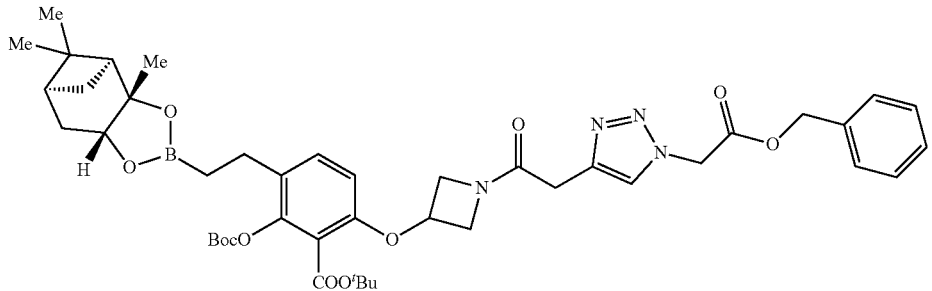

[Chemical Formula 732]

A reaction, work-up, and purification were performed using the compound of Reference Example 1-8 as the starting material by the same method described in Reference Example 36-4 to obtain the title compound.

$^1$H-NMR (CDCl$_3$) δ: 7.77 (1H, s), 7.39-7.31 (5H, m), 7.22 (1H, d, J=8.6 Hz), 6.40 (1H, d, J=8.6 Hz), 5.22 (2H, s), 5.18 (2H, d, J=1.7 Hz), 4.96-4.89 (1H, m), 4.66-4.61 (1H, m), 4.40-4.34 (1H, m), 4.29-4.22 (2H, m), 4.11-4.05 (1H, m), 3.72-3.58 (2H, m), 2.64-2.58 (2H, m), 2.36-2.28 (1H, m), 2.20-2.14 (1H, m), 2.04-2.00 (1H, m), 1.92-1.87 (1H, m), 1.83-1.77 (1H, m), 1.59-1.52 (18H, m), 1.36 (3H, s), 1.28 (3H, s), 1.13-1.09 (2H, m), 1.03 (1H, d, J=10.9 Hz), 0.83 (3H, s).

LCMS: [M+H]$^+$/Rt=829.46/4.22 min$^D$

Reference Example 47: [4-(2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-1H-1,2,3-triazol-1-yl]acetic Acid

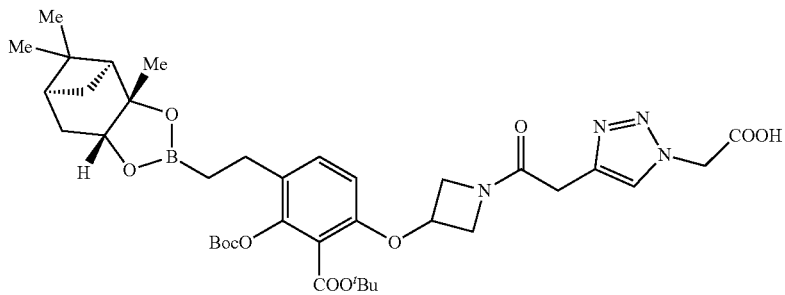

[Chemical Formula 733]

A suspension of 10% palladium on carbon (67.9 mg) in ethyl acetate was added to a methanol (4.1 mL) solution of the compound of Reference Example 47-1 (340 mg, 0.410 mmol). Subsequently, under a hydrogen atmosphere, the reaction mixture was stirred for 2 hours at room temperature. The reaction solution was filtered through celite, and the filtrate was evaporated under reduced pressure to obtain the title compound (271 mg).

$^1$H-NMR (CDCl$_3$) δ: 7.78 (1H, s), 7.21 (1H, d, J=8.6 Hz), 6.39 (1H, d, J=8.0 Hz), 5.17-4.99 (2H, m), 4.98-4.88 (1H, m), 4.61-4.55 (1H, m), 4.41-4.31 (1H, m), 4.27-4.22 (1H, m), 4.14-4.01 (2H, m), 3.70-3.62 (2H, m), 2.60 (2H, t, J=8.3 Hz), 2.37-2.13 (2H, m), 2.04-1.99 (1H, m), 1.92-1.86 (1H, m), 1.83-1.77 (1H, m), 1.55 (9H, s), 1.53 (9H, s), 1.36 (3H, S), 1.28 (3H, s), 1.10 (2H, t, J=8.3 Hz), 1.03 (1H, d, J=10.9 Hz), 0.83 (3H, s).

LCMS: [M+H]$^+$/Rt=739.28/3.84 min$^D$

Reference Example 48: tert-butyl 6-[(1-{[(tert-butoxycarbonyl)amino][1-(2-tert-butoxy-2-oxoethyl)-1H-imidazol-4-yl]acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 734]

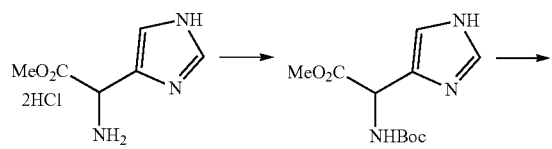
Reference Example 39-1 → Reference Example 48-1

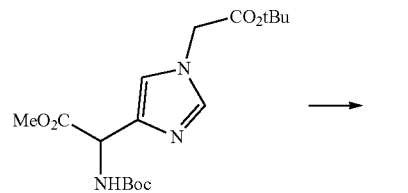
Reference Example 48-2

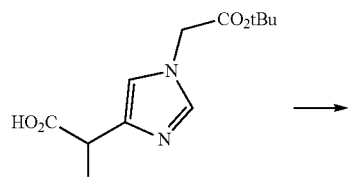
Reference Example 48-3

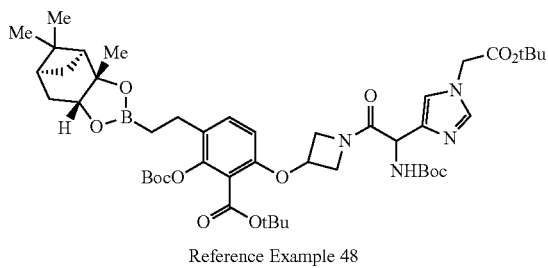
Reference Example 48

Reference Example 48-1: methyl [(tert-butoxycarbonyl)amino](1H-imidazol-4-yl)acetate

[Chemical Formula 735]

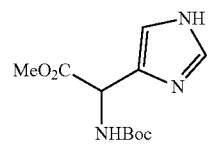

Sodium hydrogen carbonate (1.03 g, 12.2 mmol) and di-tert-butyl dicarbonate (2.06 mL, 8.95 mmol) were added to a THF-water (3:1) mixture solution (18 mL) of the compound of Reference Example 39-1 (928 mg, 4.07 mmol). The reaction mixture was stirred for 20 hours at room temperature and then stirred for 2 days at 70° C. After allowing the reaction solution to cool, water (10 mL) was added, and the mixture was extracted with ethyl acetate. The organic phase was dried over sodium sulfate, filtered, and concentrated. The resulting residue was purified by silica gel column chromatography (eluent: methylene chloride/methanol) to obtain the title compound (368 mg) as a light yellow solid.

$^1$H-NMR (CDCl$_3$) δ: 7.60 (1H, s), 7.06 (1H, s), 5.74 (1H, br), 5.40 (1H, d, J=8.1 Hz), 3.76 (3H, s), 1.45 (9H, s).

LCMS: [M+H]$^+$/Rt=256.2/0.93 min$^B$

Reference Example 48-2: methyl [(tert-butoxycarbonyl)amino][1-(2-tert-butoxy-2-oxoethyl)-1H-imidazol-4-yl]acetate

[Chemical Formula 736]

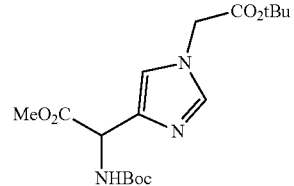

Sodium hydride (23.4 mg, 60% dispersion in liquid paraffin, 0.586 mmol) was added to a DMF solution (2.1 mL) of the compound of Reference Example 48-1 (136 mg, 0.533 mmol) under a nitrogen atmosphere at 0° C., and the reaction mixture was stirred for 30 minutes at room temperature. tert-butyl bromoacetate (86.0 μL, 0.586 mmol) was added, and the reaction mixture was stirred for 3 hours. Methanol (0.1 mL) and then saturated saline (20 mL) were added to the reaction solution, which was extracted with ethyl acetate. The organic phase was dried over sodium sulfate, filtered, and concentrated. The resulting residue was purified by silica gel column chromatography (eluent: hexane/ethyl acetate) to obtain the title compound (155 mg) as a light yellow solid.

$^1$H-NMR (CDCl$_3$) δ: 7.43 (1H, s), 6.98 (1H, s), 5.76 (1H, d, J=8.1 Hz), 5.34 (1H, d, J=8.1 Hz), 4.55 (2H, s), 3.75 (3H, s), 1.47 (9H, s), 1.40 (9H, s).

LCMS: [M+H]$^+$/Rt=370.7/1.59 min$^B$

Reference Example 48-3: [(tert-butoxycarbonyl)amino][1-(2-tert-butoxy-2-oxoethyl)-1H-imidazol-4-yl]acetic acid

[Chemical Formula 737]

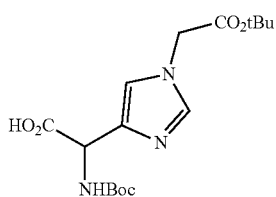

Triethylamine (0.291 mL, 2.10 mmol) was added to an aqueous solution (4.2 mL) of the compound of Reference Example 48-2 (155 mg, 0.420 mmol), and the reaction mixture was stirred for 1 hour. The reaction solution was concentrated under reduced pressure, and the resulting residue was purified by silica gel column chromatography (eluent: methylene chloride/methanol) to obtain the title compound (84.9 mg) as a colorless solid.

$^1$H-NMR (CDCl$_3$) δ: 7.82 (1H, s), 7.01 (1H, s), 5.97 (1H, s), 5.30 (1H, s), 4.62 (2H, s), 1.48 (9H, s), 1.44 (9H, s).
LCMS: [M+H]$^+$/Rt=356.2/1.35 min$^B$

Reference Example 48: tert-butyl 6-[(1-{[(tert-butoxycarbonyl)amino][1-(2-tert-butoxy-2-oxoethyl)-1H-imidazol-4-yl]acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 738]

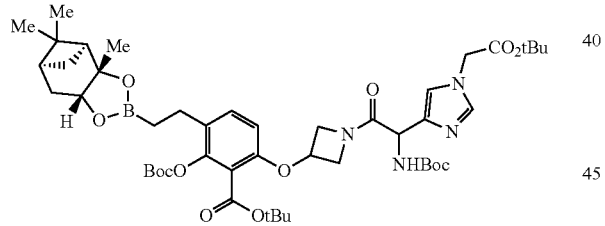

Palladium on carbon (20 mg, Pd content: 10%, wetted with ca. 55% water) was added to a methanol solution (3 mL) of the compound of Reference Example 1-7 (200 mg, 0.283 mmol), and the reaction mixture was stirred for 30 minutes under a hydrogen atmosphere at room temperature. The reaction solution was filtered through cellulose. The filtered substance was washed with methylene chloride, and the combined filtrate was concentrated. The resulting residue was dissolved in DMF (3 mL). Reference Example 48-3 (131 mg, 0.368 mmol), HATU (129 mg, 0.340 mmol), and triethylamine (0.118 mL, 0.850 mmol) were added, and the reaction mixture was stirred for 30 minutes at room temperature. Water was added to the reaction solution, which was extracted with ethyl acetate. The organic phase was washed with saturated saline, dried over sodium sulfate, filtered, and concentrated, and the resulting residue was purified by silica gel column chromatography (eluent: hexane/ethyl acetate) to obtain the title compound (208 mg) as a colorless amorphous compound.

$^1$H-NMR (CDCl$_3$) δ: 7.42 (1H, d, J=2.7 Hz), 7.20 (1H, dd, J=8.1 Hz, 5.4 Hz), 6.97 (1H, d, J=5.4 Hz), 6.36 (1H, d, J=5.4 Hz), 5.86-5.71 (1H, m), 5.26 (1H, d, J=8.1 Hz), 4.98-4.82 (1H, m), 4.76-4.05 (7H, m), 2.63-2.57 (2H, m), 2.36-2.27 (1H, m), 2.20-2.13 (1H, m), 2.04-2.00 (1H, m), 1.92-1.77 (2H, m), 1.61 (9H, s), 1.53 (9H, s), 1.48-1.42 (18H, m), 1.36 (3H, s), 1.26 (3H, s), 1.13-1.01 (3H, m), 0.83 (3H, s).
LCMS: [M+H]$^+$/Rt=910.2/2.97 min$^B$

Reference Example 49: tert-butyl 6-[(1-{[1-(2-amino-2-oxoethyl)-1H-imidazol-4-yl][(tert-butoxycarbonyl)amino]acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 739]

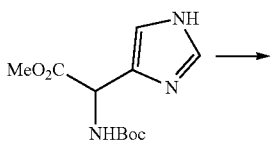

Reference Example 48-1

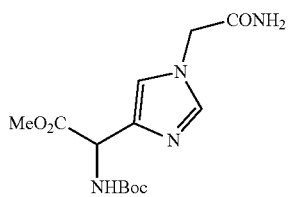

Reference Example 49-1


½ Et$_3$N complex
Reference Example 49-2

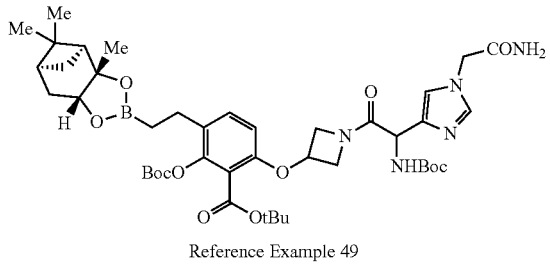

Reference Example 49

Reference Example 49-1: methyl [1-(2-amino-2-oxoethyl)-1H-imidazol-4-yl][(tert-butoxycarbonyl)amino]acetate

[Chemical Formula 740]

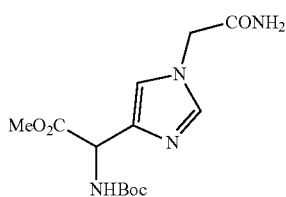

Sodium hydroxide (70.5 mg, 60% dispersion in liquid paraffin, 1.76 mmol) was added to a DMF solution (6.4 mL) of the compound of Reference Example 48-1 (409 mg, 1.60 mmol) under a nitrogen atmosphere at 0° C., and the reaction mixture was stirred for 30 minutes at room temperature. 2-bromoacetamide (243 mg, 1.76 mmol) was added, and the reaction mixture was stirred for 1.5 hours. Methanol (0.1 mL) was added to the reaction solution, and the mixture was purified by silica gel column chromatography (eluent: methylene chloride/methanol) to obtain a mixture (564 mg) of the title compound and a regioisomer thereof. The resulting mixture was further purified by silica gel column chromatography (amine silica gel, eluent: ethyl acetate/methanol). The resulting mixture (396 mg) of the title compound and a regioisomer thereof was triturated in methylene chloride, filtered, and dried and solidified under reduced pressure to obtain the title compound (198 mg) as a colorless solid.

$^1$H-NMR (DMSO-$d_6$) δ: 7.51 (1H, s), 7.47-7.19 (3H, m), 7.10 (1H, s), 5.19 (1H, d, J=8.1 Hz), 4.59 (2H, s), 3.62 (3H, s), 1.39 (9H, s).

LCMS: [M+H]$^+$/Rt=313.2/0.66 min$^B$

Reference Example 49-2: [1-(2-amino-2-oxoethyl)-1H-imidazol-4-yl][(tert-butoxycarbonyl)amino]acetic acid·1/2(triethylamine) salt

[Chemical Formula 741]

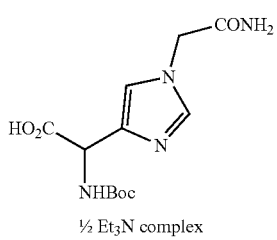

½ Et$_3$N complex

Triethylamine (0.204 mL, 1.47 mmol) was added to an aqueous solution (3.0 mL) of the compound of Reference Example 49-1 (92.0 mg, 0.295 mmol), and the reaction mixture was stirred for 30 minutes. The reaction solution was concentrated under reduced pressure to obtain the title compound (123 mg) as a colorless amorphous compound.

$^1$H-NMR (CD$_3$OD) δ: 7.69 (1H, s), 7.08 (1H, s), 5.03 (1H, s), 4.72 (2H, s), 3.62 (3H, s), 3.18 (3H, q, J=8.1 Hz), 1.42 (9H, s), 1.29 (4.5H, t, J=8.1 Hz).

LCMS: [M+H]$^+$/Rt=299.4/0.50 min$^B$

Reference Example 49: tert-butyl 6-[(1-{[1-(2-amino-2-oxoethyl)-1H-imidazol-4-yl][(tert-butoxycarbonyl)amino]acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 742]

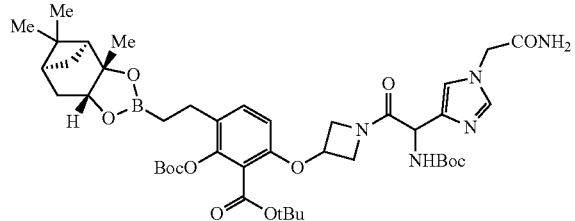

A reaction, work-up, and purification were performed using the compound of Reference Example 1-7 (200 mg, 0.283 mmol) and the compound of Reference Example 49-2 (109 mg, 0.312 mmol) as the starting materials by the same method described in Reference Example 42 to obtain the title compound (130 mg) as a colorless solid.

$^1$H-NMR (CDCl$_3$) δ: 7.46 (1H, s), 7.21 (1H, dd, J=8.1 Hz, 5.4 Hz), 6.97-6.95 (1H, m), 6.41-6.37 (1H, m), 5.88-5.59 (3H, m), 5.25-5.22 (1H, m), 5.00-4.87 (1H, m), 4.83-4.57 (3H, m), 4.48-4.33 (1H, m), 4.27-4.23 (1H, m), 4.16-4.05 (2H, m), 2.63-2.57 (2H, m), 2.36-2.27 (1H, m), 2.19-2.13 (1H, m), 2.04-2.00 (1H, m), 1.92-1.77 (2H, m), 1.62-1.53 (18H, m), 1.43 (9H, s), 1.36 (3H, s), 1.26 (3H, s), 1.13-1.00 (3H, m), 0.83 (3H, s).

LCMS: [M+H]$^+$/Rt=853.0/2.49 min$^B$

Reference Example 50: tert-butyl 6-[(1-{[(tert-butoxycarbonyl)amino](1H-1,2,3-triazol-4-yl)acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 743]

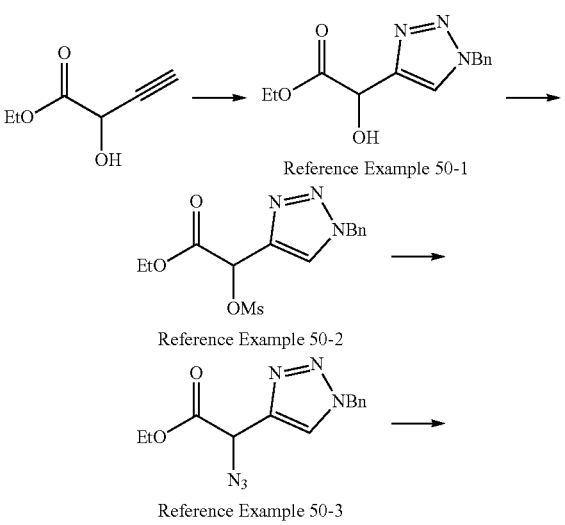

Reference Example 50-1

Reference Example 50-2

Reference Example 50-3

-continued

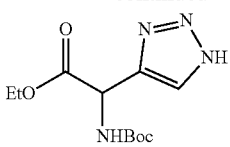

Reference Example 50-4

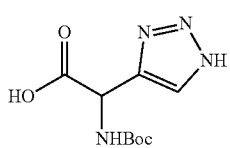

Reference Example 50-5

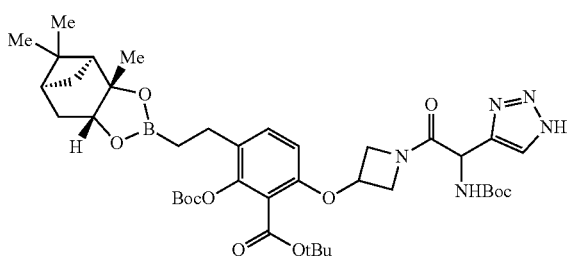

Reference Example 50

Reference Example 50-1: ethyl (1-benzyl-1H-1,2,3-triazol-4-yl)(hydroxy)acetate

[Chemical Formula 744]

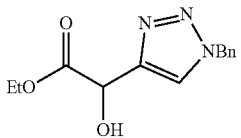

After adding benzylazide (0.10 mL), copper iodide (44.6 mg, 0.234 mmol), and tris[(1-benzyl-1H-1,2,3-triazol-4-yl)methyl]amine (41.4 mg, 78.0 μmol) to an acetonitrile (7.8 mL) solution of ethyl 2-hydroxy-3-butynoate (91 μL, 0.780 mmol) and stirring the reaction mixture for 5 hours at room temperature, a saturated aqueous potassium sodium tartrate solution was added to the reaction solution, and the mixture was extracted with chloroform. The organic phase was washed with saturated saline, and then dried over anhydrous sodium sulfate and filtered, then the filtrate was evaporated under reduced pressure. The resulting residue was purified by silica gel chromatography (eluent: hexane/ethyl acetate=1/2) to obtain the title compound (187 mg).

$^1$H-NMR (CDCl$_3$) δ: 7.45 (1H, s), 7.38-7.33 (3H, m), 7.27-7.23 (2H, m), 5.50 (2H, s), 5.34 (1H, d, J=5.7 Hz), 4.33-4.18 (2H, m), 3.44 (1H, d, J=6.3 Hz), 1.24 (3H, t, J=7.2 Hz).

Reference Example 50-2: ethyl (1-benzyl-1H-1,2,3-triazol-4-yl)[(methanesulfonyl)oxy]acetate

[Chemical Formula 745]

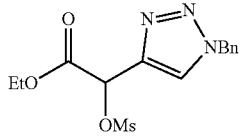

Under a nitrogen atmosphere, triethylamine (0.12 mL, 0.856 mmol) and methanesulfonyl chloride (36 μL, 0.476 mmol) were added to a dichloromethane (1.9 mL) solution of the compound of Reference Example 50-1 (102 mg, 0.389 mmol), and the reaction mixture was stirred for 4 hours at 0° C. Subsequently, a saturated aqueous sodium hydrogen carbonate solution was added to the reaction solution, which was extracted with ethyl acetate. The organic phase was washed with saturated saline, and then dried over sodium sulfate and filtered, then the filtrate was evaporated under reduced pressure to obtain the title compound (110 mg).

$^1$H-NMR (CDCl$_3$) δ: 7.59 (1H, s), 7.39-7.36 (3H, m), 7.28-7.25 (2H, m), 6.16 (1H, s), 5.57-5.47 (2H, m), 4.33-4.22 (2H, m), 3.14 (3H, s), 1.27-1.24 (3H, m).

Reference Example 50-3: ethyl azide(1-benzyl-1H-1,2,3-triazol-4-yl)acetate

[Chemical Formula 746]

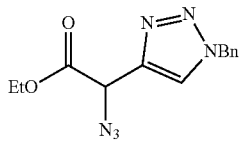

Under a nitrogen atmosphere, a DMF (4.0 mL) solution of the compound of Reference Example 50-2 (156 mg, 0.406 mmol) was cooled with ice. Sodium azide (39.6 mg, 0.609 mmol) was added, and the reaction mixture was stirred for 3.5 hours while cooling with ice. Subsequently, a saturated sodium hydrogen carbonate solution was added, and the mixture was extracted with ethyl acetate. The organic phase was washed with saturated saline, and then dried over sodium sulfate and filtered, then the filtrate was evaporated under reduced pressure. The resulting residue was purified by silica gel chromatography (eluent: hexane/ethyl acetate=2/1 to 1/1) to obtain the title compound (88.7 mg).

$^1$H-NMR (CDCl$_3$) δ: 7.56 (1H, s), 7.40-7.37 (3H, m), 7.29-7.26 (2H, m), 5.55 (2H, s), 5.14 (1H, s), 4.34-4.19 (2H, m), 1.30-1.25 (3H, m).

Reference Example 50-4: ethyl [(tert-butoxycarbonyl)amino](1H-1,2,3-triazol-4-yl)acetate

[Chemical Formula 747]

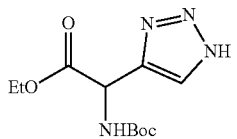

The compound of Reference Example 50-3 (101 mg, 0.349 mmol) and di-tert-butyl dicarbonate (114 mg, 0.524 mmol) were added to an ethanol (12 mL) solution of 10% palladium on carbon (10.4 mg), and then, under a hydrogen atmosphere, the reaction mixture was stirred for 2 hours at room temperature. Subsequently, 1M hydrochloric acid (0.35 mL) was added to the reaction solution, and the reaction mixture was further stirred for 44 hours at room temperature. The reaction solution was filtered through celite, and the filtrate was evaporated under reduced pressure to obtain the title compound (98.9 mg).

$^1$H-NMR (CDCl$_3$) δ: 7.74 (1H, s), 5.81-5.49 (2H, m), 4.34-4.09 (2H, m), 1.44 (9H, s), 1.27-1.21 (3H, m).

Reference Example 50-5: [(tert-butoxycarbonyl)amino](1H-1,2,3-triazol-4-yl)acetic Acid

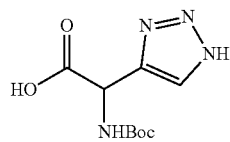

[Chemical Formula 748]

Lithium hydroxide monohydrate (14.1 mg, 0.336 mmol) was added to a THF/water (3:1) mixture solution (1.7 mL) of the compound of Reference Example 50-4 (45.4 mg, 0.168 mmol), and the reaction mixture was stirred for 3 hours at room temperature. Subsequently, 1M hydrochloric acid was added until the pH was 4, and the mixture was extracted with ethyl acetate, and then the aqueous layer was extracted again with chloroform. The organic phase was washed with saturated saline, and then dried over sodium sulfate and filtered, then the filtrate was evaporated under reduced pressure. The resulting residue was washed and purified by decantation with diethyl ether to obtain the title compound (12.7 mg).

$^1$H-NMR (CD$_3$OD) δ: 7.93-7.65 (1H, m), 5.51-5.32 (1H, m), 1.45 (9H, s).

Reference Example 50: tert-butyl 6-[(1-{[(tert-butoxycarbonyl)amino](1H-1,2,3-triazol-4-yl)acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 749]

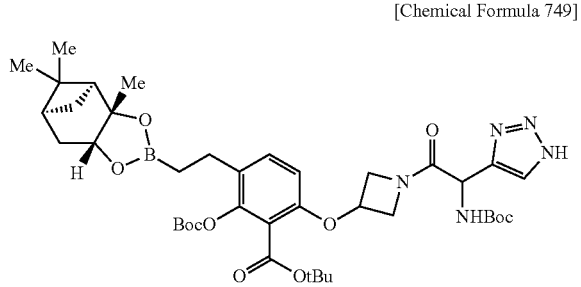

A reaction, work-up, and purification were performed using the compound of Reference Example 1-8 and the compound of Reference Example 50-5 as the starting materials by the same method described in Reference Example 36-4 to obtain the title compound.

$^1$H-NMR (CDCl$_3$) δ: 7.71-7.62 (1H, m), 7.24-7.17 (1H, m), 6.39-6.32 (1H, m), 5.96-5.78 (1H, m), 5.52-5.37 (1H, m), 5.04-4.84 (1H, m), 4.62-3.93 (5H, m), 2.67-2.58 (2H, m), 2.51-2.27 (1H, m), 2.25-2.12 (1H, m), 2.04-1.99 (1H, m), 1.95-1.86 (1H, m), 1.83-1.74 (1H, m), 1.66-1.26 (33H, m), 1.14-1.08 (2H, m), 1.04-0.99 (1H, m), 0.83 (3H, s).

LCMS: [M+H]$^+$/Rt=796.42/2.30 min$^D$

Reference Example 51: tert-butyl 2-[(tert-butoxycarbonyl)oxy]-6-({1-[(4-nitro-1H-1,2,3-triazol-1-yl)acetyl]azetidin-3-yl}oxy)-3-{2-[(3aS,4S,6S,7aR)-3a,5,5-trimethylhexahydro-2H-4,6-methano-1,3,2-benzodioxaborol-2-yl]ethyl}benzoate

[Chemical Formula 750]

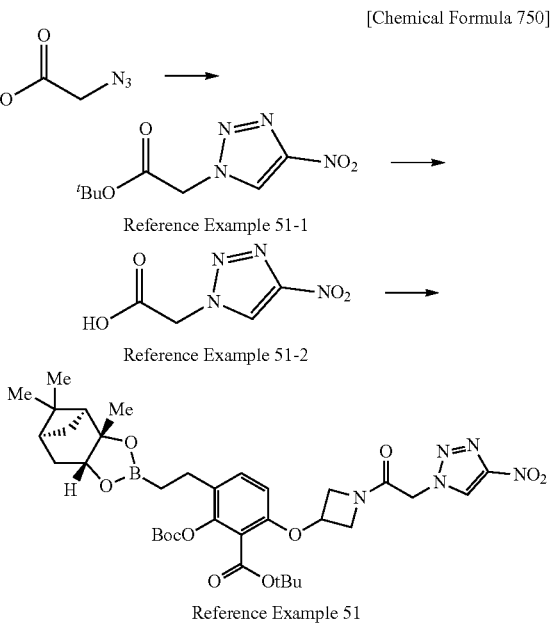

Reference Example 51-1

Reference Example 51-2

Reference Example 51

Reference Example 51-1: tert-butyl (4-nitro-1H-1,2,3-triazol-1-yl)acetate

[Chemical Formula 751]

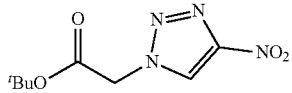

1-(dimethylamino)-2-nitroethylene (1.57 g, 13.5 mmol) was added to a 1,4-dioxane (8.2 mL) solution of tert-butyl 2-azidoacetate (1.29 g, 8.21 mmol), and the reaction mixture was stirred for 12 hours under microwave irradiation at 120° C. Subsequently, the reaction solution was evaporated under reduced pressure to obtain the title compound (226 mg).

$^1$H-NMR (CDCl$_3$) δ: 8.45 (1H, s), 5.13 (2H, s), 1.50 (9H, s).

LCMS: [M+H]$^+$/Rt=229.13/2.48 min$^D$

Reference Example 51-2: (4-nitro-1H-1,2,3-triazol-1-yl)acetic Acid

[Chemical Formula 752]

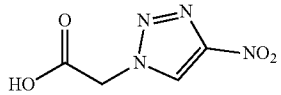

A 4 N hydrogen chloride·1,4-dioxane solution (14 mL) was added to the compound of Reference Example 51-1 (329 mg, 1.44 mmol), and the reaction mixture was stirred for 23 hours at room temperature. Subsequently, the reaction solution was evaporated under reduced pressure to obtain the title compound.

$^1$H-NMR (CD$_3$OD) δ: 8.94 (1H, s), 5.35-5.30 (2H, m).

Reference Example 51: tert-butyl 2-[(tert-butoxycarbonyl)oxy]-6-({1-[(4-nitro-1H-1,2,3-triazol-1-yl)acetyl]azetidin-3-yl}oxy)-3-{2-[(3aS,4S,6S,7aR)-3a,5,5-trimethylhexahydro-2H-4,6-methano-1,3,2-benzodioxaborol-2-yl]ethyl}benzoate

[Chemical Formula 753]

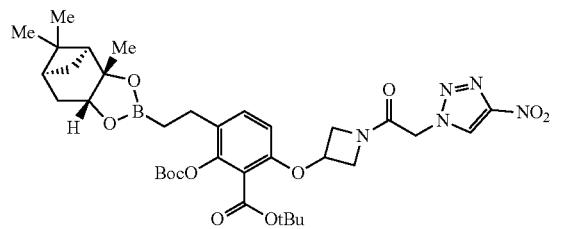

A reaction, work-up, and purification were performed using the compound of Reference Example 1-8 and the compound of Reference Example 51-2 as the starting materials by the same method described in Reference Example 36-4 to obtain the title compound.

$^1$H-NMR (CDCl$_3$) δ: 8.57 (1H, s), 6.43 (1H, d, J=8.6 Hz), 5.16-4.98 (3H, m), 4.65-4.57 (1H, m), 4.48-4.41 (1H, m), 4.36-4.29 (1H, m), 4.26-4.21 (1H, m), 4.20-4.13 (1H, m), 2.66-2.56 (2H, m), 2.33-2.28 (1H, m), 2.18-2.13 (1H, m), 2.05-1.97 (1H, m), 1.91-1.85 (1H, m), 1.82-1.75 (2H, m), 1.55 (9H, s), 1.52 (9H, s), 1.34 (3H, s), 1.26 (3H, s), 1.12-1.07 (2H, m), 1.03-0.98 (1H, m), 0.82 (3H, s).

Reference Example 52: tert-butyl 2-[(tert-butoxycarbonyl)oxy]-6-[(1-D-serylazetidin-3-yl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 754]

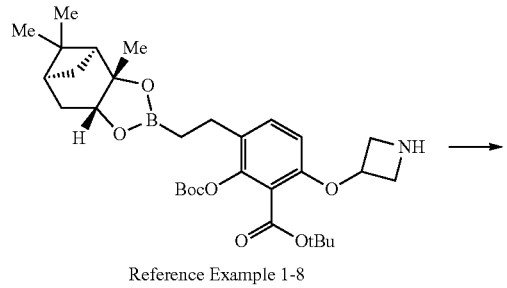

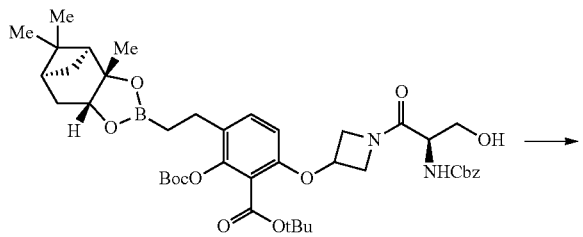

Reference Example 52-1

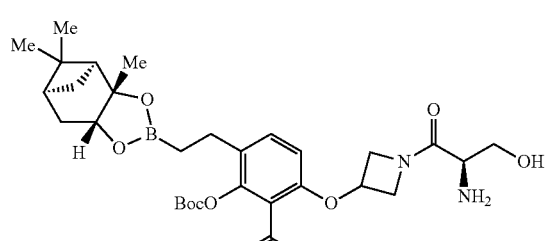

Reference Example 52

Reference Example 52-1: tert-butyl 6-[(1-{N-[(benzyloxy)carbonyl]-D-seryl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 755]

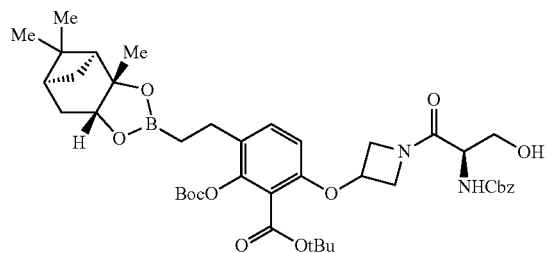

A reaction, work-up, and purification were performed using the compound of Reference Example 1-8 (114.4 mg, 0.188 mmol) and N-carbobenzoxy-D-serine (91.8 mg, 0.384 mmol) as the starting materials by the same method described in Reference Example 3 to obtain the title compound (71.4 mg).

$^1$H-NMR (CD$_3$OD) δ: 7.39-7.26 (6H, m), 6.67 (1H, d, J=8.5 Hz), 5.12-5.05 (3H, m), 4.39-4.33 (1H, m), 4.29 (2H, d, J=8.5 Hz), 4.00-3.94 (1H, m), 3.74-3.67 (2H, m), 3.34 (2H, s), 2.58 (2H, t, J=7.9 Hz), 2.39-2.32 (1H, m), 2.21-2.16 (1H, m), 1.99 (1H, t, J=5.5 Hz), 1.89-1.87 (1H, m), 1.79 (1H, d, J=15.3 Hz), 1.55 (9H, d, J=7.9 Hz), 1.52 (9H, s), 1.35 (3H, s), 1.29 (3H, s), 1.08 (2H, t, J=8.2 Hz), 0.99 (1H, d, J=10.4 Hz), 0.86 (3H, s).

LCMS: [M+H]$^+$/Rt=793.48/1.381 min$^{-1}$

Reference Example 52: tert-butyl 2-[(tert-butoxy-carbonyl)oxy]-6-[(1-D-serylazetidin-3-yl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 756]

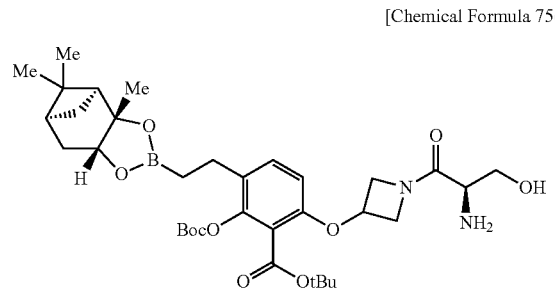

Palladium on carbon (20 mg, Pd content: 10%, wetted with ca. 55% water) was added to a methanol solution (3.0 mL) of the compound of Reference Example 52-1 (200 mg, 0.252 mmol), and the reaction mixture was stirred for 30 minutes under a hydrogen atmosphere at room temperature. The reaction solution was filtered through cellulose. The filtered substance was washed with methylene chloride, and the combined filtrate was concentrated to obtain the title compound (198 mg).

$^1$H-NMR (CDCl$_3$) δ: 7.23 (1H, d, J=8.1 Hz), 6.44-6.40 (1H, m), 5.01-4.94 (1H, m), 4.71-4.06 (5H, m), 3.74-3.49 (3H, m), 2.64-2.58 (2H, m), 2.45-2.00 (6H, m), 1.93-1.77 (2H, m), 1.56 (9H, s), 1.54 (9H, s), 1.36 (3H, s), 1.28 (3H, s), 1.14-1.01 (3H, m), 0.84 (3H, s).

LCMS: [M+H]$^+$/Rt=659.7/2.31 min$^3$

Reference Example 53: tert-butyl 6-({1-[N$^2$-(tert-butoxycarbonyl)-N-methyl-D-asparaginyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 757]

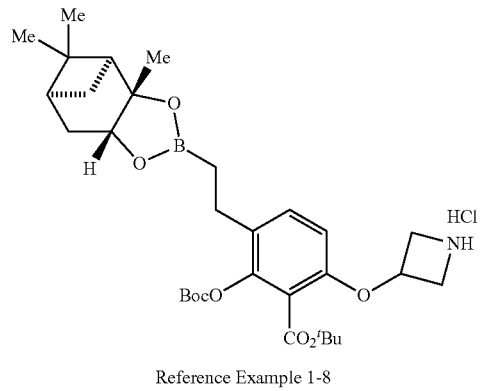
Reference Example 1-8

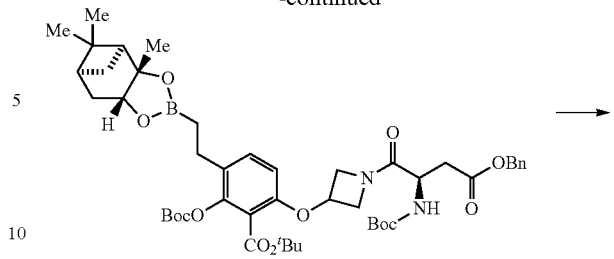
Reference Example 53-1

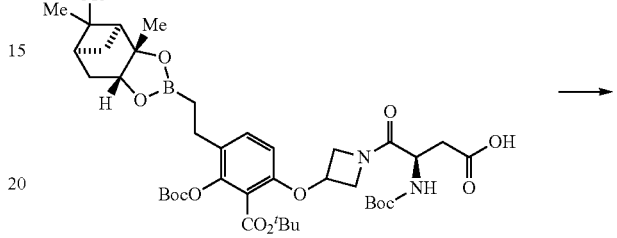
Reference Example 53-2

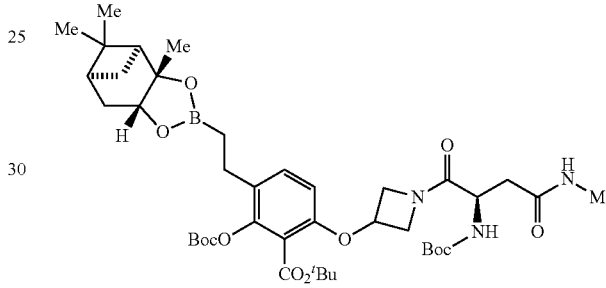
Reference Example 53

Reference Example 53-1: tert-butyl 6-[(1-{(2R)-4-(benzyloxy)-2-[(tert-butoxycarbonyl)amino]-4-oxobutanoyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 758]

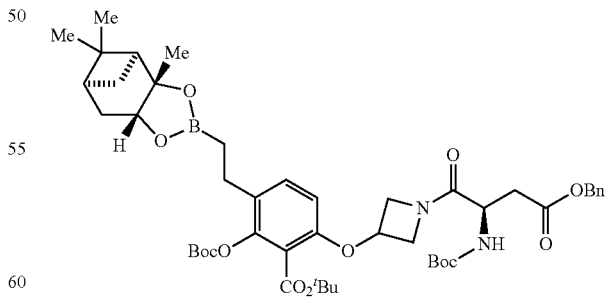

A reaction, work-up, and purification were performed using the compound of Reference Example 1-8 and benzyl (R)-3-[(tert-butoxycarbonyl)amino]-4-oxobutanoate as the starting materials by the same method described in Reference Example 3 to obtain the title compound (1.84 g).

¹H-NMR (CDCl₃) δ: 7.40-7.31 (5H, m), 7.21 (1H, d, J=8.6 Hz), 6.40-6.30 (1H, m), 5.37-5.24 (1H, m), 5.16-5.07 (2H, m), 4.97-4.54 (3H, m), 4.42-4.27 (2H, m), 4.27-4.22 (1H, m), 4.08-4.00 (1H, m), 2.84-2.73 (2H, m), 2.65-2.57 (2H, m), 2.37-2.27 (1H, m), 2.24-2.13 (1H, m), 2.04-2.00 (1H, m), 1.93-1.87 (1H, m), 1.84-1.77 (1H, m), 1.56 (9H, s), 1.53 (9H, s), 1.44-1.40 (9H, m), 1.36 (3H, s), 1.28 (3H, s), 1.15-1.08 (2H, m), 1.06-1.01 (1H, m), 0.84 (3H, s).

LCMS: [M+H]⁺/Rt=877.72/4.54 min$^D$

Reference Example 53-2: (3R)-3-[(tert-butoxycarbonyl)amino]-4-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-4-oxobutanoic Acid

[Chemical Formula 759]

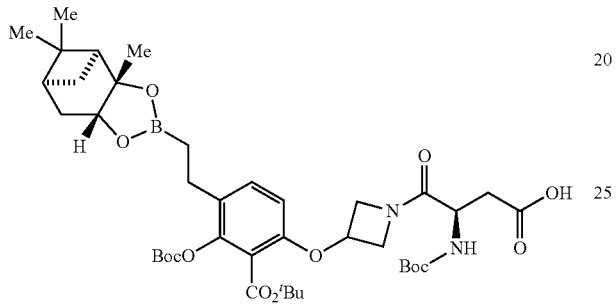

A suspension of 10% palladium on carbon (150 mg) in ethyl acetate was added to an ethyl acetate (17 mL) solution of the compound of Example 53-1 (1.50 g, 1.71 mmol). Subsequently, under a hydrogen atmosphere, the reaction mixture was stirred for 3 hours at room temperature. The reaction solution was filtered through celite, and the filtrate was evaporated under reduced pressure to obtain the title compound (1.34 g).

¹H-NMR (CD₃OD) δ: 7.32 (1H, d, J=8.0 Hz), 6.69 (1H, d, J=8.6 Hz), 5.15-5.08 (1H, m), 4.63-4.59 (1H, m), 4.55-4.27 (4H, m), 3.99-3.92 (1H, m), 2.82-2.69 (1H, m), 2.61-2.51 (3H, m), 2.40-2.31 (1H, m), 2.23-2.14 (1H, m), 2.02-1.97 (2H, m), 1.92-1.86 (1H, m), 1.83-1.76 (1H, m), 1.57 (9H, s), 1.52 (9H, s), 1.47-1.40 (9H, m), 1.36 (3H, s), 1.30 (3H, s), 1.11-1.05 (2H, m), 1.02-0.96 (1H, m), 0.86 (3H, s).

LCMS: [M+H]⁺/Rt=787.62/4.14 min$^D$

Reference Example 53: tert-butyl 6-({1-[N²-(tert-butoxycarbonyl)-N-methyl-D-asparaginyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 760]

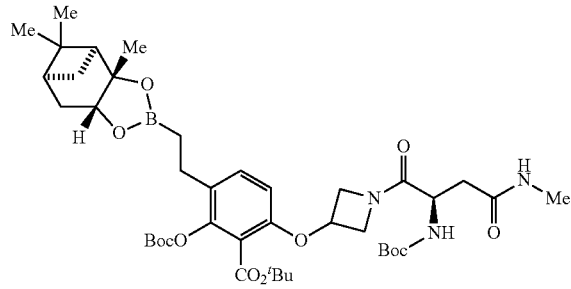

A reaction, work-up, and purification were performed using the compound of Reference Example 53-2 and methylamine hydrochloride as the starting materials by the same method described in Reference Example 36-4 to obtain the title compound (270 mg).

¹H-NMR (CD₃OD) δ: 7.32 (1H, d, J=8.6 Hz), 6.68 (1H, d, J=8.6 Hz), 5.14-5.07 (1H, m), 4.61-4.27 (5H, m), 4.00-3.91 (1H, m), 2.74-2.54 (6H, m), 2.49-2.41 (1H, m), 2.41-2.32 (1H, m), 2.23-2.14 (1H, m), 2.01-1.97 (1H, m), 1.92-1.86 (1H, m), 1.83-1.76 (1H, m), 1.57 (9H, s), 1.52 (9H, s), 1.46-1.40 (9H, m), 1.36 (3H, s), 1.30 (3H, s), 1.11-1.04 (2H, m), 1.01-0.95 (1H, m), 0.86 (3H, s).

LCMS: [M+H]⁺/Rt=800.73/4.09 min$^D$

Reference Example 54: tert-butyl 6-({1-[N²-(tert-butoxycarbonyl)-N,N-dimethyl-D-asparaginyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 761]

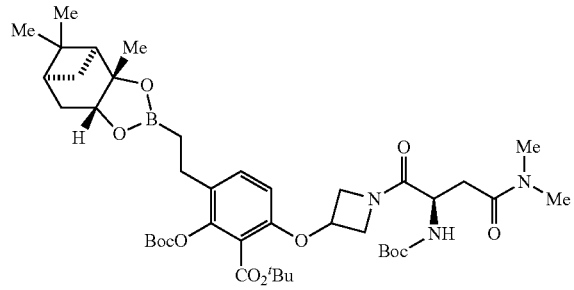

A reaction, work-up, and purification were performed using the compound of Reference Example 53-2 and dimethylamine hydrochloride as the starting materials by the same method described in Reference Example 36-4 to obtain the title compound (251 mg).

¹H-NMR (CDCl₃) δ: 7.18 (1H, d, J=8.6 Hz), 6.36 (1H, d, J=8.6 Hz), 5.82-5.50 (1H, m), 4.94-4.86 (1H, m), 4.85-4.72 (1H, m), 4.64-4.53 (1H, m), 4.43-4.31 (2H, m), 4.26-4.19 (1H, m), 4.08-3.99 (1H, m), 2.99-2.84 (8H, m), 2.62-2.54 (2H, m), 2.34-2.25 (1H, m), 2.18-2.12 (1H, m), 2.02-1.98 (1H, m), 1.90-1.85 (1H, m), 1.83-1.75 (1H, m), 1.54 (9H, s), 1.51 (9H, s), 1.40 (9H, s), 1.33 (3H, s), 1.26 (3H, s), 1.12-1.06 (2H, m), 1.03-0.99 (1H, m), 0.81 (3H, s).

LCMS: [M+H]⁺/Rt=814.69/4.15 min$^D$

531

Reference Example 55: tert-butyl 6-{[(3R)-1-{[(tert-butoxycarbonyl)amino](1H-imidazol-4-yl)acetyl}pyrrolidin-3-yl]oxy}-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 762]

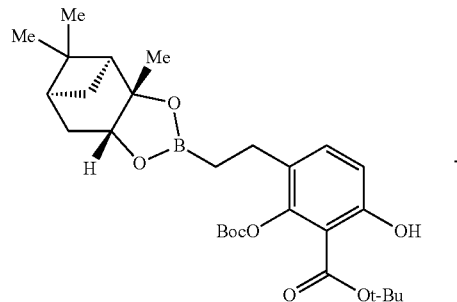

Reference Example 1-6

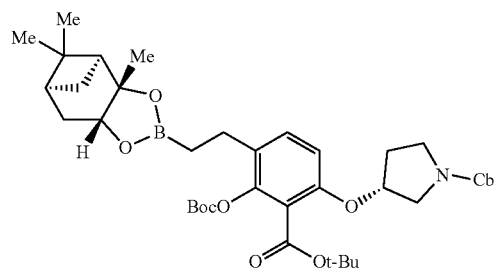

Reference Example 55-1

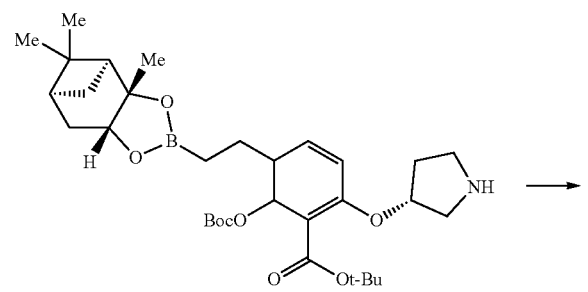

Reference Example 55-2

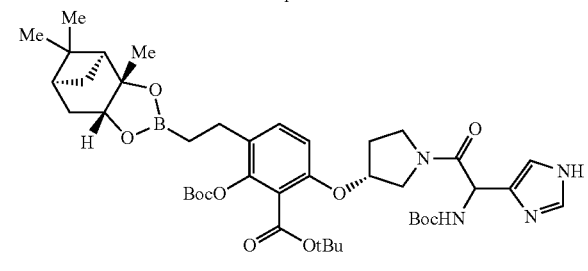

Reference Example 55

532

Reference Example 55-1: benzyl (3R)-3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]pyrrolidine-1-carboxylate

[Chemical Formula 763]

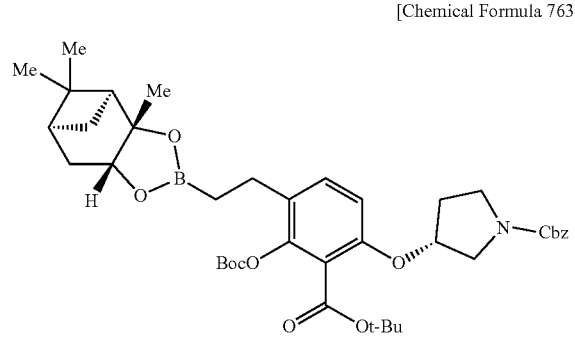

Cyanomethylenetri-n-butylphosphorane (0.762 mL, 2.90 mmol) was added dropwise to a toluene solution (5 mL) of the compound of Reference Example 1-6 (500 mg, 0.968 mmol) and (S)-1-Cbz-3-pyrrolidinol (321 mg). The reaction solution was warmed up to 100° C., and stirred for 3 hours. The reaction solution was evaporated under reduced pressure, and the resulting residue was purified by silica gel column chromatography (eluent: hexane/ethyl acetate=90/10 to 65/35) to obtain the title compound (681 mg).

$^1$H-NMR (CDCl$_3$) δ: 7.29-7.25 (5H, m), 7.14 (1H, dd, J=8.5, 3.0 Hz), 6.60 (1H, dd, J=12.2, 8.5 Hz), 5.08-5.03 (2H, m), 4.82 (1H, s), 4.18-4.16 (1H, m), 3.69-3.45 (4H, m), 2.55-2.53 (2H, m), 2.26-2.23 (1H, m), 2.14-2.10 (2H, m), 1.96-1.94 (2H, m), 1.84-1.81 (1H, m), 1.76-1.72 (1H, m), 1.45-1.44 (18H, m), 1.29 (3H, s), 1.21 (3H, s), 1.05-1.03 (2H, m), 0.97 (1H, d, J=10.4 Hz), 0.76 (3H, s).

Reference Example 55-2: tert-butyl 2-[(tert-butoxycarbonyl)oxy]-6-{[(3R)-pyrrolidin-3-yl]oxy}-3-{2-[(3aS,4S,6S,7aR)-3a,5,5-trimethylhexahydro-2H-4,6-methano-1,3,2-benzodioxaborol-2-yl]ethyl}benzoate

[Chemical Formula 764]

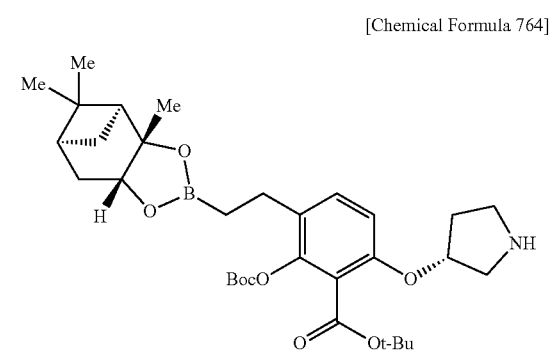

10% palladium on carbon (340 mg) was added to a methanol (5 mL) solution of the compound of Reference Example 55-1 (681 mg, 0.945 mmol), and the reaction mixture was stirred for 5 hours under a hydrogen atmosphere at room temperature. The reaction solution was filtered through celite, and the filtrate was evaporated under reduced pressure. The resulting residue was purified by silica gel column chromatography (eluent: chloroform/methanol=95/5 to 80/20) to obtain the title compound (333 mg).

LCMS: [M+H]⁺/Rt=586/0.990 min$^D$

Reference Example 55: tert-butyl 6-{[(3R)-1-{[(tert-butoxycarbonyl)amino](1H-imidazol-4-yl)acetyl}pyrrolidin-3-yl]oxy}-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 765]

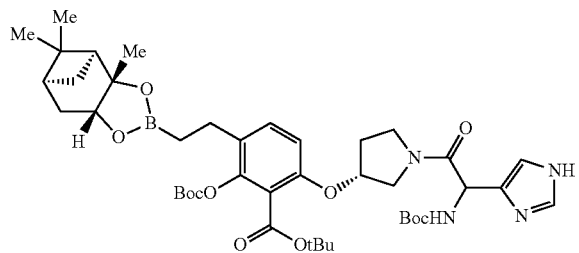

A reaction, work-up, and purification were performed using the compound of Reference Example 55-2 (86 mg, 0.138 mmol) as the starting material by the same method described in Reference Example 36-4 to obtain the title compound (90.7 mg).

LCMS: [M+H]⁺/Rt=809.53/0.874 min$^E$

Reference Example 56: tert-butyl 4-(1-[(tert-butoxycarbonyl)amino]-2-{(3S)-3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]pyrrolidin-1-yl}-2-oxoethyl)-1H-imidazole-1-carboxylate

[Chemical Formula 766]

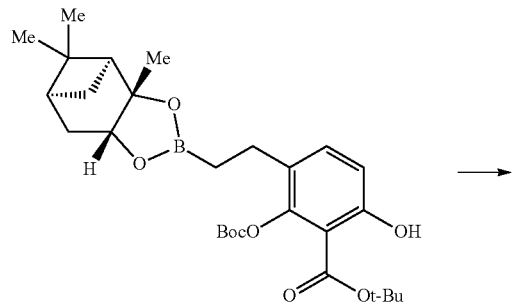

Reference Example 1-6

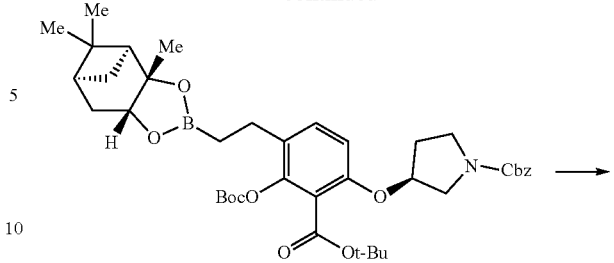

Reference Example 56-1

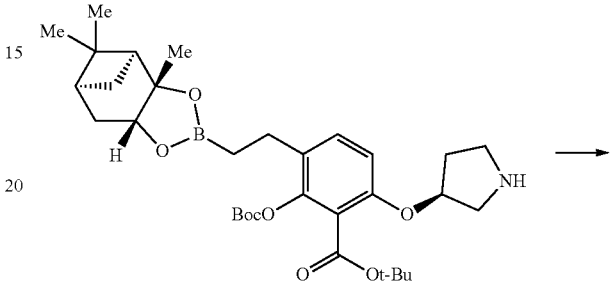

Reference Example 56-2

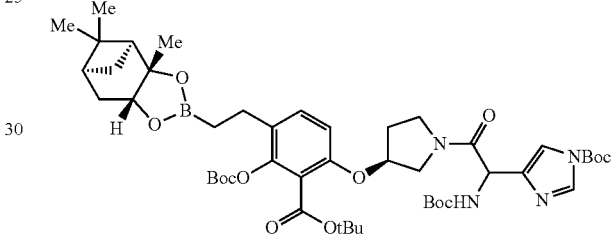

Reference Example 56

Reference Example 56-1: benzyl (3S)-3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]pyrrolidine-1-carboxylate

[Chemical Formula 767]

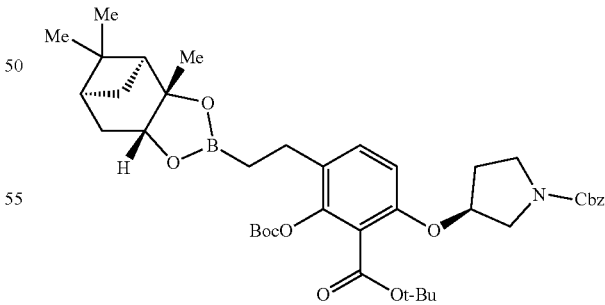

A reaction, work-up, and purification were performed using the compound of Reference Example 1-6 and (R)-1-Cbz-3-pyrrolidinol as the starting materials by the same method described in Reference Example 55-1 to obtain the title compound.

¹H-NMR (CDCl₃) δ: 7.30-7.21 (5H, m), 7.17-7.11 (1H, m), 6.60 (1H, dd, J=12.8, 8.5 Hz), 5.10-5.01 (2H, m), 4.83-4.80 (1H, m), 4.18-4.16 (1H, m), 3.69-3.45 (4H, m), 2.55-2.53 (2H, m), 2.28-2.21 (1H, m), 2.14-2.10 (2H, m), 1.95 (2H, t, J=5.5 Hz), 1.83-1.80 (1H, m), 1.76-1.72 (1H, m), 1.45-1.44 (18H, m), 1.29 (3H, s), 1.21 (3H, s), 1.05-1.03 (2H, m), 0.97 (1H, d, J=11.0 Hz), 0.76 (3H, s).

Reference Example 56-2: tert-butyl 2-[(tert-butoxycarbonyl)oxy]-6-{[(3S)-pyrrolidin-3-yl]oxy}-3-{2-[(3aS,4S,6S,7aR)-3a,5,5-trimethylhexahydro-2H-4,6-methano-1,3,2-benzodioxaborol-2-yl]ethyl}benzoate

[Chemical Formula 768]

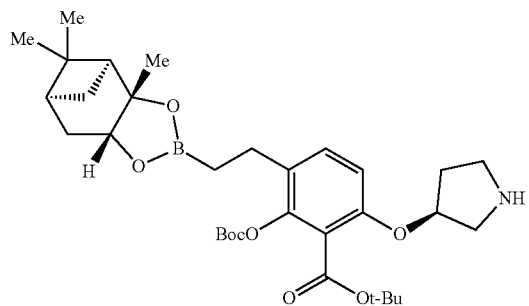

A reaction, work-up, and purification were performed using the compound of Reference Example 56-1 as the starting material by the same method described in Reference Example 55-2 to obtain the title compound.
LCMS: [M+H]$^+$/Rt=586/0.993 min$^D$ Reference Example 56: tert-butyl 4-(1-[[(tert-butoxycarbonyl)amino]-2-{(3S)-3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]pyrrolidin-1-yl}-2-oxoethyl)-1H-imidazole-1-carboxylate

[Chemical Formula 769]

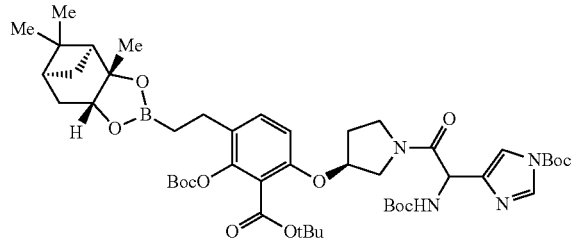

A reaction, work-up, and purification were performed using the compound of Reference Example 56-2 (54 mg, 0.093 mmol) and [(tert-butoxycarbonyl)amino][1-(tert-butoxycarbonyl)-1H-imidazol-4-yl]acetic acid (38 mg, 0.11 mmol) as the starting materials by the same method described in Reference Example 55 to obtain the title compound (47 mg).
LCMS: [M+H]$^+$/Rt=909.53/1.356 min$^E$ A reaction, work-up, and purification were performed using the compound of Reference Example 1-8 and carboxylic acid corresponding to each of the following Reference Examples as the starting materials by the same method described in Reference Example 36-4 to obtain each of Reference Example compounds 57 to 62 shown in Tables 2-7 and 2-8.

TABLE 2-7

| Reference Example | Structural formula | NMR and/or LCMS |
|---|---|---|
| 57 | 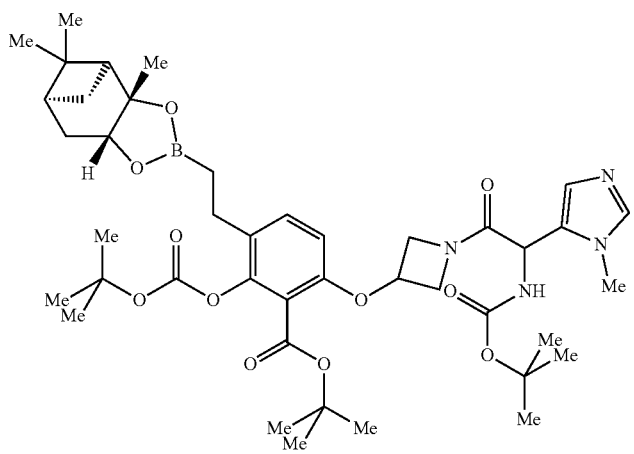 | LCMS: [M + H]$^+$/Rt = 809.49/0.973 min$^C$ |

TABLE 2-7-continued

| Reference Example | Structural formula | NMR and/or LCMS |
|---|---|---|
| 58 | | LCMS: [M + H]$^+$/Rt = 707.43/1.187 min$^A$ |
| 59 | | LCMS: [M + H]$^+$/Rt = 681.60/3.75 min$^D$<br>$^1$H-NMR (CDCl$_3$) δ: 7.66 (1H, s), 7.20 (1H, d, J = 8.0 Hz), 6.38 (1H, d, J = 8.6 Hz), 4.99-4.87 (1H, m), 4.55-4.49 (1H, m), 4.40-4.34 (1H, m), 4.28-4.20 (1H, m), 4.12-4.06 (1H, m), 3.62-3.58 (2H, m), 2.63-2.54 (2H, m), 2.33-2.24 (1H, m), 2.21-2.10 (1H, m), 2.03-1.96 (1H, m), 1.90-1.84 (1H, m), 1.81-1.74 (1H, m), 1.53-1.51 (18H, m), 1.34 (3H, s), 1.26 (3H, s), 1.11-1.07 (2H, m), 1.02-0.98 (1H, m), 0.81 (3H, s). |
| 60 | | $^1$H-NMR (CDCl$_3$) δ: 7.20 (2H, d, J = 8.5 Hz), 6.39 (1H, d, J = 8.5 Hz), 4.93-4.90 (1H, m), 4.42-4.31 (2H, m), 4.22 (1H, dd, J = 9.2, 1.8 Hz), 4.13-4.02 (2H, m), 3.59-3.55 (1H, m), 3.44-3.38 (1H, m), 3.29-3.25 (1H, m), 2.92-2.87 (1H, m), 2.59 (3H, t, J = 8.2 Hz), 2.35-2.23 (1H, m), 2.19-2.12 (3H, m), 2.09-2.02 (2H, m), 1.88-1.85 (1H, m), 1.78 (1H, d, J = 14.6 Hz), 1.54 (9H, s), 1.52 (18H, s), 1.43 (3H, s), 1.34 (3H, s), 1.09 (2H, t, J = 8.5 Hz), 1.01 (1H, d, J = 11.0 Hz), 0.82 (3H, s). |

TABLE 2-8

61 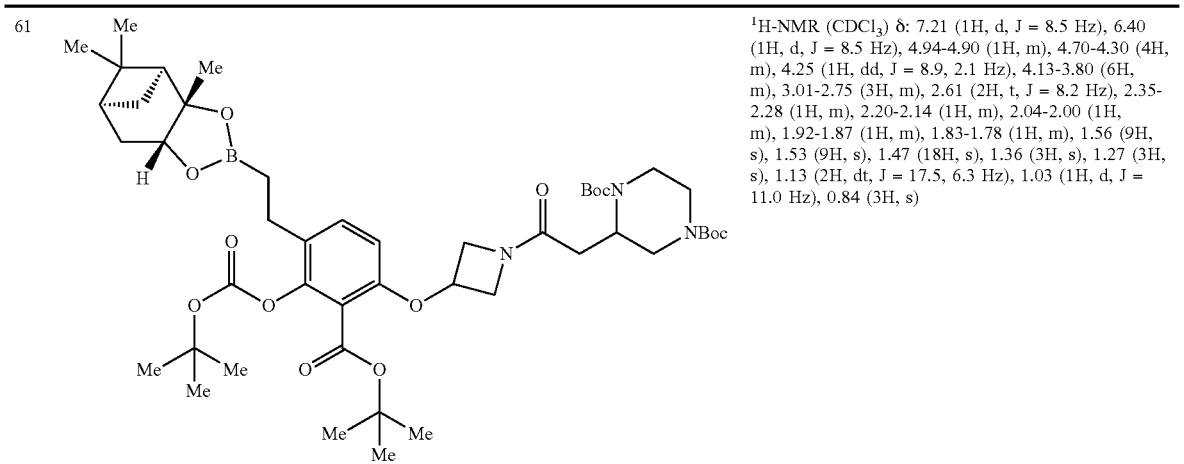

¹H-NMR (CDCl₃) δ: 7.21 (1H, d, J = 8.5 Hz), 6.40 (1H, d, J = 8.5 Hz), 4.94-4.90 (1H, m), 4.70-4.30 (4H, m), 4.25 (1H, dd, J = 8.9, 2.1 Hz), 4.13-3.80 (6H, m), 3.01-2.75 (3H, m), 2.61 (2H, t, J = 8.2 Hz), 2.35-2.28 (1H, m), 2.20-2.14 (1H, m), 2.04-2.00 (1H, m), 1.92-1.87 (1H, m), 1.83-1.78 (1H, m), 1.56 (9H, s), 1.53 (9H, s), 1.47 (18H, s), 1.36 (3H, s), 1.27 (3H, s), 1.13 (2H, dt, J = 17.5, 6.3 Hz), 1.03 (1H, d, J = 11.0 Hz), 0.84 (3H, s)

62 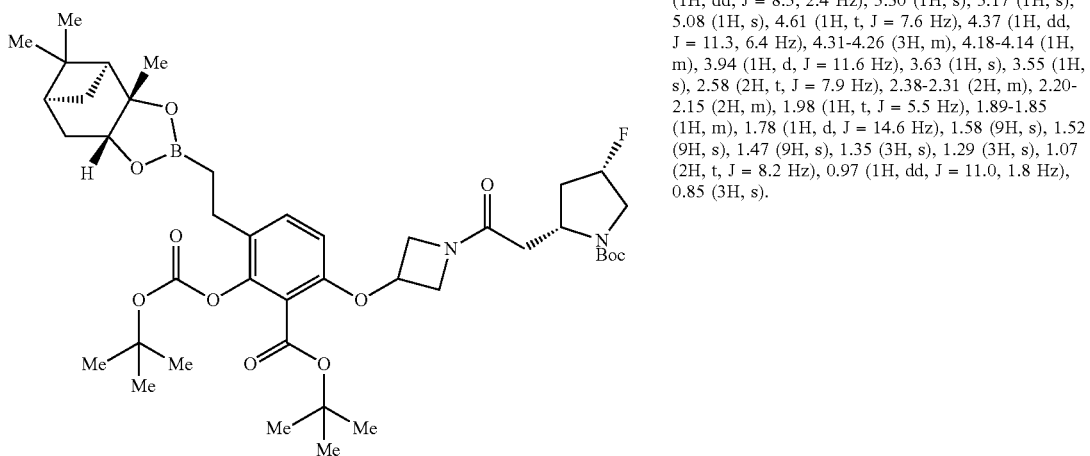

LCMS: [M + H]⁺/Rt = 801.41/1.463 min$^C$
¹H-NMR (CD₃OD) δ: 7.31 (1H, d, J = 8.5 Hz), 6.69 (1H, dd, J = 8.5, 2.4 Hz), 5.30 (1H, s), 5.17 (1H, s), 5.08 (1H, s), 4.61 (1H, t, J = 7.6 Hz), 4.37 (1H, dd, J = 11.3, 6.4 Hz), 4.31-4.26 (3H, m), 4.18-4.14 (1H, m), 3.94 (1H, d, J = 11.6 Hz), 3.63 (1H, s), 3.55 (1H, s), 2.58 (2H, t, J = 7.9 Hz), 2.38-2.31 (2H, m), 2.20-2.15 (2H, m), 1.98 (1H, t, J = 5.5 Hz), 1.89-1.85 (1H, m), 1.78 (1H, d, J = 14.6 Hz), 1.58 (9H, s), 1.52 (9H, s), 1.47 (9H, s), 1.35 (3H, s), 1.29 (3H, s), 1.07 (2H, t, J = 8.2 Hz), 0.97 (1H, dd, J = 11.0, 1.8 Hz), 0.85 (3H, s).

A reaction, work-up, and purification were performed using the compound of Reference Example 1-8 as the starting material by the same method described in Reference Example 3 to obtain each of Reference Example compounds 63 to 105 shown in Tables 2-9 to 2-16.

TABLE 2-9

| Reference Example | Structural formula | NMR and/or LCMS |
|---|---|---|
| 63 | | LCMS: [M + H]⁺/Rt = 807.2/2.91 min$^B$<br>¹H-NMR (CDCl₃) δ: 8.63-8.57 (2H, m), 7.73-7.66 (1H, m), 7.34-7.29 (1H, m), 7.20 (1H, dd, J = 8.1 Hz, 5.4 Hz), 6.34 (1H, t, J = 8.1 Hz), 6.00-5.83 (1H, m), 5.24-5.17 (1H, m), 4.98-4.78 (1H, m), 4.64-4.42 (1H, m), 4.33-4.06 (3H, m), 4.04-3.82 (1H, m), 2.64-2.56 (2H, m), 2.36-2.27 (1H, m), 2.21-2.12 (1H, m), 2.05-2.00 (1H, m), 1.91-1.77 (2H, m), 1.56-1.40 (27H, m), 1.36 (3H, s), 1.26 (3H, s), 1.13-1.00 (3H, m), 0.83 (3H, s). |

TABLE 2-9-continued

| Reference Example | Structural formula | NMR and/or LCMS |
|---|---|---|
| 64 | (structure) | LCMS: [M + H]$^+$/Rt = 810.0/2.93 min$^B$<br>$^1$H-NMR (CDCl$_3$) δ: 7.46-7.36 (2H, m), 7.22-7.18 (1H, m), 6.36-6.33 (1H, m), 5.67-5.50 (1H, m), 5.19-5.15 (1H, m), 5.05-4.93 (1H, m), 4.85-4.63 (1H, m), 4.48-4.22 (3H, m), 4.16-3.95 (1H, m), 3.88-3.66 (3H, m), 2.63-2.57 (2H, m), 2.36-2.27 (1H, m), 2.19-2.14 (1H, m), 2.05-2.00 (1H, m), 1.93-1.76 (2H, m), 1.56-1.41 (27H, m), 1.35 (3H, s), 1.28 (3H, s), 1.13-1.00 (3H, m), 0.83 (3H, s). |
| 65 | (structure) | LCMS: [M + H]$^+$/Rt = 813.0/2.97 min$^B$<br>$^1$H-NMR (CDCl$_3$) δ: 8.15 (1H, br), 7.21 (1H, d, J = 8.1 Hz), 6.71 (1H, s), 6.41 (1H, d, J = 8.1 Hz), 5.00-4.88 (1H, m), 4.54-4.49 (1H, m), 4.42-4.35 (1H, m), 4.31-4.23 (2H, m), 4.14-4.08 (1H, m), 3.49 (2H, s), 2.65-2.56 (2H, m), 2.36-2.26 (1H, m), 2.19-2.12 (1H, m), 2.06-2.00 (1H, m), 1.92-1.77 (2H, m), 1.61-1.44 (27H, m), 1.36 (3H, s), 1.28 (3H, s), 1.14-1.00 (3H, m), 0.83 (3H, s) |
| 66 | (structure) | LCMS: [M + H]$^+$/Rt = 798.8/3.05 min$^B$<br>$^1$H-NMR (CDCl$_3$) δ: 7.82 (1H, br), 7.72 (1H, s), 7.23 (1H, d, J = 8.1 Hz), 6.45 (1H, d, J = 8.1 Hz), 4.97-4.84 (2H, m), 4.56-4.52 (2H, m), 4.26-4.19 (2H, m), 2.65-2.59 (2H, m), 2.36-2.28 (1H, m), 2.22-2.14 (1H, m), 2.04-2.00 (1H, m), 1.91-1.76 (2H, m), 1.60-1.49 (27H, m), 1.36 (3H, s), 1.28 (3H, s), 1.15-1.01 (3H, m), 0.84 (3H, s). |
| 67 | (structure) | LCMS: [M + H]$^+$/Rt = 1017.7/3.24 min$^B$<br>$^1$H-NMR (CDCl$_3$) δ: 7.47-7.18 (11H, m), 6.92-6.87 (3H, m), 6.36-6.26 (1H, m), 5.86-5.69 (1H, m), 5.19-3.76 (11H, m), 2.63-2.57 (2H, m), 2.36-2.27 (1H, m), 2.18-2.13 (1H, m), 2.05-2.00 (1H, m), 1.89-1.77 (2H, m), 1.57-1.39 (27H, m), 1.35 (3H, s), 1.26 (3H, s), 1.14-1.00 (3H, m), 0.83 (3H, s). |

TABLE 2-10

| | | |
|---|---|---|
| 68 | (structure) | LCMS: [M + H]$^+$/Rt = 1017.9/3.36 min$^B$<br>$^1$H-NMR (CDCl$_3$) δ: 7.41-7.15 (12H, m), 6.61-6.53 (2H, m), 6.24-6.11 (1H, m), 5.66-5.49 (2H, m), 5.11-5.00 (4H, m), 4.81-3.72 (5H, m), 2.64-2.54 (2H, m), 2.36-2.28 (1H, m), 2.20-2.16 (1H, m), 2.09-2.00 (1H, m), 1.89-1.78 (2H, m), 1.68-1.23 (33H, m), 1.14-1.02 (3H, m), 0.83 (3H, s). |

TABLE 2-10-continued
| 69 | 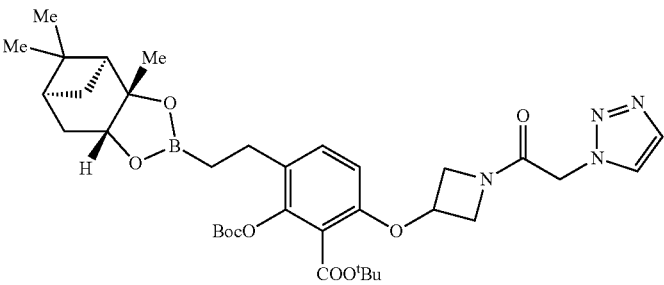 | LCMS: [M + H]⁺/Rt = 681.39/3.96 min$^D$<br>¹H-NMR (CDCl₃) δ: 7.78 (1H, d, J = 1.1 Hz), 7.73 (1H, d, J = 1.1 Hz), 7.23-7.18 (1H, m), 6.37 (1H, d, J = 8.6 Hz), 5.09 (1H, d, J = 16.0 Hz), 5.01-4.91 (2H, m), 4.53-4.45 (1H, m), 4.45-4.37 (1H, m), 4.26-4.21 (1H, m), 4.19-4.07 (2H, m), 2.63-2.56 (2H, m), 2.34-2.25 (1H, m), 2.20-2.12 (1H, m), 2.03-1.98 (1H, m), 1.92-1.85 (1H, m), 1.83-1.75 (1H, m), 1.54 (9H, s), 1.52 (9H, s), 1.34 (3H, s), 1.26 (3H, s), 1.12-1.07 (2H, m), 1.01 (1H, d, J = 11.5 Hz), 0.82 (3H, s). |
| 70 | 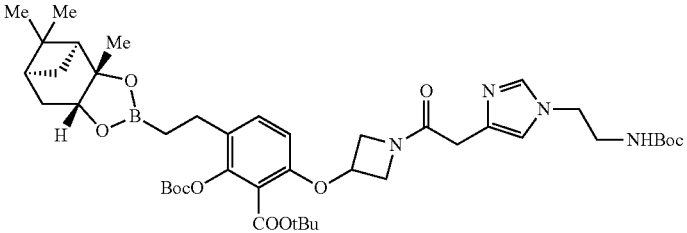 | LCMS: [M + H]⁺/Rt = 824.0/2.51 min$^B$<br>¹H-NMR (CDCl₃) δ: 7.39 (1H, s), 7.22 (1H, d, J = 8.1 Hz), 6.90 (1H, s), 6.41 (1H, d, J = 8.1 Hz), 4.93-4.61 (3H, m), 4.41-4.35 (1H, m), 4.27-4.23 (2H, m), 4.06-4.00 (2H, m), 3.52-3.37 (4H, m), 2.64-2.56 (2H, m), 2.36-2.27 (1H, m), 2.19-2.13 (1H, m), 2.05-2.00 (1H, m), 1.93-1.66 (2H, m), 1.56 (9H, s), 1.53 (9H, s), 1.44 (9H, s), 1.36 (3H, s), 1.28 (3H, s), 1.14-1.00 (3H, m), 0.86 (3H, s). |
| 71 | 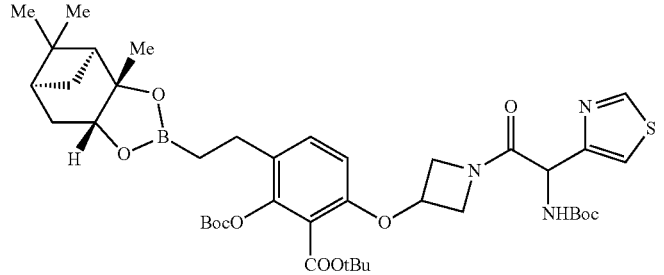 | LCMS: [M + H]⁺/Rt = 812.9/2.93 min$^B$<br>¹H-NMR (CDCl₃) δ: 8.77-8.76 (1H, m), 7.36-7.33 (1H, m), 7.22 (1H, d, J = 8.1 Hz), 6.39 (1H, d, J = 8.1 Hz), 5.98-5.92 (1H, m), 5.54-5.48 (1H, m), 5.01-4.87 (1H, m), 4.74-4.68 (1H, m), 4.48-4.03 (4H, m), 2.64-2.58 (2H, m), 2.36-2.27 (2H, m), 2.04-2.00 (1H, m), 1.92-1.76 (2H, m), 1.57-1.52 (18H, m), 1.44 (9H, s), 1.36 (3H, s), 1.28 (3H, s), 1.13-1.01 (3H, m), 0.83 (3H, s). |
| 72 | 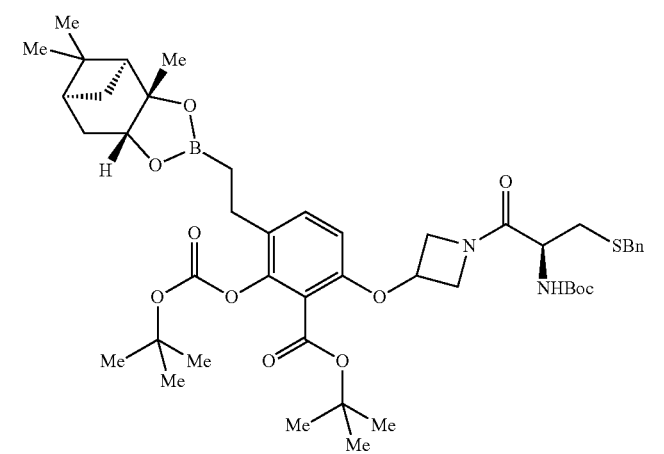 | LCMS: [M + H]⁺/Rt = 865.61/1.332 min$^E$ |

TABLE 2-11
| | | |
|---|---|---|
| 73 | 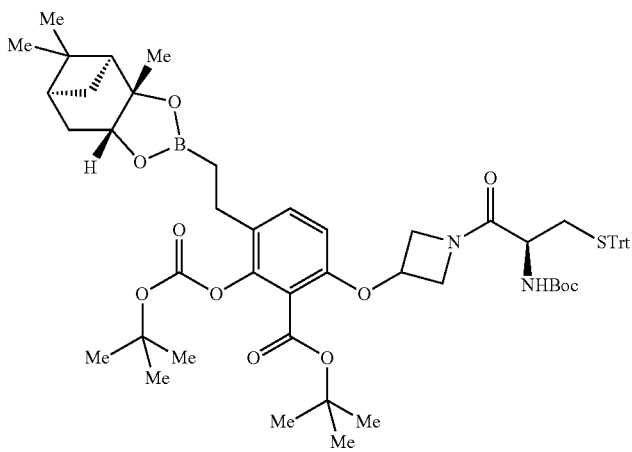 | $^1$H-NMR (400 MHz, CDCl$_3$) δ: 7.39-7.37 (6H, m), 7.27-7.12 (10H, m), 6.49 (1H, d, J = 8.5 Hz), 5.16-5.13 (1H, m), 4.92-4.90 (1H, m), 4.83-4.79 (2H, m), 4.24-4.20 (3H, m), 4.13-4.07 (1H, m), 2.64-2.56 (4H, m), 2.35-2.26 (1H, m), 2.19-2.13 (1H, m), 2.02-1.99 (1H, m), 1.90-1.86 (1H, m), 1.81-1.77 (1H, m), 1.54 (9H, s), 1.51 (9H, s), 1.41 (9H, s), 1.34 (3H, s), 1.26 (3H, s), 1.11-1.00 (2H, m), 0.82 (3H, s). |
| 74 | 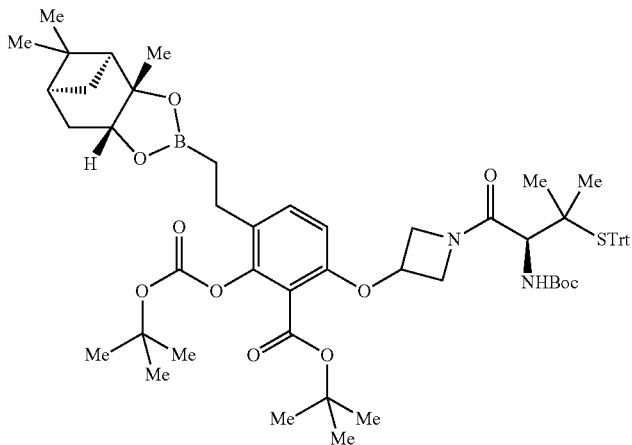 | LCMS: [M + H]$^+$/Rt = 1045/1.347 min$^C$ |
| 75 | 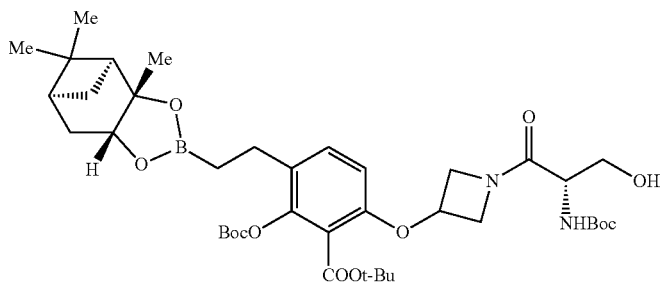 | LCMS: [M + H]$^+$/Rt = 759.20/4.09 min$^D$<br>$^1$H-NMR (CDCl$_3$) δ: 7.22-7.17 (1H, m), 6.40-6.36 (1H, m), 5.58-5.41 (1H, m), 4.98-4.89 (1H, m), 4.76-4.53 (1H, m), 4.44-4.19 (3H, m), 4.13-4.02 (1H, m), 3.91-3.80 (1H, m), 3.73-3.64 (1H, m), 2.62-2.55 (2H, m), 2.35-2.25 (1H, m), 2.19-2.11 (1H, m), 2.03-1.97 (1H, m), 1.92-1.84 (1H, m), 1.82-1.75 (1H, m), 1.54 (9H, s), 1.51 (9H, s), 1.44-1.40 (9H, m), 1.34 (3H, s), 1.26 (3H, s), 1.12-1.06 (2H, m), 1.03-0.99 (1H, m), 0.81 (3H, s). |
| 76 | 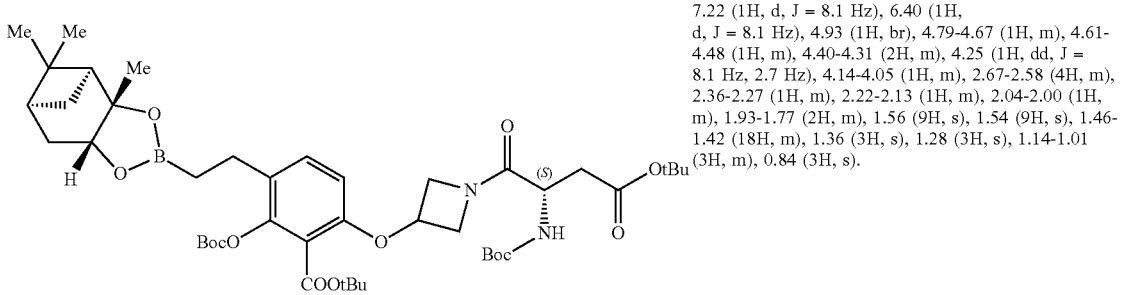 | LCMS: [M + H]$^+$/Rt = 843.8/3.14 min$^B$<br>$^1$H-NMR (CDCl$_3$) δ: 7.22 (1H, d, J = 8.1 Hz), 6.40 (1H, d, J = 8.1 Hz), 4.93 (1H, br), 4.79-4.67 (1H, m), 4.61-4.48 (1H, m), 4.40-4.31 (2H, m), 4.25 (1H, dd, J = 8.1 Hz, 2.7 Hz), 4.14-4.05 (1H, m), 2.67-2.58 (4H, m), 2.36-2.27 (1H, m), 2.22-2.13 (1H, m), 2.04-2.00 (1H, m), 1.93-1.77 (2H, m), 1.56 (9H, s), 1.54 (9H, s), 1.46-1.42 (18H, m), 1.36 (3H, s), 1.28 (3H, s), 1.14-1.01 (3H, m), 0.84 (3H, s). |

TABLE 2-11-continued

| 77 | [structure] | LCMS: [M + H]⁺/Rt = 814.7/2.89 min$^B$<br>$^1$H-NMR (CDCl$_3$) δ: 7.23 (1H, d, J = 8.1 Hz), 6.77 (1H, br), 6.41 (1H, d, J = 8.1 Hz), 5.70-4.90 (2H, m), 4.75-4.04 (7H, m), 2.65-2.59 (2H, m), 2.36-2.28 (1H, m), 2.20-2.14 (1H, m), 2.04-2.00 (1H, m), 1.91-1.78 (2H, m), 1.56 (9H, s), 1.54 (9H, s), 1.45 (9H, s), 1.36-1.23 (12H, s), 1.14-1.01 (3H, m), 0.84 (3H, s). |

TABLE 2-12

| 78 | [structure] | LCMS: [M + H]⁺/Rt = 843.7/3.21 min$^B$<br>$^1$H-NMR (CDCl$_3$) δ: 7.22 (1H, d, J = 8.1 Hz), 6.40 (1H, d, J = 8.1 Hz), 5.32-5.29 (1H, m), 5.00-4.84 (1H, m), 4.79-4.64 (1H, m), 4.59-4.48 (1H, m), 4.40-4.30 (2H, m), 4.27-4.23 (1H, m), 4.14-4.05 (1H, m), 2.67-2.56 (4H, m), 2.36-2.26 (1H, m), 2.22-2.13 (1H, m), 2.05-2.00 (1H, m), 1.92-1.77 (2H, m), 1.56 (9H, s), 1.54 (9H, s), 1.45-1.40 (18H, m), 1.36 (3H, s), 1.26 (3H, s), 1.14-1.01 (3H, m), 0.84 (3H, s). |
| 79 | [structure] | LCMS: [M + H]⁺/Rt = 785.7/1.40 min$^C$ |
| 80 | [structure] | LCMS: [M − Boc + H]⁺/Rt = 737.5/1.47 min$^C$ |

TABLE 2-12-continued
| | | |
|---|---|---|
| 81 | 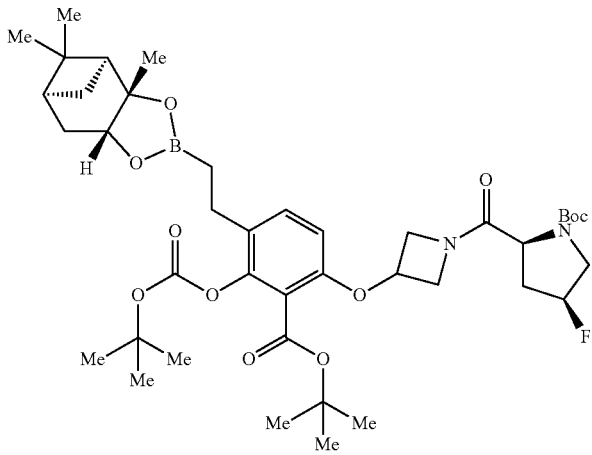 [SMILES: CC(C)(C)OC(=O)Oc1c(CCB2O[C@@H]3C[C@@H]4C[C@@H](C4(C)C)[C@]3(C)O2)ccc(OC2CN(C(=O)[C@@H]3C[C@H](F)CN3C(=O)OC(C)(C)C)C2)c1C(=O)OC(C)(C)C] | LCMS: [M + H]⁺/Rt = 787.7/1.40 min$^C$ |
| 82 | 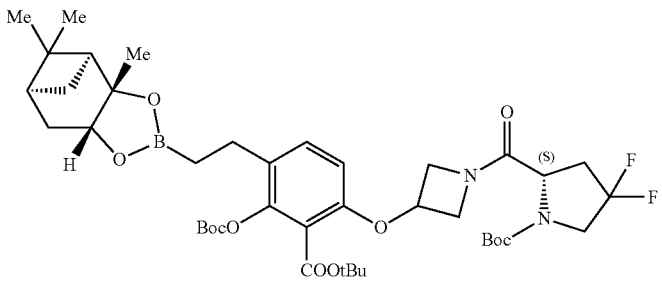 | LCMS: [M + H]⁺/Rt = 805.7/3.07 min$^B$<br>¹H-NMR (CDCl₃) δ: 7.23 (1H, d, J = 8.1 Hz), 6.41 (1H, d, J = 8.1 Hz), 5.01-4.43 (3H, m), 4.37-4.30 (1H, m), 4.27-4.00 (3H, m), 3.85-3.75 (2H, m), 2.65-2.48 (4H, m), 2.36-2.27 (1H, m), 2.20-2.14 (1H, m), 2.05-2.00 (1H, m), 1.92-1.77 (2H, m), 1.59-1.45 (27H, m), 1.36 (3H, s), 1.26 (3H, s), 1.14-1.01 (3H, m), 0.84 (3H, s). |
TABLE 2-13
| | | |
|---|---|---|
| 83 | 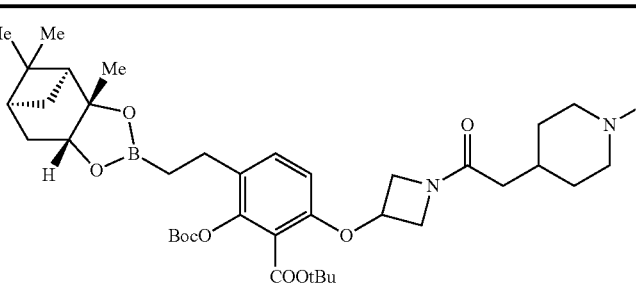 | LCMS: [M + H]⁺/Rt = 797.3/3.07 min$^B$<br>¹H-NMR (CDCl₃) δ: 7.22 (1H, d, J = 8.1 Hz), 6.42 (1H, d, J = 8.1 Hz), 4.97-4.89 (1H, m), 4.45-4.32 (2H, m), 4.27-4.23 (1H, m), 4.16-4.05 (2H, m), 2.96-2.71 (4H, m), 2.65-2.56 (2H, m), 2.36-2.27 (1H, m), 2.22-2.13 (1H, m), 2.05-2.01 (5H, m), 1.92-1.67 (5H, m), 1.56 (9H, s), 1.54 (9H, s), 1.45 (9H, s), 1.36 (3H, s), 1.26 (3H, s), 1.14-1.01 (3H, m), 0.84 (3H, s). |
| 84 | 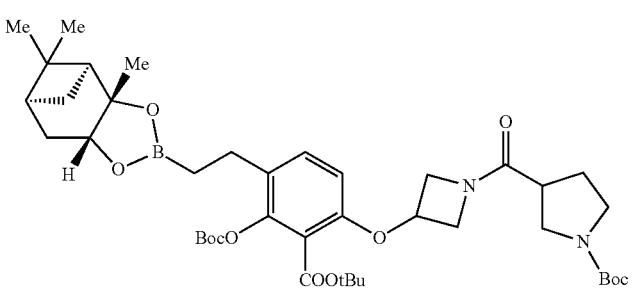 | LCMS: [M + H]⁺/Rt = 769.8/3.03 min$^B$<br>¹H-NMR (CDCl₃) δ: 7.23 (1H, d, J = 8.1 Hz), 6.43 (1H, d, J = 8.1 Hz), 4.99-4.93 (1H, m), 4.45-4.46 (1H, m), 4.40-4.34 (1H, m), 4.27-4.05 (3H, m), 3.60-3.26 (4H, m), 2.95-2.80 (1H, m), 2.65-2.59 (2H, m), 2.36-2.26 (1H, m), 2.22-2.13 (1H, m), 2.05-2.00 (3H, m), 1.90-1.76 (2H, m), 1.57 (9H, s), 1.54 (9H, s), 1.45 (9H, s), 1.36 (3H, s), 1.26 (3H, s), 1.14-1.01 (3H, m), 0.84 (3H, s). |

TABLE 2-13-continued

| | | |
|---|---|---|
| 85 | 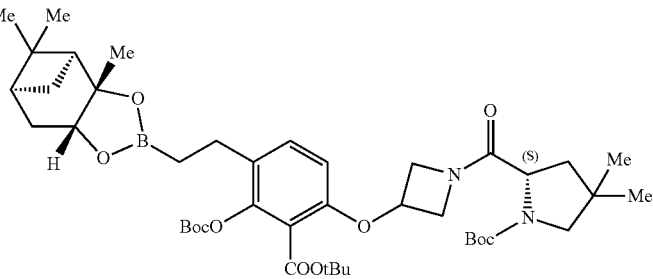 | LCMS: [M + H]⁺/Rt = 797.8/3.18 min$^B$<br>¹H-NMR (CDCl₃) δ: 7.22 (1H, d, J = 8.1 Hz), 6.41 (1H, d, J = 8.1 Hz), 5.00-4.82 (1H, m), 4.48-4.08 (7H, m), 3.40-3.12 (1H, m), 2.64-2.58 (2H, m), 2.36-2.27 (1H, m), 2.22-2.13 (1H, m), 2.05-1.76 (5H, m), 1.60-1.56 (15H, m), 1.54 (9H, s), 1.45 (9H, s), 1.36 (3H, s), 1.26 (3H, s), 1.14-1.01 (3H, m), 0.84 (3H, s). |
| 86 | 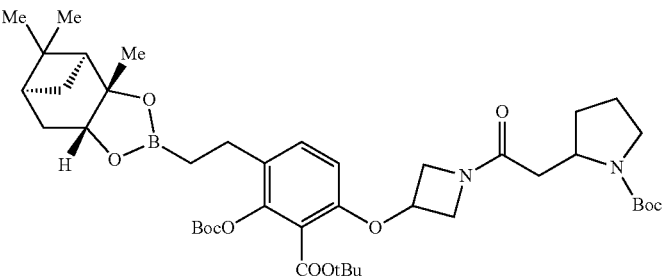 | LCMS: [M + H]⁺/Rt = 783.9/3.09 min$^B$<br>¹H-NMR (CDCl₃) δ: 7.22 (1H, d, J = 8.1 Hz), 6.42 (1H, d, J = 8.1 Hz), 4.96-4.86 (1H, m), 4.37-4.00 (6H, m), 3.37-3.26 (2H, m), 2.80-2.58 (4H, m), 2.36-2.26 (1H, m), 2.20-2.13 (1H, m), 2.09-1.77 (7H, m), 1.56 (9H, s), 1.54 (9H, s), 1.46 (9H, s), 1.36 (3H, s), 1.28 (3H, s), 1.14-1.01 (3H, m), 0.83 (3H, s). |
| 87 | 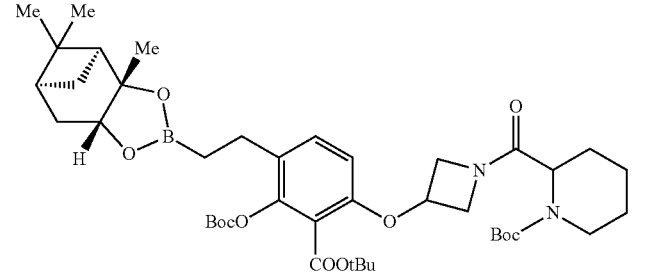 | LCMS: [M + H]⁺/Rt = 783.8/3.22 min$^B$<br>¹H-NMR (CDCl₃) δ: 7.21 (1H, d, J = 8.1 Hz), 6.39-6.33 (1H, m), 4.94-4.68 (2H, m), 4.55-3.89 (7H, m), 2.64-2.56 (2H, m), 2.36-2.27 (1H, m), 2.27-2.13 (1H, m), 2.05-2.00 (1H, m), 1.93-1.77 (2H, m), 1.70-1.23 (39H, m), 1.13-1.01 (3H, m), 0.83 (3H, s). |
| 88 | 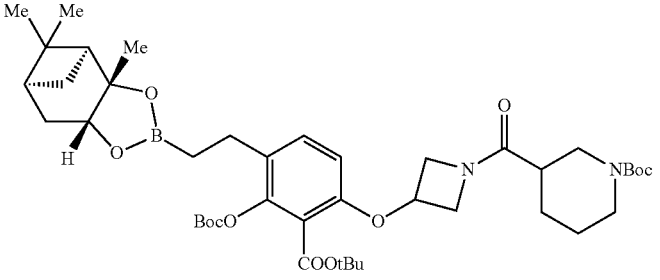 | LCMS: [M + H]⁺/RT = 783.9/3.11 min$^B$<br>¹H-NMR (CDCl₃) δ: 7.23 (1H, d, J = 8.1 Hz), 6.43 (1H, d, J = 8.1 Hz), 5.00-4.92 (1H, m), 4.51-4.04 (8H, m), 2.85-2.56 (3H, m), 2.36-2.14 (3H, m), 2.05-2.00 (1H, m), 1.93-1.77 (3H, m), 1.74-1.44 (30H, m), 1.36 (3H, s), 1.26 (3H, s), 1.14-1.01 (3H, m), 0.84 (3H, s). |

TABLE 2-14

| | | |
|---|---|---|
| 89 | 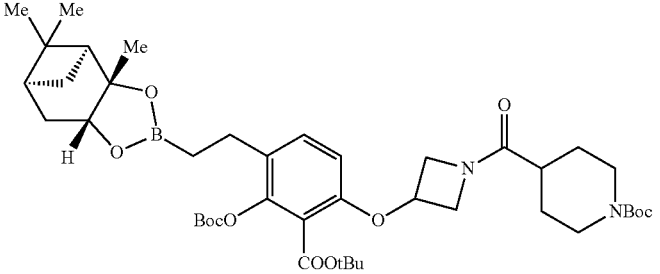 | LCMS: [M + H]⁺/Rt = 783.6/3.05 min$^B$<br>¹H-NMR (CDCl₃) δ: 7.22 (1H, d, J = 8.1 Hz), 6.43 (1H, d, J = 8.1 Hz), 4.99-4.92 (1H, m), 4.51-4.45 (1H, m), 4.39-4.32 (1H, m), 4.27-4.04 (5H, m), 2.80-2.53 (3H, m), 2.36-2.25 (2H, m), 2.20-2.13 (1H, m), 2.05-2.00 (1H, m), 1.92-1.77 (2H, m), 1.71-1.51 (23H, m), 1.45 (9H, s), 1.36 (3H, s), 1.26 (3H, s), 1.14-1.01 (3H, m), 0.84 (3H, s). |

TABLE 2-14-continued

| | | |
|---|---|---|
| 90 | (structure) | LCMS: [M + H]⁺/Rt = 670.7/2.88 min$^B$<br>¹H-NMR (CDCl₃) δ:<br>7.22 (1H, d, J = 8.1 Hz), 6.41 (1H, d, J = 8.1 Hz),<br>4.97-4.90 (1H, m), 4.76-4.63 (1H, m), 4.47-4.22 (4H, m), 4.14-4.05 (1H, m), 3.92-3.81 (2H, m),<br>2.64-2.58 (2H, m), 2.36-2.27 (1H, m), 2.21-2.11 (3H, m), 2.05-2.00 (1H, m), 1.95-1.79 (4H, m), 1.62-1.54 (18H, m), 1.36 (3H, s), 1.26 (3H, s), 1.14-1.01 (3H, m), 0.84 (3H, s). |
| 91 | (structure) | LCMS: [M + H]⁺/Rt = 845.8/3.14 min$^B$<br>¹H-NMR (CDCl₃) δ:<br>7.32-7.20 (6H, m), 6.42 (1H, d, J = 8.1 Hz), 5.05-4.86 (1H, m), 4.64-3.91 (7H, m), 3.49-3.26 (2H, m), 2.64-2.58 (2H, m), 2.36-2.27 (1H, m), 2.22-2.13 (2H, m), 2.08-2.00 (2H, m), 1.96-1.78 (2H, m), 1.56-1.45 (27H, m), 1.36 (3H, s), 1.26 (3H, s), 1.14-1.01 (3H, m), 0.83 (3H, s). |
| 92 | (structure) | LCMS: [M + H]⁺/Rt = 781.7/3.07 min$^B$<br>¹H-NMR (CDCl₃) δ:<br>7.21 (1H, d, J = 8.1 Hz), 6.39 (1H, d, J = 8.1 Hz), 4.97-4.86 (1H, m), 4.78-4.33 (3H, m), 4.26-3.98 (3H, m), 3.50-3.42 (1H, m), 2.64-2.58 (2H, m), 2.41-2.27 (1H, m), 2.22-2.13 (1H, m), 2.05-2.00 (2H, m), 1.96-1.77 (2H, m), 1.56-1.41 (29H, m), 1.36 (3H, s), 1.26 (3H, s), 1.14-1.01 (4H, m), 0.96-0.69 (4H, m). |
| 93 | (structure) | LCMS: [M + H]⁺/Rt = 684.0/2.18 min$^B$<br>¹H-NMR (CDCl₃) δ: 7.23 (1H, d, J = 8.1 Hz), 6.42 (1H, d, J = 8.1 Hz), 5.00-4.92 (1H, m), 4.67-4.57 (1H, m), 4.47-4.36 (1H, m), 4.27-4.23 (2H, m), 4.15-4.05 (1H, m), 3.25-2.94 (1H, m), 2.64-2.58 (2H, m), 2.47-2.27 (5H, m), 2.21-2.14 (1H, m), 2.05-2.00 (1H, m), 1.97-1.66 (6H, m), 1.56 (9H, s), 1.54 (9H, s), 1.36 (3H, s), 1.26 (3H, s), 1.14-1.01 (3H, m), 0.84 (3H, s). |
| 94 | (structure) | LCMS: [M + H]⁺/Rt = 797.9/3.23 min$^B$<br>¹H-NMR (CDCl₃) δ: 7.21 (1H, d, J = 8.1 Hz), 6.42 (1H, d, J = 8.1 Hz), 4.97-4.89 (1H, m), 4.47-4.33 (2H, m), 4.26-4.23 (1H, m), 4.16-4.03 (4H, m), 3.87-3.77 (2H, m), 2.65-2.58 (2H, m), 2.36-2.28 (1H, m), 2.21-2.12 (1H, m), 2.08-1.78 (10H, m), 1.60-1.44 (27H, m), 1.36 (3H, s), 1.28 (3H, s), 1.14-1.01 (3H, m), 0.84 (3H, s). |

TABLE 2-15

| 95 | 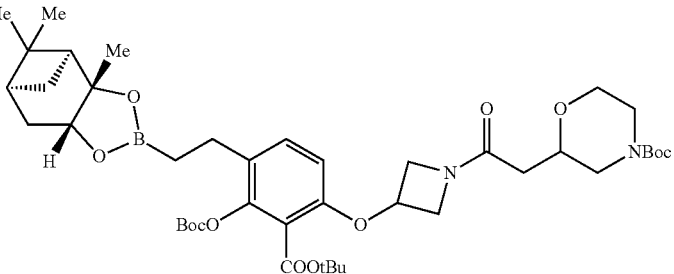 | LCMS: [M + H]⁺/Rt = 799.9/3.01 min$^B$<br>¹H-NMR (CDCl₃) δ: 7.22 (1H, d, J = 8.1 Hz), 6.41 (1H, d, J = 8.1 Hz), 4.95-4.88 (1H, m), 4.56-4.32 (2H, m), 4.26-3.81 (6H, m), 3.57-3.48 (1H, m), 2.93-2.80 (1H, m), 2.71-2.58 (3H, m), 2.36-2.26 (2H, m), 2.22-2.10 (2H, m), 2.04-2.00 (2H, m), 1.93-1.77 (2H, m), 1.56 (9H, s), 1.54 (9H, s), 1.46 (9H, s), 1.36 (3H, s), 1.28 (3H, s), 1.14-1.01 (3H, m), 0.83 (3H, s). |
| --- | --- | --- |
| 96 | 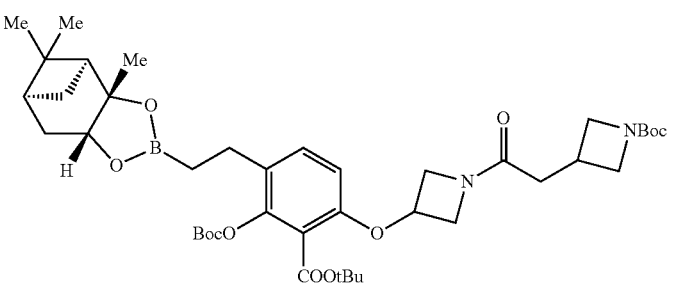 | LCMS: [M + H]⁺/Rt = 769.9/2.98 min$^B$<br>¹H-NMR (CDCl₃) δ:<br>7.23 (1H, d, J = 8.1 Hz), 6.42 (1H, d, J = 8.1 Hz), 4.98-4.91 (1H, m), 4.47-4.41 (1H, m), 4.37-4.31 (1H, m), 4.27-4.23 (1H, m), 4.18-4.02 (4H, m), 3.61-3.55 (2H, m), 2.98-2.85 (1H, m), 2.65-2.59 (2H, m), 2.42 (2H, d, J = 8.1 Hz), 2.22-2.13 (1H, m), 2.05-2.00 (1H, m), 1.92-1.76 (2H, m), 1.57 (9H, s), 1.54 (9H, s), 1.43 (9H, s), 1.36 (3H, s), 1.28 (3H, s), 1.14-1.01 (3H, m), 0.84 (3H, s). |
| 97 | 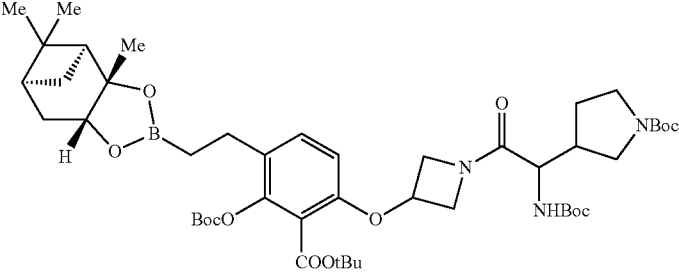 | LCMS: [M + H]⁺/Rt = 898.9/3.14 min$^B$<br>¹H-NMR (CDCl₃) δ: 7.23 (1H, d, J = 8.1 Hz), 6.41 (1H, d, J = 8.1 Hz), 5.24-5.07 (1H, m), 5.02-4.90 (1H, m), 4.55-4.00 (6H, m), 3.62-2.92 (5H, m), 2.65-2.59 (2H, m), 2.49-2.23 (2H, m), 2.22-2.12 (1H, m), 2.05-2.00 (1H, m), 1.95-1.78 (3H, m), 1.58-1.42 (36H, m), 1.36 (3H, s), 1.28 (3H, s), 1.14-1.01 (3H, m), 0.84 (3H, s). |
| 98 | 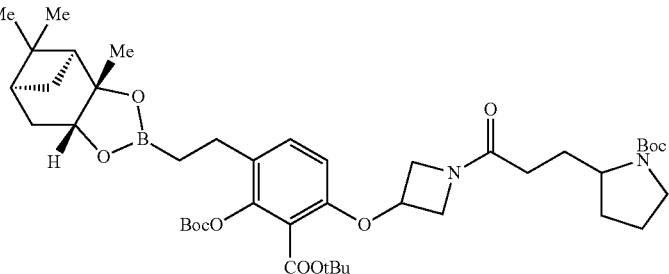 | LCMS: [M + H]⁺/Rt = 798.0/3.10 min$^B$<br>¹H-NMR (CDCl₃) δ:<br>7.22 (1H, d, J = 8.1 Hz), 6.41 (1H, d, J = 8.1 Hz), 4.96-4.89 (1H, m), 4.49-4.32 (2H, m), 4.27-4.23 (1H, m), 4.16-4.02 (3H, m), 3.89-3.75 (1H, m), 3.33-3.26 (1H, m), 2.65-2.58 (2H, m), 2.36-2.28 (1H, m), 2.22-2.07 (3H, m), 2.05-2.00 (2H, m), 1.97-1.78 (7H, m), 1.56 (9H, s), 1.54 (9H, s), 1.45 (9H, s), 1.36 (3H, s), 1.28 (3H, s), 1.14-1.01 (3H, m), 0.84 (3H, s). |
| 99 | 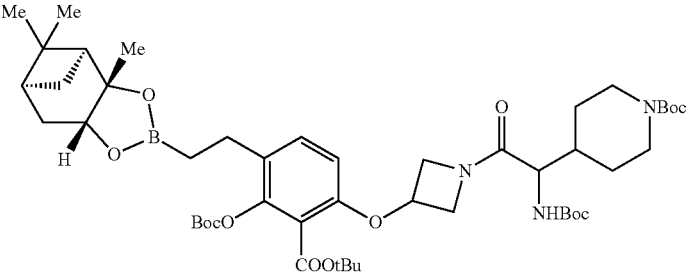 | LCMS: [M + H]⁺/Rt = 912.7/3.1 min$^B$<br>¹H-NMR (CDCl₃) δ:<br>7.23 (1H, d, J = 8.1 Hz), 6.41 (1H, d, J = 8.1 Hz), 5.13-5.09 (1H, m), 5.00-4.91 (1H, m), 4.75-4.69 (1H, m), 4.54-3.99 (8H, m), 2.70-2.59 (4H, m), 2.36-2.28 (1H, m), 2.23-2.13 (1H, m), 2.05-2.00 (1H, m), 1.94-1.87 (1H, m), 1.84-1.62 (4H, m), 1.60-1.53 (18H, m), 1.45-1.42 (18H, m), 1.36 (3H, s), 1.28 (3H, s), 1.14-1.01 (3H, m), 0.84 (3H, s). |

TABLE 2-15-continued
| 100 | 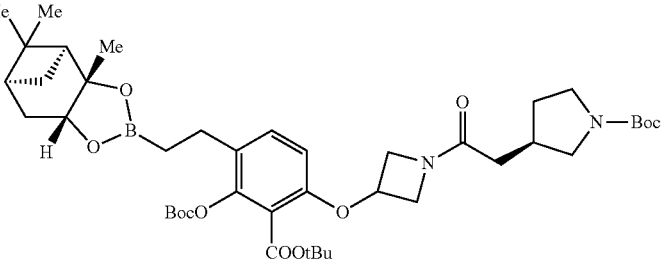 | LCMS: [M + H]⁺/Rt = 783.7/2.99 min[B] |
TABLE 2-16
| 101 | 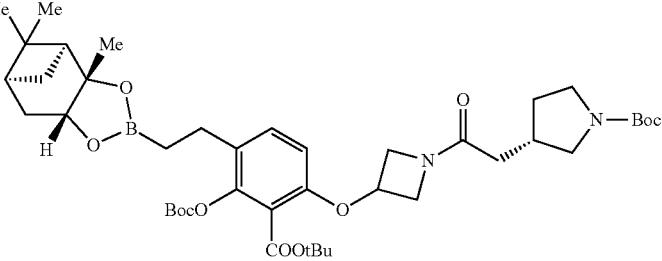 | LCMS: [M + H]⁺/Rt = 783.6/3.01 min[B] |
| 102 | 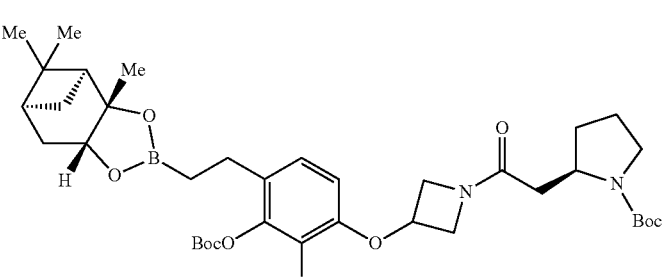 | LCMS: [M + H]⁺/Rt = 783.9/3.08 min[B] |
| 103 | 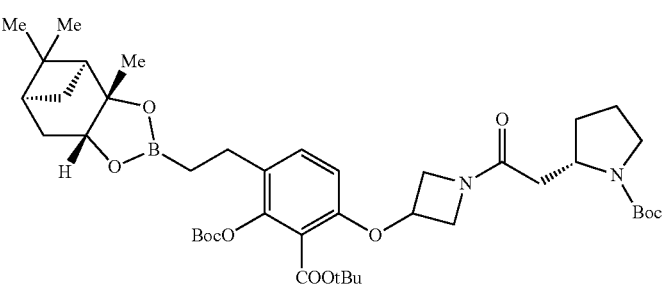 | LCMS: [M + H]⁺/Rt = 783.8/3.08 min[B] |
| 104 |  | LCMS: [M + H]⁺/Rt = 797.9/3.17 min[B]<br>¹H-NMR (CDCl₃) δ: 7.22 (1H, d, J = 8.1 Hz), 6.42 (1H, d, J = 8.1 Hz), 4.97-4.89 (1H, m), 4.68-4.40 (2H, m), 4.36-3.94 (5H, m), 2.87-2.69 (1H, m), 2.63-2.53 (2H, m), 2.47-2.13 (4H, m), 2.04-2.00 (1H, m), 1.93-1.77 (2H, m), 1.68-1.54 (24H, m), 1.46-1.45 (9H, m), 1.36 (3H, s), 1.28 (3H, s), 1.14-1.01 (3H, m), 0.84 (3H, s). |

TABLE 2-16-continued

| | | |
|---|---|---|
| 105 | [structure] | LCMS: [M + H]⁺/Rt = 794.6/2.90 min^B<br>¹H-NMR (CDCl₃) δ: 7.22 (1H, d, J = 8.1 Hz), 6.41 (1H, d, J = 8.1 Hz), 5.00-4.85 (1H, m), 4.61-3.92 (7H, m), 3.67-3.56 (1H, m), 3.50-2.98 (1H, m), 2.64-2.46 (3H, m), 2.41-2.13 (3H, m), 2.05-2.00 (1H, m), 1.92-1.77 (2H, m), 1.59-1.54 (18H, m), 1.45 (9H, s), 1.36 (3H, s), 1.28 (3H, s), 1.14-1.01 (3H, m), 0.84 (3H, s). |

A reaction, work-up, and purification were performed using the compound of Reference Example 1-7 as the starting material by the same method described in Reference Example 41 to obtain each of Reference Example compounds 106 to 108 shown in Table 2-17.

TABLE 2-17

| Reference Example | Structural formula | NMR and/or LCMS |
|---|---|---|
| 106 | [structure] | LCMS: [M + H]⁺/Rt = 702.8/2.72 min^B<br>¹H-NMR (CDCl₃) δ: 10.51 (1H, br), 7.62 (1H, s), 7.56 (1H, s), 7.18 (1H, d, J = 8.1 Hz), 6.30 (1H, d, J = 8.1 Hz), 4.76-4.71 (1H, m), 4.33-4.22 (3H, m), 4.01-3.96 (2H, m), 2.62-2.56 (2H, m), 2.36-2.27 (1H, m), 2.19-2.13 (1H, m), 2.04-2.00 (1H, m), 1.92-1.76 (2H, m), 1.53 (9H, s), 1.52 (9H, s), 1.35 (3H, s), 1.26 (3H, s), 1.11-1.00 (3H, m), 0.83 (3H, s). |
| 107 | [structure] | LCMS: [M + H]⁺/Rt = 714.0/2.96 min^B<br>¹H-NMR (CDCl₃) δ: 9.07 (1H, d, J = 2.7 Hz), 8.88 (1H, dd, J = 5.4 Hz, 2.7 Hz), 8.15-8.11 (1H, m), 7.53 (1H, dd, J = 8.1 Hz, 5.4 Hz), 7.18 (1H, d, J = 8.1 Hz), 6.37 (1H, d, J = 8.1 Hz), 4.86-4.82 (1H, m), 4.27-4.21 (3H, m), 3.87-3.82 (2H, m), 2.62-2.56 (2H, m), 2.35-2.27 (1H, m), 2.19-2.12 (1H, m), 2.03-1.99 (1H, m), 1.91-1.76 (2H, m), 1.52 (9H, s), 1.49 (9H, s), 1.35 (3H, s), 1.26 (3H, s), 1.11-0.99 (3H, m), 0.83 (3H, s). |
| 108 | [structure] | LCMS: [M + H]⁺/Rt = 729.8/2.84 min^B<br>¹H-NMR (CDCl₃) δ: 8.23 (1H, d, J = 8.1 Hz), 7.99 (1H, dd, J = 8.1 Hz, 2.7 Hz), 7.46-7.31 (2H, m), 7.20 (1H, d, J = 8.1 Hz), 6.40 (1H, d, J = 8.1 Hz), 4.99-4.90 (1H, m), 4.60-4.54 (2H, m), 4.42-4.36 (2H, m), 4.24 (1H, dd, J = 8.1 Hz, 2.7 Hz), 2.64-2.56 (2H, m), 2.36-2.27 (1H, m), 2.22-2.13 (1H, m), 2.05-2.00 (1H, m), 1.92-1.76 (2H, m), 1.56 (9H, s), 1.53 (9H, s), 1.35 (3H, s), 1.28 (3H, s), 1.13-1.00 (3H, m), 0.83 (3H, s). |

A reaction, work-up, and purification were performed using the compound of Reference Example 1-7 as the starting material by the same method described in Reference Example 42 to obtain each of Reference Example compounds 109 to 113 shown in Table 2-18.

TABLE 2-18

| Reference Example | Structural formula | NMR and/or LCMS |
|---|---|---|
| 109 | | LCMS: [M + H]⁺/Rt = 786.9/2.77 min$^B$<br>$^1$H-NMR (CDCl$_3$) δ: 7.22 (1H, d, J = 8.1 Hz), 6.41-6.37 (1H, m), 6.02 (1H, br), 5.71-5.61 (1H, m), 5.48-5.39 (1H, m), 4.95-4.89 (1H, m), 4.75-4.50 (2H, m), 4.42-4.32 (2H, m), 4.27-4.23 (1H, m), 4.10-4.03 (1H, m), 2.73-2.54 (4H, m), 2.36-2.27 (1H, m), 2.20-2.13 (1H, m), 2.04-2.00 (1H, m), 1.92-1.77 (2H, m), 1.57 (9H, s), 1.53 (9H, s), 1.43 (9H, s), 1.36 (3H, s), 1.26 (3H, s), 1.14-1.01 (3H, m), 0.83 (3H, s). |
| 110 | | LCMS: [M + H]⁺/Rt = 671.6/2.59 min$^B$<br>$^1$H-NMR (CDCl$_3$) δ: 7.32 (1H, d, J = 8.1 Hz), 6.70 (1H, d, J = 8.2 Hz), 5.12-5.06 (1H, m), 4.68-4.62 (1H, m), 4.40-4.17 (3H, m), 3.96-3.90 (1H, m), 2.60-2.49 (4H, m), 2.45-2.31 (3H, m), 2.23-2.11 (1H, m), 2.01-1.97 (1H, m), 1.90-1.66 (2H, m), 1.56 (9H, s), 1.52 (9H, s), 1.35 (3H, s), 1.29 (3H, s), 1.20-0.96 (3H, m), 0.86 (3H, s). |
| 111 | | LCMS: [M + H]⁺/Rt = 800.8/2.72 min$^B$<br>$^1$H-NMR (CDCl$_3$) δ: 7.23 (1H, d, J = 8.1 Hz), 6.43-6.39 (1H, m), 5.01-4.91 (1H, m), 4.69-4.02 (6H, m), 2.64-2.58 (2H, m), 2.36-1.76 (9H, m), 1.61-1.53 (18H, m), 1.43-1.42 (9H, m), 1.36 (3H, s), 1.28 (3H, s), 1.14-1.01 (3H, m), 0.84 (3H, s). |
| 112 | | LCMS: [M + H]⁺/Rt = 800.7/2.81 min$^B$<br>$^1$H-NMR (CDCl$_3$) δ: 7.23 (1H, d, J = 8.1 Hz), 6.41 (1H, d, J = 8.1 Hz), 6.23-6.16 (1H, m), 5.56-5.40 (1H, m), 5.00-4.92 (1H, m), 4.75-4.65 (1H, m), 4.56-4.23 (4H, m), 4.12-4.03 (1H, m), 3.67-3.27 (2H, m), 2.64-2.58 (2H, m), 2.37-2.27 (1H, m), 2.22-2.12 (1H, m), 2.04-1.98 (4H, m), 1.93-1.77 (2H, m), 1.60-1.54 (18H, m), 1.44 (9H, s), 1.36 (3H, s), 1.28 (3H, s), 1.14-1.01 (3H, m), 0.84 (3H, s). |
| 113 | | LCMS: [M + H]⁺/Rt = 801.7/2.70 min$^B$<br>$^1$H-NMR (CDCl$_3$) δ: 7.26-7.21 (1H, m), 6.43 (1H, d, J = 8.1 Hz), 6.25 (1H, br), 5.30-4.95 (2H, m), 4.75-4.52 (3H, m), 4.44-4.05 (5H, m), 3.74-3.15 (2H, m), 2.63-2.57 (2H, m), 2.37-2.28 (1H, m), 2.23-2.13 (1H, m), 2.05-2.01 (1H, m), 1.93-1.77 (2H, m), 1.57 (9H, s), 1.52 (9H, s), 1.44 (9H, s), 1.36 (3H, s), 1.28 (3H, s), 1.13-1.01 (3H, m), 0.84 (3H, s). |

A reaction, work-up, and purification were performed using the compound of Reference Example 43-2 as the starting material by the same method described in Reference Example 43 to obtain each of Reference Example compounds 114 to 116 shown in Table 2-19.

TABLE 2-19

| Reference Example | Structural formula | NMR and/or LCMS |
|---|---|---|
| 114 | 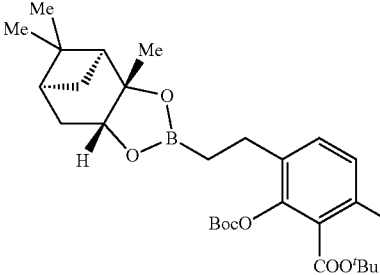 | LCMS: [M + H]⁺/Rt = 824.58/4.36 min$^D$<br>¹H-NMR (CDCl₃) δ: 7.76-7.65 (1H, m), 7.24 (1H, d, J = 8.6 Hz), 6.41 (1H, d, J = 8.6 Hz), 5.11-5.04 (1H, m), 5.02-4.96 (1H, m), 4.95-4.89 (1H, m), 4.60-4.48 (3H, m), 4.47-4.40 (1H, m), 4.31-4.20 (2H, m), 4.19-4.11 (1H, m), 2.92 (3H, s), 2.63 (2H, t, J = 8.3 Hz), 2.38-2.29 (1H, m), 2.23-2.14 (1H, m), 2.07-2.01 (1H, m), 1.94-1.88 (1H, m), 1.86-1.78 (1H, m), 1.58 (9H, s), 1.55 (9H, s), 1.48 (9H, s), 1.37 (3H, s), 1.30 (3H, s), 1.13 (2H, t, J = 8.3 Hz), 1.04 (1H, d, J = 10.9 Hz), 0.85 (3H, s). |
| 115 | 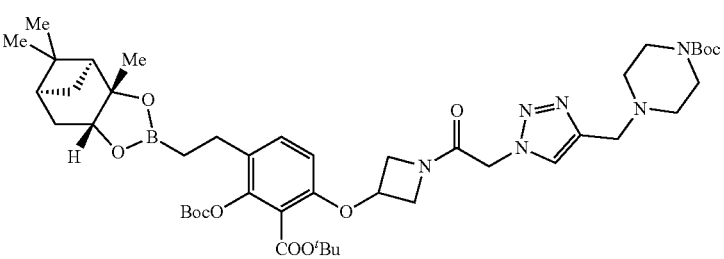 | LCMS: [M + H]⁺/Rt = 879.59/3.24 min$^D$<br>¹H-NMR (CDCl₃) δ: 7.72 (1H, s), 7.40-7.17 (1H, m), 6.48-6.36 (1H, m), 5.12-4.87 (3H, m), 4.62-4.51 (1H, m), 4.49-4.36 (1H, m), 4.30-4.21 (2H, m), 4.19-4.09 (1H, m), 3.74-3.65 (2H, m), 3.51-3.37 (4H, m), 2.67-2.56 (2H, m), 2.54-2.41 (4H, m), 2.36-2.26 (1H, m), 2.21-2.12 (1H, m), 2.06-1.99 (1H, m), 1.94-1.75 (2H, m), 1.62-1.42 (27H, m), 1.38-1.35 (3H, m), 1.30-1.27 (3H, m), 1.14-1.08 (2H, m), 1.06-1.00 (1H, m), 0.86-0.82 (3H, m). |
| 116 | 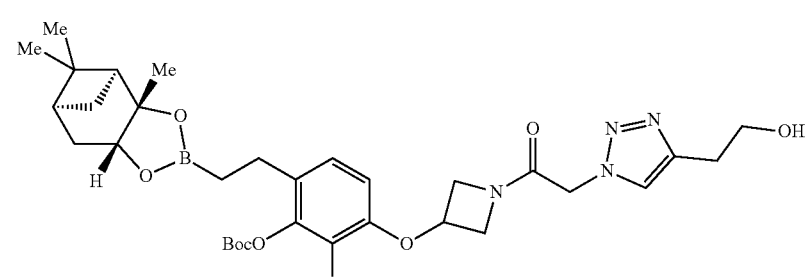 | LCMS: [M + H]⁺/Rt = 725.50/3.77 min$^D$<br>¹H-NMR (CDCl₃) δ: 7.62 (1H, s), 7.22 (1H, d, J = 8.6 Hz), 6.38 (1H, d, J = 8.6 Hz), 5.10-4.90 (3H, m), 4.53-4.39 (2H, m), 4.28-4.22 (1H, m), 4.16-4.04 (2H, m), 3.98-3.82 (2H, m), 2.96 (2H, t, J = 5.7 Hz), 2.65-2.56 (3H, m), 2.37-2.26 (1H, m), 2.21-2.12 (1H, m), 2.04-2.00 (1H, m), 1.94-1.88 (1H, m), 1.86-1.74 (1H, m), 1.57 (9H, s), 1.54 (9H, s), 1.36 (3H, s), 1.28 (3H, s), 1.13-1.08 (2H, m), 1.03 (1H, d, J = 10.9 Hz), 0.84 (3H, s). |

Reference Example 117: tert-butyl (4R)-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}-4-hydroxypyrrolidine-1-carboxylate

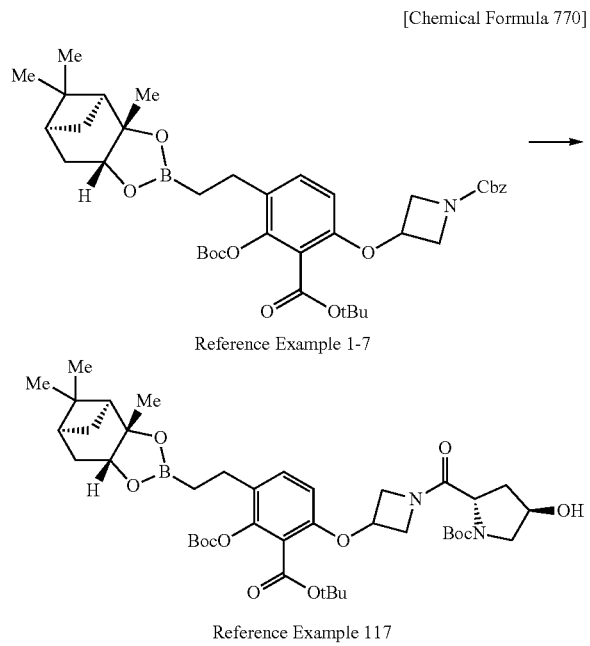

[Chemical Formula 770]

Reference Example 1-7

Reference Example 117

Palladium on carbon (20 mg, Pd content: 10%, wetted with ca. 55% water) was added to a methanol solution (3 mL) of the compound of Reference Example 1-7 (200 mg, 0.283 mmol), and the reaction mixture was stirred for 30 minutes under a hydrogen atmosphere at room temperature. The reaction solution was filtered through cellulose. The filtered substance was washed with methanol, and the combined filtrate was concentrated. The resulting residue was dissolved in DMF (2 mL) (this is referred to as "solution A"). Meanwhile, 4-(4,6-dimethoxy-1,3,5-triazin-2-yl)-4-methylmorpholinium chloride (94.1 mg, 0.340 mmol) was added to a DMF-methanol (2:1) mixture solution (3 mL) of trans-N-(tert-butoxycarbonyl)-4-hydroxy-L-proline (98.3 mg, 0.425 mmol), and the reaction mixture was stirred for 20 minutes at room temperature. The aforementioned solution A was then added, and the reaction mixture was stirred for 30 minutes at room temperature. Water was added to the reaction solution, which was extracted with ethyl acetate. The organic phase was washed with saturated saline, dried over sodium sulfate, filtered, and concentrated. The resulting residue was purified by silica gel column chromatography (methylene chloride/methanol) to obtain the title compound (222 mg).

$^1$H-NMR (CDCl$_3$) δ: 7.22 (1H, d, J=8.1 Hz), 6.41 (1H, d, J=8.1 Hz), 4.99-4.89 (1H, m), 4.58-3.99 (7H, m), 3.69-3.42 (2H, m), 2.65-2.58 (2H, m), 2.36-2.26 (1H, m), 2.22-2.07 (3H, m), 2.05-2.00 (1H, m), 1.93-1.73 (2H, m), 1.56 (9H, s), 1.54 (9H, s), 1.45-1.44 (9H, m), 1.36 (3H, s), 1.26 (3H, s), 1.14-1.01 (3H, m), 0.84 (3H, s).

LCMS: [M+H]$^+$/Rt=785.8/2.79 min$^B$

A reaction, work-up, and purification were performed using the compound of Reference Example 1-7 as the starting material by the same method described in Reference Example 117 to obtain each of Reference Example compounds 118 to 119 shown in Table 2-20.

TABLE 2-20

| Reference Example | Structural formula | NMR and/or LCMS |
|---|---|---|
| 118 | (Me,Me / Me bicyclic boronate — CH$_2$CH$_2$ — phenyl(BocO, COOtBu) — O — azetidine — N — C(=O) — (S)-pyrrolidine-(S)-OH, N-Boc) | LCMS: [M + H]$^+$/Rt = 785.8/2.94 min$^B$<br>$^1$H-NMR (CDCl$_3$) δ: 7.23 (1H, d, J = 8.1 Hz), 6.43 (1H, d, J = 8.1 Hz), 5.14-4.94 (2H, m), 4.57-4.03 (6H, m), 3.65-3.42 (2H, m), 2.65-2.59 (2H, m), 2.36-2.14 (3H, m), 2.04-1.76 (4H, m), 1.61-1.42 (27H, m), 1.36 (3H, s), 1.26 (3H, s), 1.14-1.01 (3H, m), 0.84 (3H, s). |
| 119 | (Me,Me / Me bicyclic boronate — CH$_2$CH$_2$ — phenyl(BocO, COOtBu) — O — azetidine — N — C(=O) — (S)-pyrrolidine-(R)-OH, N-Boc) | LCMS: [M + H]$^+$/Rt = 785.8/2.87 min$^B$<br>$^1$H-NMR (CDCl$_3$) δ: 8.65 (1H, br), 7.22 (1H, d, J = 8.1 Hz), 6.43 (1H, d, J = 8.1 Hz), 5.00-4.88 (1H, m), 4.59-4.05 (7H, m), 3.62-3.43 (2H, m), 2.64-2.56 (2H, m), 2.36-2.26 (1H, m), 2.19-2.00 (4H, m), 1.92-1.77 (2H, m), 1.56 (9H, s), 1.53 (9H, s), 1.45 (9H, s), 1.36 (3H, s), 1.26 (3H, s), 1.14-1.01 (3H, m), 0.84 (3H, s). |

Reference Example 120: tert-butyl (2S,4S)-4-amino-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate

[Chemical Formula 771]

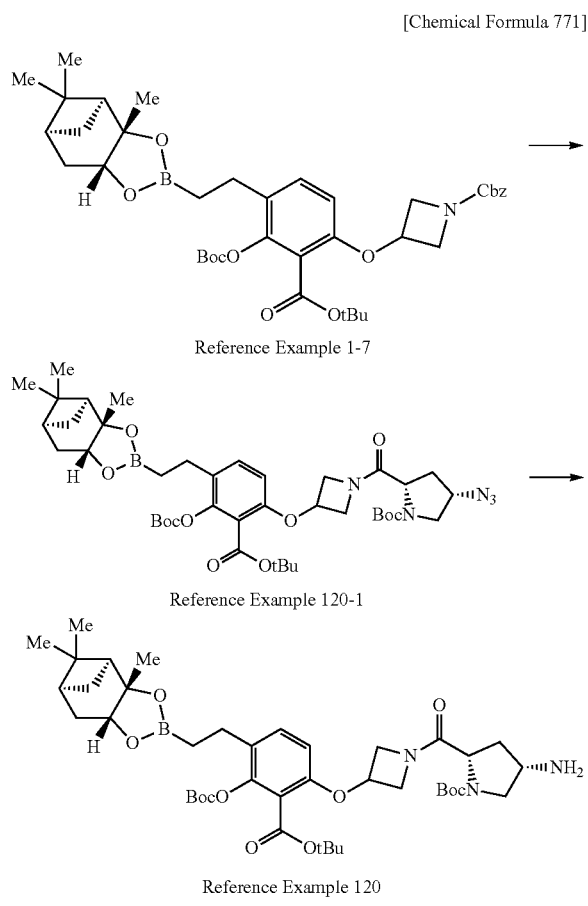

Reference Example 1-7

Reference Example 120-1

Reference Example 120

Reference Example 120-1: tert-butyl (2S,4S)-4-azido-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate

[Chemical Formula 772]

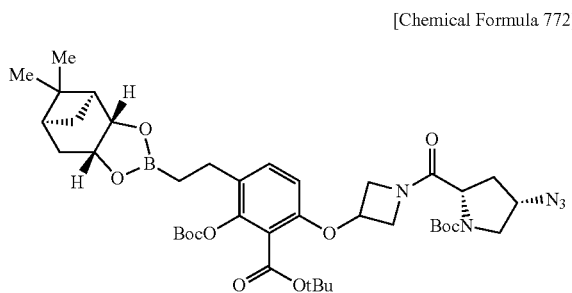

Palladium on carbon (40 mg, Pd content: 10%, wetted with ca. 55% water) was added to a methanol solution (6 mL) of the compound of Reference Example 1-7 (400 mg, 0.567 mmol), and the reaction mixture was stirred for 30 minutes under a hydrogen atmosphere at room temperature. The reaction solution was filtered through cellulose. The filtered substance was washed with methylene chloride, and the combined filtrate was concentrated. The resulting residue was dissolved in DMF (6 mL). cis-4-azido-(tert-butoxycarbonyl)-L-proline (160 mg, 0.624 mmol), HATU (259 mg, 0.680 mmol), and triethylamine (236 µL, 1.70 mmol) were added, and the reaction mixture was stirred for 30 minutes at room temperature. Water was added to the reaction solution, which was extracted with ethyl acetate. The organic phase was washed with saturated saline, dried over sodium sulfate, filtered, and concentrated. The resulting residue was purified by silica gel column chromatography (hexane/ethyl acetate) to obtain the title compound (392 mg) as a colorless amorphous compound.
$^1$H-NMR (CDCl$_3$) δ: 7.22 (1H, d, J=8.1 Hz), 6.40 (1H, d, J=8.1 Hz), 5.00-4.89 (1H, m), 4.82-4.01 (7H, m), 3.86-3.76 (1H, m), 3.39-3.32 (1H, m), 2.64-2.58 (2H, m), 2.48-2.28 (2H, m), 2.22-2.14 (1H, m), 2.04-2.00 (1H, m), 1.93-1.77 (3H, m), 1.56 (9H, s), 1.54 (9H, s), 1.45 (9H, s), 1.36 (3H, s), 1.26 (3H, s), 1.14-1.01 (3H, m), 0.84 (3H, s).
LCMS: [M+H]$^+$/Rt=810.8/3.02 min$^B$

Reference Example 120: tert-butyl (2S,4S)-4-amino-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate

[Chemical Formula 773]

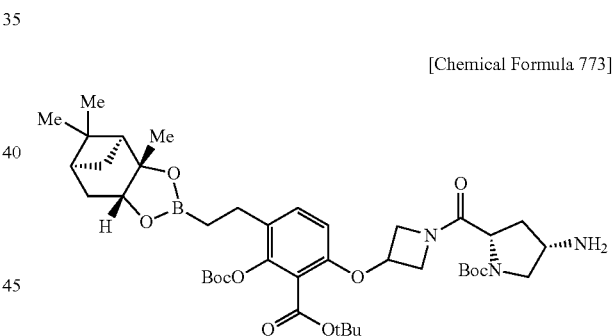

Palladium on carbon (40 mg, Pd content: 10%, wetted with ca. 55% water) was added to a methanol solution (5 mL) of the compound of Reference Example 120-1 (392 mg, 0.484 mmol), and the reaction mixture was stirred for 3 hours under a hydrogen atmosphere at room temperature. The reaction solution was filtered through cellulose. The filtered substance was washed with methanol, and the combined filtrate was concentrated. The residue was dissolved in acetonitrile (10 mL) and further filtered through cellulose. The filtered substance was washed with acetonitrile and the combined filtrate was concentrated to obtain the title compound (355 mg) as a brown solid.
$^1$H-NMR (CDCl$_3$) δ: 7.22 (1H, d, J=8.1 Hz), 6.41 (1H, d, J=8.1 Hz), 5.00-4.89 (2H, m), 4.52-4.02 (5H, m), 3.68-3.49 (2H, m), 3.33-3.29 (1H, m), 2.64-2.61 (2H, m), 2.36-2.26 (2H, m), 2.20-2.14 (1H, m), 2.04-2.01 (1H, m), 1.93-1.73 (3H, m), 1.61 (9H, s), 1.54 (9H, s), 1.45 (9H, s), 1.36 (3H, s), 1.26 (3H, s), 1.14-1.01 (3H, m), 0.84 (3H, s).
LCMS: [M+H]$^+$/Rt=785.0/2.28 min$^B$ Reference Example 121: tert-butyl (2S,4S)-4-acetamido-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate

[Chemical Formula 774]

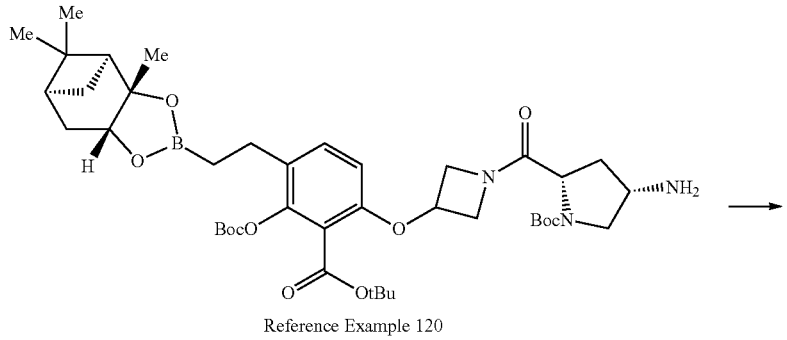

Reference Example 120

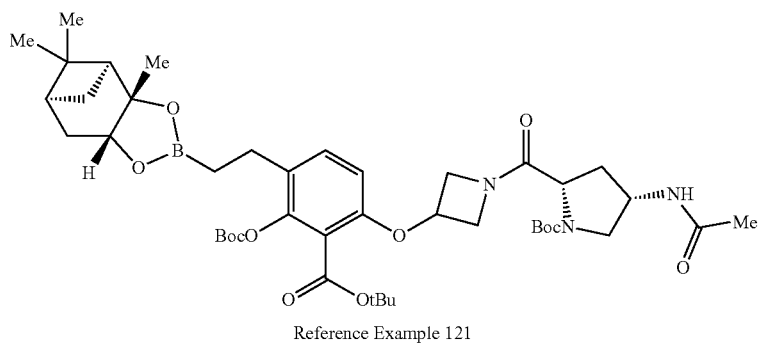

Reference Example 121

Triethylamine (101 μL, 0.727 mmol) and acetyl chloride (19 μL, 0.267 mmol) were added to a THF solution (2.4 mL) of the compound of Reference Example 120 (190 mg, 0.242 mmol), and the reaction mixture was stirred for 30 minutes. Water was added to the reaction solution, which was extracted with ethyl acetate. The organic phase was washed with saturated saline, dried over sodium sulfate, filtered, and concentrated. The resulting residue was purified by silica gel column chromatography (methylene chloride/methanol) to obtain the title compound (204 mg) as a colorless amorphous compound.

$^1$H-NMR (CDCl$_3$) δ: 8.38-8.23 (1H, m), 7.23 (1H, d, J=8.1 Hz), 6.43 (1H, d, J=8.1 Hz), 5.12-4.93 (2H, m), 4.72-4.63 (1H, m), 4.53-4.46 (1H, m), 4.32-4.02 (4H, m), 3.61-3.45 (2H, m), 2.65-2.59 (2H, m), 2.37-2.27 (2H, m), 2.21-2.14 (1H, m), 2.04-2.00 (1H, m), 1.98-1.78 (6H, m), 1.57 (9H, s), 1.54 (9H, s), 1.46-1.43 (9H, m), 1.36 (3H, s), 1.26 (3H, s), 1.14-1.01 (3H, m), 0.84 (3H, s).

LCMS: [M+H]$^+$/Rt=827.0/2.86 min$^B$

Reference Example 122: tert-butyl (2S,4R)-4-amino-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate
[Chemical Formula 775]
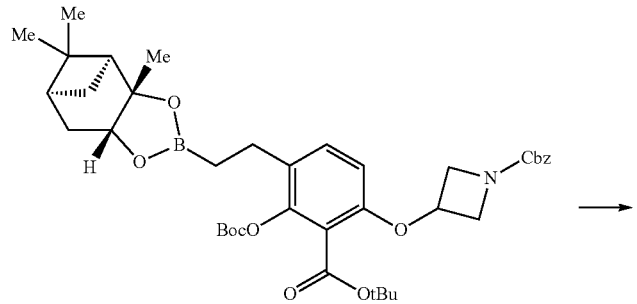
Reference Example 1-7
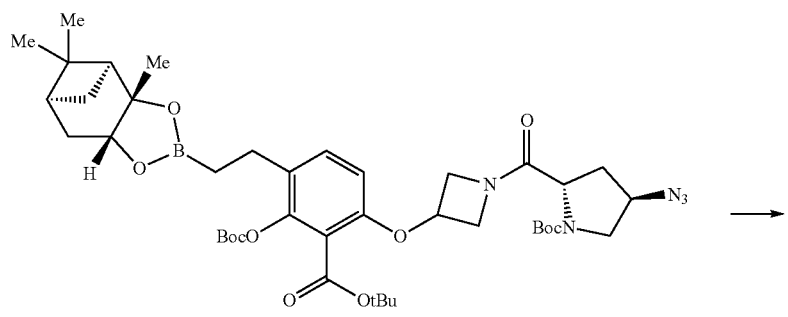
Reference Example 122-1
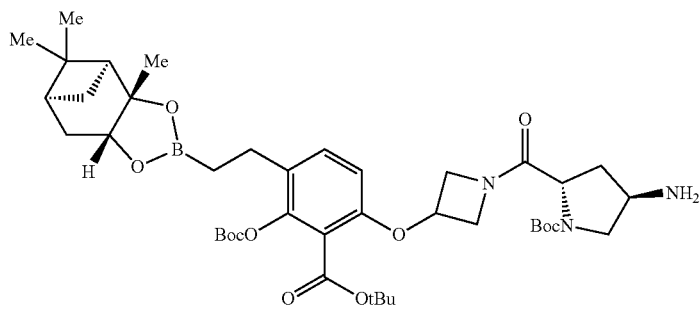
Reference Example 122

Reference Example 122-1: tert-butyl (2S,4R)-4-azido-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate

[Chemical Formula 776]

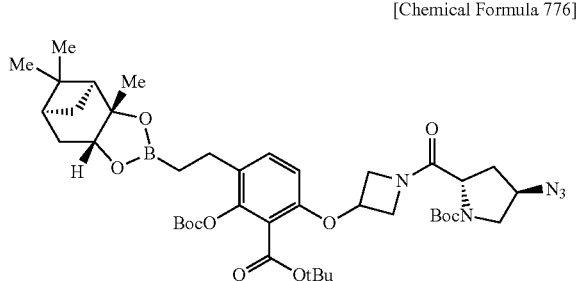

Palladium on carbon (40 mg, Pd content: 10%, wetted with ca. 55% water) was added to a methanol solution (6 mL) of the compound of Reference Example 1-7 (400 mg, 0.567 mmol), and the reaction mixture was stirred for 30 minutes under a hydrogen atmosphere at room temperature. The reaction solution was filtered through cellulose. The filtered substance was washed with methylene chloride, and the combined filtrate was concentrated. The resulting residue was dissolved in DMF (6 mL). (2S,4R)-4-azido-1-(tert-butoxycarbonyl)pyrrolidine-2-carboxylic acid (189 mg, 0.737 mmol), HATU (259 mg, 0.680 mmol), and triethylamine (236 µL, 1.70 mmol) were added, and the reaction mixture was stirred for 30 minutes at room temperature. Water was added to the reaction solution, which was extracted with ethyl acetate. The organic phase was washed with saturated saline, dried over sodium sulfate, filtered, and concentrated. The resulting residue was purified by silica gel column chromatography (hexane/ethyl acetate) to obtain the title compound (397 mg) as a colorless amorphous compound.

$^1$H-NMR (CDCl$_3$) δ: 7.23 (1H, d, J=8.1 Hz), 6.41 (1H, d, J=8.1 Hz), 5.00-4.00 (8H, m), 3.75-3.45 (2H, m), 2.74-2.58 (2H, m), 2.36-2.12 (4H, m), 2.05-2.00 (1H, m), 1.92-1.77 (2H, m), 1.60-1.54 (18H, m), 1.46-1.44 (9H, m), 1.36 (3H, s), 1.28 (3H, s), 1.14-1.01 (3H, m), 0.84 (3H, s).
LCMS: [M+H]$^+$/Rt=810.7/3.05 min$^B$ Reference Example 122: tert-butyl (2S,4R)-4-amino-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate

[Chemical Formula 777]

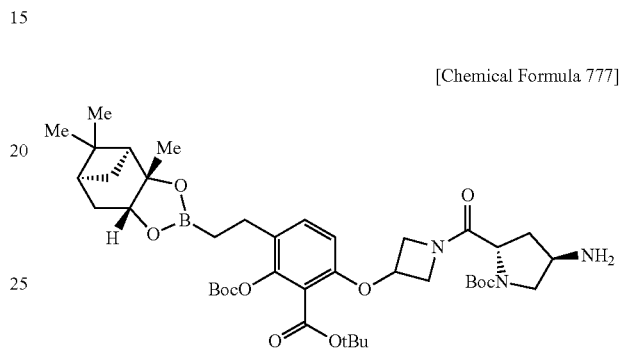

A reaction, work-up, and purification were performed using the compound of Reference Example 122-1 (397 mg, 0.490 mmol) as the starting material by the same method described in Reference Example 120 to obtain the title compound (368 mg) as a colorless amorphous compound.

$^1$H-NMR (CDCl$_3$) δ: 7.22 (1H, d, J=8.1 Hz), 6.40 (1H, d, J=8.1 Hz), 5.50-3.50 (9H, m), 3.26-3.07 (1H, m), 2.74-2.58 (2H, m), 2.36-2.28 (1H, m), 2.22-2.00 (3H, m), 1.92-1.77 (3H, m), 1.60-1.54 (18H, m), 1.45 (9H, s), 1.36 (3H, s), 1.28 (3H, s), 1.17-1.01 (3H, m), 0.84 (3H, s).
LCMS: [M+H]$^+$/Rt=784.8/2.27 min$^B$ Reference Example 123: tert-butyl (2S,4R)-4-acetamido-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidine-1-carbonyl}pyrrolidine-1-carboxylate

[Chemical Formula 778]

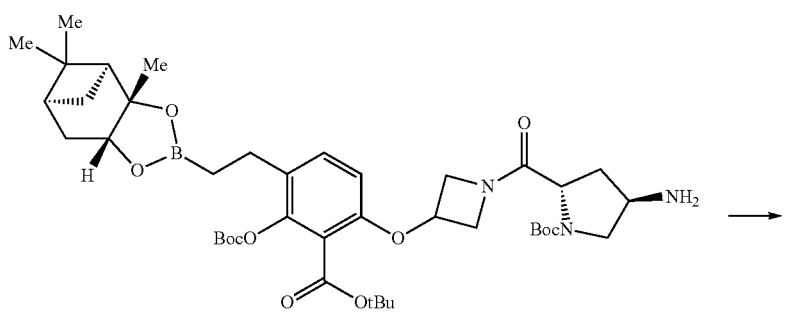

Reference Example 122

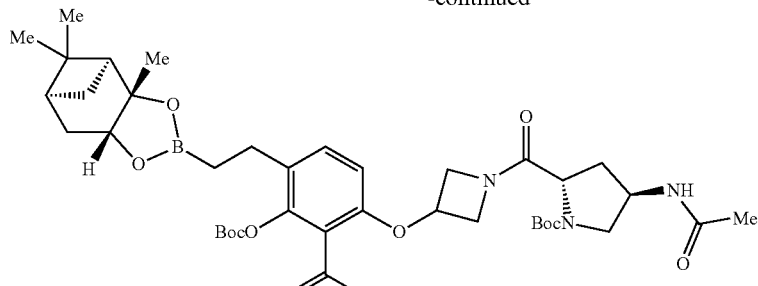

Reference Example 123

A reaction, work-up, and purification were performed using the compound of Reference Example 122 (181 mg, 0.232 mmol) as the starting material by the same method described in Reference Example 121 to obtain the title compound (162 mg) as a colorless amorphous compound.

$^1$H-NMR (CDCl$_3$) δ: 7.22 (1H, d, J=8.1 Hz), 6.42 (1H, d, J=8.1 Hz), 5.63-5.49 (1H, m), 5.00-3.94 (8H, m), 3.81-3.70 (1H, m), 3.48-3.32 (1H, m), 2.64-2.58 (2H, m), 2.36-2.14 (4H, m), 2.05-2.00 (1H, m), 1.98 (3H, s), 1.93-1.77 (2H, m), 1.56 (9H, s), 1.54 (9H, s), 1.47-1.43 (9H, m), 1.36 (3H, s), 1.28 (3H, s), 1.14-1.01 (3H, m), 0.84 (3H, s).

LCMS: [M+H]$^+$/Rt=826.7/2.81 min$^B$

Reference Example 124: tert-butyl (2S,4R)-4-(2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-2-(dimethylcarbamoyl)pyrrolidine-1-carboxylate

[Chemical Formula 779]

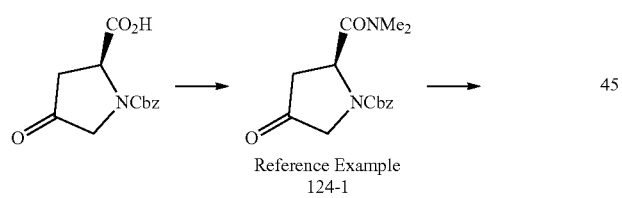

Reference Example 124-1

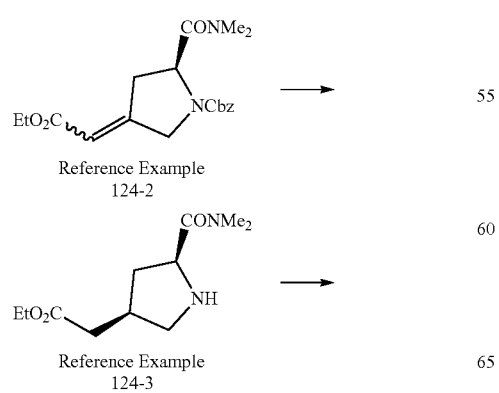

Reference Example 124-2

Reference Example 124-3

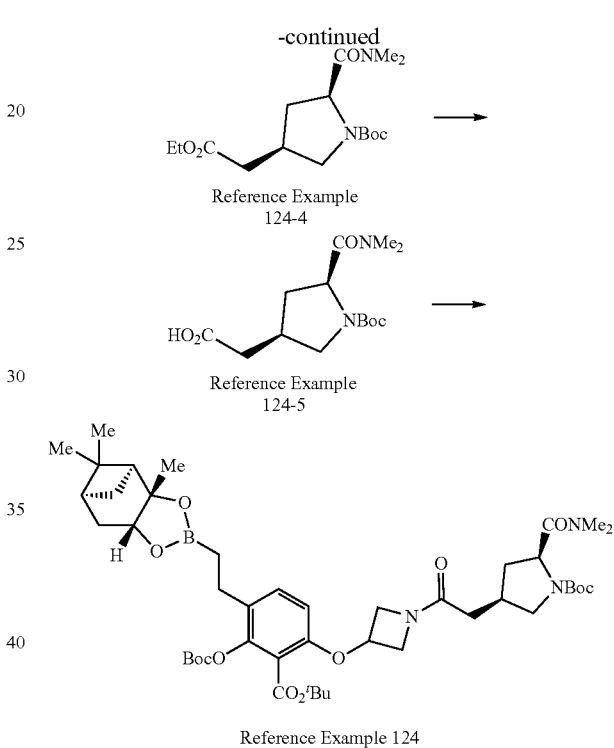

Reference Example 124-4

Reference Example 124-5

Reference Example 124

Reference Example 124-1: benzyl (2S)-2-(dimethylcarbamoyl)-4-oxopyrrolidine-1-carboxylate

[Chemical Formula 780]

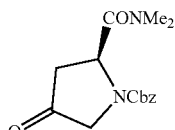

Triethylamine (0.48 mL, 3.44 mmol), HATU (873 mg, 2.30 mmol), and aqueous dimethylamine solution (about 9.5 mol/L, 0.24 mL, 2.3 mmol) were added to a THF solution (5.7 mL) of (2S)-1-benzyloxycarbonyl-4-oxopyrrolidine-2-carboxylic acid (302 mg, 1.15 mmol) while cooling with ice, and the reaction mixture was stirred for 8 hours at room temperature. A saturated aqueous sodium hydrogen carbonate solution was added to the reaction solution, which was extracted with ethyl acetate. The organic phase was washed with saturated saline, dried over sodium sulfate, filtered, and concentrated. The resulting residue was purified by silica gel column chromatography (hexane/ethyl acetate) to obtain the title compound (285 mg) as a colorless oily compound.

LCMS: [M+H]$^+$/Rt=291.14/0.582 min$^4$

Reference Example 124-2: benzyl (2S)-2-(dimethylcarbamoyl)-4-(2-ethoxy-2-oxoethylidene)pyrrolidine-1-carboxylate

[Chemical Formula 781]

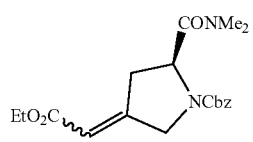

An n-butyl lithium/hexane solution (1.57 mol/L, 1.38 mL, 2.16 mmol) was slowly added to a THF solution (4.9 mL) of ethyl dimethylphosphonoacetate (423 mg, 2.16 mmol) at 78° C., and the reaction mixture was stirred for 30 minutes. A THF solution (4 ml) of the compound of Reference Example 124-1 (285 mg, 0.983 mmol) was added to the reaction solution at −78° C., and the reaction mixture was stirred for 5 hours at room temperature. A saturated aqueous ammonium chloride solution was added to the reaction solution, which was extracted with ethyl acetate. The organic phase was washed with saturated saline, dried over sodium sulfate, filtered, and concentrated. The resulting residue was purified by silica gel column chromatography (hexane/ethyl acetate) to obtain the title compound (190 mg) as a colorless oil.

LCMS: [M+H]$^+$/Rt=361.19/0.757 min$^4$, 361.19/0.795 min$^4$ (E/Z isomer mixture)

Reference Example 124-3: ethyl [(3R,5S)-5-(dimethylcarbamoyl)pyrrolidin-3-yl]acetate

[Chemical Formula 782]

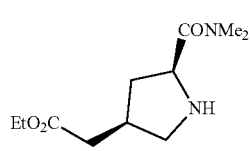

A palladium on carbon-ethylenediamine complex (180 mg, Pd content: 10%, wetted with ca. 55% water) was added to a methanol solution (3.8 mL) of the compound of Reference Example 124-2 (190 mg, 0.526 mmol), and the reaction mixture was stirred for 7.5 hours under a hydrogen atmosphere. The reaction solution was filtered through celite. The filtered substance was washed with methanol, and the combined filtrate was concentrated to obtain the title compound (116.3 mg) as a colorless oil.

$^1$H-NMR (CDCl$_3$) δ: 4.05 (2H, q, J=7.1 Hz), 3.89 (1H, t, J=7.9 Hz), 3.02 (1H, dd, J=10.4, 6.7 Hz), 2.94 (3H, s), 2.91 (3H, s), 2.76 (1H, dd, J=10.4, 7.3 Hz), 2.57-2.48 (1H, m), 2.38-2.30 (3H, m), 2.23 (1H, dd, J=15.9, 7.9 Hz), 1.18 (3H, t, J=7.0 Hz).

LCMS: [M+H]$^+$/Rt=229.12/0.244 min$^4$

Reference Example 124-4: tert-butyl (2S,4R)-2-(dimethylcarbamoyl)-4-(2-ethoxy-2-oxoethyl)pyrrolidine-1-carboxylate

[Chemical Formula 783]

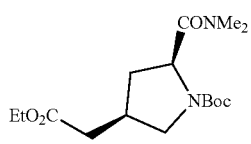

Sodium hydrogen carbonate (128 mg, 1.53 mmol) and di-tert-butyl dicarbonate (0.237 mL, 1.02 mmol) were added to a THF-water (1:1) mixture solution (3 mL) of the compound of Reference Example 124-3 (116 mg, 0.509 mmol), and the reaction mixture was stirred for 14 hours at room temperature. The reaction solution was extracted with ethyl acetate. The organic phase was washed with saturated saline, dried over sodium sulfate, filtered, and concentrated. The resulting residue was purified by silica gel column chromatography (hexane/ethyl acetate) to obtain the title compound (125 mg) as a colorless oil.

$^1$H-NMR (CDCl$_3$) δ: 5.25 (1H, s), 4.00-3.94 (1H, m), 3.78-3.72 (1H, m), 3.76 (3H, s), 3.17 (1H, s), 1.46 (3H, s), 1.43 (9H, s).

Reference Example 124-5: [(3R,5S)-1-(tert-butoxycarbonyl)-5-(dimethylcarbamoyl)pyrrolidin-3-yl]acetic Acid

[Chemical Formula 784]

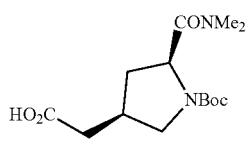

An aqueous 2 N sodium hydroxide solution (0.38 mL, 0.76 mmol) was added to a THF-water (2:1) mixture solution (1.8 mL) of the compound of Reference Example 124-4 (125 mg, 0.380 mmol) while cooling with ice, and the reaction mixture was stirred for 16 hours at room temperature. 1 N hydrochloric acid was added to the reaction solution, which was extracted with chloroform. The organic phase was washed with saturated saline, dried over sodium sulfate, filtered, and concentrated to obtain the title compound (114 mg) as a white solid.

$^1$H-NMR (CDCl$_3$) δ: 4.54 (1H, dt, J=38.8, 7.9 Hz), 3.82-3.73 (1H, m), 3.11 (1H, td, J=9.6, 4.9 Hz), 3.04-2.97 (3H, m), 2.91 (3H, s), 2.54-2.35 (3H, m), 1.60-1.50 (2H, m), 1.35 (9H, d, J=23.3 Hz).

Reference Example 124: tert-butyl (2S,4R)-4-(2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-2-(dimethylcarbamoyl)pyrrolidine-1-carboxylate

[Chemical Formula 785]

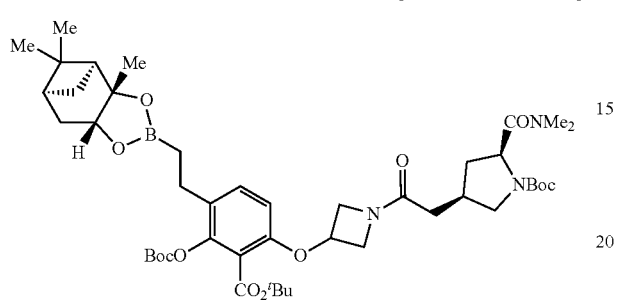

A reaction, work-up, and purification were performed using the compound of Reference Example 1-8 (145 mg, 0.253 mmol) and the compound of Reference Example 124-5 (114 mg, 0.380 mmol) as the starting materials by the same method described in Reference Example 36-4 to obtain the title compound (167 mg) as a colorless amorphous compound.

LCMS: $[M+H]^+$/RT=854.45/1.398 $min^C$

Reference Example 125: tert-butyl (2R,4S)-4-(2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-2-(dimethylcarbamoyl)pyrrolidine-1-carboxylate

[Chemical Formula 786]

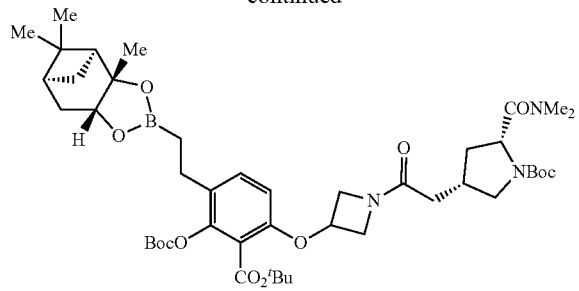

Reference Example 125

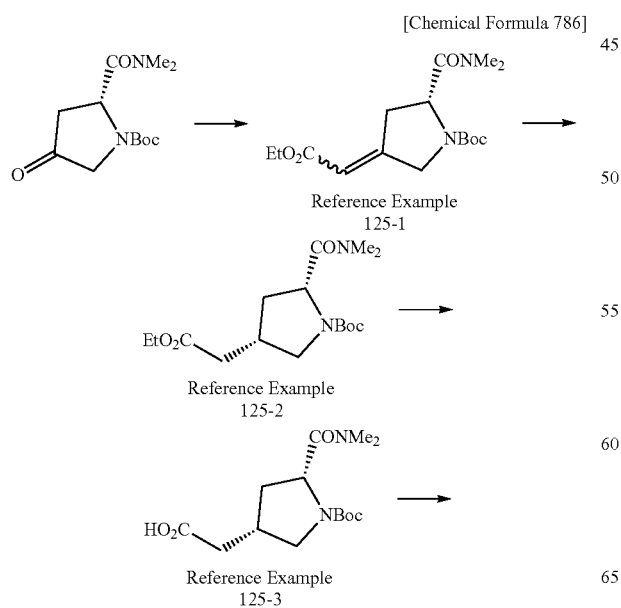

Reference Example 125-1: tert-butyl (2R)-2-(dimethylcarbamoyl)-4-(2-ethoxy-2-oxoethylidene)pyrrolidine-1-carboxylate

[Chemical Formula 787]

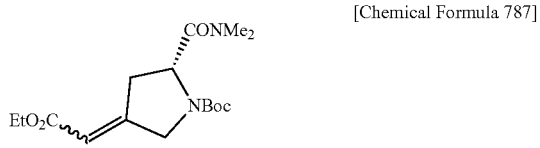

A reaction, work-up, and purification were performed using tert-butyl (R)-2-(dimethylcarbamoyl)-4-oxopyrrolidine-1-carboxylate (325 mg, 1.27 mmol) as the starting material by the same method described in Reference Example 124-2 to obtain the title compound (167 mg) as a colorless oil.

LCMS: $[M+H]^+$/Rt=327.24/0.704 $min^A$, 327.24/0.748 $min^A$ (two peaks detected due to being an E/Z isomer mixture)

Reference Example 125-2: tert-butyl (2R,4S)-2-(dimethylcarbamoyl)-4-(2-ethoxy-2-oxoethyl)pyrrolidine-1-carboxylate

[Chemical Formula 788]

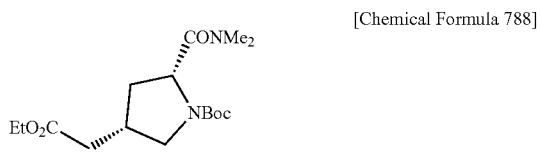

A reaction and work-up were performed using the compound of Reference Example 125-1 (167 mg, 0.511 mmol) was used as the starting material by the same method described in Reference Example 124-3 to obtain the title compound (128 mg) as a colorless oil.

LCMS: $[M+H]^+$/Rt=329.18/0.681 $min^A$

581

Reference Example 125-3: [(3S,5R)-1-(tert-butoxy-carbonyl)-5-(dimethylcarbamoyl)pyrrolidin-3-yl] acetic Acid

[Chemical Formula 789]

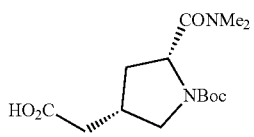

A reaction and work-up were performed using the compound of Reference Example 125-2 (128 mg, 0.388 mmol) as the starting materials by the same method described in Reference Example 124-4 to obtain the title compound (117 mg) as a white solid.

$^1$H-NMR (CDCl$_3$) δ: 4.55 (1H, dt, J=39.1, 7.9 Hz), 3.82-3.73 (1H, m), 3.10 (1H, dd, J=11.3, 7.6 Hz), 3.02 (3H, d, J=16.4 Hz), 2.91 (3H, d, J=1.2 Hz), 2.52-2.39 (3H, m), 1.60-1.50 (2H, m), 1.35 (9H, d, J=23.2 Hz).

Reference Example 125: tert-butyl (2R,4S)-4-(2-{3-[2-(tert-butoxycarbonyl)-3-[(tert-butoxycarbonyl)oxy]-4-{2-[(3aS,4S,6S,7aR)-3a,5,5-trimethylhexa-hydro-2H-4,6-methano-1,3,2-benzodioxaborol-2-yl]ethyl}phenoxy]azetidin-1-yl}-2-oxoethyl)-2-(dimethylcarbamoyl)pyrrolidine-1-carboxylate

[Chemical Formula 790]

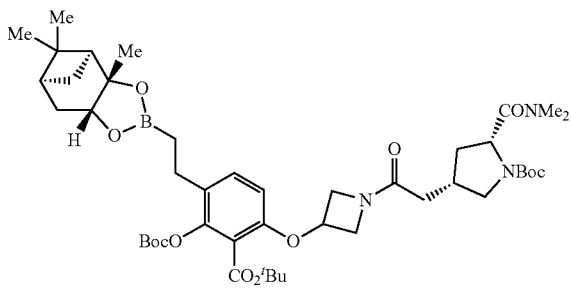

A reaction, work-up, and purification were performed using the compound of Reference Example 1-8 (149 mg, 0.260 mmol) and the compound of Reference Example 125-3 (116 mg, 0.386 mmol) as the starting materials by the same method described in Reference Example 36-4 to obtain the title compound (153 mg) as a colorless amorphous compound.

LCMS: [M+H]$^+$/RT=854.47/1.398 min$^C$

Reference Example 126: tert-butyl 2-(2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-1,1-dioxo-1λ$^6$-thiomorpholine-4-carboxylate

[Chemical Formula 791]

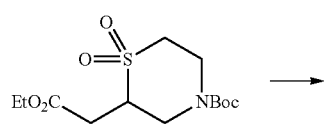

582

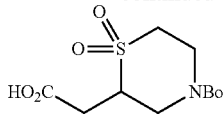

Reference Example 126-1

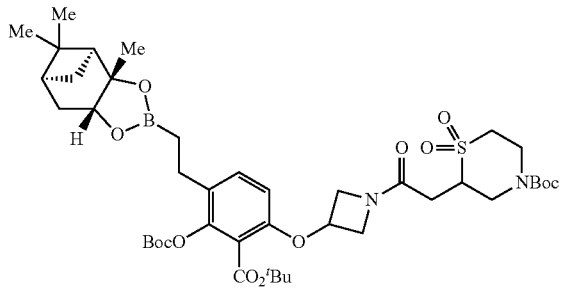

Reference Example 126

Reference Example 126-1: [4-(tert-butoxycarbonyl)-1,1-dioxo-1λ$^6$-thiomorpholin-2-yl]acetic Acid

[Chemical Formula 792]

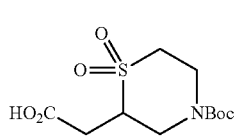

An aqueous 2 N sodium hydroxide solution (1.15 mL, 2.31 mmol) was added to a methanol solution (7 mL) of tert-butyl 2-(2-ethoxy-2-oxoethyl)thiomorpholine-4-carboxylate 1,1-dioxide (247 mg, 0.769 mmol) while cooling with ice, and the reaction mixture was stirred for 4.5 hours at room temperature. An aqueous 2 N sodium hydroxide solution (1.15 mL, 2.31 mmol) was further added, and the reaction mixture was stirred for 2 hours. 1 N hydrochloric acid was added to the reaction solution, which was extracted with ethyl acetate. The organic phase was dried over sodium sulfate, filtered, and concentrated to obtain the title compound (225 mg) as a light yellow oily compound.

LCMS: [M+H]$^+$/RT=292.13/0.521 min$^C$

Reference Example 126: tert-butyl 2-(2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-1,1-dioxo-1λ$^6$-thiomorpholine-4-carboxylate

[Chemical Formula 793]

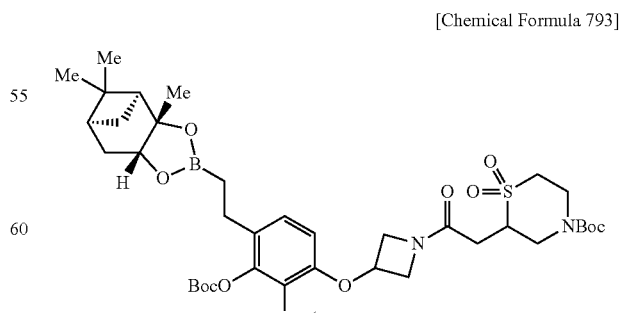

A reaction, work-up, and purification were performed using the compound of Reference Example 1-8 (0.30 g, 0.493 mmol) and the compound of Reference Example 126-1 (159 mg, 0.543 mmol) as the starting materials by the same method described in Reference Example 36-4 to obtain the title compound (225 mg) as a light yellow oil.

¹H-NMR (CDCl₃) δ: 7.22 (1H, d, J=8.7 Hz), 6.40 (1H, d, J=8.7 Hz), 4.97-4.91 (1H, m), 4.56-4.35 (3H, m), 4.31-4.16 (5H, m), 4.09-3.98 (2H, m), 3.05-3.00 (2H, m), 2.79 (1H, d, J=16.0 Hz), 2.62 (2H, t, J=8.2 Hz), 2.35-2.28 (1H, m), 2.22-2.15 (1H, m), 2.04-2.00 (1H, m), 1.95-1.85 (2H, m), 1.81 (1H, d, J=14.6 Hz), 1.56 (9H, s), 1.54 (9H, s), 1.47 (9H, s), 1.36 (3H, s), 1.28 (3H, s), 1.11 (2H, t, J=8.2 Hz), 1.03 (1H, d, J=11.0 Hz), 0.83 (3H, s).

Reference Example 127: tert-butyl 2-[(tert-butoxycarbonyl)oxy]-6-{[1-(1H-imidazole-2-carbonyl)azetidin-3-yl]oxy}-3-{2-[(3aS,4S,6S,7aR)-3a,5,5-trimethylhexahydro-2H-4,6-methano-1,3,2-benzodioxaborol-2-yl]ethyl}benzoate

[Chemical Formula 794]

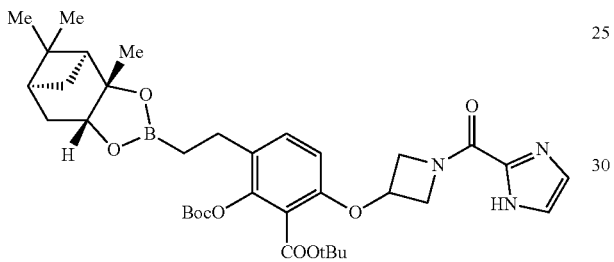

A reaction, work-up, and purification were performed using the compound of Reference Example 1-7 (200 mg, 0.283 mmol) as the starting material by the same method described in Reference Example 40 to obtain the title compound (119 mg).

¹H-NMR (CDCl₃) δ: 10.76 (1H, br), 7.23 (1H, d, J=8.1 Hz), 7.19 (1H, s), 7.13 (1H, s), 6.46 (1H, d, J=8.1 Hz), 5.15-4.99 (2H, m), 4.76-4.70 (1H, m), 4.60-4.54 (1H, m), 4.29-4.23 (2H, m), 2.65-2.59 (2H, m), 2.36-2.26 (1H, m), 2.23-2.14 (1H, m), 2.05-2.01 (1H, m), 1.93-1.78 (2H, m), 1.56 (9H, s), 1.53 (9H, s), 1.36 (3H, s), 1.29 (3H, s), 1.15-1.01 (3H, m), 0.84 (3H, s).

LCMS: [M+H]⁺/Rt=666.9/2.83 min^B

Reference Example 128: N²-(tert-butoxycarbonyl)-N-[(2R)-1-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-1-oxopropan-2-yl]-D-serinamide

[Chemical Formula 795]

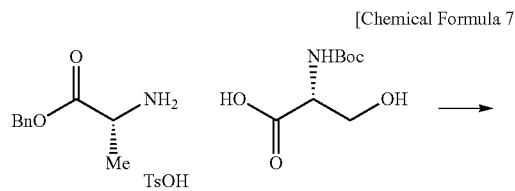

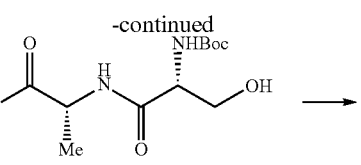

Reference Example 128-1

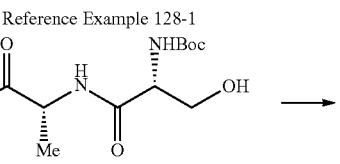

Reference Example 128-2

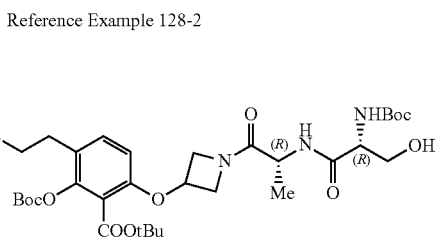

Reference Example 128

Reference Example 128-1: benzyl N-(tert-butoxycarbonyl)-D-seryl-D-alaninate

[Chemical Formula 796]

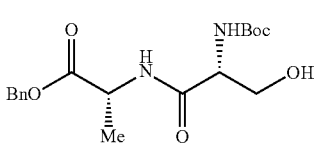

4-(4,6-dimethoxy-1,3,5-triazin-2-yl)-4-methylmorpholinium chloride (809 mg, 2.92 mmol), triethylamine (0.355 mL, 2.56 mmol), and D-alanine benzyl p-toluenesulfonate (899 mg, 2.56 mmol) were added to a methanol (24 mL) solution of N-(tert-butoxycarbonyl)-D-serine (500 mg, 2.44 mmol), and the reaction mixture was stirred for 13 hours at room temperature. Water was added to the reaction solution, which was extracted with methylene chloride and then washed with 1 N hydrochloric acid and saturated aqueous sodium hydrogen carbonate solution. The resultant was dried over anhydrous sodium sulfate, filtered, and concentrated to obtain the title compound (955 mg).

¹H-NMR (CDCl₃) δ: 7.42-7.31 (5H, m), 7.03-7.00 (1H, m), 5.53-5.50 (1H, m), 5.23-5.13 (2H, m), 4.70-4.55 (1H, m), 4.23-4.15 (1H, m), 4.09-3.94 (1H, m), 3.68-3.59 (1H, m), 3.11-3.03 (1H, m), 1.45-1.42 (12H, m).

LCMS: [M+H]⁺/Rt=367.2/1.77 min^B

Reference Example 128-2: N-(tert-butoxycarbonyl)-D-seryl-D-alanine

[Chemical Formula 797]

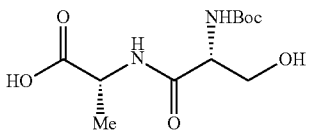

10% palladium on carbon (48 mg) was added to a methanol (18 mL) solution of the compound of Reference Example 128-1 (955 mg, 2.61 mmol). The reaction mixture was subjected to hydrogen substitution and was stirred for 2 hours at room temperature. After the reaction solution was filtered, the filtrate was concentrated to obtain the title compound (735 mg).

$^1$H-NMR (CDCl$_3$) δ: 7.50-7.42 (1H, m), 5.75-5.72 (1H, m), 4.62-4.51 (1H, m), 4.30 (1H, br), 4.03-3.66 (3H, m), 1.47-1.44 (12H, m).

LCMS: [M+H]$^+$/Rt=277.1/1.04 min$^B$

Reference Example 128: N$^2$-(tert-butoxycarbonyl)-N-[(2R)-1-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-1-oxopropan-2-yl]-D-serinamide

[Chemical Formula 798]

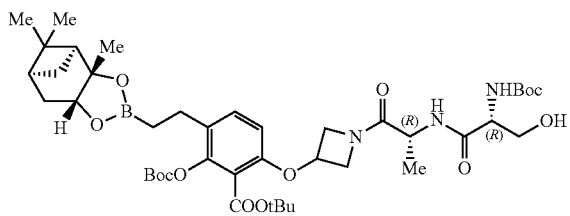

A reaction, work-up, and purification were performed using the compound of Reference Example 1-7 (200 mg, 0.283 mmol) and the compound of Reference Example 128-2 (86.1 mg, 0.312 mmol) as the starting materials by the same method described in Reference Example 117 to obtain the title compound (203 mg).

$^1$H-NMR (CDCl$_3$) δ: 7.24 (1H, d, J=8.1 Hz), 6.92-6.82 (1H, m), 6.41 (1H, d, J=8.1 Hz), 5.46-5.37 (1H, m), 5.02-4.95 (1H, m), 4.72-4.66 (1H, m), 4.51-3.94 (7H, m), 3.65-3.32 (2H, m), 2.65-2.49 (2H, m), 2.36-2.28 (1H, m), 2.22-2.13 (1H, m), 2.05-2.00 (1H, m), 1.93-1.77 (2H, m), 1.57 (9H, s), 1.54 (9H, s), 1.45 (9H, s), 1.36-1.23 (9H, m), 1.14-1.01 (3H, m), 0.84 (3H, s).

LCMS: [M+H]$^+$/Rt=830.4/2.80 min$^B$

A reaction, work-up, and purification were performed using N$^α$-(tert-butoxycarbonyl)-D-asparagine and tert-butyl N$^α$-(tert-butoxycarbonyl)-D-aspartate as the starting materials by the same method described in Reference Example 128-1 and Reference Example 128-2 to obtain each of Reference Example compounds 129 and 130 shown in Table 2-21.

TABLE 2-21

| Reference Example | Starting material | Structural formula | NMR and/or LCMS |
|---|---|---|---|
| 129 | N$^α$-(tert-butoxycarbonyl)-D-asparagine | | LCMS: [M + H]$^+$/Rt = 304.1/1.03 min$^B$ $^1$H-NMR (DMSO-d$_6$) δ: 12.6 (1H, br), 8.01 (1H, d, J = 8.1 Hz), 7.24 (1H, br), 6.91-6.88 (1H, m), 4.30-4.15 (2H, m), 3.42-3.35 (1H, m), 2.52-2.28 (2H, m), 1.37 (9H, s), 1.26 (3H, d, J = 8.1 Hz). |
| 130 | tert-Butyl N$^α$-(tert-butoxycarbonyl)-D-aspartate | | LCMS: [M + H]$^+$/Rt = 361.2/1.71 min$^B$ $^1$H-NMR (CDCl$_3$) δ: 7.19 (1H, d, J = 5.4 Hz), 6.75 (1H, d, J = 8.1 Hz), 4.64-4.46 (2H, m), 2.89-2.57 (2H, m), 1.47-1.45 (21H, m). |

A reaction, work-up, and purification were performed using the compound of Reference Example 1-7 and a corresponding commercially available carboxylic acid or the compound of Reference Example 129 as the starting materials by the same method described in Reference Example 42 to obtain each of Reference Example compounds 131 to 134 shown in Table 2-22.

TABLE 2-22

| Reference Example | Structural formula | NMR and/or LCMS |
|---|---|---|
| 131 | (structure) | LCMS: [M + H]$^+$/Rt = 814.9/2.79 min$^B$<br>$^1$H-NMR (CDCl$_3$) δ: 7.23 (1H, d, J = 8.1 Hz), 6.64-6.39 (2H, m), 5.50-5.39 (1H, m), 5.01-4.91 (1H, m), 4.63-4.00 (6H, m), 3.79-3.56 (1H, m), 3.07-2.83 (1H, m), 2.64-2.58 (2H, m), 2.37-2.26 (1H, m), 2.23-2.13 (1H, m), 2.05-1.77 (8H, m), 1.59-1.54 (18H, m), 1.44 (9H, s), 1.36 (3H, s), 1.28 (3H, s), 1.14-1.01 (3H, m), 0.84 (3H, s). |
| 132 | (structure) | LCMS: [M + H]$^+$/Rt = 786.8/2.77 min$^B$<br>$^1$H-NMR (CDCl$_3$) δ: 7.24-7.20 (1H, m), 7.00-6.86 (1H, m), 6.41 (1H, d, J = 8.1 Hz), 6.34-6.07 (1H, m), 5.43-5.35 (1H, m), 4.98-4.89 (1H, m), 4.63-4.31 (3H, m), 4.26-4.22 (1H, m), 4.17-4.00 (2H, m), 2.96-2.83 (1H, m), 2.64-2.58 (2H, m), 2.44-2.27 (2H, m), 2.21-2.13 (1H, m), 2.05-2.00 (1H, m, 1.93-1.76 (2H, m), 1.59-1.53 (18H, m), 1.45 (9H, s), 1.36 (3H, s), 1.28 (3H, s), 1.14-1.00 (3H, m), 0.83 (3H, s). |
| 133 | (structure) | LCMS: [M + H]$^+$/Rt = 814.8/2.88 min$^B$<br>$^1$H-NMR (CDCl$_3$) δ: 7.24 (1H, d, J = 8.1 Hz), 6.80-6.70 (1H, m), 6.41 (1H, d, J = 8.1 Hz), 5.05-4.90 (2H, m), 4.71-4.03 (7H, m), 2.65-2.59 (2H, m), 2.37-2.27 (1H, m), 2.22-2.13 (1H, m), 2.05-2.00 (1H, m), 1.93-1.76 (2H, m), 1.59-1.54 (18H, m), 1.45-1.44 (9H, m), 1.36-1.26 (12H, m), 1.14-1.01 (3H, m), 0.84 (3H, s). |
| 134 | (structure) | LCMS: [M + H]$^+$/Rt = 857.8/2.71 min$^B$<br>$^1$H-NMR (CDCl$_3$) δ: 7.40-7.31 (1H, m), 7.23 (1H, d, J = 8.1 Hz), 6.41 (1H, d, J = 8.1 Hz), 6.09-5.95 (1H, m), 5.90-5.79 (1H, m), 5.51-5.41 (1H, m), 5.01-4.92 (1H, m), 4.70-4.00 (7H, m), 2.97-2.88 (1H, m), 2.64-2.48 (3H, m), 2.37-2.27 (1H, m), 2.22-2.13 (1H, m), 2.05-2.00 (1H, m), 1.93-1.77 (2H, m), 1.56 (9H, s), 1.53 (9H, s), 1.46-1.45 (9H, m), 1.36 (3H, s), 1.32-1.23 (6H, m), 1.14-1.01 (3H, m), 0.84 (3H, s). |

A reaction, work-up, and purification were performed using the compound of Reference Example 1-8 and a corresponding commercially available carboxylic acid or the compound of Reference Example 130 as the starting materials by the same method described in Reference Example 3 to obtain each of Reference Example compounds 135 to 137 shown in Table 2-23.

TABLE 2-23

| Reference Example | Structural formula | NMR and/or LCMS |
|---|---|---|
| 135 | 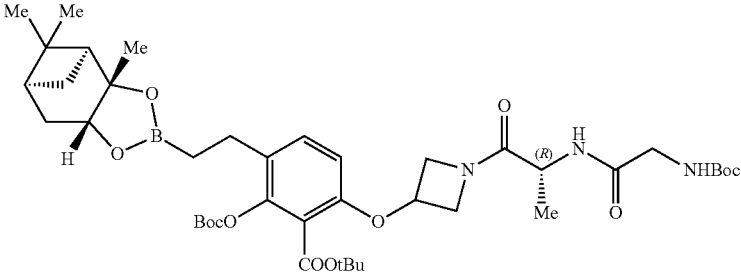 | LCMS: [M + H]$^+$/Rt = 800.7/2.83 min$^B$<br>$^1$H-NMR (CDCl$_3$) δ: 7.26-7.21 (1H, m), 6.77-6.68 (1H, m), 6.41 (1H, d, J = 8.1 Hz), 5.10-4.92 (2H, m), 4.72-4.03 (6H, m), 3.85-3.76 (2H, m), 2.65-2.59 (2H, m), 2.36-2.28 (1H, m), 2.22-2.12 (1H, m), 2.04-2.00 (1H, m), 1.93-1.76 (2H, m), 1.56-1.54 (18H, m), 1.46 (9H, s), 1.36-1.28 (9H, m), 1.14-1.01 (3H, m), 0.84 (3H, s). |
| 136 | 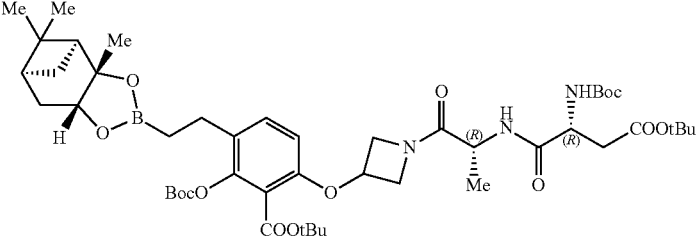 | LCMS: [M + H]$^+$/Rt = 914.7/3.07 min$^B$<br>$^1$H-NMR (CDCl$_3$) δ: 7.24-7.03 (1H, m), 6.42-6.38 (1H, m), 5.66-5.53 (1H, m), 4.99-4.91 (1H, m), 4.69-4.04 (8H, m), 2.94-2.82 (1H, m), 2.64-2.55 (3H, m), 2.36-2.27 (1H, m), 2.20-2.12 (1H, m), 2.05-2.00 (1H, m), 1.93-1.77 (2H, m), 1.59-1.53 (18H, m), 1.46-1.43 (18H, m), 1.36 (3H, s), 1.32-1.23 (6H, m), 1.14-1.01 (3H, m), 0.84 (3H, s). |
| 137 | 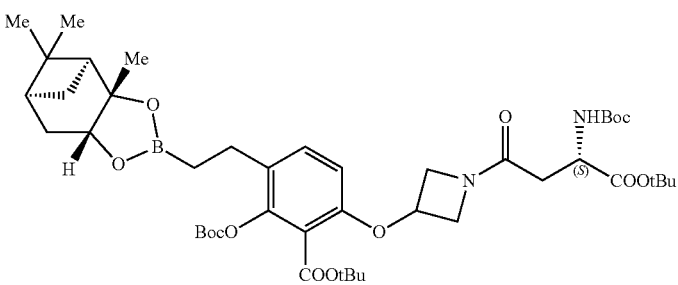 | LCMS: [M + H]$^+$/Rt = 843.6/3.14 min$^B$<br>$^1$H-NMR (CDCl$_3$) δ: 7.22 (1H, d, J = 8.1 Hz), 6.40 (1H, d, J = 8.1 Hz), 5.75-5.67 (1H, m), 4.94-4.89 (1H, m), 4.48-4.32 (3H, m), 4.26-4.22 (1H, m), 4.19-4.11 (1H, m), 4.07-4.02 (1H, m), 2.86-2.71 (1H, m), 2.64-2.48 (3H, m), 2.37-2.26 (1H, m), 2.23-2.13 (1H, m), 2.05-2.00 (1H, m), 1.92-1.77 (2H, m), 1.56 (9H, s), 1.53 (9H, s), 1.46-1.43 (18H, m), 1.36 (3H, s), 1.28 (3H, s), 1.14-1.00 (3H, m), 0.83 (3H, s). |

Reference Example 138: tert-butyl 4-[2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-1-(methylamino)-2-oxoethyl]-1H-imidazole-1-carboxylate

[Chemical Formula 799]

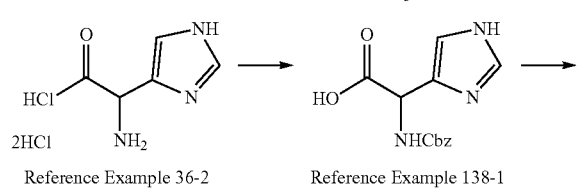

Reference Example 36-2 → Reference Example 138-1

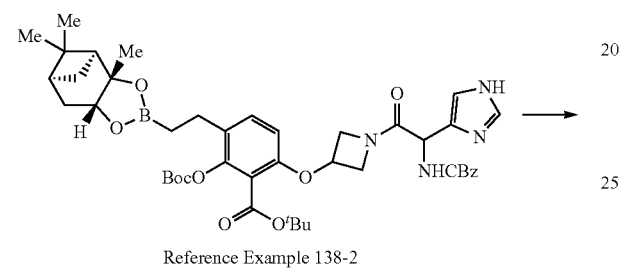

Reference Example 138-2

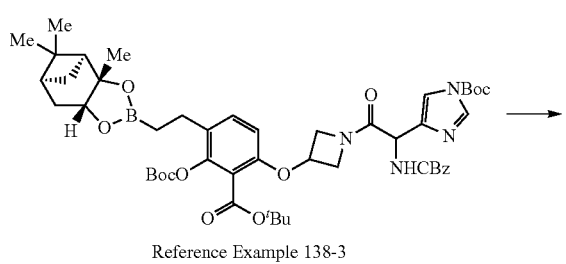

Reference Example 138-3

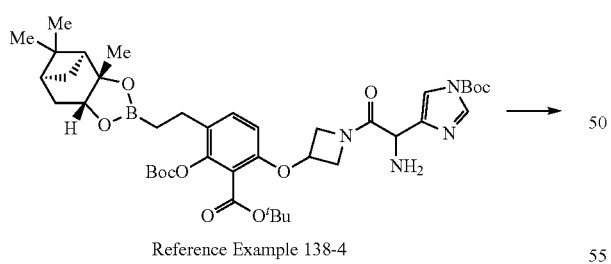

Reference Example 138-4

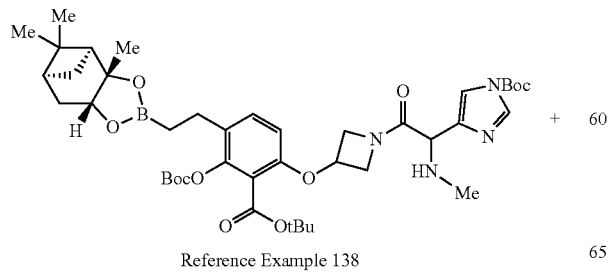

Reference Example 138

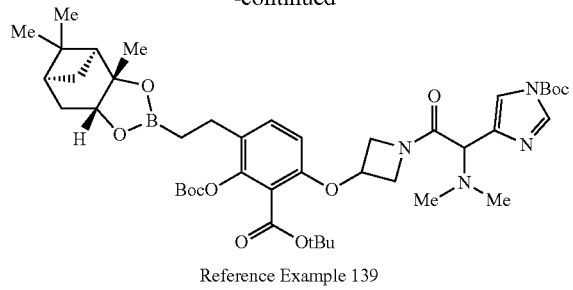

Reference Example 139

Reference Example 138-1: {[(benzyloxy)carbonyl]amino}(1H-imidazol-4-yl)acetic Acid

[Chemical Formula 800]

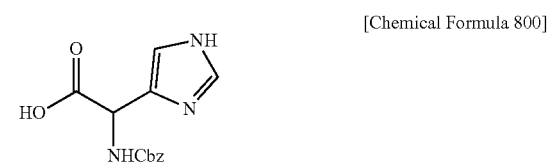 [SMILES: O=C(NC(C(=O)O)c1c[nH]cn1)OCc1ccccc1]

Sodium hydrogen carbonate (5.78 g, 68.8 mmol) and benzyl chloroformate (5.87 g, 34.4 mmol) were added to an ethanol/water (1:1) mixture solution (57 mL) of the compound of Reference Example 36-2 (3.68 g, 17.2 mmol) while cooling with ice. After stirring for 15 minutes, the reaction solution was warmed up to room temperature, and stirred for another 12 hours. Saturated ammonium chloride water was added to the reaction solution, which was extracted with ethanol (40 mL) and dichloromethane (40 mL). The organic phase was dried over sodium sulfate, filtered, and concentrated. The resulting residue was purified by chromatography (dichloromethane/methanol=10/1) to obtain the title compound (1.7 g).

$^1$H-NMR (500 MHz, CDCl$_3$) δ: 8.86-8.82 (1H, m), 7.51-7.47 (1H, m), 7.37-7.24 (5H, m), 5.57 (1H, s), 5.10 (2H, s).

Reference Example 138-2: tert-butyl 6-({1-[{[(benzyloxy)carbonyl]amino}(1H-imidazol-4-yl)acetyl]azetidin-3-yl}oxy)-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 801]

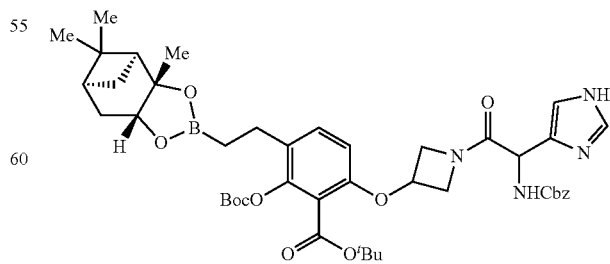

Triethylamine (5 mL, 18 mmol), ethyldicarbodiimide (1.16 g, 6 mmol), and 1-hydroxybenzotriazole (1.64 g, 12 mmol) were added to a DMF (24 mL) solution of the compound of Reference Example 138-1 (1.7 g, 6.1 mmol) and the compound of Reference Example 1-8 (1.7 g, 3.0 mmol), and the reaction mixture was stirred for 12 hours at room temperature. A saturated aqueous sodium hydrogen carbonate solution (30 mL) was added to the reaction solution, which was extracted with ethyl acetate (30 mL). The organic phase was washed with saturated saline (30 mL), then dried over sodium sulfate, filtered, and concentrated. The resulting residue was purified by column chromatography (dichloromethane/methanol=50/1) to obtain the title compound (956 mg).

$^1$H-NMR (500 MHz, CDCl$_3$) δ: 9.30 (1H, brs), 7.59 (1H, s), 7.40-7.22 (5H, m), 7.21-7.05 (2H, m), 6.03 (1H, brs), 5.48-5.32 (2H, m), 5.15-5.08 (4H, m), 4.43-4.06 (2H, m), 3.79-3.67 (3H, m), 2.63-1.79 (3H, m), 1.54 (9H, s), 1.53 (9H, s), 1.36-1.16 (6H, m), 1.13-1.01 (2H, m), 0.89-0.80 (4H, m).

Reference Example 138-3: tert-butyl 4-(1-{[(benzyloxy)carbonyl]amino}-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-1H-imidazole-1-carboxylate

[Chemical Formula 802]

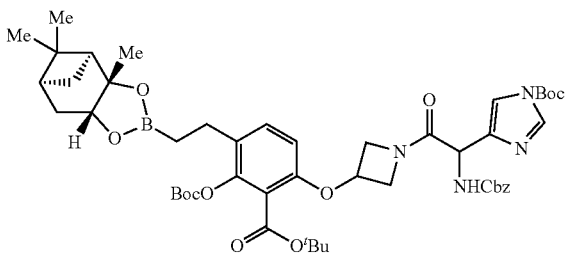

Triethylamine (0.641 mL, 4.6 mmol) and di-tert-butyl dicarbonate (503 mg, 2.3 mmol) were added to a dichloromethane (5.75 mL) solution of the compound of Reference Example 138-2 (956 mg, 1.15 mmol), and the reaction mixture was stirred overnight at room temperature. A saturated aqueous ammonium chloride solution (10 mL) was added to the reaction solution, which was extracted with dichloromethane (10 mL). The organic phase was dried over sodium sulfate, then filtered and concentrated. The resulting residue was purified by column chromatography (dichloromethane/methanol=50/1) to obtain the title compound (228 mg).

$^1$H-NMR (500 MHz, CDCl$_3$) δ: 8.02-7.98 (1H, m), 7.38-7.12 (7H, m), 6.39-6.07 (1H, m), 5.32-4.05 (5H, m), 3.50-3.49 (1H, m), 2.63-1.78 (7H, m), 1.62 (9H, s), 1.56 (9H, s), 1.52 (9H, s), 1.38-1.23 (8H, m), 1.15-1.08 (2H, m), 1.05-0.83 (5H, m).

Reference Example 138-4: tert-butyl 4-(1-amino-2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-2-oxoethyl)-1H-imidazole-1-carboxylate

[Chemical Formula 803]

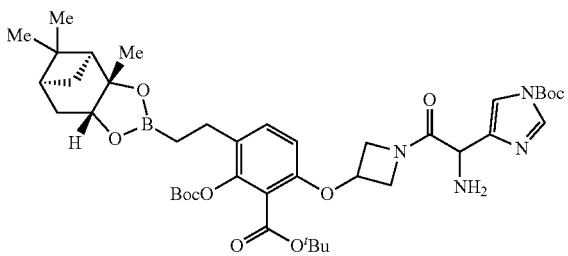

Palladium hydroxide (22 mg) was added to a methanol solution (4 mL) of the compound of Reference Example 138-3 (228 mg, 0.245 mmol), and the reaction mixture was stirred under a hydrogen atmosphere at room temperature. After 12 hours, the reaction solution was filtered through celite, and the filtrate was concentrated. The resulting residue was purified by column chromatography (dichloromethane/methanol=50/1) to obtain the title compound (123 mg).

$^1$H-NMR (500 MHz, CDCl$_3$) δ: 8.02-8.00 (1H, m), 7.35-7.20 (2H, m), 6.40-6.37 (1H, m), 4.96-4.90 (1H, brs), 4.45-4.39 (m, 1H), 4.25-4.20 (1H, m), 4.13-4.11 (1H, m), 2.63-2.60 (2H, m), 2.35-2.28 (1H, m), 2.17-2.14 (1H, m), 2.03-2.01 (1H, m), 1.61 (9H, s), 1.56 (9H, s), 1.52 (9H, s), 1.28-1.26 (6H, m), 1.13-1.10 (1H, m), 0.83 (6H, s).

Reference Example 138: tert-butyl 4-[2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-1-(methylamino)-2-oxoethyl]-1H-imidazole-1-carboxylate

[Chemical Formula 804]

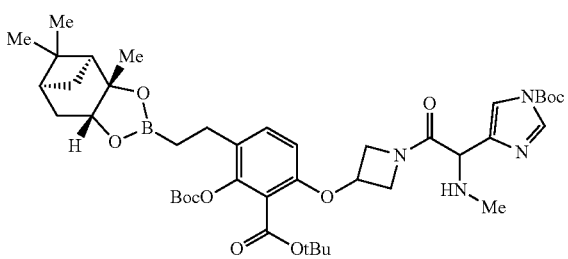

A formalin solution (30% methanol solution, 2.32 μL, 0.231 mmol) was added to a diethyl ether solution (3 mL) of the compound of Reference Example 138-4 (123 mg, 0.154 mmol), and the reaction mixture was stirred for 1.5 hours at room temperature. Dichloromethane (10 ML) was added to the reaction solution. The organic layer was washed three times with water (10 mL), dried over sodium sulfate, then filtered and concentrated. Sodium triacetoxyborohydride (65 mg, 0.308 mmol) was added to a dichloromethane/acetic acid (1:1) mixture solution (3 mL) of the resulting residue, and the reaction mixture was stirred for 1.5 hours at room temperature. The reaction solution was added to a saturated aqueous sodium hydrogen carbonate solution (10 mL) and extracted with dichloromethane (10 mL). The retrieved organic layer was dried over sodium sulfate, filtered and concentrated. The resulting residue was purified by preparative thin-layer chromatography (dichloromethane/methanol=10/1) to obtain the compound of Reference Example 138 (26 mg) and the compound of Reference Example 139 (42 mg).

$^1$H-NMR (500 MHz, CDCl$_3$) δ: 8.00 (1H, d, J=6.3 Hz), 7.35 (1H, d, J=8.6 Hz), 7.24-7.15 (1H, m), 6.38 (1H, dd, J=8.6, 8.3 Hz), 4.95-4.72 (1H, m), 4.66-4.05 (4H, m), 2.63-2.58 (2H, m), 2.41 (3H, s), 2.35-1.78 (5H, m), 1.47 (9H, s), 1.52 (9H, s), 1.52 (9H, s), 1.35 (3H, s), 1.28 (3H, s), 1.28-1.23 (2H, m), 1.24-1.08 (2H, m), 1.04-1.02 (1H, m), 0.83 (3H, s).

Reference Example 139: tert-butyl 4-[2-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-1-(dimethylamino)-2-oxoethyl]-1H-imidazole-1-carboxylate

[Chemical Formula 805]

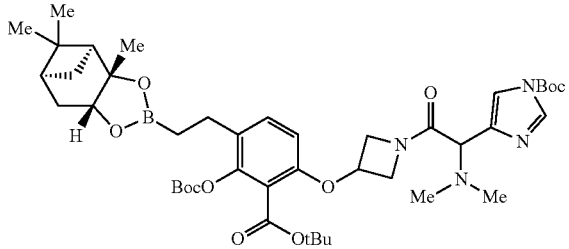

$^1$H-NMR (500 MHz, CDCl$_3$) δ: 8.04-8.03 (1H, m), 7.52-7.49 (1H, m), 7.21-7.19 (1H, m), 6.39-6.37 (1H, m), 4.91-3.98 (6H, m), 2.63-2.58 (2H, m), 2.35-1.78 (11H, m), 1.56 (9H, s), 1.53 (9H, s), 1.52 (9H, s), 1.35-1.23 (5H, m), 1.14-1.03 (3H, m), 0.83 (4H, s).

A reaction, work-up, and purification were performed using the compound of Reference Example 1-8 as the starting material by the same method described in Reference Example 3 to obtain each of Reference Example compounds 140 to 147 shown in Tables 2-24 and 2-25. Further, a reaction, work-up, and purification were performed using the compound of Reference Example 1-8 as the starting material by the same method described in Reference Example 36-4 to obtain Reference Example compounds 148 and 149 shown in Table 2-26.

TABLE 2-24

| Reference Example | Structural formula | NMR and/or LCMS |
|---|---|---|
| 140 | 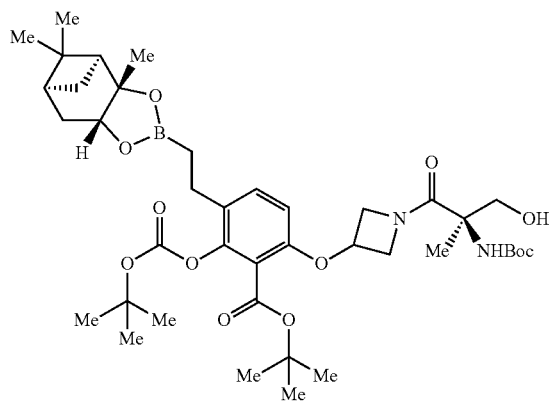 [SMILES: CC(C)(C)OC(=O)N[C@](C)(CO)C(=O)N1CC(Oc2ccc(CCB3O[C@@H]4C[C@@H]5C[C@@H](C5(C)C)[C@]4(C)O3)c(OC(=O)OC(C)(C)C)c2C(=O)OC(C)(C)C)C1] | LCMS: [M + H]$^+$/Rt = 773.00/1.394 min[41] H-NMR (CD$_3$OD) δ: 7.39-7.26 (6H, m), 6.67 (1H, d, J = 8.5 Hz), 5.12-5.05 (3H, m), 4.39-4.33 (1H, m), 4.29 (2H, d, J = 8.5 Hz), 4.00-3.94 (1H, m), 3.74-3.67 (2H, m), 3.34 (2H, s), 2.58 (2H, t, J = 7.9 Hz), 2.39-2.32 (1H, m), 2.21-2.16 (1H, m), 1.99 (1H, t, J = 5.5 Hz), 1.89-1.87 (1H, m), 1.79 (1H, d, J = 15.3 Hz), 1.55 (9H, d, J = 7.9 Hz), 1.52 (9H, s), 1.35 (3H, s), 1.29 (3H, s), 1.08 (2H, t, J = 8.2 Hz), 0.99 (1H, d, J = 10.4 Hz), 0.86 (3H, s). |

TABLE 2-24-continued

| Reference Example | Structural formula | NMR and/or LCMS |
|---|---|---|
| 141 | | LCMS: [M + H]$^+$/Rt = 773/2.275 min$^H$ |

TABLE 2-25

| | | |
|---|---|---|
| 142 | | LCMS: [M + H]$^+$/Rt = 905/2.433 min$^H$ |
| 143 | | LCMS: [M + H]$^+$/Rt = 812/2.217 min$^H$ |

TABLE 2-25-continued
| 144 | 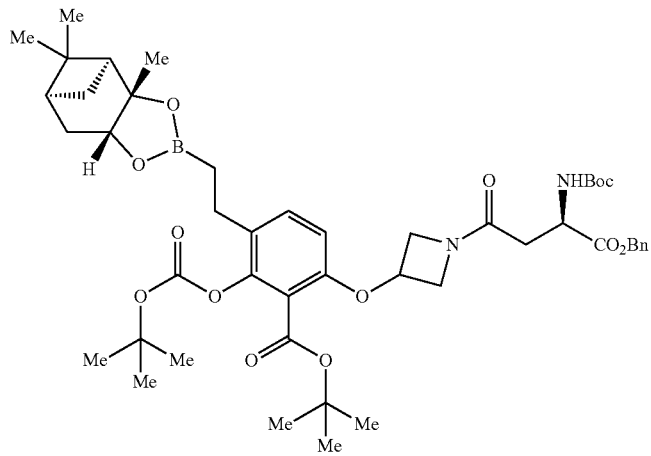 [SMILES: CC(C)(C)OC(=O)N[C@H](CC(=O)N1CC(Oc2ccc(CCB3O[C@@H]4C[C@@H]5C[C@@H](C5(C)C)[C@]4(C)O3)c(OC(=O)OC(C)(C)C)c2C(=O)OC(C)(C)C)C1)C(=O)OCc1ccccc1] | LCMS: [M + H]⁺/Rt = 877/2.150 min^H |
| 145 | 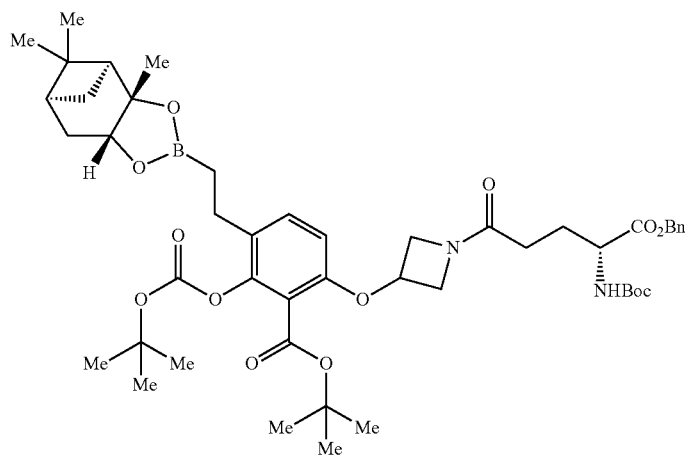 [SMILES: CC(C)(C)OC(=O)N[C@H](CCC(=O)N1CC(Oc2ccc(CCB3O[C@@H]4C[C@@H]5C[C@@H](C5(C)C)[C@]4(C)O3)c(OC(=O)OC(C)(C)C)c2C(=O)OC(C)(C)C)C1)C(=O)OCc1ccccc1] | LCMS: [M + H]⁺/Rt = 892/1.411 min^E |
| 146 | 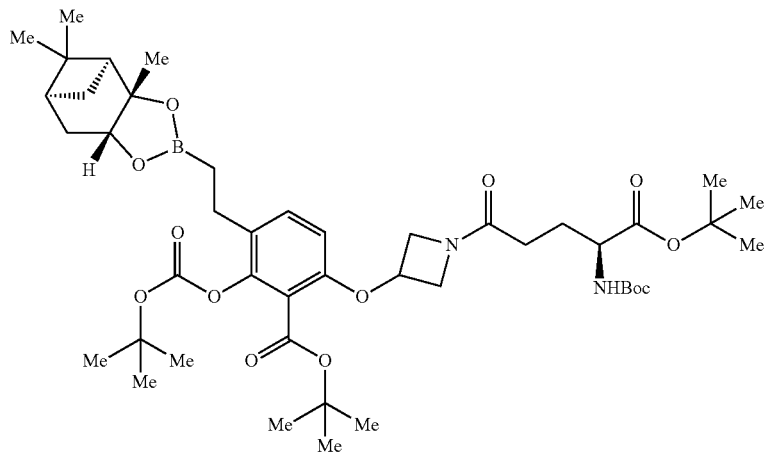 [SMILES: CC1[C@@H]2C[C@H]3OB(CCc4ccc(OC5CN(C(=O)CC[C@H](NC(=O)OC(C)(C)C)C(=O)OC(C)(C)C)C5)c(C(=O)OC(C)(C)C)c4OC(=O)OC(C)(C)C)O[C@@]3(C)[C@H]1C2 ; "Me"] | LCMS: [M + H]⁺/Rt = 857.7/3.17 min^B |

TABLE 2-25-continued
| 147 | 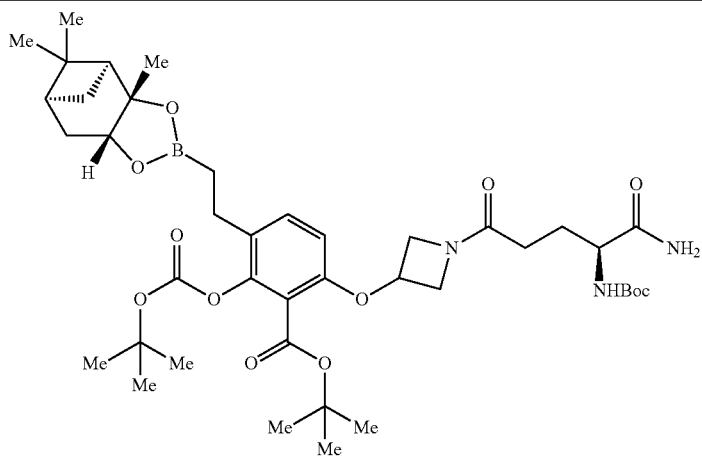 | LCMS: [M + H]+/Rt = 800.7/2.81 min[B] |
TABLE 2-26
| 148 | 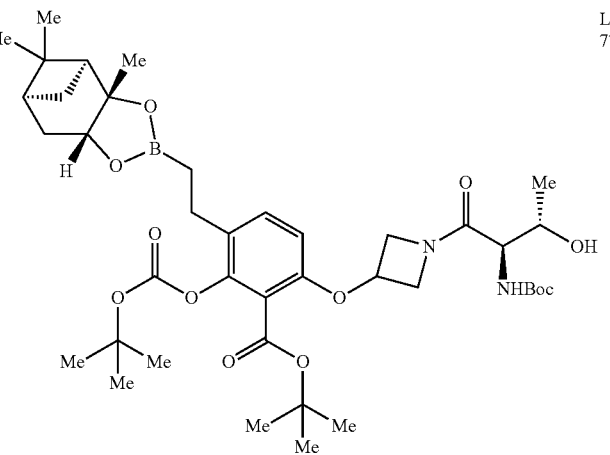 | LCMS: [M + H]+/Rt = 773.54/3.960 min[I] |
| 149 | 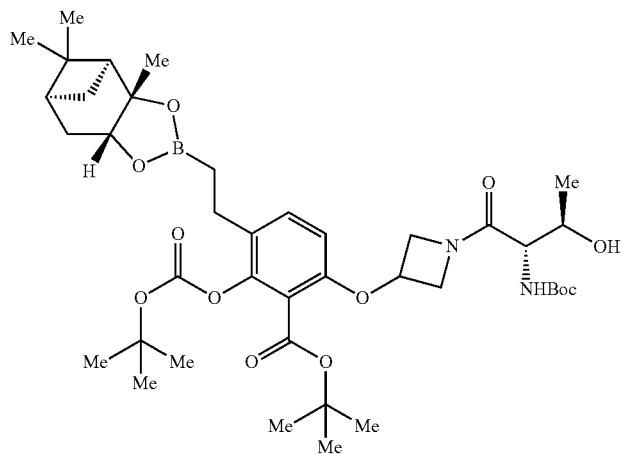 [SMILES: C[C@@H](O)[C@H](NC(=O)OC(C)(C)C)C(=O)N1CC(Oc2ccc(CCB3O[C@@H]4C[C@@H]5C[C@@H](C5(C)C)[C@]4(C)O3)c(OC(=O)OC(C)(C)C)c2C(=O)OC(C)(C)C)C1] | LCMS: [M + H]+/Rt = 773.54/3.940 min[I] |

Reference Example 150: (4S)-4-[(tert-butoxycarbonyl)amino]-6-{3-[2-(tert-butoxycarbonyl)-3-[(tert-butoxycarbonyl)oxy]-4-{2-[(3aS,4S,6S,7aR)-3a,5,5-trimethylhexahydro-2H-4,6-methano-1,3,2-benzodioxaborol-2-yl]ethyl}phenoxy]azetidin-1-yl}-6-oxohexanoic Acid

[Chemical Formula 806]

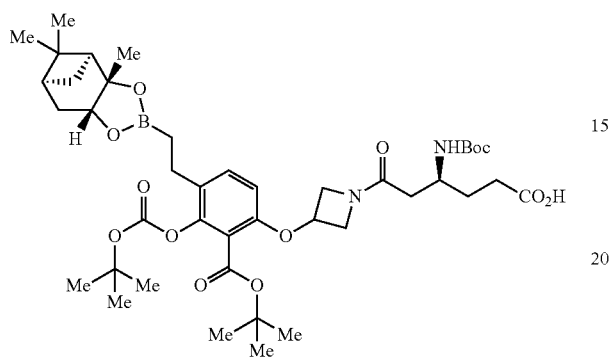

10% palladium on carbon (113 mg) was added to a methanol (7 mL) solution of the compound of Reference Example 142 (334 mg, 0.369 mmol). The reaction mixture was subjected to hydrogen substitution and was stirred for 2 hours at room temperature. After filtering the reaction solution, the filtrate was concentrated to obtain the title compound (329 mg).

LCMS: $[M+H]^+$/Rt=815.5/2.211 $min^H$

A reaction, work-up, and purification were performed using the compounds of Reference Examples 144 and 145 as the starting materials by the same method described in Reference Example 151 to obtain Reference Example compounds 151 and 152 shown in Table 2-27, respectively.

TABLE 2-27

| Reference Example | Starting material | Structural formula | NMR and/or LCMS |
|---|---|---|---|
| 151 | Reference Example 144 | 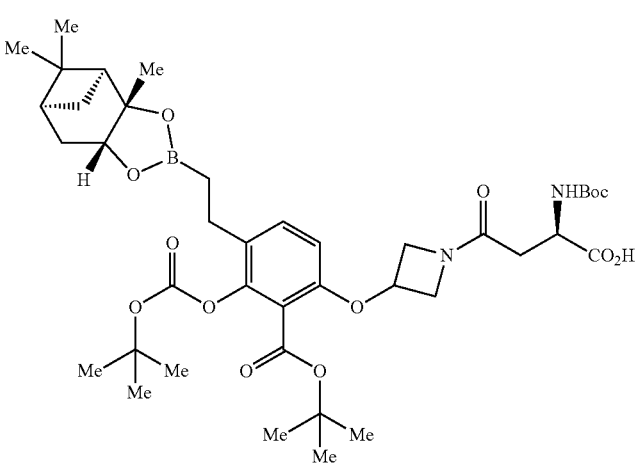 [SMILES: CC(C)(C)OC(=O)N[C@H](CC(=O)N1CC(Oc2ccc(CCB3O[C@@H]4C[C@@H]5C[C@@H](C5(C)C)[C@]4(C)O3)c(OC(=O)OC(C)(C)C)c2C(=O)OC(C)(C)C)C1)C(=O)O] | LCMS: $[M + H]^+$/Rt = 787/2.247 $min^H$ |

TABLE 2-27-continued

| Reference Example | Starting material | Structural formula | NMR and/or LCMS |
|---|---|---|---|
| 152 | Reference Example 145 | | LCMS: [M + H]$^+$/Rt = 801/2.231 min$^H$ |

Reference Example 153: tert-butyl 6-[(1-{(3S)-6-amino-3-[(tert-butoxycarbonyl)amino]-6-oxohexanoyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 807]

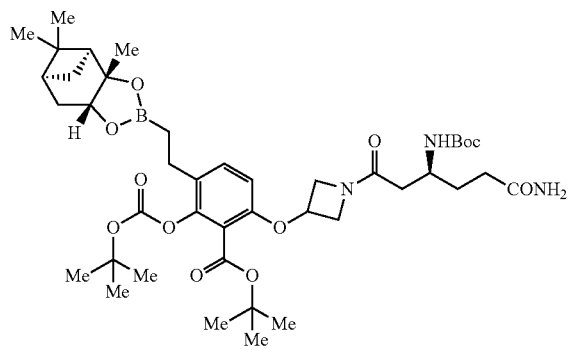

N,N-diisopropylethylamine (0.131 mL, 0.750 mmol) and HATU (107 mg, 0.281 mmol) were added to a DMF (1 mL) solution of the compound of Reference Example 150 (153 mg, 0.188 mmol), and the reaction mixture was stirred for 30 minutes at room temperature. Ammonium chloride (16.1 mg, 0,300 mmol) was added, and the reaction mixture was stirred for 2 hours at room temperature. A saturated aqueous ammonium chloride solution was added to the reaction solution, which was extracted with ethyl acetate. The organic phase was washed with a saturated aqueous sodium hydrogen carbonate solution and then saturated saline, dried over sodium sulfate and filtered, and the filtrate was concentrated. The resulting residue was purified by silica gel column chromatography (chloroform/methanol) to obtain the title compound (45.7 mg).

LCMS: [M+H]$^+$/Rt=814.5/2.204 min$^H$

A reaction, work-up, and purification were performed using the compounds of Reference Examples 151 and 152 as the starting materials by the same method described in Reference Example 153 to obtain Reference Example compounds 154 and 155 shown in Table 2-28, respectively.

TABLE 2-28

| Reference Example | Starting material | Structural formula | NMR and/or LCMS |
|---|---|---|---|
| 154 | Reference Example 151 | | LCMS: [M + H]$^+$/Rt = 786.5/2.150 min$^H$ |

TABLE 2-28-continued

| Reference Example | Starting material | Structural formula | NMR and/or LCMS |
|---|---|---|---|
| 155 | Reference Example 152 | 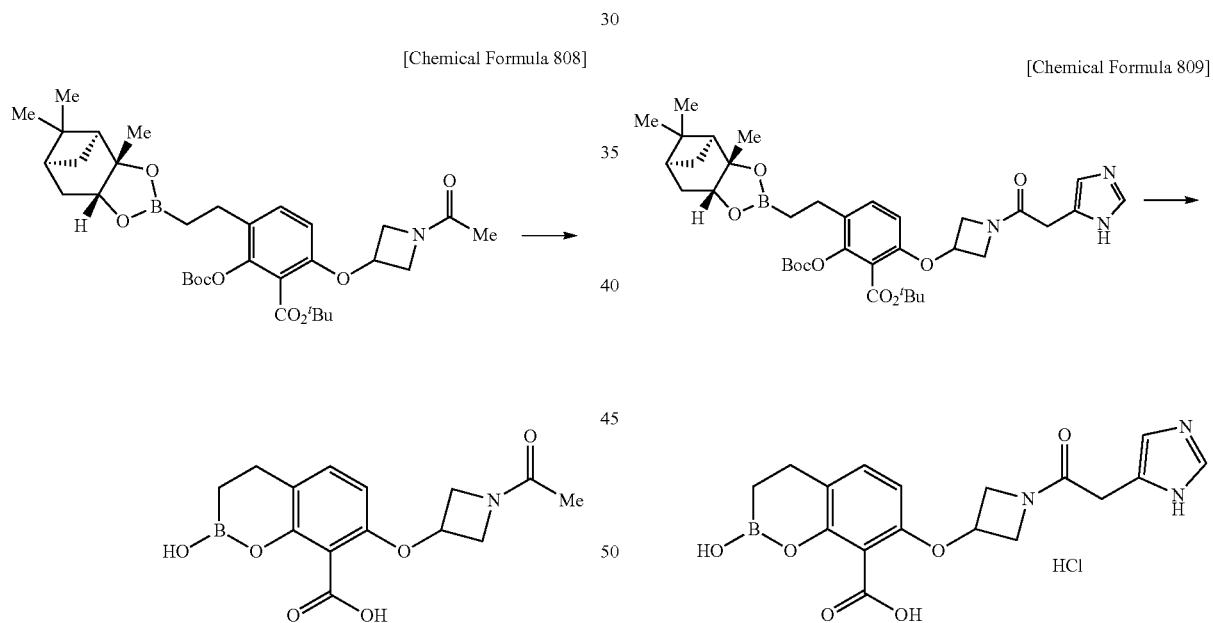 | LCMS: [M + H]⁺/Rt = 800.55/2.210 min$^H$ |

Example 1: 7-[(1-acetylazetidin-3-yl)oxy]-2-hydroxy-3,4-dihydro-2H-1,2-benzoxaborinine-8-carboxylic Acid

[Chemical Formula 808]

Example 2: 2-hydroxy-7-({1-[(1H-imidazol-5-yl)acetyl]azetidin-3-yl}oxy)-3,4-dihydro-2H-1,2-benzoxaborinine-8-carboxylic Acid Hydrochloride

[Chemical Formula 809]

The compound of Reference Example 1 (105 mg) and phenylboronic acid (19 mg) were added to CPME (0.9 mL). 3 mol/L hydrochloric acid (1.14 mL) was added thereto, and the reaction mixture was stirred overnight at room temperature. The aqueous layer was concentrated and purified by reversed phase column chromatography (eluent: acetonitrile/water=1/99 to 95/5) to obtain the title compound (9.2 mg).

$^1$H-NMR (CD$_3$OD) δ: 7.16-7.08 (1H, m), 6.35-6.25 (1H, m), 5.06-4.97 (1H, m), 4.58-4.52 (1H, m), 4.37-4.30 (1H, m), 4.22-4.17 (1H, m), 3.96-3.89 (1H, m), 2.70-2.62 (2H, m), 1.86 (3H, s), 1.05-1.01 (2H, m).

Triethylsilane (0.2 mL) and, additionally, TFA (0.9 mL) was added to the compound of Reference Example 3 (96 mg) and phenylboronic acid (14 mg), and the reaction mixture was stirred for 3 hours at room temperature. After concentrating the reaction mixture, the residue was washed with a mixture solvent of diethyl ether/hexane (1:1). The resulting solid was dissolved in methanol and purified by reversed phase chromatography and concentrated. After adding 0.2 mL of aqueous 1 N hydrochloric acid solution to the residue, the mixture was concentrated to obtain the compound of interest (21.6 mg).

LCMS: [M+H]⁺/Rt=372/0.44 min$^C$

Example 3: 2-hydroxy-7-{[1-(methanesulfonyl)azetidin-3-yl]oxy}-3,4-dihydro-2H-1,2-benzoxaborinine-8-carboxylic acid

[Chemical Formula 810]

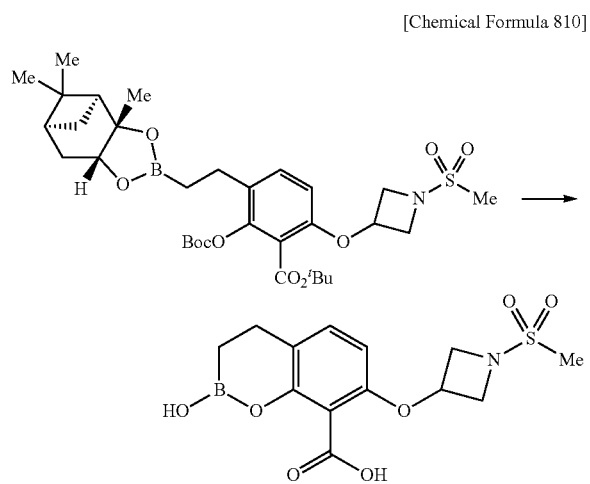

Triethylsilane (0.2 mL) and, additionally, TFA (0.9 mL) was added to the compound of Reference Example 2 (96 mg) and phenylboronic acid (14 mg), and the reaction mixture was stirred for 3 hours at room temperature. After concentrating the reaction mixture, the residue was washed with a mixture solvent of diethyl ether/hexane (1:1). The resulting solid was dissolved in methanol and purified by reversed phase chromatography and concentrated to obtain the compound of interest (28 mg).

$^1$H-NMR (CD$_3$OD) δ: 7.16-7.00 (1H, m), 6.37-6.20 (1H, m), 5.06-4.97 (1H, m), 4.31-4.25 (2H, m), 3.98-3.94 (2H, m), 2.96 (3H, s), 2.68-2.65 (2H, m), 1.05-1.01 (2H, m)

Example 4: 8-({1-[(2R)-2-amino-2-(4-hydroxyphenyl)acetyl]azetidin-3-yl}oxy)-4,4-dihydroxy-5-oxa-4-boranuidabicyclo[4.4.0]deca-1(6),7,9-triene-7-carboxylic acid disodium salt

[Chemical Formula 811]

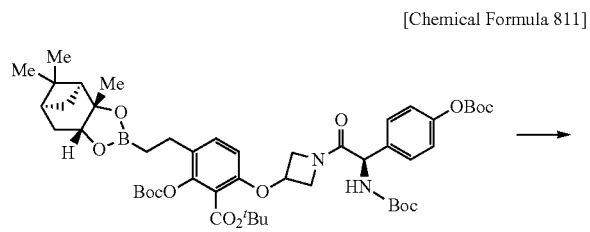

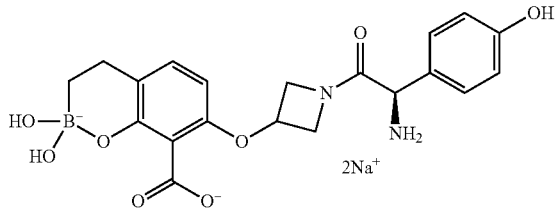

The compound of Reference Example 17 (119 mg), phenylboronic acid (16.2 mg), acetonitrile (2.0 mL), hexane (2.0 mL), and 4 N hydrochloric acid/dioxane solution (1.0 mL) were added, and the reaction mixture was stirred for 19 hours at room temperature. After allowing it to stand, the supernatant (top layer) of the reaction solution separated into two layers was removed, and the remaining bottom layer was washed 5 times with hexane and twice with diethyl ether (the washing process removes the supernatant after standing). The solid produced in the solution at the bottom layer was washed with acetonitrile (5.0 mL). The residue of the solid obtained by removing the solvent was dried under reduced pressure. The resulting dried residue was dissolved in water. An aqueous 2 N sodium hydroxide solution (0.5 mL) was added. The mixture was purified by reversed phase column chromatography to obtain the title compound (41.7 mg) as a colorless solid.

$^1$H-NMR (D$_2$O) δ: 7.20-7.13 (2H, m), 6.83-6.75 (3H, m), 5.98-5.90 (1H, m), 5.00-4.91 (1H, m), 4.63-3.90 (5H, m), 2.59-2.50 (2H, m), 0.39-0.29 (2H, m).

A reaction, work-up, and purification were performed using Reference Example compounds 4 to 16 and 18 to 33 shown in Table 2 as the starting materials by the same method described in Example 4 to obtain each of Example compounds 5 to 33. However, if a free form is the final product (Examples 5 and 34), the free form was obtained without sodium hydroxide treatment. If a hydrochloride (hydrochloride salt) is the final product (Example 6), the hydrochloride was obtained by purifying the compound by using reversed phase chromatography and then adding hydrochloric acid and concentrating. A reaction, work-up, and purification were performed using Reference Example compound 34 as the starting material by the same method described in Example 3 to obtain Example compound 34.

TABLE 3-1

| Example | Starting material | Structural formula | NMR and/or LCMS |
|---|---|---|---|
| 5 | Reference Example 4 | (free form) | LCMS: [M + H]$^+$/Rt = 447/ 0.626 min$^C$ |

TABLE 3-1-continued

| Example | Starting material | Structural formula | NMR and/or LCMS |
|---|---|---|---|
| 6 | Reference Example 5 | 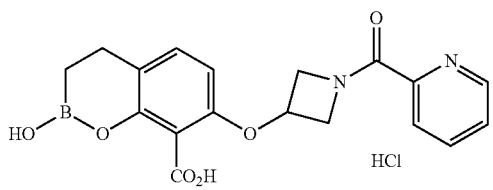<br>(hydrochloride) | ¹H-NMR (CD₃OD) δ: 8.67-8.64 (1H, m), 8.06-8.01 (2H, m), 7.59-7.56 (1H, m), 7.18-7.15 (1H, m), 6.38-6.35 (1H, m), 5.13-5.10 (2H, m), 4.72-4.69 (1H, m), 4.63-4.60 (1H, m), 4.22-4.19 (1H, m), 2.70 (2H, t, J = 7.3 Hz), 1.05 (2H, t, J = 7.3 Hz). |
| 7 | Reference Example 6 | 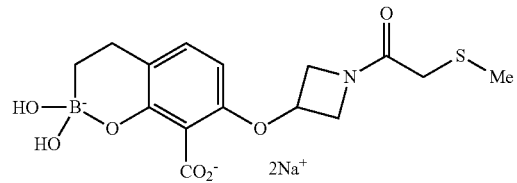<br>(disodium salt) | ¹H-NMR (D₂O) as a mixture of keto and enol forms δ: 6.87-6.82 (1H, m), 6.04-6.02 (1H, m), 5.02-4.97 (1H, m), 4.65-3.64 (4H, m), 3.20-3.13 (2H, m), 2.57-2.54 (2H, m), 2.11 and 2.07 (3H, s) and 0.36-0.33 (2H, m). |
| 8 | Reference Example 7 | 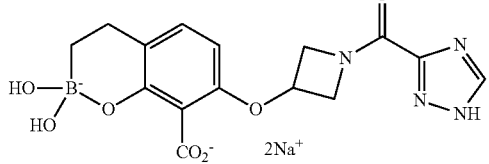<br>(disodium salt) | ¹H-NMR (D₂O) δ: 8.32-8.31 (1H, m), 6.94-6.92 (1H, m), 6.94-6.92 (1H, m), 5.13-5.11 (1H, m), 4.99-4.94 (1H, m), 4.65-4.59 (2H, m), 4.28-4.25 (1H, m), 2.63-2.60 (2H, m), and 0.45-0.42 (2H, m). |
| 9 | Reference Example 8 | 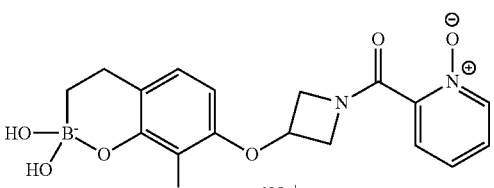<br>(disodium salt) | ¹H-NMR (D₂O) δ: 8.41 (1H, d, J = 6.4 Hz), 7.83 (1H, t, J = 7.8 Hz), 7.76 (1H, dd, J = 7.8, 1.8 Hz), 7.73-7.69 (1H, m), 6.91 (1H, d, J = 7.8 Hz), 6.07 (1H, d, J = 7.8 Hz), 5.15-5.10 (1H, m), 4.69-4.63 (1H, m), 4.47 (1H, dd, J = 9.6, 7.3 Hz), 4.32 (1H, dd, J = 13.3, 4.1 Hz), 4.20 (1H, dd, J = 9.6, 3.2 Hz), 2.61 (2H, t, J = 7.1 Hz), 0.44 (2H, s). |
| 10 | Reference Example 9 | 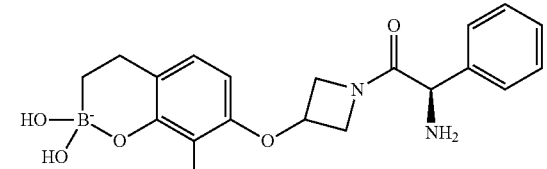<br>(disodium salt) | ¹H-NMR (D₂O) as a mixture of isomers δ: 7.46-7.38 (5H, m), 6.89-6.80 (1H, m), 6.01-5.91 (1H, m), 5.04-4.93 (0.5H, m), 4.71-4.59 (1.5H, m), 4.49-4.38 (0.5H, m), 4.22-4.07 (1H, m), 4.01-3.91 (1H, m), 2.63-2.50 (2H, m), 0.45-0.30 (2H, m). |

TABLE 3-2

| 11 | Reference Example 10 | 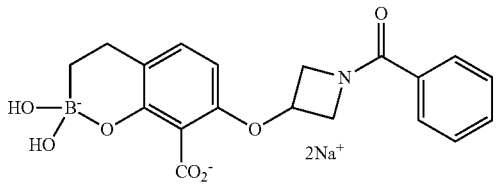 (disodium salt) | ¹H-NMR (D₂O) δ: 7.65-7.49 (5H, m), 6.88 (1H, d, J = 8.2 Hz), 6.04 (1H, d, J = 8.2 Hz), 5.04 (1H, td, J = 7.0, 3.7 Hz), 4.65 (1H, dd, J = 10.1, 6.4 Hz), 4.57 (1H, dd, J = 11.4, 6.9 Hz), 4.45 (1H, dd, J = 10.5, 2.7 Hz), 4.23 (1H, dd, J = 10.8, 3.4 Hz), 2.58 (2H, t, J = 6.9 Hz), 0.38 (2H, t, J = 7.1 Hz). |
|---|---|---|---|
| 12 | Reference Example 11 | 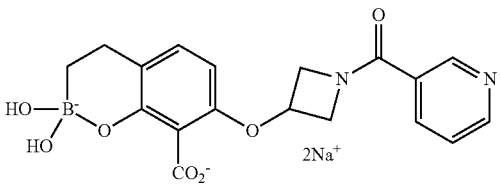 (disodium salt) | ¹H-NMR (D₂O) δ: 8.72 (1H, d, J = 1.4 Hz), 8.63 (1H, dd, J = 5.0, 1.4 Hz), 8.05 (1H, dt, J = 7.8, 1.8 Hz), 7.53 (1H, dd, J = 7.8, 5.0 Hz), 6.85 (1H, d, J = 8.2 Hz), 6.01 (1H, d, J = 8.2 Hz), 5.04 (1H, td, J = 7.9, 4.7 Hz), 4.66 (1H, t, J = 8.5 Hz), 4.56 (1H, dd, J = 11.2, 6.6 Hz), 4.44 (1H, dd, J = 10.1, 3.7 Hz), 4.23 (1H, dd, J = 11.2, 3.9 Hz), 2.55 (2H, t, J = 7.1 Hz), 0.34 (2H, t, J = 6.9 Hz). |
| 13 | Reference Example 12 | 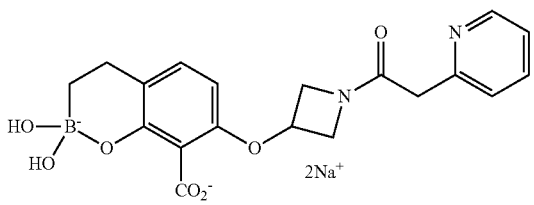 (disodium salt) | ¹H-NMR (CD₃OD) δ: 8.85-8.78 (1H, m), 8.62-8.52 (1H, m), 8.06-7.95 (2H, m), 7.18 (1H, d, J = 8.2 Hz), 6.36 (1H, d, J = 7.9 Hz), 5.19-5.06 (1H, m), 4.83-4.70 (2H, m), 4.49-4.38 (2H, m), 4.14-4.02 (2H, m), 2.71 (2H, t, J = 7.7 Hz), 1.07 (2H, t, J = 7.7 Hz). |
| 14 | Reference Example 13 | 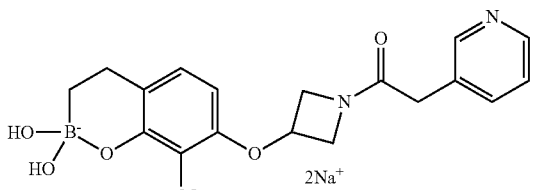 (disodium salt) | ¹H-NMR (CD₃OD)) δ: 8.87-8.74 (2H, m), 8.62-8.53 (1H, m), 8.12-8.03 (1H, m), 7.18 (1H, d, J = 8.2 Hz), 6.36 (1H, d, J = 8.2 Hz), 5.18-5.09 (1H, m), 4.82-4.70 (2H, m), 4.49-4.36 (2H, m), 4.07-3.99 (2H, m), 2.71 (2H, t, J = 7.7 Hz), 1.07 (2H, t, J = 7.7 Hz). |
| 15 | Reference Example 14 | 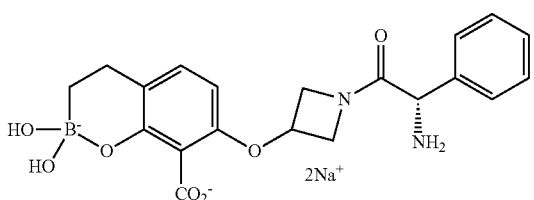 (disodium salt) | ¹H-NMR (D₂O) as a mixture of isomers δ: 7.43-7.29 (5H, m), 6.84-6.76 (1H, m), 6.01-5.89 (1H, m), 4.95-4.83 (1H, m), 4.65-4.53 (1H, m), 4.41-3.50 (4H, m), 2.52 (2H, t, J = 6.6 Hz), 0.31 (2H, q, J = 6.4 Hz). |
| 16 | Reference Example 15 | 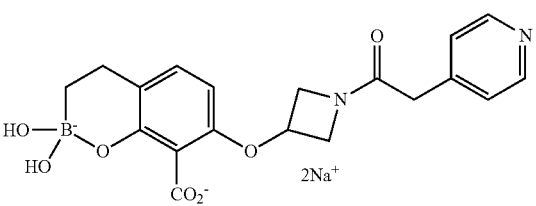 (disodium salt) | ¹H-NMR (D₂O) δ: 8.32 (2H, d, J = 6.0 Hz), 7.19 (2H, d, J = 6.0 Hz), 6.74 (1H, d, J = 8.2 Hz), 5.91 (1H, d, J = 8.2 Hz), 4.91-4.80 (1H, m), 4.52-4.49 (1H, m), 4.29-4.20 (2H, m), 3.96-3.91 (1H, m), 3.52 (2H, s), 2.44 (2H, t, J = 7.1 Hz), 0.23 (2H, t, J = 7.1 Hz). |

TABLE 3-2-continued

| 17 | Reference Example 16 | 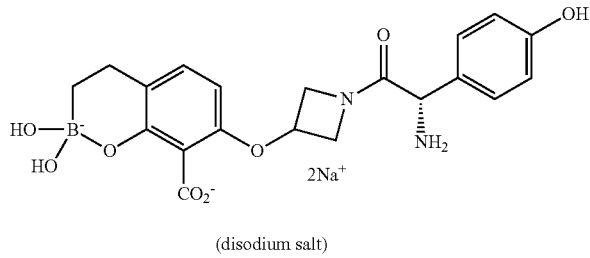 (disodium salt) | $^1$H-NMR (D$_2$O) δ: 7.03 (2H, d, J = 8.2 Hz), 6.86 (1H, d, J = 8.2 Hz), 6.67 (2H, d, J = 8.2 Hz), 6.01 (1H, d, J = 8.2 Hz), 4.99-4.38 (2H, m), m), 4.62-4.55 (1H, m), 4.29-4.38 (2H, m), 4.05-3.99 (1H, m), 3.46-3.36 (2H, m), 2.56 (2H, t, J = 7.1 Hz), 0.35 (2H, t, J = 7.1 Hz). |
| --- | --- | --- | --- |
| 18 | Reference Example 18 | 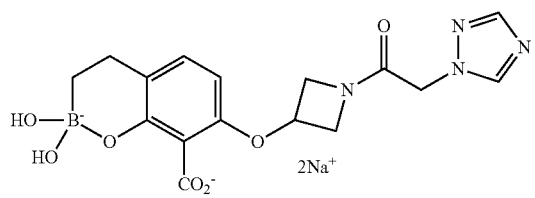 (disodium salt) | $^1$H-NMR (D$_2$O) δ: 8.51 (1H, s), 8.12 (1H, s), 6.94 (1H, d, J = 8.2 Hz), 6.11 (1H, d, J = 8.2 Hz), 5.20-5.05 (3H, m), 4.72-4.64 (1H, m), 4.52-4.45 (1H, m), 4.42-4.37 (1H, m), 4.20-4.13 (1H, m), 2.62 (2H, t, J = 6.9 Hz), 0.46 (2H, t, J = 6.9 Hz). |

TABLE 3-3

| 19 | Reference Example 19 | 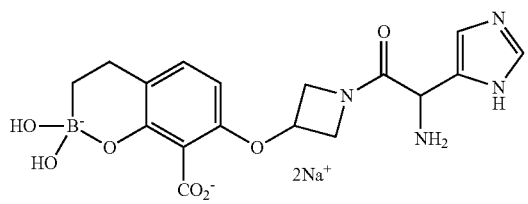 (disodium salt) | $^1$H-NMR (D$_2$O)) δ: 7.75-7.65 (1H, m), 7.42-7.35 and 7.70-7.09 (1H, m), 6.90-6.82 (1H, m), 6.02-5.96 (1H, m), 5.05-4.85 and 4.70-3.91 (6H, m), 2.62-2.50 (2H, m), 0.43-0.31 (2H, m). |
| --- | --- | --- | --- |
| 20 | Reference Example 20 | 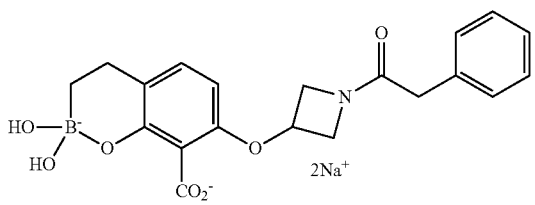 (disodium salt) | $^1$H-NMR (D$_2$O) δ: 7.41-7.24 (5H, m), 6.86 (1H, d, J = 8.2 Hz), 6.02 (1H, d, J = 8.2 Hz), 5.01-4.96 (1H, m), 4.63-4.58 (1H, m), 4.40-4.32 (2H, m), 4.08-4.01 (1H, m), 3.58 (2H, s), 2.56 (2H, t, J = 7.1 Hz), 0.35 (2H, t, J = 6.9 Hz). |
| 21 | Reference Example 21 | 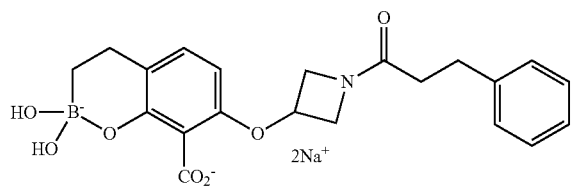 (disodium salt) | $^1$H-NMR (D$_2$O) δ: 7.39-7.28 (2H, m), 7.30-7.22 (3H, m), 6.84 (1H, d, J = 7.8 Hz), 5.92 (1H, d, J = 7.8 Hz), 4.28-4.20 (1H, m), 4.17-4.09 (1H, m), 3.98-3.88 (2H, m), 2.94-2.80 (2H, m), 2.60-2.50 (2H, m), 2.50-2.43 (2H, m), 0.40-0.31 (2H, m). |

TABLE 3-3-continued

| 22 | Reference Example 22 | 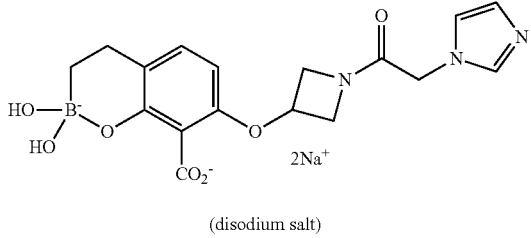<br>(disodium salt) | $^1$H-NMR (D$_2$O) δ: 7.80-7.62 (1H, m), 7.22-7.0 (2H, m), 6.96-6.85 (1H, m), 6.13-5.99 (1H, m), 5.10-5.05 (1H, m), 4.64-4.53 (1H, m), 4.47-4.38 (1H, m), 4.36-4.27 (1H, m), 4.20-4.05 (1H, m), 2.67 (2H, m), 0.50-0.38 (2H, m). |
| --- | --- | --- | --- |
| 23 | Reference Example 23 | 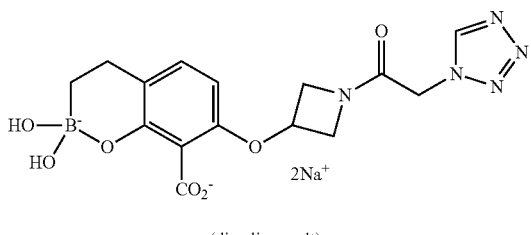<br>(disodium salt) | $^1$H-NMR (CD$_3$OD) δ: 9.18 (1H, s), 7.21-7.14 (1H, m), 6.44-6.12 (1H, m), 5.38 (2H, s), 5.22-5.08 (1H, m), 4.80-4.69 (1H, m), 4.51-4.38 (2H, m), 4.15-4.03 (1H, m), 2.78-2.65 (2H, m), 1.14-0.98 (2H, m). |
| 24 | Reference Example 24 | 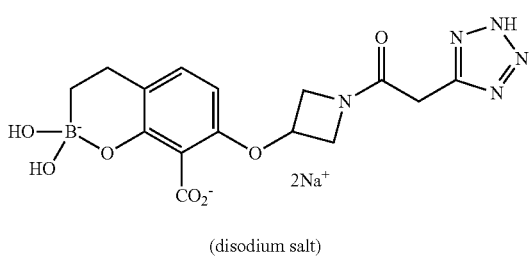<br>(disodium salt) | $^1$H-NMR (D$_2$O) δ: 6.89 (1H, d, J = 8.2 Hz), 6.05 (1H, d, J = 8.2 Hz), 5.03-4.97 (1H, m), 4.54 (1H, dd, J = 9.6, 6.9 Hz), 4.40 (1H, dd, J = 11.0, 6.9 Hz), 4.29 (1H, dd, J = 9.6, 3.7 Hz), 4.08 (1H, dd, J = 11.0, 3.7 Hz), 3.85 (1H, d, J = 16.3 Hz), 3.75 (1H, d, J = 16.3 Hz), 2.58 (2H, t, J = 6.9 Hz), 0.41 (2H, t, J = 7.1 Hz). |
| 25 | Reference Example 25 | 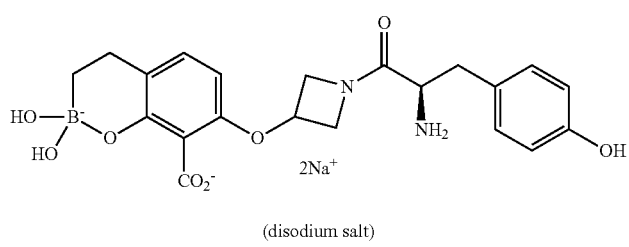<br>(disodium salt) | $^1$H-NMR (D$_2$O) δ: 7.41-7.21 (5H, m), 6.97-6.78 (1H, m), 5.93-5.80 (1H, m), 4.59-4.52, 4.33-4.25, 4.33-4.25, 4.18-4.10, 4.05-3.99, 3.91-3.82, 3.74-3.65, 3.53-3.48, 3.38-3.30 (6H, m), 2.99-2.90 (1H, m), 2.88-2.72 (1H, m), 2.60-2.50 (2H, m), 0.43-0.27 (2H, m). |
| 26 | Reference Example 26 | 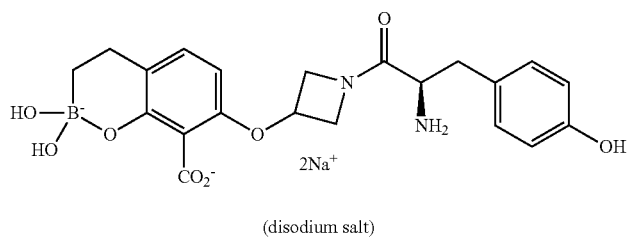<br>(disodium salt) | $^1$H-NMR (D$_2$O) δ: 7.14-7.01 (2H, m), 6.88-6.76 (3H, m), 5.86-5.70 (1H, m), 4.61-4.56, 4.30-4.12, 4.00-3.82, 3.63-3.44, 2.95-2.80, 2.72-2.48 (10H, m), 0.44-0.26 (2H, m). |
| 27 | Reference Example 27 | 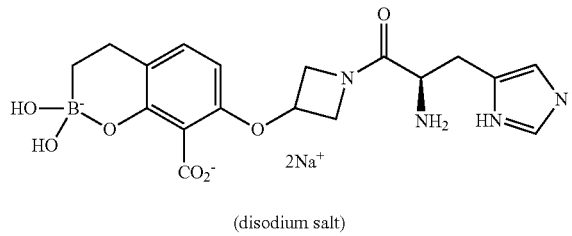<br>(disodium salt) | $^1$H-NMR (D$_2$O) δ: 7.69, 7.52 (1H, s), 6.93-6.83 (2H, m), 5.99-5.78 (1H, m), 4.42-4.07, 4.01-3.79, 3.70-3.50, 3.05-2.91 (5H, m), 2.91-2.66 (1H, m), 2.61-2.48 (2H, m), 0.42-0.28 (2H, m). |

TABLE 3-4

| 28 | Reference Example 28 | 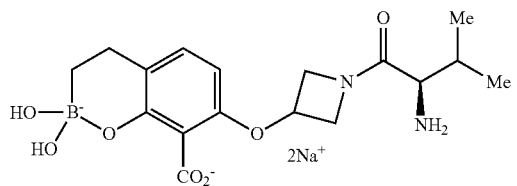<br>(disodium salt) | ¹H-NMR (D₂O) δ: 6.87 (1H, d, J = 8.2 Hz), 6.03 (1H, d, J = 8.2 Hz), 5.04-4.96 (1H, m), 4.68-4.58 (1H, m), 4.43-4.28 (2H, m), 4.08-4.00 (1H, m), 3.19-3.13 (1H, m), 2.56 (2H, t, J = 6.9 Hz), 1.81-1.73 (1H, m), 1.00-0.81 (6H, m), 0.35 (2H, t, J = 7.1 Hz). |
| --- | --- | --- | --- |
| 29 | Reference Example 29 | 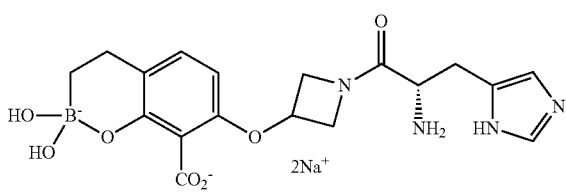<br>(disodium salt) | ¹H-NMR (D₂O) δ: 7.73, 7.54 (1H, s), 6.98-6.80 (2H, m), 5.96-5.80 (1H, m), 4.42-4.11, 4.04-3.83, 3.74-3.66, 3.65-3.57, 3.08-2.96 (5H, m), 2.90-2.74 (2H, m), 2.64-2.50 (2H, m), 0.84-0.31 (2H, m). |
| 30 | Reference Example 30 | 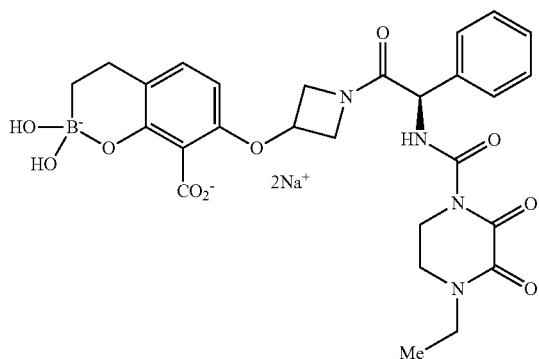<br>(disodium salt) | ¹H-NMR (D₂O) δ: 7.50-7.31 (5H, m), 6.89-6.84 (1H, m), 6.03-5.95 (1H, m), 5.33-5.27 (1H, m), 5.15-4.97 (1H, m), 4.50-4.28 (2H, m), 4.20-3.95 (2H, m), 3.33 (6H, dt, J = 28.1, 9.6 Hz), 2.63-2.48 (2H, m), 1.16-1.02 (3H, m), 0.50-0.30 (2H, m). |
| 31 | Reference Example 31 | 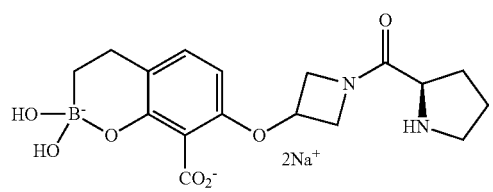<br>(disodium salt) | ¹H-NMR (D₂O) δ: 6.87 (1H, d, J = 7.9 Hz), 6.04 (1H, d, J = 7.9 Hz), 5.09-4.96 (1H, m), 4.90-4.84 (1H, m), 4.66-4.52 (1H, m), 4.43-4.30 (2H, m), 4.10-4.00 (1H, m), 3.93-3.80 (1H, m), 3.08-2.90 (2H, m), 2.57 (2H, t, J = 6.9 Hz), 2.28-2.02 (1H, m), 1.93-1.68 (3H, m), 0.36 (2H, t, J = 6.9 Hz). |
| 32 | Reference Example 32 | 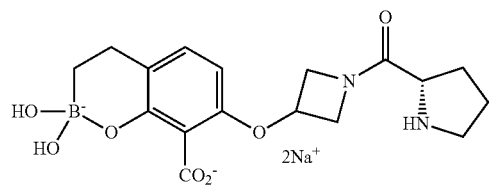<br>(disodium salt) | LCMS: [M + H]⁺/Rt = 361/0.87 min$^B$ |

TABLE 3-4-continued

| 33 | Reference Example 33 | 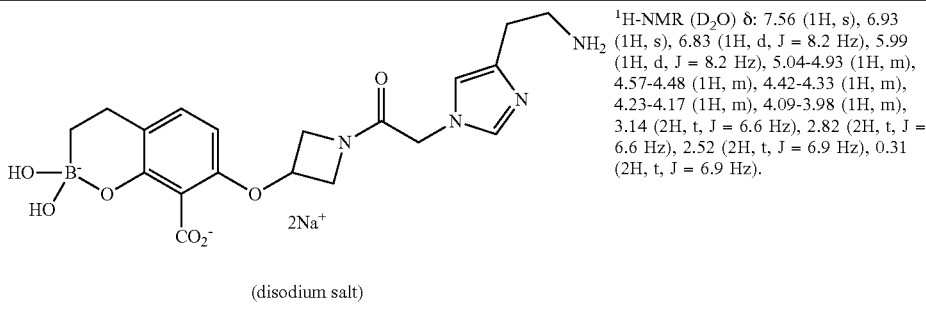 (disodium salt) | $^1$H-NMR (D$_2$O) δ: 7.56 (1H, s), 6.93 (1H, s), 6.83 (1H, d, J = 8.2 Hz), 5.99 (1H, d, J = 8.2 Hz), 5.04-4.93 (1H, m), 4.57-4.48 (1H, m), 4.42-4.33 (1H, m), 4.23-4.17 (1H, m), 4.09-3.98 (1H, m), 3.14 (2H, t, J = 6.6 Hz), 2.82 (2H, t, J = 6.6 Hz), 2.52 (2H, t, J = 6.9 Hz), 0.31 (2H, t, J = 6.9 Hz). |
|---|---|---|---|
| 34 | Reference Example 34 | 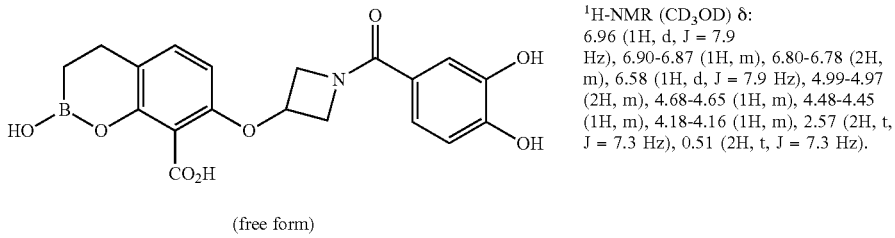 (free form) | $^1$H-NMR (CD$_3$OD) δ: 6.96 (1H, d, J = 7.9 Hz), 6.90-6.87 (1H, m), 6.80-6.78 (2H, m), 6.58 (1H, d, J = 7.9 Hz), 4.99-4.97 (2H, m), 4.68-4.65 (1H, m), 4.48-4.45 (1H, m), 4.18-4.16 (1H, m), 2.57 (2H, t, J = 7.3 Hz), 0.51 (2H, t, J = 7.3 Hz). |

The names of the compounds of Examples 5 to 34 are described below.

7-({1-[(2-amino-1,3-thiazol-4-yl)(methoxyimino)acetyl]azetidin-3-yl}oxy)-2-hydroxy-3,4-dihydro-2H-1,2-benzoxaborinine-8-carboxylic acid (Example 5)

2-hydroxy-7-{[1-(pyridine-2-carbonyl)azetidin-3-yl]oxy}-3,4-dihydro-2H-1,2-benzoxaborinine-8-carboxylic acid hydrochloride (Example 6)

4,4-dihydroxy-8-({1-[(methylsulfanyl)acetyl]azetidin-3-yl}oxy)-5-oxa-4-boranuidabicyclo[4.4.0]deca-l(6),7,9-triene-7-carboxylic acid disodium salt (Example 7)

4,4-dihydroxy-8-{[1-(1H-1,2,4-triazole-3-carbonyl)azetidin-3-yl]oxy}-5-oxa-4-boranuidabicyclo[4.4.0]deca-l(6),7,9-triene-7-carboxylic acid disodium salt (Example 8)

4,4-dihydroxy-8-{[1-(1-oxido-2-pyridinylcarbonyl)azetidin-3-yl]oxy}-5-oxa-4-boranuidabicyclo[4.4.0]deca-l(6),7,9-triene-7-carboxylic acid disodium salt (Example 9)

8-({1-[(2R)-2-amino-2-phenylacetyl]azetidin-3-yl}oxy)-4,4-dihydroxy-5-oxa-4-boranuidabicyclo[4.4.0]deca-l(6),7,9-triene-7-carboxylic acid disodium salt (Example 10)

8-[(1-benzoylazetidin-3-yl)oxy]-4,4-dihydroxy-5-oxa-4-boranuidabicyclo[4.4.0]deca-l(6),7,9-triene-7-carboxylic acid disodium salt (Example 11)

4,4-dihydroxy-8-{[1-(pyridine-3-carbonyl)azetidin-3-yl]oxy}-5-oxa-4-boranuidabicyclo[4.4.0]deca-l(6),7,9-triene-7-carboxylic acid disodium salt (Example 12)

4,4-dihydroxy-8-({1-[(pyridin-2-yl)acetyl]azetidin-3-yl}oxy)-5-oxa-4-boranuidabicyclo[4.4.0]deca-l(6),7,9-triene-7-carboxylic acid disodium salt (Example 13)

4,4-dihydroxy-8-({1-[(pyridin-3-yl)acetyl]azetidin-3-yl}oxy)-5-oxa-4-boranuidabicyclo[4.4.0]deca-l(6),7,9-triene-7-carboxylic acid disodium salt (Example 14)

8-({1-[(2S)-2-amino-2-phenylacetyl]azetidin-3-yl}oxy)-4,4-dihydroxy-5-oxa-4-boranuidabicyclo[4.4.0]deca-l(6),7,9-triene-7-carboxylic acid disodium salt (Example 15)

4,4-dihydroxy-8-({1-[(pyridin-4-yl)acetyl]azetidin-3-yl}oxy)-5-oxa-4-boranuidabicyclo[4.4.0]deca-l(6),7,9-triene-7-carboxylic acid disodium salt (Example 16)

4,4-dihydroxy-8-({1-[(4-hydroxyphenyl)acetyl]azetidin-3-yl}oxy)-5-oxa-4-boranuidabicyclo[4.4.0]deca-l(6),7,9-triene-7-carboxylic acid disodium salt (Example 17)

4,4-dihydroxy-8-({1-[(1H-1,2,4-triazol-1-yl)acetyl]azetidin-3-yl}oxy)-5-oxa-4-boranuidabicyclo[4.4.0]deca-l(6),7,9-triene-7-carboxylic acid disodium salt (Example 18)

8-({1-[amino(1H-imidazol-5-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 19)

4,4-dihydroxy-8-{[1-(phenylacetyl)azetidin-3-yl]oxy}-5-oxa-4-boranuidabicyclo[4.4.0]deca-l(6),7,9-triene-7-carboxylic acid disodium salt (Example 20)

4,4-dihydroxy-8-{[1-(3-phenylpropanoyl)azetidin-3-yl]oxy}-5-oxa-4-boranuidabicyclo[4.4.0]deca-l(6),7,9-triene-7-carboxylic acid disodium salt (Example 21)

4,4-dihydroxy-8-({1-[(1H-imidazol-1-yl)acetyl]azetidin-3-yl}oxy)-5-oxa-4-boranuidabicyclo[4.4.0]deca-l(6),7,9-triene-7-carboxylic acid disodium salt (Example 22)

4,4-dihydroxy-8-({1-[(1H-tetrazol-1-yl)acetyl]azetidin-3-yl}oxy)-5-oxa-4-boranuidabicyclo[4.4.0]deca-l(6),7,9-triene-7-carboxylic acid disodium salt (Example 23)

4,4-dihydroxy-8-({1-[(2H-tetrazol-5-yl)acetyl]azetidin-3-yl}oxy)-5-oxa-4-boranuidabicyclo[4.4.0]deca-l(6),7,9-triene-7-carboxylic acid disodium salt (Example 24)

4,4-dihydroxy-8-[(1-D-phenylalanylazetidin-3-yl)oxy]-5-oxa-4-boranuidabicyclo[4.4.0]deca-l(6),7,9-triene-7-carboxylic acid disodium salt (Example 25)

4,4-dihydroxy-8-[(1-D-tyrosylazetidin-3-yl)oxy]-5-oxa-4-boranuidabicyclo[4.4.0]deca-l(6),7,9-triene-7-carboxylic acid disodium salt (Example 26)

8-[(1-D-histidylazetidin-3-yl)oxy]-4,4-dihydroxy-5-oxa-4-boranuidabicyclo[4.4.0]deca-l(6),7,9-triene-7-carboxylic acid disodium salt (Example 27)

4,4-dihydroxy-8-[(1-D-valylazetidin-3-yl)oxy]-5-oxa-4-boranuidabicyclo[4.4.0]deca-l(6),7,9-triene-7-carboxylic acid disodium salt (Example 28)

8-[(1-L-histidylazetidin-3-yl)oxy]-4,4-dihydroxy-5-oxa-4-boranuidabicyclo[4.4.0]deca-l(6),7,9-triene-7-carboxylic acid disodium salt (Example 29)

8-[(1-{(2R)-2-[(4-ethyl-2,3-dioxopiperazine-1-carbonyl)amino]-2-phenylacetyl}azetidin-3-yl)oxy]-4,4-dihydroxy-5-oxa-4-boranuidabicyclo[4.4.0]deca-l(6),7,9-triene-7-carboxylic acid disodium salt (Example 30)

4,4-dihydroxy-8-[(1-D-prolylazetidin-3-yl)oxy]-5-oxa-4-boranuidabicyclo[4.4.0]deca-l(6),7,9-triene-7-carboxylic acid disodium salt (Example 31)

4,4-dihydroxy-8-[(1-L-prolylazetidin-3-yl)oxy]-5-oxa-4-boranuidabicyclo[4.4.0]deca-1(6),7,9-triene-7-carboxylic acid disodium salt (Example 32)

8-[(1-{[4-(2-aminoethyl)-1H-imidazol-1-yl]acetyl}azetidin-3-yl)oxy]-4,4-dihydroxy-5-oxa-4-boranuidabicyclo[4.4.0]deca-1(6),7,9-triene-7-carboxylic acid disodium salt (Example 33)

7-{[1-(3,4-dihydroxybenzoyl)azetidin-3-yl]oxy}-2-hydroxy-3,4-dihydro-2H-1,2-benzoxaborinine-8-carboxylic acid (Example 34)

Example 35: 2-hydroxy-7-{[1-(hydroxycarbamoyl)azetidin-3-yl]oxy}-3,4-dihydro-2H-1,2-benzoxaborinine-8-carboxylic Acid

[Chemical Formula 812]

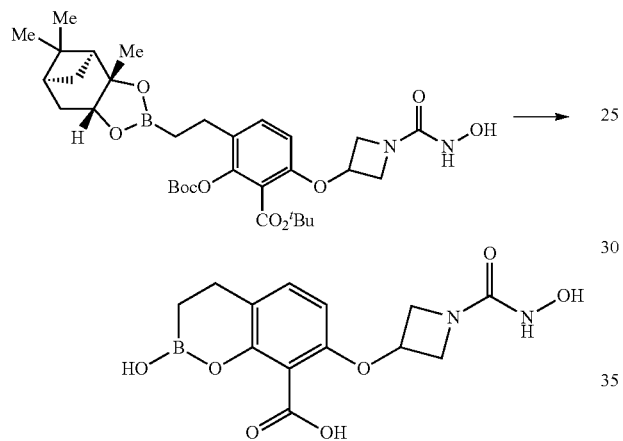

Phenylboronic acid (10.3 mg), 4 N hydrochloric acid/ethyl acetate solution, and hexane (3.6 mL) were added to an acetonitrile (0.73 mL) solution of the compound of Reference Example 35. The reaction mixture was stirred for 7 hours at room temperature and allowed to stand overnight. The acetonitrile phase was washed with hexane and concentrated. The residue was washed with acetonitrile to obtain the title compound (0.4 mg).

LCMS: [M+H]$^+$/Rt=323/0.489 min$^C$

Example 36: 7-({1-[(2R)-2-amino-2-(1H-imidazol-4-yl)acetyl]azetidin-3-yl}oxy)-2-hydroxy-3,4-dihydro-2H-1,2-benzoxaborinine-8-carboxylic Acid

[Chemical Formula 813]

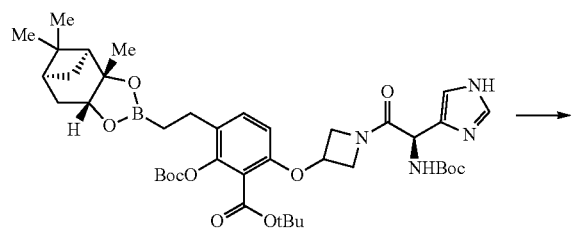

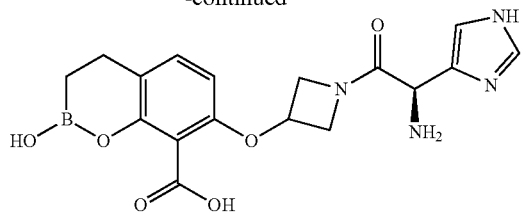

Phenylboronic acid (0.146 g) and 1 N hydrochloric acid/acetic acid solution (25.2 mL) were added to Reference Example (R)-36 (1.0 g). The reaction mixture was stirred for 1 hour at room temperature and then concentrated. The residue was dissolved in methanol (3 mL) and washed twice with heptane (6 mL) (the washing process removes the supernatant (top layer) after standing). The bottom layer was concentrated under reduced pressure, and the resulting residue was purified by reversed phase column chromatography to obtain the title compound (200 mg).

$^1$H-NMR (600 MHz, D$_2$O) δ: 7.56 (1H, m), 6.99 (1H, m), 6.73 (1H, d, J=8.4 Hz), 5.86 (1H, d, J=8.4 Hz), 4.86-4.65 (2H, m), 4.51-4.46 (0.5H, m), 4.30-4.14 (2H, m), 3.96-3.82 (1.5H, m), 2.45-2.43 (2H, m), 0.24-0.21 (2H, m).

LCMS: [M+H]$^+$/Rt=387.05/0.421 min$^C$

Example 37: 8-({1-[(2S)-2-amino-2-(1H-imidazol-4-yl)acetyl]azetidin-3-yl}oxy)-4,4-dihydroxy-5-oxa-4-boranuidabicyclo[4.4.0]deca-1(6),7,9-triene-7-carboxylic Acid Disodium Salt

[Chemical Formula 814]

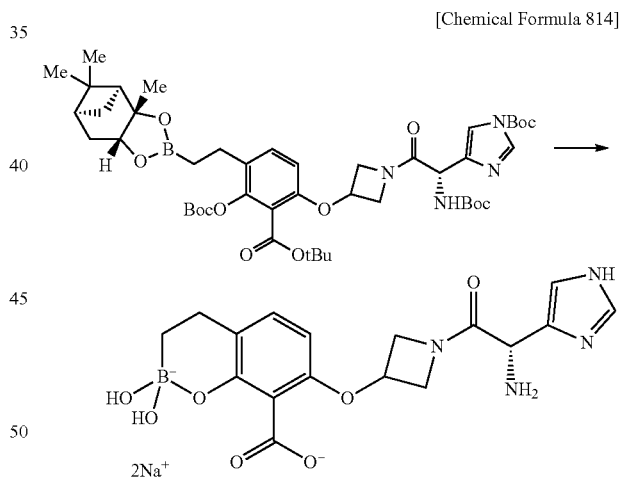

Phenylboronic acid (2.46 mg), hexane (0.337 mL), and 4 N hydrochloric acid/cyclopentyl methyl ether solution (0.151 mL) were added to an acetonitrile (0.337 mL) solution of the compound of Reference Example (S)-36 (18.1 mg), and the reaction mixture was stirred for 16 hours at room temperature. After allowing it to stand, the supernatant (top layer) of the reaction solution separated into two layers was removed, and the remaining bottom layer was washed with hexane (the washing process removes the supernatant after standing). The solid produced in the solution at the bottom layer was washed with diethyl ether. The residue of the solid obtained by removing the solvent was dried under reduced pressure. The resulting dried residue was dissolved in water. An aqueous 2 N sodium hydroxide solution (0.1 mL) was added. The mixture was purified by reversed phase column chromatography to obtain the title compound (7.8 mg) as a white solid.

LCMS: [M+H]⁺/Rt=387.00/0.428 min$^C$

The column retention times of the compound of Example 36 and the compound of Example 37 in chiral chromatography were the following.

Column: CROWNPAK CR-I(−) (0.30 cm I.D.×15 cm L) (Daicel Corporation)

Mobile phase: aqueous perchloric acid solution (pH 1.0)/acetonitrile (60% perchloric acid: 1.7%)

Flow rate: 0.5 mL/min
Temperature: 25° C.
Rt of compound of Example 36: 6.001 min
Rt of compound of Example 37: 3.968 min
Optical purity of Example 36 (computed by HPLC area percentage value): 98.5% ee
Optical purity of Example 37 (computed by HPLC area percentage value): 98.3% ee The stereostructure of the compound of Example 36 was estimated to be an R form by Mosher's method (reference document for Mosher's method include: The Journal of Organic Chemistry, 2016, 81, 7373).

Example 38: 8-({1-[amino(1-methyl-1H-imidazol-4-yl)acetyl]azetidin-3-yl}oxy)-4,4-dihydroxy-5-oxa-4-boranuidabicyclo[4.4.0]deca-l(6),7,9-triene-7-carboxylic Acid Disodium Salt

[Chemical Formula 815]

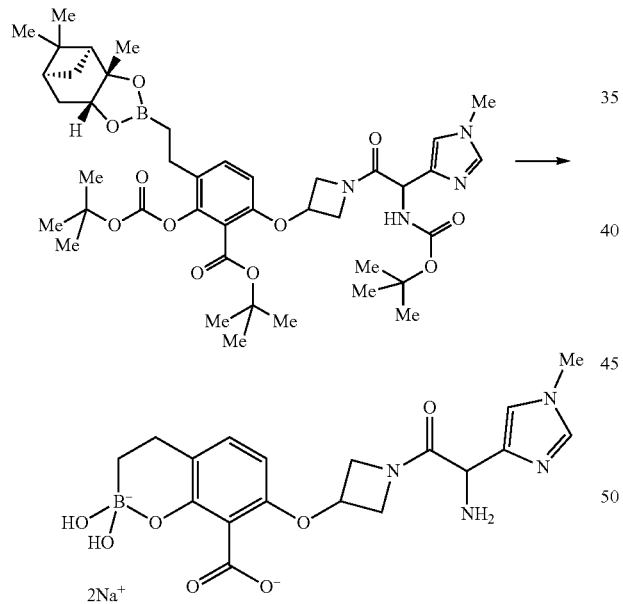

Phenylboronic acid (18.6 mg) and 4 N hydrochloric acid/cyclopentyl methyl ether solution (1.21 mL) were added to an acetic acid (1.61 mL) solution of the compound of Reference Example 37 (130 mg) while cooling with ice, and the reaction mixture was stirred for 3 hours at room temperature. The solvent was removed under reduced pressure. The resulting dried residue was dissolved in water. An aqueous 2 N sodium hydroxide solution (0.402 mL) was added, and the mixture was purified by reversed phase column chromatography to obtain the title compound (5 mg) as a white solid.

LCMS: [M+H]⁺/Rt=401.31/0.473 min$^C$

Example 39: 2-hydroxy-7-{[1-(4H-1,2,4-triazole-3-sulfonyl)azetidin-3-yl]oxy}-3,4-dihydro-2H-1,2-benzoxaborinine-8-carboxylic Acid Trifluoroacetate

[Chemical Formula 816]

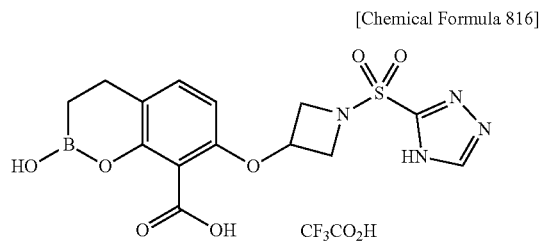 [SMILES: O=C(O)c1c(OC2CN(S(=O)(=O)c3nnc[nH]3)C2)ccc2c1OB(O)CC2 ; "CF3CO2H"]

Phenylboronic acid (35.6 mg), hexane (2.9 mL), and TFA (2.23 mL) were added to an acetonitrile (2.9 mL) solution of the compound of Reference Example 41 (205 mg), and the reaction mixture was stirred for 5 hours at room temperature. After allowing it to stand, the supernatant (top layer) of the reaction solution separated into two layers was removed, and the remaining bottom layer was washed with hexane (the washing process removes the supernatant after standing). The solid produced in the solution at the bottom layer was washed with diethyl ether. The residue of the solid obtained by removing the solvent was dried under reduced pressure. The resulting dried residue was purified by reversed phase column chromatography to obtain the title compound (39.8 mg) as a colorless solid.

¹H-NMR (CD₃OD) δ: 8.69 (1H, s), 7.11 (1H, d, J=8.1 Hz), 6.21 (1H, d, J=8.1 Hz), 4.95-4.85 (1H, m), 4.44-4.35 (2H, m), 4.04-3.99 (2H, m), 2.65 (2H, t, J=8.1 Hz), 1.04 (2H, t, J=8.1 Hz).

LCMS: [M+H]⁺/Rt=395.1/1.24 min³

Example 40: 7-({1-[2-amino-2-(1H-imidazol-4-yl)(2H)ethanoyl]azetidin-3-yl}oxy)-2-hydroxy-3,4-dihydro-2H-1,2-benzoxaborinine-8-carboxylic acid dihydrochloride

[Chemical Formula 817]

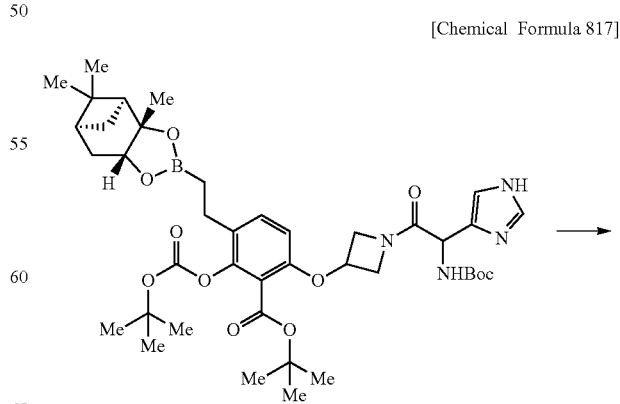

Reference Example 36-4

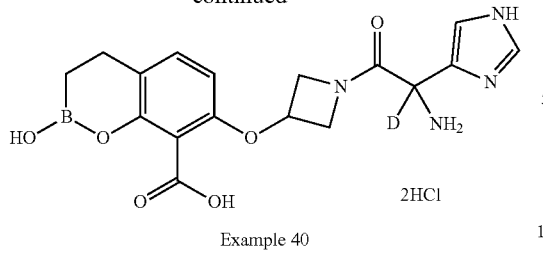

Example 40

Acetic acid-d1 (3 mL) was added to the compound of Reference Example 36-4 (0.3 g, 0.377 mmol), and the reaction mixture was stirred for 4 days at room temperature. Phenylboronic acid (46 mg, 0.377 mmol) and 4 N hydrochloric acid cyclopentyl methyl ether solution (2 mL, 8.0 mmol) were then added, and the reaction mixture was stirred for 4 hours at room temperature. The reaction mixture was dried and solidified under reduced pressure. The resulting dried residue was dissolved in methanol (1 mL), and isopropanol (10 mL) was added. The precipitated solid was filtered out, dried and solidified under reduced pressure. The resulting solid was purified by reversed phase column chromatography, and the resulting dried residue was washed with acetonitrile, dried and solidified under reduced pressure to obtain the title compound (71 mg) as a white solid.

$^1$H-NMR (0.1M $Na_2CO_3$ in $D_2O$) δ: 7.84-7.76 (1H, m), 7.30-7.20 (1H, m), 6.91-6.89 (1H, m), 6.12-6.01 (1H, m), 5.02-4.89 (1H, m), 4.58-3.76 (4H, m), 2.59 (2H, m), 0.55 (2H, m).

LCMS: $[M+H]^+$/Rt=388.12/0.410 min$^C$

Example 41: 7-({1-[2-amino-2-(1H-imidazol-4-yl)propanoyl]azetidin-3-yl}oxy)-2-hydroxy-3,4-dihydro-2H-1,2-benzoxaborinine-8-carboxylic Acid

[Chemical Formula 818]

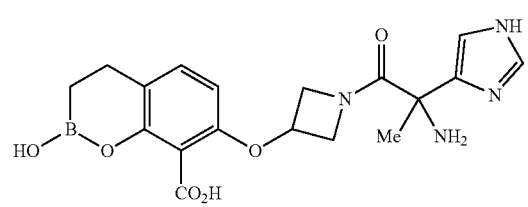

A reaction, work-up, and purification were performed using the compound of Reference Example 39 (153 mg, 0.189 mmol) as the starting material by the same method described in Example 36 to obtain the title compound (42 mg) as a white solid.

$^1$H-NMR (0.1M $Na_2CO_3$ in $D_2O$) δ: 7.77 (1H, m), 7.18 (1H, m), 6.83 (1H, m), 5.91 (1H, m), 4.35 (1H, m), 3.95-4.20 (2H, m), 3.30-3.51 (2H, m), 2.57 (2H, m), 1.63 (3H, s), 0.36 (2H, m).

LCMS: $[M+H]^+$/Rt=401.12/0.422 min$^C$

A reaction, work-up, and purification were performed using the compounds of Reference Examples 56 and 58 as the starting materials by the same method described in Example 37 to obtain Example compounds 42 and 43, respectively. However, if hydrochloride is the final product (Example 43), the hydrochloride was obtained from purifying the compound by reversed phase chromatography without sodium hydroxide treatment, followed by addition of hydrochloric acid and concentration.

TABLE 3-5

| Example | Starting material | Structural formula | NMR and/or LCMS |
|---|---|---|---|
| 42 | Reference Example 56 | | LCMS: $[M + H]^+$/Rt = 401.10/0.451 min$^C$ |
| 43 | Reference Example 58 | | LCMS: $[M + H]^+$/Rt = 399.10/0.493 min$^C$ <br> $^1$H-NMR (CD$_3$OD) δ: 8.61 (1H, s), 7.21 (1H, s), 7.17 (1H, d, J = 7.9 Hz), 6.34 (1H, d, J = 7.9 Hz). 5.18-5.15 (1H, m), 4.70-4.67 (2H, m), 4.34-4.21 (2H, m), 2.70 (2H, t, J = 7.6 Hz), 2.67 (3H, s), 1.05 (2H, t, J = 7.6 Hz). |

The names of the compounds of Examples 42 and 43 are described below.

8-({(3S)-1-[amino(1H-imidazol-4-yl)acetyl]pyrrolidin-3-yl}oxy)-4,4-dihydroxy-5-oxa-4-boranuidabicyclo[4.4.0]deca-l(6),7,9-triene-7-carboxylic acid disodium salt (Example 42)

2-hydroxy-7-{[1-(4-hydroxy-6-methylpyridine-3-carbonyl)azetidin-3-yl]oxy}-3,4-dihydro-2H-1,2-benzoxaborinine-8-carboxylic acid hydrochloride (Example 43)

A reaction, work-up, and purification were performed using the compounds of Reference Examples 38, 48, 49, 55, 57, 63, 64, and 71 as the starting materials by the same method described in Example 38 to obtain each of the following Example compounds 44 to 51. However, if hydrochloride is the final product (Examples 46 and 51), the hydrochloride was obtained from purifying the compound by reversed phase chromatography without sodium hydroxide treatment, followed by addition of hydrochloric acid and concentration.

TABLE 3-6

| Example | Starting material | Structural formula | NMR and/or LCMS |
|---|---|---|---|
| 44 | Reference Example 57 | | LCMS: [M + H]⁺/Rt = 401.20/0.393 min$^C$ |
| 45 | Reference Example 48 | | LCMS: [M + H]⁺/Rt = 445.2/0.82 min$^B$ $^1$H-NMR (CD$_3$OD) δ: 7.57 (1H, s), 7.08 (1H, s), 6.70 (1H, d, J = 8.1 Hz), 5.90 (1H, d, J = 8.1 Hz), 4.98-4.90 (1H, m), 4.62-3.93 (7H, m), 2.55 (2H, t, J = 5.4 Hz), 0.44 (2H, t, J = 5.4 Hz). |
| 46 | Reference Example 49 | | LCMS: [M + H]⁺/Rt = 444.3/0.52 min$^B$ $^1$H-NMR (CD$_3$OD) δ: 9.01 (1H, s), 7.88 (1H, s), 7.15 (1H, d, J = 8.1 Hz), 6.35-6.28 (1H, m), 5.55 (1H, d, J = 16.2 Hz), 5.20-4.97 (3H, m), 4.77-3.72 (4H, m), 2.69 (2H, t, J = 8.1 Hz), 1.05 (2H, t, J = 8.1 Hz). |
| 47 | Reference Example 63 | | LCMS: [M + H]⁺/Rt = 398.3/0.82 min$^B$ $^1$H-NMR (CD$_3$OD) δ: 8.59 (1H, s), 8.50-8.47 (1H, m), 7.90-7.84 (1H, m), 7.47-7.41 (1H, m), 6.67 (1H, d, J = 8.1 Hz), 5.89-5.85 (1H, m), 5.01-4.94 (1H, m), 4.73-3.73 (5H, m), 2.54 (2H, t, J = 5.4 Hz), 0.41 (2H, t, J = 5.4 Hz). |

TABLE 3-7

| | | Structural formula | NMR and/or LCMS |
|---|---|---|---|
| 48 | Reference Example 64 | (structure) | LCMS: [M + H]⁺/Rt = 401.3/0.92 min^B<br>¹H-NMR (CD₃OD) δ: 7.61-7.59 (1H, m), 7.47 (1H, s), 6.68 (1H, d, J = 8.1 Hz), 5.90-5.86 (1H, s), 5.00-4.94 (1H, m), 4.64-3.96 (5H, m), 3.86 (3H, s), 2.55 (2H, t, J = 8.1 Hz), 0.41 (2H, t, J = 8.1 Hz). |
| 49 | Reference Example 55 | (structure) | LCMS: [M + H]⁺/Rt = 401.05/0.442 min^C |
| 50 | Reference Example 38 | (structure) | LCMS: [M + H]⁺/RT = 401.16/0.387 min^C<br>¹H-NMR (D₂O) δ: 6.62 (1H, d, J = 12.8 Hz), 6.48 (1H, d, J = 7.9 Hz), 5.61 (1H, d, J = 7.9 Hz), 4.61-4.49 (2H, m), 4.30-4.26 (1H, m), 4.05-3.94 (1H, m), 3.90-3.81 (1H, m), 3.70-3.63 (1H, m), 2.18 (2H, t, J = 6.4 Hz), 1.94 (3H, d, J = 4.3 Hz), 0.00 (2H, t, J = 6.1 Hz). |
| 51 | Reference Example 71 | (structure) | LCMS: [M + H]⁺/Rt = 404.2/0.95 min^B<br>¹H-NMR (CD₃OD) δ: 9.13-9.10 (1H, m), 7.92-7.91 (1H, m), 7.13 (1H, d, J = 8.2 Hz), 6.27 (1H, d, J = 8.2 Hz), 5.50-5.49 (1H, m), 5.12-5.03 (1H, m), 4.73-3.62 (4H, m), 2.68 (2H, t, J = 8.1 Hz), 1.05 (2H, t, J = 8.1 Hz). |

The names of the compounds of Examples 44 to 51 are described below.

8-({1-[amino(1-methyl-1H-imidazol-5-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 44)

8-[(1-{amino[1-(carboxymethyl)-1H-imidazol-4-yl]acetyl}azetidin-3-yl)oxy]-4,4-dihydroxy-5-oxa-4-boranuidabicyclo[4.4.0]deca-l(6),7,9-triene-7-carboxylic acid trisodium salt (Example 45)

7-[(1-{amino[1-(2-amino-2-oxoethyl)-1H-imidazol-4-yl]acetyl}azetidin-3-yl)oxy]-2-hydroxy-3,4-dihydro-2H-1,2-benzoxaborinine-8-carboxylic acid hydrochloride (Example 46)

8-({1-[amino(pyridin-3-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 47)

8-({1-[amino(1-methyl-1H-pyrazol-4-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 48)

8-({(3R)-1-[amino(1H-imidazol-4-yl)acetyl]pyrrolidin-3-yl}oxy)-4,4-dihydroxy-5-oxa-4-boranuidabicyclo[4.4.0]deca-l(6),7,9-triene-7-carboxylic acid disodium salt (Example 49)

8-({1-[amino(2-methyl-1H-imidazol-4-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 50)

7-({1-[amino(1,3-thiazol-4-yl)acetyl]azetidin-3-yl}oxy)-2-hydroxy-3,4-dihydro-2H-1,2-benzoxaborinine-8-carboxylic acid hydrochloride (Example 51)

A reaction, work-up, and purification were performed using the compounds of Reference Examples 106 to 108 as the starting materials by the same method described in Example 38 to obtain the following Example compounds 52 to 54, respectively.

TABLE 3-8

| Example | Starting material | Structural formula | NMR and/or LCMS |
|---|---|---|---|
| 52 | Reference Example 106 | (structure) | LCMS: [M + H]⁺/Rt = 394.4/1.20 min^B<br>¹H-NMR (CD₃OD) δ: 8.07 (1H, s), 7.87 (1H, s), 7.12 (1H, d, J = 8.1 Hz), 6.23 (1H, d, J = 8.1 Hz), 4.93-4.87 (1H, m), 4.34-4.26 (2H, m), 3.91-3.88 (2H, m), 2.66 (2H, t, J = 8.1 Hz), 1.04 (2H, t, J = 8.1 Hz). |

TABLE 3-8-continued

| Example | Starting material | Structural formula | NMR and/or LCMS |
|---|---|---|---|
| 53 | Reference Example 107 | | LCMS: [M + H]⁺/Rt = 405.3/1.41 min$^B$<br>$^1$H-NMR (CD$_3$OD) δ: 9.00 (1H, s), 8.87 (1H, d, J = 5.4 Hz), 8.31 (1H, d, J = 8.1 Hz), 7.74-7.00 (1H, m), 7.10 (1H, d, J = 8.1 Hz), 6.22 (1H, d, J = 8.1 Hz), 4.97-4.65 (1H, m), 4.33-4.27 (2H, m), 3.83-3.77 (2H, m), 2.65 (2H, t, J = 8.1 Hz), 1.02 (2H, t, J = 8.1 Hz). |
| 54 | Reference Example 108 | | LCMS: [M + H]⁺/Rt = 421.3/1.30 min$^B$<br>$^1$H-NMR (CD$_3$OD) δ: 8.46-8.36 (1H, m), 8.06 (1H, dd, J = 5.4 Hz, 2.7 Hz), 7.70-7.57 (2H, m), 7.12 (1H, d, J = 8.1 Hz), 6.28 (1H, d, J = 8.1 Hz), 5.08-5.00 (1H, m), 4.61-4.55 (2H, m), 4.33-4.26 (2H, m), 2.65 (2H, t, J = 8.1 Hz), 1.05 (2H, t, J = 8.1 Hz). |

The names of the compounds of Examples 52 to 54 are described below.

2-hydroxy-7-{[1-(1H-imidazole-4-sulfonyl)azetidin-3-yl]oxy}-3,4-dihydro-2H-1,2-benzoxaborinine-8-carboxylic acid trifluoroacetate (Example 52)

2-hydroxy-7-{[1-(pyridine-3-sulfonyl)azetidin-3-yl]oxy}-3,4-dihydro-2H-1,2-benzoxaborinine-8-carboxylic acid trifluoroacetate (Example 53)

2-hydroxy-7-{[1-(1-oxo-1λ$^5$-pyridine-2-sulfonyl)azetidin-3-yl]oxy}-3,4-dihydro-2H-1,2-benzoxaborinine-8-carboxylic acid trifluoroacetate (Example 54)

A reaction, work-up, and purification were performed using the compounds of Reference Examples 40, 43 to 47, 50, 51, 59, 65, 66, 69, 70, 114 to 116, and 127 as the starting materials by the same method described in Example 4 to obtain the following Example compounds 55 to 71 (corresponding starting materials are not in order). However, if a free form is the final product (Examples 57, 61, 64, 65, 67, and 71), the free form was obtained from purifying the compound without sodium hydroxide treatment. If hydrochloride is the final product (Examples 58, 62, and 63), the hydrochloride was obtained from purifying the compound by reversed phase chromatography without sodium hydroxide treatment, followed by addition of hydrochloric acid and concentration.

TABLE 3-9

| Example | Starting material | Structural formula | NMR and/or LCMS |
|---|---|---|---|
| 55 | Reference Example 65 | | LCMS: [M + H]⁺/Rt = 404.4/1.03 min$^B$<br>$^1$H-NMR (CD$_3$OD) δ: 6.69 (1H, d, J = 8.2 Hz), 6.31 (1H, s), 5.90 (1H, d, J = 8.2 Hz), 5.00-4.86 (1H, m), 4.63-4.47 (1H, m), 4.39-4.21 (2H, m), 4.08-3.96 (1H, m), 3.41-3.35 (2H, m), 2.63-2.49 (2H, m), 0.48-0.35 (2H, m). |
| 56 | Reference Example 66 | | LCMS: [M + H]+/Rt = 390.2/1.16 min$^B$<br>$^1$H-NMR (CD$_3$OD) δ: 7.24 (1H, s), 6.72 (1H, d, J = 8.1 Hz), 5.94 (1H, d, J = 8.1 Hz), 4.95-4.90 (2H, m), 4.62-4.56 (1H, m), 4.47-4.41 (1H, m), 4.16-4.12 (1H, m), 2.59-2.54 (2H, m), 0.47-0.42 (2H, m). |
| 57 | Reference Example 69 | | LCMS: [M + H]⁺/Rt = 373.22/1.62 min$^D$<br>$^1$H-NMR (CD$_3$OD) δ: 8.11 (1H, d, J = 1.1 Hz), 7.91 (1H, s), 7.22-7.13 (1H, m), 6.40-6.28 (1H, m), 5.32 (2H, s), 5.16-5.10 (1H, m), 4.74-4.66 (1H, m), 4.50-4.42 (1H, m), 4.37-4.31 (1H, m), 4.10-4.02 (1H, m), 2.77-2.62 (2H, m), 1.10-1.01 (2H, m). |

TABLE 3-10

| 58 | Reference Example 70 | 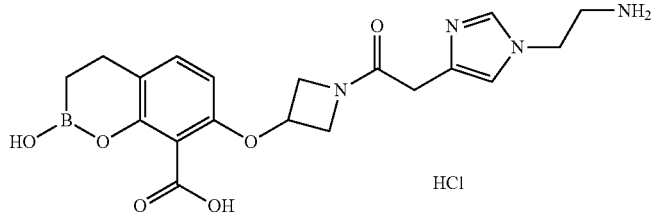 [SMILES: NCCn1cnc(CC(=O)N2CC(Oc3ccc4c(c3C(=O)O)OB(O)CC4)C2)c1 ; Cl] | LCMS: [M + H]⁺/Rt = 415.2/0.52 min^B<br>¹H-NMR (CD₃OD) δ: 9.04 (1H, s), 7.63 (1H, s), 7.18 (1H, d, J = 8.1 Hz), 6.37 (1H, d, J = 8.1 Hz), 5.15-5.12 (1H, m), 4.79-4.73 (1H, m), 4.60 (2H, t, J = 5.4 Hz), 4.54-4.33 (2H, m), 4.18-4.02 (1H, m), 3.79 (2H, s), 3.53 (2H, t, J = 5.4 Hz), 2.71-2.65 (2H, m), 1.10-1.04 (2H, m). |
| --- | --- | --- | --- |
| 59 | Reference Example 40 | 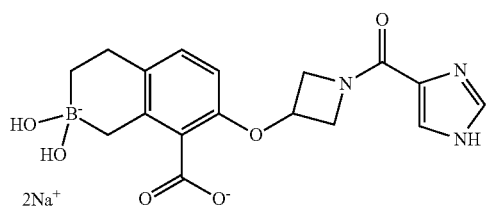 | LCMS: [M + H]⁺/Rt = 358.2/0.90 min^B<br>¹H-NMR (CD₃OD) δ: 7.81 (1H, s), 7.67 (1H, s), 6.93 (1H, d, J = 8.1 Hz), 6.11 (1H, d, J = 8.1 Hz), 5.14-5.03 (1H, m), 4.92-4.73 (1H, m), 4.59-4.52 (2H, m), 4.24-4.19 (1H, m), 2.60 (2H, t, J = 8.1 Hz), 0.40 (2H, t, J = 8.1 Hz). |
| 60 | Reference Example 127 | 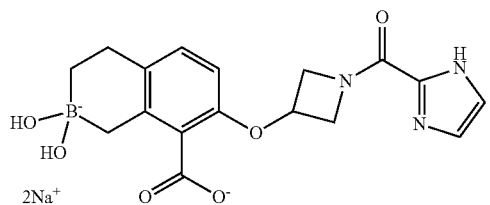 | LCMS: [M + H]⁺/Rt = 358.1/1.17 min^B<br>¹H-NMR (CD₃OD) δ: 7.28 (2H, s), 6.93 (1H, d, J = 8.1 Hz), 6.11 (1H, d, J = 8.1 Hz), 5.16-5.09 (1H, m), 5.04-4.71 (1H, m), 4.67-4.55 (2H, m), 4.27-4.21 (1H, m), 2.61 (2H, t, J = 8.1 Hz), 0.41 (2H, t, J = 8.1 Hz). |
| 61 | Reference Example 43 | 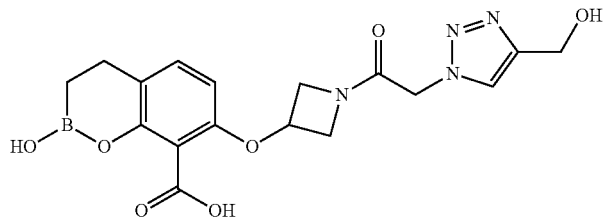 [SMILES: O=C(O)c1c(OC2CN(C(=O)Cn3cc(CO)nn3)C2)ccc2c1OB(O)CC2] | LCMS: [M + H]⁺/Rt = 403.17/1.58 min^D<br>¹H-NMR (CD₃OD) δ: 8.06 (1H, s), 7.21-7.12 (1H, m), 6.41-6.27 (1H, m), 5.31 (2H, s), 5.16-5.10 (1H, m), 4.77-4.67 (3H, m), 4.50-4.42 (1H, m), 4.38-4.31 (1H, m), 4.10-4.02 (1H, m), 2.74-2.63 (2H, m), 1.06 (2H, t, J = 7.7 Hz). |
| 62 | Reference Example 114 | 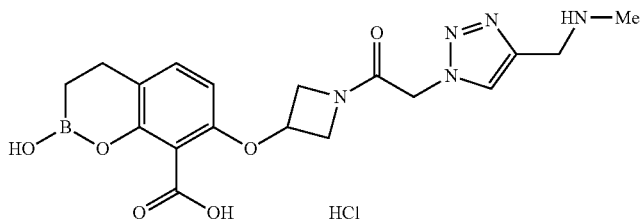 [SMILES: CNCc1cn(CC(=O)N2CC(Oc3ccc4c(c3C(=O)O)OB(O)CC4)C2)nn1 ; Cl] | LCMS: [M + H]⁺/Rt = 416.30/1.25 min^D<br>¹H-NMR (CD₃OD) δ: 8.12 (1H, s), 7.23-7.10 (1H, m), 6.41-6.29 (1H, m), 5.30 (2H, s), 5.18-5.10 (1H, m), 4.78-4.71 (1H, m), 4.50-4.43 (1H, m), 4.40-4.28 (3H, m), 4.11-4.03 (1H, m), 2.79-2.65 (5H, m), 1.10-1.02 (2H, m). |
| 63 | Reference Example 115 | 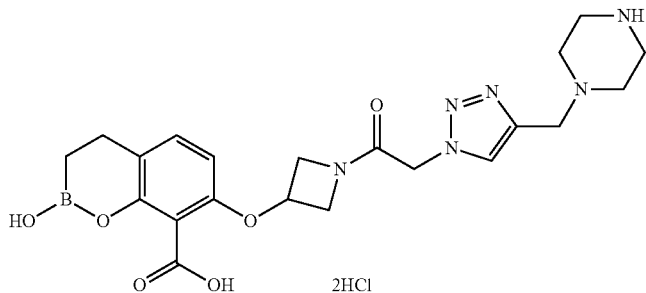 [SMILES: O=C(O)c1c(OC2CN(C(=O)Cn3cc(CN4CCNCC4)nn3)C2)ccc2c1OB(O)CC2 ; "2HCl"] | LCMS: [M + H]⁺/Rt = 471.27/1.15 min^D<br>¹H-NMR (CD₃OD) δ: 8.29 (1H, s), 7.21-7.13 (1H, m), 6.40-6.30 (1H, m), 5.34 (2H, s), 5.19-5.13 (1H, m), 4.79-4.73 (1H, m), 4.64 (2H, s), 4.50-4.45 (1H, m), 4.41-4.36 (1H, m), 4.11-4.04 (1H, m), 3.71-3.54 (8H, m), 2.74-2.66 (2H, m), 1.10-1.03 (2H, m). |

TABLE 3-11

| 64 | Reference Example 116 | 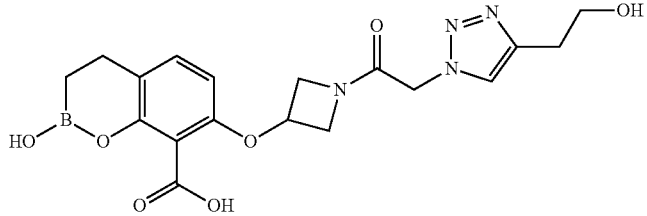 [SMILES: O=C(O)c1c(OC2CN(C(=O)Cn3cc(CCO)nn3)C2)ccc2c1OB(O)CC2] | LCMS: [M + H]⁺/Rt = 417.26/1.56 min^D<br>¹H-NMR (CD₃OD) δ: 8.10 (1H, s), 7.23-7.13 (1H, m), 6.43-6.28 (1H, m), 5.36 (2H, s), 5.19-5.12 (1H, m), 4.76-4.68 (1H, m), 4.52-4.44 (1H, m), 4.38-4.32 (1H, m), 4.13-4.06 (1H, m), 3.90-3.78 (2H, m), 3.04-2.95 (2H, m), 2.78-2.65 (2H, m), 1.12-1.00 (2H, m). |
| --- | --- | --- | --- |
| 65 | Reference Example 44 | 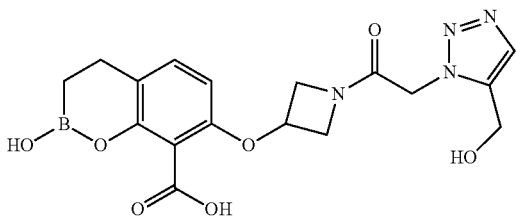 [SMILES: O=C(O)c1c(OC2CN(C(=O)Cn3nncc3CO)C2)ccc2c1OB(O)CC2] | LCMS: [M + H]⁺/Rt = 403.35/1.44 min^D<br>¹H-NMR (CD₃OD) δ: 7.77 (1H, s), 7.23-7.12 (1H, m), 6.44-6.25 (1H, m), 5.35-5.31 (2H, m), 5.16-5.12 (1H, m), 4.76-4.70 (3H, m), 4.51-4.44 (1H, m), 4.40-4.32 (1H, m), 4.11-4.04 (1H, m), 2.77-2.65 (2H, m), 1.10-1.03 (2H, m). |
| 66 | Reference Example 45 | 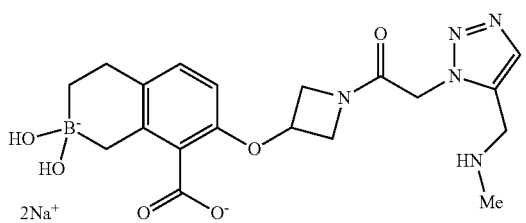 | LCMS: [M + H]⁺/Rt = 416.34/1.12 min^D<br>¹H-NMR (D₂O) δ: 7.76 (1H, s), 6.89 (1H, d, J = 8.0 Hz), 6.06 (1H, d, J = 8.0 Hz), 5.33-5.22 (2H, m), 5.12-5.06 (1H, m), 4.74-4.67 (1H, m), 4.49-4.36 (2H, m), 4.16-4.10 (1H, m), 3.79 (2H, s), 2.62-2.54 (2H, m), 2.34 (3H, s), 0.41-0.33 (2H, m). |
| 67 | Reference Example 59 | 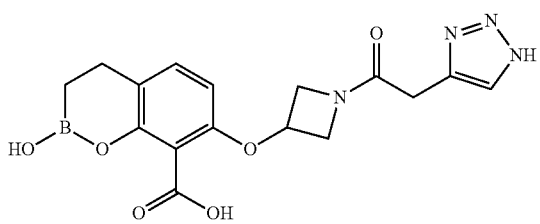 [SMILES: O=C(O)c1c(OC2CN(C(=O)Cc3c[nH]nn3)C2)ccc2c1OB(O)CC2] | LCMS: [M + H]⁺/Rt = 373.35/1.59 min^D<br>¹H-NMR (CD₃OD) δ: 8.19 (1H, s), 7.21-7.07 (1H, m), 6.42-6.21 (1H, m), 5.09-5.05 (1H, m), 4.72-4.65 (1H, m), 4.43-4.36 (1H, m), 4.35-4.28 (1H, m), 4.03-3.95 (1H, m), 3.84 (2H, s), 2.71-2.61 (2H, m), 1.06-0.97 (2H, m). |
| 68 | Reference Example 46 | 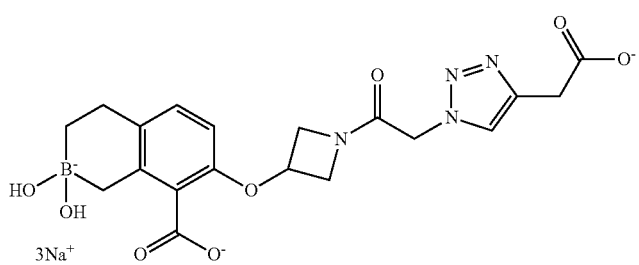 | LCMS: [M + H]⁺/Rt = 431.12/1.71 min^D<br>¹H-NMR (D₂O) δ: 7.84 (1H, d, J = 6.9 Hz), 6.92 (1H, d, J = 8.0 Hz), 6.09 (1H, d, J = 8.0 Hz), 5.33-5.22 (2H, m), 5.12-5.05 (1H, m), 4.72-4.66 (1H, m), 4.50-4.43 (1H, m), 4.43-4.37 (1H, m), 4.16-4.10 (1H, m), 3.64 (2H, s), 2.64-2.56 (2H, m), 0.51-0.42 (2H, m). |
| 69 | Reference Example 47 | 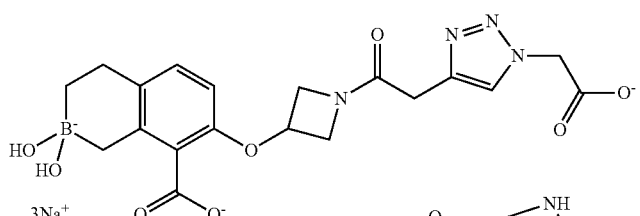 | LCMS: [M + H]⁺/Rt = 431.16/1.44 min^D<br>¹H-NMR (D₂O) δ: 7.86 (1H, s), 6.89 (1H, d, J = 8.0 Hz), 6.06 (1H, d, J = 8.0 Hz), 5.06-5.00 (3H, m), 4.70-4.65 (1H, m), 4.44-4.35 (2H, m), 4.11-4.05 (1H, m), 3.80-3.67 (2H, m), 2.62-2.55 (2H, m), 0.41-0.34 (2H, m). |
| 70 | Reference Example 50 | 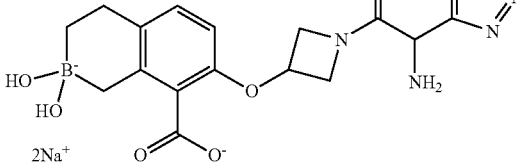 | LCMS: [M + H]⁺/R = 388.35/0.93 min^D<br>¹H-NMR (D₂O) δ: 7.77-7.72 (1H, m), 6.92-6.34 (1H, m), 6.05-5.93 (1H, m), 5.03-4.85 (2H, m), 4.64-3.91 (4H, m), 2.62-2.49 (2H, m), 0.49-0.37 (2H, m). |

TABLE 3-12

| 71 | Reference Example 51 | (structure) | LCMS: [M + H]⁺/R = 418.13/2.03 min[D]<br>¹H-NMR (CD₃OD) δ: 8.92 (1H, s), 7.22-7.13 (1H, m), 6.40-6.12 (1H, m), 5.41-5.34 (2H, m), 5.19-5.12 (1H, m), 4.78-4.71 (1H, m), 4.52-4.45 (1H, m), 4.44-4.37 (1H, m), 4.13-4.06 (1H, m), 2.76-2.66 (2H, m), 1.11-1.02 (2H, m). |
|---|---|---|---|

The names of the compounds of Examples 55 to 71 are described below.

8-({1-[(2-amino-1,3-thiazol-4-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 55)

8-{[1-(2-amino-1,3-thiazole-4-carbonyl)azetidin-3-yl]oxy}-4,4-dihydroxy-5-oxa-4-boranuidabicyclo[4.4.0]deca-l(6),7,9-triene-7-carboxylic acid disodium salt (Example 56)

2-hydroxy-7-({1-[(1H-1,2,3-triazol-1-yl)acetyl]azetidin-3-yl}oxy)-3,4-dihydro-2H-1,2-benzoxaborinine-8-carboxylic acid (Example 57)

7-[(1-{[1-(2-aminoethyl)-1H-imidazol-4-yl]acetyl}azetidin-3-yl)oxy]-2-hydroxy-3,4-dihydro-2H-1,2-benzoxaborinine-8-carboxylic acid hydrochloride (Example 58)

4,4-dihydroxy-8-{[1-(1H-imidazole-4-carbonyl)azetidin-3-yl]oxy}-5-oxa-4-boranuidabicyclo[4.4.0]deca-l(6),7,9-triene-7-carboxylic acid disodium salt (Example 59)

4,4-dihydroxy-8-{[1-(1H-imidazole-2-carbonyl)azetidin-3-yl]oxy}-5-oxa-4-boranuidabicyclo[4.4.0]deca-l(6),7,9-triene-7-carboxylic acid disodium salt (Example 60)

2-hydroxy-7-[(1-{[4-(hydroxymethyl)-1H-1,2,3-triazol-1-yl]acetyl}azetidin-3-yl)oxy]-3,4-dihydro-2H-1,2-benzoxaborinine-8-carboxylic acid (Example 61)

2-hydroxy-7-{[1-({4-[(methylamino)methyl]-1H-1,2,3-triazol-1-yl}acetyl)azetidin-3-yl]oxy}-3,4-dihydro-2H-1,2-benzoxaborinine-8-carboxylic acid hydrochloride (Example 62)

2-hydroxy-7-{[1-({4-[(piperazin-1-yl)methyl]-1H-1,2,3-triazol-1-yl}acetyl)azetidin-3-yl]oxy}-3,4-dihydro-2H-1,2-benzoxaborinine-8-carboxylic acid dihydrochloride (Example 63)

2-hydroxy-7-[(1-{[4-(2-hydroxyethyl)-1H-1,2,3-triazol-1-yl]acetyl}azetidin-3-yl)oxy]-3,4-dihydro-2H-1,2-benzoxaborinine-8-carboxylic acid (Example 64)

2-hydroxy-7-[(1-{[5-(hydroxymethyl)-1H-1,2,3-triazol-1-yl]acetyl}azetidin-3-yl)oxy]-3,4-dihydro-2H-1,2-benzoxaborinine-8-carboxylic acid (Example 65)

4,4-dihydroxy-8-{[1-({5-[(methylamino)methyl]-1H-1,2,3-triazol-1-yl}acetyl)azetidin-3-yl]oxy}-5-oxa-4-boranuidabicyclo[4.4.0]deca-l(6),7,9-triene-7-carboxylic acid disodium salt (Example 66)

2-hydroxy-7-({1-[(1H-1,2,3-triazol-4-yl)acetyl]azetidin-3-yl}oxy)-3,4-dihydro-2H-1,2-benzoxaborinine-8-carboxylic acid (Example 67)

8-[(1-{[4-(carboxymethyl)-1H-1,2,3-triazol-1-yl]acetyl}azetidin-3-yl)oxy]-4,4-dihydroxy-5-oxa-4-boranuidabicyclo[4.4.0]deca-l(6),7,9-triene-7-carboxylic acid trisodium salt (Example 68)

8-[(1-{[1-(carboxymethyl)-1H-1,2,3-triazol-4-yl]acetyl}azetidin-3-yl)oxy]-4,4-dihydroxy-5-oxa-4-boranuidabicyclo[4.4.0]deca-l(6),7,9-triene-7-carboxylic acid trisodium salt (Example 69)

8-({1-[amino(1H-1,2,3-triazol-4-yl)acetyl]azetidin-3-yl}oxy-4,4-dihydroxy-5-oxa-4-boranuidabicyclo[4.4.0]deca-l(6),7,9-triene-7-carboxylic acid disodium salt (Example 70)

2-hydroxy-7-({1-[(4-nitro-1H-1,2,3-triazol-1-yl)acetyl]azetidin-3-yl}oxy)-3,4-dihydro-2H-1,2-benzoxaborinine-8-carboxylic acid (Example 71)

Example 72: 7-({1-[amino(3,4-dihydroxyphenyl)acetyl]azetidin-3-yl}oxy)-2-hydroxy-3,4-dihydro-2H-1,2-benzoxaborinine-8-carboxylic acid hydrochloride

[Chemical Formula 819]

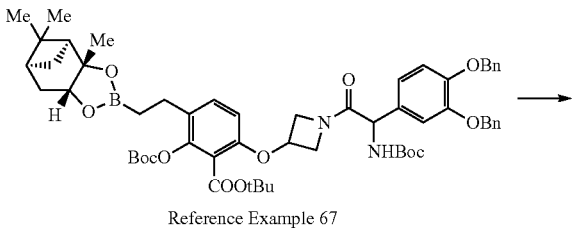

Reference Example 67

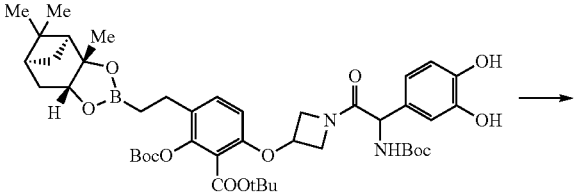

Reference Example 72-1

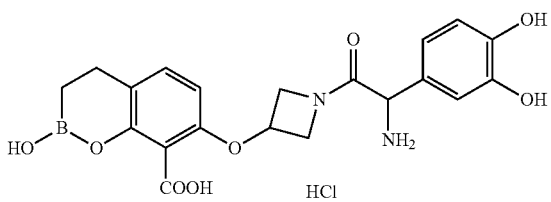

Reference Example 72

Example 72-1: tert-butyl 6-[(1-{[(tert-butoxycarbo-nyl)amino](3,4-dihydroxyphenyl)acetyl}azetidin-3-yl)oxy]-2-[(tert-butoxycarbonyl)oxy]-3-{2-[(3aS,4S,6S,7aR)-3a,5,5-trimethylhexahydro-2H-4,6-methano-1,3,2-benzodioxaborol-2-yl]ethyl}benzoate

[Chemical Formula 820]

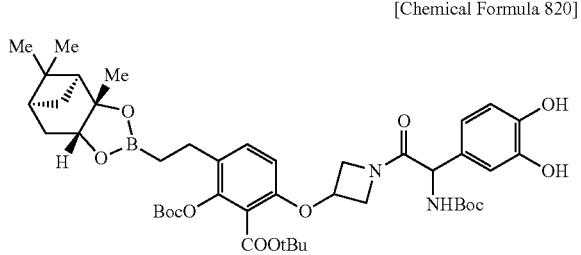

Palladium on carbon (19 mg, Pd content: 10%, wetted with ca. 55% water) was added to a methanol solution (2 mL) of the compound of Reference Example 67 (190 mg, 0.187 mmol), and the reaction mixture was stirred for 2.5 hours under a hydrogen atmosphere at room temperature. The reaction solution was filtered through cellulose. The filtered substance was washed with methanol, and the combined filtrate was concentrated to obtain the title compound (143 mg) as a colorless amorphous compound.

$^1$H-NMR (CDCl$_3$) δ: 7.19 (1H, d, J=8.1 Hz), 6.93 (1H, d, J=16.2 Hz), 6.82-6.71 (2H, m), 6.32 (1H, d, J=8.1 Hz), 5.99 (1H, br), 5.77-5.65 (1H, m), 5.08-3.80 (7H, m), 2.63-2.56 (2H, m), 2.36-2.27 (1H, m), 2.19-2.12 (1H, m), 2.04-1.99 (1H, m), 1.89-1.77 (2H, m), 1.63-1.39 (27H, m), 1.35 (3H, s), 1.28 (3H, s), 1.12-1.00 (3H, m), 0.83 (3H, s).

LCMS: [M+H]$^+$/Rt=837.7/2.83 min$^B$

Example 72: 7-({1-[amino(3,4-dihydroxyphenyl)acetyl]azetidin-3-yl}oxy)-2-hydroxy-3,4-dihydro-2H-1,2-benzoxaborinine-8-carboxylic acid hydrochloride

[Chemical Formula 821]

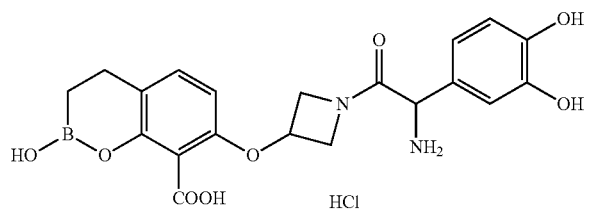

Phenylboronic acid (18.7 mg, 0.153 mmol), hexane (1.5 mL), and 4 N hydrochloric acid/dioxane solution (0.76 mL) were added to an acetonitrile solution (1.5 mL) of the compound of Example 72-1 (128 mg, 0.153 mmol), and the reaction mixture was stirred for 17 hours at room temperature. The reaction solution was allowed to stand. The supernatant (top layer) was removed, and hexane (5 mL) was added to the remaining bottom layer. After stirring and then allowing it to stand, the supernatant was removed. This was repeated 5 times. Diethyl ether (5 mL) was added to the bottom layer. After stirring and then allowing it to stand, the supernatant (top layer) was removed. This was repeated 3 times. The resulting residue was dried under reduced pressure. Since an intermediate (Boc-underprotected form of the title compound) was also found in the resulting residue, a 4 N hydrochloric acid/dioxane solution (3.0 mL) was further added. The reaction mixture was stirred for 21 hours at room temperature, and the reaction solution was concentrated. The resulting residue was dissolved in methanol (1.5 mL) and purified by reversed phase column chromatography to obtain the title compound (19.3 mg) as a light yellow solid.

$^1$H-NMR (CD$_3$OD) δ: 7.25-7.05 (1H, m), 6.91-6.79 (3H, m), 6.25-6.00 (1H, m), 5.09-4.94 (1H, m), 4.63-3.98 (3H, m), 3.76-3.53 (2H, m), 2.81-2.39 (2H, m), 1.16-0.51 (2H, m).

LCMS: [M+H]$^+$/Rt=429.2/0.96 min$^B$

Example 73: 7-({1-[amino(2,4-dihydroxyphenyl)acetyl]azetidin-3-yl}oxy)-2-hydroxy-3,4-dihydro-2H-1,2-benzoxaborinine-8-carboxylic

[Chemical Formula 822]

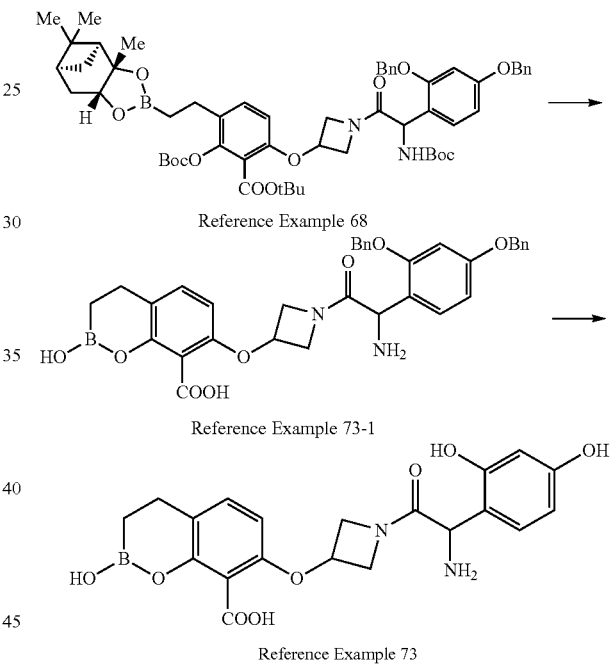

Reference Example 68

Reference Example 73-1

Reference Example 73

Example 73-1: 7-[(1-{amino[2,4-bis(benzyloxy)phenyl]acetyl}azetidin-3-yl)oxy]-2-hydroxy-3,4-dihydro-2H-1,2-benzoxaborinine-8-carboxylic Acid

[Chemical Formula 823]

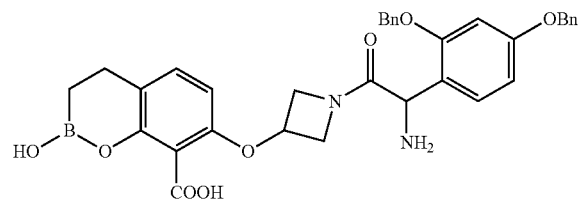

A reaction, work-up, and purification were performed using the compound of Reference Example 68 (195 mg, 0.192 mmol) as the starting material by the same method described in Example 72 to obtain the title compound (78 mg) as a colorless solid.

$^1$H-NMR (CD$_3$OD) δ: 7.45-7.26 (11H, m), 7.14-7.11 (1H, m), 6.87-6.79 (1H, m), 6.74-6.65 (1H, m), 6.16 (1H, brs), 5.25-5.04 (5H, m), 5.03-4.91 (1H, m), 4.48-3.90 (3H, m), 3.77-3.60 (1H, m), 2.73-2.64 (2H, m), 1.09-1.02 (2H, m).

LCMS: [M+H]$^+$/Rt=609.6/1.80 min$^B$

Example 73: 7-({1-[amino (2,4-dihydroxyphenyl)acetyl]azetidin-3-yl}oxy)-2-hydroxy-3,4-dihydro-2H-1,2-benzoxaborinine-8-carboxylic Acid Hydrochloride

[Chemical Formula 824]

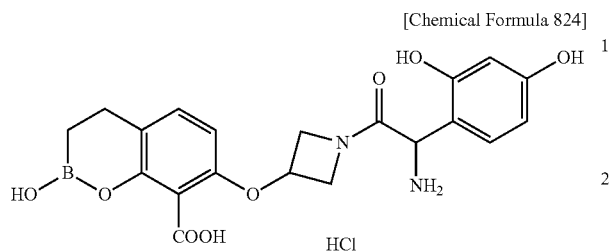

HCl

Palladium on carbon (13 mg, Pd content: 10%, wetted with ca. 55% water) was added to a THF solution (25 mL) of the compound of Example 73-1 (65.1 mg, 0.101 mmol), and the reaction mixture was stirred for 2.5 hours under a hydrogen atmosphere at room temperature. Subsequently, methanol (0.25 mL) was added, and the reaction mixture was stirred for 4 days at room temperature. Subsequently, palladium on carbon (13 mg) was added, and the reaction mixture was stirred for 1 day at room temperature. Palladium on carbon (13 mg) was further added, and the reaction mixture was stirred for 5 days at room temperature. The reaction solution was filtered through cellulose. The filtered substance was washed with methanol, and the combined filtrate was concentrated. The resulting residue was dissolved in methanol (2 mL) and purified by reversed phase column chromatography to obtain the title compound (9.0 mg) as a colorless solid.

$^1$H-NMR (CD$_3$OD) δ: 7.13-5.98 (5H, m), 5.23-5.19 (1H, m), 5.04-4.79 (1H, m), 4.51-3.47 (4H, m), 2.85-1.93 (2H, m), 1.16-0.65 (2H, m).

LCMS: [M+H]$^+$/Rt=429.2/0.94 min$^B$

Example 74: 7-{[1-(S-benzyl-D-cysteinyl)azetidin-3-yl]oxy}-2-hydroxy-3,4-dihydro-2H-1,2-benzoxaborinine 8-carboxylic Acid Trifluoroacetate

[Chemical Formula 825]

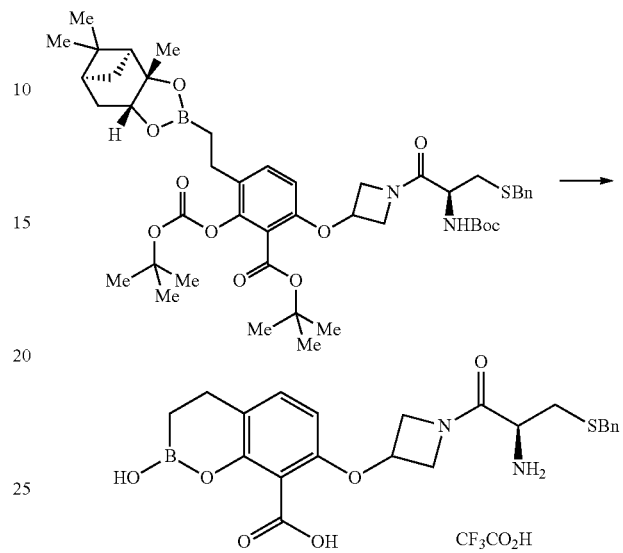

Trifluoroacetic acid (3.3 mL) was added to the compound of Reference Example 72 (106 mg), and the reaction mixture was stirred for 8 hours at room temperature. The reaction mixture was dried and solidified under reduced pressure. The resulting dried residue was purified by reversed phase column chromatography. The resulting dried residue was washed with acetonitrile, dried and solidified under reduced pressure to obtain the title compound (24.6 mg) as a white solid.

LCMS: [M+H]$^+$/Rt=865.61/1.332 min$^A$

A reaction, work-up, and purification were performed using the compounds of Reference Examples 73 and 74 as the starting materials by the same method described in Reference Example 74 to obtain the following Example compounds 75 and 76, respectively.

TABLE 3-13

| Example | Starting material | Structural formula | NMR and/or LCMS |
|---|---|---|---|
| 75 | Reference Example 73 | (structure shown) | LCMS: M + H]$^+$/Rt = 367.09/0.495 min$^C$ $^1$H-NMR (400 MHz, CD$_3$OD) δ: 7.19-7.11 (1H, m), 6.16-6.12 (1H, m), 5.07-5.02 (2H, m), 4.53-4.33 (2H, m), 4.23-4.06 (2H, m), 3.07-2.99 (1H, m), 2.89-2.82 (1H, m), 2.76-2.68 (1H, m), 2.62-2.50 (1H, m), 1.07-0.67 (2H, m). |
| 76 | Reference Example 74 | (structure shown) | LCMS: M + H]$^+$/Rt = 395.17/0.489 min$^C$ $^1$H-NMR (400 MHz, CD$_3$OD) δ: 7.19-7.12 (1H, m), 6.37-6.13 (1H, m), 5.06-5-01 (2H, m), 4-77-4.73 (1H, m), 4.52-4.39 (2H, m), 4.18-3.99 (2H, m), 2.76-2.53 (2H, m), 1.54 (3H, s), 1.46 (3H, s), 1.08-0.68 (2H, m). |

The names of the compounds of Examples 75 and 76 are described below.

7-[(1-D-cysteinylazetidin-3-yl)oxy]-2-hydroxy-3,4-dihydro-2H-1,2-benzoxaborinine-8-carboxylic acid trifluoroacetate (Example 75)

2-hydroxy-7-{[1-(3-sulfanyl-D-valyl)azetidin-3-yl]oxy}-3,4-dihydro-2H-1,2-benzoxaborinine-8-carboxylic acid trifluoroacetate (Example 76)

A reaction, work-up, and purification were performed using the compounds of Reference Examples 42, 52, 76 to 78, and 109 to 113 as the starting materials by the same method described in Example 38 to obtain the following Example compounds 77 to 86 (corresponding starting materials are not in order). However, if a free form is the final product (Example 83), the free form was obtained from purifying the compound without sodium hydroxide treatment. If hydrochloride is the final product (Examples 79, 80, 82, and 84 to 86), the hydrochloride was obtained from purifying the compound by reversed phase chromatography without sodium hydroxide treatment, followed by addition of hydrochloric acid and concentration.

TABLE 3-14

| Example | Starting material | Structural formula | NMR and/or LCMS |
|---|---|---|---|
| 77 | Reference Example 76 | | LCMS: [M + H]$^+$/Rt = 379.1/0.76 min$^B$ $^1$H-NMR (CD$_3$OD) δ: 6.71 (1H, d, J = 8.1 Hz), 5.93 (1H, d, J = 8.1 Hz), 5.00-4.93 (1H, m), 4.73-4.61 (1H, m), 4.37-4.27 (2H, m), 4.05-4.01 (1H, m), 3.79-3.71 (1H, m), 2.59-2.47 (3H, m), 2.38-2.25 (1H, m), 0.41 (2H, t, J = 8.1 Hz). |
| 78 | Reference Example 77 | | LCMS: [M + H]$^+$/Rt = 406.3/1.00 min$^B$ $^1$H-NMR (CD$_3$OD) δ: 6.73 (1H, d, J = 8.1 Hz), 5.93 (1H, d, J = 8.1 Hz), 5 05-4-95 (1H, m), 4-75-4.53 (1H, m), 4.48-4.28 (3H, m), 4.08-3.98 (1H, m), 3.66-3.42 (1H, m), 2.57 (2H, d, J = 8.1 Hz), 1.32-1.25 (6H, m), 0.45 (2H, t, J = 8.1 Hz). |
| 79 | Reference Example 42 | | LCMS: [M + H]$^+$/Rt = 378.2/0.81 min$^B$ $^1$H-NMR (CD$_3$OD) δ: 7.21-7.11 (1H, m), 6.38-6.10 (1H, m), 5.16-4.98 (1H, m), 4.78-4.64 (1H, m), 4.54-4.26 (3H, m), 4.12-4.02 (1H, m), 2.90-2.54 (4H, m), 1.10-0.64 (2H, m). |
| 80 | Reference Example 109 | | LCMS: [M + H]$^+$/Rt = 378.2/0.58 min$^B$ $^1$H-NMR (CD$_3$OD) δ: 7.18 (1H, d, J = 8.1 Hz), 6.35 (1H, d, J = 8.1 Hz), 5.17-5.07 (1H, m), 4.79-4.72 (1H, m), 4.55-4.27 (3H, m), 4.12-4.01 (1H, m), 2.92-2.64 (4H, m), 1.07 (2H, t, J = 8.1 Hz). |
| 81 | Reference Example 78 | | LCMS: [M + H]$^+$/Rt = 379.1/0.56 min$^B$ $^1$H-NMR (CD$_3$OD) δ: 6.72 (1H, d, J = 8.1 Hz), 5.94 (1H, d, J = 8.1 Hz), 5.00-4.92 (1H, m), 4.73-4.61 (1H, m), 4.37-4.27 (2H, m), 4.06-4.00 (1H, m), 3.80-3.72 (1H, m), 2.59-2.47 (3H, m), 2.39-2.26 (1H, m), 0.44 (2H, t, J = 8.1 Hz). |
| 82 | Reference Example 52 | | LCMS: [M + H]$^+$/Rt = 351.0/0.48 min$^B$ $^1$H-NMR (CD$_3$OD) δ: 7.17 (1H, d, J = 8.2 Hz), 6.35 (1H, d, J = 8.1 Hz), 5.18-5.09 (1H, m), 4.79-4.70 (1H, m), 4.55-4.33 (2H, m), 4.12-4.02 (2H, m), 3.92-3.84 (1H, m), 3.80-3.73 (1H, m), 2.70 (2H, t, J = 8.1 Hz), 1.06 (2H, t, J = 8.1 Hz). |

TABLE 3-15

| 83 | Reference Example 110 | [structure] | LCMS: [M + H]⁺/Rt = 363.0/0.97 min$^B$<br>$^1$H-NMR (CD$_3$OD) δ: 7.18-7.09 (1H, m), 6.33-6.09 (1H, m), 5.10-5.02 (1H, m), 4.67-4.62 (1H, m), 4.40-4.34 (1H, m), 4.28-4.23 (1H, m), 3.99-3.94 (1H, m), 2.72-2.38 (6H, m), 1.09-0.91 (2H, m). |
|---|---|---|---|
| 84 | Reference Example 111 | [structure] | LCMS: [M + H]⁺/Rt = 392.1/0.79 min$^B$<br>$^1$H-NMR (CD$_3$OD) δ: 7.17 (1H, d, J = 8.2 Hz), 6.40-6.30 (1H, m), 5.17-5.08 (1H, m), 4.77-4.71 (1H, m), 4.54-4.31 (2H, m), 4.14-4.02 (2H, m), 2.70 (2H, t, J = 8.1 Hz), 2.48-2.42 (2H, m), 2.15-2.00 (2H, m), 1.06 (2H, t, J = 8.1 Hz). |
| 85 | Reference Example 113 | [structure] | LCMS: [M + H]⁺/Rt = 393.1/0.47 min$^B$<br>$^1$H-NMR (CD$_3$OD) δ: 7.17 (1H, d, J = 8.2 Hz), 6.35 (1H, d, J = 8.2 Hz), 5.17-5.08 (1H, m), 4.81-4.72 (1H, m), 4.55-4.30 (2H, m), 4.17-4.03 (2H, m), 3.60-3.40 (2H, m), 2.70 (2H, t, J = 8.1 Hz), 1.06 (2H, t, J = 8.1 Hz). |
| 86 | Reference Example 112 | [structure] | LCMS: [M + H]⁺/Rt = 392.1/0.86 min$^B$<br>$^1$H-NMR (CD$_3$OD) δ: 7.18 (1H, d, J = 8.2 Hz), 6.39-6.30 (1H, m), 5.18-5.09 (1H, m), 4.80-4.72 (1H, m), 4.55-4.32 (2H, m), 4.21-4.03 (2H, m), 3.60-3.42 (2H, m), 2.70 (2H, t, J = 8.1 Hz), 2.01-1.98 (3H, m), 1.06 (2H, t, J = 8.1 Hz). |

The names of the compounds of Examples 77 to 86 are described below.

8-({1-[(2S)-2-amino-3-carboxypropanoyl]azetidin-3-yl}oxy)-4,4-dihydroxy-5-oxa-4-boranuidabicyclo[4.4.0]deca-l(6),7,9-triene-7-carboxylic acid trisodium salt (Example 77)

8-{[1-(D-alanyl-D-alanyl)azetidin-3-yl]oxy}-4,4-dihydroxy-5-oxa-4-boranuidabicyclo[4.4.0]deca-l(6),7,9-triene-7-carboxylic acid disodium salt (Example 78)

7-[(1-L-asparaginylazetidin-3-yl)oxy]-2-hydroxy-3,4-dihydro-2H-1,2-benzoxaborinine-8-carboxylic acid hydrochloride (Example 79)

7-[(1-D-asparaginylazetidin-3-yl)oxy]-2-hydroxy-3,4-dihydro-2H-1,2-benzoxaborinine-8-carboxylic acid hydrochloride (Example 80)

8-({1-[(2R)-2-amino-3-carboxypropanoyl]azetidin-3-yl}oxy)-4,4-dihydroxy-5-oxa-4-boranuidabicyclo[4.4.0]deca-l(6),7,9-triene-7-carboxylic acid trisodium salt (Example 81)

2-hydroxy-7-[(1-D-serylazetidin-3-yl)oxy]-3,4-dihydro-2H-1,2-benzoxaborinine-8-carboxylic acid hydrochloride (Example 82)

7-{[1-(4-amino-4-oxobutanoyl)azetidin-3-yl]oxy}-2-hydroxy-3,4-dihydro-2H-1,2-benzoxaborinine-8-carboxylic acid (Example 83)

7-[(1-D-glutaminylazetidin-3-yl)oxy]-2-hydroxy-3,4-dihydro-2H-1,2-benzoxaborinine-8-carboxylic acid hydrochloride (Example 84)

7-({1-[3-(carbamoylamino)-D-alanyl]azetidin-3-yl}oxy)-2-hydroxy-3,4-dihydro-2H-1,2-benzoxaborinine-8-carboxylic acid hydrochloride (Example 85)

1-(3-acetamido-D-alanyl)azetidin-3-yl]oxy}-2-hydroxy-3,4-dihydro-2H-1,2-benzoxaborinine-8-carboxylic acid hydrochloride (Example 86)

The following Example compounds 87 to 89 (corresponding starting materials are not in order) were obtained by performing a reaction and work-up using the compounds of Reference Examples 53, 54, and 75 as the starting materials by the same method described in Example 4, and purifying the compounds by reversed phase chromatography without sodium hydroxide treatment, followed by addition of hydrochloric acid and concentration.

TABLE 3-16

| Example | Starting material | Structural formula | NMR and/or LCMS |
|---|---|---|---|
| 87 | Reference Example 54 | 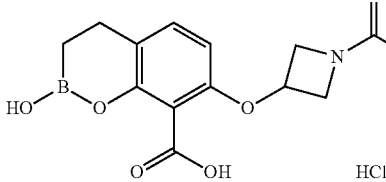 | LCMS: [M + H]+/Rt = 406.36/1.38 min$^D$<br>$^1$H-NMR (CD$_3$OD) δ: 7.22-7.12 (1H, m), 6.41-6.28 (1H, m), 5.17-5.07 (1H, m), 4.83-4.68 (1H, m), 4.54-4.24 (3H, m), 4.13-4.00 (1H, m), 3.11-2.77 (8H, m), 2.75-2.64 (21-I, m), 1.10-1.00 (2H, m). |
| 88 | Reference Example 53 | 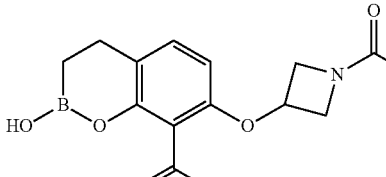 | LCMS: [M + H]+/Rt = 392.19/1.43 min$^D$<br>$^1$H-NMR (CD$_3$OD) δ: 7-24-7.10 (1H, m), 6.46-6.23 (1H, m), 5.18-5.09 (1H, m), 4.79-4.68 (1H, m), 4.57-4.27 (3H, m), 4.22-3.98 (1H, m), 2.85-2.61 (7H, m), 1.10-1.03 (2H, m). |
| 89 | Reference Example 75 | 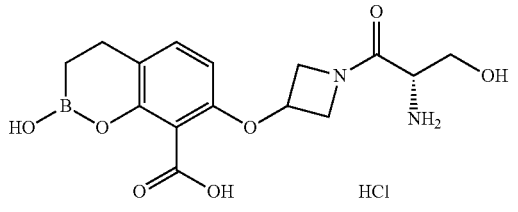 [SMILES: N[C@@H](CO)C(=O)N1CC(Oc2ccc3c(c2C(=O)O)OB(O)CC3)C1 ; Cl] | LCMS: [M + H]+/Rt = 351.21/0.97 min$^D$<br>$^1$H-NMR (CD$_3$OD) δ: 7.20-7.14 (1H, m), 6.40-6.28 (1H, m), 5.17-5.09 (1H, m), 4.78-4.70 (1H, m), 4.56-4.41 (1H, m), 4.39-4.32 (1H, m), 4.14-4.02 (2H, m), 3.92-3.85 (1H, m), 3.81-3.74 (1H, m), 2.75-2.65 (2H, m), 1.12-1.03 (2H, m). |

The names of the compounds of Examples 87 to 89 are described below.

7-{[1-(N,N-dimethyl-D-asparaginyl)azetidin-3-yl]oxy}-2-hydroxy-3,4-dihydro-2H-1,2-benzoxaborinine-8-carboxylic acid hydrochloride (Example 87)

2-hydroxy-7-{[1-(N-methyl-D-asparaginyl)azetidin-3-yl]oxy}-3,4-dihydro-2H-1,2-benzoxaborinine-8-carboxylic acid hydrochloride (Example 88)

2-hydroxy-7-[(1-L-serylazetidin-3-yl)oxy]-3,4-dihydro-2H-1,2-benzoxaborine-8-carboxylic acid hydrochloride Example 89

A reaction, work-up, and purification were performed using the compounds of Reference Examples 60, 62, 79 to 81, 124, and 125 as the starting materials by the same method described in Example 37 to obtain the following Example compounds 90 to 96 (corresponding starting materials are not in order). However, if a free form is the final product (Example 91), the free form was obtained from purifying the compound without sodium hydroxide treatment. If hydrochloride is the final product (Examples 90, 92, and 93), the hydrochloride was obtained from purifying the compound by reversed phase chromatography without sodium hydroxide treatment, followed by addition of hydrochloric acid and concentration.

TABLE 3-17

| Example | Starting material | Structural formula | NMR and/or LCMS |
|---|---|---|---|
| 90 | Reference Example 79 | 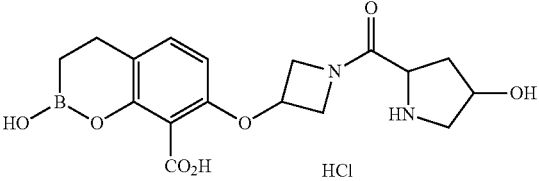 [SMILES: O=C(O)c1c(OC2CN(C(=O)C3CC(O)CN3)C2)ccc2c1OB(O)CC2 ; Cl] | LCMS: [M + H]+/Rt = 377.4/0.425 min$^C$<br>$^1$H-NMR (CD$_3$OD) δ: 7.16 (1H, d, J = 8.5 Hz), 6.34 (1H, d, J = 8.5 Hz), 5.15 (1H, s), 4.72-4.66 (1H, m), 4.54-4.48 (4H, m), 4.32-4.25 (1H, m), 4.13-4.05 (1H, m), 3.39-3.33 (1H, m), 2.72-2.67 (2H, m), 2.61-2.57 (1H, m), 2.09-2.05 (1H, m), 1.03-1.00 (2H, m). |

TABLE 3-17-continued

| Example | Starting material | Structural formula | NMR and/or LCMS |
|---|---|---|---|
| 91 | Reference Example 80 | | LCMS: [M + H]+/Rt = 429.1/0.537 min$^C$<br>$^1$H-NMR (CD$_3$OD) δ: 7.19-7.17 (1H, m), 636-6.33 (1H, m), 5.22-5-11 (2H, m), 4.58-4.50 (2H, m), 4.36-4.33 (1H, m), 4.13-4.11 (1H, m), 3.68-3.66 (1H, m), 3.52-3.50 (2H, m), 2.84-2.81 (1H, m), 2.70 (2H, t, J = 7.9 Hz), 2.11-2.09 (1H, m), 1.06 (2H, t, J = 7.6 Hz). |
| 92 | Reference Example 81 | | LCMS: [M + H]+/Rt = 379.09/0.453 min$^C$ |
| 93 | Reference Example 60 | | LCMS: [M + H]+/Rt = 375.01/0.304 min$^A$<br>$^1$H-NMR (CD$_3$OD) δ: 7.16 (1H, d, J = 7.3 Hz), 6.35-6.33 (1H, m), 5.08-5.06 (1H, m), 4.62-4.59 (1H, m), 4.39-4.37 (1H, m), 4.22 (1H, d, J = 9.8 Hz), 3.97 (1H, d, J = 11.0 Hz), 3.52 (1H, t, J = 9.8 Hz), 3.38-3.35 (1H, m), 3.25-3.23 (1H, m), 2.93 (1H, t, J = 10.4 Hz), 2.70-2.68 (3H, m), 2.48-2.45 (1H, m), 2.39-2.35 (1H, m), 2.26-2.24 (1H, m), 1.73-1.68 (1H, m), 1.07 (2H, t, J = 7.9 Hz). |
| 94 | Reference Example 124 | | LCMS: [M + H]+/Rt = 466.23/0.486 min$^C$<br>$^1$H-NMR (D$_2$O) δ: 6.51 (1H, d, J = 8.5 Hz), 5.67 (1H, dd, J = 8.5, 2.7 Hz), 4.64-4.59 (1H, m), 4.22-4.16 (1H, m), 4.00-3.84 (3H, m), 3.65 (1H, dd, J = 10.7, 3.4 Hz), 2.87-2.82 (1H, m), 2.68 (3H, d, J = 3.1 Hz), 2.57 (3H, d, J = 8.5 Hz), 2.49-2.44 (1H, m), 2.23-2.14 (4H, m), 1.99-1.90 (2H, m), 1.07-1.03 (1H, m), 0.00 (2H, t, J = 7.0 Hz). |

TABLE 3-18

| 95 | Reference Example 125 | | LCMS: [M + H]$^+$/Rt = 466.28/0.482 min$^C$<br>$^1$H-NMR (D$_2$O) δ: 6.51 (1H, d, J = 7.9 Hz), 5.67 (1H, dd, J = 7.9, 2.4 Hz), 4.64-4.59 (1H, m), 4.19 (1H, dd, J = 15.9, 9.2 Hz), 4.00-3.84 (3H, m), 3.64 (1H, dd, J = 11.0, 3.4 Hz), 2.90-2.85 (1H, m), 2.68 (3H, d, J = 3.7 Hz), 2.57 (3H, d, J = 7.9 Hz), 2.52-2.46 (1H, m), 2.23-2.17 (4H, m), 1.98-1.92 (2H, m), 1.07 (1H, dd, J = 8.9, 4.0 Hz), 0.00 (2H, t, J = 7.0 Hz). |

TABLE 3-18-continued

| | | Structural formula | NMR and/or LCMS |
|---|---|---|---|
| 96 | Reference Example 62 | 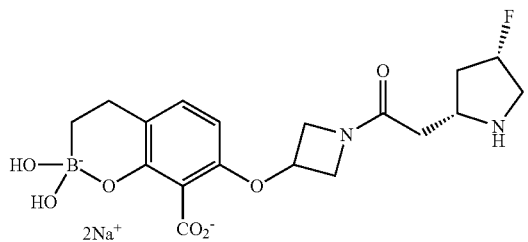 | LCMS: [M + H]$^+$/Rt = 393.10/0.477 min$^C$ $^1$H-NMR (D$_2$O) δ: 6.49 (1H, d, J = 7.9 Hz), 5.67 (1H, d, J = 7.9 Hz), 4.98 (1H, dq, J = 53.1, 4.3 Hz), 4.64-4.58 (1H, m), 4.42-4.39 (1H, m), 4.20-4.15 (1H, m), 3.97 (1H, dd, J = 10.4, 6.1 Hz), 3.88 (1H, dd, J = 10.4, 3.7 Hz), 3.64 (1H, dd, J = 11.0, 3.1 Hz), 3.41-3.31 (1H, m), 3.07 (1H, dt, J = 20.0, 13.0 Hz), 2.84-2.67 (1H, m), 2.29-2.22 (1H, m), 2.18 (2H, t, J = 7.0 Hz), 2.15-2.02 (1H, m), 1.59-1.47 (1H, m), 0.00 (2H, t, J = 7.0 Hz). |

The names of the compounds of Examples 90 to 96 are described below.

2-hydroxy-7-{[1-(4-hydroxyprolyl)azetidin-3-yl]oxy}-3,4-dihydro-2H-1,2-benzoxaborinine-8-carboxylic acid hydrochloride (Example 90)

2-hydroxy-7-({1-[(4R)-4-(trifluoromethyl)-D-prolyl]azetidin-3-yl}oxy)-3,4-dihydro-2H-1,2-benzoxaborinine-8-carboxylic acid (Example 91)

7-({1-[(4S)-4-fluoro-L-prolyl]azetidin-3-yl}oxy)-2-hydroxy-3,4-dihydro-2H-1,2-benzoxaborinine-8-carboxylic acid hydrochloride (Example 92)

2-hydroxy-7-({1-[(pyrrolidin-3-yl)acetyl]azetidin-3-yl}oxy)-3,4-dihydro-2H-1,2-benzoxaborinine-8-carboxylic acid hydrochloride (Example 93)

8-[(1-{[(3R,5S)-5-(dimethylcarbamoyl)pyrrolidin-3-yl]acetyl}azetidin-3-yl)oxy]-4,4-dihydroxy-5-oxa-4-boranuidabicyclo[4.4.0]deca-l(6),7,9-triene-7-carboxylic acid disodium salt (Example 94)

8-[(1-{[(3S,5R)-5-(dimethylcarbamoyl)pyrrolidin-3-yl]acetyl}azetidin-3-yl)oxy]-4,4-dihydroxy-5-oxa-4-boranuidabicyclo[4.4.0]deca-l(6),7,9-triene-7-carboxylic acid disodium salt (Example 95)

8-[(1-{[(2R,4S)-4-fluoropyrrolidin-2-yl]acetyl}azetidin-3-yl)oxy]-4,4-dihydroxy-5-oxa-4-boranuidabicyclo[4.4.0]deca-l(6),7,9-triene-7-carboxylic acid disodium salt (Example 96)

A reaction, work-up, and purification were performed using the compounds of Reference Examples 82 to 105 and 117 to 123 as the starting materials by the same method described in Example 38 to obtain the following Example compounds 97 to 127 (corresponding starting materials are not in order). However, if hydrochloride is the final product (Examples 119, 120, and 123), the hydrochloride was obtained from purifying the compound by reversed phase chromatography without sodium hydroxide treatment, followed by addition of hydrochloric acid and concentration.

TABLE 3-19

| Example | Starting material | Structural formula | NMR and/or LCMS |
|---|---|---|---|
| 97 | Reference Example 82 | | LCMS: [M + H]$^+$/Rt = 397.3/1.08 min$^B$ $^1$H-NMR (CD$_3$OD) δ: 7.63 (1H, d, J = 8.1 Hz), 5.95 (1H, d, J = 8.1 Hz), 5.03-4.95 (1H, m), 4.64-4.52 (1H, m), 4.39-4.25 (2H, m), 4.09-3.95 (2H, m), 3.37-3.01 (2H, m), 2.62-2.20 (4H, m), 0.46 (2H, t, J = 8.1 Hz). |
| 98 | Reference Example 117 | | LCMS: [M + H]$^+$/Rt = 377.2/0.65 min$^B$ $^1$H-NMR (CD$_3$OD) δ: 6.73 (1H, d, J = 8.1 Hz), 5.94 (1H, d, J = 8.1 Hz), 5.02-4.92 (1H, m), 4.62-4.52 (1H, m), 4.42-4.22 (3H, m), 4.08-4.00 (1H, m), 3.92-3.86 (1H, m), 3.22-3.16 (1H, m), 2.80-2.75 (1H, m), 2.57 (2H, t, J = 8.1 Hz), 2.10-2.01 (1H, m), 1.89-1.76 (1H, m), 0.45 (2H, t, J = 8.1 Hz). |
| 99 | Reference Example 83 | | LCMS: [M + H]$^+$/Rt = 389.3/0.91 min$^B$ $^1$H-NMR (CD$_3$OD) δ: 6.70 (1H, d, J = 8.1 Hz), 5.93 (1H, d, J = 8.1 Hz), 4.99-4.89 (1H, m), 4.54-4.48 (1H, m), 4.33-4.19 (2H, m), 4.02-3.97 (1H, m), 3.00-2.95 (2H, m), 2.63-2.53 (4H, m), 2.19 (2H, d, J = 8.1 Hz), 1.99-1.81 (1H, m), 1.73-1.65 (2H, m), 1.33-1.14 (2H, m), 0.43 (2H, t, J = 8.1 Hz). |

TABLE 3-19-continued

| Example | Starting material | Structural formula | NMR and/or LCMS |
|---|---|---|---|
| 100 | Reference Example 84 | 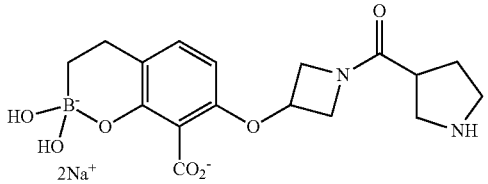 | LCMS: [M + H]⁺/Rt = 361.2/0.93 min$^B$<br>$^1$H-NMR (CD$_3$OD) δ: 6.70 (1H, d, J = 8.1 Hz), 5.93 (1H, d, J = 8.1 Hz), 5.00-4.92 (1H, m), 4.58-4.52 (1H, m), 4.32-4.25 (2H, m), 4.02-3.97 (1H, m), 3.09-2.76 (5H, m), 2.56 (2H, d, J = 8.1 Hz), 2.03-1.85 (2H, m), 0.43 (2H, t, J = 8.1 Hz). |

TABLE 3-20

| 101 | Reference Example 118 | 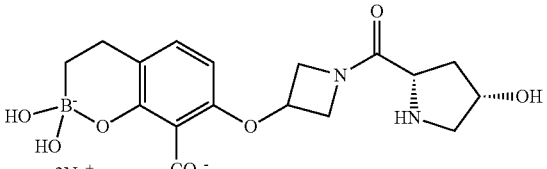 | LCMS: [M + H]⁺/Rt = 377.2/0.54 min$^B$<br>$^1$H-NMR (CD$_3$OD) δ: 6.72 (1H, d, J = 8.1 Hz), 5.94 (1H, d, J = 8.1 Hz), 5.04-4.94 (1H, m), 4.60-4.49 (1H, m), 4.40-4.24 (3H, m), 4.10-4.01 (1H, m), 3.72-3.66 (1H, m), 3.01-2.97 (1H, m), 2.81-2.75 (1H, m), 2.56 (2H, d, J = 8.1 Hz), 2.40-2.26 (1H, m), 1.76-1.67 (1H, m), 0.44 (2H, t, J = 8.1 Hz). |
| 102 | Reference Example 120 | 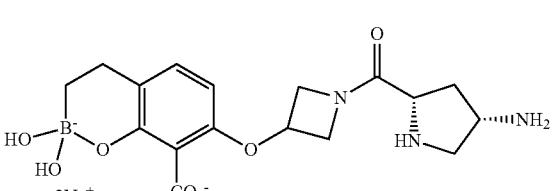 | LCMS: [M + H]⁺/Rt = 376.2/0.31 min$^B$<br>$^1$H-NMR (CD$_3$OD) δ: 6.73 (1H, d, J = 8.1 Hz), 5.95 (1H, d, J = 8.1 Hz), 5.02-4.94 (1H, m), 4.61-4.49 (1H, m), 4.38-4.21 (2H, m), 4.09-4.00 (1H, m), 3.75-3.61 (1H, m), 3.49-3.29 (1H, m), 3.00-2.78 (1H, m), 2.56 (2H, d, J = 8.1 Hz), 2.41-2.18 (1H, m), 1.64-1.29 (2H, m), 0.45 (2H, t, J = 8.1 Hz). |
| 103 | Reference Example 121 | 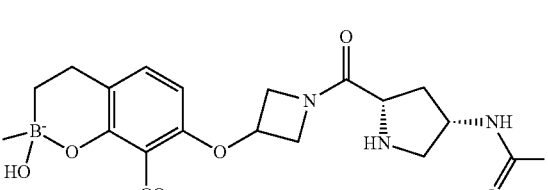 | LCMS: [M + H]⁺/Rt = 418.3/0.74 min$^B$<br>$^1$H-NMR (CD$_3$OD) δ: 6.77 (1H, d, J = 8.1 Hz), 5.97 (1H, d, J = 8.1 Hz), 5.02-4.96 (1H, m), 4.62-4.52 (1H, m), 4.40-4.23 (3H, m), 4.10-4.03 (1H, m), 3.76-3.72 (1H, m), 3.02-2.86 (2H, m), 2.57 (2H, d, J = 8.1 Hz), 2.48-2.35 (1H, m), 1.92 (3H, s), 1.75-1.63 (1H, m), 0.54-0.45 (2H, m). |
| 104 | Reference Example 119 | 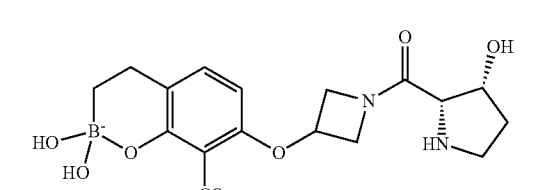 | LCMS: [M + H]⁺/Rt = 377.2/0.55 min$^B$<br>$^1$H-NMR (CD$_3$OD) δ: 6.76 (1H, d, J = 8.1 Hz), 5.98 (1H, d, J = 8.1 Hz), 5.03-4.97 (1H, m), 4.62-4.49 (2H, m), 4.39-4.22 (2H, m), 4.11-4.05 (1H, m), 3.69-3.65 (1H, m), 3.35-3.19 (1H, m), 2.89-2.80 (1H, m), 2.57 (2H, d, J = 8.1 Hz), 2.11-1.80 (2H, m), 0.50-0.42 (2H, m). |
| 105 | Reference Example 85 | 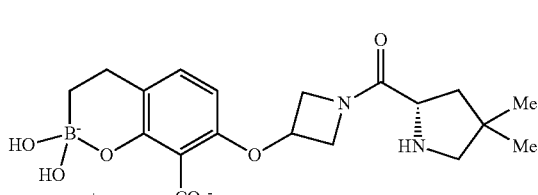 | LCMS: [M + H]⁺/Rt = 389.3/1.18 min$^B$<br>$^1$H-NMR (CD$_3$OD) δ: 6.72 (1H, d, J = 8.1 Hz), 5.93 (1H, d, J = 8.1 Hz), 5.02-4.96 (1H, m), 4.59-4.47 (1H, m), 4.39-4.20 (2H, m), 4.08-4.00 (1H, m), 3.83-3.77 (1H, m), 2.80-2.54 (4H, m), 2.00-1.88 (1H, m), 1.59-1.50 (1H, m), 1.09 (3H, s), 1.06 (3H, s), 0.44 (2H, t, J = 8.1 Hz). |
| 106 | Reference Example 86 | 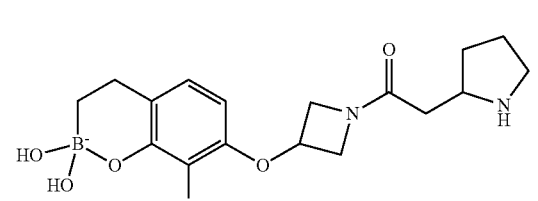 | LCMS: [M + H]⁺/Rt = 375.2/0.99 min$^B$<br>$^1$H-NMR (CD$_3$OD) δ: 6.70 (1H, d, J = 8.1 Hz), 5.92 (1H, d, J = 8.1 Hz), 4.98-4.91 (1H, m), 4.53-4.47 (1H, m), 4.33-4.19 (2H, m), 4.03-3.96 (1H, m), 3.37-3.33 (1H, m), 3.08-2.80 (2H, m), 2.56 (2H, t, J = 8.1 Hz), 2.35-2.30 (1H, m), 2.06-1.90 (1H, m), 1.85-1.72 (2H, m), 1.43-1.29 (1H, m), 0.42 (2H, t, J = 8.1 Hz). |

TABLE 3-21

| 107 | Reference Example 87 | 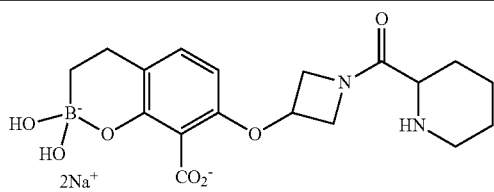 | LCMS: [M + H]⁺/Rt = 375.3/0.96 min$^B$<br>$^1$H-NMR (CD$_3$OD) δ: 6.70 (1H, d, J = 8.1 Hz), 5.93 (1H, d, J = 8.1 Hz), 5.00-4.92 (1H, m), 4.63-4.52 (1H, m), 4.36-4.22 (2H, m), 4.06-3.96 (1H, m), 3.09-3.02 (1H, m), 2.66-2.53 (3H, m), 1.94-1.75 (2H, m), 1.63-1.27 (5H, m), 0.43 (2H, t, J = 8.1 Hz). |
| --- | --- | --- | --- |
| 108 | Reference Example 88 | 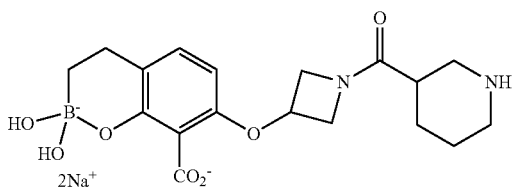 | LCMS: [M + H]⁺/Rt = 375.3/0.99 min$^B$<br>$^1$H-NMR (CD$_3$OD) δ: 6.70 (1H, d, J = 8.1 Hz), 5.93 (1H, d, J = 8.1 Hz), 4.99-4.92 (1H, m), 4.60-4.53 (1H, m), 4.31-4.25 (2H, m), 4.01-3.95 (1H, m), 2.95 (2H, t, J = 8.1 Hz), 2.66-2.39 (5H, m), 1.88-1.43 (4H, m), 0.43 (2H, t, J = 8.1 Hz). |
| 109 | Reference Example 89 | 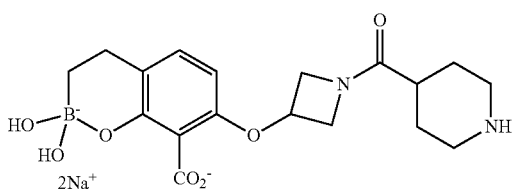 | LCMS: [M + H]⁺/Rt = 375.3/0.95 min$^B$<br>$^1$H-NMR (CD$_3$OD) δ: 6.70 (1H, d, J = 8.1 Hz), 5.93 (1H, d, J = 8.1 Hz), 4.99-4.90 (1H, m), 4.58-4.53 (1H, m), 4.31-4.25 (2H, m), 4.01-3.96 (1H, m), 3.08-2.99 (2H, m), 2.66-2.40 (5H, m), 1.71-1.51 (4H, m), 0.43 (2H, t, J = 8.1 Hz). |
| 110 | Reference Example 90 | 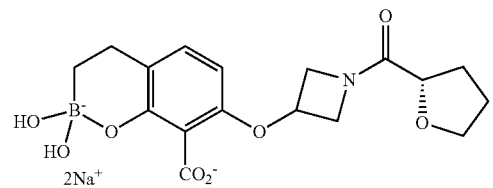 | LCMS: [M + H]⁺/Rt = 362.2/1.31 min$^B$<br>$^1$H-NMR (CD$_3$OD) δ: 6.63 (1H, d, J = 8.1 Hz), 5.84 (1H, d, J = 8.1 Hz), 4.91-4.83 (1H, m), 4.62-4.52 (1H, m), 4.35-4.21 (3H, m), 3.97-3.68 (3H, m), 2.47 (2H, t, J = 8.1 Hz), 2.19-2.01 (1H, m), 1.96-1.71 (3H, m), 0.41-0.31 (2H, m). |
| 111 | Reference Example 91 | 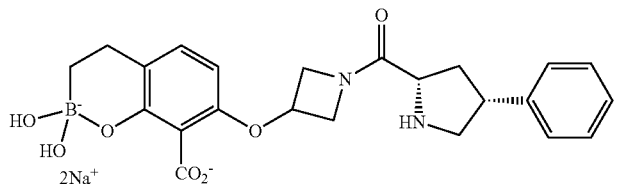 | LCMS: [M + H]⁺/Rt = 437.0/1.34 min$^B$<br>$^1$H-NMR (CD$_3$OD) δ: 7.31-7.26 (4H, m), 7.21-7.15 (1H, m), 6.70 (1H, d, J = 8.1 Hz), 5.93 (1H, d, J = 8.1 Hz), 5.05-4.94 (1H, m), 4.65-4.54 (1H, m), 4.42-4.26 (2H, m), 4.11-4.03 (1H, m), 3.89 (1H, t, J = 8.1 Hz), 3.77-3.65 (1H, m), 3.39-3.20 (1H, m), 3.07-2.96 (1H, m), 2.85-2.53 (3H, m), 1.94-1.77 (1H, m), 0.42 (2H, t, J = 8.1 Hz). |
| 112 | Reference Example 92 | 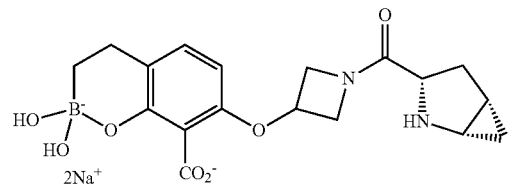 | LCMS: [M + H]⁺/Rt = 373.3/0.96 min$^B$<br>$^1$H-NMR (CD$_3$OD) δ: 6.70 (1H, d, J = 8.1 Hz), 5.91 (1H, d, J = 8.1 Hz), 5.00-4.91 (1H, m), 4.54-4.46 (1H, m), 4.36-4.26 (2H, m), 4.05-3.99 (2H, m), 2.77-2.71 (1H, m), 2.58-2.39 (3H, m), 1.95-1.87 (1H, m), 1.52-1.43 (1H, m), 0.63-0.55 (1H, m), 0.48-0.38 (3H, m). |

TABLE 3-22

| 113 | Reference Example 93 | 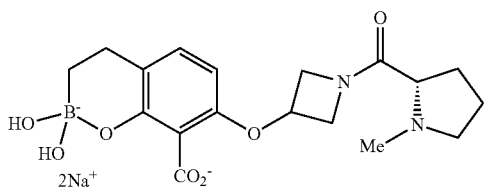 | LCMS: [M + H]⁺/Rt = 375.2/0.85 min$^B$<br>$^1$H-NMR (CD$_3$OD) δ: 6.70 (1H, d, J = 8.1 Hz), 5.92 (1H, d, J = 8.1 Hz), 5.00-4.92 (1H, m), 4.65-4.55 (1H, m), 4.38-4.26 (2H, m), 4.07-3.99 (1H, m), 3.08-3.02 (1H, m), 2.95-2.88 (1H, m), 2.56 (2H, t, J = 8.1 Hz), 2.30-2.10 (5H, m), 1.88-1.79 (3H, m), 0.43 (2H, t, J = 8.1 Hz). |
| --- | --- | --- | --- |

TABLE 3-22-continued

| 114 | Reference Example 94 | 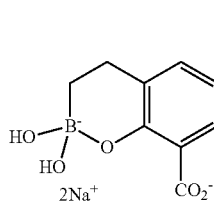 | LCMS: [M + H]+/Rt = 389.3/0.95 min[B]<br>1H-NMR (CD3OD) δ: 6.72 (1H, d, J = 8.1 Hz), 5.97-5.93 (1H, m), 4.96-4.86 (1H, m), 4.63-4.57 (1H, m), 4.31-4.20 (2H, m), 4.02-3.96 (1H, m), 3.00-2.84 (2H, m), 2.62-2.50 (3H, m), 2.35-2.23 (1H, m), 2.09-1.96 (3H, m), 1.89-1.80 (1H, m), 1.74-1.54 (2H, m), 1.26-1.10 (1H, m), 0.43 (2H, t, J = 8.1 Hz). |
| --- | --- | --- | --- |
| 115 | Reference Example 95 | 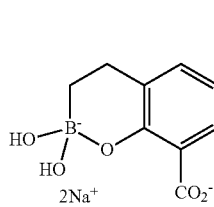 | LCMS: [M + H]+/Rt = 391.3/0.9 min[B]<br>1H-NMR (CD3OD) δ: 6.72 (1H, d, J = 8.1 Hz), 5.93 (1H, d, J = 8.1 Hz), 5.00-4.80 (1H, m), 4.58-4.49 (1H, m), 4.33-4.21 (2H, m), 4.02-3.98 (1H, m), 3.90-3.76 (2H, m), 3.64-3.51 (1H, m), 2.95-2.47 (6H, m), 2.37-2.29 (1H, m), 2.22-2.12 (1H, m), 0.44 (2H, t, J = 8.1 Hz). |
| 116 | Reference Example 96 | 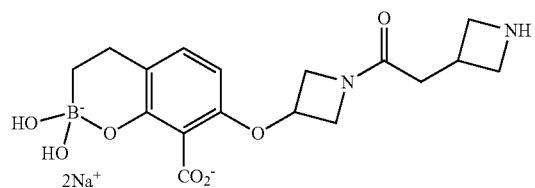 | LCMS: [M + H]+/Rt = 361.2/0.84 min[B]<br>1H-NMR (CD3OD) δ: 6.72 (1H, d, J = 8.1 Hz), 5.94 (1H, d, J = 8.1 Hz), 5.16-5.03 (1H, m), 4.56-4.50 (2H, m), 4.37-4.26 (2H, m), 3.78-3.65 (1H, m), 3.57-3.44 (3H, m), 2.89-2.68 (2H, m), 2.61-2.53 (3H, m), 0.43 (2H, t, J = 8.1 Hz). |
| 117 | Reference Example 97 | 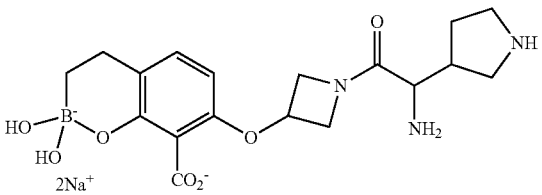 | LCMS: [M + H]+/Rt = 390.3/0.34 min[B]<br>1H-NMR (CD3OD) δ: 6.70 (1H, d, J = 8.1 Hz), 5.95-5.91 (1H, m), 5.10-4.97 (1H, m), 4.44-3.61 (4H, m), 3.35-1.52 (10H, m), 0.43 (2H, t, J = 8.1 Hz). |
| 118 | Reference Example 98 | 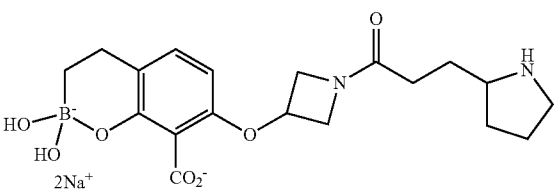 | LCMS: [M + H]+/Rt = 389.3/0.98 min[B]<br>1H-NMR (CD3OD) δ: 6.80-6.73 (1H, m), 5.98-5.91 (1H, m), 5.00-4.76 (1H, m), 4.35-3.79 (4H, m), 3.22-3.00 (3H, m), 2.65-2.51 (2H, m), 2.33-1.29 (8H, m), 0.55-0.28 (2H, m). |
| 119 | Reference Example 122 | 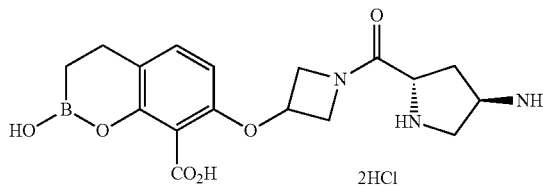 | LCMS: [M + H]+/Rt = 376.2/0.41 min[B]<br>1H-NMR (CD3OD) δ: 7.18 (1H, d, J = 8.1 Hz), 6.41-6.30 (1H, m), 5.22-5.10 (1H, m), 4.89-4.69 (2H, m), 4.57-4.26 (2H, m), 4.20-4.05 (2H, m), 3.93-3.86 (1H, m), 3.57-3.47 (1H, m), 2.70 (2H, t, J = 8.1 Hz), 2.64-2.45 (2H, m), 1.07 (2H, t, J = 8.1 Hz). |

TABLE 3-23

| 120 | Reference Example 123 | 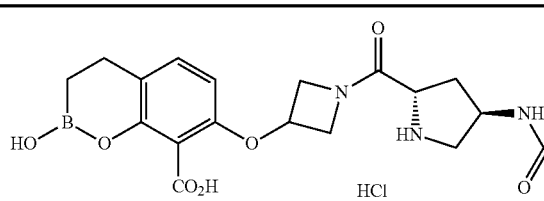 | LCMS: [M + H]+/Rt = 418.2/0.89 min[B]<br>1H-NMR (CD3OD) δ: 7.18 (1H, d, J = 8.1 Hz), 6.41-6.30 (1H, m), 5.20-5.12 (1H, m), 4.77-4.26 (5H, m), 4.14-4.05 (1H, m), 3.67-3.60 (1H, m), 3.36-3.30 (1H, m), 2.71 (2H, t, J = 8.1 Hz), 2.48-2.21 (2H, m), 1.98 (3H, s), 1.07 (2H, t, J = 8.1 Hz). |
| --- | --- | --- | --- |

TABLE 3-23-continued

| 121 | Reference Example 99 | 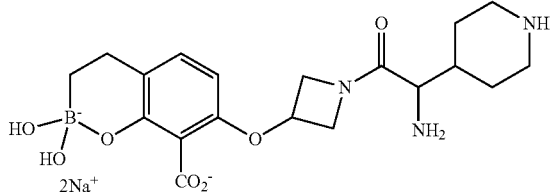 | LCMS: [M + H]⁺/Rt = 404.3/0.34 min^B<br>¹H-NMR (CD₃OD) δ: 6.74-6.69 (1H, m), 5.98-5.92 (1H, m), 5.03-4.94 (1H, m), 4.64-4.47 (1H, m), 4.39-4.19 (2H, m), 4.05-3.97 (1H, m), 3.19-2.46 (7H, m), 2.00-1.80 (1H, m), 1.71-1.28 (4H, m), 0.43 (2H, t, J = 8.1 Hz). |
|---|---|---|---|
| 122 | Reference Example 104 | 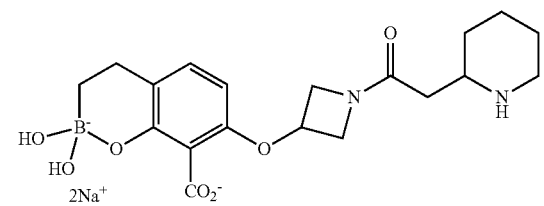 | LCMS: [M + H]⁺/Rt = 389.3/1.05 min^B<br>¹H-NMR (CD₃OD) δ: 6.74-6.69 (1H, m), 5.91-5.86 (1H, m), 4.94-4.83 (1H, m), 4.48-3.97 (4H, m), 3.12-2.86 (2H, m), 2.71-2.54 (3H, m), 2.26-2.14 (2H, m), 1.85-1.12 (6H, m), 0.42 (2H, t, J = 8.1 Hz). |
| 123 | Reference Example 105 | 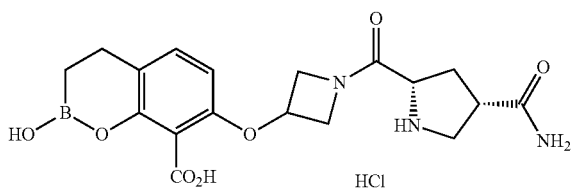 [SMILES: NC(=O)[C@@H]1CN[C@H](C(=O)N2CC(Oc3ccc4c(c3C(=O)O)OB(O)CC4)C2)C1 ; Cl] | LCMS: [M + H]⁺/Rt = 404.1/0.84 min^B<br>¹H-NMR (CD₃OD) δ: 7.18 (1H, d, J = 8.2 Hz), 6.41-6.31 (1H, m), 5.20-5.10 (1H, m), 4.81-4.64 (1H, m), 4.58-4.42 (2H, m), 4.38-4.25 (1H, m), 4.18-4.05 (1H, m), 3.68-3.50 (2H, m), 3.38-3.26 (1H, m), 2.85-2.67 (3H, m), 2.16-2.06 (1H, m), 1.06 (2H, t, J = 8.1 Hz). |
| 124 | Reference Example 100 | 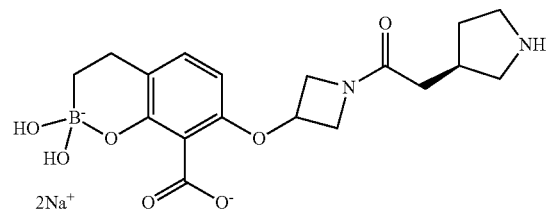 | LCMS: [M + H]+/Rt = 375.2/0.89 min^B<br>¹¹H-NMR (CD₃OD) δ: 6.77-6.62 (1H, m), 6.00-5.85 (1H, m), 4.99-4.91 (1H, m), 4.57-4.44 (1H, m), 4.35-4.16 (2H, m), 4.04-3.92 (1H, m), 3.10-2.81 (3H, m), 2.62-2.40 (4H, m), 2.29-2.19 (2H, m), 2.10-1.96 (1H, m), 1.56-1.37 (1H, m), 0.48-0.36 (2H, m). |
| 125 | Reference Example 101 | 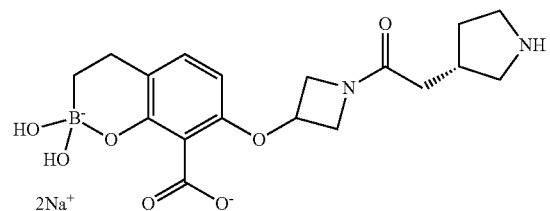 | LCMS: [M + H]+/Rt = 375.1/0.92 min^B<br>¹H-NMR (CD₃OD) δ: 6.75-6.64 (1H, m), 5.99-5.88 (1H, m), 5.01-4.89 (1H, m), 4.59-4.42 (1H, m), 4.37-4.15 (2H, m), 4.03-3.90 (1H, m), 3.12-2.84 (3H, m), 2.61-2.39 (4H, m), 2.31-2.17 (2H, m), 2.11-1.95 (1H, m), 1.59-1.40 (1H, m), 0.47-0.32 (2H, m). |
| 126 | Reference Example 102 | 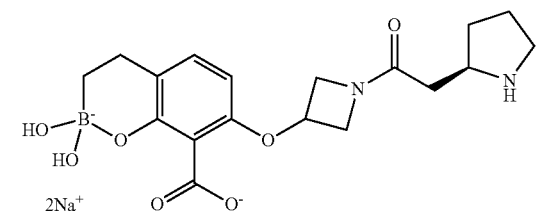 | LCMS: [M + H]+/Rt = 375.1/0.99 min^B<br>¹H-NMR (CD₃OD) δ: 6.77-6.65 (1H, m), 5.96-5.86 (1H, m), 4.97-4.84 (1H, m), 4.56-3.94 (4H, m), 3.41-3.26 (1H, m), 3.09-2.75 (2H, m), 2.62-2.49 (2H, m), 2.37-2.23 (2H, m), 2.09-1.70 (3H, m), 1.47-1.25 (1H, m), 0.49-0.33 (2H, m). |

TABLE 3-24

| 127 | Reference Example 103 | 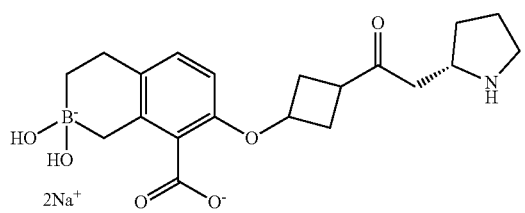 | LCMS: [M + H]+/Rt = 375.0/0.93 min^B<br>¹H-NMR (CD₃OD) δ: 6.69 (1H, d, J = 8.2 Hz), 5.91 (1H, d, J = 8.2 Hz), 4.98-4.85 (1H, m), 4.56-4.46 (1H, m), 4.35-4.17 (2H, m), 4.05-3.94 (1H, m), 3.38-3.26 (1H, m), 3.03-2.73 (2H, m), 2.61-2.49 (2H, m), 2.37-2.26 (2H, m), 2.03-1.88 (1H, m), 1.85-1.67 (2H, m), 1.46-1.24 (1H, m), 0.46-0.37 (2H, m). |
|---|---|---|---|

The names of the compounds of Examples 97 to 127 are described below.

8-{[1-(4,4-difluoro-L-prolyl)azetidin-3-yl]oxy}-4,4-dihydroxy-5-oxa-4-boranuidabicyclo[4.4.0]deca-l(6),7,9-triene-7-carboxylic acid disodium salt (Example 97)

4,4-dihydroxy-8-({1-[(4R)-4-hydroxy-L-prolyl]azetidin-3-yl}oxy)-5-oxa-4-boranuidabicyclo[4.4.0]deca-l(6),7,9-triene-7-carboxylic acid disodium salt (Example 98)

4,4-dihydroxy-8-({1-[(piperidin-4-yl)acetyl]azetidin-3-yl}oxy)-5-oxa-4-boranuidabicyclo[4.4.0]deca-l(6),7,9-triene-7-carboxylic acid disodium salt (Example 99)

4,4-dihydroxy-8-{[1-(pyrrolidine-3-carbonyl)azetidin-3-yl]oxy}-5-oxa-4-boranuidabicyclo[4.4.0]deca-l(6),7,9-triene-7-carboxylic acid disodium salt (Example 100)

4,4-dihydroxy-8-({1-[(4S)-4-hydroxy-L-prolyl]azetidin-3-yl}oxy)-5-oxa-4-boranuidabicyclo[4.4.0]deca-l(6),7,9-triene-7-carboxylic acid disodium salt (Example 101)

8-({1-[(4S)-4-amino-L-prolyl]azetidin-3-yl}oxy)-4,4-dihydroxy-5-oxa-4-boranuidabicyclo[4.4.0]deca-l(6),7,9-triene-7-carboxylic acid disodium salt (Example 102)

8-({1-[(4S)-4-acetamido-L-prolyl]azetidin-3-yl}oxy)-4,4-dihydroxy-5-oxa-4-boranuidabicyclo[4.4.0]deca-l(6),7,9-triene-7-carboxylic acid disodium salt (Example 103)

4,4-dihydroxy-8-({1-[(3R)-3-hydroxy-L-prolyl]azetidin-3-yl}oxy)-5-oxa-4-boranuidabicyclo[4.4.0]deca-l(6),7,9-triene-7-carboxylic acid disodium salt (Example 104)

8-{[1-(4,4-dimethyl-L-prolyl)azetidin-3-yl]oxy}-4,4-dihydroxy-5-oxa-4-boranuidabicyclo[4.4.0]deca-l(6),7,9-triene-7-carboxylic acid disodium salt (Example 105)

4,4-dihydroxy-8-({1-[(pyrrolidin-2-yl)acetyl]azetidin-3-yl}oxy)-5-oxa-4-boranuidabicyclo[4.4.0]deca-l(6),7,9-triene-7-carboxylic acid disodium salt (Example 106)

4,4-dihydroxy-8-{[1-(piperidine-2-carbonyl)azetidin-3-yl]oxy}-5-oxa-4-boranuidabicyclo[4.4.0]deca-l(6),7,9-triene-7-carboxylic acid disodium salt (Example 107)

4,4-dihydroxy-8-{[1-(piperidine-3-carbonyl)azetidin-3-yl]oxy}-5-oxa-4-boranuidabicyclo[4.4.0]deca-l(6),7,9-triene-7-carboxylic acid disodium salt (Example 108)

4,4-dihydroxy-8-{[1-(piperidine-4-carbonyl)azetidin-3-yl]oxy}-5-oxa-4-boranuidabicyclo[4.4.0]deca-l(6),7,9-triene-7-carboxylic acid disodium salt (Example 109)

4,4-dihydroxy-8-({1-[(2S)-oxolane-2-carbonyl]azetidin-3-yl}oxy)-5-oxa-4-boranuidabicyclo[4.4.0]deca-l(6),7,9-triene-7-carboxylic acid disodium salt (Example 110)

4,4-dihydroxy-8-({1-[(4R)-4-phenyl-L-prolyl]azetidin-3-yl}oxy)-5-oxa-4-boranuidabicyclo[4.4.0]deca-l(6),7,9-triene-7-carboxylic acid disodium salt (Example 111)

8-({1-[(1S,3S,5S)-2-azabicyclo[3.1.0]hexane-3-carbonyl]azetidin-3-yl}oxy)-4,4-dihydroxy-5-oxa-4-boranuidabicyclo[4.4.0]deca-l(6),7,9-triene-7-carboxylic acid disodium salt (Example 112)

4,4-dihydroxy-8-{[1-(1-methyl-L-prolyl)azetidin-3-yl]oxy}-5-oxa-4-boranuidabicyclo[4.4.0]deca-l(6),7,9-triene-7-carboxylic acid disodium salt (Example 113)

4,4-dihydroxy-8-({1-[(piperidin-3-yl)acetyl]azetidin-3-yl}oxy)-5-oxa-4-boranuidabicyclo[4.4.0]deca-l(6),7,9-triene-7-carboxylic acid disodium salt (Example 114)

4,4-dihydroxy-8-({1-[(morpholin-2-yl)acetyl]azetidin-3-yl}oxy)-5-oxa-4-boranuidabicyclo[4.4.0]deca-l(6),7,9-triene-7-carboxylic acid disodium salt (Example 115)

8-({1-[(azetidin-3-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 116)

8-({1-[amino(pyrrolidin-3-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 117)

4,4-dihydroxy-8-({1-[3-(pyrrolidin-2-yl)propanoyl]azetidin-3-yl}oxy)-5-oxa-4-boranuidabicyclo[4.4.0]deca-l(6),7,9-triene-7-carboxylic acid disodium salt (Example 118)

7-({1-[(4R)-4-amino-L-prolyl]azetidin-3-yl}oxy)-2-hydroxy-3,4-dihydro-2H-1,2-benzoxaborinine-8-carboxylic acid dihydrochloride (Example 119)

7-({1-[(4R)-4-acetamido-L-prolyl]azetidin-3-yl}oxy)-2-hydroxy-3,4-dihydro-2H-1,2-benzoxaborinine-8-carboxylic acid hydrochloride (Example 120)

8-({1-[amino(piperidin-4-yl)acetyl]azetidin-3-yl}oxy)-4,4-dihydroxy-5-oxa-4-boranuidabicyclo[4.4.0]deca-l(6),7,9-triene-7-carboxylic acid disodium salt (Example 121)

4,4-dihydroxy-8-({1-[(piperidin-2-yl)acetyl]azetidin-3-yl}oxy)-5-oxa-4-boranuidabicyclo[4.4.0]deca-l(6),7,9-triene-7-carboxylic acid disodium salt (Example 122)

7-({1-[(4S)-4-carbamoyl-L-prolyl]azetidin-3-yl}oxy)-2-hydroxy-3,4-dihydro-2H-1,2-benzoxaborinine-8-carboxylic acid hydrochloride (Example 123)

4,4-dihydroxy-8-[(1-{[(3R)-pyrrolidin-3-yl]acetyl}azetidin-3-yl)oxy]-5-oxa-4-boranuidabicyclo[4.4.0]deca-l(6),7,9-triene-7-carboxylic acid disodium salt (Example 124)

4,4-dihydroxy-8-[(1-{[(3S)-pyrrolidin-3-yl]acetyl}azetidin-3-yl)oxy]-5-oxa-4-boranuidabicyclo[4.4.0]deca-l(6),7,9-triene-7-carboxylic acid disodium salt (Example 125)

4,4-dihydroxy-8-[(1-{[(2R)-pyrrolidin-2-yl]acetyl}azetidin-3-yl)oxy]-5-oxa-4-boranuidabicyclo[4.4.0]deca-l(6),7,9-triene-7-carboxylic acid disodium salt (Example 126)

4,4-dihydroxy-8-[(1-{[(2S)-pyrrolidin-2-yl]acetyl}azetidin-3-yl)oxy]-5-oxa-4-boranuidabicyclo[4.4.0]deca-l(6),7,9-triene-7-carboxylic acid disodium salt (Example 127)

The following Example compounds 128 and 129 were obtained by performing a reaction, work-up, and purification using the compounds of Reference Examples 61 and 126, respectively, as the starting materials by the same method described in Example 36, further dissolving the resulting crude product in water, adding an aqueous 2 N sodium hydroxide solution, and purifying by reversed phase chromatography.

TABLE 3-25

| Example | Starting material | Structural formula | NMR and/or LCMS |
|---|---|---|---|
| 128 | Reference Example 61 | | LCMS: [M + H]⁺/Rt = 389.96/0.446 min$^F$<br>$^1$H-NMR (D$_2$O) δ: 6.90 (1H, d, J = 8.2 Hz), 6.07 (1H, d, J = 8.2 Hz), 5.01 (1H, m), 4.60 (1H, m), 4.28-4.40 (2H, m), 4.05 (1H, m), 2.94-3.09 (4H, m), 2.58-2.81 (4H, m), 2.45 (1H, m), 2.22-2.31 (2H, m), 0.38 (2H, m). |

TABLE 3-25-continued

| Example | Starting material | Structural formula | NMR and/or LCMS |
|---|---|---|---|
| 129 | Reference Example 126 | (structure shown) | LCMS: $[M + H]^+$/Rt = 438.95/0.555 min$^F$<br>$^1$H-NMR (D$_2$O) δ: 6.90 (1H, d, J = 8.2 Hz), 6.07 (1H, d, J = 8.2 Hz), 5.03 (1H, m), 4.65 (1H, m), 4.42-4.32 (2H, m), 4.08 (1H, m), 3.60 (1H, m), 3.47-3.12 (5H, m), 2.96-2.79 (2H, m), 2.60 (2H, m), 2.40 (1H, m), 0.39 (2H, m). |

The names of the compounds of Examples 128 and 129 are described below.
4,4-dihydroxy-8-({1-[(piperazin-2-yl)acetyl]azetidin-3-yl}oxy)-5-oxa-4-boranuidabicyclo[4.4.0]deca-1(6),7,9-triene-7-carboxylic acid disodium salt (Example 128)
8-({1-[(1,1-dioxo-1λ$^6$-thiomorpholin-2-yl)acetyl]azetidin-3-yl}oxy)-4,4-dihydroxy-5-oxa-4-boranuidabicyclo[4.4.0]deca-1(6),7,9-triene-7-carboxylic acid disodium salt (Example 129)

The following Example compounds 130 to 137 were obtained by performing a reaction, work-up, and purification using the compounds of Reference Examples 128 and 131 to 137 as the starting materials (corresponding starting materials are not in order) by the same method described in Example 38, purifying the compound by reversed phase chromatography without sodium hydroxide treatment, followed by addition of hydrochloric acid and concentration.

TABLE 3-26

| Example | Starting material | Structural formula | NMR and/or LCMS |
|---|---|---|---|
| 130 | Reference Example 131 | (structure shown) | LCMS: $[M + H]^+$/Rt=406.1/0.86 min$^B$<br>$^1$H-NMR (CD$_3$OD) δ: 7.19-7.11 (1H, m), 6.36-6.14 (1H, m), 5.16-4.99 (1H, m), 4.74-4.65 (1H, m), 4.54-4.27 (2H, m), 4.12-3.96 (2H, m), 3.42-3.20 (2H, m), 2.73-2.54 (2H, m), 2.11-1.89 (5H, m), 1.09-0.68 (2H, m). |
| 131 | Reference Example 132 | (structure shown) | LCMS: $[M + H]^+$/Rt = 378.1/0.54 min$^B$<br>$^1$H-NMR (CD$_3$OD) δ: 7.19-7.11 (1H, m), 6.34-6.10 (1H, m), 5.13-4.99 (1H, m), 4.66-4.52 (1H, m), 4.47-4.01 (4H, m), 2.94-2.50 (4H, m), 1.09-0.64 (2H, m). |
| 132 | Reference Example 133 | (structure shown) | LCMS: $[M + H]^+$/Rt = 406.1/0.94 min$^B$<br>$^1$H-NMR (CD$_3$OD) δ: 7.18-7.10 (1H, m), 6.64-6.09 (1H, m), 5.14-5.03 (1H, m), 4.80-4.66 (1H, m), 4.46-4.27 (3H, m), 4.04-3.87 (2H, m), 2.80-2.52 (2H, m), 1.51-1.46 (3H, m), 1.36-1.33 (3H, m), 1.09-0.65 (2H, m). |
| 133 | Reference Example 135 | (structure shown) | LCMS: $[M + H]^+$/Rt = 392.1/0.88 min$^B$<br>$^1$H-NMR (CD$_3$OD) δ: 7.17 (1H, d, J = 8.1 Hz), 6.39-6.28 (1H, m), 5.17-5.06 (1H, m), 4.99-4.80 (1H, m), 4.73-3.94 (4H, m), 3.74-3.67 (2H, m), 2.70 (2H, t, J = 8.1 Hz), 1.34 (3H, d, J = 8.1 Hz), 1.06 (2H, t, J = 8.1 Hz). |

TABLE 3-26-continued

| Example | Starting material | Structural formula | NMR and/or LCMS |
|---|---|---|---|
| 134 | Reference Example 136 | | LCMS: [M + H]$^+$/Rt = 450.1/ 0.92 min$^B$<br>$^1$H-NMR (CD$_3$OD) δ: 8.67-8.56 (1H, m), 7.18-7.10 (1H, m), 6.34-6.10 (1H, m), 5.13-5.05 (1H, m), 4.93-4.66 (1H, m), 4.52-4.27 (3H, m), 4.23-4.13 (1H, m), 4.04-3.95 (1H, m), 3.08-2.52 (4H, m), 1.36-1.33 (3H, m), 1.09-0.66 (2H, m). |
| 135 | Reference Example 134 | | LCMS: [M + H]$^+$/Rt = 449.1/ 0.85 min$^B$<br>$^1$H-NMR (CD$_3$OD) δ: 7.17 (1H, d, J = 8.1 Hz), 6.38-6.28 (1H, m), 5.15-5.05 (1H, m), 4.92-4.64 (1H, m), 4.47-4.27 (3H, m), 4.22-4.15 (1H, m), 4.03-3.95 (1H, m), 2.96-2.86 (1H, m), 2.76-2.65 (3H, m), 1.34 (3H, d, J = 5.4 Hz), 1.07 (2H, t, J = 8.1 Hz). |

TABLE 3-27

| 136 | Reference Example 128 | | LCMS: [M + H]$^+$/Rt = 422.1/0.88 min$^B$<br>$^1$H-NMR (CD$_3$OD) δ: 8.84-8.56 (1H, m), 7.18-7.10 (1H, m), 6.34-6.09 (1H, m), 5.13-4.59 (2H, m), 4.51-4.26 (3H, m), 4.13-3.77 (4H, m), 2.79-2.51 (2H, m), 1.37-1.33 (3H, m), 1.09-0.64 (2H, m). |
|---|---|---|---|
| 137 | Reference Example 137 | | LCMS: [M + H]$^+$/Rt = 379.0/0.71 min$^B$<br>$^1$H-NMR (CD$_3$OD) δ: 7.17 (1H, d, J = 8.2 Hz), 6.78-6.32 (1H, m), 5.14-5.04 (1H, m), 4.67-4.61 (1H, m), 4.47-4.38 (1H, m), 4.31-4.22 (2H, m), 4.05-3.61 (1H, m), 3.00-2.78 (2H, m), 2.70 (2H, t, J = 8.1 Hz), 1.06 (2H, t, J = 8.1 Hz). |

The names of the compounds of Examples 130 to 137 are described below.

7-({1-[(2S)-4-acetamido-2-aminobutanoyl]azetidin-3-yl}oxy)-2-hydroxy-3,4-dihydro-2H-1,2-benzoxaborinine-8-carboxylic acid hydrochloride (Example 130)

7-{[1-(L-α-asparaginyl)azetidin-3-yl]oxy}-2-hydroxy-3,4-dihydro-2H-1,2-benzoxaborinine-8-carboxylic acid hydrochloride (Example 131)

7-{[1-(L-alanyl-L-alanyl)azetidin-3-yl]oxy}-2-hydroxy-3,4-dihydro-2H-1,2-benzoxaborinine-8-carboxylic acid hydrochloride (Example 132)

7-{[1-(glycyl-D-alanyl)azetidin-3-yl]oxy}-2-hydroxy-3,4-dihydro-2H-1,2-benzoxaborinine-8-carboxylic acid hydrochloride (Example 133)

N-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-α-asparagine hydrochloride (Example 134)

N$^1$-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-aspartamide hydrochloride (Example 135)

N-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-serinamide hydrochloride (Example 136)

7-({1-[(3S)-3-amino-3-carboxypropanoyl]azetidin-3-yl}oxy)-2-hydroxy-3,4-dihydro-2H-1,2-benzoxaborinine-8-carboxylic acid hydrochloride (Example 137)

The compounds of Reference Examples 138 and 139 were used as the starting materials to perform a reaction and work-up by the same method described in Example 4. Each of Example compounds 138 and 139 were obtained from purifying the compound by reversed phase chromatography without sodium hydroxide treatment, followed by addition of hydrochloric acid and concentration.

TABLE 3-28

| Example | Starting material | Structural formula | NMR and/or LCMS |
|---|---|---|---|
| 138 | Reference Example 138 | (structure shown) 2HCl | LCMS: [M + H]⁺/Rt = 401.26/0.58 min$^I$<br>¹H-NMR (500 MHz, CD₃OD) δ: 9.10-9.07 (1H, m), 7.93 (brs, 1H), 7.15 (1H, d, J = 8.0 Hz), 6.37-6.22 (1H, m), 5.61-5.54 (1H, m), 5.16-4.75 (2H, m), 4.61-3.76 (3H, m), 2.74-2.69 (5H, m), 1.06 (2H, t, J = 8.0 Hz). |
| 139 | Reference Example 139 | (structure shown) 2HCl | LCMS: [M + H]⁺/Rt = 415.25/1.03 min$^I$<br>¹H-NMR (500 MHz, CD₃OD) δ: 8.91 (1H, brs), 7.95 (1H, brs), 7.14 (1H, d, J = 8.0 Hz), 6.38-6.23 (1H, m), 5.75-5.58 (1H, m), 5.16-3.94 (6H, m), 3.01-3.81 (5H, m), 2.75-2.65 (5H, m), 1.06 (2H, t, J = 8.0 Hz). |

The names of the compounds of Examples 138 and 139 are described below.

2-hydroxy-7-({1-[(1H-imidazol-4-yl)(methylamino)acetyl]azetidin-3-yl}oxy)-3,4-dihydro-2H-1,2-benzoxaborinine-8-carboxylic acid dihydrochloride (Example 138)

2-hydroxy-7-({1-[(1H-imidazol-4-yl)(methylamino)acetyl]azetidin-3-yl}oxy)-3,4-dihydro-2H-1,2-benzoxaborinine-8-carboxylic acid dihydrochloride Example 139

Example 140: 2-hydroxy-7-{[1-(2-methyl-D-seryl)azetidin-3-yl]oxy}-3,4-dihydro-2H-1,2-benzoxaborinine-8-carboxylic Acid

[Chemical Formula 826]

A reaction, work-up, and purification were performed using the compound of Reference Example 140 (245 mg, 0.317 mmol) as the starting material by the same method described in Example 36 to obtain the title compound (21.8 mg) as a white solid.

¹H-NMR (0.1M HCl in CD₃OD) δ: 7.18 (1H, d, J=8.5 Hz), 6.35 (1H, d, J=8.5 Hz), 5.14-5.10 (2H, m), 4.50-4.43 (2H, m), 4.12-4.04 (1H, m), 3.91 (1H, d, J=12.2 Hz), 3.72 (1H, d, J=12.2 Hz), 2.70 (2H, t, J=7.6 Hz), 1.52 (3H, s), 1.05 (2H, t, J=7.6 Hz).

LCMS: [M+H]⁺/Rt=365.09/0.447 min$^C$

The following Example compounds 141 to 148 were obtained by performing a reaction using the compounds of Reference Examples 141, 143, and 150 to 155, respectively, as the starting materials by the same method described in Example 36, followed by, as a work-up, concentrating a reaction mixture under reduced pressure and then purifying the mixture by reversed phase chromatography (Column: YMC-Actus pro C18, solution A: 0.05% TFA/water, solution B: 0.03% TFA/acetonitrile). However, if hydrochloride is the final product (Example 145), the hydrochloride was obtained from purifying the compound by reversed phase chromatography, followed by addition of hydrochloric acid and concentration.

TABLE 3-29

| Example | Starting material | Structural formula | NMR and/or LCMS |
|---|---|---|---|
| 141 | Reference Example 141 | (structure shown) CF₃CO₂H | LCMS: [M + H]⁺/Rt = 365/1.414 min$^G$<br>¹H-NMR (D₂O) δ: 7.08-6.89 (1H, m), 6.14-5.94 (1H, m), 4.96-4.67 (2H, m), 4.36-4.29 (2H, m), 4.02-3.92 (1H, m), 3.81-3.73 (1H, m), 3.63-3.56 (1H, m), 2.52-2.25 (2H, m), 1.38-1.33 (3H, m), 0.92-0.43 (2H, m). |

TABLE 3-29-continued

| Example | Starting material | Structural formula | NMR and/or LCMS |
|---|---|---|---|
| 142 | Reference Example 143 | 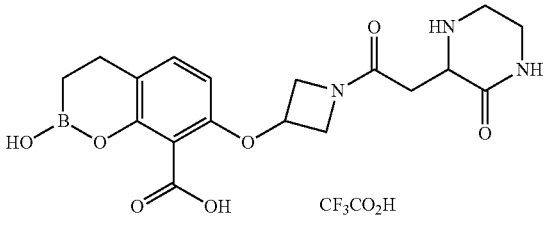 [SMILES: O=C(O)c1c(OC2CN(C(=O)CC3NCCNC3=O)C2)ccc2c1OB(O)CC2 ; "CF3CO2H"] | LCMS: [M + H]⁺/Rt = 404/1.400 min$^G$<br>¹H-NMR (D₂O) δ: 7.11-6.91 (1H, m), 6.15-5.89 (1H, m), 4.95-4.81 (1H, m), 4.48-4.38 (1H, m), 4.32-3.84 (4H, m), 3.57-3.39 (3H, m), 3.36-3.29 (1H, m), 2.99-2.67 (2H, m), 2.53-2.36 (2H, m), 0.94-0.45 (2H, m). |
| 143 | Reference Example 150 | 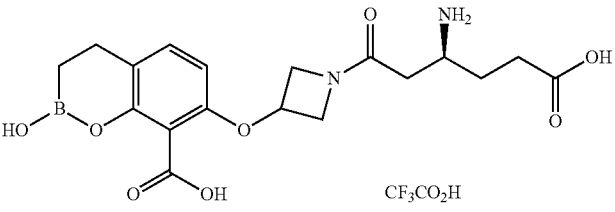 [SMILES: N[C@@H](CCC(=O)O)CC(=O)N1CC(Oc2ccc3c(c2C(=O)O)OB(O)CC3)C1 ; "CF3CO2H"] | LCMS: [M + H]⁺/Rt = 407/1.175 min$^G$<br>¹H-NMR (D₂O) δ: 7.09-6.89 (1H, m), 6.15-5.91 (1H, m), 4.94-4.63 (2H, m), 4.50-3.84 (4H, m), 2.53-2.33 (6H, m), 1.92-1.74 (2H, m), 0.93-0.43 (2H, m). |
| 144 | Reference Example 151 | 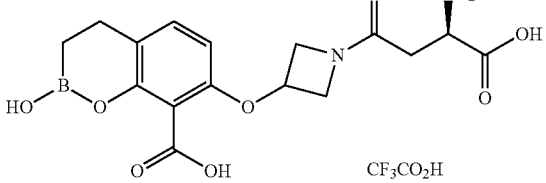 | LCMS: [M + H]⁺/Rt = 379/1.400 min$^G$<br>¹H-NMR (D₂O) δ: 6.94-6.80 (1H, m), 5.98-5.78 (1H, m), 4.35-3.36 (6H, m), 2.67 (2H, s), 2.35-2.20 (2H, m), 0.91-0.60 (2H, m). |

TABLE 3-30

| Example | Starting material | Structural formula | NMR and/or LCMS |
|---|---|---|---|
| 145 | Reference Example 152 | 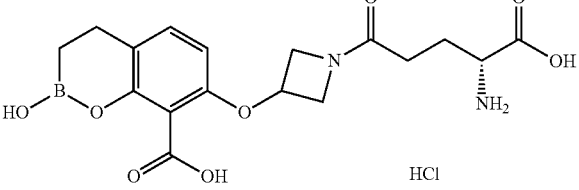 | LCMS: [M + H]⁺/Rt = 393/1.217 min$^G$<br>¹H-NMR (D₂O) δ: 7.05-6.84 (1H, m), 6.13-5.85 (1H, m), 4.91-4.71 (1H, m), 4.47-3.87 (5H, m), 2.52-2.21 (4H, m), 2.01 (2H, brs), 0.91-0.40 (2H, m). |
| 146 | Reference Example 153 | 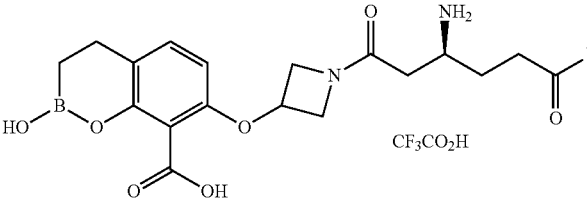 | LCMS: [M + H]⁺/Rt = 406/1.223 min$^G$<br>¹H-NMR (D₂O) δ: 7.05-6.82 (1H, m), 6.14-5.87 (1H, m), 4.92-4.74 (1H, m), 4.28-4.03 (4H, m), 3.46 (1H, brs), 2.50-1.74 (8H, m), 0.92-0.39 (2H, m). |
| 147 | Reference Example 154 | 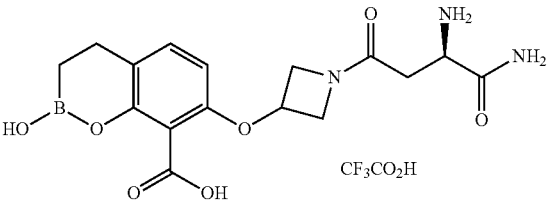 [SMILES: NC(=O)[C@H](N)CC(=O)N1CC(Oc2ccc3c(c2C(=O)O)OB(O)CC3)C1 ; "CF3CO2H"] | LCMS: [M + H]⁺/Rt = 378/1.208 min$^G$<br>¹H-NMR (D₂O) δ: 7.02-6.82 (1H, m), 6.08-5.83 (1H, m), 4.88-4.71 (1H, m), 4.39-3.83 (5H, m), 2.68 (2H, brs), 2.52-2.16 (2H, m), 0.70-0.37 (2H, m). |

TABLE 3-30-continued

| | | | |
|---|---|---|---|
| 148 | Reference Example 155 | 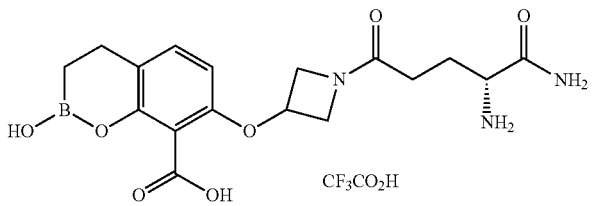 [SMILES: NC(=O)[C@H](N)CCC(=O)N1CC(Oc2ccc3c(c2C(=O)O)OB(O)CC3)C1 ; "CF3CO2H"] CF$_3$CO$_2$H | LCMS: [M + H]$^+$/Rt = 392/1.171 min$^G$<br>$^1$H-NMR (D$_2$O) δ: 7.07-6.81 (1H, m), 6.10-5.84 (1H, m), 4.78-4.67 (1H, m), 4.42-3.80 (5H, m), 2.50-2.33 (2H, m), 2.17 (2H, brs), 1.98-1.96 (2H, m), 0.91-0.38 (2H, m). |

The names of the compounds of Examples 141 to 148 are described below.

2-hydroxy-7-{[1-(2-methyl-L-seryl)azetidin-3-yl]oxy}-3,4-dihydro-2H-1,2-benzoxaborinine-8-carboxylic acid trifluoroacetate (Example 141)

2-hydroxy-7-({1-[(3-oxopiperazin-2-yl)acetyl]azetidin-3-yl}oxy)-3,4-dihydro-2H-1,2-benzoxaborinine-8-carboxylic acid trifluoroacetate (Example 142)

7-({1-[(3S)-3-amino-5-carboxypentanoyl]azetidin-3-yl}oxy)-2-hydroxy-3,4-dihydro-2H-1,2-benzoxaborinine-8-carboxylic acid trifluoroacetate (Example 143)

7-({1-[(3R)-3-amino-3-carboxypropanoyl]azetidin-3-yl}oxy)-2-hydroxy-3,4-dihydro-2H-1,2-benzoxaborinine-8-carboxylic acid trifluoroacetate (Example 144)

7-({1-[(4R)-4-amino-4-carboxybutanoyl]azetidin-3-yl}oxy)-2-hydroxy-3,4-dihydro-2H-1,2-benzoxaborinine-8-carboxylic acid hydrochloride (Example 145)

7-({1-[(3S)-3,6-diamino-6-oxohexanoyl]azetidin-3-yl}oxy)-2-hydroxy-3,4-dihydro-2H-1,2-benzoxaborinine-8-carboxylic acid trifluoroacetate (Example 146)

7-{[1-(D-α-asparaginyl)azetidin-3-yl]oxy}-2-hydroxy-3,4-dihydro-2H-1,2-benzoxaborinine-8-carboxylic acid trifluoroacetate (Example 147)

7-{[1-(D-α-glutaminyl)azetidin-3-yl]oxy}-2-hydroxy-3,4-dihydro-2H-1,2-benzoxaborinine-8-carboxylic acid trifluoroacetate (Example 148)

The following Example compounds 149 and 150 were obtained by performing a reaction and work-up using the compounds of Reference Examples 146 and 147, respectively, as the starting materials by the same method described in Example 38, and purifying the compound by reversed phase chromatography without sodium hydroxide treatment, followed by addition of hydrochloric acid and concentration.

TABLE 3-31

| Example | Starting material | Structural formula | NMR and/or LCMS |
|---|---|---|---|
| 149 | Reference Example 146 | | LCMS: [M + H]+/Rt = 393.1/0.86 min$^B$<br>1H-NMR (CD3OD) δ: 7.22-7.08 (1H, m), 6.38-6.06 (1H, m), 5.13-5.01 (1H, m), 4.67-4.52 (1H, m), 4.47-4.32 (1H, m), 4.28-4.18 (1H, m), 4.11-3.92 (2H, m), 2.76-2.62 (2H, m), 2.53-2.38 (2H, m), 2.28-2.04 (2H, m), 1.13-0.61 (2H, m). |
| 150 | Reference Example 147 | | LCMS: [M + H]$^+$/Rt = 392.1/0.86 min$^B$<br>1H-NMR (CD3OD) δ: 7.24-7.08 (1H, m), 6.41-6.07 (1H, m), 5.14-5.00 (1H, m), 4.67-4.51 (1H, m), 4.46-4.32 (1H, m), 4.29-4.16 (1H, m), 4.08-3.88 (2H, m), 2.81-2.50 (2H, m), 2.49-2.34 (2H, m), 2.21-2.02 (2H, m), 1.14-0.64 (2H, m). |

The names of the compounds of Examples 149 and 150 are described below.
7-({1-[(4S)-4-amino-4-carboxybutanoyl]azetidin-3-yl}oxy)-2-hydroxy-3,4-dihydro-2H-1,2-benzoxaborinine-8-carboxylic acid hydrochloride (Example 149)
7-{[1-(L-α-glutaminyl)azetidin-3-yl]oxy}-2-hydroxy-3,4-dihydro-2H-1,2-benzoxaborinine-8-carboxylic acid hydrochloride (Example 150)

The following Example compounds 151 and 152 were obtained by performing a reaction and work-up using the compounds of Reference Examples 148 and 149, respectively, as the starting materials by the same method described in Example 4 and purifying the compound by reversed phase chromatography without sodium hydroxide treatment, followed by addition of hydrochloric acid and concentration.

TABLE 3-32

| Example | Starting material | Structural formula | NMR and/or LCMS |
|---|---|---|---|
| 151 | Reference Example 148 | 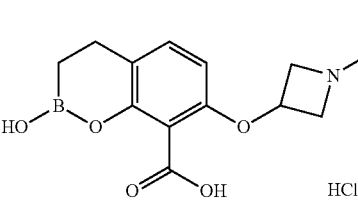 | LCMS: [M + H]⁺/Rt = 365.24/1.27 min$^f$. $^1$H-NMR (500 MHz, CDCl$_3$) δ: 7.18-7.09 (1H, s), 6.32 (1H, brs), 5.13-5.07 (1H, m), 4.78-4.69 (1H, m), 4.50-4.29 (2H, m), 4.10-3.96 (2H, m), 3.81-3.78 (1H, m), 2.67 (2H, t, J = 7.4 Hz), 1.26 (3H, t, J = 5.7 Hz), 1.03 (2H, t, J = 8.1 Hz). |
| 152 | Reference Example 149 | 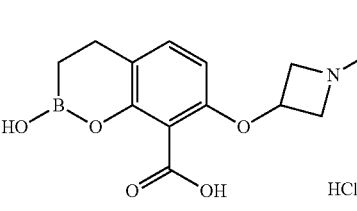 | LCMS: [M + H]⁺/Rt = 365.24/1.23 min$^f$. $^1$H-NMR (500 MHz, CDCl$_3$) δ: 7.17-7.10 (1H, s), 6.33 (1H, brs), 5.12-5.07 (1H, m), 4.76-4.70 (1H, m), 4.51-4.30 (2H, m), 4.09-3.78 (3H, m), 2.67 (2H, brs), 1.26 (3H, t, J = 6.3 Hz), 1.03 (2H, t, J = 8.0 Hz). |

The names of the compounds of Examples 151 and 152 are described below.
2-hydroxy-7-[(1-D-threonylazetidin-3-yl)oxy]-3,4-dihydro-2H-1,2-benzoxaborinine-8-carboxylic acid hydrochloride (Example 151)
2-hydroxy-7-[(1-L-threonylazetidin-3-yl)oxy]-3,4-dihydro-2H-1,2-benzoxaborinine-8-carboxylic acid hydrochloride (Example 152)

Pharmacological testing methods and results thereof for representative compounds of the invention are shown hereinafter, but the present invention is not limited to the Test Examples.

Test Example 1: Evaluation of Minimum Inhibitory Concentration (MIC) of MEPM Against β-Lactamase Producing Bacteria To evaluate the β-lactamase inhibitory activity of test compounds, the effect of combination of a test compound and a β-lactam agent against β-lactamase producing bacteria was evaluated. Meropenem (MEPM) was used as a β-lactam antimicrobial agent. The minimum inhibitory concentration (MIC) of MEPM against D-lactamase producing bacteria when a test compound was added at a fixed concentration (4 μg/mL) was measured by broth microdilution method (common ratio: 2). MIC of MEPM decreasing to less than 1/32 in combination with a test compound is indicated by A, decreasing from 1/32 to 1/16 is indicated by B, decreasing from 1/8 to 1/4 is indicated by C, and decreasing to 1/2 or others are indicated by D. "-" represents untested cases.

TABLE 4

| Example number | E. coli ATCC BAA-2340 (KPC) | K. pneumoniae ATCC BAA-2344 (KPC) | K. pneumoniae ATCC BAA-2524 (OXA-48) |
|---|---|---|---|
| 1 | A | A | B |
| 2 | A | A | B |
| 3 | A | A | B |
| 4 | A | A | A |
| 5 | A | B | C |

TABLE 4-continued

| Example number | E. coli ATCC BAA-2340 (KPC) | K. pneumoniae ATCC BAA-2344 (KPC) | K. pneumoniae ATCC BAA-2524 (OXA-48) |
|---|---|---|---|
| 6 | A | A | B |
| 7 | A | A | B |
| 8 | A | A | B |
| 9 | A | A | A |
| 10 | A | A | B |
| 11 | A | B | B |
| 12 | A | A | B |
| 13 | A | A | B |
| 14 | A | A | B |
| 15 | A | A | B |
| 16 | A | — | B |
| 17 | A | B | B |
| 18 | A | A | B |
| 19 | A | A | B |
| 20 | A | B | B |
| 21 | A | B | C |
| 22 | A | A | B |
| 23 | — | A | B |
| 24 | A | A | B |
| 25 | A | A | B |
| 26 | A | A | A |
| 27 | — | A | B |
| 28 | A | A | B |
| 29 | — | A | B |
| 30 | — | A | B |

TABLE 4-continued

| Example number | E. coli ATCC BAA-2340 (KPC) | K. pneumoniae ATCC BAA-2344 (KPC) | K. pneumoniae ATCC BAA-2524 (OXA-48) |
|---|---|---|---|
| 31 | — | A | B |
| 32 | — | A | B |
| 33 | — | A | B |
| 34 | — | A | B |
| 35 | A | A | B |

Test Example 2: Evaluation of Minimum Inhibitory Concentration (MIC) of MEPM Against β-Lactamase Producing Bacteria In the same manner as Test Example 1, E. coli ATCC BAA-2469 (NDM-1), K. pneumomiae ATCC BAA-2470 (NDM-1), K. pneumomiae NCTC 13439 (VIM-1), K. pneumomiae NCTC 13440 (VIM-1), E. coli NCTC 13476 (IMP), and the like can be used to evaluate metallo-β-lactamase inhibitory activity of test compounds.

Test Example 3: Evaluation of Minimum Inhibitory Concentration (MIC) of MEPM Against β-Lactamase Producing Bacteria To evaluate the β-lactamase inhibitory activity of test compounds, the effect of combination of a test compound and a β-lactam agent against β-lactamase producing bacteria was evaluated. Meropenem (MEPM) was used as a D-lactam antimicrobial agent. The minimum inhibitory concentration (MIC) of MEPM against β-lactamase producing bacteria when a test compound was added at a fixed concentration (4 μg/mL) was measured by broth microdilution method (common ratio: 2).

The numerical value of (MIC of MEPM in combination with a test compound)/(MIC of MEPM alone) are shown below ("-" represents untested cases).

TABLE 5-1

| Example number | E. coli ATCC BAA-2340 (KPC) | K. pneumoniae ATCC BAA-2344 (KPC) | K. pneumoniae ATCC BAA-2524 (OXA-48) |
|---|---|---|---|
| 1 | 0.031/8 | 0.063/32 | 0.063/1 |
| 2 | 0.031/8 | 0.031/32 | 0.063/1 |
| 3 | 0.031/8 | 0.063/32 | 0.063/1 |
| 4 | 0.016/4 | 0.031/32 | 0.031/2 |
| 5 | 0.125/8 | 2/32 | 0.125/1 |
| 6 | 0.031/4 | 0.125/32 | 0.063/1 |
| 7 | 0.031/4 | 0.031/32 | 0.063/1 |
| 8 | 0.031/8 | 0.063/32 | 0.063/2 |
| 9 | 0.016/4 | 0.063/32 | 0.031/2 |
| 10 | 0.031/4 | 0.063/32 | 0.063/2 |
| 11 | 0.063/4 | 2/32 | 0.063/1 |
| 12 | 0.031/4 | 0.063/32 | 0.063/1 |
| 13 | 0.031/8 | 0.063/32 | 0.063/2 |
| 14 | 0.031/8 | 0.125/32 | 0.063/2 |
| 15 | 0.031/8 | 0.063/32 | 0.063/1 |
| 16 | 0.031/8 | 0.125/32 | 0.063/1 |
| 17 | 0.031/8 | 2/32 | 0.063/1 |
| 18 | 0.016/8 | 0.031/32 | 0.063/2 |
| 19 | 0.016/8 | 0.031/32 | 0.063/2 |
| 20 | 0.031/8 | 2/32 | 0.063/1 |
| 21 | 0.125/8 | 2/32 | 0.125/1 |
| 22 | 0.016/8 | 0.031/32 | 0.063/2 |
| 23 | — | 0.063/32 | 0.063/2 |
| 24 | 0.016/8 | 0.5/32 | 0.063/2 |
| 25 | 0.016/8 | 0.063/32 | 0.063/2 |
| 26 | 0.016/8 | 0.063/32 | 0.031/2 |
| 27 | — | 0.063/32 | 0.063/2 |
| 28 | 0.016/8 | 0.031/32 | 0.063/2 |
| 29 | — | 0.063/32 | 0.063/2 |
| 30 | — | 0.125/32 | 0.125/2 |
| 31 | — | 0.063/32 | 0.063/2 |
| 32 | — | 0.063/32 | 0.063/2 |
| 33 | — | ≤0.063/32 | ≤0.063/1 |
| 34 | — | 0.063/32 | 0.063/2 |
| 35 | 0.031/4 | 0.063/32 | 0.063/1 |
| 36 | — | ≤0.063/16 | ≤0.063/1 |
| 37 | — | ≤0.031/16 | ≤0.031/1 |
| 38 | — | ≤0.063/16 | ≤0.063/2 |
| 39 | — | 1/16 | ≤0.063/2 |
| 40 | — | ≤0.063/16 | ≤0.063/1 |
| 41 | — | ≤0.063/16 | ≤0.063/1 |
| 42 | — | ≤0.063/16 | ≤0.063/2 |
| 43 | — | ≤0.063/16 | ≤0.063/1 |

TABLE 5-2

| Example number | E. coli ATCC BAA-2340 (KPC) | K. pneumoniae ATCC BAA-2344 (KPC) | K. pneumoniae ATCC BAA-2524 (OXA-48) |
|---|---|---|---|
| 44 | — | ≤0.063/16 | ≤0.063/1 |
| 45 | — | ≤0.063/16 | ≤0.063/2 |
| 46 | — | ≤0.063/16 | ≤0.063/2 |
| 47 | — | ≤0.063/16 | ≤0.063/2 |
| 48 | — | ≤0.063/16 | ≤0.063/2 |
| 49 | — | ≤0.063/16 | ≤0.063/2 |
| 50 | — | ≤0.063/16 | ≤0.063/1 |
| 51 | — | ≤0.063/32 | ≤0.063/2 |
| 52 | — | ≤0.063/16 | ≤0.063/1 |
| 53 | — | 0.25/16 | ≤0.063/1 |
| 54 | — | 0.25/16 | ≤0.063/2 |
| 55 | — | ≤0.031/32 | ≤0.031/1 |
| 56 | — | 0.125/32 | ≤0.031/1 |
| 57 | — | ≤0.063/16 | ≤0.063/1 |
| 58 | — | ≤0.063/16 | ≤0.063/2 |
| 59 | — | ≤0.063/32 | ≤0.063/2 |
| 60 | — | 0.125/32 | ≤0.063/2 |
| 61 | — | ≤0.063/16 | ≤0.063/2 |
| 62 | — | ≤0.063/16 | ≤0.063/2 |
| 63 | — | ≤0.063/16 | ≤0.063/2 |
| 64 | — | ≤0.063/16 | ≤0.063/2 |
| 65 | — | ≤0.063/16 | ≤0.063/2 |
| 66 | — | ≤0.063/16 | ≤0.063/2 |
| 67 | — | ≤0.063/16 | ≤0.063/2 |
| 68 | — | ≤0.063/16 | ≤0.063/1 |
| 69 | — | ≤0.063/16 | ≤0.063/1 |
| 70 | — | ≤0.063/16 | ≤0.063/2 |
| 71 | — | ≤0.063/16 | ≤0.063/1 |
| 72 | — | ≤0.063/16 | ≤0.063/1 |
| 73 | — | ≤0.063/16 | ≤0.063/2 |
| 74 | — | 0.25/32 | 0.125/1 |
| 75 | — | 1/32 | ≤0.063/1 |
| 76 | — | 4/32 | 0.25/1 |
| 77 | — | ≤0.063/16 | ≤0.063/2 |
| 78 | — | ≤0.063/16 | ≤0.063/1 |
| 79 | — | ≤0.063/16 | ≤0.063/1 |
| 80 | — | ≤0.063/16 | ≤0.063/1 |
| 81 | — | ≤0.063/16 | ≤0.063/1 |
| 82 | — | ≤0.063/16 | ≤0.063/1 |
| 83 | — | ≤0.063/32 | ≤0.063/2 |
| 84 | — | ≤0.063/32 | ≤0.063/2 |
| 85 | — | ≤0.063/32 | ≤0.063/2 |
| 86 | — | ≤0.063/32 | ≤0.063/2 |
| 87 | — | ≤0.063/16 | ≤0.063/1 |
| 88 | — | ≤0.063/32 | ≤0.063/2 |
| 89 | — | ≤0.063/16 | ≤0.063/1 |
| 90 | — | ≤0.063/16 | ≤0.063/1 |
| 91 | — | ≤0.063/16 | ≤0.063/1 |

TABLE 5-3

| | | | |
|---|---|---|---|
| 92 | — | ≤0.063/16 | ≤0.063/2 |
| 93 | — | ≤0.063/16 | ≤0.063/2 |
| 94 | — | ≤0.063/16 | ≤0.063/1 |
| 95 | — | ≤0.063/16 | ≤0.063/1 |
| 96 | — | ≤0.063/16 | ≤0.063/1 |
| 97 | — | ≤0.063/16 | ≤0.063/2 |
| 98 | — | ≤0.063/16 | ≤0.063/2 |
| 99 | — | ≤0.063/16 | ≤0.063/2 |
| 100 | — | ≤0.063/16 | ≤0.063/2 |
| 101 | — | ≤0.063/16 | ≤0.063/2 |
| 102 | — | ≤0.063/16 | ≤0.063/2 |
| 103 | — | ≤0.063/16 | ≤0.063/2 |
| 104 | — | ≤0.063/32 | ≤0.063/2 |
| 105 | — | ≤0.063/32 | ≤0.063/2 |
| 106 | — | ≤0.063/16 | ≤0.063/2 |
| 107 | — | ≤0.063/16 | ≤0.063/2 |
| 108 | — | ≤0.063/16 | ≤0.063/2 |
| 109 | — | ≤0.063/16 | ≤0.063/2 |
| 110 | — | ≤0.063/16 | ≤0.063/2 |
| 111 | — | ≤0.063/16 | ≤0.063/2 |
| 112 | — | ≤0.063/16 | ≤0.063/2 |
| 113 | — | ≤0.063/16 | ≤0.063/2 |
| 114 | — | ≤0.063/16 | ≤0.063/2 |
| 115 | — | ≤0.063/16 | ≤0.063/2 |
| 116 | — | ≤0.063/16 | ≤0.063/2 |
| 117 | — | ≤0.063/16 | ≤0.063/2 |
| 118 | — | ≤0.063/16 | ≤0.063/2 |
| 119 | — | 0.125/16 | ≤0.063/1 |
| 120 | — | ≤0.063/16 | ≤0.063/1 |
| 121 | — | ≤0.063/16 | ≤0.063/2 |
| 122 | — | ≤0.063/16 | ≤0.063/2 |
| 123 | — | ≤0.063/32 | ≤0.063/2 |
| 124 | — | ≤0.063/16 | ≤0.063/2 |
| 125 | — | ≤0.063/16 | ≤0.063/2 |
| 126 | — | ≤0.063/16 | ≤0.063/2 |
| 127 | — | ≤0.063/16 | ≤0.063/2 |
| 128 | — | ≤0.063/16 | ≤0.063/1 |
| 129 | — | ≤0.063/16 | ≤0.063/1 |
| 130 | — | ≤0.063/16 | ≤0.063/1 |
| 131 | — | ≤0.063/16 | ≤0.063/1 |
| 132 | — | ≤0.063/16 | ≤0.063/1 |
| 133 | — | ≤0.063/16 | ≤0.063/1 |
| 134 | — | ≤0.063/16 | ≤0.063/1 |
| 135 | — | ≤0.063/16 | ≤0.063/1 |
| 136 | — | ≤0.063/16 | ≤0.063/1 |
| 137 | — | ≤0.063/32 | ≤0.063/2 |
| 138 | — | ≤0.063/16 | ≤0.063/2 |
| 139 | — | ≤0.063/16 | ≤0.063/2 |

TABLE 5-4

| | | | |
|---|---|---|---|
| 140 | — | ≤0.063/64 | ≤0.063/2 |
| 141 | — | ≤0.063/64 | ≤0.063/2 |
| 142 | — | ≤0.063/64 | ≤0.063/2 |
| 143 | — | ≤0.063/64 | ≤0.063/2 |
| 144 | — | ≤0.063/64 | ≤0.063/2 |
| 145 | — | ≤0.063/64 | ≤0.063/2 |
| 146 | — | ≤0.063/64 | ≤0.063/2 |
| 147 | — | ≤0.063/64 | ≤0.063/2 |
| 148 | — | ≤0.063/64 | ≤0.063/2 |
| 149 | — | 0.125/64 | ≤0.063/2 |
| 150 | — | ≤0.063/64 | ≤0.063/2 |
| 151 | — | ≤0.063/64 | ≤0.063/2 |
| 152 | — | ≤0.063/64 | ≤0.063/2 |

As disclosed above, the present invention is exemplified by the use of its preferred embodiments. However, it is understood that the scope of the present invention should be interpreted based solely on the Claims. It is also understood that any patent, any patent application, and any other references cited herein should be incorporated herein by reference in the same manner as the contents are specifically described herein.

INDUSTRIAL APPLICABILITY

The compound of the invention exhibits a potent inhibitory action against β-lactamase and is useful as a therapeutic agent and/or prophylactic agent for sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, deep skin infection, lymphangitis/lymphadenitis, secondary infection of trauma, burn injury, surgical wound, or the like, urinary tract infection, genital infection, eye infection, or odontogenic infection.

The invention claimed is:
1. A compound represented by formula (5a) or (5b):

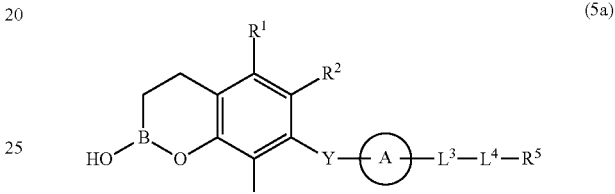

(5a)

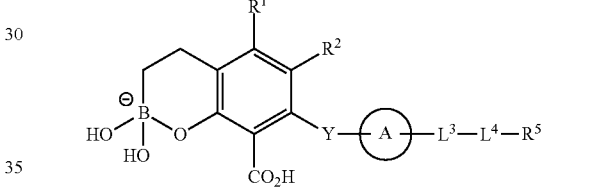

(5b)

or a pharmaceutically acceptable salt thereof,
wherein
Y is an oxygen atom,
ring A is an optionally substituted 4- to 20-membered non-aryl heterocycle,
$L^3$ is —C(=O)—,
$L^4$ is
1) a single bond,
2) a $C_{1-6}$ alkylene group,
3) a $C_{3-10}$ cycloalkylene group,
4) a $C_{6-10}$ arylene group,
5) a 5- or 6-membered heteroarylene group,
6) a 4- to 10-membered non-aryl heterocyclylene group, or
7) —C(=N—$OR^{h1}$)—,
8) —CD($NH_2$)— wherein D represents a heavy hydrogen atom
wherein each substituent from 2) to 6) is optionally substituted, and
$R^5$ is
1) a hydrogen atom,
2) a $C_{1-6}$ alkyl group,
3) a $C_{3-10}$ alicyclic group,
4) a 4- to 10-membered non-aryl heterocycle,
5) $C_{6-10}$ aryl,
6) 5- or 6-membered heteroaryl,
7) a $C_{1-6}$ alkylthio group,
wherein each substituent from 2) to 7) is optionally substituted, or
8) —$NR^{e1}OH$, $R^1$ and $R^2$ are the same or different, each independently a hydrogen atom, a halogen atom, an optionally substituted $C_{1-6}$ alkyl group, an optionally substituted $C_{1-6}$ alkoxy group, an optionally substituted $C_{1-6}$ alkylthio group, an optionally substituted 5- or 6-membered heteroaryl, or —$NR^{a3}R^{b2}$, $R^{e1}$ and are the same or different, each independently a hydrogen atom, an optionally substituted $C_{1-6}$ alkyl group, an optionally substituted $C_{3-10}$ alicyclic group, optionally substituted $C_{6-10}$ aryl, optionally substituted 5- or 6-membered heteroaryl, or an optionally substituted 4- to 10-membered non-aryl heterocycle, $R^{a3}$ and are the same or different, each independently
1) a hydrogen atom,
2) a $C_{1-6}$ alkyl group,
3) a $C_{3-10}$ alicyclic group,
4) $C_{6-10}$ aryl
5) 5- or 6-membered heteroaryl,
6) a 4- to 10-membered non-aryl heterocycle,
7) a $C_{1-6}$ alkylcarbonyl group,
8) a $C_{3-10}$ alicyclic carbonyl group,
9) a $C_{6-10}$ arylcarbonyl group,
10) a 5- or 6-membered heteroarylcarbonyl group,
11) a $C_{4-6}$ alkysulfonyl group,
12) a $C_{3-10}$ alicyclic sulfonyl group,
13) a $C_{6-10}$ arylsulfonyl group,
14) a 5- or 6-membered heteroarylsulfonyl group, or
15) —$OR^{c1}$,
wherein each substituent from 2) to 14) is optionally substituted,
$R^{c1}$ is
1) a hydrogen atom,
2) a $C_{1-6}$ alkyl group,
3) a $C_{3-10}$ alicyclic group,
4) $C_{6-10}$ aryl,
5) 5- or 6-membered heteroaryl, or
6) a 4- to 10-membered non-aryl heterocycle,
wherein each substituent from 2) to 6) is optionally substituted,
wherein a combination of $R^{a3}$ and $R^{b2}$, when attached to the same nitrogen atom, together may form an optionally substituted 4- to 10-membered nitrogen-containing non-aryl heterocycle.

2. The compound or the pharmaceutically acceptable salt thereof according to claim 1, wherein
$R^1$ and $R^2$ are the same or different, each independently a hydrogen atom, a halogen atom, a $C_{1-6}$ alkyl group, or a $C_{1-6}$ alkoxy group, wherein the $C_{1-6}$ alkyl group and the $C_{1-6}$ alkoxy group are optionally substituted with 1 to 5 halogen atoms.

3. The compound or the pharmaceutically acceptable salt thereof according to claim 1, wherein ring A is an optionally substituted 4- to 10-membered non-aryl heterocycle.

4. The compound or the pharmaceutically acceptable salt thereof according to claim 1, wherein ring A is an optionally substituted 4- to 7-membered non-aryl heterocycle.

5. The compound or the pharmaceutically acceptable salt thereof according to claim 1, wherein ring A is an optionally substituted 4- to 6-membered nitrogen-containing non-aryl heterocycle.

6. The compound or the pharmaceutically acceptable salt thereof according to claim 1, wherein $L^4$ is a single bond, —C(=N—$OR^{h1}$)—, or an optionally substituted $C_{1-6}$ alkylene group, wherein $R^{h1}$ is an optionally substituted $C_{1-6}$ alkyl group.

7. The compound or the pharmaceutically acceptable salt thereof according to claim 1, wherein $R^1$ and $R^2$ are the same or different, each independently selected from the group consisting of
1) a hydrogen atom,
2) a halogen atom,
3) a $C_1$-6 alkyl group,
4) a $C_{1-6}$ alkoxy group, and
5) a $C_{1-6}$ alkylthio group,
wherein each substituent from 3) to 5) is optionally substituted.

8. The compound or the pharmaceutically acceptable salt thereof according to claim 1, wherein $R^1$ and $R^2$ are the same or different, each independently selected from the group consisting of
1) a hydrogen atom,
2) a halogen atom, and
3) an optionally substituted $C_{1-6}$ alkyl group.

9. The compound or the pharmaceutically acceptable salt thereof according to claim 1, wherein $R^1$ and $R^2$ are both hydrogen atoms.

10. The compound or the pharmaceutically acceptable salt thereof according to claim 9, wherein the compounds of formulas (5a) and (5b) are represented by formulas (6a) and (6b), respectively:

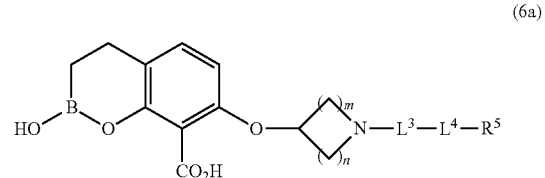

(6a)

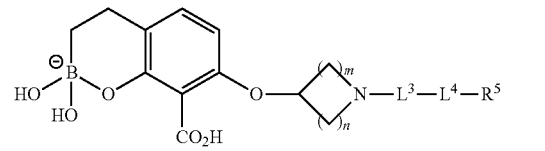

(6b)

wherein
m is an integer 1, 2, or 3,
n is an integer 1, 2, or 3, and
m+n is 2, 3, or 4.

11. The compound or the pharmaceutically acceptable salt thereof according to claim 10, wherein m is 1 or 2, n is 1 or 2, and m+n is 2 or 3.

12. The compound or the pharmaceutically acceptable salt thereof according to claim 11, wherein m is 1 and n is 1.

13. The compound or the pharmaceutically acceptable salt thereof according to claim 1, wherein $L^4$ is a single bond, or a $C_{1-6}$ alkylene group optionally substituted with —$NR^{21}R^{22}$ or =$NOR^{23}$, wherein $R^{21}$, $R^{22}$, and $R^{23}$ are each independently a hydrogen atom, an optionally substituted $C_{1-6}$ alkyl group, or an optionally substituted 4- to 10-membered non-aryl heterocyclyl carbonyl group.

14. The compound or the pharmaceutically acceptable salt thereof according to claim 13, wherein $L^4$ is a single bond, —$CH_2$—, —$CH(NH_2)$—, or —$CH(NH_2)$—$CH_2$—, wherein if an amino group is present in $L^4$, carbon that attaches to the amino group attaches to $L^3$.

15. The compound or the pharmaceutically acceptable salt thereof according to claim 13, wherein $L^4$ is a single bond, —$CH_2$—, —$C(Me)(NH_2)$—, —$CH(NHMe)$-, —CD (NH₂)—, wherein —CD(NH₂)—, wherein D represents a heavy hydrogen atom, —CH(NH₂)—, or —CH₂CH₂—.

16. The compound or the pharmaceutically acceptable salt thereof according to claim 15, wherein L⁴ is a single bond, —CH₂—, or —CH(NH₂)—.

17. The compound or the pharmaceutically acceptable salt thereof according to claim 1, wherein R⁵ is a hydrogen atom, an optionally substituted $C_{1-6}$ alkyl group, an optionally substituted 4- to 10-membered non-aryl heterocycle, optionally substituted $C_{6-10}$ aryl, optionally substituted 5- or 6-membered heteroaryl, an optionally substituted $C_{1-6}$ alkylthio group, or —NR$^{e1}$OH, wherein R$^{e1}$ is a hydrogen atom or an optionally substituted $C_{1-6}$ alkyl group.

18. The compound or the pharmaceutically acceptable salt thereof according to claim 17, wherein R⁵ is optionally substituted 5- or 6-membered heteroaryl or optionally substituted $C_{6-10}$ aryl.

19. The compound or the pharmaceutically acceptable salt thereof according to claim 17, wherein R⁵ is optionally substituted 5- or 6-membered heteroaryl.

20. The compound or the pharmaceutically acceptable salt thereof according to claim 16, wherein R⁵ is an optionally substituted 4- to 10-membered non-aryl heterocycle.

21. The compound or the pharmaceutically acceptable salt thereof according to claim 16, wherein L⁴ is a single bond, and R⁵ is —NR$^{e1}$OH, wherein R$^{e1}$ is a hydrogen atom or an optionally substituted $C_{1-6}$ alkyl group.

22. The compound or the pharmaceutically acceptable salt thereof according to claim 1, wherein L⁴ is
1) —(CH₂)$_p$—CR¹⁰(NHR¹¹)—,
2) —(CH₂)$_q$—CR¹²R¹³—, or
3) —(CH₂)$_p$—CR¹⁰(NHR¹¹)—(CH₂)$_q$—CR¹²R¹³—
wherein p and q are independently 0 or 1,
R¹⁰ is
1) a hydrogen atom,
2) a carboxyl group, or
3) —C(=O)NR$^{10a}$R$^{10b}$,
R¹¹ is
1) a hydrogen atom,
2) —C(=O)R$^{11a}$, or
3) an optionally substituted 5- or 6-membered non-aryl heterocyclyl carbonyl group, wherein if R¹⁰ is —C(=O)NR$^{10a}$R$^{10b}$, R$^{10b}$ and R¹¹ together may form —CH₂CH₂—,
R¹² is
1) a hydrogen atom, or
2) an optionally substituted $C_{1-4}$ alkyl group,
R¹³ is
1) a hydrogen atom,
2) a hydroxyl group,
3) an optionally substituted $C_{1-6}$ alkyl group,
4) a sulfanyl group,
5) a carboxyl group,
6) an optionally substituted $C_{1-4}$ alkylthio group,
7) —NR$^{13a}$R$^{13b}$,
8) —NR$^{13a}$—C(=O)R$^{13b}$,
9) an optionally substituted 5- or 6-membered non-aryl heterocyclyl carbonylamino group,
10) —NR$^{13a}$—C(=O)NR$^{13b}$R$^{13c}$,
11) —C(=O)NR$^{13a}$R$^{13b}$,
12) —C(=O)NR$^{13a}$OR$^{13b}$,
13) —S(=O)₂—R$^{13a}$,
14) —S(=O)₂—NR$^{13a}$R$^{13b}$,
15) —C(=O)NR$^{13a}$—S(=O)₂—R$^{13b}$, or
16) —C(=O)NR$^{13a}$—S(=O)₂—NR$^{13b}$R$^{13c}$, and R$^{10a}$, R$^{10b}$, R$^{11a}$, R$^{13a}$, R$^{13b}$, and R$^{13c}$ are each independently a hydrogen atom or an optionally substituted $C_{1-4}$ alkyl group.

23. The compound or the pharmaceutically acceptable salt thereof according to claim 22, wherein R⁵ is a hydrogen atom or an optionally substituted $C_{1-4}$ alkyl group.

24. The compound or the pharmaceutically acceptable salt thereof according to claim 19, wherein
R⁵ is selected from the group consisting of

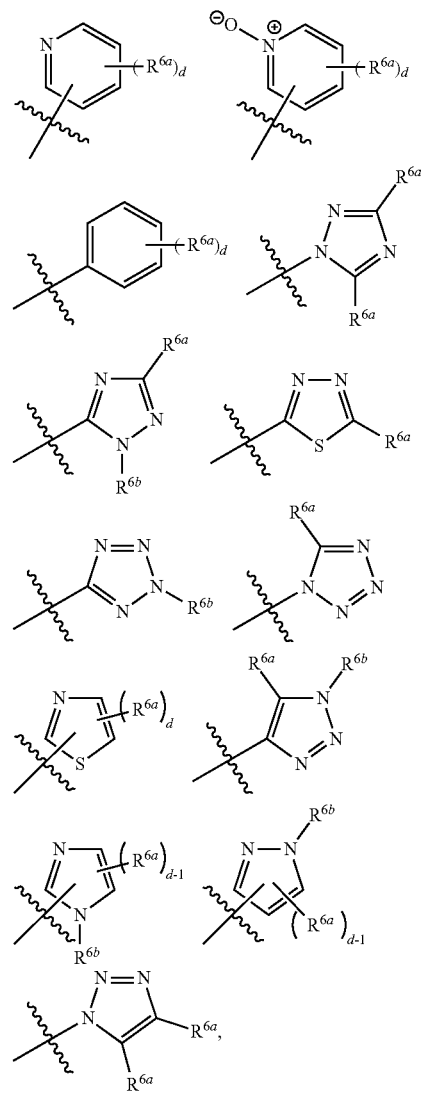

and subscript d is the number of substitutable positions on a ring of R⁵,
each R$^{6a}$ is independently selected from the group consisting of
1) a hydrogen atom,
2) a hydroxyl group,
3) a cyano group,
4) a nitro group,
5) halogen,
6) a $C_{1-4}$ alkyl group,
7) a $C_{3-10}$ alicyclic group,
8) a $C_{1-4}$ alkoxy group,
9) a $C_{3-10}$ alicyclic oxy group, 10) a $C_{6-10}$ aryloxy group,
11) a 5- or 6-membered heteroaryloxy group,
12) a 4- to 10-membered non-aryl heterocyclyl oxy group,
wherein each substituent from 6) to 12) is optionally substituted,
13) —$SO_2$—$NR^{e2}R^{f2}$,
14) —$NR^{g2}$—$CR^{e2}(=NR^{f2})$,
15) —$NR^{g2}$—$CR^{g2}(=N—OR^{f2})$,
16) —$NR^{h2}$—$C(=NR^{g2})NR^{e2}R^{f2}$,
17) —$NR^{h2}$—$C(=N—OR^{g2})NR^{e2}R^{f2}$,
18) —$NR^{i2}$—$C(=NR^{h2})NR^{g2}$—$NR^{e2}R^{f2}$,
19) —$NR^{i2}$—$C(=N—OR^{h2})NR^{g2}$—$NR^{e2}R^{f2}$,
20) —$C(=NR^{e2})R^{f2}$,
21) —$C(=N—OR^{e2})R^{f2}$,
22) —$C(=NR^{h2})$—$NR^{e2}R^{f2}$,
23) —$C(=NR^{h2})NR^{g2}$—$NR^{e2}R^{f2}$,
24) —$C(=N—OR^{h2})NR^{g2}$—$NR^{e2}R^{f2}$,
25) —$NR^{e2}R^{f2}$,
26) —$NR^{g2}$—$NR^{e2}R^{f2}$,
27) —$NR^{e2}OR^{f2}$,
28) —$NR^{e2}$—$C(=O)R^{f2}$,
29) —$C(=O)NR^{e2}R^{f2}$,
30) —$C(=O)NR^{e2}OR^{f2}$,
31) —$C(=O)NR^{g2}$—$NR^{e2}R^{f2}$,
32) —$C(=O)R^{e2}$,
33) —$C(=O)OR^{e2}$, and
34) —$C(=N—OR^{h2})NR^{e2}R^{f2}$, and
each $R^{6b}$ is independently selected from the group consisting of
1) a hydrogen atom,
2) a hydroxyl group,
3) A $C_{1-4}$ alkyl group
wherein the alkyl group is optionally substituted,
4) a $C_{3-10}$ alicyclic group
wherein the alicyclic group is optionally substituted,
5) —$C(=NR^{e2})R^{f2}$,
6) —$C(=N—OR^{e2})R^{f2}$,
7) —$SO_2$—$NR^{e2}R^{f2}$,
8) —$C(=NR^{h2})$—$N^{e2}R^{f2}$,
9) —$C(=NR^{h2})NR^{g2}$—$NR^{e2}R^{f2}$,
10) —$C(=N—OR^{h2})NR^{g2}$—$NR^{e2}R^{f2}$,
11) —$C(=O)NR^{e2}R^{f2}$,
12) —$C(=O)NR^{e2}OR^{f2}$,
13) —$C(=O)NR^{g2}$—$NR^{e2}R^{f2}$,
14) —$C(=O)R^{e2}$, and
15) —$C(=N—OR^{h2})NR^{e2}Rf^2$.

25. The compound or the pharmaceutically acceptable salt thereof according to claim 24, wherein $R^5$ is 5- or 6-membered aryl or heteroaryl selected from the group consisting of

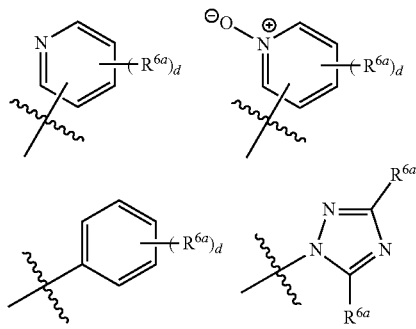

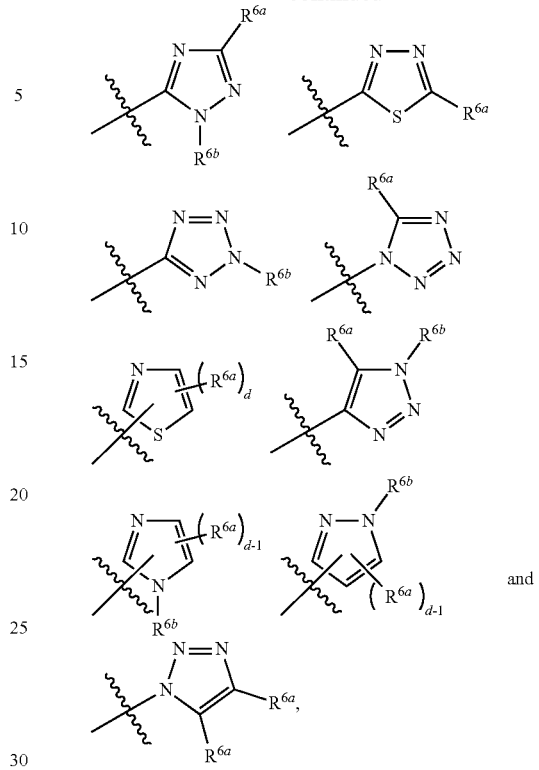

subscript d is the number of substitutable positions on a ring of $R^5$,
each $R^{6a}$ is independently selected from the group consisting of
1) a hydrogen atom,
2) A hydroxyl group,
3) halogen,
4) A $C_{1-6}$ alkyl group
wherein the alkyl group is optionally substituted with $NR^{e2}R^{f2}$, a 5- or 6-membered non-aryl heterocycle, —$C(=O)OR^{f2}$, or a hydroxyl group,
5) a $C_{1-4}$ alkoxy group
6) —$NR^{e2}R^{f2}$, and
7) —$C(=O)OR^{e2}$, and
each $R^{6b}$ is independently selected from the group consisting of
1) a hydrogen atom,
2) a hydroxyl group, and
3) a $C_{1-4}$ alkyl group
wherein the alkyl group is optionally substituted with $NR^{e2}R^{f2}$, —$C(=O)NR^{e2}R^{f2}$, —$C(=O)OR^{f2}$, or a hydroxyl group.

26. The compound or the pharmaceutically acceptable salt thereof according to claim 25, wherein $R^{e2}$ and $R^{f2}$ are the same or different, each independently a hydrogen atom, an optionally substituted $C_{1-6}$ alkyl group, or an optionally substituted $C_{3-10}$ alicyclic group.

27. The compound or the pharmaceutically acceptable salt thereof according to claim 26, wherein $R^{e2}$ and $R^{f2}$ are the same or different, each independently a hydrogen atom or an optionally substituted $C_{1-6}$ alkyl group.

28. The compound or the pharmaceutically acceptable salt thereof according to claim 27, wherein $R^{e2}$ and $R^{f2}$ are hydrogen atoms.

29. The compound or the pharmaceutically acceptable salt thereof according to claim 27, wherein $R^{6a}$ is —$NR^{e2}R^{f2}$, and one of $R^{e2}$ and $R^{f2}$ is a hydrogen atom and the other is a $C_{1-4}$ alkyl group (wherein the alkyl group is optionally substituted with an amino group or a hydroxyl group).

30. The compound or the pharmaceutically acceptable salt thereof according to claim 20, wherein $R^5$ is a 4- to 6-membered non-aryl heterocycle selected from the group consisting of

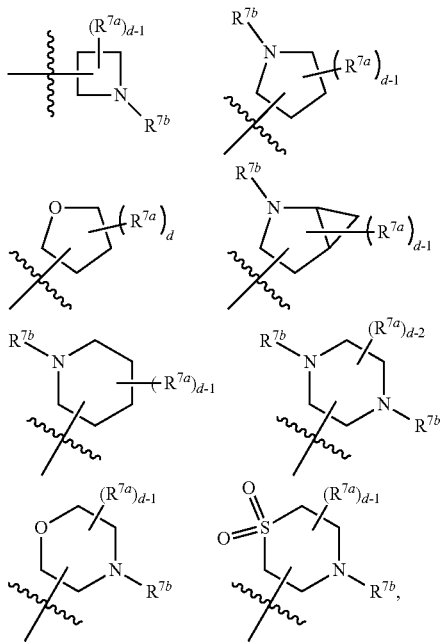

subscript d is the number of substitutable positions on a ring of $R^5$, each $R^{7a}$ is independently selected from the group consisting of
1) a hydrogen atom,
2) a hydroxyl group,
3) a cyano group,
4) halogen,
5) a $C_{1-4}$ alkyl group,
6) a $C_{3-10}$ alicyclic group,
7) a $C_{1-4}$ alkoxy group,
8) a $C_{3-10}$ alicyclic oxy group,
9) a $C_{6-10}$ aryloxy group,
10) a 5- or 6-membered heteroaryloxy group,
11) a 4- to 10-membered non-aryl heterocyclyl oxy group,
wherein each substituent from 5) to 11) is optionally substituted,
12) —$SO_2$—$NR^{e3}R^{f3}$,
13) —$NR^{g2}$—$CR^{e3}(=NR^{f3})$,
14) —$NR^{g2}$—$CR^{e3}(=N-OR^{f3})$,
15) —$NR^{h2}$—$C(=NR^{g2})NR^{e3}R^{f3}$,
16) —$NR^{h2}$—$C(=N-OR^{g2})NR^{e3}R^{f3}$,
17) —$NR^{i2}$—$C(=NR^{h2})NR^{g2}$—$NR^{e3}R^{f3}$,
18) —$NR^{i2}$—$C(=N-OR^{h2})NR^{g2}$—$NR^{g3}R^{f3}$,
19) —$C(=NR^{e3})R^{f3}$,
20) —$C(=N-OR^{e3})R^{f3}$,
21) —$C(=NR^{h2})$—$NR^{e3}R^{f3}$,
22) —$C(=NR^{h2})NR^{g2}$—$NR^{e3}R^{f3}$,
23) —$C(=N-OR^{h2})NR^{g2}$—$NR^{e3}R^{f3}$,
24) —$NR^{e3}R^{f3}$,
25) —$NR^{g2}$—$NR^{e3}R^{f3}$,
26) —$NR^{e3}OR^{f3}$,
27) —$NR^{e3}$—$C(=O)R^{f3}$,
28) —$C(=O)NR^{e3}R^{f3}$,
29) —$C(=O)NR^{e3}OR^{f3}$,
30) —$C(=O)NR^{g2}$—$NR^{e3}R^{f3}$,
31) —$C(=O)R^{e3}$,
32) —$C(=O)OR^{e3}$, and
33) —$C(=N-OR^{h2})NR^{e3}R^{f3}$, each $R^{7b}$ is independently selected from the group consisting of
1) a hydrogen atom,
2) a hydroxyl group,
3) a $C_{1-4}$ alkyl group
wherein the alkyl group is optionally substituted,
4) a $C_{3-10}$ alicyclic group
wherein the alicyclic group is optionally substituted,
5) —$C(=NR^{e3})R^{f3}$,
6) —$C(=N-OR^{e3})R^{f3}$,
7) —$SO_2$—$NR^{e3}R^{f3}$,
8) —$C(=NR^{h2})$—$NR^{e3}R^{f3}$,
9) —$C(=NR^{h2})NR^{g2}$—$NR^{e3}R^{f3}$,
10) —$C(=N-OR^{h2})NR^{g2}$—$NR^{e3}R^{f3}$,
11) —$C(=O)NR^{e3}R^{f3}$,
12) —$C(=O)NR^{e3}OR^{f3}$,
13) —$C(=O)NR^{g2}$—$NR^{e3}R^{f3}$,
14) —$C(=O)R^{e3}$, and
15) —$C(=N-OR^{h2})NR^{e3}R^{f3}$, and $R^{e3}$ and $R^{f3}$ are the same or different, each independently hydrogen atom, an optionally substituted $C_{1-6}$ alkyl group, an optionally substituted $C_{3-10}$ alicyclic group, optionally substituted $C_{6-10}$ aryl, optionally substituted 5- or 6-membered heteroaryl, or an optionally substituted 4- to 10-membered non-aryl heterocycle, a combination of $R^{e3}$ and $R^{f3}$, when attached to the same nitrogen atom, together may form an optionally substituted 4- to 10-membered nitrogen-containing non-aryl heterocycle.

31. The compound or the pharmaceutically acceptable salt thereof according to claim 30, wherein $R^5$ is a 4- to 6-membered non-aryl heterocycle selected from the group consisting of

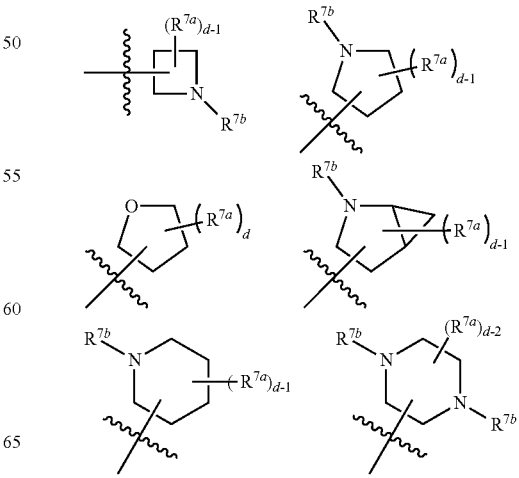

-continued

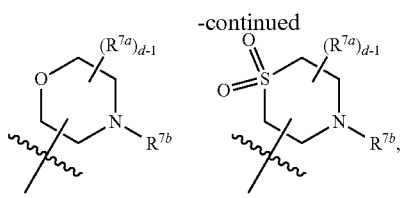

subscript d is the number of substitutable positions on a ring of $R^5$,
each $R^{7a}$ is independently selected from the group consisting of
1) a hydrogen atom,
2) a hydroxyl group,
3) halogen,
4) a $C_{1-4}$ alkyl group
wherein the alkyl group is optionally substituted with $NR^{e3}R^{f3}$, a 5- or 6-membered non-aryl heterocycle, $-C(=O)OR^{f3}$, or a hydroxyl group,
5) A $C_{1-4}$ alkoxy group
6) $-NR^{e3}R^{f3}$,
7) $-C(=O)OR^{e3}$,
8) $C_{6-10}$ aryl, and
9) $-C(=O)NR^{e3}R^{f3}$,
each $R^{7b}$ is independently selected from the group consisting of
1) a hydrogen atom,
2) a hydroxyl group, and
3) a $C_{1-4}$ alkyl group
wherein the alkyl group is optionally substituted with $NR^{e2}R^{f2}$, $-C(=O)OR^{f2}$, or a hydroxyl group, and
$R^{e3}$ and $R^{f3}$ wherein $R^{e3}$ and $R^{f3}$ are the same or different, each independently a hydrogen atom, an optionally substituted $C_{1-6}$ alkyl group, or an optionally substituted $C_{3-10}$ alicyclic group.

32. The compound or the pharmaceutically acceptable salt thereof according to claim 23, wherein
$L^4$ is $-CH(NH_2)-CHR^{13}-$, wherein carbon that attaches to the $NH_2$ attaches to $L^3$,
$R^5$ is a hydrogen atom, and
$R^{13}$ is
1) $-NH-C(=O)CH_3$,
2) $-NH-C(=O)NH_2$,
3) $-NH-C(=O)CH(NH_2)-CH_2C(=O)NH_2$,
4) $-NH-C(=O)CH_2-NH_2$,
5) $-NH-C(=O)CH(NH_2)-CH_2OH$, or
6) a pyrrolidin-2-ylcarbonylamino group.

33. The compound or the pharmaceutically acceptable salt thereof according to claim 23, wherein $L^4$ is $-CH(NH_2)-CR^{12}R^{13}-$, wherein carbon that attaches to the $NH_2$ attaches to $L^3$,
$R^5$ is a hydrogen atom or methyl,
$R^{12}$ is a hydrogen atom or methyl, and
$R^{13}$ is a benzylthio group or a sulfanyl group.

34. The compound or the pharmaceutically acceptable salt thereof according to claim 23, wherein
$L^4$ is $-CH(NH_2)-(CH_2)_q-CHR^3-$, wherein q is 0 or 1, and carbon that attaches to the $NH_2$ attaches to $L^3$,
$R^5$ is a hydrogen atom, and
$R^{13}$ is
1) a carboxyl group,
2) $-C(=O)NH_2$,
3) $-C(=O)NH(CH_3)$,
4) $-C(=O)N(CH_3)_2$,
5) $-C(=O)NH-(CH_2)_2-OH$,
6) $-C(=O)NH-(CH_2)_2-NH_2$,
7) $-C(=O)NH-S(=O)_2-CH_3$,
8) $-C(=O)NHOH$,
9) $-S(=O)_2-NH_2$,
10) $-S(=O)_2-CH_3$, or
11) a hydroxyl group.

35. The compound or the pharmaceutically acceptable salt thereof according to claim 23, wherein
$L^4$ is $-CH(NHR^{11})-CH_2-$, wherein carbon that attaches to the $NHR^{11}$ attaches to $L^3$,
$R^5$ is hydrogen, and
$R^{11}$ is
1) $-C(=O)CH(NH_2)-CH_2C(=O)NH_2$,
2) $-C(=O)CH_2-NH_2-$,
3) $-C(=O)CH(CH_3)-NH_2$,
4) $-C(=O)CH(NH_2)-CH_2OH$, or
5) pyrrolidin-2-ylcarbonyl.

36. The compound or the pharmaceutically acceptable salt thereof according to claim 23, wherein
$L^4$ is $-CH(NHR^{11})-CH(COOH)-$, wherein carbon that attaches to the $NHR^{11}$ attaches to $L^3$,
$R^5$ is hydrogen, and
$R^{11}$ is
1) $-C(=O)CH(NH_2)-CH_2C(=O)NH_2$,
2) $-C(=O)CH_2-NH_2$,
3) $-C(=O)CH(CH_3)-NH_2$,
4) $-C(=O)CH(NH_2)-CH_2OH$, or
5) pyrrolidin-2-ylcarbonyl.

37. The compound or the pharmaceutically acceptable salt thereof according to claim 23, wherein
$L^4$ is $-CHR^{13}-$ or $-CH_2-CHR^{13}-$,
$R^5$ is hydrogen, and
$R^{13}$ is $-C(=O)NH_2$ or $-C(=O)NHOH$.

38. The compound or the pharmaceutically acceptable salt thereof according to claim 23, wherein
$L^4$ is $-CH_2-CR^{10}(NH_2)-$, wherein the $CH_2$ attaches to $L^3$,
$R^5$ is hydrogen, and
$R^{10}$ is a carboxy group or $-C(=O)NH_2$.

39. The compound or the pharmaceutically acceptable salt thereof according to claim 23, wherein
$L^4$ is $-(CH_2)_p-CR^{10}(NHR^{11})-(CH_2)_q-CHR^{13}-$ or $-CHR^{13}-(CH_2)_q-CR^{10}(NHR^{11})(CH_2)_p-$, wherein q is 0 or 1,
$R^5$ is hydrogen,
(1) if $L^4$ is $-CHR^{13}-(CH_2)_q-CR^{10}(NHR^{11})-(CH_2)_p-$, carbon of the $-CHR^{13}-$ group attaches to $L^3$,
p is 0,
$R^{10}$ is a hydrogen atom, a carboxyl group, or $-C(=O)NHR^{10b}$,
$R^{11}$ is a hydrogen atom,
$R^{10b}$ is a hydrogen atom,
wherein if $R^{10}$ is $-C(=O)NHR^{10b}$, $R^{10b}$ and $R^{11}$ together may form $-CH_2CH_2-$, and
$R^{13}$ is a hydrogen atom, and
(2) if $L^4$ is $-(CH_2)_p-CR^{10}(NHR^{11})-(CH_2)_q-CHR^{13}-$, carbon of the $-(CH_2)_p-$ group attaches to $L^3$,
p is 1,
$R^{10}$ and $R^{11}$ are both hydrogen atoms,
$R^{13}$ is a carboxyl group or $-C(=O)NR^{13a}R^{13b}$, and
$R^{13a}$ and $R^{13b}$ are each independently a hydrogen atom or an optionally substituted $C_{1-6}$ alkyl group.

40. The compound or the pharmaceutically acceptable salt thereof according to claim 23, wherein
$L^4$ is $-CR^{12}(NH_2)-$,
$R^{12}$ is a hydrogen atom or a methyl group, and
$R^5$ is a $C_{1-4}$ alkyl group optionally substituted with a hydroxyl group.

41. The compound or the pharmaceutically acceptable salt thereof according to claim 1, selected from the group consisting of:

7-[(1-acetylazetidin-3-yl)oxy]-2-hydroxy-3,4-dihydro-2H-1,2-benzoxaborinine-8-carboxylic

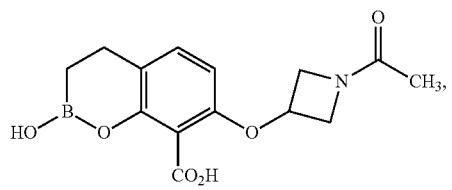 [SMILES: CC(=O)N1CC(Oc2ccc3c(c2C(=O)O)OB(O)CC3)C1]

8-[(1-acetylazetidin-3-yl)oxy]-4,4-dihydroxy-5-oxa-4-boranuidabicyclo[4.4.0]deca-1(6),7,9-triene-7-carboxylic acid

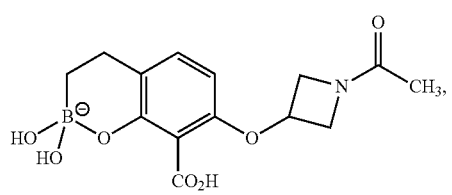 [SMILES: CC(=O)N1CC(Oc2ccc3c(c2C(=O)O)O[B-](O)(O)CC3)C1]

2-hydroxy-7-({1-[(1H-imidazol-5-yl)acetyl]azetidin-3-yl}oxy)-3,4-dihydro-2H-1,2-benzoxaborinine-8-carboxylic acid

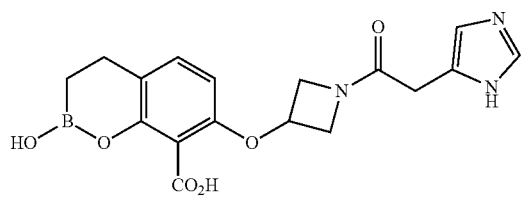

4,4-dihydroxy-8-({1-[(1H-imidazol-5-yl)acetyl]azetidin-3-yl}oxy)-5-oxa-4-boranuidabicyclo[4.4.0]deca-1(6),7,9-triene-7-carboxylic acid

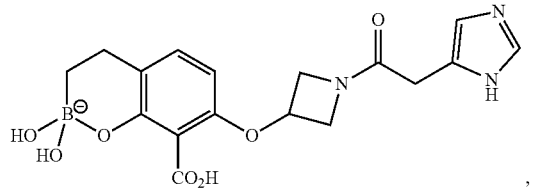 [SMILES: O=C(O)c1c(OC2CN(C(=O)Cc3cnc[nH]3)C2)ccc2c1O[B-](O)(O)CC2]

7-({1-[(2R)-2-amino-2-(4-hydroxyphenyl)acetyl]azetidin-3-yl}oxy)-4-hydroxy-3,4-dihydro-2H-1,2-benzoxaborinine-8-carboxylic acid

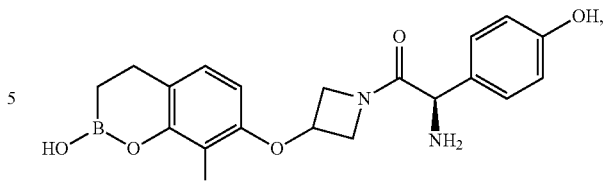

8-({1-[(2R)-2-amino-2-(4-hydroxyphenyl)acetyl]azetidin-3-yl}oxy)-4,4-dihydroxy-5-oxa-4-boranuidabicyclo[4.4.0]deca-1(6),7,9-triene-7-carboxylic acid

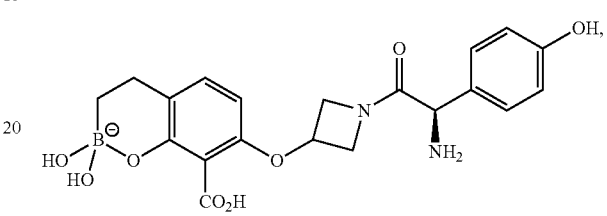

7-({1-[(2-amino-1,3-thiazol-4-yl)(methoxyimino)acetyl]azetidin-3-yl}oxy)-2-hydroxy-3,4-dihydro-2H-1,2-benzoxaborinine-8-carboxylic acid

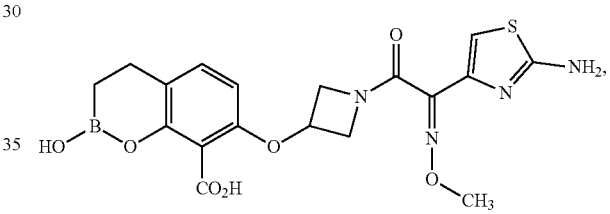

8-({1-[(2-amino-1,3-thiazol-4-yl)(methoxyimino)acetyl]azetidin-3-yl}oxy)-4,4-dihydroxy-5-oxa-4-boranuidabicyclo[4.4.0]deca-1(6),7,9-triene-7-carboxylic acid

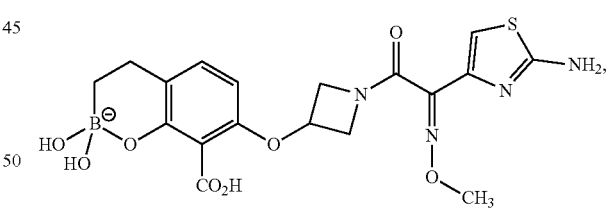

2-hydroxy-7-{[1-(pyridine-2-carbonyl)azetidin-3-yl]oxy}-3,4-dihydro-2H-1,2-benzoxaborinine-8-carboxylic acid

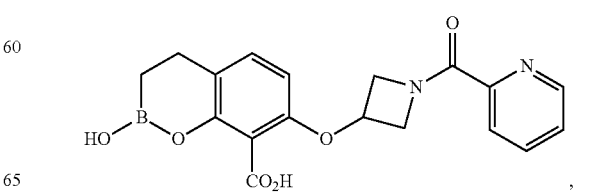

693

4,4-dihydroxy-8-{[1-(pyridine-2-carbonyl)azetidin-3-yl]oxy}-5-oxa-4-boranuidabicyclo[4.4.0]deca-1(6),7,9-triene-7-carboxylic acid

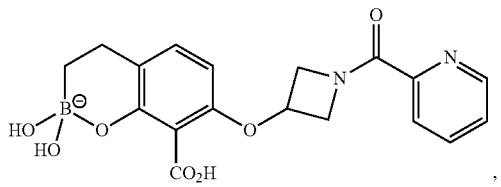 [SMILES: O=C(O)c1c(OC2CN(C(=O)c3ccccn3)C2)ccc2c1O[B-](O)(O)CC2]
, 2-hydroxy-7-({1-[(methylsulfanyl)acetyl]azetidin-3-yl}oxy)-3,4-dihydro-2H-1,2-benzoxaborinine-8-carboxylic acid

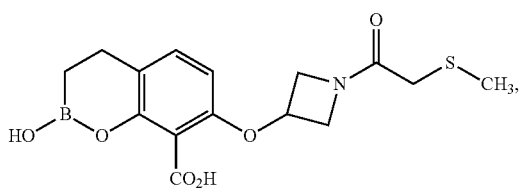 [SMILES: CSCC(=O)N1CC(Oc2ccc3c(c2C(=O)O)OB(O)CC3)C1]
, 4,4-dihydroxy-8-({1-[(methylsulfanyl)acetyl]azetidin-3-yl}oxy)-5-oxa-4-boranuidabicyclo[4.4.0]deca-1(6),7,9-triene-7-carboxylic acid

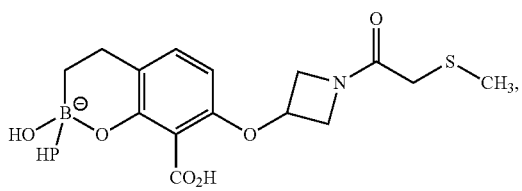
, 2-hydroxy-7-{[1-(1H-1,2,4-triazole-3-carbonyl)azetidin-3-yl]oxy}-3,4-dihydro-2H-1,2-benzoxaborinine-8-carboxylic acid

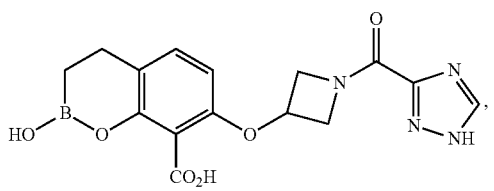 [SMILES: O=C(O)c1c(OC2CN(C(=O)c3nc[nH]n3)C2)ccc2c1OB(O)CC2]
, 4,4-dihydroxy-8-{[1-(1H-1,2,4-triazole-3-carbonyl)azetidin-3-yl]oxy}-5-oxa-4-boranuidabicyclo[4.4.0]deca-1(6),7,9-triene-7-carboxylic acid

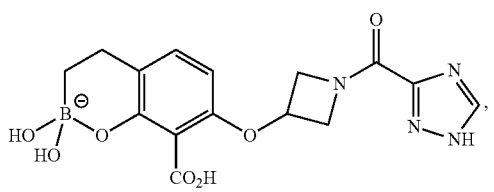 [SMILES: O=C(O)c1c(OC2CN(C(=O)c3nc[nH]n3)C2)ccc2c1O[B-](O)(O)CC2]
,

694

2-hydroxy-7-{[1-(1-oxido-2-pyridinylcarbonyl)azetidin-3-yl]oxy}-3,4-dihydro-2H-1,2-benzoxaborinine-8-carboxylic acid

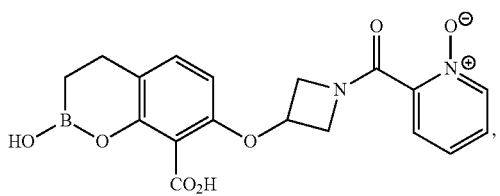 [SMILES: O=C(O)c1c(OC2CN(C(=O)c3cccc[n+]3[O-])C2)ccc2c1OB(O)CC2]
, 4,4-dihydroxy-8-{[1-(1-oxido-2-pyridinylcarbonyl)azetidin-3-yl]oxy}-5-oxa-4-boranuidabicyclo[4.4.0]deca-1(6),7,9-triene-7-carboxylic acid

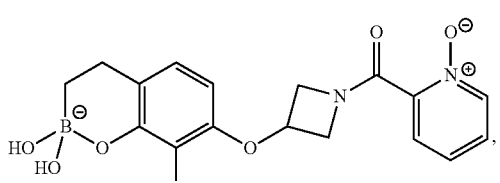
, 7-({1-[(2R)-2-amino-2-phenylacetyl]azetidin-3-yl}oxy)-2-hydroxy-3,4-dihydro-2H-1,2-benzoxaborinine-8-carboxylic acid

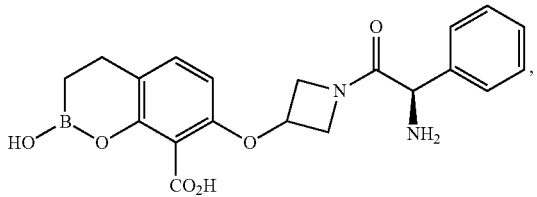 [SMILES: N[C@@H](C(=O)N1CC(Oc2ccc3c(c2C(=O)O)OB(O)CC3)C1)c1ccccc1]
, 8-({1-[(2R)-2-amino-2-phenylacetyl]azetidin-3-yl}oxy)-4,4-dihydroxy-5-oxa-4-boranuidabicyclo[4.4.0]deca-1(6),7,9-triene-7-carboxylic acid

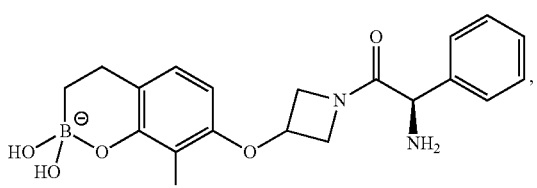
,

7-[(1-benzoylazetidin-3-yl)oxy]-2-hydroxy-3,4-dihydro-2H-1,2-benzoxaborinine-8-carboxylic acid

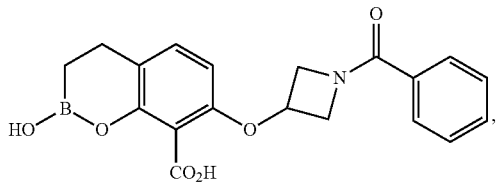

8-[(1-benzoylazetidin-3-yl)oxy]-4,4-dihydroxy-5-oxa-4-boranuidabicyclo[4.4.0]deca-1(6),7,9-triene-7-carboxylic acid

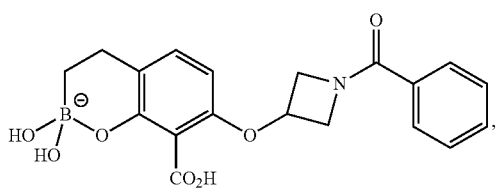

2-hydroxy-7-{[1-(pyridine-3-carbonyl)azetidin-3-yl]oxy}-3,4-dihydro-2H-1,2-benzoxaborinine-8-carboxylic acid

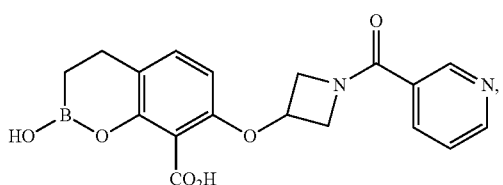

4,4-dihydroxy-8-{[1-(pyridine-3-carbonyl)azetidin-3-yl]oxy}-5-oxa-4-boranuidabicyclo[4.4.0]deca-1(6),7,9-triene-7-carboxylic acid

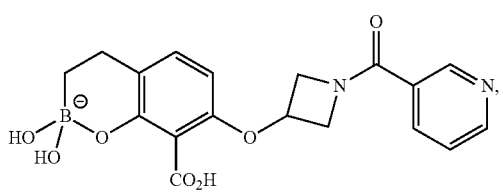 [SMILES: O=C(O)c1c(OC2CN(C(=O)c3cccnc3)C2)ccc2c1O[B-](O)(O)CC2]

2-hydroxy-7-({1-[(pyridin-2-yl)acetyl]azetidin-3-yl}oxy)-3,4-dihydro-2H-1,2-benzoxaborinine-8-carboxylic acid

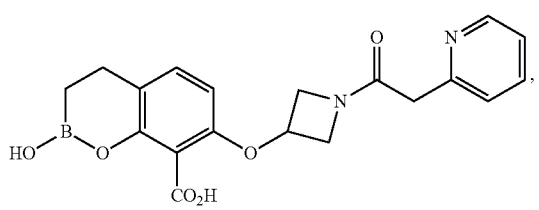

4,4-dihydroxy-8-({1-[(pyridin-2-yl)acetyl]azetidin-3-yl}oxy)-5-oxa-4-boranuidabicyclo[4.4.0]deca-1(6),7,9-triene-7-carboxylic acid

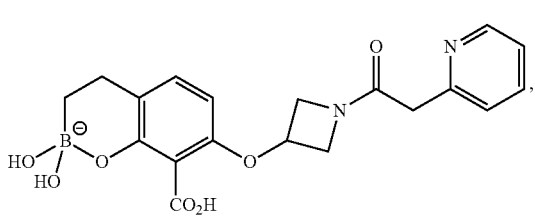

2-hydroxy-7-({1-[(pyridin-3-yl)acetyl]azetidin-3-yl}oxy)-3,4-dihydro-2H-1,2-benzoxaborinine-8-carboxylic acid

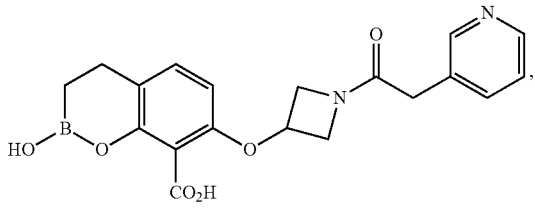 [SMILES: O=C(O)c1c(OC2CN(C(=O)Cc3cccnc3)C2)ccc2c1OB(O)CC2]

4,4-dihydroxy-8-({1-[(pyridin-3-yl)acetyl]azetidin-3-yl}oxy)-5-oxa-4-boranuidabicyclo[4.4.0]deca-1(6),7,9-triene-7-carboxylic acid

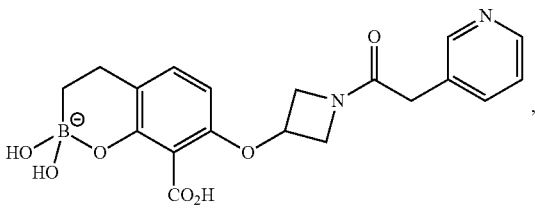 [SMILES: O=C(O)c1c(OC2CN(C(=O)Cc3cccnc3)C2)ccc2c1O[B-](O)(O)CC2]

7-({1-[(2S)-2-amino-2-phenylacetyl]azetidin-3-yl}oxy)-2-hydroxy-3,4-dihydro-2H-1,2-benzoxaborinine-8-carboxylic acid

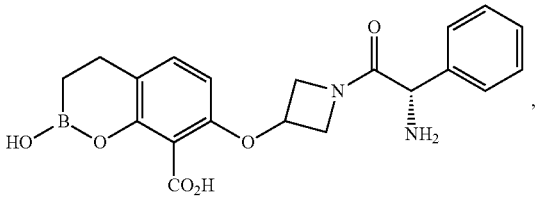 [SMILES: N[C@H](C(=O)N1CC(Oc2ccc3c(c2C(=O)O)OB(O)CC3)C1)c1ccccc1]

697

8-({1-[(2S)-2-amino-2-phenylacetyl]azetidin-3-yl}oxy)-4,4-dihydroxy-5-oxa-4-boranuidabicyclo[4.4.0]deca-1(6),7,9-triene-7-carboxylic acid

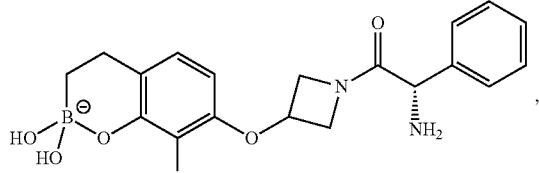

2-hydroxy-7-({1-[(pyridin-4-yl)acetyl]azetidin-3-yl}oxy)-3,4-dihydro-2H-1,2-benzoxaborinine-8-carboxylic acid

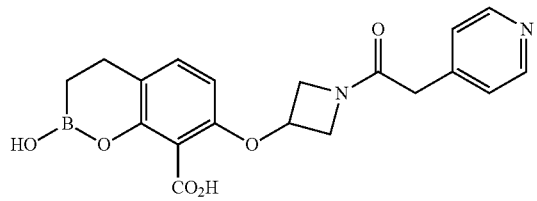 [SMILES: O=C(O)c1c(OC2CN(C(=O)Cc3ccncc3)C2)ccc2c1OB(O)CC2]

4,4-dihydroxy-8-({1-[(pyridin-4-yl)acetyl]azetidin-3-yl}oxy)-5-oxa-4-boranuidabicyclo[4.4.0]deca-1(6),7,9-triene-7-carboxylic acid

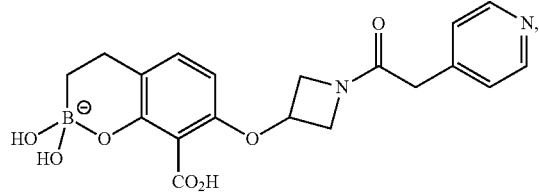

2-hydroxy-7-({1-[(4-hydroxyphenyl)acetyl]azetidin-3-yl}oxy)-3,4-dihydro-2H-1,2-benzoxaborinine-8-carboxylic acid

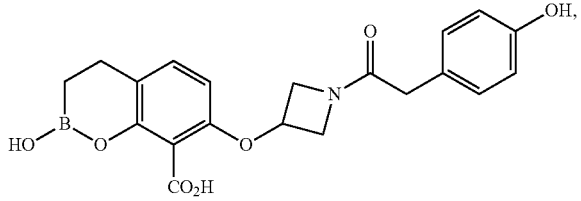 [SMILES: O=C(O)c1c(OC2CN(C(=O)Cc3ccc(O)cc3)C2)ccc2c1OB(O)CC2]

4,4-dihydroxy-8-({1-[(4-hydroxyphenyl)acetyl]azetidin-3-yl}oxy)-5-oxa-4-boranuidabicyclo[4.4.0]deca-1(6),7,9-triene-7-carboxylic acid

698

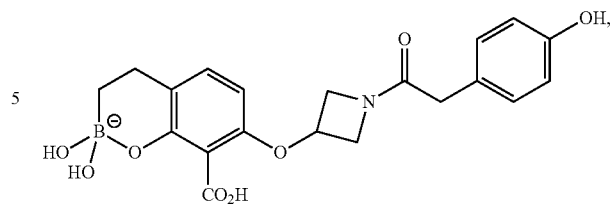

2-hydroxy-7-({1-[(1H-1,2,4-triazol-1-yl)acetyl]azetidin-3-yl}oxy)-3,4-dihydro-2H-1,2-benzoxaborinine-8-carboxylic acid

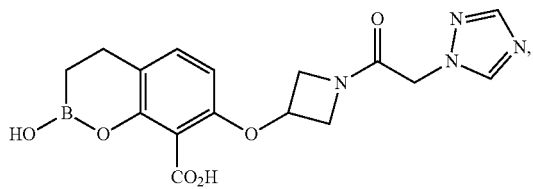

4,4-dihydroxy-8-({1-[(1H-1,2,4-triazol-1-yl)acetyl]azetidin-3-yl}oxy)-5-oxa-4-boranuidabicyclo[4.4.0]deca-1(6),7,9-triene-7-carboxylic acid

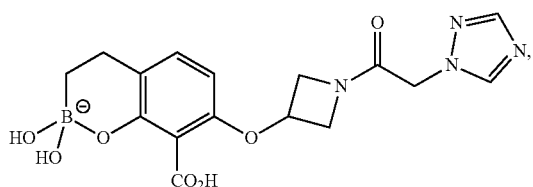

7-({1-[amino(1H-imidazol-5-yl)acetyl]azetidin-3-yl}oxy)-2-hydroxy-3,4-dihydro-2H-1,2-benzoxaborinine-8-carboxylic acid

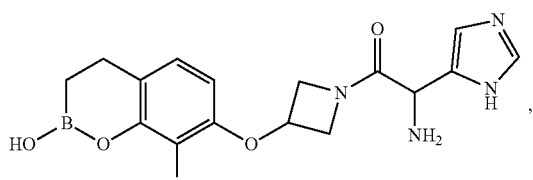

8-({1-[amino(1H-imidazol-5-yl)acetyl]azetidin-3-yl}oxy)-4,4-dihydroxy-5-oxa-4-boranuidabicyclo[4.4.0]deca-1(6),7,9-triene-7-carboxylic acid

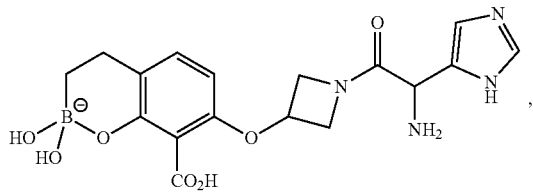

2-hydroxy-7-{[1-(phenylacetyl)azetidin-3-yl]oxy}-3,4-dihydro-2H-1,2-benzoxaborinine-8-carboxylic acid

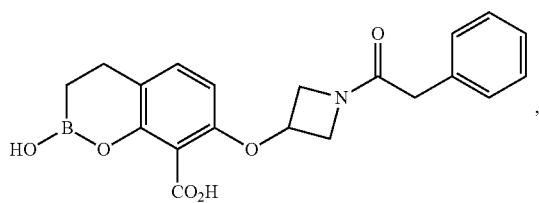 [SMILES: O=C(O)c1c(OC2CN(C(=O)Cc3ccccc3)C2)ccc2c1OB(O)CC2]

4,4-dihydroxy-8-{[1-(phenylacetyl)azetidin-3-yl]oxy}-5-oxa-4-boranuidabicyclo[4.4.0]deca-1(6),7,9-triene-7-carboxylic acid

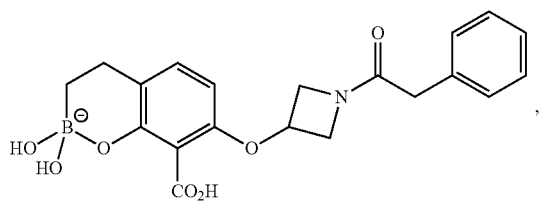 [SMILES: O=C(O)c1c(OC2CN(C(=O)Cc3ccccc3)C2)ccc2c1O[B-](O)(O)CC2]

2-hydroxy-7-{[1-(3-phenylpropanoyl)azetidin-3-yl]oxy}-3,4-dihydro-2H-1,2-benzoxaborinine-8-carboxylic acid

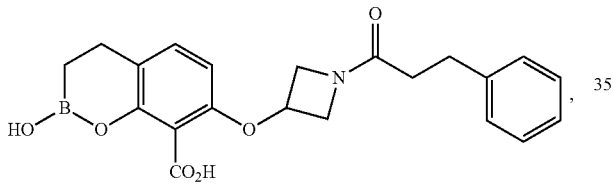

4,4-dihydroxy-8-{[1-(3-phenylpropanoyl)azetidin-3-yl]oxy}-5-oxa-4-boranuidabicyclo[4.4.0]deca-1(6),7,9-triene-7-carboxylic acid

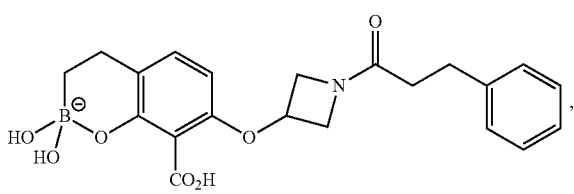 [SMILES: O=C(O)c1c(OC2CN(C(=O)CCc3ccccc3)C2)ccc2c1O[B-](O)(O)CC2]

2-hydroxy-7-({1-[(1H-imidazol-1-yl)acetyl]azetidin-3-yl}oxy)-3,4-dihydro-2H-1,2-benzoxaborinine-8-carboxylic acid

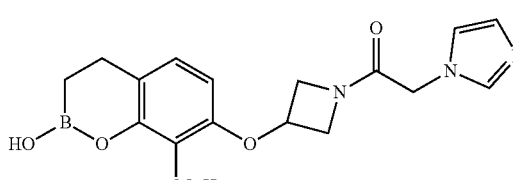
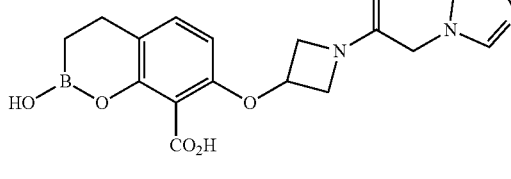

4,4-dihydroxy-8-({1-[(1H-imidazol-1-yl)acetyl]azetidin-3-yl}oxy)-5-oxa-4-boranuidabicyclo[4.4.0]deca-1(6),7,9-triene-7-carboxylic acid

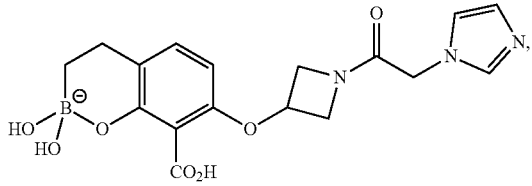

2-hydroxy-7-({1-[(1H-tetrazol-1-yl)acetyl]azetidin-3-yl}oxy)-3,4-dihydro-2H-1,2-benzoxaborinine-8-carboxylic acid

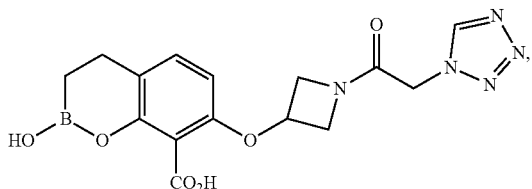

4,4-dihydroxy-8-({1-[(1H-tetrazol-1-yl)acetyl]azetidin-3-yl}oxy)-5-oxa-4-boranuidabicyclo[4.4.0]deca-1(6),7,9-triene-7-carboxylic acid

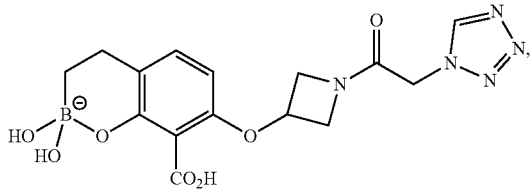 [SMILES: O=C(O)c1c(OC2CN(C(=O)Cn3cnnn3)C2)ccc2c1O[B-](O)(O)CC2]

2-hydroxy-7-({1-[(2H-tetrazol-5-yl)acetyl]azetidin-3-yl}oxy)-3,4-dihydro-2H-1,2-benzoxaborinine-8-carboxylic acid

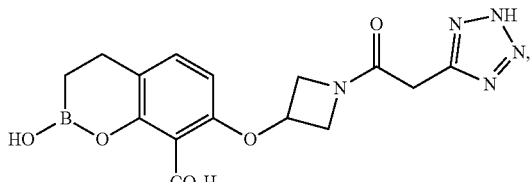
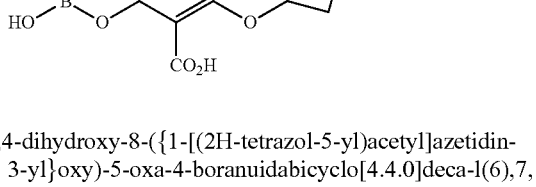

4,4-dihydroxy-8-({1-[(2H-tetrazol-5-yl)acetyl]azetidin-3-yl}oxy)-5-oxa-4-boranuidabicyclo[4.4.0]deca-1(6),7,9-triene-7-carboxylic acid

701

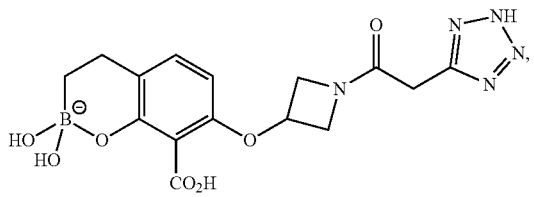 [SMILES: O=C(O)c1c(OC2CN(C(=O)Cc3nn[nH]n3)C2)ccc2c1O[B-](O)(O)CC2]

2-hydroxy-7-[(1-D-phenylalanylazetidin-3-yl)oxy]-3,4-dihydro-2H-1,2-benzoxaborinine-8-carboxylic acid

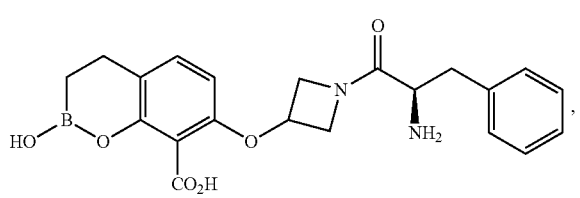 [SMILES: N[C@H](Cc1ccccc1)C(=O)N1CC(Oc2ccc3c(c2C(=O)O)OB(O)CC3)C1]

4,4-dihydroxy-8-[(1-D-phenylalanylazetidin-3-yl)oxy]-5-oxa-4-boranuidabicyclo[4.4.0]deca-1(6),7,9-triene-7-carboxylic acid

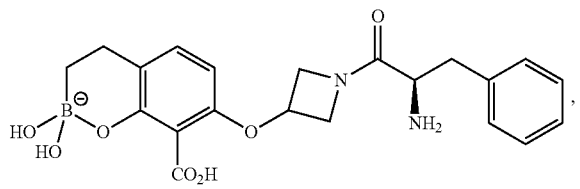 [SMILES: N[C@H](Cc1ccccc1)C(=O)N1CC(Oc2ccc3c(c2C(=O)O)O[B-](O)(O)CC3)C1]

2-hydroxy-7-[(1-D-tyrosylazetidin-3-yl)oxy]-3,4-dihydro-2H-1,2-benzoxaborinine-8-carboxylic acid

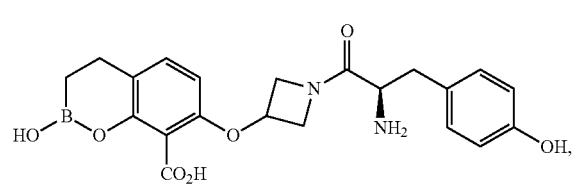 [SMILES: N[C@H](Cc1ccc(O)cc1)C(=O)N1CC(Oc2ccc3c(c2C(=O)O)OB(O)CC3)C1]

4,4-dihydroxy-8-[(1-D-tyrosylazetidin-3-yl)oxy]-5-oxa-4-boranuidabicyclo[4.4.0]deca-1(6),7,9-triene-7-carboxylic acid

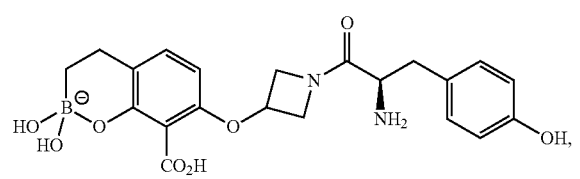 [SMILES: N[C@H](Cc1ccc(O)cc1)C(=O)N1CC(Oc2ccc3c(c2C(=O)O)O[B-](O)(O)CC3)C1]

702

7-[(1-D-histidylazetidin-3-yl)oxy]-2-hydroxy-3,4-dihydro-2H-1,2-benzoxaborinine-8-carboxylic acid

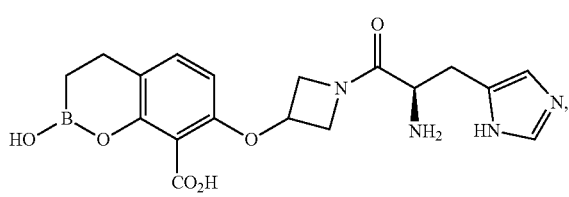 [SMILES: N[C@H](Cc1cnc[nH]1)C(=O)N1CC(Oc2ccc3c(c2C(=O)O)OB(O)CC3)C1]

8-[(1-D-histidylazetidin-3-yl)oxy]-4,4-dihydroxy-5-oxa-4-boranuidabicyclo[4.4.0]deca-1(6),7,9-triene-7-carboxylic acid

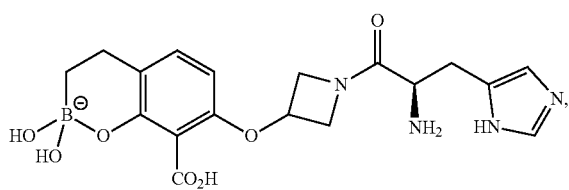 [SMILES: N[C@H](Cc1cnc[nH]1)C(=O)N1CC(Oc2ccc3c(c2C(=O)O)O[B-](O)(O)CC3)C1]

2-hydroxy-7-[(1-D-valylazetidin-3-yl)oxy]-3,4-dihydro-2H-1,2-benzoxaborinine-8-carboxylic acid

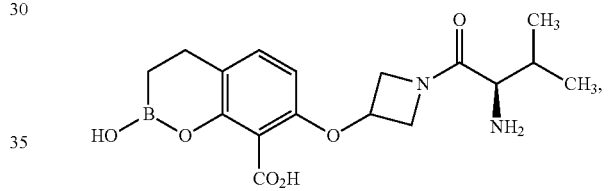

4,4-dihydroxy-8-[(1-D-valylazetidin-3-yl)oxy]-5-oxa-4-boranuidabicyclo[4.4.0]deca-1(6),7,9-triene-7-carboxylic acid

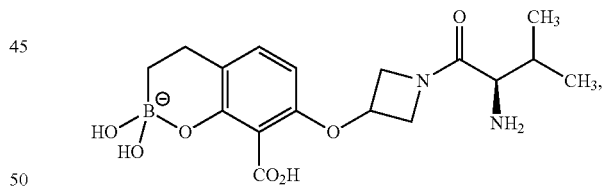

7-[(1-L-histidylazetidin-3-yl)oxy]-2-hydroxy-3,4-dihydro-2H-1,2-benzoxaborinine-8-carboxylic acid

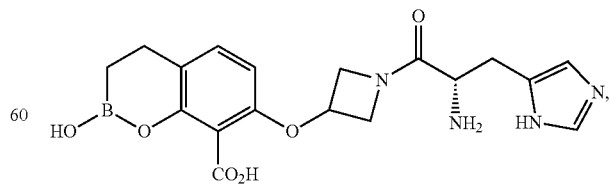

8-[(1-L-histidylazetidin-3-yl)oxy]-4,4-dihydroxy-5-oxa-4-boranuidabicyclo[4.4.0]deca-1(6),7,9-triene-7-carboxylic acid

703

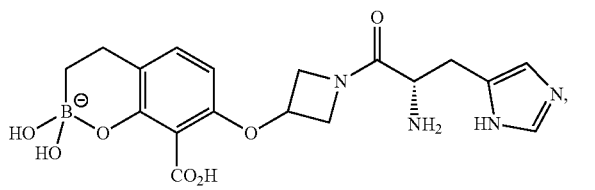 [SMILES: N[C@@H](Cc1cnc[nH]1)C(=O)N1CC(Oc2ccc3c(c2C(=O)O)O[B-](O)(O)CC3)C1]

7-[(1-({2R)-2-[(4-ethyl-2,3-dioxopiperazine-1-carbonyl)
amino]-2-phenylacetyl}azetidin-3-yl)oxy]-2-hydroxy-
3,4-dihydro-2H-1,2-benzoxaborinine-8-carboxylic
acid

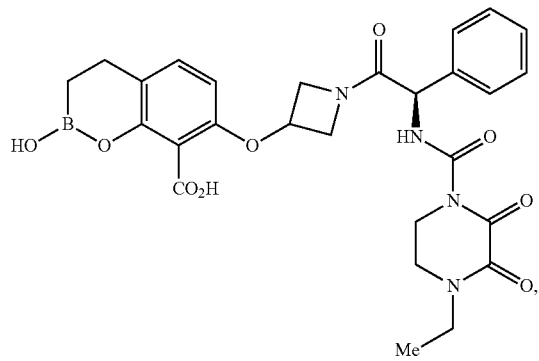 [SMILES: CCN1CCN(C(=O)N[C@@H](C(=O)N2CC(Oc3ccc4c(c3C(=O)O)OB(O)CC4)C2)c2ccccc2)C(=O)C1=O]

8-[(1-({2R)-2-[(4-ethyl-2,3-dioxopiperazine-1-carbonyl)
amino]-2-phenylacetyl}azetidin-3-yl)oxy]-4,4-dihy-
droxy-5-oxa-4-boranuidabicyclo[4.4.0]deca-1(6),7,9-
triene-7-carboxylic acid

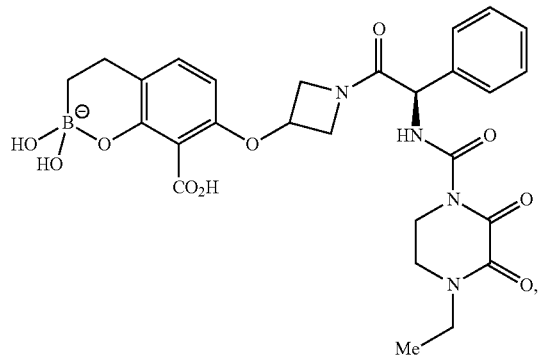 [SMILES: CCN1CCN(C(=O)N[C@@H](C(=O)N2CC(Oc3ccc4c(c3C(=O)O)O[B-](O)(O)CC4)C2)c2ccccc2)C(=O)C1=O]

2-hydroxy-7-[(1-D-prolylazetidin-3-yl)oxy]-3,4-dihydro-
2H-1,2-benzoxaborinine-8-carboxylic acid

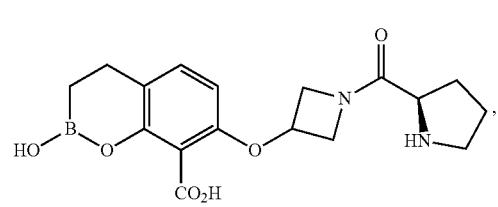

4,4-dihydroxy-8-[(1-D-prolylazetidin-3-yl)oxy]-5-oxa-4-
boranuidabicyclo[4.4.0]deca-1(6),7,9-triene-7-carbox-
ylic acid

704

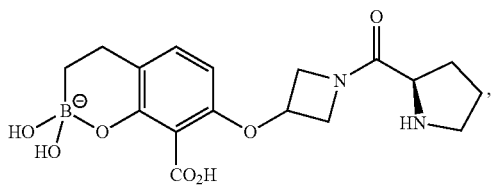 [SMILES: O=C(O)c1c(OC2CN(C(=O)[C@H]3CCCN3)C2)ccc2c1O[B-](O)(O)CC2]

2-hydroxy-7-[(1-L-prolylazetidin-3-yl)oxy]-3,4-dihydro-
2H-1,2-benzoxaborinine-8-carboxylic acid

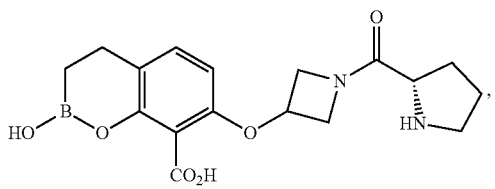 [SMILES: O=C(O)c1c(OC2CN(C(=O)[C@@H]3CCCN3)C2)ccc2c1OB(O)CC2]

4,4-dihydroxy-8-[(1-L-prolylazetidin-3-yl)oxy]-5-oxa-4-
boranuidabicyclo[4.4.0]deca-1(6),7,9-triene-7-carbox-
ylic acid

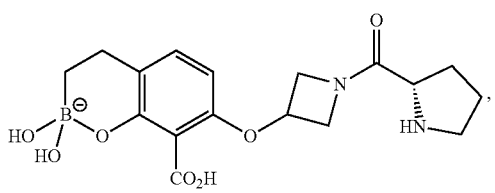 [SMILES: O=C(O)c1c(OC2CN(C(=O)[C@@H]3CCCN3)C2)ccc2c1O[B-](O)(O)CC2]

7-[(1-{[4-(2-aminoethyl)-1H-imidazol-1-yl]
acetyl}azetidin-3-yl)oxy]-2-hydroxy-3,4-dihydro-2H-
1,2-benzoxaborinine-8-carboxylic acid

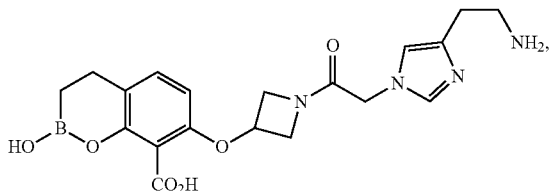

8-[(1-{[4-(2-aminoethyl)-1H-imidazol-1-yl]
acetyl}azetidin-3-yl)oxy]-4,4-dihydroxy-5-oxa-4-bo-
ranuidabicyclo[4.4.0]deca-1(6),7,9-triene-7-carboxylic
acid

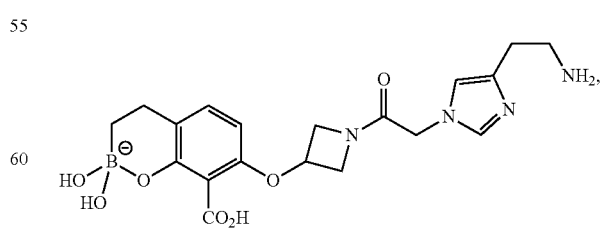

7-{[1-(3,4-dihydroxybenzoyl)azetidin-3-yl]oxy}-2-hy-
droxy-3,4-dihydro-2H-1,2-benzoxaborinine-8-carbox-
ylic acid

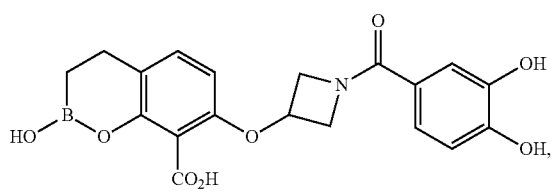 [SMILES: O=C(O)c1c(OC2CN(C(=O)c3ccc(O)c(O)c3)C2)ccc2c1OB(O)CC2]

8-{[1-(3,4-dihydroxybenzoyl)azetidin-3-yl]oxy}-4,4-dihydroxy-5-oxa-4-boranuidabicyclo[4.4.0]deca-1(6),7,9-triene-7-carboxylic acid

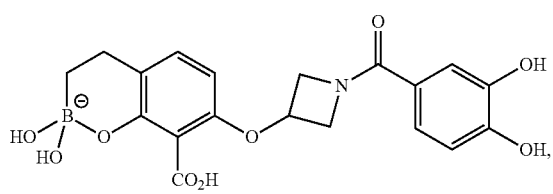 [SMILES: O=C(O)c1c(OC2CN(C(=O)c3ccc(O)c(O)c3)C2)ccc2c1O[B-](O)(O)CC2]

2-hydroxy-7-{[1-(hydroxycarbamoyl)azetidin-3-yl]oxy}-3,4-dihydro-2H-1,2-benzoxaborinine-8-carboxylic acid

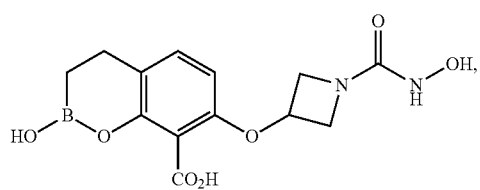 [SMILES: O=C(O)c1c(OC2CN(C(=O)NO)C2)ccc2c1OB(O)CC2]

4,4-dihydroxy-8-{[1-(hydroxycarbamoyl)azetidin-3-yl]oxy}-5-oxa-4-boranuidabicyclo[4.4.0]deca-1(6),7,9-triene-7-carboxylic acid

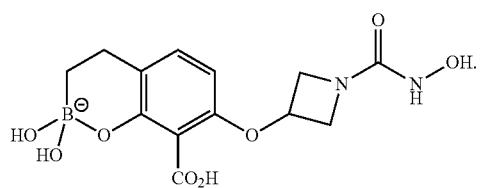 [SMILES: O=C(O)c1c(OC2CN(C(=O)NO)C2)ccc2c1O[B-](O)(O)CC2]

42. The compound or the pharmaceutically acceptable salt thereof of claim 1, represented by the following compound name or structural formula:

7-({1-[(2R)-2-amino-2-(1H-imidazol-4-yl)acetyl]azetidin-3-yl}oxy)-2-hydroxy-3,4-dihydro-2H-1,2-benzoxaborinine-8-carboxylic acid

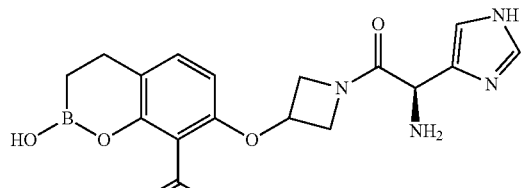

8-({1-[(2R)-2-amino-2-(1H-imidazol-4-yl)acetyl]azetidin-3-yl}oxy)-4,4-dihydroxy-5-oxa-4-boranuidabicyclo[4.4.0]deca-1(6),7,9-triene-7-carboxylic acid

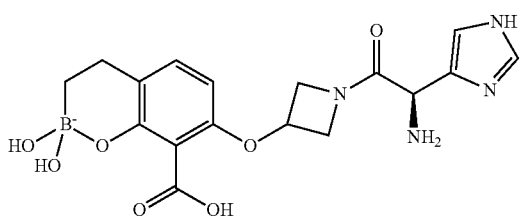

7-({1-[(2S)-2-amino-2-(1H-imidazol-4-yl)acetyl]azetidin-3-yl}oxy)-2-hydroxy-3,4-dihydro-2H-1,2-benzoxaborinine-8-carboxylic acid

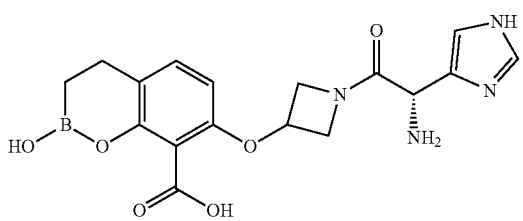

8-({1-[(2S)-2-amino-2-(1H-imidazol-4-yl)acetyl]azetidin-3-yl}oxy)-4,4-dihydroxy-5-oxa-4-boranuidabicyclo[4.4.0]deca-1(6),7,9-triene-7-carboxylic acid

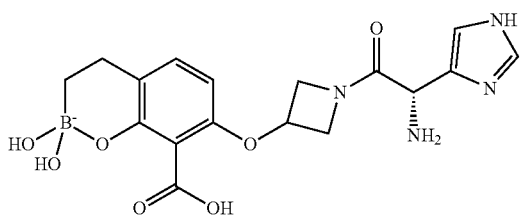

7-({1-[amino(1-methyl-1H-imidazol-4-yl)acetyl]azetidin-3-yl}oxy)-2-hydroxy-3,4-dihydro-2H-1,2-benzoxaborinine-8-carboxylic acid

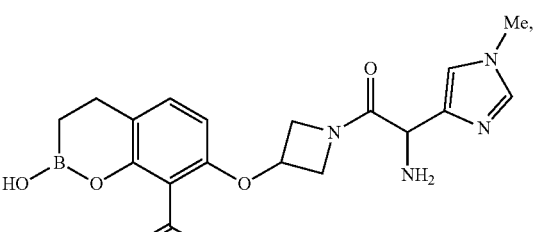

8-({1-[amino(1-methyl-1H-imidazol-4-yl)acetyl]azetidin-3-yl}oxy)-4,4-dihydroxy-5-oxa-4-boranuidabicyclo[4.4.0]deca-1(6),7,9-triene-7-carboxylic acid

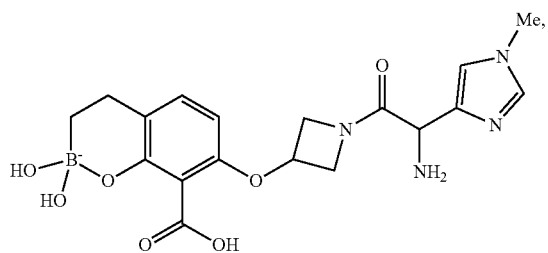 [SMILES: Cn1cnc(C(N)C(=O)N2CC(Oc3ccc4c(c3C(=O)O)O[B-](O)(O)CC4)C2)c1]

7-({1-[2-amino-2-(1H-imidazol-4-yl)(²H)ethanoyl]azetidin-3-yl}oxy)-2-hydroxy-3,4-dihydro-2H-1,2-benzoxaborinine-8-carboxylic acid

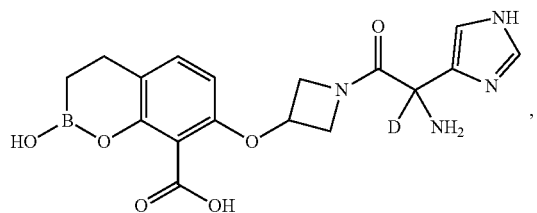 [SMILES: [2H]C(N)(C(=O)N1CC(Oc2ccc3c(c2C(=O)O)OB(O)CC3)C1)c1c[nH]cn1]

8-({1-[2-amino-2-(H-imidazol-4-yl)(²H)ethanoyl]azetidin-3-yl}oxy)-4,4-dihydroxy-5-oxa-4-boranuidabicyclo[4.4.0]deca-1(6),7,9-triene-7-carboxylic acid

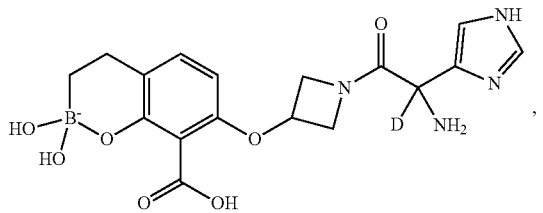 [SMILES: [2H]C(N)(C(=O)N1CC(Oc2ccc3c(c2C(=O)O)O[B-](O)(O)CC3)C1)c1c[nH]cn1]

7-({1-[2-amino-2-(1H-imidazol-4-yl)propanoyl]azetidin-3-yl}oxy)-2-hydroxy-3,4-dihydro-2H-1,2-benzoxaborinine-8-carboxylic acid

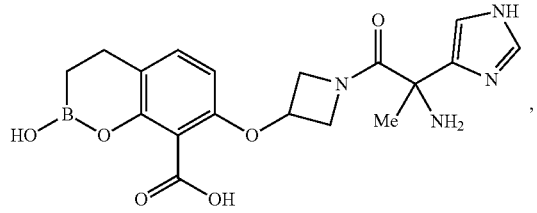 [SMILES: CC(N)(C(=O)N1CC(Oc2ccc3c(c2C(=O)O)OB(O)CC3)C1)c1c[nH]cn1]

8-({1-[2-amino-2-(1H-imidazol-4-yl)propanoyl]azetidin-3-yl}oxy)-4,4-dihydroxy-5-oxa-4-boranuidabicyclo[4.4.0]deca-1(6),7,9-triene-7-carboxylic acid

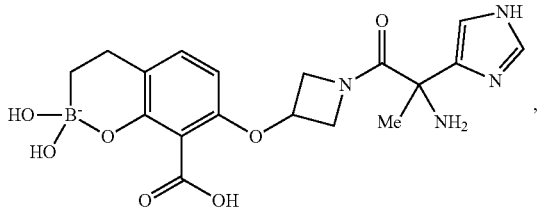 [SMILES: CC(N)(C(=O)N1CC(Oc2ccc3c(c2C(=O)O)O[B-](O)(O)CC3)C1)c1c[nH]cn1]

7-({(3S)-1-[amino(1H-imidazol-4-yl)acetyl]pyrrolidin-3-yl}oxy)-2-hydroxy-3,4-dihydro-2H-1,2-benzoxaborinine-8-carboxylic acid

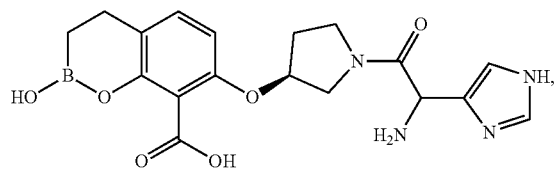 [SMILES: NC(C(=O)N1CC[C@H](Oc2ccc3c(c2C(=O)O)OB(O)CC3)C1)c1c[nH]cn1]

8-({(3S)-1-[amino(1H-imidazol-4-yl)acetyl]pyrolidin-3-yl}oxy)-4,4-dihydroxy-5-oxa-4-boranuidabicyclo[4.4.0]deca-1(6),7,9-triene-7-carboxylic acid

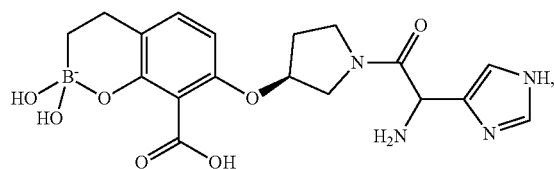 [SMILES: NC(C(=O)N1CC[C@H](Oc2ccc3c(c2C(=O)O)O[B-](O)(O)CC3)C1)c1c[nH]cn1]

2-hydroxy-7-{[1-(4-hydroxy-6-methylpyridine-3-carbonyl)azetidin-3-yl]oxy}-3,4-dihydro-2H-1,2-benzoxaborinine-8-carboxylic acid

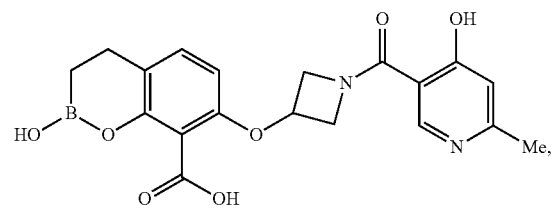 [SMILES: Cc1cc(O)c(C(=O)N2CC(Oc3ccc4c(c3C(=O)O)OB(O)CC4)C2)cn1]

4,4-dihydroxy-8-{[1-(4-hydroxy-6-methylpyridine-3-carbonyl)azetidin-3-yl]oxy}-5-oxa-4-boranuidabicyclo[4.4.0]deca-1(6),7,9-triene-7-carboxylic acid

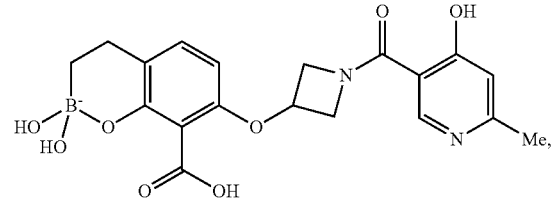 [SMILES: Cc1cc(O)c(C(=O)N2CC(Oc3ccc4c(c3C(=O)O)O[B-](O)(O)CC4)C2)cn1]

7-({1-[amino(1-methyl-1H-imidazol-5-yl)acetyl]azetidin-3-yl}oxy)-2-hydroxy-3,4-dihydro-2H-1,2-benzoxaborinine-8-carboxylic acid

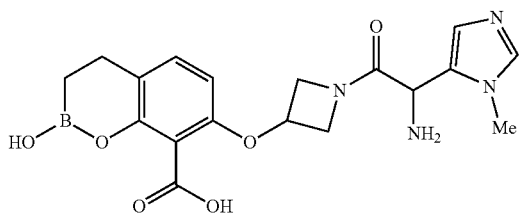

8-({1-[amino(1-methyl-1H-imidazol-5-yl)acetyl]azetidin-3-yl}oxy)-4,4-dihydroxy-5-oxa-4-boranuidabicyclo[4.4.0]deca-1(6),7,9-triene-7-carboxylic acid

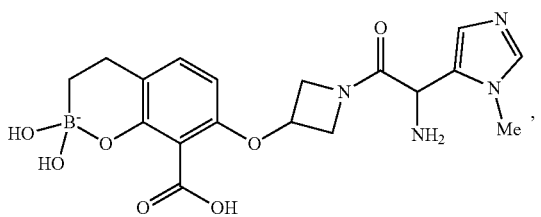 [SMILES: Cn1cncc1C(N)C(=O)N1CC(Oc2ccc3c(c2C(=O)O)O[B-](O)(O)CC3)C1]

7-[(1-{amino[1-(carboxymethyl)-1H-imidazol-4-yl]acetyl}azetidin-3-yl)oxy]-2-hydroxy-3,4-dihydro-2H-1,2-benzoxaborinine-8-carboxylic acid

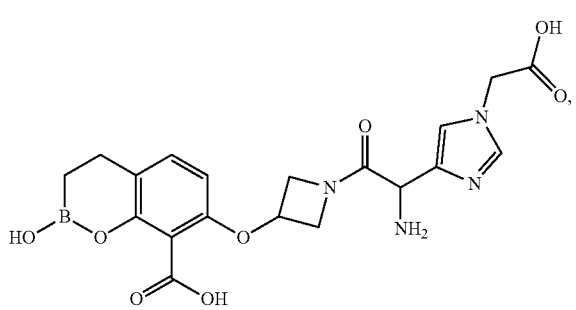

8-[(1-{amino[1-(carboxymethyl)-1H-imidazol-4-yl]acetyl}azetidin-3-yl)oxy]-4,4-dihydroxy-5-oxa-4-boranuidabicyclo[4.4.0]deca-1(6),7,9-triene-7-carboxylic acid

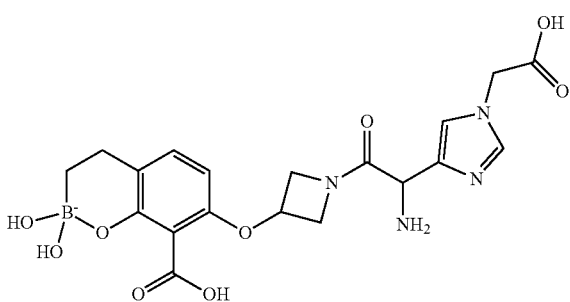 [SMILES: NC(C(=O)N1CC(Oc2ccc3c(c2C(=O)O)O[B-](O)(O)CC3)C1)c1cn(CC(=O)O)cn1]

7-[(1-{amino[1-(2-amino-2-oxoethyl)-1H-imidazol-4-yl]acetyl}azetidin-3-yl)oxy]-2-hydroxy-3,4-dihydro-2H-1,2-benzoxaborinine-8-carboxylic acid

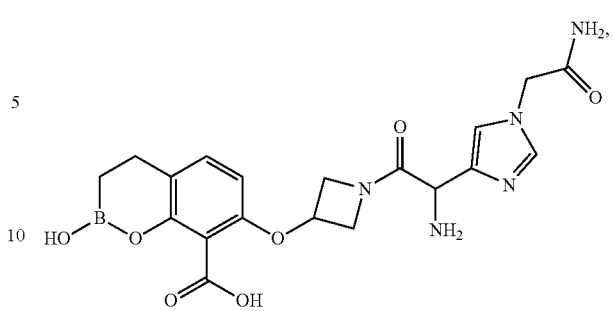

8-[(1-{amino[1-(2-amino-2-oxoethyl)-1H-imidazol-4-yl]acetyl}azetidin-3-yl)oxy]-4,4-dihydroxy-5-oxa-4-boranuidabicyclo[4.4.0]deca-1(6),7,9-triene-7-carboxylic acid

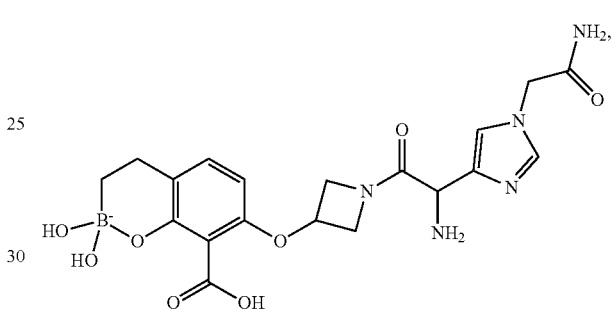

7-({1-[amino(pyridin-3-yl)acetyl]azetidin-3-yl}oxy)-2-hydroxy-3,4-dihydro-2H-1,2-benzoxaborinine-8-carboxylic acid

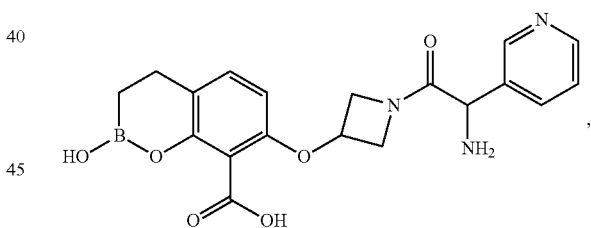

8-({1-[amino(pyridin-3-yl)acetyl]azetidin-3-yl}oxy)-4,4-dihydroxy-5-oxa-4-boranuidabicyclo[4.4.0]deca-1(6),7,9-triene-7-carboxylic acid

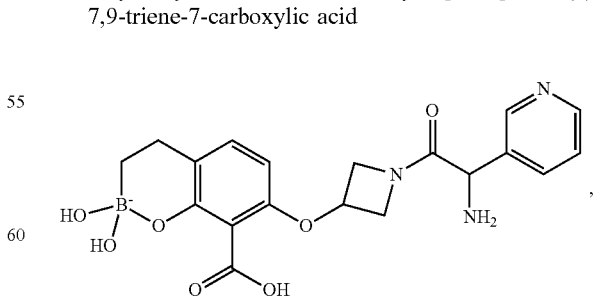

7-({1-[amino(1-methyl-1H-pyrazol-4-yl)acetyl]azetidin-3-yl}oxy)-2-hydroxy-3,4-dihydro-2H-1,2-benzoxaborinine-8-carboxylic acid

711

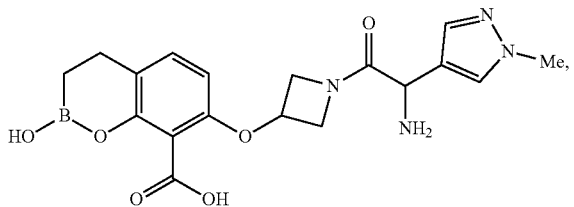 [SMILES: Cn1cc(C(N)C(=O)N2CC(Oc3ccc4c(c3C(=O)O)OB(O)CC4)C2)cn1]

8-({1-[amino(1-methyl-1H-pyrazol-4-yl)acetyl]azetidin-3-yl}oxy)-4,4-dihydroxy-5-oxa-4-boranuidabicyclo[4.4.0]deca-l(6),7,9-triene-7-carboxylic acid

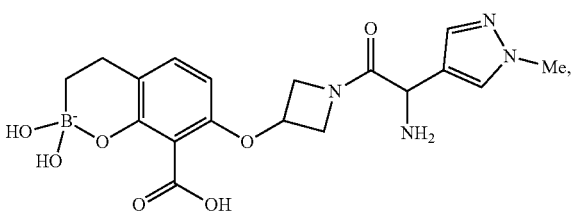 [SMILES: Cn1cc(C(N)C(=O)N2CC(Oc3ccc4c(c3C(=O)O)O[B-](O)(O)CC4)C2)cn1]

7-({(3R)-1-[amino(1H-imidazol-4-yl)acetyl]pyrrolidin-3-yl}oxy)-2-hydroxy-3,4-dihydro-2H-1,2-benzoxaborinine-8-carboxylic acid

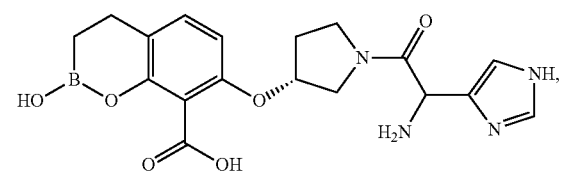 [SMILES: NC(C(=O)N1CC[C@@H](Oc2ccc3c(c2C(=O)O)OB(O)CC3)C1)c1c[nH]cn1]

8-({(3R)-1-[amino(1H-imidazol-4-Yl)cetyl]pyrolidin-3-yl}oxy)-4,4-dihydroxy-5-oxa-4-boranuidabicyclo[4.4.0]deca-l(6),7,9-triene-7-carboxylic acid

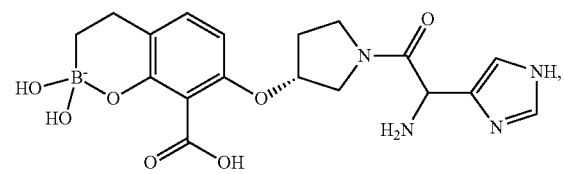 [SMILES: NC(C(=O)N1CC[C@@H](Oc2ccc3c(c2C(=O)O)O[B-](O)(O)CC3)C1)c1c[nH]cn1]

7-({1-[amino(2-methyl-1H-imidazol-4-yl)acetyl]azetidin-3-yl}oxy)-2-hydroxy-3,4-dihydro-2H-1,2-benzoxaborinine-8-carboxylic acid

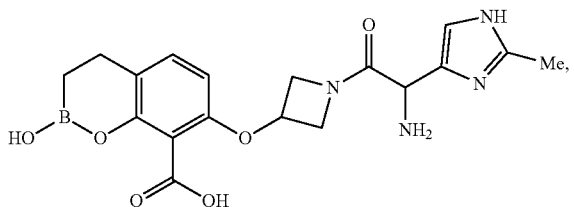 [SMILES: Cc1nc(C(N)C(=O)N2CC(Oc3ccc4c(c3C(=O)O)OB(O)CC4)C2)c[nH]1]

8-({1-[amino(2-methyl-1H-imidazol-4-yl)acetyl]azetidin-3-yl}oxy)-4,4-dihydroxy-5-oxa-4-boranuidabicyclo[4.4.0]deca-l(6),7,9-triene-7-carboxylic acid

712

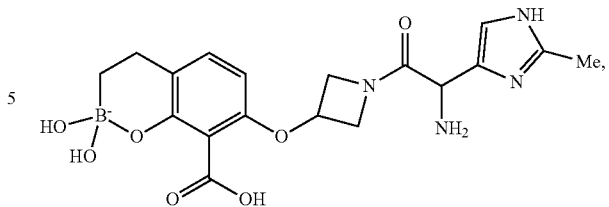

7-({1-[amino(1,3-thiazol-4-yl)acetyl]azetidin-3-yl}oxy)-2-hydroxy-3,4-dihydro-2H-1,2-benzoxaborinine-8-carboxylic acid

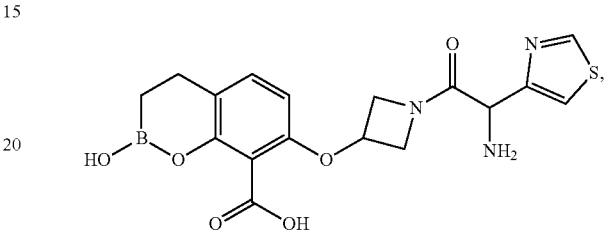

8-({1-[amino(1,3-thiazol-4-yl)acetyl]azetidin-3-yl}oxy)-4,4-dihydroxy-5-oxa-4-boranuidabicyclo[4.4.0]deca-l(6),7,9-triene-7-carboxylic acid

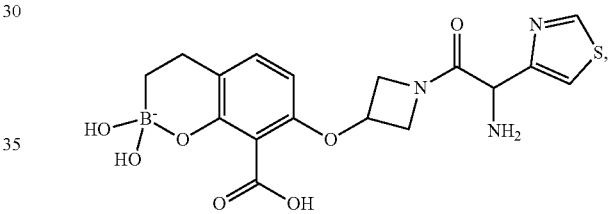

7-({1-[(2-amino-1,3-thiazol-4-yl)acetyl]azetidin-3-yl}oxy)-2-hydroxy-3,4-dihydro-2H-1,2-benzoxaborinine-8-carboxylic acid

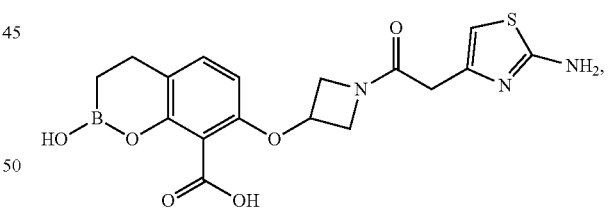

8-({1-[(2-amino-1,3-thiazol-4-yl)acetyl]azetidin-3-yl}oxy-4,4-dihydroxy-5-oxa-4-boranuidabicyclo[4.4.0]deca-l(6),7,9-triene-7-carboxylic acid

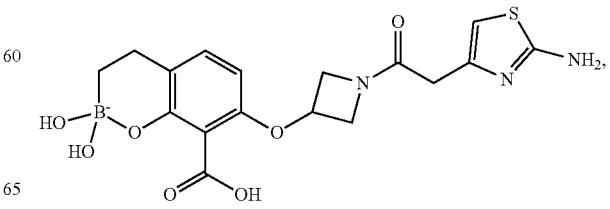

713

7-{[1-(2-amino-1,3-thiazole-4-carbonyl)azetidin-3-yl]
oxy}-2-hydroxy-3,4-dihydro-2H-1,2-benzoxaborinine-
8-carboxylic acid

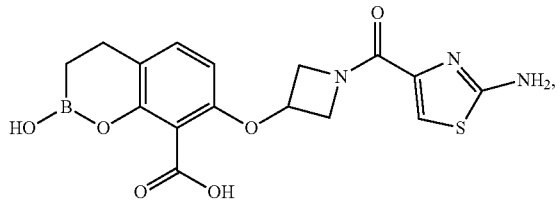 [SMILES: Nc1nc(C(=O)N2CC(Oc3ccc4c(c3C(=O)O)OB(O)CC4)C2)cs1]

8-{[1-(2-amino-1,3-thiazole-4-carbonyl)azetidin-3-yl]
oxy}-4,4-dihydroxy-5-oxa-4-boranuidabicyclo[4.4.0]
deca-1(6),7,9-triene-7-carboxylic acid

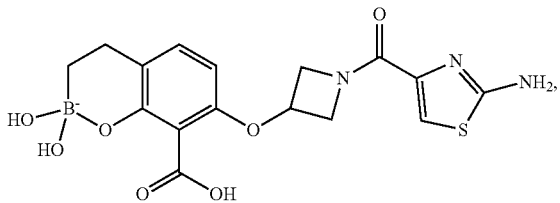 [SMILES: Nc1nc(C(=O)N2CC(Oc3ccc4c(c3C(=O)O)O[B-](O)(O)CC4)C2)cs1]

2-hydroxy-7-({1-[(1H-1,2,3-triazol-1-yl)acetyl]azetidin-
3-yl}oxy)-3,4-dihydro-2H-1,2-benzoxaborinine-8-car-
boxylic acid

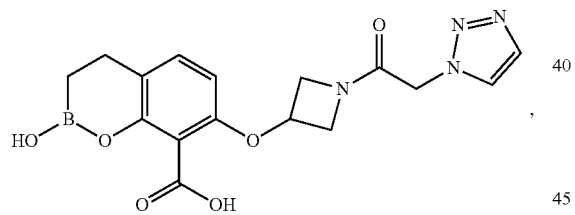

4,4-dihydroxy-8-({1-[(1H-1,2,3-triazol-1-yl)acetyl]azeti-
din-3-yl}oxy)-5-oxa-4-boranuidabicyclo[4.4.0]deca-1
(6),7,9-triene-7-carboxylic acid

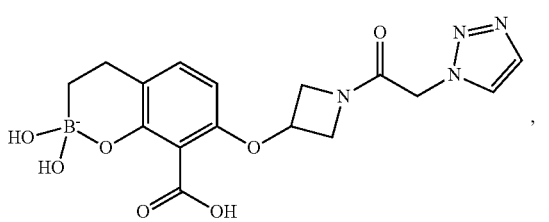 [SMILES: O=C(O)c1c(OC2CN(C(=O)Cn3ccnn3)C2)ccc2c1O[B-](O)(O)CC2]

7-[(1-{[1-(2-aminoethyl)-1H-imidazol-4-yl]
acetyl}azetidin-3-yl)oxy]-2-hydroxy-3,4-dihydro-2H-
1,2-benzoxaborinine-8-carboxylic acid

714

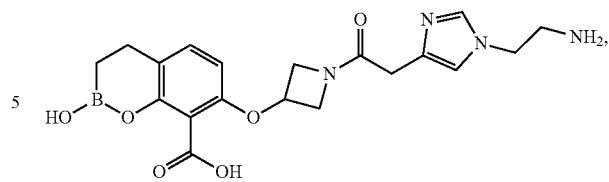

8-[(1-{[1-(2-aminoethyl)-1H-imidazol-4-yl]
acetyl}azetidin-3-yl)oxy]-4,4-dihydroxy-5-oxa-4-bo-
ranuidabicyclo[4.4.0]deca-1(6),7,9-triene-7-carboxylic
acid

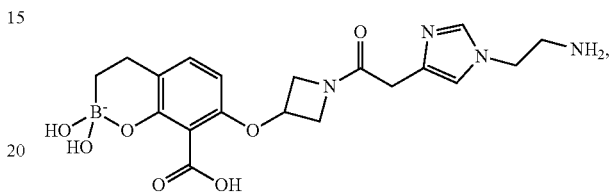

2-hydroxy-7-{[1-(1H-imidazole-4-carbonyl)azetidin-3-
yl]oxy}-3,4-dihydro-2H-1,2-benzoxaborinine-8-car-
boxylic acid

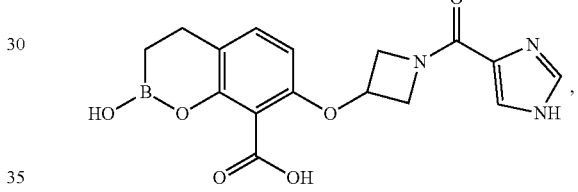

4,4-dihydroxy-8-{[1-(H-imidazole-4-carbonyl)azetidin-
3-yl]oxy}-5-oxa-4-boranuidabicyclo[4.4.0]deca-1(6),7,
9-triene-7-carboxylic acid

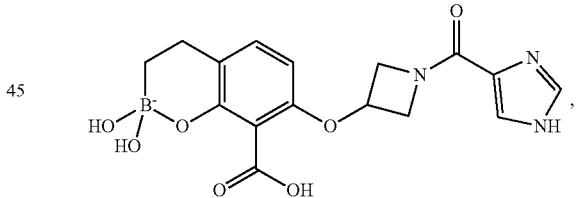

2-hydroxy-7-{[1-(1H-imidazole-2-carbonyl)azetidin-3-
yl]oxy}-3,4-dihydro-2H-1,2-benzoxaborinine-8-car-
boxylic acid

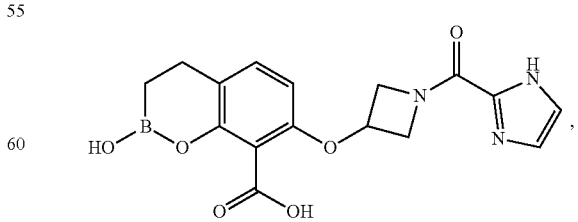

4,4-dihydroxy-8-{[1-(1H-imidazole-2-carbonyl)azetidin-
3-yl]oxy}-5-oxa-4-boranuidabicyclo[4.4.0]deca-1(6),7,
9-triene-7-carboxylic acid

715

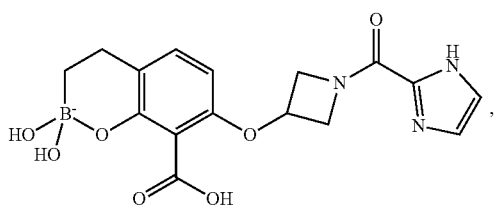 [SMILES: O=C(O)c1c(OC2CN(C(=O)c3ncc[nH]3)C2)ccc2c1O[B-](O)(O)CC2]

2-hydroxy-7-[(1-{[4-(hydroxymethyl)-1H-1,2,3-triazol-1-yl]acetyl}azetidin-3-yl)oxy]-3,4-dihydro-2H-1,2-benzoxaborinine-8-carboxylic acid

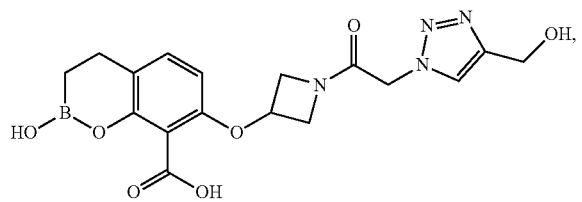 [SMILES: O=C(O)c1c(OC2CN(C(=O)Cn3cc(CO)nn3)C2)ccc2c1OB(O)CC2]

4,4-dihydroxy-8-[(1-{[4-(hydroxymethyl)-1H-1,2,3-triazol-1-yl]acetyl}azetidin-3-yl)oxy]-5-oxa-4-boranuidabicyclo[4.4.0]deca-1(6),7,9-triene-7-carboxylic acid

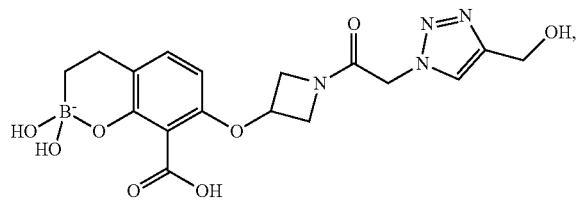 [SMILES: O=C(O)c1c(OC2CN(C(=O)Cn3cc(CO)nn3)C2)ccc2c1O[B-](O)(O)CC2]

2-hydroxy-7-{1-[({4-[(methylamino)methyl]-1H-1,2,3-triazol-1-yl}acetyl)azetidin-3-yl]oxy}-3,4-dihydro-2H-1,2-benzoxaborinine-8-carboxylic acid

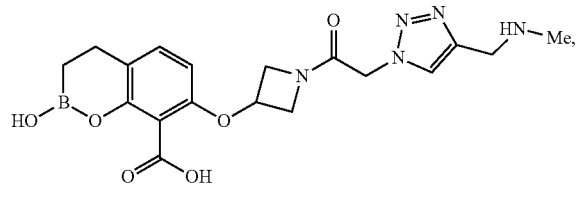 [SMILES: CNCc1cn(CC(=O)N2CC(Oc3ccc4c(c3C(=O)O)OB(O)CC4)C2)nn1]

4,4-dihydroxy-8-{[1-({4-[(methylamino)methyl]-1H-1,2,3-triazol-1-yl}acetyl)azetidin-3-yl]oxy}-5-oxa-4-boranuidabicyclo[4.4.0]deca-1(6),7,9-triene-7-carboxylic acid

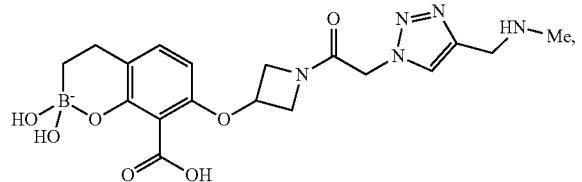 [SMILES: CNCc1cn(CC(=O)N2CC(Oc3ccc4c(c3C(=O)O)O[B-](O)(O)CC4)C2)nn1]

716

2-hydroxy-7-{[1-({4-[(piperazin-1-yl)methyl]-1H-1,2,3-triazol-1-yl}acetyl)azetidin-3-yl]oxy}-3,4-dihydro-2H-1,2-benzoxaborinine-8-carboxylic acid

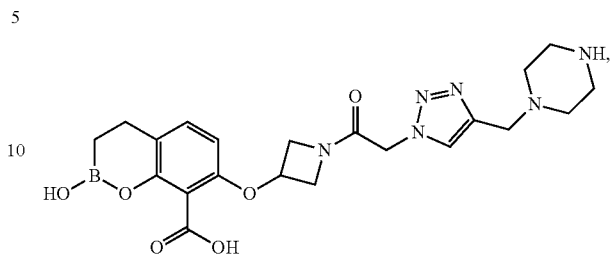

4,4-dihydroxy-8-{[1-({4-[(piperazin-1-yl)methyl]-1H-1,2,3-triazol-1-yl}acetyl)azetidin-3-yl]oxy}-5-oxa-4-boranuidabicyclo[4.4.0]deca-1(6),7,9-triene-7-carboxylic acid

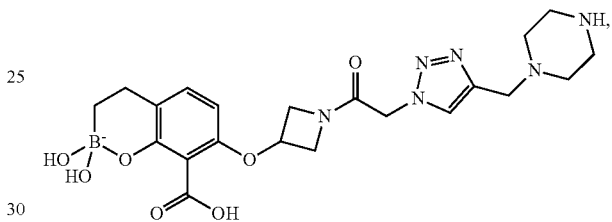

2-hydroxy-7-[(1-({4-(2-hydroxyethyl)-1H-1,2,3-triazol-1-yl]acetyl}azetidin-3-yl)oxy]-3,4-dihydro-2H-1,2-benzoxaborinine-8-carboxylic acid

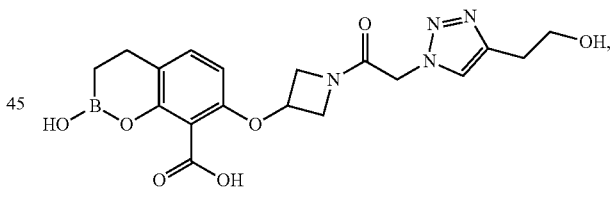

4,4-dihydroxy-8-[(1-{[4-(2-hydroxyethyl)-1H-1,2,3-triazol-1-yl]acetyl}azetidin-3-yl)oxy]-5-oxa-4-boranuidabicyclo[4.4.0]deca-1(6),7,9-triene-7-carboxylic acid

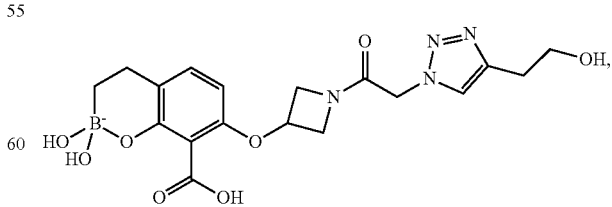

2-hydroxy-7-[(1-{[5-(hydroxymethyl)-1H-1,2,3-triazol-1-yl]acetyl}azetidin-3-yl)oxy]-3,4-dihydro-2H-1,2-benzoxaborinine-8-carboxylic acid

717

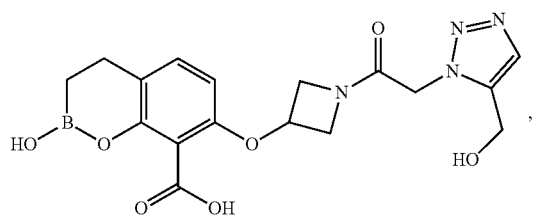 [SMILES: O=C(O)c1c(OC2CN(C(=O)Cn3nncc3CO)C2)ccc2c1OB(O)CC2]

4,4-dihydroxy-8-[(1-{[5-(hydroxymethyl)-1H-1,2,3-triazol-1-yl]acetyl}azetidin-3-yl)oxy]-5-oxa-4-boranuidabicyclo[4.4.0]deca-1(6),7,9-triene-7-carboxylic acid

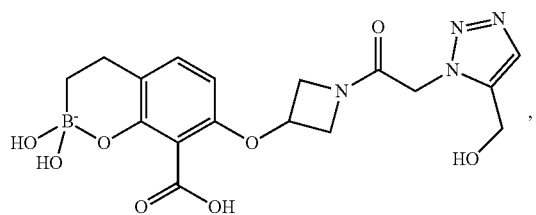 [SMILES: O=C(O)c1c(OC2CN(C(=O)Cn3nncc3CO)C2)ccc2c1O[B-](O)(O)CC2]

2-hydroxy-7-{[1-({5-[(methylamino)methyl]-1H-1,2,3-triazol-1-yl}acetyl)azetidin-3-yl]oxy}-3,4-dihydro-2H-1,2-benzoxaborinine-8-carboxylic acid

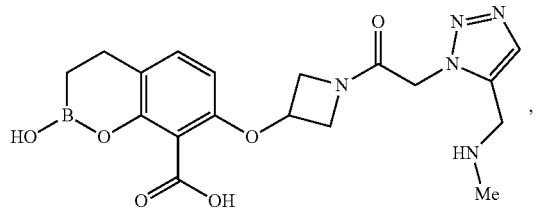 [SMILES: CNCc1cnnn1CC(=O)N1CC(Oc2ccc3c(c2C(=O)O)OB(O)CC3)C1]

4,4-dihydroxy-8-{[1-({5-[(methylamino)methyl]-1H-1,2,3-triazol-1-yl}acetyl)azetidin-3-yl]oxy}-5-oxa-4-boranuidabicyclo[4.4.0]deca-1(6),7,9-triene-7-carboxylic acid

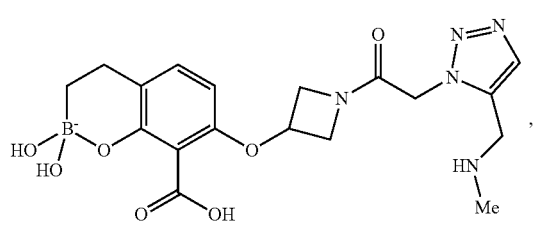 [SMILES: CNCc1cnnn1CC(=O)N1CC(Oc2ccc3c(c2C(=O)O)O[B-](O)(O)CC3)C1]

2-hydroxy-7-({1-[(1H-1,2,3-triazol-4-yl)acetyl]azetidin-3-yl}oxy)-3,4-dihydro-2H-1,2-benzoxaborinine-8-carboxylic acid

718

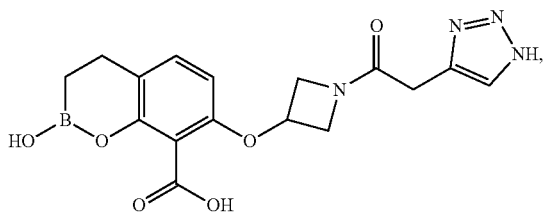 [SMILES: O=C(O)c1c(OC2CN(C(=O)Cc3c[nH]nn3)C2)ccc2c1OB(O)CC2]

4,4-dihydroxy-8-({1-[(1H-1,2,3-triazol-4-yl)acetyl]azetidin-3-yl}oxy)-5-oxa-4-boranuidabicyclo[4.4.0]deca-1(6),7,9-triene-7-carboxylic acid

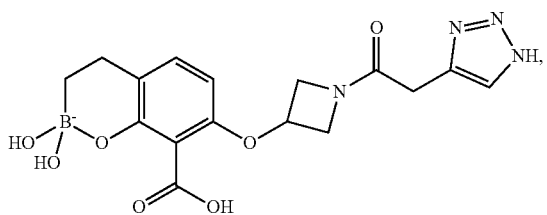 [SMILES: O=C(O)c1c(OC2CN(C(=O)Cc3c[nH]nn3)C2)ccc2c1O[B-](O)(O)CC2]

7-[(1-{[4-(carboxymethyl)-1H-1,2,3-triazol-1-yl]acetyl}azetidin-3-yl)oxy]-2-hydroxy-3,4-dihydro-2H-1,2-benzoxaborinine-8-carboxylic acid

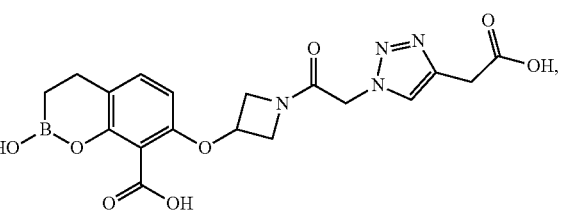

8-[(1-{[4-(carboxymethyl)-1H-1,2,3-triazol-1-yl]acetyl}azetidin-3-yl)oxy]-4,4-dihydroxy-5-oxa-4-boranuidabicyclo[4.4.0]deca-1(6),7,9-triene-7-carboxylic acid

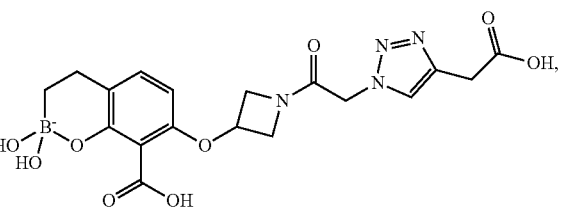

[(1-{[1-(carboxymethyl)-1H-1,2,3-triazol-4-yl]acetyl}azetidin-3-yl)oxy]-2-hydroxy-3,4-dihydro-2H-1,2-benzoxaborinine-8-carboxylic acid

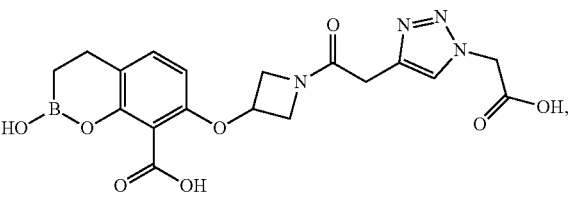 [SMILES: O=C(O)Cn1cc(CC(=O)N2CC(Oc3ccc4c(c3C(=O)O)OB(O)CC4)C2)nn1]

719

8-[(1-{[1-(carboxymethyl)-1H-1,2,3-triazol-4-yl]
acetyl}azetidin-3-yl)oxy]-4,4-dihydroxy-5-oxa-4-bo-
ranuidabicyclo[4.4.0]deca-1(6),7,9-triene-7-carboxylic
acid

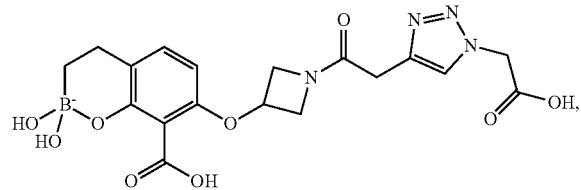 [SMILES: O=C(O)Cn1cc(CC(=O)N2CC(Oc3ccc4c(c3C(=O)O)O[B-](O)(O)CC4)C2)nn1]

7-({1-[amino(1H-2,3-triazol-4-yl)acetyl]azetidin-3-
yl}oxy)-2-hydroxy-3,4-dihydro-2H-1,2-benzoxabori-
nine-8-carboxylic acid

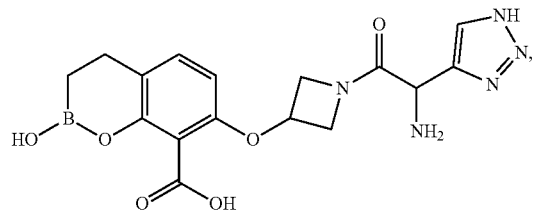

8-({1-[amino(1H-1,2,3-triazol-4-yl}acetyl]azetidin-3-yl)
oxy-4,4-dihydroxy-5-oxa-4-boranuidabicyclo[4.4.0]
deca-1(6),7,9-triene-7-carboxylic acid

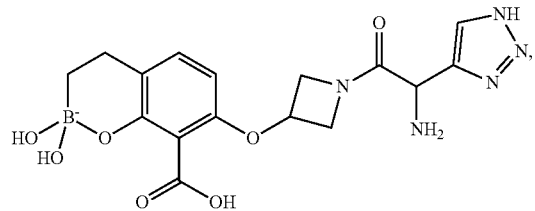

2-hydroxy-7-({1-[(4-nitro-1H-1,2,3-triazol-1-yl)acetyl]
azetidin-3-yl}oxy)-3,4-dihydro-2H-1,2-benzoxabori-
nine-8-carboxylic acid

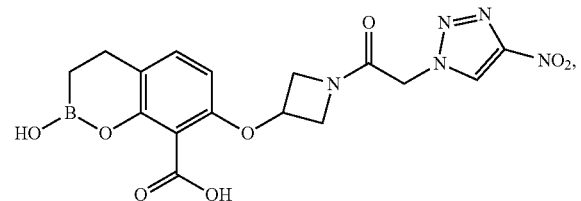 [SMILES: O=C(O)c1c(OC2CN(C(=O)Cn3cc([N+](=O)[O-])nn3)C2)ccc2c1OB(O)CC2]

4,4-dihydroxy-8-({1-[(4-nitro-1H-1,2,3-triazol-1-yl)
acetyl]azetidin-3-yl}oxy)-5-oxa-4-boranuidabicyclo
[4.4.0]deca-1(6),7,9-triene-7-carboxylic acid

720

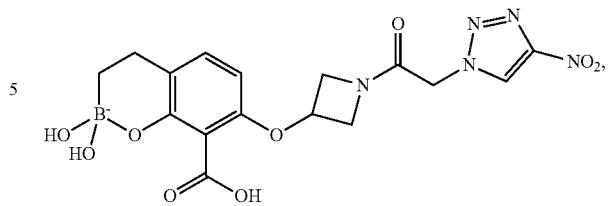

7-({1-[amino(3,4-dihydroxyphenyl)acetyl]azetidin-3-
yl}oxy)-2-hydroxy-3,4-dihydro-2H-1,2-benzoxabori-
nine-8-carboxylic acid

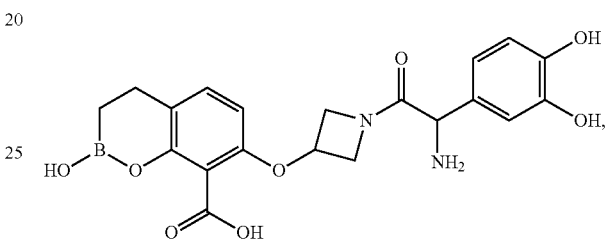

8-({1-[amino(3,4-dihydroxyphenyl)acetyl]azetidin-3-
yl}oxy)-4,4-dihydroxy-5-oxa-4-boranuidabicyclo
[4.4.0]deca-1(6),7,9-triene-7-carboxylic acid

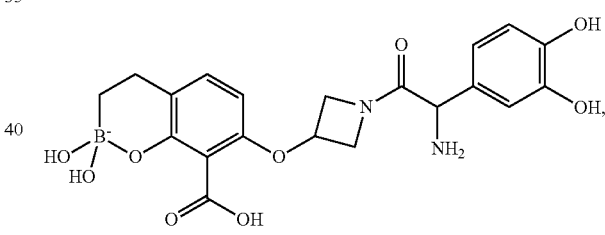

7-({1-[amino(2,4-dihydroxyphenyl)acetyl]azetidin-3-
yl}oxy)-2-hydroxy-3,4-dihydro-2H-1,2-benzoxabori-
nine-8-carboxylic acid

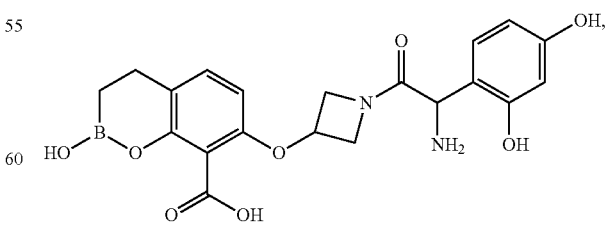

8-({1-[amino(2,4-dihydroxyphenyl)acetyl]azetidin-3-
yl}oxy)-4,4-dihydroxy-5-oxa-4-boranuidabicyclo
[4.4.0]deca-1(6),7,9-triene-7-carboxylic acid

721

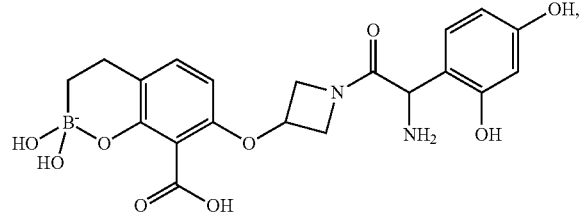 [SMILES: NC(C(=O)N1CC(Oc2ccc3c(c2C(=O)O)O[B-](O)(O)CC3)C1)c1ccc(O)cc1O]

7-{([1-(S-benzyl-D-cysteinyl)azetidin-3-yl]oxy}-2-hydroxy-3,4-dihydro-2H-1,2-benzoxaborinine-8-carboxylic acid

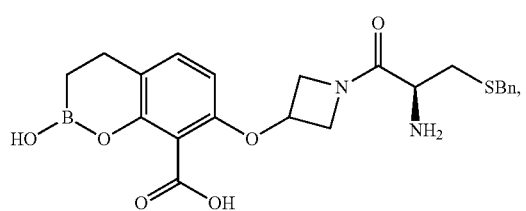

8-{[1-(S-benzyl-D-cysteinyl)azetidin-3-yl]oxy}-4,4-dihydroxy-5-oxa-4-boranuidabicyclo[4.4.0]deca-1(6),7,9-triene-7-carboxylic acid

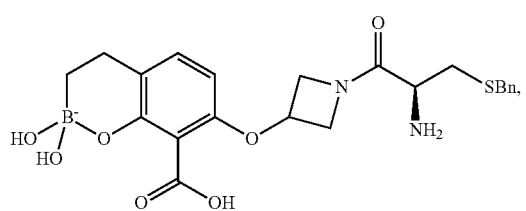

7-[(1-D-cysteinylazetidin-3-yl)oxy]-2-hydroxy-3,4-dihydro-2H-1,2-benzoxaborinine-8-carboxylic acid

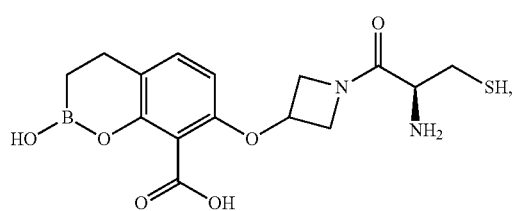

7-[(1-D-cysteinylazetidin-3-yl)oxy]-4,4-dihydroxy-5-oxa-4-boranuidabicyclo[4.4.0]deca-1(6),7,9-triene-7-carboxylic acid

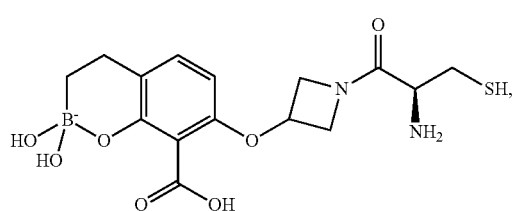

722

2-hydroxy-7-{[1-(3-sulfanyl-D-valyl)azetidin-3-yl]oxy}-3,4-dihydro-2H-1,2-benzoxaborinine-8-carboxylic acid

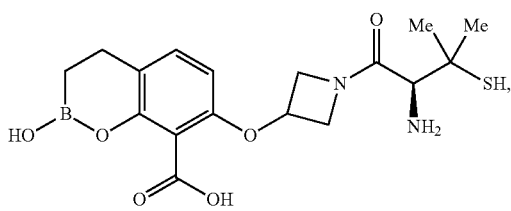 [SMILES: CC(C)(S)[C@@H](N)C(=O)N1CC(Oc2ccc3c(c2C(=O)O)OB(O)CC3)C1]

4,4-dihydroxy-8-{[1-(3-sulfanyl-D-valyl)azetidin-3-yl]oxy}-5-oxa-4-boranuidabicyclo[4.4.0]deca-1(6),7,9-triene-7-carboxylic acid

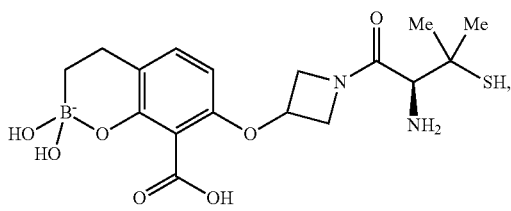 [SMILES: CC(C)(S)[C@@H](N)C(=O)N1CC(Oc2ccc3c(c2C(=O)O)O[B-](O)(O)CC3)C1]

7-({1-[(2S)-2-amino-3-carboxypropanoyl]azetidin-3-yl}oxy)-2-hydroxy-3,4-dihydro-2H-1,2-benzoxaborinine-8-carboxylic acid

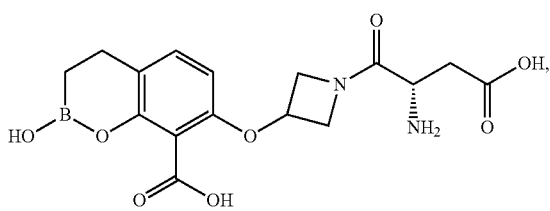

8-({1-[(2S)-2-amino-3-carboxypropanoyl]azetidin-3-yl}oxy)-4,4-dihydroxy-5-oxa-4-boranuidabicyclo[4.4.0]deca-1(6),7,9-triene-7-carboxylic acid

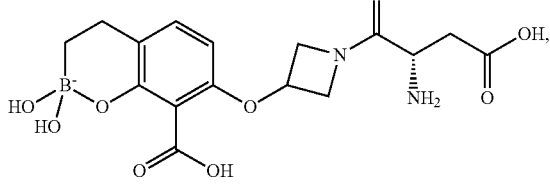

723

7-{[1-(D-alanyl-D-alanyl)azetidin-3-yl]oxy}-2-hydroxy-3,4-dihydro-2H-1,2-benzoxaborinine-8-carboxylic acid

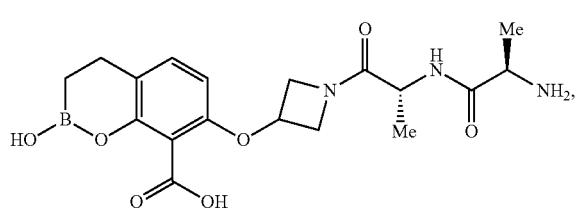 [SMILES: C[C@@H](N)C(=O)N[C@H](C)C(=O)N1CC(Oc2ccc3c(c2C(=O)O)OB(O)CC3)C1]

8-{[1-(D-alanyl-D-alanyl)azetidin-3-yl]oxy}-4,4-dihydroxy-5-oxa-4-boranuidabicyclo[4.4.0]deca-1(6),7,9-triene-7-carboxylic acid

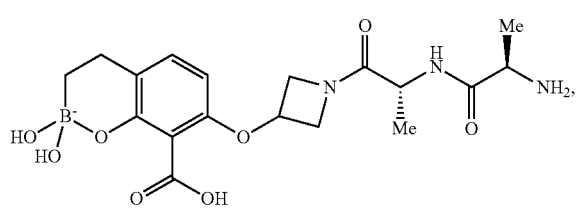 [SMILES: C[C@@H](N)C(=O)N[C@H](C)C(=O)N1CC(Oc2ccc3c(c2C(=O)O)O[B-](O)(O)CC3)C1]

7-[(1-L-asparaginylazetidin-3-yl)oxy]-2-hydroxy-3,4-dihydro-2H-1,2-benzoxaborinine-8-carboxylic acid

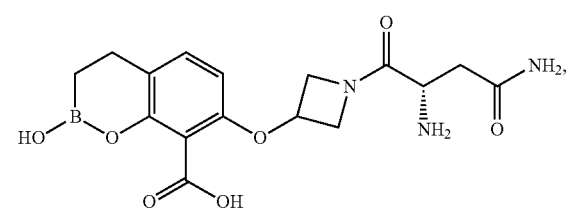 [SMILES: NC(=O)C[C@H](N)C(=O)N1CC(Oc2ccc3c(c2C(=O)O)OB(O)CC3)C1]

8-[(1-L-asparaginylazetidin-3-yl)oxy]-4,4-dihydroxy-5-oxa-4-boranuidabicyclo[4.4.0]deca-1(6),7,9-triene-7-carboxylic acid

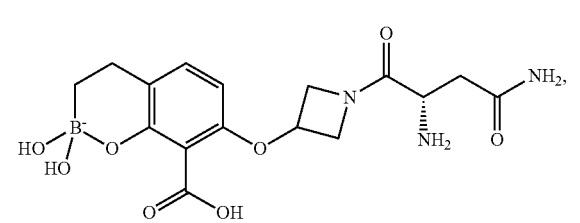 [SMILES: NC(=O)C[C@H](N)C(=O)N1CC(Oc2ccc3c(c2C(=O)O)O[B-](O)(O)CC3)C1]

7-[(1-D-asparaginylazetidin-3-yl)oxy]-2-hydroxy-3,4-dihydro-2H-1,2-benzoxaborinine-8-carboxylic acid

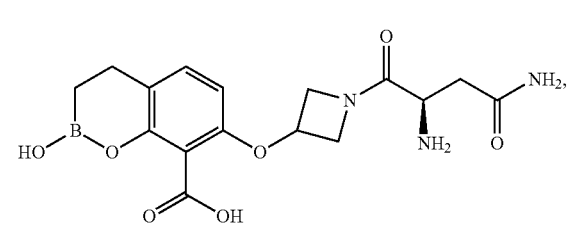

724

8-[(1-D-asparaginylazetidin-3-yl)oxy]-4,4-dihydroxy-5-oxa-4-boranuidabicyclo[4.4.0]deca-1(6),7,9-triene-7-carboxylic acid

7-({1-[(2R)-2-amino-3-carboxypropanoyl]azetidin-3-yl}oxy)-2-hydroxy-3,4-dihydro-2H-1,2-benzoxaborinine-8-carboxylic acid

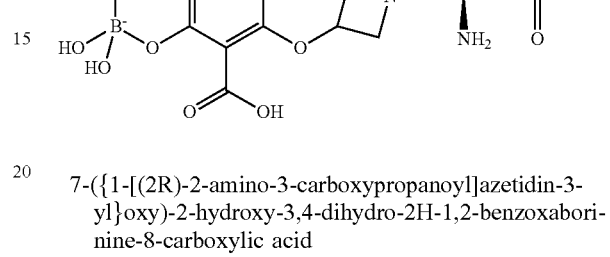

8-({1-[(2R)-2-amino-3-carboxypropanoyl]azetidin-3-yl}oxy)-4,4-dihydroxy-5-oxa-4-boranuidabicyclo[4.4.0]deca-1(6),7,9-triene-7-carboxylic acid

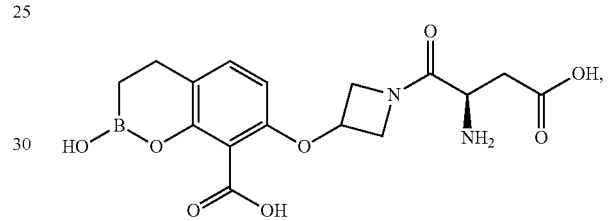

2-hydroxy-7-[(1-D-serylazetidin-3-yl)oxy]-3,4-dihydro-2H-1,2-benzoxaborinine-8-carboxylic acid

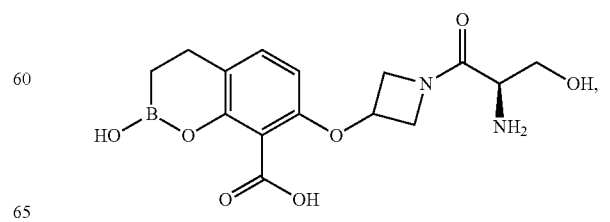

725

4,4-dihydroxy-8-[(1-D-serylazetidin-3-yl)oxy]-5-oxa-4-boranuidabicyclo[4.4.0]deca-1(6),7,9-triene-7-carboxylic acid

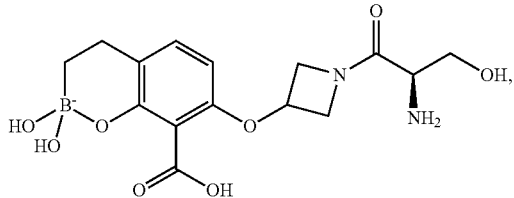

7-{[1-(4-amino-4-oxobutanoyl)azetidin-3-yl]oxy}-2-hydroxy-3,4-dihydro-2H-1,2-benzoxaborinine-8-carboxylic acid

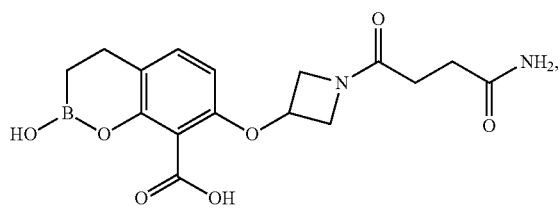 [SMILES: NC(=O)CCC(=O)N1CC(Oc2ccc3c(c2C(=O)O)OB(O)CC3)C1]

8-{[1-(4-amino-4-oxobutanoyl)azetidin-3-yl]oxy}-4,4-dihydroxy-5-oxa-4-boranuidabicyclo[4.4.0]deca-1(6),7,9-triene-7-carboxylic acid

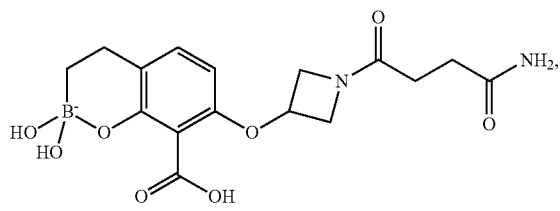 [SMILES: NC(=O)CCC(=O)N1CC(Oc2ccc3c(c2C(=O)O)O[B-](O)(O)CC3)C1]

7-[(1-D-glutaminylazetidin-3-yl)oxy]-2-hydroxy-3,4-dihydro-2H-1,2-benzoxaborinine-8-carboxylic acid

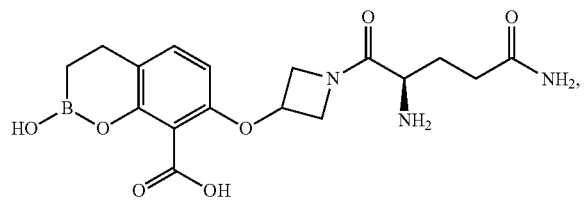 [SMILES: NC(=O)CC[C@@H](N)C(=O)N1CC(Oc2ccc3c(c2C(=O)O)OB(O)CC3)C1]

726

8-[(1-D-glutaminylazetidin-3-yl)oxy]-4,4-dihydroxy-5-oxa-4-boranuidabicyclo[4.4.0]deca-1(6),7,9-triene-7-carboxylic acid

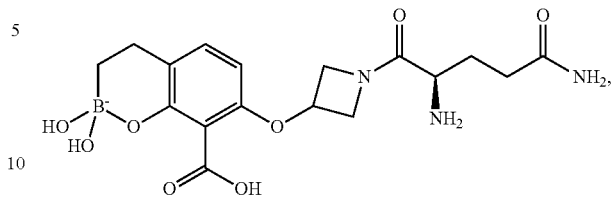

7-({1-[3-(carbamoylamino)-D-alanyl]azetidin-3-yl}oxy)-2-hydroxy-3,4-dihydro-2H-1,2-benzoxaborinine-8-carboxylic acid

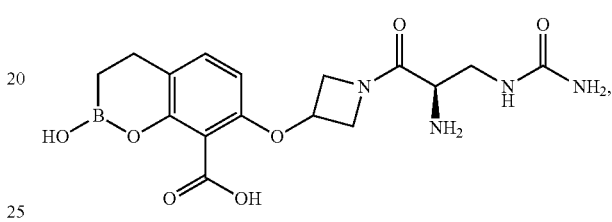

8-({1-[3-(carbamoylamino)-D-alanyl]azetidin-3-yl}oxy)-4,4-dihydroxy-5-oxa-4-boranuidabicyclo[4.4.0]deca-1(6),7,9-triene-7-carboxylic acid

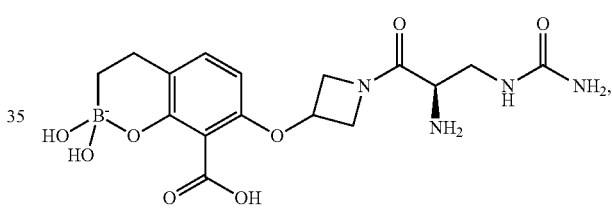

7-{[1-(3-acetamido-D-alanyl)azetidin-3-yl]oxy}-2-hydroxy-3,4-dihydro-2H-1,2-benzoxaborinine-8-carboxylic acid

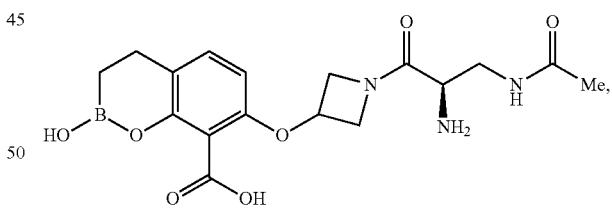

8-{[1-(3-acetamido-D-alanyl)azetidin-3-yl]oxy-4,4-dihydroxy-5-oxa-4-boranuidabicyclo[4.4.0]deca-1(6),7,9-triene-7-carboxylic acid

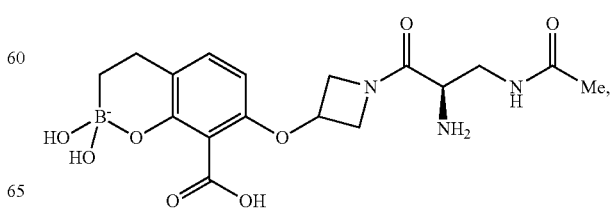

727

7-{[1-(N,N-dimethyl-D-asparaginyl)azetidin-3-yl]oxy}-2-hydroxy-3,4-dihydro-2H-1,2-benzoxaborinine-8-carboxylic acid

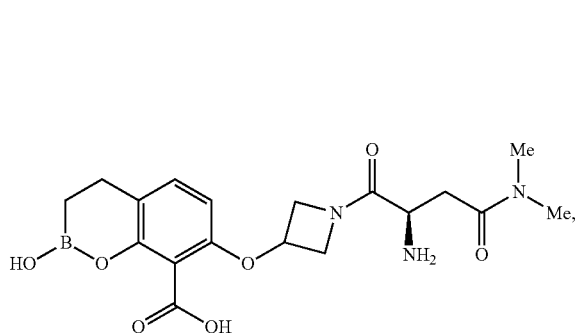 [SMILES: CN(C)C(=O)C[C@@H](N)C(=O)N1CC(Oc2ccc3c(c2C(=O)O)OB(O)CC3)C1]

8-{[1-(N,N-dimethyl-D-asparaginyl)azetidin-3-yl]oxy}-4,4-dihydroxy-5-oxa-4-boranuidabicyclo[4.4.0]deca-1(6),7,9-triene-7-carboxylic acid

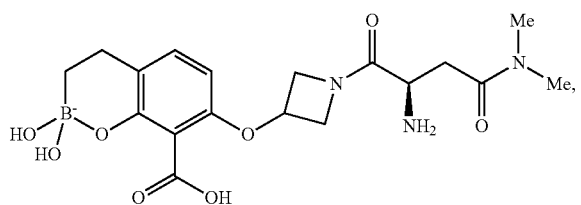 [SMILES: CN(C)C(=O)C[C@@H](N)C(=O)N1CC(Oc2ccc3c(c2C(=O)O)O[B-](O)(O)CC3)C1]

2-hydroxy-7-{[1-(N-methyl-D-asparaginyl)azetidin-3-yl]oxy}-3,4-dihydro-2H-1,2-benzoxaborinine-8-carboxylic acid

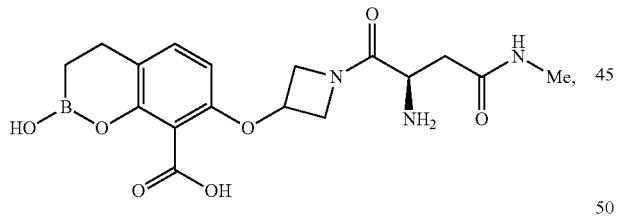

4,4-dihydroxy-8-{[1-(N-methyl-D-asparaginyl)azetidin-3-yl]oxy}-5-oxa-4-boranuidabicyclo[4.4.0]deca-1(6),7,9-triene-7-carboxylic acid

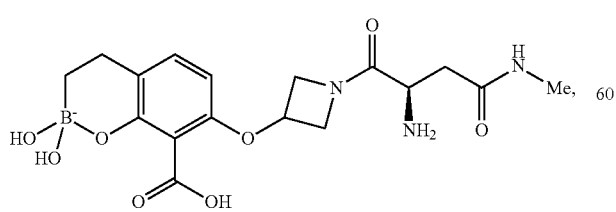

728

2-hydroxy-7-[(1-L-serylazetidin-3-yl)oxy]-3,4-dihydro-2H-1,2-benzoxaborine-8-carboxylic acid

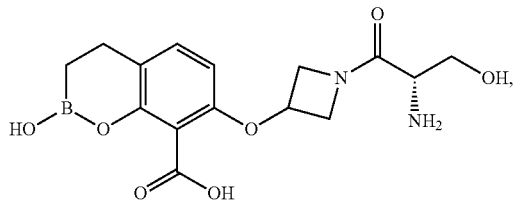 [SMILES: N[C@@H](CO)C(=O)N1CC(Oc2ccc3c(c2C(=O)O)OB(O)CC3)C1]

4,4-dihydroxy-8-[(1-L-serylazetidin-3-yl)oxy]-5-oxa-4-boranuidabicyclo[4.4.0]deca-1(6),7,9-triene-7-carboxylic acid

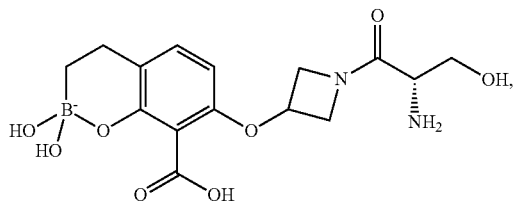 [SMILES: N[C@@H](CO)C(=O)N1CC(Oc2ccc3c(c2C(=O)O)O[B-](O)(O)CC3)C1]

2-hydroxy-7-{[1-(4-hydroxyprolyl)azetidin-3-yl]oxy}-3,4-dihydro-2H-1,2-benzoxaborinine-8-carboxylic acid

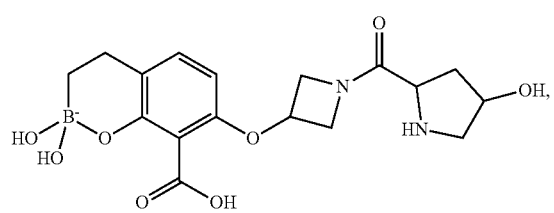 [SMILES: O=C(O)c1c(OC2CN(C(=O)C3CC(O)CN3)C2)ccc2c1O[B-](O)(O)CC2]

4,4-dihydroxy-8-{[1-(4-hydroxyprolyl)azetidin-3-yl]oxy}-5-oxa-4-boranuidabicyclo[4.4.0]deca-1(6),7,9-triene-7-carboxylic acid 2-hydroxy-7-({1-[(4R)-4-(trifluoromethyl)-D-prolyl]azetidin-3-yl}oxy)-3,4-dihydro-2H-1,2-benzoxaborinine-8-carboxylic acid

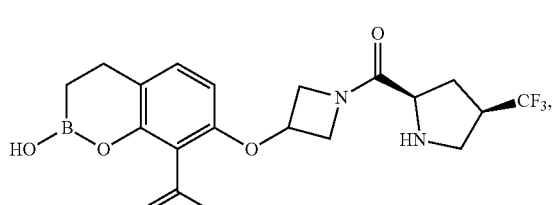

729

4,4-dihydroxy-8-({1-[(4R)-4-(trifluoromethyl)-D-prolyl]
azetidin-3-yl}oxy)-5-oxa-4-boranuidabicyclo[4.4.0]
deca-1(6),7,9-triene-7-carboxylic acid

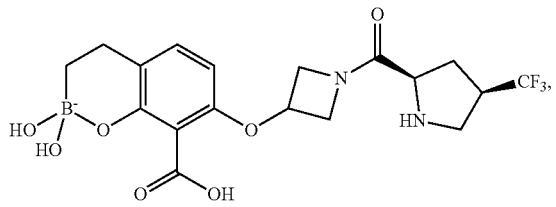 [SMILES: O=C(O)c1c(OC2CN(C(=O)[C@H]3C[C@@H](C(F)(F)F)CN3)C2)ccc2c1O[B-](O)(O)CC2]

7-({1-[(4S)-4-fluoro-L-prolyl]azetidin-3-yl}oxy)-2-hy-
droxy-3,4-dihydro-2H-1,2-benzoxaborinine-8-carbox-
ylic acid

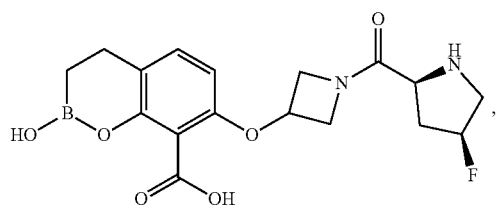 [SMILES: O=C(O)c1c(OC2CN(C(=O)[C@@H]3C[C@H](F)CN3)C2)ccc2c1OB(O)CC2]

8-({1-[(4S)-4-fluoro-L-prolyl]azetidin-3-yl}oxy)-4,4-di-
hydroxy-5-oxa-4-boranuidabicyclo[4.4.0]deca-1(6),7,
9-triene-7-carboxylic acid

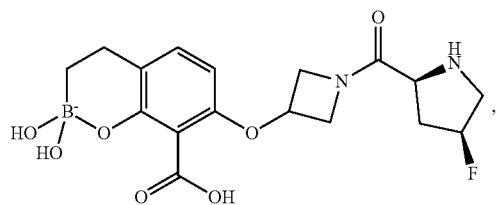 [SMILES: O=C(O)c1c(OC2CN(C(=O)[C@@H]3C[C@H](F)CN3)C2)ccc2c1O[B-](O)(O)CC2]

2-hydroxy-7-({1-[(pyrrolidin-3-yl)acetyl]azetidin-3-
yl}oxy)-3,4-dihydro-2H-1,2-benzoxaborinine-8-car-
boxylic acid

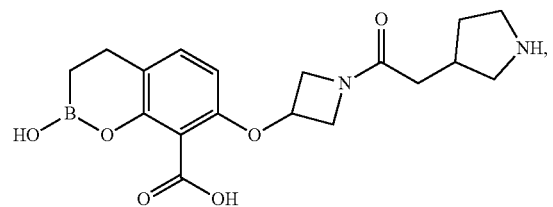 [SMILES: O=C(O)c1c(OC2CN(C(=O)CC3CCNC3)C2)ccc2c1OB(O)CC2]

730

4,4-dihydroxy-8-({1-[(pyrrolidin-3-yl)acetyl]azetidin-3-
yl}oxy)-5-oxa-4-boranuidabicyclo[4.4.0]deca-1(6),7,9-
triene-7-carboxylic acid

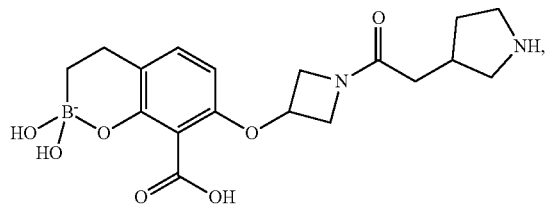 [SMILES: O=C(O)c1c(OC2CN(C(=O)CC3CCNC3)C2)ccc2c1O[B-](O)(O)CC2]

7-[(1-{[(3R,5S)-5-(dimethylcarbamoyl)pyrrolidin-3-yl]
acetyl}azetidin-3-yl)oxy]-2-hydroxy-3,4-dihydro-2H-
1,2-benzoxaborinine-8-carboxylic acid

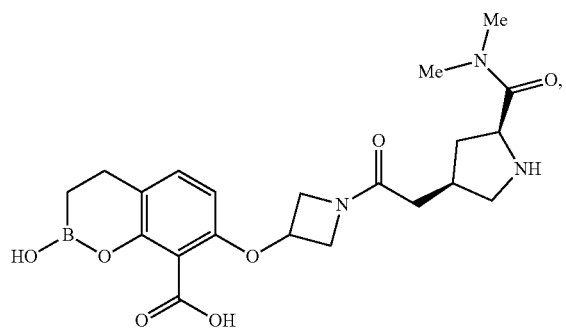 [SMILES: CN(C)C(=O)[C@@H]1C[C@H](CC(=O)N2CC(Oc3ccc4c(c3C(=O)O)OB(O)CC4)C2)CN1]

8-[(1-{[(3R,5S)-5-(dimethylcarbamoyl)pyrrolidin-3-yl]
acetyl}azetidin-3-yl)oxy]-4,4-dihydroxy-5-oxa-4-bo-
ranuidabicyclo[4.4.0]deca-1(6),7,9-triene-7-carboxylic
acid

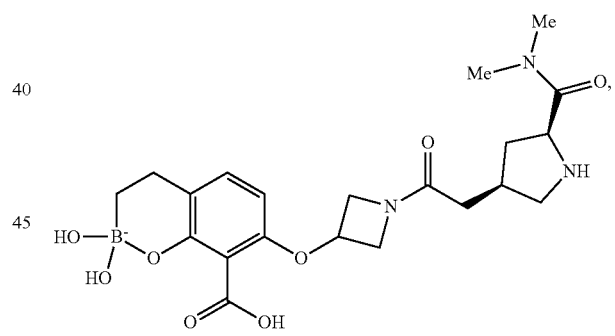

7-[(1-{[(3S,5R)-5-(dimethylcarbamoyl)pyrrolidin-3-yl]
acetyl}azetidin-3-yl)oxy]-2-hydroxy-3,4-dihydro-2H-
1,2-benzoxaborinine-8-carboxylic acid

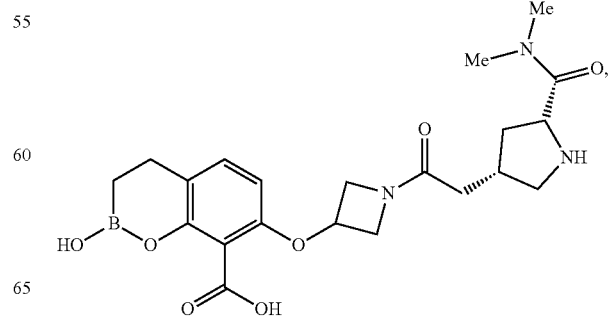

731

8-[(1-{[(3S,5R)-5-(dimethylcarbamoyl)pyrrolidin-3-yl]
 acetyl}azetidin-3-yl)oxy]-4,4-dihydroxy-5-oxa-4-bo-
 ranuidabicyclo[4.4.0]deca-1(6),7,9-triene-7-carboxylic
 acid

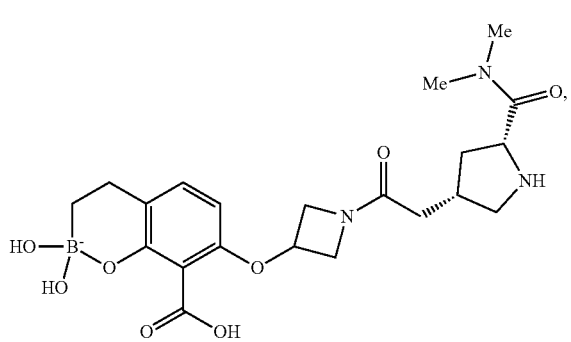 [SMILES: CN(C)C(=O)[C@H]1C[C@@H](CC(=O)N2CC(Oc3ccc4c(c3C(=O)O)O[B-](O)(O)CC4)C2)CN1]

7-[(1-{[(2R,4S)-4-fluoropyrrolidin-2-yl]acetyl}azetidin-
 3-yl)oxy]-2-hydroxy-3,4-dihydro-2H-1,2-benzoxa-
 borinine-8-carboxylic acid

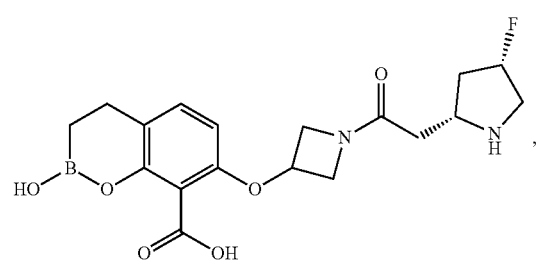 [SMILES: O=C(O)c1c(OC2CN(C(=O)C[C@@H]3C[C@H](F)CN3)C2)ccc2c1OB(O)CC2]

8-[(1-{[(2R,4S)-4-fluoropyrrolidin-2-yl]acetyl}azetidin-
 3-yl)oxy]-4,4-dihydroxy-5-oxa-4-boranuidabicyclo
 [4.4.0]deca-1(6),7,9-triene-7-carboxylic acid

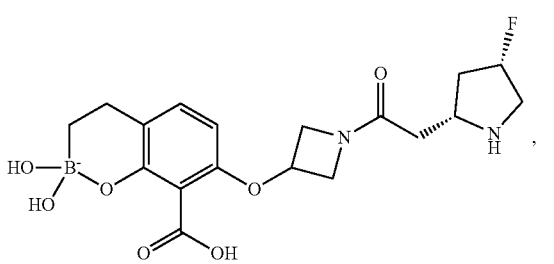 [SMILES: O=C(O)c1c(OC2CN(C(=O)C[C@@H]3C[C@H](F)CN3)C2)ccc2c1O[B-](O)(O)CC2]

7-{[1-(4,4-difluoro-L-prolyl)azetidin-3-yl]oxy}-2-hy-
 droxy-3,4-dihydro-2H-1,2-benzoxaborinine-8-carbox-
 ylic acid

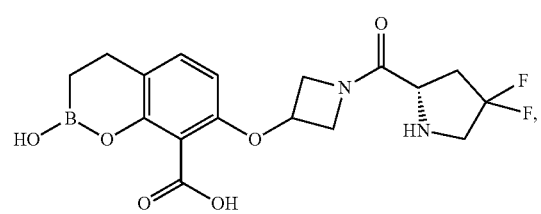 [SMILES: O=C(O)c1c(OC2CN(C(=O)[C@@H]3CC(F)(F)CN3)C2)ccc2c1OB(O)CC2]

8-{[1-(4,4-difluoro-L-prolyl)azetidin-3-yl]oxy}-4,4-di-
 hydroxy-5-oxa-4-boranuidabicyclo[4.4.0]deca-1(6),7,
 9-triene-7-carboxylic acid

732

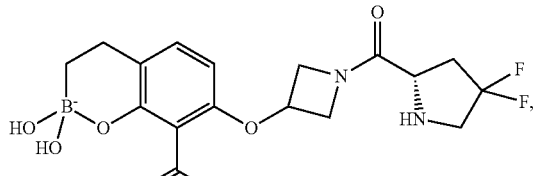

2-hydroxy-7-({1-[(4R)-4-hydroxy-L-prolyl]azetidin-3-
 yl}oxy)-3,4-dihydro-2H-1,2-benzoxaborinine-8-car-
 boxylic acid

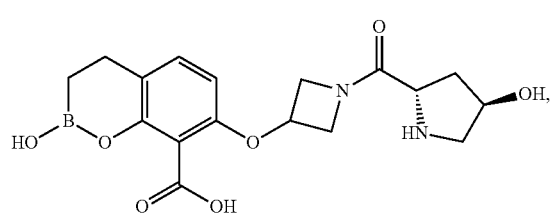 [SMILES: O=C(O)c1c(OC2CN(C(=O)[C@@H]3C[C@@H](O)CN3)C2)ccc2c1OB(O)CC2]

4,4-dihydroxy-8-({1-[(4R)-4-hydroxy-L-prolyl]azetidin-
 3-yl}oxy)-5-oxa-4-boranuidabicyclo[4.4.0]deca-1(6),7,
 9-triene-7-carboxylic acid

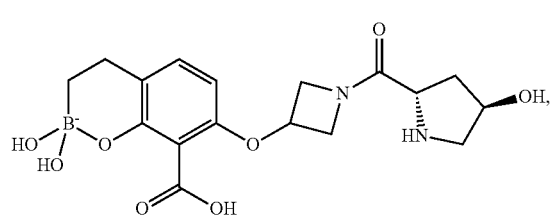 [SMILES: O=C(O)c1c(OC2CN(C(=O)[C@@H]3C[C@@H](O)CN3)C2)ccc2c1O[B-](O)(O)CC2]

2-hydroxy-7-({1-[(piperidin-4-yl)acetyl]azetidin-3-
 yl}oxy)-3,4-dihydro-2H-1,2-benzoxaborinine-8-car-
 boxylic acid

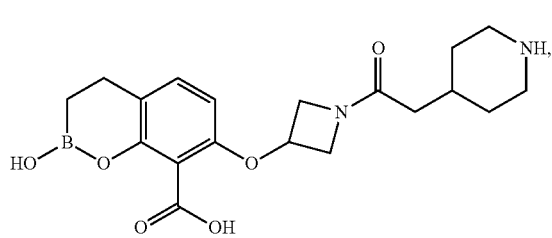 [SMILES: O=C(O)c1c(OC2CN(C(=O)CC3CCNCC3)C2)ccc2c1OB(O)CC2]

4,4-dihydroxy-8-({1-[(piperidin-4-yl)acetyl]azetidin-3-
 yl}oxy)-5-oxa-4-boranuidabicyclo[4.4.0]deca-1(6),7,9-
 triene-7-carboxylic acid

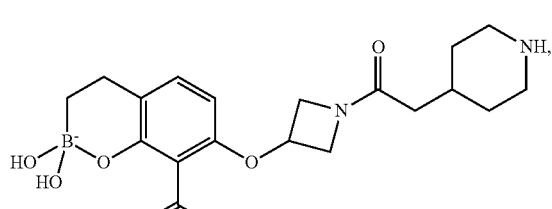

733

2-hydroxy-7-{[1-(pyrolidine-3-carbonyl)azetidin-3-yl]
oxy}-3,4-dihydro-2H-1,2-benzoxaborinine-8-carbox-
ylic acid

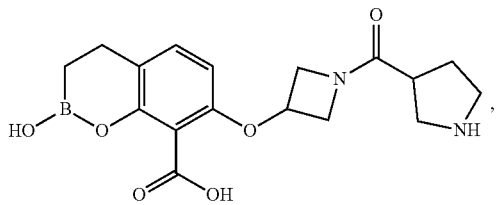 [SMILES: O=C(O)c1c(OC2CN(C(=O)C3CCNC3)C2)ccc2c1OB(O)CC2]

4,4-dihydroxy-8-{[1-(pyrolidine-3-cabonyl)azetidin-3-
yl]oxy}-5-oxa-4-boranuidabicyclo[4.4.0]deca-1(6),7,9-
triene-7-carboxylic acid

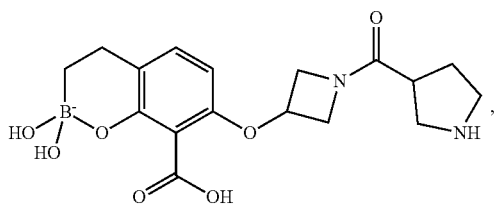 [SMILES: O=C(O)c1c(OC2CN(C(=O)C3CCNC3)C2)ccc2c1O[B-](O)(O)CC2]

2-hydroxy-7-({1-[(4S)-4-hydroxy-L-prolyl]azetidin-3-
yl}oxy)-3,4-dihydro-2H-1,2-benzoxaborinine-8-car-
boxylic acid

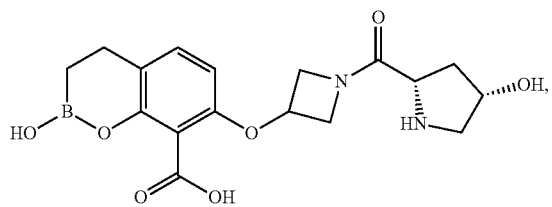 [SMILES: O=C(O)c1c(OC2CN(C(=O)[C@@H]3C[C@H](O)CN3)C2)ccc2c1OB(O)CC2]

4,4-dihydroxy-8-({1-[(4S)-4-hydroxy-L-prolyl]azetidin-
3-yl}oxy)-5-oxa-4-boranuidabicyclo[4.4.0]deca-1(6),7,
9-triene-7-carboxylic acid

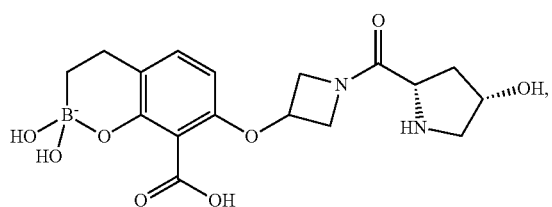 [SMILES: O=C(O)c1c(OC2CN(C(=O)[C@@H]3C[C@H](O)CN3)C2)ccc2c1O[B-](O)(O)CC2]

734

7-({1-[(4S)-4-amino-L-prolyl]azetidin-3-yl}oxy)-2-hy-
droxy-3,4-dihydro-2H-1,2-benzoxaborinine-8-carbox-
ylic acid

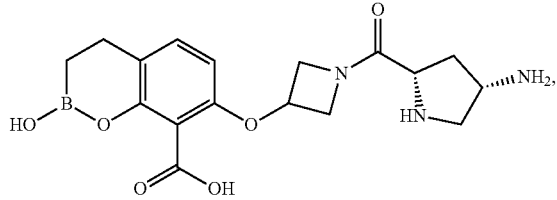 [SMILES: N[C@@H]1CN[C@H](C(=O)N2CC(Oc3ccc4c(c3C(=O)O)OB(O)CC4)C2)C1]

8-({1-[(4S)-4-amino-L-prolyl]azetidin-3-yl}oxy)-4,4-di-
hydroxy-5-oxa-4-boranuidabicyclo[4.4.0]deca-1(6),7,
9-triene-7-carboxylic acid

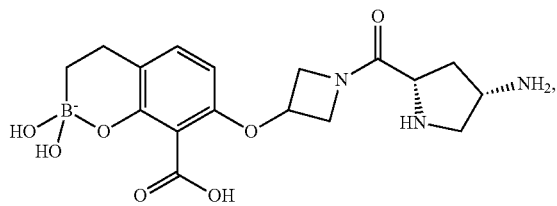 [SMILES: N[C@@H]1CN[C@H](C(=O)N2CC(Oc3ccc4c(c3C(=O)O)O[B-](O)(O)CC4)C2)C1]

7-({1-[(4S)-4-acetamido-L-prolyl]azetidin-3-yl}oxy)-2-
hydroxy-3,4-dihydro-2H-1,2-benzoxaborinine-8-car-
boxylic acid

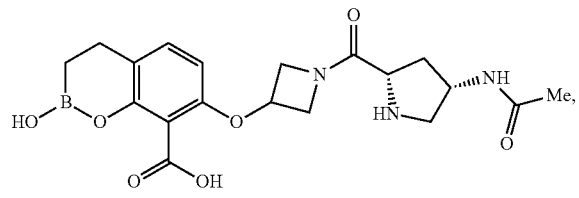 [SMILES: CC(=O)N[C@@H]1CN[C@H](C(=O)N2CC(Oc3ccc4c(c3C(=O)O)OB(O)CC4)C2)C1]

8-({1-[(4S)-4-acetamido-L-prolyl]azetidin-3-yl}oxy)-4,
4-dihydroxy-5-oxa-4-boranuidabicyclo[4.4.0]deca-1
(6),7,9-triene-7-carboxylic acid

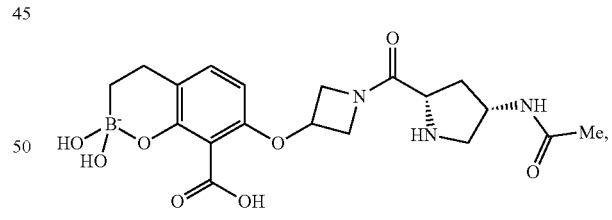

2-hydroxy-7-({1-[(3R)-3-hydroxy-L-prolyl]azetidin-3-
yl}oxy)-3,4-dihydro-2H-1,2-benzoxaborinine-8-car-
boxylic acid

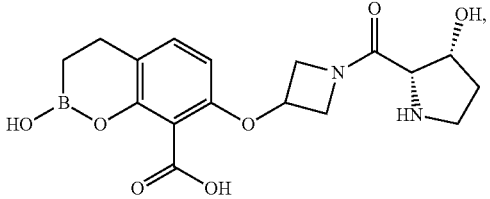 [SMILES: O=C(O)c1c(OC2CN(C(=O)[C@H]3NCC[C@H]3O)C2)ccc2c1OB(O)CC2]

735

4,4-dihydroxy-8-({1-[(3R)-3-hydroxy-L-prolyl]azetidin-3-yl}oxy)-5-oxa-4-boranuidabicyclo[4.4.0]deca-1(6),7,9-triene-7-carboxylic acid

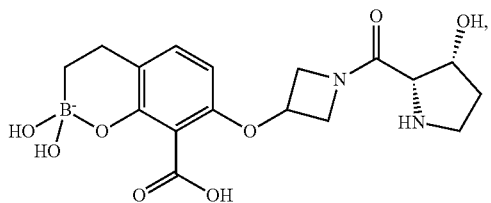 [SMILES: O=C(O)c1c(OC2CN(C(=O)[C@H]3NCC[C@H]3O)C2)ccc2c1O[B-](O)(O)CC2]

7-{[1-(4,4-dimethyl-L-prolyl)azetidin-3-yl]oxy}-2-hydroxy-3,4-dihydro-2H-1,2-benzoxaborinine-8-carboxylic acid

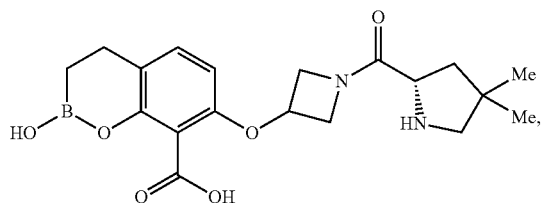 [SMILES: CC1(C)CN[C@H](C(=O)N2CC(Oc3ccc4c(c3C(=O)O)OB(O)CC4)C2)C1]

8-{[1-(4,4-dimethyl-L-prolyl)azetidin-3-yl]oxy}-4,4-dihydroxy-5-oxa-4-boranuidabicyclo[4.4.0]deca-1(6),7,9-triene-7-carboxylic acid

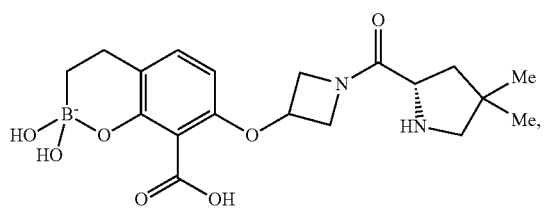 [SMILES: CC1(C)CN[C@H](C(=O)N2CC(Oc3ccc4c(c3C(=O)O)O[B-](O)(O)CC4)C2)C1]

2-hydroxy-7-({1-[(pyrrolidin-2-yl)acetyl]azetidin-3-yl}oxy)-3,4-dihydro-2H-1,2-benzoxaborinine-8-carboxylic acid

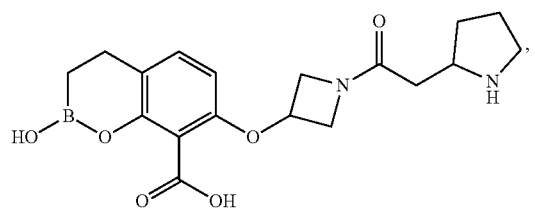 [SMILES: O=C(O)c1c(OC2CN(C(=O)CC3CCCN3)C2)ccc2c1OB(O)CC2]

4,4-dihydroxy-8-({1-[(pyrrolidin-2-yl)acetyl]azetidin-3-yl}oxy)-5-oxa-4-boranuidabicyclo[4.4.0]deca-1(6),7,9-triene-7-carboxylic acid

736

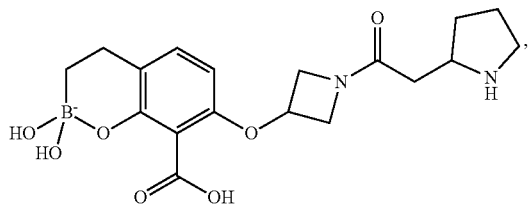 [SMILES: O=C(O)c1c(OC2CN(C(=O)CC3CCCN3)C2)ccc2c1O[B-](O)(O)CC2]

2-hydroxy-7-{[1-(piperidine-2-carbonyl)azetidin-3-yl]oxy}-3,4-dihydro-2H-1,2-benzoxaborinine-8-carboxylic acid

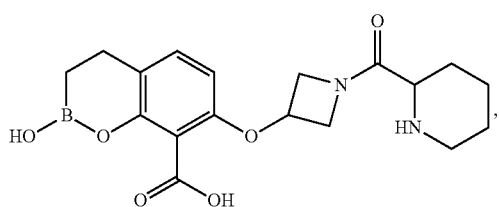

4,4-dihydroxy-8-{[1-(piperidine-2-carbonyl)azetidin-3-yl]oxy}-5-oxa-4-boranuidabicyclo[4.4.0]deca-1(6),7,9-triene-7-carboxylic acid

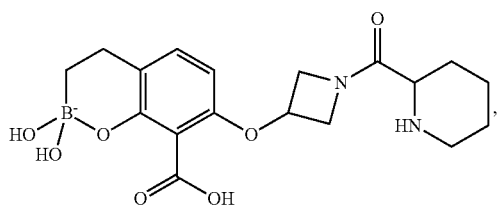 [SMILES: O=C(O)c1c(OC2CN(C(=O)C3CCCCN3)C2)ccc2c1O[B-](O)(O)CC2]

2-hydroxy-7-{[1-(piperidine-3-carbonyl)azetidin-3-yl]oxy}-3,4-dihydro-2H-1,2-benzoxaborinine-8-carboxylic acid

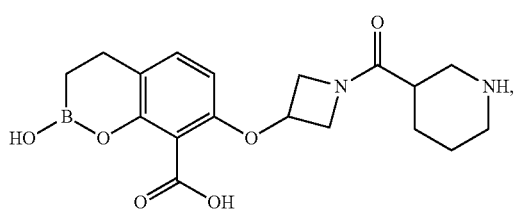 [SMILES: O=C(O)c1c(OC2CN(C(=O)C3CCCNC3)C2)ccc2c1OB(O)CC2]

4,4-dihydroxy-8-{[1-(piperidine-3-carbonyl)azetidin-3-yl]oxy}-5-oxa-4-boranuidabicyclo[4.4.0]deca-1(6),7,9-triene-7-carboxylic acid

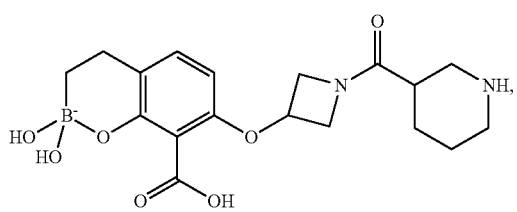 [SMILES: O=C(O)c1c(OC2CN(C(=O)C3CCCNC3)C2)ccc2c1O[B-](O)(O)CC2]

737

2-hydroxy-7-{[1-(piperidine-4-carbonyl)azetidin-3-yl]
oxy}-3,4-dihydro-2H-1,2-benzoxaborinine-8-carbox-
ylic acid

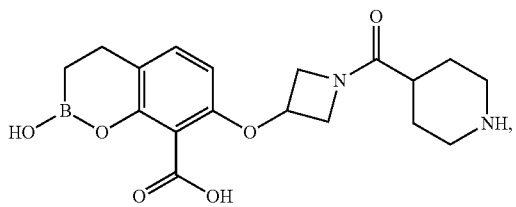 [SMILES: O=C(O)c1c(OC2CN(C(=O)C3CCNCC3)C2)ccc2c1OB(O)CC2]

4,4-dihydroxy-8-{[1-(piperidine-4-carbonyl)azetidin-3-
yl]oxy}-5-oxa-4-boranuidabicyclo[4.4.0]deca-1(6),7,9-
triene-7-carboxylic acid

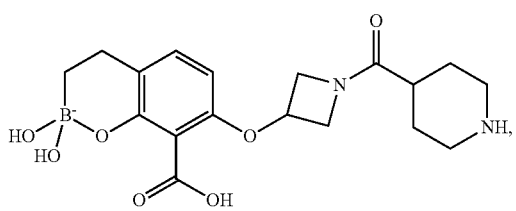 [SMILES: O=C(O)c1c(OC2CN(C(=O)C3CCNCC3)C2)ccc2c1O[B-](O)(O)CC2]

2-hydroxy-7-({1-[(2S)-oxolane-2-carbonyl]azetidin-3-
yl}oxy)-3,4-dihydro-2H-1,2-benzoxaborinine-8-car-
boxylic acid

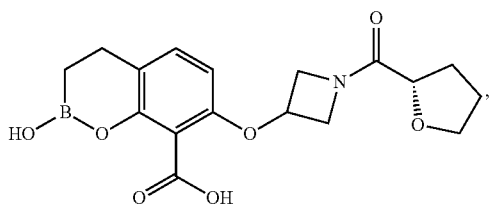 [SMILES: O=C(O)c1c(OC2CN(C(=O)[C@@H]3CCCO3)C2)ccc2c1OB(O)CC2]

4,4-dihydroxy-8-({1-[(2S)-oxolane-2-carbonyl]azetidin-
3-yl}oxy)-5-oxa-4-boranuidabicyclo[4.4.0]deca-1(6),7,
9-triene-7-carboxylic acid

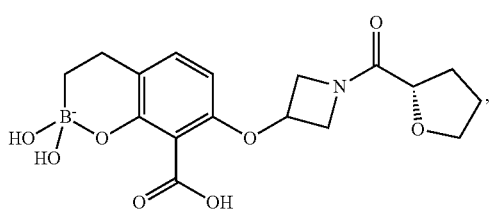 [SMILES: O=C(O)c1c(OC2CN(C(=O)[C@@H]3CCCO3)C2)ccc2c1O[B-](O)(O)CC2]

738

2-hydroxy-7-({1-[(4R)-4-phenyl-L-prolyl]azetidin-3-
yl}oxy)-3,4-dihydro-2H-1,2-benzoxaborinine-8-car-
boxylic acid

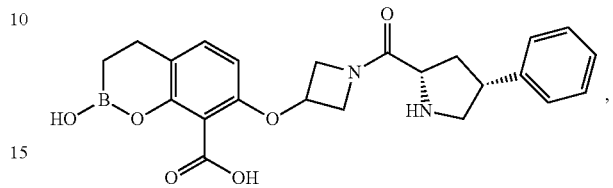

4,4-dihydroxy-8-({1-[(4R)-phenyl-L-prolyl]azetidin-3-
yl}oxy)-5-oxa-4-boranuidabicyclo[4.4.0]deca-1(6),7,9-
triene-7-carboxylic acid

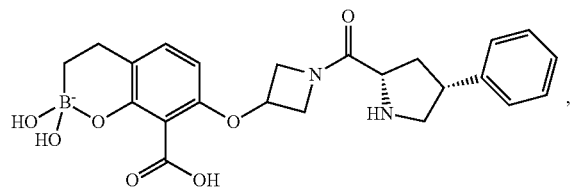 [SMILES: O=C(O)c1c(OC2CN(C(=O)[C@@H]3C[C@H](c4ccccc4)CN3)C2)ccc2c1O[B-](O)(O)CC2]

7-({1-[(1S,3S,5S)-2-azabicyclo[3.1.0]hexane-3-carbo-
nyl]azetidin 3-yl}oxy)-2-hydroxy-3,4-dihydro-2H-1,2-
benzoxaborinine-8-carboxylic acid

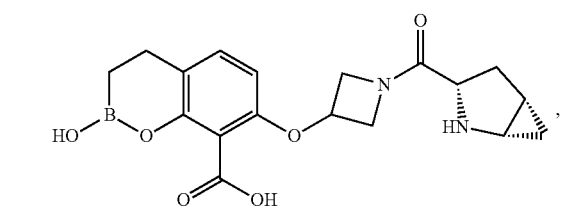 [SMILES: O=C(O)c1c(OC2CN(C(=O)[C@@H]3C[C@@H]4C[C@@H]4N3)C2)ccc2c1OB(O)CC2]

8-({1-[(1S,3S,5S)-2-azabicyclo[3.1.0]hexane-3-carbo-
nyl]azetidin-3-yl}oxy)-4,4-dihydroxy-5-oxa-4-boranu-
idabicyclo[4.4.0]deca-1(6),7,9-triene-7-carboxylic acid

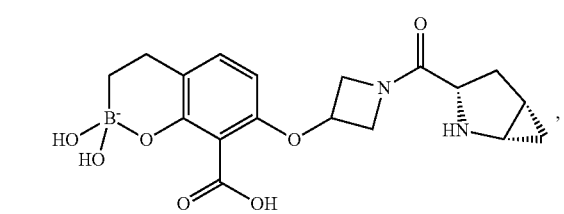 [SMILES: O=C(O)c1c(OC2CN(C(=O)[C@@H]3C[C@@H]4C[C@@H]4N3)C2)ccc2c1O[B-](O)(O)CC2]

2-hydroxy-7-{[1-(1-methyl-L-prolyl)azetidin-3-yl]oxy}-3,4-dihydro-2H-1,2-benzoxaborinine-8-carboxylic acid

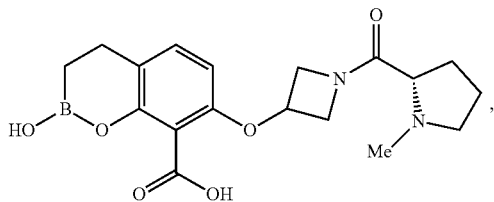 [SMILES: CN1CCC[C@H]1C(=O)N1CC(Oc2ccc3c(c2C(=O)O)OB(O)CC3)C1]

4,4-dihydroxy-8-{[1-(1-methyl-L-prolyl)azetidin-3-yl]oxy}-5-oxa-4-boranuidabicyclo[4.4.0]deca-1(6),7,9-triene-7-carboxylic acid

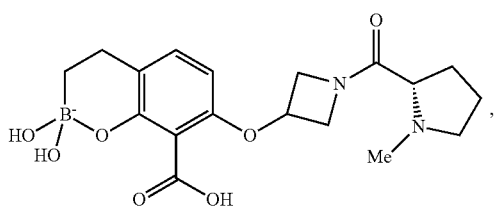 [SMILES: CN1CCC[C@H]1C(=O)N1CC(Oc2ccc3c(c2C(=O)O)O[B-](O)(O)CC3)C1]

2-hydroxy-7-({1-[(piperidin-3-yl)acetyl]azetidin-3-yl}oxy)-3,4-dihydro-2H-1,2-benzoxaborinine-8-carboxylic acid

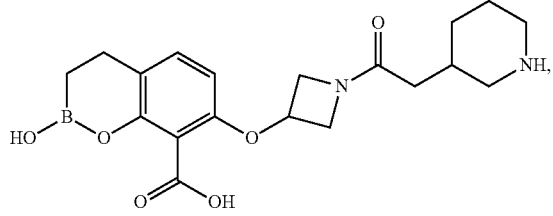 [SMILES: O=C(O)c1c(OC2CN(C(=O)CC3CCCNC3)C2)ccc2c1OB(O)CC2]

4,4-dihydroxy-8-({1-[(piperidin-3-yl)acetyl]azetidin-3-yl}oxy)-5-oxa-4-boranuidabicyclo[4.4.0]deca-1(6),7,9-triene-7-carboxylic acid

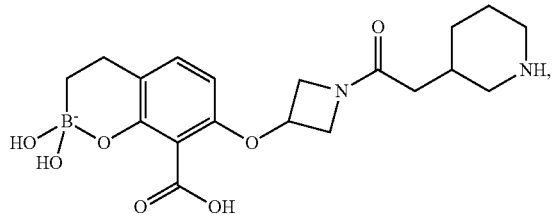 [SMILES: O=C(O)c1c(OC2CN(C(=O)CC3CCCNC3)C2)ccc2c1O[B-](O)(O)CC2]

2-hydroxy-7-({1-[(morpholin-2-yl)acetyl]azetidin-3-yl}oxy)-3,4-dihydro-2H-1,2-benzoxaborinine-8-carboxylic acid

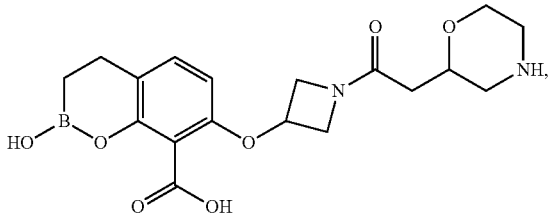

4,4-dihydroxy-8-({1-[(morpholin-2-yl)acetyl]azetidin-3-yl}oxy)-5-oxa-4-boranuidabicyclo[4.4.0]deca-1(6),7,9-triene-7-carboxylic acid

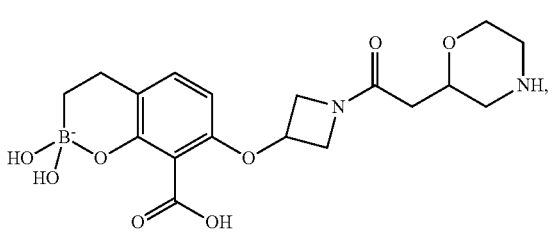

7-({1-[(azetidin-3-yl)acetyl]azetidin-3-yl}oxy)-2-hydroxy-3,4-dihydro-2H-1,2-benzoxaborinine-8-carboxylic acid

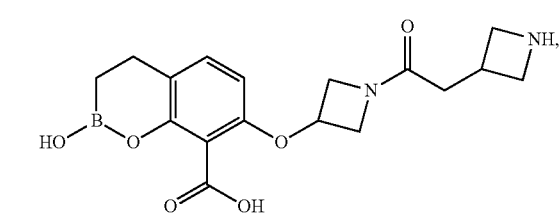 [SMILES: O=C(O)c1c(OC2CN(C(=O)CC3CNC3)C2)ccc2c1OB(O)CC2]

8-({1-[(azetidin-3-yl)acetyl]azetidin-3-yl}oxy)-4,4-dihydroxy-5-oxa-4-boranuidabicyclo[4.4.0]deca-1(6),7,9-triene-7-carboxylic acid

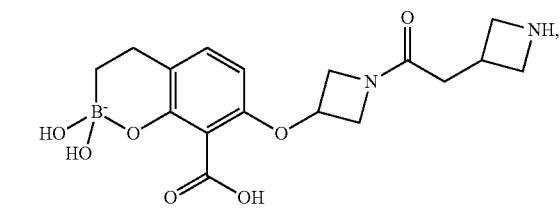 [SMILES: O=C(O)c1c(OC2CN(C(=O)CC3CNC3)C2)ccc2c1O[B-](O)(O)CC2]

7-({1-[amino(pyrolidin-3-yl)acetyl]azetidin-3-yl}oxy)-2-hydroxy-3,4-dihydro-2H-1,2-benzoxaborinine-8-carboxylic acid

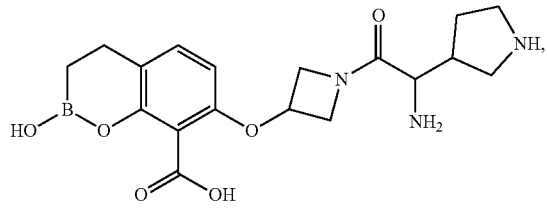 [SMILES: NC(C(=O)N1CC(Oc2ccc3c(c2C(=O)O)OB(O)CC3)C1)C1CCNC1]

741

8-({1-[amino(pyrrolidin-3-yl)acetyl]azetidin-3-yl}oxy)-4,4-dihydroxy-5-oxa-4-boranuidabicyclo[4.4.0]deca-1(6),7,9-triene-7-carboxylic acid

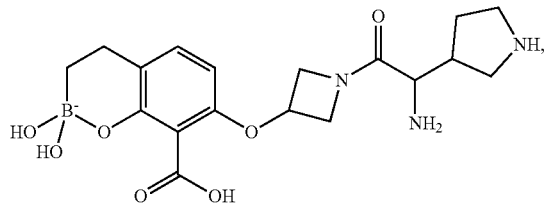 [SMILES: NC(C(=O)N1CC(Oc2ccc3c(c2C(=O)O)O[B-](O)(O)CC3)C1)C1CCNC1]

2-hydroxy-7-({1-[3-(pyrrolidin-2-yl)propanoyl]azetidin-3-yl}oxy)-3,4-dihydro-2H-1,2-benzoxaborinine-8-carboxylic acid

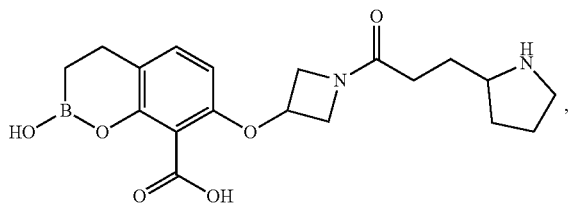 [SMILES: O=C(O)c1c(OC2CN(C(=O)CCC3CCCN3)C2)ccc2c1OB(O)CC2]

4,4-dihydroxy-8-({1-[3-(pyrrolidin-2-yl)propanoyl]azetidin-3-yl}oxy)-5-oxa-4-boranuidabicyclo[4.4.0]deca-1(6),7,9-triene-7-carboxylic acid

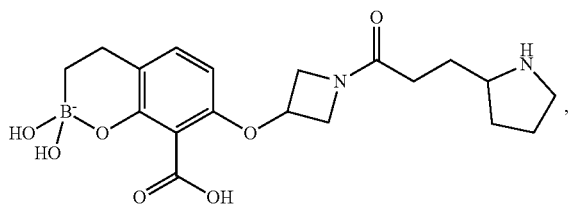 [SMILES: O=C(O)c1c(OC2CN(C(=O)CCC3CCCN3)C2)ccc2c1O[B-](O)(O)CC2]

7-({1-[(4R)-4-amino-L-prolyl]azetidin-3-yl}oxy)-2-hydroxy-3,4-dihydro-2H-1,2-benzoxaborinine-8-carboxylic acid

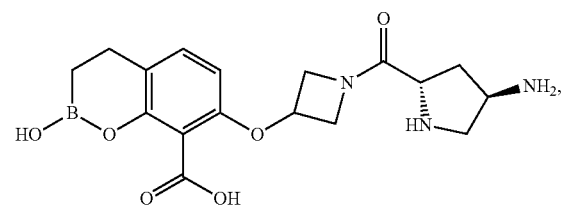 [SMILES: N[C@H]1CN[C@H](C(=O)N2CC(Oc3ccc4c(c3C(=O)O)OB(O)CC4)C2)C1]

8-({1-[(4R)-4-amino-L-prolyl]azetidin-3-yl}oxy)-4,4-dihydroxy-5-oxa-4-boranuidabicyclo[4.4.0]deca-1(6),7,9-triene-7-carboxylic acid

742

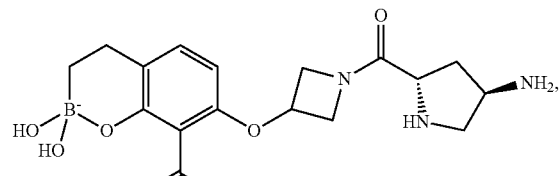

7-({1-[(4R)-4-acetamido-L-prolyl]azetidin-3-yl}oxy)-2-hydroxy-3,4-dihydro-2H-1,2-benzoxaborinine-8-carboxylic acid

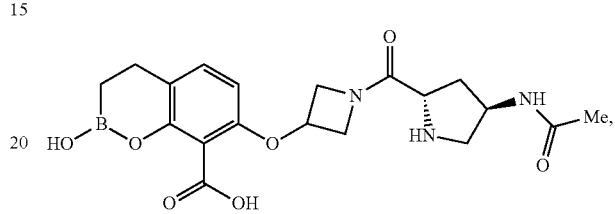

8-({1-[(4R)-4-acetamido-L-prolyl]azetidin-3-yl}oxy)-4,4-dihydroxy-5-oxa-4-boranuidabicyclo[4.4.0]deca-1(6),7,9-triene-7-carboxylic acid

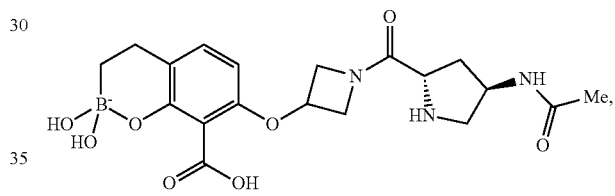

7-({1-[amino(piperidin-4-yl)acetyl]azetidin-3-yl}oxy)-2-hydroxy-3,4-dihydro-2H-1,2-benzoxaborinine-8-carboxylic acid

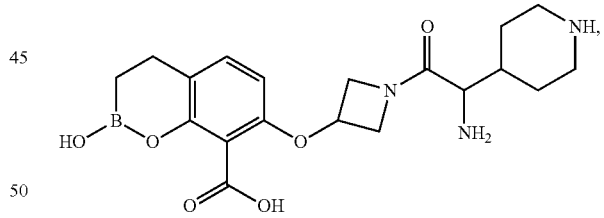

8-({-[amino(piperidin-4-yl}acetyl]azetidin-3-yloxy)-4,4-dihydroxy-5-oxa-4-boranuidabicyclo[4.4.0]deca-1(6),7,9-triene-7-carboxylic acid

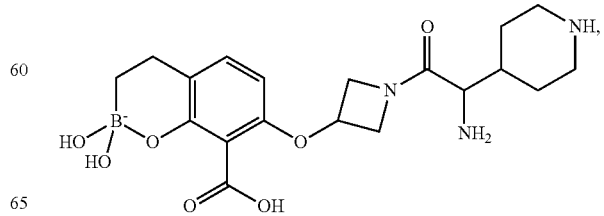

743

2-hydroxy-7-({1-[(piperidin-2-yl)acetyl]azetidin-3-yl}oxy)-3,4-dihydro-2H-1,2-benzoxaborinine-8-carboxylic acid

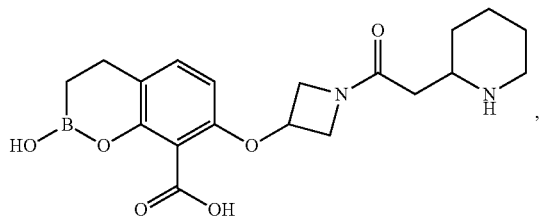 [SMILES: O=C(O)c1c(OC2CN(C(=O)CC3CCCCN3)C2)ccc2c1OB(O)CC2]

4,4-dihydroxy-8-({1-[(piperidin-2-yl)acetyl]azetidin-3-yl}oxy)-5-oxa-4-boranuidabicyclo[4.4.0]deca-1(6),7,9-triene-7-carboxylic acid

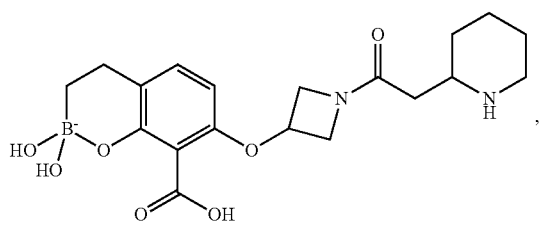 [SMILES: O=C(O)c1c(OC2CN(C(=O)CC3CCCCN3)C2)ccc2c1O[B-](O)(O)CC2]

7-({1-[(4S)-4-carbamoyl-L-prolyl]azetidin-3-yl}oxy)-2-hydroxy-3,4-dihydro-2H-1,2-benzoxaborinine-8-carboxylic acid

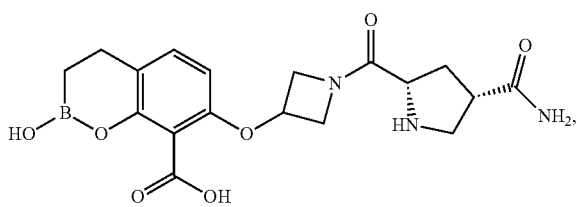 [SMILES: NC(=O)[C@@H]1CN[C@H](C(=O)N2CC(Oc3ccc4c(c3C(=O)O)OB(O)CC4)C2)C1]

8-({1-[(4S)-4-carbamoyl-L-prolyl]azetidin-3-yl}oxy)-4,4-dihydroxy-5-oxa-4-boranuidabicyclo[4.4.0]deca-1(6),7,9-triene-7-carboxylic acid

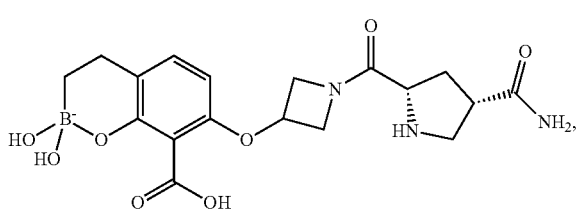 [SMILES: NC(=O)[C@@H]1CN[C@H](C(=O)N2CC(Oc3ccc4c(c3C(=O)O)O[B-](O)(O)CC4)C2)C1]

2-hydroxy-7-[(1-{[(3R)-pyrrolidin-3-yl]acetyl}azetidin-3-yl)oxy]-3,4-dihydro-2H-1,2-benzoxaborine-8-carboxylic acid

744

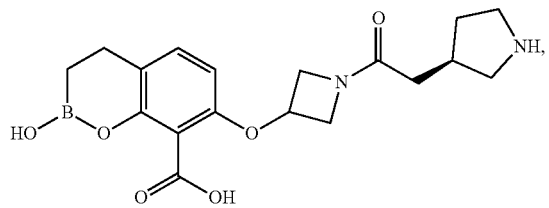 [SMILES: O=C(O)c1c(OC2CN(C(=O)C[C@H]3CCNC3)C2)ccc2c1OB(O)CC2]

4,4-dihydroxy-8-[(1-{[(3R)-pyrrolidin-3-yl]acetyl}azetidin-3-yl)oxy]-5-oxa-4-boranuidabicyclo[4.4.0]deca-1(6),7,9-triene-7-carboxylic acid

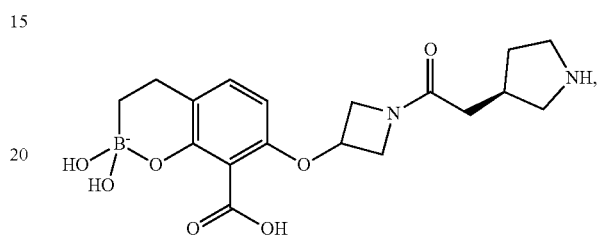

2-hydroxy-7-[(1-{[(3S)-pyrrolidin-3-yl]acetyl}azetidin-3-yl)oxy]-3,4-dihydro-2H-1,2-benzoxaborine-8-carboxylic acid

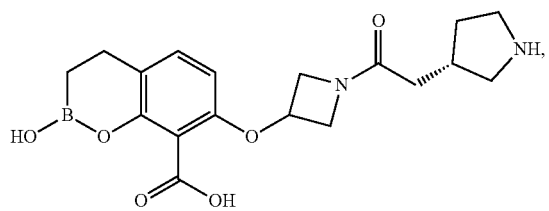 [SMILES: O=C(O)c1c(OC2CN(C(=O)C[C@@H]3CCNC3)C2)ccc2c1OB(O)CC2]

4,4-dihydroxy-8-[(1-{[(3S)-pyrrolidin-3-yl]acetyl}azetidin-3-yl)oxy]-5-oxa-4-boranuidabicyclo[4.4.0]deca-1(6),7,9-triene-7-carboxylic acid

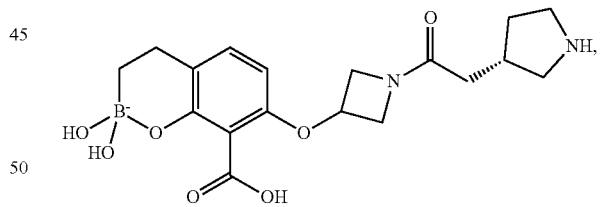

2-hydroxy-7-[(1-{[(2R)-pyrrolidin-2-yl]acetyl}azetidin-3-yl)oxy]-3,4-dihydro-2H-1,2-benzoxaborine-8-carboxylic acid

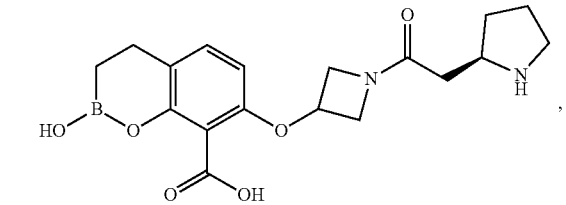 [SMILES: O=C(O)c1c(OC2CN(C(=O)C[C@H]3CCCN3)C2)ccc2c1OB(O)CC2]

745

4,4-dihydroxy-8-[(1-{[(2R)-pyrrolidin-2-yl]
acetyl}azetidin-3-yl)oxy]-5-oxa-4-boranuidabicyclo
[4.4.0]deca-1(6),7,9-triene-7-carboxylic acid

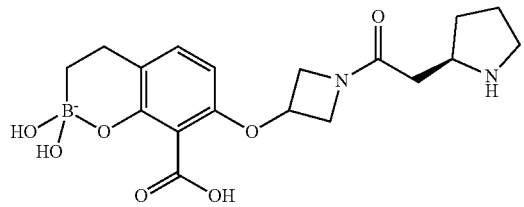

2-hydroxy-7-[(1-{[(2S)-pyrrolidin-2-yl]acetyl}azetidin-
3-yl)oxy]-3,4-dihydro-2H-1,2-benzoxaborine-8-car-
boxylic acid

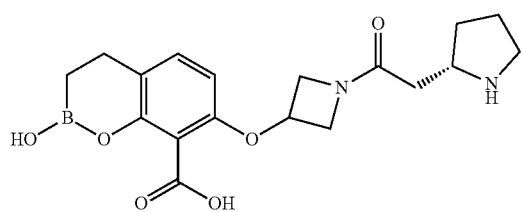

4,4-dihydroxy-8-[(1-{[(2S)-pyrrolidin-2-yl]
acetyl}azetidin-3-yl)oxy]-5-oxa-4-boranuidabicyclo
[4.4.0]deca-1(6),7,9-triene-7-carboxylic acid

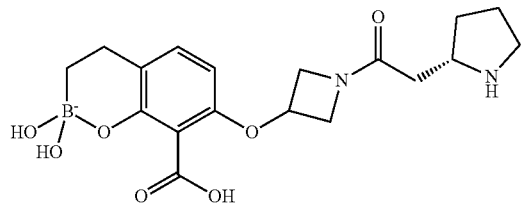

2-hydroxy-7-({1-[(piperazin-2-yl)acetyl]azetidin-3-
yl}oxy)-3,4-dihydro-2H-1,2-benzoxaborinine-8-car-
boxylic acid

746

4,4-dihydroxy-8-({1-[(piperazin-2-yl)acetyl]azetidin-3-
yl}oxy)-5-oxa-4-boranuidabicyclo[4.4.0]deca-1(6),7,9-
triene-7-carboxylic acid

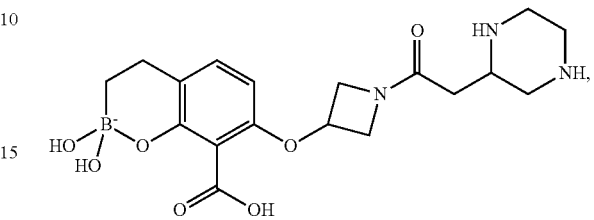

7-({1-[(1,1-dioxo-1$\lambda^6$-thiomorpholin-2-yl)acetyl]azeti-
din-3-yl}oxy)-2-hydroxy-3,4-dihydro-2H-1,2-benzo-
xaborinine-8-carboxylic acid

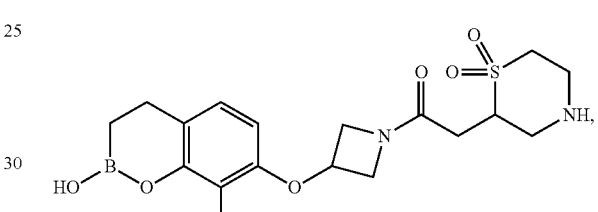

8-({1-[(1,1-dioxo-1$\lambda^d$-thiomorpholin-2-yl)acetyl]azeti-
din-3-yl}oxy)-4,4-dihydroxy-5-oxa-4-boranuidabicy-
clo[4.4.0]deca-(6),7,9-triene-7-carboxylic acid

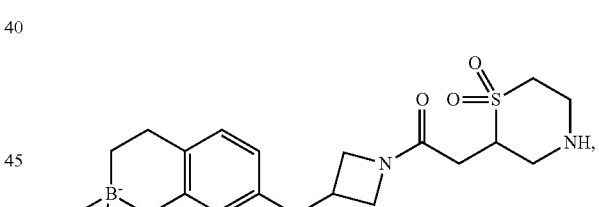

7-({1-[(2S)-4-acetamido-2-aminobutanoyl]azetidin-3-
yl}oxy)-2-hydroxy-3,4-dihydro-2H-1,2-benzoxabori-
nine-8-carboxylic acid

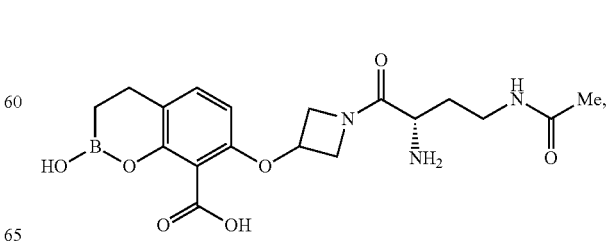

747

8-({1-[(2S)-4-acetamido-2-aminobutanoyl]azetidin-3-yl}oxy)-4,4-dihydroxy-5-oxa-4-boranuidabicyclo[4.4.0]deca-1(6),7,9-triene-7-carboxylic acid

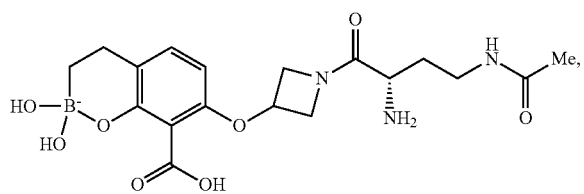 [SMILES: CC(=O)NCC[C@H](N)C(=O)N1CC(Oc2ccc3c(c2C(=O)O)O[B-](O)(O)CC3)C1]

7-{[1-(L-α-asparaginyl)azetidin-3-yl]oxy}-2-hydroxy-3,4-dihydro-2H-1,2-benzoxaborinine-8-carboxylic acid

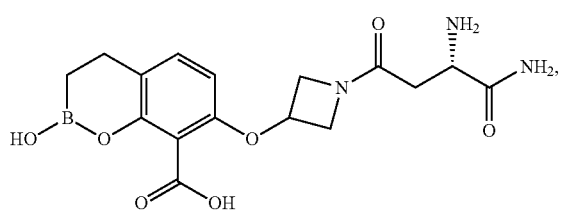 [SMILES: NC(=O)[C@@H](N)CC(=O)N1CC(Oc2ccc3c(c2C(=O)O)OB(O)CC3)C1]

8-{[1-(L-α-asparaginyl)azetidin-3-yl]oxy}-4,4-dihydroxy-5-oxa-4-boranuidabicyclo[4.4.0]deca-1(6),7,9-triene-7-carboxylic acid

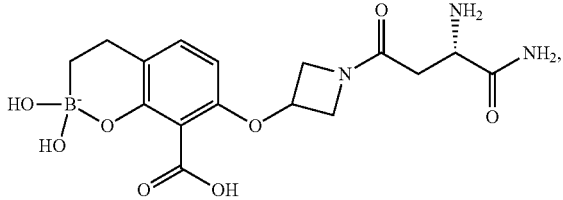 [SMILES: NC(=O)[C@@H](N)CC(=O)N1CC(Oc2ccc3c(c2C(=O)O)O[B-](O)(O)CC3)C1]

7-{[1-(L-alanyl-L-alanyl)azetidin-3-yl]oxy}-2-hydroxy-3,4-dihydro-2H-1,2-benzoxaborinine-8-carboxylic acid

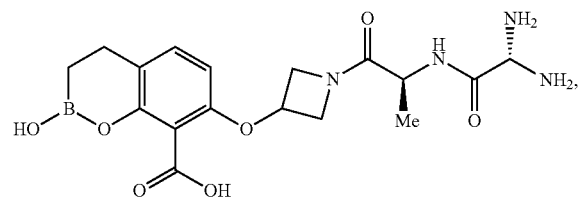

748

8-{([1-(L-alanyl-L-alanyl)azetidin-3-yl]oxy}-4,4-dihydroxy-5-oxa-4-boranuidabicyclo[4.4.0]deca-1(6),7,9-triene-7-carboxylic acid

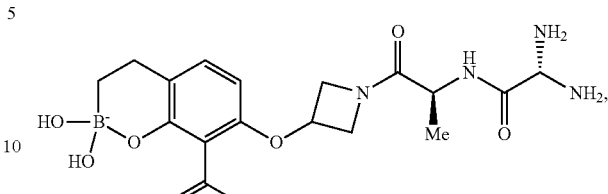

7-{[1-(glycyl-D-alanyl)azetidin-3-yl]oxy}-2-hydroxy-3,4-dihydro-2H-1,2-benzoxaborinine-8-carboxylic acid

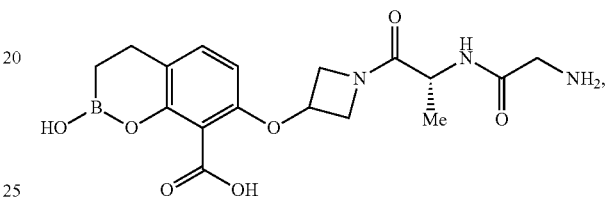

8-{[1-(glycyl-D-alanyl)azetidin-3-yl]oxy}-4,4-dihydroxy-5-oxa-4-boranuidabicyclo[4.4.0]deca-1(6),7,9-triene-7-carboxylic acid

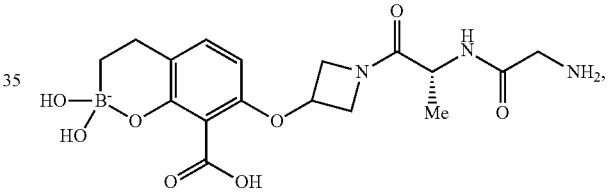

N-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-α-asparagine

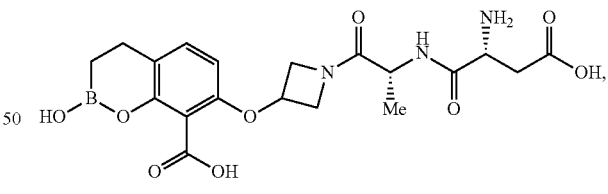

N-[(2R)-1-{3-[(7-carboxy-4,4-hydroxy-5-oxa-4-boranuidabicyclo[4.4.0]deca-1(6),7,9-trien-8-yl)oxy]azetidin-1-yl}-1-oxopropan-2-yl]-D-α-asparagine

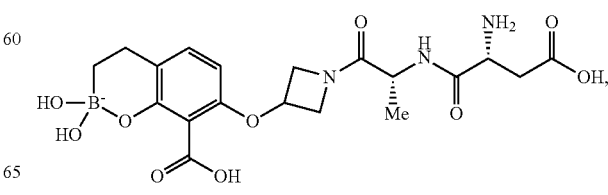

749

N¹-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-aspartamide

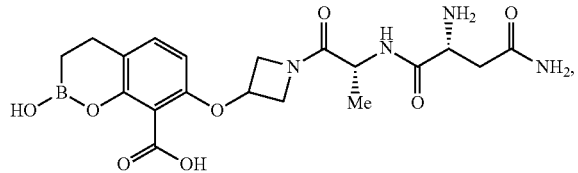 [SMILES: C[C@@H](NC(=O)[C@H](N)CC(N)=O)C(=O)N1CC(Oc2ccc3c(c2C(=O)O)OB(O)CC3)C1]

N¹-[(2R)-1-{3-[(7-carboxy-4,4-hydroxy-5-oxa-4-boranuidabicyclo[4.4.0]deca-1(6),7,9-trien-8-yl)oxy]azetidin-1-yl}-1-oxopropan-2-yl]-D-aspartamide

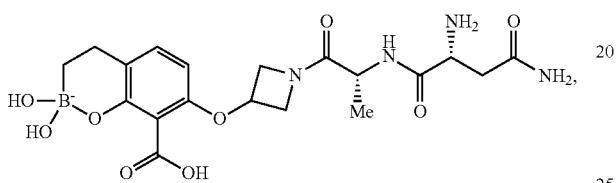

N-[(2R)-1-{3-[(8-carboxy-2-hydroxy-3,4-dihydro-2H-1,2-benzoxaborinine-7-yl)oxy]azetidin-1-yl}-1-oxopropan-2-yl]-D-serinamide

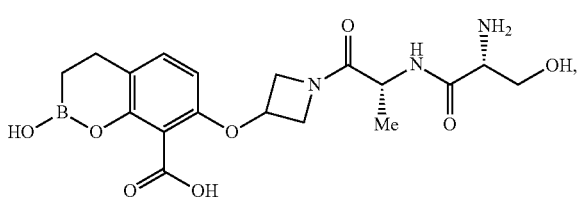 [SMILES: C[C@@H](NC(=O)[C@H](N)CO)C(=O)N1CC(Oc2ccc3c(c2C(=O)O)OB(O)CC3)C1]

N-[(2R)-1-{3-[(7-carboxy-4,4-hydroxy-5-oxa-4-boranuidabicyclo[4.4.0]deca-1(6),7,9-trien-8-yl)oxy]azetidin-1-yl}-1-oxopropan-2-yl]-D-serinamide

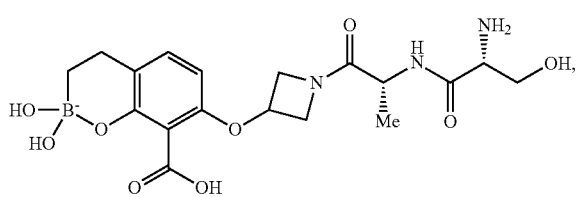 [SMILES: C[C@@H](NC(=O)[C@H](N)CO)C(=O)N1CC(Oc2ccc3c(c2C(=O)O)O[B-](O)(O)CC3)C1]

7-({1-[(3S)-3-amino-3-carboxypropanoyl]azetidin-3-yl}oxy)-2-hydroxy-3,4-dihydro-2H-1,2-benzoxaborinine-8-carboxylic acid

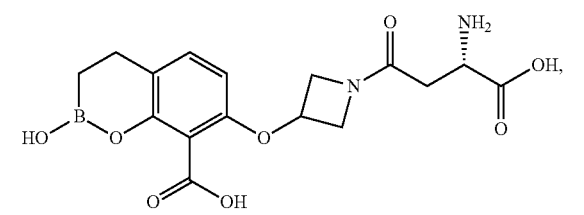 [SMILES: N[C@@H](CC(=O)N1CC(Oc2ccc3c(c2C(=O)O)OB(O)CC3)C1)C(=O)O]

750

8-({1-[(3S)-3-amino-3-carboxypropanoyl]azetidin-3-yl}oxy)-4,4-dihydroxy-5-oxa-4-boranuidabicyclo[4.4.0]deca-1(6),7,9-triene-7-carboxylic acid

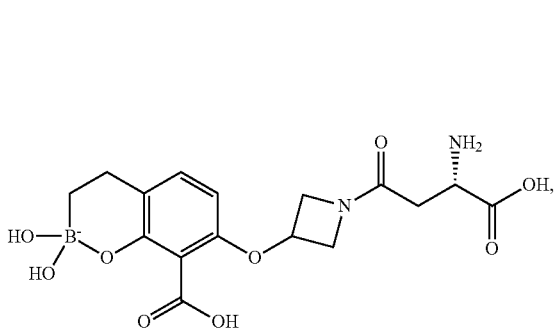 [SMILES: N[C@@H](CC(=O)N1CC(Oc2ccc3c(c2C(=O)O)O[B-](O)(O)CC3)C1)C(=O)O]

2-hydroxy-7-({1-[(1H-imidazol-4-yl)(methylamino)acetyl]azetidin-3-yl}oxy)-3,4-dihydro-2H-1,2-benzoxaborinine-8-carboxylic acid

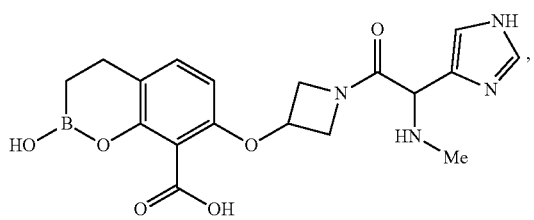 [SMILES: CNC(C(=O)N1CC(Oc2ccc3c(c2C(=O)O)OB(O)CC3)C1)c1c[nH]cn1]

4,4-dihydroxy-8-({1-[(1H-imidazol-4-yl)(methylamino)acetyl]azetidin-3-yl}oxy)-5-oxa-4-boranuidabicyclo[4.4.0]deca-1(6),7,9-triene-7-carboxylic acid

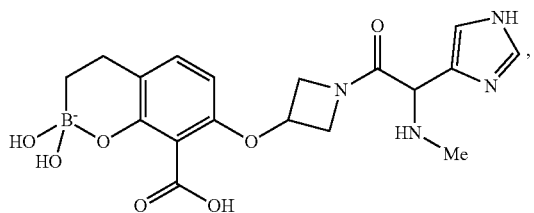 [SMILES: CNC(C(=O)N1CC(Oc2ccc3c(c2C(=O)O)O[B-](O)(O)CC3)C1)c1c[nH]cn1]

2-hydroxy-7-({1-[(1H-imidazol-4-yl)(methylamino)acetyl]azetidin-3-yl}oxy)-3,4-dihydro-2H-1,2-benzoxaborinine-8-carboxylic acid

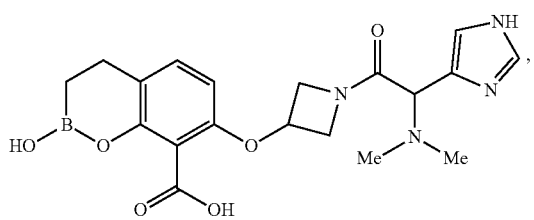 [SMILES: CN(C)C(C(=O)N1CC(Oc2ccc3c(c2C(=O)O)OB(O)CC3)C1)c1c[nH]cn1]

751

4,4-dihydroxy-8-({1-[(1H-imidazol-4-yl)(methylamino)
acetyl]azetidin-3-yl}oxy)-5-oxa-4-boranuidabicyclo
[4.4.0]deca-1(6),7,9-triene-7-carboxylic acid

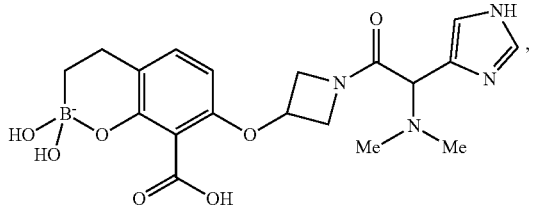 [SMILES: CN(C)C(C(=O)N1CC(Oc2ccc3c(c2C(=O)O)O[B-](O)(O)CC3)C1)c1c[nH]cn1]

2-hydroxy-7-{[1-(2-methyl-D-seryl)azetidin-3-yl]oxy}-
3,4-dihydro-2H-1,2-benzoxaborinine-8-carboxylic
acid

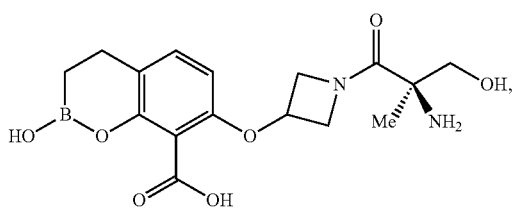 [SMILES: C[C@@](N)(CO)C(=O)N1CC(Oc2ccc3c(c2C(=O)O)OB(O)CC3)C1]

4,4-dihydroxy-8-{[1-(2-methyl-D-seryl)azetidin-3-yl]
oxy}-5-oxa-4-boranuidabicyclo[4.4.0]deca-1(6),7,9-
triene-7-carboxylic acid

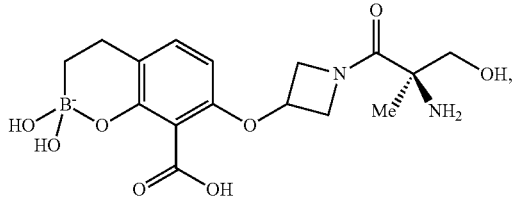 [SMILES: C[C@@](N)(CO)C(=O)N1CC(Oc2ccc3c(c2C(=O)O)O[B-](O)(O)CC3)C1]

2-hydroxy-7-{[1-(2-methyl-L-seryl)azetidin-3-yl]oxy}-3,
4-dihydro-2H-1,2-benzoxaborinine-8-carboxylic acid

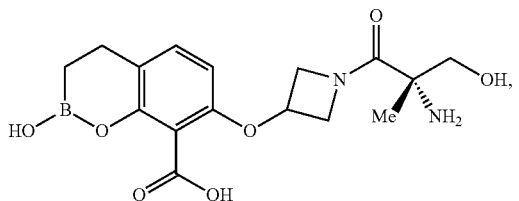 [SMILES: C[C@](N)(CO)C(=O)N1CC(Oc2ccc3c(c2C(=O)O)OB(O)CC3)C1]

752

4,4-dihydroxy-8-{[1-(2-methyl-L-seryl)azetidin-3-yl]
oxy}-5-oxa-4-boranuidabicyclo[4.4.0]deca-1(6),7,9-
triene-7-carboxylic acid

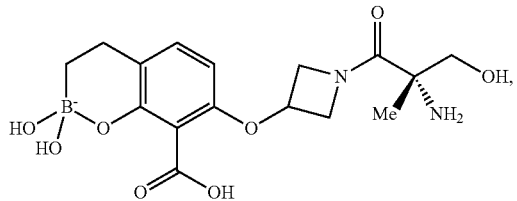 [SMILES: C[C@](N)(CO)C(=O)N1CC(Oc2ccc3c(c2C(=O)O)O[B-](O)(O)CC3)C1]

2-hydroxy-7-({1-[(3-oxopiperazin-2-yl)acetyl]azetidin-
3-yl}oxy)-3,4-dihydro-2H-1,2-benzoxaborinine-8-car-
boxylic acid

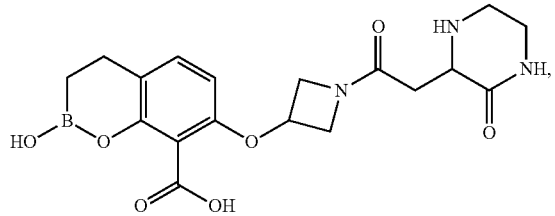 [SMILES: O=C(O)c1c(OC2CN(C(=O)CC3NCCNC3=O)C2)ccc2c1OB(O)CC2]

4,4-dihydroxy-8-({1-[(3-oxopiperazin-2-yl)acetyl]azeti-
din-3-yl}oxy)-5-oxa-4-boranuidabicyclo[4.4.0]deca-1
(6),7,9-triene-7-carboxylic acid

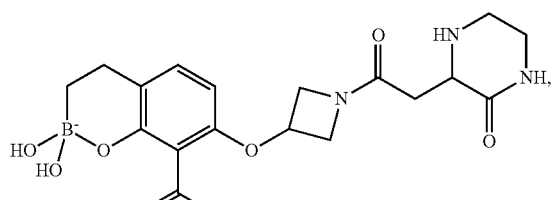

7-({1-[(3S)-3-amino-5-carboxypentanoyl]azetidin-3-
yl}oxy)-2-hydroxy-3,4-dihydro-2H-1,2-benzoxabori-
nine-8-carboxylic acid

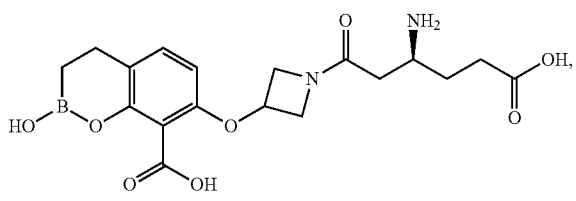 [SMILES: N[C@@H](CCC(=O)O)CC(=O)N1CC(Oc2ccc3c(c2C(=O)O)OB(O)CC3)C1]

8-({1-[(3S)-3-amino-5-carboxypentanoyl]azetidin-3-
yl}oxy)-4,4-dihydroxy-5-oxa-4-boranuidabicyclo
[4.4.0]deca-1(6),7,9-triene-7-carboxylic acid

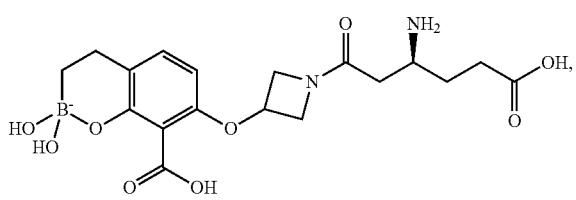 [SMILES: N[C@@H](CCC(=O)O)CC(=O)N1CC(Oc2ccc3c(c2C(=O)O)O[B-](O)(O)CC3)C1]

753

7-({1-[(3R)-3-amino-3-carboxypropanoyl]azetidin-3-yl}oxy)-2-hydroxy-3,4-dihydro-2H-1,2-benzoxaborinine-8-carboxylic acid

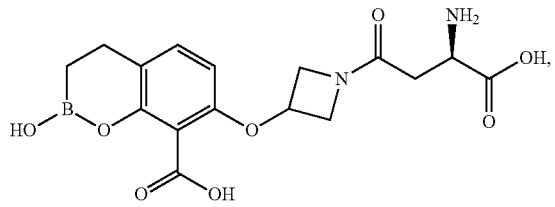 [SMILES: N[C@H](CC(=O)N1CC(Oc2ccc3c(c2C(=O)O)OB(O)CC3)C1)C(=O)O]

8-({1-[(3R)-3-amino-3-carboxypropanoyl]azetidin-3-yl}oxy)-4,4-dihydroxy-5-oxa-4-boranuidabicyclo[4.4.0]deca-1(6),7,9-triene-7-carboxylic acid

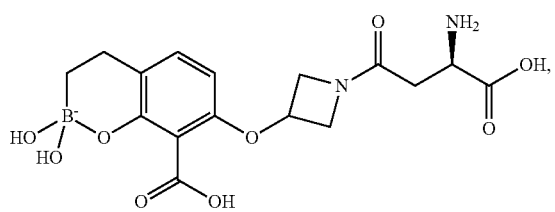 [SMILES: N[C@H](CC(=O)N1CC(Oc2ccc3c(c2C(=O)O)O[B-](O)(O)CC3)C1)C(=O)O]

7-({1-[(4R)-4-amino-4-carboxybutanoyl]azetidin-3-yl}oxy)-2-hydroxy-3,4-dihydro-2H-1,2-benzoxaborinine-8-carboxylic acid

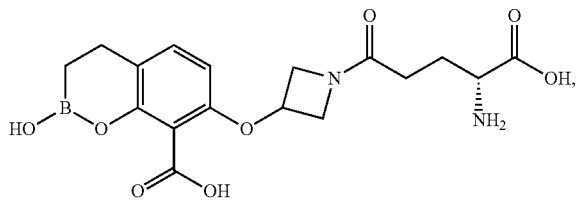 [SMILES: N[C@H](CCC(=O)N1CC(Oc2ccc3c(c2C(=O)O)OB(O)CC3)C1)C(=O)O]

8-({1-[(3R)-3-amino-3-carboxypropanoyl]azetidin-3-yl}oxy)-4,4-dihydroxy-5-oxa-4-boranuidabicyclo[4.4.0]deca-1(6),7,9-triene-7-carboxylic acid

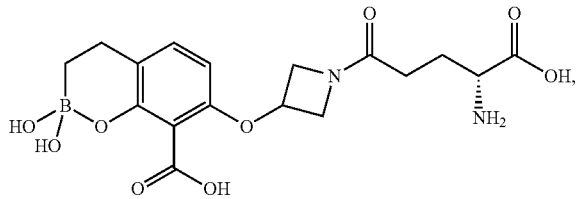

754

7-({1-[(3S)-3,6-diamino-6-oxoexanoyl]azetidin-3-yl}oxy)-2-hydroxy-3,4-dihydro-2H-1,2-benzoxaborinine-8-carboxylic acid

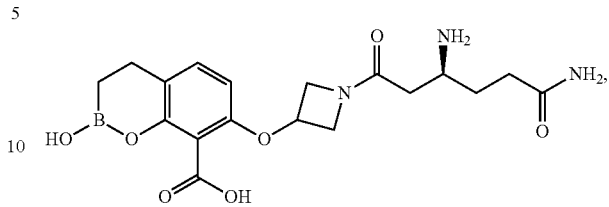

8-({1-[(3S)-3,6-diamino-6-oxohexanoyl]azetidin-3-yl}oxy)-4,4-dihydroxy-5-oxa-4-boranuidabicyclo[4.4.0]deca-1(6),7,9-triene-7-carboxylic acid

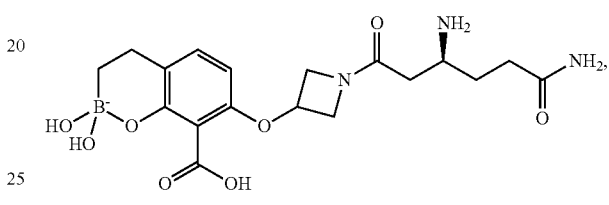

7-{[1-(D-α-asparaginyl)azetidin-3-yl]oxy}-2-hydroxy-3,4-dihydro-2H-1,2-benzoxaborinine-8-carboxylic acid

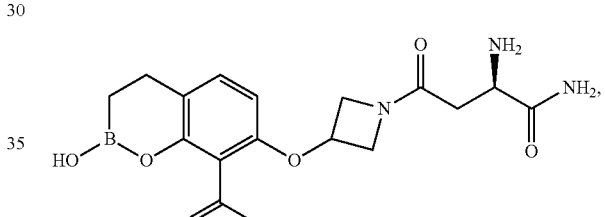

8-{[1-(D-α-asparaginyl)azetidin-3-yl]oxy}-4,4-dihydroxy-5-oxa-4-boranuidabicyclo[4.4.0]deca-1(6),7,9-triene-7-carboxylic acid

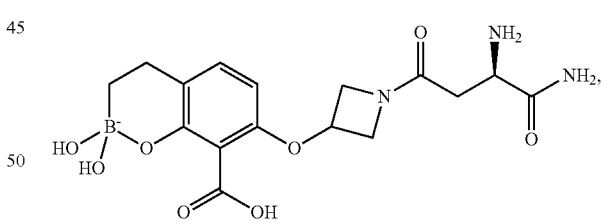

7-{[1-(D-α-glutaminyl)azetidin-3-yl]oxy}-2-hydroxy-3,4-dihydro-2H-1,2-benzoxaborinine-8-carboxylic acid

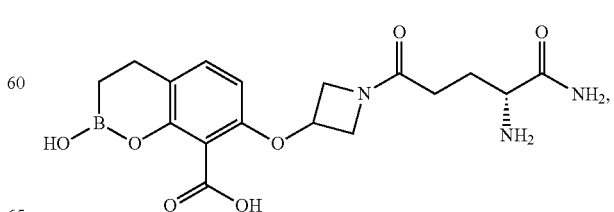

8-{[1-(D-α-glutaminyl)azetidin-3-yl]oxy}-4,4-dihydroxy-5-oxa-4-boranuidabicyclo[4.4.0]deca-1(6),7,9-triene-7-carboxylic acid

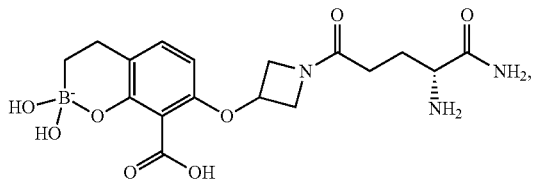 [SMILES: NC(=O)[C@H](N)CCC(=O)N1CC(Oc2ccc3c(c2C(=O)O)O[B-](O)(O)CC3)C1]

7-({1-[(4S)-4-amino-4-carboxybutanoyl]azetidin-3-yl}oxy)-2-hydroxy-3,4-dihydro-2H-1,2-benzoxaborinine-8-carboxylic acid

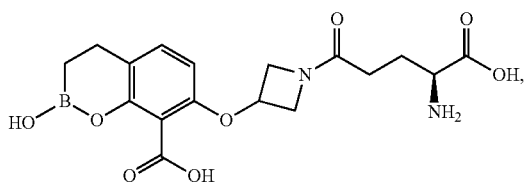 [SMILES: N[C@@H](CCC(=O)N1CC(Oc2ccc3c(c2C(=O)O)OB(O)CC3)C1)C(=O)O]

8-({1-[(4S)-4-amino-4-carboxybutanoyl]azetidin-3-yl}oxy)-4,4-dihydroxy-5-oxa-4-boranuidabicyclo[4.4.0]deca-1(6),7,9-triene-7-carboxylic acid

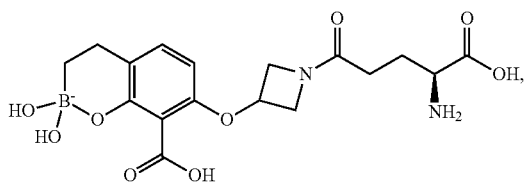 [SMILES: N[C@@H](CCC(=O)N1CC(Oc2ccc3c(c2C(=O)O)O[B-](O)(O)CC3)C1)C(=O)O]

7-{[1-(L-α-glutaminyl)azetidin-3-yl]oxy}-2-hydroxy-3,4-dihydro-2H-1,2-benzoxaborinine-8-carboxylic acid

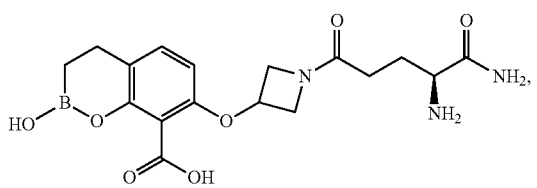 [SMILES: NC(=O)[C@@H](N)CCC(=O)N1CC(Oc2ccc3c(c2C(=O)O)OB(O)CC3)C1]

8-{[1-(L-α-glutaminyl)azetidin-3-yl]oxy}-4,4-dihydroxy-5-oxa-4-boranuidabicyclo[4.4.0]deca-1(6),7,9-triene-7-carboxylic acid

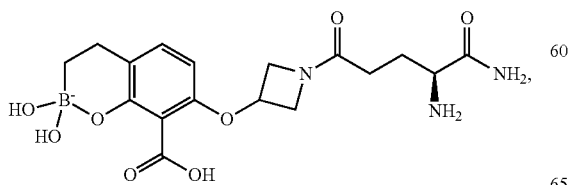

2-hydroxy-7-[(1-D-threonylazetidin-3-yl)oxy]-3,4-dihydro-2H-1,2-benzoxaborinine-8-carboxylic acid

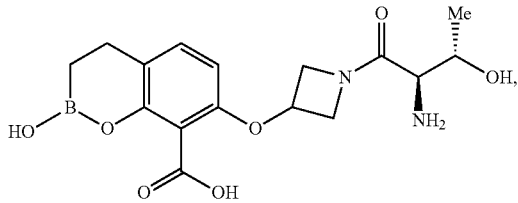 [SMILES: C[C@H](O)[C@@H](N)C(=O)N1CC(Oc2ccc3c(c2C(=O)O)OB(O)CC3)C1]

4,4-dihydroxy-8-[(1-D-threonylazetidin-3-yl)oxy]-5-oxa-4-boranuidabicyclo[4.4.0]deca-1(6),7,9-triene-7-carboxylic acid

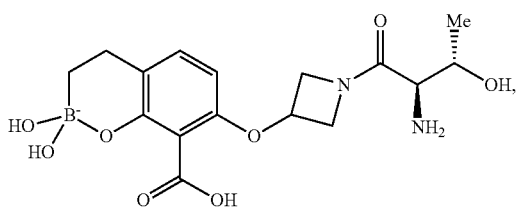 [SMILES: C[C@H](O)[C@@H](N)C(=O)N1CC(Oc2ccc3c(c2C(=O)O)O[B-](O)(O)CC3)C1]

2-hydroxy-7-[(1-L-threonylazetidin-3-yl)oxy]-3,4-dihydro-2H-1,2-benzoxaborinine-8-carboxylic acid

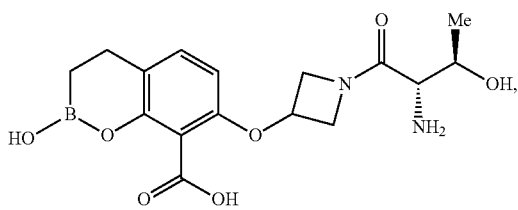 [SMILES: C[C@@H](O)[C@H](N)C(=O)N1CC(Oc2ccc3c(c2C(=O)O)OB(O)CC3)C1]

4,4-dihydroxy-8-[(1-L-threonylazetidin-3-yl)oxy]-5-oxa-4-boranuidabicyclo[4.4.0]deca-1(6),7,9-triene-7-carboxylic acid; and

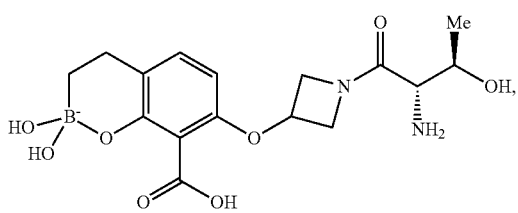 [SMILES: C[C@@H](O)[C@H](N)C(=O)N1CC(Oc2ccc3c(c2C(=O)O)O[B-](O)(O)CC3)C1]

43. A compound or the pharmaceutically acceptable salt thereof, selected from the group consisting of the following compounds:

6-[(1-acetylazetidin-3-yl)oxy]-3-(2-boronoethyl)-2-hydroxybenzoic acid

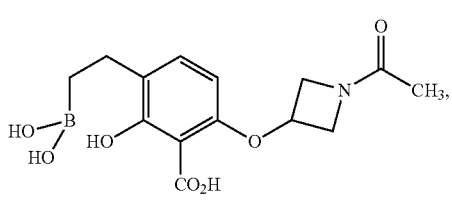 [SMILES: CC(=O)N1CC(Oc2ccc(CCB(O)O)c(O)c2C(=O)O)C1]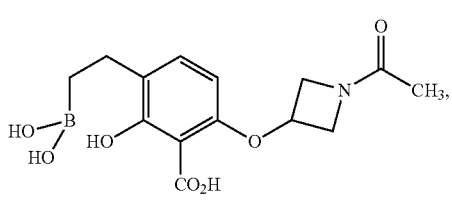 [SMILES: CC(=O)N1CC(Oc2ccc(CCB(O)O)c(O)c2C(=O)O)C1]

757

3-(2-boronoethyl)-2-hydroxy-6-({1-[(1H-imidazol-5-yl)acetyl]azetidin-3-yl}oxy)benzoic acid

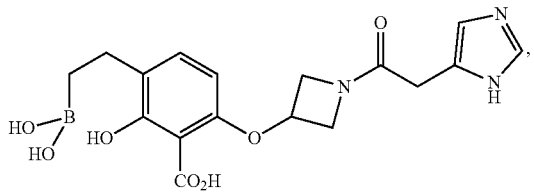 [SMILES: O=C(O)c1c(OC2CN(C(=O)Cc3cnc[nH]3)C2)ccc(CCB(O)O)c1O]

6-({1-[(2R)-2-amino-2-(4-hydroxyphenyl)acetyl]azetidin-3-yl}oxy)-3-(2-boronoethyl)-2-hydroxybenzoic acid

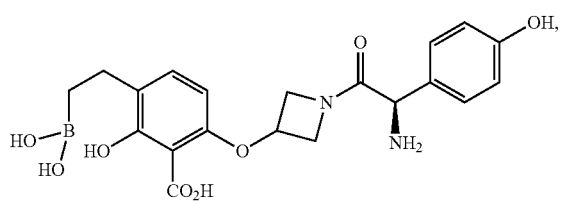 [SMILES: N[C@@H](C(=O)N1CC(Oc2ccc(CCB(O)O)c(O)c2C(=O)O)C1)c1ccc(O)cc1]

6-({1-[(2-amino-1,3-thiazol-4-yl)(methoxyimino)acetyl]azetidin-3-yl}oxy)-3-(2-boronoethyl)-2-hydroxybenzoic acid

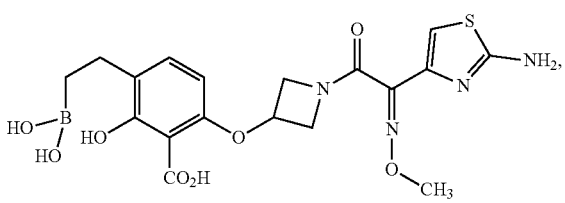 [SMILES: CON=C(C(=O)N1CC(Oc2ccc(CCB(O)O)c(O)c2C(=O)O)C1)c1csc(N)n1]

3-(2-boronoethyl)-2-hydroxy-6-{[1-(pyridine-2-carbonyl)azetidin-3-yl]oxy}benzoic acid

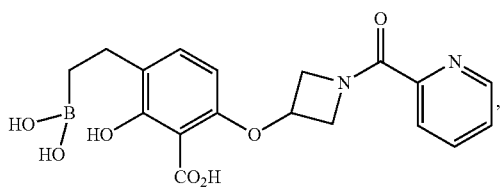

3-(2-boronoethyl)-2-hydroxy-6-({1-[(methylsulfanyl)acetyl]azetidin-3-yl}oxy)benzoic acid

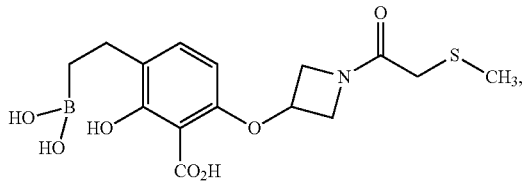 [SMILES: CSCC(=O)N1CC(Oc2ccc(CCB(O)O)c(O)c2C(=O)O)C1]

758

3-(2-boronoethyl)-2-hydroxy-6-{[1-(1H-1,2,4-triazole-3-carbonyl)azetidin-3-yl]oxy}benzoic acid

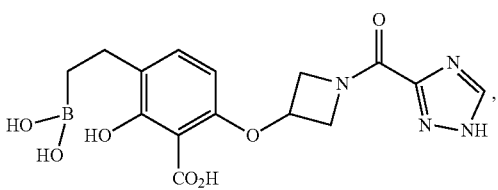 [SMILES: O=C(O)c1c(OC2CN(C(=O)c3nc[nH]n3)C2)ccc(CCB(O)O)c1O]

3-(2-boronoethyl)-2-hydroxy-6-{[1-1-oxido-2-pyridinylcarbonyl)azetidin-3-yl]oxy}benzoic acid

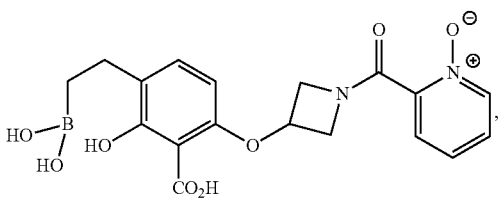 [SMILES: O=C(O)c1c(OC2CN(C(=O)c3cccc[n+]3[O-])C2)ccc(CCB(O)O)c1O]

6-({1-[(2R)-2-amino-2-phenylacetyl]azetidin-3-yl}oxy)-3-(2-boronoethyl)-2-hydroxybenzoic acid

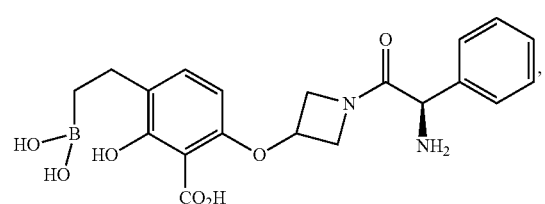

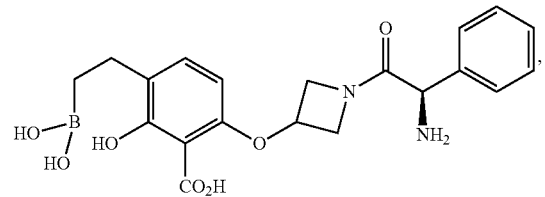 [SMILES: N[C@@H](C(=O)N1CC(Oc2ccc(CCB(O)O)c(O)c2C(=O)O)C1)c1ccccc1]

6-[(1-benzoylazetidin-3-yl)oxy]-3-(2-boronoethyl)-2-hydroxybenzoic acid

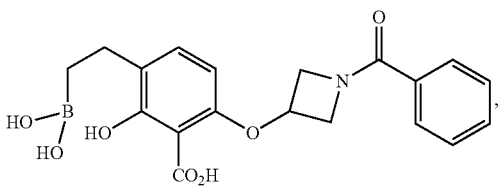

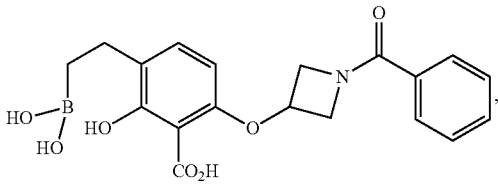 [SMILES: O=C(O)c1c(OC2CN(C(=O)c3ccccc3)C2)ccc(CCB(O)O)c1O]

3-(2-boronoethyl)-2-hydroxy-6-{[1-(pyridine-3-carbonyl)azetidin-3-yl]oxy}benzoic acid

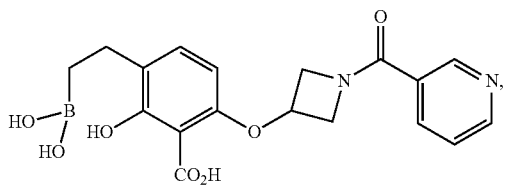 [SMILES: O=C(O)c1c(OC2CN(C(=O)c3cccnc3)C2)ccc(CCB(O)O)c1O]

3-(2-boronoethyl)-2-hydroxy-6-({1-[(pyridin-2-yl)acetyl]azetidin-3-yl}oxy)benzoic acid

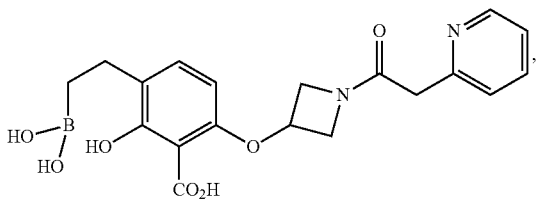

3-(2-boronoethyl)-2-hydroxy-6-({1-[(pyridin-3-yl)acetyl]azetidin-3-yl}oxy)benzoic acid

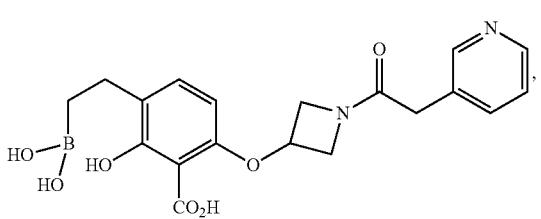 [SMILES: O=C(O)c1c(OC2CN(C(=O)Cc3cccnc3)C2)ccc(CCB(O)O)c1O]

6-({1-[(2S)-2-amino-2-phenylacetyl]azetidin-3-yl}oxy)-3-(2-boronoethyl)-2-hydroxybenzoic acid

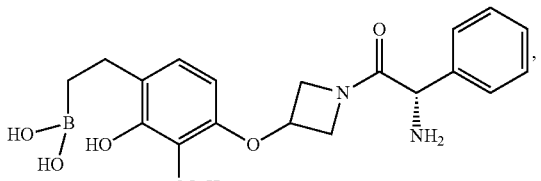

3-(2-boronoethyl)-2-hydroxy-6-({1-[(pyridin-4-yl)acetyl]azetidin-3-yl}oxy)benzoic acid

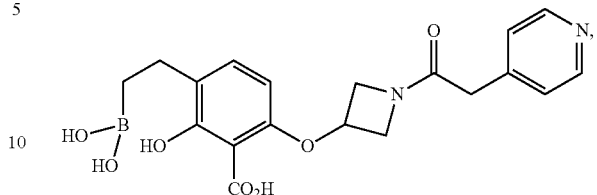

3-(2-boronoethyl)-2-hydroxy-6-({1-[(4-hydroxyphenyl)acetyl]azetidin-3-yl}oxy)benzoic acid

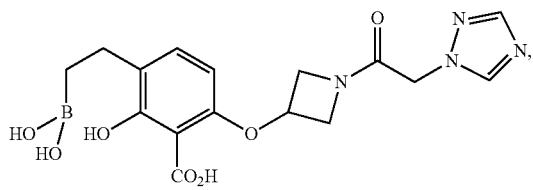 [SMILES: O=C(O)c1c(OC2CN(C(=O)Cn3cncn3)C2)ccc(CCB(O)O)c1O]

3-(2-boronoethyl)-2-hydroxy-6-({1-[(1H-1,2,4-triazol-1-yl)acetyl]azetidin-3-yl}oxy)benzoic acid

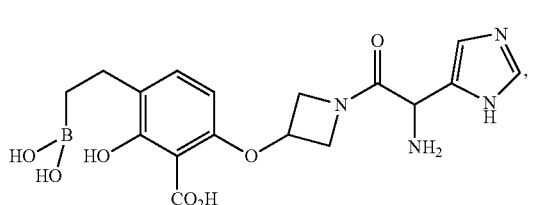

6-({1-[amino(1H-imidazol-5-yl)acetyl]azetidin-3-yl}oxy)-3-(2-boronoethyl)-2-hydroxybenzoic acid

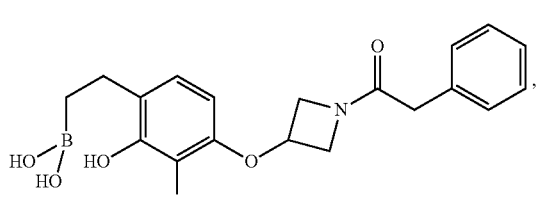

3-(2-boronoethyl)-2-hydroxy-6-{[1-(phenylacetyl)azetidin-3-yl]oxy}benzoic acid

761

3-(2-boronoethyl)-2-hydroxy-6-{[1-(3-phenylpropanoyl)azetidin-3-yl]oxy}benzoic acid

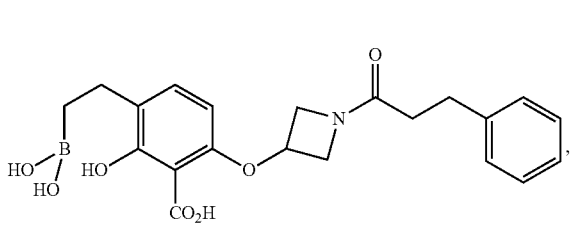 [SMILES: O=C(O)c1c(OC2CN(C(=O)CCc3ccccc3)C2)ccc(CCB(O)O)c1O]

3-(2-boronoethyl)-2-hydroxy-6-({1-[(1H-imidazol-1-yl)acetyl]azetidin-3-yl}oxy)benzoic acid

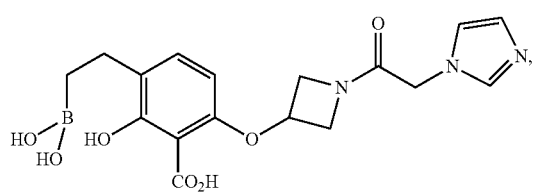 [SMILES: O=C(O)c1c(OC2CN(C(=O)Cn3ccnc3)C2)ccc(CCB(O)O)c1O]

3-(2-boronoethyl)-2-hydroxy-6-({1-[(1H-tetrazol-1-yl)acetyl]azetidin-3-yl}oxy)benzoic acid

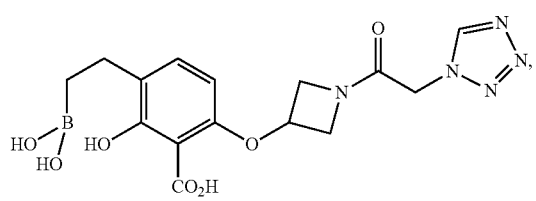 [SMILES: O=C(O)c1c(OC2CN(C(=O)Cn3cnnn3)C2)ccc(CCB(O)O)c1O]

3-(2-boronoethyl)-2-hydroxy-6-({1-[(2H-tetrazol-5-yl)acetyl]azetidin-3-yl}oxy)benzoic acid

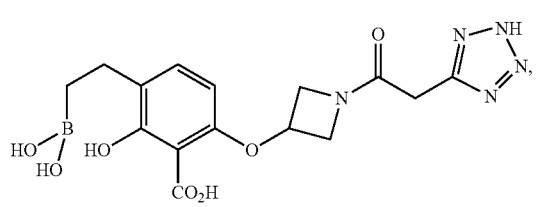 [SMILES: O=C(O)c1c(OC2CN(C(=O)Cc3nn[nH]n3)C2)ccc(CCB(O)O)c1O]

3-(2-boronoethyl)-2-hydroxy-6-[(1-D-phenylalanylazetidin-3-yl)oxy]benzoic acid

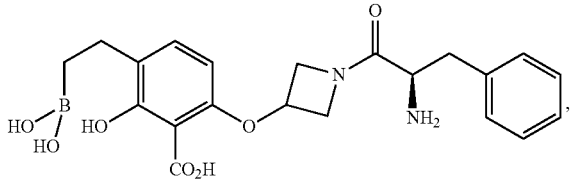 [SMILES: N[C@H](Cc1ccccc1)C(=O)N1CC(Oc2ccc(CCB(O)O)c(O)c2C(=O)O)C1]

762

3-(2-boronoethyl)-2-hydroxy-6-[(1-D-tyrosylazetidin-3-yl)oxy]benzoic acid

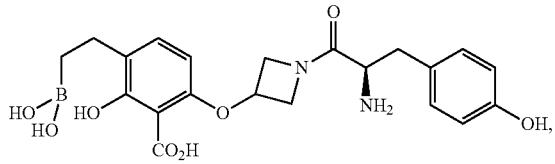 [SMILES: N[C@H](Cc1ccc(O)cc1)C(=O)N1CC(Oc2ccc(CCB(O)O)c(O)c2C(=O)O)C1]

3-(2-boronoethyl)-6-[(1-D-histidylazetidin-3-yl)oxy]-2-hydroxybenzoic acid

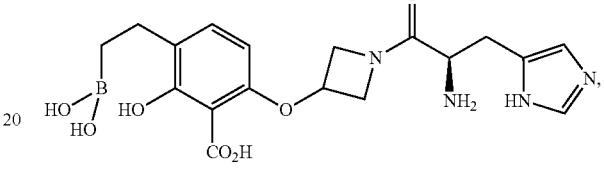

3-(2-boronoethyl)-2-hydroxy-6-[(1-D-valylazetidin-3-yl)oxy]benzoic acid

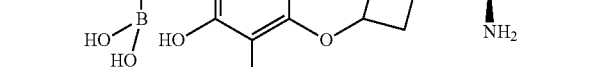

3-(2-boronoethyl)-6-[(1-L-histidylazetidin-3-yl)oxy]-2-hydroxybenzoic acid

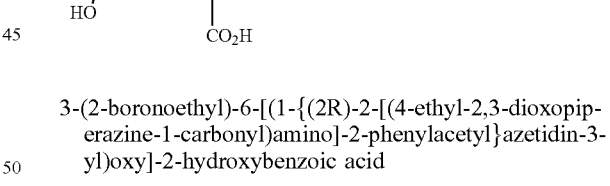

3-(2-boronoethyl)-6-[(1-{(2R)-2-[(4-ethyl-2,3-dioxopiperazine-1-carbonyl)amino]-2-phenylacetyl}azetidin-3-yl)oxy]-2-hydroxybenzoic acid

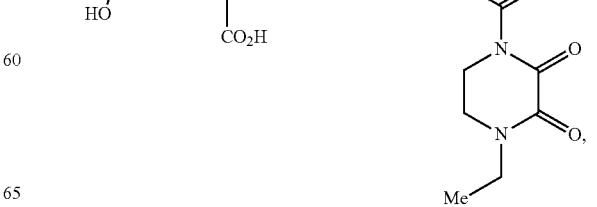

763

3-(2-boronoethyl)-2-hydroxy-6-[(1-D-prolylazetidin-3-yl)oxy]benzoic acid

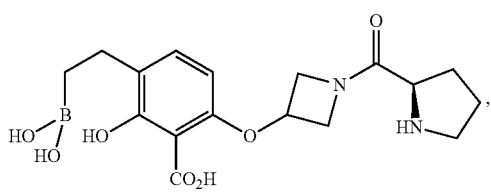 [SMILES: O=C(O)c1c(OC2CN(C(=O)[C@H]3CCCN3)C2)ccc(CCB(O)O)c1O]

3-(2-boronoethyl)-2-hydroxy-6-[(1-L-prolylazetidin-3-yl)oxy]benzoic acid

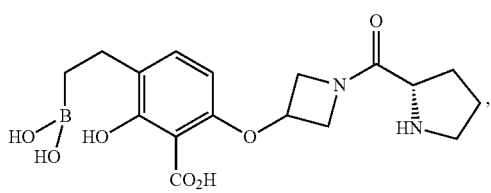

6-[(1-{[4-(2-aminoethyl)-1H-imidazol-1-yl]acetyl}azetidin-3-yl)oxy]-3-(2-boronoethyl)-2-hydroxybenzoic acid

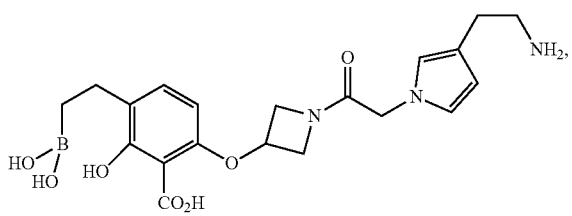 [SMILES: NCCc1ccn(CC(=O)N2CC(Oc3ccc(CCB(O)O)c(O)c3C(=O)O)C2)c1]

3-(2-boronoethyl)-6-{[1-(3,4-dihydroxybenzoyl)azetidin-3-yl]oxy}-2-hydroxybenzoic acid

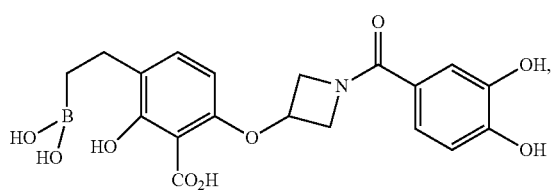 [SMILES: O=C(O)c1c(OC2CN(C(=O)c3ccc(O)c(O)c3)C2)ccc(CCB(O)O)c1O]

3-(2-boronoethyl)-2-hydroxy-6-{[1-(hydroxycarbamoyl)azetidin-3-yl]oxy}benzoic acid

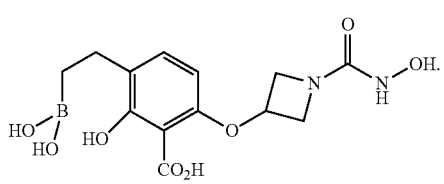 [SMILES: O=C(O)c1c(OC2CN(C(=O)NO)C2)ccc(CCB(O)O)c1O]

44. A compound or the pharmaceutically acceptable salt, selected from the group consisting of the following compounds:

764

6-({1-[(2R)-2-amino-2-(1H-imidazol-4-yl)acetyl]azetidin-3-yl}oxy)-3-(2-boronoethyl)-2-hydroxybenzoic acid

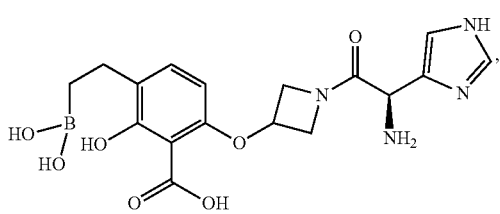 [SMILES: N[C@@H](C(=O)N1CC(Oc2ccc(CCB(O)O)c(O)c2C(=O)O)C1)c1c[nH]cn1]

6-({1-[(2 S)-2-amino-2-(1 H-imidazol-4-yl)acetyl]azetidin-3-yl}oxy)-3-(2-boronoethyl)-2-hydroxybenzoic acid

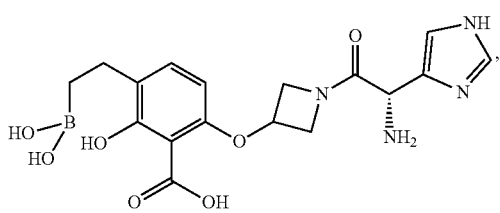 [SMILES: N[C@H](C(=O)N1CC(Oc2ccc(CCB(O)O)c(O)c2C(=O)O)C1)c1c[nH]cn1]

6-({1-[amino(1-methyl-1H-imidazol-4-yl)acetyl]azetidin-3-yl}oxy)-3-(2-boronoethyl)-2-hydroxybenzoic acid

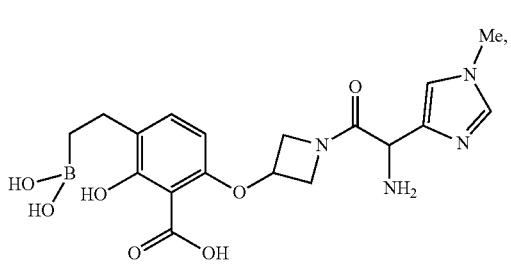 [SMILES: Cn1cnc(C(N)C(=O)N2CC(Oc3ccc(CCB(O)O)c(O)c3C(=O)O)C2)c1]

6-({1-[2-amino-2-(1H-imidazo-4-yl)($^{2}$H)ethanoyl]azetidin-3-yl}oxy)-3-(2-boronoethyl)-2-hydroxybenzoic acid

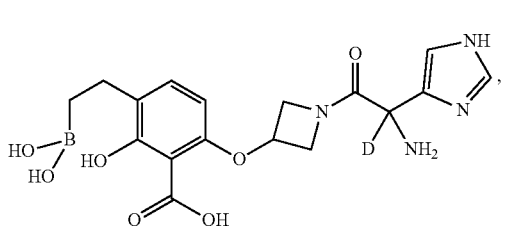 [SMILES: [2H]C(N)(C(=O)N1CC(Oc2ccc(CCB(O)O)c(O)c2C(=O)O)C1)c1c[nH]cn1]

765

6-({1-[2-amino-2-(1H-imidazol-4-yl)propanoyl]azetidin-3-yl}oxy)-3-(2-boronoethyl)-2-hydroxybenzoic acid

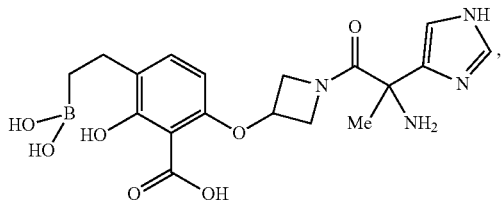 [SMILES: CC(N)(C(=O)N1CC(Oc2ccc(CCB(O)O)c(O)c2C(=O)O)C1)c1c[nH]cn1]

6-({(3S)-1-[amino(1H-imidazol-4-yl)acetyl]pyrolidin-3-yl}oxy)-3-(2-boronoethyl)-2-hydroxybenzoic acid

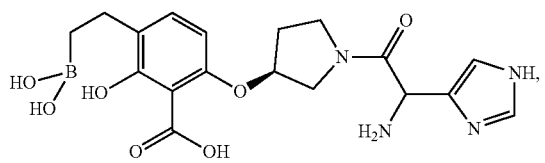 [SMILES: NC(C(=O)N1CC[C@H](Oc2ccc(CCB(O)O)c(O)c2C(=O)O)C1)c1c[nH]cn1]

3-(2-boronoethyl)-2-hydroxy-6-{[1-(4-hydroxy-6-methylpyridine-3-carbonyl)azetidin-3-yl]oxy}benzoic acid

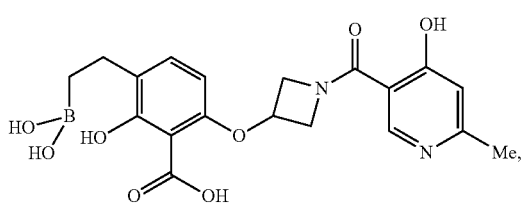 [SMILES: Cc1cc(O)c(C(=O)N2CC(Oc3ccc(CCB(O)O)c(O)c3C(=O)O)C2)cn1]

6-({1-[amino(1-methyl-1H-imidazol-5-yl)acetyl]azetidin-3-yl}oxy)-3-(2-boronoethyl)-2-hydroxybenzoic acid

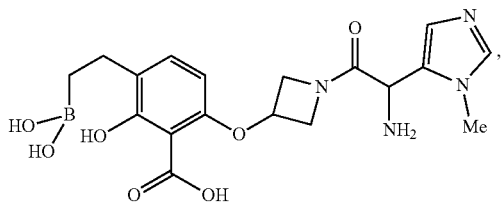 [SMILES: Cn1cncc1C(N)C(=O)N1CC(Oc2ccc(CCB(O)O)c(O)c2C(=O)O)C1]

6-[(1-{amino[1-(carboxymethyl)-1H-imidazol-4-yl]acetyl}azetidin-3-yl)oxy]-3-(2-boronoethyl)-2-hydroxybenzoic acid

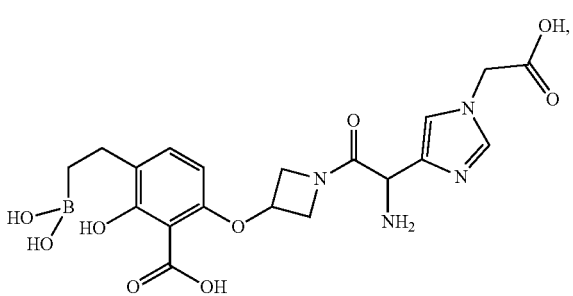 [SMILES: NC(C(=O)N1CC(Oc2ccc(CCB(O)O)c(O)c2C(=O)O)C1)c1cn(CC(=O)O)cn1]

766

6-[(1-{amino[1-(2-amino-2-oxoethyl)-1H-imidazol-4-yl]acetyl}azetidin-3-yl)oxy]-3-(2-boronoethyl)-2-hydroxybenzoic acid

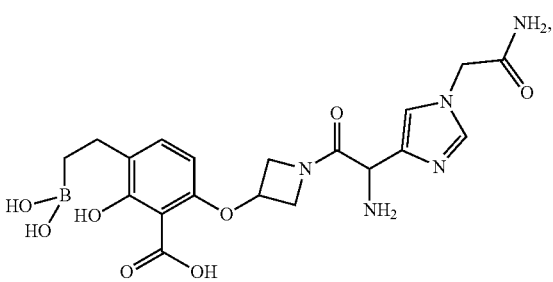 [SMILES: NC(=O)Cn1cnc(C(N)C(=O)N2CC(Oc3ccc(CCB(O)O)c(O)c3C(=O)O)C2)c1]

6-({1-[amino(pyridin-3-yl)acetyl]azetidin-3-yl}oxy)-3-(2-boronoethyl)-2-hydroxybenzoic acid

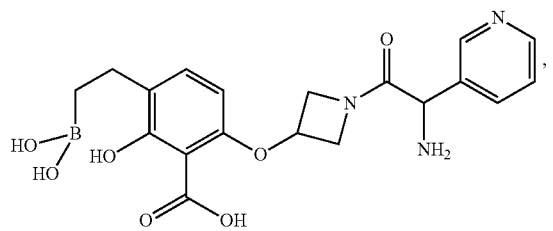 [SMILES: NC(C(=O)N1CC(Oc2ccc(CCB(O)O)c(O)c2C(=O)O)C1)c1cccnc1]

6-({1-[amino(1-methyl-1H-pyrazol-4-yl)acetyl]azetidin-3-yl}oxy)-3-(2-boronoethyl)-2-hydroxybenzoic acid

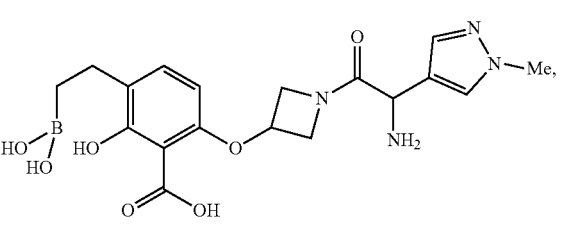 [SMILES: Cn1cc(C(N)C(=O)N2CC(Oc3ccc(CCB(O)O)c(O)c3C(=O)O)C2)cn1]

6-({(3R)-1-[amino(1H-imidazol-4-yl)acetyl]pyrrolidin-3-yl}oxy)-3-(2-boronoethyl)-2-hydroxybenzoic acid

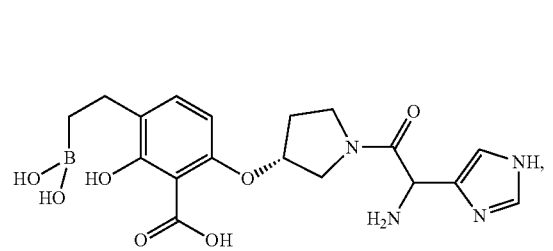 [SMILES: NC(C(=O)N1CC[C@@H](Oc2ccc(CCB(O)O)c(O)c2C(=O)O)C1)c1c[nH]cn1]

767

6-({1-[amino(2-methyl-1H-imidazol-4-yl)acetyl]azetidin-3-yl}oxy)-3-(2-boronoethyl)-2-hydroxybenzoic acid

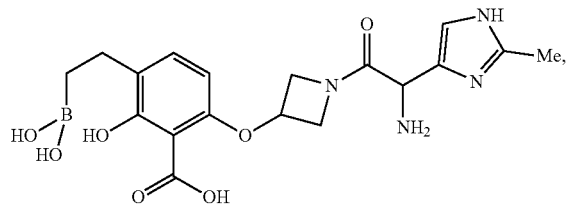 [SMILES: Cc1nc(C(N)C(=O)N2CC(Oc3ccc(CCB(O)O)c(O)c3C(=O)O)C2)c[nH]1]

6-({1-[amino(1,3-thiazol-4-yl)acetyl]azetidin-3-yl}oxy)-3-(2-boronoethyl)-2-hydroxybenzoic

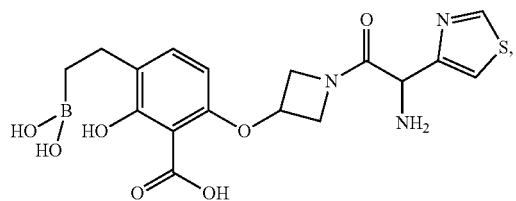 [SMILES: NC(C(=O)N1CC(Oc2ccc(CCB(O)O)c(O)c2C(=O)O)C1)c1cscn1]

6-({1-[(2-amino-1,3-thiazol-4-yl)acetyl]azetidin-3-yl}oxy)-3-(2-boronoethyl)-2-hydroxybenzoic acid

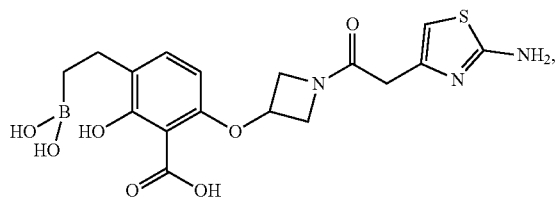 [SMILES: Nc1nc(CC(=O)N2CC(Oc3ccc(CCB(O)O)c(O)c3C(=O)O)C2)cs1]

6-{[1-(2-amino-1,3-thiazole-4-carbonyl)azetidin-3-yl]oxyl-3-(2-boronoethyl)-2-hydroxybenzoic acid

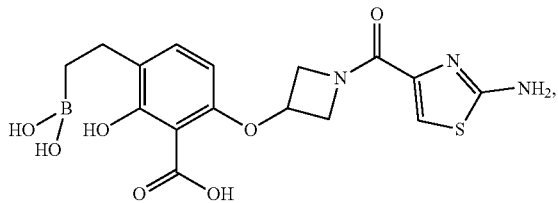 [SMILES: Nc1nc(C(=O)N2CC(Oc3ccc(CCB(O)O)c(O)c3C(=O)O)C2)cs1]

3-(2-boronoethyl)-2-hydroxy-6-({1-[(1H-1,2,3-triazol-1-yl)acetyl]azetidin-3-yl}oxy)benzoic acid

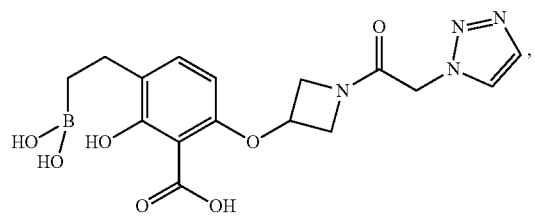 [SMILES: O=C(O)c1c(OC2CN(C(=O)Cn3ccnn3)C2)ccc(CCB(O)O)c1O]

768

6-[(1-{[1-(2-aminoethyl)-1H-imidazol-4-yl]acetyl}azetidin-3-yl)oxy]-3-(2-boronoethyl)-2-hydroxybenzoic acid

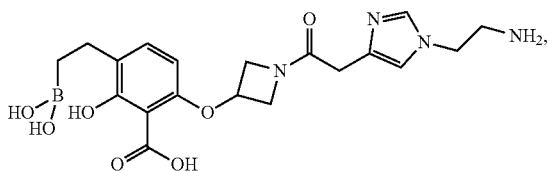 [SMILES: NCCn1cnc(CC(=O)N2CC(Oc3ccc(CCB(O)O)c(O)c3C(=O)O)C2)c1]

3-(2-boronoethyl)-2-hydroxy-6-([1-(1H-imidazole-4-carbonyl)azetidin-3-yl]oxy}benzoic acid

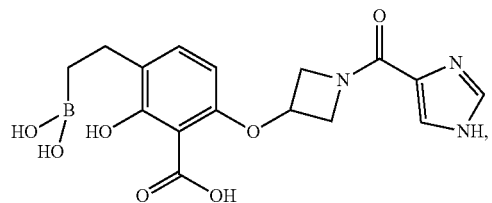 [SMILES: O=C(O)c1c(OC2CN(C(=O)c3c[nH]cn3)C2)ccc(CCB(O)O)c1O]

3-(2-boronoethyl)-2-hydroxy-6-{[1-(1H-imidazole-2-carbonyl)azetidin-3-yl]oxy}benzoic acid

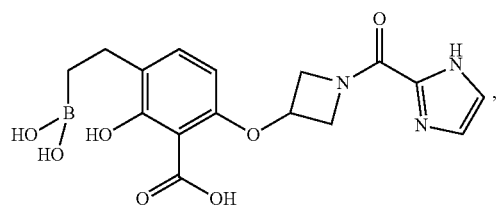 [SMILES: O=C(O)c1c(OC2CN(C(=O)c3ncc[nH]3)C2)ccc(CCB(O)O)c1O]

3-(2-boronoethyl)-2-hydroxy-6-[(1-{[4-(hydroxymethyl)-1H-1,2,3-triazol-1-yl]acetyl}azetidin-3-yl)oxy]benzoic acid

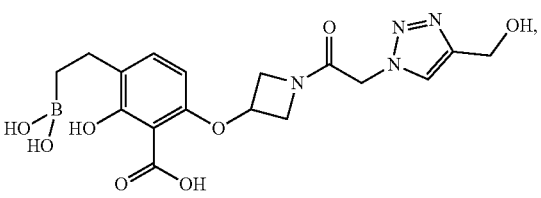 [SMILES: O=C(O)c1c(OC2CN(C(=O)Cn3cc(CO)nn3)C2)ccc(CCB(O)O)c1O]

3-(2-boronoethyl)-2-hydroxy-6-{[1-({4-[(methylamino)methyl]-1H-1,2,3-triazol-1-yl}acetyl)azetidin-3-yl]oxy}benzoic acid

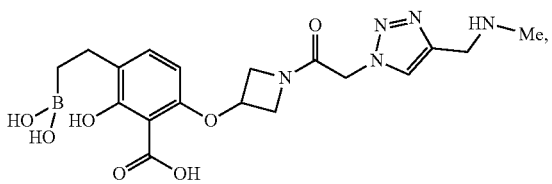 [SMILES: CNCc1cn(CC(=O)N2CC(Oc3ccc(CCB(O)O)c(O)c3C(=O)O)C2)nn1]

769

3-(2-boronoethyl)-2-hydroxy-6-{[1-({4-[(piperazin-1-yl)
methyl]-1H-1,2,3-triazol-1-yl}acetyl)azetidin-3-yl]
oxy}benzoic acid

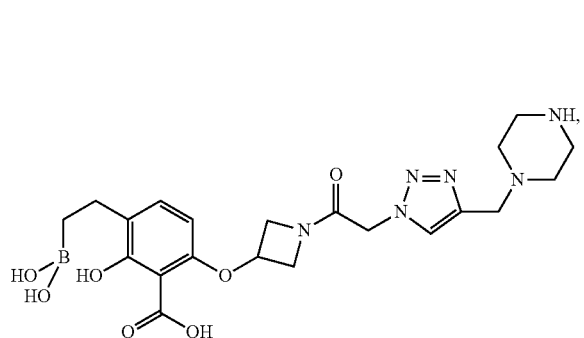 [SMILES: O=C(O)c1c(OC2CN(C(=O)Cn3cc(CN4CCNCC4)nn3)C2)ccc(CCB(O)O)c1O]

3-(2-boronoethyl)-2-hydroxy-6-[(1-{[4-(2-hydroxy-
ethyl)-1H-1,2,3-triazol-1-yl]acetyl}azetidin-3-yl)oxy]
benzoic acid

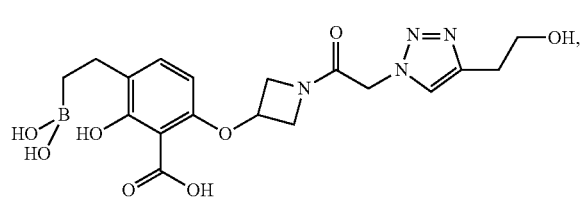 [SMILES: O=C(O)c1c(OC2CN(C(=O)Cn3cc(CCO)nn3)C2)ccc(CCB(O)O)c1O]

3-(2-boronoethyl)-2-hydroxy-6-[(1-{[5-(hydroxym-
ethyl)-1H-1,2,3-triazol-1-yl]acetyl}azetidin-3-yl)oxy]
benzoic acid

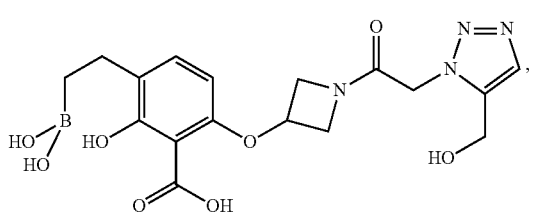 [SMILES: O=C(O)c1c(OC2CN(C(=O)Cn3nncc3CO)C2)ccc(CCB(O)O)c1O]

3-(2-boronoethyl)-2-hydroxy-6-{[1-({5-[(methylamino)
methyl]-1H-1,2,3-triazol-1-yl}acetyl)azetidin-3-yl]
oxy}benzoic acid

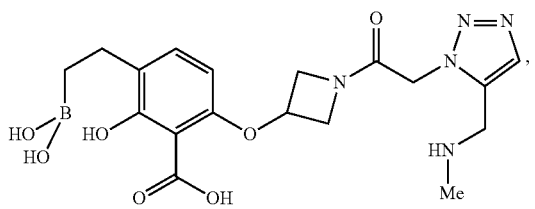 [SMILES: CNCc1cnnn1CC(=O)N1CC(Oc2ccc(CCB(O)O)c(O)c2C(=O)O)C1]

770

3-(2-boronoethyl)-2-hydroxy-6-({1-[(1H-1,2,3-triazol-4-
yl)acetyl]azetidin-3-yl}oxy)benzoic acid

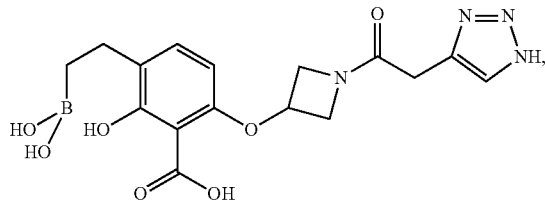 [SMILES: O=C(O)c1c(OC2CN(C(=O)Cc3c[nH]nn3)C2)ccc(CCB(O)O)c1O]

3-(2-boronoethyl)-6-[(1-{[4-(carboxymethyl)-1H-1,2,3-
triazol-1-yl]acetyl}azetidin-3-yl)oxy]-2-hydroxyben-
zoic acid

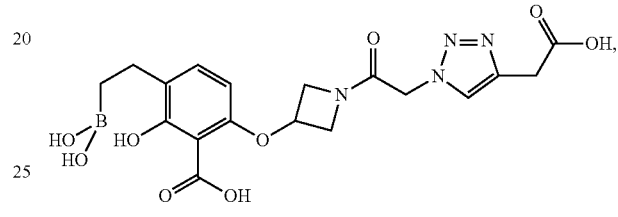

3-(2-boronoethyl)-6-[(1-{[1-(carboxymethyl)-1H-1,2,3-
triazol-4-yl]acetyl}azetidin-3-yl)oxy]-2-hydroxyben-
zoic acid

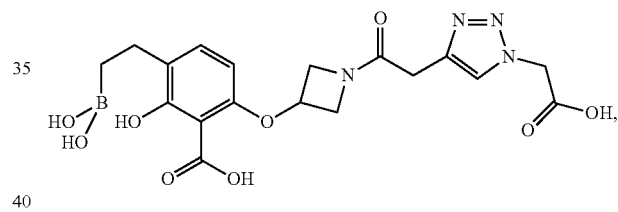

6-({1-[amino(1H-1,2,3-triazol-4-yl)acetyl]azetidin-3-
yl}oxy)-3-(2-boronoethyl)-2-hydroxybenzoic acid

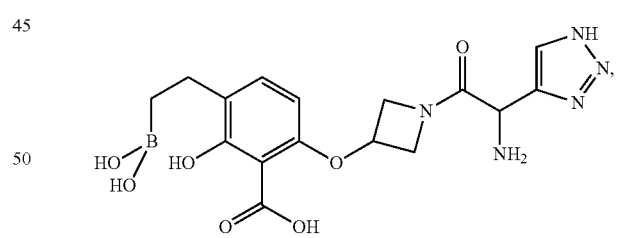

3-(2-boronoethyl)-2-hydroxy-6-({1-[(4-nitro-1H-1,2,3-
triazol-1-yl)acetyl]azetidin-3-yl}oxy)benzoic acid

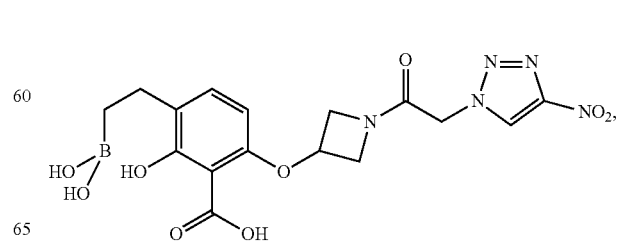

771

6-({1-[amino(3,4-dihydroxyphenyl)acetyl]azetidin-3-yl}oxy)-3-(2-boronoethyl)-2-hydroxybenzoic acid

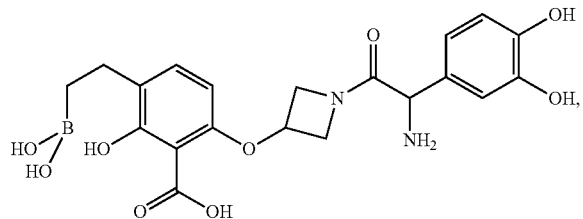 [SMILES: NC(C(=O)N1CC(Oc2ccc(CCB(O)O)c(O)c2C(=O)O)C1)c1ccc(O)c(O)c1]

6-({1-[amino(2,4-dihydroxyphenyl)acetyl]azetidin-3-yl}oxy)-3-(2-boronoethyl)-2-hydroxybenzoic acid

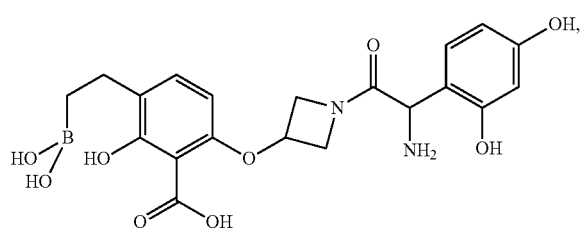 [SMILES: NC(C(=O)N1CC(Oc2ccc(CCB(O)O)c(O)c2C(=O)O)C1)c1ccc(O)cc1O]

6-{[1-(S-benzyl-D-cysteinyl)azetidin-3-yl]oxy}-3-(2-boronoethyl)-2-hydroxybenzoic acid

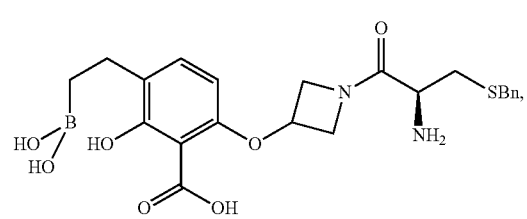

3-(2-boronoethyl)-6-[(1-D-cysteinylazetidin-3-yl)oxy]-2-hydroxybenzoic acid

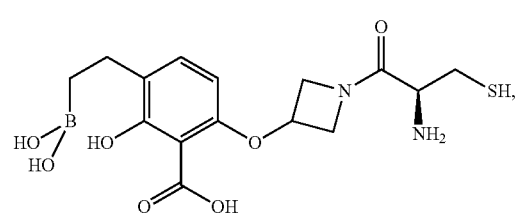 [SMILES: N[C@H](CS)C(=O)N1CC(Oc2ccc(CCB(O)O)c(O)c2C(=O)O)C1]

3-(2-boronoethyl)-2-hydroxy-6-{[1-(3-sulfanyl-D-valyl)azetidin-3-yl]oxy}benzoic acid

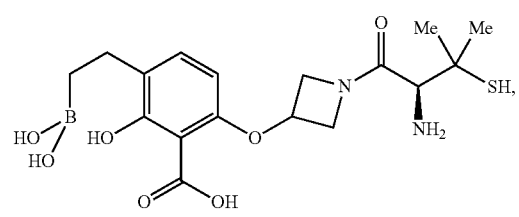 [SMILES: CC(C)(S)[C@@H](N)C(=O)N1CC(Oc2ccc(CCB(O)O)c(O)c2C(=O)O)C1]

772

6-({1-[(2S)-2-amino-3-carboxypropanoyl]azetidin-3-yl}oxy)-3-(2-boronoethyl)-2-hydroxybenzoic acid

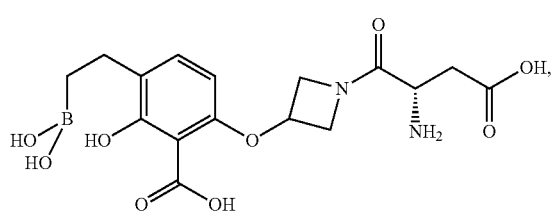 [SMILES: N[C@@H](CC(=O)O)C(=O)N1CC(Oc2ccc(CCB(O)O)c(O)c2C(=O)O)C1]

6-{[1-(D-alanyl-D-alanyl)azetidin-3-yl]oxy}-3-(2-boronoethyl)-2-hydroxybenzoic acid

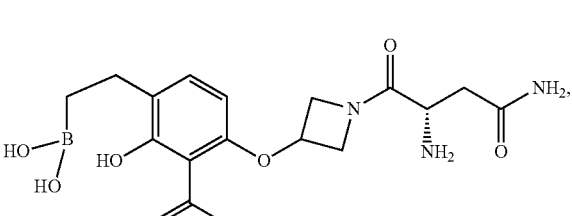

6-[(1-L-asparaginylazetidin-3-yl)oxy]-3-(2-boronoethyl)-2-hydroxybenzoic acid

6-[(1-D-asparaginylazetidin-3-yl)oxy]-3-(2-boronoethyl)-2-hydroxybenzoic acid 6-({1-[(2R)-2-amino-3-carboxypropanoyl]azetidin-3-yl}oxy)-3-(2-boronoethyl)-2-hydroxybenzoic acid

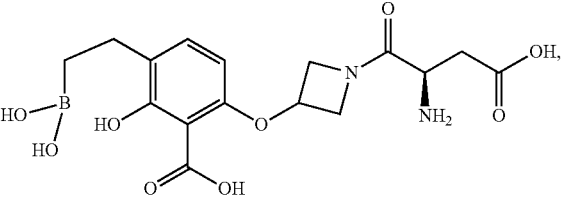 [SMILES: N[C@H](CC(=O)O)C(=O)N1CC(Oc2ccc(CCB(O)O)c(O)c2C(=O)O)C1]

773

3-(2-boronoethyl)-2-hydroxy-6-[(1-D-serylazetidin-3-yl)oxy]benzoic acid

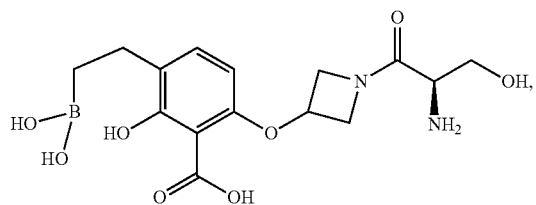 [SMILES: N[C@H](CO)C(=O)N1CC(Oc2ccc(CCB(O)O)c(O)c2C(=O)O)C1]

6-{[1-(4-amino-4-oxobutanoyl)azetidin-3-yl]oxy}-3-(2-boronoethyl)-2-hydroxybenzoic acid

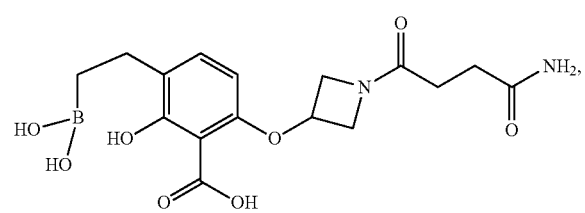 [SMILES: NC(=O)CCC(=O)N1CC(Oc2ccc(CCB(O)O)c(O)c2C(=O)O)C1]

3-(2-boronoethyl)-6-[(1-D-glutaminylazetidin-3-yl)oxy]-2-hydroxybenzoic acid

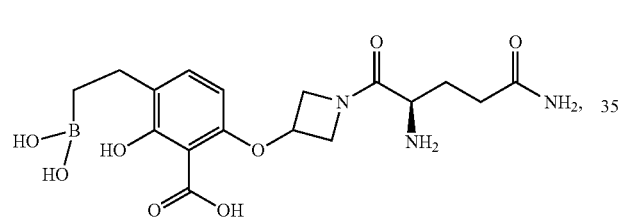

3-(2-boronoethyl)-6-({1-[3-(carbamoylamino)-D-alanyl]azetidin-3-yl}oxy)-2-hydroxybenzoic acid

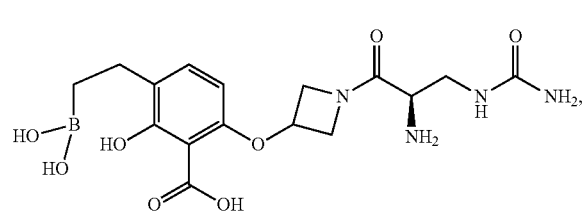 [SMILES: NC(=O)NC[C@@H](N)C(=O)N1CC(Oc2ccc(CCB(O)O)c(O)c2C(=O)O)C1]

6-{[1-(3-acetamido-D-alanyl)azetidin-3-yl]oxy}-3-(2-boronoethyl)-2-hydroxybenzoic acid

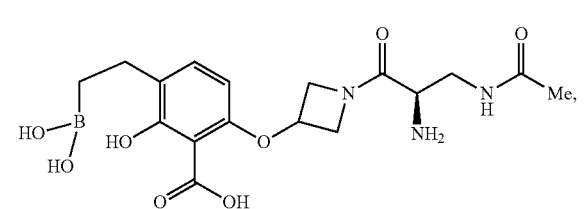 [SMILES: CC(=O)NC[C@@H](N)C(=O)N1CC(Oc2ccc(CCB(O)O)c(O)c2C(=O)O)C1]

774

3-(2-boronoethyl)-6-{[1-(N,N-dimethyl-D-asparaginyl)azetidin-3-yl]oxy}-2-hydroxybenzoic acid

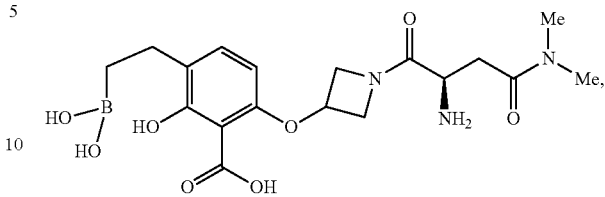

3-(2-boronoethyl)-2-hydroxy-6-{[1-(N-methyl-D-asparaginyl)azetidin-3-yl]oxy}benzoic acid

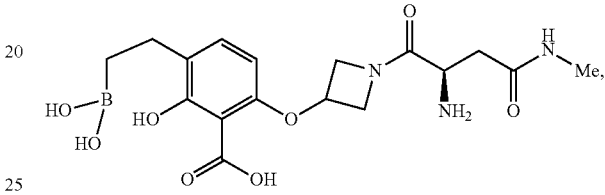

3-(2-boronoethyl)-2-hydroxy-6-[(1-L-serylazetidin-3-yl)oxy]benzoic acid

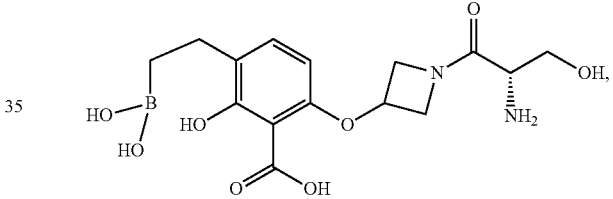

3-(2-boronoethyl)-2-hydroxy-6-{[1-(4-hydroxyprolyl)azetidin-3-yl]oxy}benzoic acid

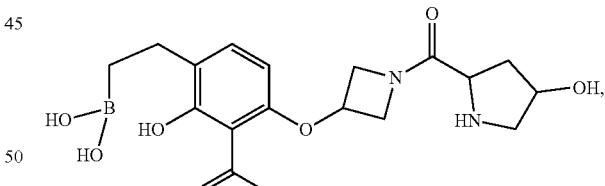

3-(2-boronoethyl)-2-hydroxy-6-({1-[(4R)-4-(trifluoromethyl)-D-prolyl]azetidin-3-yl}oxy)benzoic acid

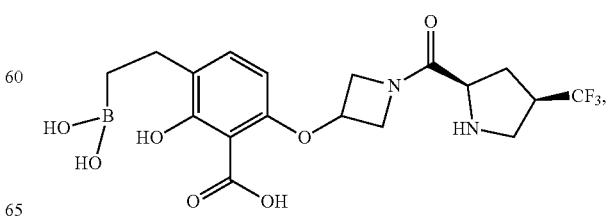

775

3-(2-boronoethyl)-6-({1-[(4S)-4-fluoro-L-prolyl]azetidin-3-yl}oxy)-2-hydroxybenzoic acid

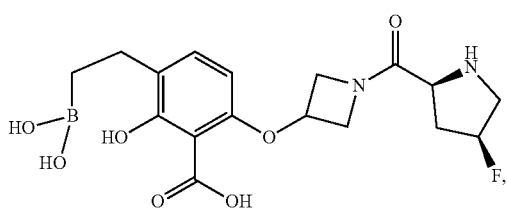 [SMILES: O=C(O)c1c(OC2CN(C(=O)[C@@H]3C[C@H](F)CN3)C2)ccc(CCB(O)O)c1O]

3-(2-boronoethyl)-2-hydroxy-6-({1-[(pyrrolidin-3-yl)acetyl]azetidin-3-yl}oxy)benzoic acid

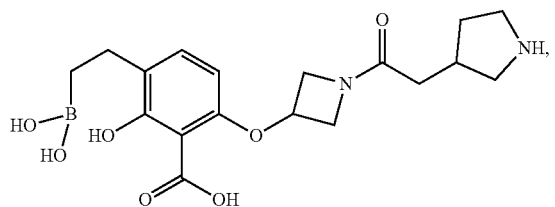 [SMILES: O=C(O)c1c(OC2CN(C(=O)CC3CCNC3)C2)ccc(CCB(O)O)c1O]

3-(2-boronoethyl)-6-[(1-{[(3R,5S)-5-(dimethylcarbamoyl)pyrrolidin-3-yl]acetyl}azetidin-3-yl)oxy]-2-hydroxybenzoic acid

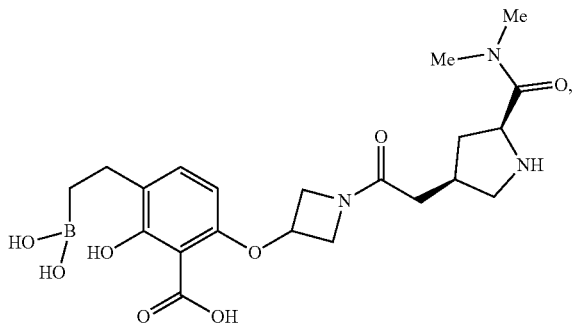 [SMILES: CN(C)C(=O)[C@@H]1C[C@H](CC(=O)N2CC(Oc3ccc(CCB(O)O)c(O)c3C(=O)O)C2)CN1]

3-(2-boronoethyl)-6-[(1-{[(3S,5R)-5-(dimethylcarbamoyl)pyrrolidin-3-yl]acetyl}azetidin-3-yl)oxy]-2-hydroxybenzoic acid

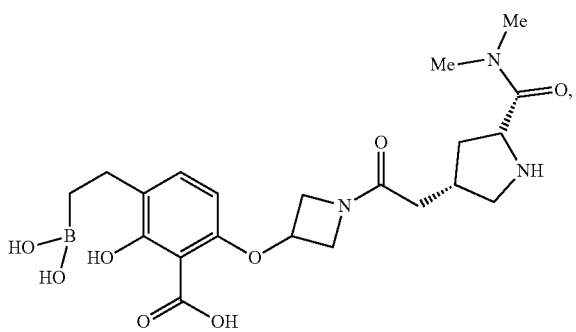

776

3-(2-boronoethyl)-6-[(1-{[(2R,4S)-4-fluoropyrrolidin-2-yl]acetyl}azetidin-3-yl)oxy]-2-hydroxybenzoic acid

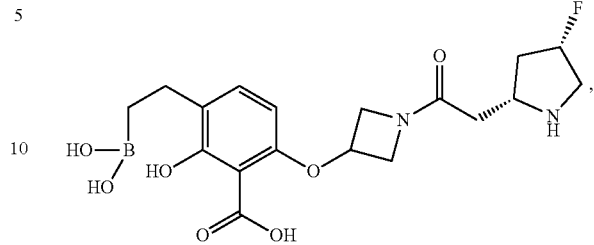

3-(2-boronoethyl)-6-{[1-(4,4-difluoro-L-prolyl)azetidin-3-yl]oxy}-2-hydroxybenzoic acid

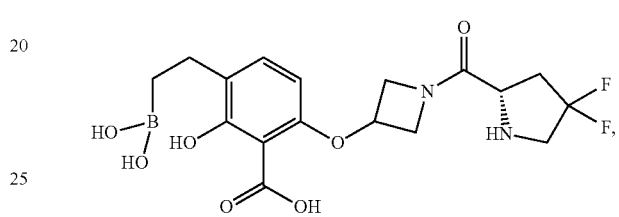

3-(2-boronoethyl)-2-hydroxy-6-({1-[(4R)-4-hydroxy-L-prolyl]azetidin-3-yl}oxy)benzoic acid

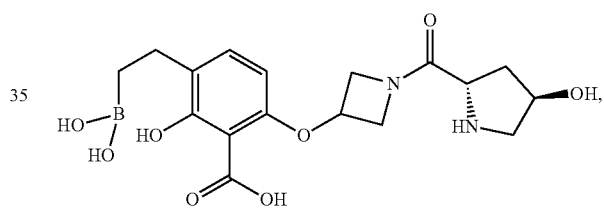

3-(2-boronoethyl)-2-hydroxy-6-({1-[(piperidin-4-yl)acetyl]azetidin-3-yl}oxy)benzoic acid

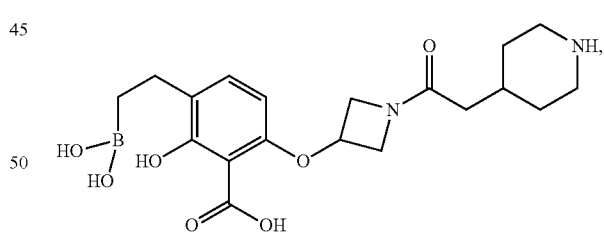

3-(2-boronoethyl)-2-hydroxy-6-{[1-(pyrrolidine-3-carbonyl)azetidin-3-yl]oxy}benzoic acid

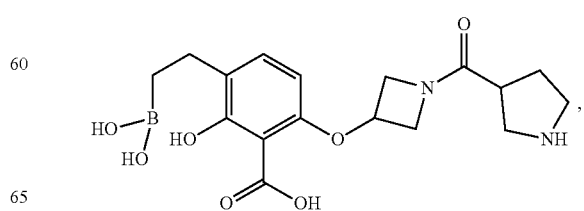

777

3-(2-boronoethyl)-2-hydroxy-6-({1-[(4S)-4-hydroxy-L-prolyl]azetidin-3-yl}oxy)benzoic acid

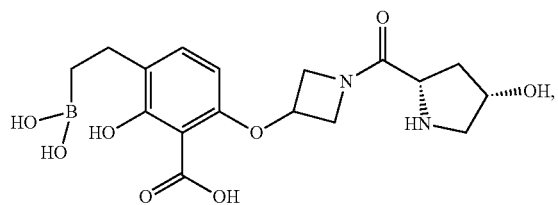 [SMILES: O=C(O)c1c(OC2CN(C(=O)[C@@H]3C[C@H](O)CN3)C2)ccc(CCB(O)O)c1O]

6-({1-[(4S)-4-amino-L-prolyl]azetidin-3-yl}oxy)-3-(2-boronoethyl)-2-hydroxybenzoic acid

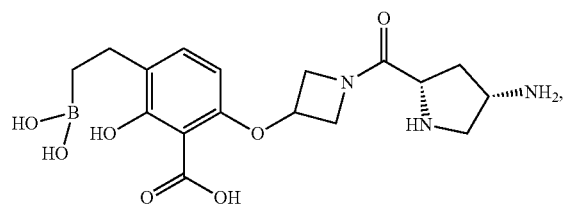 [SMILES: N[C@@H]1CN[C@H](C(=O)N2CC(Oc3ccc(CCB(O)O)c(O)c3C(=O)O)C2)C1]

6-({1-[(4S)-4-acetamido-L-prolyl]azetidin-3-yl}oxy)-3-(2-boronoethyl)-2-hydroxybenzoic acid

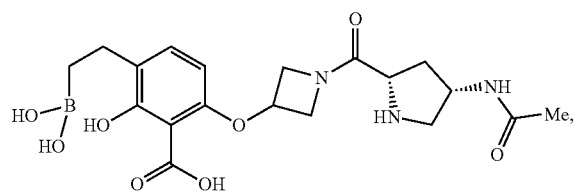 [SMILES: CC(=O)N[C@@H]1CN[C@H](C(=O)N2CC(Oc3ccc(CCB(O)O)c(O)c3C(=O)O)C2)C1]

3-(2-boronoethyl)-2-hydroxy-6-({1-[(3R)-3-hydroxy-L-prolyl]azetidin-3-yl}oxy)benzoic acid

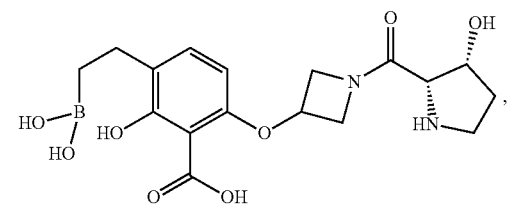 [SMILES: O=C(O)c1c(OC2CN(C(=O)[C@H]3NCC[C@H]3O)C2)ccc(CCB(O)O)c1O]

3-(2-boronoethyl)-6-{[1-(4,4-dimethyl-L-prolyl)azetidin-3-yl]oxy}-2-hydroxybenzoic acid

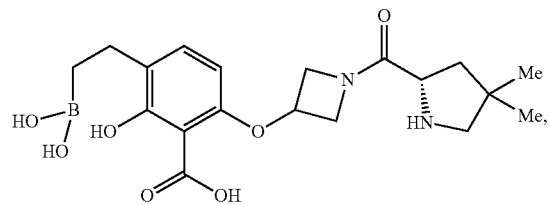 [SMILES: CC1(C)CN[C@H](C(=O)N2CC(Oc3ccc(CCB(O)O)c(O)c3C(=O)O)C2)C1]

778

3-(2-boronoethyl)-2-hydroxy-6-({1-[(pyrrolidin-2-yl)acetyl]azetidin-3-yl}oxy)benzoic acid

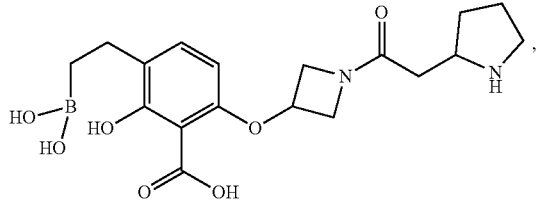 [SMILES: O=C(O)c1c(OC2CN(C(=O)CC3CCCN3)C2)ccc(CCB(O)O)c1O]

3-(2-boronoethyl)-2-hydroxy-6-{[1-(piperidine-2-carbonyl)azetidin-3-yl]oxy}benzoic acid

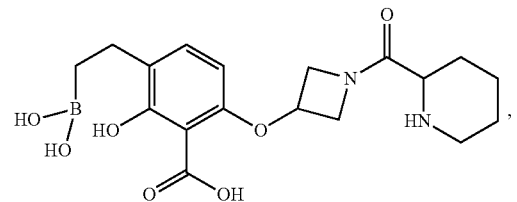 [SMILES: O=C(O)c1c(OC2CN(C(=O)C3CCCCN3)C2)ccc(CCB(O)O)c1O]

3-(2-boronoethyl)-2-hydroxy-6-{[1-(piperidine-3-carbonyl)azetidin-3-yl]oxy}benzoic acid

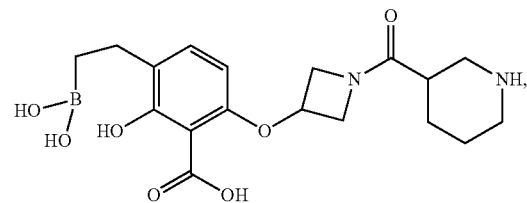 [SMILES: O=C(O)c1c(OC2CN(C(=O)C3CCCNC3)C2)ccc(CCB(O)O)c1O]

3-(2-boronoethyl)-2-hydroxy-6-{[1-(piperidine-4-carbonyl)azetidin-3-yl]oxy}benzoic acid

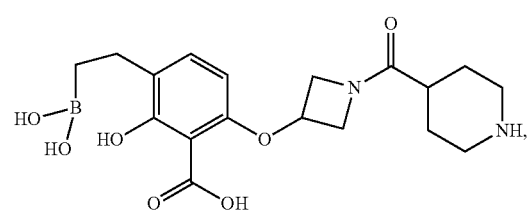 [SMILES: O=C(O)c1c(OC2CN(C(=O)C3CCNCC3)C2)ccc(CCB(O)O)c1O]

3-(2-boronoethyl)-2-hydroxy-6-({1-[(2S)-oxolane-2-carbonyl]azetidin-3-yl}oxy)benzoic acid

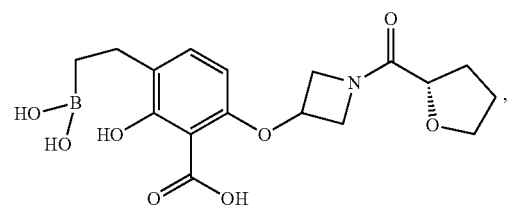 [SMILES: O=C(O)c1c(OC2CN(C(=O)[C@@H]3CCCO3)C2)ccc(CCB(O)O)c1O]

779

3-(2-boronoethyl)-2-hydroxy-6-({1-[(4R)-4-phenyl-L-prolyl]azetidin-3-yl}oxy)benzoic acid

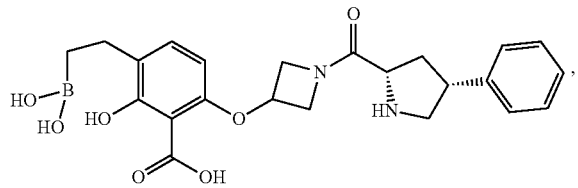 [SMILES: O=C(O)c1c(OC2CN(C(=O)[C@@H]3C[C@H](c4ccccc4)CN3)C2)ccc(CCB(O)O)c1O]

6-({1-[(1S,3S,5S)-2-azabicyclo[3.1.0]hexane-3-carbonyl]azetidin-3-yl}oxy)-3-(2-boronoethyl)-2-hydroxybenzoic acid

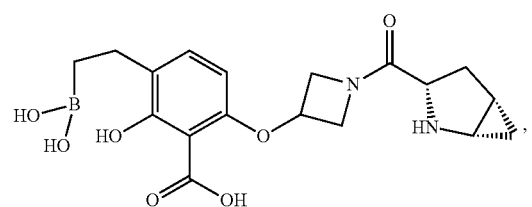 [SMILES: O=C(O)c1c(OC2CN(C(=O)[C@@H]3C[C@@H]4C[C@@H]4N3)C2)ccc(CCB(O)O)c1O]

3-(2-boronoethyl)-2-hydroxy-6-{[1(1-methyl-L-prolyl)azetidin-3-yl]oxy}benzoic acid

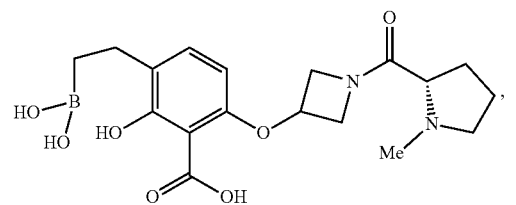 [SMILES: CN1CCC[C@H]1C(=O)N1CC(Oc2ccc(CCB(O)O)c(O)c2C(=O)O)C1]

3-(2-boronoethyl)-2-hydroxy-6-({1-[(piperidin-3-yl)acetyl]azetidin-3-yl}oxy)benzoic acid

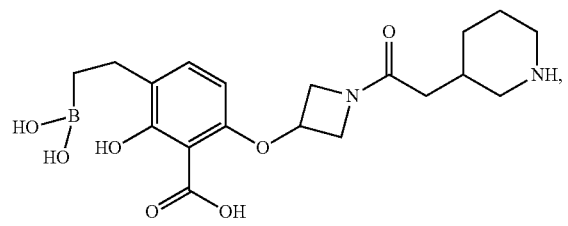 [SMILES: O=C(O)c1c(OC2CN(C(=O)CC3CCCNC3)C2)ccc(CCB(O)O)c1O]

3-(2-boronoethyl)-2-hydroxy-6-({1-[(morpholin-2-yl)acetyl]azetidin-3-yl}oxy)benzoic acid

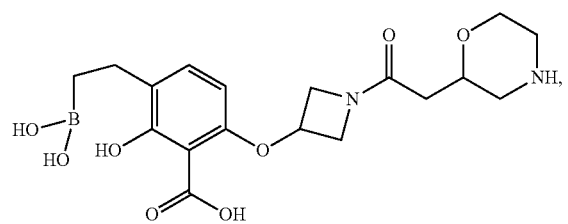 [SMILES: O=C(O)c1c(OC2CN(C(=O)CC3CNCCO3)C2)ccc(CCB(O)O)c1O]

780

6-({1-[(azetidin-3-yl)acetyl]azetidin-3-yl}oxy)-3-(2-boronoethyl)-2-hydroxybenzoic acid

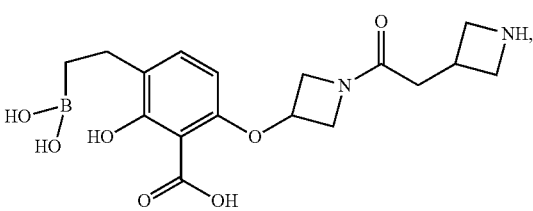 [SMILES: O=C(O)c1c(OC2CN(C(=O)CC3CNC3)C2)ccc(CCB(O)O)c1O]

6-({1-[amino(pyrrolidin-3-yl)acetyl]azetidin-3-yl}oxy)-3-(2-boronoethyl)-2-hydroxybenzoic

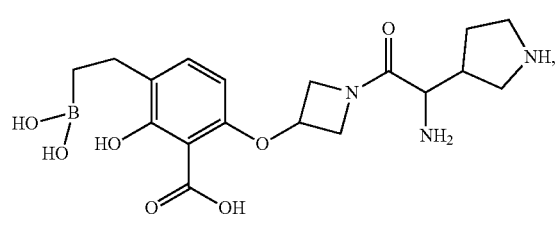 [SMILES: NC(C(=O)N1CC(Oc2ccc(CCB(O)O)c(O)c2C(=O)O)C1)C1CCNC1]

3-(2-boronoethyl)-2-hydroxy-6-({1-[3-(pyrrolidin-2-yl)propanoyl]azetidin-3-yl}oxy)benzoic

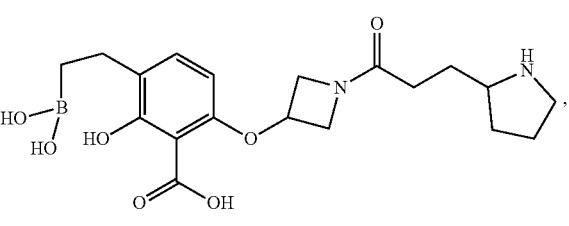 [SMILES: O=C(O)c1c(OC2CN(C(=O)CCC3CCCN3)C2)ccc(CCB(O)O)c1O]

6-({1-[(4R)-4-amino-L-prolyl]azetidin-3-yl}oxy)-3-(2-boronoethyl)-2-hydroxybenzoic acid

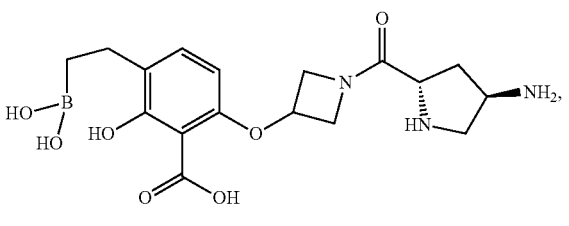 [SMILES: N[C@H]1CN[C@H](C(=O)N2CC(Oc3ccc(CCB(O)O)c(O)c3C(=O)O)C2)C1]

6-({1-[(4R)-4-acetamido-L-prolyl]azetidin-3-yl}oxy)-3-(2-boronoethyl)-2-hydroxybenzoic acid

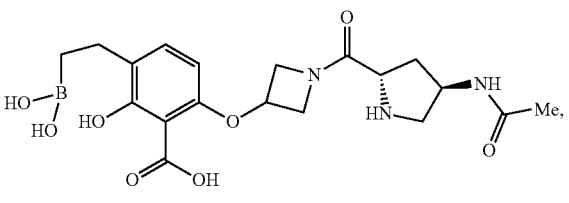 [SMILES: CC(=O)N[C@H]1CN[C@H](C(=O)N2CC(Oc3ccc(CCB(O)O)c(O)c3C(=O)O)C2)C1]

781

6-({1-[amino(piperidin-4-yl)acetyl]azetidin-3-yl}oxy)-3-(2-boronoethyl)-2-hydroxybenzoic acid

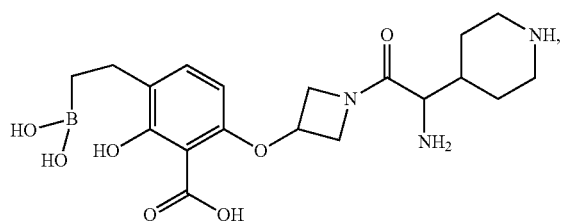 [SMILES: NC(C(=O)N1CC(Oc2ccc(CCB(O)O)c(O)c2C(=O)O)C1)C1CCNCC1]

3-(2-boronoethyl)-2-hydroxy-6-({1-[(piperidin-2-yl)acetyl]azetidin-3-yl}oxy)benzoic acid

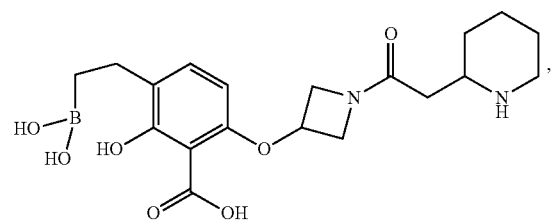 [SMILES: O=C(O)c1c(OC2CN(C(=O)CC3CCCCN3)C2)ccc(CCB(O)O)c1O]

3-(2-boronoethyl)-6-({1-[(4S)-4-carbamoyl-L-prolyl]azetidin-3-yl}oxy)-2-hydroxybenzoic acid

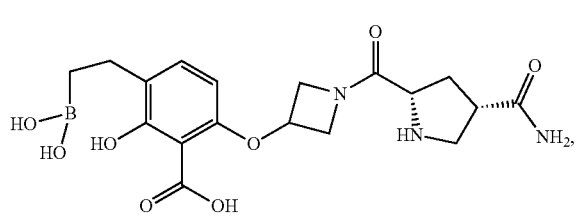 [SMILES: NC(=O)[C@@H]1CN[C@H](C(=O)N2CC(Oc3ccc(CCB(O)O)c(O)c3C(=O)O)C2)C1]

3-(2-boronoethyl)-2-hydroxy-6-[(1-{[(3R)-pyrrolidin-3-yl]acetyl}azetidin-3-yl)oxy]benzoic acid

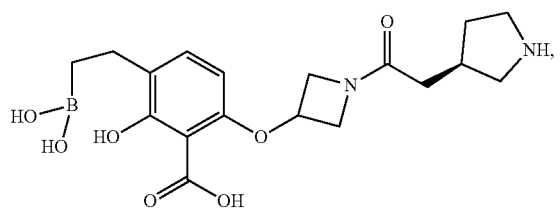 [SMILES: O=C(O)c1c(OC2CN(C(=O)C[C@H]3CCNC3)C2)ccc(CCB(O)O)c1O]

3-(2-boronoethyl)-2-hydroxy-6-[(1-{[(3S)-pyrrolidin-3-yl]acetyl}azetidin-3-yl)oxy]benzoic acid

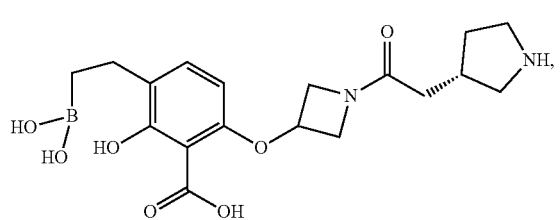 [SMILES: O=C(O)c1c(OC2CN(C(=O)C[C@@H]3CCNC3)C2)ccc(CCB(O)O)c1O]

782

3-(2-boronoethyl)-2-hydroxy-6-[(1-{[(2R)-pyrrolidin-2-yl]acetyl}azetidin-3-yl)oxy]benzoic acid

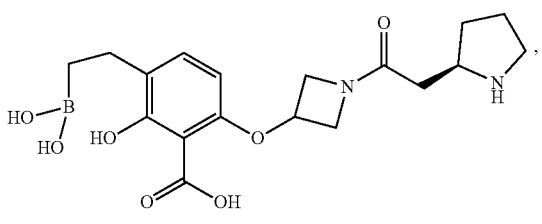 [SMILES: O=C(O)c1c(OC2CN(C(=O)C[C@H]3CCCN3)C2)ccc(CCB(O)O)c1O]

3-(2-boronoethyl)-2-hydroxy-6-[(1-{[(2S)-pyrrolidin-2-yl]acetyl}azetidin-3-yl)oxy]benzoic acid

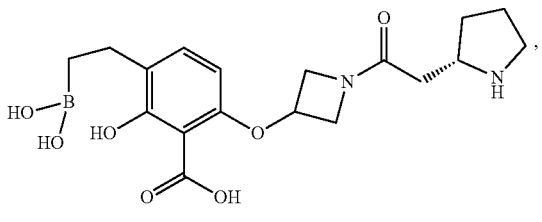 [SMILES: O=C(O)c1c(OC2CN(C(=O)C[C@@H]3CCCN3)C2)ccc(CCB(O)O)c1O]

3-(2-boronoethyl)-2-hydroxy-6-({1-[(piperazin-2-yl)acetyl]azetidin-3-yl}oxy)benzoic acid

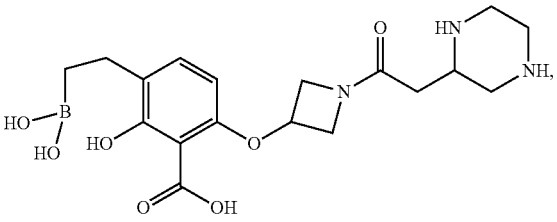 [SMILES: O=C(O)c1c(OC2CN(C(=O)CC3CNCCN3)C2)ccc(CCB(O)O)c1O]

3-(2-boronoethyl)-6-({1-[(1,1-dioxo-1$\lambda^6$-thiomorpholin-2-yl)acetyl]azetidin-3-yl}oxy)-2-hydroxybenzoic acid

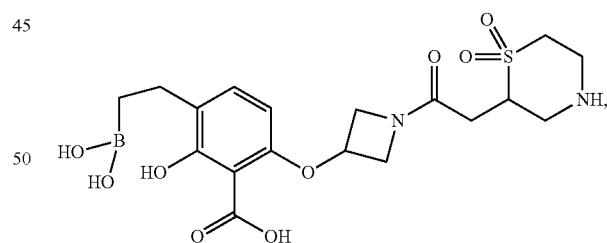

6-({1-[(2S)-4-acetamido-2-aminobutanoyl]azetidin-3-yl}oxy)-3-(2-boronoethyl)-2-hydroxybenzoic acid

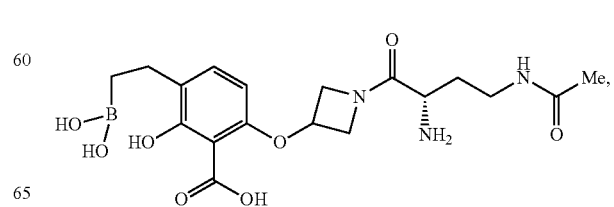

6-{[1-(L-α-asparaginyl)azetidin-3-yl]oxy}-3-(2-borono-ethyl)-2-hydroxybenzoic acid

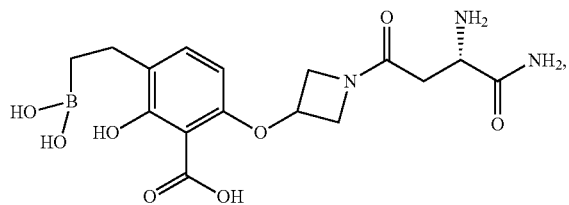 [SMILES: NC(=O)[C@@H](N)CC(=O)N1CC(Oc2ccc(CCB(O)O)c(O)c2C(=O)O)C1]

6-{[1-(L-alanyl-L-alanyl)azetidin-3-yl]oxy}-3-(2-bo-ronoethyl)-2-hydroxybenzoic acid

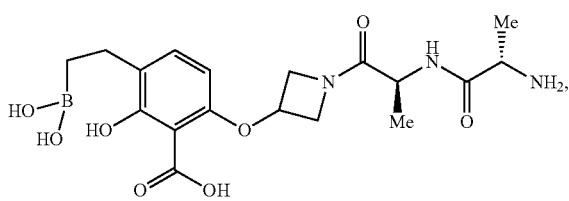 [SMILES: C[C@H](N)C(=O)N[C@@H](C)C(=O)N1CC(Oc2ccc(CCB(O)O)c(O)c2C(=O)O)C1]

3-(2-boronoethyl)-6-{[1-(glycyl-D-alanyl)azetidin-3-yl]oxy}-2-hydroxybenzoic acid

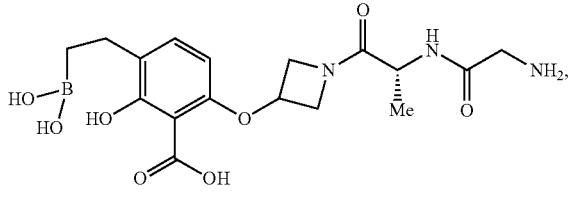

N-[(2R)-1-{3-[4-(2-boronoethyl)-2-carboxy-3-hydroxy-phenoxy]azetidin-1-yl}-1-oxopropan-2-yl]-D-α-as-paragine

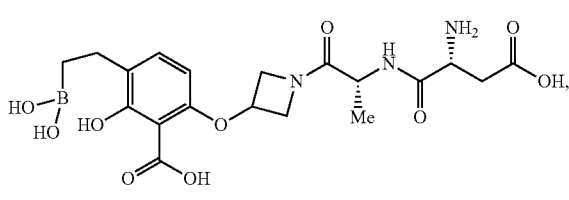 [SMILES: C[C@@H](NC(=O)[C@H](N)CC(=O)O)C(=O)N1CC(Oc2ccc(CCB(O)O)c(O)c2C(=O)O)C1]

N¹-[(2R)-1-{3-[4-(2-boronoethyl)-2-carboxy-3-hydroxy-phenoxy]azetidin-1-yl}-1-oxopropan-2-yl]-D-aspart-amide

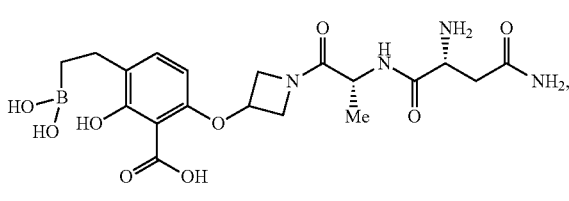

N-[(2R)-1-{3-[4-(2-boronoethyl)-2-carboxy-3-hydroxy-phenoxy]azetidin-1-yl}-1-oxopropan-2-yl]-D-serina-mide

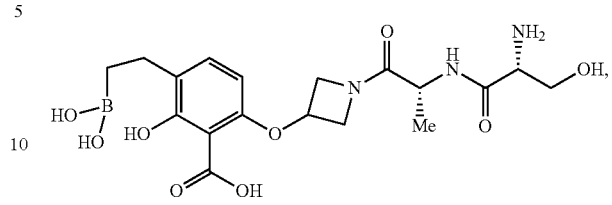

6-({1-[(3S)-3-amino-3-carboxypropanoyl]azetidin-3-yl}oxy)-3-(2-boronoethyl)-2-hydroxybenzoic acid

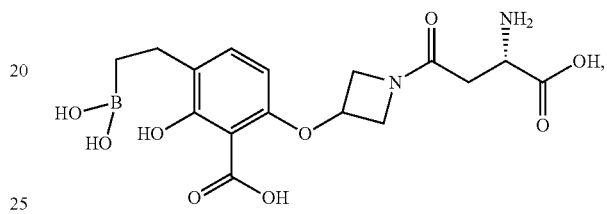

3-(2-boronoethyl)-2-hydroxy-6-({1-[(1H-imidazol-4-yl)(methylamino)acetyl]azetidin-3-yl}oxy)benzoic acid

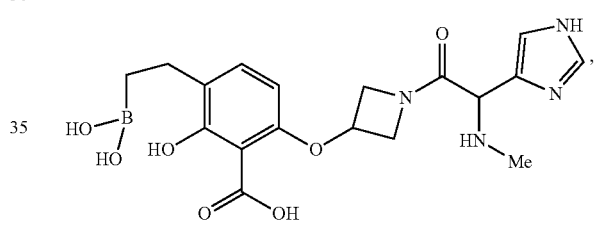

3-(2-boronoethyl)-6-({1-[(dimethylamino)(1H-imidazol-4-yl)acetyl]azetidin-3-yl}oxy)-2-hydroxybenzoic acid

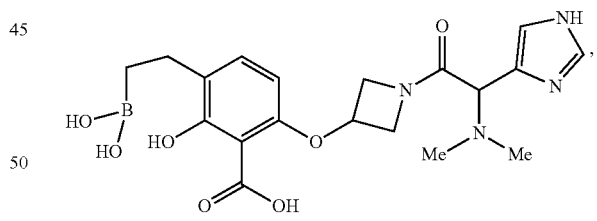

3-(2-boronoethyl)-2-hydroxy-6-{[1-(2-methyl-D-seryl)azetidin-3-yl]oxy}benzoic acid

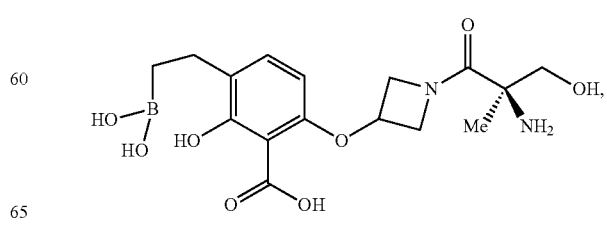

785

3-(2-boronoethyl)-2-hydroxy-6-{[1-(2-methyl-L-seryl)azetidin-3-yl]oxy}benzoic acid

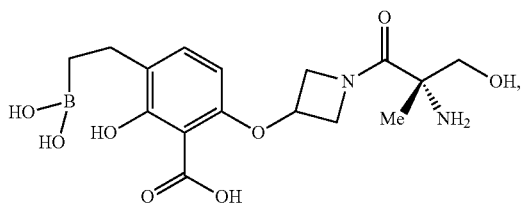 [SMILES: C[C@](N)(CO)C(=O)N1CC(Oc2ccc(CCB(O)O)c(O)c2C(=O)O)C1]

3-(2-boronoethyl)-2-hydroxy-6-({1-[(3-oxopiperazin-2-yl)acetyl]azetidin-3-yl}oxy)benzoic acid

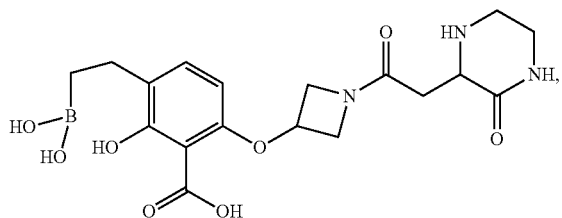 [SMILES: O=C(O)c1c(OC2CN(C(=O)CC3NCCNC3=O)C2)ccc(CCB(O)O)c1O]

6-({1-[(3S)-3-amino-5-carboxypentanoyl]azetidin-3-yl}oxy)-3-(2-boronoethyl)-2-hydroxybenzoic acid

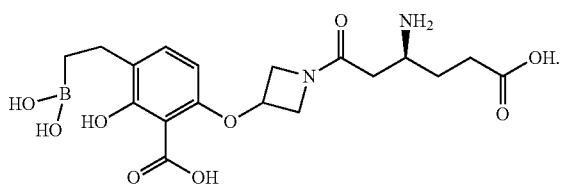 [SMILES: N[C@@H](CCC(=O)O)CC(=O)N1CC(Oc2ccc(CCB(O)O)c(O)c2C(=O)O)C1]

6-({1-[(3R)-3-amino-3-carboxypropanoyl]azetidin-3-yl}oxy)-3-(2-boronoethyl)-2-hydroxybenzoic acid

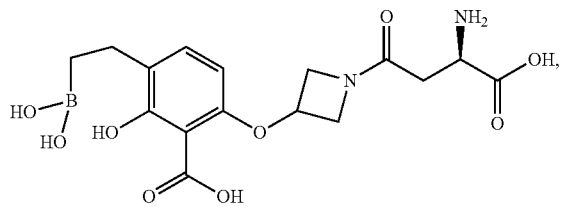 [SMILES: N[C@H](CC(=O)N1CC(Oc2ccc(CCB(O)O)c(O)c2C(=O)O)C1)C(=O)O]

6-({1-[(4R)-4-amino-4-carboxybutanoyl]azetidin-3-yl}oxy)-3-(2-boronoethyl)-2-hydroxybenzoic acid

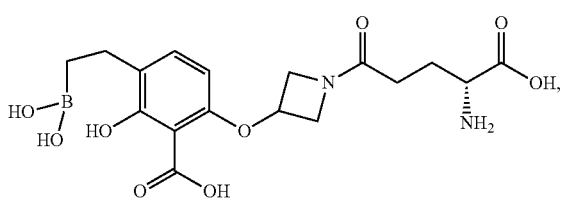 [SMILES: N[C@H](CCC(=O)N1CC(Oc2ccc(CCB(O)O)c(O)c2C(=O)O)C1)C(=O)O]

786

3-(2-boronoethyl)-6-({1-[(3S)-3,6-diamino-6-oxohexanoyl]azetidin-3-yl}oxy)-2-hydroxybenzoic acid

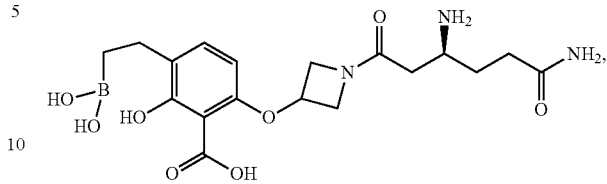

6-{[1-(D-α-asparaginyl)azetidin-3-yl]oxy}-3-(2-boronoethyl)-2-hydroxybenzoic acid

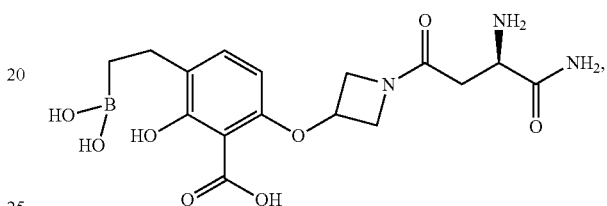

3-(2-boronoethyl)-6-{[1-(D-α-glutaminyl)azetidin-3-yl]oxy}-2-hydroxybenzoic acid

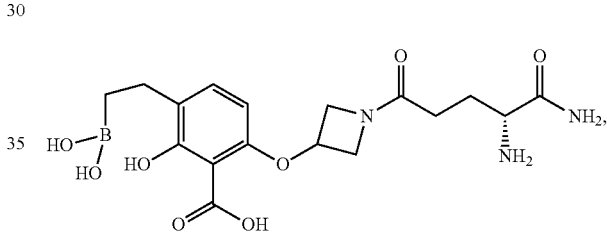

6-({1-[(4S)-4-amino-4-carboxybutanoyl]azetidin-3-yl}oxy)-3-(2-boronoethyl)-2-hydroxybenzoic acid

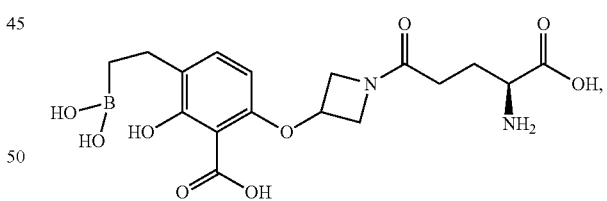

3-(2-boronoethyl)-6-{[1-(L-α-glutaminyl)azetidin-3-yl]oxy}-2-hydroxybenzoic acid

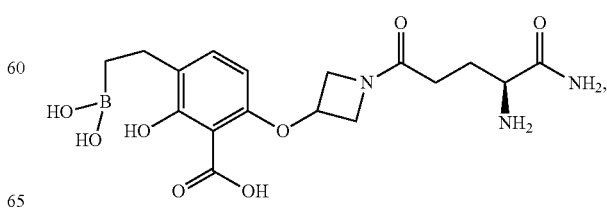

3-(2-boronoethyl)-2-hydroxy-6-[(1-D-threonylazetidin-3-yl)oxy]benzoic acid

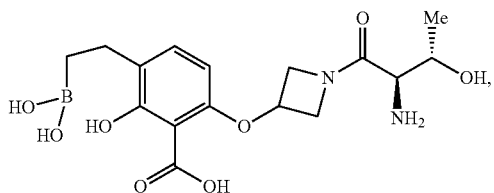 [SMILES: C[C@H](O)[C@@H](N)C(=O)N1CC(Oc2ccc(CCB(O)O)c(O)c2C(=O)O)C1]

and 3-(2-boronoethyl)-2-hydroxy-6-[(1-L-threonylazetidin-3-yl)oxy]benzoic acid; and

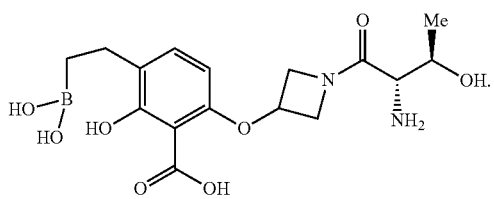 [SMILES: C[C@@H](O)[C@H](N)C(=O)N1CC(Oc2ccc(CCB(O)O)c(O)c2C(=O)O)C1]

45. A medicament comprising the compound or the pharmaceutically acceptable salt thereof according to claim 1.

46. The medicament according to claim 45, which is a therapeutic drug or a prophylactic drug for a bacterial infection.

47. A β-lactamase inhibiting agent comprising the compound or the pharmaceutically acceptable salt thereof according to claim 1 as an active ingredient.

48. A pharmaceutical composition comprising the compound or the pharmaceutically acceptable salt thereof according to claim 1 and a pharmaceutically acceptable carrier.

49. The pharmaceutical composition according to claim 48, further comprising an additional agent.

50. The pharmaceutical composition according to claim 49, wherein the additional agent is selected from the group consisting of an antibacterial agent, an antifungal agent, an antiviral agent, an anti-inflammatory agent, and an anti-allergic agent.

51. The pharmaceutical composition according to claim 49, wherein the additional agent is a β-lactam agent.

52. The pharmaceutical composition according to claim 51, wherein a β-lactam agent, which is the additional agent, is selected from the group consisting of amoxicillin, ampicillin (pivampicillin, hetacillin, bacampicillin, metampicillin, and talampicillin), epicillin, carbenicillin (carindacillin), ticarcillin, temocillin, azlocillin, piperacillin, mezlocillin, mecillinam (pivmecillinam), sulbenicillin, benzylpenicillin (G), clometocillin, benzathine benzylpenicillin, procaine benzylpenicillin, azidocillin, penamecillin, phenoxymethyl penicillin (V), propicillin, benzathine phenoxymethylpenicillin, phenethicillin, cloxacillin (dicloxacillin and flucloxacillin), oxacillin, methicillin, nafcillin, faropenem, biapenem doripenem, ertapenem, imipenem, meropenem, panipenem, tomopenem, razupenem, cefazolin, cefacetrile, cefadroxil, cephalexin, cefaloglycin, cefalonium, cefaloridine, cephalothin, cephapirin, cefatrizine, cefazedone, cefazaflur, cefradine, cefroxadine, ceftezole, cefaclor, cefamandole, cefminox, cefonicide, ceforanide, cefotiam, cefprozil, cefbuperazone, cefuroxime, cefuzonam, cefoxitin, cefotetan, cefmetazole, loracarbef, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, flomoxef, latamoxef, cefepime, cefozopran, cefpirome, cefquinome, ceftobiprole, ceftaroline, CXA-101, RWJ-54428, MC-04546, ME1036, BAL30072, SYN2416, ceftiofur, cefquinome, cefovecin, aztreonam, tigemonam, carumonam, RWJ-442831, RWJ-333441, and RWJ-333442.

53. The pharmaceutical composition according to claim 52, wherein the β-lactam agent is selected from ceftazidime, biapenem, doripenem, ertapenem, imipenem, meropenem, or panipenem.

54. The pharmaceutical composition according to claim 52, wherein the β-lactam agent is selected from aztreonam, tigemonam, BAL30072, SYN2416, or carumonam.

55. The pharmaceutical composition according to claim 48, characterized in that an additional agent is concomitantly administered.

56. The pharmaceutical composition according to claim 55, wherein the additional agent is selected from an antibacterial agent, an antifungal agent, an antiviral agent, an anti-inflammatory agent, or an anti-allergic agent.

57. The pharmaceutical composition according to claim 56, wherein the additional agent is a β-lactam agent.

58. The pharmaceutical composition according to claim 57, wherein a β-lactam agent, which is the additional agent, is selected from the group consisting of amoxicillin, ampicillin (pivampicillin, hetacillin, bacampicillin, metampicillin, and talampicillin), epicillin, carbenicillin (carindacillin), ticarcillin, temocillin, azlocillin, piperacillin, mezlocillin, mecillinam (pivmecillinam), sulbenicillin, benzylpenicillin (G), clometocillin, benzathine benzylpenicillin, procaine benzylpenicillin, azidocillin, penamecillin, phenoxymethyl penicillin (V), propicillin, benzathine phenoxymethylpenicillin, phenethicillin, cloxacillin (dicloxacillin and flucloxacillin), oxacillin, methicillin, nafcillin, faropenem, biapenem, doripenem, ertapenem, imipenem, meropenem, panipenem, tomopenem, razupenem, cefazolin, cefacetrile, cefadroxil, cephalexin, cefaloglycin, cefalonium, cefaloridine, cephalothin, cephapirin, cefatrizine, cefazedone, cefazaflur, cefradine, cefroxadine, ceftezole, cefaclor, cefamandole, cefminox, cefonicide, ceforanide, cefotiam, cefprozil, cefbuperazone, cefuroxime, cefuzonam, cefoxitin, cefotetan, cefmetazole, loracarbef, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, flomoxef, latamoxef, cefepime, cefozopran, cefpirome, cefquinome, ceftobiprole, ceftaroline, CXA-101, RWJ-54428, MC-04546, ME1036, BAL30072, SYN2416, ceftiofur, cefquinome, cefovecin, aztreonam, tigemonam, carumonam, RWJ-442831, RWJ-333441, and RWJ-333442.

59. The pharmaceutical composition according to claim 58, wherein the β-lactam agent is selected from the group consisting of ceftazidime, biapenem, doripenem, ertapenem, imipenem meropenem, and panipenem.

60. The pharmaceutical composition according to claim 58, wherein the β-lactam agent is selected from the group consisting of aztreonam, tigemonam, BAL30072, SYN2416, and carumonam.

61. The compound or the pharmaceutically acceptable salt thereof according to claim 1 for treating a bacterial infection.

62. The compound or the pharmaceutically acceptable salt thereof according to claim 61, wherein the bacterial infection is a bacterial infection in which a bacteria that can have a β-lactamase is involved.

63. The compound or the pharmaceutically acceptable salt thereof according to claim 62, wherein the bacterial infection is sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, eye infection, or an odontogenic infection.

64. A medicament comprised of a combination of the compound or the pharmaceutically acceptable salt thereof according to claim 1 and at least one agent selected from the group consisting of therapeutic agents for sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, eye infection, and an odontogenic infection.

65. A method for treating a bacterial infection, comprising administering a therapeutically effective amount of the compound or the pharmaceutically acceptable salt thereof according to claim 1 is administered to a patient in need thereof.

66. The method according to claim 65, wherein the bacterial infection is a bacterial infection in which a bacteria that can have a β-lactamase is involved.

67. The method according to claim 66, wherein the bacterial infection is sepsis, febrile neutropenia, bacterial meningitis, bacterial endocarditis, otitis media, sinusitis, pneumonia, lung abscess, empyema, secondary infection of a chronic respiratory disease, pharyngolaryngitis, tonsillitis, osteomyelitis, arthritis, peritonitis, intraperitoneal abscess, cholecystitis, cholangitis, liver abscess, a deep skin infection, lymphangitis/lymphadenitis, secondary infection of trauma, burn injury, surgical wound, or the like, a urinary tract infection, a genital infection, an eye infection, or an odontogenic infection.

68. The method of claim 67, wherein an additional agent is concomitantly administered.

* * * * *